US012208136B2

(12) United States Patent
Muik et al.

(10) Patent No.: US 12,208,136 B2
(45) **Date of Patent: *Jan. 28, 2025**

(54) CORONAVIRUS VACCINE

(71) Applicant: BioNTech SE, Mainz (DE)

(72) Inventors: Alexander Muik, Seeheim-Jugenheim (DE); Kena Anne Swanson, Pearl River, NY (US); Qi Yang, Orangeburg, NY (US); Hui Cai, Ridgewood, NJ (US); Ugur Sahin, Mainz (DE); Kayvon Modjarrad, Chevy Chase, MD (US)

(73) Assignee: BioNTech SE, Mainz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/186,914

(22) Filed: Mar. 20, 2023

(65) Prior Publication Data

US 2024/0042011 A1 Feb. 8, 2024

Related U.S. Application Data

(63) Continuation of application No. 18/071,499, filed on Nov. 29, 2022.

(60) Provisional application No. 63/425,290, filed on Nov. 14, 2022, provisional application No. 63/422,404, filed on Nov. 3, 2022, provisional application No. 63/417,680, filed on Oct. 19, 2022, provisional application No. 63/402,444, filed on Aug. 30, 2022, provisional application No. 63/394,571, filed on Aug. 2, 2022, provisional application No. 63/358,522, filed on Jul. 5, 2022, provisional application No. 63/357,628, filed on Jun. 30, 2022, provisional application No. 63/355,648, filed on Jun. 26, 2022, provisional application No. 63/355,597, filed on Jun. 25, 2022, provisional application No. 63/342,614, filed on May 16, 2022, provisional application No. 63/324,586, filed on Mar. 28, 2022, provisional application No. 63/302,997, filed on Jan. 25, 2022, provisional application No. 63/291,347, filed on Dec. 17, 2021, provisional application No. 63/287,486, filed on Dec. 8, 2021, provisional application No. 63/283,976, filed on Nov. 29, 2021.

(51) Int. Cl.

| | |
|---|---|
| ***A61K 39/215*** | (2006.01) |
| ***A61K 9/127*** | (2006.01) |
| ***A61K 39/145*** | (2006.01) |
| ***A61K 45/06*** | (2006.01) |
| ***A61K 47/26*** | (2006.01) |
| ***C12N 15/86*** | (2006.01) |
| *A61K 39/00* | (2006.01) |

(52) U.S. Cl.

CPC .......... *A61K 39/215* (2013.01); *A61K 9/1272* (2013.01); *A61K 39/145* (2013.01); *A61K 45/06* (2013.01); *A61K 47/26* (2013.01); *C12N 15/86* (2013.01); *A61K 2039/53* (2013.01); *A61K 2039/54* (2013.01); *A61K 2039/545* (2013.01); *A61K 2039/55555* (2013.01); *C12N 2310/335* (2013.01); *C12N 2760/16022* (2013.01); *C12N 2760/16034* (2013.01); *C12N 2770/20022* (2013.01); *C12N 2770/20034* (2013.01); *C12N 2770/20043* (2013.01); *C12N 2770/20071* (2013.01)

(58) Field of Classification Search

None

See application file for complete search history.

(56) References Cited

U.S. PATENT DOCUMENTS

| | | | |
|---|---|---|---|
| 4,898,278 | A | 2/1990 | Leoncavallo et al. |
| 6,381,981 | B1 | 5/2002 | Yaddgo et al. |
| 7,736,850 | B2 | 6/2010 | Van Der Werf et al. |
| 7,901,708 | B2 | 3/2011 | MacLachlan et al. |
| 8,058,069 | B2 | 11/2011 | Yaworski et al. |
| 8,153,773 | B2 | 4/2012 | Jemielity et al. |
| 8,278,036 | B2 | 10/2012 | Kariko et al. |
| 8,329,070 | B2 | 12/2012 | MacLachlan et al. |
| 8,691,966 | B2 | 4/2014 | Kariko et al. |
| 8,710,200 | B2 | 4/2014 | Schrum et al. |
| 8,748,089 | B2 | 6/2014 | Kariko et al. |

(Continued)

FOREIGN PATENT DOCUMENTS

| | | | |
|---|---|---|---|
| AU | 2015210364 | A1 | 8/2015 |
| AU | 2019264591 | A1 | 12/2019 |

(Continued)

OTHER PUBLICATIONS

U.S. Appl. No. 18/341,590, Muik et al.

(Continued)

*Primary Examiner* — Benjamin P Blumel
*Assistant Examiner* — Jeffrey Mark Sifford
(74) *Attorney, Agent, or Firm* — Choate, Hall & Stewart LLP; Brenda Herschbach Jarrell; Rolando Medina

(57) ABSTRACT

This disclosure relates to the field of RNA to prevent or treat coronavirus infection. In particular, the present disclosure relates to methods and agents for vaccination against coronavirus infection and inducing effective coronavirus antigen-specific immune responses such as antibody and/or T cell responses. Specifically, in one embodiment, the present disclosure relates to methods comprising administering to a subject RNA encoding a peptide or protein comprising an epitope of SARS-CoV-2 spike protein (S protein) for inducing an immune response against coronavirus S protein, in particular S protein of SARS-CoV-2, in the subject, i.e., vaccine RNA encoding vaccine antigen.

28 Claims, 108 Drawing Sheets

Specification includes a Sequence Listing.

(56) References Cited

U.S. PATENT DOCUMENTS

| | | | |
|---|---|---|---|
| 8,754,062 B2 | 6/2014 | de Fougerolles et al. | |
| 8,822,663 B2 | 9/2014 | Schrum et al. | |
| 8,835,108 B2 | 9/2014 | Kariko et al. | |
| 8,999,380 B2 | 4/2015 | Bancel et al. | |
| 9,220,755 B2 | 12/2015 | Chakraborty et al. | |
| 9,221,891 B2 | 12/2015 | Bancel et al. | |
| 9,283,287 B2 | 3/2016 | Chakraborty et al. | |
| 9,295,717 B2 | 3/2016 | Sahin et al. | |
| 9,303,079 B2 | 4/2016 | Chakraborty et al. | |
| 9,334,328 B2 | 5/2016 | Schrum et al. | |
| 9,364,435 B2 | 6/2016 | Yaworski et al. | |
| 9,428,535 B2 | 8/2016 | de Fougerolles et al. | |
| 9,464,124 B2 | 10/2016 | Bancel et al. | |
| 9,476,055 B2 | 10/2016 | Sahin et al. | |
| 9,492,386 B2 | 11/2016 | MacLachlan et al. | |
| 9,504,651 B2 | 11/2016 | MacLachlan et al. | |
| 9,512,456 B2 | 12/2016 | Wang et al. | |
| 9,533,047 B2 | 1/2017 | de Fougerolles et al. | |
| 9,597,380 B2 | 3/2017 | Chakraborty et al. | |
| 9,657,295 B2 | 5/2017 | Schrum et al. | |
| 9,669,089 B2 | 6/2017 | Thess et al. | |
| 9,737,619 B2 | 8/2017 | Ansell et al. | |
| 9,738,593 B2 | 8/2017 | Ansell et al. | |
| 9,750,824 B2 | 9/2017 | Kariko et al. | |
| 9,850,269 B2 | 12/2017 | DeRosa et al. | |
| 9,868,691 B2 | 1/2018 | Benenato | |
| 9,868,692 B2 | 1/2018 | Benenato | |
| 9,872,900 B2 | 1/2018 | Ciaramella et al. | |
| 9,957,499 B2 | 5/2018 | Heartlein et al. | |
| 9,970,047 B2 | 5/2018 | Heartlein et al. | |
| 10,022,435 B2 | 7/2018 | Ciaramella et al. | |
| 10,064,934 B2 | 9/2018 | Ciaramella et al. | |
| 10,064,935 B2 | 9/2018 | Ciaramella et al. | |
| 10,064,959 B2 | 9/2018 | Schrum et al. | |
| 10,106,490 B2 | 10/2018 | Du | |
| 10,106,800 B2 | 10/2018 | Sahin et al. | |
| 10,124,055 B2 | 11/2018 | Ciaramella et al. | |
| 10,166,298 B2 | 1/2019 | Ansell et al. | |
| 10,207,010 B2 | 2/2019 | Besin et al. | |
| 10,232,055 B2 | 3/2019 | Kariko et al. | |
| 10,238,754 B2 | 3/2019 | Guild et al. | |
| 10,266,485 B2 | 4/2019 | Benenato | |
| 10,272,150 B2 | 4/2019 | Ciaramella et al. | |
| 10,273,269 B2 | 4/2019 | Ciaramella | |
| 10,286,086 B2 | 5/2019 | Roy et al. | |
| 10,350,303 B1 | 7/2019 | Guild et al. | |
| 10,385,088 B2 | 8/2019 | Fraley et al. | |
| 10,413,618 B2 | 9/2019 | Guild et al. | |
| 10,442,756 B2 | 10/2019 | Benenato et al. | |
| 10,449,244 B2 | 10/2019 | Ciaramella et al. | |
| 10,465,190 B1 | 11/2019 | Chen et al. | |
| 10,487,332 B2 | 11/2019 | Geall | |
| 10,493,143 B2 | 12/2019 | Ciaramella et al. | |
| 10,493,167 B2 | 12/2019 | de Fougerolles et al. | |
| 10,494,399 B2 | 12/2019 | Hogrefe et al. | |
| 10,519,189 B2 | 12/2019 | Hogrefe et al. | |
| 10,526,629 B2 | 1/2020 | Rabideau et al. | |
| 10,543,269 B2 | 1/2020 | Ciaramella et al. | |
| 10,577,403 B2 | 3/2020 | De Fougerolles et al. | |
| 10,583,203 B2 | 3/2020 | De Fougerolles et al. | |
| 10,648,017 B2 | 5/2020 | Wochner | |
| 10,653,712 B2 | 5/2020 | Hoge et al. | |
| 10,653,767 B2 | 5/2020 | Ciaramella et al. | |
| 10,695,419 B2 | 6/2020 | Ciaramella et al. | |
| 10,702,599 B2 | 7/2020 | Ciaramella et al. | |
| 10,702,600 B1 | 7/2020 | Ciaramella et al. | |
| 10,703,789 B2 | 7/2020 | De Fougerolles et al. | |
| 10,709,779 B2 | 7/2020 | Ciaramella et al. | |
| 10,717,982 B2 | 7/2020 | Eberle et al. | |
| 10,723,692 B2 | 7/2020 | Ansell et al. | |
| 10,738,306 B2 | 8/2020 | Thess | |
| 10,760,070 B2 | 9/2020 | Funkner et al. | |
| 10,772,975 B2 | 9/2020 | Bancel et al. | |
| 10,808,242 B2 | 10/2020 | Kariko et al. | |
| 10,857,105 B2 | 12/2020 | Benenato et al. | |
| 10,858,647 B2 | 12/2020 | Issa et al. | |
| 10,906,944 B2 | 2/2021 | He et al. | |
| 10,912,826 B2 | 2/2021 | Thess et al. | |
| 10,913,768 B2 | 2/2021 | Hogrefe et al. | |
| 10,925,935 B2 | 2/2021 | Chakraborty et al. | |
| 10,925,958 B2 | 2/2021 | Ciaramella | |
| 10,933,127 B2 | 3/2021 | Ciaramella et al. | |
| 10,960,070 B2 | 3/2021 | Graham et al. | |
| 10,973,909 B1 | 4/2021 | Csiszovszki et al. | |
| 11,040,112 B2 | 6/2021 | Ansell et al. | |
| 11,045,540 B2 | 6/2021 | Ciaramella | |
| 11,110,166 B2 | 9/2021 | Fotin-Mleczek et al. | |
| 11,213,482 B1 | 1/2022 | Gambotto et al. | |
| 11,241,493 B2 | 2/2022 | Rauch et al. | |
| 11,278,617 B2 | 3/2022 | Mosharraf et al. | |
| 11,498,944 B2 | 11/2022 | Langedijk et al. | |
| 11,510,977 B2 | 11/2022 | Ying | |
| 11,547,673 B1 | 1/2023 | Sahin et al. | |
| 11,634,379 B2 | 4/2023 | Ansell et al. | |
| 11,872,280 B2 | 1/2024 | Roth et al. | |
| 11,878,055 B1 * | 1/2024 | Muik | A61K 39/215 |
| 11,918,643 B2 | 3/2024 | Roth et al. | |
| 2003/0194759 A1 | 10/2003 | Darzynkiewiz et al. | |
| 2005/0002953 A1 | 1/2005 | Herold | |
| 2005/0095582 A1 | 5/2005 | Gillim-Ross et al. | |
| 2005/0112554 A1 | 5/2005 | Zhao et al. | |
| 2005/0178142 A1 | 8/2005 | Perry et al. | |
| 2005/0249742 A1 | 11/2005 | Ruprecht et al. | |
| 2006/0121580 A1 | 6/2006 | ter Meulen et al. | |
| 2006/0196193 A1 | 9/2006 | Byrne | |
| 2007/0128217 A1 | 6/2007 | ter Meulen et al. | |
| 2007/0270361 A1 | 11/2007 | Lu et al. | |
| 2009/0093433 A1 | 4/2009 | Woolf et al. | |
| 2009/0286852 A1 | 11/2009 | Kariko et al. | |
| 2010/0017904 A1 | 1/2010 | Abad et al. | |
| 2011/0300205 A1 | 12/2011 | Geall et al. | |
| 2012/0082693 A1 | 4/2012 | Van Der Werf et al. | |
| 2012/0101148 A1 | 4/2012 | Aking et al. | |
| 2013/0102034 A1 | 4/2013 | Schrum | |
| 2013/0115272 A1 | 5/2013 | de Fougerolles et al. | |
| 2013/0236974 A1 | 9/2013 | de Fougerolles | |
| 2013/0245103 A1 | 9/2013 | de Fougerolles et al. | |
| 2013/0259923 A1 | 10/2013 | Bancel et al. | |
| 2013/0266640 A1 | 10/2013 | de Fougerolles et al. | |
| 2014/0147432 A1 | 5/2014 | Bancel et al. | |
| 2014/0148502 A1 | 5/2014 | Bancel et al. | |
| 2014/0193482 A1 | 7/2014 | Bancel et al. | |
| 2014/0206752 A1 | 7/2014 | Afeyan et al. | |
| 2014/0308304 A1 | 10/2014 | Manoharan et al. | |
| 2014/0378538 A1 | 12/2014 | Bancel | |
| 2015/0051268 A1 | 2/2015 | Bancel et al. | |
| 2015/0056253 A1 | 2/2015 | Bancel et al. | |
| 2015/0141499 A1 | 5/2015 | Bancel et al. | |
| 2015/0265698 A1 | 9/2015 | Pushko et al. | |
| 2015/0307542 A1 | 10/2015 | Roy et al. | |
| 2015/0315541 A1 | 11/2015 | Bancel et al. | |
| 2015/0376115 A1 | 12/2015 | Ansell et al. | |
| 2016/0022580 A1 | 1/2016 | Ramsay et al. | |
| 2016/0024140 A1 | 1/2016 | Issa et al. | |
| 2016/0024141 A1 | 1/2016 | Issa et al. | |
| 2016/0032273 A1 | 2/2016 | Shahrokh et al. | |
| 2016/0038612 A1 | 2/2016 | Hoge et al. | |
| 2016/0235864 A1 | 8/2016 | Schlake et al. | |
| 2016/0243221 A1 | 8/2016 | Hoge et al. | |
| 2016/0317647 A1 | 11/2016 | Ciaramella et al. | |
| 2017/0043037 A1 | 2/2017 | Kariko et al. | |
| 2017/0056528 A1 | 3/2017 | De Fougerolles et al. | |
| 2017/0130255 A1 | 5/2017 | Wang et al. | |
| 2017/0166905 A1 | 6/2017 | Eberle et al. | |
| 2017/0202979 A1 | 7/2017 | Chakraborty et al. | |
| 2017/0204152 A1 | 7/2017 | Nelson et al. | |
| 2017/0362627 A1 | 12/2017 | Reynders, III et al. | |
| 2018/0000953 A1 | 1/2018 | Almarsson et al. | |
| 2018/0002393 A1 | 1/2018 | Bancel et al. | |
| 2018/0086816 A1 | 3/2018 | Hoge et al. | |
| 2018/0112221 A1 | 4/2018 | Schrum et al. | |
| 2018/0161422 A1 | 6/2018 | Thess et al. | |
| 2018/0237766 A1 | 8/2018 | Heartlein et al. | |
| 2018/0237849 A1 | 8/2018 | Thompson | |

(56) References Cited

U.S. PATENT DOCUMENTS

| | | | |
|---|---|---|---|
| 2018/0243225 | A1 | 8/2018 | Ciaramella |
| 2018/0243230 | A1 | 8/2018 | Smith |
| 2018/0256628 | A1 | 9/2018 | Hoge et al. |
| 2018/0256750 | A1 | 9/2018 | Butora et al. |
| 2018/0271795 | A1 | 9/2018 | Martini et al. |
| 2018/0271970 | A1 | 9/2018 | Ciaramella et al. |
| 2018/0273576 | A1 | 9/2018 | Hogrefe et al. |
| 2018/0273977 | A1 | 9/2018 | Mousavi et al. |
| 2018/0274009 | A1 | 9/2018 | Marquardt et al. |
| 2018/0291425 | A1 | 10/2018 | Heartlein et al. |
| 2018/0303925 | A1 | 10/2018 | Weissman et al. |
| 2018/0303929 | A1 | 10/2018 | Ciaramella et al. |
| 2018/0311336 | A1 | 11/2018 | Ciaramella et al. |
| 2018/0311343 | A1 | 11/2018 | Huang et al. |
| 2018/0318409 | A1 | 11/2018 | Valiante et al. |
| 2018/0318446 | A1 | 11/2018 | Bancel et al. |
| 2018/0353618 | A1 | 12/2018 | Burkhardt et al. |
| 2018/0369374 | A1 | 12/2018 | Frederick et al. |
| 2018/0369419 | A1 | 12/2018 | Benenato et al. |
| 2018/0371047 | A1 | 12/2018 | Ticho et al. |
| 2019/0000959 | A1 | 1/2019 | Ciaramella et al. |
| 2019/0002890 | A1 | 1/2019 | Martini et al. |
| 2019/0008938 | A1 | 1/2019 | Ciaramella et al. |
| 2019/0008948 | A1 | 1/2019 | Ciaramella et al. |
| 2019/0015501 | A1 | 1/2019 | Ciaramella et al. |
| 2019/0030129 | A1 | 1/2019 | Schrum et al. |
| 2019/0060458 | A1 | 2/2019 | De Fougerolles et al. |
| 2019/0062762 | A1 | 2/2019 | Sahin et al. |
| 2019/0071682 | A1 | 3/2019 | Orlandini Von Niessen et al. |
| 2019/0078087 | A1 | 3/2019 | Butora et al. |
| 2019/0085368 | A1 | 3/2019 | Bancel et al. |
| 2019/0100748 | A1 | 4/2019 | Issa et al. |
| 2019/0144480 | A1 | 5/2019 | DeRosa et al. |
| 2019/0153428 | A1 | 5/2019 | Kariko et al. |
| 2019/0160185 | A1 | 5/2019 | Schrum et al. |
| 2019/0167811 | A1 | 6/2019 | Benenato et al. |
| 2019/0175517 | A1 | 6/2019 | Martini et al. |
| 2019/0175727 | A1 | 6/2019 | Huang et al. |
| 2019/0192646 | A1 | 6/2019 | Cohen et al. |
| 2019/0192653 | A1 | 6/2019 | Hoge et al. |
| 2019/0211368 | A1 | 7/2019 | Butora et al. |
| 2019/0216951 | A1 | 7/2019 | Baumhof |
| 2019/0218546 | A1 | 7/2019 | Butora et al. |
| 2019/0225644 | A1 | 7/2019 | Butora et al. |
| 2019/0240317 | A1 | 8/2019 | Ciaramella et al. |
| 2019/0241633 | A1 | 8/2019 | Fotin-Mleczek et al. |
| 2019/0247417 | A1 | 8/2019 | Hoge et al. |
| 2019/0255194 | A1 | 8/2019 | Roy et al. |
| 2019/0275170 | A1 | 9/2019 | Benenato et al. |
| 2019/0298657 | A1 | 10/2019 | Martini et al. |
| 2019/0298658 | A1 | 10/2019 | Benenato et al. |
| 2019/0300906 | A1 | 10/2019 | Martini et al. |
| 2019/0314291 | A1 | 10/2019 | Besin et al. |
| 2019/0314292 | A1 | 10/2019 | Benenato et al. |
| 2019/0314524 | A1 | 10/2019 | Ansell et al. |
| 2019/0336452 | A1 | 11/2019 | Brader |
| 2019/0336595 | A1 | 11/2019 | Ciaramella |
| 2019/0351040 | A1 | 11/2019 | Valiante et al. |
| 2019/0351048 | A1 | 11/2019 | Rauch |
| 2019/0382774 | A1 | 12/2019 | Hoge et al. |
| 2019/0390181 | A1 | 12/2019 | Benenato et al. |
| 2020/0010528 | A1 | 1/2020 | Seidel, III et al. |
| 2020/0030432 | A1 | 1/2020 | Ciaramella et al. |
| 2020/0030460 | A1 | 1/2020 | Kariko et al. |
| 2020/0032274 | A1 | 1/2020 | Mauger et al. |
| 2020/0038499 | A1 | 2/2020 | Narayanan et al. |
| 2020/0054737 | A1 | 2/2020 | Ciaramella et al. |
| 2020/0060971 | A1 | 2/2020 | Eber et al. |
| 2020/0061185 | A1 | 2/2020 | Graham et al. |
| 2020/0069599 | A1 | 3/2020 | Smith et al. |
| 2020/0069793 | A1 | 3/2020 | Ciaramella |
| 2020/0069794 | A1 | 3/2020 | Ciaramella et al. |
| 2020/0071689 | A1 | 3/2020 | Miracco |
| 2020/0085916 | A1 | 3/2020 | Martini et al. |
| 2020/0109420 | A1 | 4/2020 | Brito et al. |
| 2020/0113832 | A1 | 4/2020 | Yaworski et al. |
| 2020/0121809 | A1 | 4/2020 | Hope et al. |
| 2020/0123100 | A1 | 4/2020 | Benenato et al. |
| 2020/0129445 | A1 | 4/2020 | Patel et al. |
| 2020/0129608 | A1 | 4/2020 | Ciaramella et al. |
| 2020/0129615 | A1 | 4/2020 | Ciaramella et al. |
| 2020/0147176 | A1 | 5/2020 | Gieseke et al. |
| 2020/0155706 | A1 | 5/2020 | De Fougerolles et al. |
| 2020/0163878 | A1 | 5/2020 | Baumhof et al. |
| 2020/0164038 | A1 | 5/2020 | De Fougerolles et al. |
| 2020/0206362 | A1 | 7/2020 | Besin et al. |
| 2020/0208145 | A1 | 7/2020 | Moore et al. |
| 2020/0216878 | A1 | 7/2020 | Wochner |
| 2020/0230058 | A1 | 7/2020 | Geall et al. |
| 2020/0239869 | A1 | 7/2020 | Issa et al. |
| 2020/0247861 | A1 | 8/2020 | De Fougerolles et al. |
| 2020/0254086 | A1 | 8/2020 | Hoge et al. |
| 2020/0268664 | A1 | 8/2020 | MacLachlan et al. |
| 2020/0282046 | A1 | 9/2020 | Ciaramella et al. |
| 2020/0282047 | A1 | 9/2020 | Ciaramella et al. |
| 2020/0332293 | A1 | 10/2020 | Thess |
| 2020/0338214 | A1 | 10/2020 | Guild et al. |
| 2020/0354423 | A1 | 11/2020 | De Fougerolles et al. |
| 2020/0383922 | A1 | 12/2020 | Ketterer et al. |
| 2020/0392518 | A1 | 12/2020 | Eberle et al. |
| 2020/0399629 | A1 | 12/2020 | Kariko et al. |
| 2020/0405844 | A1 | 12/2020 | Ciaramella et al. |
| 2021/0023199 | A1 | 1/2021 | Kallen et al. |
| 2021/0030683 | A1 | 2/2021 | Eber et al. |
| 2021/0030866 | A1 | 2/2021 | Kallen et al. |
| 2021/0040473 | A1 | 2/2021 | Funkner et al. |
| 2021/0046173 | A1 | 2/2021 | Ciaramella et al. |
| 2021/0060175 | A1 | 3/2021 | Fotin-Mleczek et al. |
| 2021/0077634 | A1 | 3/2021 | De Fougerolles et al. |
| 2021/0107861 | A1 | 4/2021 | Ansell et al. |
| 2021/0128716 | A1 | 5/2021 | Thess et al. |
| 2021/0139543 | A1 | 5/2021 | He et al. |
| 2021/0163919 | A1 | 6/2021 | Issa et al. |
| 2021/0187097 | A1 | 6/2021 | Ciaramella et al. |
| 2021/0217484 | A1 | 7/2021 | Giessel et al. |
| 2021/0220467 | A1 | 7/2021 | Ciaramella et al. |
| 2021/0228707 | A1 | 7/2021 | Metkar et al. |
| 2021/0228708 | A1 | 7/2021 | Smith et al. |
| 2021/0230578 | A1 | 7/2021 | Issa et al. |
| 2021/0246170 | A1 | 8/2021 | Langedijk et al. |
| 2021/0251898 | A1 | 8/2021 | Baumhof et al. |
| 2021/0261597 | A1 | 8/2021 | Hogrefe et al. |
| 2021/0275664 | A1 | 9/2021 | Graham et al. |
| 2021/0290756 | A1 | 9/2021 | Sullivan et al. |
| 2021/0299244 | A1 | 9/2021 | Mosharraf et al. |
| 2021/0299251 | A1 | 9/2021 | Mosharraf et al. |
| 2021/0299278 | A1 | 9/2021 | Bancel et al. |
| 2021/0308257 | A1 | 10/2021 | Kuo et al. |
| 2021/0322541 | A1 | 10/2021 | Akahata et al. |
| 2021/0332085 | A1 | 10/2021 | Chen |
| 2021/0346493 | A1 | 11/2021 | Zhou et al. |
| 2021/0355170 | A1 | 11/2021 | Whitehead et al. |
| 2021/0371452 | A1 | 12/2021 | Hogrefe et al. |
| 2021/0379181 | A1 | 12/2021 | Rauch et al. |
| 2021/0388032 | A1 | 12/2021 | Langedijk et al. |
| 2022/0011039 | A1 | 1/2022 | Hou et al. |
| 2022/0016234 | A1 | 1/2022 | Rice et al. |
| 2022/0040285 | A1 | 2/2022 | Weissman et al. |
| 2022/0040292 | A1 | 2/2022 | Tang et al. |
| 2022/0048954 | A1 | 2/2022 | Pao et al. |
| 2022/0072155 | A1 | 3/2022 | Ansell et al. |
| 2022/0105201 | A1 | 4/2022 | Guild et al. |
| 2022/0193226 | A1 | 6/2022 | Rauch et al. |
| 2022/0202930 | A1 | 6/2022 | Roth et al. |
| 2022/0211838 | A1 | 7/2022 | Oostvogels et al. |
| 2022/0211841 | A1 | 7/2022 | Oostvogels et al. |
| 2022/0218815 | A1 | 7/2022 | Rauch et al. |
| 2022/0218816 | A1 | 7/2022 | Ying |
| 2022/0249654 | A1 | 8/2022 | Oostvogels et al. |
| 2022/0249704 | A1 | 8/2022 | Sahin et al. |
| 2022/0273820 | A1 | 9/2022 | Sahin et al. |
| 2022/0307040 | A1 | 9/2022 | Thess et al. |
| 2022/0323572 | A1 | 10/2022 | Metkar et al. |
| 2022/0347097 | A1 | 11/2022 | Geall |

(56) References Cited

U.S. PATENT DOCUMENTS

| | | | |
|---|---|---|---|
| 2022/0347289 A1 | 11/2022 | Chen et al. | |
| 2022/0395562 A1 | 12/2022 | Chakraborty et al. | |
| 2022/0395570 A1 | 12/2022 | Rauch et al. | |
| 2022/0401550 A1 | 12/2022 | Simon-Loriere et al. | |
| 2023/0073461 A1 | 3/2023 | Sahin et al. | |
| 2023/0075979 A1 | 3/2023 | Sahin et al. | |
| 2023/0167159 A1 | 6/2023 | Mwangi et al. | |
| 2023/0173057 A1 | 6/2023 | Zhang et al. | |
| 2023/0233665 A1 | 7/2023 | Wei et al. | |
| 2023/0277652 A1 | 9/2023 | Ying | |
| 2023/0285540 A1 | 9/2023 | Aurisicchio et al. | |
| 2023/0285545 A1 | 9/2023 | Zhang et al. | |
| 2023/0338512 A1* | 10/2023 | Muik | A61P 31/14 |

FOREIGN PATENT DOCUMENTS

| | | | |
|---|---|---|---|
| AU | 2016253972 | B2 | 1/2020 |
| AU | 2015280499 | B2 | 3/2020 |
| CN | 107033250 | A | 8/2017 |
| CN | 110167587 | A | 8/2019 |
| CN | 106795096 | B | 5/2020 |
| CN | 111088283 | B | 6/2020 |
| CN | 111303254 | A | 6/2020 |
| CN | 110951756 | B | 8/2020 |
| CN | 110974950 | B | 8/2020 |
| CN | 111518175 | A | 8/2020 |
| CN | 111592602 | A | 8/2020 |
| CN | 111139241 | B | 9/2020 |
| CN | 111218459 | B | 9/2020 |
| CN | 111363858 | B | 9/2020 |
| CN | 111748557 | A | 10/2020 |
| CN | 111778254 | A | 10/2020 |
| CN | 111848753 | A | 10/2020 |
| CN | 111218458 | B | 11/2020 |
| CN | 111876419 | A | 11/2020 |
| CN | 111939250 | A | 11/2020 |
| CN | 111978377 | A | 11/2020 |
| CN | 112023035 | A | 12/2020 |
| CN | 112028976 | A | 12/2020 |
| CN | 112043825 | A | 12/2020 |
| CN | 112048005 | A | 12/2020 |
| CN | 112094327 | A | 12/2020 |
| CN | 112220920 | A | 1/2021 |
| CN | 112226445 | A | 1/2021 |
| CN | 112266411 | A | 1/2021 |
| CN | 112321688 | A | 2/2021 |
| CN | 112358533 | A | 2/2021 |
| CN | 112480217 | A | 3/2021 |
| CN | 112626089 | A | 4/2021 |
| CN | 112794884 | A | 5/2021 |
| CN | 113186203 | A | 7/2021 |
| DE | 20 2021 003 575 | U1 | 1/2022 |
| EP | 1291300 | A2 | 3/2003 |
| EP | 1392341 | B1 | 3/2003 |
| EP | 1685844 | B1 | 3/2003 |
| EP | 1857122 | B1 | 12/2010 |
| EP | 2691101 | A2 | 2/2014 |
| EP | 2791160 | A1 | 10/2014 |
| EP | 2833892 | A2 | 2/2015 |
| EP | 2833894 | A1 | 2/2015 |
| EP | 3134131 | A1 | 3/2017 |
| EP | 3169693 | A1 | 5/2017 |
| EP | 3190361 | A1 | 7/2017 |
| EP | 2958588 | B1 | 8/2017 |
| EP | 3218508 | A1 | 9/2017 |
| EP | 2506857 | B1 | 2/2018 |
| EP | 3289083 | A1 | 3/2018 |
| EP | 2971102 | B1 | 6/2018 |
| EP | 3334828 | A1 | 6/2018 |
| EP | 3350157 | A2 | 7/2018 |
| EP | 3350333 | A2 | 7/2018 |
| EP | 3362460 | A1 | 8/2018 |
| EP | 3362461 | A1 | 8/2018 |
| EP | 3364949 | A1 | 8/2018 |
| EP | 3364983 | A2 | 8/2018 |
| EP | 3036330 | B1 | 9/2018 |
| EP | 3368507 | A1 | 9/2018 |
| EP | 3386484 | A1 | 10/2018 |
| EP | 3394030 | A1 | 10/2018 |
| EP | 2970955 | B1 | 11/2018 |
| EP | 2763701 | B1 | 12/2018 |
| EP | 3090060 | B1 | 2/2019 |
| EP | 3452101 | A2 | 3/2019 |
| EP | 3318248 | B1 | 4/2019 |
| EP | 3468537 | A1 | 4/2019 |
| EP | 2717893 | B1 | 5/2019 |
| EP | 3260541 | B1 | 5/2019 |
| EP | 3292873 | B1 | 5/2019 |
| EP | 3492109 | A1 | 6/2019 |
| EP | 3501550 | A1 | 6/2019 |
| EP | 1797886 | B1 | 7/2019 |
| EP | 3505176 | A1 | 7/2019 |
| EP | 3512944 | A1 | 7/2019 |
| EP | 3134506 | B1 | 8/2019 |
| EP | 3520820 | A1 | 8/2019 |
| EP | 3520821 | A1 | 8/2019 |
| EP | 3532070 | A1 | 9/2019 |
| EP | 3538067 | A1 | 9/2019 |
| EP | 3540060 | A1 | 9/2019 |
| EP | 3577221 | A1 | 12/2019 |
| EP | 3578200 | A1 | 12/2019 |
| EP | 3578205 | A1 | 12/2019 |
| EP | 3578659 | A1 | 1/2020 |
| EP | 3586861 | A1 | 1/2020 |
| EP | 3590949 | A1 | 1/2020 |
| EP | 3595676 | A1 | 1/2020 |
| EP | 3595727 | A1 | 1/2020 |
| EP | 3596041 | A1 | 1/2020 |
| EP | 3596042 | A1 | 1/2020 |
| EP | 3607074 | A1 | 2/2020 |
| EP | 3492109 | B1 | 3/2020 |
| EP | 3625345 | A1 | 3/2020 |
| EP | 3638215 | A1 | 4/2020 |
| EP | 3062798 | B1 | 5/2020 |
| EP | 3668522 | A2 | 6/2020 |
| EP | 3294885 | B1 | 7/2020 |
| EP | 3682905 | A1 | 7/2020 |
| EP | 3160938 | B1 | 9/2020 |
| EP | 3718565 | A1 | 10/2020 |
| EP | 3838294 | A1 | 6/2021 |
| EP | 3886897 | A1 | 10/2021 |
| EP | 3901260 | A1 | 10/2021 |
| EP | 3901261 | A1 | 10/2021 |
| EP | 3981437 | A1 | 4/2022 |
| EP | 4096710 | A1 | 12/2022 |
| EP | 4097122 | A1 | 12/2022 |
| EP | 4103228 | A1 | 12/2022 |
| EP | 4103229 | A1 | 12/2022 |
| EP | 4217370 | A2 | 8/2023 |
| EP | 4221739 | A1 | 8/2023 |
| EP | 4226938 | A2 | 8/2023 |
| EP | 4277655 | A1 | 11/2023 |
| EP | 4295862 | A2 | 12/2023 |
| JP | H10-113117 | A | 5/1998 |
| JP | 6594421 | B2 | 10/2019 |
| RU | 2731342 | C1 | 9/2020 |
| RU | 2731356 | C1 | 9/2020 |
| RU | 2733834 | C1 | 10/2020 |
| TW | 200515917 | A | 5/2005 |
| WO | WO-1998/051278 | A2 | 11/1998 |
| WO | WO-1999/14346 | A2 | 3/1999 |
| WO | WO-02/098443 | A2 | 12/2002 |
| WO | WO-2004/002453 | A1 | 1/2004 |
| WO | WO-2004/004743 | A1 | 1/2004 |
| WO | WO-2004/096842 | A2 | 11/2004 |
| WO | WO-2004/110081 | A1 | 12/2004 |
| WO | WO-2005/027963 | A2 | 3/2005 |
| WO | WO-2005/118813 | A2 | 12/2005 |
| WO | WO-2006/138380 | A2 | 12/2006 |
| WO | WO-2007/024708 | A2 | 3/2007 |
| WO | WO-2007/036366 | A2 | 4/2007 |
| WO | WO-2008/016473 | A2 | 2/2008 |
| WO | WO-2008/027942 | A2 | 3/2008 |
| WO | WO-2008/052770 | A2 | 5/2008 |

(56) References Cited

FOREIGN PATENT DOCUMENTS

| | | | | |
|---|---|---|---|---|
| WO | WO-2008/157688 | A2 | 12/2008 | |
| WO | WO-2009/127060 | A1 | 10/2009 | |
| WO | WO-2009/149253 | A2 | 12/2009 | |
| WO | WO-2011/015347 | A1 | 2/2011 | |
| WO | WO-2011/068810 | A1 | 6/2011 | |
| WO | WO-2012/006369 | A2 | 1/2012 | |
| WO | WO-2012/019168 | A2 | 2/2012 | |
| WO | WO-2012/045075 | A1 | 4/2012 | |
| WO | WO-2012/135805 | A2 | 10/2012 | |
| WO | WO-2012/170930 | A1 | 12/2012 | |
| WO | WO-2013/052523 | A1 | 4/2013 | |
| WO | WO-2013/090648 | A1 | 6/2013 | |
| WO | WO-2013/143699 | A1 | 10/2013 | |
| WO | WO-2013/151668 | A2 | 10/2013 | |
| WO | WO-2013/151671 | A1 | 10/2013 | |
| WO | WO-2013/151672 | A2 | 10/2013 | |
| WO | WO-2013/151736 | A2 | 10/2013 | |
| WO | WO-2014/089239 | A1 | 6/2014 | |
| WO | WO-2014/127917 | A1 | 8/2014 | |
| WO | WO-2014/144711 | A1 | 9/2014 | |
| WO | WO-2014/152659 | A1 | 9/2014 | |
| WO | WO-2014/152966 | A1 | 9/2014 | |
| WO | WO-2014/159813 | A1 | 10/2014 | |
| WO | WO-2014/164253 | A1 | 10/2014 | |
| WO | WO-2015/005253 | A1 | 1/2015 | |
| WO | WO-2015/024667 | A1 | 2/2015 | |
| WO | WO-2015/062738 | A1 | 5/2015 | |
| WO | WO-2015/101416 | A1 | 7/2015 | |
| WO | WO-2015/130584 | A2 | 9/2015 | |
| WO | WO-2015/164674 | A1 | 10/2015 | |
| WO | WO-2015/164773 | A1 | 10/2015 | |
| WO | WO-2015/199952 | A1 | 12/2015 | |
| WO | WO-2016/005004 | A1 | 1/2016 | |
| WO | WO-2016/005324 | A1 | 1/2016 | |
| WO | WO-2016/010840 | A1 | 1/2016 | |
| WO | WO-2016/011226 | A1 | 1/2016 | |
| WO | WO-2016/045732 | A1 | 3/2016 | |
| WO | WO-2016/077123 | A1 | 5/2016 | |
| WO | WO-2016/091391 | A1 | 6/2016 | |
| WO | WO-2016/164762 | A1 | 10/2016 | |
| WO | WO-2016/165831 | A1 | 10/2016 | |
| WO | WO-2016/176330 | A1 | 11/2016 | |
| WO | WO-2016/180430 | A1 | 11/2016 | |
| WO | WO-2016/184575 | A1 | 11/2016 | |
| WO | WO-2016/184576 | A2 | 11/2016 | |
| WO | WO-2016/193206 | A1 | 12/2016 | |
| WO | WO-2016/201377 | A1 | 12/2016 | |
| WO | WO-2017/015457 | A1 | 1/2017 | |
| WO | WO-2017/025447 | A1 | 2/2017 | |
| WO | WO-2017/036889 | A1 | 3/2017 | |
| WO | WO-2017/049245 | A2 | 3/2017 | |
| WO | WO-2017/049275 | A2 | 3/2017 | |
| WO | WO-2017/053297 | A1 | 3/2017 | |
| WO | WO-2017/059902 | A1 | 4/2017 | |
| WO | WO-2017/060314 | A2 | 4/2017 | |
| WO | WO-2017/066781 | A1 | 4/2017 | |
| WO | WO-2017/066789 | A1 | 4/2017 | |
| WO | WO-2017/066793 | A1 | 4/2017 | |
| WO | WO-2017/070601 | A1 | 4/2017 | |
| WO | WO-2017/070618 | A1 | 4/2017 | |
| WO | WO-2017070626 | A2 * | 4/2017 | ............. A61K 39/12 |
| WO | WO-2017/075531 | A1 | 5/2017 | |
| WO | WO-2017/081082 | A2 | 5/2017 | |
| WO | WO-2017/099823 | A1 | 6/2017 | |
| WO | WO-2017/112865 | A1 | 6/2017 | |
| WO | WO-2017/127750 | A1 | 7/2017 | |
| WO | WO-2017/191274 | A2 | 11/2017 | |
| WO | WO-2017/201333 | A1 | 11/2017 | |
| WO | WO-2017/218704 | A1 | 12/2017 | |
| WO | WO-2017/220954 | A1 | 12/2017 | |
| WO | WO-2018/053209 | A1 | 3/2018 | |
| WO | WO-2018/075827 | A1 | 4/2018 | |
| WO | WO-2018/078053 | A1 | 5/2018 | |
| WO | WO-2018/081318 | A1 | 5/2018 | |
| WO | WO-2018/081459 | A1 | 5/2018 | |
| WO | WO-2018/081462 | A1 | 5/2018 | |
| WO | WO-2018/081480 | A1 | 5/2018 | |
| WO | WO-2018/089540 | A1 | 5/2018 | |
| WO | WO-2018/089851 | A2 | 5/2018 | |
| WO | WO-2018/115527 | A2 | 6/2018 | |
| WO | WO-2018/144778 | A1 | 8/2018 | |
| WO | WO-2018/157009 | A1 | 9/2018 | |
| WO | WO-2018/170245 | A1 | 9/2018 | |
| WO | WO-2018/170306 | A1 | 9/2018 | |
| WO | WO-2018/170322 | A1 | 9/2018 | |
| WO | WO-2018/170336 | A1 | 9/2018 | |
| WO | WO-2018/170347 | A1 | 9/2018 | |
| WO | WO-2018/187590 | A1 | 10/2018 | |
| WO | WO-2018/213789 | A1 | 11/2018 | |
| WO | WO-2018/232355 | A1 | 12/2018 | |
| WO | WO-2018/232357 | A1 | 12/2018 | |
| WO | WO-2019/035998 | A1 | 2/2019 | |
| WO | WO-2019/036670 | A2 | 2/2019 | |
| WO | WO-2019/036683 | A1 | 2/2019 | |
| WO | WO-2019/036685 | A1 | 2/2019 | |
| WO | WO-2019/092002 | A1 | 5/2019 | |
| WO | WO-2019/092437 | A1 | 5/2019 | |
| WO | WO-2019/148101 | A1 | 8/2019 | |
| WO | WO-2019/209914 | A2 | 10/2019 | |
| WO | WO-2019/232097 | A1 | 12/2019 | |
| WO | WO-2020/006242 | A1 | 1/2020 | |
| WO | WO-2020/025576 | A1 | 2/2020 | |
| WO | WO-2020/056370 | A1 | 3/2020 | |
| WO | WO-2020/061284 | A1 | 3/2020 | |
| WO | WO-2020/061295 | A1 | 3/2020 | |
| WO | WO-2020/061367 | A1 | 3/2020 | |
| WO | WO-2020/061457 | A1 | 3/2020 | |
| WO | WO-2020/072605 | A1 | 4/2020 | |
| WO | WO-2020/097291 | A1 | 5/2020 | |
| WO | WO-2020/150152 | A1 | 7/2020 | |
| WO | WO-2020/160397 | A1 | 8/2020 | |
| WO | WO-2020/172239 | A1 | 8/2020 | |
| WO | WO-2020/185811 | A1 | 9/2020 | |
| WO | WO-2020/190750 | A1 | 9/2020 | |
| WO | WO-2020/198337 | A1 | 10/2020 | |
| WO | WO-2020/243561 | A1 | 12/2020 | |
| WO | WO-2020/263985 | A1 | 12/2020 | |
| WO | WO-2021/000968 | A2 | 1/2021 | |
| WO | WO-2021/000969 | A2 | 1/2021 | |
| WO | WO-2021/04081 | A1 | 1/2021 | |
| WO | WO-2021/030533 | A1 | 2/2021 | |
| WO | WO-2021/030701 | A1 | 2/2021 | |
| WO | WO-2021/050864 | A1 | 3/2021 | |
| WO | WO-2021/055811 | A1 | 3/2021 | |
| WO | WO-2021/084282 | A1 | 5/2021 | |
| WO | WO-2021/123332 | A1 | 6/2021 | |
| WO | WO-2021/138447 | A1 | 7/2021 | |
| WO | WO-2021/147025 | A1 | 7/2021 | |
| WO | WO-2021/154763 | A1 | 8/2021 | |
| WO | WO-2021/154812 | A1 | 8/2021 | |
| WO | WO-2021/155243 | A1 | 8/2021 | |
| WO | WO-2021/155323 | A1 | 8/2021 | |
| WO | WO-2021/155733 | A1 | 8/2021 | |
| WO | WO-2021/155760 | A1 | 8/2021 | |
| WO | WO-2021/156267 | A1 | 8/2021 | |
| WO | WO-2021/159040 | A2 | 8/2021 | |
| WO | WO-2021/159118 | A2 | 8/2021 | |
| WO | WO-2021/159130 | A2 | 8/2021 | |
| WO | WO-2021/159648 | A1 | 8/2021 | |
| WO | WO-2021/159985 | A1 | 8/2021 | |
| WO | WO-2021/160346 | A1 | 8/2021 | |
| WO | WO-2021/160850 | A1 | 8/2021 | |
| WO | WO-2021/163365 | A1 | 8/2021 | |
| WO | WO-2021/163371 | A1 | 8/2021 | |
| WO | WO-2021/163398 | A1 | 8/2021 | |
| WO | WO-2021/163427 | A1 | 8/2021 | |
| WO | WO-2021/163456 | A1 | 8/2021 | |
| WO | WO-2021/165667 | A1 | 8/2021 | |
| WO | WO-2021/181100 | A1 | 9/2021 | |
| WO | WO-2021/188906 | A1 | 9/2021 | |
| WO | WO-2021/188969 | A2 | 9/2021 | |
| WO | WO-2021/189056 | A2 | 9/2021 | |
| WO | WO-2021/191630 | A1 | 9/2021 | |
| WO | WO-2021/194826 | A2 | 9/2021 | |

(56) References Cited

FOREIGN PATENT DOCUMENTS

| | | | | |
|---|---|---|---|---|
| WO | WO-2021/198705 A1 | | 10/2021 | |
| WO | WO-2021/198706 A2 | | 10/2021 | |
| WO | WO-2021/200800 A1 | | 10/2021 | |
| WO | WO-2021/201612 A1 | | 10/2021 | |
| WO | WO-2021/202599 A2 | | 10/2021 | |
| WO | WO-2021/202772 A1 | | 10/2021 | |
| WO | WO-2021/203017 A2 | | 10/2021 | |
| WO | WO-2021/203018 A1 | | 10/2021 | |
| WO | WO-2021/203044 A2 | | 10/2021 | |
| WO | WO-2021/204179 A1 | | 10/2021 | |
| WO | WO-2021/205455 A1 | | 10/2021 | |
| WO | WO-2021/206581 A1 | | 10/2021 | |
| WO | WO-2021/209824 A1 | | 10/2021 | |
| WO | WO-2021/210686 A1 | | 10/2021 | |
| WO | WO-2021/211279 A1 | | 10/2021 | |
| WO | WO-2021/211688 A1 | | 10/2021 | |
| WO | WO-2021/211748 A1 | | 10/2021 | |
| WO | WO-2021/211749 A1 | | 10/2021 | |
| WO | WO-2021/211760 A1 | | 10/2021 | |
| WO | WO-2021/212568 A1 | | 10/2021 | |
| WO | WO-2021/213924 A1 | | 10/2021 | |
| WO | WO-2021/214204 A1 | | 10/2021 | |
| WO | WO-2021/216729 A1 | | 10/2021 | |
| WO | WO-2021/216738 A2 | | 10/2021 | |
| WO | WO-2021/216743 A2 | | 10/2021 | |
| WO | WO-2021213945 A1 | * | 10/2021 | ......... A61K 31/7105 |
| WO | WO-2021/203017 A3 | | 11/2021 | |
| WO | WO-2021/220319 A1 | | 11/2021 | |
| WO | WO-2021/221486 A1 | | 11/2021 | |
| WO | WO-2021/222304 A1 | | 11/2021 | |
| WO | WO-2021/223647 A1 | | 11/2021 | |
| WO | WO-2021/224946 A1 | | 11/2021 | |
| WO | WO-2021/226436 A1 | | 11/2021 | |
| WO | WO-2021/227401 A1 | | 11/2021 | |
| WO | WO-2021/231560 A1 | | 11/2021 | |
| WO | WO-2021/231929 A1 | | 11/2021 | |
| WO | WO-2021/231963 A1 | | 11/2021 | |
| WO | WO-2021/237174 A1 | | 11/2021 | |
| WO | WO-2021/214081 A3 | | 12/2021 | |
| WO | WO-2021/239880 A1 | | 12/2021 | |
| WO | WO-2021/253172 A1 | | 12/2021 | |
| WO | WO-2022/003119 A1 | | 1/2022 | |
| WO | WO-2022/005503 A1 | | 1/2022 | |
| WO | WO-2022/009121 A1 | | 1/2022 | |
| WO | WO-2022/011092 A1 | | 1/2022 | |
| WO | WO-2022/011332 A2 | | 1/2022 | |
| WO | WO-2022/043551 A2 | | 3/2022 | |
| WO | WO-2022/064494 A2 | | 3/2022 | |
| WO | WO-2022/072910 A1 | | 4/2022 | |
| WO | WO-2022/073131 A1 | | 4/2022 | |
| WO | WO-2022/101469 A1 | | 5/2022 | |
| WO | WO-2022/110099 A1 | | 6/2022 | |
| WO | WO-2022/131832 A1 | | 6/2022 | |
| WO | WO-2022/137133 A1 | | 6/2022 | |
| WO | WO-2022/155524 A1 | | 7/2022 | |
| WO | WO-2022/155530 A1 | | 7/2022 | |
| WO | WO-2022/191377 A1 | | 9/2022 | |
| WO | WO-2022/192594 A2 | | 9/2022 | |
| WO | WO-2022/197720 A2 | | 9/2022 | |
| WO | WO-2022/212659 A1 | | 10/2022 | |
| WO | WO-2022/221335 A1 | | 10/2022 | |
| WO | WO-2022/221440 A1 | | 10/2022 | |
| WO | WO-2022/223617 A1 | | 10/2022 | |
| WO | WO-2022/234405 A1 | | 11/2022 | |
| WO | WO-2023/004415 A2 | | 1/2023 | |
| WO | WO-2023/286076 A1 | | 1/2023 | |
| WO | WO-2023/042099 A2 | | 3/2023 | |
| WO | WO-2023/049272 A1 | | 3/2023 | |
| WO | WO-2023/056911 A1 | | 4/2023 | |
| WO | WO-2023/064708 A1 | | 4/2023 | |
| WO | WO-2023/064907 A1 | | 4/2023 | |
| WO | WO-2023/073190 A9 | | 6/2023 | |
| WO | WO-2023/094713 A2 | | 6/2023 | |
| WO | WO-2023/094713 A3 | | 6/2023 | |
| WO | WO-2023/098842 A1 | | 6/2023 | |
| WO | WO-2023/102448 A2 | | 6/2023 | |
| WO | WO-2023/111725 A1 | | 6/2023 | |
| WO | WO-2023/089071 A1 | | 7/2023 | |
| WO | WO-2023/137550 A1 | | 7/2023 | |
| WO | WO-2023/142786 A1 | | 8/2023 | |
| WO | WO-2023/147092 A2 | | 8/2023 | |
| WO | WO-2023/150838 A1 | | 8/2023 | |
| WO | WO-2023/151172 A1 | | 8/2023 | |
| WO | WO-2023/151173 A1 | | 8/2023 | |
| WO | WO-2023/185121 A1 | | 10/2023 | |
| WO | WO-2024/002985 A1 | | 1/2024 | |
| WO | WO-2024/021817 A1 | | 2/2024 | |
| WO | WO-2024/050483 A1 | | 3/2024 | |
| WO | WO-2024/082795 A1 | | 4/2024 | |
| WO | WO-2024/089638 A1 | | 5/2024 | |
| WO | WO-2024/097259 A1 | | 5/2024 | |

OTHER PUBLICATIONS

[No Author Listed] "CureVac Announces Positive Results in Low Dose—1 μg—Rabies Vaccine Clinical Phase 1 Study." Globalnewswire.com. Jan. 7, 2020.

[No Author Listed], 10 Million Doses of mRNA-based COVID-19 Vaccine to be supplied to Taiwan Region, 2 pages (Jul. 12, 2021).

[No Author Listed], An In Vitro Study Shows Pfizer-BioNTech COVID-19 Vaccine Elicits Antibodies that Neutralize SARS-COV-2 with a Mutation Associated with Rapid Transmission, 3 pages (Jan. 8, 2021).

[No Author Listed], Assessment Report—Comirnaty, 140 pages Jan. 19, 2021.

[No Author Listed], BioNTech and Fosun Pharma Announce Start of Clinical Trial of mRNA-based COVID-19 Vaccine Candidate in China, 2 pages (Aug. 5, 2020).

[No Author Listed], BioNTech and Fosun Pharma Announce the Start of a Phase 2 Clinical Trial of Lead mRNA COVID-19 Vaccine BNT162b2 in China, 2 pages (Nov. 25, 2020).

[No Author Listed], BioNTech and Fosun Pharma form COVID-19 vaccine strategic alliance in China, 2 pages (Mar. 16, 2020).

[No Author Listed], BioNTech and Fosun Pharma Receive Authorization for Emergency Use in Hong Kong for COVID-19 Vaccine, 2 pages (Jan. 25, 2021).

[No Author Listed], BioNTech and Fosun Pharma Receive Special Import Authorization in Macau for COVID-19 Vaccine, 2 pages (Feb. 25, 2021).

[No Author Listed], BioNTech and Fosun Pharma to Potentially Supply 10 Million Doses of BioNTech's NT162 mRNA-based Vaccine Candidate Against SARS-COV-2 to Hong Kong SAR and Macao SAR, 2 pages (Aug. 27, 2020).

[No Author Listed], BioNTech and Fosun Pharma to Supply China with mRNA-based COVID-19 Vaccine, 2 pages (Dec. 16, 2020).

[No Author Listed], BioNTech and Pfizer announce completion of dosing for first cohort of Phase 1/2 trial of COVID-19 vaccine candidates in Germany, 2 pages (Apr. 29, 2020).

[No Author Listed], BioNTech and Pfizer Announce Nature Publication of German Phase 1/2 Study Data from mRNA-based Vaccine Candidate BNT162b1 Against SARS-COV-2, 3 pages (Sep. 30, 2020).

[No Author Listed], BioNTech and Pfizer announce regulatory approval from German authority Paul-Ehrlich-Institut to commence first clinical trial of COVID-19 vaccine candidates, 3 pages (Apr. 22, 2020).

[No Author Listed], BioNTech and Pfizer Initiate Rolling Submission to European Medicines Agency for SARS-COV-2 Vaccine Candidate BNT162b2, 3 pages (Oct. 6, 2020).

[No Author Listed], BioNTech and Pfizer Receive Regulatory Approval From Paul-Ehrlich-Institut to commence German Part of Global Phase 2/3 Trial for COVID-19 Vaccine Candidate BNT162b2, 3 pages (Sep. 7, 2020).

[No Author Listed], BioNTech Recognizes Employees and Partners for Their Support in Developing Historic Vaccine, 2 pages (Dec. 31, 2020).

(56) References Cited

OTHER PUBLICATIONS

[No Author Listed], BioNTech reports rapid progress on COVID-19 vaccine program to address global public health threat, 2 pages (Mar. 16, 2020).
[No Author Listed], BioNTech to Acquire GMP Manufacturing Site to Expand COVID-19 Vaccine Production Capacity in First Half 2021, 2 pages (Sep. 17, 2020).
[No Author Listed], BioNTech to Hold Press Conference to Provide an Update on COVID-19 Vaccine Development Program, 1 page (Dec. 2, 2020).
[No Author Listed], BioNTech to Hold Press Conference to Provide an Update on COVID-19 Vaccine Development Program, 1 page (Dec. 21, 2020).
[No Author Listed], BioNTech to Hold Webcast to Present Early Positive Data from Ongoing Phase 1/2 Study of mRNA-based Vaccine Candidate Against SARS-COV-2, 1 page (Jul. 1, 2020).
[No Author Listed], BioNTech to Receive up to €375M in Funding from German Federal Ministry of Education and Research to Support COVID-19 Vaccine Program BNT162, 2 pages (Sep. 15, 2020).
[No Author Listed], Canada Exercises Increased Option for 20 Million Doses of mRNA Vaccine Against COVID-19 (mRNA-1273), Moderna Press Release, 2 pages (Sep. 22, 2020).
[No Author Listed], EMA Approves New Storage Option for Pfizer-BioNTech Vaccine, Easing Distribution and Storage of Doses Across European Union, 3 pages (Mar. 26, 2021).
[No Author Listed], Experimental COVID-19 Vaccine Protects Upper and Lower Airways in Nonhuman Primates, NIH News Release, 2 pages (Jul. 28, 2020).
[No Author Listed], Experimental COVID-19 Vaccine Safe, Generates Immune Response, NIH News Release, 2 pages (Jul. 14, 2020).
[No Author Listed], In Vitro Studies Demonstrate Pfizer and BioNTech COVID-19 Vaccine Elicits Antibodies that Neutralize SARS-COV-2 with Key Mutations Present in U.K. and South African Variants, 3 pages (Jan. 27, 2021).
[No Author Listed], In Vitro Study Published in The New England Journal of Medicine Demonstrates Sera from Individuals Immunized with the Pfizer-BioNTech COVID-19 Vaccine Neutralize SARS-COV-2 with South African Variant Spike Mutations, 3 pages (Feb. 17, 2021).
[No Author Listed], Investment Plan for Europe: European Investment Bank to provide BioNTech with up to €100 million in debt financing for COVID-19 vaccine development and manufacturing, 2 pages (Jun. 11, 2020).
[No Author Listed], Moderna Advances Late-Stage Development of its Vaccine (mRNA-1273) Against COVID-19, Moderna Press Release, 3 pages (Jun. 11, 2020).
[No Author Listed], Moderna and Lonza Announce Worldwide Strategic Collaboration to Manufacture Moderna's Vaccine (mRNA-1273) Against Novel Coronavirus, Moderna Press Release, 3 pages (May 1, 2020).
[No Author Listed], Moderna Announces Award from U.S. Government Agency BARDA for up to $483 Million to Accelerate Development of mRNA Vaccine (mRNA-1273) Against Novel Coronavirus, Moderna Press Release, 3 pages (Apr. 16, 2020).
[No Author Listed], Moderna Announces Expansion of BARDA Agreement to Support Larger Phase 3 Program forVaccine (mRNA-1273) Against COVID-19, Moderna Press Release, 3 pages (Jul. 26, 2020).
[No Author Listed], Moderna Announces First Participant Dosed in NIH-led Phase 1 Study of mRNA Vaccine (mRNA-1273) Against Novel Coronavirus, Moderna Press Release, 2 pages (Mar. 16, 2020).
[No Author Listed], Moderna Announces First Participants in Each Age Cohort Dosed in Phase 2 Study of mRNA Vaccine (mRNA-1273) Against Novel Coronavirus, Moderna Press Release, 2 pages (May 29, 2020).
[No Author Listed], Moderna Announces IND Submitted to U.S. FDA for Phase 2 Study of mRNA Vaccine (mRNA-1273) Against Novel Coronavirus, Moderna Press Release, 3 pages (Apr. 27, 2020).
[No Author Listed], Moderna Announces Phase 3 COVE Study of mRNA Vaccine Against COVID-19 (mRNA-1273) Begins, Moderna Press Release, 3 pages (Jul. 27, 2020).
[No Author Listed], Moderna Announces Positive Interim Phase 1 Data for its mRNA Vaccine (mRNA-1273) Against Novel Coronavirus, Moderna Press Release, 3 pages (May 18, 2020).
[No Author Listed], Moderna Announces Progress Across Broad Portfolio and all Three Clinical Stage Therapeutic Areas at 2020 R&D Day, Moderna Press Release, 4 pages (Sep. 17, 2020).
[No Author Listed], Moderna Announces Publication in The New England Journal of Medicine of Interim Results From Phase 1 Study of Its mRNA Vaccine Against COVID-19 (mRNA-1273), Moderna Press Release, 5 pages (Jul. 14, 2020).
[No Author Listed], Moderna Announces Publication in The New England Journal of Medicine of Non-Human Primate Preclinical Viral Challenge Study of its mRNA Vaccine Against COVID-19 (mRNA-1273), Moderna Press Release, 3 pages (Jul. 28, 2020).
[No Author Listed], Moderna Announces Supply Agreement with U.S. Government for Initial 100 Million Doses of mRNA Vaccine Against COVID-19 (mRNA-1273), Moderna Press Release, 3 pages (Aug. 11, 2020).
[No Author Listed], Moderna Completes Enrollment of Phase 2 Study of its mRNA Vaccine Against COVID-19 (mRNA-1273), Moderna Press Release, 2 pages (Jul. 8, 2020).
[No Author Listed], Moderna Confirms Advanced Discussions with European Commission to Supply Europe with 80 Million Doses of mRNA Vaccine Against COVID-19 (mRNA-1273), Moderna Press Release, 3 pages (Aug. 24, 2020).
[No Author Listed], Moderna Confirms Discussions with the Ministry of Health, Labour and Welfare to Supply Japan with 40 Million Doses of mRNA Vaccine Against COVID-19 (mRNA-1273), Moderna Press Release, 2 pages (Aug. 28, 2020).
[No Author Listed], Moderna Receives FDA Fast Track Designation for mRNA Vaccine (mRNA-1273) Against Novel Coronavirus, Moderna Press Release, 2 pages (May 12, 2020).
[No Author Listed], Moderna Ships mRNA Vaccine Against Novel Coronavirus (mRNA-1273) for Phase 1 Study, Moderna Press Release, 2 pages (Feb. 24, 2020).
[No Author Listed], NIH Clinical Trial NCT04283461, Safety and Immunogenicity Study of 2019-nCoV Vaccine (mRNA-1273) for Prophylaxis of SARS-CoV-2 Infection (COVID-19), 6 pages (Feb. 11, 2021).
[No Author Listed], NIH Clinical Trial NCT04283461, Safety and Immunogenicity Study of 2019-nCoV Vaccine (mRNA-1273) for Prophylaxis of SARS-CoV-2 Infection (COVID-19), 8 pages (Apr. 30, 2020).
[No Author Listed], NIH Clinical Trial NCT04283461, Safety and Immunogenicity Study of 2019-nCoV Vaccine (mRNA-1273) for Prophylaxis of SARS-CoV-2 Infection (COVID-19), 8 pages (May 28, 2020).
[No Author Listed], NIH Clinical Trial NCT04283461, Safety and Immunogenicity Study of 2019-nCoV Vaccine (mRNA-1273) for Prophylaxis of SARS-CoV-2 Infection (COVID-19), First Posted: Feb. 25, 2020, 18 pages, <https://clinicaltrials.gov/ct2/show/NCT04283461>.
[No Author Listed], NIH Clinical Trial NCT04283461, Safety and Immunogenicity Study of 2019-nCoV Vaccine (mRNA-1273) to Treat Novel Coronavirus, 6 pages (Feb. 21, 2020).
[No Author Listed], NIH Clinical Trial of Investigational Vaccine for COVID-19 begins, NIH News Release, 3 pages (Mar. 16, 2020).
[No Author Listed], NIH-Moderna Investigational COVID-19 Vaccine Shows Promise in Mouse Studies, NIH News Release, 2 pages (Aug. 5, 2020).
[No Author Listed], Pfizer and BioNTech Achieve First Authorization in the World for a Vaccine to Combat COVID-19, 3 pages (Dec. 2, 2020).
[No Author Listed], Pfizer and BioNTech Achieve Health Canada Authorization for Their Vaccine to Combat COVID-19, 2 pages (Dec. 9, 2020).

(56) References Cited

OTHER PUBLICATIONS

[No Author Listed], Pfizer and BioNTech Announce Agreement with the United Kingdom for 30 Million Doses of mRNA-based Vaccine Candidate Against SARS-CoV-2, 3 pages (Jul. 20, 2020).
[No Author Listed], Pfizer and BioNTech Announce an Agreement with U. S. Government for up to 600 Million Doses of mRNA-based Vaccine Candidate Against SARS-CoV-2, 3 pages (Jul. 22, 2020).
[No Author Listed], Pfizer and BioNTech Announce Collaboration with Biovac to Manufacture and Distribute COVID-19 Vaccine Doses within Africa, 4 pages (Jul. 21, 2021).
[No Author Listed], Pfizer and BioNTech Announce Data From Preclinical Studies of mRNA-Based Vaccine Candidate Against COVID-19, 3 pages (Sep. 9, 2020).
[No Author Listed], Pfizer and BioNTech Announce Early Positive Data from an Ongoing Phase 1/2 Study of mRNA-based Vaccine Candidate Against SARS-CoV-2, 3 pages (Jul. 1, 2020).
[No Author Listed], Pfizer and BioNTech Announce Early Positive Update from German Phase 1/2 COVID-19 Vaccine Study, Including First T Cell Response Data, 3 pages (Jul. 20, 2020).
[No Author Listed], Pfizer and BioNTech Announce Further Details on Collaboration to Accelerate Global COVID-19 Vaccine Development, 2 pages (Apr. 9, 2020).
[No Author Listed], Pfizer and BioNTech Announce New England Journal of Medicine Publication of Phase 1 Data on Lead mRNA Vaccine Candidate BNT162b2 Against COVID-19, 2 pages (Oct. 14, 2020).
[No Author Listed], Pfizer and BioNTech Announce Publication of Peer-Reviewed Data from Ongoing Phase 1/2 study of mRNA-based Vaccine Candidate, BNT162b1, Against SARS-CoV-2 in Nature, 4 pages (Aug. 12, 2020).
[No Author Listed], Pfizer and BioNTech Announce Publication of Results from Landmark Phase 3 Trial of BNT162b2 COVID-19 Vaccine Candidate in The New England Journal of Medicine, 3 pages (Dec. 10, 2020).
[No Author Listed], Pfizer and BioNTech Announce Vaccine Candidate Against COVID-19 Achieved Success in First Interim Analysis from Phase 3 Study, 3 pages (Nov. 9, 2020).
[No Author Listed], Pfizer and BioNTech Choose Lead mRNA Vaccine Candidate Against COVID-19 and Commence Pivotal Phase 2/3 Global Study, 3 pages (Jul. 27, 2020).
[No Author Listed], Pfizer and BioNTech Commence Global Clinical Trial to Evaluate COVID-19 Vaccine in Pregnant Women, 3 pages (Feb. 18, 2021).
[No Author Listed], Pfizer and BioNTech Confirm High Efficacy and No Serious Safety Concerns Through Up to Six Months Following Second Dose in Updated Topline Analysis of Landmark COVID-19 Vaccine Study, 4 pages (Apr. 1, 2021).
[No Author Listed], Pfizer and BioNTech Dose First Participants in the U.S. as Part of Global COVID-19 mRNA Vaccine Development Program, 2 pages (May 5, 2020).
[No Author Listed], Pfizer and BioNTech Granted FDA Fast Track Designation for Two Investigational mRNA-based Vaccine Candidates Against SARS-CoV-2, 2 pages (Jul. 13, 2020).
[No Author Listed], Pfizer and BioNTech Initiate a Study as Part of Broad Development Plan to Evaluate COVID-19 Booster and New Vaccine Variants, 3 pages (Feb. 25, 2021).
[No Author Listed], Pfizer and BioNTech Initiate Rolling Submission of Biologics License Application for U.S. FDA Approval of their COVID-19 Vaccine, 3 pages (May 7, 2021).
[No Author Listed], Pfizer and BioNTech Propose Expansion of Pivotal COVID-19 Vaccine Trial, 2 pages (Sep. 12, 2020).
[No Author Listed], Pfizer and BioNTech Provide Data from German Phase 1/2 Study Further Characterizing Immune Response Following Immunization with Lead COVID-19 Vaccine Candidate BNT162b2, 3 pages (Dec. 14, 2020).
[No Author Listed], Pfizer and BioNTech Publish Data from In Vitro Studies in Nature Medicine Demonstrating COVID-19 Vaccine Elicits Antibodies that Neutralize SARS-CoV-2 with Key Mutations Present in U.K. and South African Variants, 3 pages (Feb. 8, 2021).
[No Author Listed], Pfizer and BioNTech Publish Data on COVID-19 Vaccine-Induced Antibodies' Ability to Neutralize SARS-CoV-2 U.K. Strain Pseudovirus in Cell Culture in Science, 3 pages (Jan. 29, 2021).
[No Author Listed], Pfizer and BioNTech Publish Preclinical Data from Investigational COVID-19 Vaccine Program in Nature, 3 pages (Feb. 1, 2021).
[No Author Listed], Pfizer and BioNTech Publish Results of Study Showing COVID-19 Vaccine Elicits Antibodies that Neutralize Pseudovirus Bearing the SARS-CoV-2 U.K. Strain Spike Protein in Cell Culture, 3 pages (Jan. 20, 2021).
[No Author Listed], Pfizer and BioNTech Reach Agreement with COVAX for Advance Purchase of Vaccine to Help Combat COVID-19, 3 pages (Jan. 22, 2021).
[No Author Listed], Pfizer and BioNTech Reach an Agreement to Supply the EU with 200 Million Doses of Their BNT162b2 mRNA-based Vaccine Candidate against COVID-19, 3 pages (Nov. 11, 2020).
[No Author Listed], Pfizer and BioNTech Receive Authorization in the European Union for COVID-19 Vaccine, 4 pages (Dec. 21, 2020).
[No Author Listed], Pfizer and BioNTech Receive CHMP Positive Opinion for their COVID-19 Vaccine, 3 pages (Dec. 21, 2020).
[No Author Listed], Pfizer and BioNTech Receive Conditional Marketing Authorization by Swissmedic for COVID-19 Vaccine, 3 pages (Dec. 19, 2020).
[No Author Listed], Pfizer and BioNTech Receive FDA Advisory Committee Vote Supporting Potential First Emergency Use Authorization for Vaccine to Combat COVID-19 in the U.S., 3 pages (Dec. 10, 2020).
[No Author Listed], Pfizer and BioNTech Receive First Authorization in European Union for COVID-19 Vaccine in Adolescents, 3 pages (May 28, 2021).
[No Author Listed], Pfizer and BioNTech Receive First U.S. Authorization for Emergency Use of COVID-19 Vaccine in Adolescents, 4 pages (May 11, 2021).
[No Author Listed], Pfizer and BioNTech Receive Health Canada Authorization of COVID-19 Vaccine in Adolescents, 2 pages (May 5, 2021).
[No Author Listed], Pfizer and BioNTech Request Regulatory Agencies Expand Emergency Use of Their COVID-19 Vaccine to Adolescents, 3 pages (Apr. 9, 2021).
[No Author Listed], Pfizer and BioNTech Share Positive Early Data on Lead mRNA Vaccine Candidate BNT162b2 Against COVID-19, 3 pages (Aug. 20, 2020).
[No Author Listed], Pfizer and BioNTech Sign Agreement for Additional Supply to Turkey of 60 Million Doses of their COVID-19 Vaccine, 3 pages (May 20, 2021).
[No Author Listed], Pfizer and BioNTech Submit COVID-19 Vaccine Stability Data at Standard Freezer Temperature to the U.S. FDA, 3 pages (Feb. 19, 2021).
[No Author Listed], Pfizer and BioNTech Submitted Application for Conditional Marketing Authorization for COVID-19 Vaccine to the EMA, 3 pages (Dec. 1, 2020).
[No Author Listed], Pfizer and BioNTech to Co-develop Potential COVID-19 Vaccine, 2 pages (Mar. 17, 2020).
[No Author Listed], Pfizer and BioNTech to Potentially Supply the EU with 200 Million Doses of mRNA-based Vaccine Candidate Against SARS-CoV-2, 3 pages (Sep. 9, 2020).
[No Author Listed], Pfizer and BioNTech to Provide 500 Million Doses of COVID-19 Vaccine to U.S. Government for Donation to Poorest Nations, 4 pages (Jun. 10, 2021).
[No Author Listed], Pfizer and BioNTech to Provide COVID-19 Vaccine Doses for Olympic Athletes at the 2020 Tokyo Games, 4 pages (May 6, 2021).
[No Author Listed], Pfizer and BioNTech to Supply Canada with their BNT162 mRNA-Based Vaccine Candidate, 3 pages (Aug. 5, 2020).
[No Author Listed], Pfizer and BioNTech to Supply Japan with 120 Million Doses of Their BNT162 mRNA-Based Vaccine Candidate, 3 pages (Jul. 31, 2020).

(56) References Cited

OTHER PUBLICATIONS

[No Author Listed], Pfizer and BioNTech to Supply the U.S. with 100 Million Additional Doses of COVID-19 Vaccine, 3 pages (Dec. 23, 2020).
[No Author Listed], Pfizer and BioNTech to Supply the United States with 100 Million Additional Doses of COVID-19 Vaccine, 3 pages (Feb. 12, 2021).
[No Author Listed], Pfizer And BioNTech to Supply U.S. Government with an Additional 200 Million Doses of COVID-19 Vaccine to Help Meet Continued Need for Vaccine Supply in the U.S., 3 pages (Jul. 23, 2021).
[No Author Listed], Pfizer Canada and BioNTech Initiate Rolling Submission to Health Canada for SARS-CoV-2 Vaccine Candidate BNT162b2, 2 pages (Oct. 9, 2020).
[No Author Listed], Pfizer-BioNTech Announce Positive Topline Results of Pivotal COVID-19 Vaccine Study in Adolescents, 3 pages (Mar. 31, 2021).
[No Author Listed], Pfizer-BioNTech's COVID-19 Vaccine Arrives in Rwanda, 3 pages (Mar. 3, 2021).
[No Author Listed], Phase 3 Clinical Trial of Investigational Vaccine for COVID-19 Begins, NIH News Release, 3 pages (Jul. 27, 2020).
[No Author Listed], Real-World Evidence Confirms High Effectiveness of Pfizer-BioNTech COVID-19 Vaccine and Profound Public Health Impact of Vaccination One Year After Pandemic Declared, 4 pages (Mar. 11, 2021).
[No Author Listed], Severe acute respiratory syndrome coronavirus 2 isolate Wuhan-Hu-1, complete genome, Gen Bank: Accession No. 045512, 16 pages (published on Jan. 2020).
[No Author Listed], Severe acute respiratory syndrome coronavirus 2 isolate Wuhan-Hu-1, complete genome, Genbank Accession No. MN908947.3, 11 pages (Mar. 18, 2020).
[No Author Listed], Statement on Voluntary COVID-19 Vaccination for BioNTech Employees and Suppliers to Ensure Undisrupted Manufacturing and Distribution of COVID-19 Vaccine Doses, 1 page (Jan. 11, 2021).
[No Author Listed], U.S. CDC Committee of Independent Health Experts Recommends Vaccination with Pfizer and BioNTech COVID-19 Vaccine for Persons Ages 16 Years and Older, 3 pages (Dec. 12, 2020).
[No Author Listed], U.S. FDA Grants Priority Review for the Biologics License Application for Pfizer-BioNTech COVID-19 Vaccine, 3 pages (Jul. 16, 2021).
[No Author Listed], Update on vaccine production at BioNTech's manufacturing site in Marburg, 2 pages (Feb. 10, 2021).
Abu-Raddad, L. J. et al., Effectiveness of the BNT162b2 Covid-19 Vaccine against the B.1.1.7 and B.1.351 Variants, N. Engl. J. Med., 3 pages (2021).
Adams, P. et al., PHENIX: a comprehensive Python-based system for macromolecular structure solution, Acta Crystallogr D Biol Crystallogr, 66(Pt 2):213-21 (2010).
Adney, D. et al., Efficacy of an Adjuvanted Middle East Respiratory Syndrome Coronavirus Spike Protein Vaccine in Dromedary Camels and Alpacas, Viruses, 11(3):212 (2019).
Agnihothram, S. et al., Development of a Broadly Accessible Venezuelan Equine Encephalitis Virus Replicon Particle Vaccine Platform, J Virol, 92(11):e00027-18 (2018).
Akinc, A. et al., The onpattro story and the clinical translation of the nanomedicines containing nucleic acid-based drugs, Nature Nanotechnology, 14:1084-1087 (2019).
Al Kahlout, R. et al., Comparative Serological Study for the Prevalence of Anti-MERS Coronavirus Antibodies in High- and Low-Risk Groups in Qatar, J Immunol Res, 2019:1386740, 8 pages (2019).
Al-Amri, S. et al., Immunogenicity of Candidate MERS-Cov DNA Vaccines Based on the Spike Protein, Sci Rep, 7:44875, 8 pages (2017).
Aldrich, C. et al., Proof-of-concept of a low-dose unmodified MRNA-based rabies vaccine formulated with lipid nanoparticles in human volunteers: A phase 1 trial, Vaccine, 39:1310-1318 (2021).
Anderson, E.J. et al., Safety and Immunogenicity of SARS-CoV-2 mRNA-1273 Vaccine in Older Adults, N. Engl. J. Med., 383(25):2427-2438 (2020).
Andries, O. et al., N(I)-methylpseudouridine-incorporated mRNA outperforms pseudouridineincorporated mRNA by providing enhanced protein expression and reduced immunogenicity in mammalian cell lines and mice, J Control Release, 217:337-44 (2015).
Bao, L. et al., Reinfection could not occur in SARS-CoV-2 infected rhesus macaques, bioRXiv, 20 pages (2020).
Bao, L. et al., The Pathogenicity of SARS-CoV-2 in hACE2 Transgenic Mice, bioRxiv, 24 pages (2020).
Battles, M. B. et al., Structure and immunogenicity of pre-fusion-stabilized human metapneumovirus F glycoprotein, Nature Communications, 8(1528):1-11 (2017).
Berger Rentsch, M. and Zimmer, G., A vesicular stomatitis virus replicon-based bioassay for the rapid and sensitive determination of multi-species type I interferon, PLoS One,6(10):e25858, 8 pages (2011).
Bergtold, A. et al., Cell Surface Recycling of Internalized Antigen Permits Dendritic Cell Priming of B Cells, Immunity, 23:503-514 (2005).
Berkhout, B. and Van Hemert, F., On the biased nucleotide composition of the human coronavirus RNA genome, Virus Research, 202:41-47 (2015).
BioNTech and Fosun Pharma Announce Full Regulatory Approval of their Mono- and Bivalent COVID-19 Vaccine COMIRNATY® in Individuals 12 Years and Older in Hong Kong—Dec. 23, 2022.
BioNTech Announces Second Quarter Financial Results and Corporate Update—Aug. 8, 2022.
Boon, S. et al., Temporal-Geographical Dispersion of SARS-CoV-2 Spike Glycoprotein Variant Lineages and Their Functional Prediction Using in Silico Approach, Mbio 12(5), e02687-21, 19 pages (2021).
Boone, L. et al., Selection and interpretation of clinical pathology indicators of hepatic injury in preclinical studies, Vet Clin Pathol., 34(3):182-8 (2005).
Bouloy, M. et al., Both the 7-methyl and the 2'-0-methyl groups in the CAP of mRNA strongly influence its ability to act as primer for influenza virus RNA transcription, Proceedings of The National Academy of Sciences of The USA, 77(7):3952-3956 (1980).
Braathen, R. et al., The Magnitude and IgG Subclass of Antibodies Elicited by Targeted DNA Vaccines Are Influenced by Specificity for APC Surface Molecules, ImmunoHorizons, 2(1):21pgs (2018).
Brooks, M. et al., Non-Lethal Endotoxin Injection: A Rat Model of Hypercoagulability, PLoS One, 12(1):e0169976 (2017).
Brown, E. L. and Essigmann, H. T., Original Antigenic Sin: the Downside of Immunological Memory and Implications for COVID-19, Amer. Soc. Microbio., 6(2):e00056-21, 6 pages (2021).
Bruun, T. et al., Engineering a Rugged Nanoscaffold to Enhance Plug-and-Display Vaccination, ACS Nano, 12(9):8855-8866 (2018).
Cai, Y. et al., Distinct conformational states of SARS-CoV-2 spike protein, Science, 369(6511):1586-1592 (2020).
Callaway, E. and Ledford, H., How to Redesign Covid Vaccines So They Protect Against Variants, 590(7844):15-16 (2021).
Chan, J. et al., Genomic characterization of the 2019 novel human-pathogenic coronavirus isolated from a patient with atypical pneumonia after visiting Wuhan, Emerg Microbes Infect, 9(1):221-236 (2020).
Chan, J. et al., NCBI GenBank: MN938384.1, Severe acute respiratory syndrome coronavirus 2 isolate 2019_nCOV_HKU_SZ_002a_2020, complete genome, NCBI GenBank (Feb. 11, 2020).
Chan, J. F. et al., A familial cluster of pneumonia associated with the 2019 novel coronavirus indicating person-to-person transmission a study of a family cluster, Lancet, 395(10223):514-523 (2020).
Chandrashekar, A. et al., SARS-CoV-2 infection protects against rechallenge in rhesus macaques, Sci. Mag., 12 pages (2020).
Chen, J. et al., Prediction and mitigation of mutation threats to COVID-19 vaccines and anibody therapies, Arxiv. org, Cornell University Library, 28 pages (2021).
Chen, Y. et al., Emerging Coronaviruses: Genome structure, replication, and pathogenesis, J Med Virol., 92:418-423, (2020).

(56) References Cited

OTHER PUBLICATIONS

Chi, X. et al., A neutralizing human antibody binds to the N-terminal domain of the Spike protein of SARS-CoV-2, Science, 369(6504):650-655 (2020).
Cohen, A. et al., Mosaic RBD nanoparticles protect against challenge by diverse sarbecoviruses in animal models, Science, retrieved from the Internet: https://www.science.org/doi/pdf/10.1126/science.abf6840, 30 pages (2022).
Cohen, Jon, Scientists are moving at record speed to create new coronavirus vaccines but they may come too late, Science; AAAS, retrieved from the Internet: https://www.sciencemag.org/news/2020/01/scientists-are-moving-record-speed-create-new-coronavirus-vaccines-they-may-come-too, 6 pages (May 25, 2021).
Corbett, K. S. et al., SARS-CoV-2 mRNA Vaccine Development Enabled by Prototype Pathogen Preparedness, posted on bioRxiv (Jun. 2020), 39 pages.
Corbett, K.S. et al., Evaluation of mRNA-1273 against SARS-CoV-2 B.1.351 Infection in Nonhuman Primates, posted on bioRxiv (May 2021), 33 pages.
Corbett, K.S. et al., Evaluation of the mRNA-1273 Vaccine against SARS-CoV-2 in Nonhuman Primates, N. Engl. J. Med., 383(16):1544-1555 (2020).
Corbett, K.S. et al., Immune Correlates of Protection by mRNA-1273 Immunization against SARS-CoV-2 Infection in Nonhuman Primates, posted on bioRxiv (Apr. 2021), 33 pages.
Corbett, K.So et al., SARS-CoV-2mRNA vaccine design enabled by prototype pathogen preparedness, Nature, 586:567-571 (2020).
Cossarizza, A. et al., SARS-CoV-2, the Virus that Causes COVID-19: Cytometry and the New Challenge for Global Health, Cytometry Part A, 4 pages (2020).
Cullis, P. and Hope, M., Lipid Nanoparticle Systems for Enabling Gene Therapies, Mol Ther, 25(7):1467-1475 (2017).
CureVac Provides Update on Phase 2b/3 Trial of First-Generation COVID-19 Vaccine Candidate, CVnCoV, Jun. 16, 2021, press release, <https://www.curevac.com/en/curevac-provides-update-on-phase-2b-3-trial-of-first-generation-covid-19-vaccine-candidate-cvncov/>, 4 pages.
CureVac's COVID-19 vaccine (CVnCoV): Withdrawal from the rolling review process, Oct. 12, 2021, European Medical Agency (EMA), ema.europa.eu/en/medicines/human/withdrawn-applications/curevacs-covid-19-vaccine-cvncov, 3 pages.
Database EMBL [Online] EBI; Jan. 15, 2020 (Jan. 15, 2020), Zhang Y. et al: "Wuhan seafood market pneumonia virus isolate Wuhan-Hu-1, complete genome.", XP055796635, Database accession No. MN908947 the whole document.
Database UniParc, Database accession No. UPI00131F240A, retrieved from UniProt, 4 pages Aug. 23, 2021.
Database UniParc, Database accession No. UPI0013753F0, retrieved from UniProt, one page (Sep. 2, 2021).
De Wit, E. et al., SARS and MERS: recent insights into emerging coronaviruses, Nat Rev Microbiol., 14(8):523-34 (2016).
Dearlove, B. et al., A SARS-CoV-2 vaccine candidate would likely match all currently circulating variants, PNAS, 117(38):23652-23662 (2020).
Den Dunnon, J.T. and Antonarakis, S.E., Nomenclature for the description of sequence variations, Human Genet., 109(1):121-124 (2001).
Diao, B. et al., Human kidney is a target for novel severe acute respiratory syndrome coronavirus 2 infection, Nat Commun., 12(1):2506, 9 pages (2021).
Doremalen, N. et al., ChAdOx1 nCoV-19 vaccination prevents SARS-CoV-2 pneumonia in rhesus macaques, bioRxiv, 23 pages (2020).
Du, L. et al., Recombinant adeno-associated virus expressing the receptor-binding domain of severe acute respiratory syndrome coronavirus S protein elicits neutralizing antibodies: Implication for developing SARS vaccines, Virology, 353(1):6-16 (2006).
Emsley, P. et al., Features and development of Coot, Acta Crystallogr D Biol Crystallogr, 66(Pt 4):486-501 (2010).
Ennulat, D. et al., Diagnostic performance of traditional hepatobiliary biomarkers of drug-induced liver injury in the rat, Toxicol Sci., 116(2):397-412 (2010).
Fan, X. et al., Cryo-EM analysis of the post-fusion structure of the SARS-CoV spike glycoprotein, Nat Commun., 11(1):3618, 10 pages (2020).
Fang, Z. et al., Omicron-specific mRNA vaccination alone and as a heterogous booster against SARS-CoV-2, Nature Communications, 13:3250, 12 pages (2022).
Faria, N. et al., Genomic characterisation of an emergent SARS-CoV-2 lineage in Manaus: preliminary findings—SARS-CoV-2 coronavirus / nCoV-2019 Genomic Epidemiology-Virological, retrieved from the Internet: https//virological.org/t/genomic-characterisation-of-an- emergent-sars-cov-2-lineage-in-manaus-preliminary-findings/586, 6 pages (May 31, 2021).
Farooq, F. et al., Circulating follicular T helper cells and cytokine profile in humans following vaccination with the rVSV-ZEBOV Ebola vaccine, Scientific Reports, 6(27944):1-9 (2016).
Feldstein, L. R. et al., Multisystem Inflammatory Syndrome in U.S. Children and Adolescents, N. Engl. Med., 383(4):334-346 (2020).
Fierz, W. and Walz, B., Antibody Dependent Enhancement Due to Original Antigenic Sin and the Development of SARS, Front. Immun., 11(1120):1-5 (2020).
Folegatti, P. et al., Safety and immunogenicity of the ChAdOx1 nCoV-19 vaccine against SARS-CoV-2: a preliminary report of a phase 1/2, single-blind, randomised controlled trial, Lancet, 396(10249):467-478 (2020).
Follis, K. et al., Furin cleavage of the SARS coronavirus spike glycoprotein enhances cell-cell fusion but does not affect virion entry, Virology, 350(2):358-69 (2006).
Funk, C. et al., A Snapshot of the Global Race for Vaccines Targeting SARS-CoV-2 and the COVID-19 Pandemic, Front Pharmacol., 11:937, 17 pages (2020).
Furuichi, Y. and Shatkin, A., Viral and cellular mRNA capping: past and prospects, Adv Virus Res, 55:135-84 (2000).
Furuichi, Yasuhiro, Caps on Eukaryotic mRNAs, John Wiley & Sons, pp. 1-12 (Jul. 2014).
Gallie, Daniel R., The cap and poly(A) tail function synergistically to regulate mRNA translational efficiency, Genes Dev, 5(11):2108-16 (1991).
Garcia-Doval, C. and Van Raaij, M. J., Structure of the receptor-binding carboxy-terminal domain of bacteriophage T7 tail fibers, PNAS, 109(24):9390-9395 (2012).
Garrido, C. et al., SARS-CoV-2 vaccines elicit durable immune responses in infant rhesus macaques, Sci. Immunol., 23 pages (2021).
Gautam, U. et al., In vivo inhibition of tryptophan catabolismreorganizes the tuberculoma and augments immune-mediated control of *Mycobacterium tuberculosis*, Proc Natl Acad Sci USA, 115(1):E62-E71 (2018).
Gebre, M. S. et al., Optimization of Non-Coding Regions Improves Protective Efficacy of an mRNA SARS-CoV-2 Vaccine in Nonhuman Primates, bioRxiv, 36 pages (2021).
GenBank MN975262.1 "Wuhan seafood market pneumonia virus isolate 2019-nCoV_HKU-SZ-005b_2020, complete genome" (Jan. 24, 2020) [retrieved on Jun. 2, 2021, https://www.ncbi.nlm.nih.gov/nuccore/1800242661 ?sat=48&satkey=350763] whole doc.
GenBank QHN73810.1 "surface glycoprotein [Wuhan seafood market pneumonia virus]" (Jan. 24, 2020) [retrieved on Jun. 2, 2021, https://www.ncbi.nlm.nih.gov/protein/QHN73810.1/] whole doc.
Gomes, A. C. et al., Type of RNA Packed in VLPs Impacts IgG Class Switching-Implications for an Influenza Vaccine Design, MDPI, 7(47):1-13 (2019).
Graham, Barney S., Rapid COVID-19 vaccine development, Science, 368(6494):945-946 (2020).
Grudzen, E. et al., Differential Inhibition of mRNA Degradation Pathways by Novel Cap Analogs, The Journal of Biological Chemistry, 281(4):1857-1867 (2006).
Habjan, M. et al., Sequestration by IFIT1 impairs translation of 2'0-unmethylated capped RNA, PLOS Pathogens, 9(10):e1003663 (2013).

(56) References Cited

OTHER PUBLICATIONS

Hahn, S. et al., FDA Statement on Following the Authorized Dosing Schedules for COVID-19 Vaccines, FDA website, Jan. 4, 2021, 3 pages.
Hait, S. H. et al., Early T Follicular Helper Cell Responses and Germinal Center Reactions Are Associated with Viremia Control in Immunized Rhesus Macaques, Journal of Virology, 93(4):1-22 (2019).
Hassett, K. et al., Optimization of Lipid Nanoparticles for Intramuscular Administration of mRNA Vaccines, Mol Ther Nucleic Acids, 15:1-11 (2019).
He, Y. et al., Receptor-binding domain of SARS-CoV spike protein induces highly potent neutralizing antibodies: implication for developing subunit vaccine, Biochem Biophys Res Commun, 324(2):773-81 (2004).
Henderson, R. et al., Controlling the SARS-CoV-2 spike glycoprotein conformation, Nat Struct Mol Biol., 27(10):925-933 (2020).
Hie, B. et al., Learning the language of viral evolution and escape, Science, 371(6526):284-288 (2021).
Hodcroft, Emma, CoVariants: Shared Mutations, Covariants.org, 4 pages (2022).
Hodgson, J., The pandemic pipeline, Nature Biotechnology, 38(5):523-532 (2020).
Hodgson, J., The pandemic pipeline, Nature Biotechnology, Gale Group Inc, New York, 38(5):523-532 (2020).
Hoffman, M. et al., SARS-CoV-2 variants B.1.351 and B.1.1.248: Escape from the therapeutic antibodies and antibodies induced by infection and vaccination, bioRxiv, retrieved from the Internet: https//www.biorxiv.org/content/10.1101/2021.02.11.430787v1.full.pdf (Aug. 23, 2021).
Hoffmann, M. et al., SARS-CoV-2 Cell Entry Depends on ACE2 and TMPRSS2 and Is Blocked by a Clinically Proven Protease Inhibitor, Cell, 181(2):271-280 (2020).
Holdsworth, S. R. et al., Th1 and Th2 T helper cell subsets affect patterns of injury and outcomes in glomerulonephritis, Kidney International, 55:1198-1216 (1999).
Honda-Okubo, Y. et al., Severe Acute Respiratory Syndrome-Associated Coronavirus Vaccines Formulated with Delta Inulin Adjuvants Provide Enhanced Protection while Ameliorating Lung Eosinophilic Immunopathology, Journal of Virology, 89(6):2995-3007 (2015).
Hsieh, C. et al., Structure-based design of prefusion-stabilized SARS-CoV-2 spikes, Science, 369:1501-1505 (2020).
Hsieh, C. et al., Structure-based Design of Prefusion-stabilized SARS-CoV-2 Spikes, bioRxiv, retrieved from the Internet: https://www.ncbi.nlm.nih.gov/pmc/articles/PMC7302215/pdf/nihpp-2020.5.30.125484.pdf, 39 pages (May 30, 2020).
Huang, C. et al., Clinical features of patients infected with 2019 novel coronavirus in Wuhan, China, Lancet, 395(10223)497-506 (2020).
Huang, Q. et al., A single-dose mRNA vaccine provides a long-term protection for hACE2 transgenic mice from SARS-CoV-2, Nat. Comm., 12(776):1-10 (2021).
Huang, Y. et al., Structural and functional properties of SARS-CoV-2 spike protein: potential antivirus drug development for COVID-19, Acta Pharma. Sinica, 41:1141-1149 (2020).
Huber, V. C. et al., Distinct Contributions of Vaccine-Induced Immunoglobulin G1 (IgG1) and IgG2a Antibodies to Protective Immunity against Influenza, Clinical and Vaccine Immunology, 13(9):981-990 (2006).
Hui, A. et al., Immunogenicity and safety of BNT162b2 mRNA vaccine in Chinese adults: A phase 2 randomised clinical trial. The Lancet Regional Health-Western Pacific 29 (2022): 100586.
Hulswit, R. et al., Coronavirus Spike Protein and Tropism Changes, Adv Virus Res., 96:29-57 (2016).
Hyde, J. L. et al., A viral RNA structural element alters host recognition of nonself RNA, Science, 343(6172):783-787 (2014).
Hyde, J. L. et al., Supplementary Information, SCIENCE, 343(6172):783-787 (2014).
Iadevaia, V. et al., All translation elongation factors and the e, f, and h subunits of translation initiation factor 3 are encoded by 5'-terminal oligopyrimidine (TOP) mRNAs, RNA, 14:1730-1736 (2008).
International Nonproprietary Names for Pharmaceautical Substances (INN), WHO Drug Information, vol. 33, No. 3, 139 pages, (2019).
International Search Report and Written Opinion for Application No. PCT/US2021/015145, 5 pages, mailed May 3, 2021.
International Search Report for PCT/EP2021/059947, 6 pages (mailed Aug. 5, 2021).
International Search Report for PCT/EP2021/060004, 7 pages (Sep. 8, 2021).
International Search Report for PCT/EP2021/060508, 7 pages (mailed Aug. 5, 2021).
International Search Report for PCT/EP2022/060417, 6 pages (Aug. 4, 2022).
International Search Report for PCT/EP2022/083740, 9 pages (Jun. 2, 2023).
Ishikawa, M. et al., Preparation of eukaryotic mRNA having differently methylated adenosine at the 5'-terminus and the effect of the methyl group in translation, Nucleic Acids Symposium Series, Oxford, 53:129-130 (2009).
Ivens, I. et al., PEGylated Biopharmaceuticals: Current Experience and Considerations for Nonclinical Development, Toxicol Pathol., 43(7):959-83 (2015).
Jackson, L.A. et al., An mRNA Vaccine against SARS-CoV-2—Preliminary Report, N. Engl. J. Med., 383:1920-1931 (2020).
Jackson, N. A. C. et al., The promise of mRNA vaccines: a biotech and industrial perspective, NPJ Vaccines, 5(11):1-6 (2020).
Jafarzadeh, H. et al., Contribution of monocytes and macrophages to the local tissue inflammation and cytokine storm in COVID-19: Lessons from SARS and MERS, and potential therapeutic interventions, Life Sci., 257:118102, 16 pages (2020).
Jaimes, J. et al., Phylogenetic Analysis and Structural Modeling of SARS-CoV-2 Spike Protein Reveals an Evolutionary Distinct and Proteolytically Sensitive Activation Loop, J Mol Biol., 432(10):3309-3325 (2020).
Jeong, D. et al., Assemblies-of-putative-SARS-CoV2-spike-encoding-mRNA-sequences-for-vaccines-BNT-162b2-and-mRNA-1273, 4 pages (2021).
Ji, R. et al., BNT162b2 Vaccine Encoding the SARS-CoV-2 P2 S Protects Transgenic hACE2 Mice against COVID-19, Vaccines, 9(324):1-7 (2021).
Jiang, S. et al., Neutralizing Antibodies against SARS-CoV-2 and Other Human Coronaviruses, Trends in Immunology, 41(5):355-359 (2020).
Kaku, C. et al., Recall of pre-existing cross-reactive B cell memory following Omicron BA. 1 breakthrough infection. Science immunology (2022): eabq3511.
Kanekiyo, M. et al., New Vaccine Design and Delivery Technologies, The Journal of Infectious Diseases, 219(S1):S88-96 (2019).
Kauffman, K. et al., Materials for non-viral intracellular delivery of messenger RNA therapeutics, J Control Release, 240:227-234 (2016).
Ke, Z. et al., Structures, conformations and distributions of SARs-CoV-2 spike protein trimers on intact virions, bioRxiv (2020).
Kielian, M. and Rey, F. A., Virus membrane-fusion proteins: more than one way to make a hairpin, Nature Reviews Microbiology, 4:67-76 (2006).
Kim, A. et al., A mouse model of anemia of inflammation: complex pathogenesis with partial dependence on hepcidinm, Blood, 123(8):1129-36 (2014).
Kim, A. et al., Isocitrate treatment of acute anemia of inflammation in a mouse model. Blood Cells Mol Dis., 56(1):31-6 (2016).
Kim, J. et al., Viral Load Kinetics of SARS-CoV-2 Infection in First Two Patients in Korea, J Korean Med Sci., 35(7):e86 (2020).
Kirchdoerfer, R. N. et al., Stabilized coronavirus spikes are resistant to conformational changes induced by receptor recognition or proteolysis, Sci. Repo., 8(15701):1-11 (2018).
Kleine-Weber, H., et al., Functional analysis of potential cleavage sites in the MERS-coronavirus spike protein, Sci Rep., 8(1):16597 (2018).

(56) References Cited

OTHER PUBLICATIONS

Klimek, L. et al., Severe allergic reactions after COVID-19 vaccination with the Pfizer/BioNTech vaccine in Great Britain and USA, Allergo J. Int., 5 pages (2021).
Koukhareva I. I. and Lebedev, A. V., Chemical Route to the Capped RNAs, Nucleosides, Nucleotides and Nucleic Acids, 23(10):1667-1780 (2004).
Kozauer, N. et al., Cross-Discipline Team Leader Review, Center for Drug Evaluation and Research 210922, 485 pages (2020).
Kozma, G. T. et al., Pseudo-anaphylaxis to Polyethylene Glycol (PEG)-Coated Liposomes: Roles of Anti-PEG IgM and Complement Activation in a Porcine Model of Human Infusion Reactions, ACS Nano, 13:9315-9324 (2019).
Krarup, A. et al., A highly stable prefusion RSV F vaccine derived from structural analysis of the fusion mechanism, Nature Communications, 6(8143):1-12 (2015).
Kremsner, P. et al., Phase 1 Assessment of the Safety and Immunogenicity of an mRNALipid Nanoparticle Vaccine Candidate Against SARS-CoV-2 in Human Volunteers, medRxiv, pp. 1-38 (2020).
Kuhn, A. et al., Phosphorothioate cap analogs increase stability and translational efficiency of RNA vaccines in immature dentritic cells and induce superior immune responses in vivo, Gene Therapy, 17:961-971 (2010).
Kumar, A. et al., Status Report on COVID-19 Vaccines Development, Current Infectious Disease Reports, 23(6):1-12 (2021).
Kurhade, C. et al., Neutralization of Omicron BA. 1, BA. 2, and BA. 3 SARS-CoV-2 by 3 doses of BNT162b2 vaccine. Nature communications 13.1 (2022): 1-4.
Kurhade, C. et al., Neutralization of Omicron sublineages and Deltacron SARS-CoV-2 by 3 doses of BNT162b2 vaccine or BA. 1 infection. bioRxiv (2022).
Kurimoto, S. et al., PEG-OligoRNA Hybridization of mRNA for Developing Sterically Stable Lipid Nanoparticles toward In Vivo Administration, Molecules, 24(7):1303, 16 pages (2019).
Laczkó, D. et al., A Single Immunization with Nucleoside-Modified mRNA Vaccines Elicits Strong Cellular and Humoral Immune Responses against SARS-CoV-2 in Mice, Immunity, 53(4):724-732 (2020).
Lambert, P. et al., Consensus summary report for CEPI/BC Mar. 12-13, 2020 meeting: Assessment of risk of disease enhancement with COVID-19 vaccines, Vaccine, 38(31):4783-4791 (2020).
Lan, J. et al., Structure of the SARS-CoV-2 spike receptor-binding domain bound to the ACE2 receptor, Nature, 581:215-220 (2020).
Lee, W. S. et al., Antibody-dependent enhancement and SARS-CoV-2 vaccines and therapies, Nature Microbiology, 5:1185-1191 (2020).
Lee, Y. et al., Cross Protection against Influenza A Virus by Yeast-Expressed Heterologous Tandem Repeat M2 Extracellular Proteins, PLoS One, 10(9):e0137822 (15).
Lester, S. et al., Middle East respiratory coronavirus (MERS-CoV) spike (S) protein vesicular stomatitis virus pseudoparticle neutralization assays offer a reliable alternative to the conventional neutralization assay in human seroepidemiological studies, Access Microbiol., 1(9):e000057, 9 pages (2019).
Leung, A. K.K et al., Lipid Nanoparticles for Short Interfering RNA Delivery, Advances in Genetics 88:71-110 (2014).
Li, Fang, Structure, Function, and Evolution of Corona virus Spike Proteins, Annu Rev Viral, 3(1):237-261 (2016).
Li, R. et al., The challenge of emerging SARS-CoV-2 mutants to vaccine development, Journal of Genetics and Genomics, 48(2):102-106 (2021).
Limbach, P. A. et al., Summary: the modified nucleosides of RNA, Nucleic Acids Research, 22(12):2183-2196 (1994).
Liu Y. et al., Neutralizing activity of BNT162b2-elicited serum. New England Journal of Medicine 384.15 (2021): 1466-1468.
Liu, J. et al., BNT162b2-elicited neutralization of B. 1.617 and other SARS-CoV-2 variants. Nature 596.7871 (2021): 273-275.
Liu, J. et al., BNT162b2-elicited neutralization of Delta plus, Lambda, Mu, B. 1.1. 519, and Theta SARS-CoV-2 variants. npj Vaccines 7.1 (2022): 1-4.
Liu, Y. et al., BNT162b2-elicited neutralization against new SARS-CoV-2 spike variants. New England Journal of Medicine 385.5 (2021): 472-474.
Liu, Y. et al., Neutralizing Activity of BNT162b2-Elicited Serum, N. Eng. J. Med., 384(15):1-3 (2021).
Lu, R. et al., Genomic characterisation and epidemiology of 2019 novel coronavirus: implications for virus origins and receptor binding, Lancet, 395(10224):565-574 (2020).
Lucey, Daniel R., Moderna to test a "multivalent" COVID vaccine as well as single-valent boosters, retrieved from Internet: https://www.idsociety.org/science-speaks-blog/2021/moderna-to-test-a-multivalent-covid-vaccine-as-well-as-single-valent-boosters/#/+/0/publishedDate_na_dt/desc/, 2 pages (2021).
Mccown, P. J. et al., Naturally occurring modified ribonucleosides, WIREs RNA, 11(e1595):1-71 (2020).
Mckay, P. et al., Self-amplifying RN A SARS-Co V -2 lipid nanoparticle vaccine candidate induces high neutralizing antibody titers in mice, Nat Commun, 11(1):3523, 7 pages (2020).
Mclean, G. et al., The impact of evolving SARS-CoV-2 mutations and variants on COVID-19 vaccines. Mbio 13.2 (2022): e02979-21.
Meier, S. et al., Foldon, The Natural Trimerization Domain of T4 Fibritin, Dissociates into a Monomeric A-state Form containing a Stable B-Hairpin: Atomic Details of Trimer Dissociation and Local β-Hairpin Stability from Residual Dipolar Couplings, J. Mol. Biol., 344(4):1051-1069 (2004).
Mishra, S. and Carnahan, R. et al., Coronavirus: A new type of vaccine using RNA could help defeat COVID-19, The Conversation, 4 pages (2020).
Moderna TX Clinical Trial, NCT04283461, Safety and Immunogenicity Study of 2019-nCoV Vaccine (mRNA-1273) for Prophylaxis of SARS-CoV-2 Infection (COVID-19), 18 pages (2020).
Muik, A. et al., Exposure to BA. 4/5 S protein drives neutralization of Omicron BA. 1, BA. 2, BA. 2.12. 1, and BA. 4/5 in vaccine-experienced humans and mice. Science Immunology (2022): eade9888.
Muik, A. et al., Exposure to BA. 4/BA. 5 Spike glycoprotein drives pan-Omicron neutralization in vaccine-experienced humans and mice. bioRxiv (2022).
Muik, A. et al., Neutralization of SARS-CoV-2 lineage B. 1.1. 7 pseudovirus by BNT162b2 vaccine-elicited human sera. Science 371.6534 (2021): 1152-1153.
Muik, A. et al., Neutralization of SARS-CoV-2 Omicron by BNT162b2 mRNA vaccine-elicited human sera. Science 375.6581 (2022): 678-680.
Muik, A. et al., Neutralization of SARS-CoV-2 Omicron pseudovirus by BNT162b2 vaccine-elicited human sera. medRxiv (2021).
Muik, A. et al., Omicron BA. 2 breakthrough infection enhances cross-neutralization of BA. 2.12. 1 and BA. 4/BA. 5. Science Immunology 7.77 (2022): eade2283.
Muik, A. et al., Progressive loss of conserved spike protein neutralizing antibody sites in Omicron sublineages is balanced by preserved T-cell recognition epitopes. bioRxiv (2022).
Mulligan, M. et al., Phase I/II study of COVID-19 RNA vaccine BNT162b1 in adults, Nature, 586(7830):589-593 (2020).
Mulligan, M. J. et al., Phase 1/2 Study to Describe the Safety and Immunogenicity of a COVID-19 RNA Vaccine Candidate (BNT162b1) in Adults 18 to 55 Years of Age: Interim Report, bioRxiv, 586:16pgs (2020).
Munoz-Fontela, C. et al., Animal models for COVID-19, Nature, 586:509-515 (2020).
Munster, et al., Respiratory disease and virus shedding in rhesus macaques inoculated with SARS-CoV-2, bioRxiv (2020).
Muruato, A. et al., A high-throughput neutralizing antibody assay for COVID-19 diagnosis and vaccine evaluation, Nat Commun., 11(1):4059 (2020).
Muthumani, K. et al., A synthetic consensus anti-spike protein DNA vaccine induces protective immunity against Middle East respiratory syndrome coronavirus in nonhuman primates, Science Translational Medicine, 7(301):1-14 (2015).
Nathan, A. et al., Structure-guided T cell vaccine design for SARS-CoV-2 variants and sarbecovriuses, Cell, 184:1-13 (2021).
Nawrat, A., Q&A with CureVac: resolving the ultra-cold chain logistics of Covid-19 mRNA vaccines, Pharmaceutical Technology,

(56) References Cited

OTHER PUBLICATIONS

Dec. 5, 2020, <https://www.pharmaceutical-technology.com/analysis/mrna-vaccines-covid19-pandemic-curevac/>, 23 pages.
No Author Listed, Messenger RNA encoding the full-length SARS-CoV-2 spike glycoprotein, WHO International Nonproprietary Names Progamme, 4 pages (Jun. 2021).
Nurieva, R. I. et al., Generation of T Follicular Helper Cells is Mediated by Interleukin-21 but Independent of T Helper 1,2, or 17 Cell Lineages, Immunity, 29:138-149 (2008).
Oany, A. et al., Design of an epitope-based peptide vaccine against spike protein of human coronavirus: an in silico approach, Drug Des Devel Ther., 8:1139-49 (2014).
Ogando, N. S. et al., SARS-coronavirus-2 replication in Vero E6 cells: replication kinetics, rapid adaptation and cytopathology, bioRxiv, 40 pages (2020).
ONPATTRO (patisiran) lipid complex injection, for intravenous use, Initial U.S. Approval: 2018, Highlights of prescribing information, 14 pages, Revised: Jan. 2023.
Orlandini Von Niessen, A. G. et al., Improving mRNA-Based Therapeautic Gene Delivery by Expression-Augmenting 3' UTRs Identified by Cellular Library Screening, Molecular Therapy Original Article, 27(4):824-836 (2019).
Ou, X. et al., Characterization of spike glycoprotein of SARS-CoV-2 on virus entry and its immune cross-reactivity with SARS-CoV, Nat Commun., 11(1):1620, 12 pages (2020).
Pallesen, J. et al., Immunogenicity and structures of a rationally designed prefusion MERS-CoV spike antigen, Proc Natl Acad Sci USA, 114(35):E7348-E7357 (2017).
Pape, K. A. et al., The Humoral Immune Response is Initiated in Lymph Nodes by B Cells that Acquire Soluble Antigen Directly in the Follicles, Immunity, 26:491-502 (2007).
Pardi, et al., Nucleoside-modified mRNA vaccines induce potent T follicular helper and germinal center B cell responses, J. Exp. Med. 215(6):1571-1588 (2018).
Pardi, N. et al., Characterization of HIV-1 Nucleoside-Modified mRNA Vaccines in Rabbits and Rhesus Macaques, Molecular Therapy: Nucleic Acids, 15:36-47 (2019).
Pardi, N. et al., mRNA vaccines—a new era in vaccinology, Nat Rev Drug Discov, 17(4):261-279 (2018).
Pardi, N. et al., Nucleoside-modified mRNA immunization elicits influenza virus hemagglutinin stalk-specific antibodies, Nat Commun., 22;9(1):3361 (2018).
Pardi, N. et al., Zika virus protection by a single low-dose nucleoside-modified mRNA vaccination, Nature, 543(7644):248-251 (2017).
Pardi, Norbert, COVID-19 Symposium: Nucleoside-modified mRNA Vaccines Against SARS-CoV-2, Penn Medicine, 10 pages (2020).
Pardi, Norbert, Developement of nucleoside modified mRNA Vaccines against SARS-CoV-2, Penn Medicine, 10 pages (2020).
Pegu, A. et al., Durability of mRNA-1273-induced antibodies against SARS-CoV-2 variants, posted on bioRxiv (May 2021), 39 pages.
Peng, Y. et al., Broad and strong memory $CD4^+$ and $CD8^+$ T cells induced by SARS-CoV-2 in UK convalescent individuals following COVID-19, Nat. Immun., 21:1336-1345 (2020).
Pfizer and BioNTech Advance COVID-19 Vaccine Strategy With Study Start of Next-Generation Vaccine Candidate Based on Enhanced Spike Protein Design—Jul. 27, 2022.
Pfizer and BioNTech Announce Data Demonstrating High Immune Response Following a Booster Dose of Their COVID-19 Vaccine in Children 5 Through 11 Years of Age—Apr. 14, 2022.
Pfizer and BioNTech Announce Omicron-Adapted COVID-19 Vaccine Candidates Demonstrate High Immune Response Against Omicron—Jun. 25, 2022.
Pfizer and BioNTech Announce Positive Early Data From Clinical Trial of Omicron BA.4/BA.5-Adapted Bivalent Booster in Individuals 18 Years and Older—Oct. 13, 2022.
Pfizer and BioNTech Announce Updated Clinical Data for Omicron BA.4/BA.5-Adapted Bivalent Booster Demonstrating Substantially Higher Immune Response in Adults Compared to the Original COVID-19 Vaccine—Nov. 4, 2022.
Pfizer and BioNTech Announce Updated COVID-19 Vaccine Data Supporting Efficacy in Children 6 Months through 4 Years of Age—Aug. 23, 2022.
Pfizer and BioNTech Complete Submission to European Medicines Agency for Omicron BA.4/BA.5 Adapted Bivalent Vaccine—Aug. 26, 2022.
Pfizer and BioNTech Complete Submission to European Medicines Agency for Omicron BA.4/BA.5-Adapted Bivalent Vaccine Booster in Children 5 Through 11 Years of Age—Sep. 28, 2022.
Pfizer and BioNTech Granted FDA Emergency Use Authorization of Omicron BA.4/BA.5-Adapted Bivalent COVID-19 Vaccine Booster for Ages 12 Years and Older—Aug. 31, 2022.
Pfizer and BioNTech Initiate Study to Evaluate Omicron-Based COVID-19 Vaccine in Adults 18 to 55 Years of Age—Jan. 25, 2022.
Pfizer and BioNTech Provide Update on Omicron Variant—Dec. 8, 2021.
Pfizer and BioNTech Provide Update on Rolling Submission to European Medicines Agency for a Potential Variant-Adapted Vaccine—Jun. 15, 2022.
Pfizer and BioNTech Publish Data from Two Laboratory Studies on COVID-19 Vaccine-induced Antibodies Ability to Neutralize SARS-CoV-2 Omicron Variant—Jan. 24, 2022.
Pfizer and BioNTech Receive Positive CHMP Opinion for Omicron BA.1-Adapted Bivalent COVID-19 Vaccine Booster in European Union—Sep. 1, 2022.
Pfizer and BioNTech Receive Positive CHMP Opinion for Omicron BA.4/BA.5-Adapted Bivalent COVID-19 Vaccine Booster for Children 5 Through 11 Years of Age in European Union—Nov. 10, 2022.
Pfizer and BioNTech Receive Positive CHMP Opinion for Omicron BA.4/BA.5-Adapted Bivalent COVID-19 Vaccine Booster in European Union—Sep. 12, 2022.
Pfizer and BioNTech Receive U.S. FDA Emergency Use Authorization for Omicron BA.4/BA.5-Adapted Bivalent COVID-19 Vaccine Booster in Children 5 Through 11 Years of Age—Oct. 12, 2022.
Pfizer and BioNTech Receive U.S. FDA Emergency Use Authorization for Omicron BA.4/BA.5-Adapted Bivalent COVID-19 Vaccine in Children Under 5 Years—Dec. 8, 2022.
Pfizer and BioNTech Report New Data on Omicron BA.4/BA.5-Adapted Bivalent Booster Demonstrating Improved Immune Response Against Emerging Omicron Sublineages—Nov. 18, 2022.
Pfizer and BioNTech Submit Application to U.S. FDA for Emergency Use Authorization of Omicron BA.4/BA.5-Adapted Bivalent COVID-19 Vaccine—Aug. 22, 2022.
Pfizer and BioNTech Submit Application to U.S. FDA for Emergency Use Authorization of Omicron BA.4/BA.5-Adapted Bivalent COVID-19 Vaccine in Children Under 5 Years—Dec. 8, 2022.
Pfizer and BioNTech Submit Application to U.S. FDA for Emergency Use Authorization of Omicron BA.4/BA.5-Adapted Bivalent Vaccine Booster in Children 5 Through 11 Years of Age—Sep. 26, 2022.
Pfizer and BioNTech Submit for U.S. Emergency Use Authorization of an Additional Booster Dose of their COVID-19 Vaccine for Older Adults—Mar. 15, 2022.
Pfizer and BioNTech's Omicron BA.4/BA.5-Adapted Bivalent COVID-19 Vaccine Booster Receives Health Canada Authorization for Individuals 12 Years of Age and Older—Oct. 7, 2022.
Pfizer-BioNTech COVID-19 Vaccine Demonstrates Strong Immune Response, High Efficacy and Favorable Safety in Children 6 Months to Under 5 Years of Age Following Third Dose—May 23, 2022.
Polack, F. P. et al., Safety and Efficacy of the BNT162b2 mRNA Covid-19 Vaccine, N. Engl. J. Med., 383(27):2603-2615 (2020).
Program leaflet of the "1st International mRNA Health Conference".
Qiao, H. et al., Specific single or double proline substitutions in the "spring-loaded" coiled-coil region of the influenza hemagglutinin impair or abolish membrane fusion activity, The Journal of Cell Biology, 141(6):1335-1347 (1998).
Quandt, J. et al., Omicron BA. 1 breakthrough infection drives cross-variant neutralization and memory B cell formation against conserved epitopes. Science Immunology (2022): eabq2427.
Quandt, J. et al., Omicron breakthrough infection drives cross-variant neutralization and memory B cell formation. bioRxiv (2022).

(56) References Cited

OTHER PUBLICATIONS

Quinlan, B. D. et al., The SARS-COV-2 receptor-binding domain elicits a potent neutralizing response without antibody-dependent enhancement, bioRxiv, 24 pages (2020).
Rabaan, A. A. et al., SARS-CoV-2, SARS-CoV, and MERS-CoV: a comparative overview, Le Infezioni in Medicina, 2:174-184 (2020).
Ralph, R. et al., 2019-nCoV (Wuhan virus), a novel Coronavirus: human-to-human transmission, travel-related cases, and vaccine readiness, J Infect Dev Ctries., 14(1):3-17 (2020).
Ramanathan, A. et al., mRNA capping: biological functions and applications, Nucleic Acids Research, 44(16) 7511-752:7511-7526 (2016).
Rambaut, A. et al., A dynamic nomenclature proposal for SARS-CoV-2 lineages to assist genomic epidemiology, Nat Microbiol., 5(11):1403-1407 (2020).
Rambaut, A. et al., Preliminary genomic characterisation of an emergent SARS-CoV-2 lineage in the UK defined by a novel set of spike mutations—SARS-CoV-2 coronavirus / nCoV—2019 Genomic Epidemiology-Virological, retrieved from Internet: https://virological.org/t/preliminary-genomic-characterisation-of-an-emergent-sars-cov-2-lineage-in-the-uk-defined-by-a-novel-set-of-spike-mutations/563, 9 pages (May 7, 2021).
Rauch, S. et al., mRNA-based SARS-CoV-2 vaccine candidate CVnCoV induces high levels of virus-neutralising antibodies and mediates protection in rodents, NPJ, 57:1-9 (2021).
Rauch, S. et al., New Vaccine Technologies to Combat Outbreak Situations, Frontiers in Immunology, 9(1963):1-24 (2018).
Reichmuth, A. et al., mRNA vaccine delivery using lipid nanoparticles, Ther. Deliv., 7(5):319-334 (2016).
Rohou, A. and Grigorieff, N., CTFFIND4: Fast and accurate defocus estimation from electron micrographs, J Struct Biol., 192(2):216-21 (2015).
Roth, N. et al., CV2COV, an enhanced mRNA based SARS-CoV-2 vaccine candidate supports higher protein expression and improved immunogenicity in rats, bioRxiv, 12 pages (2021).
Sahin, U. et al., BNT162b2 induces SARS-CoV-2-neutralising antibodies and T cells in humans. MedRxiv (2020).
Sahin, U. et al., BNT162b2 vaccine induces neutralizing antibodies and poly-specific T cells in humans. Nature 595.7868 (2021): 572-577.
Sahin, U. et al., Concurrent human antibody and TH1 type T-cell responses elicited by a COVID-19 RNA vaccine, medRXiv, 27 pages (2020).
Sahin, U. et al., COVID-19 vaccine BNT162b1 elicits human antibody and TH1 T cell responses, Nature, 586(7830):594-599 (2020).
Sahin, U. et al., mRNA-based therapeutics—developing a new class of drugs. Nat Rev Drug Discov., 13(10):759-80 (2014).
Sanders, R. W. et al., A next-generation cleaved, soluble HIV-1 Env Trimer, BG505 SOSIP.664 gp140, expresses multiple epitopes for broadly neutralizing but not non-neutralizing antibodies, PLOS Pathogens, 9(9):e1003618 (2013).
Scheaffer, S. et al., Bivalent SARS-CoV-2 mRNA vaccines increase breadth of neutralization and protect against the BA.5 Omicron variant, bioRxiv preprint, 39 pages (posted Sep. 13, 2022).
Schlake, T. et al., Developing mRNA-vaccine technologies, RNA Biol, 9(11):1319-30 (2012).
Selisko, B. et al., Biochemical characterization of the (nucleoside-2'O)-methyltransferase activity of dengue virus protein NS5 using purified capped RNA oligonucleotides (7Me)GpppAC(n) and GpppAC(n), Journal of General Virology, 91(Pt1):112-121 (2010).
Sellers, R. et al., Scientific and Regulatory Policy Committee Points to Consider *: Approaches to the Conduct and Interpretation of Vaccine Safety Studies for Clinical and Anatomic Pathologists, Toxicol Pathol., 48(2):257-276 (2020).
Seq Id No. 7 alignments with Seq Id 84 and 86 in U.S. Appl. No. 10/953,089 with Jan. 27, 2020 earliest priority.
Sequence Alignment for Seq Id No. 7, 3 pages (2022).
Sequence Alignment for Seq Id No. 9, 6 pages (2022).
Sesterhenn, F. et al., Structure-based immunogen design—leading the way to the new age of precision vaccines, Current Opinion in Structural Biology, 51:163-169 (2018).
Shang, J. et al., Structural basis of receptor recognition by SARS-CoV-2, Nature, 581(7807):221-224 (2020).
Shi, P. et al., Neutralization of SARS-CoV-2 variants B. 1.617. 1 and B. 1.525 by BNT162b2-elicited sera. (2021).
Singh, D. et al., Responses to acute infection with SARS-CoV-2 in the lungs of rhesus macaques, baboons and marmosets, Nat Microbiol., 6(1):73-86 (2021).
Singh, D. et al., SARS-CoV-2 infection leads to acute infection with dynamic cellular and inflammatory flux in the lung that varies across nonhuman primate species, bioRxiv (2020).
Sinopeg Data Sheet, 10 pages (2022).
Song, E. et al., Divergent and self-reactive immune responses in the CNS of COVID-19 patients with neurological symptoms, Cell Repo. Med., 2(100288):24 pages (2021).
Song, W. et al., Cryo-EM structure of the SARS coronavirus spike glycoprotein in complex with its host cell receptor ACE2, PLOS Pathogens, 1-19 (2018).
Song, Z. et al., From SARS to MERS, Thrusting Coronaviruses into the Spotlight, Viruses, 11(1):59, 28 pages (2019).
Stadler, K. et al., SARS Beginning to Understand a New Virus, Nature Reviews, 1:209-218 (2003).
Stertz, S. et al., The intracellular sites of early replication and budding of SARS-coronavirus, Virology, 361:304-315 (2007).
Tang, X. et al., On the origin and continuing evolution of SARS-CoV-2, National Science Review, 7:1012-1023 (2020).
Tegally, H. et al., Continued Emergence and Evolution of Omicron in South Africa: New BA.4 and BA.5 Lineages, medRxiv, (May 2, 2022), XP093032398, DOI: 10.1101/2022.05.01.22274406 Retrieved from the internet: URL: https://www.medrxiv.org/content/10.1101/2022.05.01.22274406v1.full.pdf [retrieved on Mar. 16, 2023) the whole document.
Tegunov, D. and Cramer, P., Real-time cryo-electron microscopy data preprocessing with Warp, Nat Methods, 16(11):1146-1152 (2019).
Thanh, Le, T. et al., The COVID-19 vaccine development landscape, Nat Rev Drug Discov., 19(5):305-306 (2020).
Tian, J. et al., SARS-CoV-2 spike glycoprotein vaccine candidate NVX-CoV2373 immunogenicity in baboons and protection in mice, Nat Commun, 12(1):372 (2021).
Tseng, C. et al., Immunization with SARS coronavirus vaccines leads to pulmonary immunopathology on challenge with the SARS virus, PLoS One, 7(4):e35421, 13 pages (2012).
Turner, J. S. et al., SARS-CoV-2 mRNA vaccines induce persistent human germinal centre responses, Nat., 25 pages (2021).
UK Health Security Agency: “SARS-CoV-2 Variants of concern and variants under investigation in England: Technical Briefing 29”, (Nov. 26, 2021), XP093032319, Retrieved from the internet: URL: https://assets.publishing.service.gov.uk/government/uploads/attachment_data/file/1036501/technical_briefing_29_published_26_november_2021.pdf [retrieved on Mar. 16, 2023] p. 18.
Van Doremalen, N. et al., ChAdOx1 nCoV-19 vaccine prevents SARS-CoV-2 pneumonia in rhesus macaques, Nature, 586(7830):578-582 (2020).
Viner, R. et al., Kawasaki-like disease: emerging complication during the COVID-19 pandemic, Lancet, 395(10239):1741-1743 (2020).
Vogel, A. B. et al., A prefusion SARS-CoV-2 spike RNA vaccine is highly immunogenic and prevents lung infection in non-human primates, posted on bioRxiv (Sep. 2020), 38 pages.
Vogel, A. B. et al., BNT162b vaccines are immunogenic and protect non-human primates against SARS-CoV-2, posted on bioRxiv (Dec. 2020), 71 pages.
Vogel, A. B. et al., BNT162b vaccines protect rhesus macaques from SARS-CoV-2 (with supplementary materials), Nature, 44 pages (2021).
Vogel, A.B. et al., BNT162b vaccines protect rhesus macaques from SARS-CoV-2, Nature, 592:283-289 (Feb. 2021).
Vojdani, A. et al., Reaction of Human Monoclonal Antibodies to SARS-CoV-2 Proteins With Tissue Antigens: Implications for Autoimmune Diseases, Front. Immun., 11(617089):1-16 (2021).

(56) References Cited

OTHER PUBLICATIONS

Walls, A. et al., Elicitation of Potent Neutralizing Antibody Responses by Designed Protein Nanoparticle Vaccines for SARS-CoV-2, Cell, 183(5):1367-1382 (2020).
Walsh, E. E. et al., Safety and Immunogenicity of Two RNA-Based Covid-19 Vaccine Candidates, N. Engl. J. Med., 383:2439-2450 (2020).
Wang, F. et al., An Evidence Based Perspective on mRN A-SARS-Co V -2 Vaccine Development, Med Sci Monit, 26:e924701-e924700-8 (2020).
Wang, L. et al., Evaluation of candidate vaccine approaches for MERS-CoV, Nature Communications, 6(7712):1-11 (2015).
Wang, N. et al., Structural Definition of a Neutralization-sensitive Epitope on the MERS-CoV SI-NTD, Cell Rep, 28(13):3395-3405 (2019).
Wang, Z. et al., mRNA vaccine-elicited antibodies to SARS-CoV-2 and circulating variants, Nature, 592(7855):616-622 (2021).
WHO Drug Information 2021, vol. 35, 2 [full issue], WHO Drug Information 35(2):270-605 (2021).
Winkler, E. S. et al., SARS-CoV-2 infection of human ACE2-transgenic mice causes severe lung inflammation and impaired function, Nat. Immun., 21:1327-1335 (2020).
World Health Organization—WHO guidelines on nonclinical evaluation of vaccines, Annex 1 in World Health Organization, WHO technical report series, No. 927, Geneva, Switzerland; World Health Organization; 31-63 (2005).
World Health Organization, Annex 2, Guidelines on nonclinical evaluation of vaccine adjuvants and adjuvanted vaccines, In WHO technical report series No. 987, Geneva, Switzerland; World Health Organization; 59-100 (2014).
Wrapp D. et al., Prefusion 2019-nCoV spike glycoprotein with a single receptor-binding domain up, 78 pages, (Jan. 16, 2021), deposited on Feb. 10, 2020, Retrieved from the Internet: URL:https://www.rcsb.org/structure/6vsb [retrieved on May 21, 2021] the whole document.
Wrapp, D. et al., Cryo-EM structure of the 2019-nCoV spike in the prefusion conformation, Science, 367(6483):1260-1263 (2020).
Wrapp, D. et al., Cryo-EM structure of the 2019-nCoV spike in the prefusion conformation, Supplementary Materials, Science, 19 pages (2020).
Wrapp, D. et al., Prefusion 2019-nCoV spike glycoprotein with a single receptor-binding domain up, PDB: database, 4 pages (2020).
Written Opinion for PCT/EP2021/059947, 9 pages (mailed Aug. 5, 2021).
Written Opinion for PCT/EP2021/060004, 14 pages (Sep. 8, 2021).
Written Opinion for PCT/EP2021/060508, 11 pages (mailed Aug. 5, 2021).
Written Opinion for PCT/EP2022/060417, 10 pages (Aug. 4, 2022).
Written Opinion for PCT/EP2022/083740, 15 pages (Jun. 2, 2023).
Wu, F. et al., A new coronavirus associated with human respiratory disease in China, Nature, 579(7798):265-269 (2020).
Wu, J. et al., Nowcasting and forecasting the potential domestic and international spread of the 2019-nCoV outbreak originating in Wuhan, China: a modelling study, Lancet, 395(10225):689-697 (2020).
Wu, K. et al., mRNA-1273 vaccine induces neutralizing antibodies against spike mutants from global SARS-CoV-2 variants, posted on bioRxiv (Jan. 2021), 20 pages.
Wu, K. et al., Variant SARS-CoV-2 mRNA vaccines confer broad neutralization as primary or booster series in mice, posted on bioRxiv (Apr. 2021), 28 pages.
Wu, Y. et al., A noncompeting pair of human neutralizing antibodies block COVID-19 virus binding to its receptor ACE2, Science, 368(6496):1274-1278 (2020).
Xia, H. et al., Neutralization and durability of 2 or 3 doses of the BNT162b2 vaccine against Omicron SARS-CoV-2. Cell Host & Microbe 30.4 (2022): 485-488.
Xia, H. et al., Neutralization of Omicron SARS-CoV-2 by 2 or 3 doses of BNT162b2 vaccine. bioRxiv (2022).
Xia, X., Detailed Dissection and Critical Evaluation of the Pfizer/BioNTech and Moderna mRNA Vaccines, Vaccines, 9(734):1-19 (2021).
Xie, X. et al., Neutralization of SARS-CoV-2 spike 69/70 deletion, E484K and N501Y variants by BNT162b2 vaccine-elicited sera, Nat. Med., 6 pages (2021).
Xu, J. et al., Antibodies and vaccines against Middle East respiratory syndrome coronavirus, Emerging Microbes and Infections, 8:841-856 (2019).
Yan, R. et al., Structural basis for the recognition of the SARS-CoV-2 by full-length human ACE2, Sci. Mag., 10 pages (2020).
Yang, D. et al., Attenuated Interferon and Proinflammatory Response in SARS-CoV-2-Infected Human Dendritic Cells Is Associated With Viral Antagonism of STAT1 Phosphorylation, J Infect Dis., 222(5):734-745 (2020).
Yang, X. et al., Highly Stable Timers Formed by Human Immunodeficiency Virus Type 1 Envelope Glycoproteins Fused with the Trimeric Motif of T4 Bacteriophage Fibritin, Journal of Virology, 76(9):4634-4642 (2002).
Yi, C. et al., Key residues of the receptor binding motif in the spike protein of SARS-CoV-2 that interact with ACE2 and neutralizing antibodies, Cell Mol Immunol., 17(6):621-630 (2020).
Yong, C. et al., Recent Advances in the Vaccine Development Against Middle East Respiratory Syndrome-Coronavirus, Front Microbiol., 10:1781 (2019).
Yu, F. et al., Measures for diagnosing and treating infections by a novel coronavirus responsible for a pneumonia outbreak originating in Wuhan, China, Microbes Infect., 22(2):74-79 (2020).
Yu, J. et al., DNA vaccine protection against SARS-CoV-2 in rhesus macaques, Sci. Mag., 11 pages (2020).
Yuan, M. et al., A highly conserved cryptic epitope in the receptor binding domains of SARS-CoV-2 and SARS-CoV, Science, 368(6491):630-633 (2020).
Zakhartchouk, A. et al., Immunogenicity of a receptor-binding domain of SARS coronavirus spike protein in mice: implications for a subunit vaccine, Vaccine, 25(1):136-43 (2007).
Zeng, C. et al., Leveraging mRNAs sequences to express SARS-CoV-2 antigens in vivo, bioRxiv, 16 pages (2020), Retrieved from the Internet: URL:https://www.biorxiv.org/content/10.1101/2020.04.01.019877vl.full.pdf.
Zeng, C. et al., Leveraging mRNAs sequences to express SARS-CoV-2 antigens in vivo, Supplementary Information, bioRxiv, 13 pages (2020).
Zhang, J. et al., Progress and Prospects on Vaccine Developement against SARS-CoV-2, Vaccines, 8(153):1-12 (2020).
Zhang, N. et al., A Thermostable mRNA Vaccine against COVID-19, Cell, 182(5):1271-1283 (2020).
Zhang, Y. et al., Wuhan seafood market pneumonia virus isolate Wuhan-Hu-1, complete genome, Database EMBL, Database Accession No. MN908947 (Jan. 15, 2020).
Zhao, L. et al., Nanoparticle vaccines, Vaccine, 32(3):327-37 (2014).
Zhou, M. et al., Coronavirus disease 2019 (COVID-19): a clinical update, Front Med., 14(2):126-135 (2020).
Zhou, P. et al., A pneumonia outbreak associated with a new coronavirus of probable bat origin, Nature, vol. 579, online publication: Feb. 3, 2020.
Zhou, Y. et al., Enhancement versus neutralization by SARS-CoV-2 antibodies from a convalescent donor associates with distinct epitopes on the RBD, Cell Repo., 34(108699):1-23 (2021).
Zhu, F. et al., Safety, tolerability, and immunogenicity of a recombinant adenovirus type-5 vectored COVID-19 vaccine: a dose-escalation, open-label, non-randomised, first-in-human trial, Lancet, 395(10240):1845-1854 (2020).
Zhu, N. et al., A Novel Coronavirus from Patients with Pneumonia in China, 2019, N Engl J Med., 382(8):727-733 (2020).
Zhu, X. et al., Receptor-binding domain as a target for developing SARS vaccines, J Thorac Dis., 5 Suppl 2(Suppl 2):S142-8 (2013).
Zimmer, Katarina, A Guide to Emerging SARS-CoV-2 Variants, retrieved from the Internet: https://www.the-scientist.com/news-opinion/a-guide-to-emerging-sars-cov-2-variants-68387, 7 pages (May 31, 2021).

(56) References Cited

OTHER PUBLICATIONS

Zivanov, J. et al., New tools for automated high-resolution cryo-EM structure determination in RELION-3, Elife, 7:e42166, 22 pages (2018).
Zost, S. et al., Rapid isolation and profiling of a diverse panel of human monoclonal antibodies targeting the SARS-CoV-2 spike protein, Nat Med., 26(9):1422-1427 (2020).
Zou, J. et al., Improved Neutralization of Omicron BA. 4/5, BA. 4.6, BA. 2.75. 2, BQ. 1.1, and XBB. 1 with Bivalent BA. 4/5 Vaccine. BioRxiv (2022).
Zou, L. et al., SARS-CoV-2 Viral Load in Upper Respiratory Specimens of Infected Patients, N Engl J Med., 382(12):1177-1179 (2020).
U.S. Appl. No. 17/988,742, filed Nov. 16, 2022.
International Search Report for PCT/EP2023/067350, 11 pages (Dec. 1, 2023).
Li, Q. et al., Antigenicity comparison of SARS-CoV-2 Omicron sublineages with other variants contained multiple mutations in RBD, MedComm, 3:e130, 12 pages (2022).
Morais, P. et al., The Critical Contribution of Pseudouridine to mRNA COVID-19 Vaccines. Front Cell Dev Biol. 9:789427 (9 pages) (2021).
Written Opinion for PCT/EP2023/067350, 26 pages (Dec. 1, 2023).
Becerra-Flores, M. and Cardozo, T., SARS-CoV-2 viral spike G614 mutation exhibits higher case fatality rate, Int. J. Clin. Pract., 74e:e13525, 4 pages (2020).
Bhattacharyya, C. et al., Global Spread of SARS-CoV-2 Subtype with Spike Protein Mutation D614G is Shaped by Human Genomic Variations that Regulate Expression of TMPRSS2 and MX1 Genes, bioRxiv, 30 pages (2020).
Brito, L. et al., A cationic nanoemulsion for the delivery of next-generation RNA vaccines, Mol Ther., 22(12):2118-2129 (2014).
Defrancesco, Laura, The 'anti-hype' vaccine, Nat Biotechnol., 35(3):193-197 (2017).
Du, L. et al., The spike protein of SARS-CoV—a target for vaccine and therapeutic development, Nat Rev Microbiol., 7(3):226-36 (2009).
International Search Report for PCT/IB2024/051778, 6 pages (Jun. 7, 2024).
Jaume, M. et al., Anti-severe acute respiratory syndrome coronavirus spike antibodies trigger infection of human immune cells via a pH- and cysteine protease-independent Fc?R pathway, J Virol., 85(20):10582-97 (2011).
Kallen, K. et al., A novel, disruptive vaccination technology: self-adjuvanted RNActive(®) vaccines, Hum Vaccin Immunother., 9(10):2263-76 (2013).
Korber, B. et al., Spike mutation pipeline reveals the emergence of a more transmissible form of SARS-CoV-2, BioRxiv, 33 pages 2020).
Koyama, T. et al., Emergence of Drift Variants That May Affect COVID-19 Vaccine Development and Antibody Treatment, Pathogens, 9:324, 7 pages (2020).
Li, Zhe, et al., Memory B cells dominate the early antibody-secreting cell response to SARS-CoV-2 mRNA vaccination in naive individuals independently of their antibody affinity, bioRxiv (2023): 2023-12.
Parums, Dinah V., Editorial: The XBB.1.5 ('Kraken') Subvariant of Omicron SARS-CoV-2 and its Rapid Global Spread, Med Sci Monit., 1;29:e939580, 3 pages (2023).
Petsch, B. et al., Protective efficacy of in vitro synthesized, specific mRNA vaccines against influenza A virus infection, Nat Biotechnol., 30(12):1210-6 (2012).
Phan, Tung, Genetic diversity and evolution of SARS-CoV-2, Infection, Genetics and Evolution, 81:104260, 4 pages (2020).
Song, S. et al., Sequential immunization with SARS-CoV-2 Rbd vaccine induces potent and broad neutralization against variants in mice, Virology Journal, 19(2): 5 pages (2022).
Stefanelli, P. et al., Whole genome and phylogenetic analysis of two SARS-CoV-2 strains isolated in Italy in Jan. and Feb. 2020: additional clues on multiple introductions and further circulation in Europe, Euro Surveill., 25(13): 5 pages (2020).
Vennema, H. et al., Early death after feline infectious peritonitis virus challenge due to recombinant vaccinia virus immunization, J Virol., 64(3):1407-9 (1990).
Written Opinion for PCT/IB2024/051778, 10 pages (Jun. 7, 2024).
Yang, Z. et al., A DNA vaccine induces SARS coronavirus neutralization and protective immunity in mice, Nature, 428(6982):561-4 (2004).
Zang, J. et al., Neutralizing Potency of Prototype and Omicron RBD mRNA Vaccines Against Omicron Variant, Frontiers in Immunology, 13(Article 908478): 10 pages (2022).
Zehender, G. et al., Genomic characterization and phylogenetic analysis of SARS-CoV-2 in Italy, Journal of Medical Virology, 92:1637-1640 (2020).
Zhang, Z. et al., A Heterologous V-01 or Variant-Matched Bivalent V-01D-351 Booster following Primary Series of Inactivated Vaccine Enhances the Neutralizing Capacity against SARS-CoV-2 Delta and Omicron Strains, Journal of Clinical Medicine, 11:4164, 10 pages (2022).

* cited by examiner

Figure 10

| HLA-Allele | No of MHC-I epitopes* | No. of epitopes affected by mutations in different VOCs | | | | |
|---|---|---|---|---|---|---|
| | | Alpha | Beta | Gamma | Delta | Omicron |
| A*01:01 | 1 | 0 | 0 | 0 | 0 | 0 |
| A*02:01 | 2 | 0 | 0 | 0 | 0 | 0 |
| **A*03:01** | **2** | 0 | 0 | 0 | 0 | **1** |
| A*11:01 | 2 | 0 | 0 | 0 | 0 | 0 |
| **A*24:02** | **5** | 0 | 0 | 0 | **1** | **1** |
| A*26:01 | 2 | 0 | 0 | 0 | 0 | 0 |
| **A*29:02** | 1 | 0 | 0 | 0 | 0 | **1** |
| **A*68:01** | 4 | 0 | 0 | 0 | 0 | **1** |
| B*07:02 | 1 | 0 | 0 | 0 | 0 | 0 |
| **B*15:01** | **3** | **1** | **2** | **1** | **1** | **2** |
| B*35:01 | 6 | 0 | 0 | 0 | 0 | 0 |
| C*03:03 | 1 | 0 | 0 | 0 | 0 | 0 |
| C*04:01 | 1 | 0 | 0 | 0 | 0 | 0 |
| **Total affected<br>Total unaffected** | **31** | **1 (4%)<br>30 (96%)** | **2 (7%)<br>26 (93%)** | **1 (4%)<br>30 (96%)** | **2 (7%)<br>26 (93%)** | **6 (22%)<br>25 (78%)** |

| Booster vaccine | Trial ID | Omicron neutralization by variant-specific booster compared to 3rd dose BNT162b2 [%] |
|---|---|---|
| BNT162b2 | NCT04380701 | 100% |
| Alpha Variant | NCT05004181 | 466% |
| Beta Variant | NCT04949490 | Pending |
| Delta Variant | NCT05004181 | 165% |
| Alpha/Delta Variant Mix | NCT05004181 | 155% |

SARS-CoV-2 mRNA Variant Vaccine Technical Adaptation Process

A
VSV/SARS-CoV-2-S pVNT
pVN50 titer [serum dilution$^{-1}$]
$10^4$
$10^3$
$10^2$
$10^1$
LOD
P<0.005
P<0.0001
P<0.0001
P<0.0001
160 90 26 71 7 14 6
Wuhan
Alpha
Beta
Delta
Omicron BA.1
Omicron BA.2
SARS-CoV-1
BNT162b2 (n=20)
P<0.01
P<0.0001
398 714 222 370 160 211 20
BNT162b3 (n=19)
P<0.01
740 1245 740 571 880 523 49
BNT162b2 + Omi (n=8)
P<0.005
1182 2206 1182 1103 1029 835 72
BNT162b3 + Omi (n=10)

A

C

D

E

WT and Beta neut from 30 open label subjects that received the beta booster twice, 1 month apart WT and Beta neut from 30 open label subjects that received the beta booster twice, 1 month apart

<u>D7PD4 GMR vs. b2-30 µg</u>

*Subjects with evidence of existing (POS PCR) or preexisting (POS N-Ig-Binding) SARS-CoV-2 infection excluded*

| | b2-60 µg | OMI 30 µg | OMI 60 µg | Bivalent 30 µg | Bivalent 60 µg |
|---|---|---|---|---|---|
| WT | 1.38 | 0.77 | 1.06 | 1.36 | 1.11 |
| Delta | 1.55 | 0.81 | 1.14 | 1.67 | 1.29 |
| Omicron | 1.50 | 1.26 | 2.00 | 1.78 | 1.95 |

*All subjects included*

| | b2-60 µg | OMI 30 µg | OMI 60 µg | Bivalent 30 µg | Bivalent 60 µg |
|---|---|---|---|---|---|
| WT | 1.05 | 0.68 | 0.95 | 1.39 | 0.90 |
| Delta | 1.21 | 0.78 | 1.05 | 1.77 | 1.07 |
| Omicron | 1.09 | 1.15 | 1.83 | 2.03 | 1.54 |

C

| Geometric mean ratio | Alpha | Beta | Delta | Omi BA.1 | Omi BA.2 | Omi BA.4/5 | SARS-CoV-1 |
|---|---|---|---|---|---|---|---|
| BNT162b2[2] (n=20) | 0.56 | 0.16 | 0.46 | 0.04 | 0.09 | 0.05 | 0.04 |
| BNT162b2[3] (n=19) | 1.79 | 0.56 | 0.93 | 0.40 | 0.53 | 0.19 | 0.05 |
| BNT162b2[2] + Omi (n=8) | 1.68 | 1.00 | 0.77 | 1.19 | 0.71 | 0.18 | 0.07 |
| BNT162b2[3] + Omi (n=8) | 1.87 | 1.00 | 0.93 | 0.87 | 0.71 | 0.17 | 0.06 |

Figure 28

RBD

*Wuhan WT strain*

VOD ALPHA

VOC DELTA

VOC OMICRON BA.1

VOC OMICRON BA.4/5

```
301 CTLKSFTVEKGIYQTSNFRVQPTESIVRFPNITNLCPFGEVFNATRFASV
301 CTLKSFTVEKGIYQTSNFRVQPTESIVRFPNITNLCPFGEVFNATRFASV
301 CTLKSFTVEKGIYQTSNFRVQPTESIVRFPNITNLCPFGEVFNATRFASV
301 CTLKSFTVEKGIYQTSNFRVQPTESIVRFPNITNLCPFDEVFNATRFASV
301 CTLKSFTVEKGIYQTSNFRVQPTESIVRFPNITNLCPFDEVFNATRFASV

351 YAWNRKRISNCVADYSVLYNSASFSTFKCYGVSPTKLNDLCFTNVYADSF
351 YAWNRKRISNCVADYSVLYNSASFSTFKCYGVSPTKLNDLCFTNVYADSF
351 YAWNRKRISNCVADYSVLYNSASFSTFKCYGVSPTKLNDLCFTNVYADSF
351 YAWNRKRISNCVADYSVLYNLAPFFTFKCYGVSPTKLNDLCFTNVYADSF
351 YAWNRKRISNCVADYSVLYNFAPFFAFKCYGVSPTKLNDLCFTNVYADSF

401 VIRGDEVRQIAPGQTGKIADYNYKLPDDFTGCVIAWNSNNLDSKVGGNYN
401 VIRGDEVRQIAPGQTGKIADYNYKLPDDFTGCVIAWNSNNLDSKVGGNYN
401 VIRGDEVRQIAPGQTGKIADYNYKLPDDFTGCVIAWNSNNLDSKVGGNYN
401 VIRGDEVRQIAPGQTGNIADYNYKLPDDFTGCVIAWNSNKLDSKVSGNYN
401 VIRGNEVSQIAPGQTGNIADYNYKLPDDFTGCVIAWNSNKLDSKVGGNYN

451 YLYRLFRKSNLKPFERDISTEIYQAGSTPCNGVEGFNCYFPLQSYGFQPT
451 YLYRLFRKSNLKPFERDISTEIYQAGSTPCNGVEGFNCYFPLQSYGFQPT
451 YRYRLFRKSNLKPFERDISTEIYQAGSKPCNGVEGFNCYFPLQSYGFQPT
451 YLYRLFRKSNLKPFERDISTEIYQAGNKPCNGVAGVNCYFPLRSYSFRPT
451 YRYRLFRKSNLKPFERDISTEIYQAGNKPCNGVAGVNCYFPLQSYGFRPT

501 NGVGYQPYRVVVLSFELLHAPATVCGPKKSTNLVKNKCVNFNFNGLTGTG
501 YGVGYQPYRVVVLSFELLHAPATVCGPKKSTNLVKNKCVNFNFNGLTGTG
501 NGVGYQPYRVVVLSFELLHAPATVCGPKKSTNLVKNKCVNFNFNGLTGTG
501 YGVGHQPYRVVVLSFELLHAPATVCGPKKSTNLVKNKCVNFNFNGLKGTG
501 YGVGHQPYRVVVLSFELLHAPATVCGPKKSTNLVKNKCVNFNFNGLTGTG
```

C

| Geometric mean ratio | Alpha | Beta | Delta | Omi BA.1 | Omi BA.2 | Omi BA.2.12.1 | Omi BA.4/5 | SARS-CoV-1 |
|---|---|---|---|---|---|---|---|---|
| -●- BNT162b2³ (n=19) | 1.79 | 0.56 | 0.93 | 0.40 | 0.53 | 0.28 | 0.19 | 0.05 |
| -▲- all Vax + Omi BA.1 (n=15) | 1.82 | 0.91 | 0.91 | 0.76 | 0.66 | 0.44 | 0.20 | 0.06 |
| -□- all Vax + Omi BA.2 (n=17) | 1.57 | 0.64 | 0.85 | 0.46 | 0.85 | 0.59 | 0.42 | 0.01 |

Translation:
Ausgewählte proben = selected samples
Blutabnahme = blood draw
Immunisierung = immunization
Mitteis = by means of
Pra = pre
Serologische untersuchung = serological investigation
Spezifischen = specific
Versuchsende = trial end
Wochen = weeks

| Geometric mean ratio | Omi BA.1 | Omi BA.2 | Omi BA.2.12.1 | Omi BA.4/BA.5 |
|---|---|---|---|---|
| BNT162b2 | 0.32 | 0.11 | 0.10 | 0.07 |
| Omi BA.1 | 0.09 | 0.11 | 0.04 | 0.04 |
| Omi BA.4/5 | 0.18 | 0.15 | 0.05 | 0.05 |
| b2 + Omi BA.1 | 0.11 | 0.13 | 0.08 | 0.07 |
| b2 + Omi BA.4/5 | 0.13 | 0.13 | 0.09 | 0.06 |
| Omi BA.1 + BA.4/5 | 0.10 | 0.10 | 0.05 | 0.04 |
| b2 + Omi BA.1 + BA.4/5 | 0.16 | 0.12 | 0.07 | 0.06 |

| Geometric mean ratio | Omi BA.1 | Omi BA.2 | Omi BA.2.12.1 | Omi BA.4/BA.5 |
|---|---|---|---|---|
| BNT162b2 | 0.21 | 0.09 | 0.10 | 0.08 |
| Omi BA.1 | 0.84 | 0.27 | 0.15 | 0.11 |
| Omi BA.4/5 | 0.42 | 0.59 | 0.50 | 0.50 |
| b2 + Omi BA.1 | 0.23 | 0.25 | 0.19 | 0.19 |
| b2 + Omi BA.4/5 | 0.35 | 0.46 | 0.55 | 0.35 |
| Omi BA.1 + BA.4/5 | 0.42 | 0.42 | 0.30 | 0.23 |
| b2 + Omi BA.1 + BA.4/5 | 0.39 | 0.27 | 0.32 | 0.25 |

B

| Geometric mean ratio | Alpha | Beta | Delta | Omi BA.1 | Omi BA.2 | Omi BA.2.12.1 | Omi BA.4/5 |
|---|---|---|---|---|---|---|---|
| BNT162b2[3] (n=18) | 1.78 | 0.54 | 0.89 | 0.38 | 0.51 | 0.26 | 0.17 |
| mRNA-Vax[3] + BA.1 (n=14) | 1.72 | 0.86 | 0.91 | 0.78 | 0.64 | 0.43 | 0.18 |
| mRNA-Vax[3] + BA.2 (n=13) | 1.53 | 0.59 | 0.90 | 0.45 | 0.77 | 0.52 | 0.38 |

A

B

| Geometric mean ratio | Alpha | Beta | Delta | Omi BA.1 | Omi BA.2 | Omi BA.4 |
|---|---|---|---|---|---|---|
| -●- BNT162b2³ (n=18) | 0.62 | 0.30 | 0.50 | 0.16 | 0.17 | 0.07 |
| -▲- mRNA-Vax3 + BA.1 (n=14) | 1.45 | 1.08 | 1.52 | 0.84 | 1.03 | 0.20 |
| -□- mRNA-Vax3 + BA.2 (n=13) | 2.83 | 1.00 | 1.49 | 0.65 | 1.03 | 0.39 |

B

C

| Geometric mean ratio | Alpha | Beta | Delta | Omi BA.1 | Omi BA.2 | Omi BA.4 | Omi BA.4/5 |
|---|---|---|---|---|---|---|---|
| BNT162b2[3] (n=18) | 1.78 | 0.54 | 0.89 | 0.38 | 0.51 | 0.26 | 0.17 |
| BNT162b2[3] + BA.1 (n=10) | 1.87 | 1.00 | 0.93 | 0.87 | 0.71 | 0.51 | 0.17 |
| BNT162b2[3] + BA.2 (n=8) | 1.41 | 0.55 | 0.84 | 0.32 | 0.71 | 0.44 | 0.42 |

F

| Geometric mean ratio | Alpha | Beta | Delta | Omi BA.1 | Omi BA.2 | Omi BA.4 |
|---|---|---|---|---|---|---|
| BNT162b2$^{3}$ (n=18) | 0.62 | 0.30 | 0.50 | 0.16 | 0.17 | 0.07 |
| BNT162b2$^{3}$ + BA.1 (n=10) | 1.80 | 1.32 | 1.74 | 1.07 | 1.19 | 0.26 |
| BNT162b2$^{3}$ + BA.2 (n=8) | 3.22 | 0.88 | 1.54 | 0.55 | 1.09 | 0.44 |

| Geometric mean ratio | Omi BA.1 | Omi BA.2 | Omi BA.2.12.1 | Omi BA.4/BA.5 |
|---|---|---|---|---|
| BNT162b2[3] (n=18) | 0.38 | 0.51 | 0.26 | 0.17 |
| mRNA-Vax3 + BA.1 (n=14) | 0.78 | 0.64 | 0.43 | 0.18 |
| mRNA-Vax3 + BA.2 (n=19) | 0.48 | 0.77 | 0.53 | 0.37 |
| mRNA-Vax3 + BA.4/BA.5 (n=17) | 0.46 | 0.57 | 0.57 | 0.48 |

| Geometric mean ratio | Omi BA.1 | Omi BA.2 | Omi BA.4 |
|---|---|---|---|
| BNT162b2$^3$ (n=18) | 0.16 | 0.17 | 0.07 |
| mRNA-Vax$^3$ + BA.1 (n=14) | 0.84 | 1.03 | 0.20 |
| mRNA-Vax$^3$ + BA.2 (n=13) | 0.65 | 1.03 | 0.39 |
| mRNA-Vax$^3$ + BA.4/BA.5 (n=6) | 0.40 | 0.94 | 0.71 |

d21D3

C

VSV/SARS-CoV-2-S pVNT

| Geometric mean ratio | Omi BA.1 | Omi BA.2 | Omi BA.2.12.1 | Omi BA.4/BA.5 |
|---|---|---|---|---|
| BNT162b2 | 0.23 | 0.11 | 0.10 | 0.09 |
| Omi BA.1 | 0.77 | 0.39 | 0.16 | 0.07 |
| Omi BA.4/5 | 0.65 | 0.77 | 0.77 | 0.65 |
| BNT162b2 + Omi BA.1 | 0.35 | 0.25 | 0.23 | 0.16 |
| BNT162b2 + Omi BA.4/5 | 0.27 | 0.46 | 0.32 | 0.27 |

F

| Geometric mean ratio | Omi BA.1 | Omi BA.2 | Omi BA.4 |
|---|---|---|---|
| BNT162b2 | 0.17 | 0.07 | 0.02 |
| Omi BA.1 | 0.07 | 0.03 | <0.01 |
| Omi BA.4/5 | 0.68 | 0.50 | 0.39 |
| BNT162b2 + Omi BA.1 | 0.16 | 0.19 | 0.05 |
| BNT162b2 + Omi BA.4/5 | 0.31 | 0.26 | 0.13 |

| Geometric mean ratio | Omi BA.1 | Omi BA.2 | Omi BA.2.12.1 | Omi BA.4/BA.5 |
|---|---|---|---|---|
| pre-BNT162b2 | 0.32 | 0.11 | 0.10 | 0.07 |
| pre-Omi BA.1 | 0.09 | 0.11 | 0.04 | 0.04 |
| pre-Omi BA.4/5 | 0.18 | 0.15 | 0.05 | 0.05 |
| pre-BNT162b2 + Omi BA.1 | 0.11 | 0.13 | 0.08 | 0.07 |
| pre-BNT162b2 + Omi BA.4/5 | 0.13 | 0.13 | 0.09 | 0.06 |

C

| Geometric mean ratio | Omi BA.1 | Omi BA.2 | Omi BA.2.12.1 | Omi BA.4/BA.5 |
|---|---|---|---|---|
| BNT162b2 | 0.21 | 0.09 | 0.10 | 0.08 |
| Omi BA.1 | 0.84 | 0.27 | 0.15 | 0.11 |
| Omi BA.4/5 | 0.42 | 0.59 | 0.50 | 0.50 |
| b2 + Omi BA.1 | 0.23 | 0.25 | 0.19 | 0.19 |
| b2 + Omi BA.4/5 | 0.35 | 0.46 | 0.55 | 0.35 |

C VSV/SARS-CoV-2-S pVNT

| Geometric mean ratio | Omi BA.1 | Omi BA.2 | Omi BA.2.12.1 | Omi BA.4/BA.5 |
| --- | --- | --- | --- | --- |
| BNT162b2 | 0.27 | 0.10 | 0.10 | 0.10 |
| Omi BA.1 | 1.09 | 0.59 | 0.25 | 0.13 |
| Omi BA.4/5 | 0.65 | 0.55 | 0.46 | 0.42 |
| BNT162b2 + Omi BA.1 | 0.23 | 0.18 | 0.13 | 0.10 |
| BNT162b2 + Omi BA.4/5 | 0.42 | 0.50 | 0.35 | 0.46 |

E

| Geometric mean ratio | Omi BA.1 | Omi BA.2 | Omi BA.4 |
|---|---|---|---|
| BNT162b2 | 0.09 | 0.04 | 0.03 |
| Omi BA.1 | 0.71 | 0.25 | 0.04 |
| Omi BA.4/5 | 0.50 | 0.50 | 0.32 |
| BNT162b2 + Omi BA.1 | 0.13 | 0.10 | 0.03 |
| BNT162b2 + Omi BA.4/5 | 0.23 | 0.16 | 0.08 |

A

B

| Geometric mean ratio | Omi BA.4/5 | Omi BA.4.6/BF.7 | Omi BQ1.1 | Omi BA.2.75 | Omi BA.2.75.2 | Omi XBB |
|---|---|---|---|---|---|---|
| BNT162b2³ (n=18) | 0.17 | 0.12 | 0.04 | 0.20 | 0.05 | 0.02 |
| BNT162b2⁴ (n=15) | 0.19 | 0.09 | 0.03 | 0.22 | 0.04 | 0.02 |
| mRNA-Vax³ + BA.1 (n=14) | 0.18 | 0.19 | 0.03 | 0.37 | 0.06 | 0.02 |
| mRNA-Vax³ + BA.2 (n=19) | 0.37 | 0.23 | 0.10 | 0.30 | 0.05 | 0.02 |
| mRNA-Vax³ + BA.4/5 (n=17) | 0.48 | 0.41 | 0.14 | 0.27 | 0.05 | 0.03 |

Figure 65

| | | NTD | | | | | | | | | | | | | | | | | | | | |
|---|---|---|---|---|---|---|---|---|---|---|---|---|---|---|---|---|---|---|---|---|---|---|
| | | T19I | Δ24-26 | A27S | A67V | Δ69-70 | V83A | T95I | G142D | Δ143-145 | Δ144 | H146Q | K147E | W152R | F157L | Q183E | I210V | Δ211 | L212I | V213 | ins214EPE | G257S |
| BA.1 | | | | | ■ | ■ | | ■ | ■ | ■ | | | | | | | | ■ | ■ | | ■ | |
| BA.2 | | ■ | ■ | ■ | | | | | ■ | | | | | | | | | | | G | | |
| BA.2.12.1 | | ■ | ■ | ■ | | | | | ■ | | | | | | | | | | | G | | |
| BA.4/BA.5 | | ■ | ■ | ■ | | ■ | | | ■ | | | | | | | | | | | G | | |
| BA.4.6/BF.7 | | ■ | ■ | ■ | | ■ | | | ■ | | | | | | | | | | | G | | |
| BQ.1 | | ■ | ■ | ■ | | ■ | | | ■ | | | | | | | | | | | G | | |
| BQ.1.1 | | ■ | ■ | ■ | | ■ | | | ■ | | | | | | | | | | | G | | |
| BA.2.75 | | ■ | ■ | ■ | | | | | ■ | | | | ■ | ■ | ■ | | ■ | | | G | | ■ |
| BA.2.75.2 | | ■ | ■ | ■ | | | | | ■ | | | | ■ | ■ | ■ | | ■ | | | G | | ■ |
| XBB | | ■ | ■ | ■ | | | ■ | | ■ | | ■ | ■ | | | | ■ | | | | E | | |

| | RBD | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|
| | G339 | R346T | L368I | S371 | S373P | S375F | T376A | D405N | R408S | K417N | N440K | K444T | V445P | G446S | L452 | N460K | S477N | T478K | E484A | F486 | F490S | Q493R | G496S | Q498R | N501Y | Y505H | T547K | D614G | H655Y | N679K | P681H | S704L | N764K | D796Y | N856K | Q954H | N969K | L981F | D1199N |
| BA.1 | D | | | L | ■ | ■ | | | | ■ | ■ | | | ■ | | | ■ | ■ | ■ | | | ■ | ■ | ■ | ■ | ■ | ■ | ■ | ■ | ■ | ■ | | ■ | ■ | ■ | ■ | ■ | ■ | |
| BA.2 | D | | | F | ■ | ■ | ■ | ■ | ■ | ■ | ■ | | | | | | ■ | ■ | ■ | | | ■ | | ■ | ■ | ■ | | ■ | ■ | ■ | ■ | | ■ | ■ | | ■ | ■ | | |
| BA.2.12.1 | D | | | F | ■ | ■ | ■ | ■ | ■ | ■ | ■ | | | | Q | | ■ | ■ | ■ | | | ■ | | ■ | ■ | ■ | | ■ | ■ | ■ | ■ | ■ | ■ | ■ | | ■ | ■ | | |
| BA.4/BA.5 | D | | | F | ■ | ■ | ■ | ■ | ■ | ■ | ■ | | | | R | | ■ | ■ | ■ | V | | | | ■ | ■ | ■ | | ■ | ■ | ■ | ■ | | ■ | ■ | | ■ | ■ | | |
| BA.4.6/BF.7 | D | ■ | | F | ■ | ■ | ■ | ■ | ■ | ■ | ■ | | | | R | | ■ | ■ | ■ | V | | | | ■ | ■ | ■ | | ■ | ■ | ■ | ■ | | ■ | ■ | | ■ | ■ | | |
| BQ.1 | D | | | F | ■ | ■ | ■ | ■ | ■ | ■ | ■ | ■ | | | R | ■ | ■ | ■ | ■ | V | | | | ■ | ■ | ■ | | ■ | ■ | ■ | ■ | | ■ | ■ | | ■ | ■ | | |
| BQ.1.1 | D | ■ | | F | ■ | ■ | ■ | ■ | ■ | ■ | ■ | ■ | | | R | ■ | ■ | ■ | ■ | V | | | | ■ | ■ | ■ | | ■ | ■ | ■ | ■ | | ■ | ■ | | ■ | ■ | | |
| BA.2.75 | H | | | F | ■ | ■ | ■ | ■ | ■ | ■ | ■ | | | ■ | | ■ | ■ | ■ | ■ | | | | | ■ | ■ | ■ | | ■ | ■ | ■ | ■ | | ■ | ■ | | ■ | ■ | | |
| BA.2.75.2 | H | ■ | | F | ■ | ■ | ■ | ■ | ■ | ■ | ■ | | | ■ | | ■ | ■ | ■ | ■ | S | | | | ■ | ■ | ■ | | ■ | ■ | ■ | ■ | | ■ | ■ | | ■ | ■ | | ■ |
| XBB | H | ■ | ■ | F | ■ | ■ | ■ | ■ | ■ | ■ | ■ | | ■ | ■ | | ■ | ■ | ■ | ■ | S | ■ | | | ■ | ■ | ■ | | ■ | ■ | ■ | ■ | | ■ | ■ | | ■ | ■ | | |

A

SEQUENCE LISTING

```
Sequence total quantity: 157
SEQ ID NO: 1           moltype = AA  length = 1273
FEATURE                Location/Qualifiers
REGION                 1..1273
                       note = S protein
source                 1..1273
                       mol_type = protein
                       organism = synthetic construct
SEQUENCE: 1
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDKVEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 2           moltype = RNA  length = 3819
FEATURE                Location/Qualifiers
misc_feature           1..3819
                       note = Coding Sequence
source                 1..3819
                       mol_type = other RNA
                       organism = synthetic construct
SEQUENCE: 2
atgtttgtgt ttcttgtgct gctgcctctt gtgtcttctc agtgtgtgaa tttgacaaca  60
agaacacagc tgccaccagc ttatacaaat tcttttacca gaggagtgta ttatcctgat  120
aaagtgttta gatcttctgt gctgcacagc acacaggacc tgtttctgcc atttttttagc  180
aatgtgacat ggtttcatgc aattcatgtg tctggaacaa atggaacaaa aagatttgat  240
aatcctgtgc tgccttttaa tgatggagtg tattttgctt caacagaaaa gtcaaatatt  300
attagaggat ggatttttgg aacaacactg gattctaaaa cacagtctct gctgattgtg  360
aataatgcaa caaatgtggt gattaaagtg tgtgaatttc agttttgtaa tgatcctttt  420
ctgggagtgt attatcacaa aaataataaa tcttggatgg aatctgaatt tagagtgtat  480
tcctctgcaa ataattgtac atttgaatat gtgtctcagc ctttctgat ggatctggaa  540
ggaaaacagg gcaattttaa aaatctgaga gaatttgtgt ttaaaaatat tgatggatat  600
```

-continued

```
tttaaaattt attctaaaca cacaccaatt aatttagtga gagatctgcc tcagggattt  660
tctgctctgg aacctctggt ggatctgcca attggcatta atattacaag atttcagaca  720
ctgctggctc tgcacagatc ttatctgaca cctggagatt cttcttctgg atggacagcc  780
ggagctgcag cttattatgt gggctatctg cagccaagaa catttctgct gaaatataat  840
gaaaatggaa caattacaga tgctgtggat tgtgctctgg atcctctgtc tgaaacaaaa  900
tgtacattaa aatcttttac agtggaaaaa ggcatttatc agacatctaa ttttagagtg  960
cagccaacag aatctattgt gagatttcca aatattacaa atctgtgtcc atttggagaa  1020
gtgtttaatg caacaagatt tgcatctgtg tatgcatgga atagaaaaag aatttctaat  1080
tgtgtggctg attattctgt gctgtataat agtgcttctt tttccacatt taaatgttat  1140
ggagtgtctc caacaaaatt aaatgattta tgttttacaa atgtgtatgc tgattctttt  1200
gtgatcagag gtgatgaagt gagacagatt gccccggac agacaggaaa aattgctgat  1260
tacaattaca aactgcctga tgattttaca ggatgtgtga ttgcttggaa ttctaataat  1320
ttagattcta aagtgggagg aaattacaat tatctgtaca gactgtttag aaaatcaaat  1380
ctgaaacctt ttgaaagaga tatttcaaca gaaatttatc aggctggatc aacaccttgt  1440
aatggagtgg aaggatttaa ttgttatttt ccattacaga gctatggatt tcagccaacc  1500
aatggtgtgg gatatcagcc atatagagtg gtggtgctgt cttttgaact gctgcatgca  1560
cctgcaacag tgtgtggacc taaaaaatct acaaatttag tgaaaaataa atgtgtgaat  1620
tttaatttta atggattaac aggaacagga gtgctgacag aatctaataa aaaatttctg  1680
ccttttcagc agtttggcag agatattgca gataccacag atgcagtgag agatcctcag  1740
acattagaaa ttctggatat tacaccttgt tcttttgggg gtgtgtctgt gattacacct  1800
ggaacaaata catctaatca ggtggctgtg ctgtatcagg atgtgaattg tacagaagtg  1860
ccagtggcaa ttcatgcaga tcagctgaca ccaacatgga gagtgtattc tacaggatct  1920
aatgtgtttc agacaagagc aggatgtctg attggagcag aacatgtgaa taattcttat  1980
gaatgtgata ttccaattgg agcaggcatt tgtgcatctt atcagacaca gacaaattcc  2040
ccaaggagag caagatctgt ggcatctcag tctattattg catacaccat gtctctggga  2100
gcagaaaatt ctgtggcata ttctaataat tctattgcta ttccaacaaa ttttaccatt  2160
tctgtgacaa cagaaatttt acctgtgtct atgacaaaaa catctgtgga ttgtaccatg  2220
tacatttgtg gagattctac agaatgttct aatctgctgc tgcagtatgg atctttttgt  2280
acacagctga atagagcttt aacaggaatt gctgtggaac aggataaaaa tacacaggaa  2340
gtgtttgctc aggtgaaaca gatttacaaa acaccaccaa ttaaagattt tggaggattt  2400
aattttagcc agattctgcc tgatccttct aaaccttcta aaagatcttt tattgaagat  2460
ctgctgttta ataaagtgac actggcagat gcaggattta ttaaacagta tggagattgc  2520
ctgggtgata ttgctgcaag agatctgatt tgtgctcaga aatttaatgg actgacagtg  2580
ctgcctcctc tgctgacaga tgaaatgatt gctcagtaca catctgcttt actggctgga  2640
acaattacaa gcggatggac atttggagct ggagctgctc tgcagattcc ttttgcaatg  2700
cagatggctt acagatttaa tggaattgga gtgacacaga atgtgttata tgaaaatcag  2760
aaactgattg caaatcagtt taattctgca attggcaaaa ttcaggattc tctgtcttct  2820
acagcttctg ctctgggaaa actgcaggat gtggtgaatc agaatgcaca ggcactgaat  2880
actctggtga aacagctgtc tagcaatttt ggggcaattt cttctgtgct gaatgatatt  2940
ctgtctagac tggataaagt ggaagctgaa gtgcagattg atagactgat cacaggaaga  3000
ctgcagtctc tgcagactta tgtgacacag cagctgatta gagctgctga aattagagct  3060
tctgctaatc tggctgctac aaaaatgtct gaatgtgtgc tgggacagtc aaaaagagtg  3120
gatttttgtg gaaaaggata tcatctgatg tcttttccac agtctgctcc acatggagtg  3180
gtgtttttac atgtgacata tgtgccagca caggaaaaga attttaccac agcaccagca  3240
atttgtcatg atggaaaagc acattttcca agagaaggag tgtttgtgtc taatggaaca  3300
cattggtttg tgacacagag aaatttttat gaacctcaga ttattacaac agataataca  3360
tttgtgtcag gaaattgtga tgtggtgatt ggaattgtga ataatacagt gtatgatcca  3420
ctgcagccag aactggattc ttttaaagaa gaactggata aatattttaa aaatcacaca  3480
tctcctgatg tggatttagg agatatttct ggaatcaatg catctgtggt gaatattcag  3540
aaagaaattg atagactgaa tgaagtggcc aaaaatctga atgaatctct gattgatctg  3600
caggaacttg gaaaatatga acagtacatt aaatggcctt ggtacatttg gcttggattt  3660
attgcaggat taattgcaat tgtgatggtg acaattatgt tatgttgtat gacatcatgt  3720
tgttcttgtt taaaaggatg ttgttcttgt ggaagctgtt gtaaatttga tgaagatgat  3780
tctgaacctg tgttaaaagg agtgaaattg cattacaca                        3819
```

```
SEQ ID NO: 3            moltype = AA  length = 218
FEATURE                 Location/Qualifiers
REGION                  1..218
                        note = S Protein RBD Fusion
source                  1..218
                        mol_type = protein
                        organism = synthetic construct
SEQUENCE: 3
MFVFLVLLPL VSSQCVVRFP NITNLCPFGE VFNATRFASV YAWNRKRISN CVADYSVLYN  60
SASFSTFKCY GVSPTKLNDL CFTNVYADSF VIRGDEVRQI APGQTGKIAD YNYKLPDDFT  120
GCVIAWNSNN LDSKVGGNYN YLYRLFRKSN LKPFERDIST EIYQAGSTPC NGVEGFNCYF  180
PLQSYGFQPT NGVGYQPYRV VVLSFELLHA PATVCGPK                        218
```

```
SEQ ID NO: 4            moltype = RNA  length = 654
FEATURE                 Location/Qualifiers
misc_feature            1..654
                        note = Coding Sequence
source                  1..654
                        mol_type = other RNA
                        organism = synthetic construct
SEQUENCE: 4
atgtttgtgt ttcttgtgct gctgcctctt gtgtcttctc agtgtgtggt gagatttcca  60
aatattacaa atctgtgtcc atttggagaa gtgtttaatg caacaagatt tgcatctgtg  120
tatgcatgga atagaaaaag aatttctaat tgtgtggctg attattctgt gctgtataat  180
```

```
agtgcttctt tttccacatt taaatgttat ggagtgtctc caacaaaatt aaatgattta  240
tgttttacaa atgtgtatgc tgattctttt gtgatcagag gtgatgaagt gagacagatt  300
gcccccggac agacaggaaa aattgctgat tacaattaca aactgcctga tgattttaca  360
ggatgtgtga ttgcttggaa ttctaataat ttagattcta aagtgggagg aaattacaat  420
tatctgtaca gactgtttag aaaatcaaat ctgaaacctt ttgaaagaga tatttcaaca  480
gaaatttatc aggctggatc aacaccttgt aatggagtgg aaggatttaa ttgttatttt  540
ccattacaga gctatggatt tcagccaacc aatggtgtgg gatatcagcc atatagagtg  600
gtggtgctgt cttttgaact gctgcatgca cctgcaacag tgtgtggacc taaa        654

SEQ ID NO: 5            moltype = AA  length = 266
FEATURE                 Location/Qualifiers
REGION                  1..266
                        note = S Protein RBD Fusion
source                  1..266
                        mol_type = protein
                        organism = synthetic construct
SEQUENCE: 5
MFVFLVLLPL VSSQCVVRFP NITNLCPFGE VFNATRFASV YAWNRKRISN CVADYSVLYN  60
SASFSTFKCY GVSPTKLNDL CFTNVYADSF VIRGDEVRQI APGQTGKIAD YNYKLPDDFT  120
GCVIAWNSNN LDSKVGGNYN YLYRLFRKSN LKPFERDIST EIYQAGSTPC NGVEGFNCYF  180
PLQSYGFQPT NGVGYQPYRV VVLSFELLHA PATVCGPKGS PGSGSGSGYI PEAPRDGQAY  240
VRKDGEWVLL STFLGRSLEV LFQGPG                                        266

SEQ ID NO: 6            moltype = RNA  length = 798
FEATURE                 Location/Qualifiers
misc_feature            1..798
                        note = Coding Sequence
source                  1..798
                        mol_type = other RNA
                        organism = synthetic construct
SEQUENCE: 6
atgtttgtgt ttcttgtgct gctgcctctt gtgtcttctc agtgtgtggt gagatttcca  60
aatattacaa atctgtgtcc atttggagaa gtgtttaatg caacaagatt tgcatctgtg  120
tatgcatgga atagaaaaag aatttctaat tgtgtggctg attattctgt gctgtataat  180
agtgcttctt tttccacatt taaatgttat ggagtgtctc caacaaaatt aaatgattta  240
tgttttacaa atgtgtatgc tgattctttt gtgatcagag gtgatgaagt gagacagatt  300
gcccccggac agacaggaaa aattgctgat tacaattaca aactgcctga tgattttaca  360
ggatgtgtga ttgcttggaa ttctaataat ttagattcta aagtgggagg aaattacaat  420
tatctgtaca gactgtttag aaaatcaaat ctgaaacctt ttgaaagaga tatttcaaca  480
gaaatttatc aggctggatc aacaccttgt aatggagtgg aaggatttaa ttgttatttt  540
ccattacaga gctatggatt tcagccaacc aatggtgtgg gatatcagcc atatagagtg  600
gtggtgctgt cttttgaact gctgcatgca cctgcaacag tgtgtggacc taaaggctcc  660
cccggctccg gctccggatc tggttatatt cctgaagctc caagagatgg gcaagcttac  720
gttcgtaaag atggcgaatg ggtattactt tctacctttt taggccggtc cctggaggtg  780
ctgttccagg gccccggc                                                798

SEQ ID NO: 7            moltype = AA  length = 1273
FEATURE                 Location/Qualifiers
REGION                  1..1273
                        note = S Protein Variant
source                  1..1273
                        mol_type = protein
                        organism = synthetic construct
SEQUENCE: 7
MFVFLVLLPL VSSQCVNLTT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
LLALHRSYLT PGDSSSGWTA GAAAYYVGYL QPRTFLLKYN ENGTITDAVD CALDPLSETK  300
CTLKSFTVEK GIYQTSNFRV QPTESIVRFP NITNLCPFGE VFNATRFASV YAWNRKRISN  360
CVADYSVLYN SASFSTFKCY GVSPTKLNDL CFTNVYADSF VIRGDEVRQI APGQTGKIAD  420
YNYKLPDDFT GCVIAWNSNN LDSKVGGNYN YLYRLFRKSN LKPFERDIST EIYQAGSTPC  480
NGVEGFNCYF PLQSYGFQPT NGVGYQPYRV VVLSFELLHA PATVCGPKKS TNLVKNKCVN  540
FNFNGLTGTG VLTESNKKFL PFQQFGRDIA DTTDAVRDPQ TLEILDITPC SFGGVSVITP  600
GTNTSNQVAV LYQDVNCTEV PVAIHADQLT PTWRVYSTGS NVFQTRAGCL IGAEHVNNSY  660
ECDIPIGAGI CASYQTQTNS PRRARSVASQ SIIAYTMSLG AENSVAYSNN SIAIPTNFTI  720
SVTTEILPVS MTKTSVDCTM YICGDSTECS NLLLQYGSFC TQLNRALTGI AVEQDKNTQE  780
VFAQVKQIYK TPPIKDFGGF NFSQILPDPS KPSKRSFIED LLFNKVTLAD AGFIKQYGDC  840
LGDIAARDLI CAQKFNGLTV LPPLLTDEMI AQYTSALLAG TITSGWTFGA GAALQIPFAM  900
QMAYRFNGIG VTQNVLYENQ KLIANQFNSA IGKIQDSLSS TASALGKLQD VVNQNAQALN  960
TLVKQLSSNF GAISSVLNDI LSRLDPPEAE VQIDRLITGR LQSLQTYVTQ QLIRAAEIRA  1020
SANLAATKMS ECVLGQSKRV DFCGKGYHLM SFPQSAPHGV VFLHVTYVPA QEKNFTTAPA  1080
ICHDGKAHFP REGVFVSNGT HWFVTQRNFY EPQIITTDNT FVSGNCDVVI GIVNNTVYDP  1140
LQPELDSFKE ELDKYFKNHT SPDVDLGDIS GINASVVNIQ KEIDRLNEVA KNLNESLIDL  1200
QELGKYEQYI KWPWYIWLGF IAGLIAIVMV TIMLCCMTSC CSCLKGCCSC GSCCKFDEDD  1260
SEPVLKGVKL HYT                                                     1273

SEQ ID NO: 8            moltype = RNA  length = 3819
FEATURE                 Location/Qualifiers
```

```
misc_feature           1..3819
                       note = Coding Sequence
source                 1..3819
                       mol_type = other RNA
                       organism = synthetic construct
SEQUENCE: 8
atgtttgtgt ttcttgtgct gctgcctctt gtgtcttctc agtgtgtgaa tttgacaaca  60
agaacacagc tgccaccagc ttatacaaat tcttttacca gaggagtgta ttatcctgat  120
aaagtgttta gatcttctgt gctgcacagc acacaggacc tgtttctgcc atttttttagc  180
aatgtgacat ggtttcatgc aattcatgtg tctggaacaa atggaacaaa aagatttgat  240
aatcctgtgc tgccttttaa tgatggagtg tattttgctt caacagaaaa gtcaaatatt  300
attagaggat ggatttttgg aacaacactg gattctaaaa cacagtctct gctgattgtg  360
aataatgcaa caaatgtggt gattaaagtg tgtgaatttc agttttgtaa tgatcctttt  420
ctgggagtgt attatcacaa aaataataaa tcttggatgg aatctgaatt tagagtgtat  480
tcctctgcaa ataattgtac atttgaatat gtgtctcagc cttttctgat ggatctggaa  540
ggaaaacagg gcaattttaa aaatctgaga gaatttgtgt ttaaaaatat tgatggatat  600
tttaaaattt attctaaaca cacaccaatt aatttagtga gagatctgcc tcagggattt  660
tctgctctgg aacctctggt ggatctgcca attggcatta atattacaag atttcagaca  720
ctgctggctc tgcacagatc ttatctgaca cctggagatt cttcttctgg atggacagcc  780
ggagctgcag cttattatgt gggctatctg cagccaagaa catttctgct gaaatataat  840
gaaaatggaa caattacaga tgctgtggat tgtgctctgg atcctctgtc tgaaacaaaa  900
tgtacattaa aatcttttac agtggaaaaa ggcatttatc agacatctaa ttttagagtg  960
cagccaacag aatctattgt gagatttcca aatattacaa atctgtgtcc atttggagaa  1020
gtgtttaatg caacaagatt tgcatctgtg tatgcatgga atagaaaaag aatttctaat  1080
tgtgtggctg attattctgt gctgtataat agtgcttctt tttccacatt taaatgttat  1140
ggagtgtctc caacaaaatt aaatgattta tgttttacaa atgtgtatgc tgattctttt  1200
gtgatcagag gtgatgaagt gagacagatt gcccccggac agacaggaaa aattgctgat  1260
tacaattaca aactgcctga tgattttaca ggatgtgtga ttgcttggaa ttctaataat  1320
ttagattcta aagtgggagg aaattacaat tatctgtaca gactgtttag aaaatcaaat  1380
ctgaaacctt ttgaaagaga tatttcaaca gaaatttatc aggctggatc aacaccttgt  1440
aatggagtgg aaggatttaa ttgttatttt ccattacaga gctatggatt tcagccaacc  1500
aatggtgtgg gatatcagcc atatagagtg gtggtgctgt cttttgaact gctgcatgca  1560
cctgcaacag tgtgtggacc taaaaaatct acaaatttag tgaaaaataa atgtgtgaat  1620
tttaatttta atggattaac aggaacagga gtgctgacag aatctaataa aaaatttctg  1680
ccttttcagc agtttggcag agatattgca gataccacag atgcagtgag agatcctcag  1740
acattagaaa ttctggatat tacaccttgt tcttttgggg gtgtgtctgt gattacacct  1800
ggaacaaata catctaatca ggtggctgtg ctgtatcagg atgtgaattg tacagaagtg  1860
ccagtggcaa ttcatgcaga tcagctgaca ccaacatgga gagtgtattc tacaggatct  1920
aatgtgtttc agacaagagc aggatgtctg attggagcag aacatgtgaa taattcttat  1980
gaatgtgata ttccaattgg agcaggcatt tgtgcatctt atcagacaca gacaaattcc  2040
ccaaggagag caagatctgt ggcatctcag tctattattg catacaccat gtctctggga  2100
gcagaaaatt ctgtggcata ttctaataat tctattgcta ttccaacaaa ttttaccatt  2160
tctgtgacaa cagaaatttt acctgtgtct atgacaaaaa catctgtgga ttgtaccatg  2220
tacatttgtg gagattctac agaatgttct aatctgctgc tgcagtatgg atctttttgt  2280
acacagctga atagagcttt aacaggaatt gctgtggaac aggataaaaa tacacaggaa  2340
gtgtttgctc aggtgaaaca gatttacaaa acaccaccaa ttaaagattt tggaggattt  2400
aattttagcc agattctgcc tgatccttct aaaccttcta aaagatcttt tattgaagat  2460
ctgctgttta ataaagtgac actggcagat gcaggattta ttaaacagta tggagattgc  2520
ctgggtgata ttgctgcaag agatctgatt tgtgctcaga aatttaatgg actgacagtg  2580
ctgcctcctc tgctgacaga tgaaatgatt gctcagtaca catctgcttt actggctgga  2640
acaattacaa gcggatggac atttggagct ggagctgctc tgcagattcc ttttgcaatg  2700
cagatggctt acagatttaa tggaattgga gtgacacaga atgtgttata tgaaaatcag  2760
aaactgattg caaatcagtt taattctgca attggcaaaa ttcaggattc tctgtcttct  2820
acagcttctg ctctgggaaa actgcaggat gtggtgaatc agaatgcaca ggcactgaat  2880
actctggtga aacagctgtc tagcaatttt ggggcaattt cttctgtgct gaatgatatt  2940
ctgtctagac tggatcctcc tgaagctgaa gtgcagattg atagactgat cacaggaaga  3000
ctgcagtctc tgcagactta tgtgacacag cagctgatta gagctgctga aattagagct  3060
tctgctaatc tggctgctac aaaaatgtct gaatgtgtgc tgggacagtc aaaaagagtg  3120
gatttttgtg gaaaaggata tcatctgatg tcttttccac agtctgctcc acatggagtg  3180
gtgtttttac atgtgacata tgtgccagca caggaaaaga attttaccac agcaccagca  3240
atttgtcatg atggaaaagc acattttcca agagaaggag tgtttgtgtc taatggaaca  3300
cattggtttg tgacacagag aaatttttat gaacctcaga ttattacaac agataataca  3360
tttgtgtcag gaaattgtga tgtggtgatt ggaattgtga ataatacagt gtatgatcca  3420
ctgcagccag aactggattc ttttaaagaa gaactggata aatattttaa aaatcacaca  3480
tctcctgatg tggatttagg agatatttct ggaatcaatg catctgtggt gaatattcag  3540
aaagaaattg atagactgaa tgaagtggcc aaaaatctga atgaatctct gattgatctg  3600
caggaacttg gaaaatatga acagtacatt aaatggcctt ggtacatttg gcttggattt  3660
attgcaggat taattgcaat tgtgatggtg acaattatgt tatgttgtat gacatcatgt  3720
tgttcttgtt taaaaggatg ttgttcttgt ggaagctgtt gtaaatttga tgaagatgat  3780
tctgaacctg tgttaaaagg agtgaaattg cattacaca                        3819

SEQ ID NO: 9           moltype = RNA  length = 3819
FEATURE                Location/Qualifiers
misc_feature           1..3819
                       note = Coding Sequence
source                 1..3819
                       mol_type = other RNA
                       organism = synthetic construct
SEQUENCE: 9
```

```
atgttcgtgt tcctggtgct gctgcctctg gtgtccagcc agtgtgtgaa cctgaccacc  60
agaacacagc tgcctccagc ctacaccaac agctttacca gaggcgtgta ctaccccgac  120
aaggtgttca gatccagcgt gctgcactct acccaggacc tgttcctgcc tttcttcagc  180
aacgtgacct ggttccacgc catccacgtg tccggcacca atggcaccaa gagattcgac  240
aaccccgtgc tgcccttcaa cgacggggtg tactttgcca gcaccgagaa gtccaacatc  300
atcagaggct ggatcttcgg caccacactg gacagcaaga cccagagcct gctgatcgtg  360
aacaacgcca ccaacgtggt catcaaagtg tgcgagttcc agttctgcaa cgaccccttc  420
ctgggcgtct actaccacaa gaacaacaag agctggatgg aaagcgagtt ccgggtgtac  480
agcagcgcca acaactgcac cttcgagtac gtgtcccagc ctttcctgat ggacctggaa  540
ggcaagcagg gcaacttcaa gaacctgcgc gagttcgtgt ttaagaacat cgacggctac  600
ttcaagatct acagcaagca cacccctatc aacctcgtgc gggatctgcc tcagggcttc  660
tctgctctgg aaccccctggt ggatctgccc atcggcatca acatcacccg gtttcagaca  720
ctgctggccc tgcacagaag ctacctgaca cctggcgata gcagcagcgg atggacagct  780
ggtgccgccg cttactatgt gggctacctg cagcctagaa ccttcctgct gaagtacaac  840
gagaacggca ccatcaccga cgccgtggat tgtgctctgg atcctctgag cgagacaaag  900
tgcaccctga agtccttcac cgtggaaaag ggcatctacc agaccagcaa cttccgggtg  960
cagcccaccg aatccatcgt gcggttcccc aatatcacca atctgtgccc cttcggcgag  1020
gtgttcaatg ccaccagatt cgcctctgtg tacgcctgga accggaagcg gatcagcaat  1080
tgcgtggccg actactccgt gctgtacaac tccgccagct tcagcacctt caagtgctac  1140
ggcgtgtccc ctaccaagct gaacgacctg tgcttcacaa acgtgtacgc cgacagcttc  1200
gtgatccggg gagatgaagt gcggcagatt gcccctggac agacaggcaa gatcgccgac  1260
tacaactaca agctgcccga cgacttcacc ggctgtgtga ttgcctggaa cagcaacaac  1320
ctggactcca aagtcggcgg caactacaat tacctgtacc ggctgttccg gaagtccaat  1380
ctgaagccct tcgagcggga catctccacc gagatctatc aggccggcag cacccccttgt  1440
aacggcgtgg aaggcttcaa ctgctacttc ccactgcagt cctacggctt tcagcccaca  1500
aatggcgtgg gctatcagcc ctacagagtg gtggtgctga gcttcgaact gctgcatgcc  1560
cctgccacag tgtgcggccc taagaaaagc accaatctcg tgaagaacaa atgcgtgaac  1620
ttcaacttca acggcctgac cggcaccggc gtgctgacag agagcaacaa gaagttcctg  1680
ccattccagc agtttggccg ggatatcgcc gataccacag acgccgttag agatccccag  1740
acactggaaa tcctggacat caccccttgc agcttcggcg gagtgtctgt gatcacccct  1800
ggcaccaaca ccagcaatca ggtggcagtg ctgtaccagg acgtgaactg taccgaagtg  1860
cccgtggcca ttcacgccga tcagctgaca cctacatggc gggtgtactc caccggcagc  1920
aatgtgtttc agaccagagc cggctgtctg atcggagccg agcacgtgaa caatagctac  1980
gagtgcgaca tccccatcgg cgctggaatc tgcgccagct accagacaca gacaaacagc  2040
cctcggagag ccagaagcgt ggccagccag agcatcattg cctacacaat gtctctgggc  2100
gccgagaaca gcgtggccta ctccaacaac tctatcgcta tccccaccaa cttcaccatc  2160
agcgtgacca cagagatcct gcctgtgtcc atgaccaaga ccagcgtgga ctgcaccatg  2220
tacatctgcg gcgattccac cgagtgctcc aacctgctgc tgcagtacgg cagcttctgc  2280
acccagctga atagagccct gacagggatc gccgtggaac aggacaagaa cacccaagag  2340
gtgttcgccc aagtgaagca gatctacaag accccctccta tcaaggactt cggcggcttc  2400
aatttcagcc agattctgcc cgatcctagc aagcccagca agcggagctt catcgaggac  2460
ctgctgttca acaaagtgac actggccgac gccggcttca tcaagcagta tggcgattgt  2520
ctgggcgaca ttgccgccag ggatctgatt tgcgcccaga agtttaacgg actgacagtg  2580
ctgcctcctc tgctgaccga tgagatgatc gcccagtaca catctgccct gctggccggc  2640
acaatcacaa gcggctggac atttggagca ggcgccgctc tgcagatccc ctttgctatg  2700
cagatggcct accggttcaa cggcatcgga gtgacccaga atgtgctgta cgagaaccag  2760
aagctgatcg ccaaccagtt caacagcgcc atcggcaaga tccaggacag cctgagcagc  2820
acagcaagcg ccctgggaaa gctgcaggac gtggtcaacc agaatgccca ggcactgaac  2880
accctggtca agcagctgtc ctccaacttc ggcgccatca gctctgtgct gaacgatatc  2940
ctgagcagac tggaccctcc tgaggccgag gtgcagatcg acagactgat cacaggcaga  3000
ctgcagagcc tccagacata cgtgacccag cagctgatca gagccgccga gattagagcc  3060
tctgccaatc tggccgccac caagatgtct gagtgtgtgc tgggccagag caagagagtg  3120
gacttttgcg gcaagggcta ccacctgatg agcttccctc agtctgcccc tcacggcgtg  3180
gtgtttctgc acgtgacata tgtgcccgct caagagaaga atttcaccac cgctccagcc  3240
atctgccacg acggcaaagc ccactttcct agagaaggcg tgttcgtgtc caacggcacc  3300
cattggttcg tgacacagcg gaacttctac gagccccaga tcatcaccac cgacaacacc  3360
ttcgtgtctg gcaactgcga cgtcgtgatc ggcattgtga acaataccgt gtacgaccct  3420
ctgcagcccg agctggacag cttcaaagag gaactggaca agtactttaa gaaccacaca  3480
agccccgacg tggacctggg cgatatcagc ggaatcaatg ccagcgtcgt gaacatccag  3540
aaagagatcg accggctgaa cgaggtggcc aagaatctga acgagagcct gatcgacctg  3600
caagaactgg ggaagtacga gcagtacatc aagtggccct ggtacatctg gctgggcttt  3660
atcgccggac tgattgccat cgtgatggtc acaatcatgc tgtgttgcat gaccagctgc  3720
tgtagctgcc tgaagggctg ttgtagctgt ggcagctgct gcaagttcga cgaggacgat  3780
tctgagcccg tgctgaaggg cgtgaaactg cactacaca                        3819
```

```
SEQ ID NO: 10          moltype = AA  length = 41
FEATURE                Location/Qualifiers
REGION                 1..41
                       note = Foldon Sequence
source                 1..41
                       mol_type = protein
                       organism = synthetic construct
SEQUENCE: 10
GSGYIPEAPR DGQAYVRKDG EWVLLSTFLG RSLEVLFQGP G                     41

SEQ ID NO: 11          moltype = RNA  length = 123
FEATURE                Location/Qualifiers
misc_feature           1..123
                       note = Coding Sequence
```

```
source                  1..123
                        mol_type = other RNA
                        organism = synthetic construct
SEQUENCE: 11
ggatctggtt atattcctga agctccaaga gatgggcaag cttacgttcg taaagatggc  60
gaatgggtat tactttctac ctttttaggc cggtccctgg aggtgctgtt ccagggcccc  120
ggc                                                                123

SEQ ID NO: 12           moltype = RNA  length = 47
FEATURE                 Location/Qualifiers
misc_feature            1..47
                        note = 5'-UTR
source                  1..47
                        mol_type = other RNA
                        organism = synthetic construct
SEQUENCE: 12
aactagtatt cttctggtcc ccacagactc agagagaacc cgccacc               47

SEQ ID NO: 13           moltype = RNA  length = 278
FEATURE                 Location/Qualifiers
misc_feature            1..278
                        note = 3'-UTR
source                  1..278
                        mol_type = other RNA
                        organism = synthetic construct
SEQUENCE: 13
ctggtactgc atgcacgcaa tgctagctgc ccctttcccg tcctgggtac cccgagtctc  60
ccccgacctc gggtcccagg tatgctccca cctccacctg ccccactcac cacctctgct  120
agttccagac acctcccaag cacgcagcaa tgcagctcaa aacgcttagc ctagccacac  180
ccccacggga aacagcagtg attaaccttt agcaataaac gaaagtttaa ctaagctata  240
ctaaccccag ggttggtcaa tttcgtgcca gccacacc                          278

SEQ ID NO: 14           moltype = RNA  length = 110
FEATURE                 Location/Qualifiers
misc_feature            1..110
                        note = A30L70
source                  1..110
                        mol_type = other RNA
                        organism = synthetic construct
SEQUENCE: 14
aaaaaaaaaa aaaaaaaaaa aaaaaaaaaa gcatatgact aaaaaaaaaa aaaaaaaaaa  60
aaaaaaaaaa aaaaaaaaaa aaaaaaaaaa aaaaaaaaaa aaaaaaaaaa             110

SEQ ID NO: 15           moltype = RNA  length = 4282
FEATURE                 Location/Qualifiers
misc_feature            1..4282
                        note = RBL063.1
source                  1..4282
                        mol_type = other RNA
                        organism = synthetic construct
SEQUENCE: 15
gggcgaacta gtattcttct ggtccccaca gactcagaga gaacccgcca ccatgtttgt  60
gtttcttgtg ctgctgcctc ttgtgtcttc tcagtgtgtg aatttgacaa caagaacaca  120
gctgccacca gcttatacaa attcttttac cagaggagtg tattatcctg ataaagtgtt  180
tagatcttct gtgctgcaca gcacacagga cctgtttctg ccattttttta gcaatgtgac  240
atggtttcat gcaattcatg tgtctggaac aaatggaaca aaaagatttg ataatcctgt  300
gctgcctttt aatgatggag tgtattttgc ttcaacagaa aagtcaaata ttattagagg  360
atggattttt ggaacaacac tggattctaa aacacagtct ctgctgattg tgaataatgc  420
aacaaatgtg gtgattaaag tgtgtgaatt tcagttttgt aatgatcctt ttctgggagt  480
gtattatcac aaaaataata aatcttggat ggaatctgaa tttagagtgt attcctctgc  540
aaataattgt acatttgaat atgtgtctca gccttttctg atggatctgg aaggaaaaca  600
gggcaatttt aaaaatctga gagaatttgt gtttaaaaat attgatggat attttaaaat  660
ttattctaaa cacacaccaa ttaatttagt gagagatctg cctcagggat ttctgctct  720
ggaacctctg gtggatctgc caattggcat taatattaca agatttcaga cactgctggc  780
tctgcacaga tcttatctga cacctggaga ttcttcttct ggatggacag ccggagctgc  840
agcttattat gtgggctatc tgcagccaag aacatttctg ctgaaatata atgaaaatgg  900
aacaattaca gatgctgtgg attgtgctct ggatcctctg tctgaaacaa aatgtacatt  960
aaaatctttt acagtggaaa aaggcattta tcagacatct aattttagag tgcagccaac  1020
agaatctatt gtgagatttc caaatattac aaatctgtgt ccatttggag aagtgtttaa  1080
tgcaacaaga tttgcatctg tgtatgcatg gaatagaaaa agaatttcta attgtgtggc  1140
tgattattct gtgctgtata atagtgcttc tttttccaca tttaaatgtt atggagtgtc  1200
tccaacaaaa ttaaatgatt tatgttttac aaatgtgtat gctgattctt ttgtgatcag  1260
aggtgatgaa gtgagacaga ttgcccccgg acagacagga aaaattgctg attacaatta  1320
caaactgcct gatgatttta caggatgtgt gattgcttgg aattctaata atttagattc  1380
taaagtggga ggaaattaca attatctgta cagactgttt agaaaatcaa atctgaaacc  1440
ttttgaaaga gatatttcaa cagaaattta tcaggctgga tcaacacctt gtaatggagt  1500
ggaaggattt aattgttatt ttccattaca gagctatgga tttcagccaa ccaatggtgt  1560
gggatatcag ccatatagag tggtggtgct gtcttttgaa ctgctgcatg cacctgcaac  1620
agtgtgtgga cctaaaaaat ctacaaattt agtgaaaaat aaatgtgtga attttaattt  1680
```

```
taatggatta acaggaacag gagtgctgac agaatctaat aaaaaatttc tgccttttca  1740
gcagtttggc agagatattg cagataccac agatgcagtg agagatcctc agacattaga  1800
aattctggat attacacctt gttcttttgg gggtgtgtct gtgattacac ctggaacaaa  1860
tacatctaat caggtggctg tgctgtatca ggatgtgaat tgtacagaag tgccagtggc  1920
aattcatgca gatcagctga caccaacatg gagagtgtat tctacaggat ctaatgtgtt  1980
tcagacaaga gcaggatgtc tgattggagc agaacatgtg aataattctt atgaatgtga  2040
tattccaatt ggagcaggca tttgtgcatc ttatcagaca cagacaaatt ccccaaggag  2100
agcaagatct gtggcatctc agtctattat tgcatacacc atgtctctgg gagcagaaaa  2160
ttctgtggca tattctaata attctattgc tattccaaca aattttacca tttctgtgac  2220
aacagaaatt ttacctgtgt ctatgacaaa aacatctgtg gattgtacca tgtacatttg  2280
tggagattct acagaatgtt ctaatctgct gctgcagtat ggatcttttt gtacacagct  2340
gaatagagct ttaacaggaa ttgctgtgga acaggataaa aatacacagg aagtgtttgc  2400
tcaggtgaaa cagatttaca aaacaccacc aattaaagat tttggaggat ttaattttag  2460
ccagattctg cctgatcctt ctaaaccttc taaaagatct tttattgaag atctgctgtt  2520
taataaagtg acactggcag atgcaggatt tattaaacag tatggagatt gcctgggtga  2580
tattgctgca agagatctga tttgtgctca gaaatttaat ggactgacag tgctgcctcc  2640
tctgctgaca gatgaaatga ttgctcagta cacatctgct ttactggctg gaacaattac  2700
aagcggatgg acatttggag ctggagctgc tctgcagatt ccttttgcaa tgcagatggc  2760
ttacagattt aatggaattg gagtgacaca gaatgtgtta tatgaaaatc agaaactgat  2820
tgcaaatcag tttaattctg caattggcaa aattcaggat tctctgtctt ctacagcttc  2880
tgctctggga aaactgcagg atgtggtgaa tcagaatgca caggcactga atactctggt  2940
gaaacagctg tctagcaatt ttggggcaat ttcttctgtg ctgaatgata ttctgtctag  3000
actggatcct cctgaagctg aagtgcagat tgatagactg atcacaggaa gactgcagtc  3060
tctgcagact tatgtgacac agcagctgat tagagctgct gaaattagag cttctgctaa  3120
tctggctgct acaaaaatgt ctgaatgtgt gctgggacag tcaaaaagag tggatttttg  3180
tggaaaagga tatcatctga tgtcttttcc acagtctgct ccacatggag tggtgttttt  3240
acatgtgaca tatgtgccag cacaggaaaa gaattttacc acagcaccag caatttgtca  3300
tgatggaaaa gcacatttc caagagaagg agtgtttgtg tctaatggaa cacattggtt  3360
tgtgacacag agaaattttt atgaacctca gattattaca acagataata catttgtgtc  3420
aggaaattgt gatgtggtga ttggaattgt gaataataca gtgtatgatc cactgcagcc  3480
agaactggat tcttttaaag aagaactgga taaatatttt aaaaatcaca catctcctga  3540
tgtggattta ggagatattt ctggaatcaa tgcatctgtg gtgaatattc agaaagaaat  3600
tgatagactg aatgaagtgg ccaaaaatct gaatgaatct ctgattgatc tgcaggaact  3660
tggaaaatat gaacagtaca ttaaatggcc ttggtacatt tggcttggat ttattgcagg  3720
attaattgca attgtgatgg tgacaattat gttatgttgt atgacatcat gttgttcttg  3780
tttaaaagga tgttgttctt gtggaagctg ttgtaaattt gatgaagatg attctgaacc  3840
tgtgttaaaa ggagtgaaat tgcattacac atgatgactc gagctggtac tgcatgcacg  3900
caatgctagc tgcccctttc ccgtcctggg taccccgagt ctcccccgac ctcgggtccc  3960
aggtatgctc ccacctccac ctgccccact caccacctct gctagttcca gacacctccc  4020
aagcacgcag caatgcagct caaaacgctt agcctagcca cacccccacg ggaaacagca  4080
gtgattaacc tttagcaata aacgaaagtt taactaagct atactaaccc cagggttggt  4140
caatttcgtg ccagccacac cctggagcta gcaaaaaaaa aaaaaaaaaa aaaaaaaaaa  4200
aagcatatga ctaaaaaaaa aaaaaaaaaa aaaaaaaaaa aaaaaaaaaa aaaaaaaaaa  4260
aaaaaaaaaa aaaaaaaaaa aa                                          4282

SEQ ID NO: 16           moltype = RNA  length = 4282
FEATURE                 Location/Qualifiers
misc_feature            1..4282
                        note = RBL063.2
source                  1..4282
                        mol_type = other RNA
                        organism = synthetic construct
SEQUENCE: 16
gggcgaacta gtattcttct ggtccccaca gactcagaga gaacccgcca ccatgttcgt  60
gttcctggtg ctgctgcctc tggtgtccag ccagtgtgtg aacctgacca ccagaacaca  120
gctgcctcca gcctacacca acagctttac cagaggcgtg tactaccccg acaaggtgtt  180
cagatccagc gtgctgcact ctacccagga cctgttcctg cctttcttca gcaacgtgac  240
ctggttccac gccatccacg tgtccggcac caatggcacc aagagattcg acaaccccgt  300
gctgcccttc aacgacgggg tgtactttgc cagcaccgag aagtccaaca tcatcagagg  360
ctggatcttc ggcaccacac tggacagcaa gacccagagc ctgctgatcg tgaacaacgc  420
caccaacgtg gtcatcaaag tgtgcgagtt ccagttctgc aacgacccct tcctgggcgt  480
ctactaccac aagaacaaca agagctggat ggaaagcgag ttccgggtgt acagcagcgc  540
caacaactgc accttcgagt acgtgtccca gcctttcctg atggacctgg aaggcaagca  600
gggcaacttc aagaacctgc gcgagttcgt gtttaagaac atcgacggct acttcaagat  660
ctacagcaag cacaccccta tcaacctcgt gcgggatctg cctcagggct tctctgctct  720
ggaacccctg gtggatctgc ccatcggcat caacatcacc cggtttcaga cactgctggc  780
cctgcacaga agctacctga cacctggcga tagcagcagc ggatggacag ctggtgccgc  840
cgcttactat gtgggctacc tgcagcctag aaccttcctg ctgaagtaca acgagaacgg  900
caccatcacc gacgccgtgg attgtgctct ggatcctctg agcgagacaa agtgcaccct  960
gaagtccttc accgtggaaa agggcatcta ccagaccagc aacttccggg tgcagcccac  1020
cgaatccatc gtgcggttcc ccaatatcac caatctgtgc cccttcggcg aggtgttcaa  1080
tgccaccaga ttcgcctctg tgtacgcctg gaaccggaag cggatcagca attgcgtggc  1140
cgactactcc gtgctgtaca actccgccag cttcagcacc ttcaagtgct acggcgtgtc  1200
ccctaccaag ctgaacgacc tgtgcttcac aaacgtgtac gccgacagct tcgtgatccg  1260
gggagatgaa gtgcggcaga ttgccccctgg acagacaggc aagatcgccg actacaacta  1320
caagctgccc gacgacttca ccggctgtgt gattgcctgg aacagcaaca acctggactc  1380
caaagtcggc ggcaactaca attacctgta ccggctgttc cggaagtcca atctgaagcc  1440
cttcgagcgg gacatctcca ccgagatcta tcaggccggc agcacccctt gtaacggcgt  1500
ggaaggcttc aactgctact tcccactgca gtcctacggc tttcagccca caaatggcgt  1560
```

-continued

```
gggctatcag ccctacagag tggtggtgct gagcttcgaa ctgctgcatg cccctgccac  1620
agtgtgcggc cctaagaaaa gcaccaatct cgtgaagaac aaatgcgtga acttcaactt  1680
caacggcctg accggcaccg gcgtgctgac agagagcaac aagaagttcc tgccattcca  1740
gcagtttggc cgggatatcg ccgataccac agacgccgtt agagatcccc agacactgga  1800
aatcctggac atcacccctt gcagcttcgg cggagtgtct gtgatcaccc ctggcaccaa  1860
caccagcaat caggtggcag tgctgtacca ggacgtgaac tgtaccgaag tgcccgtggc  1920
cattcacgcc gatcagctga cacctacatg gcgggtgtac tccaccggca gcaatgtgtt  1980
tcagaccaga gccggctgtc tgatcggagc cgagcacgtg aacaatagct acgagtgcga  2040
catccccatc ggcgctggaa tctgcgccag ctaccagaca cagacaaaca gccctcggag  2100
agccagaagc gtggccagcc agagcatcat tgcctacaca atgtctctgg gcgccgagaa  2160
cagcgtggcc tactccaaca actctatcgc tatccccacc aacttcacca tcagcgtgac  2220
cacagagatc ctgcctgtgt ccatgaccaa gaccagcgtg gactgcacca tgtacatctg  2280
cggcgattcc accgagtgct ccaacctgct gctgcagtac ggcagcttct gcacccagct  2340
gaatagagcc ctgacaggga tcgccgtgga acaggacaag aacacccaag aggtgttcgc  2400
ccaagtgaag cagatctaca agacccctcc tatcaaggac ttcggcggct tcaatttcag  2460
ccagattctg cccgatccta gcaagcccag caagcggagc ttcatcgagg acctgctgtt  2520
caacaaagtg acactggccg acgccggctt catcaagcag tatggcgatt gtctgggcga  2580
cattgccgcc agggatctga tttgcgccca gaagtttaac ggactgacag tgctgcctcc  2640
tctgctgacc gatgagatga tcgcccagta cacatctgcc ctgctggccg gcacaatcac  2700
aagcggctgg acatttggag caggcgccgc tctgcagatc ccctttgcta tgcagatggc  2760
ctaccggttc aacggcatcg gagtgaccca gaatgtgctg tacgagaacc agaagctgat  2820
cgccaaccag ttcaacagcg ccatcggcaa gatccaggac agcctgagca gcacagcaag  2880
cgccctggga aagctgcagg acgtggtcaa ccagaatgcc caggcactga acaccctggt  2940
caagcagctg tcctccaact tcggcgccat cagctctgtg ctgaacgata tcctgagcag  3000
actggaccct cctgaggccg aggtgcagat cgacagactg atcacaggca gactgcagag  3060
cctccagaca tacgtgaccc agcagctgat cagagccgcc gagattagag cctctgccaa  3120
tctggccgcc accaagatgt ctgagtgtgt gctgggccag agcaagagag tggacttttg  3180
cggcaagggc taccacctga tgagcttccc tcagtctgcc cctcacggcg tggtgtttct  3240
gcacgtgaca tatgtgcccg ctcaagagaa gaatttcacc accgctccag ccatctgcca  3300
cgacggcaaa gcccactttc ctagagaagg cgtgttcgtg tccaacggca cccattggtt  3360
cgtgacacag cggaacttct acgagcccca gatcatcacc accgacaaca ccttcgtgtc  3420
tggcaactgc gacgtcgtga tcggcattgt gaacaatacc gtgtacgacc ctctgcagcc  3480
cgagctggac agcttcaaag aggaactgga caagtacttt aagaaccaca caagccccga  3540
cgtggacctg ggcgatatca gcggaatcaa tgccagcgtc gtgaacatcc agaaagagat  3600
cgaccggctg aacgaggtgg ccaagaatct gaacgagagc ctgatcgacc tgcaagaact  3660
ggggaagtac gagcagtaca tcaagtggcc ctggtacatc tggctgggct ttatcgccgg  3720
actgattgcc atcgtgatgg tcacaatcat gctgtgttgc atgaccagct gctgtagctg  3780
cctgaagggc tgttgtagct gtggcagctg ctgcaagttc gacgaggacg attctgagcc  3840
cgtgctgaag ggcgtgaaac tgcactacac atgatgactc gagctggtac tgcatgcacg  3900
caatgctagc tgccccttc ccgtcctggg taccccgagt ctcccccgac ctcgggtccc  3960
aggtatgctc ccacctccac ctgccccact caccacctct gctagttcca gacacctccc  4020
aagcacgcag caatgcagct caaaacgctt agcctagcca cacccccacg ggaaacagca  4080
gtgattaacc tttagcaata aacgaaagtt taactaagct atactaaccc cagggttggt  4140
caatttcgtg ccagccacac cctggagcta gcaaaaaaaa aaaaaaaaaa aaaaaaaaaa  4200
aagcatatga ctaaaaaaaa aaaaaaaaaa aaaaaaaaaa aaaaaaaaaa aaaaaaaaaa  4260
aaaaaaaaaa aaaaaaaaaa aa                                          4282
```

```
SEQ ID NO: 17          moltype = RNA  length = 1261
FEATURE                Location/Qualifiers
misc_feature           1..1261
                       note = RBL063.3
source                 1..1261
                       mol_type = other RNA
                       organism = synthetic construct
SEQUENCE: 17
gggcgaacta gtattcttct ggtccccaca gactcagaga gaacccgcca ccatgtttgt  60
gtttcttgtg ctgctgcctc ttgtgtcttc tcagtgtgtg gtgagatttc caaatattac  120
aaatctgtgt ccatttggag aagtgtttaa tgcaacaaga tttgcatctg tgtatgcatg  180
gaatagaaaa agaatttcta attgtgtggc tgattattct gtgctgtata atagtgcttc  240
tttttccaca tttaaatgtt atggagtgtc tccaacaaaa ttaaatgatt tatgttttac  300
aaatgtgtat gctgattctt ttgtgatcag aggtgatgaa gtgagacaga ttgccccccgg  360
acagacagga aaaattgctg attacaatta caaactgcct gatgatttta caggatgtgt  420
gattgcttgg aattctaata atttagattc taaagtggga ggaaattaca attatctgta  480
cagactgttt agaaaatcaa atctgaaacc ttttgaaaga gatatttcaa cagaaattta  540
tcaggctgga tcaacacctt gtaatggagt ggaaggattt aattgttatt ttccattaca  600
gagctatgga tttcagccaa ccaatggtgt gggatatcag ccatatagag tggtggtgct  660
gtcttttgaa ctgctgcatg cacctgcaac agtgtgtgga cctaaaggct cccccggctc  720
cggctccgga tctggttata ttcctgaagc tccaagagat gggcaagctt acgttcgtaa  780
agatggcgaa tgggtattac tttctacctt tttaggccgg tccctggagg tgctgttcca  840
gggccccggc tgatgactcg agctggtact gcatgcacgc aatgctagct gcccctttcc  900
cgtcctgggt accccgagtc tcccccgacc tcgggtccca ggtatgctcc cacctccacc  960
tgccccactc accacctctg ctagttccag acacctccca agcacgcagc aatgcagctc  1020
aaaacgctta gcctagccac accccccacgg gaaacagcag tgattaacct ttagcaataa  1080
acgaaagttt aactaagcta tactaacccc agggttggtc aatttcgtgc cagccacacc  1140
ctggagctag caaaaaaaaa aaaaaaaaaa aaaaaaaaaa agcatatgac taaaaaaaaa  1200
aaaaaaaaaa aaaaaaaaaa aaaaaaaaaa aaaaaaaaaa aaaaaaaaaa aaaaaaaaaa  1260
a                                                                 1261

SEQ ID NO: 18          moltype = AA  length = 250
```

-continued

```
FEATURE                 Location/Qualifiers
REGION                  1..250
                        note = S Protein RBD Fusion
source                  1..250
                        mol_type = protein
                        organism = synthetic construct
SEQUENCE: 18
VRFPNITNLC PFGEVFNATR FASVYAWNRK RISNCVADYS VLYNSASFST FKCYGVSPTK  60
LNDLCFTNVY ADSFVIRGDE VRQIAPGQTG KIADYNYKLP DDFTGCVIAW NSNNLDSKVG  120
GNYNYLYRLF RKSNLKPFER DISTEIYQAG STPCNGVEGF NCYFPLQSYG FQPTNGVGYQ  180
PYRVVVLSFE LLHAPATVCG PKGSPGSGSG SGYIPEAPRD GQAYVRKDGE WVLLSTFLGR  240
SLEVLFQGPG                                                        250

SEQ ID NO: 19           moltype = RNA  length = 4283
FEATURE                 Location/Qualifiers
misc_feature            1..4283
                        note = RBP020.1
source                  1..4283
                        mol_type = other RNA
                        organism = synthetic construct
SEQUENCE: 19
agaataaact agtattcttc tggtccccac agactcagag agaacccgcc accatgtttg  60
tgtttcttgt gctgctgcct cttgtgtctt ctcagtgtgt gaatttgaca acaagaacac  120
agctgccacc agcttataca aattctttta ccagaggagt gtattatcct gataaagtgt  180
ttagatcttc tgtgctgcac agcacacagg acctgtttct gccatttttt agcaatgtga  240
catggtttca tgcaattcat gtgtctggaa caaatggaac aaaaagattt gataatcctg  300
tgctgccttt taatgatgga gtgtattttg cttcaacaga aaagtcaaat attattagag  360
gatggatttt tggaacaaca ctggattcta aaacacagtc tctgctgatt gtgaataatg  420
caacaaatgt ggtgattaaa gtgtgtgaat ttcagttttg taatgatcct tttctgggag  480
tgtattatca caaaaaataat aaatcttgga tggaatctga atttagagtg tattcctctg  540
caaataattg tacatttgaa tatgtgtctc agccttttct gatggatctg gaaggaaaac  600
agggcaattt taaaaatctg agagaatttg tgtttaaaaa tattgatgga tattttaaaa  660
tttattctaa acacacacca attaatttag tgagagatct gcctcaggga ttttctgctc  720
tggaacctct ggtggatctg ccaattggca ttaatattac aagatttcag acactgctgg  780
ctctgcacag atcttatctg acacctggag attcttcttc tggatggaca gccggagctg  840
cagcttatta tgtgggctat ctgcagccaa gaacatttct gctgaaatat aatgaaaatg  900
gaacaattac agatgctgtg gattgtgctc tggatcctct gtctgaaaca aaatgtacat  960
taaaatcttt tacagtggaa aaaggcattt atcagacatc taattttaga gtgcagccaa  1020
cagaatctat tgtgagattt ccaaatatta caaatctgtg tccatttgga gaagtgttta  1080
atgcaacaag atttgcatct gtgtatgcat ggaatagaaa aagaatttct aattgtgtgg  1140
ctgattattc tgtgctgtat aatagtgctt ctttttccac atttaaatgt tatggagtgt  1200
ctccaacaaa attaaatgat ttatgtttta caaatgtgta tgctgattct tttgtgatca  1260
gaggtgatga agtgagacag attgcccccg gacagacagg aaaaattgct gattacaatt  1320
acaaactgcc tgatgatttt acaggatgtg tgattgcttg gaattctaat aatttagatt  1380
ctaaagtggg aggaaattac aattatctgt acagactgtt tagaaaatca aatctgaaac  1440
cttttgaaag agatatttca acagaaattt atcaggctgg atcaacacct tgtaatggag  1500
tggaaggatt taattgttat tttccattac agagctatgg atttcagcca accaatggtg  1560
tgggatatca gccatataga gtggtggtgc tgtcttttga actgctgcat gcacctgcaa  1620
cagtgtgtgg acctaaaaaa tctacaaatt tagtgaaaaa taaatgtgtg aattttaatt  1680
ttaatggatt aacaggaaca ggagtgctga cagaatctaa taaaaaattt ctgccttttc  1740
agcagtttgg cagagatatt gcagatacca cagatgcagt gagagatcct cagacattag  1800
aaattctgga tattacacct tgttcttttg ggggtgtgtc tgtgattaca cctggaacaa  1860
atacatctaa tcaggtggct gtgctgtatc aggatgtgaa ttgtacagaa gtgccagtgg  1920
caattcatgc agatcagctg acaccaacat ggagagtgta ttctacagga tctaatgtgt  1980
ttcagacaag agcaggatgt ctgattggag cagaacatgt gaataattct tatgaatgtg  2040
atattccaat tggagcaggc atttgtgcat cttatcagac acagacaaat tccccaagga  2100
gagcaagatc tgtggcatct cagtctatta ttgcatacac catgtctctg ggagcagaaa  2160
attctgtggc atattctaat aattctattg ctattccaac aaattttacc atttctgtga  2220
caacagaaat tttacctgtg tctatgacaa aaacatctgt ggattgtacc atgtacattt  2280
gtggagattc tacagaatgt tctaatctgc tgctgcagta tggatctttt tgtacacagc  2340
tgaatagagc tttaacagga attgctgtgg aacaggataa aaatacacag gaagtgtttg  2400
ctcaggtgaa acagatttac aaaacaccac caattaaaga ttttggagga tttaatttta  2460
gccagattct gcctgatcct tctaaacctt ctaaaagatc ttttattgaa gatctgctgt  2520
ttaataaagt gacactggca gatgcaggat ttattaaaca gtatggagat tgcctgggtg  2580
atattgctgc aagagatctg atttgtgctc agaaatttaa tggactgaca gtgctgcctc  2640
ctctgctgac agatgaaatg attgctcagt acacatctgc tttactggct ggaacaatta  2700
caagcggatg gacatttgga gctggagctg ctctgcagat tccttttgca atgcagatgg  2760
cttacagatt taatggaatt ggagtgacac agaatgtgtt atatgaaaat cagaaactga  2820
ttgcaaatca gtttaattct gcaattggca aaattcagga ttctctgtct tctacagctt  2880
ctgctctggg aaaactgcag gatgtggtga atcagaatgc acaggcactg aatactctgg  2940
tgaaacagct gtctagcaat tttggggcaa tttcttctgt gctgaatgat attctgtcta  3000
gactggatcc tcctgaagct gaagtgcaga ttgatagact gatcacagga agactgcagt  3060
ctctgcagac ttatgtgaca cagcagctga ttagagctgc tgaaattaga gcttctgcta  3120
atctggctgc tacaaaaatg tctgaatgtg tgctgggaca gtcaaaaaga gtggattttt  3180
gtggaaaagg atatcatctg atgtcttttc cacagtctgc tccacatgga gtggtgtttt  3240
tacatgtgac atatgtgcca gcacaggaaa agaattttac cacagcacca gcaatttgtc  3300
atgatggaaa agcacatttt ccaagagaag gagtgtttgt gtctaatgga acacattggt  3360
ttgtgacaca gagaaatttt tatgaacctc agattattac aacagataat acatttgtgt  3420
caggaaattg tgatgtggtg attggaattg tgaataatac agtgtatgat ccactgcagc  3480
```

```
cagaactgga ttcttttaaa gaagaactgg ataaatattt taaaaatcac acatctcctg  3540
atgtggattt aggagatatt tctggaatca atgcatctgt ggtgaatatt cagaaagaaa  3600
ttgatagact gaatgaagtg gccaaaaatc tgaatgaatc tctgattgat ctgcaggaac  3660
ttggaaaata tgaacagtac attaaatggc cttggtacat ttggcttgga tttattgcag  3720
gattaattgc aattgtgatg gtgacaatta tgttatgttg tatgacatca tgttgttctt  3780
gtttaaaagg atgttgttct tgtggaagct gttgtaaatt tgatgaagat gattctgaac  3840
ctgtgttaaa aggagtgaaa ttgcattaca catgatgact cgagctggta ctgcatgcac  3900
gcaatgctag ctgccccttt cccgtcctgg gtaccccgag tctcccccga cctcgggtcc  3960
caggtatgct cccacctcca cctgccccac tcaccacctc tgctagttcc agacacctcc  4020
caagcacgca gcaatgcagc tcaaaacgct tagcctagcc acacccccac gggaaacagc  4080
agtgattaac ctttagcaat aaacgaaagt ttaactaagc tatactaacc ccagggttgg  4140
tcaatttcgt gccagccaca ccctggagct agcaaaaaaa aaaaaaaaaa aaaaaaaaaa  4200
aaagcatatg actaaaaaaa aaaaaaaaaa aaaaaaaaaa aaaaaaaaaa aaaaaaaaaa  4260
aaaaaaaaaa aaaaaaaaaa aaa                                         4283

SEQ ID NO: 20          moltype = RNA  length = 4283
FEATURE                Location/Qualifiers
misc_feature           1..4283
                       note = RBP020.2
source                 1..4283
                       mol_type = other RNA
                       organism = synthetic construct
SEQUENCE: 20
agaataaact agtattcttc tggtccccac agactcagag agaacccgcc accatgttcg  60
tgttcctggt gctgctgcct ctggtgtcca gccagtgtgt gaacctgacc accagaacac  120
agctgcctcc agcctacacc aacagcttta ccagaggcgt gtactacccc gacaaggtgt  180
tcagatccag cgtgctgcac tctacccagg acctgttcct gcctttcttc agcaacgtga  240
cctggttcca cgccatccac gtgtccggca ccaatggcac caagagattc gacaaccccg  300
tgctgccctt caacgacggg gtgtactttg ccagcaccga gaagtccaac atcatcagag  360
gctggatctt cggcaccaca ctggacagca agacccagag cctgctgatc gtgaacaacg  420
ccaccaacgt ggtcatcaaa gtgtgcgagt tccagttctg caacgacccc ttcctgggcg  480
tctactacca caagaacaac aagagctgga tggaaagcga gttccgggtg tacagcagcg  540
ccaacaactg caccttcgag tacgtgtccc agcctttcct gatggacctg gaaggcaagc  600
agggcaactt caagaacctg cgcgagttcg tgtttaagaa catcgacggc tacttcaaga  660
tctacagcaa gcacacccct atcaacctcg tgcgggatct gcctcagggc ttctctgctc  720
tggaacccct ggtggatctg cccatcggca tcaacatcac ccggtttcag acactgctgg  780
ccctgcacag aagctacctg acacctggcg atagcagcag cggatggaca gctggtgccg  840
ccgcttacta tgtgggctac ctgcagccta gaaccttcct gctgaagtac aacgagaacg  900
gcaccatcac cgacgccgtg gattgtgctc tggatcctct gagcgagaca aagtgcaccc  960
tgaagtcctt caccgtggaa aagggcatct accagaccag caacttccgg gtgcagccca  1020
ccgaatccat cgtgcggttc cccaatatca ccaatctgtg ccccttcggc gaggtgttca  1080
atgccaccag attcgcctct gtgtacgcct ggaaccggaa gcggatcagc aattgcgtgg  1140
ccgactactc cgtgctgtac aactccgcca gcttcagcac cttcaagtgc tacggcgtgt  1200
cccctaccaa gctgaacgac ctgtgcttca caaacgtgta cgccgacagc ttcgtgatcc  1260
ggggagatga agtgcggcag attgcccctg gacagacagg caagatcgcc gactacaact  1320
acaagctgcc cgacgacttc accggctgtg tgattgcctg gaacagcaac aacctggact  1380
ccaaagtcgg cggcaactac aattacctgt accggctgtt ccggaagtcc aatctgaagc  1440
ccttcgagcg ggacatctcc accgagatct atcaggccgg cagcacccct tgtaacggcg  1500
tggaaggctt caactgctac ttcccactgc agtcctacgg ctttcagccc acaaatggcg  1560
tgggctatca gccctacaga gtggtggtgc tgagcttcga actgctgcat gcccctgcca  1620
cagtgtgcgg ccctaagaaa agcaccaatc tcgtgaagaa caaatgcgtg aacttcaact  1680
tcaacggcct gaccggcacc ggcgtgctga cagagagcaa caagaagttc ctgccattcc  1740
agcagtttgg ccgggatatc gccgatacca cagacgccgt tagagatccc cagacactgg  1800
aaatcctgga catcacccct tgcagcttcg gcggagtgtc tgtgatcacc cctggcacca  1860
acaccagcaa tcaggtggca gtgctgtacc aggacgtgaa ctgtaccgaa gtgcccgtgg  1920
ccattcacgc cgatcagctg acacctacat ggcgggtgta ctccaccggc agcaatgtgt  1980
ttcagaccag agccggctgt ctgatcggag ccgagcacgt gaacaatagc tacgagtgcg  2040
acatccccat cggcgctgga atctgcgcca gctaccagac acagacaaac agccctcgga  2100
gagccagaag cgtggccagc cagagcatca ttgcctacac aatgtctctg ggcgccgaga  2160
acagcgtggc ctactccaac aactctatcg ctatccccac caacttcacc atcagcgtga  2220
ccacagagat cctgcctgtg tccatgacca agaccagcgt ggactgcacc atgtacatct  2280
gcggcgattc caccgagtgc tccaacctgc tgctgcagta cggcagcttc tgcacccagc  2340
tgaatagagc cctgacaggg atcgccgtgg aacaggacaa gaacacccaa gaggtgttcg  2400
cccaagtgaa gcagatctac aagacccctc ctatcaagga cttcggcggc ttcaatttca  2460
gccagattct gcccgatcct agcaagccca gcaagcggag cttcatcgag gacctgctgt  2520
tcaacaaagt gacactggcc gacgccggct tcatcaagca gtatggcgat tgtctgggcg  2580
acattgccgc cagggatctg atttgcgccc agaagtttaa cggactgaca gtgctgcctc  2640
ctctgctgac cgatgagatg atcgcccagt acacatctgc cctgctggcc ggcacaatca  2700
caagcggctg gacatttgga gcaggcgccg ctctgcagat cccctttgct atgcagatgg  2760
cctaccggtt caacggcatc ggagtgaccc agaatgtgct gtacgagaac cagaagctga  2820
tcgccaacca gttcaacagc gccatcggca agatccagga cagcctgagc agcacagcaa  2880
gcgccctggg aaagctgcag gacgtggtca accagaatgc ccaggcactg aacaccctgg  2940
tcaagcagct gtcctccaac ttcggcgcca tcagctctgt gctgaacgat atcctgagca  3000
gactggaccc tcctgaggcc gaggtgcaga tcgacagact gatcacaggc agactgcaga  3060
gcctccagac atacgtgacc cagcagctga tcagagccgc cgagattaga gcctctgcca  3120
atctggccgc caccaagatg tctgagtgtg tgctgggcca gagcaagaga gtggactttt  3180
gcggcaaggg ctaccacctg atgagcttcc ctcagtctgc ccctcacggc gtggtgtttc  3240
tgcacgtgac atatgtgccc gctcaagaga agaatttcac caccgctcca gccatctgcc  3300
acgacggcaa agcccacttt cctagagaag gcgtgttcgt gtccaacggc acccattggt  3360
```

```
tcgtgacaca gcggaacttc tacgagcccc agatcatcac caccgacaac accttcgtgt  3420
ctggcaactg cgacgtcgtg atcggcattg tgaacaatac cgtgtacgac cctctgcagc  3480
ccgagctgga cagcttcaaa gaggaactgg acaagtactt taagaaccac acaagccccg  3540
acgtggacct gggcgatatc agcggaatca atgccagcgt cgtgaacatc cagaaagaga  3600
tcgaccggct gaacgaggtg gccaagaatc tgaacgagag cctgatcgac ctgcaagaac  3660
tggggaagta cgagcagtac atcaagtggc cctggtacat ctggctgggc tttatcgccg  3720
gactgattgc catcgtgatg gtcacaatca tgctgtgttg catgaccagc tgctgtagct  3780
gcctgaaggg ctgttgtagc tgtggcagct gctgcaagtt cgacgaggac gattctgagc  3840
ccgtgctgaa gggcgtgaaa ctgcactaca catgatgact cgagctggta ctgcatgcac  3900
gcaatgctag ctgcccctt cccgtcctgg gtaccccgag tctcccccga cctcgggtcc  3960
caggtatgct cccacctcca cctgccccac tcaccacctc tgctagttcc agacacctcc  4020
caagcacgca gcaatgcagc tcaaaacgct tagcctagcc acacccccac gggaaacagc  4080
agtgattaac ctttagcaat aaacgaaagt ttaactaagc tatactaacc ccagggttgg  4140
tcaatttcgt gccagccaca ccctggagct agcaaaaaaa aaaaaaaaaa aaaaaaaaaa  4200
aaagcatatg actaaaaaaa aaaaaaaaaa aaaaaaaaaa aaaaaaaaaa aaaaaaaaaa  4260
aaaaaaaaaa aaaaaaaaaa aaa                                          4283

SEQ ID NO: 21          moltype = RNA  length = 1262
FEATURE                Location/Qualifiers
misc_feature           1..1262
                       note = RBP020.3
source                 1..1262
                       mol_type = other RNA
                       organism = synthetic construct
SEQUENCE: 21
agaataaact agtattcttc tggtccccac agactcagag agaacccgcc accatgtttg  60
tgtttcttgt gctgctgcct cttgtgtctt ctcagtgtgt ggtgagattt ccaaatatta  120
caaatctgtg tccatttgga gaagtgttta atgcaacaag atttgcatct gtgtatgcat  180
ggaatagaaa aagaatttct aattgtgtgg ctgattattc tgtgctgtat aatagtgctt  240
ctttttccac atttaaatgt tatggagtgt ctccaacaaa attaaatgat ttatgtttta  300
caaatgtgta tgctgattct tttgtgatca gaggtgatga agtgagacag attgcccccg  360
gacagacagg aaaaattgct gattacaatt acaaactgcc tgatgatttt acaggatgtg  420
tgattgcttg gaattctaat aatttagatt ctaaagtggg aggaaattac aattatctgt  480
acagactgtt tagaaaatca aatctgaaac cttttgaaag agatatttca acagaaattt  540
atcaggctgg atcaacacct tgtaatggag tggaaggatt taattgttat tttccattac  600
agagctatgg atttcagcca accaatggtg tgggatatca gccatataga gtggtggtgc  660
tgtcttttga actgctgcat gcacctgcaa cagtgtgtgg acctaaaggc tcccccggct  720
ccggctccgg atctggttat attcctgaag ctccaagaga tggcaagct tacgttcgta  780
aagatggcga atgggtatta ctttctacct ttttaggccg gtccctggag gtgctgttcc  840
agggccccgg ctgatgactc gagctggtac tgcatgcacg caatgctagc tgcccctttc  900
ccgtcctggg taccccgagt ctcccccgac ctcgggtccc aggtatgctc ccacctccac  960
ctgccccact caccacctct gctagttcca gacacctccc aagcacgcag caatgcagct  1020
caaaacgctt agcctagcca cacccccacg ggaaacagca gtgattaacc tttagcaata  1080
aacgaaagtt taactaagct atactaaccc cagggttggt caatttcgtg ccagccacac  1140
cctggagcta gcaaaaaaaa aaaaaaaaaa aaaaaaaaaa aagcatatga ctaaaaaaaa  1200
aaaaaaaaaa aaaaaaaaaa aaaaaaaaaa aaaaaaaaaa aaaaaaaaaa aaaaaaaaaa  1260
aa                                                                 1262

SEQ ID NO: 22          moltype = AA  length = 1879
FEATURE                Location/Qualifiers
REGION                 1..1879
                       note = Viral Protein
source                 1..1879
                       mol_type = protein
                       organism = synthetic construct
SEQUENCE: 22
MEKVHVDIEE DSPFLRALQR SFPQFEVEAK QVTDNDHANA RAFSHLASKL IETEVDPSDT  60
ILDIGSAPAR RMYSKHKYHC ICPMRCAEDP DRLYKYATKL KKNCKEITDK ELDKKMKELA  120
AVMSDPDLET ETMCLHDDES CRYEGQVAVY QDVYAVDGPT SLYHQANKGV RVAYWIGFDT  180
TPFMFKNLAG AYPSYSTNWA DETVLTARNI GLCSSDVMER SRRGMSILRK KYLKPSNNVL  240
FSVGSTIYHE KRDLLRSWHL PSVFHLRGKQ NYTCRCETIV SCDGYVVKRI AISPGLYGKP  300
SGYAATMHRE GFLCCKVTDT LNGERVSFPV CTYVPATLCD QMTGILATDV SADDAQKLLV  360
GLNQRIVVNG RTQRNTNTMK NYLLPVVAQA FARWAKEYKE DQEDERPLGL RDRQLVMGCC  420
WAFRRHKITS IYKRPDTQTI IKVNSDFHSF VLPRIGSNTL EIGLRTRIRK MLEEHKEPSP  480
LITAEDVQEA KCAADEAKEV REAEELRAAL PPLAADVEEP TLEADVDLML QEAGAGSVET  540
PRGLIKVTSY AGEDKIGSYA VLSPQAVLKS EKLSCIHPLA EQVIVITHSG RKGRYAVEPY  600
HGKVVVPEGH AIPVQDFQAL SESATIVYNE REFVNRYLHH IATHGGALNT DEEYYKTVKP  660
SEHDGEYLYD IDRKQCVKKE LVTGLGLTGE LVDPPFHEFA YESLRTRPAA PYQVPTIGVY  720
GVPGSGKSGI IKSAVTKKDL VVSAKKENCA EIIRDVKKMK GLDVNARTVD SVLLNGCKHP  780
VETLYIDEAF ACHAGTLRAL IAIIRPKKAV LCGDPKQCGF FNMMCLKVHF NHEICTQVFH  840
KSISRRCTKS VTSVVSTLFY DKKMRTTNPK ETKIVIDTTG STKPKQDDLI LTCFRGWVKQ  900
LQIDYKGNEI MTAAASQGLT RKGVYAVRYK VNENPLYAPT SEHVNVLLTR TEDRIVWKTL  960
AGDPWIKTLT AKYPGNFTAT IEEWQAEHDA IMRHILERPD PTDVFQNKAN VCWAKALVPV  1020
LKTAGIDMTT EQWNTVDYFE TDKAHSAEIV LNQLCVRFFG LDLDSGLFSA PTVPLSIRNN  1080
HWDNSPSPNM YGLNKEVVRQ LSRRYPQLPR AVATGRVYDM NTGTLRNYDP RINLVPVNRR  1140
LPHALVLHHN EHPQSDFSSF VSKLKGRTVL VVGEKLSVPG KMVDWLSDRP EATFRARLDL  1200
GIPGDVPKYD IIFVNVRTPY KYHHYQQCED HAIKLSMLTK KACLHLNPGG TCVSIGYGYA  1260
DRASESIIGA IARQFKFSRV CKPKSSLEET EVLFVFIGYD RKARTHNPYK LSSTLTNIYT  1320
GSRLHEAGCA PSYHVVRGDI ATATEGVIIN AANSKGQPGG GVCGALYKKF PESFDLQPIE  1380
```

-continued

```
VGKARLVKGA AKHIIHAVGP NFNKVSEVEG DKQLAEAYES IAKIVNDNNY KSVAIPLLST  1440
GIFSGNKDRL TQSLNHLLTA LDTTDADVAI YCRDKKWEMT LKEAVARREA VEEICISDDS  1500
SVTEPDAELV RVHPKSSLAG RKGYSTSDGK TFSYLEGTKF HQAAKDIAEI NAMWPVATEA  1560
NEQVCMYILG ESMSSIRSKC PVEESEASTP PSTLPCLCIH AMTPERVQRL KASRPEQITV  1620
CSSFPLPKYR ITGVQKIQCS QPILFSPKVP AYIHPRKYLV ETPPVDETPE PSAENQSTEG  1680
TPEQPPLITE DETRTRTPEP IIIEEEEEDS ISLLSDGPTH QVLQVEADIH GPPSVSSSSW  1740
SIPHASDFDV DSLSILDTLE GASVTSGATS AETNSYFAKS MEFLARPVPA PRTVFRNPPH  1800
PAPRTRTPSL APSRACSRTS LVSTPPGVNR VITREELEAL TPSRTPSRSV SRTSLVSNPP  1860
GVNRVITREE FEAFVAQQQ                                                1879

SEQ ID NO: 23           moltype = AA  length = 613
FEATURE                 Location/Qualifiers
REGION                  1..613
                        note = Viral Protein
source                  1..613
                        mol_type = protein
                        organism = synthetic construct
SEQUENCE: 23
RFDAGAYIFS SDTGQGHLQQ KSVRQTVLSE VVLERTELEI SYAPRLDQEK EELLRKKLQL  60
NPTPANRSRY QSRKVENMKA ITARRILQGL GHYLKAEGKV ECYRTLHPVP LYSSSVNRAF  120
SSPKVAVEAC NAMLKENFPT VASYCIIPEY DAYLDMVDGA SCCLDTASFC PAKLRSFPKK  180
HSYLEPTIRS AVPSAIQNTL QNVLAAATKR NCNVTQMREL PVLDSAAFNV ECFKKYACNN  240
EYWETFKENP IRLTEENVVN YITKLKGPKA AALFAKTHNL NMLQDIPMDR FVMDLKRDVK  300
VTPGTKHTEE RPKVQVIQAA DPLATAYLCG IHRELVRRLN AVLLPNIHTL FDMSAEDFDA  360
IIAEHFQPGD CVLETDIASF DKSEDDAMAL TALMILEDLG VDAELLTLIE AAFGEISSIH  420
LPTKTKFKFG AMMKSGMFLT LFVNTVINIV IASRVLRERL TGSPCAAFIG DDNIVKGVKS  480
DKLMADRCAT WLNMEVKIID AVVGEKAPYF CGGFILCDSV TGTACRVADP LKRLFKLGKP  540
LAADDEHDDD RRRALHEEST RWNRVGILSE LCKAVESRYE TVGTSIIVMA MTTLASSVKS  600
FSYLRGAPIT LYG                                                      613

SEQ ID NO: 24           moltype = RNA  length = 11917
FEATURE                 Location/Qualifiers
misc_feature            1..11917
                        note = RBS004.1
source                  1..11917
                        mol_type = other RNA
                        organism = synthetic construct
SEQUENCE: 24
gatgggcggc gcatgagaga agcccagacc aattacctac ccaaaatgga gaaagttcac  60
gttgacatcg aggaagacag cccattcctc agagctttgc agcggagctt cccgcagttt  120
gaggtagaag ccaagcaggt cactgataat gaccatgcta atgccagagc gttttcgcat  180
ctggcttcaa aactgatcga aacggaggtg gacccatccg acacgatcct tgacattgga  240
agtgcgcccg cccgcagaat gtattctaag cacaagtatc attgtatctg tccgatgaga  300
tgtgcggaag atccggacag attgtataag tatgcaacta agctgaagaa aaactgtaag  360
gaaataactg ataaggaatt ggacaagaaa atgaaggagc tcgccgccgt catgagcgac  420
cctgacctgg aaactgagac tatgtgcctc cacgacgacg agtcgtgtcg ctacgaaggg  480
caagtcgctg tttaccagga tgtatacgcg gttgacggac cgacaagtct ctatcaccaa  540
gccaataagg gagttagagt cgcctactgg ataggctttg acaccacccc ttttatgttt  600
aagaacttgg ctggagcata tccatcatac tctaccaact gggccgacga aaccgtgtta  660
acggctcgta acataggcct atgcagctct gacgttatgg agcggtcacg tagagggatg  720
tccattctta gaaagaagta tttgaaacca tccaacaatg ttctattctc tgttggctcg  780
accatctacc acgaaaagag ggacttactg aggagctggc acctgccgtc tgtatttcac  840
ttacgtggca agcaaaatta cacatgtcgg tgtgagacta tagttagttg cgacgggtac  900
gtcgttaaaa gaatagctat cagtccaggc ctgtatggga agccttcagg ctatgctgct  960
acgatgcacc gcgagggatt cttgtgctgc aaagtgacag acacattgaa cggggagagg  1020
gtctcttttc ccgtgtgcac gtatgtgcca gctacattgt gtgaccaaat gactggcata  1080
ctggcaacag atgtcagtgc ggacgacgcg caaaaactgc tggttgggct caaccagcgt  1140
atagtcgtca acggtcgcac ccagagaaac accaatacca tgaaaaatta cctttttgccc  1200
gtagtggccc aggcatttgc taggtgggca aaggaatata aggaagatca agaagatgaa  1260
aggccactag gactacgaga tagacagtta gtcatggggt gttgttgggc ttttagaagg  1320
cacaagataa catctattta taagcgcccg gatacccaaa ccatcatcaa agtgaacagc  1380
gatttccact cattcgtgct gcccaggata ggcagtaaca cattggagat cgggctgaga  1440
acaagaatca ggaaaatgtt agaggagcac aaggagccgt cacctctcat taccgccgag  1500
gacgtacaag aagctaagtg cgcagccgat gaggctaagg aggtgcgtga agccgaggag  1560
ttgcgcgcag ctctaccacc tttggcagct gatgttgagg agcccactct ggaagccgat  1620
gtcgacttga tgttacaaga ggctggggcc ggctcagtgg agacacctcg tggcttgata  1680
aaggttacca gctacgctgg cgaggacaag atcggctctt acgctgtgct ttctccgcag  1740
gctgtactca agagtgaaaa attatcttgc atccaccctc tcgctgaaca agtcatagtg  1800
ataacacact ctggccgaaa agggcgttat gccgtggaac cataccatgg taaagtagtg  1860
gtgccagagg gacatgcaat acccgtccag gactttcaag ctctgagtga aagtgccacc  1920
attgtgtaca acgaacgtga gttcgtaaac aggtacctgc accatattgc cacacatgga  1980
ggagcgctga acactgatga agaatattac aaaactgtca agcccagcga gcacgacggc  2040
gaatacctgt acgacatcga caggaaacag tgcgtcaaga aagagctagt cactgggcta  2100
gggctcacag gcgagctggt cgatcctccc ttccatgaat tcgcctacga gagtctgaga  2160
acacgaccag ccgctcctta ccaagtacca accatagggg tgtatggcgt gccaggatca  2220
ggcaagtctg gcatcattaa aagcgcagtc accaaaaaag atctagtggt gagcgccaag  2280
aaagaaaact gtgcagaaat tataagggac gtcaagaaaa tgaaagggct ggacgtcaat  2340
gccagaactg tggactcagt gctcttgaat ggatgcaaac accccgtaga gaccctgtat  2400
attgacgagg cttttgcttg tcatgcaggt actctcagag cgctcatagc cattataaga  2460
```

-continued

```
cctaaaaagg cagtgctctg cggagatccc aaacagtgcg gttttttaa catgatgtgc  2520
ctgaaagtgc attttaacca cgagatttgc acacaagtct tccacaaaag catctctcgc  2580
cgttgcacta aatctgtgac ttcggtcgtc tcaaccttgt tttacgacaa aaaaatgaga  2640
acgacgaatc cgaaagagac taagattgtg attgacacta ccggcagtac caaacctaag  2700
caggacgatc tcattctcac ttgtttcaga gggtgggtga agcagttgca aatagattac  2760
aaaggcaacg aaataatgac ggcagctgcc tctcaagggc tgacccgtaa aggtgtgtat  2820
gccgttcggt acaaggtgaa tgaaaatcct ctgtacgcac ccacctcaga acatgtgaac  2880
gtcctactga cccgcacgga ggaccgcatc gtgtggaaaa cactagccgg cgacccatgg  2940
ataaaaacac tgactgccaa gtaccctggg aatttcactg ccacgataga ggagtggcaa  3000
gcagagcatg atgccatcat gaggcacatc ttggagagac cggaccctac cgacgtcttc  3060
cagaataagg caaacgtgtg ttgggccaag gctttagtgc cggtgctgaa gaccgctggc  3120
atagacatga ccactgaaca atggaacact gtggattatt ttgaaacgga caaagctcac  3180
tcagcagaga tagtattgaa ccaactatgc gtgaggttct ttggactcga tctggactcc  3240
ggtctatttt ctgcacccac tgttccgtta tccattagga ataatcactg ggataactcc  3300
ccgtcgccta acatgtacgg gctgaataaa gaagtggtcc gtcagctctc tcgcaggtac  3360
ccacaactgc ctcgggcagt tgccactggt agagtctatg acatgaacac tggtacactg  3420
cgcaattatg atccgcgcat aaacctagta cctgtaaaca gaagactgcc tcatgcttta  3480
gtcctccacc ataatgaaca cccacagagt gacttttctt cattcgtcag caaattgaag  3540
ggcagaactg tcctggtggt cggggaaaag ttgtccgtcc caggcaaaat ggttgactgg  3600
ttgtcagacc ggcctgaggc taccttcaga gctcggctgg atttaggcat cccaggtgat  3660
gtgcccaaat atgacataat atttgttaat gtgaggaccc catataaata ccatcactat  3720
cagcagtgtg aagaccatgc cattaagcta agcatgttga ccaagaaagc atgtctgcat  3780
ctgaatcccg gcggaacctg tgtcagcata ggttatggtt acgctgacag ggccagcgaa  3840
agcatcattg gtgctatagc gcggcagttc aagttttccc gagtatgcaa accgaaatcc  3900
tcacttgagg agacggaagt tctgtttgta ttcattgggt acgatcgcaa ggcccgtacg  3960
cacaatcctt acaagctatc atcaaccttg accaacattt atacaggttc cagactccac  4020
gaagccggat gtgcaccctc atatcatgtg gtgcgagggg atattgccac ggccaccgaa  4080
ggagtgatta taaatgctgc taacagcaaa ggacaacctg gcggaggggt gtgcggagcg  4140
ctgtataaga aattcccgga aagtttcgat ttacagccga tcgaagtagg aaaagcgcga  4200
ctggtcaaag gtgcagctaa acatatcatt catgccgtag gaccaaactt caacaaagtt  4260
tcggaggttg aaggtgacaa acagttggca gaggcttatg agtccatcgc taagattgtc  4320
aacgataaca attacaagtc agtagcgatt ccactgttgt ccaccggcat cttttccggg  4380
aacaaagatc gactaaccca atcattgaac catttgctga cagctttaga caccactgat  4440
gcagatgtag ccatatactg cagggacaag aaatgggaaa tgactctcaa ggaagcagtg  4500
gctaggagag aagcagtgga ggagatatgc atatccgacg attcttcagt gacagaacct  4560
gatgcagagc tggtgagggt gcatcccaag agttctttgg ctggaaggaa gggctacagc  4620
acaagcgatg gcaaaacttt ctcatatttg gaagggacca agtttcacca ggcggccaag  4680
gatatagcag aaattaatgc catgtggccc gttgcaacgg aggccaatga gcaggtatgc  4740
atgtatatcc tcggagaaag catgagcagt attaggtcga aatgccccgt cgaggagtcg  4800
gaagcctcca caccacctag cacgctgcct tgcttgtgca tccatgccat gactccagaa  4860
agagtacagc gcctaaaagc ctcacgtcca gaacaaatta ctgtgtgctc atcctttcca  4920
ttgccgaagt atagaatcac tggtgtgcag aagatccaat gctcccagcc tatattgttc  4980
tcaccgaaag tgcctgcgta tattcatcca aggaagtatc tcgtggaaac accaccggta  5040
gacgagactc cggagccatc ggcagagaac caatccacag aggggacacc tgaacaacca  5100
ccacttataa ccgaggatga gaccaggact agaacgcctg agccgatcat catcgaagaa  5160
gaagaagaag atagcataag tttgctgtca gatggcccga cccaccaggt gctgcaagtc  5220
gaggcagaca ttcacgggcc gccctctgta tctagctcat cctggtccat tcctcatgca  5280
tccgactttg atgtggacag tttatccata cttgacaccc tggagggagc tagcgtgacc  5340
agcggggcaa cgtcagccga gactaactct tacttcgcaa agagtatgga gtttctggcg  5400
cgaccggtgc ctgcgcctcg aacagtattc aggaaccctc cacatcccgc tccgcgcaca  5460
agaacaccgt cacttgcacc cagcagggcc tgctccagaa ccagcctagt ttccaccccg  5520
ccaggcgtga atagggtgat cactagagag gagctcgaag cgcttacccc gtcacgcact  5580
cctagcaggt cggtctccag aaccagcctg gtctccaacc cgccaggcgt aaatagggtg  5640
attacaagag aggagtttga ggcgttcgta gcacaacaac aatgacggtt tgatgcgggt  5700
gcatacatct tttcctccga caccggtcaa gggcatttac aacaaaaatc agtaaggcaa  5760
acggtgctat ccgaagtggt gttggagagg accgaattgg agatttcgta tgccccgcgc  5820
ctcgaccaag aaaaagaaga attactacgc aagaaattac agttaaatcc cacacctgct  5880
aacagaagca gataccagtc caggaaggtg gagaacatga aagccataac agctagacgt  5940
attctgcaag gcctagggca ttatttgaag gcagaaggaa aagtggagtg ctaccgaacc  6000
ctgcatcctg ttcctttgta ttcatctagt gtgaaccgtg ccttttcaag ccccaaggtc  6060
gcagtggaag cctgtaacgc catgttgaaa gagaactttc cgactgtggc ttcttactgt  6120
attattccag agtacgatgc ctatttggac atggttgacg gagcttcatg ctgcttagac  6180
actgccagtt tttgccctgc aaagctgcgc agctttccaa agaaacactc ctatttggaa  6240
cccacaatac gatcggcagt gccttcagcg atccagaaca cgctccagaa cgtcctggca  6300
gctgccacaa aaagaaattg caatgtcacg caaatgagag aattgcccgt attggattcg  6360
gcggccttta atgtggaatg cttcaagaaa tatgcgtgta ataatgaata ttgggaaacg  6420
tttaaagaaa accccatcag gcttactgaa gaaaacgtgg taaattacat taccaaatta  6480
aaaggaccaa aagctgctgc tctttttgcg aagacacata atttgaatat gttgcaggac  6540
ataccaatgg acaggtttgt aatggactta aagagagacg tgaaagtgac tccaggaaca  6600
aaacatactg aagaacggcc caaggtacag gtgatccagg ctgccgatcc gctagcaaca  6660
gcgtatctgt gcggaatcca ccgagagctg gttaggagat taaatgcggt cctgcttccg  6720
aacattcata cactgtttga tatgtcggct gaagactttg acgctattat agccgagcac  6780
ttccagcctg gggattgtgt tctggaaact gacatcgcgt cgtttgataa aagtgaggac  6840
gacgccatgg ctctgaccgc gttaatgatt ctggaagact taggtgtgga cgcagagctg  6900
ttgacgctga ttgaggcggc tttcggcgaa atttcatcaa tacatttgcc cactaaaact  6960
aaatttaaat tcggagccat gatgaaatct ggaatgttcc tcacactgtt tgtgaacaca  7020
gtcattaaca ttgtaatcgc aagcagagtg ttgagagaac ggctaaccgg atcaccatgt  7080
gcagcattca ttggagatga caatatcgtg aaaggagtca aatcggacaa attaatggca  7140
gacaggtgcg ccacctggtt gaatatggaa gtcaagatta tagatgctgt ggtgggcgag  7200
```

-continued

```
aaagcgcctt atttctgtgg agggtttatt ttgtgtgact ccgtgaccgg cacagcgtgc  7260
cgtgtggcag accccctaaa aaggctgttt aagctaggca aacctctggc agcagacgat  7320
gaacatgatg atgacaggag aagggcattg catgaggagt caacacgctg gaaccgagtg  7380
ggtattcttt cagagctgtg caaggcagta gaatcaaggt atgaaaccgt aggaacttcc  7440
atcatagtta tggccatgac tactctagct agcagtgtta aatcattcag ctacctgaga  7500
ggggccccta taactctcta cggctaacct gaatggacta cgacatagtc tagtccgcca  7560
agactagtat gtttgtgttt cttgtgctgc tgcctcttgt gtcttctcag tgtgtgaatt  7620
tgacaacaag aacacagctg ccaccagctt atacaaattc ttttaccaga ggagtgtatt  7680
atcctgataa agtgtttaga tcttctgtgc tgcacagcac acaggacctg tttctgccat  7740
tttttagcaa tgtgacatgg tttcatgcaa ttcatgtgtc tggaacaaat ggaacaaaaa  7800
gatttgataa tcctgtgctg ccttttaatg atggagtgta ttttgcttca acagaaaagt  7860
caaatattat tagaggatgg atttttggaa caacactgga ttctaaaaca cagtctctgc  7920
tgattgtgaa taatgcaaca aatgtggtga ttaaagtgtg tgaatttcag ttttgtaatg  7980
atcctttttct gggagtgtat tatcacaaaa ataataaatc ttggatggaa tctgaattta  8040
gagtgtattc ctctgcaaat aattgtacat ttgaatatgt gtctcagcct ttttctgatgg  8100
atctggaagg aaaacagggc aattttaaaa atctgagaga atttgtgttt aaaaatattg  8160
atggatattt taaaatttat tctaaacaca caccaattaa tttagtgaga gatctgcctc  8220
agggattttc tgctctggaa cctctggtgg atctgccaat tggcattaat attacaagat  8280
ttcagacact gctggctctg cacagatctt atctgacacc tggagattct tcttctggat  8340
ggacagccgg agctgcagct tattatgtgg gctatctgca gccaagaaca tttctgctga  8400
aatataatga aaatggaaca attacagatg ctgtggattg tgctctggat cctctgtctg  8460
aaacaaaatg tacattaaaa tcttttacag tggaaaaagg catttatcag acatctaatt  8520
ttagagtgca gccaacagaa tctattgtga gatttccaaa tattacaaat ctgtgtccat  8580
ttggagaagt gtttaatgca acaagatttg catctgtgta tgcatggaat agaaaaagaa  8640
tttctaattg tgtggctgat tattctgtgc tgtataatag tgcttctttt tccacattta  8700
aatgttatgg agtgtctcca acaaaattaa atgatttatg ttttacaaat gtgtatgctg  8760
attcttttgt gatcagaggt gatgaagtga gacagattgc cccggacag acaggaaaaa  8820
ttgctgatta caattacaaa ctgcctgatg attttacagg atgtgtgatt gcttggaatt  8880
ctaataattt agattctaaa gtgggaggaa attacaatta tctgtacaga ctgtttagaa  8940
aatcaaatct gaaacctttt gaaagagata tttcaacaga aatttatcag gctggatcaa  9000
caccttgtaa tggagtggaa ggatttaatt gttattttcc attacagagc tatggatttc  9060
agccaaccaa tggtgtggga tatcagccat atagagtggt ggtgctgtct tttgaactgc  9120
tgcatgcacc tgcaacagtg tgtggaccta aaaaatctac aaatttagtg aaaaataaat  9180
gtgtgaattt taattttaat ggattaacag gaacaggagt gctgacagaa tctaataaaa  9240
aatttctgcc ttttcagcag tttggcagag atattgcaga taccacagat gcagtgagag  9300
atcctcagac attagaaatt ctggatatta caccttgttc ttttgggggt gtgtctgtga  9360
ttacacctgg aacaaataca tctaatcagg tggctgtgct gtatcaggat gtgaattgta  9420
cagaagtgcc agtggcaatt catgcagatc agctgacacc aacatggaga gtgtattcta  9480
caggatctaa tgtgtttcag acaagagcag gatgtctgat tggagcagaa catgtgaata  9540
attcttatga atgtgatatt ccaattggag caggcatttg tgcatcttat cagacacaga  9600
caaattcccc aaggagagca agatctgtgg catctcagtc tattattgca tacaccatgt  9660
ctctgggagc agaaaattct gtggcatatt ctaataattc tattgctatt ccaacaaatt  9720
ttaccatttc tgtgacaaca gaaattttac ctgtgtctat gacaaaaaca tctgtggatt  9780
gtaccatgta catttgtgga gattctacag aatgttctaa tctgctgctg cagtatggat  9840
ctttttgtac acagctgaat agagctttaa caggaattgc tgtggaacag gataaaaata  9900
cacaggaagt gtttgctcag gtgaaacaga tttacaaaac accaccaatt aaagattttg  9960
gaggatttaa ttttagccag attctgcctg atccttctaa accttctaaa agatctttta  10020
ttgaagatct gctgtttaat aaagtgacac tggcagatgc aggatttatt aaacagtatg  10080
gagattgcct gggtgatatt gctgcaagag atctgatttg tgctcagaaa tttaatggac  10140
tgacagtgct gcctcctctg ctgacagatg aaatgattgc tcagtacaca tctgctttac  10200
tggctggaac aattacaagc ggatggacat ttggagctgg agctgctctg cagattcctt  10260
ttgcaatgca gatggcttac agatttaatg gaattggagt gacacagaat gtgttatatg  10320
aaaatcagaa actgattgca aatcagttta attctgcaat tggcaaaatt caggattctc  10380
tgtcttctac agcttctgct ctgggaaaac tgcaggatgt ggtgaatcag aatgcacagg  10440
cactgaatac tctggtgaaa cagctgtcta gcaattttgg ggcaatttct tctgtgctga  10500
atgatattct gtctagactg gatcctcctg aagctgaagt gcagattgat agactgatca  10560
caggaagact gcagtctctg cagacttatg tgacacagca gctgattaga gctgctgaaa  10620
ttagagcttc tgctaatctg gctgctacaa aaatgtctga atgtgtgctg ggacagtcaa  10680
aaagagtgga tttttgtgga aaaggatatc atctgatgtc ttttccacag tctgctccac  10740
atggagtggt gtttttacat gtgacatatg tgccagcaca ggaaaaagaat tttaccacag  10800
caccagcaat ttgtcatgat ggaaaagcac attttccaag agaaggagtg tttgtgtcta  10860
atggaacaca ttggtttgtg acacagagaa atttttatga acctcagatt attacaacag  10920
ataatacatt tgtgtcagga aattgtgatg tggtgattgg aattgtgaat aatacagtgt  10980
atgatccact gcagccagaa ctggattctt ttaaagaaga actggataaa tattttaaaa  11040
atcacacatc tcctgatgtg gatttaggag atatttctgg aatcaatgca tctgtggtga  11100
atattcagaa agaaattgat agactgaatg aagtggccaa aaatctgaat gaatctctga  11160
ttgatctgca ggaacttgga aaatatgaac agtacattaa atggccttgg tacatttggc  11220
ttggatttat tgcaggatta attgcaattg tgatggtgac aattatgtta tgttgtatga  11280
catcatgttg ttcttgttta aaaggatgtt gttcttgtgg aagctgttgt aaatttgatg  11340
aagatgattc tgaacctgtg ttaaaaggag tgaaattgca ttacacatga tgactcgagc  11400
tggtactgca tgcacgcaat gctagctgcc cctttcccgt cctgggtacc ccgagtctcc  11460
cccgacctcg ggtcccaggt atgctcccac ctccacctgc ccactcacc acctctgcta  11520
gttccagaca cctcccaagc acgcagcaat gcagctcaaa acgcttagcc tagccacacc  11580
cccacgggaa acagcagtga ttaaccttta gcaataaacg aaagtttaac taagctatac  11640
taaccccagg gttggtcaat ttcgtgccag ccacaccgcg gccgcatgaa tacagcagca  11700
attggcaagc tgcttacata gaactcgcgg cgattggcat gccgccttaa aatttttatt  11760
ttatttttc ttttctttc cgaatcggat tttgttttta atatttcaaa aaaaaaaaaa  11820
aaaaaaaaaa aaaaaaagca tatgactaaa aaaaaaaaaa aaaaaaaaaa aaaaaaaaaa  11880
aaaaaaaaaa aaaaaaaaaa aaaaaaaaaa aaaaaaa                          11917
```

```
SEQ ID NO: 25           moltype = RNA  length = 11917
FEATURE                 Location/Qualifiers
misc_feature            1..11917
                        note = RBS004.2
source                  1..11917
                        mol_type = other RNA
                        organism = synthetic construct
SEQUENCE: 25
gatgggcggc gcatgagaga agcccagacc aattacctac ccaaaatgga gaaagttcac  60
gttgacatcg aggaagacag cccattcctc agagctttgc agcggagctt cccgcagttt  120
gaggtagaag ccaagcaggt cactgataat gaccatgcta atgccagagc gttttcgcat  180
ctggcttcaa aactgatcga aacggaggtg gacccatccg acacgatcct tgacattgga  240
agtgcgcccg cccgcagaat gtattctaag cacaagtatc attgtatctg tccgatgaga  300
tgtgcggaag atccggacag attgtataag tatgcaacta agctgaagaa aaactgtaag  360
gaaataactg ataaggaatt ggacaagaaa atgaaggagc tcgccgccgt catgagcgac  420
cctgacctgg aaactgagac tatgtgcctc cacgacgacg agtcgtgtcg ctacgaaggg  480
caagtcgctg tttaccagga tgtatacgcg gttgacggac cgacaagtct ctatcaccaa  540
gccaataagg gagttagagt cgcctactgg ataggctttg acaccacccc ttttatgttt  600
aagaacttgg ctggagcata tccatcatac tctaccaact gggccgacga aaccgtgtta  660
acggctcgta acataggcct atgcagctct gacgttatgg agcggtcacg tagagggatg  720
tccattctta gaaagaagta tttgaaacca tccaacaatg ttctattctc tgttggctcg  780
accatctacc acgaaaagag ggacttactg aggagctggc acctgccgtc tgtatttcac  840
ttacgtggca agcaaaatta cacatgtcgg tgtgagacta tagttagttg cgacgggtac  900
gtcgttaaaa gaatagctat cagtccaggc ctgtatggga agccttcagg ctatgctgct  960
acgatgcacc gcgagggatt cttgtgctgc aaagtgacag acacattgaa cggggagagg  1020
gtctcttttc ccgtgtgcac gtatgtgcca gctacattgt gtgaccaaat gactggcata  1080
ctggcaacag atgtcagtgc ggacgacgcg caaaaactgc tggttgggct caaccagcgt  1140
atagtcgtca acggtcgcac ccagagaaac accaatacca tgaaaaatta ccttttgccc  1200
gtagtggccc aggcatttgc taggtgggca aaggaatata aggaagatca agaagatgaa  1260
aggccactag gactacgaga tagacagtta gtcatggggt gttgttgggc ttttagaagg  1320
cacaagataa catctattta taagcgcccg gatacccaaa ccatcatcaa agtgaacagc  1380
gatttccact cattcgtgct gcccaggata ggcagtaaca cattggagat cgggctgaga  1440
acaagaatca ggaaaatgtt agaggagcac aaggagccgt cacctctcat taccgccgag  1500
gacgtacaag aagctaagtg cgcagccgat gaggctaagg aggtgcgtga agccgaggag  1560
ttgcgcgcag ctctaccacc tttggcagct gatgttgagg agcccactct ggaagccgat  1620
gtcgacttga tgttacaaga ggctggggcc ggctcagtgg agacacctcg tggcttgata  1680
aaggttacca gctacgctgg cgaggacaag atcggctctt acgctgtgct ttctccgcag  1740
gctgtactca agagtgaaaa attatcttgc atccaccctc tcgctgaaca agtcatagtg  1800
ataacacact ctggccgaaa agggcgttat gccgtggaac cataccatgg taaagtagtg  1860
gtgccagagg gacatgcaat acccgtccag gactttcaag ctctgagtga aagtgccacc  1920
attgtgtaca acgaacgtga gttcgtaaac aggtacctgc accatattgc cacacatgga  1980
ggagcgctga acactgatga agaatattac aaaactgtca agcccagcga gcacgacggc  2040
gaatacctgt acgacatcga caggaaacag tgcgtcaaga aagagctagt cactgggcta  2100
gggctcacag gcgagctggt cgatcctccc ttccatgaat tcgcctacga gagtctgaga  2160
acacgaccag ccgctcctta ccaagtacca accatagggg tgtatggcgt gccaggatca  2220
ggcaagtctg gcatcattaa aagcgcagtc accaaaaaag atctagtggt gagcgccaag  2280
aaagaaaact gtgcagaaat tataagggac gtcaagaaaa tgaaagggct ggacgtcaat  2340
gccagaactg tggactcagt gctcttgaat ggatgcaaac accccgtaga gaccctgtat  2400
attgacgagg cttttgcttg tcatgcaggt actctcagag cgctcatagc cattataaga  2460
cctaaaaagg cagtgctctg cggagatccc aaacagtgcg gtttttttaa catgatgtgc  2520
ctgaaagtgc attttaacca cgagatttgc acacaagtct tccacaaaag catctctcgc  2580
cgttgcacta aatctgtgac ttcggtcgtc tcaaccttgt tttacgacaa aaaaatgaga  2640
acgacgaatc cgaaagagac taagattgtg attgacacta ccggcagtac caaacctaag  2700
caggacgatc tcattctcac ttgtttcaga gggtgggtga agcagttgca aatagattac  2760
aaaggcaacg aaataatgac ggcagctgcc tctcaagggc tgacccgtaa aggtgtgtat  2820
gccgttcggt acaaggtgaa tgaaaatcct ctgtacgcac ccacctcaga acatgtgaac  2880
gtcctactga cccgcacgga ggaccgcatc gtgtggaaaa cactagccgg cgacccatgg  2940
ataaaaacac tgactgccaa gtaccctggg aatttcactg ccacgataga ggagtggcaa  3000
gcagagcatg atgccatcat gaggcacatc ttggagagac cggaccctac cgacgtcttc  3060
cagaataagg caaacgtgtg ttgggccaag gctttagtgc cggtgctgaa gaccgctggc  3120
atagacatga ccactgaaca atggaacact gtggattatt ttgaaacgga caaagctcac  3180
tcagcagaga tagtattgaa ccaactatgc gtgaggttct ttggactcga tctggactcc  3240
ggtctatttt ctgcacccac tgttccgtta tccattagga ataatcactg ggataactcc  3300
ccgtcgccta acatgtacgg gctgaataaa gaagtggtcc gtcagctctc tcgcaggtac  3360
ccacaactgc ctcgggcagt tgccactggt agagtctatg acatgaacac tggtacactg  3420
cgcaattatg atccgcgcat aaacctagta cctgtaaaca gaagactgcc tcatgcttta  3480
gtcctccacc ataatgaaca cccacagagt gacttttctt cattcgtcag caaattgaag  3540
ggcagaactg tcctggtggt cggggaaaag ttgtccgtcc caggcaaaat ggttgactgg  3600
ttgtcagacc ggcctgaggc taccttcaga gctcggctgg atttaggcat cccaggtgat  3660
gtgcccaaat atgacataat atttgttaat gtgaggaccc catataaata ccatcactat  3720
cagcagtgtg aagaccatgc cattaagcta agcatgttga ccaagaaagc atgtctgcat  3780
ctgaatcccg gcggaacctg tgtcagcata ggttatggtt acgctgacag ggccagcgaa  3840
agcatcattg gtgctatagc gcggcagttc aagttttccc gagtatgcaa accgaaatcc  3900
tcacttgagg agacggaagt tctgtttgta ttcattgggt acgatcgcaa ggcccgtacg  3960
cacaatcctt acaagctatc atcaaccttg accaacattt atacaggttc cagactccac  4020
gaagccggat gtgcaccctc atatcatgtg gtgcgagggg atattgccac ggccaccgaa  4080
ggagtgatta taaatgctgc taacagcaaa ggacaacctg gcggaggggt gtgcggagcg  4140
ctgtataaga aattcccgga aagtttcgat ttacagccga tcgaagtagg aaaagcgcga  4200
```

-continued

```
ctggtcaaag gtgcagctaa acatatcatt catgccgtag gaccaaactt caacaaagtt  4260
tcggaggttg aaggtgacaa acagttggca gaggcttatg agtccatcgc taagattgtc  4320
aacgataaca attacaagtc agtagcgatt ccactgttgt ccaccggcat cttttccggg  4380
aacaaagatc gactaaccca atcattgaac catttgctga cagctttaga caccactgat  4440
gcagatgtag ccatatactg cagggacaag aaatgggaaa tgactctcaa ggaagcagtg  4500
gctaggagag aagcagtgga ggagatatgc atatccgacg attcttcagt gacagaacct  4560
gatgcagagc tggtgagggt gcatcccaag agttctttgg ctggaaggaa gggctacagc  4620
acaagcgatg gcaaaacttt ctcatatttg gaagggacca agtttcacca ggcggccaag  4680
gatatagcag aaattaatgc catgtggccc gttgcaacgg aggccaatga gcaggtatgc  4740
atgtatatcc tcggagaaag catgagcagt attaggtcga aatgccccgt cgaggagtcg  4800
gaagcctcca caccacctag cacgctgcct tgcttgtgca tccatgccat gactccagaa  4860
agagtacagc gcctaaaagc ctcacgtcca gaacaaatta ctgtgtgctc atcctttcca  4920
ttgccgaagt atagaatcac tggtgtgcag aagatccaat gctcccagcc tatattgttc  4980
tcaccgaaag tgcctgcgta tattcatcca aggaagtatc tcgtggaaac accaccggta  5040
gacgagactc cggagccatc ggcagagaac caatccacag aggggacacc tgaacaacca  5100
ccacttataa ccgaggatga gaccaggact agaacgcctg agccgatcat catcgaagaa  5160
gaagaagaag atagcataag tttgctgtca gatggcccga cccaccaggt gctgcaagtc  5220
gaggcagaca ttcacgggcc gccctctgta tctagctcat cctggtccat tcctcatgca  5280
tccgactttg atgtggacag tttatccata cttgacaccc tggagggagc tagcgtgacc  5340
agcggggcaa cgtcagccga gactaactct tacttcgcaa agagtatgga gtttctggcg  5400
cgaccggtgc ctgcgcctcg aacagtattc aggaaccctc cacatcccgc tccgcgcaca  5460
agaacaccgt cacttgcacc cagcagggcc tgctccagaa ccagcctagt ttccaccccg  5520
ccaggcgtga atagggtgat cactagagag gagctcgaag cgcttacccc gtcacgcact  5580
cctagcaggt cggtctccag aaccagcctg gtctccaacc cgccaggcgt aaatagggtg  5640
attacaagag aggagtttga ggcgttcgta gcacaacaac aatgacggtt tgatgcgggt  5700
gcatacatct tttcctccga caccggtcaa gggcatttac aacaaaaatc agtaaggcaa  5760
acggtgctat ccgaagtggt gttggagagg accgaattgg agatttcgta tgccccgcgc  5820
ctcgaccaag aaaaagaaga attactacgc aagaaattac agttaaatcc cacacctgct  5880
aacagaagca gataccagtc caggaaggtg gagaacatga aagccataac agctagacgt  5940
attctgcaag gcctagggca ttatttgaag gcagaaggaa aagtggagtg ctaccgaacc  6000
ctgcatcctg ttcctttgta ttcatctagt gtgaaccgtg ccttttcaag ccccaaggtc  6060
gcagtggaag cctgtaacgc catgttgaaa gagaactttc cgactgtggc ttcttactgt  6120
attattccag agtacgatgc ctatttggac atggttgacg gagcttcatg ctgcttagac  6180
actgccagtt tttgccctgc aaagctgcgc agctttccaa agaaacactc ctatttggaa  6240
cccacaatac gatcggcagt gccttcagcg atccagaaca cgctccagaa cgtcctggca  6300
gctgccacaa aaagaaattg caatgtcacg caaatgagag aattgcccgt attggattcg  6360
gcggccttta atgtggaatg cttcaagaaa tatgcgtgta ataatgaata ttgggaaacg  6420
tttaaagaaa accccatcag gcttactgaa gaaaacgtgg taaattacat taccaaatta  6480
aaaggaccaa aagctgctgc tctttttgcg aagacacata atttgaatat gttgcaggac  6540
ataccaatgg acaggtttgt aatggactta aagagagacg tgaaagtgac tccaggaaca  6600
aaacatactg aagaacggcc caaggtacag gtgatccagg ctgccgatcc gctagcaaca  6660
gcgtatctgt gcggaatcca ccgagagctg gttaggagat taaatgcggt cctgcttccg  6720
aacattcata cactgtttga tatgtcggct gaagactttg acgctattat agccgagcac  6780
ttccagcctg ggattgtgt tctggaaact gacatcgcgt cgtttgataa aagtgaggac  6840
gacgccatgg ctctgaccgc gttaatgatt ctggaagact taggtgtgga cgcagagctg  6900
ttgacgctga ttgaggcggc tttcggcgaa atttcatcaa tacatttgcc cactaaaact  6960
aaatttaaat tcggagccat gatgaaatct ggaatgttcc tcacactgtt tgtgaacaca  7020
gtcattaaca ttgtaatcgc aagcagagtg ttgagagaac ggctaaccgg atcaccatgt  7080
gcagcattca ttggagatga caatatcgtg aaaggagtca aatcggacaa attaatggca  7140
gacaggtgcg ccacctggtt gaatatggaa gtcaagatta tagatgctgt ggtgggcgag  7200
aaagcgcctt atttctgtgg agggtttatt ttgtgtgact ccgtgaccgg cacagcgtgc  7260
cgtgtggcag acccccctaaa aaggctgttt aagctaggca aacctctggc agcagacgat  7320
gaacatgatg atgacaggag aagggcattg catgaggagt caacacgctg gaaccgagtg  7380
ggtattcttt cagagctgtg caaggcagta gaatcaaggt atgaaaccgt aggaacttcc  7440
atcatagtta tggccatgac tactctagct agcagtgtta aatcattcag ctacctgaga  7500
ggggccccta taactctcta cggctaacct gaatggacta cgacatagtc tagtccgcca  7560
agactagtat gttcgtgttc ctggtgctgc tgcctctggt gtccagccag tgtgtgaacc  7620
tgaccaccag aacacagctg cctccagcct acaccaacag ctttaccaga ggcgtgtact  7680
accccgacaa ggtgttcaga tccagcgtgc tgcactctac ccaggacctg ttcctgcctt  7740
tcttcagcaa cgtgacctgg ttccacgcca tccacgtgtc cggcaccaat ggcaccaaga  7800
gattcgacaa ccccgtgctg cccttcaacg acggggtgta ctttgccagc accgagaagt  7860
ccaacatcat cagaggctgg atcttcggca ccacactgga cagcaagacc cagagcctgc  7920
tgatcgtgaa caacgccacc aacgtggtca tcaaagtgtg cgagttccag ttctgcaacg  7980
accccttcct gggcgtctac taccacaaga acaacaagag ctggatggaa agcgagttcc  8040
gggtgtacag cagcgccaac aactgcacct tcgagtacgt gtcccagcct ttcctgatgg  8100
acctggaagg caagcagggc aacttcaaga acctgcgcga gttcgtgttt aagaacatcg  8160
acggctactt caagatctac agcaagcaca cccctatcaa cctcgtgcgg gatctgcctc  8220
agggcttctc tgctctggaa cccctggtgg atctgcccat cggcatcaac atcacccggt  8280
ttcagacact gctggccctg cacagaagct acctgacacc tggcgatagc agcagcggat  8340
ggacagctgg tgccgccgct tactatgtgg gctacctgca gcctagaacc ttcctgctga  8400
agtacaacga gaacggcacc atcaccgacg ccgtggattg tgctctggat cctctgagcg  8460
agacaaagtg caccctgaag tccttcaccg tggaaaaggg catctaccag accagcaact  8520
tccgggtgca gcccaccgaa tccatcgtgc ggttccccaa tatcaccaat ctgtgcccct  8580
tcggcgaggt gttcaatgcc accagattcg cctctgtgta cgcctggaac cggaagcgga  8640
tcagcaattg cgtggccgac tactccgtgc tgtacaactc cgccagcttc agcaccttca  8700
agtgctacgg cgtgtccccct accaagctga acgacctgtg cttcacaaac gtgtacgccg  8760
acagcttcgt gatccgggga gatgaagtgc ggcagattgc ccctggacag acaggcaaga  8820
tcgccgacta caactacaag ctgcccgacg acttcaccgg ctgtgtgatt gcctggaaca  8880
gcaacaacct ggactccaaa gtcggcggca actacaatta cctgtaccgg ctgttccgga  8940
```

-continued

```
agtccaatct gaagcccttc gagcgggaca tctccaccga gatctatcag gccggcagca  9000
ccccttgtaa cggcgtggaa ggcttcaact gctacttccc actgcagtcc tacggctttc  9060
agcccacaaa tggcgtgggc tatcagccct acagagtggt ggtgctgagc ttcgaactgc  9120
tgcatgcccc tgccacagtg tgcggcccta agaaaagcac caatctcgtg aagaacaaat  9180
gcgtgaactt caacttcaac ggcctgaccg gcaccggcgt gctgacagag agcaacaaga  9240
agttcctgcc attccagcag tttggccggg atatcgccga taccacagac gccgttagag  9300
atccccagac actggaaatc ctggacatca ccccttgcag cttcggcgga gtgtctgtga  9360
tcacccctgg caccaacacc agcaatcagg tggcagtgct gtaccaggac gtgaactgta  9420
ccgaagtgcc cgtggccatt cacgccgatc agctgacacc tacatggcgg gtgtactcca  9480
ccggcagcaa tgtgtttcag accagagccg gctgtctgat cggagccgag cacgtgaaca  9540
atagctacga gtgcgacatc cccatcggcg ctggaatctg cgccagctac cagacacaga  9600
caaacagccc tcggagagcc agaagcgtgg ccagccagag catcattgcc tacacaatgt  9660
ctctgggcgc cgagaacagc gtggcctact ccaacaactc tatcgctatc cccaccaact  9720
tcaccatcag cgtgaccaca gagatcctgc ctgtgtccat gaccaagacc agcgtggact  9780
gcaccatgta catctgcggc gattccaccg agtgctccaa cctgctgctg cagtacggca  9840
gcttctgcac ccagctgaat agagccctga cagggatcgc cgtggaacag gacaagaaca  9900
cccaagaggt gttcgcccaa gtgaagcaga tctacaagac ccctcctatc aaggacttcg  9960
gcggcttcaa tttcagccag attctgcccg atcctagcaa gcccagcaag cggagcttca  10020
tcgaggacct gctgttcaac aaagtgacac tggccgacgc cggcttcatc aagcagtatg  10080
gcgattgtct gggcgacatt gccgccaggg atctgatttg cgcccagaag tttaacggac  10140
tgacagtgct gcctcctctg ctgaccgatg agatgatcgc ccagtacaca tctgccctgc  10200
tggccggcac aatcacaagc ggctggacat ttggagcagg cgccgctctg cagatcccct  10260
ttgctatgca gatggcctac cggttcaacg gcatcggagt gacccagaat gtgctgtacg  10320
agaaccagaa gctgatcgcc aaccagttca acagcgccat cggcaagatc caggacagcc  10380
tgagcagcac agcaagcgcc ctgggaaagc tgcaggacgt ggtcaaccag aatgcccagg  10440
cactgaacac cctggtcaag cagctgtcct ccaacttcgg cgccatcagc tctgtgctga  10500
acgatatcct gagcagactg gaccctcctg aggccgaggt gcagatcgac agactgatca  10560
caggcagact gcagagcctc cagacatacg tgacccagca gctgatcaga gccgccgaga  10620
ttagagcctc tgccaatctg gccgccacca agatgtctga gtgtgtgctg ggccagagca  10680
agagagtgga cttttgcggc aagggctacc acctgatgag cttccctcag tctgcccctc  10740
acggcgtggt gtttctgcac gtgacatatg tgcccgctca agagaagaat ttcaccaccg  10800
ctccagccat ctgccacgac ggcaaagccc actttcctag agaaggcgtg ttcgtgtcca  10860
acggcaccca ttggttcgtg acacagcgga acttctacga gccccagatc atcaccaccg  10920
acaacacctt cgtgtctggc aactgcgacg tcgtgatcgg cattgtgaac aataccgtgt  10980
acgaccctct gcagcccgag ctggacagct tcaaagagga actggacaag tactttaaga  11040
accacacaag ccccgacgtg gacctgggcg atatcagcgg aatcaatgcc agcgtcgtga  11100
acatccagaa agagatcgac cggctgaacg aggtggccaa gaatctgaac gagagcctga  11160
tcgacctgca agaactgggg aagtacgagc agtacatcaa gtggccctgg tacatctggc  11220
tgggctttat cgccggactg attgccatcg tgatggtcac aatcatgctg tgttgcatga  11280
ccagctgctg tagctgcctg aagggctgtt gtagctgtgg cagctgctgc aagttcgacg  11340
aggacgattc tgagcccgtg ctgaagggcg tgaaactgca ctacacatga tgactcgagc  11400
tggtactgca tgcacgcaat gctagctgcc cctttcccgt cctgggtacc ccgagtctcc  11460
cccgacctcg ggtcccaggt atgctcccac ctccacctgc ccactcacc acctctgcta  11520
gttccagaca cctcccaagc acgcagcaat gcagctcaaa acgcttagcc tagccacacc  11580
cccacgggaa acagcagtga ttaaccttta gcaataaacg aaagtttaac taagctatac  11640
taaccccagg gttggtcaat ttcgtgccag ccacaccgcg gccgcatgaa tacagcagca  11700
attggcaagc tgcttacata gaactcgcgg cgattggcat gccgccttaa aatttttatt  11760
ttattttttc ttttcttttc cgaatcggat tttgttttta atatttcaaa aaaaaaaaaa  11820
aaaaaaaaaa aaaaaaagca tatgactaaa aaaaaaaaaa aaaaaaaaaa aaaaaaaaaa  11880
aaaaaaaaaa aaaaaaaaaa aaaaaaaaaa aaaaaaa                          11917

SEQ ID NO: 26           moltype = RNA  length = 8896
FEATURE                 Location/Qualifiers
misc_feature            1..8896
                        note = RBS004.3
source                  1..8896
                        mol_type = other RNA
                        organism = synthetic construct
SEQUENCE: 26
gatgggcggc gcatgagaga agcccagacc aattacctac ccaaaatgga gaaagttcac  60
gttgacatcg aggaagacag cccattcctc agagctttgc agcggagctt cccgcagttt  120
gaggtagaag ccaagcaggt cactgataat gaccatgcta atgccagagc gttttcgcat  180
ctggcttcaa aactgatcga aacggaggtg gacccatccg acacgatcct tgacattgga  240
agtgcgcccg cccgcagaat gtattctaag cacaagtatc attgtatctg tccgatgaga  300
tgtgcggaag atccggacag attgtataag tatgcaacta agctgaagaa aaactgtaag  360
gaaataactg ataaggaatt ggacaagaaa atgaaggagc tcgccgccgt catgagcgac  420
cctgacctgg aaactgagac tatgtgcctc cacgacgacg agtcgtgtcg ctacgaaggg  480
caagtcgctg tttaccagga tgtatacgcg gttgacggac cgacaagtct ctatcaccaa  540
gccaataagg gagttagagt cgcctactgg ataggctttg acaccacccc ttttatgttt  600
aagaacttgg ctggagcata tccatcatac tctaccaact gggccgacga aaccgtgtta  660
acggctcgta acataggcct atgcagctct gacgttatgg agcggtcacg tagagggatg  720
tccattctta gaaagaagta tttgaaacca tccaacaatg ttctattctc tgttggctcg  780
accatctacc acgaaaagag ggacttactg aggagctggc acctgccgtc tgtatttcac  840
ttacgtggca agcaaaatta cacatgtcgg tgtgagacta tagttagttg cgacgggtac  900
gtcgttaaaa gaatagctat cagtccaggc ctgtatggga agccttcagg ctatgctgct  960
acgatgcacc gcgagggatt cttgtgctgc aaagtgacag acacattgaa cggggagagg  1020
gtctcttttc ccgtgtgcac gtatgtgcca gctacattgt gtgaccaaat gactggcata  1080
ctggcaacag atgtcagtgc ggacgacgcg caaaaactgc tggttgggct caaccagcgt  1140
atagtcgtca acggtcgcac ccagagaaac accaatacca tgaaaaatta ccttttgccc  1200
```

-continued

```
gtagtggccc aggcatttgc taggtgggca aaggaatata aggaagatca agaagatgaa  1260
aggccactag gactacgaga tagacagtta gtcatggggt gttgttgggc ttttagaagg  1320
cacaagataa catctattta taagcgcccg gatacccaaa ccatcatcaa agtgaacagc  1380
gatttccact cattcgtgct gcccaggata ggcagtaaca cattggagat cgggctgaga  1440
acaagaatca ggaaaatgtt agaggagcac aaggagccgt cacctctcat taccgccgag  1500
gacgtacaag aagctaagtg cgcagccgat gaggctaagg aggtgcgtga agccgaggag  1560
ttgcgcgcag ctctaccacc tttggcagct gatgttgagg agcccactct ggaagccgat  1620
gtcgacttga tgttacaaga ggctggggcc ggctcagtgg agacacctcg tggcttgata  1680
aaggttacca gctacgctgg cgaggacaag atcggctctt acgctgtgct ttctccgcag  1740
gctgtactca agagtgaaaa attatcttgc atccaccctc tcgctgaaca agtcatagtg  1800
ataacacact ctggccgaaa agggcgttat gccgtggaac cataccatgg taaagtagtg  1860
gtgccagagg gacatgcaat acccgtccag gactttcaag ctctgagtga aagtgccacc  1920
attgtgtaca acgaacgtga gttcgtaaac aggtacctgc accatattgc cacacatgga  1980
ggagcgctga acactgatga agaatattac aaaactgtca agcccagcga gcacgacggc  2040
gaatacctgt acgacatcga caggaaacag tgcgtcaaga aagagctagt cactgggcta  2100
gggctcacag gcgagctggt cgatcctccc ttccatgaat tcgcctacga gagtctgaga  2160
acacgaccag ccgctcctta ccaagtacca accatagggg tgtatggcgt gccaggatca  2220
ggcaagtctg gcatcattaa aagcgcagtc accaaaaaag atctagtggt gagcgccaag  2280
aaagaaaact gtgcagaaat tataagggac gtcaagaaaa tgaaagggct ggacgtcaat  2340
gccagaactg tggactcagt gctcttgaat ggatgcaaac accccgtaga gaccctgtat  2400
attgacgagg cttttgcttg tcatgcaggt actctcagag cgctcatagc cattataaga  2460
cctaaaaagg cagtgctctg cggagatccc aaacagtgcg gttttttaa catgatgtgc  2520
ctgaaagtgc attttaacca cgagatttgc acacaagtct tccacaaaag catctctcgc  2580
cgttgcacta aatctgtgac ttcggtcgtc tcaaccttgt tttacgacaa aaaaatgaga  2640
acgacgaatc cgaaagagac taagattgtg attgacacta ccggcagtac caaacctaag  2700
caggacgatc tcattctcac ttgtttcaga gggtgggtga agcagttgca aatagattac  2760
aaaggcaacg aaataatgac ggcagctgcc tctcaagggc tgacccgtaa aggtgtgtat  2820
gccgttcggt acaaggtgaa tgaaaatcct ctgtacgcac ccacctcaga acatgtgaac  2880
gtcctactga cccgcacgga ggaccgcatc gtgtggaaaa cactagccgg cgacccatgg  2940
ataaaaacac tgactgccaa gtaccctggg aatttcactg ccacgataga ggagtggcaa  3000
gcagagcatg atgccatcat gaggcacatc ttggagagac cggaccctac cgacgtcttc  3060
cagaataagg caaacgtgtg ttgggccaag gctttagtgc cggtgctgaa gaccgctggc  3120
atagacatga ccactgaaca atggaacact gtggattatt ttgaaacgga caaagctcac  3180
tcagcagaga tagtattgaa ccaactatgc gtgaggttct ttggactcga tctggactcc  3240
ggtctatttt ctgcacccac tgttccgtta tccattagga ataatcactg ggataactcc  3300
ccgtcgccta acatgtacgg gctgaataaa gaagtggtcc gtcagctctc tcgcaggtac  3360
ccacaactgc ctcgggcagt tgccactggt agagtctatg acatgaacac tggtacactg  3420
cgcaattatg atccgcgcat aaacctagta cctgtaaaca gaagactgcc tcatgcttta  3480
gtcctccacc ataatgaaca cccacagagt gacttttctt cattcgtcag caaattgaag  3540
ggcagaactg tcctggtggt cggggaaaag ttgtccgtcc caggcaaaat ggttgactgg  3600
ttgtcagacc ggcctgaggc taccttcaga gctcggctgg atttaggcat cccaggtgat  3660
gtgcccaaat atgacataat atttgttaat gtgaggaccc catataaata ccatcactat  3720
cagcagtgtg aagaccatgc cattaagcta agcatgttga ccaagaaagc atgtctgcat  3780
ctgaatcccg gcggaacctg tgtcagcata ggttatggtt acgctgacag ggccagcgaa  3840
agcatcattg gtgctatagc gcggcagttc aagttttccc gagtatgcaa accgaaatcc  3900
tcacttgagg agacggaagt tctgtttgta ttcattgggt acgatcgcaa ggcccgtacg  3960
cacaatcctt acaagctatc atcaaccttg accaacattt atacaggttc cagactccac  4020
gaagccggat gtgcaccctc atatcatgtg gtgcgagggg atattgccac ggccaccgaa  4080
ggagtgatta taaatgctgc taacagcaaa ggacaacctg gcggaggggt gtgcggagcg  4140
ctgtataaga aattcccgga aagtttcgat ttacagccga tcgaagtagg aaaagcgcga  4200
ctggtcaaag gtgcagctaa acatatcatt catgccgtag gaccaaactt caacaaagtt  4260
tcggaggttg aaggtgacaa acagttggca gaggcttatg agtccatcgc taagattgtc  4320
aacgataaca attacaagtc agtagcgatt ccactgttgt ccaccggcat cttttccggg  4380
aacaaagatc gactaaccca atcattgaac catttgctga cagctttaga caccactgat  4440
gcagatgtag ccatatactg cagggacaag aaatgggaaa tgactctcaa ggaagcagtg  4500
gctaggagag aagcagtgga ggagatatgc atatccgacg attcttcagt gacagaacct  4560
gatgcagagc tggtgagggt gcatcccaag agttctttgg ctggaaggaa gggctacagc  4620
acaagcgatg gcaaaacttt ctcatatttg gaagggacca agtttcacca ggcggccaag  4680
gatatagcag aaattaatgc catgtggccc gttgcaacgg aggccaatga gcaggtatgc  4740
atgtatatcc tcggagaaag catgagcagt attaggtcga aatgccccgt cgaggagtcg  4800
gaagcctcca caccacctag cacgctgcct tgcttgtgca tccatgccat gactccagaa  4860
agagtacagc gcctaaaagc ctcacgtcca gaacaaatta ctgtgtgctc atcctttcca  4920
ttgccgaagt atagaatcac tggtgtgcag aagatccaat gctcccagcc tatattgttc  4980
tcaccgaaag tgcctgcgta tattcatcca aggaagtatc tcgtggaaac accaccggta  5040
gacgagactc cggagccatc ggcagagaac caatccacag aggggacacc tgaacaacca  5100
ccacttataa ccgaggatga gaccaggact agaacgcctg agccgatcat catcgaagaa  5160
gaagaagaag atagcataag tttgctgtca gatggcccga cccaccaggt gctgcaagtc  5220
gaggcagaca ttcacgggcc gccctctgta tctagctcat cctggtccat tcctcatgca  5280
tccgactttg atgtggacag tttatccata cttgacaccc tggagggagc tagcgtgacc  5340
agcggggcaa cgtcagccga gactaactct tacttcgcaa agagtatgga gtttctggcg  5400
cgaccggtgc ctgcgcctcg aacagtattc aggaaccctc cacatcccgc tccgcgcaca  5460
agaacaccgt cacttgcacc cagcagggcc tgctccagaa ccagcctagt ttccaccccg  5520
ccaggcgtga atagggtgat cactagagag gagctcgaag cgcttacccc gtcacgcact  5580
cctagcaggt cggtctccag aaccagcctg gtctccaacc cgccaggcgt aaatagggtg  5640
attacaagag aggagtttga ggcgttcgta gcacaacaac aatgacggtt tgatgcgggt  5700
gcatacatct tttcctccga caccggtcaa gggcatttac aacaaaaatc agtaaggcaa  5760
acggtgctat ccgaagtggt gttggagagg accgaattgg agatttcgta tgccccgcgc  5820
ctcgaccaag aaaaagaaga attactacgc aagaaattac agttaaatcc cacacctgct  5880
aacagaagca gataccagtc caggaaggtg gagaacatga aagccataac agctagacgt  5940
```

-continued

```
attctgcaag gcctagggca ttatttgaag gcagaaggaa aagtggagtg ctaccgaacc  6000
ctgcatcctg ttcctttgta ttcatctagt gtgaaccgtg ccttttcaag ccccaaggtc  6060
gcagtggaag cctgtaacgc catgttgaaa gagaactttc cgactgtggc ttcttactgt  6120
attattccag agtacgatgc ctatttggac atggttgacg gagcttcatg ctgcttagac  6180
actgccagtt tttgccctgc aaagctgcgc agctttccaa agaaacactc ctatttggaa  6240
cccacaatac gatcggcagt gccttcagcg atccagaaca cgctccagaa cgtcctggca  6300
gctgccacaa aaagaaattg caatgtcacg caaatgagag aattgcccgt attggattcg  6360
gcggcccttta atgtggaatg cttcaagaaa tatgcgtgta ataatgaata ttgggaaacg  6420
tttaaagaaa accccatcag gcttactgaa gaaaacgtgg taaattacat taccaaatta  6480
aaaggaccaa aagctgctgc tctttttgcg aagacacata atttgaatat gttgcaggac  6540
ataccaatgg acaggtttgt aatggactta aagagagacg tgaaagtgac tccaggaaca  6600
aaacatactg aagaacggcc caaggtacag gtgatccagg ctgccgatcc gctagcaaca  6660
gcgtatctgt gcggaatcca ccgagagctg gttaggagat taaatgcggt cctgcttccg  6720
aacattcata cactgtttga tatgtcggct gaagactttg acgctattat agccgagcac  6780
ttccagcctg ggattgtgt tctggaaact gacatcgcgt cgtttgataa aagtgaggac  6840
gacgccatgg ctctgaccgc gttaatgatt ctggaagact taggtgtgga cgcagagctg  6900
ttgacgctga ttgaggcggc tttcggcgaa atttcatcaa tacatttgcc cactaaaact  6960
aaatttaaat tcggagccat gatgaaatct ggaatgttcc tcacactgtt tgtgaacaca  7020
gtcattaaca ttgtaatcgc aagcagagtg ttgagagaac ggctaaccgg atcaccatgt  7080
gcagcattca ttggagatga caatatcgtg aaaggagtca aatcggacaa attaatggca  7140
gacaggtgcg ccacctggtt gaatatggaa gtcaagatta tagatgctgt ggtgggcgag  7200
aaagcgcctt atttctgtgg agggtttatt ttgtgtgact ccgtgaccgg cacagcgtgc  7260
cgtgtggcag accccctaaa aaggctgttt aagctaggca aacctctggc agcagacgat  7320
gaacatgatg atgacaggag aagggcattg catgaggagt caacacgctg gaaccgagtg  7380
ggtattcttt cagagctgtg caaggcagta gaatcaaggt atgaaaccgt aggaacttcc  7440
atcatagtta tggccatgac tactctagct agcagtgtta aatcattcag ctacctgaga  7500
ggggccccta taactctcta cggctaacct gaatggacta cgacatagtc tagtccgcca  7560
agactagtat gtttgtgttt cttgtgctgc tgcctcttgt gtcttctcag tgtgtggtga  7620
gatttccaaa tattacaaat ctgtgtccat ttggagaagt gtttaatgca acaagatttg  7680
catctgtgta tgcatggaat agaaaaagaa tttctaattg tgtggctgat tattctgtgc  7740
tgtataatag tgcttctttt tccacattta aatgttatgg agtgtctcca acaaaattaa  7800
atgatttatg ttttacaaat gtgtatgctg attcttttgt gatcagaggt gatgaagtga  7860
gacagattgc cccccggacag acaggaaaaa ttgctgatta caattacaaa ctgcctgatg  7920
attttacagg atgtgtgatt gcttggaatt ctaataattt agattctaaa gtgggaggaa  7980
attacaatta tctgtacaga ctgtttagaa aatcaaatct gaaacctttt gaaagagata  8040
tttcaacaga aatttatcag gctggatcaa caccttgtaa tggagtggaa ggatttaatt  8100
gttattttcc attacagagc tatggatttc agccaaccaa tggtgtggga tatcagccat  8160
atagagtggt ggtgctgtct tttgaactgc tgcatgcacc tgcaacagtg tgtggaccta  8220
aaggctcccc cggctccggc tccggatctg gttatattcc tgaagctcca agagatgggc  8280
aagcttacgt tcgtaaagat ggcgaatggg tattactttc taccttttta ggccggtccc  8340
tggaggtgct gttccagggc cccggctgat gactcgagct ggtactgcat gcacgcaatg  8400
ctagctgccc ctttcccgtc ctgggtaccc cgagtctccc ccgacctcgg gtcccaggta  8460
tgctcccacc tccacctgcc ccactcacca cctctgctag ttccagacac ctcccaagca  8520
cgcagcaatg cagctcaaaa cgcttagcct agccacaccc ccacgggaaa cagcagtgat  8580
taacctttag caataaacga aagtttaact aagctatact aaccccaggg ttggtcaatt  8640
tcgtgccagc cacaccgcgg ccgcatgaat acagcagcaa ttggcaagct gcttacatag  8700
aactcgcggc gattggcatg ccgccttaaa atttttattt tattttttct ttcttttcc  8760
gaatcggatt ttgtttttaa tatttcaaaa aaaaaaaaaa aaaaaaaaaa aaaaaagcat  8820
atgactaaaa aaaaaaaaaa aaaaaaaaaa aaaaaaaaaa aaaaaaaaaa aaaaaaaaaa  8880
aaaaaaaaaa aaaaaa                                                  8896
```

```
SEQ ID NO: 27          moltype = RNA  length = 9079
FEATURE                Location/Qualifiers
misc_feature           1..9079
                       note = RBS004.4
source                 1..9079
                       mol_type = other RNA
                       organism = synthetic construct
SEQUENCE: 27
gatgggcggc gcatgagaga agcccagacc aattacctac ccaaaatgga gaaagttcac  60
gttgacatcg aggaagacag cccattcctc agagctttgc agcggagctt cccgcagttt  120
gaggtagaag ccaagcaggt cactgataat gaccatgcta atgccagagc gttttcgcat  180
ctggcttcaa aactgatcga aacggaggtg gacccatccg acacgatcct tgacattgga  240
agtgcgcccg cccgcagaat gtattctaag cacaagtatc attgtatctg tccgatgaga  300
tgtgcggaag atccggacag attgtataag tatgcaacta agctgaagaa aaactgtaag  360
gaaataactg ataaggaatt ggacaagaaa atgaaggagc tcgccgccgt catgagcgac  420
cctgacctgg aaactgagac tatgtgcctc cacgacgacg agtcgtgtcg ctacgaaggg  480
caagtcgctg tttaccagga tgtatacgcg gttgacggac cgacaagtct ctatcaccaa  540
gccaataagg gagttagagt cgcctactgg ataggctttg acaccacccc ttttatgttt  600
aagaacttgg ctggagcata tccatcatac tctaccaact gggccgacga aaccgtgtta  660
acggctcgta acataggcct atgcagctct gacgttatgg agcggtcacg tagagggatg  720
tccattctta gaaagaagta tttgaaacca tccaacaatg ttctattctc tgttggctcg  780
accatctacc acgaaaagag ggacttactg aggagctggc acctgccgtc tgtatttcac  840
ttacgtggca agcaaaatta cacatgtcgg tgtgagacta tagttagttg cgacgggtac  900
gtcgttaaaa gaatagctat cagtccaggc ctgtatggga agccttcagg ctatgctgct  960
acgatgcacc gcgagggatt cttgtgctgc aaagtgacag acacattgaa cggggagagg  1020
gtctcttttc ccgtgtgcac gtatgtgcca gctacattgt gtgaccaaat gactggcata  1080
ctggcaacag atgtcagtgc ggacgacgcg caaaaactgc tggttgggct caaccagcgt  1140
atagtcgtca acggtcgcac ccagagaaac accaatacca tgaaaaatta ccttttgccc  1200
```

```
gtagtggccc aggcatttgc taggtgggca aaggaatata aggaagatca agaagatgaa  1260
aggccactag gactacgaga tagacagtta gtcatggggt gttgttgggc ttttagaagg  1320
cacaagataa catctattta taagcgcccg gatacccaaa ccatcatcaa agtgaacagc  1380
gatttccact cattcgtgct gcccaggata ggcagtaaca cattggagat cgggctgaga  1440
acaagaatca ggaaaatgtt agaggagcac aaggagccgt cacctctcat taccgccgag  1500
gacgtacaag aagctaagtg cgcagccgat gaggctaagg aggtgcgtga agccgaggag  1560
ttgcgcgcag ctctaccacc tttggcagct gatgttgagg agcccactct ggaagccgat  1620
gtcgacttga tgttacaaga ggctggggcc ggctcagtgg agacacctcg tggcttgata  1680
aaggttacca gctacgctgg cgaggacaag atcggctctt acgctgtgct ttctccgcag  1740
gctgtactca agagtgaaaa attatcttgc atccaccctc tcgctgaaca agtcatagtg  1800
ataacacact ctggccgaaa agggcgttat gccgtggaac cataccatgg taaagtagtg  1860
gtgccagagg gacatgcaat acccgtccag gactttcaag ctctgagtga aagtgccacc  1920
attgtgtaca acgaacgtga gttcgtaaac aggtacctgc accatattgc cacacatgga  1980
ggagcgctga acactgatga agaatattac aaaactgtca agcccagcga gcacgacggc  2040
gaatacctgt acgacatcga caggaaacag tgcgtcaaga aagagctagt cactgggcta  2100
gggctcacag gcgagctggt cgatcctccc ttccatgaat tcgcctacga gagtctgaga  2160
acacgaccag ccgctcctta ccaagtacca accatagggg tgtatggcgt gccaggatca  2220
ggcaagtctg gcatcattaa aagcgcagtc accaaaaaag atctagtggt gagcgccaag  2280
aaagaaaact gtgcagaaat tataagggac gtcaagaaaa tgaaagggct ggacgtcaat  2340
gccagaactg tggactcagt gctcttgaat ggatgcaaac accccgtaga gaccctgtat  2400
attgacgagg cttttgcttg tcatgcaggt actctcagag cgctcatagc cattataaga  2460
cctaaaaagg cagtgctctg cggagatccc aaacagtgcg gtttttttaa catgatgtgc  2520
ctgaaagtgc attttaacca cgagatttgc acacaagtct tccacaaaag catctctcgc  2580
cgttgcacta aatctgtgac ttcggtcgtc tcaaccttgt tttacgacaa aaaaatgaga  2640
acgacgaatc cgaaagagac taagattgtg attgacacta ccggcagtac caaacctaag  2700
caggacgatc tcattctcac ttgtttcaga gggtgggtga agcagttgca aatagattac  2760
aaaggcaacg aaataatgac ggcagctgcc tctcaagggc tgacccgtaa aggtgtgtat  2820
gccgttcggt acaaggtgaa tgaaaatcct ctgtacgcac ccacctcaga acatgtgaac  2880
gtcctactga cccgcacgga ggaccgcatc gtgtggaaaa cactagccgg cgacccatgg  2940
ataaaaacac tgactgccaa gtaccctggg aatttcactg ccacgataga ggagtggcaa  3000
gcagagcatg atgccatcat gaggcacatc ttggagagac cggaccctac cgacgtcttc  3060
cagaataagg caaacgtgtg ttgggccaag gctttagtgc cggtgctgaa gaccgctggc  3120
atagacatga ccactgaaca atggaacact gtggattatt ttgaaacgga caaagctcac  3180
tcagcagaga tagtattgaa ccaactatgc gtgaggttct ttggactcga tctggactcc  3240
ggtctatttt ctgcacccac tgttccgtta tccattagga ataatcactg ggataactcc  3300
ccgtcgccta acatgtacgg gctgaataaa gaagtggtcc gtcagctctc tcgcaggtac  3360
ccacaactgc ctcgggcagt tgccactggt agagtctatg acatgaacac tggtacactg  3420
cgcaattatg atccgcgcat aaacctagta cctgtaaaca gaagactgcc tcatgcttta  3480
gtcctccacc ataatgaaca cccacagagt gacttttctt cattcgtcag caaattgaag  3540
ggcagaactg tcctggtggt cggggaaaag ttgtccgtcc caggcaaaat ggttgactgg  3600
ttgtcagacc ggcctgaggc taccttcaga gctcggctgg atttaggcat cccaggtgat  3660
gtgcccaaat atgacataat atttgttaat gtgaggaccc catataaata ccatcactat  3720
cagcagtgtg aagaccatgc cattaagcta agcatgttga ccaagaaagc atgtctgcat  3780
ctgaatcccg gcggaacctg tgtcagcata ggttatggtt acgctgacag ggccagcgaa  3840
agcatcattg gtgctatagc gcggcagttc aagttttccc gagtatgcaa accgaaatcc  3900
tcacttgagg agacggaagt tctgtttgta ttcattgggt acgatcgcaa ggcccgtacg  3960
cacaatcctt acaagctatc atcaaccttg accaacattt atacaggttc cagactccac  4020
gaagccggat gtgcaccctc atatcatgtg gtgcgagggg atattgccac ggccaccgaa  4080
ggagtgatta taaatgctgc taacagcaaa ggacaacctg gcggaggggt gtgcggagcg  4140
ctgtataaga aattcccgga aagtttcgat ttacagccga tcgaagtagg aaaagcgcga  4200
ctggtcaaag gtgcagctaa acatatcatt catgccgtag gaccaaactt caacaaagtt  4260
tcggaggttg aaggtgacaa acagttggca gaggcttatg agtccatcgc taagattgtc  4320
aacgataaca attacaagtc agtagcgatt ccactgttgt ccaccggcat cttttccggg  4380
aacaaagatc gactaaccca atcattgaac catttgctga cagctttaga caccactgat  4440
gcagatgtag ccatatactg cagggacaag aaatgggaaa tgactctcaa ggaagcagtg  4500
gctaggagag aagcagtgga ggagatatgc atatccgacg attcttcagt gacagaacct  4560
gatgcagagc tggtgagggt gcatcccaag agttctttgg ctggaaggaa gggctacagc  4620
acaagcgatg gcaaaacttt ctcatatttg gaagggacca agtttcacca ggcggccaag  4680
gatatagcag aaattaatgc catgtggccc gttgcaacgg aggccaatga gcaggtatgc  4740
atgtatatcc tcggagaaag catgagcagt attaggtcga aatgccccgt cgaggagtcg  4800
gaagcctcca caccacctag cacgctgcct tgcttgtgca tccatgccat gactccagaa  4860
agagtacagc gcctaaaagc ctcacgtcca gaacaaatta ctgtgtgctc atcctttcca  4920
ttgccgaagt atagaatcac tggtgtgcag aagatccaat gctcccagcc tatattgttc  4980
tcaccgaaag tgcctgcgta tattcatcca aggaagtatc tcgtggaaac accaccggta  5040
gacgagactc cggagccatc ggcagagaac caatccacag aggggacacc tgaacaacca  5100
ccacttataa ccgaggatga gaccaggact agaacgcctg agccgatcat catcgaagaa  5160
gaagaagaag atagcataag tttgctgtca gatggcccga cccaccaggt gctgcaagtc  5220
gaggcagaca ttcacgggcc gccctctgta tctagctcat cctggtccat tcctcatgca  5280
tccgactttg atgtggacag tttatccata cttgacaccc tggagggagc tagcgtgacc  5340
agcggggcaa cgtcagccga gactaactct tacttcgcaa agagtatgga gtttctggcg  5400
cgaccggtgc ctgcgcctcg aacagtattc aggaaccctc cacatcccgc tccgcgcaca  5460
agaacaccgt cacttgcacc cagcagggcc tgctccagaa ccagcctagt ttccaccccg  5520
ccaggcgtga atagggtgat cactagagag gagctcgaag cgcttacccc gtcacgcact  5580
cctagcaggt cggtctccag aaccagcctg gtctccaacc cgccaggcgt aaatagggtg  5640
attacaagag aggagtttga ggcgttcgta gcacaacaac aatgacggtt tgatgcgggt  5700
gcatacatct tttcctccga caccggtcaa gggcatttac aacaaaaatc agtaaggcaa  5760
acggtgctat ccgaagtggt gttggagagg accgaattgg agatttcgta tgccccgcgc  5820
ctcgaccaag aaaaagaaga attactacgc aagaaattac agttaaatcc cacacctgct  5880
aacagaagca gataccagtc caggaaggtg gagaacatga aagccataac agctagacgt  5940
```

```
attctgcaag gcctagggca ttatttgaag gcagaaggaa aagtggagtg ctaccgaacc  6000
ctgcatcctg ttcctttgta ttcatctagt gtgaaccgtg ccttttcaag ccccaaggtc  6060
gcagtggaag cctgtaacgc catgttgaaa gagaactttc cgactgtggc ttcttactgt  6120
attattccag agtacgatgc ctatttggac atggttgacg gagcttcatg ctgcttagac  6180
actgccagtt tttgccctgc aaagctgcgc agctttccaa agaaacactc ctatttggaa  6240
cccacaatac gatcggcagt gccttcagcg atccagaaca cgctccagaa cgtcctggca  6300
gctgccacaa aaagaaattg caatgtcacg caaatgagag aattgcccgt attggattcg  6360
gcggccttta atgtggaatg cttcaagaaa tatgcgtgta ataatgaata ttgggaaacg  6420
tttaaagaaa accccatcag gcttactgaa gaaaacgtgg taaattacat taccaaatta  6480
aaaggaccaa aagctgctgc tctttttgcg aagacacata atttgaatat gttgcaggac  6540
ataccaatgg acaggtttgt aatggactta aagagagacg tgaaagtgac tccaggaaca  6600
aaacatactg aagaacggcc caaggtacag gtgatccagg ctgccgatcc gctagcaaca  6660
gcgtatctgt gcggaatcca ccgagagctg gttaggagat taaatgcggt cctgcttccg  6720
aacattcata cactgtttga tatgtcggct gaagactttg acgctattat agccgagcac  6780
ttccagcctg gggattgtgt tctggaaact gacatcgcgt cgtttgataa aagtgaggac  6840
gacgccatgg ctctgaccgc gttaatgatt ctggaagact taggtgtgga cgcagagctg  6900
ttgacgctga ttgaggcggc tttcggcgaa atttcatcaa tacatttgcc cactaaaact  6960
aaatttaaat tcggagccat gatgaaatct ggaatgttcc tcacactgtt tgtgaacaca  7020
gtcattaaca ttgtaatcgc aagcagagtg ttgagagaac ggctaaccgg atcaccatgt  7080
gcagcattca ttggagatga caatatcgtg aaaggagtca aatcggacaa attaatggca  7140
gacaggtgcg ccacctggtt gaatatggaa gtcaagatta tagatgctgt ggtgggcgag  7200
aaagcgcctt atttctgtgg agggtttatt ttgtgtgact ccgtgaccgg cacagcgtgc  7260
cgtgtggcag accccctaaa aaggctgttt aagctaggca aacctctggc agcagacgat  7320
gaacatgatg atgacaggag aagggcattg catgaggagt caacacgctg gaaccgagtg  7380
ggtattcttt cagagctgtg caaggcagta gaatcaaggt atgaaaccgt aggaacttcc  7440
atcatagtta tggccatgac tactctagct agcagtgtta aatcattcag ctacctgaga  7500
ggggccccta taactctcta cggctaacct gaatggacta cgacatagtc tagtccgcca  7560
agactagtat gtttgtgttt cttgtgctgc tgcctcttgt gtcttctcag tgtgtggtga  7620
gatttccaaa tattacaaat ctgtgtccat ttggagaagt gtttaatgca acaagatttg  7680
catctgtgta tgcatggaat agaaaaagaa tttctaattg tgtggctgat tattctgtgc  7740
tgtataatag tgcttctttt tccacattta aatgttatgg agtgtctcca acaaaattaa  7800
atgatttatg ttttacaaat gtgtatgctg attcttttgt gatcagaggt gatgaagtga  7860
gacagattgc ccccggacag acaggaaaaa ttgctgatta caattacaaa ctgcctgatg  7920
attttacagg atgtgtgatt gcttggaatt ctaataattt agattctaaa gtgggaggaa  7980
attacaatta tctgtacaga ctgtttagaa aatcaaatct gaaacctttt gaaagagata  8040
tttcaacaga aatttatcag gctggatcaa caccttgtaa tggagtggaa ggatttaatt  8100
gttattttcc attacagagc tatggatttc agccaaccaa tggtgtggga tatcagccat  8160
atagagtggt ggtgctgtct tttgaactgc tgcatgcacc tgcaacagtg tgtggaccta  8220
aaggctcccc cggctccggc tccggatctg gttatattcc tgaagctcca agagatgggc  8280
aagcttacgt tcgtaaagat ggcgaatggg tattactttc tacctttta ggaagcggca  8340
gcggatctga acagtacatt aaatggcctt ggtacatttg gcttggattt attgcaggat  8400
taattgcaat tgtgatggtg acaattatgt tatgttgtat gacatcatgt tgttcttgtt  8460
taaaaggatg ttgttcttgt ggaagctgtt gtaaatttga tgaagatgat tctgaacctg  8520
tgttaaaagg agtgaaattg cattacacat gatgactcga gctggtactg catgcacgca  8580
atgctagctg cccctttccc gtcctgggta ccccgagtct cccccgacct cgggtcccag  8640
gtatgctccc acctccacct gccccactca ccacctctgc tagttccaga cacctcccaa  8700
gcacgcagca atgcagctca aaacgcttag cctagccaca cccccacggg aaacagcagt  8760
gattaacctt tagcaataaa cgaaagttta actaagctat actaacccca gggttggtca  8820
atttcgtgcc agccacaccg cggccgcatg aatacagcag caattggcaa gctgcttaca  8880
tagaactcgc ggcgattggc atgccgcctt aaaattttta ttttattttt tcttttcttt  8940
tccgaatcgg attttgtttt taatatttca aaaaaaaaaa aaaaaaaaaa aaaaaaaaag  9000
catatgacta aaaaaaaaaa aaaaaaaaaa aaaaaaaaaa aaaaaaaaaa aaaaaaaaaa  9060
aaaaaaaaaa aaaaaaaaa                                              9079
```

```
SEQ ID NO: 28          moltype = AA  length = 327
FEATURE                Location/Qualifiers
REGION                 1..327
                       note = Vaccine Antigen
source                 1..327
                       mol_type = protein
                       organism = synthetic construct
SEQUENCE: 28
MFVFLVLLPL VSSQCVVRFP NITNLCPFGE VFNATRFASV YAWNRKRISN CVADYSVLYN  60
SASFSTFKCY GVSPTKLNDL CFTNVYADSF VIRGDEVRQI APGQTGKIAD YNYKLPDDFT  120
GCVIAWNSNN LDSKVGGNYN YLYRLFRKSN LKPFERDIST EIYQAGSTPC NGVEGFNCYF  180
PLQSYGFQPT NGVGYQPYRV VVLSFELLHA PATVCGPKGS PGSGSGSGYI PEAPRDGQAY  240
VRKDGEWVLL STFLGSGSGS EQYIKWPWYI WLGFIAGLIA IVMVTIMLCC MTSCCSCLKG  300
CCSCGSCCKF DEDDSEPVLK GVKLHYT                                     327
```

```
SEQ ID NO: 29          moltype = AA  length = 311
FEATURE                Location/Qualifiers
REGION                 1..311
                       note = BNT162b3c
source                 1..311
                       mol_type = protein
                       organism = synthetic construct
SEQUENCE: 29
MFVFLVLLPL VSSQCVNLTV RFPNITNLCP FGEVFNATRF ASVYAWNRKR ISNCVADYSV  60
LYNSASFSTF KCYGVSPTKL NDLCFTNVYA DSFVIRGDEV RQIAPGQTGK IADYNYKLPD  120
```

-continued

```
DFTGCVIAWN SNNLDSKVGG NYNYLYRLFR KSNLKPFERD ISTEIYQAGS TPCNGVEGFN  180
CYFPLQSYGF QPTNGVGYQP YRVVVLSFEL LHAPATVCGP KGSPGSGSGS GYIPEAPRDG  240
QAYVRKDGEW VLLSTFLGSG SGSEQYIKWP WYIWLGFIAG LIAIVMVTIM LCCMTSCCSC  300
LKGCCSCGSC C                                                       311

SEQ ID NO: 30          moltype = RNA  length = 1397
FEATURE                Location/Qualifiers
misc_feature           1..1397
                       note = BNT162b3c
source                 1..1397
                       mol_type = other RNA
                       organism = synthetic construct
SEQUENCE: 30
agaataaact agtattcttc tggtccccac agactcagag agaacccgcc accatgtttg  60
tgtttcttgt gctgctgcct cttgtgtctt ctcagtgtgt gaatttgaca gtgagatttc  120
caaatattac aaatctgtgt ccatttggag aagtgtttaa tgcaacaaga tttgcatctg  180
tgtatgcatg gaatagaaaa agaatttcta attgtgtggc tgattattct gtgctgtata  240
atagtgcttc tttttccaca tttaaatgtt atggagtgtc tccaacaaaa ttaaatgatt  300
tatgttttac aaatgtgtat gctgattctt ttgtgatcag aggtgatgaa gtgagacaga  360
ttgcccccgg acagacagga aaaattgctg attacaatta caaactgcct gatgatttta  420
caggatgtgt gattgcttgg aattctaata atttagattc taaagtggga ggaaattaca  480
attatctgta cagactgttt agaaaatcaa atctgaaacc ttttgaaaga gatatttcaa  540
cagaaattta tcaggctgga tcaacacctt gtaatggagt ggaaggattt aattgttatt  600
ttccattaca gagctatgga tttcagccaa ccaatggtgt gggatatcag ccatatagag  660
tggtggtgct gtcttttgaa ctgctgcatg cacctgcaac agtgtgtgga cctaaaggct  720
cccccggctc cggctccgga tctggttata ttcctgaagc tccaagagat gggcaagctt  780
acgttcgtaa agatggcgaa tgggtattac tttctacctt tttaggaagc ggcagcggat  840
ctgaacagta cattaaatgg ccttggtaca tttggcttgg atttattgca ggattaattg  900
caattgtgat ggtgacaatt atgttatgtt gtatgacatc atgttgttct tgtttaaaag  960
gatgttgttc ttgtggaagc tgttgttgat gactcgagct ggtactgcat gcacgcaatg  1020
ctagctgccc ctttcccgtc ctgggtaccc cgagtctccc ccgacctcgg gtcccaggta  1080
tgctcccacc tccacctgcc ccactcacca cctctgctag ttccagacac ctcccaagca  1140
cgcagcaatg cagctcaaaa cgcttagcct agccacaccc ccacgggaaa cagcagtgat  1200
taacctttag caataaacga aagtttaact aagctatact aaccccaggg ttggtcaatt  1260
tcgtgccagc cacaccctgg agctagcaaa aaaaaaaaaa aaaaaaaaaa aaaaaaagca  1320
tatgactaaa aaaaaaaaaa aaaaaaaaaa aaaaaaaaaa aaaaaaaaaa aaaaaaaaaa  1380
aaaaaaaaaa aaaaaaa                                                 1397

SEQ ID NO: 31          moltype = AA  length = 314
FEATURE                Location/Qualifiers
REGION                 1..314
                       note = BNT162b3d
source                 1..314
                       mol_type = protein
                       organism = synthetic construct
SEQUENCE: 31
MDWIWRILFL VGAATGAHSQ MQVRFPNITN LCPFGEVFNA TRFASVYAWN RKRISNCVAD  60
YSVLYNSASF STFKCYGVSP TKLNDLCFTN VYADSFVIRG DEVRQIAPGQ TGKIADYNYK  120
LPDDFTGCVI AWNSNNLDSK VGGNYNYLYR LFRKSNLKPF ERDISTEIYQ AGSTPCNGVE  180
GFNCYFPLQS YGFQPTNGVG YQPYRVVVLS FELLHAPATV CGPKGSPGSG SGSGYIPEAP  240
RDGQAYVRKD GEWVLLSTFL GSGSGSEQYI KWPWYIWLGF IAGLIAIVMV TIMLCCMTSC  300
CSCLKGCCSC GSCC                                                    314

SEQ ID NO: 32          moltype = RNA  length = 1406
FEATURE                Location/Qualifiers
misc_feature           1..1406
                       note = BNT162b3d
source                 1..1406
                       mol_type = other RNA
                       organism = synthetic construct
SEQUENCE: 32
agaataaact agtattcttc tggtccccac agactcagag agaacccgcc accatggatt  60
ggatttggag aatcctgttc ctcgtgggag ccgctacagg agcccactcc cagatgcagg  120
tgagatttcc aaatattaca aatctgtgtc catttggaga agtgtttaat gcaacaagat  180
ttgcatctgt gtatgcatgg aatagaaaaa gaatttctaa ttgtgtggct gattattctg  240
tgctgtataa tagtgcttct ttttccacat ttaaatgtta tggagtgtct ccaacaaaat  300
taaatgattt atgttttaca aatgtgtatg ctgattcttt tgtgatcaga ggtgatgaag  360
tgagacagat tgcccccgga cagacaggaa aaattgctga ttacaattac aaactgcctg  420
atgattttac aggatgtgtg attgcttgga attctaataa tttagattct aaagtgggag  480
gaaattacaa ttatctgtac agactgttta gaaaatcaaa tctgaaacct tttgaaagag  540
atatttcaac agaaatttat caggctggat caacaccttg taatggagtg gaaggattta  600
attgttattt tccattacag agctatggat ttcagccaac caatggtgtg ggatatcagc  660
catatagagt ggtggtgctg tcttttgaac tgctgcatgc acctgcaaca gtgtgtggac  720
ctaaaggctc ccccggctcc ggctccggat ctggttatat tcctgaagct ccaagagatg  780
ggcaagctta cgttcgtaaa gatggcgaat gggtattact ttctaccttt ttaggaagcg  840
gcagcggatc tgaacagtac attaaatggc cttggtacat ttggcttgga tttattgcag  900
gattaattgc aattgtgatg gtgacaatta tgttatgttg tatgacatca tgttgttctt  960
gtttaaaagg atgttgttct tgtggaagct gttgttgatg actcgagctg gtactgcatg  1020
cacgcaatgc tagctgcccc tttcccgtcc tgggtacccc gagtctcccc cgacctcggg  1080
```

-continued

```
tcccaggtat gctcccacct ccacctgccc cactcaccac ctctgctagt tccagacacc  1140
tcccaagcac gcagcaatgc agctcaaaac gcttagccta gccacacccc cacgggaaac  1200
agcagtgatt aacctttagc aataaacgaa agtttaacta agctatacta accccagggt  1260
tggtcaattt cgtgccagcc acaccctgga gctagcaaaa aaaaaaaaaa aaaaaaaaaa  1320
aaaaaagcat atgactaaaa aaaaaaaaaa aaaaaaaaaa aaaaaaaaaa aaaaaaaaaa  1380
aaaaaaaaaa aaaaaaaaaa aaaaaa                                        1406

SEQ ID NO: 33          moltype = AA  length = 9
FEATURE                Location/Qualifiers
REGION                 1..9
                       note = Linker
source                 1..9
                       mol_type = protein
                       organism = synthetic construct
SEQUENCE: 33
GSPGSGSGS                                                           9

SEQ ID NO: 34          moltype = AA  length = 6
FEATURE                Location/Qualifiers
REGION                 1..6
                       note = Linker
source                 1..6
                       mol_type = protein
                       organism = synthetic construct
SEQUENCE: 34
GSGSGS                                                              6

SEQ ID NO: 35          moltype = AA  length = 9
FEATURE                Location/Qualifiers
REGION                 1..9
                       note = Epitope
source                 1..9
                       mol_type = protein
                       organism = synthetic construct
SEQUENCE: 35
YLQPRTFLL                                                           9

SEQ ID NO: 36          moltype = AA  length = 9
FEATURE                Location/Qualifiers
REGION                 1..9
                       note = Epitope
source                 1..9
                       mol_type = protein
                       organism = synthetic construct
SEQUENCE: 36
RLQSLQTYV                                                           9

SEQ ID NO: 37          moltype = AA  length = 9
FEATURE                Location/Qualifiers
REGION                 1..9
                       note = Epitope
source                 1..9
                       mol_type = protein
                       organism = synthetic construct
SEQUENCE: 37
QYIKWPWYI                                                           9

SEQ ID NO: 38          moltype = AA  length = 9
FEATURE                Location/Qualifiers
REGION                 1..9
                       note = Epitope
source                 1..9
                       mol_type = protein
                       organism = synthetic construct
SEQUENCE: 38
NYNYLYRLF                                                           9

SEQ ID NO: 39          moltype = AA  length = 10
FEATURE                Location/Qualifiers
REGION                 1..10
                       note = Epitope
source                 1..10
                       mol_type = protein
                       organism = synthetic construct
SEQUENCE: 39
KWPWYIWLGF                                                          10

SEQ ID NO: 40          moltype = AA  length = 9
FEATURE                Location/Qualifiers
```

```
REGION                1..9
                      note = Epitope
source                1..9
                      mol_type = protein
                      organism = synthetic construct
SEQUENCE: 40
QPTESIVRF                                                    9

SEQ ID NO: 41         moltype = AA  length = 9
FEATURE               Location/Qualifiers
REGION                1..9
                      note = Epitope
source                1..9
                      mol_type = protein
                      organism = synthetic construct
SEQUENCE: 41
IPFAMQMAY                                                    9

SEQ ID NO: 42         moltype = AA  length = 9
FEATURE               Location/Qualifiers
REGION                1..9
                      note = Epitope
source                1..9
                      mol_type = protein
                      organism = synthetic construct
SEQUENCE: 42
LPFNDGVYF                                                    9

SEQ ID NO: 43         moltype = AA  length = 9
FEATURE               Location/Qualifiers
REGION                1..9
                      note = Epitope
source                1..9
                      mol_type = protein
                      organism = synthetic construct
SEQUENCE: 43
GVYFASTEK                                                    9

SEQ ID NO: 44         moltype = AA  length = 9
FEATURE               Location/Qualifiers
REGION                1..9
                      note = Epitope
source                1..9
                      mol_type = protein
                      organism = synthetic construct
SEQUENCE: 44
CVADYSVLY                                                    9

SEQ ID NO: 45         moltype = AA  length = 9
FEATURE               Location/Qualifiers
REGION                1..9
                      note = Epitope
source                1..9
                      mol_type = protein
                      organism = synthetic construct
SEQUENCE: 45
KCYGVSPTK                                                    9

SEQ ID NO: 46         moltype = AA  length = 9
FEATURE               Location/Qualifiers
REGION                1..9
                      note = Epitope
source                1..9
                      mol_type = protein
                      organism = synthetic construct
SEQUENCE: 46
FQPTNGVGY                                                    9

SEQ ID NO: 47         moltype = AA  length = 9
FEATURE               Location/Qualifiers
REGION                1..9
                      note = Epitope
source                1..9
                      mol_type = protein
                      organism = synthetic construct
SEQUENCE: 47
GTHWFVTQR                                                    9

SEQ ID NO: 48         moltype = AA  length = 9
```

-continued

```
FEATURE                Location/Qualifiers
REGION                 1..9
                       note = Epitope
source                 1..9
                       mol_type = protein
                       organism = synthetic construct
SEQUENCE: 48
VYDPLQPEL                                                        9

SEQ ID NO: 49          moltype = AA  length = 1270
FEATURE                Location/Qualifiers
REGION                 1..1270
                       note = Vaccine sequence
source                 1..1270
                       mol_type = protein
                       organism = synthetic construct
SEQUENCE: 49
MFVFLVLLPL VSSQCVNLTT RTQLPPAYTN SFTRGVYYPD KVFRSSVLHS TQDLFLPFFS  60
NVTWFHVISG TNGTKRFDNP VLPFNDGVYF ASIEKSNIIR GWIFGTTLDS KTQSLLIVNN  120
ATNVVIKVCE FQFCNDPFLD HKNNKSWMES EFRVYSSANN CTFEYVSQPF LMDLEGKQGN  180
FKNLREFVFK NIDGYFKIYS KHTPIIVREP EDLPQGFSAL EPLVDLPIGI NITRFQTLLA  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFDEVFN ATRFASVYAW NRKRISNCVA  360
DYSVLYNLAP FFTFKCYGVS PTKLNDLCFT NVYADSFVIR GDEVRQIAPG QTGNIADYNY  420
KLPDDFTGCV IAWNSNKLDS KVSGNYNYLY RLFRKSNLKP FERDISTEIY QAGNKPCNGV  480
AGFNCYFPLR SYSFRPTYGV GHQPYRVVVL SFELLHAPAT VCGPKKSTNL VKNKCVNFNF  540
NGLKGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTKSHRR ARSVASQSII AYTMSLGAEN SVAYSNNSIA IPTNFTISVT  720
TEILPVSMTK TSVDCTMYIC GDSTECSNLL LQYGSFCTQL KRALTGIAVE QDKNTQEVFA  780
QVKQIYKTPP IKYFGGFNFS QILPDPSKPS KRSFIEDLLF NKVTLADAGF IKQYGDCLGD  840
IAARDLICAQ KFKGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN HNAQALNTLV  960
KQLSSKFGAI SSVLNDIFSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                       1270

SEQ ID NO: 50          moltype = RNA  length = 3816
FEATURE                Location/Qualifiers
misc_feature           1..3816
                       note = Coding sequence
source                 1..3816
                       mol_type = other RNA
                       organism = synthetic construct
SEQUENCE: 50
atgttcgtgt tcctggtgct gctgcctctg gtgtccagcc agtgtgtgaa cctgaccacc  60
agaacacagc tgcctccagc ctacaccaac agctttacca gaggcgtgta ctaccccgac  120
aaggtgttca gatccagcgt gctgcactct acccaggacc tgttcctgcc tttcttcagc  180
aacgtgacct ggttccacgt gatctccggc accaatggca ccaagagatt cgacaacccc  240
gtgctgccct tcaacgacgg ggtgtacttt gccagcatcg agaagtccaa catcatcaga  300
ggctggatct tcggcaccac actggacagc aagacccaga gcctgctgat cgtgaacaac  360
gccaccaacg tggtcatcaa agtgtgcgag ttccagttct gcaacgaccc cttcctgggc  420
cacaagaaca acaagagctg gatggaaagc gagttccggg tgtacagcag cgccaacaac  480
tgcaccttcg agtacgtgtc ccagcctttc ctgatggacc tggaaggcaa gcagggcaac  540
ttcaagaacc tgcgcgagtt cgtgtttaag aacatcgacg gctacttcaa gatctacagc  600
aagcacaccc ctatcatcgt gagagagccc gaggatctgc ctcagggctt ctctgctctg  660
gaacccctgg tggatctgcc catcggcatc aacatcaccc ggtttcagac actgctggcc  720
ctgcacagaa gctacctgac acctggcgat agcagcagcg gatggacagc tggtgccgcc  780
gcttactatg tgggctacct gcagcctaga accttcctgc tgaagtacaa cgagaacggc  840
accatcaccg acgccgtgga ttgtgctctg gatcctctga gcgagacaaa gtgcaccctg  900
aagtccttca ccgtggaaaa gggcatctac cagaccagca acttccgggt gcagcccacc  960
gaatccatcg tgcggttccc caatatcacc aatctgtgcc ccttcgacga ggtgttcaat  1020
gccaccagat tcgcctctgt gtacgcctgg aaccggaagc ggatcagcaa ttgcgtggcc  1080
gactactccg tgctgtacaa cctggccccc ttcttcacct tcaagtgcta cggcgtgtcc  1140
cctaccaagc tgaacgacct gtgcttcaca aacgtgtacg ccgacagctt cgtgatccgg  1200
ggagatgaag tgcggcagat tgcccctgga cagacaggca acatcgccga ctacaactac  1260
aagctgcccg acgacttcac cggctgtgtg attgcctgga acagcaacaa gctggactcc  1320
aaagtcagcg gcaactacaa ttacctgtac cggctgttcc ggaagtccaa tctgaagccc  1380
ttcgagcggg acatctccac cgagatctat caggccggca acaagccttg taacggcgtg  1440
gccggcttca actgctactt cccactgcgg tcctacagct ttaggcccac atacggcgtg  1500
ggccaccagc cctacagagt ggtggtgctg agcttcgaac tgctgcatgc ccctgccaca  1560
gtgtgcggcc ctaagaaaag caccaatctc gtgaagaaca aatgcgtgaa cttcaacttc  1620
aacggcctga agggcaccgg cgtgctgaca gagagcaaca agaagttcct gccattccag  1680
cagtttggcc gggatatcgc cgataccaca gacgccgtta gagatcccca gacactggaa  1740
atcctggaca tcaccccttg cagcttcggc ggagtgtctg tgatcacccc tggcaccaac  1800
accagcaatc aggtggcagt gctgtaccag ggcgtgaact gtaccgaagt gcccgtggcc  1860
```

-continued

```
attcacgccg atcagctgac acctacatgg cgggtgtact ccaccggcag caatgtgttt  1920
cagaccagag ccggctgtct gatcggagcc gagtacgtga acaatagcta cgagtgcgac  1980
atccccatcg gcgctggaat ctgcgccagc taccagacac agacaaagag ccaccggaga  2040
gccagaagcg tggccagcca gagcatcatt gcctacacaa tgtctctggg cgccgagaac  2100
agcgtggcct actccaacaa ctctatcgct atccccacca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aaaagagccc tgacagggat cgccgtggaa caggacaaga acacccaaga ggtgttcgcc  2340
caagtgaagc agatctacaa gacccctcct atcaagtact tcggcggctt caatttcagc  2400
cagattctgc ccgatcctag caagcccagc aagcggagct tcatcgagga cctgctgttc  2460
aacaaagtga cactggccga cgccggcttc atcaagcagt atggcgattg tctgggcgac  2520
attgccgcca gggatctgat ttgcgcccag aagtttaagg gactgacagt gctgcctcct  2580
ctgctgaccg atgagatgat cgcccagtac acatctgccc tgctggccgg cacaatcaca  2640
agcggctgga catttggagc aggcgccgct ctgcagatcc cctttgctat gcagatggcc  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctgggaa agctgcagga cgtggtcaac cacaatgccc aggcactgaa caccctggtc  2880
aagcagctgt cctccaagtt cggcgccatc agctctgtgc tgaacgatat cttcagcaga  2940
ctggaccctc ctgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctgggccaga gcaagagagt ggacttttgc  3120
ggcaagggct accacctgat gagcttccct cagtctgccc ctcacggcgt ggtgtttctg  3180
cacgtgacat atgtgcccgc tcaagagaag aatttcacca ccgctccagc catctgccac  3240
gacggcaaag cccactttcc tagagaaggc gtgttcgtgt ccaacggcac ccattggttc  3300
gtgacacagc ggaacttcta cgagccccag atcatcacca ccgacaacac cttcgtgtct  3360
ggcaactgcg acgtcgtgat cggcattgtg aacaataccg tgtacgaccc tctgcagccc  3420
gagctggaca gcttcaaaga ggaactggac aagtacttta agaaccacac aagccccgac  3480
gtggacctgg gcgatatcag cggaatcaat gccagcgtcg tgaacatcca gaaagagatc  3540
gaccggctga acgaggtggc caagaatctg aacgagagcc tgatcgacct gcaagaactg  3600
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
gtgctgaagg gcgtgaaact gcactacaca tgatga                            3816

SEQ ID NO: 51          moltype = RNA  length = 4274
FEATURE                Location/Qualifiers
misc_feature           1..4274
                       note = Vaccine RNA
source                 1..4274
                       mol_type = other RNA
                       organism = synthetic construct
SEQUENCE: 51
agaataaact agtattcttc tggtccccac agactcagag agaacccgcc accatgttcg  60
tgttcctggt gctgctgcct ctggtgtcca gccagtgtgt gaacctgacc accagaacac  120
agctgcctcc agcctacacc aacagcttta ccagaggcgt gtactacccc gacaaggtgt  180
tcagatccag cgtgctgcac tctacccagg acctgttcct gcctttcttc agcaacgtga  240
cctggttcca cgtgatctcc ggcaccaatg gcaccaagag attcgacaac cccgtgctgc  300
ccttcaacga cggggtgtac tttgccagca tcgagaagtc caacatcatc agaggctgga  360
tcttcggcac cacactggac agcaagaccc agagcctgct gatcgtgaac aacgccacca  420
acgtggtcat caaagtgtgc gagttccagt tctgcaacga ccccttcctg gaccacaaga  480
acaacaagag ctggatggaa agcgagttcc gggtgtacag cagcgccaac aactgcacct  540
tcgagtacgt gtcccagcct ttcctgatgg acctggaagg caagcagggc aacttcaaga  600
acctgcgcga gttcgtgttt aagaacatcg acggctactt caagatctac agcaagcaca  660
cccctatcat cgtgagagag cccgaggatc tgcctcaggg cttctctgct ctggaacccc  720
tggtggatct gcccatcggc atcaacatca cccggtttca gacactgctg gccctgcaca  780
gaagctacct gacacctggc gatagcagca gcggatggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca  1020
tcgtgcggtt ccccaatatc accaatctgt gccccttcga cgaggtgttc aatgccacca  1080
gattcgcctc tgtgtacgcc tggaaccgga agcggatcag caattgcgtg gccgactact  1140
ccgtgctgta caacctggcc cccttcttca ccttcaagtg ctacggcgtg tcccctacca  1200
agctgaacga cctgtgcttc acaaacgtgt acgccgacag cttcgtgatc cggggagatg  1260
aagtgcggca gattgcccct ggacagacag gcaacatcgc cgactacaac tacaagctgc  1320
ccgacgactt caccggctgt gtgattgcct ggaacagcaa caagctggac tccaaagtca  1380
gcggcaacta caattacctg taccggctgt tccggaagtc caatctgaag cccttcgagc  1440
gggacatctc caccgagatc tatcaggccg gcaacaagcc ttgtaacggc gtggccggct  1500
tcaactgcta cttcccactg cggtcctaca gctttaggcc cacatacggc gtgggccacc  1560
agccctacag agtggtggtg ctgagcttcg aactgctgca tgcccctgcc acagtgtgcg  1620
gccctaagaa aagcaccaat ctcgtgaaga acaaatgcgt gaacttcaac ttcaacggcc  1680
tgaagggcac cggcgtgctg acagagagca acaagaagtt cctgccattc cagcagtttg  1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagccggctg tctgatcgga gccgagtacg tgaacaatag ctacgagtgc gacatcccca  2040
tcggcgctgg aatctgcgcc agctaccaga cacagacaaa gagccaccgg agagccagaa  2100
gcgtggccag ccagagcatc attgcctaca caatgtctct gggcgccgag aacagcgtgg  2160
cctactccaa caactctatc gctatcccca ccaacttcac catcagcgtg accacagaga  2220
```

-continued

```
tcctgcctgt gtccatgacc aagaccagcg tggactgcac catgtacatc tgcggcgatt  2280
ccaccgagtg ctccaacctg ctgctgcagt acggcagctt ctgcacccag ctgaaaagag  2340
ccctgacagg gatcgccgtg gaacaggaca agaacaccca agaggtgttc gcccaagtga  2400
agcagatcta caagacccct cctatcaagt acttcggcgg cttcaatttc agccagattc  2460
tgcccgatcc tagcaagccc agcaagcgga gcttcatcga ggacctgctg ttcaacaaag  2520
tgacactggc cgacgccggc ttcatcaagc agtatggcga ttgtctgggc gacattgccg  2580
ccagggatct gatttgcgcc cagaagttta agggactgac agtgctgcct cctctgctga  2640
ccgatgagat gatcgcccag tacacatctg ccctgctggc cggcacaatc acaagcggct  2700
ggacatttgg agcaggcgcc gctctgcaga tcccctttgc tatgcagatg gcctaccggt  2760
tcaacggcat cggagtgacc cagaatgtgc tgtacgagaa ccagaagctg atcgccaacc  2820
agttcaacag cgccatcggc aagatccagg acagcctgag cagcacagca agcgccctgg  2880
gaaagctgca ggacgtggtc aaccacaatg cccaggcact gaacaccctg gtcaagcagc  2940
tgtcctccaa gttcggcgcc atcagctctg tgctgaacga tatcttcagc agactggacc  3000
ctcctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctgggcc agagcaagag agtggacttt tgcggcaagg  3180
gctaccacct gatgagcttc cctcagtctg cccctcacgg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccaccgacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcga cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgac tcgagctggt actgcatgca cgcaatgcta  3900
gctgcccctt tcccgtcctg ggtaccccga gtctcccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cgggaaacag cagtgattaa  4080
cctttagcaa taaacgaaag tttaactaag ctatactaac cccagggttg gtcaatttcg  4140
tgccagccac accctggagc tagcaaaaaa aaaaaaaaaa aaaaaaaaaa aaaagcatat  4200
gactaaaaaa aaaaaaaaaa aaaaaaaaaa aaaaaaaaaa aaaaaaaaaa aaaaaaaaaa  4260
aaaaaaaaaa aaaa                                                    4274

SEQ ID NO: 52          moltype = AA  length = 1270
FEATURE                Location/Qualifiers
REGION                 1..1270
                       note = Vaccine sequence
source                 1..1270
                       mol_type = protein
                       organism = synthetic construct
SEQUENCE: 52
MFVFLVLLPL VSSQCVNLTT RTQLPPAYTN SFTRGVYYPD KVFRSSVLHS TQDLFLPFFS  60
NVTWFHVISG TNGTKRFDNP VLPFNDGVYF ASIEKSNIIR GWIFGTTLDS KTQSLLIVNN  120
ATNVVIKVCE FQFCNDPFLD HKNNKSWMES EFRVYSSANN CTFEYVSQPF LMDLEGKQGN  180
FKNLREFVFK NIDGYFKIYS KHTPIIVREP EDLPQGFSAL EPLVDLPIGI NITRFQTLLA  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFDEVFN ATRFASVYAW NRKRISNCVA  360
DYSVLYNLAP FFTFKCYGVS PTKLNDLCFT NVYADSFVIR GDEVRQIAPG QTGKIADYNY  420
KLPDDFTGCV IAWNSNNLDS KVGGNYNYLY RLFRKSNLKP FERDISTEIY QAGNKPCNGV  480
AGFNCYFPLR SYSFRPTYGV GHQPYRVVVL SFELLHAPAT VCGPKKSTNL VKNKCVNFNF  540
NGLKGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTKSHRR ARSVASQSII AYTMSLGAEN SVAYSNNSIA IPTNFTISVT  720
TEILPVSMTK TSVDCTMYIC GDSTECSNLL LQYGSFCTQL KRALTGIAVE QDKNTQEVFA  780
QVKQIYKTPP IKYFGGFNFS QILPDPSKPS KRSFIEDLLF NKVTLADAGF IKQYGDCLGD  840
IAARDLICAQ KFKGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN HNAQALNTLV  960
KQLSSKFGAI SSVLNDIFSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                         1270

SEQ ID NO: 53          moltype = RNA  length = 3816
FEATURE                Location/Qualifiers
misc_feature           1..3816
                       note = Coding sequence
source                 1..3816
                       mol_type = other RNA
                       organism = synthetic construct
SEQUENCE: 53
atgttcgtgt tcctggtgct gctgcctctg gtgtccagcc agtgtgtgaa cctgaccacc  60
agaacacagc tgcctccagc ctacaccaac agctttacca gaggcgtgta ctaccccgac  120
aaggtgttca gatccagcgt gctgcactct acccaggacc tgttcctgcc tttcttcagc  180
aacgtgacct ggttccacgt gatctccggc accaatggca ccaagagatt cgacaacccc  240
```

-continued gtgctgccct tcaacgacgg ggtgtacttt gccagcatcg agaagtccaa catcatcaga 300
ggctggatct tcggcaccac actggacagc aagacccaga gcctgctgat cgtgaacaac 360
gccaccaacg tggtcatcaa agtgtgcgag ttccagttct gcaacgaccc cttcctggac 420
cacaagaaca acaagagctg gatggaaagc gagttccggg tgtacagcag cgccaacaac 480
tgcaccttcg agtacgtgtc ccagcctttc ctgatggacc tggaaggcaa gcagggcaac 540
ttcaagaacc tgcgcgagtt cgtgtttaag aacatcgacg gctacttcaa gatctacagc 600
aagcacaccc ctatcatcgt gagagagccc gaggatctgc ctcagggctt ctctgctctg 660
gaacccctgg tggatctgcc catcggcatc aacatcaccc ggtttcagac actgctggcc 720
ctgcacagaa gctacctgac acctggcgat agcagcagcg gatggacagc tggtgccgcc 780
gcttactatg tgggctacct gcagcctaga accttcctgc tgaagtacaa cgagaacggc 840
accatcaccg acgccgtgga ttgtgctctg gatcctctga gcgagacaaa gtgcaccctg 900
aagtccttca ccgtggaaaa gggcatctac cagaccagca acttccgggt gcagcccacc 960
gaatccatcg tgcggttccc caatatcacc aatctgtgcc ccttcgacga ggtgttcaat 1020
gccaccagat tcgcctctgt gtacgcctgg aaccggaagc ggatcagcaa ttgcgtggcc 1080
gactactccg tgctgtacaa cctggccccc ttcttcacct tcaagtgcta cggcgtgtcc 1140
cctaccaagc tgaacgacct gtgcttcaca aacgtgtacg ccgacagctt cgtgatccgg 1200
ggagatgaag tgcggcagat tgcccctgga cagacaggca agatcgccga ctacaactac 1260
aagctgcccg acgacttcac cggctgtgtg attgcctgga acagcaacaa cctggactcc 1320
aaagtcggcg gcaactacaa ttacctgtac cggctgttcc ggaagtccaa tctgaagccc 1380
ttcgagcggg acatctccac cgagatctat caggccggca acaagccttg taacggcgtg 1440
gccggcttca actgctactt cccactgcgg tcctacagct ttaggcccac atacggcgtg 1500
ggccaccagc cctacagagt ggtggtgctg agcttcgaac tgctgcatgc ccctgccaca 1560
gtgtgcggcc ctaagaaaag caccaatctc gtgaagaaca aatgcgtgaa cttcaacttc 1620
aacggcctga agggcaccgg cgtgctgaca gagagcaaca agaagttcct gccattccag 1680
cagtttggcc gggatatcgc cgataccaca gacgccgtta gagatcccca gacactggaa 1740
atcctggaca tcacccctg cagcttcggc ggagtgtctg tgatcacccc tggcaccaac 1800
accagcaatc aggtggcagt gctgtaccag ggcgtgaact gtaccgaagt gcccgtggcc 1860
attcacgccg atcagctgac acctacatgg cgggtgtact ccaccggcag caatgtgttt 1920
cagaccagag ccggctgtct gatcggagcc gagtacgtga acaatagcta cgagtgcgac 1980
atccccatcg gcgctggaat ctgcgccagc taccagacac agacaaagag ccaccggaga 2040
gccagaagcg tggccagcca gagcatcatt gcctacacaa tgtctctggg cgccgagaac 2100
agcgtggcct actccaacaa ctctatcgct atccccacca acttcaccat cagcgtgacc 2160
acagagatcc tgcctgtgtc catgaccaag accagcgtgg actgcaccat gtacatctgc 2220
ggcgattcca ccgagtgctc caacctgctg ctgcagtacg gcagcttctg cacccagctg 2280
aaaagagccc tgacagggat cgccgtggaa caggacaaga acacccaaga ggtgttcgcc 2340
caagtgaagc agatctacaa gacccctcct atcaagtact tcggcggctt caatttcagc 2400
cagattctgc ccgatcctag caagcccagc aagcggagct tcatcgagga cctgctgttc 2460
aacaaagtga cactggccga cgccggcttc atcaagcagt atggcgattg tctgggcgac 2520
attgccgcca gggatctgat ttgcgcccag aagtttaagg gactgacagt gctgcctcct 2580
ctgctgaccg atgagatgat cgcccagtac acatctgccc tgctggccgg cacaatcaca 2640
agcggctgga catttggagc aggcgccgct ctgcagatcc cctttgctat gcagatggcc 2700
taccggttca acggcatcgg agtgacccag aatgtgctgt acgagaacca gaagctgatc 2760
gccaaccagt tcaacagcgc catcggcaag atccaggaca gcctgagcag cacagcaagc 2820
gccctgggaa agctgcagga cgtggtcaac cacaatgccc aggcactgaa caccctggtc 2880
aagcagctgt cctccaagtt cggcgccatc agctctgtgc tgaacgatat cttcagcaga 2940
ctggaccctc ctgaggccga ggtgcagatc gacagactga tcacaggcag actgcagagc 3000
ctccagacat acgtgaccca gcagctgatc agagccgccg agattagagc ctctgccaat 3060
ctggccgcca ccaagatgtc tgagtgtgtg ctgggccaga gcaagagagt ggacttttgc 3120
ggcaagggct accacctgat gagcttccct cagtctgccc ctcacggcgt ggtgtttctg 3180
cacgtgacat atgtgcccgc tcaagagaag aatttcacca ccgctccagc catctgccac 3240
gacggcaaag cccactttcc tagagaaggc gtgttcgtgt ccaacggcac ccattggttc 3300
gtgacacagc ggaacttcta cgagccccag atcatcacca ccgacaacac cttcgtgtct 3360
ggcaactgcg acgtcgtgat cggcattgtg aacaataccg tgtacgaccc tctgcagccc 3420
gagctggaca gcttcaaaga ggaactggac aagtacttta agaaccacac aagccccgac 3480
gtggacctgg gcgatatcag cggaatcaat gccagcgtcg tgaacatcca gaaagagatc 3540
gaccggctga acgaggtggc caagaatctg aacgagagcc tgatcgacct gcaagaactg 3600
ggaagtacg agcagtacat caagtggccc tggtacatct ggctgggctt tatcgccgga 3660
ctgattgcca tcgtgatggt cacaatcatg ctgtgttgca tgaccagctg ctgtagctgc 3720
ctgaagggct gttgtagctg tggcagctgc tgcaagttcg acgaggacga ttctgagccc 3780
gtgctgaagg gcgtgaaact gcactacaca tgatga 3816

SEQ ID NO: 54 moltype = RNA length = 4274
FEATURE Location/Qualifiers
misc_feature 1..4274
note = Vaccine RNA
source 1..4274
mol_type = other RNA
organism = synthetic construct
SEQUENCE: 54
agaataaact agtattcttc tggtccccac agactcagag agaacccgcc accatgttcg 60
tgttcctggt gctgctgcct ctggtgtcca gccagtgtgt gaacctgacc accagaacac 120
agctgcctcc agcctacacc aacagcttta ccagaggcgt gtactacccc gacaaggtgt 180
tcagatccag cgtgctgcac tctacccagg acctgttcct gcctttcttc agcaacgtga 240
cctggttcca cgtgatctcc ggcaccaatg gcaccaagag attcgacaac cccgtgctgc 300
ccttcaacga cggggtgtac tttgccagca tcgagaagtc caacatcatc agaggctgga 360
tcttcggcac cacactggac agcaagaccc agagcctgct gatcgtgaac aacgccacca 420
acgtggtcat caaagtgtgc gagttccagt tctgcaacga ccccttcctg gaccacaaga 480
acaacaagag ctggatggaa agcgagttcc gggtgtacag cagcgccaac aactgcacct 540
tcgagtacgt gtcccagcct ttcctgatgg acctggaagg caagcagggc aacttcaaga 600

-continued

```
acctgcgcga gttcgtgttt aagaacatcg acggctactt caagatctac agcaagcaca  660
cccctatcat cgtgagagag cccgaggatc tgcctcaggg cttctctgct ctggaacccc  720
tggtggatct gcccatcggc atcaacatca cccggtttca gacactgctg gccctgcaca  780
gaagctacct gacacctggc gatagcagca gcggatggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca  1020
tcgtgcggtt ccccaatatc accaatctgt gccccttcga cgaggtgttc aatgccacca  1080
gattcgcctc tgtgtacgcc tggaaccgga agcggatcag caattgcgtg gccgactact  1140
ccgtgctgta caacctggcc cccttcttca ccttcaagtg ctacggcgtg tcccctacca  1200
agctgaacga cctgtgcttc acaaacgtgt acgccgacag cttcgtgatc cggggagatg  1260
aagtgcggca gattgcccct ggacagacag gcaagatcgc cgactacaac tacaagctgc  1320
ccgacgactt caccggctgt gtgattgcct ggaacagcaa caacctggac tccaaagtcg  1380
gcggcaacta caattacctg taccggctgt tccggaagtc caatctgaag cccttcgagc  1440
gggacatctc caccgagatc tatcaggccg gcaacaagcc ttgtaacggc gtggccggct  1500
tcaactgcta cttcccactg cggtcctaca gctttaggcc cacatacggc gtgggccacc  1560
agccctacag agtggtggtg ctgagcttcg aactgctgca tgcccctgcc acagtgtgcg  1620
gccctaagaa aagcaccaat ctcgtgaaga acaaatgcgt gaacttcaac ttcaacggcc  1680
tgaagggcac cggcgtgctg acagagagca acaagaagtt cctgccattc cagcagtttg  1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagccggctg tctgatcgga gccgagtacg tgaacaatag ctacgagtgc gacatcccca  2040
tcggcgctgg aatctgcgcc agctaccaga cacagacaaa gagccaccgg agagccagaa  2100
gcgtggccag ccagagcatc attgcctaca caatgtctct gggcgccgag aacagcgtgg  2160
cctactccaa caactctatc gctatcccca ccaacttcac catcagcgtg accacagaga  2220
tcctgcctgt gtccatgacc aagaccagcg tggactgcac catgtacatc tgcggcgatt  2280
ccaccgagtg ctccaacctg ctgctgcagt acggcagctt ctgcacccag ctgaaaagag  2340
ccctgacagg gatcgccgtg gaacaggaca agaacaccca agaggtgttc gcccaagtga  2400
agcagatcta caagacccct cctatcaagt acttcggcgg cttcaatttc agccagattc  2460
tgcccgatcc tagcaagccc agcaagcgga gcttcatcga ggacctgctg ttcaacaaag  2520
tgacactggc cgacgccggc ttcatcaagc agtatggcga ttgtctgggc gacattgccg  2580
ccagggatct gatttgcgcc cagaagttta agggactgac agtgctgcct cctctgctga  2640
ccgatgagat gatcgcccag tacacatctg ccctgctggc cggcacaatc acaagcggct  2700
ggacatttgg agcaggcgcc gctctgcaga tccccttTgc tatgcagatg gcctaccggt  2760
tcaacggcat cggagtgacc cagaatgtgc tgtacgagaa ccagaagctg atcgccaacc  2820
agttcaacag cgccatcggc aagatccagg acagcctgag cagcacagca agcgccctgg  2880
gaaagctgca ggacgtggtc aaccacaatg cccaggcact gaacaccctg gtcaagcagc  2940
tgtcctccaa gttcggcgcc atcagctctg tgctgaacga tatcttcagc agactggacc  3000
ctcctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctgggcc agagcaagag agtggacttt tgcggcaagg  3180
gctaccacct gatgagcttc cctcagtctg cccctcacgg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccaccgacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcga cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgac tcgagctggt actgcatgca cgcaatgcta  3900
gctgcccctt tcccgtcctg ggtaccccga gtctcccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cgggaaacag cagtgattaa  4080
cctttagcaa taaacgaaag tttaactaag ctatactaac cccagggttg gtcaatttcg  4140
tgccagccac accctggagc tagcaaaaaa aaaaaaaaaa aaaaaaaaaa aaaagcatat  4200
gactaaaaaa aaaaaaaaaa aaaaaaaaaa aaaaaaaaaa aaaaaaaaaa aaaaaaaaaa  4260
aaaaaaaaaa aaaa                                                    4274

SEQ ID NO: 55          moltype = AA  length = 1270
FEATURE                Location/Qualifiers
source                 1..1270
                       mol_type = protein
                       organism = synthetic construct
SEQUENCE: 55
MFVFLVLLPL VSSQCVNFTT RTQLPPAYTN SFTRGVYYPD KVFRSSVLHS TQDLFLPFFS  60
NVTWFHAIHV SGTNGTKRFA NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRGLPQGF SALEPLVDLP IGINITRFQT  240
LHISYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFGEVFN ATRFASVYAW NRKRISNCVA  360
DYSVLYNSAS FSTFKCYGVS PTKLNDLCFT NVYADSFVIR GDEVRQIAPG QTGNIADYNY  420
KLPDDFTGCV IAWNSNNLDS KVGGNYNYLY RLFRKSNLKP FERDISTEIY QAGSTPCNGV  480
KGFNCYFPLQ SYGFQPTYGV GYQPYRVVVL SFELLHAPAT VCGPKKSTNL VKNKCVNFNF  540
NGLTGTGVLT ESNKKFLPFQ QFGRDIADTT DAVRDPQTLE ILDITPCSFG GVSVITPGTN  600
```

```
TSNQVAVLYQ GVNCTEVPVA IHADQLTPTW RVYSTGSNVF QTRAGCLIGA EHVNNSYECD  660
IPIGAGICAS YQTQTNSPRR ARSVASQSII AYTMSLGVEN SVAYSNNSIA IPTNFTISVT  720
TEILPVSMTK TSVDCTMYIC GDSTECSNLL LQYGSFCTQL NRALTGIAVE QDKNTQEVFA  780
QVKQIYKTPP IKDFGGFNFS QILPDPSKPS KRSFIEDLLF NKVTLADAGF IKQYGDCLGD  840
IAARDLICAQ KFNGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN QNAQALNTLV  960
KQLSSNFGAI SSVLNDILSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                         1270

SEQ ID NO: 56           moltype = RNA  length = 3817
FEATURE                 Location/Qualifiers
source                  1..3817
                        mol_type = other RNA
                        organism = synthetic construct
SEQUENCE: 56
atgttcgtgt tcctggtgct gctgcctctg gtgtccagcc agtgtgtgaa cttcaccacc  60
agaacacagc tgcctccagc ctacaccaac agctttacca gaggcgtgta ctaccccgac  120
aaggtgttca gatccagcgt gctgcactct acccaggacc tgttcctgcc tttcttcagc  180
aacgtgacct ggttccacgc catccacgtg tccggcacca atggcaccaa gagattcgcc  240
aaccccgtgc tgcccttcaa cgacggggtg tactttgcca gcaccgagaa gtccaacatc  300
atcagaggct ggatcttcgg caccacactg gacagcaaga cccagagcct gctgatcgtg  360
aacaacgcca ccaacgtggt catcaaagtg tgcgagttcc agttctgcaa cgaccccttc  420
ctgggcgtct actaccacaa gaacaacaag agctggatgg aaagcgagtt ccgggtgtac  480
agcagcgcca acaactgcac cttcgagtac gtgtcccagc ctttcctgat ggacctggaa  540
ggcaagcagg gcaacttcaa gaacctgcgc gagttcgtgt ttaagaacat cgacggctac  600
ttcaagatct acagcaagca cacccctatc aacctcgtgc ggggcctgcc tcagggcttc  660
tctgctctgg aacccctggt ggatctgccc atcggcatca acatcacccg gtttcagaca  720
ctgcacatca gctacctgac acctggcgat agcagcagcg gatggacagc tggtgccgcc  780
gcttactatg tgggctacct gcagcctaga accttcctgc tgaagtacaa cgagaacggc  840
accatcaccg acgccgtgga ttgtgctctg gatcctctga gcgagacaaa gtgcaccctg  900
aagtccttca ccgtggaaaa gggcatctac cagaccagca acttccgggt gcagcccacc  960
gaatccatcg tgcggttccc caatatcacc aatctgtgcc ccttcggcga ggtgttcaat  1020
gccaccagat tcgcctctgt gtacgcctgg aaccggaagc ggatcagcaa ttgcgtggcc  1080
gactactccg tgctgtacaa ctccgccagc ttcagcacct tcaagtgcta cggcgtgtcc  1140
cctaccaagc tgaacgacct gtgcttcaca aacgtgtacg ccgacagctt cgtgatccgg  1200
ggagatgaag tgcggcagat tgcccctgga cagacaggca acatcgccga ctacaactac  1260
aagctgcccg acgacttcac cggctgtgtg attgcctgga acagcaacaa cctggactcc  1320
aaagtcggcg gcaactacaa ttacctgtac cggctgttcc ggaagtccaa tctgaagccc  1380
ttcgagcggg acatctccac cgagatctat caggccggca gcaccccttg taacggcgtg  1440
aagggcttca actgctactt cccactgcag tcctacggct ttcagcccac atacggcgtg  1500
ggctatcagc cctacagagt ggtggtgctg agcttcgaac tgctgcatgc ccctgccaca  1560
gtgtgcggcc ctaagaaaag caccaatctc gtgaagaaca aatgcgtgaa cttcaacttc  1620
aacggcctga ccggcaccgg cgtgctgaca gagagcaaca agaagttcct gccattccag  1680
cagtttggcc gggatatcgc cgataccaca gacgccgtta gagatcccca gacactggaa  1740
atcctggaca tcacccttg cagcttcggc ggagtgtctg tgatcacccc tggcaccaac  1800
accagcaatc aggtggcagt gctgtaccag ggcgtgaact gtaccgaagt gcccgtggcc  1860
attcacgccg atcagctgac acctacatgg cgggtgtact ccaccggcag caatgtgttt  1920
cagaccagag ccggctgtct gatcggagcc gagcacgtga acaatagcta cgagtgcgac  1980
atccccatcg gcgctggaat ctgcgccagc taccagacac agacaaacag ccctcggaga  2040
gccagaagcg tggccagcca gagcatcatt gcctacacaa tgtctctggg cgtcgagaac  2100
agcgtggcct actccaacaa ctctatcgct atccccacca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aatagagccc tgacagggat cgccgtggaa caggacaaga acacccaaga ggtgttcgcc  2340
caagtgaagc agatctacaa gacccctcct atcaaggact tcggcggctt caatttcagc  2400
cagattctgc ccgatcctag caagcccagc aagcggagct tcatcgagga cctgctgttc  2460
aacaaagtga cactggccga cgccggcttc atcaagcagt atggcgattg tctgggcgac  2520
attgccgcca gggatctgat ttgcgcccag aagtttaacg gactgacagt gctgcctcct  2580
ctgctgaccg atgagatgat cgcccagtac acatctgccc tgctggccgg cacaatcaca  2640
agcggctgga catttggagc aggcgccgct ctgcagatcc cctttgctat gcagatggcc  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctgggaa agctgcagga cgtggtcaac cagaatgccc aggcactgaa caccctggtc  2880
aagcagctgt cctccaactt cggcgccatc agctctgtgc tgaacgatat cctgagcaga  2940
ctggaccctc ctgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctgggccaga gcaagagagt ggacttttgc  3120
ggcaagggct accacctgat gagcttccct cagtctgccc ctcacggcgt ggtgtttctg  3180
cacgtgacat atgtgcccgc tcaagagaag aatttcacca ccgctccagc catctgccac  3240
gacggcaaag cccactttcc tagagaaggc gtgttcgtgt ccaacggcac ccattggttc  3300
gtgacacagc ggaacttcta cgagccccag atcatcacca ccgacaacac cttcgtgtct  3360
ggcaactgcg acgtcgtgat cggcattgtg aacaataccg tgtacgaccc tctgcagccc  3420
gagctggaca gcttcaaaga ggaactggac aagtacttta agaaccacac aagccccgac  3480
gtggacctgg gcgatatcag cggaatcaat gccagcgtcg tgaacatcca gaaagagatc  3540
gaccggctga acgaggtggc caagaatctg aacgagagcc tgatcgacct gcaagaactg  3600
```

-continued

```
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
gtgctgaagg gcgtgaaact gcactacaca tgatgac                           3817

SEQ ID NO: 57          moltype = RNA  length = 4274
FEATURE                Location/Qualifiers
source                 1..4274
                       mol_type = other RNA
                       organism = synthetic construct
SEQUENCE: 57
agaataaact agtattcttc tggtccccac agactcagag agaacccgcc accatgttcg  60
tgttcctggt gctgctgcct ctggtgtcca gccagtgtgt gaacttcacc accagaacac  120
agctgcctcc agcctacacc aacagcttta ccagaggcgt gtactacccc gacaaggtgt  180
tcagatccag cgtgctgcac tctacccagg acctgttcct gcctttcttc agcaacgtga  240
cctggttcca cgccatccac gtgtccggca ccaatggcac caagagattc gccaaccccg  300
tgctgccctt caacgacggg gtgtactttg ccagcaccga gaagtccaac atcatcagag  360
gctggatctt cggcaccaca ctggacagca agacccagag cctgctgatc gtgaacaacg  420
ccaccaacgt ggtcatcaaa gtgtgcgagt tccagttctg caacgacccc ttcctgggcg  480
tctactacca caagaacaac aagagctgga tggaaagcga gttccgggtg tacagcagcg  540
ccaacaactg caccttcgag tacgtgtccc agcctttcct gatggacctg gaaggcaagc  600
agggcaactt caagaacctg cgcgagttcg tgtttaagaa catcgacggc tacttcaaga  660
tctacagcaa gcacacccct atcaacctcg tgcggggcct gcctcagggc ttctctgctc  720
tggaaccccct ggtggatctg cccatcggca tcaacatcac ccggtttcag acactgcaca  780
tcagctacct gacacctggc gatagcagca gcggatggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca  1020
tcgtgcggtt ccccaatatc accaatctgt gccccttcgg cgaggtgttc aatgccacca  1080
gattcgcctc tgtgtacgcc tggaaccgga agcggatcag caattgcgtg gccgactact  1140
ccgtgctgta caactccgcc agcttcagca ccttcaagtg ctacggcgtg tcccctacca  1200
agctgaacga cctgtgcttc acaaacgtgt acgccgacag cttcgtgatc cggggagatg  1260
aagtgcggca gattgcccct ggacagacag gcaacatcgc cgactacaac tacaagctgc  1320
ccgacgactt caccggctgt gtgattgcct ggaacagcaa caacctggac tccaaagtcg  1380
gcggcaacta caattacctg taccggctgt tccggaagtc caatctgaag cccttcgagc  1440
gggacatctc caccgagatc tatcaggccg gcagcacccc ttgtaacggc gtgaagggct  1500
tcaactgcta cttcccactg cagtcctacg gctttcagcc cacatacggc gtgggctatc  1560
agccctacag agtggtggtg ctgagcttcg aactgctgca tgcccctgcc acagtgtgcg  1620
gccctaagaa aagcaccaat ctcgtgaaga acaaatgcgt gaacttcaac ttcaacggcc  1680
tgaccggcac cggcgtgctg acagagagca acaagaagtt cctgccattc cagcagtttg  1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagccggctg tctgatcgga gccgagcacg tgaacaatag ctacgagtgc gacatcccca  2040
tcggcgctgg aatctgcgcc agctaccaga cacagacaaa cagccctcgg agagccagaa  2100
gcgtggccag ccagagcatc attgcctaca caatgtctct gggcgtcgag aacagcgtgg  2160
cctactccaa caactctatc gctatcccca ccaacttcac catcagcgtg accacagaga  2220
tcctgcctgt gtccatgacc aagaccagcg tggactgcac catgtacatc tgcggcgatt  2280
ccaccgagtg ctccaacctg ctgctgcagt acggcagctt ctgcacccag ctgaatagag  2340
ccctgacagg gatcgccgtg gaacaggaca agaacaccca agaggtgttc gcccaagtga  2400
agcagatcta caagacccct cctatcaagg acttcggcgg cttcaatttc agccagattc  2460
tgcccgatcc tagcaagccc agcaagcgga gcttcatcga ggacctgctg ttcaacaaag  2520
tgacactggc cgacgccggc ttcatcaagc agtatggcga ttgtctgggc gacattgccg  2580
ccagggatct gatttgcgcc cagaagttta acggactgac agtgctgcct cctctgctga  2640
ccgatgagat gatcgcccag tacacatctg ccctgctggc cggcacaatc acaagcggct  2700
ggacatttgg agcaggcgcc gctctgcaga tcccctttgc tatgcagatg gcctaccggt  2760
tcaacggcat cggagtgacc cagaatgtgc tgtacgagaa ccagaagctg atcgccaacc  2820
agttcaacag cgccatcggc aagatccagg acagcctgag cagcacagca agcgccctgg  2880
gaaagctgca ggacgtggtc aaccagaatg cccaggcact gaacaccctg gtcaagcagc  2940
tgtcctccaa cttcggcgcc atcagctctg tgctgaacga tatcctgagc agactggacc  3000
ctcctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctgggcc agagcaagag agtggacttt tgcggcaagg  3180
gctaccacct gatgagcttc cctcagtctg cccctcacgg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccaccgacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcga cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgac tcgagctggt actgcatgca cgcaatgcta  3900
gctgcccctt tcccgtcctg ggtaccccga gtctcccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cgggaaacag cagtgattaa  4080
```

-continued

```
cctttagcaa taaacgaaag tttaactaag ctatactaac cccagggttg gtcaatttcg  4140
tgccagccac accctggagc tagcaaaaaa aaaaaaaaaa aaaaaaaaaa aaaagcatat  4200
gactaaaaaa aaaaaaaaaa aaaaaaaaaa aaaaaaaaaa aaaaaaaaaa aaaaaaaaaa  4260
aaaaaaaaaa aaaa                                                    4274

SEQ ID NO: 58          moltype = AA  length = 1270
FEATURE                Location/Qualifiers
source                 1..1270
                       mol_type = protein
                       organism = synthetic construct
SEQUENCE: 58
MFVFLVLLPL VSSQCVNLTT RTQLPPAYTN SFTRGVYYPD KVFRSSVLHS TQDLFLPFFS  60
NVTWFHAISG TNGTKRFDNP VLPFNDGVYF ASTEKSNIIR GWIFGTTLDS KTQSLLIVNN  120
ATNVVIKVCE FQFCNDPFLG VYHKNNKSWM ESEFRVYSSA NNCTFEYVSQ PFLMDLEGKQ  180
GNFKNLREFV FKNIDGYFKI YSKHTPINLV RDLPQGFSAL EPLVDLPIGI NITRFQTLLA  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFGEVFN ATRFASVYAW NRKRISNCVA  360
DYSVLYNSAS FSTFKCYGVS PTKLNDLCFT NVYADSFVIR GDEVRQIAPG QTGKIADYNY  420
KLPDDFTGCV IAWNSNNLDS KVGGNYNYLY RLFRKSNLKP FERDISTEIY QAGSTPCNGV  480
EGFNCYFPLQ SYGFQPTYGV GYQPYRVVVL SFELLHAPAT VCGPKKSTNL VKNKCVNFNF  540
NGLTGTGVLT ESNKKFLPFQ QFGRDIDDTT DAVRDPQTLE ILDITPCSFG GVSVITPGTN  600
TSNQVAVLYQ GVNCTEVPVA IHADQLTPTW RVYSTGSNVF QTRAGCLIGA EHVNNSYECD  660
IPIGAGICAS YQTQTNSHRR ARSVASQSII AYTMSLGAEN SVAYSNNSIA IPINFTISVT  720
TEILPVSMTK TSVDCTMYIC GDSTECSNLL LQYGSFCTQL NRALTGIAVE QDKNTQEVFA  780
QVKQIYKTPP IKDFGGFNFS QILPDPSKPS KRSFIEDLLF NKVTLADAGF IKQYGDCLGD  840
IAARDLICAQ KFNGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN QNAQALNTLV  960
KQLSSNFGAI SSVLNDILAR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTHNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                         1270

SEQ ID NO: 59          moltype = RNA  length = 3816
FEATURE                Location/Qualifiers
source                 1..3816
                       mol_type = other RNA
                       organism = synthetic construct
SEQUENCE: 59
atgttcgtgt tcctggtgct gctgcctctg gtgtccagcc agtgtgtgaa cctgaccacc  60
agaacacagc tgcctccagc ctacaccaac agctttacca gaggcgtgta ctaccccgac  120
aaggtgttca gatccagcgt gctgcactct acccaggacc tgttcctgcc tttcttcagc  180
aacgtgacct ggttccacgc catctccggc accaatggca ccaagagatt cgacaacccc  240
gtgctgccct tcaacgacgg ggtgtacttt gccagcaccg agaagtccaa catcatcaga  300
ggctggatct tcggcaccac actggacagc aagacccaga gcctgctgat cgtgaacaac  360
gccaccaacg tggtcatcaa agtgtgcgag ttccagttct gcaacgaccc cttcctgggc  420
gtctaccaca agaacaacaa gagctggatg gaaagcgagt tccgggtgta cagcagcgcc  480
aacaactgca ccttcgagta cgtgtcccag cctttcctga tggacctgga aggcaagcag  540
ggcaacttca agaacctgcg cgagttcgtg tttaagaaca tcgacggcta cttcaagatc  600
tacagcaagc acacccctat caacctcgtg cgggatctgc ctcagggctt ctctgctctg  660
gaacccctgg tggatctgcc catcggcatc aacatcaccc ggtttcagac actgctggcc  720
ctgcacagaa gctacctgac acctggcgat agcagcagcg gatggacagc tggtgccgcc  780
gcttactatg tgggctacct gcagcctaga accttcctgc tgaagtacaa cgagaacggc  840
accatcaccg acgccgtgga ttgtgctctg gatcctctga gcgagacaaa gtgcaccctg  900
aagtccttca ccgtggaaaa gggcatctac cagaccagca acttccgggt gcagcccacc  960
gaatccatcg tgcggttccc caatatcacc aatctgtgcc ccttcggcga ggtgttcaat  1020
gccaccagat tcgcctctgt gtacgcctgg aaccggaagc ggatcagcaa ttgcgtggcc  1080
gactactccg tgctgtacaa ctccgccagc ttcagcacct tcaagtgcta cggcgtgtcc  1140
cctaccaagc tgaacgacct gtgcttcaca aacgtgtacg ccgacagctt cgtgatccgg  1200
ggagatgaag tgcggcagat tgcccctgga cagacaggca agatcgccga ctacaactac  1260
aagctgcccg acgacttcac cggctgtgtg attgcctgga acagcaacaa cctggactcc  1320
aaagtcggcg gcaactacaa ttacctgtac cggctgttcc ggaagtccaa tctgaagccc  1380
ttcgagcggg acatctccac cgagatctat caggccggca gcaccccttg taacggcgtg  1440
gaaggcttca actgctactt cccactgcag tcctacggct ttcagcccac atacggcgtg  1500
ggctatcagc cctacagagt ggtggtgctg agcttcgaac tgctgcatgc ccctgccaca  1560
gtgtgcggcc ctaagaaaag caccaatctc gtgaagaaca aatgcgtgaa cttcaacttc  1620
aacggcctga ccggcaccgg cgtgctgaca gagagcaaca agaagttcct gccattccag  1680
cagtttggcc gggatatcga cgataccaca gacgccgtta gagatcccca gacactggaa  1740
atcctggaca tcaccccttg cagcttcggc ggagtgtctg tgatcacccc tggcaccaac  1800
accagcaatc aggtggcagt gctgtaccag ggcgtgaact gtaccgaagt gcccgtggcc  1860
attcacgccg atcagctgac acctacatgg cgggtgtact ccaccggcag caatgtgttt  1920
cagaccagag ccggctgtct gatcggagcc gagcacgtga acaatagcta cgagtgcgac  1980
atccccatcg gcgctggaat ctgcgccagc taccagacac agacaaacag ccaccggaga  2040
gccagaagcg tggccagcca gagcatcatt gcctacacaa tgtctctggg cgccgagaac  2100
agcgtggcct actccaacaa ctctatcgct atccccatca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aatagagccc tgacagggat cgccgtggaa caggacaaga acacccaaga ggtgttcgcc  2340
```

-continued

```
caagtgaagc agatctacaa gacccctcct atcaaggact tcggcggctt caatttcagc  2400
cagattctgc ccgatcctag caagcccagc aagcggagct tcatcgagga cctgctgttc  2460
aacaaagtga cactggccga cgccggcttc atcaagcagt atggcgattg tctgggcgac  2520
attgccgcca gggatctgat ttgcgcccag aagtttaacg gactgacagt gctgcctcct  2580
ctgctgaccg atgagatgat cgcccagtac acatctgccc tgctggccgg cacaatcaca  2640
agcggctgga catttggagc aggcgccgct ctgcagatcc cctttgctat gcagatggcc  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctgggaa agctgcagga cgtggtcaac cagaatgccc aggcactgaa caccctggtc  2880
aagcagctgt cctccaactt cggcgccatc agctctgtgc tgaacgatat cctggccaga  2940
ctggaccctc ctgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctgggccaga gcaagagagt ggacttttgc  3120
ggcaagggct accacctgat gagcttccct cagtctgccc ctcacggcgt ggtgtttctg  3180
cacgtgacat atgtgcccgc tcaagagaag aatttcacca ccgctccagc catctgccac  3240
gacggcaaag cccactttcc tagagaaggc gtgttcgtgt ccaacggcac ccattggttc  3300
gtgacacagc ggaacttcta cgagccccag atcatcacca cccacaacac cttcgtgtct  3360
ggcaactgcg acgtcgtgat cggcattgtg aacaataccg tgtacgaccc tctgcagccc  3420
gagctggaca gcttcaaaga ggaactggac aagtacttta agaaccacac aagccccgac  3480
gtggacctgg gcgatatcag cggaatcaat gccagcgtcg tgaacatcca gaaagagatc  3540
gaccggctga acgaggtggc caagaatctg aacgagagcc tgatcgacct gcaagaactg  3600
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
gtgctgaagg gcgtgaaact gcactacaca tgatga                            3816

SEQ ID NO: 60          moltype = RNA  length = 4274
FEATURE                Location/Qualifiers
source                 1..4274
                       mol_type = other RNA
                       organism = synthetic construct
SEQUENCE: 60
agaataaact agtattcttc tggtccccac agactcagag agaacccgcc accatgttcg  60
tgttcctggt gctgctgcct ctggtgtcca gccagtgtgt gaacctgacc accagaacac  120
agctgcctcc agcctacacc aacagcttta ccagaggcgt gtactacccc gacaaggtgt  180
tcagatccag cgtgctgcac tctacccagg acctgttcct gcctttcttc agcaacgtga  240
cctggttcca cgccatctcc ggcaccaatg gcaccaagag attcgacaac cccgtgctgc  300
ccttcaacga cggggtgtac tttgccagca ccgagaagtc caacatcatc agaggctgga  360
tcttcggcac cacactggac agcaagaccc agagcctgct gatcgtgaac aacgccacca  420
acgtggtcat caaagtgtgc gagttccagt tctgcaacga ccccttcctg ggcgtctacc  480
acaagaacaa caagagctgg atggaaagcg agttccgggt gtacagcagc gccaacaact  540
gcaccttcga gtacgtgtcc cagccttttcc tgatggacct ggaaggcaag cagggcaact  600
tcaagaacct gcgcgagttc gtgtttaaga acatcgacgg ctacttcaag atctacagca  660
agcacacccc tatcaacctc gtgcgggatc tgcctcaggg cttctctgct ctggaacccc  720
tggtggatct gcccatcggc atcaacatca cccggtttca gacactgctg gccctgcaca  780
gaagctacct gacacctggc gatagcagca gcggatggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca  1020
tcgtgcggtt ccccaatatc accaatctgt gccccttcgg cgaggtgttc aatgccacca  1080
gattcgcctc tgtgtacgcc tggaaccgga agcggatcag caattgcgtg gccgactact  1140
ccgtgctgta caactccgcc agcttcagca ccttcaagtg ctacggcgtg tcccctacca  1200
agctgaacga cctgtgcttc acaaacgtgt acgccgacag cttcgtgatc cggggagatg  1260
aagtgcggca gattgcccct ggacagacag gcaagatcgc cgactacaac tacaagctgc  1320
ccgacgactt caccggctgt gtgattgcct ggaacagcaa caacctggac tccaaagtcg  1380
gcggcaacta caattacctg taccggctgt tccggaagtc caatctgaag cccttcgagc  1440
gggacatctc caccgagatc tatcaggccg gcagcacccc ttgtaacggc gtggaaggct  1500
tcaactgcta cttcccactg cagtcctacg gctttcagcc cacatacggc gtgggctatc  1560
agccctacag agtggtggtg ctgagcttcg aactgctgca tgcccctgcc acagtgtgcg  1620
gccctaagaa aagcaccaat ctcgtgaaga acaaatgcgt gaacttcaac ttcaacggcc  1680
tgaccggcac cggcgtgctg acagagagca acaagaagtt cctgccattc cagcagtttg  1740
gccgggatat cgacgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagccggctg tctgatcgga gccgagcacg tgaacaatag ctacgagtgc gacatcccca  2040
tcggcgctgg aatctgcgcc agctaccaga cacagacaaa cagccaccgg agagccagaa  2100
gcgtggccag ccagagcatc attgcctaca caatgtctct gggcgccgag aacagcgtgg  2160
cctactccaa caactctatc gctatcccca tcaacttcac catcagcgtg accacagaga  2220
tcctgcctgt gtccatgacc aagaccagcg tggactgcac catgtacatc tgcggcgatt  2280
ccaccgagtg ctccaacctg ctgctgcagt acggcagctt ctgcacccag ctgaatagag  2340
ccctgacagg gatcgccgtg gaacaggaca agaacaccca agaggtgttc gcccaagtga  2400
agcagatcta caagacccct cctatcaagg acttcggcgg cttcaatttc agccagattc  2460
tgcccgatcc tagcaagccc agcaagcgga gcttcatcga ggacctgctg ttcaacaaag  2520
tgacactggc cgacgccggc ttcatcaagc agtatggcga ttgtctgggc gacattgccg  2580
ccagggatct gatttgcgcc cagaagttta acggactgac agtgctgcct cctctgctga  2640
ccgatgagat gatcgcccag tacacatctg ccctgctggc cggcacaatc acaagcggct  2700
ggacatttgg agcaggcgcc gctctgcaga tcccctttgc tatgcagatg gcctaccggt  2760
tcaacggcat cggagtgacc cagaatgtgc tgtacgagaa ccagaagctg atcgccaacc  2820
```

-continued

```
agttcaacag cgccatcggc aagatccagg acagcctgag cagcacagca agcgccctgg  2880
gaaagctgca ggacgtggtc aaccagaatg cccaggcact gaacaccctg gtcaagcagc  2940
tgtcctccaa cttcggcgcc atcagctctg tgctgaacga tatcctggcc agactggacc  3000
ctcctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctgggcc agagcaagag agtggacttt tgcggcaagg  3180
gctaccacct gatgagcttc cctcagtctg cccctcacgg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccacccacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcga cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgag atctgctggt actgcatgca cgcaatgcta  3900
gctgcccctt tcccgtcctg ggtaccccga gtctcccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cgggaaacag cagtgattaa  4080
cctttagcaa taaacgaaag tttaactaag ctatactaac cccagggttg gtcaatttcg  4140
tgccagccac accctggagc tagcaaaaaa aaaaaaaaaa aaaaaaaaaa aaaagcatat  4200
gactaaaaaa aaaaaaaaaa aaaaaaaaaa aaaaaaaaaa aaaaaaaaaa aaaaaaaaaa  4260
aaaaaaaaaa aaaa                                                    4274

SEQ ID NO: 61          moltype = AA  length = 1271
FEATURE                Location/Qualifiers
source                 1..1271
                       mol_type = protein
                       organism = synthetic construct
SEQUENCE: 61
MFVFLVLLPL VSSQCVNLRT RTQLPPAYTN SFTRGVYYPD KVFRSSVLHS TQDLFLPFFS  60
NVTWFHAIHV SGTNGTKRFD NPVLPFNDGV YFASTEKSNI IRGWIFGTTL DSKTQSLLIV  120
NNATNVVIKV CEFQFCNDPF LDVYYHKNNK SWMESGVYSS ANNCTFEYVS QPFLMDLEGK  180
QGNFKNLREF VFKNIDGYFK IYSKHTPINL VRDLPQGFSA LEPLVDLPIG INITRFQTLL  240
ALHRSYLTPG DSSSGWTAGA AAYYVGYLQP RTFLLKYNEN GTITDAVDCA LDPLSETKCT  300
LKSFTVEKGI YQTSNFRVQP TESIVRFPNI TNLCPFGEVF NATRFASVYA WNRKRISNCV  360
ADYSVLYNSA SFSTFKCYGV SPTKLNDLCF TNVYADSFVI RGDEVRQIAP GQTGKIADYN  420
YKLPDDFTGC VIAWNSNNLD SKVGGNYNYR YRLFRKSNLK PFERDISTEI YQAGSKPCNG  480
VEGFNCYFPL QSYGFQPTNG VGYQPYRVVV LSFELLHAPA TVCGPKKSTN LVKNKCVNFN  540
FNGLTGTGVL TESNKKFLPF QQFGRDIADT TDAVRDPQTL EILDITPCSF GGVSVITPGT  600
NTSNQVAVLY QGVNCTEVPV AIHADQLTPT WRVYSTGSNV FQTRAGCLIG AEHVNNSYEC  660
DIPIGAGICA SYQTQTNSRR RARSVASQSI IAYTMSLGAE NSVAYSNNSI AIPTNFTISV  720
TTEILPVSMT KTSVDCTMYI CGDSTECSNL LLQYGSFCTQ LNRALTGIAV EQDKNTQEVF  780
AQVKQIYKTP PIKDFGGFNF SQILPDPSKP SKRSFIEDLL FNKVTLADAG FIKQYGDCLG  840
DIAARDLICA QKFNGLTVLP PLLTDEMIAQ YTSALLAGTI TSGWTFGAGA ALQIPFAMQM  900
AYRFNGIGVT QNVLYENQKL IANQFNSAIG KIQDSLSSTA SALGKLQNVV NQNAQALNTL  960
VKQLSSNFGA ISSVLNDILS RLDPPEAEVQ IDRLITGRLQ SLQTYVTQQL IRAAEIRASA  1020
NLAATKMSEC VLGQSKRVDF CGKGYHLMSF PQSAPHGVVF LHVTYVPAQE KNFTTAPAIC  1080
HDGKAHFPRE GVFVSNGTHW FVTQRNFYEP QIITTDNTFV SGNCDVVIGI VNNTVYDPLQ  1140
PELDSFKEEL DKYFKNHTSP DVDLGDISGI NASVVNIQKE IDRLNEVAKN LNESLIDLQE  1200
LGKYEQYIKW PWYIWLGFIA GLIAIVMVTI MLCCMTSCCS CLKGCCSCGS CCKFDEDDSE  1260
PVLKGVKLHY T                                                       1271

SEQ ID NO: 62          moltype = DNA  length = 3819
FEATURE                Location/Qualifiers
source                 1..3819
                       mol_type = other DNA
                       organism = synthetic construct
SEQUENCE: 62
atgttcgtgt tcctggtgct gctgcctctg gtgtccagcc agtgtgtgaa cctgagaacc  60
agaacacagc tgcctccagc ctacaccaac agctttacca gaggcgtgta ctacccgac   120
aaggtgttca gatccagcgt gctgcactct acccaggacc tgttcctgcc tttcttcagc  180
aacgtgacct ggttccacgc catccacgtg tccggcacca atggcaccaa gagattcgac  240
aaccccgtgc tgcccttcaa cgacggggtg tactttgcca gcaccgagaa gtccaacatc  300
atcagaggct ggatcttcgg caccacactg gacagcaaga cccagagcct gctgatcgtg  360
aacaacgcca ccaacgtggt catcaaagtg tgcgagttcc agttctgcaa cgaccccttc  420
ctggacgtct actaccacaa gaacaacaag agctggatgg aaagcggcgt gtacagcagc  480
gccaacaact gcaccttcga gtacgtgtcc cagcctttcc tgatggacct ggaaggcaag  540
cagggcaact tcaagaacct gcgcgagttc gtgtttaaga acatcgacgg ctacttcaag  600
atctacagca agcacacccc tatcaacctc gtgcgggatc tgcctcaggg cttctctgct  660
ctggaacccc tggtggatct gcccatcggc atcaacatca cccggtttca gacactgctg  720
gccctgcaca gaagctacct gacacctggc gatagcagca gcggatggac agctggtgcc  780
gccgcttact atgtgggcta cctgcagcct agaaccttcc tgctgaagta caacgagaac  840
ggcaccatca ccgacgccgt ggattgtgct ctggatcctc tgagcgagac aaagtgcacc  900
ctgaagtcct tcaccgtgga aaagggcatc taccagacca gcaacttccg ggtgcagccc  960
accgaatcca tcgtgcggtt ccccaatatc accaatctgt gccccttcgg cgaggtgttc  1020
aatgccacca gattcgcctc tgtgtacgcc tggaaccgga agcggatcag caattgcgtg  1080
```

```
gccgactact ccgtgctgta caactccgcc agcttcagca ccttcaagtg ctacggcgtg  1140
tcccctacca agctgaacga cctgtgcttc acaaacgtgt acgccgacag cttcgtgatc  1200
cggggagatg aagtgcggca gattgcccct ggacagacag gcaagatcgc cgactacaac  1260
tacaagctgc ccgacgactt caccggctgt gtgattgcct ggaacagcaa caacctggac  1320
tccaaagtcg gcggcaacta caattacagg taccggctgt tccggaagtc caatctgaag  1380
cccttcgagc gggacatctc caccgagatc tatcaggccg gcagcaagcc ttgtaacggc  1440
gtggaaggct tcaactgcta cttcccactg cagtcctacg gctttcagcc cacaaatggc  1500
gtgggctatc agccctacag agtggtggtg ctgagcttcg aactgctgca tgcccctgcc  1560
acagtgtgcg gccctaagaa aagcaccaat ctcgtgaaga acaaatgcgt gaacttcaac  1620
ttcaacggcc tgaccggcac cggcgtgctg acagagagca acaagaagtt cctgccattc  1680
cagcagtttg gccgggatat cgccgatacc acagacgccg ttagagatcc ccagacactg  1740
gaaatcctgg acatcacccc ttgcagcttc ggcggagtgt ctgtgatcac ccctggcacc  1800
aacaccagca atcaggtggc agtgctgtac cagggcgtga actgtaccga agtgcccgtg  1860
gccattcacg ccgatcagct gacacctaca tggcgggtgt actccaccgg cagcaatgtg  1920
tttcagacca gagccggctg tctgatcgga gccgagcacg tgaacaatag ctacgagtgc  1980
gacatcccca tcggcgctgg aatctgcgcc agctaccaga cacagacaaa cagcaggcgg  2040
agagccagaa gcgtggccag ccagagcatc attgcctaca caatgtctct gggcgccgag  2100
aacagcgtgg cctactccaa caactctatc gctatcccca ccaacttcac catcagcgtg  2160
accacagaga tcctgcctgt gtccatgacc aagaccagcg tggactgcac catgtacatc  2220
tgcggcgatt ccaccgagtg ctccaacctg ctgctgcagt acggcagctt ctgcacccag  2280
ctgaatagag ccctgacagg gatcgccgtg gaacaggaca agaacaccca agaggtgttc  2340
gcccaagtga agcagatcta caagacccct cctatcaagg acttcggcgg cttcaatttc  2400
agccagattc tgcccgatcc tagcaagccc agcaagcgga gcttcatcga ggacctgctg  2460
ttcaacaaag tgacactggc cgacgccggc ttcatcaagc agtatggcga ttgtctgggc  2520
gacattgccg ccagggatct gatttgcgcc cagaagttta acggactgac agtgctgcct  2580
cctctgctga ccgatgagat gatcgcccag tacacatctg ccctgctggc cggcacaatc  2640
acaagcggct ggacatttgg agcaggcgcc gctctgcaga tcccctttgc tatgcagatg  2700
gcctaccggt tcaacggcat cggagtgacc cagaatgtgc tgtacgagaa ccagaagctg  2760
atcgccaacc agttcaacag cgccatcggc aagatccagg acagcctgag cagcacagca  2820
agcgccctgg gaaagctgca gaacgtggtc aaccagaatg cccaggcact gaacaccctg  2880
gtcaagcagc tgtcctccaa cttcggcgcc atcagctctg tgctgaacga tatcctgagc  2940
agactggacc ctcctgaggc cgaggtgcag atcgacagac tgatcacagg cagactgcag  3000
agcctccaga catacgtgac ccagcagctg atcagagccg ccgagattag agcctctgcc  3060
aatctggccg ccaccaagat gtctgagtgt gtgctgggcc agagcaagag agtggacttt  3120
tgcggcaagg gctaccacct gatgagcttc cctcagtctg cccctcacgg cgtggtgttt  3180
ctgcacgtga catatgtgcc cgctcaagag aagaatttca ccaccgctcc agccatctgc  3240
cacgacggca aagcccactt tcctagagaa ggcgtgttcg tgtccaacgg cacccattgg  3300
ttcgtgacac agcggaactt ctacgagccc cagatcatca ccaccgacaa caccttcgtg  3360
tctggcaact gcgacgtcgt gatcggcatt gtgaacaata ccgtgtacga ccctctgcag  3420
cccgagctgg acagcttcaa agaggaactg gacaagtact ttaagaacca cacaagcccc  3480
gacgtggacc tgggcgatat cagcggaatc aatgccagcg tcgtgaacat ccagaaagag  3540
atcgaccggc tgaacgaggt ggccaagaat ctgaacgaga gcctgatcga cctgcaagaa  3600
ctggggaagt acgagcagta catcaagtgg ccctggtaca tctggctggg ctttatcgcc  3660
ggactgattg ccatcgtgat ggtcacaatc atgctgtgtt gcatgaccag ctgctgtagc  3720
tgcctgaagg gctgttgtag ctgtggcagc tgctgcaagt tcgacgagga cgattctgag  3780
cccgtgctga agggcgtgaa actgcactac acatgatga                          3819
```

```
SEQ ID NO: 63          moltype = DNA  length = 4277
FEATURE                Location/Qualifiers
source                 1..4277
                       mol_type = other DNA
                       organism = synthetic construct
SEQUENCE: 63
agaataaact agtattcttc tggtccccac agactcagag agaacccgcc accatgttcg  60
tgttcctggt gctgctgcct ctggtgtcca gccagtgtgt gaacctgaga accagaacac  120
agctgcctcc agcctacacc aacagcttta ccagaggcgt gtactacccc gacaaggtgt  180
tcagatccag cgtgctgcac tctacccagg acctgttcct gcctttcttc agcaacgtga  240
cctggttcca cgccatccac gtgtccggca ccaatggcac caagagattc gacaaccccg  300
tgctgccctt caacgacggg gtgtactttg ccagcaccga gaagtccaac atcatcagag  360
gctggatctt cggcaccaca ctggacagca agacccagag cctgctgatc gtgaacaacg  420
ccaccaacgt ggtcatcaaa gtgtgcgagt tccagttctg caacgacccc ttcctggacg  480
tctactacca caagaacaac aagagctgga tggaaagcgg cgtgtacagc agcgccaaca  540
actgcacctt cgagtacgtg tcccagcctt tcctgatgga cctggaaggc aagcagggca  600
acttcaagaa cctgcgcgag ttcgtgttta agaacatcga cggctacttc aagatctaca  660
gcaagcacac ccctatcaac ctcgtgcggg atctgcctca gggcttctct gctctggaac  720
ccctggtgga tctgcccatc ggcatcaaca tcacccggtt tcagacactg ctggccctgc  780
acagaagcta cctgacacct ggcgatagca gcagcggatg gacagctggt gccgccgctt  840
actatgtggg ctacctgcag cctagaacct tcctgctgaa gtacaacgag aacggcacca  900
tcaccgacgc cgtggattgt gctctggatc ctctgagcga gacaaagtgc accctgaagt  960
ccttcaccgt ggaaaagggc atctaccaga ccagcaactt ccgggtgcag cccaccgaat  1020
ccatcgtgcg gttccccaat atcaccaatc tgtgcccctt cggcgaggtg ttcaatgcca  1080
ccagattcgc ctctgtgtac gcctggaacc ggaagcggat cagcaattgc gtggccgact  1140
actccgtgct gtacaactcc gccagcttca gcaccttcaa gtgctacggc gtgtccccta  1200
ccaagctgaa cgacctgtgc ttcacaaacg tgtacgccga cagcttcgtg atccggggag  1260
atgaagtgcg gcagattgcc cctggacaga caggcaagat cgccgactac aactacaagc  1320
tgcccgacga cttcaccggc tgtgtgattg cctggaacag caacaacctg gactccaaag  1380
tcggcggcaa ctacaattac aggtaccggc tgttccggaa gtccaatctg aagcccttcg  1440
agcgggacat ctccaccgag atctatcagg ccggcagcaa gccttgtaac ggcgtggaag  1500
gcttcaactg ctacttccca ctgcagtcct acggctttca gcccacaaat ggcgtgggct  1560
```

-continued

```
atcagcccta cagagtggtg gtgctgagct tcgaactgct gcatgcccct gccacagtgt  1620
gcggccctaa gaaaagcacc aatctcgtga agaacaaatg cgtgaacttc aacttcaacg  1680
gcctgaccgg caccggcgtg ctgacagaga gcaacaagaa gttcctgcca ttccagcagt  1740
ttggccggga tatcgccgat accacagacg ccgttagaga tccccagaca ctggaaatcc  1800
tggacatcac cccttgcagc ttcggcggag tgtctgtgat caccccctggc accaacacca  1860
gcaatcaggt ggcagtgctg taccagggcg tgaactgtac cgaagtgccc gtggccattc  1920
acgccgatca gctgacacct acatggcggg tgtactccac cggcagcaat gtgtttcaga  1980
ccagagccgg ctgtctgatc ggagccgagc acgtgaacaa tagctacgag tgcgacatcc  2040
ccatcggcgc tggaatctgc gccagctacc agacacagac aaacagcagg cggagagcca  2100
gaagcgtggc cagccagagc atcattgcct acacaatgtc tctgggcgcc gagaacagcg  2160
tggcctactc caacaactct atcgctatcc ccaccaactt caccatcagc gtgaccacag  2220
agatcctgcc tgtgtccatg accaagacca gcgtggactg caccatgtac atctgcggcg  2280
attccaccga gtgctccaac ctgctgctgc agtacggcag cttctgcacc cagctgaata  2340
gagccctgac agggatcgcc gtggaacagg acaagaacac ccaagaggtg ttcgcccaag  2400
tgaagcagat ctacaagacc cctcctatca aggacttcgg cggcttcaat ttcagccaga  2460
ttctgcccga tcctagcaag cccagcaagc ggagcttcat cgaggacctg ctgttcaaca  2520
aagtgacact ggccgacgcc ggcttcatca agcagtatgg cgattgtctg ggcgacattg  2580
ccgccaggga tctgatttgc gcccagaagt ttaacggact gacagtgctg cctcctctgc  2640
tgaccgatga gatgatcgcc cagtacacat ctgccctgct ggccggcaca atcacaagcg  2700
gctggacatt tggagcaggc gccgctctgc agatcccctt tgctatgcag atggcctacc  2760
ggttcaacgg catcggagtg acccagaatg tgctgtacga gaaccagaag ctgatcgcca  2820
accagttcaa cagcgccatc ggcaagatcc aggacagcct gagcagcaca gcaagcgccc  2880
tgggaaagct gcagaacgtg gtcaaccaga atgcccaggc actgaacacc ctggtcaagc  2940
agctgtcctc caacttcggc gccatcagct ctgtgctgaa cgatatcctg agcagactgg  3000
accctcctga ggccgaggtg cagatcgaca gactgatcac aggcagactg cagagcctcc  3060
agacatacgt gacccagcag ctgatcagag ccgccgagat tagagcctct gccaatctgg  3120
ccgccaccaa gatgtctgag tgtgtgctgg gccagagcaa gagagtggac ttttgcggca  3180
agggctacca cctgatgagc ttccctcagt ctgcccctca cggcgtggtg tttctgcacg  3240
tgacatatgt gcccgctcaa gagaagaatt tcaccaccgc tccagccatc tgccacgacg  3300
gcaaagccca ctttcctaga gaaggcgtgt tcgtgtccaa cggcacccat tggttcgtga  3360
cacagcggaa cttctacgag ccccagatca tcaccaccga caacaccttc gtgtctggca  3420
actgcgacgt cgtgatcggc attgtgaaca ataccgtgta cgaccctctg cagcccgagc  3480
tggacagctt caaagaggaa ctggacaagt actttaagaa ccacacaagc cccgacgtgg  3540
acctgggcga tatcagcgga atcaatgcca gcgtcgtgaa catccagaaa gagatcgacc  3600
ggctgaacga ggtggccaag aatctgaacg agagcctgat cgacctgcaa gaactgggga  3660
agtacgagca gtacatcaag tggccctggt acatctggct gggctttatc gccggactga  3720
ttgccatcgt gatggtcaca atcatgctgt gttgcatgac cagctgctgt agctgcctga  3780
agggctgttg tagctgtggc agctgctgca agttcgacga ggacgattct gagcccgtgc  3840
tgaagggcgt gaaactgcac tacacatgat gatttcacct ggtactgcat gcacgcaatg  3900
ctagctgccc ctttcccgtc ctgggtaccc cgagtctccc ccgacctcgg gtcccaggta  3960
tgctcccacc tccacctgcc ccactcacca cctctgctag ttccagacac ctcccaagca  4020
cgcagcaatg cagctcaaaa cgcttagcct agccacaccc ccacgggaaa cagcagtgat  4080
taacctttag caataaacga aagtttaact aagctatact aaccccaggg ttggtcaatt  4140
tcgtgccagc cacaccctgg agctagcaaa aaaaaaaaaa aaaaaaaaaa aaaaaaagca  4200
tatgactaaa aaaaaaaaaa aaaaaaaaaa aaaaaaaaaa aaaaaaaaaa aaaaaaaaaa  4260
aaaaaaaaaa aaaaaaa                                                 4277

SEQ ID NO: 64          moltype = AA  length = 1270
FEATURE                Location/Qualifiers
source                 1..1270
                       mol_type = protein
                       organism = synthetic construct
SEQUENCE: 64
MFVFLVLLPL VSSQCVNLIT RTQSYTNSFT RGVYYPDKVF RSSVLHSTQD LFLPFFSNVT  60
WFHAIHVSGT NGTKRFDNPV LPFNDGVYFA STEKSNIIRG WIFGTTLDSK TQSLLIVNNA  120
TNVVIKVCEF QFCNDPFLDV YYHKNNKSWM ESEFRVYSSA NNCTFEYVSQ PFLMDLEGKQ  180
GNFKNLREFV FKNIDGYFKI YSKHTPINLG RDLPQGFSAL EPLVDLPIGI NITRFQTLLA  240
LHRSYLTPGD SSSGWTAGAA AYYVGYLQPR TFLLKYNENG TITDAVDCAL DPLSETKCTL  300
KSFTVEKGIY QTSNFRVQPT ESIVRFPNIT NLCPFDEVFN ATRFASVYAW NRKRISNCVA  360
DYSVLYNFAP FFAFKCYGVS PTKLNDLCFT NVYADSFVIR GNEVSQIAPG QTGNIADYNY  420
KLPDDFTGCV IAWNSNKLDS KVGGNYNYLY RLFRKSNLKP FERDISTEIY QAGNKPCNGV  480
AGFNCYFPLR SYGFRPTYGV GHQPYRVVVL SFELLHAPAT VCGPKKSTNL VKNKCVNFNF  540
NGLTGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTKSHRR ARSVASQSII AYTMSLGAEN SVAYSNNSIA IPTNFTISVT  720
TEILPVSMTK TSVDCTMYIC GDSTECSNLL LQYGSFCTQL KRALTGIAVE QDKNTQEVFA  780
QVKQIYKTPP IKYFGGFNFS QILPDPSKPS KRSFIEDLLF NKVTLADAGF IKQYGDCLGD  840
IAARDLICAQ KFNGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN HNAQALNTLV  960
KQLSSKFGAI SSVLNDILSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                         1270

SEQ ID NO: 65          moltype = RNA  length = 3816
FEATURE                Location/Qualifiers
source                 1..3816
```

mol_type = other RNA
organism = synthetic construct
SEQUENCE: 65
atgttcgtgt tcctggtgct gctgcctctg gtgtccagcc agtgtgtgaa cctgatcacc 60
agaacacagt catacaccaa cagctttacc agaggcgtgt actaccccga caaggtgttc 120
agatccagcg tgctgcactc tacccaggac ctgttcctgc ctttcttcag caacgtgacc 180
tggttccacg ccatccacgt gtccggcacc aatggcacca agagattcga caaccccgtg 240
ctgcccttca acgacggggt gtactttgcc agcaccgaga agtccaacat catcagaggc 300
tggatcttcg gcaccacact ggacagcaag acccagagcc tgctgatcgt gaacaacgcc 360
accaacgtgg tcatcaaagt gtgcgagttc cagttctgca acgacccctt cctggacgtc 420
tactaccaca agaacaacaa gagctggatg gaaagcgagt tccgggtgta cagcagcgcc 480
aacaactgca ccttcgagta cgtgtcccag cctttcctga tggacctgga aggcaagcag 540
ggcaacttca agaacctgcg cgagttcgtg tttaagaaca tcgacggcta cttcaagatc 600
tacagcaagc acacccctat caacctcggc cgggatctgc ctcagggctt ctctgctctg 660
gaacccctgg tggatctgcc catcggcatc aacatcaccc ggtttcagac actgctggcc 720
ctgcacagaa gctacctgac acctggcgat agcagcagcg gatggacagc tggtgccgcc 780
gcttactatg tgggctacct gcagcctaga accttcctgc tgaagtacaa cgagaacggc 840
accatcaccg acgccgtgga ttgtgctctg gatcctctga gcgagacaaa gtgcaccctg 900
aagtccttca ccgtggaaaa gggcatctac cagaccagca acttccgggt gcagcccacc 960
gaatccatcg tgcggttccc caatatcacc aatctgtgcc ccttcgacga ggtgttcaat 1020
gccaccagat tcgcctctgt gtacgcctgg aaccggaagc ggatcagcaa ttgcgtggcc 1080
gactactccg tgctgtacaa cttcgccccc ttcttcgcat tcaagtgcta cggcgtgtcc 1140
cctaccaagc tgaacgacct gtgcttcaca aacgtgtacg ccgacagctt cgtgatccgg 1200
ggaaacgaag tgtcacagat tgcccctgga cagacaggca acatcgccga ctacaactac 1260
aagctgcccg acgacttcac cggctgtgtg attgcctgga acagcaacaa gctggactcc 1320
aaagtcggcg gcaactacaa ttacctgtac cggctgttcc ggaagtccaa tctgaagccc 1380
ttcgagcggg acatctccac cgagatctat caggccggca acaagccttg taacggcgtg 1440
gcaggcttca actgctactt cccactgagg tcctacggct ttaggcccac atacggcgtg 1500
ggccaccagc cctacagagt ggtggtgctg agcttcgaac tgctgcatgc ccctgccaca 1560
gtgtgcggcc ctaagaaaag caccaatctc gtgaagaaca aatgcgtgaa cttcaacttc 1620
aacggcctga ccggcaccgg cgtgctgaca gagagcaaca agaagttcct gccattccag 1680
cagtttggcc gggatatcgc cgataccaca gacgccgtta gagatcccca gacactggaa 1740
atcctggaca tcaccccttg cagcttcggc ggagtgtctg tgatcacccc tggcaccaac 1800
accagcaatc aggtggcagt gctgtaccag ggcgtgaact gtaccgaagt gcccgtggcc 1860
attcacgccg atcagctgac acctacatgg cgggtgtact ccaccggcag caatgtgttt 1920
cagaccagag ccggctgtct gatcggagcc gagtacgtga acaatagcta cgagtgcgac 1980
atccccatcg gcgctggaat ctgcgccagc taccagacac agacaaagag ccaccggaga 2040
gccagaagcg tggccagcca gagcatcatt gcctacacaa tgtctctggg cgccgagaac 2100
agcgtggcct actccaacaa ctctatcgct atccccacca acttcaccat cagcgtgacc 2160
acagagatcc tgcctgtgtc catgaccaag accagcgtgg actgcaccat gtacatctgc 2220
ggcgattcca ccgagtgctc caacctgctg ctgcagtacg gcagcttctg cacccagctg 2280
aaaagagccc tgacagggat cgccgtggaa caggacaaga acacccaaga ggtgttcgcc 2340
caagtgaagc agatctacaa gacccctcct atcaagtact tcggcggctt caatttcagc 2400
cagattctgc ccgatcctag caagcccagc aagcggagct tcatcgagga cctgctgttc 2460
aacaaagtga cactggccga cgccggcttc atcaagcagt atggcgattg tctgggcgac 2520
attgccgcca gggatctgat ttgcgcccag aagtttaacg gactgacagt gctgcctcct 2580
ctgctgaccg atgagatgat cgcccagtac acatctgccc tgctggccgg cacaatcaca 2640
agcggctgga catttggagc aggcgccgct ctgcagatcc cctttgctat gcagatggcc 2700
taccggttca acggcatcgg agtgacccag aatgtgctgt acgagaacca gaagctgatc 2760
gccaaccagt tcaacagcgc catcggcaag atccaggaca gcctgagcag cacagcaagc 2820
gccctgggaa agctgcagga cgtggtcaac cacaatgccc aggcactgaa caccctggtc 2880
aagcagctgt cctccaagtt cggcgccatc agctctgtgc tgaacgatat cctgagcaga 2940
ctggaccctc ctgaggccga ggtgcagatc gacagactga tcacaggcag actgcagagc 3000
ctccagacat acgtgaccca gcagctgatc agagccgccg agattagagc ctctgccaat 3060
ctggccgcca ccaagatgtc tgagtgtgtg ctgggccaga gcaagagagt ggacttttgc 3120
ggcaagggct accacctgat gagcttccct cagtctgccc ctcacggcgt ggtgtttctg 3180
cacgtgacat atgtgcccgc tcaagagaag aatttcacca ccgctccagc catctgccac 3240
gacggcaaag cccactttcc tagagaaggc gtgttcgtgt ccaacggcac ccattggttc 3300
gtgacacagc ggaacttcta cgagccccag atcatcacca ccgacaacac cttcgtgtct 3360
ggcaactgcg acgtcgtgat cggcattgtg aacaataccg tgtacgaccc tctgcagccc 3420
gagctggaca gcttcaaaga ggaactggac aagtacttta agaaccacac aagccccgac 3480
gtggacctgg gcgatatcag cggaatcaat gccagcgtcg tgaacatcca gaaagagatc 3540
gaccggctga acgaggtggc caagaatctg aacgagagcc tgatcgacct gcaagaactg 3600
gggaagtacg agcagtacat caagtggccc tggtacatct ggctgggctt tatcgccgga 3660
ctgattgcca tcgtgatggt cacaatcatg ctgtgttgca tgaccagctg ctgtagctgc 3720
ctgaagggct gttgtagctg tggcagctgc tgcaagttcg acgaggacga ttctgagccc 3780
gtgctgaagg gcgtgaaact gcactacaca tgatga 3816

SEQ ID NO: 66 moltype = DNA length = 3816
FEATURE Location/Qualifiers
source 1..3816
mol_type = other DNA
organism = synthetic construct
SEQUENCE: 66
atgttcgtgt tcctggtgct gctgcctctg gtgtccagcc agtgtgtgaa cctgatcacc 60
agaacacagt catacaccaa cagctttacc agaggcgtgt actaccccga caaggtgttc 120
agatccagcg tgctgcactc tacccaggac ctgttcctgc ctttcttcag caacgtgacc 180
tggttccacg ccatccacgt gtccggcacc aatggcacca agagattcga caaccccgtg 240
ctgcccttca acgacggggt gtactttgcc agcaccgaga agtccaacat catcagaggc 300

-continued

```
tggatcttcg gcaccacact ggacagcaag acccagagcc tgctgatcgt gaacaacgcc  360
accaacgtgg tcatcaaagt gtgcgagttc cagttctgca acgacccctt cctggacgtc  420
tactaccaca agaacaacaa gagctggatg gaaagcgagt tccgggtgta cagcagcgcc  480
aacaactgca ccttcgagta cgtgtcccag cctttcctga tggacctgga aggcaagcag  540
ggcaacttca agaacctgcg cgagttcgtg tttaagaaca tcgacggcta cttcaagatc  600
tacagcaagc acacccctat caacctcggc cgggatctgc ctcagggctt ctctgctctg  660
gaacccctgg tggatctgcc catcggcatc aacatcaccc ggtttcagac actgctggcc  720
ctgcacagaa gctacctgac acctggcgat agcagcagcg gatggacagc tggtgccgcc  780
gcttactatg tgggctacct gcagcctaga accttcctgc tgaagtacaa cgagaacggc  840
accatcaccg acgccgtgga ttgtgctctg gatcctctga gcgagacaaa gtgcaccctg  900
aagtccttca ccgtggaaaa gggcatctac cagaccagca acttccgggt gcagcccacc  960
gaatccatcg tgcggttccc caatatcacc aatctgtgcc ccttcgacga ggtgttcaat  1020
gccaccagat tcgcctctgt gtacgcctgg aaccggaagc ggatcagcaa ttgcgtggcc  1080
gactactccg tgctgtacaa cttcgccccc ttcttcgcat tcaagtgcta cggcgtgtcc  1140
cctaccaagc tgaacgacct gtgcttcaca aacgtgtacg ccgacagctt cgtgatccgg  1200
ggaaacgaag tgtcacagat tgcccctgga cagacaggca acatcgccga ctacaactac  1260
aagctgcccg acgacttcac cggctgtgtg attgcctgga acagcaacaa gctggactcc  1320
aaagtcggcg gcaactacaa ttacctgtac cggctgttcc ggaagtccaa tctgaagccc  1380
ttcgagcggg acatctccac cgagatctat caggccggca acaagccttg taacggcgtg  1440
gcaggcttca actgctactt cccactgagg tcctacggct ttaggcccac atacggcgtg  1500
ggccaccagc cctacagagt ggtggtgctg agcttcgaac tgctgcatgc ccctgccaca  1560
gtgtgcggcc ctaagaaaag caccaatctc gtgaagaaca aatgcgtgaa cttcaacttc  1620
aacggcctga ccggcaccgg cgtgctgaca gagagcaaca agaagttcct gccattccag  1680
cagtttggcc gggatatcgc cgataccaca gacgccgtta gagatcccca gacactggaa  1740
atcctggaca tcaccccttg cagcttcggc ggagtgtctg tgatcacccc tggcaccaac  1800
accagcaatc aggtggcagt gctgtaccag ggcgtgaact gtaccgaagt gcccgtggcc  1860
attcacgccg atcagctgac acctacatgg cgggtgtact ccaccggcag caatgtgttt  1920
cagaccagag ccggctgtct gatcggagcc gagtacgtga acaatagcta cgagtgcgac  1980
atccccatcg gcgctggaat ctgcgccagc taccagacac agacaaagag ccaccggaga  2040
gccagaagcg tggccagcca gagcatcatt gcctacacaa tgtctctggg cgccgagaac  2100
agcgtggcct actccaacaa ctctatcgct atccccacca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aaaagagccc tgacagggat cgccgtggaa caggacaaga acacccaaga ggtgttcgcc  2340
caagtgaagc agatctacaa gacccctcct atcaagtact tcggcggctt caatttcagc  2400
cagattctgc ccgatcctag caagcccagc aagcggagct tcatcgagga cctgctgttc  2460
aacaaagtga cactggccga cgccggcttc atcaagcagt atggcgattg tctgggcgac  2520
attgccgcca gggatctgat ttgcgcccag aagtttaacg gactgacagt gctgcctcct  2580
ctgctgaccg atgagatgat cgcccagtac acatctgccc tgctggccgg cacaatcaca  2640
agcggctgga catttggagc aggcgccgct ctgcagatcc cctttgctat gcagatggcc  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctgggaa agctgcagga cgtggtcaac cacaatgccc aggcactgaa caccctggtc  2880
aagcagctgt cctccaagtt cggcgccatc agctctgtgc tgaacgatat cctgagcaga  2940
ctggaccctc ctgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctgggccaga gcaagagagt ggacttttgc  3120
ggcaagggct accacctgat gagcttccct cagtctgccc ctcacggcgt ggtgtttctg  3180
cacgtgacat atgtgcccgc tcaagagaag aatttcacca ccgctccagc catctgccac  3240
gacggcaaag cccactttcc tagagaaggc gtgttcgtgt ccaacggcac ccattggttc  3300
gtgacacagc ggaacttcta cgagccccag atcatcacca ccgacaacac cttcgtgtct  3360
ggcaactgcg acgtcgtgat cggcattgtg aacaataccg tgtacgaccc tctgcagccc  3420
gagctggaca gcttcaaaga ggaactggac aagtacttta agaaccacac aagccccgac  3480
gtggacctgg gcgatatcag cggaatcaat gccagcgtcg tgaacatcca gaaagagatc  3540
gaccggctga acgaggtggc caagaatctg aacgagagcc tgatcgacct gcaagaactg  3600
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
gtgctgaagg gcgtgaaact gcactacaca tgatga                            3816

SEQ ID NO: 67          moltype = RNA  length = 4274
FEATURE                Location/Qualifiers
source                 1..4274
                       mol_type = other RNA
                       organism = synthetic construct
SEQUENCE: 67
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatcca cgtgtccggc accaatggca ccaagagatt cgacaacccc gtgctgccct  300
tcaacgacgg ggtgtacttt gccagcaccg agaagtccaa catcatcaga ggctggatct  360
tcggcaccac actggacagc aagacccaga gcctgctgat cgtgaacaac gccaccaacg  420
tggtcatcaa agtgtgcgag ttccagttct gcaacgaccc cttcctggac gtctactacc  480
acaagaacaa caagagctgg atggaaagcg agttccgggt gtacagcagc gccaacaact  540
gcaccttcga gtacgtgtcc cagcctttcc tgatggacct ggaaggcaag cagggcaact  600
tcaagaacct gcgcgagttc gtgtttaaga acatcgacgg ctacttcaag atctacagca  660
agcacacccc tatcaacctc ggccgggatc tgcctcaggg cttctctgct ctggaacccc  720
tggtggatct gcccatcggc atcaacatca cccggtttca gacactgctg gccctgcaca  780
```

-continued

```
gaagctacct gacacctggc gatagcagca gcggatggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca  1020
tcgtgcggtt ccccaatatc accaatctgt gccccttcga cgaggtgttc aatgccacca  1080
gattcgcctc tgtgtacgcc tggaaccgga agcggatcag caattgcgtg gccgactact  1140
ccgtgctgta caacttcgcc cccttcttcg cattcaagtg ctacggcgtg tcccctacca  1200
agctgaacga cctgtgcttc acaaacgtgt acgccgacag cttcgtgatc cggggaaacg  1260
aagtgtcaca gattgcccct ggacagacag gcaacatcgc cgactacaac tacaagctgc  1320
ccgacgactt caccggctgt gtgattgcct ggaacagcaa caagctggac tccaaagtcg  1380
gcggcaacta caattacctg taccggctgt tccggaagtc caatctgaag cccttcgagc  1440
gggacatctc caccgagatc tatcaggccg gcaacaagcc ttgtaacggc gtggcaggct  1500
tcaactgcta cttcccactg aggtcctacg gctttaggcc cacatacggc gtgggccacc  1560
agccctacag agtggtggtg ctgagcttcg aactgctgca tgcccctgcc acagtgtgcg  1620
gccctaagaa aagcaccaat ctcgtgaaga acaaatgcgt gaacttcaac ttcaacggcc  1680
tgaccggcac cggcgtgctg acagagagca acaagaagtt cctgccattc cagcagtttg  1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagccggctg tctgatcgga gccgagtacg tgaacaatag ctacgagtgc gacatcccca  2040
tcggcgctgg aatctgcgcc agctaccaga cacagacaaa gagccaccgg agagccagaa  2100
gcgtggccag ccagagcatc attgcctaca caatgtctct gggcgccgag aacagcgtgg  2160
cctactccaa caactctatc gctatcccca ccaacttcac catcagcgtg accacagaga  2220
tcctgcctgt gtccatgacc aagaccagcg tggactgcac catgtacatc tgcggcgatt  2280
ccaccgagtg ctccaacctg ctgctgcagt acggcagctt ctgcacccag ctgaaaagag  2340
ccctgacagg gatcgccgtg gaacaggaca agaacaccca agaggtgttc gcccaagtga  2400
agcagatcta caagacccct cctatcaagt acttcggcgg cttcaatttc agccagattc  2460
tgcccgatcc tagcaagccc agcaagcgga gcttcatcga ggacctgctg ttcaacaaag  2520
tgacactggc cgacgccggc ttcatcaagc agtatggcga ttgtctgggc gacattgccg  2580
ccagggatct gatttgcgcc cagaagttta acggactgac agtgctgcct cctctgctga  2640
ccgatgagat gatcgcccag tacacatctg ccctgctggc cggcacaatc acaagcggct  2700
ggacatttgg agcaggcgcc gctctgcaga tcccctttgc tatgcagatg gcctaccggt  2760
tcaacggcat cggagtgacc cagaatgtgc tgtacgagaa ccagaagctg atcgccaacc  2820
agttcaacag cgccatcggc aagatccagg acagcctgag cagcacagca agcgccctgg  2880
gaaagctgca ggacgtggtc aaccacaatg cccaggcact gaacaccctg gtcaagcagc  2940
tgtcctccaa gttcggcgcc atcagctctg tgctgaacga tatcctgagc agactggacc  3000
ctcctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctgggcc agagcaagag agtggacttt tgcggcaagg  3180
gctaccacct gatgagcttc cctcagtctg cccctcacgg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccaccgacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcga cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgac tcgagctggt actgcatgca cgcaatgcta  3900
gctgcccctt tcccgtcctg ggtaccccga gtctcccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cgggaaacag cagtgattaa  4080
cctttagcaa taaacgaaag tttaactaag ctatactaac cccagggttg gtcaatttcg  4140
tgccagccac accctggagc tagcaaaaaa aaaaaaaaaa aaaaaaaaaa aaaagcatat  4200
gactaaaaaa aaaaaaaaaa aaaaaaaaaa aaaaaaaaaa aaaaaaaaaa aaaaaaaaaa  4260
aaaaaaaaaa aaaa                                                   4274
```

```
SEQ ID NO: 68          moltype = DNA  length = 4274
FEATURE                Location/Qualifiers
source                 1..4274
                       mol_type = other DNA
                       organism = synthetic construct
SEQUENCE: 68
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatcca cgtgtccggc accaatggca ccaagagatt cgacaacccc gtgctgccct  300
tcaacgacgg ggtgtacttt gccagcaccg agaagtccaa catcatcaga ggctggatct  360
tcggcaccac actggacagc aagacccaga gcctgctgat cgtgaacaac gccaccaacg  420
tggtcatcaa agtgtgcgag ttccagttct gcaacgaccc cttcctggac gtctactacc  480
acaagaacaa caagagctgg atggaaagcg agttccgggt gtacagcagc gccaacaact  540
gcacccttcga gtacgtgtcc cagcctttcc tgatggacct ggaaggcaag cagggcaact  600
tcaagaacct gcgcgagttc gtgtttaaga acatcgacgg ctacttcaag atctacagca  660
agcacacccc tatcaacctc ggccgggatc tgcctcaggg cttctctgct ctggaacccc  720
tggtggatct gcccatcggc atcaacatca cccggtttca gacactgctg gccctgcaca  780
```

-continued

```
gaagctacct gacacctggc gatagcagca gcggatggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca  1020
tcgtgcggtt ccccaatatc accaatctgt gccccttcga cgaggtgttc aatgccacca  1080
gattcgcctc tgtgtacgcc tggaaccgga agcggatcag caattgcgtg gccgactact  1140
ccgtgctgta caacttcgcc cccttcttcg cattcaagtg ctacggcgtg tcccctacca  1200
agctgaacga cctgtgcttc acaaacgtgt acgccgacag cttcgtgatc cggggaaacg  1260
aagtgtcaca gattgcccct ggacagacag gcaacatcgc cgactacaac tacaagctgc  1320
ccgacgactt caccggctgt gtgattgcct ggaacagcaa caagctggac tccaaagtcg  1380
gcggcaacta caattacctg taccggctgt tccggaagtc caatctgaag cccttcgagc  1440
gggacatctc caccgagatc tatcaggccg gcaacaagcc ttgtaacggc gtggcaggct  1500
tcaactgcta cttcccactg aggtcctacg gctttaggcc cacatacggc gtgggccacc  1560
agccctacag agtggtggtg ctgagcttcg aactgctgca tgcccctgcc acagtgtgcg  1620
gccctaagaa aagcaccaat ctcgtgaaga acaaatgcgt gaacttcaac ttcaacggcc  1680
tgaccggcac cggcgtgctg acagagagca acaagaagtt cctgccattc cagcagtttg  1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagccggctg tctgatcgga gccgagtacg tgaacaatag ctacgagtgc gacatcccca  2040
tcggcgctgg aatctgcgcc agctaccaga cacagacaaa gagccaccgg agagccagaa  2100
gcgtggccag ccagagcatc attgcctaca caatgtctct gggcgccgag aacagcgtgg  2160
cctactccaa caactctatc gctatcccca ccaacttcac catcagcgtg accacagaga  2220
tcctgcctgt gtccatgacc aagaccagcg tggactgcac catgtacatc tgcggcgatt  2280
ccaccgagtg ctccaacctg ctgctgcagt acggcagctt ctgcacccag ctgaaaagag  2340
ccctgacagg gatcgccgtg gaacaggaca agaacaccca agaggtgttc gcccaagtga  2400
agcagatcta caagacccct cctatcaagt acttcggcgg cttcaatttc agccagattc  2460
tgcccgatcc tagcaagccc agcaagcgga gcttcatcga ggacctgctg ttcaacaaag  2520
tgacactggc cgacgccggc ttcatcaagc agtatggcga ttgtctgggc gacattgccg  2580
ccagggatct gatttgcgcc cagaagttta acggactgac agtgctgcct cctctgctga  2640
ccgatgagat gatcgcccag tacacatctg ccctgctggc cggcacaatc acaagcggct  2700
ggacatttgg agcaggcgcc gctctgcaga tcccctttgc tatgcagatg gcctaccggt  2760
tcaacggcat cggagtgacc cagaatgtgc tgtacgagaa ccagaagctg atcgccaacc  2820
agttcaacag cgccatcggc aagatccagg acagcctgag cagcacagca agcgccctgg  2880
gaaagctgca ggacgtggtc aaccacaatg cccaggcact gaacaccctg gtcaagcagc  2940
tgtcctccaa gttcggcgcc atcagctctg tgctgaacga tatcctgagc agactggacc  3000
ctcctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctgggcc agagcaagag agtggacttt tgcggcaagg  3180
gctaccacct gatgagcttc cctcagtctg cccctcacgg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccaccgacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcga cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgac tcgagctggt actgcatgca cgcaatgcta  3900
gctgcccctt tcccgtcctg ggtaccccga gtctcccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cgggaaacag cagtgattaa  4080
cctttagcaa taaacgaaag tttaactaag ctatactaac cccagggttg gtcaatttcg  4140
tgccagccac accctggagc tagcaaaaaa aaaaaaaaaa aaaaaaaaaa aaaagcatat  4200
gactaaaaaa aaaaaaaaaa aaaaaaaaaa aaaaaaaaaa aaaaaaaaaa aaaaaaaaaa  4260
aaaaaaaaaa aaaa                                                  4274
```

```
SEQ ID NO: 69          moltype = AA  length = 1268
FEATURE                Location/Qualifiers
source                 1..1268
                       mol_type = protein
                       organism = synthetic construct
SEQUENCE: 69
MFVFLVLLPL VSSQCVNLIT RTQSYTNSFT RGVYYPDKVF RSSVLHSTQD LFLPFFSNVT  60
WFHAISGTNG TKRFDNPVLP FNDGVYFAST EKSNIIRGWI FGTTLDSKTQ SLLIVNNATN  120
VVIKVCEFQF CNDPFLDVYY HKNNKSWMES EFRVYSSANN CTFEYVSQPF LMDLEGKQGN  180
FKNLREFVFK NIDGYFKIYS KHTPINLGRD LPQGFSALEP LVDLPIGINI TRFQTLLALH  240
RSYLTPGDSS SGWTAGAAAY YVGYLQPRTF LLKYNENGTI TDAVDCALDP LSETKCTLKS  300
FTVEKGIYQT SNFRVQPTES IVRFPNITNL CPFDEVFNAT RFASVYAWNR KRISNCVADY  360
SVLYNFAPFF AFKCYGVSPT KLNDLCFTNV YADSFVIRGN EVRQIAPGQT GNIADYNYKL  420
PDDFTGCVIA WNSNKLDSKV GGNYNYRYRL FRKSNLKPFE RDISTEIYQA GNKPCNGVAG  480
VNCYFPLQSY GFRPTYGVGH QPYRVVVLSF ELLHAPATVC GPKKSTNLVK NKCVNFNFNG  540
LTGTGVLTES NKKFLPFQQF GRDIADTTDA VRDPQTLEIL DITPCSFGGV SVITPGTNTS  600
NQVAVLYQGV NCTEVPVAIH ADQLTPTWRV YSTGSNVFQT RAGCLIGAEY VNNSYECDIP  660
IGAGICASYQ TQTKSHRRAR SVASQSIIAY TMSLGAENSV AYSNNSIAIP TNFTISVTTE  720
ILPVSMTKTS VDCTMYICGD STECSNLLLQ YGSFCTQLKR ALTGIAVEQD KNTQEVFAQV  780
```

-continued

```
KQIYKTPPIK YFGGFNFSQI LPDPSKPSKR SFIEDLLFNK VTLADAGFIK QYGDCLGDIA  840
ARDLICAQKF NGLTVLPPLL TDEMIAQYTS ALLAGTITSG WTFGAGAALQ IPFAMQMAYR  900
FNGIGVTQNV LYENQKLIAN QFNSAIGKIQ DSLSSTASAL GKLQDVVNHN AQALNTLVKQ  960
LSSKFGAISS VLNDILSRLD PPEAEVQIDR LITGRLQSLQ TYVTQQLIRA AEIRASANLA  1020
ATKMSECVLG QSKRVDFCGK GYHLMSFPQS APHGVVFLHV TYVPAQEKNF TTAPAICHDG  1080
KAHFPREGVF VSNGTHWFVT QRNFYEPQII TTDNTFVSGN CDVVIGIVNN TVYDPLQPEL  1140
DSFKEELDKY FKNHTSPDVD LGDISGINAS VVNIQKEIDR LNEVAKNLNE SLIDLQELGK  1200
YEQYIKWPWY IWLGFIAGLI AIVMVTIMLC CMTSCCSCLK GCCSCGSCCK FDEDDSEPVL  1260
KGVKLHYT                                                          1268

SEQ ID NO: 70          moltype = RNA  length = 3810
FEATURE                Location/Qualifiers
source                 1..3810
                       mol_type = other RNA
                       organism = synthetic construct
SEQUENCE: 70
atgttcgtgt tcctggtgct gctgcctctg gtgtccagcc agtgtgtgaa cctgatcacc  60
agaacacagt catacaccaa cagctttacc agaggcgtgt actaccccga caaggtgttc  120
agatccagcg tgctgcactc tacccaggac ctgttcctgc ctttcttcag caacgtgacc  180
tggttccacg ccatctccgg caccaatggc accaagagat tcgacaaccc cgtgctgccc  240
ttcaacgacg gggtgtactt tgccagcacc gagaagtcca acatcatcag aggctggatc  300
ttcggcacca cactggacag caagacccag agcctgctga tcgtgaacaa cgccaccaac  360
gtggtcatca aagtgtgcga gttccagttc tgcaacgacc ccttcctgga cgtctactac  420
cacaagaaca acaagagctg gatggaaagc gagttccggg tgtacagcag cgccaacaac  480
tgcaccttcg agtacgtgtc ccagcctttc ctgatggacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caaagtgcac cctgaagtcc  900
ttcaccgtgg aaaagggcat ctaccagacc agcaacttcc gggtgcagcc caccgaatcc  960
atcgtgcggt tccccaatat caccaatctg tgccccttcg acgaggtgtt caatgccacc  1020
agattcgcct ctgtgtacgc ctggaaccgg aagcggatca gcaattgcgt ggccgactac  1080
tccgtgctgt acaacttcgc cccattcttc gcattcaagt gctacggcgt gtcccctacc  1140
aagctgaacg acctgtgctt cacaaacgtg tacgccgaca gcttcgtgat ccggggaaac  1200
gaagtgcggc agattgcccc tggacagaca ggcaacatcg ccgactacaa ctacaagctg  1260
cccgacgact tcaccggctg tgtgattgcc tggaacagca acaagctgga ctccaaagtc  1320
ggcggcaact acaattacag gtaccggctg ttccggaagt ccaatctgaa gcccttcgag  1380
cgggacatct ccaccgagat ctatcaggcc ggcaacaagc cttgtaacgg cgtggcaggc  1440
gtgaactgct acttcccact gcagtcctac ggctttaggc ccacatacgg cgtgggccac  1500
cagccctaca gagtggtggt gctgagcttc gaactgctgc atgcccctgc cacagtgtgc  1560
ggccctaaga aaagcaccaa tctcgtgaag aacaaatgcg tgaacttcaa cttcaacggc  1620
ctgaccggca ccggcgtgct gacagagagc aacaagaagt tcctgccatt ccagcagttt  1680
ggccgggata tcgccgatac cacagacgcc gttagagatc cccagacact ggaaatcctg  1740
gacatcaccc cttgcagctt cggcggagtg tctgtgatca cccctggcac caacaccagc  1800
aatcaggtgg cagtgctgta ccagggcgtg aactgtaccg aagtgcccgt ggccattcac  1860
gccgatcagc tgacacctac atggcgggtg tactccaccg gcagcaatgt gtttcagacc  1920
agagccggct gtctgatcgg agccgagtac gtgaacaata gctacgagtg cgacatcccc  1980
atcggcgctg gaatctgcgc cagctaccag acacagacaa agagccaccg gagagccaga  2040
agcgtggcca gccagagcat cattgcctac acaatgtctc tgggcgccga gaacagcgtg  2100
gcctactcca acaactctat cgctatcccc accaacttca ccatcagcgt gaccacagag  2160
atcctgcctg tgtccatgac caagaccagc gtggactgca ccatgtacat ctgcggcgat  2220
tccaccgagt gctccaacct gctgctgcag tacggcagct tctgcaccca gctgaaaaga  2280
gccctgacag ggatcgccgt ggaacaggac aagaacaccc aagaggtgtt cgcccaagtg  2340
aagcagatct acaagacccc tcctatcaag tacttcggcg gcttcaattt cagccagatt  2400
ctgcccgatc ctagcaagcc cagcaagcgg agcttcatcg aggacctgct gttcaacaaa  2460
gtgacactgg ccgacgccgg cttcatcaag cagtatggcg attgtctggg cgacattgcc  2520
gccagggatc tgatttgcgc ccagaagttt aacggactga cagtgctgcc tcctctgctg  2580
accgatgaga tgatcgccca gtacacatct gccctgctgg ccggcacaat cacaagcggc  2640
tggacatttg gagcaggcgc cgctctgcag atcccctttg ctatgcagat ggcctaccgg  2700
ttcaacggca tcggagtgac ccagaatgtg ctgtacgaga accagaagct gatcgccaac  2760
cagttcaaca gcgccatcgg caagatccag gacagcctga gcagcacagc aagcgccctg  2820
ggaaagctgc aggacgtggt caaccacaat gcccaggcac tgaacaccct ggtcaagcag  2880
ctgtcctcca agttcggcgc catcagctct gtgctgaacg atatcctgag cagactggac  2940
cctcctgagg ccgaggtgca gatcgacaga ctgatcacag gcagactgca gagcctccag  3000
acatacgtga cccagcagct gatcagagcc gccgagatta gagcctctgc caatctggcc  3060
gccaccaaga tgtctgagtg tgtgctgggc cagagcaaga gagtggactt ttgcggcaag  3120
ggctaccacc tgatgagctt ccctcagtct gcccctcacg gcgtggtgtt tctgcacgtg  3180
acatatgtgc ccgctcaaga gaagaatttc accaccgctc cagccatctg ccacgacggc  3240
aaagcccact ttcctagaga aggcgtgttc gtgtccaacg gcacccattg gttcgtgaca  3300
cagcggaact tctacgagcc ccagatcatc accaccgaca acaccttcgt gtctggcaac  3360
tgcgacgtcg tgatcggcat tgtgaacaat accgtgtacg accctctgca gcccgagctg  3420
gacagcttca aagaggaact ggacaagtac tttaagaacc acacaagccc cgacgtggac  3480
ctgggcgata tcagcggaat caatgccagc gtcgtgaaca tccagaaaga gatcgaccgg  3540
ctgaacgagg tggccaagaa tctgaacgag agcctgatcg acctgcaaga actggggaag  3600
tacgagcagt acatcaagtg gccctggtac atctggctgg gctttatcgc cggactgatt  3660
gccatcgtga tggtcacaat catgctgtgt tgcatgacca gctgctgtag ctgcctgaag  3720
ggctgttgta gctgtggcag ctgctgcaag ttcgacgagg acgattctga gcccgtgctg  3780
```

```
aagggcgtga aactgcacta cacatgatga                                3810

SEQ ID NO: 71          moltype = DNA  length = 3810
FEATURE                Location/Qualifiers
source                 1..3810
                       mol_type = other DNA
                       organism = synthetic construct
SEQUENCE: 71
atgttcgtgt tcctggtgct gctgcctctg gtgtccagcc agtgtgtgaa cctgatcacc  60
agaacacagt catacaccaa cagctttacc agaggcgtgt actaccccga caaggtgttc  120
agatccagcg tgctgcactc tacccaggac ctgttcctgc ctttcttcag caacgtgacc  180
tggttccacg ccatctccgg caccaatggc accaagagat tcgacaaccc cgtgctgccc  240
ttcaacgacg ggtgtactt tgccagcacc gagaagtcca acatcatcag aggctggatc  300
ttcggcacca cactggacag caagacccag agcctgctga tcgtgaacaa cgccaccaac  360
gtggtcatca aagtgtgcga gttccagttc tgcaacgacc ccttcctgga cgtctactac  420
cacaagaaca acaagagctg gatggaaagc gagttccggg tgtacagcag cgccaacaac  480
tgcaccttcg agtacgtgtc ccagcctttc ctgatggacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caaagtgcac cctgaagtcc  900
ttcaccgtgg aaaagggcat ctaccagacc agcaacttcc gggtgcagcc caccgaatcc  960
atcgtgcggt tccccaatat caccaatctg tgcccctteg acgaggtgtt caatgccacc  1020
agattcgcct ctgtgtacgc ctggaaccgg aagcggatca gcaattgcgt ggccgactac  1080
tccgtgctgt acaacttcgc cccctteftc gcattcaagt gctacggcgt gtcccctacc  1140
aagctgaacg acctgtgctt cacaaacgtg tacgccgaca gcttcgtgat ccggggaaac  1200
gaagtgcggc agattgcccc tggacagaca ggcaacatcg ccgactacaa ctacaagctg  1260
cccgacgact tcaccggctg tgtgattgcc tggaacagca acaagctgga ctccaaagtc  1320
ggcggcaact acaattacag gtaccggctg ttccggaagt ccaatctgaa gcccttcgag  1380
cgggacatct ccaccgagat ctatcaggcc ggcaacaagc cttgtaacgg cgtggcaggc  1440
gtgaactgct acttcccact gcagtcctac ggctttaggc ccacatacgg cgtgggccac  1500
cagccctaca gagtggtggt gctgagcttc gaactgctgc atgcccctgc cacagtgtgc  1560
ggccctaaga aaagcaccaa tctcgtgaag aacaaatgcg tgaacttcaa cttcaacggc  1620
ctgaccggca ccggcgtgct gacagagagc aacaagaagt tcctgccatt ccagcagttt  1680
ggccgggata tcgccgatac cacagacgcc gttagagatc cccagacact ggaaatcctg  1740
gacatcaccc cttgcagctt cggcggagtg tctgtgatca cccctggcac caacaccagc  1800
aatcaggtgg cagtgctgta ccagggcgtg aactgtaccg aagtgcccgt ggccattcac  1860
gccgatcagc tgacacctac atggcgggtg tactccaccg gcagcaatgt gtttcagacc  1920
agagccggct gtctgatcgg agccgagtac gtgaacaata gctacgagtg cgacatcccc  1980
atcggcgctg gaatctgcgc cagctaccag acacagacaa agagccaccg gagagccaga  2040
agcgtggcca gccagagcat cattgcctac acaatgtctc tgggcgccga gaacagcgtg  2100
gcctactcca acaactctat cgctatcccc accaacttca ccatcagcgt gaccacagag  2160
atcctgcctg tgtccatgac caagaccagc gtggactgca ccatgtacat ctgcggcgat  2220
tccaccgagt gctccaacct gctgctgcag tacggcagct tctgcaccca gctgaaaaga  2280
gccctgacag ggatcgccgt ggaacaggac aagaacaccc aagaggtgtt cgcccaagtg  2340
aagcagatct acaagacccc tcctatcaag tacttcggcg gcttcaattt cagccagatt  2400
ctgcccgatc ctagcaagcc cagcaagcgg agcttcatcg aggacctgct gttcaacaaa  2460
gtgacactgg ccgacgccgg cttcatcaag cagtatggcg attgtctggg cgacattgcc  2520
gccagggatc tgatttgcgc ccagaagttt aacggactga cagtgctgcc tcctctgctg  2580
accgatgaga tgatcgccca gtacacatct gccctgctgg ccggcacaat cacaagcggc  2640
tggacatttg gagcaggcgc cgctctgcag atcccctttg ctatgcagat ggcctaccgg  2700
ttcaacggca tcggagtgac ccagaatgtg ctgtacgaga accagaagct gatcgccaac  2760
cagttcaaca gcgccatcgg caagatccag gacagcctga gcagcacagc aagcgccctg  2820
ggaaagctgc aggacgtggt caaccacaat gcccaggcac tgaacaccct ggtcaagcag  2880
ctgtcctcca agttcggcgc catcagctct gtgctgaacg atatcctgag cagactggac  2940
cctcctgagg ccgaggtgca gatcgacaga ctgatcacag gcagactgca gagcctccag  3000
acatacgtga cccagcagct gatcagagcc gccgagatta gagcctctgc caatctggcc  3060
gccaccaaga tgtctgagtg tgtgctgggc cagagcaaga gagtggactt ttgcggcaag  3120
ggctaccacc tgatgagctt ccctcagtct gcccctcacg gcgtggtgtt tctgcacgtg  3180
acatatgtgc ccgctcaaga gaagaatttc accaccgctc cagccatctg ccacgacggc  3240
aaagcccact ttcctagaga aggcgtgttc gtgtccaacg gcacccattg gttcgtgaca  3300
cagcggaact tctacgagcc ccagatcatc accaccgaca acaccttcgt gtctggcaac  3360
tgcgacgtcg tgatcggcat tgtgaacaat accgtgtacg accctctgca gcccgagctg  3420
gacagcttca aagaggaact ggacaagtac tttaagaacc acacaagccc cgacgtggac  3480
ctgggcgata tcagcggaat caatgccagc gtcgtgaaca tccagaaaga gatcgaccgg  3540
ctgaacgagg tggccaagaa tctgaacgag agcctgatcg acctgcaaga actggggaag  3600
tacgagcagt acatcaagtg gccctggtac atctggctgg gctttatcgc cggactgatt  3660
gccatcgtga tggtcacaat catgctgtgt tgcatgacca gctgctgtag ctgcctgaag  3720
ggctgttgta gctgtggcag ctgctgcaag ttcgacgagg acgattctga gcccgtgctg  3780
aagggcgtga aactgcacta cacatgatga                                3810

SEQ ID NO: 72          moltype = RNA  length = 4268
FEATURE                Location/Qualifiers
source                 1..4268
                       mol_type = other RNA
                       organism = synthetic construct
SEQUENCE: 72
```

-continued

```
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatctc cggcaccaat ggcaccaaga gattcgacaa ccccgtgctg cccttcaacg  300
acggggtgta ctttgccagc accgagaagt ccaacatcat cagaggctgg atcttcggca  360
ccacactgga cagcaagacc cagagcctgc tgatcgtgaa caacgccacc aacgtggtca  420
tcaaagtgtg cgagttccag ttctgcaacg acccccttcct ggacgtctac taccacaaga  480
acaacaagag ctggatggaa agcgagttcc gggtgtacag cagcgccaac aactgcacct  540
tcgagtacgt gtcccagcct ttcctgatgg acctggaagg caagcagggc aacttcaaga  600
acctgcgcga gttcgtgttt aagaacatcg acggctactt caagatctac agcaagcaca  660
cccctatcaa cctcggccgg gatctgcctc agggcttctc tgctctggaa cccctggtgg  720
atctgcccat cggcatcaac atcacccggt ttcagacact gctggccctg cacagaagct  780
acctgacacc tggcgatagc agcagcggat ggacagctgg tgccgccgct tactatgtgg  840
gctacctgca gcctagaacc ttcctgctga agtacaacga gaacggcacc atcaccgacg  900
ccgtggattg tgctctggat cctctgagcg agacaaagtg caccctgaag tccttcaccg  960
tggaaaaggg catctaccag accagcaact tccgggtgca gcccaccgaa tccatcgtgc  1020
ggttccccaa tatcaccaat ctgtgccccct tcgacgaggt gttcaatgcc accagattcg  1080
cctctgtgta cgcctggaac cggaagcgga tcagcaattg cgtggccgac tactccgtgc  1140
tgtacaactt cgccccccttc ttcgcattca agtgctacgg cgtgtcccct accaagctga  1200
acgacctgtg cttcacaaac gtgtacgccg acagcttcgt gatccgggga aacgaagtgc  1260
ggcagattgc ccctggacag acaggcaaca tcgccgacta caactacaag ctgcccgacg  1320
acttcaccgg ctgtgtgatt gcctggaaca gcaacaagct ggactccaaa gtcggcggca  1380
actacaatta caggtaccgg ctgttccgga agtccaatct gaagcccttc gagcgggaca  1440
tctccaccga gatctatcag gccggcaaca agccttgtaa cggcgtggca ggcgtgaact  1500
gctacttccc actgcagtcc tacggcttta ggcccacata cggcgtgggc caccagccct  1560
acagagtggt ggtgctgagc ttcgaactgc tgcatgcccc tgccacagtg tgcggcccta  1620
agaaaagcac caatctcgtg aagaacaaat gcgtgaactt caacttcaac ggcctgaccg  1680
gcaccggcgt gctgacagag agcaacaaga agttcctgcc attccagcag tttggccggg  1740
atatcgccga taccacagac gccgttagag atccccagac actggaaatc ctggacatca  1800
cccccttgcag cttcggcgga gtgtctgtga tcacccctgg caccaacacc agcaatcagg  1860
tggcagtgct gtaccagggc gtgaactgta ccgaagtgcc cgtggccatt cacgccgatc  1920
agctgacacc tacatggcgg gtgtactcca ccggcagcaa tgtgtttcag accagagccg  1980
gctgtctgat cggagccgag tacgtgaaca atagctacga gtgcgacatc cccatcggcg  2040
ctggaatctg cgccagctac cagacacaga caaagagcca ccggagagcc agaagcgtgg  2100
ccagccagag catcattgcc tacacaatgt ctctgggcgc cgagaacagc gtggcctact  2160
ccaacaactc tatcgctatc cccaccaact tcaccatcag cgtgaccaca gagatcctgc  2220
ctgtgtccat gaccaagacc agcgtggact gcaccatgta catctgcggc gattccaccg  2280
agtgctccaa cctgctgctg cagtacggca gcttctgcac ccagctgaaa agagccctga  2340
cagggatcgc cgtggaacag gacaagaaca cccaagaggt gttcgcccaa gtgaagcaga  2400
tctacaagac ccctcctatc aagtacttcg gcggcttcaa tttcagccag attctgcccg  2460
atcctagcaa gcccagcaag cggagcttca tcgaggacct gctgttcaac aaagtgacac  2520
tggccgacgc cggcttcatc aagcagtatg gcgattgtct gggcgacatt gccgccaggg  2580
atctgatttg cgcccagaag tttaacggac tgacagtgct gcctcctctg ctgaccgatg  2640
agatgatcgc ccagtacaca tctgccctgc tggccggcac aatcacaagc ggctggacat  2700
ttggagcagg cgccgctctg cagatcccct ttgctatgca gatggcctac cggttcaacg  2760
gcatcggagt gacccagaat gtgctgtacg agaaccagaa gctgatcgcc aaccagttca  2820
acagcgccat cggcaagatc caggacagcc tgagcagcac agcaagcgcc ctgggaaagc  2880
tgcaggacgt ggtcaaccac aatgcccagg cactgaacac cctggtcaag cagctgtcct  2940
ccaagttcgg cgccatcagc tctgtgctga acgatatcct gagcagactg gaccctcctg  3000
aggccgaggt gcagatcgac agactgatca caggcagact gcagagcctc cagacatacg  3060
tgacccagca gctgatcaga gccgccgaga ttagagcctc tgccaatctg gccgccacca  3120
agatgtctga gtgtgtgctg ggccagagca agagagtgga cttttgcggc aagggctacc  3180
acctgatgag cttccctcag tctgcccctc acggcgtggt gtttctgcac gtgacatatg  3240
tgcccgctca agagaagaat ttcaccaccg ctccagccat ctgccacgac ggcaaagccc  3300
actttcctag agaaggcgtg ttcgtgtcca acggcaccca ttggttcgtg acacagcgga  3360
acttctacga gccccagatc atcaccaccg acaacacctt cgtgtctggc aactgcgacg  3420
tcgtgatcgg cattgtgaac aataccgtgt acgaccctct gcagcccgag ctggacagct  3480
tcaaagagga actggacaag tactttaaga accacacaag ccccgacgtg gacctgggcg  3540
atatcagcgg aatcaatgcc agcgtcgtga acatccagaa agagatcgac cggctgaacg  3600
aggtggccaa gaatctgaac gagagcctga tcgacctgca agaactgggg aagtacgagc  3660
agtacatcaa gtggccctgg tacatctggc tgggctttat cgccggactg attgccatcg  3720
tgatggtcac aatcatgctg tgttgcatga ccagctgctg tagctgcctg aagggctgtt  3780
gtagctgtgg cagctgctgc aagttcgacg aggacgattc tgagcccgtg ctgaagggcg  3840
tgaaactgca ctacacatga tgactcgagc tggtactgca tgcacgcaat gctagctgcc  3900
cctttcccgt cctgggtacc ccgagtctcc cccgacctcg ggtcccaggt atgctcccac  3960
ctccacctgc cccactcacc acctctgcta gttccagaca cctcccaagc acgcagcaat  4020
gcagctcaaa acgcttagcc tagccacacc cccacgggaa acagcagtga ttaacccttta  4080
gcaataaacg aaagtttaac taagctatac taaccccagg gttggtcaat ttcgtgccag  4140
ccacaccctg gagctagcaa aaaaaaaaaa aaaaaaaaaa aaaaaaaagc atatgactaa  4200
aaaaaaaaaa aaaaaaaaaa aaaaaaaaaa aaaaaaaaaa aaaaaaaaaa aaaaaaaaaa  4260
aaaaaaaa                                                          4268
```

```
SEQ ID NO: 73          moltype = DNA  length = 4268
FEATURE                Location/Qualifiers
source                 1..4268
                       mol_type = other DNA
                       organism = synthetic construct
SEQUENCE: 73
```

-continued

```
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatctc cggcaccaat ggcaccaaga gattcgacaa ccccgtgctg cccttcaacg  300
acggggtgta ctttgccagc accgagaagt ccaacatcat cagaggctgg atcttcggca  360
ccacactgga cagcaagacc cagagcctgc tgatcgtgaa caacgccacc aacgtggtca  420
tcaaagtgtg cgagttccag ttctgcaacg accccttcct ggacgtctac taccacaaga  480
acaacaagag ctggatggaa agcgagttcc gggtgtacag cagcgccaac aactgcacct  540
tcgagtacgt gtcccagcct ttcctgatgg acctggaagg caagcagggc aacttcaaga  600
acctgcgcga gttcgtgttt aagaacatcg acggctactt caagatctac agcaagcaca  660
cccctatcaa cctcggccgg gatctgcctc agggcttctc tgctctggaa cccctggtgg  720
atctgcccat cggcatcaac atcacccggt ttcagacact gctggccctg cacagaagct  780
acctgacacc tggcgatagc agcagcggat ggacagctgg tgccgccgct tactatgtgg  840
gctacctgca gcctagaacc ttcctgctga agtacaacga gaacggcacc atcaccgacg  900
ccgtggattg tgctctggat cctctgagcg agacaaagtg caccctgaag tccttcaccg  960
tggaaaaggg catctaccag accagcaact tccgggtgca gcccaccgaa tccatcgtgc  1020
ggttccccaa tatcaccaat ctgtgccct tcgacgaggt gttcaatgcc accagattcg  1080
cctctgtgta cgcctggaac cggaagcgga tcagcaattg cgtggccgac tactccgtgc  1140
tgtacaactt cgccccctc ttcgcattca agtgctacgg cgtgtcccct accaagctga  1200
acgacctgtg cttcacaaac gtgtacgccg acagcttcgt gatccgggga aacgaagtgc  1260
ggcagattgc ccctggacag acaggcaaca tcgccgacta caactacaag ctgcccgacg  1320
acttcaccgg ctgtgtgatt gcctggaaca gcaacaagct ggactccaaa gtcggcggca  1380
actacaatta caggtaccgg ctgttccgga agtccaatct gaagcccttc gagcgggaca  1440
tctccaccga gatctatcag gccggcaaca agccttgtaa cggcgtggca ggcgtgaact  1500
gctacttccc actgcagtcc tacggcttta ggcccacata cggcgtgggc caccagccct  1560
acagagtggt ggtgctgagc ttcgaactgc tgcatgcccc tgccacagtg tgcggcccta  1620
agaaaagcac caatctcgtg aagaacaaat gcgtgaactt caacttcaac ggcctgaccg  1680
gcaccggcgt gctgacagag agcaacaaga agttcctgcc attccagcag tttggccggg  1740
atatcgccga taccacagac gccgttagag atccccagac actggaaatc ctggacatca  1800
cccttgcag cttcggcgga gtgtctgtga tcacccctgg caccaacacc agcaatcagg  1860
tggcagtgct gtaccagggc gtgaactgta ccgaagtgcc cgtggccatt cacgccgatc  1920
agctgacacc tacatggcgg gtgtactcca ccggcagcaa tgtgtttcag accagagccg  1980
gctgtctgat cggagccgag tacgtgaaca atagctacga gtgcgacatc cccatcggcg  2040
ctggaatctg cgccagctac cagacacaga caaagagcca ccggagagcc agaagcgtgg  2100
ccagccagag catcattgcc tacacaatgt ctctgggcgc cgagaacagc gtggcctact  2160
ccaacaactc tatcgctatc cccaccaact tcaccatcag cgtgaccaca gagatcctgc  2220
ctgtgtccat gaccaagacc agcgtggact gcaccatgta catctgcggc gattccaccg  2280
agtgctccaa cctgctgctg cagtacggca gcttctgcac ccagctgaaa agagccctga  2340
cagggatcgc cgtggaacag gacaagaaca cccaagaggt gttcgcccaa gtgaagcaga  2400
tctacaagac ccctcctatc aagtacttcg gcggcttcaa tttcagccag attctgcccg  2460
atcctagcaa gcccagcaag cggagcttca tcgaggacct gctgttcaac aaagtgacac  2520
tggccgacgc cggcttcatc aagcagtatg gcgattgtct gggcgacatt gccgccaggg  2580
atctgatttg cgcccagaag tttaacggac tgacagtgct gcctcctctg ctgaccgatg  2640
agatgatcgc ccagtacaca tctgccctgc tggccggcac aatcacaagc ggctggacat  2700
ttggagcagg cgccgctctg cagatcccct ttgctatgca gatggcctac cggttcaacg  2760
gcatcggagt gacccagaat gtgctgtacg agaaccagaa gctgatcgcc aaccagttca  2820
acagcgccat cggcaagatc caggacagcc tgagcagcac agcaagcgcc ctgggaaagc  2880
tgcaggacgt ggtcaaccac aatgcccagg cactgaacac cctggtcaag cagctgtcct  2940
ccaagttcgg cgccatcagc tctgtgctga acgatatcct gagcagactg gaccctcctg  3000
aggccgaggt gcagatcgac agactgatca caggcagact gcagagcctc cagacatacg  3060
tgacccagca gctgatcaga gccgccgaga ttagagcctc tgccaatctg gccgccacca  3120
agatgtctga gtgtgtgctg ggccagagca agagagtgga cttttgcggc aagggctacc  3180
acctgatgag cttccctcag tctgcccctc acggcgtggt gtttctgcac gtgacatatg  3240
tgcccgctca agagaagaat ttcaccaccg ctccagccat ctgccacgac ggcaaagccc  3300
actttcctag agaaggcgtg ttcgtgtcca acggcaccca ttggttcgtg acacagcgga  3360
acttctacga gccccagatc atcaccaccg acaacacctt cgtgtctggc aactgcgacg  3420
tcgtgatcgg cattgtgaac aataccgtgt acgaccctct gcagcccgag ctggacagct  3480
tcaaagagga actggacaag tactttaaga accacacaag ccccgacgtg gacctgggcg  3540
atatcagcgg aatcaatgcc agcgtcgtga acatccagaa agagatcgac cggctgaacg  3600
aggtggccaa gaatctgaac gagagcctga tcgacctgca agaactgggg aagtacgagc  3660
agtacatcaa gtggccctgg tacatctggc tgggctttat cgccggactg attgccatcg  3720
tgatggtcac aatcatgctg tgttgcatga ccagctgctg tagctgcctg aagggctgtt  3780
gtagctgtgg cagctgctgc aagttcgacg aggacgattc tgagcccgtg ctgaagggcg  3840
tgaaactgca ctacacatga tgactcgagc tggtactgca tgcacgcaat gctagctgcc  3900
cctttcccgt cctgggtacc ccgagtctcc cccgacctcg ggtcccaggt atgctcccac  3960
ctccacctgc cccactcacc acctctgcta gttccagaca cctcccaagc acgcagcaat  4020
gcagctcaaa acgcttagcc tagccacacc cccacgggaa acagcagtga ttaacctta  4080
gcaataaacg aaagtttaac taagctatac taaccccagg gttggtcaat ttcgtgccag  4140
ccacaccctg gagctagcaa aaaaaaaaa aaaaaaaaa aaaaaaaagc atatgactaa  4200
aaaaaaaaaa aaaaaaaaa aaaaaaaaaa aaaaaaaaa aaaaaaaaa aaaaaaaaaa  4260
aaaaaaaa                                                          4268
```

```
SEQ ID NO: 74          moltype = AA  length = 1268
FEATURE                Location/Qualifiers
source                 1..1268
                       mol_type = protein
                       organism = synthetic construct
SEQUENCE: 74
```

-continued

```
MFVFLVLLPL VSSQCVNLIT RTQSYTNSFT RGVYYPDKVF RSSVLHSTQD LFLPFFSNVT  60
WFHAISGTNG TKRFDNPVLP FNDGVYFAST EKSNIIRGWI FGTTLDSKTQ SLLIVNNATN  120
VVIKVCEFQF CNDPFLDVYY HKNNKSWMES EFRVYSSANN CTFEYVSQPF LMDLEGKQGN  180
FKNLREFVFK NIDGYFKIYS KHTPINLGRD LPQGFSALEP LVDLPIGINI TRFQTLLALH  240
RSYLTPGDSS SGWTAGAAAY YVGYLQPRTF LLKYNENGTI TDAVDCALDP LSETKCTLKS  300
FTVEKGIYQT SNFRVQPTES IVRFPNITNL CPFDEVFNAT RFASVYAWNR KRISNCVADY  360
SVLYNFAPFF AFKCYGVSPT KLNDLCFTNV YADSFVIRGN EVSQIAPGQT GNIADYNYKL  420
PDDFTGCVIA WNSNKLDSKV GGNYNYRYRL FRKSNLKPFE RDISTEIYQA GNKPCNGVAG  480
VNCYFPLQSY GFRPTYGVGH QPYRVVVLSF ELLHAPATVC GPKKSTNLVK NKCVNFNFNG  540
LTGTGVLTES NKKFLPFQQF GRDIADTTDA VRDPQTLEIL DITPCSFGGV SVITPGTNTS  600
NQVAVLYQGV NCTEVPVAIH ADQLTPTWRV YSTGSNVFQT RAGCLIGAEY VNNSYECDIP  660
IGAGICASYQ TQTKSHRRAR SVASQSIIAY TMSLGAENSV AYSNNSIAIP TNFTISVTTE  720
ILPVSMTKTS VDCTMYICGD STECSNLLLQ YGSFCTQLKR ALTGIAVEQD KNTQEVFAQV  780
KQIYKTPPIK YFGGFNFSQI LPDPSKPSKR SFIEDLLFNK VTLADAGFIK QYGDCLGDIA  840
ARDLICAQKF NGLTVLPPLL TDEMIAQYTS ALLAGTITSG WTFGAGAALQ IPFAMQMAYR  900
FNGIGVTQNV LYENQKLIAN QFNSAIGKIQ DSLSSTASAL GKLQDVVNHN AQALNTLVKQ  960
LSSKFGAISS VLNDILSRLD PPEAEVQIDR LITGRLQSLQ TYVTQQLIRA AEIRASANLA  1020
ATKMSECVLG QSKRVDFCGK GYHLMSFPQS APHGVVFLHV TYVPAQEKNF TTAPAICHDG  1080
KAHFPREGVF VSNGTHWFVT QRNFYEPQII TTDNTFVSGN CDVVIGIVNN TVYDPLQPEL  1140
DSFKEELDKY FKNHTSPDVD LGDISGINAS VVNIQKEIDR LNEVAKNLNE SLIDLQELGK  1200
YEQYIKWPWY IWLGFIAGLI AIVMVTIMLC CMTSCCSCLK GCCSCGSCCK FDEDDSEPVL  1260
KGVKLHYT                                                          1268

SEQ ID NO: 75          moltype = RNA  length = 3810
FEATURE                Location/Qualifiers
source                 1..3810
                       mol_type = other RNA
                       organism = synthetic construct
SEQUENCE: 75
atgttcgtgt tcctggtgct gctgcctctg gtgtccagcc agtgtgtgaa cctgatcacc  60
agaacacaga gctacaccaa cagctttacc agaggcgtgt actaccccga caaggtgttc  120
agatccagcg tgctgcactc tacccaggac ctgttcctgc ctttcttcag caacgtgacc  180
tggttccacg ccatctccgg caccaatggc accaagagat tcgacaaccc cgtgctgccc  240
ttcaacgacg gggtgtactt tgccagcacc gagaagtcca acatcatcag aggctggatc  300
ttcggcacca cactggacag caagacccag agcctgctga tcgtgaacaa cgccaccaac  360
gtggtcatca aagtgtgcga gttccagttc tgcaacgacc ccttcctgga cgtgtactac  420
cacaagaaca acaagagctg gatggaaagc gagttccggg tgtacagcag cgccaacaac  480
tgcaccttcg agtacgtgtc ccagcctttc ctgatggacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caaagtgcac cctgaagtcc  900
ttcaccgtgg aaaagggcat ctaccagacc agcaacttcc gggtgcagcc caccgaatcc  960
atcgtgcggt tccccaatat caccaatctg tgccccttcg acgaggtgtt caatgccacc  1020
agattcgcct ctgtgtacgc ctggaaccgg aagcggatca gcaattgcgt ggccgactac  1080
tccgtgctgt acaacttcgc cccctttctc gccttcaagt gctacggcgt gtcccctacc  1140
aagctgaacg acctgtgctt cacaaacgtg tacgccgaca gcttcgtgat ccggggaaac  1200
gaagtgagcc agattgcccc tggacagaca ggcaacatcg ccgactacaa ctacaagctg  1260
cccgacgact tcaccggctg tgtgattgcc tggaacagca acaagctgga ctccaaagtc  1320
ggcggcaact acaattacag gtaccggctg ttccggaagt ccaatctgaa gcccttcgag  1380
cgggacatct ccaccgagat ctatcaggcc ggcaacaagc cttgtaacgg cgtggccggc  1440
gtgaactgct acttcccact gcagtcctac ggctttaggc ccacatatgg cgtgggccat  1500
cagccctaca gagtggtggt gctgagcttc gaactgctgc atgcccctgc cacagtgtgc  1560
ggccctaaga aaagcaccaa tctcgtgaag aacaaatgcg tgaacttcaa cttcaacggc  1620
ctgaccggca ccggcgtgct gacagagagc aacaagaagt tcctgccatt ccagcagttt  1680
ggccgggata tcgccgatac cacagacgcc gttagagatc cccagacact ggaaatcctg  1740
gacatcaccc cttgcagctt cggcggagtg tctgtgatca cccctggcac caacaccagc  1800
aatcaggtgg cagtgctgta ccagggcgtg aactgtaccg aagtgcccgt ggccattcac  1860
gccgatcagc tgacacctac atggcgggtg tactccaccg gcagcaatgt gtttcagacc  1920
agagccggct gtctgatcgg agccgagtac gtgaacaata gctacgagtg cgacatcccc  1980
atcggcgctg gaatctgcgc cagctaccag acacagacaa agagccaccg gagagccaga  2040
agcgtggcca gccagagcat cattgcctac acaatgtctc tgggcgccga gaacagcgtg  2100
gcctactcca acaactctat cgctatcccc accaacttca ccatcagcgt gaccacagag  2160
atcctgcctg tgtccatgac caagaccagc gtggactgca ccatgtacat ctgcggcgat  2220
tccaccgagt gctccaacct gctgctgcag tacggcagct tctgcaccca gctgaagaga  2280
gccctgacag ggatcgccgt ggaacaggac aagaacaccc aagaggtgtt cgcccaagtg  2340
aagcagatct acaagacccc tcctatcaag tacttcggcg gcttcaattt cagccagatt  2400
ctgcccgatc ctagcaagcc cagcaagcgg agcttcatcg aggacctgct gttcaacaaa  2460
gtgacactgg ccgacgccgg cttcatcaag cagtatggcg attgtctggg cgacattgcc  2520
gccagggatc tgatttgcgc ccagaagttt aacggactga cagtgctgcc tcctctgctg  2580
accgatgaga tgatcgccca gtacacatct gccctgctgg ccggcacaat cacaagcggc  2640
tggacatttg gagcaggcgc cgctctgcag atcccctttg ctatgcagat ggcctaccgg  2700
ttcaacggca tcggagtgac ccagaatgtg ctgtacgaga accagaagct gatcgccaac  2760
cagttcaaca gcgccatcgg caagatccag gacagcctga gcagcacagc aagcgccctg  2820
ggaaagctgc aggacgtggt caaccacaat gcccaggcac tgaacaccct ggtcaagcag  2880
ctgtcctcca agttcggcgc catcagctct gtgctgaacg atatcctgag cagactggac  2940
cctcctgagg ccgaggtgca gatcgacaga ctgatcacag gcagactgca gagcctccag  3000
```

```
acatacgtga cccagcagct gatcagagcc gccgagatta gagcctctgc caatctggcc  3060
gccaccaaga tgtctgagtg tgtgctgggc cagagcaaga gagtggactt ttgcggcaag  3120
ggctaccacc tgatgagctt ccctcagtct gcccctcacg gcgtggtgtt tctgcacgtg  3180
acatatgtgc ccgctcaaga gaagaatttc accaccgctc cagccatctg ccacgacggc  3240
aaagcccact ttcctagaga aggcgtgttc gtgtccaacg gcacccattg gttcgtgaca  3300
cagcggaact tctacgagcc ccagatcatc accaccgaca acaccttcgt gtctggcaac  3360
tgcgacgtcg tgatcggcat tgtgaacaat accgtgtacg accctctgca gcccgagctg  3420
gacagcttca aagaggaact ggacaagtac tttaagaacc acacaagccc cgacgtggac  3480
ctgggcgata tcagcggaat caatgccagc gtcgtgaaca tccagaaaga gatcgaccgg  3540
ctgaacgagg tggccaagaa tctgaacgag agcctgatcg acctgcaaga actggggaag  3600
tacgagcagt acatcaagtg gccctggtac atctggctgg gctttatcgc cggactgatt  3660
gccatcgtga tggtcacaat catgctgtgt tgcatgacca gctgctgtag ctgcctgaag  3720
ggctgttgta gctgtggcag ctgctgcaag ttcgacgagg acgattctga gcccgtgctg  3780
aagggcgtga aactgcacta cacatgatga                                   3810
```

```
SEQ ID NO: 76           moltype = DNA  length = 3810
FEATURE                 Location/Qualifiers
source                  1..3810
                        mol_type = other DNA
                        organism = synthetic construct
SEQUENCE: 76
atgttcgtgt tcctggtgct gctgcctctg gtgtccagcc agtgtgtgaa cctgatcacc  60
agaacacaga gctacaccaa cagctttacc agaggcgtgt actaccccga caaggtgttc  120
agatccagcg tgctgcactc tacccaggac ctgttcctgc ctttcttcag caacgtgacc  180
tggttccacg ccatctccgg caccaatggc accaagagat tcgacaaccc cgtgctgccc  240
ttcaacgacg gggtgtactt tgccagcacc gagaagtcca acatcatcag aggctggatc  300
ttcggcacca cactggacag caagacccag agcctgctga tcgtgaacaa cgccaccaac  360
gtggtcatca aagtgtgcga gttccagttc tgcaacgacc ccttcctgga cgtgtactac  420
cacaagaaca acaagagctg gatggaaagc gagttccggg tgtacagcag cgccaacaac  480
tgcaccttcg agtacgtgtc ccagcctttc ctgatggacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caaagtgcac cctgaagtcc  900
ttcaccgtgg aaaagggcat ctaccagacc agcaacttcc gggtgcagcc caccgaatcc  960
atcgtgcggt tccccaatat caccaatctg tgccccttcg acgaggtgtt caatgccacc  1020
agattcgcct ctgtgtacgc ctggaaccgg aagcggatca gcaattgcgt ggccgactac  1080
tccgtgctgt acaacttcgc cccctcttc gccttcaagt gctacggcgt gtcccctacc  1140
aagctgaacg acctgtgctt cacaaacgtg tacgccgaca gcttcgtgat ccggggaaac  1200
gaagtgagcc agattgcccc tggacagaca ggcaacatcg ccgactacaa ctacaagctg  1260
cccgacgact tcaccggctg tgtgattgcc tggaacagca acaagctgga ctccaaagtc  1320
ggcggcaact acaattacag gtaccggctg ttccggaagt ccaatctgaa gcccttcgag  1380
cgggacatct ccaccgagat ctatcaggcc ggcaacaagc cttgtaacgg cgtggccggc  1440
gtgaactgct acttcccact gcagtcctac ggctttaggc ccacatatgg cgtgggccat  1500
cagccctaca gagtggtggt gctgagcttc gaactgctgc atgcccctgc cacagtgtgc  1560
ggccctaaga aaagcaccaa tctcgtgaag aacaaatgcg tgaacttcaa cttcaacggc  1620
ctgaccggca ccggcgtgct gacagagagc aacaagaagt tcctgccatt ccagcagttt  1680
ggccgggata tcgccgatac cacagacgcc gttagagatc cccagacact ggaaatcctg  1740
gacatcaccc cttgcagctt cggcggagtg tctgtgatca cccctggcac caacaccagc  1800
aatcaggtgg cagtgctgta ccagggcgtg aactgtaccg aagtgcccgt ggccattcac  1860
gccgatcagc tgacacctac atggcgggtg tactccaccg gcagcaatgt gtttcagacc  1920
agagccggct gtctgatcgg agccgagtac gtgaacaata gctacgagtg cgacatcccc  1980
atcggcgctg gaatctgcgc cagctaccag acacagacaa agagccaccg gagagccaga  2040
agcgtggcca gccagagcat cattgcctac acaatgtctc tgggcgccga gaacagcgtg  2100
gcctactcca acaactctat cgctatcccc accaacttca ccatcagcgt gaccacagag  2160
atcctgcctg tgtccatgac caagaccagc gtggactgca ccatgtacat ctgcggcgat  2220
tccaccgagt gctccaacct gctgctgcag tacggcagct tctgcaccca gctgaagaga  2280
gccctgacag ggatcgccgt ggaacaggac aagaacaccc aagaggtgtt cgcccaagtg  2340
aagcagatct acaagacccc tcctatcaag tacttcggcg gcttcaattt cagccagatt  2400
ctgcccgatc ctagcaagcc cagcaagcgg agcttcatcg aggacctgct gttcaacaaa  2460
gtgacactgg ccgacgccgg cttcatcaag cagtatggcg attgtctggg cgacattgcc  2520
gccagggatc tgatttgcgc ccagaagttt aacggactga cagtgctgcc tcctctgctg  2580
accgatgaga tgatcgccca gtacacatct gccctgctgg ccggcacaat cacaagcggc  2640
tggacatttg gagcaggcgc cgctctgcag atcccctttg ctatgcagat ggcctaccgg  2700
ttcaacggca tcggagtgac ccagaatgtg ctgtacgaga accagaagct gatcgccaac  2760
cagttcaaca gcgccatcgg caagatccag gacagcctga gcagcacagc aagcgccctg  2820
ggaaagctgc aggacgtggt caaccacaat gcccaggcac tgaacaccct ggtcaagcag  2880
ctgtcctcca agttcggcgc catcagctct gtgctgaacg atatcctgag cagactggac  2940
cctcctgagg ccgaggtgca gatcgacaga ctgatcacag gcagactgca gagcctccag  3000
acatacgtga cccagcagct gatcagagcc gccgagatta gagcctctgc caatctggcc  3060
gccaccaaga tgtctgagtg tgtgctgggc cagagcaaga gagtggactt ttgcggcaag  3120
ggctaccacc tgatgagctt ccctcagtct gcccctcacg gcgtggtgtt tctgcacgtg  3180
acatatgtgc ccgctcaaga gaagaatttc accaccgctc cagccatctg ccacgacggc  3240
aaagcccact ttcctagaga aggcgtgttc gtgtccaacg gcacccattg gttcgtgaca  3300
cagcggaact tctacgagcc ccagatcatc accaccgaca acaccttcgt gtctggcaac  3360
tgcgacgtcg tgatcggcat tgtgaacaat accgtgtacg accctctgca gcccgagctg  3420
gacagcttca aagaggaact ggacaagtac tttaagaacc acacaagccc cgacgtggac  3480
```

-continued

```
ctgggcgata tcagcggaat caatgccagc gtcgtgaaca tccagaaaga gatcgaccgg  3540
ctgaacgagg tggccaagaa tctgaacgag agcctgatcg acctgcaaga actggggaag  3600
tacgagcagt acatcaagtg gccctggtac atctggctgg gctttatcgc cggactgatt  3660
gccatcgtga tggtcacaat catgctgtgt tgcatgacca gctgctgtag ctgcctgaag  3720
ggctgttgta gctgtggcag ctgctgcaag ttcgacgagg acgattctga gcccgtgctg  3780
aagggcgtga aactgcacta cacatgatga                                  3810

SEQ ID NO: 77          moltype = AA  length = 1268
FEATURE                Location/Qualifiers
source                 1..1268
                       mol_type = protein
                       organism = synthetic construct
SEQUENCE: 77
MFVFLVLLPL VSSQCVNLIT RTQSYTNSFT RGVYYPDKVF RSSVLHSTQD LFLPFFSNVT  60
WFHAISGTNG TKRFDNPVLP FNDGVYFAST EKSNIIRGWI FGTTLDSKTQ SLLIVNNATN  120
VVIKVCEFQF CNDPFLDVYY HKNNKSWMES EFRVYSSANN CTFEYVSQPF LMDLEGKQGN  180
FKNLREFVFK NIDGYFKIYS KHTPINLGRD LPQGFSALEP LVDLPIGINI TRFQTLLALH  240
RSYLTPGDSS SGWTAGAAAY YVGYLQPRTF LLKYNENGTI TDAVDCALDP LSETKCTLKS  300
FTVEKGIYQT SNFRVQPTES IVRFPNITNL CPFDEVFNAT RFASVYAWNR KRISNCVADY  360
SVLYNFAPFF AFKCYGVSPT KLNDLCFTNV YADSFVIRGN EVRQIAPGQT GNIADYNYKL  420
PDDFTGCVIA WNSNKLDSKV GGNYNYRYRL FRKSNLKPFE RDISTEIYQA GNKPCNGVAG  480
VNCYFPLQSY GFRPTYGVGH QPYRVVVLSF ELLHAPATVC GPKKSTNLVK NKCVNFNFNG  540
LTGTGVLTES NKKFLPFQQF GRDIADTTDA VRDPQTLEIL DITPCSFGGV SVITPGTNTS  600
NQVAVLYQGV NCTEVPVAIH ADQLTPTWRV YSTGSNVFQT RAGCLIGAEY VNNSYECDIP  660
IGAGICASYQ TQTKSHRRAR SVASQSIIAY TMSLGAENSV AYSNNSIAIP TNFTISVTTE  720
ILPVSMTKTS VDCTMYICGD STECSNLLLQ YGSFCTQLKR ALTGIAVEQD KNTQEVFAQV  780
KQIYKTPPIK YFGGFNFSQI LPDPSKPSKR SFIEDLLFNK VTLADAGFIK QYGDCLGDIA  840
ARDLICAQKF NGLTVLPPLL TDEMIAQYTS ALLAGTITSG WTFGAGAALQ IPFAMQMAYR  900
FNGIGVTQNV LYENQKLIAN QFNSAIGKIQ DSLSSTASAL GKLQDVVNHN AQALNTLVKQ  960
LSSKFGAISS VLNDILSRLD PPEAEVQIDR LITGRLQSLQ TYVTQQLIRA AEIRASANLA  1020
ATKMSECVLG QSKRVDFCGK GYHLMSFPQS APHGVVFLHV TYVPAQEKNF TTAPAICHDG  1080
KAHFPREGVF VSNGTHWFVT QRNFYEPQII TTDNTFVSGN CDVVIGIVNN TVYDPLQPEL  1140
DSFKEELDKY FKNHTSPDVD LGDISGINAS VVNIQKEIDR LNEVAKNLNE SLIDLQELGK  1200
YEQYIKWPWY IWLGFIAGLI AIVMVTIMLC CMTSCCSCLK GCCSCGSCCK FDEDDSEPVL  1260
KGVKLHYT                                                          1268

SEQ ID NO: 78          moltype = RNA  length = 3810
FEATURE                Location/Qualifiers
source                 1..3810
                       mol_type = other RNA
                       organism = synthetic construct
SEQUENCE: 78
atgttcgtgt tcctggtgct gctgcctctg gtgtccagcc agtgtgtgaa cctgatcacc  60
agaacacagt catacaccaa cagctttacc agaggcgtgt actacccgga caaggtgttc  120
agatccagcg tgctgcactc tacccaggac ctgttcctgc ctttcttcag caacgtgacc  180
tggttccacg ccatctccgg caccaatggc accaagagat tcgacaaccc cgtgctgccc  240
ttcaacgacg gggtgtactt tgccagcacc gagaagtcca acatcatcag aggctggatc  300
ttcggcacca cactggacag caagacccag agcctgctga tcgtgaacaa cgccaccaac  360
gtggtcatca aagtgtgcga gttccagttc tgcaacgacc ccttcctgga cgtctactac  420
cacaagaaca acaagagctg gatggaaagc gagttccggg tgtacagcag cgccaacaac  480
tgcaccttcg agtacgtgtc ccagcctttc ctgatggacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caaagtgcac cctgaagtcc  900
ttcaccgtgg aaaagggcat ctaccagacc agcaacttcc gggtgcagcc caccgaatcc  960
atcgtgcggt tccccaatat caccaatctg tgccccttcg acgaggtgtt caatgccacc  1020
agattcgcct ctgtgtacgc ctggaaccgg aagcggatca gcaattgcgt ggccgactac  1080
tccgtgctgt acaacttcgc cccttcttc gcattcaagt gctacggcgt gtcccctacc  1140
aagctgaacg acctgtgctt cacaaacgtg tacgccgaca gcttcgtgat ccggggaaac  1200
gaagtgcggc agattgcccc tggacagaca ggcaacatcg ccgactacaa ctacaagctg  1260
cccgacgact tcaccggctg tgtgattgcc tggaacagca acaagctgga ctccaaagtc  1320
ggcggcaact acaattacag gtaccggctg ttccggaagt ccaatctgaa gcccttcgag  1380
cgggacatct ccaccgagat ctatcaggcc ggcaacaagc cttgtaacgg cgtggcaggc  1440
gtgaactgct acttcccact gcagtcctac ggctttaggc ccacatacgg cgtgggccac  1500
cagccctaca gagtggtggt gctgagcttc gaactgctgc atgcccctgc cacagtgtgc  1560
ggccctaaga aaagcaccaa tctcgtgaag aacaaatgcg tgaacttcaa cttcaacggc  1620
ctgaccggca ccggcgtgct gacagagagc aacaagaagt tcctgccatt ccagcagttt  1680
ggccgggata tcgccgatac cacagacgcc gttagagatc cccagacact ggaaatcctg  1740
gacatcaccc cttgcagctt cggcggagtg tctgtgatca cccctggcac caacaccagc  1800
aatcaggtgg cagtgctgta ccagggcgtg aactgtaccg aagtgcccgt ggccattcac  1860
gccgatcagc tgacacctac atggcgggtg tactccaccg gcagcaatgt gtttcagacc  1920
agagccggct gtctgatcgg agccgagtac gtgaacaata gctacgagtg cgacatcccc  1980
atcggcgctg gaatctgcgc cagctaccag acacagacaa agagccaccg gagagccaga  2040
agcgtggcca gccagagcat cattgcctac acaatgtctc tgggcgccga gaacagcgtg  2100
gcctactcca acaactctat cgctatcccc accaacttca ccatcagcgt gaccacagag  2160
atcctgcctg tgtccatgac caagaccagc gtggactgca ccatgtacat ctgcggcgat  2220
```

```
tccaccgagt gctccaacct gctgctgcag tacggcagct tctgcaccca gctgaaaaga  2280
gccctgacag ggatcgccgt ggaacaggac aagaacaccc aagaggtgtt cgcccaagtg  2340
aagcagatct acaagacccc tcctatcaag tacttcggcg gcttcaattt cagccagatt  2400
ctgcccgatc ctagcaagcc cagcaagcgg agcttcatcg aggacctgct gttcaacaaa  2460
gtgacactgg ccgacgccgg cttcatcaag cagtatggcg attgtctggg cgacattgcc  2520
gccagggatc tgatttgcgc ccagaagttt aacggactga cagtgctgcc tcctctgctg  2580
accgatgaga tgatcgccca gtacacatct gccctgctgg ccggcacaat cacaagcggc  2640
tggacatttg gagcaggcgc cgctctgcag atcccctttg ctatgcagat ggcctaccgg  2700
ttcaacggca tcggagtgac ccagaatgtg ctgtacgaga accagaagct gatcgccaac  2760
cagttcaaca gcgccatcgg caagatccag gacagcctga gcagcacagc aagcgccctg  2820
ggaaagctgc aggacgtggt caaccacaat gcccaggcac tgaacaccct ggtcaagcag  2880
ctgtcctcca agttcggcgc catcagctct gtgctgaacg atatcctgag cagactggac  2940
cctcctgagg ccgaggtgca gatcgacaga ctgatcacag gcagactgca gagcctccag  3000
acatacgtga cccagcagct gatcagagcc gccgagatta gagcctctgc caatctggcc  3060
gccaccaaga tgtctgagtg tgtgctgggc cagagcaaga gagtggactt ttgcggcaag  3120
ggctaccacc tgatgagctt ccctcagtct gcccctcacg gcgtggtgtt tctgcacgtg  3180
acatatgtgc ccgctcaaga gaagaatttc accaccgctc cagccatctg ccacgacggc  3240
aaagcccact ttcctagaga aggcgtgttc gtgtccaacg gcacccattg gttcgtgaca  3300
cagcggaact tctacgagcc ccagatcatc accaccgaca acaccttcgt gtctggcaac  3360
tgcgacgtcg tgatcggcat tgtgaacaat accgtgtacg accctctgca gcccgagctg  3420
gacagcttca aagaggaact ggacaagtac tttaagaacc acacaagccc cgacgtggac  3480
ctgggcgata tcagcggaat caatgccagc gtcgtgaaca tccagaaaga gatcgaccgg  3540
ctgaacgagg tggccaagaa tctgaacgag agcctgatcg acctgcaaga actggggaag  3600
tacgagcagt acatcaagtg gccctggtac atctggctgg gctttatcgc cggactgatt  3660
gccatcgtga tggtcacaat catgctgtgt tgcatgacca gctgctgtag ctgcctgaag  3720
ggctgttgta gctgtggcag ctgctgcaag ttcgacgagg acgattctga gcccgtgctg  3780
aagggcgtga aactgcacta cacatgatga                                  3810
```

```
SEQ ID NO: 79           moltype = DNA  length = 3810
FEATURE                 Location/Qualifiers
source                  1..3810
                        mol_type = other DNA
                        organism = synthetic construct
SEQUENCE: 79
atgttcgtgt tcctggtgct gctgcctctg gtgtccagcc agtgtgtgaa cctgatcacc  60
agaacacagt catacaccaa cagctttacc agaggcgtgt actaccccga caaggtgttc  120
agatccagcg tgctgcactc tacccaggac ctgttcctgc ctttcttcag caacgtgacc  180
tggttccacg ccatctccgg caccaatggc accaagagat tcgacaaccc cgtgctgccc  240
ttcaacgacg gggtgtactt tgccagcacc gagaagtcca acatcatcag aggctggatc  300
ttcggcacca cactggacag caagacccag agcctgctga tcgtgaacaa cgccaccaac  360
gtggtcatca aagtgtgcga gttccagttc tgcaacgacc ccttcctgga cgtctactac  420
cacaagaaca acaagagctg gatggaaagc gagttccggg tgtacagcag cgccaacaac  480
tgcaccttcg agtacgtgtc ccagcctttc ctgatggacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caaagtgcac cctgaagtcc  900
ttcaccgtgg aaaagggcat ctaccagacc agcaacttcc gggtgcagcc caccgaatcc  960
atcgtgcggt tccccaatat caccaatctg tgccccttcg acgaggtgtt caatgccacc  1020
agattcgcct ctgtgtacgc ctggaaccgg aagcggatca gcaattgcgt ggccgactac  1080
tccgtgctgt acaacttcgc cccattcttc gcattcaagt gctacggcgt gtcccctacc  1140
aagctgaacg acctgtgctt cacaaacgtg tacgccgaca gcttcgtgat ccggggaaac  1200
gaagtgcggc agattgcccc tggacagaca ggcaacatcg ccgactacaa ctacaagctg  1260
cccgacgact tcaccggctg tgtgattgcc tggaacagca acaagctgga ctccaaagtc  1320
ggcggcaact acaattacag gtaccggctg ttccggaagt ccaatctgaa gcccttcgag  1380
cgggacatct ccaccgagat ctatcaggcc ggcaacaagc cttgtaacgg cgtggcaggc  1440
gtgaactgct acttcccact gcagtcctac ggctttaggc ccacatacgg cgtgggccac  1500
cagccctaca gagtggtggt gctgagcttc gaactgctgc atgcccctgc cacagtgtgc  1560
ggccctaaga aaagcaccaa tctcgtgaag aacaaatgcg tgaacttcaa cttcaacggc  1620
ctgaccggca ccggcgtgct gacagagagc aacaagaagt tcctgccatt ccagcagttt  1680
ggccgggata tcgccgatac cacagacgcc gttagagatc cccagacact ggaaatcctg  1740
gacatcaccc cttgcagctt cggcggagtg tctgtgatca cccctggcac caacaccagc  1800
aatcaggtgg cagtgctgta ccagggcgtg aactgtaccg aagtgcccgt ggccattcac  1860
gccgatcagc tgacacctac atggcgggtg tactccaccg gcagcaatgt gtttcagacc  1920
agagccggct gtctgatcgg agccgagtac gtgaacaata gctacgagtg cgacatcccc  1980
atcggcgctg gaatctgcgc cagctaccag acacagacaa agagccaccg gagagccaga  2040
agcgtggcca gccagagcat cattgcctac acaatgtctc tgggcgccga gaacagcgtg  2100
gcctactcca acaactctat cgctatcccc accaacttca ccatcagcgt gaccacagag  2160
atcctgcctg tgtccatgac caagaccagc gtggactgca ccatgtacat ctgcggcgat  2220
tccaccgagt gctccaacct gctgctgcag tacggcagct tctgcaccca gctgaaaaga  2280
gccctgacag ggatcgccgt ggaacaggac aagaacaccc aagaggtgtt cgcccaagtg  2340
aagcagatct acaagacccc tcctatcaag tacttcggcg gcttcaattt cagccagatt  2400
ctgcccgatc ctagcaagcc cagcaagcgg agcttcatcg aggacctgct gttcaacaaa  2460
gtgacactgg ccgacgccgg cttcatcaag cagtatggcg attgtctggg cgacattgcc  2520
gccagggatc tgatttgcgc ccagaagttt aacggactga cagtgctgcc tcctctgctg  2580
accgatgaga tgatcgccca gtacacatct gccctgctgg ccggcacaat cacaagcggc  2640
tggacatttg gagcaggcgc cgctctgcag atcccctttg ctatgcagat ggcctaccgg  2700
```

-continued

```
ttcaacggca tcggagtgac ccagaatgtg ctgtacgaga accagaagct gatcgccaac  2760
cagttcaaca gcgccatcgg caagatccag gacagcctga gcagcacagc aagcgccctg  2820
ggaaagctgc aggacgtggt caaccacaat gcccaggcac tgaacaccct ggtcaagcag  2880
ctgtcctcca agttcggcgc catcagctct gtgctgaacg atatcctgag cagactggac  2940
cctcctgagg ccgaggtgca gatcgacaga ctgatcacag gcagactgca gagcctccag  3000
acatacgtga cccagcagct gatcagagcc gccgagatta gagcctctgc caatctggcc  3060
gccaccaaga tgtctgagtg tgtgctgggc cagagcaaga gagtggactt ttgcggcaag  3120
ggctaccacc tgatgagctt ccctcagtct gcccctcacg gcgtggtgtt tctgcacgtg  3180
acatatgtgc ccgctcaaga gaagaatttc accaccgctc cagccatctg ccacgacggc  3240
aaagcccact ttcctagaga aggcgtgttc gtgtccaacg gcacccattg gttcgtgaca  3300
cagcggaact tctacgagcc ccagatcatc accaccgaca acaccttcgt gtctggcaac  3360
tgcgacgtcg tgatcggcat tgtgaacaat accgtgtacg accctctgca gcccgagctg  3420
gacagcttca aagaggaact ggacaagtac tttaagaacc acacaagccc cgacgtggac  3480
ctgggcgata tcagcggaat caatgccagc gtcgtgaaca tccagaaaga gatcgaccgg  3540
ctgaacgagg tggccaagaa tctgaacgag agcctgatcg acctgcaaga actggggaag  3600
tacgagcagt acatcaagtg gccctggtac atctggctgg gctttatcgc cggactgatt  3660
gccatcgtga tggtcacaat catgctgtgt tgcatgacca gctgctgtag ctgcctgaag  3720
ggctgttgta gctgtggcag ctgctgcaag ttcgacgagg acgattctga gcccgtgctg  3780
aagggcgtga aactgcacta cacatgatga                                  3810

SEQ ID NO: 80          moltype = AA  length = 1270
FEATURE                Location/Qualifiers
source                 1..1270
                       mol_type = protein
                       organism = synthetic construct
SEQUENCE: 80
MFVFLVLLPL VSSQCVNLIT RTQSYTNSFT RGVYYPDKVF RSSVLHSTQD LFLPFFSNVT  60
WFHAIHVSGT NGTKRFDNPV LPFNDGVYFA STEKSNIIRG WIFGTTLDSK TQSLLIVNNA  120
TNVVIKVCEF QFCNDPFLDV YYHENNKSRM ESELRVYSSA NNCTFEYVSQ PFLMDLEGKQ  180
GNFKNLREFV FKNIDGYFKI YSKHTPVNLG RDLPQGFSAL EPLVDLPIGI NITRFQTLLA  240
LHRSYLTPGD SSSSWTAGAA AYYVGYLQPR TFLLKYNENG TITDAVDCAL DPLSETKCTL  300
KSFTVEKGIY QTSNFRVQPT ESIVRFPNIT NLCPFHEVFN ATRFASVYAW NRKRISNCVA  360
DYSVLYNFAP FFAFKCYGVS PTKLNDLCFT NVYADSFVIR GNEVSQIAPG QTGNIADYNY  420
KLPDDFTGCV IAWNSNKLDS KVSGNYNYLY RLFRKSKLKP FERDISTEIY QAGNKPCNGV  480
AGFNCYFPLQ SYGFRPTYGV GHQPYRVVVL SFELLHAPAT VCGPKKSTNL VKNKCVNFNF  540
NGLTGTGVLT ESNKKFLPFQ QFGRDIADTT DAVRDPQTLE ILDITPCSFG GVSVITPGTN  600
TSNQVAVLYQ GVNCTEVPVA IHADQLTPTW RVYSTGSNVF QTRAGCLIGA EYVNNSYECD  660
IPIGAGICAS YQTQTKSHRR ARSVASQSII AYTMSLGAEN SVAYSNNSIA IPTNFTISVT  720
TEILPVSMTK TSVDCTMYIC GDSTECSNLL LQYGSFCTQL KRALTGIAVE QDKNTQEVFA  780
QVKQIYKTPP IKYFGGFNFS QILPDPSKPS KRSFIEDLLF NKVTLADAGF IKQYGDCLGD  840
IAARDLICAQ KFNGLTVLPP LLTDEMIAQY TSALLAGTIT SGWTFGAGAA LQIPFAMQMA  900
YRFNGIGVTQ NVLYENQKLI ANQFNSAIGK IQDSLSSTAS ALGKLQDVVN HNAQALNTLV  960
KQLSSKFGAI SSVLNDILSR LDPPEAEVQI DRLITGRLQS LQTYVTQQLI RAAEIRASAN  1020
LAATKMSECV LGQSKRVDFC GKGYHLMSFP QSAPHGVVFL HVTYVPAQEK NFTTAPAICH  1080
DGKAHFPREG VFVSNGTHWF VTQRNFYEPQ IITTDNTFVS GNCDVVIGIV NNTVYDPLQP  1140
ELDSFKEELD KYFKNHTSPD VDLGDISGIN ASVVNIQKEI DRLNEVAKNL NESLIDLQEL  1200
GKYEQYIKWP WYIWLGFIAG LIAIVMVTIM LCCMTSCCSC LKGCCSCGSC CKFDEDDSEP  1260
VLKGVKLHYT                                                        1270

SEQ ID NO: 81          moltype = RNA  length = 3816
FEATURE                Location/Qualifiers
source                 1..3816
                       mol_type = other RNA
                       organism = synthetic construct
SEQUENCE: 81
atgttcgtgt tcctggtgct gctgcctctg gtgtccagcc agtgtgtgaa cctgatcacc  60
agaacacagt catacaccaa cagctttacc agaggcgtgt actaccccga caaggtgttc  120
agatccagcg tgctgcactc tacccaggac ctgttcctgc ctttcttcag caacgtgacc  180
tggttccacg ccatccacgt gtccggcacc aatggcacca agagattcga caaccccgtg  240
ctgcccttca acgacggggt gtactttgcc agcaccgaga agtccaacat catcagaggc  300
tggatcttcg gcaccacact ggacagcaag acccagagcc tgctgatcgt gaacaacgcc  360
accaacgtgg tcatcaaagt gtgcgagttc cagttctgca acgacccctt cctggacgtc  420
tactaccacg agaacaacaa gagcaggatg gaaagcgagc tccgggtgta cagcagcgcc  480
aacaactgca ccttcgagta cgtgtcccag cctttcctga tggacctgga aggcaagcag  540
ggcaacttca agaacctgcg cgagttcgtg tttaagaaca tcgacggcta cttcaagatc  600
tacagcaagc acacccctgt gaacctcggc cgggatctgc ctcagggctt ctctgctctg  660
gaacccctgg tggatctgcc catcggcatc aacatcaccc ggtttcagac actgctggcc  720
ctgcacagaa gctacctgac acctggcgat agcagcagca gctggacagc tggtgccgcc  780
gcttactatg tgggctacct gcagcctaga accttcctgc tgaagtacaa cgagaacggc  840
accatcaccg acgccgtgga ttgtgctctg gatcctctga gcgagacaaa gtgcaccctg  900
aagtccttca ccgtggaaaa gggcatctac cagaccagca acttccgggt gcagcccacc  960
gaatccatcg tgcggttccc caatatcacc aatctgtgcc ccttccacga ggtgttcaat  1020
gccaccagat tcgcctctgt gtacgcctgg aaccggaagc ggatcagcaa ttgcgtggcc  1080
gactactccg tgctgtacaa cttcgccccc ttcttcgcat tcaagtgcta cggcgtgtcc  1140
cctaccaagc tgaacgacct gtgcttcaca aacgtgtacg ccgacagctt cgtgatccgg  1200
ggaaacgaag tgtcacagat tgcccctgga cagacaggca acatcgccga ctacaactac  1260
aagctgcccg acgacttcac cggctgtgtg attgcctgga acagcaacaa gctggactcc  1320
aaagtcagcg gcaactacaa ttacctgtac cggctgttcc ggaagtccaa gctgaagccc  1380
ttcgagcggg acatctccac cgagatctat caggccggca acaagccttg taacggcgtg  1440
```

```
gcaggcttca actgctactt cccactgcag tcctacggct ttaggcccac atacggcgtg  1500
ggccaccagc cctacagagt ggtggtgctg agcttcgaac tgctgcatgc ccctgccaca  1560
gtgtgcggcc ctaagaaaag caccaatctc gtgaagaaca aatgcgtgaa cttcaacttc  1620
aacggcctga ccggcaccgg cgtgctgaca gagagcaaca agaagttcct gccattccag  1680
cagtttggcc gggatatcgc cgataccaca gacgccgtta gagatcccca gacactggaa  1740
atcctggaca tcaccccttg cagcttcggc ggagtgtctg tgatcacccc tggcaccaac  1800
accagcaatc aggtggcagt gctgtaccag ggcgtgaact gtaccgaagt gcccgtggcc  1860
attcacgccg atcagctgac acctacatgg cgggtgtact ccaccggcag caatgtgttt  1920
cagaccagag ccggctgtct gatcggagcc gagtacgtga acaatagcta cgagtgcgac  1980
atccccatcg gcgctggaat ctgcgccagc taccagacac agacaaagag ccaccggaga  2040
gccagaagcg tggccagcca gagcatcatt gcctacacaa tgtctctggg cgccgagaac  2100
agcgtggcct actccaacaa ctctatcgct atccccacca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aaaagagccc tgacagggat cgccgtggaa caggacaaga acacccaaga ggtgttcgcc  2340
caagtgaagc agatctacaa gacccctcct atcaagtact tcggcggctt caatttcagc  2400
cagattctgc ccgatcctag caagcccagc aagcggagct tcatcgagga cctgctgttc  2460
aacaaagtga cactggccga cgccggcttc atcaagcagt atggcgattg tctgggcgac  2520
attgccgcca gggatctgat ttgcgcccag aagtttaacg gactgacagt gctgcctcct  2580
ctgctgaccg atgagatgat cgcccagtac acatctgccc tgctggccgg cacaatcaca  2640
agcggctgga catttggagc aggcgccgct ctgcagatcc cctttgctat gcagatggcc  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctgggaa agctgcagga cgtggtcaac cacaatgccc aggcactgaa caccctggtc  2880
aagcagctgt cctccaagtt cggcgccatc agctctgtgc tgaacgatat cctgagcaga  2940
ctggaccctc ctgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctgggccaga gcaagagagt ggacttttgc  3120
ggcaagggct accacctgat gagcttccct cagtctgccc ctcacggcgt ggtgtttctg  3180
cacgtgacat atgtgcccgc tcaagagaag aatttcacca ccgctccagc catctgccac  3240
gacggcaaag cccactttcc tagagaaggc gtgttcgtgt ccaacggcac ccattggttc  3300
gtgacacagc ggaacttcta cgagccccag atcatcacca ccgacaacac cttcgtgtct  3360
ggcaactgcg acgtcgtgat cggcattgtg aacaataccg tgtacgaccc tctgcagccc  3420
gagctggaca gcttcaaaga ggaactggac aagtacttta agaaccacac aagccccgac  3480
gtggacctgg gcgatatcag cggaatcaat gccagcgtcg tgaacatcca gaaagagatc  3540
gaccggctga acgaggtggc caagaatctg aacgagagcc tgatcgacct gcaagaactg  3600
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
gtgctgaagg gcgtgaaact gcactacaca tgatga                            3816

SEQ ID NO: 82           moltype = DNA  length = 3816
FEATURE                 Location/Qualifiers
source                  1..3816
                        mol_type = other DNA
                        organism = synthetic construct
SEQUENCE: 82
atgttcgtgt tcctggtgct gctgcctctg gtgtccagcc agtgtgtgaa cctgatcacc  60
agaacacagt catacaccaa cagctttacc agaggcgtgt actaccccga caaggtgttc  120
agatccagcg tgctgcactc tacccaggac ctgttcctgc ctttcttcag caacgtgacc  180
tggttccacg ccatccacgt gtccggcacc aatggcacca agagattcga caaccccgtg  240
ctgcccttca acgacggggt gtactttgcc agcaccgaga agtccaacat catcagaggc  300
tggatcttcg gcaccacact ggacagcaag acccagagcc tgctgatcgt gaacaacgcc  360
accaacgtgg tcatcaaagt gtgcgagttc cagttctgca acgacccctt cctggacgtc  420
tactaccacg agaacaacaa gagcaggatg gaaagcgagc tccgggtgta cagcagcgcc  480
aacaactgca ccttcgagta cgtgtcccag cctttcctga tggacctgga aggcaagcag  540
ggcaacttca agaacctgcg cgagttcgtg tttaagaaca tcgacggcta cttcaagatc  600
tacagcaagc acacccctgt gaacctcggc cgggatctgc ctcagggctt ctctgctctg  660
gaacccctgg tggatctgcc catcggcatc aacatcaccc ggtttcagac actgctggcc  720
ctgcacagaa gctacctgac acctggcgat agcagcagca gctggacagc tggtgccgcc  780
gcttactatg tgggctacct gcagcctaga accttcctgc tgaagtacaa cgagaacggc  840
accatcaccg acgccgtgga ttgtgctctg gatcctctga gcgagacaaa gtgcaccctg  900
aagtccttca ccgtggaaaa gggcatctac cagaccagca acttccgggt gcagcccacc  960
gaatccatcg tgcggttccc caatatcacc aatctgtgcc ccttccacga ggtgttcaat  1020
gccaccagat tcgcctctgt gtacgcctgg aaccggaagc ggatcagcaa ttgcgtggcc  1080
gactactccg tgctgtacaa cttcgccccc ttcttcgcat tcaagtgcta cggcgtgtcc  1140
cctaccaagc tgaacgacct gtgcttcaca aacgtgtacg ccgacagctt cgtgatccgg  1200
ggaaacgaag tgtcacagat tgcccctgga cagacaggca acatcgccga ctacaactac  1260
aagctgcccg acgacttcac cggctgtgtg attgcctgga acagcaacaa gctggactcc  1320
aaagtcagcg gcaactacaa ttacctgtac cggctgttcc ggaagtccaa gctgaagccc  1380
ttcgagcggg acatctccac cgagatctat caggccggca acaagccttg taacggcgtg  1440
gcaggcttca actgctactt cccactgcag tcctacggct ttaggcccac atacggcgtg  1500
ggccaccagc cctacagagt ggtggtgctg agcttcgaac tgctgcatgc ccctgccaca  1560
gtgtgcggcc ctaagaaaag caccaatctc gtgaagaaca aatgcgtgaa cttcaacttc  1620
aacggcctga ccggcaccgg cgtgctgaca gagagcaaca agaagttcct gccattccag  1680
cagtttggcc gggatatcgc cgataccaca gacgccgtta gagatcccca gacactggaa  1740
atcctggaca tcaccccttg cagcttcggc ggagtgtctg tgatcacccc tggcaccaac  1800
accagcaatc aggtggcagt gctgtaccag ggcgtgaact gtaccgaagt gcccgtggcc  1860
attcacgccg atcagctgac acctacatgg cgggtgtact ccaccggcag caatgtgttt  1920
```

```
cagaccagag ccggctgtct gatcggagcc gagtacgtga acaatagcta cgagtgcgac  1980
atccccatcg gcgctggaat ctgcgccagc taccagacac agacaaagag ccaccggaga  2040
gccagaagcg tggccagcca gagcatcatt gcctacacaa tgtctctggg cgccgagaac  2100
agcgtggcct actccaacaa ctctatcgct atccccacca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aaaagagccc tgacagggat cgccgtggaa caggacaaga acacccaaga ggtgttcgcc  2340
caagtgaagc agatctacaa gacccctcct atcaagtact tcggcggctt caatttcagc  2400
cagattctgc ccgatcctag caagcccagc aagcggagct tcatcgagga cctgctgttc  2460
aacaaagtga cactggccga cgccggcttc atcaagcagt atggcgattg tctgggcgac  2520
attgccgcca gggatctgat ttgcgcccag aagtttaacg gactgacagt gctgcctcct  2580
ctgctgaccg atgagatgat cgcccagtac acatctgccc tgctggccgg cacaatcaca  2640
agcggctgga catttggagc aggcgccgct ctgcagatcc cctttgctat gcagatggcc  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctgggaa agctgcagga cgtggtcaac cacaatgccc aggcactgaa caccctggtc  2880
aagcagctgt cctccaagtt cggcgccatc agctctgtgc tgaacgatat cctgagcaga  2940
ctggaccctc ctgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctgggccaga gcaagagagt ggacttttgc  3120
ggcaagggct accacctgat gagcttccct cagtctgccc ctcacggcgt ggtgtttctg  3180
cacgtgacat atgtgcccgc tcaagagaag aatttcacca ccgctccagc catctgccac  3240
gacggcaaag cccactttcc tagagaaggc gtgttcgtgt ccaacggcac ccattggttc  3300
gtgacacagc ggaacttcta cgagccccag atcatcacca ccgacaacac cttcgtgtct  3360
ggcaactgcg acgtcgtgat cggcattgtg aacaataccg tgtacgaccc tctgcagccc  3420
gagctggaca gcttcaaaga ggaactggac aagtacttta agaaccacac aagccccgac  3480
gtggacctgg gcgatatcag cggaatcaat gccagcgtcg tgaacatcca gaaagagatc  3540
gaccggctga acgaggtggc caagaatctg aacgagagcc tgatcgacct gcaagaactg  3600
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
gtgctgaagg gcgtgaaact gcactacaca tgatga                            3816

SEQ ID NO: 83          moltype = RNA  length = 4273
FEATURE                Location/Qualifiers
source                 1..4273
                       mol_type = other RNA
                       organism = synthetic construct
SEQUENCE: 83
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatcca cgtgtccggc accaatggca ccaagagatt cgacaacccc gtgctgccct  300
tcaacgacgg ggtgtacttt gccagcaccg agaagtccaa catcatcaga ggctggatct  360
tcggcaccac actggacagc aagacccaga gcctgctgat cgtgaacaac gccaccaacg  420
tggtcatcaa agtgtgcgag ttccagttct gcaacgaccc cttcctggac gtctactacc  480
acgagaacaa caagagcagg atggaaagcg agctccgggt gtacagcagc gccaacaact  540
gcaccttcga gtacgtgtcc cagcctttcc tgatggacct ggaaggcaag cagggcaact  600
tcaagaacct gcgcgagttc gtgtttaaga acatcgacgg ctacttcaag atctacagca  660
agcacacccc tgtgaacctc ggccgggatc tgcctcaggg cttctctgct ctggaacccc  720
tggtggatct gcccatcggc atcaacatca cccggtttca gacactgctg gccctgcaca  780
gaagctacct gacacctggc gatagcagca gcagctggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca  1020
tcgtgcggtt ccccaatatc accaatctgt gccccttcca cgaggtgttc aatgccacca  1080
gattcgcctc tgtgtacgcc tggaaccgga agcggatcag caattgcgtg gccgactact  1140
ccgtgctgta caacttcgcc cccttcttcg cattcaagtg ctacggcgtg tcccctacca  1200
agctgaacga cctgtgcttc acaaacgtgt acgccgacag cttcgtgatc cggggaaacg  1260
aagtgtcaca gattgcccct ggacagacag gcaacatcgc cgactacaac tacaagctgc  1320
ccgacgactt caccggctgt gtgattgcct ggaacagcaa caagctggac tccaaagtca  1380
gcggcaacta caattacctg taccggctgt tccggaagtc caagctgaag cccttcgagc  1440
gggacatctc caccgagatc tatcaggccg gcaacaagcc ttgtaacggc gtggcaggct  1500
tcaactgcta cttcccactg cagtcctacg gctttaggcc cacatacggc gtgggccacc  1560
agccctacag agtggtggtg ctgagcttcg aactgctgca tgcccctgcc acagtgtgcg  1620
gccctaagaa aagcaccaat ctcgtgaaga acaaatgcgt gaacttcaac ttcaacggcc  1680
tgaccggcac cggcgtgctg acagagagca acaagaagtt cctgccattc cagcagtttg  1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagccggctg tctgatcgga gccgagtacg tgaacaatag ctacgagtgc gacatcccca  2040
tcggcgctgg aatctgcgcc agctaccaga cacagacaaa gagccaccgg agagccagaa  2100
gcgtggccag ccagagcatc attgcctaca caatgtctct gggcgccgag aacagcgtgg  2160
cctactccaa caactctatc gctatcccca ccaacttcac catcagcgtg accacagaga  2220
tcctgcctgt gtccatgacc aagaccagcg tggactgcac catgtacatc tgcggcgatt  2280
ccaccgagtg ctccaacctg ctgctgcagt acggcagctt ctgcacccag ctgaaaagag  2340
ccctgacagg gatcgccgtg gaacaggaca agaacaccca agaggtgttc gcccaagtga  2400
```

```
agcagatcta caagacccct cctatcaagt acttcggcgg cttcaatttc agccagattc  2460
tgcccgatcc tagcaagccc agcaagcgga gcttcatcga ggacctgctg ttcaacaaag  2520
tgacactggc cgacgccggc ttcatcaagc agtatggcga ttgtctgggc gacattgccg  2580
ccagggatct gatttgcgcc cagaagttta acggactgac agtgctgcct cctctgctga  2640
ccgatgagat gatcgcccag tacacatctg ccctgctggc cggcacaatc acaagcggct  2700
ggacatttgg agcaggcgcc gctctgcaga tcccctttgc tatgcagatg gcctaccggt  2760
tcaacggcat cggagtgacc cagaatgtgc tgtacgagaa ccagaagctg atcgccaacc  2820
agttcaacag cgccatcggc aagatccagg acagcctgag cagcacagca agcgccctgg  2880
gaaagctgca ggacgtggtc aaccacaatg cccaggcact gaacaccctg gtcaagcagc  2940
tgtcctccaa gttcggcgcc atcagctctg tgctgaacga tatcctgagc agactggacc  3000
ctcctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctgggcc agagcaagag agtggacttt tgcggcaagg  3180
gctaccacct gatgagcttc cctcagtctg cccctcacgg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccaccgacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcga cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgac tcgagctggt actgcatgca cgcaatgcta  3900
gctgcccctt tcccgtcctg ggtaccccga gtctcccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cgggaaacag cagtgattaa  4080
cctttagcaa taaacgaaag tttaactaag ctatactaac cccagggttg gtcaatttcg  4140
tgccagccac accctggagc tagcaaaaaa aaaaaaaaaa aaaaaaaaaa aaaagcatat  4200
gactaaaaaa aaaaaaaaaa aaaaaaaaaa aaaaaaaaaa aaaaaaaaaa aaaaaaaaaa  4260
aaaaaaaaaa aaa                                                     4273

SEQ ID NO: 84          moltype = DNA  length = 4273
FEATURE                Location/Qualifiers
source                 1..4273
                       mol_type = other DNA
                       organism = synthetic construct
SEQUENCE: 84
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatcca cgtgtccggc accaatggca ccaagagatt cgacaacccc gtgctgccct  300
tcaacgacgg ggtgtacttt gccagcaccg agaagtccaa catcatcaga ggctggatct  360
tcggcaccac actggacagc aagacccaga gcctgctgat cgtgaacaac gccaccaacg  420
tggtcatcaa agtgtgcgag ttccagttct gcaacgaccc cttcctggac gtctactacc  480
acgagaacaa caagagcagg atggaaagcg agctccgggt gtacagcagc gccaacaact  540
gcaccttcga gtacgtgtcc cagcctttcc tgatggacct ggaaggcaag cagggcaact  600
tcaagaacct gcgcgagttc gtgtttaaga acatcgacgg ctacttcaag atctacagca  660
agcacacccc tgtgaacctc ggccgggatc tgcctcaggg cttctctgct ctggaacccc  720
tggtggatct gcccatcggc atcaacatca cccggtttca gacactgctg gccctgcaca  780
gaagctacct gacacctggc gatagcagca gcagctggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca  1020
tcgtgcggtt ccccaatatc accaatctgt gccccttcca cgaggtgttc aatgccacca  1080
gattcgcctc tgtgtacgcc tggaaccgga agcggatcag caattgcgtg gccgactact  1140
ccgtgctgta caacttcgcc cccttcttcg cattcaagtg ctacggcgtg tcccctacca  1200
agctgaacga cctgtgcttc acaaacgtgt acgccgacag cttcgtgatc cggggaaacg  1260
aagtgtcaca gattgcccct ggacagacag gcaacatcgc cgactacaac tacaagctgc  1320
ccgacgactt caccggctgt gtgattgcct ggaacagcaa caagctggac tccaaagtca  1380
gcggcaacta caattacctg taccggctgt tccggaagtc caagctgaag cccttcgagc  1440
gggacatctc caccgagatc tatcaggccg gcaacaagcc ttgtaacggc gtggcaggct  1500
tcaactgcta cttcccactg cagtcctacg gctttaggcc cacatacggc gtgggccacc  1560
agccctacag agtggtggtg ctgagcttcg aactgctgca tgcccctgcc acagtgtgcg  1620
gccctaagaa aagcaccaat ctcgtgaaga acaaatgcgt gaacttcaac ttcaacggcc  1680
tgaccggcac cggcgtgctg acagagagca acaagaagtt cctgccattc cagcagtttg  1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagccggctg tctgatcgga gccgagtacg tgaacaatag ctacgagtgc gacatcccca  2040
tcggcgctgg aatctgcgcc agctaccaga cacagacaaa gagccaccgg agagccagaa  2100
gcgtggccag ccagagcatc attgcctaca caatgtctct gggcgccgag aacagcgtgg  2160
cctactccaa caactctatc gctatcccca ccaacttcac catcagcgtg accacagaga  2220
tcctgcctgt gtccatgacc aagaccagcg tggactgcac catgtacatc tgcggcgatt  2280
ccaccgagtg ctccaacctg ctgctgcagt acggcagctt ctgcacccag ctgaaaagag  2340
ccctgacagg gatcgccgtg gaacaggaca agaacaccca agaggtgttc gcccaagtga  2400
```

-continued agcagatcta caagacccct cctatcaagt acttcggcgg cttcaatttc agccagattc 2460
tgcccgatcc tagcaagccc agcaagcgga gcttcatcga ggacctgctg ttcaacaaag 2520
tgacactggc cgacgccggc ttcatcaagc agtatggcga ttgtctgggc gacattgccg 2580
ccagggatct gatttgcgcc cagaagttta acggactgac agtgctgcct cctctgctga 2640
ccgatgagat gatcgcccag tacacatctg ccctgctggc cggcacaatc acaagcggct 2700
ggacatttgg agcaggcgcc gctctgcaga tcccctttgc tatgcagatg gcctaccggt 2760
tcaacggcat cggagtgacc cagaatgtgc tgtacgagaa ccagaagctg atcgccaacc 2820
agttcaacag cgccatcggc aagatccagg acagcctgag cagcacagca agcgccctgg 2880
gaaagctgca ggacgtggtc aaccacaatg cccaggcact gaacaccctg gtcaagcagc 2940
tgtcctccaa gttcggcgcc atcagctctg tgctgaacga tatcctgagc agactggacc 3000
ctcctgaggc cgaggtgcag atcgacagac tgatcacagg cagactgcag agcctccaga 3060
catacgtgac ccagcagctg atcagagccg ccgagattag agcctctgcc aatctggccg 3120
ccaccaagat gtctgagtgt gtgctgggcc agagcaagag agtggacttt tgcggcaagg 3180
gctaccacct gatgagcttc cctcagtctg cccctcacgg cgtggtgttt ctgcacgtga 3240
catatgtgcc cgctcaagag aagaatttca ccaccgctcc agccatctgc cacgacggca 3300
aagcccactt tcctagagaa ggcgtgttcg tgtccaacgg cacccattgg ttcgtgacac 3360
agcggaactt ctacgagccc cagatcatca ccaccgacaa caccttcgtg tctggcaact 3420
gcgacgtcgt gatcggcatt gtgaacaata ccgtgtacga ccctctgcag cccgagctgg 3480
acagcttcaa agaggaactg gacaagtact ttaagaacca cacaagcccc gacgtggacc 3540
tgggcgatat cagcggaatc aatgccagcg tcgtgaacat ccagaaagag atcgaccggc 3600
tgaacgaggt ggccaagaat ctgaacgaga gcctgatcga cctgcaagaa ctggggaagt 3660
acgagcagta catcaagtgg ccctggtaca tctggctggg ctttatcgcc ggactgattg 3720
ccatcgtgat ggtcacaatc atgctgtgtt gcatgaccag ctgctgtagc tgcctgaagg 3780
gctgttgtag ctgtggcagc tgctgcaagt tcgacgagga cgattctgag cccgtgctga 3840
agggcgtgaa actgcactac acatgatgac tcgagctggt actgcatgca cgcaatgcta 3900
gctgcccctt tcccgtcctg ggtaccccga gtctcccccg acctcgggtc ccaggtatgc 3960
tcccacctcc acctgcccca ctcaccacct ctgctagttc cagacacctc ccaagcacgc 4020
agcaatgcag ctcaaaacgc ttagcctagc cacaccccca cgggaaacag cagtgattaa 4080
cctttagcaa taaacgaaag tttaactaag ctatactaac cccagggttg gtcaatttcg 4140
tgccagccac accctggagc tagcaaaaaa aaaaaaaaaa aaaaaaaaaa aaaagcatat 4200
gactaaaaaa aaaaaaaaaa aaaaaaaaaa aaaaaaaaaa aaaaaaaaaa aaaaaaaaaa 4260
aaaaaaaaaa aaa 4273

SEQ ID NO: 85 moltype = AA length = 1270
FEATURE Location/Qualifiers
source 1..1270
mol_type = protein
organism = synthetic construct
SEQUENCE: 85
MFVFLVLLPL VSSQCVNLIT RTQSYTNSFT RGVYYPDKVF RSSVLHSTQD LFLPFFSNVT 60
WFHAIHVSGT NGTKRFDNPV LPFNDGVYFA STEKSNIIRG WIFGTTLDSK TQSLLIVNNA 120
TNVVIKVCEF QFCNDPFLDV YYHENNKSRM ESELRVYSSA NNCTFEYVSQ PFLMDLEGKQ 180
GNFKNLREFV FKNIDGYFKI YSKHTPVNLG RDLPQGFSAL EPLVDLPIGI NITRFQTLLA 240
LHRSYLTPGD SSSSWTAGAA AYYVGYLQPR TFLLKYNENG TITDAVDCAL DPLSETKCTL 300
KSFTVEKGIY QTSNFRVQPT ESIVRFPNIT NLCPFHEVFN ATTFASVYAW NRKRISNCVA 360
DYSVLYNFAP FFAFKCYGVS PTKLNDLCFT NVYADSFVIR GNEVSQIAPG QTGNIADYNY 420
KLPDDFTGCV IAWNSNKLDS KVSGNYNYLY RLFRKSKLKP FERDISTEIY QAGNKPCNGV 480
AGSNCYFPLQ SYGFRPTYGV GHQPYRVVVL SFELLHAPAT VCGPKKSTNL VKNKCVNFNF 540
NGLTGTGVLT ESNKKFLPFQ QFGRDIADTT DAVRDPQTLE ILDITPCSFG GVSVITPGTN 600
TSNQVAVLYQ GVNCTEVPVA IHADQLTPTW RVYSTGSNVF QTRAGCLIGA EYVNNSYECD 660
IPIGAGICAS YQTQTKSHRR ARSVASQSII AYTMSLGAEN SVAYSNNSIA IPTNFTISVT 720
TEILPVSMTK TSVDCTMYIC GDSTECSNLL LQYGSFCTQL KRALTGIAVE QDKNTQEVFA 780
QVKQIYKTPP IKYFGGFNFS QILPDPSKPS KRSFIEDLLF NKVTLADAGF IKQYGDCLGD 840
IAARDLICAQ KFNGLTVLPP LLTDEMIAQY TSALLAGTIT SGWTFGAGAA LQIPFAMQMA 900
YRFNGIGVTQ NVLYENQKLI ANQFNSAIGK IQDSLSSTAS ALGKLQDVVN HNAQALNTLV 960
KQLSSKFGAI SSVLNDILSR LDPPEAEVQI DRLITGRLQS LQTYVTQQLI RAAEIRASAN 1020
LAATKMSECV LGQSKRVDFC GKGYHLMSFP QSAPHGVVFL HVTYVPAQEK NFTTAPAICH 1080
DGKAHFPREG VFVSNGTHWF VTQRNFYEPQ IITTDNTFVS GNCDVVIGIV NNTVYDPLQP 1140
ELDSFKEELD KYFKNHTSPD VDLGDISGIN ASVVNIQKEI DRLNEVAKNL NESLINLQEL 1200
GKYEQYIKWP WYIWLGFIAG LIAIVMVTIM LCCMTSCCSC LKGCCSCGSC CKFDEDDSEP 1260
VLKGVKLHYT 1270

SEQ ID NO: 86 moltype = RNA length = 3816
FEATURE Location/Qualifiers
source 1..3816
mol_type = other RNA
organism = synthetic construct
SEQUENCE: 86
atgttcgtgt tcctggtgct gctgcctctg gtgtccagcc agtgtgtgaa cctgatcacc 60
agaacacagt catacaccaa cagctttacc agaggcgtgt actacccega caaggtgttc 120
agatccagcg tgctgcactc tacccaggac ctgttcctgc ctttcttcag caacgtgacc 180
tggttccacg ccatccacgt gtccggcacc aatggcacca agagattcga caaccccgtg 240
ctgcccttca acgacggggt gtactttgcc agcaccgaga agtccaacat catcagaggc 300
tggatcttcg gcaccacact ggacagcaag acccagagcc tgctgatcgt gaacaacgcc 360
accaacgtgg tcatcaaagt gtgcgagttc cagttctgca acgacccctt cctggacgtc 420
tactaccacg agaacaacaa gagcaggatg gaaagcgagc tccgggtgta cagcagcgcc 480
aacaactgca ccttcgagta cgtgtcccag cctttcctga tggacctgga aggcaagcag 540
ggcaacttca agaacctgcg cgagttcgtg tttaagaaca tcgacggcta cttcaagatc 600
tacagcaagc acacccctgt gaacctcggc cgggatctgc ctcagggctt ctctgctctg 660

```
gaacccctgg tggatctgcc catcggcatc aacatcaccc ggtttcagac actgctggcc  720
ctgcacagaa gctacctgac acctggcgat agcagcagca gctggacagc tggtgccgcc  780
gcttactatg tgggctacct gcagcctaga accttcctgc tgaagtacaa cgagaacggc  840
accatcaccg acgccgtgga ttgtgctctg gatcctctga gcgagacaaa gtgcaccctg  900
aagtccttca ccgtggaaaa gggcatctac cagaccagca acttccgggt gcagcccacc  960
gaatccatcg tgcggttccc caatatcacc aatctgtgcc ccttccacga ggtgttcaat  1020
gccaccacct tcgcctctgt gtacgcctgg aaccggaagc ggatcagcaa ttgcgtggcc  1080
gactactccg tgctgtacaa cttcgccccc ttcttcgcat tcaagtgcta cggcgtgtcc  1140
cctaccaagc tgaacgacct gtgcttcaca aacgtgtacg ccgacagctt cgtgatccgg  1200
ggaaacgaag tgtcacagat tgcccctgga cagacaggca acatcgccga ctacaactac  1260
aagctgcccg acgacttcac cggctgtgtg attgcctgga acagcaacaa gctggactcc  1320
aaagtcagcg gcaactacaa ttacctgtac cggctgttcc ggaagtccaa gctgaagccc  1380
ttcgagcggg acatctccac cgagatctat caggccggca acaagccttg taacggcgtg  1440
gcaggcagca actgctactt cccactgcag tcctacggct ttaggcccac atacggcgtg  1500
ggccaccagc cctacagagt ggtggtgctg agcttcgaac tgctgcatgc ccctgccaca  1560
gtgtgcggcc ctaagaaaag caccaatctc gtgaagaaca aatgcgtgaa cttcaacttc  1620
aacggcctga ccggcaccgg cgtgctgaca gagagcaaca agaagttcct gccattccag  1680
cagtttggcc gggatatcgc cgataccaca gacgccgtta gagatcccca gacactggaa  1740
atcctggaca tcaccccttg cagcttcggc ggagtgtctg tgatcacccc tggcaccaac  1800
accagcaatc aggtggcagt gctgtaccag ggcgtgaact gtaccgaagt gcccgtggcc  1860
attcacgccg atcagctgac acctacatgg cgggtgtact ccaccggcag caatgtgttt  1920
cagaccagag ccggctgtct gatcggagcc gagtacgtga acaatagcta cgagtgcgac  1980
atccccatcg gcgctggaat ctgcgccagc taccagacac agacaaagag ccaccggaga  2040
gccagaagcg tggccagcca gagcatcatt gcctacacaa tgtctctggg cgccgagaac  2100
agcgtggcct actccaacaa ctctatcgct atccccacca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aaaagagccc tgacagggat cgccgtggaa caggacaaga acacccaaga ggtgttcgcc  2340
caagtgaagc agatctacaa gacccctcct atcaagtact tcggcggctt caatttcagc  2400
cagattctgc ccgatcctag caagcccagc aagcggagct tcatcgagga cctgctgttc  2460
aacaaagtga cactggccga cgccggcttc atcaagcagt atggcgattg tctgggcgac  2520
attgccgcca gggatctgat ttgcgcccag aagtttaacg gactgacagt gctgcctcct  2580
ctgctgaccg atgagatgat cgcccagtac acatctgccc tgctggccgg cacaatcaca  2640
agcggctgga catttggagc aggcgccgct ctgcagatcc cctttgctat gcagatggcc  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctgggaa agctgcagga cgtggtcaac cacaatgccc aggcactgaa caccctggtc  2880
aagcagctgt cctccaagtt cggcgccatc agctctgtgc tgaacgatat cctgagcaga  2940
ctggaccctc ctgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctgggccaga gcaagagagt ggacttttgc  3120
ggcaagggct accacctgat gagcttccct cagtctgccc ctcacggcgt ggtgtttctg  3180
cacgtgacat atgtgcccgc tcaagagaag aatttcacca ccgctccagc catctgccac  3240
gacggcaaag cccactttcc tagagaaggc gtgttcgtgt ccaacggcac ccattggttc  3300
gtgacacagc ggaacttcta cgagccccag atcatcacca ccgacaacac cttcgtgtct  3360
ggcaactgcg acgtcgtgat cggcattgtg aacaataccg tgtacgaccc tctgcagccc  3420
gagctggaca gcttcaaaga ggaactggac aagtacttta agaaccacac aagccccgac  3480
gtggacctgg gcgatatcag cggaatcaat gccagcgtcg tgaacatcca gaaagagatc  3540
gaccggctga acgaggtggc caagaatctg aacgagagcc tgatcaacct gcaagaactg  3600
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
gtgctgaagg gcgtgaaact gcactacaca tgatga                            3816

SEQ ID NO: 87           moltype = DNA  length = 3816
FEATURE                 Location/Qualifiers
source                  1..3816
                        mol_type = other DNA
                        organism = synthetic construct
SEQUENCE: 87
atgttcgtgt tcctggtgct gctgcctctg gtgtccagcc agtgtgtgaa cctgatcacc  60
agaacacagt catacaccaa cagctttacc agaggcgtgt actacccoga caaggtgttc  120
agatccagcg tgctgcactc tacccaggac ctgttcctgc ctttcttcag caacgtgacc  180
tggttccacg ccatccacgt gtccggcacc aatggcacca agagattcga caaccccgtg  240
ctgcccttca acgacggggt gtactttgcc agcaccgaga agtccaacat catcagaggc  300
tggatcttcg gcaccacact ggacagcaag acccagagcc tgctgatcgt gaacaacgcc  360
accaacgtgg tcatcaaagt gtgcgagttc cagttctgca acgacccctt cctggacgtc  420
tactaccacg agaacaacaa gagcaggatg gaaagcgagc tccgggtgta cagcagcgcc  480
aacaactgca ccttcgagta cgtgtcccag cctttcctga tggacctgga aggcaagcag  540
ggcaacttca agaacctgcg cgagttcgtg tttaagaaca tcgacggcta cttcaagatc  600
tacagcaagc acacccctgt gaacctcggc cgggatctgc ctcagggctt ctctgctctg  660
gaacccctgg tggatctgcc catcggcatc aacatcaccc ggtttcagac actgctggcc  720
ctgcacagaa gctacctgac acctggcgat agcagcagca gctggacagc tggtgccgcc  780
gcttactatg tgggctacct gcagcctaga accttcctgc tgaagtacaa cgagaacggc  840
accatcaccg acgccgtgga ttgtgctctg gatcctctga gcgagacaaa gtgcaccctg  900
aagtccttca ccgtggaaaa gggcatctac cagaccagca acttccgggt gcagcccacc  960
gaatccatcg tgcggttccc caatatcacc aatctgtgcc ccttccacga ggtgttcaat  1020
gccaccacct tcgcctctgt gtacgcctgg aaccggaagc ggatcagcaa ttgcgtggcc  1080
gactactccg tgctgtacaa cttcgccccc ttcttcgcat tcaagtgcta cggcgtgtcc  1140
```

```
cctaccaagc tgaacgacct gtgcttcaca aacgtgtacg ccgacagctt cgtgatccgg  1200
ggaaacgaag tgtcacagat tgcccctgga cagacaggca acatcgccga ctacaactac  1260
aagctgcccg acgacttcac cggctgtgtg attgcctgga acagcaacaa gctggactcc  1320
aaagtcagcg gcaactacaa ttacctgtac cggctgttcc ggaagtccaa gctgaagccc  1380
ttcgagcggg acatctccac cgagatctat caggccggca acaagccttg taacggcgtg  1440
gcaggcagca actgctactt cccactgcag tcctacggct ttaggcccac atacggcgtg  1500
ggccaccagc cctacagagt ggtggtgctg agcttcgaac tgctgcatgc ccctgccaca  1560
gtgtgcggcc ctaagaaaag caccaatctc gtgaagaaca aatgcgtgaa cttcaacttc  1620
aacggcctga ccggcaccgg cgtgctgaca gagagcaaca agaagttcct gccattccag  1680
cagtttggcc gggatatcgc cgataccaca gacgccgtta gagatcccca gacactggaa  1740
atcctggaca tcaccccttg cagcttcggc ggagtgtctg tgatcacccc tggcaccaac  1800
accagcaatc aggtggcagt gctgtaccag ggcgtgaact gtaccgaagt gcccgtggcc  1860
attcacgccg atcagctgac acctacatgg cgggtgtact ccaccggcag caatgtgttt  1920
cagaccagag ccggctgtct gatcggagcc gagtacgtga acaatagcta cgagtgcgac  1980
atccccatcg gcgctggaat ctgcgccagc taccagacac agacaaagag ccaccggaga  2040
gccagaagcg tggccagcca gagcatcatt gcctacacaa tgtctctggg cgccgagaac  2100
agcgtggcct actccaacaa ctctatcgct atccccacca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aaaagagccc tgacagggat cgccgtggaa caggacaaga acacccaaga ggtgttcgcc  2340
caagtgaagc agatctacaa gacccctcct atcaagtact tcggcggctt caatttcagc  2400
cagattctgc ccgatcctag caagcccagc aagcggagct tcatcgagga cctgctgttc  2460
aacaaagtga cactggccga cgccggcttc atcaagcagt atggcgattg tctgggcgac  2520
attgccgcca gggatctgat ttgcgcccag aagtttaacg gactgacagt gctgcctcct  2580
ctgctgaccg atgagatgat cgcccagtac acatctgccc tgctggccgg cacaatcaca  2640
agcggctgga catttggagc aggcgccgct ctgcagatcc cctttgctat gcagatggcc  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctgggaa agctgcagga cgtggtcaac cacaatgccc aggcactgaa caccctggtc  2880
aagcagctgt cctccaagtt cggcgccatc agctctgtgc tgaacgatat cctgagcaga  2940
ctggaccctc ctgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctgggccaga gcaagagagt ggacttttgc  3120
ggcaagggct accacctgat gagcttccct cagtctgccc ctcacggcgt ggtgtttctg  3180
cacgtgacat atgtgcccgc tcaagagaag aatttcacca ccgctccagc catctgccac  3240
gacggcaaag cccactttcc tagagaaggc gtgttcgtgt ccaacggcac ccattggttc  3300
gtgacacagc ggaacttcta cgagccccag atcatcacca ccgacaacac cttcgtgtct  3360
ggcaactgcg acgtcgtgat cggcattgtg aacaataccg tgtacgaccc tctgcagccc  3420
gagctggaca gcttcaaaga ggaactggac aagtacttta agaaccacac aagccccgac  3480
gtggacctgg gcgatatcag cggaatcaat gccagcgtcg tgaacatcca gaaagagatc  3540
gaccggctga acgaggtggc caagaatctg aacgagagcc tgatcaacct gcaagaactg  3600
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
gtgctgaagg gcgtgaaact gcactacaca tgatga                            3816
```

```
SEQ ID NO: 88          moltype = RNA  length = 4273
FEATURE                Location/Qualifiers
source                 1..4273
                       mol_type = other RNA
                       organism = synthetic construct
SEQUENCE: 88
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatcca cgtgtccggc accaatggca ccaagagatt cgacaacccc gtgctgccct  300
tcaacgacgg ggtgtacttt gccagcaccg agaagtccaa catcatcaga ggctggatct  360
tcggcaccac actggacagc aagacccaga gcctgctgat cgtgaacaac gccaccaacg  420
tggtcatcaa agtgtgcgag ttccagttct gcaacgaccc cttcctggac gtctactacc  480
acgagaacaa caagagcagg atggaaagcg agctccgggt gtacagcagc gccaacaact  540
gcaccttcga gtacgtgtcc cagcctttcc tgatggacct ggaaggcaag cagggcaact  600
tcaagaacct gcgcgagttc gtgtttaaga acatcgacgg ctacttcaag atctacagca  660
agcacacccc tgtgaacctc ggccgggatc tgcctcaggg cttctctgct ctggaacccc  720
tggtggatct gcccatcggc atcaacatca cccggtttca gacactgctg gccctgcaca  780
gaagctacct gacacctggc gatagcagca gcagctggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca  1020
tcgtgcggtt ccccaatatc accaatctgt gccccttcca cgaggtgttc aatgccacca  1080
ccttcgcctc tgtgtacgcc tggaaccgga agcggatcag caattgcgtg gccgactact  1140
ccgtgctgta caacttcgcc cccttcttcg cattcaagtg ctacggcgtg tcccctacca  1200
agctgaacga cctgtgcttc acaaacgtgt acgccgacag cttcgtgatc cggggaaacg  1260
aagtgtcaca gattgcccct ggacagacag gcaacatcgc cgactacaac tacaagctgc  1320
ccgacgactt caccggctgt gtgattgcct ggaacagcaa caagctggac tccaaagtca  1380
gcggcaacta caattacctg taccggctgt tccggaagtc caagctgaag cccttcgagc  1440
gggacatctc caccgagatc tatcaggccg gcaacaagcc ttgtaacggc gtggcaggca  1500
gcaactgcta cttcccactg cagtcctacg gctttaggcc cacatacggc gtgggccacc  1560
agccctacag agtggtggtg ctgagcttcg aactgctgca tgcccctgcc acagtgtgcg  1620
```

```
gccctaagaa aagcaccaat ctcgtgaaga acaaatgcgt gaacttcaac ttcaacggcc  1680
tgaccggcac cggcgtgctg acagagagca acaagaagtt cctgccattc cagcagtttg  1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagccggctg tctgatcgga gccgagtacg tgaacaatag ctacgagtgc gacatcccca  2040
tcggcgctgg aatctgcgcc agctaccaga cacagacaaa gagccaccgg agagccagaa  2100
gcgtggccag ccagagcatc attgcctaca caatgtctct gggcgccgag aacagcgtgg  2160
cctactccaa caactctatc gctatcccca ccaacttcac catcagcgtg accacagaga  2220
tcctgcctgt gtccatgacc aagaccagcg tggactgcac catgtacatc tgcggcgatt  2280
ccaccgagtg ctccaacctg ctgctgcagt acggcagctt ctgcacccag ctgaaaagag  2340
ccctgacagg gatcgccgtg gaacaggaca agaacaccca agaggtgttc gcccaagtga  2400
agcagatcta caagacccct cctatcaagt acttcggcgg cttcaatttc agccagattc  2460
tgcccgatcc tagcaagccc agcaagcgga gcttcatcga ggacctgctg ttcaacaaag  2520
tgacactggc cgacgccggc ttcatcaagc agtatggcga ttgtctgggc gacattgccg  2580
ccagggatct gatttgcgcc cagaagttta acggactgac agtgctgcct cctctgctga  2640
ccgatgagat gatcgcccag tacacatctg ccctgctggc cggcacaatc acaagcggct  2700
ggacatttgg agcaggcgcc gctctgcaga tcccctttgc tatgcagatg gcctaccggt  2760
tcaacggcat cggagtgacc cagaatgtgc tgtacgagaa ccagaagctg atcgccaacc  2820
agttcaacag cgccatcggc aagatccagg acagcctgag cagcacagca agcgccctgg  2880
gaaagctgca ggacgtggtc aaccacaatg cccaggcact gaacaccctg gtcaagcagc  2940
tgtcctccaa gttcggcgcc atcagctctg tgctgaacga tatcctgagc agactggacc  3000
ctcctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctgggcc agagcaagag agtggacttt tgcggcaagg  3180
gctaccacct gatgagcttc cctcagtctg cccctcacgg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccaccgacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcaa cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgac tcgagctggt actgcatgca cgcaatgcta  3900
gctgcccctt tcccgtcctg ggtaccccga gtctcccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cgggaaacag cagtgattaa  4080
cctttagcaa taaacgaaag tttaactaag ctatactaac cccagggttg gtcaatttcg  4140
tgccagccac accctggagc tagcaaaaaa aaaaaaaaaa aaaaaaaaaa aaaagcatat  4200
gactaaaaaa aaaaaaaaaa aaaaaaaaaa aaaaaaaaaa aaaaaaaaaa aaaaaaaaaa  4260
aaaaaaaaaa aaa                                                     4273

SEQ ID NO: 89          moltype = DNA  length = 4273
FEATURE                Location/Qualifiers
source                 1..4273
                       mol_type = other DNA
                       organism = synthetic construct
SEQUENCE: 89
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatcca cgtgtccggc accaatggca ccaagagatt cgacaacccc gtgctgccct  300
tcaacgacgg ggtgtacttt gccagcaccg agaagtccaa catcatcaga ggctggatct  360
tcggcaccac actggacagc aagacccaga gcctgctgat cgtgaacaac gccaccaacg  420
tggtcatcaa agtgtgcgag ttccagttct gcaacgaccc cttcctggac gtctactacc  480
acgagaacaa caagagcagg atggaaagcg agctccgggt gtacagcagc gccaacaact  540
gcaccttcga gtacgtgtcc cagcctttcc tgatggacct ggaaggcaag cagggcaact  600
tcaagaacct gcgcgagttc gtgtttaaga acatcgacgg ctacttcaag atctacagca  660
agcacacccc tgtgaacctc ggccgggatc tgcctcaggg cttctctgct ctggaacccc  720
tggtggatct gcccatcggc atcaacatca cccggtttca gacactgctg gccctgcaca  780
gaagctacct gacacctggc gatagcagca gcagctggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca  1020
tcgtgcggtt ccccaatatc accaatctgt gccccttcca cgaggtgttc aatgccacca  1080
ccttcgcctc tgtgtacgcc tggaaccgga agcggatcag caattgcgtg gccgactact  1140
ccgtgctgta caacttcgcc cccttcttcg cattcaagtg ctacggcgtg tcccctacca  1200
agctgaacga cctgtgcttc acaaacgtgt acgccgacag cttcgtgatc cggggaaacg  1260
aagtgtcaca gattgcccct ggacagacag gcaacatcgc cgactacaac tacaagctgc  1320
ccgacgactt caccggctgt gtgattgcct ggaacagcaa caagctggac tccaaagtca  1380
gcggcaacta caattacctg taccggctgt tccggaagtc caagctgaag cccttcgagc  1440
gggacatctc caccgagatc tatcaggccg gcaacaagcc ttgtaacggc gtggcaggca  1500
gcaactgcta cttcccactg cagtcctacg gctttaggcc cacatacggc gtgggccacc  1560
agccctacag agtggtggtg ctgagcttcg aactgctgca tgcccctgcc acagtgtgcg  1620
```

-continued

```
gccctaagaa aagcaccaat ctcgtgaaga acaaatgcgt gaacttcaac ttcaacggcc  1680
tgaccggcac cggcgtgctg acagagagca acaagaagtt cctgccattc cagcagtttg  1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagccggctg tctgatcgga gccgagtacg tgaacaatag ctacgagtgc gacatcccca  2040
tcggcgctgg aatctgcgcc agctaccaga cacagacaaa gagccaccgg agagccagaa  2100
gcgtggccag ccagagcatc attgcctaca caatgtctct gggcgccgag aacagcgtgg  2160
cctactccaa caactctatc gctatcccca ccaacttcac catcagcgtg accacagaga  2220
tcctgcctgt gtccatgacc aagaccagcg tggactgcac catgtacatc tgcggcgatt  2280
ccaccgagtg ctccaacctg ctgctgcagt acggcagctt ctgcacccag ctgaaaagag  2340
ccctgacagg gatcgccgtg gaacaggaca agaacaccca agaggtgttc gcccaagtga  2400
agcagatcta caagacccct cctatcaagt acttcggcgg cttcaatttc agccagattc  2460
tgcccgatcc tagcaagccc agcaagcgga gcttcatcga ggacctgctg ttcaacaaag  2520
tgacactggc cgacgccggc ttcatcaagc agtatggcga ttgtctgggc gacattgccg  2580
ccagggatct gatttgcgcc cagaagttta acggactgac agtgctgcct cctctgctga  2640
ccgatgagat gatcgcccag tacacatctg ccctgctggc cggcacaatc acaagcggct  2700
ggacatttgg agcaggcgcc gctctgcaga tcccctttgc tatgcagatg gcctaccggt  2760
tcaacggcat cggagtgacc cagaatgtgc tgtacgagaa ccagaagctg atcgccaacc  2820
agttcaacag cgccatcggc aagatccagg acagcctgag cagcacagca agcgccctgg  2880
gaaagctgca ggacgtggtc aaccacaatg cccaggcact gaacaccctg gtcaagcagc  2940
tgtcctccaa gttcggcgcc atcagctctg tgctgaacga tatcctgagc agactggacc  3000
ctcctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctgggcc agagcaagag agtggacttt tgcggcaagg  3180
gctaccacct gatgagcttc cctcagtctg cccctcacgg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccaccgacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcaa cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgac tcgagctggt actgcatgca cgcaatgcta  3900
gctgcccctt tcccgtcctg ggtaccccga gtctcccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cgggaaacag cagtgattaa  4080
cctttagcaa taaacgaaag tttaactaag ctatactaac cccagggttg gtcaatttcg  4140
tgccagccac accctggagc tagcaaaaaa aaaaaaaaaa aaaaaaaaaa aaaagcatat  4200
gactaaaaaa aaaaaaaaaa aaaaaaaaaa aaaaaaaaaa aaaaaaaaaa aaaaaaaaaa  4260
aaaaaaaaaa aaa                                                   4273

SEQ ID NO: 90          moltype = AA  length = 1268
FEATURE                Location/Qualifiers
source                 1..1268
                       mol_type = protein
                       organism = synthetic construct
SEQUENCE: 90
MFVFLVLLPL VSSQCVNLIT RTQSYTNSFT RGVYYPDKVF RSSVLHSTQD LFLPFFSNVT  60
WFHAISGTNG TKRFDNPVLP FNDGVYFAST EKSNIIRGWI FGTTLDSKTQ SLLIVNNATN  120
VVIKVCEFQF CNDPFLDVYY HKNNKSWMES EFRVYSSANN CTFEYVSQPF LMDLEGKQGN  180
FKNLREFVFK NIDGYFKIYS KHTPINLGRD LPQGFSALEP LVDLPIGINI TRFQTLLALH  240
RSYLTPGDSS SGWTAGAAAY YVGYLQPRTF LLKYNENGTI TDAVDCALDP LSETKCTLKS  300
FTVEKGIYQT SNFRVQPTES IVRFPNITNL CPFDEVFNAT TFASVYAWNR KRISNCVADY  360
SVLYNFAPFF AFKCYGVSPT KLNDLCFTNV YADSFVIRGN EVRQIAPGQT GNIADYNYKL  420
PDDFTGCVIA WNSNKLDSKV GGNYNYRYRL FRKSNLKPFE RDISTEIYQA GNKPCNGVAG  480
VNCYFPLQSY GFRPTYGVGH QPYRVVVLSF ELLHAPATVC GPKKSTNLVK NKCVNFNFNG  540
LTGTGVLTES NKKFLPFQQF GRDIADTTDA VRDPQTLEIL DITPCSFGGV SVITPGTNTS  600
NQVAVLYQGV NCTEVPVAIH ADQLTPTWRV YSTGSNVFQT RAGCLIGAEY VNNSYECDIP  660
IGAGICASYQ TQTKSHRRAR SVASQSIIAY TMSLGAENSV AYSNNSIAIP TNFTISVTTE  720
ILPVSMTKTS VDCTMYICGD STECSNLLLQ YGSFCTQLKR ALTGIAVEQD KNTQEVFAQV  780
KQIYKTPPIK YFGGFNFSQI LPDPSKPSKR SFIEDLLFNK VTLADAGFIK QYGDCLGDIA  840
ARDLICAQKF NGLTVLPPLL TDEMIAQYTS ALLAGTITSG WTFGAGAALQ IPFAMQMAYR  900
FNGIGVTQNV LYENQKLIAN QFNSAIGKIQ DSLSSTASAL GKLQDVVNHN AQALNTLVKQ  960
LSSKFGAISS VLNDILSRLD PPEAEVQIDR LITGRLQSLQ TYVTQQLIRA AEIRASANLA  1020
ATKMSECVLG QSKRVDFCGK GYHLMSFPQS APHGVVFLHV TYVPAQEKNF TTAPAICHDG  1080
KAHFPREGVF VSNGTHWFVT QRNFYEPQII TTDNTFVSGN CDVVIGIVNN TVYDPLQPEL  1140
DSFKEELDKY FKNHTSPDVD LGDISGINAS VVNIQKEIDR LNEVAKNLNE SLIDLQELGK  1200
YEQYIKWPWY IWLGFIAGLI AIVMVTIMLC CMTSCCSCLK GCCSCGSCCK FDEDDSEPVL  1260
KGVKLHYT                                                         1268

SEQ ID NO: 91          moltype = RNA  length = 3810
FEATURE                Location/Qualifiers
source                 1..3810
                       mol_type = other RNA
```

-continued

```
                         organism = synthetic construct
SEQUENCE: 91
atgttcgtgt tcctggtgct gctgcctctg gtgtccagcc agtgtgtgaa cctgatcacc  60
agaacacagt catacaccaa cagctttacc agaggcgtgt actaccccga caaggtgttc  120
agatccagcg tgctgcactc tacccaggac ctgttcctgc ctttcttcag caacgtgacc  180
tggttccacg ccatctccgg caccaatggc accaagagat tcgacaaccc cgtgctgccc  240
ttcaacgacg gggtgtactt tgccagcacc gagaagtcca acatcatcag aggctggatc  300
ttcggcacca cactggacag caagacccag agcctgctga tcgtgaacaa cgccaccaac  360
gtggtcatca aagtgtgcga gttccagttc tgcaacgacc ccttcctgga cgtctactac  420
cacaagaaca acaagagctg gatggaaagc gagttccggg tgtacagcag cgccaacaac  480
tgcaccttcg agtacgtgtc ccagcctttc ctgatggacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caaagtgcac cctgaagtcc  900
ttcaccgtgg aaaagggcat ctaccagacc agcaacttcc gggtgcagcc caccgaatcc  960
atcgtgcggt tccccaatat caccaatctg tgccccttcg acgaggtgtt caatgccacc  1020
accttcgcct ctgtgtacgc ctggaaccgg aagcggatca gcaattgcgt ggccgactac  1080
tccgtgctgt acaacttcgc ccccttcttc gcattcaagt gctacggcgt gtcccctacc  1140
aagctgaacg acctgtgctt cacaaacgtg tacgccgaca gcttcgtgat ccggggaaac  1200
gaagtgcggc agattgcccc tggacagaca ggcaacatcg ccgactacaa ctacaagctg  1260
cccgacgact tcaccggctg tgtgattgcc tggaacagca acaagctgga ctccaaagtc  1320
ggcggcaact acaattacag gtaccggctg ttccggaagt ccaatctgaa gcccttcgag  1380
cgggacatct ccaccgagat ctatcaggcc ggcaacaagc cttgtaacgg cgtggcaggc  1440
gtgaactgct acttcccact gcagtcctac ggctttaggc ccacatacgg cgtgggccac  1500
cagccctaca gagtggtggt gctgagcttc gaactgctgc atgcccctgc cacagtgtgc  1560
ggccctaaga aaagcaccaa tctcgtgaag aacaaatgcg tgaacttcaa cttcaacggc  1620
ctgaccggca ccggcgtgct gacagagagc aacaagaagt tcctgccatt ccagcagttt  1680
ggccgggata tcgccgatac cacagacgcc gttagagatc cccagacact ggaaatcctg  1740
gacatcaccc cttgcagctt cggcggagtg tctgtgatca cccctggcac caacaccagc  1800
aatcaggtgg cagtgctgta ccagggcgtg aactgtaccg aagtgcccgt ggccattcac  1860
gccgatcagc tgacacctac atggcgggtg tactccaccg gcagcaatgt gtttcagacc  1920
agagccggct gtctgatcgg agccgagtac gtgaacaata gctacgagtg cgacatcccc  1980
atcggcgctg gaatctgcgc cagctaccag acacagacaa agagccaccg gagagccaga  2040
agcgtggcca gccagagcat cattgcctac acaatgtctc tgggcgccga gaacagcgtg  2100
gcctactcca acaactctat cgctatcccc accaacttca ccatcagcgt gaccacagag  2160
atcctgcctg tgtccatgac caagaccagc gtggactgca ccatgtacat ctgcggcgat  2220
tccaccgagt gctccaacct gctgctgcag tacggcagct tctgcaccca gctgaaaaga  2280
gccctgacag ggatcgccgt ggaacaggac aagaacaccc aagaggtgtt cgcccaagtg  2340
aagcagatct acaagacccc tcctatcaag tacttcggcg gcttcaattt cagccagatt  2400
ctgcccgatc ctagcaagcc cagcaagcgg agcttcatcg aggacctgct gttcaacaaa  2460
gtgacactgg ccgacgccgg cttcatcaag cagtatggcg attgtctggg cgacattgcc  2520
gccagggatc tgatttgcgc ccagaagttt aacggactga cagtgctgcc tcctctgctg  2580
accgatgaga tgatcgccca gtacacatct gccctgctgg ccggcacaat cacaagcggc  2640
tggacatttg gagcaggcgc cgctctgcag atccccttg ctatgcagat ggcctaccgg  2700
ttcaacggca tcggagtgac ccagaatgtg ctgtacgaga accagaagct gatcgccaac  2760
cagttcaaca gcgccatcgg caagatccag gacagcctga gcagcacagc aagcgccctg  2820
ggaaagctgc aggacgtggt caaccacaat gcccaggcac tgaacaccct ggtcaagcag  2880
ctgtcctcca agttcggcgc catcagctct gtgctgaacg atatcctgag cagactggac  2940
cctcctgagg ccgaggtgca gatcgacaga ctgatcacag gcagactgca gagcctccag  3000
acatacgtga cccagcagct gatcagagcc gccgagatta gagcctctgc caatctggcc  3060
gccaccaaga tgtctgagtg tgtgctgggc cagagcaaga gagtggactt ttgcggcaag  3120
ggctaccacc tgatgagctt ccctcagtct gcccctcacg gcgtggtgtt tctgcacgtg  3180
acatatgtgc ccgctcaaga gaagaatttc accaccgctc cagccatctg ccacgacggc  3240
aaagcccact ttcctagaga aggcgtgttc gtgtccaacg gcacccattg gttcgtgaca  3300
cagcggaact tctacgagcc ccagatcatc accaccgaca acaccttcgt gtctggcaac  3360
tgcgacgtcg tgatcggcat tgtgaacaat accgtgtacg accctctgca gcccgagctg  3420
gacagcttca aagaggaact ggacaagtac tttaagaacc acacaagccc cgacgtggac  3480
ctgggcgata tcagcggaat caatgccagc gtcgtgaaca tccagaaaga gatcgaccgg  3540
ctgaacgagg tggccaagaa tctgaacgag agcctgatcg acctgcaaga actggggaag  3600
tacgagcagt acatcaagtg gccctggtac atctggctgg gctttatcgc cggactgatt  3660
gccatcgtga tggtcacaat catgctgtgt tgcatgacca gctgctgtag ctgcctgaag  3720
ggctgttgta gctgtggcag ctgctgcaag ttcgacgagg acgattctga gcccgtgctg  3780
aagggcgtga aactgcacta cacatgatga                                    3810

SEQ ID NO: 92            moltype = DNA  length = 3810
FEATURE                  Location/Qualifiers
source                   1..3810
                         mol_type = other DNA
                         organism = synthetic construct
SEQUENCE: 92
atgttcgtgt tcctggtgct gctgcctctg gtgtccagcc agtgtgtgaa cctgatcacc  60
agaacacagt catacaccaa cagctttacc agaggcgtgt actaccccga caaggtgttc  120
agatccagcg tgctgcactc tacccaggac ctgttcctgc ctttcttcag caacgtgacc  180
tggttccacg ccatctccgg caccaatggc accaagagat tcgacaaccc cgtgctgccc  240
ttcaacgacg gggtgtactt tgccagcacc gagaagtcca acatcatcag aggctggatc  300
ttcggcacca cactggacag caagacccag agcctgctga tcgtgaacaa cgccaccaac  360
```

-continued

```
gtggtcatca aagtgtgcga gttccagttc tgcaacgacc ccttcctgga cgtctactac  420
cacaagaaca acaagagctg gatggaaagc gagttccggg tgtacagcag cgccaacaac  480
tgcaccttcg agtacgtgtc ccagcctttc ctgatggacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caaagtgcac cctgaagtcc  900
ttcaccgtgg aaaagggcat ctaccagacc agcaacttcc gggtgcagcc caccgaatcc  960
atcgtgcggt tccccaatat caccaatctg tgccccttcg acgaggtgtt caatgccacc  1020
accttcgcct ctgtgtacgc ctggaaccgg aagcggatca gcaattgcgt ggccgactac  1080
tccgtgctgt acaacttcgc cccettcttc gcattcaagt gctacggcgt gtcccctacc  1140
aagctgaacg acctgtgctt cacaaacgtg tacgccgaca gcttcgtgat ccggggaaac  1200
gaagtgcggc agattgcccc tggacagaca ggcaacatcg ccgactacaa ctacaagctg  1260
cccgacgact tcaccggctg tgtgattgcc tggaacagca acaagctgga ctccaaagtc  1320
ggcggcaact acaattacag gtaccggctg ttccggaagt ccaatctgaa gcccttcgag  1380
cgggacatct ccaccgagat ctatcaggcc ggcaacaagc cttgtaacgg cgtggcaggc  1440
gtgaactgct acttcccact gcagtcctac ggctttaggc ccacatacgg cgtgggccac  1500
cagccctaca gagtggtggt gctgagcttc gaactgctgc atgcccctgc cacagtgtgc  1560
ggccctaaga aaagcaccaa tctcgtgaag aacaaatgcg tgaacttcaa cttcaacggc  1620
ctgaccggca ccggcgtgct gacagagagc aacaagaagt tcctgccatt ccagcagttt  1680
ggccgggata tcgccgatac cacagacgcc gttagagatc cccagacact ggaaatcctg  1740
gacatcaccc cttgcagctt cggcggagtg tctgtgatca cccctggcac caacaccagc  1800
aatcaggtgg cagtgctgta ccagggcgtg aactgtaccg aagtgcccgt ggccattcac  1860
gccgatcagc tgacacctac atggcgggtg tactccaccg gcagcaatgt gtttcagacc  1920
agagccggct gtctgatcgg agccgagtac gtgaacaata gctacgagtg cgacatcccc  1980
atcggcgctg gaatctgcgc cagctaccag acacagacaa agagccaccg gagagccaga  2040
agcgtggcca gccagagcat cattgcctac acaatgtctc tgggcgccga gaacagcgtg  2100
gcctactcca acaactctat cgctatcccc accaacttca ccatcagcgt gaccacagag  2160
atcctgcctg tgtccatgac caagaccagc gtggactgca ccatgtacat ctgcggcgat  2220
tccaccgagt gctccaacct gctgctgcag tacggcagct tctgcaccca gctgaaaaga  2280
gccctgacag ggatcgccgt ggaacaggac aagaacaccc aagaggtgtt cgcccaagtg  2340
aagcagatct acaagacccc tcctatcaag tacttcggcg gcttcaattt cagccagatt  2400
ctgcccgatc ctagcaagcc cagcaagcgg agcttcatcg aggacctgct gttcaacaaa  2460
gtgacactgg ccgacgccgg cttcatcaag cagtatggcg attgtctggg cgacattgcc  2520
gccagggatc tgatttgcgc ccagaagttt aacggactga cagtgctgcc tcctctgctg  2580
accgatgaga tgatcgccca gtacacatct gccctgctgg ccggcacaat cacaagcggc  2640
tggacatttg gagcaggcgc cgctctgcag atcccctttg ctatgcagat ggcctaccgg  2700
ttcaacggca tcggagtgac ccagaatgtg ctgtacgaga accagaagct gatcgccaac  2760
cagttcaaca gcgccatcgg caagatccag gacagcctga gcagcacagc aagcgccctg  2820
ggaaagctgc aggacgtggt caaccacaat gcccaggcac tgaacaccct ggtcaagcag  2880
ctgtcctcca agttcggcgc catcagctct gtgctgaacg atatcctgag cagactggac  2940
cctcctgagg ccgaggtgca gatcgacaga ctgatcacag gcagactgca gagcctccag  3000
acatacgtga cccagcagct gatcagagcc gccgagatta gagcctctgc caatctggcc  3060
gccaccaaga tgtctgagtg tgtgctgggc cagagcaaga gagtggactt ttgcggcaag  3120
ggctaccacc tgatgagctt ccctcagtct gcccctcacg gcgtggtgtt tctgcacgtg  3180
acatatgtgc ccgctcaaga gaagaatttc accaccgctc cagccatctg ccacgacggc  3240
aaagcccact ttcctagaga aggcgtgttc gtgtccaacg gcacccattg gttcgtgaca  3300
cagcggaact tctacgagcc ccagatcatc accaccgaca acaccttcgt gtctggcaac  3360
tgcgacgtcg tgatcggcat tgtgaacaat accgtgtacg accctctgca gcccgagctg  3420
gacagcttca aagaggaact ggacaagtac tttaagaacc acacaagccc cgacgtggac  3480
ctgggcgata tcagcggaat caatgccagc gtcgtgaaca tccagaaaga gatcgaccgg  3540
ctgaacgagg tggccaagaa tctgaacgag agcctgatcg acctgcaaga actggggaag  3600
tacgagcagt acatcaagtg gccctggtac atctggctgg gctttatcgc cggactgatt  3660
gccatcgtga tggtcacaat catgctgtgt tgcatgacca gctgctgtag ctgcctgaag  3720
ggctgttgta gctgtggcag ctgctgcaag ttcgacgagg acgattctga gcccgtgctg  3780
aagggcgtga aactgcacta cacatgatga                                    3810
```

```
SEQ ID NO: 93           moltype = RNA  length = 4267
FEATURE                 Location/Qualifiers
source                  1..4267
                        mol_type = other RNA
                        organism = synthetic construct
SEQUENCE: 93
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatctc cggcaccaat ggcaccaaga gattcgacaa ccccgtgctg cccttcaacg  300
acggggtgta ctttgccagc accgagaagt ccaacatcat cagaggctgg atcttcggca  360
ccacactgga cagcaagacc cagagcctgc tgatcgtgaa caacgccacc aacgtggtca  420
tcaaagtgtg cgagttccag ttctgcaacg accccttcct ggacgtctac taccacaaga  480
acaacaagag ctggatggaa agcgagttcc gggtgtacag cagcgccaac aactgcacct  540
tcgagtacgt gtcccagcct ttcctgatgg acctggaagg caagcagggc aacttcaaga  600
acctgcgcga gttcgtgttt aagaacatcg acggctactt caagatctac agcaagcaca  660
cccctatcaa cctcggccgg gatctgcctc agggcttctc tgctctggaa cccctggtgg  720
atctgcccat cggcatcaac atcacccggt ttcagacact gctggccctg cacagaagct  780
acctgacacc tggcgatagc agcagcggat ggacagctgg tgccgccgct tactatgtgg  840
```

```
gctacctgca gcctagaacc ttcctgctga agtacaacga gaacggcacc atcaccgacg  900
ccgtggattg tgctctggat cctctgagcg agacaaagtg caccctgaag tccttcaccg  960
tggaaaaggg catctaccag accagcaact tccgggtgca gcccaccgaa tccatcgtgc  1020
ggttccccaa tatcaccaat ctgtgccccct tcgacgaggt gttcaatgcc accaccttcg  1080
cctctgtgta cgcctggaac cggaagcgga tcagcaattg cgtggccgac tactccgtgc  1140
tgtacaactt cgcccccttc ttcgcattca agtgctacgg cgtgtcccct accaagctga  1200
acgacctgtg cttcacaaac gtgtacgccg acagcttcgt gatccgggga aacgaagtgc  1260
ggcagattgc ccctggacag acaggcaaca tcgccgacta caactacaag ctgcccgacg  1320
acttcaccgg ctgtgtgatt gcctggaaca gcaacaagct ggactccaaa gtcggcggca  1380
actacaatta caggtaccgg ctgttccgga agtccaatct gaagcccttc gagcgggaca  1440
tctccaccga gatctatcag gccggcaaca agccttgtaa cggcgtggca ggcgtgaact  1500
gctacttccc actgcagtcc tacggcttta ggcccacata cggcgtgggc caccagccct  1560
acagagtggt ggtgctgagc ttcgaactgc tgcatgcccc tgccacagtg tgcggcccta  1620
agaaaagcac caatctcgtg aagaacaaat gcgtgaactt caacttcaac ggcctgaccg  1680
gcaccggcgt gctgacagag agcaacaaga agttcctgcc attccagcag tttggccggg  1740
atatcgccga taccacagac gccgttagag atccccagac actggaaatc ctggacatca  1800
cccccttgcag cttcggcgga gtgtctgtga tcacccctgg caccaacacc agcaatcagg  1860
tggcagtgct gtaccagggc gtgaactgta ccgaagtgcc cgtggccatt cacgccgatc  1920
agctgacacc tacatggcgg gtgtactcca ccggcagcaa tgtgtttcag accagagccg  1980
gctgtctgat cggagccgag tacgtgaaca atagctacga gtgcgacatc cccatcggcg  2040
ctggaatctg cgccagctac cagacacaga caaagagcca ccggagagcc agaagcgtgg  2100
ccagccagag catcattgcc tacacaatgt ctctgggcgc cgagaacagc gtggcctact  2160
ccaacaactc tatcgctatc cccaccaact tcaccatcag cgtgaccaca gagatcctgc  2220
ctgtgtccat gaccaagacc agcgtggact gcaccatgta catctgcggc gattccaccg  2280
agtgctccaa cctgctgctg cagtacggca gcttctgcac ccagctgaaa agagccctga  2340
cagggatcgc cgtggaacag gacaagaaca cccaagaggt gttcgcccaa gtgaagcaga  2400
tctacaagac ccctcctatc aagtacttcg gcggcttcaa tttcagccag attctgcccg  2460
atcctagcaa gcccagcaag cggagcttca tcgaggacct gctgttcaac aaagtgacac  2520
tggccgacgc cggcttcatc aagcagtatg gcgattgtct gggcgacatt gccgccaggg  2580
atctgatttg cgcccagaag tttaacggac tgacagtgct gcctcctctg ctgaccgatg  2640
agatgatcgc ccagtacaca tctgccctgc tggccggcac aatcacaagc ggctggacat  2700
ttggagcagg cgccgctctg cagatcccct ttgctatgca gatggcctac cggttcaacg  2760
gcatcggagt gacccagaat gtgctgtacg agaaccagaa gctgatcgcc aaccagttca  2820
acagcgccat cggcaagatc caggacagcc tgagcagcac agcaagcgcc ctgggaaagc  2880
tgcaggacgt ggtcaaccac aatgcccagg cactgaacac cctggtcaag cagctgtcct  2940
ccaagttcgg cgccatcagc tctgtgctga acgatatcct gagcagactg gaccctcctg  3000
aggccgaggt gcagatcgac agactgatca caggcagact gcagagcctc cagacatacg  3060
tgacccagca gctgatcaga gccgccgaga ttagagcctc tgccaatctg gccgccacca  3120
agatgtctga gtgtgtgctg ggccagagca agagagtgga cttttgcggc aagggctacc  3180
acctgatgag cttccctcag tctgcccctc acggcgtggt gtttctgcac gtgacatatg  3240
tgcccgctca agagaagaat ttcaccaccg ctccagccat ctgccacgac ggcaaagccc  3300
actttcctag agaaggcgtg ttcgtgtcca acggcaccca ttggttcgtg acacagcgga  3360
acttctacga gccccagatc atcaccaccg acaacacctt cgtgtctggc aactgcgacg  3420
tcgtgatcgg cattgtgaac aataccgtgt acgaccctct gcagcccgag ctggacagct  3480
tcaaagagga actggacaag tactttaaga accacacaag ccccgacgtg gacctgggcg  3540
atatcagcgg aatcaatgcc agcgtcgtga acatccagaa agagatcgac cggctgaacg  3600
aggtggccaa gaatctgaac gagagcctga tcgacctgca agaactgggg aagtacgagc  3660
agtacatcaa gtggccctgg tacatctggc tgggctttat cgccggactg attgccatcg  3720
tgatggtcac aatcatgctg tgttgcatga ccagctgctg tagctgcctg aagggctgtt  3780
gtagctgtgg cagctgctgc aagttcgacg aggacgattc tgagcccgtg ctgaagggcg  3840
tgaaactgca ctacacatga tgactcgagc tggtactgca tgcacgcaat gctagctgcc  3900
cctttcccgt cctgggtacc ccgagtctcc cccgacctcg ggtcccaggt atgctcccac  3960
ctccacctgc cccactcacc acctctgcta gttccagaca cctcccaagc acgcagcaat  4020
gcagctcaaa acgcttagcc tagccacacc cccacgggaa acagcagtga ttaacctta  4080
gcaataaacg aaagtttaac taagctatac taaccccagg gttggtcaat ttcgtgccag  4140
ccacaccctg gagctagcaa aaaaaaaaaa aaaaaaaaaa aaaaaaaagc atatgactaa  4200
aaaaaaaaaa aaaaaaaaaa aaaaaaaaaa aaaaaaaaaa aaaaaaaaaa aaaaaaaaaa  4260
aaaaaaa                                                            4267

SEQ ID NO: 94          moltype = DNA  length = 4267
FEATURE                Location/Qualifiers
source                 1..4267
                       mol_type = other DNA
                       organism = synthetic construct
SEQUENCE: 94
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatctc cggcaccaat ggcaccaaga gattcgacaa ccccgtgctg cccttcaacg  300
acggggtgta ctttgccagc accgagaagt ccaacatcat cagaggctgg atcttcggca  360
ccacactgga cagcaagacc cagagcctgc tgatcgtgaa caacgccacc aacgtggtca  420
tcaaagtgtg cgagttccag ttctgcaacg accccttcct ggacgtctac taccacaaga  480
acaacaagag ctggatggaa agcgagttcc gggtgtacag cagcgccaac aactgcacct  540
tcgagtacgt gtcccagcct ttcctgatgg acctggaagg caagcagggc aacttcaaga  600
acctgcgcga gttcgtgttt aagaacatcg acggctactt caagatctac agcaagcaca  660
cccctatcaa cctcggccgg gatctgcctc agggcttctc tgctctggaa cccctggtgg  720
atctgcccat cggcatcaac atcacccggt ttcagacact gctggccctg cacagaagct  780
acctgacacc tggcgatagc agcagcggat ggacagctgg tgccgccgct tactatgtgg  840
```

-continued

```
gctacctgca gcctagaacc ttcctgctga agtacaacga gaacggcacc atcaccgacg  900
ccgtggattg tgctctggat cctctgagcg agacaaagtg caccctgaag tccttcaccg  960
tggaaaaggg catctaccag accagcaact tccgggtgca gcccaccgaa tccatcgtgc  1020
ggttccccaa tatcaccaat ctgtgcccct tcgacgaggt gttcaatgcc accaccttcg  1080
cctctgtgta cgcctggaac cggaagcgga tcagcaattg cgtggccgac tactccgtgc  1140
tgtacaactt cgcccccttc ttcgcattca agtgctacgg cgtgtcccct accaagctga  1200
acgacctgtg cttcacaaac gtgtacgccg acagcttcgt gatccgggga aacgaagtgc  1260
ggcagattgc ccctggacag acaggcaaca tcgccgacta caactacaag ctgcccgacg  1320
acttcaccgg ctgtgtgatt gcctggaaca gcaacaagct ggactccaaa gtcggcggca  1380
actacaatta caggtaccgg ctgttccgga agtccaatct gaagcccttc gagcgggaca  1440
tctccaccga gatctatcag gccggcaaca agccttgtaa cggcgtggca ggcgtgaact  1500
gctacttccc actgcagtcc tacggcttta ggcccacata cggcgtgggc caccagccct  1560
acagagtggt ggtgctgagc ttcgaactgc tgcatgcccc tgccacagtg tgcggcccta  1620
agaaaagcac caatctcgtg aagaacaaat gcgtgaactt caacttcaac ggcctgaccg  1680
gcaccggcgt gctgacagag agcaacaaga agttcctgcc attccagcag tttggccggg  1740
atatcgccga taccacagac gccgttagag atccccagac actggaaatc ctggacatca  1800
cccccttgcag cttcggcgga gtgtctgtga tcacccctgg caccaacacc agcaatcagg  1860
tggcagtgct gtaccagggc gtgaactgta ccgaagtgcc cgtggccatt cacgccgatc  1920
agctgacacc tacatggcgg gtgtactcca ccggcagcaa tgtgtttcag accagagccg  1980
gctgtctgat cggagccgag tacgtgaaca atagctacga gtgcgacatc cccatcggcg  2040
ctggaatctg cgccagctac cagacacaga caaagagcca ccggagagcc agaagcgtgg  2100
ccagccagag catcattgcc tacacaatgt ctctgggcgc cgagaacagc gtggcctact  2160
ccaacaactc tatcgctatc cccaccaact tcaccatcag cgtgaccaca gagatcctgc  2220
ctgtgtccat gaccaagacc agcgtggact gcaccatgta catctgcggc gattccaccg  2280
agtgctccaa cctgctgctg cagtacggca gcttctgcac ccagctgaaa agagccctga  2340
cagggatcgc cgtggaacag gacaagaaca cccaagaggt gttcgcccaa gtgaagcaga  2400
tctacaagac ccctcctatc aagtacttcg gcggcttcaa tttcagccag attctgcccg  2460
atcctagcaa gcccagcaag cggagcttca tcgaggacct gctgttcaac aaagtgacac  2520
tggccgacgc cggcttcatc aagcagtatg gcgattgtct gggcgacatt gccgccaggg  2580
atctgatttg cgcccagaag tttaacggac tgacagtgct gcctcctctg ctgaccgatg  2640
agatgatcgc ccagtacaca tctgccctgc tggccggcac aatcacaagc ggctggacat  2700
ttggagcagg cgccgctctg cagatcccct ttgctatgca gatggcctac cggttcaacg  2760
gcatcggagt gacccagaat gtgctgtacg agaaccagaa gctgatcgcc aaccagttca  2820
acagcgccat cggcaagatc caggacagcc tgagcagcac agcaagcgcc ctgggaaagc  2880
tgcaggacgt ggtcaaccac aatgcccagg cactgaacac cctggtcaag cagctgtcct  2940
ccaagttcgg cgccatcagc tctgtgctga acgatatcct gagcagactg gaccctcctg  3000
aggccgaggt gcagatcgac agactgatca caggcagact gcagagcctc cagacatacg  3060
tgacccagca gctgatcaga gccgccgaga ttagagcctc tgccaatctg gccgccacca  3120
agatgtctga gtgtgtgctg ggccagagca agagagtgga cttttgcggc aagggctacc  3180
acctgatgag cttccctcag tctgccccctc acggcgtggt gtttctgcac gtgacatatg  3240
tgcccgctca agagaagaat ttcaccaccg ctccagccat ctgccacgac ggcaaagccc  3300
actttcctag agaaggcgtg ttcgtgtcca acggcaccca ttggttcgtg acacagcgga  3360
acttctacga gccccagatc atcaccaccg acaacacctt cgtgtctggc aactgcgacg  3420
tcgtgatcgg cattgtgaac aataccgtgt acgaccctct gcagcccgag ctggacagct  3480
tcaaagagga actggacaag tactttaaga accacacaag ccccgacgtg gacctgggcg  3540
atatcagcgg aatcaatgcc agcgtcgtga acatccagaa agagatcgac cggctgaacg  3600
aggtggccaa gaatctgaac gagagcctga tcgacctgca agaactgggg aagtacgagc  3660
agtacatcaa gtggccctgg tacatctggc tgggctttat cgccggactg attgccatcg  3720
tgatggtcac aatcatgctg tgttgcatga ccagctgctg tagctgcctg aagggctgtt  3780
gtagctgtgg cagctgctgc aagttcgacg aggacgattc tgagcccgtg ctgaagggcg  3840
tgaaactgca ctacacatga tgactcgagc tggtactgca tgcacgcaat gctagctgcc  3900
cctttcccgt cctgggtacc ccgagtctcc cccgacctcg ggtcccaggt atgctcccac  3960
ctccacctgc cccactcacc acctctgcta gttccagaca cctcccaagc acgcagcaat  4020
gcagctcaaa acgcttagcc tagccacacc cccacgggaa acagcagtga ttaacccttta  4080
gcaataaacg aaagtttaac taagctatac taaccccagg gttggtcaat ttcgtgccag  4140
ccacaccctg gagctagcaa aaaaaaaaaa aaaaaaaaaa aaaaaaaagc atatgactaa  4200
aaaaaaaaaa aaaaaaaaaa aaaaaaaaaa aaaaaaaaaa aaaaaaaaaa aaaaaaaaaa  4260
aaaaaaa                                                            4267

SEQ ID NO: 95          moltype = AA  length = 1269
FEATURE                Location/Qualifiers
source                 1..1269
                       mol_type = protein
                       organism = synthetic construct
SEQUENCE: 95
MFVFLVLLPL VSSQCVNLIT RTQSYTNSFT RGVYYPDKVF RSSVLHSTQD LFLPFFSNVT  60
WFHAIHVSGT NGTKRFDNPA LPFNDGVYFA STEKSNIIRG WIFGTTLDSK TQSLLIVNNA  120
TNVVIKVCEF QFCNDPFLDV YQKNNKSWME SEFRVYSSAN NCTFEYVSQP FLMDLEGKEG  180
NFKNLREFVF KNIDGYFKIY SKHTPINLER DLPQGFSALE PLVDLPIGIN ITRFQTLLAL  240
HRSYLTPGDS SSGWTAGAAA YYVGYLQPRT FLLKYNENGT ITDAVDCALD PLSETKCTLK  300
SFTVEKGIYQ TSNFRVQPTE SIVRFPNITN LCPFHEVFNA TTFASVYAWN RKRISNCVAD  360
YSVIYNFAPF FAFKCYGVSP TKLNDLCFTN VYADSFVIRG NEVSQIAPGQ TGNIADYNYK  420
LPDDFTGCVI AWNSNKLDSK PSGNYNYLYR LFRKSKLKPF ERDISTEIYQ AGNKPCNGVA  480
GSNCYSPLQS YGFRPTYGVG HQPYRVVVLS FELLHAPATV CGPKKSTNLV KNKCVNFNFN  540
GLTGTGVLTE SNKKFLPFQQ FGRDIADTTD AVRDPQTLEI LDITPCSFGG VSVITPGTNT  600
SNQVAVLYQG VNCTEVPVAI HADQLTPTWR VYSTGSNVFQ TRAGCLIGAE YVNNSYECDI  660
PIGAGICASY QTQTKSHRRA RSVASQSIIA YTMSLGAENS VAYSNNSIAI PTNFTISVTT  720
EILPVSMTKT SVDCTMYICG DSTECSNLLL QYGSFCTQLK RALTGIAVEQ DKNTQEVFAQ  780
VKQIYKTPPI KYFGGFNFSQ ILPDPSKPSK RSFIEDLLFN KVTLADAGFI KQYGDCLGDI  840
```

```
AARDLICAQK FNGLTVLPPL LTDEMIAQYT SALLAGTITS GWTFGAGAAL QIPFAMQMAY  900
RFNGIGVTQN VLYENQKLIA NQFNSAIGKI QDSLSSTASA LGKLQDVVNH NAQALNTLVK  960
QLSSKFGAIS SVLNDILSRL DPPEAEVQID RLITGRLQSL QTYVTQQLIR AAEIRASANL  1020
AATKMSECVL GQSKRVDFCG KGYHLMSFPQ SAPHGVVFLH VTYVPAQEKN FTTAPAICHD  1080
GKAHFPREGV FVSNGTHWFV TQRNFYEPQI ITTDNTFVSG NCDVVIGIVN NTVYDPLQPE  1140
LDSFKEELDK YFKNHTSPDV DLGDISGINA SVVNIQKEID RLNEVAKNLN ESLIDLQELG  1200
KYEQYIKWPW YIWLGFIAGL IAIVMVTIML CCMTSCCSCL KGCCSCGSCC KFDEDDSEPV  1260
LKGVKLHYT                                                          1269

SEQ ID NO: 96           moltype = RNA  length = 3813
FEATURE                 Location/Qualifiers
source                  1..3813
                        mol_type = other RNA
                        organism = synthetic construct
SEQUENCE: 96
atgttcgtgt tcctggtgct gctgcctctg gtgtccagcc agtgtgtgaa cctgatcacc  60
agaacacagt catacaccaa cagctttacc agaggcgtgt actaccccga caaggtgttc  120
agatccagcg tgctgcactc tacccaggac ctgttcctgc ctttcttcag caacgtgacc  180
tggttccacg ccatccacgt gtccggcacc aatggcacca agagattcga caaccccgcc  240
ctgcccttca acgacggggt gtactttgcc agcaccgaga agtccaacat catcagaggc  300
tggatcttcg gcaccacact ggacagcaag acccagagcc tgctgatcgt gaacaacgcc  360
accaacgtgg tcatcaaagt gtgcgagttc cagttctgca acgacccctt cctggacgtc  420
taccagaaga acaacaagag ctggatggaa agcgagttcc gggtgtacag cagcgccaac  480
aactgcacct tcgagtacgt gtcccagcct ttcctgatgg acctggaagg caaggagggc  540
aacttcaaga acctgcgcga gttcgtgttt aagaacatcg acggctactt caagatctac  600
agcaagcaca cccctatcaa cctcgagcgg gatctgcctc agggcttctc tgctctggaa  660
cccctggtgg atctgcccat cggcatcaac atcacccggt ttcagacact gctggccctg  720
cacagaagct acctgacacc tggcgatagc agcagcggat ggacagctgg tgccgccgct  780
tactatgtgg gctacctgca gcctagaacc ttcctgctga agtacaacga gaacggcacc  840
atcaccgacg ccgtggattg tgctctggat cctctgagcg agacaaagtg caccctgaag  900
tccttcaccg tggaaaaggg catctaccag accagcaact tccgggtgca gcccaccgaa  960
tccatcgtgc ggttccccaa tatcaccaat ctgtgcccct tccacgaggt gttcaatgcc  1020
accaccttcg cctctgtgta cgcctggaac cggaagcgga tcagcaattg cgtggccgac  1080
tactccgtga tctacaactt cgccccccttc ttcgcattca agtgctacgg cgtgtcccct  1140
accaagctga acgacctgtg cttcacaaac gtgtacgccg acagcttcgt gatccgggga  1200
aacgaagtgt cacagattgc ccctggacag acaggcaaca tcgccgacta caactacaag  1260
ctgcccgacg acttcaccgg ctgtgtgatt gcctggaaca gcaacaagct ggactccaaa  1320
cccagcggca actacaatta cctgtaccgg ctgttccgga agtccaagct gaagcccttc  1380
gagcgggaca tctccaccga gatctatcag gccggcaaca agccttgtaa cggcgtggca  1440
ggcagcaact gctacagccc actgcagtcc tacggcttta ggcccacata cggcgtgggc  1500
caccagccct acagagtggt ggtgctgagc ttcgaactgc tgcatgcccc tgccacagtg  1560
tgcggcccta agaaaagcac caatctcgtg aagaacaaat gcgtgaactt caacttcaac  1620
ggcctgaccg gcaccggcgt gctgacagag agcaacaaga agttcctgcc attccagcag  1680
tttggccggg atatcgccga taccacagac gccgttagag atccccagac actggaaatc  1740
ctggacatca cccctgcag cttcggcgga gtgtctgtga tcacccctgg caccaacacc  1800
agcaatcagg tggcagtgct gtaccagggc gtgaactgta ccgaagtgcc cgtggccatt  1860
cacgccgatc agctgacacc tacatggcgg gtgtactcca ccggcagcaa tgtgtttcag  1920
accagagccg gctgtctgat cggagccgag tacgtgaaca atagctacga gtgcgacatc  1980
cccatcggcg ctggaatctg cgccagctac cagacacaga caaagagcca ccggagagcc  2040
agaagcgtgg ccagccagag catcattgcc tacacaatgt ctctgggcgc cgagaacagc  2100
gtggcctact ccaacaactc tatcgctatc cccaccaact tcaccatcag cgtgaccaca  2160
gagatcctgc ctgtgtccat gaccaagacc agcgtggact gcaccatgta catctgcggc  2220
gattccaccg agtgctccaa cctgctgctg cagtacggca gcttctgcac ccagctgaaa  2280
agagccctga cagggatcgc cgtggaacag gacaagaaca cccaagaggt gttcgcccaa  2340
gtgaagcaga tctacaagac ccctcctatc aagtacttcg gcggcttcaa tttcagccag  2400
attctgcccg atcctagcaa gcccagcaag cggagcttca tcgaggacct gctgttcaac  2460
aaagtgacac tggccgacgc cggcttcatc aagcagtatg gcgattgtct gggcgacatt  2520
gccgccaggg atctgatttg cgcccagaag tttaacggac tgacagtgct gcctcctctg  2580
ctgaccgatg agatgatcgc ccagtacaca tctgccctgc tggccggcac aatcacaagc  2640
ggctggacat ttggagcagg cgccgctctg cagatcccct ttgctatgca gatggcctac  2700
cggttcaacg gcatcggagt gacccagaat gtgctgtacg agaaccagaa gctgatcgcc  2760
aaccagttca acagcgccat cggcaagatc caggacagcc tgagcagcac agcaagcgcc  2820
ctgggaaagc tgcaggacgt ggtcaaccac aatgcccagg cactgaacac cctggtcaag  2880
cagctgtcct ccaagttcgg cgccatcagc tctgtgctga acgatatcct gagcagactg  2940
gaccctcctg aggccgaggt gcagatcgac agactgatca caggcagact gcagagcctc  3000
cagacatacg tgacccagca gctgatcaga gccgccgaga ttagagcctc tgccaatctg  3060
gccgccacca agatgtctga gtgtgtgctg ggccagagca agagagtgga cttttgcggc  3120
aagggctacc acctgatgag cttccctcag tctgcccctc acggcgtggt gtttctgcac  3180
gtgacatatg tgcccgctca agagaagaat ttcaccaccg ctccagccat ctgccacgac  3240
ggcaaagccc actttcctag agaaggcgtg ttcgtgtcca acggcaccca ttggttcgtg  3300
acacagcgga acttctacga gccccagatc atcaccaccg acaacacctt cgtgtctggc  3360
aactgcgacg tcgtgatcgg cattgtgaac aataccgtgt acgaccctct gcagcccgag  3420
ctggacagct tcaaagagga actggacaag tactttaaga accacacaag ccccgacgtg  3480
gacctgggcg atatcagcgg aatcaatgcc agcgtcgtga acatccagaa agagatcgac  3540
cggctgaacg aggtggccaa gaatctgaac gagagcctga tcgacctgca agaactgggg  3600
aagtacgagc agtacatcaa gtggccctgg tacatctggc tgggctttat cgccggactg  3660
attgccatcg tgatggtcac aatcatgctg tgttgcatga ccagctgctg tagctgcctg  3720
aagggctgtt gtagctgtgg cagctgctgc aagttcgacg aggacgattc tgagcccgtg  3780
ctgaagggcg tgaaactgca ctacacatga tga                               3813
```

```
SEQ ID NO: 97          moltype = DNA  length = 3813
FEATURE                Location/Qualifiers
source                 1..3813
                       mol_type = other DNA
                       organism = synthetic construct
SEQUENCE: 97
atgttcgtgt tcctggtgct gctgcctctg gtgtccagcc agtgtgtgaa cctgatcacc  60
agaacacagt catacaccaa cagctttacc agaggcgtgt actaccccga caaggtgttc  120
agatccagcg tgctgcactc tacccaggac ctgttcctgc ctttcttcag caacgtgacc  180
tggttccacg ccatccacgt gtccggcacc aatggcacca agagattcga caaccccgcc  240
ctgcccttca acgacggggt gtactttgcc agcaccgaga agtccaacat catcagaggc  300
tggatcttcg gcaccacact ggacagcaag acccagagcc tgctgatcgt gaacaacgcc  360
accaacgtgg tcatcaaagt gtgcgagttc cagttctgca acgacccctt cctggacgtc  420
taccagaaga acaacaagag ctggatggaa agcgagttcc gggtgtacag cagcgccaac  480
aactgcacct tcgagtacgt gtcccagcct ttcctgatgg acctggaagg caaggagggc  540
aacttcaaga acctgcgcga gttcgtgttt aagaacatcg acggctactt caagatctac  600
agcaagcaca cccctatcaa cctcgagcgg gatctgcctc agggcttctc tgctctggaa  660
cccctggtgg atctgcccat cggcatcaac atcacccggt ttcagacact gctggccctg  720
cacagaagct acctgacacc tggcgatagc agcagcggat ggacagctgg tgccgccgct  780
tactatgtgg gctacctgca gcctagaacc ttcctgctga agtacaacga gaacggcacc  840
atcaccgacg ccgtggattg tgctctggat cctctgagcg agacaaagtg caccctgaag  900
tccttcaccg tggaaaaggg catctaccag accagcaact tccgggtgca gcccaccgaa  960
tccatcgtgc ggttccccaa tatcaccaat ctgtgcccct tccacgaggt gttcaatgcc  1020
accaccttcg cctctgtgta cgcctggaac cggaagcgga tcagcaattg cgtggccgac  1080
tactccgtga tctacaactt cgcccccttc ttcgcattca agtgctacgg cgtgtcccct  1140
accaagctga acgacctgtg cttcacaaac gtgtacgccg acagcttcgt gatccgggga  1200
aacgaagtgt cacagattgc ccctggacag acaggcaaca tcgccgacta caactacaag  1260
ctgcccgacg acttcaccgg ctgtgtgatt gcctggaaca gcaacaagct ggactccaaa  1320
cccagcggca actacaatta cctgtaccgg ctgttccgga agtccaagct gaagcccttc  1380
gagcgggaca tctccaccga gatctatcag gccggcaaca agccttgtaa cggcgtggca  1440
ggcagcaact gctacagccc actgcagtcc tacggcttta ggcccacata cggcgtgggc  1500
caccagccct acagagtggt ggtgctgagc ttcgaactgc tgcatgcccc tgccacagtg  1560
tgcggcccta agaaaagcac caatctcgtg aagaacaaat gcgtgaactt caacttcaac  1620
ggcctgaccg gcaccggcgt gctgacagag agcaacaaga agttcctgcc attccagcag  1680
tttggccggg atatcgccga taccacagac gccgttagag atccccagac actggaaatc  1740
ctggacatca cccctgcag cttcggcgga gtgtctgtga tcacccctgg caccaacacc  1800
agcaatcagg tggcagtgct gtaccagggc gtgaactgta ccgaagtgcc cgtggccatt  1860
cacgccgatc agctgacacc tacatggcgg gtgtactcca ccggcagcaa tgtgtttcag  1920
accagagccg gctgtctgat cggagccgag tacgtgaaca atagctacga gtgcgacatc  1980
cccatcggcg ctggaatctg cgccagctac cagacacaga caaagagcca ccggagagcc  2040
agaagcgtgg ccagccagag catcattgcc tacacaatgt ctctgggcgc cgagaacagc  2100
gtggcctact ccaacaactc tatcgctatc cccaccaact tcaccatcag cgtgaccaca  2160
gagatcctgc ctgtgtccat gaccaagacc agcgtggact gcaccatgta catctgcggc  2220
gattccaccg agtgctccaa cctgctgctg cagtacggca gcttctgcac ccagctgaaa  2280
agagccctga cagggatcgc cgtggaacag gacaagaaca cccaagaggt gttcgcccaa  2340
gtgaagcaga tctacaagac cctcctatc aagtacttcg gcggcttcaa tttcagccag  2400
attctgcccg atcctagcaa gcccagcaag cggagcttca tcgaggacct gctgttcaac  2460
aaagtgacac tggccgacgc cggcttcatc aagcagtatg gcgattgtct gggcgacatt  2520
gccgccaggg atctgatttg cgcccagaag tttaacggac tgacagtgct gcctcctctg  2580
ctgaccgatg agatgatcgc ccagtacaca tctgccctgc tggccggcac aatcacaagc  2640
ggctggacat ttggagcagg cgccgctctg cagatcccct ttgctatgca gatggcctac  2700
cggttcaacg gcatcggagt gacccagaat gtgctgtacg agaaccagaa gctgatcgcc  2760
aaccagttca acagcgccat cggcaagatc caggacagcc tgagcagcac agcaagcgcc  2820
ctgggaaagc tgcaggacgt ggtcaaccac aatgcccagg cactgaacac cctggtcaag  2880
cagctgtcct ccaagttcgg cgccatcagc tctgtgctga acgatatcct gagcagactg  2940
gaccctcctg aggccgaggt gcagatcgac agactgatca caggcagact gcagagcctc  3000
cagacatacg tgacccagca gctgatcaga gccgccgaga ttagagcctc tgccaatctg  3060
gccgccacca agatgtctga gtgtgtgctg ggccagagca agagagtgga cttttgcggc  3120
aagggctacc acctgatgag cttccctcag tctgcccctc acggcgtggt gtttctgcac  3180
gtgacatatg tgcccgctca agagaagaat ttcaccaccg ctccagccat ctgccacgac  3240
ggcaaagccc actttcctag agaaggcgtg ttcgtgtcca acggcaccca ttggttcgtg  3300
acacagcgga acttctacga gccccagatc atcaccaccg acaacacctt cgtgtctggc  3360
aactgcgacg tcgtgatcgg cattgtgaac aataccgtgt acgaccctct gcagcccgag  3420
ctggacagct tcaaagagga actggacaag tactttaaga accacacaag ccccgacgtg  3480
gacctgggcg atatcagcgg aatcaatgcc agcgtcgtga acatccagaa agagatcgac  3540
cggctgaacg aggtggccaa gaatctgaac gagagcctga tcgacctgca agaactgggg  3600
aagtacgagc agtacatcaa gtggccctgg tacatctggc tgggctttat cgccggactg  3660
attgccatcg tgatggtcac aatcatgctg tgttgcatga ccagctgctg tagctgcctg  3720
aagggctgtt gtagctgtgg cagctgctgc aagttcgacg aggacgattc tgagcccgtg  3780
ctgaagggcg tgaaactgca ctacacatga tga                              3813

SEQ ID NO: 98          moltype = RNA  length = 4270
FEATURE                Location/Qualifiers
source                 1..4270
                       mol_type = other RNA
                       organism = synthetic construct
SEQUENCE: 98
agaataaact agtattcttc tggtccccac agactcagag agaacccgcc accatgttcg  60
```

-continued

```
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatcca cgtgtccggc accaatggca ccaagagatt cgacaacccc gccctgccct  300
tcaacgacgg ggtgtacttt gccagcaccg agaagtccaa catcatcaga ggctggatct  360
tcggcaccac actggacagc aagacccaga gcctgctgat cgtgaacaac gccaccaacg  420
tggtcatcaa agtgtgcgag ttccagttct gcaacgaccc cttcctggac gtctaccaga  480
agaacaacaa gagctggatg gaaagcgagt tccgggtgta cagcagcgcc aacaactgca  540
ccttcgagta cgtgtcccag cctttcctga tggacctgga aggcaaggag ggcaacttca  600
agaacctgcg cgagttcgtg tttaagaaca tcgacggcta cttcaagatc tacagcaagc  660
acacccctat caacctcgag cgggatctgc ctcagggctt ctctgctctg gaacccctgg  720
tggatctgcc catcggcatc aacatcaccc ggtttcagac actgctggcc ctgcacagaa  780
gctacctgac acctggcgat agcagcagcg gatggacagc tggtgccgcc gcttactatg  840
tgggctacct gcagcctaga accttcctgc tgaagtacaa cgagaacggc accatcaccg  900
acgccgtgga ttgtgctctg gatcctctga gcgagacaaa gtgcaccctg aagtccttca  960
ccgtggaaaa gggcatctac cagaccagca acttccgggt gcagcccacc gaatccatcg  1020
tgcggttccc caatatcacc aatctgtgcc ccttccacga ggtgttcaat gccaccacct  1080
tcgcctctgt gtacgcctgg aaccggaagc ggatcagcaa ttgcgtggcc gactactccg  1140
tgatctacaa cttcgccccc ttcttcgcat tcaagtgcta cggcgtgtcc cctaccaagc  1200
tgaacgacct gtgcttcaca aacgtgtacg ccgacagctt cgtgatccgg ggaaacgaag  1260
tgtcacagat tgcccctgga cagacaggca acatcgccga ctacaactac aagctgcccg  1320
acgacttcac cggctgtgtg attgcctgga acagcaacaa gctggactcc aaacccagcg  1380
gcaactacaa ttacctgtac cggctgttcc ggaagtccaa gctgaagccc ttcgagcggg  1440
acatctccac cgagatctat caggccggca acaagccttg taacggcgtg gcaggcagca  1500
actgctacag cccactgcag tcctacggct ttaggcccac atacggcgtg ggccaccagc  1560
cctacagagt ggtggtgctg agcttcgaac tgctgcatgc ccctgccaca gtgtgcggcc  1620
ctaagaaaag caccaatctc gtgaagaaca aatgcgtgaa cttcaacttc aacggcctga  1680
ccggcaccgg cgtgctgaca gagagcaaca agaagttcct gccattccag cagtttggcc  1740
gggatatcgc cgataccaca gacgccgtta gagatcccca gacactggaa atcctggaca  1800
tcaccccttg cagcttcggc ggagtgtctg tgatcacccc tggcaccaac accagcaatc  1860
aggtggcagt gctgtaccag ggcgtgaact gtaccgaagt gcccgtggcc attcacgccg  1920
atcagctgac acctacatgg cgggtgtact ccaccggcag caatgtgttt cagaccagag  1980
ccggctgtct gatcggagcc gagtacgtga acaatagcta cgagtgcgac atccccatcg  2040
gcgctggaat ctgcgccagc taccagacac agacaaagag ccaccggaga gccagaagcg  2100
tggccagcca gagcatcatt gcctacacaa tgtctctggg cgccgagaac agcgtggcct  2160
actccaacaa ctctatcgct atccccacca acttcaccat cagcgtgacc acagagatcc  2220
tgcctgtgtc catgaccaag accagcgtgg actgcaccat gtacatctgc ggcgattcca  2280
ccgagtgctc caacctgctg ctgcagtacg gcagcttctg cacccagctg aaaagagccc  2340
tgacagggat cgccgtggaa caggacaaga acacccaaga ggtgttcgcc caagtgaagc  2400
agatctacaa gacccctcct atcaagtact tcggcggctt caatttcagc cagattctgc  2460
ccgatcctag caagcccagc aagcggagct tcatcgagga cctgctgttc aacaaagtga  2520
cactggccga cgccggcttc atcaagcagt atggcgattg tctgggcgac attgccgcca  2580
gggatctgat ttgcgcccag aagtttaacg gactgacagt gctgcctcct ctgctgaccg  2640
atgagatgat cgcccagtac acatctgccc tgctggccgg cacaatcaca agcggctgga  2700
catttggagc aggcgccgct ctgcagatcc cctttgctat gcagatggcc taccggttca  2760
acggcatcgg agtgacccag aatgtgctgt acgagaacca gaagctgatc gccaaccagt  2820
tcaacagcgc catcggcaag atccaggaca gcctgagcag cacagcaagc gccctgggaa  2880
agctgcagga cgtggtcaac cacaatgccc aggcactgaa caccctggtc aagcagctgt  2940
cctccaagtt cggcgccatc agctctgtgc tgaacgatat cctgagcaga ctggaccctc  3000
ctgaggccga ggtgcagatc gacagactga tcacaggcag actgcagagc ctccagacat  3060
acgtgaccca gcagctgatc agagccgccg agattagagc ctctgccaat ctggccgcca  3120
ccaagatgtc tgagtgtgtg ctgggccaga gcaagagagt ggacttttgc ggcaagggct  3180
accacctgat gagcttccct cagtctgccc ctcacggcgt ggtgtttctg cacgtgacat  3240
atgtgcccgc tcaagagaag aatttcacca ccgctccagc catctgccac gacggcaaag  3300
cccactttcc tagagaaggc gtgttcgtgt ccaacggcac ccattggttc gtgacacagc  3360
ggaacttcta cgagccccag atcatcacca ccgacaacac cttcgtgtct ggcaactgcg  3420
acgtcgtgat cggcattgtg aacaataccg tgtacgaccc tctgcagccc gagctggaca  3480
gcttcaaaga ggaactggac aagtacttta agaaccacac aagccccgac gtggacctgg  3540
gcgatatcag cggaatcaat gccagcgtcg tgaacatcca gaaagagatc gaccggctga  3600
acgaggtggc caagaatctg aacgagagcc tgatcgacct gcaagaactg ggaagtacg  3660
agcagtacat caagtggccc tggtacatct ggctgggctt tatcgccgga ctgattgcca  3720
tcgtgatggt cacaatcatg ctgtgttgca tgaccagctg ctgtagctgc ctgaagggct  3780
gttgtagctg tggcagctgc tgcaagttcg acgaggacga ttctgagccc gtgctgaagg  3840
gcgtgaaact gcactacaca tgatgactcg agctggtact gcatgcacgc aatgctagct  3900
gcccctttcc cgtcctgggt accccgagtc tcccccgacc tcgggtccca ggtatgctcc  3960
cacctccacc tgccccactc accacctctg ctagttccag acacctccca agcacgcagc  4020
aatgcagctc aaaacgctta gcctagccac acccccacgg gaaacagcag tgattaacct  4080
ttagcaataa acgaaagttt aactaagcta tactaacccc agggttggtc aatttcgtgc  4140
cagccacacc ctggagctag caaaaaaaaa aaaaaaaaaa aaaaaaaaaa agcatatgac  4200
taaaaaaaaa aaaaaaaaaa aaaaaaaaaa aaaaaaaaaa aaaaaaaaaa aaaaaaaaaa  4260
aaaaaaaaaa                                                         4270

SEQ ID NO: 99          moltype = DNA  length = 4270
FEATURE                Location/Qualifiers
source                 1..4270
                       mol_type = other DNA
                       organism = synthetic construct
SEQUENCE: 99
agaataaact agtattcttc tggtccccac agactcagag agaacccgcc accatgttcg  60
```

```
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatcca cgtgtccggc accaatggca ccaagagatt cgacaacccc gccctgccct  300
tcaacgacgg ggtgtacttt gccagcaccg agaagtccaa catcatcaga ggctggatct  360
tcggcaccac actggacagc aagacccaga gcctgctgat cgtgaacaac gccaccaacg  420
tggtcatcaa agtgtgcgag ttccagttct gcaacgaccc cttcctggac gtctaccaga  480
agaacaacaa gagctggatg gaaagcgagt tccgggtgta cagcagcgcc aacaactgca  540
ccttcgagta cgtgtcccag cctttcctga tggacctgga aggcaaggag ggcaacttca  600
agaacctgcg cgagttcgtg tttaagaaca tcgacggcta cttcaagatc tacagcaagc  660
acacccctat caacctcgag cgggatctgc ctcagggctt ctctgctctg gaacccctgg  720
tggatctgcc catcggcatc aacatcaccc ggtttcagac actgctggcc ctgcacagaa  780
gctacctgac acctggcgat agcagcagcg gatggacagc tggtgccgcc gcttactatg  840
tgggctacct gcagcctaga accttcctgc tgaagtacaa cgagaacggc accatcaccg  900
acgccgtgga ttgtgctctg gatcctctga gcgagacaaa gtgcaccctg aagtccttca  960
ccgtggaaaa gggcatctac cagaccagca acttccgggt gcagcccacc gaatccatcg  1020
tgcggttccc caatatcacc aatctgtgcc ccttccacga ggtgttcaat gccaccacct  1080
tcgcctctgt gtacgcctgg aaccggaagc ggatcagcaa ttgcgtggcc gactactccg  1140
tgatctacaa cttcgccccc ttcttcgcat tcaagtgcta cggcgtgtcc cctaccaagc  1200
tgaacgacct gtgcttcaca aacgtgtacg ccgacagctt cgtgatccgg ggaaacgaag  1260
tgtcacagat tgcccctgga cagacaggca acatcgccga ctacaactac aagctgcccg  1320
acgacttcac cggctgtgtg attgcctgga acagcaacaa gctggactcc aaacccagcg  1380
gcaactacaa ttacctgtac cggctgttcc ggaagtccaa gctgaagccc ttcgagcggg  1440
acatctccac cgagatctat caggccggca acaagccttg taacggcgtg gcaggcagca  1500
actgctacag cccactgcag tcctacggct ttaggcccac atacggcgtg ggccaccagc  1560
cctacagagt ggtggtgctg agcttcgaac tgctgcatgc ccctgccaca gtgtgcggcc  1620
ctaagaaaag caccaatctc gtgaagaaca aatgcgtgaa cttcaacttc aacggcctga  1680
ccggcaccgg cgtgctgaca gagagcaaca agaagttcct gccattccag cagtttggcc  1740
gggatatcgc cgataccaca gacgccgtta gagatcccca gacactggaa atcctggaca  1800
tcaccccttg cagcttcggc ggagtgtctg tgatcacccc tggcaccaac accagcaatc  1860
aggtggcagt gctgtaccag ggcgtgaact gtaccgaagt gcccgtggcc attcacgccg  1920
atcagctgac acctacatgg cgggtgtact ccaccggcag caatgtgttt cagaccagag  1980
ccggctgtct gatcggagcc gagtacgtga acaatagcta cgagtgcgac atccccatcg  2040
gcgctggaat ctgcgccagc taccagacac agacaaagag ccaccggaga gccagaagcg  2100
tggccagcca gagcatcatt gcctacacaa tgtctctggg cgccgagaac agcgtggcct  2160
actccaacaa ctctatcgct atccccacca acttcaccat cagcgtgacc acagagatcc  2220
tgcctgtgtc catgaccaag accagcgtgg actgcaccat gtacatctgc ggcgattcca  2280
ccgagtgctc caacctgctg ctgcagtacg gcagcttctg cacccagctg aaaagagccc  2340
tgacagggat cgccgtggaa caggacaaga acacccaaga ggtgttcgcc caagtgaagc  2400
agatctacaa gacccctcct atcaagtact tcggcggctt caatttcagc cagattctgc  2460
ccgatcctag caagcccagc aagcggagct tcatcgagga cctgctgttc aacaaagtga  2520
cactggccga cgccggcttc atcaagcagt atggcgattg tctgggcgac attgccgcca  2580
gggatctgat ttgcgcccag aagtttaacg gactgacagt gctgcctcct ctgctgaccg  2640
atgagatgat cgcccagtac acatctgccc tgctggccgg cacaatcaca agcggctgga  2700
catttggagc aggcgccgct ctgcagatcc cctttgctat gcagatggcc taccggttca  2760
acggcatcgg agtgacccag aatgtgctgt acgagaacca gaagctgatc gccaaccagt  2820
tcaacagcgc catcggcaag atccaggaca gcctgagcag cacagcaagc gccctgggaa  2880
agctgcagga cgtggtcaac cacaatgccc aggcactgaa caccctggtc aagcagctgt  2940
cctccaagtt cggcgccatc agctctgtgc tgaacgatat cctgagcaga ctggaccctc  3000
ctgaggccga ggtgcagatc gacagactga tcacaggcag actgcagagc ctccagacat  3060
acgtgaccca gcagctgatc agagccgccg agattagagc ctctgccaat ctggccgcca  3120
ccaagatgtc tgagtgtgtg ctgggccaga gcaagagagt ggacttttgc ggcaagggct  3180
accacctgat gagcttccct cagtctgccc ctcacggcgt ggtgtttctg cacgtgacat  3240
atgtgcccgc tcaagagaag aatttcacca ccgctccagc catctgccac gacggcaaag  3300
cccactttcc tagagaaggc gtgttcgtgt ccaacggcac ccattggttc gtgacacagc  3360
ggaacttcta cgagccccag atcatcacca ccgacaacac cttcgtgtct ggcaactgcg  3420
acgtcgtgat cggcattgtg aacaataccg tgtacgaccc tctgcagccc gagctggaca  3480
gcttcaaaga ggaactggac aagtacttta agaaccacac aagccccgac gtggacctgg  3540
gcgatatcag cggaatcaat gccagcgtcg tgaacatcca gaaagagatc gaccggctga  3600
acgaggtggc caagaatctg aacgagagcc tgatcgacct gcaagaactg ggaagtacg  3660
agcagtacat caagtggccc tggtacatct ggctgggctt tatcgccgga ctgattgcca  3720
tcgtgatggt cacaatcatg ctgtgttgca tgaccagctg ctgtagctgc ctgaagggct  3780
gttgtagctg tggcagctgc tgcaagttcg acgaggacga ttctgagccc gtgctgaagg  3840
gcgtgaaact gcactacaca tgatgactcg agctggtact gcatgcacgc aatgctagct  3900
gcccctttcc cgtcctgggt accccgagtc tcccccgacc tcgggtccca ggtatgctcc  3960
cacctccacc tgccccactc accacctctg ctagttccag acacctccca agcacgcagc  4020
aatgcagctc aaaacgctta gcctagccac acccccacgg gaaacagcag tgattaacct  4080
ttagcaataa acgaaagttt aactaagcta tactaacccc agggttggtc aatttcgtgc  4140
cagccacacc ctggagctag caaaaaaaaa aaaaaaaaaa aaaaaaaaaa agcatatgac  4200
taaaaaaaaa aaaaaaaaaa aaaaaaaaaa aaaaaaaaaa aaaaaaaaaa aaaaaaaaaa  4260
aaaaaaaaaa                                                        4270
```

```
SEQ ID NO: 100          moltype = AA  length = 1268
FEATURE                 Location/Qualifiers
source                  1..1268
                        mol_type = protein
                        organism = synthetic construct
SEQUENCE: 100
MFVFLVLLPL VSSQCVNLIT RTQSYTNSFT RGVYYPDKVF RSSVLHSTQD LFLPFFSNVT  60
```

-continued

```
WFHAISGTNG TKRFDNPVLP FNDGVYFAST EKSNIIRGWI FGTTLDSKTQ SLLIVNNATN  120
VVIKVCEFQF CNDPFLDVYY HKNNKSWMES EFRVYSSANN CTFEYVSQPF LMDLEGKQGN  180
FKNLREFVFK NIDGYFKIYS KHTPINLGRD LPQGFSALEP LVDLPIGINI TRFQTLLALH  240
RSYLTPGDSS SGWTAGAAAY YVGYLQPRTF LLKYNENGTI TDAVDCALDP LSETKCTLKS  300
FTVEKGIYQT SNFRVQPTES IVRFPNITNL CPFDEVFNAT TFASVYAWNR KRISNCVADY  360
SVLYNFAPFF AFKCYGVSPT KLNDLCFTNV YADSFVIRGN EVSQIAPGQT GNIADYNYKL  420
PDDFTGCVIA WNSNKLDSTV GGNYNYRYRL FRKSKLKPFE RDISTEIYQA GNKPCNGVAG  480
VNCYFPLQSY GFRPTYGVGH QPYRVVVLSF ELLHAPATVC GPKKSTNLVK NKCVNFNFNG  540
LTGTGVLTES NKKFLPFQQF GRDIADTTDA VRDPQTLEIL DITPCSFGGV SVITPGTNTS  600
NQVAVLYQGV NCTEVPVAIH ADQLTPTWRV YSTGSNVFQT RAGCLIGAEY VNNSYECDIP  660
IGAGICASYQ TQTKSHRRAR SVASQSIIAY TMSLGAENSV AYSNNSIAIP TNFTISVTTE  720
ILPVSMTKTS VDCTMYICGD STECSNLLLQ YGSFCTQLKR ALTGIAVEQD KNTQEVFAQV  780
KQIYKTPPIK YFGGFNFSQI LPDPSKPSKR SFIEDLLFNK VTLADAGFIK QYGDCLGDIA  840
ARDLICAQKF NGLTVLPPLL TDEMIAQYTS ALLAGTITSG WTFGAGAALQ IPFAMQMAYR  900
FNGIGVTQNV LYENQKLIAN QFNSAIGKIQ DSLSSTASAL GKLQDVVNHN AQALNTLVKQ  960
LSSKFGAISS VLNDILSRLD PPEAEVQIDR LITGRLQSLQ TYVTQQLIRA AEIRASANLA  1020
ATKMSECVLG QSKRVDFCGK GYHLMSFPQS APHGVVFLHV TYVPAQEKNF TTAPAICHDG  1080
KAHFPREGVF VSNGTHWFVT QRNFYEPQII TTDNTFVSGN CDVVIGIVNN TVYDPLQPEL  1140
DSFKEELDKY FKNHTSPDVD LGDISGINAS VVNIQKEIDR LNEVAKNLNE SLIDLQELGK  1200
YEQYIKWPWY IWLGFIAGLI AIVMVTIMLC CMTSCCSCLK GCCSCGSCCK FDEDDSEPVL  1260
KGVKLHYT                                                          1268

SEQ ID NO: 101          moltype = RNA  length = 3810
FEATURE                 Location/Qualifiers
source                  1..3810
                        mol_type = other RNA
                        organism = synthetic construct
SEQUENCE: 101
atgttcgtgt tcctggtgct gctgcctctg gtgtccagcc agtgtgtgaa cctgatcacc  60
agaacacagt catacaccaa cagctttacc agaggcgtgt actaccccga caaggtgttc  120
agatccagcg tgctgcactc tacccaggac ctgttcctgc ctttcttcag caacgtgacc  180
tggttccacg ccatctccgg caccaatggc accaagagat tcgacaaccc cgtgctgccc  240
ttcaacgacg gggtgtactt tgccagcacc gagaagtcca acatcatcag aggctggatc  300
ttcggcacca cactggacag caagacccag agcctgctga tcgtgaacaa cgccaccaac  360
gtggtcatca aagtgtgcga gttccagttc tgcaacgacc ccttcctgga cgtctactac  420
cacaagaaca acaagagctg gatggaaagc gagttccggg tgtacagcag cgccaacaac  480
tgcaccttcg agtacgtgtc ccagcctttc ctgatggacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caaagtgcac cctgaagtcc  900
ttcaccgtgg aaaagggcat ctaccagacc agcaacttcc gggtgcagcc caccgaatcc  960
atcgtgcggt tccccaatat caccaatctg tgccccttcg acgaggtgtt caatgccacc  1020
accttcgcct ctgtgtacgc ctggaaccgg aagcggatca gcaattgcgt ggccgactac  1080
tccgtgctgt acaacttcgc cccttcttc gcattcaagt gctacggcgt gtcccctacc  1140
aagctgaacg acctgtgctt cacaaacgtg tacgccgaca gcttcgtgat ccggggaaac  1200
gaagtgtcac agattgcccc tggacagaca ggcaacatcg ccgactacaa ctacaagctg  1260
cccgacgact tcaccggctg tgtgattgcc tggaacagca acaagctgga ctccaccgtc  1320
ggcggcaact acaattacag gtaccggctg ttccggaagt ccaagctgaa gcccttcgag  1380
cgggacatct ccaccgagat ctatcaggcc ggcaacaagc cttgtaacgg cgtggcaggc  1440
gtgaactgct acttcccact gcagtcctac ggctttaggc ccacatacgg cgtgggccac  1500
cagccctaca gagtggtggt gctgagcttc gaactgctgc atgcccctgc cacagtgtgc  1560
ggccctaaga aaagcaccaa tctcgtgaag aacaaatgcg tgaacttcaa cttcaacggc  1620
ctgaccggca ccggcgtgct gacagagagc aacaagaagt tcctgccatt ccagcagttt  1680
ggccgggata tcgccgatac cacagacgcc gttagagatc cccagacact ggaaatcctg  1740
gacatcaccc cttgcagctt cggcggagtg tctgtgatca cccctggcac caacaccagc  1800
aatcaggtgg cagtgctgta ccagggcgtg aactgtaccg aagtgcccgt ggccattcac  1860
gccgatcagc tgacacctac atggcgggtg tactccaccg gcagcaatgt gtttcagacc  1920
agagccggct gtctgatcgg agccgagtac gtgaacaata gctacgagtg cgacatcccc  1980
atcggcgctg gaatctgcgc cagctaccag acacagacaa agagccaccg gagagccaga  2040
agcgtggcca gccagagcat cattgcctac acaatgtctc tgggcgccga gaacagcgtg  2100
gcctactcca acaactctat cgctatcccc accaacttca ccatcagcgt gaccacagag  2160
atcctgcctg tgtccatgac caagaccagc gtggactgca ccatgtacat ctgcggcgat  2220
tccaccgagt gctccaacct gctgctgcag tacggcagct tctgcaccca gctgaaaaga  2280
gccctgacag ggatcgccgt ggaacaggac aagaacaccc aagaggtgtt cgcccaagtg  2340
aagcagatct acaagacccc tcctatcaag tacttcggcg gcttcaattt cagccagatt  2400
ctgcccgatc ctagcaagcc cagcaagcgg agcttcatcg aggacctgct gttcaacaaa  2460
gtgacactgg ccgacgccgg cttcatcaag cagtatggcg attgtctggg cgacattgcc  2520
gccagggatc tgatttgcgc ccagaagttt aacggactga cagtgctgcc tcctctgctg  2580
accgatgaga tgatcgccca gtacacatct gccctgctgg ccggcacaat cacaagcggc  2640
tggacatttg gagcaggcgc cgctctgcag atcccctttg ctatgcagat ggcctaccgg  2700
ttcaacggca tcggagtgac ccagaatgtg ctgtacgaga accagaagct gatcgccaac  2760
cagttcaaca gcgccatcgg caagatccag gacagcctga gcagcacagc aagcgccctg  2820
ggaaagctgc aggacgtggt caaccacaat gcccaggcac tgaacaccct ggtcaagcag  2880
ctgtcctcca agttcggcgc catcagctct gtgctgaacg atatcctgag cagactggac  2940
cctcctgagg ccgaggtgca gatcgacaga ctgatcacag gcagactgca gagcctccag  3000
acatacgtga cccagcagct gatcagagcc gccgagatta gagcctctgc caatctggcc  3060
```

-continued

```
gccaccaaga tgtctgagtg tgtgctgggc cagagcaaga gagtggactt ttgcggcaag  3120
ggctaccacc tgatgagctt ccctcagtct gcccctcacg gcgtggtgtt tctgcacgtg  3180
acatatgtgc ccgctcaaga gaagaatttc accaccgctc cagccatctg ccacgacggc  3240
aaagcccact ttcctagaga aggcgtgttc gtgtccaacg gcacccattg gttcgtgaca  3300
cagcggaact tctacgagcc ccagatcatc accaccgaca acaccttcgt gtctggcaac  3360
tgcgacgtcg tgatcggcat tgtgaacaat accgtgtacg accctctgca gcccgagctg  3420
gacagcttca aagaggaact ggacaagtac tttaagaacc acacaagccc cgacgtggac  3480
ctgggcgata tcagcggaat caatgccagc gtcgtgaaca tccagaaaga gatcgaccgg  3540
ctgaacgagg tggccaagaa tctgaacgag agcctgatcg acctgcaaga actggggaag  3600
tacgagcagt acatcaagtg gccctggtac atctggctgg gctttatcgc cggactgatt  3660
gccatcgtga tggtcacaat catgctgtgt tgcatgacca gctgctgtag ctgcctgaag  3720
ggctgttgta gctgtggcag ctgctgcaag ttcgacgagg acgattctga gcccgtgctg  3780
aagggcgtga aactgcacta cacatgatga                                  3810

SEQ ID NO: 102          moltype = DNA  length = 3810
FEATURE                 Location/Qualifiers
source                  1..3810
                        mol_type = other DNA
                        organism = synthetic construct
SEQUENCE: 102
atgttcgtgt tcctggtgct gctgcctctg gtgtccagcc agtgtgtgaa cctgatcacc  60
agaacacagt catacaccaa cagctttacc agaggcgtgt actaccccga caaggtgttc  120
agatccagcg tgctgcactc tacccaggac ctgttcctgc ctttcttcag caacgtgacc  180
tggttccacg ccatctccgg caccaatggc accaagagat tcgacaaccc cgtgctgccc  240
ttcaacgacg gggtgtactt tgccagcacc gagaagtcca acatcatcag aggctggatc  300
ttcggcacca cactggacag caagacccag agcctgctga tcgtgaacaa cgccaccaac  360
gtggtcatca aagtgtgcga gttccagttc tgcaacgacc ccttcctgga cgtctactac  420
cacaagaaca acaagagctg gatggaaagc gagttccggg tgtacagcag cgccaacaac  480
tgcaccttcg agtacgtgtc ccagcctttc ctgatggacc tggaaggcaa gcagggcaac  540
ttcaagaacc tgcgcgagtt cgtgtttaag aacatcgacg gctacttcaa gatctacagc  600
aagcacaccc ctatcaacct cggccgggat ctgcctcagg gcttctctgc tctggaaccc  660
ctggtggatc tgcccatcgg catcaacatc acccggtttc agacactgct ggccctgcac  720
agaagctacc tgacacctgg cgatagcagc agcggatgga cagctggtgc cgccgcttac  780
tatgtgggct acctgcagcc tagaaccttc ctgctgaagt acaacgagaa cggcaccatc  840
accgacgccg tggattgtgc tctggatcct ctgagcgaga caaagtgcac cctgaagtcc  900
ttcaccgtgg aaaagggcat ctaccagacc agcaacttcc gggtgcagcc caccgaatcc  960
atcgtgcggt tccccaatat caccaatctg tgccccttcg acgaggtgtt caatgccacc  1020
accttcgcct ctgtgtacgc ctggaaccgg aagcggatca gcaattgcgt ggccgactac  1080
tccgtgctgt acaacttcgc cccctcttc gcattcaagt gctacggcgt gtcccctacc  1140
aagctgaacg acctgtgctt cacaaacgtg tacgccgaca gcttcgtgat ccggggaaac  1200
gaagtgtcac agattgcccc tggacagaca ggcaacatcg ccgactacaa ctacaagctg  1260
cccgacgact tcaccggctg tgtgattgcc tggaacagca acaagctgga ctccaccgtc  1320
ggcggcaact acaattacag gtaccggctg ttccggaagt ccaagctgaa gcccttcgag  1380
cgggacatct ccaccgagat ctatcaggcc ggcaacaagc cttgtaacgg cgtggcaggc  1440
gtgaactgct acttcccact gcagtcctac ggctttaggc ccacatacgg cgtgggccac  1500
cagccctaca gagtggtggt gctgagcttc gaactgctgc atgcccctgc cacagtgtgc  1560
ggccctaaga aaagcaccaa tctcgtgaag aacaaatgcg tgaacttcaa cttcaacggc  1620
ctgaccggca ccggcgtgct gacagagagc aacaagaagt tcctgccatt ccagcagttt  1680
ggccgggata tcgccgatac cacagacgcc gttagagatc cccagacact ggaaatcctg  1740
gacatcaccc cttgcagctt cggcggagtg tctgtgatca cccctggcac caacaccagc  1800
aatcaggtgg cagtgctgta ccagggcgtg aactgtaccg aagtgcccgt ggccattcac  1860
gccgatcagc tgacacctac atggcgggtg tactccaccg gcagcaatgt gtttcagacc  1920
agagccggct gtctgatcgg agccgagtac gtgaacaata gctacgagtg cgacatcccc  1980
atcggcgctg gaatctgcgc cagctaccag acacagacaa agagccaccg gagagccaga  2040
agcgtggcca gccagagcat cattgcctac acaatgtctc tgggcgccga gaacagcgtg  2100
gcctactcca acaactctat cgctatcccc accaacttca ccatcagcgt gaccacagag  2160
atcctgcctg tgtccatgac caagaccagc gtggactgca ccatgtacat ctgcggcgat  2220
tccaccgagt gctccaacct gctgctgcag tacggcagct tctgcaccca gctgaaaaga  2280
gccctgacag ggatcgccgt ggaacaggac aagaacaccc aagaggtgtt cgcccaagtg  2340
aagcagatct acaagacccc tcctatcaag tacttcggcg gcttcaattt cagccagatt  2400
ctgcccgatc ctagcaagcc cagcaagcgg agcttcatcg aggacctgct gttcaacaaa  2460
gtgacactgg ccgacgccgg cttcatcaag cagtatggcg attgtctggg cgacattgcc  2520
gccagggatc tgatttgcgc ccagaagttt aacggactga cagtgctgcc tcctctgctg  2580
accgatgaga tgatcgccca gtacacatct gccctgctgg ccggcacaat cacaagcggc  2640
tggacatttg gagcaggcgc cgctctgcag atccccttg ctatgcagat ggcctaccgg  2700
ttcaacggca tcggagtgac ccagaatgtg ctgtacgaga accagaagct gatcgccaac  2760
cagttcaaca gcgccatcgg caagatccag gacagcctga gcagcacagc aagcgccctg  2820
ggaaagctgc aggacgtggt caaccacaat gcccaggcac tgaacaccct ggtcaagcag  2880
ctgtcctcca agttcggcgc catcagctct gtgctgaacg atatcctgag cagactggac  2940
cctcctgagg ccgaggtgca gatcgacaga ctgatcacag gcagactgca gagcctccag  3000
acatacgtga cccagcagct gatcagagcc gccgagatta gagcctctgc caatctggcc  3060
gccaccaaga tgtctgagtg tgtgctgggc cagagcaaga gagtggactt ttgcggcaag  3120
ggctaccacc tgatgagctt ccctcagtct gcccctcacg gcgtggtgtt tctgcacgtg  3180
acatatgtgc ccgctcaaga gaagaatttc accaccgctc cagccatctg ccacgacggc  3240
aaagcccact ttcctagaga aggcgtgttc gtgtccaacg gcacccattg gttcgtgaca  3300
cagcggaact tctacgagcc ccagatcatc accaccgaca acaccttcgt gtctggcaac  3360
tgcgacgtcg tgatcggcat tgtgaacaat accgtgtacg accctctgca gcccgagctg  3420
gacagcttca aagaggaact ggacaagtac tttaagaacc acacaagccc cgacgtggac  3480
ctgggcgata tcagcggaat caatgccagc gtcgtgaaca tccagaaaga gatcgaccgg  3540
```

-continued

```
ctgaacgagg tggccaagaa tctgaacgag agcctgatcg acctgcaaga actggggaag  3600
tacgagcagt acatcaagtg gccctggtac atctggctgg gctttatcgc cggactgatt  3660
gccatcgtga tggtcacaat catgctgtgt tgcatgacca gctgctgtag ctgcctgaag  3720
ggctgttgta gctgtggcag ctgctgcaag ttcgacgagg acgattctga gcccgtgctg  3780
aagggcgtga aactgcacta cacatgatga                                  3810

SEQ ID NO: 103          moltype = RNA  length = 4267
FEATURE                 Location/Qualifiers
source                  1..4267
                        mol_type = other RNA
                        organism = synthetic construct
SEQUENCE: 103
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatctc cggcaccaat ggcaccaaga gattcgacaa ccccgtgctg cccttcaacg  300
acggggtgta ctttgccagc accgagaagt ccaacatcat cagaggctgg atcttcggca  360
ccacactgga cagcaagacc cagagcctgc tgatcgtgaa caacgccacc aacgtggtca  420
tcaaagtgtg cgagttccag ttctgcaacg accccttcct ggacgtctac taccacaaga  480
acaacaagag ctggatggaa agcgagttcc gggtgtacag cagcgccaac aactgcacct  540
tcgagtacgt gtcccagcct ttcctgatgg acctggaagg caagcagggc aacttcaaga  600
acctgcgcga gttcgtgttt aagaacatcg acggctactt caagatctac agcaagcaca  660
cccctatcaa cctcggccgg gatctgcctc agggcttctc tgctctggaa cccctggtgg  720
atctgcccat cggcatcaac atcacccggt ttcagacact gctggccctg cacagaagct  780
acctgacacc tggcgatagc agcagcggat ggacagctgg tgccgccgct tactatgtgg  840
gctacctgca gcctagaacc ttcctgctga agtacaacga gaacggcacc atcaccgacg  900
ccgtggattg tgctctggat cctctgagcg agacaaagtg caccctgaag tccttcaccg  960
tggaaaaggg catctaccag accagcaact tccgggtgca gcccaccgaa tccatcgtgc  1020
ggttccccaa tatcaccaat ctgtgcccct tcgacgaggt gttcaatgcc accaccttcg  1080
cctctgtgta cgcctggaac cggaagcgga tcagcaattg cgtggccgac tactccgtgc  1140
tgtacaactt cgccccctc ttcgcattca agtgctacgg cgtgtcccct accaagctga  1200
acgacctgtg cttcacaaac gtgtacgccg acagcttcgt gatccgggga aacgaagtgt  1260
cacagattgc ccctggacag acaggcaaca tcgccgacta caactacaag ctgcccgacg  1320
acttcaccgg ctgtgtgatt gcctggaaca gcaacaagct ggactccacc gtcggcggca  1380
actacaatta caggtaccgg ctgttccgga agtccaagct gaagcccttc gagcgggaca  1440
tctccaccga gatctatcag gccggcaaca agccttgtaa cggcgtggca ggcgtgaact  1500
gctacttccc actgcagtcc tacggcttta ggcccacata cggcgtgggc caccagccct  1560
acagagtggt ggtgctgagc ttcgaactgc tgcatgcccc tgccacagtg tgcggcccta  1620
agaaaagcac caatctcgtg aagaacaaat gcgtgaactt caacttcaac ggcctgaccg  1680
gcaccggcgt gctgacagag agcaacaaga agttcctgcc attccagcag tttggccggg  1740
atatcgccga taccacagac gccgttagag atccccagac actggaaatc ctggacatca  1800
ccccttgcag cttcggcgga gtgtctgtga tcacccctgg caccaacacc agcaatcagg  1860
tggcagtgct gtaccagggc gtgaactgta ccgaagtgcc cgtggccatt cacgccgatc  1920
agctgacacc tacatggcgg gtgtactcca ccggcagcaa tgtgtttcag accagagccg  1980
gctgtctgat cggagccgag tacgtgaaca atagctacga gtgcgacatc cccatcggcg  2040
ctggaatctg cgccagctac cagacacaga caaagagcca ccggagagcc agaagcgtgg  2100
ccagccagag catcattgcc tacacaatgt ctctgggcgc cgagaacagc gtggcctact  2160
ccaacaactc tatcgctatc cccaccaact tcaccatcag cgtgaccaca gagatcctgc  2220
ctgtgtccat gaccaagacc agcgtggact gcaccatgta catctgcggc gattccaccg  2280
agtgctccaa cctgctgctg cagtacggca gcttctgcac ccagctgaaa agagccctga  2340
cagggatcgc cgtggaacag gacaagaaca cccaagaggt gttcgcccaa gtgaagcaga  2400
tctacaagac ccctcctatc aagtacttcg gcggcttcaa tttcagccag attctgcccg  2460
atcctagcaa gcccagcaag cggagcttca tcgaggacct gctgttcaac aaagtgacac  2520
tggccgacgc cggcttcatc aagcagtatg gcgattgtct gggcgacatt gccgccaggg  2580
atctgatttg cgcccagaag tttaacggac tgacagtgct gcctcctctg ctgaccgatg  2640
agatgatcgc ccagtacaca tctgccctgc tggccggcac aatcacaagc ggctggacat  2700
ttggagcagg cgccgctctg cagatcccct ttgctatgca gatggcctac cggttcaacg  2760
gcatcggagt gacccagaat gtgctgtacg agaaccagaa gctgatcgcc aaccagttca  2820
acagcgccat cggcaagatc caggacagcc tgagcagcac agcaagcgcc ctgggaaagc  2880
tgcaggacgt ggtcaaccac aatgcccagg cactgaacac cctggtcaag cagctgtcct  2940
ccaagttcgg cgccatcagc tctgtgctga acgatatcct gagcagactg gaccctcctg  3000
aggccgaggt gcagatcgac agactgatca caggcagact gcagagcctc cagacatacg  3060
tgacccagca gctgatcaga gccgccgaga ttagagcctc tgccaatctg gccgccacca  3120
agatgtctga gtgtgtgctg ggccagagca agagagtgga cttttgcggc aagggctacc  3180
acctgatgag cttccctcag tctgcccctc acggcgtggt gtttctgcac gtgacatatg  3240
tgcccgctca agagaagaat ttcaccaccg ctccagccat ctgccacgac ggcaaagccc  3300
actttcctag agaaggcgtg ttcgtgtcca acggcaccca ttggttcgtg acacagcgga  3360
acttctacga gccccagatc atcaccacag acaacacctt cgtgtctggc aactgcgacg  3420
tcgtgatcgg cattgtgaac aataccgtgt acgaccctct gcagcccgag ctggacagct  3480
tcaaagagga actggacaag tactttaaga accacacaag ccccgacgtg gacctgggcg  3540
atatcagcgg aatcaatgcc agcgtcgtga acatccagaa agagatcgac cggctgaacg  3600
aggtggccaa gaatctgaac gagagcctga tcgacctgca agaactgggg aagtacgagc  3660
agtacatcaa gtggccctgg tacatctggc tgggctttat cgccggactg attgccatcg  3720
tgatggtcac aatcatgctg tgttgcatga ccagctgctg tagctgcctg aagggctgtt  3780
gtagctgtgg cagctgctgc aagttcgacg aggacgattc tgagcccgtg ctgaagggcg  3840
tgaaactgca ctacacatga tgactcgagc tggtactgca tgcacgcaat gctagctgcc  3900
cctttcccgt cctgggtacc ccgagtctcc cccgacctcg ggtcccaggt atgctcccac  3960
ctccacctgc cccactcacc acctctgcta gttccagaca cctcccaagc acgcagcaat  4020
```

-continued

```
gcagctcaaa acgcttagcc tagccacacc cccacgggaa acagcagtga ttaaccttta  4080
gcaataaacg aaagtttaac taagctatac taaccccagg gttggtcaat ttcgtgccag  4140
ccacaccctg gagctagcaa aaaaaaaaaa aaaaaaaaaa aaaaaaaaagc atatgactaa  4200
aaaaaaaaaa aaaaaaaaaa aaaaaaaaaa aaaaaaaaaa aaaaaaaaaa aaaaaaaaaa  4260
aaaaaaa                                                            4267

SEQ ID NO: 104         moltype = DNA  length = 4267
FEATURE                Location/Qualifiers
source                 1..4267
                       mol_type = other DNA
                       organism = synthetic construct
SEQUENCE: 104
agaataaact agtattcttc tggtccccac agactcagag agaacccgcc accatgttcg  60
tgttcctggt gctgctgcct ctggtgtcca gccagtgtgt gaacctgatc accagaacac  120
agtcatacac caacagcttt accagaggcg tgtactaccc cgacaaggtg ttcagatcca  180
gcgtgctgca ctctacccag gacctgttcc tgcctttctt cagcaacgtg acctggttcc  240
acgccatctc cggcaccaat ggcaccaaga gattcgacaa ccccgtgctg cccttcaacg  300
acggggtgta ctttgccagc accgagaagt ccaacatcat cagaggctgg atcttcggca  360
ccacactgga cagcaagacc cagagcctgc tgatcgtgaa caacgccacc aacgtggtca  420
tcaaagtgtg cgagttccag ttctgcaacg accccttcct ggacgtctac taccacaaga  480
acaacaagag ctggatggaa agcgagttcc gggtgtacag cagcgccaac aactgcacct  540
tcgagtacgt gtcccagcct ttcctgatgg acctggaagg caagcagggc aacttcaaga  600
acctgcgcga gttcgtgttt aagaacatcg acggctactt caagatctac agcaagcaca  660
cccctatcaa cctcggccgg gatctgcctc agggcttctc tgctctggaa cccctggtgg  720
atctgcccat cggcatcaac atcacccggt ttcagacact gctggccctg cacagaagct  780
acctgacacc tggcgatagc agcagcggat ggacagctgg tgccgccgct tactatgtgg  840
gctacctgca gcctagaacc ttcctgctga agtacaacga gaacggcacc atcaccgacg  900
ccgtggattg tgctctggat cctctgagcg agacaaagtg caccctgaag tccttcaccg  960
tggaaaaggg catctaccag accagcaact tccgggtgca gcccaccgaa tccatcgtgc  1020
ggttccccaa tatcaccaat ctgtgcccct tcgacgaggt gttcaatgcc accaccttcg  1080
cctctgtgta cgcctggaac cggaagcgga tcagcaattg cgtggccgac tactccgtgc  1140
tgtacaactt cgcccccttc ttcgcattca agtgctacgg cgtgtcccct accaagctga  1200
acgacctgtg cttcacaaac gtgtacgccg acagcttcgt gatccgggga aacgaagtgt  1260
cacagattgc ccctggacag acaggcaaca tcgccgacta caactacaag ctgcccgacg  1320
acttcaccgg ctgtgtgatt gcctggaaca gcaacaagct ggactccacc gtcggcggca  1380
actacaatta caggtaccgg ctgttccgga agtccaagct gaagcccttc gagcgggaca  1440
tctccaccga gatctatcag gccggcaaca agccttgtaa cggcgtggca ggcgtgaact  1500
gctacttccc actgcagtcc tacggcttta ggcccacata cggcgtgggc caccagccct  1560
acagagtggt ggtgctgagc ttcgaactgc tgcatgcccc tgccacagtg tgcggcccta  1620
agaaaagcac caatctcgtg aagaacaaat gcgtgaactt caacttcaac ggcctgaccg  1680
gcaccggcgt gctgacagag agcaacaaga agttcctgcc attccagcag tttggccggg  1740
atatcgccga taccacagac gccgttagag atccccagac actggaaatc ctggacatca  1800
ccccttgcag cttcggcgga gtgtctgtga tcacccctgg caccaacacc agcaatcagg  1860
tggcagtgct gtaccagggc gtgaactgta ccgaagtgcc cgtggccatt cacgccgatc  1920
agctgacacc tacatggcgg gtgtactcca ccggcagcaa tgtgtttcag accagagccg  1980
gctgtctgat cggagccgag tacgtgaaca atagctacga gtgcgacatc cccatcggcg  2040
ctggaatctg cgccagctac cagacacaga caaagagcca ccggagagcc agaagcgtgg  2100
ccagccagag catcattgcc tacacaatgt ctctgggcgc cgagaacagc gtggcctact  2160
ccaacaactc tatcgctatc cccaccaact tcaccatcag cgtgaccaca gagatcctgc  2220
ctgtgtccat gaccaagacc agcgtggact gcaccatgta catctgcggc gattccaccg  2280
agtgctccaa cctgctgctg cagtacggca gcttctgcac ccagctgaaa agagccctga  2340
cagggatcgc cgtggaacag gacaagaaca cccaagaggt gttcgcccaa gtgaagcaga  2400
tctacaagac ccctcctatc aagtacttcg gcggcttcaa tttcagccag attctgcccg  2460
atcctagcaa gcccagcaag cggagcttca tcgaggacct gctgttcaac aaagtgacac  2520
tggccgacgc cggcttcatc aagcagtatg gcgattgtct gggcgacatt gccgccaggg  2580
atctgatttg cgcccagaag tttaacggac tgacagtgct gcctcctctg ctgaccgatg  2640
agatgatcgc ccagtacaca tctgccctgc tggccggcac aatcacaagc ggctggacat  2700
ttggagcagg cgccgctctg cagatcccct ttgctatgca gatggcctac cggttcaacg  2760
gcatcggagt gacccagaat gtgctgtacg agaaccagaa gctgatcgcc aaccagttca  2820
acagcgccat cggcaagatc caggacagcc tgagcagcac agcaagcgcc ctgggaaagc  2880
tgcaggacgt ggtcaaccac aatgcccagg cactgaacac cctggtcaag cagctgtcct  2940
ccaagttcgg cgccatcagc tctgtgctga acgatatcct gagcagactg gaccctcctg  3000
aggccgaggt gcagatcgac agactgatca caggcagact gcagagcctc cagacatacg  3060
tgacccagca gctgatcaga gccgccgaga ttagagcctc tgccaatctg gccgccacca  3120
agatgtctga gtgtgtgctg ggccagagca agagagtgga cttttgcggc aagggctacc  3180
acctgatgag cttccctcag tctgcccctc acggcgtggt gtttctgcac gtgacatatg  3240
tgcccgctca agagaagaat ttcaccaccg ctccagccat ctgccacgac ggcaaagccc  3300
actttcctag agaaggcgtg ttcgtgtcca acggcaccca ttggttcgtg acacagcgga  3360
acttctacga gccccagatc atcaccaccg acaacacctt cgtgtctggc aactgcgacg  3420
tcgtgatcgg cattgtgaac aataccgtgt acgaccctct gcagcccgag ctggacagct  3480
tcaaagagga actggacaag tactttaaga accacacaag ccccgacgtg gacctgggcg  3540
atatcagcgg aatcaatgcc agcgtcgtga acatccagaa agagatcgac cggctgaacg  3600
aggtggccaa gaatctgaac gagagcctga tcgacctgca agaactgggg aagtacgagc  3660
agtacatcaa gtggccctgg tacatctggc tgggctttat cgccggactg attgccatcg  3720
tgatggtcac aatcatgctg tgttgcatga ccagctgctg tagctgcctg aagggctgtt  3780
gtagctgtgg cagctgctgc aagttcgacg aggacgattc tgagcccgtg ctgaagggcg  3840
tgaaactgca ctacacatga tgactcgagc tggtactgca tgcacgcaat gctagctgcc  3900
cctttcccgt cctgggtacc ccgagtctcc cccgacctcg ggtcccaggt atgctcccac  3960
ctccacctgc cccactcacc acctctgcta gttccagaca cctcccaagc acgcagcaat  4020
```

-continued

```
gcagctcaaa acgcttagcc tagccacacc cccacgggaa acagcagtga ttaaccttta  4080
gcaataaacg aaagtttaac taagctatac taaccccagg gttggtcaat ttcgtgccag  4140
ccacaccctg gagctagcaa aaaaaaaaaa aaaaaaaaaa aaaaaaaagc atatgactaa  4200
aaaaaaaaaa aaaaaaaaaa aaaaaaaaaa aaaaaaaaaa aaaaaaaaaa aaaaaaaaaa  4260
aaaaaaa                                                            4267

SEQ ID NO: 105          moltype = AA  length = 27
FEATURE                 Location/Qualifiers
source                  1..27
                        mol_type = protein
                        organism = synthetic construct
SEQUENCE: 105
MGGAAARLGA VILFVVIVGL HGVRSKY                                      27

SEQ ID NO: 106          moltype = AA  length = 25
FEATURE                 Location/Qualifiers
source                  1..25
                        mol_type = protein
                        organism = synthetic construct
SEQUENCE: 106
MGRLTSGVGT AALLVVAVGL RVVCA                                        25

SEQ ID NO: 107          moltype = AA  length = 28
FEATURE                 Location/Qualifiers
source                  1..28
                        mol_type = protein
                        organism = synthetic construct
SEQUENCE: 107
MGRLTSGVGT AALLVVAVGL RVVCAKYA                                     28

SEQ ID NO: 108          moltype = AA  length = 19
FEATURE                 Location/Qualifiers
source                  1..19
                        mol_type = protein
                        organism = synthetic construct
SEQUENCE: 108
MFVFLVLLPL VSSQCVNLT                                               19

SEQ ID NO: 109          moltype = AA  length = 21
FEATURE                 Location/Qualifiers
source                  1..21
                        mol_type = protein
                        organism = synthetic construct
SEQUENCE: 109
MDWIWRILFL VGAATGAHSQ M                                            21

SEQ ID NO: 110          moltype = AA  length = 20
FEATURE                 Location/Qualifiers
source                  1..20
                        mol_type = protein
                        organism = synthetic construct
SEQUENCE: 110
METPAQLLFL LLLWLPDTTG                                              20

SEQ ID NO: 111          moltype = AA  length = 18
FEATURE                 Location/Qualifiers
source                  1..18
                        mol_type = protein
                        organism = synthetic construct
SEQUENCE: 111
MDWTWILFLV AAATRVHS                                                18

SEQ ID NO: 112          moltype = AA  length = 24
FEATURE                 Location/Qualifiers
source                  1..24
                        mol_type = protein
                        organism = synthetic construct
SEQUENCE: 112
MLGSNSGQRV VFTILLLLVA PAYS                                         24

SEQ ID NO: 113          moltype = AA  length = 17
FEATURE                 Location/Qualifiers
source                  1..17
                        mol_type = protein
                        organism = synthetic construct
SEQUENCE: 113
MKCLLYLAFL FIGVNCA                                                 17

SEQ ID NO: 114          moltype = AA  length = 18
```

```
FEATURE                Location/Qualifiers
source                 1..18
                       mol_type = protein
                       organism = synthetic construct
SEQUENCE: 114
MDWTWILFLV AAATRVHS                                            18

SEQ ID NO: 115         moltype = AA  length = 19
FEATURE                Location/Qualifiers
source                 1..19
                       mol_type = protein
                       organism = synthetic construct
SEQUENCE: 115
ETPAQLLFLL LLWLPDTTG                                           19

SEQ ID NO: 116         moltype = AA  length = 24
FEATURE                Location/Qualifiers
source                 1..24
                       mol_type = protein
                       organism = synthetic construct
SEQUENCE: 116
MLGSNSGQRV VFTILLLLVA PAYS                                     24

SEQ ID NO: 117         moltype = AA  length = 17
FEATURE                Location/Qualifiers
source                 1..17
                       mol_type = protein
                       organism = synthetic construct
SEQUENCE: 117
MKCLLYLAFL FIGVNCA                                             17

SEQ ID NO: 118         moltype = AA  length = 15
FEATURE                Location/Qualifiers
source                 1..15
                       mol_type = protein
                       organism = synthetic construct
SEQUENCE: 118
MWLVSLAIVT ACAGA                                               15

SEQ ID NO: 119         moltype = AA  length = 15
FEATURE                Location/Qualifiers
source                 1..15
                       mol_type = protein
                       organism = synthetic construct
SEQUENCE: 119
MFVFLVLLPL VSSQC                                               15

SEQ ID NO: 120         moltype = DNA  length = 81
FEATURE                Location/Qualifiers
source                 1..81
                       mol_type = other DNA
                       organism = synthetic construct
SEQUENCE: 120
atgggggggg ctgccgccag gttgggggcc gtgattttgt ttgtcgtcat agtgggcctc  60
catggggtcc gcagcaaata t                                        81

SEQ ID NO: 121         moltype = DNA  length = 81
FEATURE                Location/Qualifiers
source                 1..81
                       mol_type = other DNA
                       organism = synthetic construct
SEQUENCE: 121
atgggaggag ccgccgccag actgggagcc gtgatcctgt tcgtggtgat cgtgggactg  60
catggagtga gaagcaagta c                                        81

SEQ ID NO: 122         moltype = DNA  length = 57
FEATURE                Location/Qualifiers
source                 1..57
                       mol_type = other DNA
                       organism = synthetic construct
SEQUENCE: 122
atgtttgtgt ttcttgtgct gctgcctctt gtgtcttctc agtgtgtgaa tttgaca     57

SEQ ID NO: 123         moltype = DNA  length = 63
FEATURE                Location/Qualifiers
source                 1..63
                       mol_type = other DNA
                       organism = synthetic construct
SEQUENCE: 123
```

-continued

```
atggattgga tttggagaat cctgttcctc gtgggagccg ctacaggagc ccactcccag  60
atg                                                                63

SEQ ID NO: 124         moltype = AA  length = 5
FEATURE                Location/Qualifiers
source                 1..5
                       mol_type = protein
                       organism = synthetic construct
SEQUENCE: 124
YLYRL                                                              5

SEQ ID NO: 125         moltype = AA  length = 5
FEATURE                Location/Qualifiers
source                 1..5
                       mol_type = protein
                       organism = synthetic construct
SEQUENCE: 125
YRYRL                                                              5

SEQ ID NO: 126         moltype = AA  length = 5
FEATURE                Location/Qualifiers
source                 1..5
                       mol_type = protein
                       organism = synthetic construct
SEQUENCE: 126
AGSTP                                                              5

SEQ ID NO: 127         moltype = AA  length = 5
FEATURE                Location/Qualifiers
source                 1..5
                       mol_type = protein
                       organism = synthetic construct
SEQUENCE: 127
AGSKP                                                              5

SEQ ID NO: 128         moltype = AA  length = 5
FEATURE                Location/Qualifiers
source                 1..5
                       mol_type = protein
                       organism = synthetic construct
SEQUENCE: 128
AGNKP                                                              5

SEQ ID NO: 129         moltype = AA  length = 250
FEATURE                Location/Qualifiers
source                 1..250
                       mol_type = protein
                       organism = synthetic construct
SEQUENCE: 129
CTLKSFTVEK GIYQTSNFRV QPTESIVRFP NITNLCPFGE VFNATRFASV YAWNRKRISN  60
CVADYSVLYN SASFSTFKCY GVSPTKLNDL CFTNVYADSF VIRGDEVRQI APGQTGKIAD  120
YNYKLPDDFT GCVIAWNSNN LDSKVGGNYN YLYRLFRKSN LKPFERDIST EIYQAGSTPC  180
NGVEGFNCYF PLQSYGFQPT NGVGYQPYRV VVLSFELLHA PATVCGPKKS TNLVKNKCVN  240
FNFNGLTGTG                                                         250

SEQ ID NO: 130         moltype = AA  length = 250
FEATURE                Location/Qualifiers
source                 1..250
                       mol_type = protein
                       organism = synthetic construct
SEQUENCE: 130
CTLKSFTVEK GIYQTSNFRV QPTESIVRFP NITNLCPFGE VFNATRFASV YAWNRKRISN  60
CVADYSVLYN SASFSTFKCY GVSPTKLNDL CFTNVYADSF VIRGDEVRQI APGQTGKIAD  120
YNYKLPDDFT GCVIAWNSNN LDSKVGGNYN YLYRLFRKSN LKPFERDIST EIYQAGSTPC  180
NGVEGFNCYF PLQSYGFQPT YGVGYQPYRV VVLSFELLHA PATVCGPKKS TNLVKNKCVN  240
FNFNGLTGTG                                                         250

SEQ ID NO: 131         moltype = AA  length = 250
FEATURE                Location/Qualifiers
source                 1..250
                       mol_type = protein
                       organism = synthetic construct
SEQUENCE: 131
CTLKSFTVEK GIYQTSNFRV QPTESIVRFP NITNLCPFGE VFNATRFASV YAWNRKRISN  60
CVADYSVLYN SASFSTFKCY GVSPTKLNDL CFTNVYADSF VIRGDEVRQI APGQTGKIAD  120
YNYKLPDDFT GCVIAWNSNN LDSKVGGNYN YRYRLFRKSN LKPFERDIST EIYQAGSKPC  180
NGVEGFNCYF PLQSYGFQPT NGVGYQPYRV VVLSFELLHA PATVCGPKKS TNLVKNKCVN  240
FNFNGLTGTG                                                         250
```

-continued

```
SEQ ID NO: 132          moltype = AA  length = 250
FEATURE                 Location/Qualifiers
source                  1..250
                        mol_type = protein
                        organism = synthetic construct
SEQUENCE: 132
CTLKSFTVEK GIYQTSNFRV QPTESIVRFP NITNLCPFDE VFNATRFASV YAWNRKRISN  60
CVADYSVLYN LAPFFTFKCY GVSPTKLNDL CFTNVYADSF VIRGDEVRQI APGQTGNIAD  120
YNYKLPDDFT GCVIAWNSNK LDSKVSGNYN YLYRLFRKSN LKPFERDIST EIYQAGNKPC  180
NGVAGFNCYF PLRSYSFRPT YGVGHQPYRV VVLSFELLHA PATVCGPKKS TNLVKNKCVN  240
FNFNGLKGTG                                                         250

SEQ ID NO: 133          moltype = AA  length = 250
FEATURE                 Location/Qualifiers
source                  1..250
                        mol_type = protein
                        organism = synthetic construct
SEQUENCE: 133
CTLKSFTVEK GIYQTSNFRV QPTESIVRFP NITNLCPFDE VFNATRFASV YAWNRKRISN  60
CVADYSVLYN FAPFFAFKCY GVSPTKLNDL CFTNVYADSF VIRGNEVSQI APGQTGNIAD  120
YNYKLPDDFT GCVIAWNSNK LDSKVGGNYN YRYRLFRKSN LKPFERDIST EIYQAGNKPC  180
NGVAGVNCYF PLQSYGFRPT YGVGHQPYRV VVLSFELLHA PATVCGPKKS TNLVKNKCVN  240
FNFNGLTGTG                                                         250

SEQ ID NO: 134          moltype = AA  length = 9
FEATURE                 Location/Qualifiers
source                  1..9
                        mol_type = protein
                        organism = synthetic construct
SEQUENCE: 134
GSPGSGSGS                                                          9

SEQ ID NO: 135          moltype = AA  length = 6
FEATURE                 Location/Qualifiers
source                  1..6
                        mol_type = protein
                        organism = synthetic construct
SEQUENCE: 135
GSGSGS                                                             6

SEQ ID NO: 136          moltype = AA  length = 4
FEATURE                 Location/Qualifiers
source                  1..4
                        mol_type = protein
                        organism = synthetic construct
SEQUENCE: 136
RRAR                                                               4

SEQ ID NO: 137          moltype = AA  length = 12
FEATURE                 Location/Qualifiers
source                  1..12
                        mol_type = protein
                        organism = synthetic construct
SEQUENCE: 137
CGGAGAGCCA GA                                                      12

SEQ ID NO: 138          moltype = AA  length = 9
FEATURE                 Location/Qualifiers
source                  1..9
                        mol_type = protein
                        organism = synthetic construct
SEQUENCE: 138
YLQPRTFLL                                                          9

SEQ ID NO: 139          moltype = AA  length = 9
FEATURE                 Location/Qualifiers
source                  1..9
                        mol_type = protein
                        organism = synthetic construct
SEQUENCE: 139
RLQSLQTYV                                                          9

SEQ ID NO: 140          moltype = AA  length = 9
FEATURE                 Location/Qualifiers
source                  1..9
                        mol_type = protein
                        organism = synthetic construct
SEQUENCE: 140
QYIKWPWYI                                                          9
```

```
SEQ ID NO: 141          moltype = AA  length = 9
FEATURE                 Location/Qualifiers
source                  1..9
                        mol_type = protein
                        organism = synthetic construct
SEQUENCE: 141
NYNYLYRLF                                                                9

SEQ ID NO: 142          moltype = AA  length = 10
FEATURE                 Location/Qualifiers
source                  1..10
                        mol_type = protein
                        organism = synthetic construct
SEQUENCE: 142
KWPWYIWLGF                                                               10

SEQ ID NO: 143          moltype = AA  length = 9
FEATURE                 Location/Qualifiers
source                  1..9
                        mol_type = protein
                        organism = synthetic construct
SEQUENCE: 143
QPTESIVRF                                                                9

SEQ ID NO: 144          moltype = AA  length = 9
FEATURE                 Location/Qualifiers
source                  1..9
                        mol_type = protein
                        organism = synthetic construct
SEQUENCE: 144
IPFAMQMAY                                                                9

SEQ ID NO: 145          moltype = AA  length = 9
FEATURE                 Location/Qualifiers
source                  1..9
                        mol_type = protein
                        organism = synthetic construct
SEQUENCE: 145
LPFNDGVYF                                                                9

SEQ ID NO: 146          moltype = AA  length = 9
FEATURE                 Location/Qualifiers
source                  1..9
                        mol_type = protein
                        organism = synthetic construct
SEQUENCE: 146
GVYFASTEK                                                                9

SEQ ID NO: 147          moltype = AA  length = 9
FEATURE                 Location/Qualifiers
source                  1..9
                        mol_type = protein
                        organism = synthetic construct
SEQUENCE: 147
CVADYSVLY                                                                9

SEQ ID NO: 148          moltype = AA  length = 9
FEATURE                 Location/Qualifiers
source                  1..9
                        mol_type = protein
                        organism = synthetic construct
SEQUENCE: 148
FQPTNGVGY                                                                9

SEQ ID NO: 149          moltype = AA  length = 9
FEATURE                 Location/Qualifiers
source                  1..9
                        mol_type = protein
                        organism = synthetic construct
SEQUENCE: 149
GTHWFVTQR                                                                9

SEQ ID NO: 150          moltype = AA  length = 9
FEATURE                 Location/Qualifiers
source                  1..9
                        mol_type = protein
                        organism = synthetic construct
SEQUENCE: 150
```

```
VYDPLQPEL                                                   9

SEQ ID NO: 151          moltype = AA  length = 9
FEATURE                 Location/Qualifiers
source                  1..9
                        mol_type = protein
                        organism = synthetic construct
SEQUENCE: 151
KCYGVSPTK                                                   9

SEQ ID NO: 152          moltype = DNA  length = 3817
FEATURE                 Location/Qualifiers
source                  1..3817
                        mol_type = other DNA
                        organism = synthetic construct
SEQUENCE: 152
atgttcgtgt tcctggtgct gctgcctctg gtgtccagcc agtgtgtgaa cttcaccacc  60
agaacacagc tgcctccagc ctacaccaac agctttacca gaggcgtgta ctaccccgac  120
aaggtgttca gatccagcgt gctgcactct acccaggacc tgttcctgcc tttcttcagc  180
aacgtgacct ggttccacgc catccacgtg tccggcacca atggcaccaa gagattcgcc  240
aaccccgtgc tgcccttcaa cgacggggtg tactttgcca gcaccgagaa gtccaacatc  300
atcagaggct ggatcttcgg caccacactg gacagcaaga cccagagcct gctgatcgtg  360
aacaacgcca ccaacgtggt catcaaagtg tgcgagttcc agttctgcaa cgaccccttc  420
ctgggcgtct actaccacaa gaacaacaag agctggatgg aaagcgagtt ccgggtgtac  480
agcagcgcca acaactgcac cttcgagtac gtgtcccagc ctttcctgat ggacctggaa  540
ggcaagcagg gcaacttcaa gaacctgcgc gagttcgtgt ttaagaacat cgacggctac  600
ttcaagatct acagcaagca cacccctatc aacctcgtgc ggggcctgcc tcagggcttc  660
tctgctctgg aacccctggt ggatctgccc atcggcatca acatcacccg gtttcagaca  720
ctgcacatca gctacctgac acctggcgat agcagcagcg gatggacagc tggtgccgcc  780
gcttactatg tgggctacct gcagcctaga accttcctgc tgaagtacaa cgagaacggc  840
accatcaccg acgccgtgga ttgtgctctg gatcctctga gcgagacaaa gtgcaccctg  900
aagtccttca ccgtggaaaa gggcatctac cagaccagca acttccgggt gcagcccacc  960
gaatccatcg tgcggttccc caatatcacc aatctgtgcc ccttcggcga ggtgttcaat  1020
gccaccagat tcgcctctgt gtacgcctgg aaccggaagc ggatcagcaa ttgcgtggcc  1080
gactactccg tgctgtacaa ctccgccagc ttcagcacct tcaagtgcta cggcgtgtcc  1140
cctaccaagc tgaacgacct gtgcttcaca aacgtgtacg ccgacagctt cgtgatccgg  1200
ggagatgaag tgcggcagat tgcccctgga cagacaggca acatcgccga ctacaactac  1260
aagctgcccg acgacttcac cggctgtgtg attgcctgga acagcaacaa cctggactcc  1320
aaagtcggcg gcaactacaa ttacctgtac cggctgttcc ggaagtccaa tctgaagccc  1380
ttcgagcggg acatctccac cgagatctat caggccggca gcaccccttg taacggcgtg  1440
aagggcttca actgctactt cccactgcag tcctacggct ttcagcccac atacggcgtg  1500
ggctatcagc cctacagagt ggtggtgctg agcttcgaac tgctgcatgc ccctgccaca  1560
gtgtgcggcc ctaagaaaag caccaatctc gtgaagaaca aatgcgtgaa cttcaacttc  1620
aacggcctga ccggcaccgg cgtgctgaca gagagcaaca agaagttcct gccattccag  1680
cagtttggcc gggatatcgc cgataccaca gacgccgtta gagatcccca gacactggaa  1740
atcctggaca tcacccccttg cagcttcggc ggagtgtctg tgatcacccc tggcaccaac  1800
accagcaatc aggtggcagt gctgtaccag ggcgtgaact gtaccgaagt gcccgtggcc  1860
attcacgccg atcagctgac acctacatgg cgggtgtact ccaccggcag caatgtgttt  1920
cagaccagag ccggctgtct gatcggagcc gagcacgtga acaatagcta cgagtgcgac  1980
atccccatcg gcgctggaat ctgcgccagc taccagacac agacaaacag ccctcggaga  2040
gccagaagcg tggccagcca gagcatcatt gcctacacaa tgtctctggg cgtcgagaac  2100
agcgtggcct actccaacaa ctctatcgct atccccacca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aatagagccc tgacagggat cgccgtggaa caggacaaga acacccaaga ggtgttcgcc  2340
caagtgaagc agatctacaa gacccctcct atcaaggact tcggcggctt caatttcagc  2400
cagattctgc ccgatcctag caagcccagc aagcggagct tcatcgagga cctgctgttc  2460
aacaaagtga cactggccga cgccggcttc atcaagcagt atggcgattg tctgggcgac  2520
attgccgcca gggatctgat ttgcgcccag aagtttaacg gactgacagt gctgcctcct  2580
ctgctgaccg atgagatgat cgcccagtac acatctgccc tgctggccgg cacaatcaca  2640
agcggctgga catttggagc aggcgccgct ctgcagatcc cctttgctat gcagatggcc  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctgggaa agctgcagga cgtggtcaac cagaatgccc aggcactgaa caccctggtc  2880
aagcagctgt cctccaactt cggcgccatc agctctgtgc tgaacgatat cctgagcaga  2940
ctggaccctc ctgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctgggccaga gcaagagagt ggacttttgc  3120
ggcaagggct accacctgat gagcttccct cagtctgccc ctcacggcgt ggtgtttctg  3180
cacgtgacat atgtgcccgc tcaagagaag aatttcacca ccgctccagc catctgccac  3240
gacggcaaag cccactttcc tagagaaggc gtgttcgtgt ccaacggcac ccattggttc  3300
gtgacacagc ggaacttcta cgagccccag atcatcacca ccgacaacac cttcgtgtct  3360
ggcaactgcg acgtcgtgat cggcattgtg aacaataccg tgtacgaccc tctgcagccc  3420
gagctggaca gcttcaaaga ggaactggac aagtacttta agaaccacac aagccccgac  3480
gtggacctgg gcgatatcag cggaatcaat gccagcgtcg tgaacatcca gaaagagatc  3540
gaccggctga acgaggtggc caagaatctg aacgagagcc tgatcgacct gcaagaactg  3600
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
```

-continued

```
gtgctgaagg gcgtgaaact gcactacaca tgatgac                          3817

SEQ ID NO: 153          moltype = DNA  length = 4274
FEATURE                 Location/Qualifiers
source                  1..4274
                        mol_type = other DNA
                        organism = synthetic construct
SEQUENCE: 153
agaataaact agtattcttc tggtccccac agactcagag agaacccgcc accatgttcg  60
tgttcctggt gctgctgcct ctggtgtcca gccagtgtgt gaacttcacc accagaacac  120
agctgcctcc agcctacacc aacagcttta ccagaggcgt gtactacccc gacaaggtgt  180
tcagatccag cgtgctgcac tctacccagg acctgttcct gcctttcttc agcaacgtga  240
cctggttcca cgccatccac gtgtccggca ccaatggcac caagagattc gccaaccccg  300
tgctgccctt caacgacggg gtgtactttg ccagcaccga gaagtccaac atcatcagag  360
gctggatctt cggcaccaca ctggacagca agacccagag cctgctgatc gtgaacaacg  420
ccaccaacgt ggtcatcaaa gtgtgcgagt tccagttctg caacgacccc ttcctgggcg  480
tctactacca caagaacaac aagagctgga tggaaagcga gttccgggtg tacagcagcg  540
ccaacaactg caccttcgag tacgtgtccc agcctttcct gatggacctg gaaggcaagc  600
agggcaactt caagaacctg cgcgagttcg tgtttaagaa catcgacggc tacttcaaga  660
tctacagcaa gcacacccct atcaacctcg tgcggggcct gcctcagggc ttctctgctc  720
tggaacccct ggtggatctg cccatcggca tcaacatcac ccggtttcag acactgcaca  780
tcagctacct gacacctggc gatagcagca gcggatggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca  1020
tcgtgcggtt ccccaatatc accaatctgt gccccttcgg cgaggtgttc aatgccacca  1080
gattcgcctc tgtgtacgcc tggaaccgga agcggatcag caattgcgtg gccgactact  1140
ccgtgctgta caactccgcc agcttcagca ccttcaagtg ctacggcgtg tcccctacca  1200
agctgaacga cctgtgcttc acaaacgtgt acgccgacag cttcgtgatc cggggagatg  1260
aagtgcggca gattgcccct ggacagacag gcaacatcgc cgactacaac tacaagctgc  1320
ccgacgactt caccggctgt gtgattgcct ggaacagcaa caacctggac tccaaagtcg  1380
gcggcaacta caattacctg taccggctgt tccggaagtc caatctgaag cccttcgagc  1440
gggacatctc caccgagatc tatcaggccg gcagcacccc ttgtaacggc gtgaagggct  1500
tcaactgcta cttcccactg cagtcctacg gctttcagcc cacatacggc gtgggctatc  1560
agccctacag agtggtggtg ctgagcttcg aactgctgca tgcccctgcc acagtgtgcg  1620
gccctaagaa aagcaccaat ctcgtgaaga acaaatgcgt gaacttcaac ttcaacggcc  1680
tgaccggcac cggcgtgctg acagagagca acaagaagtt cctgccattc cagcagtttg  1740
gccgggatat cgccgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagccggctg tctgatcgga gccgagcacg tgaacaatag ctacgagtgc gacatcccca  2040
tcggcgctgg aatctgcgcc agctaccaga cacagacaaa cagccctcgg agagccagaa  2100
gcgtggccag ccagagcatc attgcctaca caatgtctct gggcgtcgag aacagcgtgg  2160
cctactccaa caactctatc gctatcccca ccaacttcac catcagcgtg accacagaga  2220
tcctgcctgt gtccatgacc aagaccagcg tggactgcac catgtacatc tgcggcgatt  2280
ccaccgagtg ctccaacctg ctgctgcagt acggcagctt ctgcacccag ctgaatagag  2340
ccctgacagg gatcgccgtg gaacaggaca agaacaccca agaggtgttc gcccaagtga  2400
agcagatcta caagacccct cctatcaagg acttcggcgg cttcaatttc agccagattc  2460
tgcccgatcc tagcaagccc agcaagcgga gcttcatcga ggacctgctg ttcaacaaag  2520
tgacactggc cgacgccggc ttcatcaagc agtatggcga ttgtctgggc gacattgccg  2580
ccagggatct gatttgcgcc cagaagttta acggactgac agtgctgcct cctctgctga  2640
ccgatgagat gatcgcccag tacacatctg ccctgctggc cggcacaatc acaagcggct  2700
ggacatttgg agcaggcgcc gctctgcaga tccccttTgc tatgcagatg gcctaccggt  2760
tcaacggcat cggagtgacc cagaatgtgc tgtacgagaa ccagaagctg atcgccaacc  2820
agttcaacag cgccatcggc aagatccagg acagcctgag cagcacagca agcgccctgg  2880
gaaagctgca ggacgtggtc aaccagaatg cccaggcact gaacaccctg gtcaagcagc  2940
tgtcctccaa cttcggcgcc atcagctctg tgctgaacga tatcctgagc agactggacc  3000
ctcctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctgggcc agagcaagag agtggacttt tgcggcaagg  3180
gctaccacct gatgagcttc cctcagtctg cccctcacgg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccaccgacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcga cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgac tcgagctggt actgcatgca cgcaatgcta  3900
gctgcccctt tcccgtcctg ggtaccccga gtctcccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cgggaaacag cagtgattaa  4080
cctttagcaa taaacgaaag tttaactaag ctatactaac cccagggttg gtcaatttcg  4140
tgccagccac accctggagc tagcaaaaaa aaaaaaaaaa aaaaaaaaaa aaaagcatat  4200
gactaaaaaa aaaaaaaaaa aaaaaaaaaa aaaaaaaaaa aaaaaaaaaa aaaaaaaaaa  4260
```

-continued

```
aaaaaaaaaa aaaa                                                     4274

SEQ ID NO: 154          moltype = DNA  length = 3816
FEATURE                 Location/Qualifiers
source                  1..3816
                        mol_type = other DNA
                        organism = synthetic construct
SEQUENCE: 154
atgttcgtgt tcctggtgct gctgcctctg gtgtccagcc agtgtgtgaa cctgaccacc  60
agaacacagc tgcctccagc ctacaccaac agctttacca gaggcgtgta ctaccccgac  120
aaggtgttca gatccagcgt gctgcactct acccaggacc tgttcctgcc tttcttcagc  180
aacgtgacct ggttccacgc catctccggc accaatggca ccaagagatt cgacaacccc  240
gtgctgccct tcaacgacgg ggtgtacttt gccagcaccg agaagtccaa catcatcaga  300
ggctggatct tcggcaccac actggacagc aagacccaga gcctgctgat cgtgaacaac  360
gccaccaacg tggtcatcaa agtgtgcgag ttccagttct gcaacgaccc cttcctgggc  420
gtctaccaca agaacaacaa gagctggatg gaaagcgagt tccgggtgta cagcagcgcc  480
aacaactgca ccttcgagta cgtgtcccag cctttcctga tggacctgga aggcaagcag  540
ggcaacttca agaacctgcg cgagttcgtg tttaagaaca tcgacggcta cttcaagatc  600
tacagcaagc acacccctat caacctcgtg cgggatctgc ctcagggctt ctctgctctg  660
gaacccctgg tggatctgcc catcggcatc aacatcaccc ggtttcagac actgctggcc  720
ctgcacagaa gctacctgac acctggcgat agcagcagcg gatggacagc tggtgccgcc  780
gcttactatg tgggctacct gcagcctaga accttcctgc tgaagtacaa cgagaacggc  840
accatcaccg acgccgtgga ttgtgctctg gatcctctga gcgagacaaa gtgcaccctg  900
aagtccttca ccgtggaaaa gggcatctac cagaccagca acttccgggt gcagcccacc  960
gaatccatcg tgcggttccc caatatcacc aatctgtgcc ccttcggcga ggtgttcaat  1020
gccaccagat tcgcctctgt gtacgcctgg aaccggaagc ggatcagcaa ttgcgtggcc  1080
gactactccg tgctgtacaa ctccgccagc ttcagcacct tcaagtgcta cggcgtgtcc  1140
cctaccaagc tgaacgacct gtgcttcaca aacgtgtacg ccgacagctt cgtgatccgg  1200
ggagatgaag tgcggcagat tgcccctgga cagacaggca agatcgccga ctacaactac  1260
aagctgcccg acgacttcac cggctgtgtg attgcctgga acagcaacaa cctggactcc  1320
aaagtcggcg gcaactacaa ttacctgtac cggctgttcc ggaagtccaa tctgaagccc  1380
ttcgagcggg acatctccac cgagatctat caggccggca gcaccccttg taacggcgtg  1440
gaaggcttca actgctactt cccactgcag tcctacggct ttcagcccac atacggcgtg  1500
ggctatcagc cctacagagt ggtggtgctg agcttcgaac tgctgcatgc ccctgccaca  1560
gtgtgcggcc ctaagaaaag caccaatctc gtgaagaaca aatgcgtgaa cttcaacttc  1620
aacggcctga ccggcaccgg cgtgctgaca gagagcaaca agaagttcct gccattccag  1680
cagtttggcc gggatatcga cgataccaca gacgccgtta gagatcccca gacactggaa  1740
atcctggaca tcaccccttg cagcttcggc ggagtgtctg tgatcacccc tggcaccaac  1800
accagcaatc aggtggcagt gctgtaccag ggcgtgaact gtaccgaagt gcccgtggcc  1860
attcacgccg atcagctgac acctacatgg cgggtgtact ccaccggcag caatgtgttt  1920
cagaccagag ccggctgtct gatcggagcc gagcacgtga acaatagcta cgagtgcgac  1980
atccccatcg gcgctggaat ctgcgccagc taccagacac agacaaacag ccaccggaga  2040
gccagaagcg tggccagcca gagcatcatt gcctacacaa tgtctctggg cgccgagaac  2100
agcgtggcct actccaacaa ctctatcgct atccccatca acttcaccat cagcgtgacc  2160
acagagatcc tgcctgtgtc catgaccaag accagcgtgg actgcaccat gtacatctgc  2220
ggcgattcca ccgagtgctc caacctgctg ctgcagtacg gcagcttctg cacccagctg  2280
aatagagccc tgacagggat cgccgtggaa caggacaaga acacccaaga ggtgttcgcc  2340
caagtgaagc agatctacaa gacccctcct atcaaggact tcggcggctt caatttcagc  2400
cagattctgc ccgatcctag caagcccagc aagcggagct tcatcgagga cctgctgttc  2460
aacaaagtga cactggccga cgccggcttc atcaagcagt atggcgattg tctgggcgac  2520
attgccgcca gggatctgat ttgcgcccag aagtttaacg gactgacagt gctgcctcct  2580
ctgctgaccg atgagatgat cgcccagtac acatctgccc tgctggccgg cacaatcaca  2640
agcggctgga catttggagc aggcgccgct ctgcagatcc cctttgctat gcagatggcc  2700
taccggttca acggcatcgg agtgacccag aatgtgctgt acgagaacca gaagctgatc  2760
gccaaccagt tcaacagcgc catcggcaag atccaggaca gcctgagcag cacagcaagc  2820
gccctgggaa agctgcagga cgtggtcaac cagaatgccc aggcactgaa caccctggtc  2880
aagcagctgt cctccaactt cggcgccatc agctctgtgc tgaacgatat cctggccaga  2940
ctggaccctc ctgaggccga ggtgcagatc gacagactga tcacaggcag actgcagagc  3000
ctccagacat acgtgaccca gcagctgatc agagccgccg agattagagc ctctgccaat  3060
ctggccgcca ccaagatgtc tgagtgtgtg ctgggccaga gcaagagagt ggacttttgc  3120
ggcaagggct accacctgat gagcttccct cagtctgccc ctcacggcgt ggtgtttctg  3180
cacgtgacat atgtgcccgc tcaagagaag aatttcacca ccgctccagc catctgccac  3240
gacggcaaag cccactttcc tagagaaggc gtgttcgtgt ccaacggcac ccattggttc  3300
gtgacacagc ggaacttcta cgagccccag atcatcacca cccacaacac cttcgtgtct  3360
ggcaactgcg acgtcgtgat cggcattgtg aacaataccg tgtacgaccc tctgcagccc  3420
gagctggaca gcttcaaaga ggaactggac aagtacttta agaaccacac aagccccgac  3480
gtggacctgg gcgatatcag cggaatcaat gccagcgtcg tgaacatcca gaaagagatc  3540
gaccggctga acgaggtggc caagaatctg aacgagagcc tgatcgacct gcaagaactg  3600
gggaagtacg agcagtacat caagtggccc tggtacatct ggctgggctt tatcgccgga  3660
ctgattgcca tcgtgatggt cacaatcatg ctgtgttgca tgaccagctg ctgtagctgc  3720
ctgaagggct gttgtagctg tggcagctgc tgcaagttcg acgaggacga ttctgagccc  3780
gtgctgaagg gcgtgaaact gcactacaca tgatga                             3816

SEQ ID NO: 155          moltype = DNA  length = 4274
FEATURE                 Location/Qualifiers
source                  1..4274
                        mol_type = other DNA
                        organism = synthetic construct
SEQUENCE: 155
```

-continued

```
agaataaact agtattcttc tggtccccac agactcagag agaacccgcc accatgttcg  60
tgttcctggt gctgctgcct ctggtgtcca gccagtgtgt gaacctgacc accagaacac  120
agctgcctcc agcctacacc aacagcttta ccagaggcgt gtactacccc gacaaggtgt  180
tcagatccag cgtgctgcac tctacccagg acctgttcct gcctttcttc agcaacgtga  240
cctggttcca cgccatctcc ggcaccaatg gcaccaagag attcgacaac cccgtgctgc  300
ccttcaacga cggggtgtac tttgccagca ccgagaagtc caacatcatc agaggctgga  360
tcttcggcac cacactggac agcaagaccc agagcctgct gatcgtgaac aacgccacca  420
acgtggtcat caaagtgtgc gagttccagt tctgcaacga ccccttcctg ggcgtctacc  480
acaagaacaa caagagctgg atggaaagcg agttccgggt gtacagcagc gccaacaact  540
gcaccttcga gtacgtgtcc cagcctttcc tgatggacct ggaaggcaag cagggcaact  600
tcaagaacct gcgcgagttc gtgtttaaga acatcgacgg ctacttcaag atctacagca  660
agcacacccc tatcaacctc gtgcgggatc tgcctcaggg cttctctgct ctggaacccc  720
tggtggatct gcccatcggc atcaacatca cccggtttca gacactgctg gccctgcaca  780
gaagctacct gacacctggc gatagcagca gcggatggac agctggtgcc gccgcttact  840
atgtgggcta cctgcagcct agaaccttcc tgctgaagta caacgagaac ggcaccatca  900
ccgacgccgt ggattgtgct ctggatcctc tgagcgagac aaagtgcacc ctgaagtcct  960
tcaccgtgga aaagggcatc taccagacca gcaacttccg ggtgcagccc accgaatcca  1020
tcgtgcggtt ccccaatatc accaatctgt gccccttcgg cgaggtgttc aatgccacca  1080
gattcgcctc tgtgtacgcc tggaaccgga agcggatcag caattgcgtg gccgactact  1140
ccgtgctgta caactccgcc agcttcagca ccttcaagtg ctacggcgtg tcccctacca  1200
agctgaacga cctgtgcttc acaaacgtgt acgccgacag cttcgtgatc cggggagatg  1260
aagtgcggca gattgcccct ggacagacag gcaagatcgc cgactacaac tacaagctgc  1320
ccgacgactt caccggctgt gtgattgcct ggaacagcaa caacctggac tccaaagtcg  1380
gcggcaacta caattacctg taccggctgt tccggaagtc caatctgaag cccttcgagc  1440
gggacatctc caccgagatc tatcaggccg gcagcacccc ttgtaacggc gtggaaggct  1500
tcaactgcta cttcccactg cagtcctacg gctttcagcc cacatacggc gtgggctatc  1560
agccctacag agtggtggtg ctgagcttcg aactgctgca tgcccctgcc acagtgtgcg  1620
gccctaagaa aagcaccaat ctcgtgaaga acaaatgcgt gaacttcaac ttcaacggcc  1680
tgaccggcac cggcgtgctg acagagagca acaagaagtt cctgccattc cagcagtttg  1740
gccgggatat cgacgatacc acagacgccg ttagagatcc ccagacactg gaaatcctgg  1800
acatcacccc ttgcagcttc ggcggagtgt ctgtgatcac ccctggcacc aacaccagca  1860
atcaggtggc agtgctgtac cagggcgtga actgtaccga agtgcccgtg gccattcacg  1920
ccgatcagct gacacctaca tggcgggtgt actccaccgg cagcaatgtg tttcagacca  1980
gagccggctg tctgatcgga gccgagcacg tgaacaatag ctacgagtgc gacatcccca  2040
tcggcgctgg aatctgcgcc agctaccaga cacagacaaa cagccaccgg agagccagaa  2100
gcgtggccag ccagagcatc attgcctaca caatgtctct gggcgccgag aacagcgtgg  2160
cctactccaa caactctatc gctatcccca tcaacttcac catcagcgtg accacagaga  2220
tcctgcctgt gtccatgacc aagaccagcg tggactgcac catgtacatc tgcggcgatt  2280
ccaccgagtg ctccaacctg ctgctgcagt acggcagctt ctgcacccag ctgaatagag  2340
ccctgacagg gatcgccgtg gaacaggaca agaacaccca agaggtgttc gcccaagtga  2400
agcagatcta caagacccct cctatcaagg acttcggcgg cttcaatttc agccagattc  2460
tgcccgatcc tagcaagccc agcaagcgga gcttcatcga ggacctgctg ttcaacaaag  2520
tgacactggc cgacgccggc ttcatcaagc agtatggcga ttgtctgggc gacattgccg  2580
ccagggatct gatttgcgcc cagaagttta acggactgac agtgctgcct cctctgctga  2640
ccgatgagat gatcgcccag tacacatctg ccctgctggc cggcacaatc acaagcggct  2700
ggacatttgg agcaggcgcc gctctgcaga tcccctttgc tatgcagatg gcctaccggt  2760
tcaacggcat cggagtgacc cagaatgtgc tgtacgagaa ccagaagctg atcgccaacc  2820
agttcaacag cgccatcggc aagatccagg acagcctgag cagcacagca agcgccctgg  2880
gaaagctgca ggacgtggtc aaccagaatg cccaggcact gaacaccctg gtcaagcagc  2940
tgtcctccaa cttcggcgcc atcagctctg tgctgaacga tatcctggcc agactggacc  3000
ctcctgaggc cgaggtgcag atcgacagac tgatcacagg cagactgcag agcctccaga  3060
catacgtgac ccagcagctg atcagagccg ccgagattag agcctctgcc aatctggccg  3120
ccaccaagat gtctgagtgt gtgctgggcc agagcaagag agtggacttt tgcggcaagg  3180
gctaccacct gatgagcttc cctcagtctg cccctcacgg cgtggtgttt ctgcacgtga  3240
catatgtgcc cgctcaagag aagaatttca ccaccgctcc agccatctgc cacgacggca  3300
aagcccactt tcctagagaa ggcgtgttcg tgtccaacgg cacccattgg ttcgtgacac  3360
agcggaactt ctacgagccc cagatcatca ccacccacaa caccttcgtg tctggcaact  3420
gcgacgtcgt gatcggcatt gtgaacaata ccgtgtacga ccctctgcag cccgagctgg  3480
acagcttcaa agaggaactg gacaagtact ttaagaacca cacaagcccc gacgtggacc  3540
tgggcgatat cagcggaatc aatgccagcg tcgtgaacat ccagaaagag atcgaccggc  3600
tgaacgaggt ggccaagaat ctgaacgaga gcctgatcga cctgcaagaa ctggggaagt  3660
acgagcagta catcaagtgg ccctggtaca tctggctggg ctttatcgcc ggactgattg  3720
ccatcgtgat ggtcacaatc atgctgtgtt gcatgaccag ctgctgtagc tgcctgaagg  3780
gctgttgtag ctgtggcagc tgctgcaagt tcgacgagga cgattctgag cccgtgctga  3840
agggcgtgaa actgcactac acatgatgag atctgctggt actgcatgca cgcaatgcta  3900
gctgcccctt tcccgtcctg ggtaccccga gtctcccccg acctcgggtc ccaggtatgc  3960
tcccacctcc acctgcccca ctcaccacct ctgctagttc cagacacctc ccaagcacgc  4020
agcaatgcag ctcaaaacgc ttagcctagc cacaccccca cgggaaacag cagtgattaa  4080
cctttagcaa taaacgaaag tttaactaag ctatactaac cccagggttg gtcaatttcg  4140
tgccagccac accctggagc tagcaaaaaa aaaaaaaaaa aaaaaaaaaa aaaagcatat  4200
gactaaaaaa aaaaaaaaaa aaaaaaaaaa aaaaaaaaaa aaaaaaaaaa aaaaaaaaaa  4260
aaaaaaaaaa aaaa                                                   4274

SEQ ID NO: 156         moltype = RNA  length = 3819
FEATURE                Location/Qualifiers
source                 1..3819
                       mol_type = other RNA
                       organism = synthetic construct
SEQUENCE: 156
```

-continued

```
atgttcgtgt tcctggtgct gctgcctctg gtgtccagcc agtgtgtgaa cctgagaacc  60
agaacacagc tgcctccagc ctacaccaac agctttacca gaggcgtgta ctaccccgac  120
aaggtgttca gatccagcgt gctgcactct acccaggacc tgttcctgcc tttcttcagc  180
aacgtgacct ggttccacgc catccacgtg tccggcacca atggcaccaa gagattcgac  240
aaccccgtgc tgcccttcaa cgacggggtg tactttgcca gcaccgagaa gtccaacatc  300
atcagaggct ggatcttcgg caccacactg gacagcaaga cccagagcct gctgatcgtg  360
aacaacgcca ccaacgtggt catcaaagtg tgcgagttcc agttctgcaa cgacccccttc  420
ctggacgtct actaccacaa gaacaacaag agctggatgg aaagcggcgt gtacagcagc  480
gccaacaact gcaccttcga gtacgtgtcc cagcctttcc tgatggacct ggaaggcaag  540
cagggcaact tcaagaacct gcgcgagttc gtgtttaaga acatcgacgg ctacttcaag  600
atctacagca agcacacccc tatcaacctc gtgcgggatc tgcctcaggg cttctctgct  660
ctggaacccc tggtggatct gcccatcggc atcaacatca cccggtttca gacactgctg  720
gccctgcaca gaagctacct gacacctggc gatagcagca gcggatggac agctggtgcc  780
gccgcttact atgtgggcta cctgcagcct agaaccttcc tgctgaagta caacgagaac  840
ggcaccatca ccgacgccgt ggattgtgct ctggatcctc tgagcgagac aaagtgcacc  900
ctgaagtcct tcaccgtgga aaagggcatc taccagacca gcaacttccg ggtgcagccc  960
accgaatcca tcgtgcggtt ccccaatatc accaatctgt gccccttcgg cgaggtgttc  1020
aatgccacca gattcgcctc tgtgtacgcc tggaaccgga agcggatcag caattgcgtg  1080
gccgactact ccgtgctgta caactccgcc agcttcagca ccttcaagtg ctacggcgtg  1140
tcccctacca agctgaacga cctgtgcttc acaaacgtgt acgccgacag cttcgtgatc  1200
cggggagatg aagtgcggca gattgcccct ggacagacag gcaagatcgc cgactacaac  1260
tacaagctgc ccgacgactt caccggctgt gtgattgcct ggaacagcaa caacctggac  1320
tccaaagtcg gcggcaacta caattacagg taccggctgt tccggaagtc caatctgaag  1380
cccttcgagc gggacatctc caccgagatc tatcaggccg gcagcaagcc ttgtaacggc  1440
gtggaaggct tcaactgcta cttcccactg cagtcctacg gctttcagcc cacaaatggc  1500
gtgggctatc agccctacag agtggtggtg ctgagcttcg aactgctgca tgcccctgcc  1560
acagtgtgcg gccctaagaa aagcaccaat ctcgtgaaga acaaatgcgt gaacttcaac  1620
ttcaacggcc tgaccggcac cggcgtgctg acagagagca acaagaagtt cctgccattc  1680
cagcagtttg gccgggatat cgccgatacc acagacgccg ttagagatcc ccagacactg  1740
gaaatcctgg acatcacccc ttgcagcttc ggcggagtgt ctgtgatcac ccctggcacc  1800
aacaccagca atcaggtggc agtgctgtac cagggcgtga actgtaccga agtgcccgtg  1860
gccattcacg ccgatcagct gacacctaca tggcgggtgt actccaccgg cagcaatgtg  1920
tttcagacca gagccggctg tctgatcgga gccgagcacg tgaacaatag ctacgagtgc  1980
gacatcccca tcggcgctgg aatctgcgcc agctaccaga cacagacaaa cagcaggcgg  2040
agagccagaa gcgtggccag ccagagcatc attgcctaca caatgtctct gggcgccgag  2100
aacagcgtgg cctactccaa caactctatc gctatcccca ccaacttcac catcagcgtg  2160
accacagaga tcctgcctgt gtccatgacc aagaccagcg tggactgcac catgtacatc  2220
tgcggcgatt ccaccgagtg ctccaacctg ctgctgcagt acggcagctt ctgcacccag  2280
ctgaatagag ccctgacagg gatcgccgtg gaacaggaca agaacaccca agaggtgttc  2340
gcccaagtga agcagatcta caagacccct cctatcaagg acttcggcgg cttcaatttc  2400
agccagattc tgcccgatcc tagcaagccc agcaagcgga gcttcatcga ggacctgctg  2460
ttcaacaaag tgacactggc cgacgccggc ttcatcaagc agtatggcga ttgtctgggc  2520
gacattgccg ccagggatct gatttgcgcc cagaagttta acggactgac agtgctgcct  2580
cctctgctga ccgatgagat gatcgcccag tacacatctg ccctgctggc cggcacaatc  2640
acaagcggct ggacatttgg agcaggcgcc gctctgcaga tcccctttgc tatgcagatg  2700
gcctaccggt tcaacggcat cggagtgacc cagaatgtgc tgtacgagaa ccagaagctg  2760
atcgccaacc agttcaacag cgccatcggc aagatccagg acagcctgag cagcacagca  2820
agcgccctgg gaaagctgca gaacgtggtc aaccagaatg cccaggcact gaacaccctg  2880
gtcaagcagc tgtcctccaa cttcggcgcc atcagctctg tgctgaacga tatcctgagc  2940
agactggacc ctcctgaggc cgaggtgcag atcgacagac tgatcacagg cagactgcag  3000
agcctccaga catacgtgac ccagcagctg atcagagccg ccgagattag agcctctgcc  3060
aatctggccg ccaccaagat gtctgagtgt gtgctgggcc agagcaagag agtggacttt  3120
tgcggcaagg gctaccacct gatgagcttc cctcagtctg cccctcacgg cgtggtgttt  3180
ctgcacgtga catatgtgcc cgctcaagag aagaatttca ccaccgctcc agccatctgc  3240
cacgacggca aagcccactt tcctagagaa ggcgtgttcg tgtccaacgg cacccattgg  3300
ttcgtgacac agcggaactt ctacgagccc cagatcatca ccaccgacaa caccttcgtg  3360
tctggcaact gcgacgtcgt gatcggcatt gtgaacaata ccgtgtacga ccctctgcag  3420
cccgagctgg acagcttcaa agaggaactg gacaagtact ttaagaacca cacaagcccc  3480
gacgtggacc tgggcgatat cagcggaatc aatgccagcg tcgtgaacat ccagaaagag  3540
atcgaccggc tgaacgaggt ggccaagaat ctgaacgaga gcctgatcga cctgcaagaa  3600
ctggggaagt acgagcagta catcaagtgg ccctggtaca tctggctggg ctttatcgcc  3660
ggactgattg ccatcgtgat ggtcacaatc atgctgtgtt gcatgaccag ctgctgtagc  3720
tgcctgaagg gctgttgtag ctgtggcagc tgctgcaagt tcgacgagga cgattctgag  3780
cccgtgctga agggcgtgaa actgcactac acatgatga  3819
```

```
SEQ ID NO: 157          moltype = RNA  length = 4277
FEATURE                 Location/Qualifiers
source                  1..4277
                        mol_type = other RNA
                        organism = synthetic construct
SEQUENCE: 157
agaataaact agtattcttc tggtccccac agactcagag agaacccgcc accatgttcg  60
tgttcctggt gctgctgcct ctggtgtcca gccagtgtgt gaacctgaga accagaacac  120
agctgcctcc agcctacacc aacagcttta ccagaggcgt gtactacccc gacaaggtgt  180
tcagatccag cgtgctgcac tctacccagg acctgttcct gcctttcttc agcaacgtga  240
cctggttcca cgccatccac gtgtccggca ccaatggcac caagagattc gacaaccccg  300
tgctgccctt caacgacggg gtgtactttg ccagcaccga gaagtccaac atcatcagag  360
gctggatctt cggcaccaca ctggacagca agacccagag cctgctgatc gtgaacaacg  420
ccaccaacgt ggtcatcaaa gtgtgcgagt tccagttctg caacgacccc ttcctggacg  480
```

-continued

```
tctactacca caagaacaac aagagctgga tggaaagcgg cgtgtacagc agcgccaaca  540
actgcacctt cgagtacgtg tcccagcctt tcctgatgga cctggaaggc aagcagggca  600
acttcaagaa cctgcgcgag ttcgtgttta agaacatcga cggctacttc aagatctaca  660
gcaagcacac ccctatcaac ctcgtgcggg atctgcctca gggcttctct gctctggaac  720
ccctggtgga tctgcccatc ggcatcaaca tcacccggtt tcagacactg ctggccctgc  780
acagaagcta cctgacacct ggcgatagca gcagcggatg gacagctggt gccgccgctt  840
actatgtggg ctacctgcag cctagaacct tcctgctgaa gtacaacgag aacggcacca  900
tcaccgacgc cgtggattgt gctctggatc ctctgagcga gacaaagtgc accctgaagt  960
ccttcaccgt ggaaaagggc atctaccaga ccagcaactt ccgggtgcag cccaccgaat  1020
ccatcgtgcg gttccccaat atcaccaatc tgtgcccctt cggcgaggtg ttcaatgcca  1080
ccagattcgc ctctgtgtac gcctggaacc ggaagcggat cagcaattgc gtggccgact  1140
actccgtgct gtacaactcc gccagcttca gcaccttcaa gtgctacggc gtgtccccta  1200
ccaagctgaa cgacctgtgc ttcacaaacg tgtacgccga cagcttcgtg atccggggag  1260
atgaagtgcg gcagattgcc cctggacaga caggcaagat cgccgactac aactacaagc  1320
tgcccgacga cttcaccggc tgtgtgattg cctggaacag caacaacctg gactccaaag  1380
tcggcggcaa ctacaattac aggtaccggc tgttccggaa gtccaatctg aagcccttcg  1440
agcgggacat ctccaccgag atctatcagg ccggcagcaa gccttgtaac ggcgtggaag  1500
gcttcaactg ctacttccca ctgcagtcct acggctttca gcccacaaat ggcgtgggct  1560
atcagcccta cagagtggtg gtgctgagct tcgaactgct gcatgcccct gccacagtgt  1620
gcggccctaa gaaaagcacc aatctcgtga agaacaaatg cgtgaacttc aacttcaacg  1680
gcctgaccgg caccggcgtg ctgacagaga gcaacaagaa gttcctgcca ttccagcagt  1740
ttggccggga tatcgccgat accacagacg ccgttagaga tccccagaca ctggaaatcc  1800
tggacatcac cccttgcagc ttcggcggag tgtctgtgat caccccctggc accaacacca  1860
gcaatcaggt ggcagtgctg taccagggcg tgaactgtac cgaagtgccc gtggccattc  1920
acgccgatca gctgacacct acatggcggg tgtactccac cggcagcaat gtgtttcaga  1980
ccagagccgg ctgtctgatc ggagccgagc acgtgaacaa tagctacgag tgcgacatcc  2040
ccatcggcgc tggaatctgc gccagctacc agacacagac aaacagcagg cggagagcca  2100
gaagcgtggc cagccagagc atcattgcct acacaatgtc tctgggcgcc gagaacagcg  2160
tggcctactc caacaactct atcgctatcc ccaccaactt caccatcagc gtgaccacag  2220
agatcctgcc tgtgtccatg accaagacca gcgtggactg caccatgtac atctgcggcg  2280
attccaccga gtgctccaac ctgctgctgc agtacggcag cttctgcacc cagctgaata  2340
gagccctgac agggatcgcc gtggaacagg acaagaacac ccaagaggtg ttcgcccaag  2400
tgaagcagat ctacaagacc cctcctatca aggacttcgg cggcttcaat ttcagccaga  2460
ttctgcccga tcctagcaag cccagcaagc ggagcttcat cgaggacctg ctgttcaaca  2520
aagtgacact ggccgacgcc ggcttcatca agcagtatgg cgattgtctg ggcgacattg  2580
ccgccaggga tctgatttgc gcccagaagt ttaacggact gacagtgctg cctcctctgc  2640
tgaccgatga gatgatcgcc cagtacacat ctgccctgct ggccggcaca atcacaagcg  2700
gctggacatt tggagcaggc gccgctctgc agatcccctt tgctatgcag atggcctacc  2760
ggttcaacgg catcggagtg acccagaatg tgctgtacga gaaccagaag ctgatcgcca  2820
accagttcaa cagcgccatc ggcaagatcc aggacagcct gagcagcaca gcaagcgccc  2880
tgggaaagct gcagaacgtg gtcaaccaga atgcccaggc actgaacacc ctggtcaagc  2940
agctgtcctc caacttcggc gccatcagct ctgtgctgaa cgatatcctg agcagactgg  3000
accctcctga ggccgaggtg cagatcgaca gactgatcac aggcagactg cagagcctcc  3060
agacatacgt gacccagcag ctgatcagag ccgccgagat tagagcctct gccaatctgg  3120
ccgccaccaa gatgtctgag tgtgtgctgg gccagagcaa gagagtggac ttttgcggca  3180
agggctacca cctgatgagc ttccctcagt ctgcccctca cggcgtggtg tttctgcacg  3240
tgacatatgt gcccgctcaa gagaagaatt tcaccaccgc tccagccatc tgccacgacg  3300
gcaaagccca ctttcctaga gaaggcgtgt tcgtgtccaa cggcacccat tggttcgtga  3360
cacagcggaa cttctacgag ccccagatca tcaccaccga caacaccttc gtgtctggca  3420
actgcgacgt cgtgatcggc attgtgaaca ataccgtgta cgaccctctg cagcccgagc  3480
tggacagctt caaagaggaa ctggacaagt actttaagaa ccacacaagc cccgacgtgg  3540
acctgggcga tatcagcgga atcaatgcca gcgtcgtgaa catccagaaa gagatcgacc  3600
ggctgaacga ggtggccaag aatctgaacg agagcctgat cgacctgcaa gaactgggga  3660
agtacgagca gtacatcaag tggccctggt acatctggct gggctttatc gccggactga  3720
ttgccatcgt gatggtcaca atcatgctgt gttgcatgac cagctgctgt agctgcctga  3780
agggctgttg tagctgtggc agctgctgca agttcgacga ggacgattct gagcccgtgc  3840
tgaagggcgt gaaactgcac tacacatgat gatttcacct ggtactgcat gcacgcaatg  3900
ctagctgccc ctttcccgtc ctgggtaccc cgagtctccc ccgacctcgg gtcccaggta  3960
tgctcccacc tccacctgcc ccactcacca cctctgctag ttccagacac ctcccaagca  4020
cgcagcaatg cagctcaaaa cgcttagcct agccacaccc ccacgggaaa cagcagtgat  4080
taacctttag caataaacga aagtttaact aagctatact aaccccaggg ttggtcaatt  4140
tcgtgccagc cacaccctgg agctagcaaa aaaaaaaaaa aaaaaaaaaa aaaaaaagca  4200
tatgactaaa aaaaaaaaaa aaaaaaaaaa aaaaaaaaaa aaaaaaaaaa aaaaaaaaaa  4260
aaaaaaaaaa aaaaaaa                                                 4277
```

CORONAVIRUS VACCINE

This disclosure relates to the field of RNA to prevent or treat coronavirus infection. In particular, the present disclosure relates to methods and agents for vaccination against coronavirus infection and inducing effective coronavirus antigen-specific immune responses such as antibody and/or T cell responses. These methods and agents are, in particular, useful for the prevention or treatment of coronavirus infection. Administration of RNA disclosed herein to a subject can protect the subject against coronavirus infection. Specifically, in one embodiment, the present disclosure relates to methods comprising administering to a subject RNA encoding a peptide or protein comprising an epitope of SARS-CoV-2 spike protein (S protein) for inducing an immune response against coronavirus S protein, in particular S protein of SARS-CoV-2, in the subject, i.e., vaccine RNA encoding vaccine antigen. Administering to the subject RNA encoding vaccine antigen may provide (following expression of the RNA by appropriate target cells) vaccine antigen for inducing an immune response against vaccine antigen (and disease-associated antigen) in the subject.

Coronaviruses are positive-sense, single-stranded RNA ((+)ssRNA) enveloped viruses that encode for a total of four structural proteins, spike protein (S), envelope protein (E), membrane protein (M) and nucleocapsid protein (N). The spike protein (S protein) is responsible for receptor-recognition, attachment to the cell, infection via the endosomal pathway, and the genomic release driven by fusion of viral and endosomal membranes. Though sequences between the different family members vary, there are conserved regions and motifs within the S protein making it possible to divide the S protein into two subdomains: S1 and S2. While the S2, with its transmembrane domain, is responsible for membrane fusion, the S1 domain recognizes the virus-specific receptor and binds to the target host cell. Within several coronavirus isolates, the receptor binding domain (RBD) was identified and a general structure of the S protein defined (FIG. 1).

In December 2019, a pneumonia outbreak of unknown cause occurred in Wuhan, China and it became clear that a novel coronavirus (severe acute respiratory syndrome coronavirus 2; SARS-CoV-2) was the underlying cause. The genetic sequence of SARS-CoV-2 became available to the WHO and public (MN908947.3) and the virus was categorized into the betacoronavirus subfamily. By sequence analysis, the phylogenetic tree revealed a closer relationship to severe acute respiratory syndrome (SARS) virus isolates than to another coronavirus infecting humans, namely the Middle East respiratory syndrome (MERS) virus.

SARS-CoV-2 infections and the resulting disease COVID-19 have spread globally, affecting a growing number of countries. On 11 Mar. 2020 the WHO characterized the COVID-19 outbreak as a pandemic. As of 1 Dec. 2020, there have been >63 million globally confirmed COVID-19 cases and >1.4 million deaths, with 191 countries/regions affected. The ongoing pandemic remains a significant challenge to public health and economic stability worldwide.

Every individual is at risk of infection as there is no pre-existing immunity to SARS-CoV-2. Following infection some but not all individuals develop protective immunity in terms of neutralising antibody responses and cell mediated immunity. However, it is currently unknown to what extent and for how long this protection lasts. According to WHO 80% of infected individuals recover without need for hospital care, while 15% develop more severe disease and 5% need intensive care. Increasing age and underlying medical conditions are considered risk factors for developing severe disease.

The presentation of COVID-19 is generally with cough and fever, with chest radiography showing ground-glass opacities or patchy shadowing. However, many patients present without fever or radiographic changes, and infections may be asymptomatic which is relevant to controlling transmission. For symptomatic subjects, progression of disease may lead to acute respiratory distress syndrome requiring ventilation and subsequent multi-organ failure and death. Common symptoms in hospitalized patients (in order of highest to lowest frequency) include fever, dry cough, shortness of breath, fatigue, myalgias, nausea/vomiting or diarrhoea, headache, weakness, and rhinorrhoea. Anosmia (loss of smell) or ageusia (loss of taste) may be the sole presenting symptom in approximately 3% of individuals who have COVID-19.

All ages may present with the disease, but notably case fatality rates (CFR) are elevated in persons >60 years of age. Comorbidities are also associated with increased CFR, including cardiovascular disease, diabetes, hypertension, and chronic respiratory disease. Healthcare workers are overrepresented among COVID-19 patients due to occupational exposure to infected patients.

In most situations, a molecular test is used to detect SARS-CoV-2 and confirm infection. The reverse transcription polymerase chain reaction (RT-PCR) test methods targeting SARS-CoV-2 viral RNA are the gold standard in vitro methods for diagnosing suspected cases of COVID-19. Samples to be tested are collected from the nose and/or throat with a swab.

Among other things, the present disclosure provides insights into immune responses elicited by exposure to (e.g., by vaccination and/or infection) different SARS-CoV-2 variants or immunogenic polypeptides (e.g., S protein), or immunogenic fragments thereof. For example, in some embodiments, administering RNA encoding an S protein of a BA.2 and/or BA.4/5 Omicron SARS-CoV-2 variant, or an immunogenic fragment thereof, can result in an improved immune response, which includes, e.g., improved neutralization of Omicron BA.4 and/or Omicron BA.5 SARS-CoV-2 variants and/or broader cross-neutralization of Omicron variants of concern (e.g., higher neutralization titers against a larger number of Omicron variants of concern). In some embodiments, the present disclosure provides an insight that a bivalent coronavirus vaccine (e.g., a bivalent BA.4/5 vaccine comprising a first RNA encoding a SARS-CoV-2 S protein of a Wuhan strain or an immunogenic fragment thereof, and a second RNA encoding a SARS-CoV-2 S protein comprising one or more mutations that are characteristic of a BA.4/5 Omicron variant or an immunogenic fragment thereof) can provide broader cross-neutralization against SARS-CoV-2 Wuhan strain and certain variants thereof (e.g., in some embodiments variants that are prevalent and/or rapidly spreading in a relevant jurisdiction, e.g., certain Omicron variants) in certain subjects as compared to a monovalent coronavirus vaccine (e.g., a vaccine comprising RNA encoding a SARS-CoV-2 S protein of a coronavirus strain or variant thereof). In some embodiments, such broader cross-neutralization can be observed in vaccine-naïve subjects. In some embodiments, such broader cross-neutralization can be observed in subjects without a coronavirus infection (e.g., a SARS-CoV-2 infection). In some embodiments, such broader cross-neutralization can be observed in subjects who previously received a SARS-CoV-2 vaccine (e.g., in some embodiments an RNA vaccine encoding a SARS-CoV-2 S protein, e.g., in some embodiments of a Wuhan strain). In some embodiments, such broader cross-neutralization can be observed in in young pediatric subjects (e.g., subjects aged 6 months to less than 2 years, and/or 2 years to less than 5 years). In some embodiments, the present disclosure provides an insight that exposure to at least two certain SARS-CoV-2 variants or immunogenic polypeptides (e.g., S protein), or immunogenic fragments thereof can result in a synergistic improvement in immune response (e.g., higher neutralization titers, broader cross-neutralization, and/or an immune response that is less susceptible to immune escape) as compared to exposure to one SARS-CoV-2 strain and/or other combination of SARS-CoV-2 variants. In some embodiments, the present disclosure provides an insight that exposure to a SARS-CoV-2 S protein from a Wuhan strain or an immunogenic fragment thereof (e.g., by vaccination and/or infection), and exposure to a SARS-CoV-2 S protein of an Omicron BA.1 variant or an immunogenic fragment thereof (e.g., by vaccination and/or infection) can result in a synergistic improvement in immune response (e.g., higher neutralization titers, broader cross-neutralization, and/or an immune response that is less susceptible to immune escape) as compared to exposure to one SARS-CoV-2 strain and/or other combinations of SARS-CoV-2 variants. In some embodiments, the present disclosure provides an insight that exposure to a SARS-CoV-2 S protein from a Wuhan strain or an immunogenic fragment thereof (e.g., by vaccination and/or infection), and exposure to a SARS-CoV-2 S protein of an Omicron BA.4 or BA.5 variant or an immunogenic fragment thereof (e.g., by vaccination and/or infection) can result in an synergistic improvement in immune response (e.g., higher neutralization titers, broader cross-neutralization, and/or an immune response that is less susceptible to immune escape) as compared to exposure to one SARS-CoV-2 strain and/or other combinations of SARS-CoV-2 variants. In some embodiments, the present disclosure provides an insight that (i) exposure to a SARS-CoV-2 S protein from a strain/variant selected from the group consisting of Wuhan strain, an alpha variant, beta variant, delta variant, Omicron BA.1, and sublineages derived from any of the aforementioned strains/variants, or immunogenic fragments thereof (e.g., by vaccination and/or infection), combined with (ii) exposure to a SARS-CoV-2 S protein from a strain/variant selected from the group consisting of Omicron BA.2, Omicron BA.4, Omicron BA.5, and sublineages derived from any of the aforementioned strains/variants, or immunogenic fragments thereof (e.g., by vaccination and/or infection) can result in a synergistic improvement in immune response (e.g., higher neutralization titers, broader cross-neutralization, and/or an immune response that is less susceptible to immune escape) as compared to exposure to one SARS-CoV-2 strain and/or other combinations of SARS-CoV-2 variants).

The present disclosure also provides significant insights into how an immune response develops in subjects following exposures to (e.g., vaccinations and/or infections) multiple, different SARS-CoV-2 strains. Among other things, disclosed herein is a finding that different combinations of SARS-CoV-2 variants elicit different immune responses. Specifically, the present disclosure provides an insight that exposure to certain combinations of SARS-CoV-2 variants can elicit an improved immune response (e.g., higher neutralization titers, broader cross-neutralization, and/or an immune response that is less susceptible to immune escape). In some embodiments, an improved immune response can be produced when subjects are delivered two or more antigens (e.g., as polypeptides or RNAs encoding such polypeptides), each having few shared epitopes. In some embodiments, an improved immune response can be produced when subjects are delivered a combination of SARS-CoV-2 S proteins (e.g., as polypeptides or RNAs encoding such polypeptides) sharing no more than 50% (e.g., no more than 40%, no more than 30%, no more 20% or more) of epitopes (including, e.g., amino acid mutations) that can be bound by neutralization antibodies. In some embodiments, an improved immune response can be produced by delivering, as polypeptides or RNAs encoding such polypeptides, (a) a SARS-CoV-2 S protein from a Wuhan strain, an Alpha variant, Beta variant, or a Delta variant of SARS-CoV-2 or an immunogenic fragment thereof, and (b) an S protein from a SARS-CoV-2 Omicron variant or an immunogenic fragment thereof. In some embodiments, an improved immune response can be produced by delivering, as polypeptides or RNAs encoding such polypeptides, (a) a SARS-CoV-2 S protein from a Wuhan strain, an Alpha variant, a Beta variant, or a Delta variant of SARS-CoV-2 or an immunogenic fragment thereof, and (b) an S protein of a SARS-CoV-2 Omicron variant that is not a BA.1 Omicron variant or an immunogenic fragment thereof. In some embodiments, an improved immune response can be produced by delivering, as polypeptides or RNAs encoding such polypeptides, (a) an S protein from a Wuhan strain, an Alpha variant, a Beta Variant, a Delta SARS-CoV-2 variant, or a BA.1 Omicron variant or an immunogenic fragment thereof and (b) an S protein of a SARS-CoV-2 Omicron variant that is not a BA.1 Omicron variant or an immunogenic fragment thereof. In some embodiments, an improved immune response can be produced by delivering, as polypeptides or RNAs encoding such polypeptides, (a) a SARS-CoV-2 S protein from a Wuhan strain, an Alpha variant, a Beta variant, or a Delta variant, or an immunogenic fragment thereof and (b) an S protein of a BA.2 or a BA.4 or BA.5 SARS-CoV-2 Omicron variant or an immunogenic fragment thereof.

In some embodiments, the present disclosure also provides an insight that administration of multiple doses (e.g., at least 2, at least 3, at least 4, or more doses) of a coronavirus vaccine described herein (e.g., a bivalent vaccine described herein such as a bivalent BA.4/5 vaccine) may provide certain beneficial effect(s) on affinity of antibodies against one or more SARS-CoV-2 strain or variants thereof. In some embodiments, such beneficial effect(s) on affinity of antibodies may be observed with respect to antibodies against certain Omicron variants. By way of example only, in some embodiments, such beneficial effect(s) on affinity of antibodies may be observed with respect to antibodies against certain Omicron variants that share at least one or more common epitopes, for example, with a Wuhan strain.

Also disclosed herein are compositions that can produce an improved immune response (e.g., an immune response having broader cross-neutralization activity, stronger neutralization, and/or which is less susceptible to immune escape). In some embodiments, a composition described herein comprises two or more antigens or nucleic acids (e.g., RNA) that encodes such antigens that have few shared epitopes. In some embodiments, a composition described herein delivers, as polypeptides or nucleic acids encoding such polypeptides, a combination of SARS-CoV-2 S proteins or immunogenic fragments thereof sharing no more than 50% (e.g., no more than 40%, no more than 30%, no more than 20% or more) of epitopes (including, e.g., amino acid mutations) that can be bound by neutralization antibodies. In some embodiments, a composition described herein comprises (a) RNA encoding a SARS-CoV-2 S protein from a Wuhan strain, an Alpha variant, a Beta variant, or a Delta variant or an immunogenic fragment thereof and (b) RNA encoding an S protein from an Omicron variant of SARS-CoV-2 (e.g., in some embodiments an S protein from a BA.1, BA.2, or BA.4/S Omicron variant) or an immunogenic fragment thereof. In some embodiments, a composition described herein comprises (a) RNA encoding a SARS-CoV-2 S protein from a Wuhan strain, an Alpha variant, a Beta variant, or a Delta variant or an immunogenic fragment thereof and (b) RNA encoding an S protein of an Omicron variant of SARS-CoV-2 that is not a BA.1 Omicron variant or an immunogenic fragment thereof. In some embodiments, a composition described herein comprises (a) RNA encoding a SARS-CoV-2 S protein of a Wuhan strain, an Alpha variant, a Beta variant, or a Delta variant or a BA.1 Omicron variant or an immunogenic fragment thereof and (b) RNA encoding an S protein of a Omicron variant that is not a BA.1 Omicron variant or an immunogenic fragment thereof. In some embodiments, a composition described herein comprises (a) RNA encoding a SARS-CoV-2 S protein of a Wuhan strain, an Alpha variant, a Beta variant or a Delta variant of SARS-CoV-2 and (b) RNA encoding an S protein from a BA.2 or a BA.4 or BA.5 Omicron variant of SARS-CoV-2 or an immunogenic fragment thereof. In some embodiments, a composition described herein comprises RNA encoding an S protein from a BA.2 Omicron variant of SARS-CoV-2 or an immunogenic fragment thereof. In some embodiments, a composition comprises RNA encoding an S protein from a BA.4 or BA.5 Omicron variant of SARS-CoV-2 or an immunogenic fragment thereof. SARS-CoV-2 is an RNA virus with four structural proteins. One of them, the spike protein is a surface protein which binds the angiotensin-converting enzyme 2 (ACE-2) present on host cells. Therefore, the spike protein is considered a relevant antigen for vaccine development. BNT162b2 (SEQ ID NO: 20) is an mRNA vaccine for prevention of COVID-19 and demonstrated an efficacy of 95% or more at preventing COVID-19. The vaccine is made of a 5'capped mRNA encoding for the full-length SARS-CoV-2 spike glycoprotein (S) encapsulated in lipid nanoparticles (LNPs). The finished product is presented as a concentrate for dispersion for injection containing BNT162b2 as active substance. Other ingredients are: ALC-0315 (4-hydroxybutyl)azanediyl)bis(hexane-6,1-diyl)bis(2-hexyldecanoate), ALC-0159 (2-[(polyethylene glycol)-2000]-N,N-ditetradecylacetamide), 1,2-Distearoyl-sn-glycero-3-phosphocholine (DSPC), cholesterol, potassium chloride, potassium dihydrogen phosphate, sodium chloride, disodium phosphate dihydrate, sucrose and water for injection.

In some embodiments, a different buffer may be used in lieu of PBS. In some embodiments, the buffer is formulated in a Tris-buffered solution. In some embodiments, the formulation comprises ALC-0315 (4-hydroxybutyl)azanediyl) bis(hexane-6,1-diyl)bis(2-hexyldecanoate), ALC-0159 (2-[(polyethylene glycol)-2000]-N,N-ditetradecylacetamide), DSPC (1,2-distearoyl-sn-glycero-3-phosphocholine), cholesterol, sucrose, trometamol (Tris), trometamol hydrochloride and water.

In some embodiments, the concentration of RNA in a pharmaceutical RNA preparation is about 0.1 mg/ml. In some embodiments about 30 μg of RNA is administered by administering about 200 μL of RNA preparation. In some embodiments, RNA in a pharmaceutical RNA preparation is diluted prior to administration (e.g., diluted to a concentration of about 0.05 mg/ml). In some embodiments, administration volumes are between about 200 Il and about 300 μl. In some embodiments, RNA in a pharmaceutical RNA preparation is formulated in about 10 mM Tris buffer, and about 10% sucrose.

In some embodiments, the concentration of RNA in a pharmaceutical RNA preparation is about 0.1 mg/ml, and is formulated in about 10 mM Tris buffer, about 10% sucrose and a dose of about 10 μg or RNA is administered by diluting a pharmaceutical RNA preparation about 1:1 and administering about 200 μl of diluted pharmaceutical RNA preparation. In some embodiments, the concentration of RNA in a pharmaceutical RNA preparation is about 0.1 mg/ml, and is formulated in about 10 mM Tris buffer, about 10% sucrose and a dose of RNA of about 10 μg is administered by diluting a pharmaceutical RNA preparation about 1:5.75 and administering about 200 μl of diluted pharmaceutical RNA preparation.

The amino acid sequence of the S protein encoded by BNT162b2 was chosen based on the sequence for the "SARS-CoV-2 isolate Wuhan-Hu-1": GenBank: MN908947.3 (complete genome) and GenBank: QHD43416.1 (spike surface glycoprotein). The BNT162b2 active substance consists of a single-stranded, 5'-capped codon-optimized mRNA that is translated into the spike antigen of SARS-CoV-2. The spike antigen protein sequence encoded by BNT162b2 contains two proline mutations, which stabilizes an antigenically improved pre-fusion confirmation (P2 S). BNT162b2 does not contain any uridines; instead of uridine the modified N1-methylpseudouridine is used in RNA synthesis. BNT162b2 mRNA is translated into a SARS-CoV-2 S protein in host cells. The S protein is then expressed on the cell surface where it induces an adaptive immune response. The S protein encoded by BNT162b2 is identified as a target for neutralising antibodies against the virus and is considered a relevant vaccine component. For adult vaccine naïve subjects (i.e., subjects 16 years and older who have not previously been administered a SARS-CoV-2 vaccine), the dosing regimen of BNT162b2 approved by the FDA comprises administering intramuscularly (IM) two 30 μg doses of the diluted vaccine solution approximately 21 days apart.

The recent emergence of novel circulating variants of SARS-CoV-2 has raised significant concerns about geographic and temporal efficacy of vaccine interventions. One of the earliest variants that emerged and rapidly became globally dominant was D614G.

The alpha variant (also known as B.1.1.7, VOC202012/01, 501Y.V1 or GRY) was initially detected in the United Kingdom. The alpha variant has a large number of mutations, including several mutations in the S gene. It has been shown to be inherently more transmissible, with a growth rate that has been estimated to be 40-70% higher than other SARS-CoV-2 lineages in multiple countries (Volz et al., 2021, Nature, doi_org/10_1038/s41586-021-03470-x; Washington et al., 2021, Cell doi_org/10_1016/j_cell_2021_03_052).

The beta variant (also known as B.1.351 or GH/501Y.V2) was first detected in South Africa. The beta variant carries several mutations in the S gene. Three of these mutations are at sites in the RBD that are associated with immune evasion: N501Y (shared with alpha) and E484K and K417N.

The gamma variant (also known as P.1 or GR/501Y.V3) was first detected in Brazil. The gamma variant carries several mutations that affect the spike protein, including two shared with beta (N501Y and E484K), as well as a different mutation at position 417 (K417T).

The delta variant (also known as B.1.617.2 or G/478K.V1) was first documented in India. The delta variant has several point mutations that affect the spike protein, including P681R (a mutation position shared with alpha and adjacent to the furin cleavage site), and L452R, which is in the RBD and has been linked with increased binding to ACE2 and neutralizing antibody resistance. There is also a deletion in the spike protein at position 156/157.

These four VOCs have circulated globally and became dominant variants in the geographic regions where they were first identified.

On 24 Nov. 2021, the Omicron (B.1.1.529) variant was first reported to WHO from South Africa. SARS-CoV-2 Omicron and its sublineages have had a major impact on the epidemiological landscape of the COVID-19 pandemic since initial emergence in November 2021 (WHO Technical Advisory Group on SARS-CoV-2 Virus Evolution (TAG-VE): Classification of Omicron (B.1.1.259): SARS-CoV-2 Variant of Concern (2021); WHO Headquarters (HQ), WHO Health Emergencies Programme, Enhancing Response to Omicron SARS-CoV-2 variant: Technical brief and priority actions for Member States (2022)). Significant alterations in the spike (S) glycoprotein of the first Omicron variant BA.1 leading to the loss of many neutralizing antibody epitopes (M. Hoffmann et al., "The Omicron variant is highly resistant against antibody mediated neutralization: Implications for control of the COVID-19 pandemic", Cell 185, 447-456.e11 (2022)) rendered BA.1 capable of partially escaping previously established SARS-CoV-2 wild-type strain (Wuhan-Hu-1)-based immunity (V. Servellita, et al., "Neutralizing immunity in vaccine breakthrough infections from the SARS-CoV-2 Omicron and Delta variants", Cell 185, 1539-1548.e5 (2022); Y. Cao et al., "Omicron escapes the majority of existing SARS-CoV-2 neutralizing antibodies", Nature 602, 657-663 (2022)). Hence, breakthrough infection of vaccinated individuals with Omicron are more common than with previous Variants of Concern (VOCs). While Omicron BA.1 was displaced by the BA.2 variant in many countries around the globe, other variants such as BA.1.1 and BA.3 temporarily and/or locally gained momentum but did not become globally dominant (S. Xia et al., "Origin, virological features, immune evasion and intervention of SARS-CoV-2 Omicron sublineages. Signal Transduct. Target. Ther. 7, 241 (2022); H. Gruell et al., "SARS-CoV-2 Omicron sublineages exhibit distinct antibody escape patterns, Cell Host Microbe 7, 241 (2022).). Omicron BA.2.12.1 subsequently displaced BA.2 to become dominant in the United States, whereas BA.4 and BA.5 displaced BA.2 in Europe, parts of Africa, and Asia/Pacific (H. Gruell et al., "SARS-CoV-2 Omicron sublineages exhibit distinct antibody escape patterns," Cell Host Microbe 7, 241 (2022); European Centre for Disease Prevention and Control, Weekly COVID-19 country overview—Country overview report: Week 31 2022 (2022); J. Hadfield et al., "Nextstrain: Real-time tracking of pathogen evolution," Bioinformatics 34, 4121-4123 (2018)). Currently, Omicron BA.5 is dominant globally, including in the United States (Centers for Disease Control and Prevention. COVID Data Tracker. Atlanta, GA: US Department of Health and Human Services, CDC; 2022, August 12. covid_cdc_gov/coviddata-tracker (2022)).

Omicron has acquired numerous alterations (amino acid exchanges, insertions, or deletions) in the S glycoprotein, among which some are shared between all Omicron VOCs while others are specific to one or more Omicron sublineages. Antigenically, BA.2.12.1 exhibits high similarity with BA.2 but not BA.1, whereas BA.4 and BA.5 differ considerably from their ancestor BA.2 and even more so from BA.1, in line with their genealogy (A. Z. Mykytyn et al., "Antigenic cartography of SARS-CoV-2 reveals that Omicron BA.1 and BA.2 are antigenically distinct," Sci. Immunol. 7, eabq4450 (2022).). Major differences of BA.1 from the remaining Omicron VOCs include A143-145, L212I, or ins214EPE in the S glycoprotein N-terminal domain and G446S or G496S in the receptor binding domain (RBD). Amino acid changes T376A, D405N, and R408S in the RBD are in turn common to BA.2 and its descendants but not found in BA.1. In addition, some alterations are specific for individual BA.2-descendant VOCs, including L452Q for BA.2.12.1 or L452R and F486V for BA.4 and BA.5 (BA.4 and BA.5 encode for the same S sequence). Most of these shared and VOC-specific alterations were shown to play an important role in immune escape from monoclonal antibodies and polyclonal sera raised against the wild-type S glycoprotein. In particular, the BA.4/BA.5-specific alterations are strongly implicated in immune escape of these VOCs (P. Wang et al., "Antibody resistance of SARS-CoV-2 variants B.1.351 and B.1.1.7. Nature 593, 130-135 (2021); Q. Wang et al., "Antibody evasion by SARS-CoV-2 Omicron subvariants BA.2.12.1, BA.4, & BA.5. Nature 608, 603-608 (2022)).

SUMMARY

The present disclosure generally embraces immunotherapeutic treatment of a subject comprising administration of RNA, e.g., vaccine RNA, encoding an amino acid sequence, e.g., a vaccine antigen, comprising a SARS-CoV-2 S protein, an immunogenic variant thereof, or an immunogenic fragment of the SARS-CoV-2 S protein or the immunogenic variant thereof, i.e., an antigenic peptide or protein. Thus, vaccine antigen comprises an epitope of SARS-CoV-2 S protein for inducing an immune response against coronavirus S protein, in particular SARS-CoV-2 S protein, in the subject. RNA encoding vaccine antigen is administered to provide (following expression of the polynucleotide by appropriate target cells) antigen for induction, i.e., stimulation, priming and/or expansion, of an immune response, e.g., antibodies and/or immune effector cells, which is targeted to target antigen (coronavirus S protein, in particular SARS-CoV-2 S protein) or a procession product thereof. In one embodiment, the immune response which is to be induced according to the present disclosure is a B cell-mediated immune response, i.e., an antibody-mediated immune response. Additionally or alternatively, in one embodiment, the immune response which is to be induced according to the present disclosure is a T cell-mediated immune response. In one embodiment, the immune response is an anti-coronavirus, in particular anti-SARS-CoV-2 immune response.

Vaccines described herein comprise as an active principle single-stranded RNA that may be translated into protein upon entering cells of a recipient. In addition to wildtype or codon-optimized sequences encoding an antigen sequence, RNA may contain one or more structural elements optimized for maximal efficacy with respect to stability and translational efficiency (e.g., 5' cap, 5' UTR, 3' UTR, poly(A)-tail, and combinations thereof). In one embodiment, RNA contains all of these elements. In one embodiment, a cap1 structure may be utilized as specific capping structure at the 5'-end of an RNA drug substance. In one embodiment, beta-S-ARCA(D1) ($m_2^{7,2'-O}$GppSpG) or $m_2^{7,3'-O}$Gppp($m_1^{2'-O}$)ApG may be utilized as specific capping structure at the 5'-end of an RNA drug substance. As 5'-UTR sequence, the 5'-UTR sequence of the human alpha-globin mRNA, optionally with an optimized 'Kozak sequence' to increase translational efficiency (e.g., SEQ ID NO: 12) may be used. As 3'-UTR sequence, a combination of two sequence elements (FI element) derived from the "amino terminal enhancer of split" (AES) mRNA (called F) and the mitochondrial encoded 12S ribosomal RNA (called 1) (e.g., SEQ ID NO: 13) placed between the coding sequence and the poly(A)-tail to assure higher maximum protein levels and prolonged persistence of the mRNA may be used. These features were identified by an ex vivo selection process for sequences that confer RNA stability and augment total protein expression (see WO 2017/060314, herein incorporated by reference). Alternatively, the 3'-UTR may be two re-iterated 3'-UTRs of the human beta-globin mRNA. Additionally or alternatively, in some embodiments, a poly(A)-tail may comprise a length of at least 100 adenosine residues (including, e.g., at least 110 adenosine residues, at least 120 adenosine residues, 130 adenosine residues, or longer). In some embodiments, a poly(A)-tail may comprise a length of about 100 to about 150 adenosine residues. In some embodiments a poly(A)-tail may comprise an interrupted poly(A)-tail. For example, in some such embodiments, a poly(A)-tail measuring 110 nucleotides in length, consisting of a stretch of 30 adenosine residues, followed by a 10 nucleotide linker sequence (of random nucleotides) and another 70 adenosine residues (e.g., SEQ ID NO: 14) may be used. This poly(A)-tail sequence was designed to enhance RNA stability and translational efficiency.

Furthermore, in some embodiments, a nucleotide sequence encoding a secretory signal peptide (sec) may be fused to antigen-encoding regions of an RNA, preferably in some embodiments in a way that the sec is translated as an N terminal tag. In one embodiment, sec corresponds to the secretory signal peptide of a SARS-CoV-2 S protein (e.g., of a Wuhan strain). In some embodiments, sequences coding for short linker peptides predominantly consisting of the amino acids glycine (G) and serine (S), as commonly used for fusion proteins, may be used as GS/Linkers between sec and an antigen.

Vaccine RNA described herein may be complexed with proteins and/or lipids, preferably lipids, to generate RNA-particles for administration. If a combination of different RNAs is used, RNAs may be complexed together or complexed separately with proteins and/or lipids to generate RNA-particles for administration.

In one aspect, the present disclosure relates to a composition or medical preparation comprising RNA encoding an amino acid sequence comprising a SARS-CoV-2 S protein, an immunogenic variant thereof, or an immunogenic fragment of the SARS-CoV-2 S protein or the immunogenic variant thereof.

In one embodiment, an immunogenic fragment of the SARS-CoV-2 S protein comprises the S1 subunit of the SARS-CoV-2 S protein, or the receptor binding domain (RBD) of the S1 subunit of the SARS-CoV-2 S protein.

In one embodiment, an amino acid sequence comprising a SARS-CoV-2 S protein, an immunogenic variant thereof, or an immunogenic fragment of the SARS-CoV-2 S protein or the immunogenic variant thereof is able to form a multimeric complex, in particular a trimeric complex. To this end, an amino acid sequence comprising a SARS-CoV-2 S protein, an immunogenic variant thereof, or an immunogenic fragment of the SARS-CoV-2 S protein or the immunogenic variant thereof may comprise a domain allowing the formation of a multimeric complex, in particular a trimeric complex of the amino acid sequence comprising a SARS-CoV-2 S protein, an immunogenic variant thereof, or an immunogenic fragment of the SARS-CoV-2 S protein or the immunogenic variant thereof. In one embodiment, the domain allowing formation of a multimeric complex comprises a trimerization domain, for example, a trimerization domain as described herein, e.g., SARS-CoV-2 S protein trimerization domain. In one embodiment, trimerization is achieved by addition of a trimerization domain, e.g., a T4-fibritin-derived "foldon" trimerization domain (e.g., SEQ ID NO: 10), in particular if the amino acid sequence comprising a SARS-CoV-2 S protein, an immunogenic variant thereof, or an immunogenic fragment of the SARS-CoV-2 S protein or the immunogenic variant thereof corresponds to a portion of a SARS-CoV-2 S protein that does not comprise the SARS-CoV-2 S protein trimerization domain.

In one embodiment, the amino acid sequence comprising a SARS-CoV-2 S protein, an immunogenic variant thereof, or an immunogenic fragment of the SARS-CoV-2 S protein or the immunogenic variant thereof is encoded by a coding sequence which is codon-optimized and/or the G/C content of which is increased compared to wild type coding sequence, wherein the codon-optimization and/or the increase in the G/C content preferably does not change the sequence of the encoded amino acid sequence. Those skilled in the art will appreciate that codon optimization involves choosing between or among alternative codons encoding the same amino acid residue. Codon optimization typically includes consideration of codon(s) preferred by a particular host in which a sequence is to be expressed. In accordance with the present disclosure, in many embodiments, a preferred host is a human. In some embodiments, a preferred host may be a domestic animal. Alternatively or additionally, in some embodiments, selection between or among possible codons encoding the same amino acid may consider one or more other features such as, for example, overall G/C content (as noted above) and/or similarity to a particular reference. For example, in some embodiments of the present disclosure, a provided coding sequence that encodes a SARS-CoV-2 S protein or immunogenic variant thereof that differs in amino acid sequence from that encoded by a BNT162b2 construct described herein utilizes a codon, in at least one position of such difference, that preserves greater similarity to the BNT162b2 construct sequence relative to at least one alternative codon encoding the same amino acid at such position of difference.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 979 to 1584 of SEQ ID NO: 2, 8 or 9, a nucleotide sequence having at least 99%, 98%, 97%, 96%, 95%, 90%, 85%, or 80% identity to the nucleotide sequence of nucleotides 979 to 1584 of SEQ ID NO: 2, 8 or 9, or a fragment of the nucleotide sequence of nucleotides 979 to 1584 of SEQ ID NO: 2, 8 or 9, or the nucleotide sequence having at least 99%, 98%, 97%, 96%, 95%, 90%, 85%, or 80% identity to the nucleotide sequence of nucleotides 979 to 1584 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 327 to 528 of SEQ ID NO: 1, an amino acid sequence having at least 99%, 98%, 97%, 96%, 95%, 90%, 85%, or 80% identity to the amino acid sequence of amino acids 327 to 528 of SEQ ID NO: 1, or an immunogenic fragment of the amino acid sequence of amino acids 327 to 528 of SEQ ID NO: 1, or the amino acid sequence having at least 99%, 98%, 97%, 96%, 95%, 90%, 85%, or 80% identity to the amino acid sequence of amino acids 327 to 528 of SEQ ID NO: 1.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 111 to 986 of SEQ ID NO: 30, a nucleotide sequence having at least 99%, 98%, 97%, 96%, 95%, 90%, 85%, or 80% identity to the nucleotide sequence of nucleotides 111 to 986 of SEQ ID NO: 30, or a fragment of the nucleotide sequence of nucleotides 111 to 986 of SEQ ID NO: 30, or the nucleotide sequence having at least 99%, 98%, 97%, 96%, 95%, 90%, 85%, or 80% identity to the nucleotide sequence of nucleotides 111 to 986 of SEQ ID NO: 30; and/or (ii) a SARS-CoV-2 S protein, an immunogenic variant thereof, or an immunogenic fragment of the SARS-CoV-2 S protein or the immunogenic variant thereof comprises the amino acid sequence of amino acids 20 to 311 of SEQ ID NO: 29, an amino acid sequence having at least 99%, 98%, 97%, 96%, 95%, 90%, 85%, or 80% identity to the amino acid sequence of amino acids 20 to 311 of SEQ ID NO: 29, or an immunogenic fragment of the amino acid sequence of amino acids 20 to 311 of SEQ ID NO: 29, or the amino acid sequence having at least 99%, 98%, 97%, 96%, 95%, 90%, 85%, or 80% identity to the amino acid sequence of amino acids 20 to 311 of SEQ ID NO: 29.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 2055 of SEQ ID NO: 2, 8 or 9, a nucleotide sequence having at least 99%, 98%, 97%, 96%, 95%, 90%, 85%, or 80% identity to the nucleotide sequence of nucleotides 49 to 2055 of SEQ ID NO: 2, 8 or 9, or a fragment of the nucleotide sequence of nucleotides 49 to 2055 of SEQ ID NO: 2, 8 or 9, or the nucleotide sequence having at least 99%, 98%, 97%, 96%, 95%, 90%, 85%, or 80% identity to the nucleotide sequence of nucleotides 49 to 2055 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 685 of SEQ ID NO: 1, an amino acid sequence having at least 99%, 98%, 97%, 96%, 95%, 90%, 85%, or 80% identity to the amino acid sequence of amino acids 17 to 685 of SEQ ID NO: 1, or an immunogenic fragment of the amino acid sequence of amino acids 17 to 685 of SEQ ID NO: 1, or the amino acid sequence having at least 99%, 98%, 97%, 96%, 95%, 90%, 85%, or 80% identity to the amino acid sequence of amino acids 17 to 685 of SEQ ID NO: 1.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 3819 of SEQ ID NO: 2, 8 or 9, a nucleotide sequence having at least 99%, 98%, 97%, 96%, 95%, 90%, 85%, or 80% identity to the nucleotide sequence of nucleotides 49 to 3819 of SEQ ID NO: 2, 8 or 9, or a fragment of the nucleotide sequence of nucleotides 49 to 3819 of SEQ ID NO: 2, 8 or 9, or the nucleotide sequence having at least 99%, 98%, 97%, 96%, 95%, 90%, 85%, or 80% identity to the nucleotide sequence of nucleotides 49 to 3819 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 1273 of SEQ ID NO: 1 or 7, an amino acid sequence having at least 99%, 98%, 97%, 96%, 95%, 90%, 85%, or 80% identity to the amino acid sequence of amino acids 17 to 1273 of SEQ ID NO: 1 or 7, or an immunogenic fragment of the amino acid sequence of amino acids 17 to 1273 of SEQ ID NO: 1 or 7, or the amino acid sequence having at least 99%, 98%, 97%, 96%, 95%, 90%, 85%, or 80% identity to the amino acid sequence of amino acids 17 to 1273 of SEQ ID NO: 1 or 7.

In one embodiment, the amino acid sequence comprising a SARS-CoV-2 S protein, an immunogenic variant thereof, or an immunogenic fragment of the SARS-CoV-2 S protein or the immunogenic variant thereof comprises a secretory signal peptide.

In one embodiment, the secretory signal peptide is fused, preferably N-terminally, to a SARS-CoV-2 S protein, an immunogenic variant thereof, or an immunogenic fragment of the SARS-CoV-2 S protein or the immunogenic variant thereof.

In one embodiment, (i) the RNA encoding the secretory signal peptide comprises the nucleotide sequence of nucleotides 1 to 48 of SEQ ID NO: 2, 8 or 9, a nucleotide sequence having at least 99%, 98%, 97%, 96%, 95%, 90%, 85%, or 80% identity to the nucleotide sequence of nucleotides 1 to 48 of SEQ ID NO: 2, 8 or 9, or a fragment of the nucleotide sequence of nucleotides 1 to 48 of SEQ ID NO: 2, 8 or 9, or the nucleotide sequence having at least 99%, 98%, 97%, 96%, 95%, 90%, 85%, or 80% identity to the nucleotide sequence of nucleotides 1 to 48 of SEQ ID NO: 2, 8 or 9; and/or (ii) the secretory signal peptide comprises the amino acid sequence of amino acids 1 to 16 of SEQ ID NO: 1, an amino acid sequence having at least 99%, 98%, 97%, 96%, 95%, 90%, 85%, or 80% identity to the amino acid sequence of amino acids 1 to 16 of SEQ ID NO: 1, or a functional fragment of the amino acid sequence of amino acids 1 to 16 of SEQ ID NO: 1, or the amino acid sequence having at least 99%, 98%, 97%, 96%, 95%, 90%, 85%, or 80% identity to the amino acid sequence of amino acids 1 to 16 of SEQ ID NO: 1.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of SEQ ID NO: 6, a nucleotide sequence having at least 99%, 98%, 97%, 96%, 95%, 90%, 85%, or 80% identity to the nucleotide sequence of SEQ ID NO: 6, or a fragment of the nucleotide sequence of SEQ ID NO: 6, or the nucleotide sequence having at least 99%, 98%, 97%, 96%, 95%, 90%, 85%, or 80% identity to the nucleotide sequence of SEQ ID NO: 6; and/or (ii) a SARS-CoV-2 S protein, an immunogenic variant thereof, or an immunogenic fragment of the SARS-CoV-2 S protein or the immunogenic variant thereof comprises the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 54 to 986 of SEQ ID NO: 30, a nucleotide sequence having at least 99%, 98%, 97%, 96%, 95%, 90%, 85%, or 80% identity to the nucleotide sequence of nucleotides 54 to 986 of SEQ ID NO: 30, or a fragment of the nucleotide sequence of nucleotides 54 to 986 of SEQ ID NO: 30, or the nucleotide sequence having at least 99%, 98%, 97%, 96%, 95%, 90%, 85%, or 80% identity to the nucleotide sequence of nucleotides 54 to 986 of SEQ ID NO: 30; and/or (ii) a SARS-CoV-2 S protein, an immunogenic variant thereof, or an immunogenic fragment of the SARS-CoV-2 S protein or the immunogenic variant thereof comprises the amino acid sequence of amino acids 1 to 311 of SEQ ID NO: 29, an amino acid sequence having at least 99%, 98%, 97%, 96%, 95%, 90%, 85%, or 80% identity to the amino acid sequence of amino acids 1 to 311 of SEQ ID NO: 29, or an immunogenic fragment of the amino acid sequence of amino acids 1 to 311 of SEQ ID NO: 29, or the amino acid sequence having at least 99%, 98%, 97%, 96%, 95%, 90%, 85%, or 80% identity to the amino acid sequence of amino acids 1 to 311 of SEQ ID NO: 29.

In one embodiment, the RNA is a modified RNA, in particular a stabilized mRNA. In one embodiment, the RNA comprises a modified nucleoside in place of at least one uridine. In one embodiment, the RNA comprises a modified nucleoside in place of each uridine. In one embodiment, the modified nucleoside is independently selected from pseudouridine (ψ), N1-methyl-pseudouridine (m1ψ), and 5-methyl-uridine (m5U).

In one embodiment, RNA comprises a modified nucleoside in place of uridine.

In one embodiment, the modified nucleoside is selected from pseudouridine (ψ), N1-methyl-pseudouridine (m1ψ), and 5-methyl-uridine (m5U).

In one embodiment, RNA comprises a 5' cap.

In one embodiment, RNA encoding an amino acid sequence comprising a SARS-CoV-2 S protein, an immunogenic variant thereof, or an immunogenic fragment of the SARS-CoV-2 S protein or the immunogenic variant thereof comprises a 5' UTR comprising the nucleotide sequence of SEQ ID NO: 12, or a nucleotide sequence having at least 99%, 98%, 97%, 96%, 95%, 90%, 85%, or 80% identity to the nucleotide sequence of SEQ ID NO: 12.

In one embodiment, RNA encoding an amino acid sequence comprising a SARS-CoV-2 S protein, an immunogenic variant thereof, or an immunogenic fragment of the SARS-CoV-2 S protein or the immunogenic variant thereof comprises a 3' UTR comprising the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

In one embodiment, RNA encoding an amino acid sequence comprising a SARS-CoV-2 S protein, an immunogenic variant thereof, or an immunogenic fragment of the SARS-CoV-2 S protein or the immunogenic variant thereof comprises a poly-A sequence.

In one embodiment, the poly-A sequence comprises at least 100 nucleotides.

In one embodiment, the poly-A sequence comprises or consists of the nucleotide sequence of SEQ ID NO: 14.

In one embodiment, RNA is formulated or is to be formulated as a liquid, a solid, or a combination thereof.

In one embodiment, RNA is formulated or is to be formulated for injection.

In one embodiment, RNA is formulated or is to be formulated for intramuscular administration.

In one embodiment, RNA is formulated or is to be formulated as particles.

In one embodiment, particles are lipid nanoparticles (LNP) or lipoplex (LPX) particles.

In one embodiment, LNPs comprise ((4-hydroxybutyl) azanediyl)bis(hexane-6,1-diyl)bis(2-hexyldecanoate), 2-[(polyethylene glycol)-2000]-N,N-ditetradecylacetamide, 1,2-Distearoyl-sn-glycero-3-phosphocholine, and cholesterol.

In one embodiment, RNA lipoplex particles are obtainable by mixing RNA with liposomes. In one embodiment, RNA lipoplex particles are obtainable by mixing RNA with lipids.

In one embodiment, RNA is formulated or is to be formulated as colloid. In one embodiment, RNA is formulated or is to be formulated as particles, forming the dispersed phase of a colloid. In one embodiment, 50% or more, 75% or more, or 85% or more of RNA is present in the dispersed phase. In one embodiment, RNA is formulated or is to be formulated as particles comprising RNA and lipids. In one embodiment, particles are formed by exposing RNA, dissolved in an aqueous phase, with lipids, dissolved in an organic phase. In one embodiment, the organic phase comprises ethanol. In one embodiment, particles are formed by exposing RNA, dissolved in an aqueous phase, with lipids, dispersed in an aqueous phase. In one embodiment, the lipids dispersed in an aqueous phase form liposomes.

In one embodiment, RNA is mRNA or saRNA.

In one embodiment, a composition or medical preparation is a pharmaceutical composition.

In one embodiment, a composition or medical preparation is a vaccine.

In one embodiment, a pharmaceutical composition further comprises one or more pharmaceutically acceptable carriers, diluents and/or excipients.

In one embodiment, a composition or medical preparation is a kit.

In one embodiment, RNA and optionally the particle forming components are in separate vials.

In one embodiment, a kit further comprises instructions for use of a composition or medical preparation for inducing an immune response against coronavirus in a subject.

In one aspect, the present disclosure relates to a composition or medical preparation described herein for pharmaceutical use.

In one embodiment, a pharmaceutical use comprises inducing an immune response against coronavirus in a subject.

In one embodiment, a pharmaceutical use comprises a therapeutic or prophylactic treatment of a coronavirus infection.

In one embodiment, a composition or medical preparation described herein is for administration to a human.

In one embodiment, the coronavirus is a betacoronavirus.

In one embodiment, the coronavirus is a sarbecovirus.

In one embodiment, the coronavirus is SARS-CoV-2.

In one aspect, the present disclosure relates to a method of inducing an immune response against coronavirus in a subject comprising administering to the subject a composition comprising RNA encoding an amino acid sequence comprising a SARS-CoV-2 S protein, an immunogenic variant thereof, or an immunogenic fragment of the SARS-CoV-2 S protein or the immunogenic variant thereof.

In one embodiment, an immunogenic fragment of the SARS-CoV-2 S protein comprises the S1 subunit of the SARS-CoV-2 S protein, or the receptor binding domain (RBD) of the 51 subunit of the SARS-CoV-2 S protein.

In one embodiment, an amino acid sequence comprising a SARS-CoV-2 S protein, an immunogenic variant thereof, or an immunogenic fragment of the SARS-CoV-2 S protein or the immunogenic variant thereof is able to form a multimeric complex, in particular a trimeric complex. To this end, an amino acid sequence comprising a SARS-CoV-2 S protein, an immunogenic variant thereof, or an immunogenic fragment of the SARS-CoV-2 S protein or the immunogenic variant thereof may comprise a domain allowing the formation of a multimeric complex, in particular a trimeric complex of the amino acid sequence comprising a SARS-CoV-2 S protein, an immunogenic variant thereof, or an immunogenic fragment of the SARS-CoV-2 S protein or the immunogenic variant thereof. In one embodiment, the domain allowing the formation of a multimeric complex comprises a trimerization domain, for example, a trimerization domain as described herein.

In one embodiment, an amino acid sequence comprising a SARS-CoV-2 S protein, an immunogenic variant thereof, or an immunogenic fragment of the SARS-CoV-2 S protein or the immunogenic variant thereof is encoded by a coding sequence which is codon-optimized and/or the G/C content of which is increased compared to wild type coding sequence, wherein the codon-optimization and/or the increase in the G/C content preferably does not change the sequence of the encoded amino acid sequence.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 979 to 1584 of SEQ ID NO: 2, 8 or 9, a nucleotide sequence having at least 99%, 98%, 97%, 96%, 95%, 90%, 85%, or 80% identity to the nucleotide sequence of nucleotides 979 to 1584 of SEQ ID NO: 2, 8 or 9, or a fragment of the nucleotide sequence of nucleotides 979 to 1584 of SEQ ID NO: 2, 8 or 9, or the nucleotide sequence having at least 99%, 98%, 97%, 96%, 95%, 90%, 85%, or 80% identity to the nucleotide sequence of nucleotides 979 to 1584 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 327 to 528 of SEQ ID NO: 1, an amino acid sequence having at least 99%, 98%, 97%, 96%, 95%, 90%, 85%, or 80% identity to the amino acid sequence of amino acids 327 to 528 of SEQ ID NO: 1, or an immunogenic fragment of the amino acid sequence of amino acids 327 to 528 of SEQ ID NO: 1, or the amino acid sequence having at least 99%, 98%, 97%, 96%, 95%, 90%, 85%, or 80% identity to the amino acid sequence of amino acids 327 to 528 of SEQ ID NO: 1.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 111 to 986 of SEQ ID NO: 30, a nucleotide sequence having at least 99%, 98%, 97%, 96%, 95%, 90%, 85%, or 80% identity to the nucleotide sequence of nucleotides 111 to 986 of SEQ ID NO: 30, or a fragment of the nucleotide sequence of nucleotides 111 to 986 of SEQ ID NO: 30, or the nucleotide sequence having at least 99%, 98%, 97%, 96%, 95%, 90%, 85%, or 80% identity to the nucleotide sequence of nucleotides 111 to 986 of SEQ ID NO: 30; and/or (ii) a SARS-CoV-2 S protein, an immunogenic variant thereof, or an immunogenic fragment of the SARS-CoV-2 S protein or the immunogenic variant thereof comprises the amino acid sequence of amino acids 20 to 311 of SEQ ID NO: 29, an amino acid sequence having at least 99%, 98%, 97%, 96%, 95%, 90%, 85%, or 80% identity to the amino acid sequence of amino acids 20 to 311 of SEQ ID NO: 29, or an immunogenic fragment of the amino acid sequence of amino acids 20 to 311 of SEQ ID NO: 29, or the amino acid sequence having at least 99%, 98%, 97%, 96%, 95%, 90%, 85%, or 80% identity to the amino acid sequence of amino acids 20 to 311 of SEQ ID NO: 29.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 2055 of SEQ ID NO: 2, 8 or 9, a nucleotide sequence having at least 99%, 98%, 97%, 96%, 95%, 90%, 85%, or 80% identity to the nucleotide sequence of nucleotides 49 to 2055 of SEQ ID NO: 2, 8 or 9, or a fragment of the nucleotide sequence of nucleotides 49 to 2055 of SEQ ID NO: 2, 8 or 9, or the nucleotide sequence having at least 99%, 98%, 97%, 96%, 95%, 90%, 85%, or 80% identity to the nucleotide sequence of nucleotides 49 to 2055 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 685 of SEQ ID NO: 1, an amino acid sequence having at least 99%, 98%, 97%, 96%, 95%, 90%, 85%, or 80% identity to the amino acid sequence of amino acids 17 to 685 of SEQ ID NO: 1, or an immunogenic fragment of the amino acid sequence of amino acids 17 to 685 of SEQ ID NO: 1, or the amino acid sequence having at least 99%, 98%, 97%, 96%, 95%, 90%, 85%, or 80% identity to the amino acid sequence of amino acids 17 to 685 of SEQ ID NO: 1.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 3819 of SEQ ID NO: 2, 8 or 9, a nucleotide sequence having at least 99%, 98%, 97%, 96%, 95%, 90%, 85%, or 80% identity to the nucleotide sequence of nucleotides 49 to 3819 of SEQ ID NO: 2, 8 or 9, or a fragment of the nucleotide sequence of nucleotides 49 to 3819 of SEQ ID NO: 2, 8 or 9, or the nucleotide sequence having at least 99%, 98%, 97%, 96%, 95%, 90%, 85%, or 80% identity to the nucleotide sequence of nucleotides 49 to 3819 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 1273 of SEQ ID NO: 1 or 7, an amino acid sequence having at least 99%, 98%, 97%, 96%, 95%, 90%, 85%, or 80% identity to the amino acid sequence of amino acids 17 to 1273 of SEQ ID NO: 1 or 7, or an immunogenic fragment of the amino acid sequence of amino acids 17 to 1273 of SEQ ID NO: 1 or 7, or the amino acid sequence having at least 99%, 98%, 97%, 96%, 95%, 90%, 85%, or 80% identity to the amino acid sequence of amino acids 17 to 1273 of SEQ ID NO: 1 or 7.

In one embodiment, an amino acid sequence comprising a SARS-CoV-2 S protein, an immunogenic variant thereof, or an immunogenic fragment of the SARS-CoV-2 S protein or the immunogenic variant thereof comprises a secretory signal peptide.

In one embodiment, a secretory signal peptide is fused, preferably N-terminally, to a SARS-CoV-2 S protein, an immunogenic variant thereof, or an immunogenic fragment of the SARS-CoV-2 S protein or the immunogenic variant thereof.

In one embodiment, (i) the RNA encoding the secretory signal peptide comprises the nucleotide sequence of nucleotides 1 to 48 of SEQ ID NO: 2, 8 or 9, a nucleotide sequence having at least 99%, 98%, 97%, 96%, 95%, 90%, 85%, or 80% identity to the nucleotide sequence of nucleotides 1 to 48 of SEQ ID NO: 2, 8 or 9, or a fragment of the nucleotide sequence of nucleotides 1 to 48 of SEQ ID NO: 2, 8 or 9, or the nucleotide sequence having at least 99%, 98%, 97%, 96%, 95%, 90%, 85%, or 80% identity to the nucleotide sequence of nucleotides 1 to 48 of SEQ ID NO: 2, 8 or 9; and/or (ii) the secretory signal peptide comprises the amino acid sequence of amino acids 1 to 16 of SEQ ID NO: 1, an amino acid sequence having at least 99%, 98%, 97%, 96%, 95%, 90%, 85%, or 80% identity to the amino acid sequence of amino acids 1 to 16 of SEQ ID NO: 1, or a functional fragment of the amino acid sequence of amino acids 1 to 16 of SEQ ID NO: 1, or the amino acid sequence having at least 99%, 98%, 97%, 96%, 95%, 90%, 85%, or 80% identity to the amino acid sequence of amino acids 1 to 16 of SEQ ID NO: 1.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of SEQ ID NO: 6, a nucleotide sequence having at least 99%, 98%, 97%, 96%, 95%, 90%, 85%, or 80% identity to the nucleotide sequence of SEQ ID NO: 6, or a fragment of the nucleotide sequence of SEQ ID NO: 6, or the nucleotide sequence having at least 99%, 98%, 97%, 96%, 95%, 90%, 85%, or 80% identity to the nucleotide sequence of SEQ ID NO: 6; and/or (ii) a SARS-CoV-2 S protein, an immunogenic variant thereof, or an immunogenic fragment of the SARS-CoV-2 S protein or the immunogenic variant thereof comprises the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5.

In one embodiment, (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 54 to 986 of SEQ ID NO: 30, a nucleotide sequence having at least 99%, 98%, 97%, 96%, 95%, 90%, 85%, or 80% identity to the nucleotide sequence of nucleotides 54 to 986 of SEQ ID NO: 30, or a fragment of the nucleotide sequence of nucleotides 54 to 986 of SEQ ID NO: 30, or the nucleotide sequence having at least 99%, 98%, 97%, 96%, 95%, 90%, 85%, or 80% identity to the nucleotide sequence of nucleotides 54 to 986 of SEQ ID NO: 30; and/or (ii) a SARS-CoV-2 S protein, an immunogenic variant thereof, or an immunogenic fragment of the SARS-CoV-2 S protein or the immunogenic variant thereof comprises the amino acid sequence of amino acids 1 to 311 of SEQ ID NO: 29, an amino acid sequence having at least 99%, 98%, 97%, 96%, 95%, 90%, 85%, or 80% identity to the amino acid sequence of amino acids 1 to 311 of SEQ ID NO: 29, or an immunogenic fragment of the amino acid sequence of amino acids 1 to 311 of SEQ ID NO: 29, or the amino acid sequence having at least 99%, 98%, 97%, 96%, 95%, 90%, 85%, or 80% identity to the amino acid sequence of amino acids 1 to 311 of SEQ ID NO: 29.

In one embodiment, RNA is modified RNA, in particular stabilized mRNA. In one embodiment, RNA comprises a modified nucleoside in place of at least one uridine. In one embodiment, RNA comprises a modified nucleoside in place of each uridine. In one embodiment, a modified nucleoside is independently selected from pseudouridine (ψ), N1-methyl-pseudouridine (m1ψ), and 5-methyl-uridine (m5U).

In one embodiment, RNA comprises a modified nucleoside in place of uridine.

In one embodiment, the modified nucleoside is selected from pseudouridine (ψ), N1-methyl-pseudouridine (m1ψ), and 5-methyl-uridine (m5U).

In one embodiment, RNA comprises a cap.

In one embodiment, RNA encoding an amino acid sequence comprising a SARS-CoV-2 S protein, an immunogenic variant thereof, or an immunogenic fragment of the SARS-CoV-2 S protein or the immunogenic variant thereof comprises a 5' UTR comprising the nucleotide sequence of SEQ ID NO: 12, or a nucleotide sequence having at least 99%, 98%, 97%, 96%, 95%, 90%, 85%, or 80% identity to the nucleotide sequence of SEQ ID NO: 12.

In one embodiment, RNA encoding an amino acid sequence comprising a SARS-CoV-2 S protein, an immunogenic variant thereof, or an immunogenic fragment of the SARS-CoV-2 S protein or the immunogenic variant thereof comprises a 3' UTR comprising the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

In one embodiment, RNA encoding an amino acid sequence comprising a SARS-CoV-2 S protein, an immunogenic variant thereof, or an immunogenic fragment of the SARS-CoV-2 S protein or the immunogenic variant thereof comprises a poly-A sequence.

In one embodiment, a poly-A sequence comprises at least 100 nucleotides.

In one embodiment, a poly-A sequence comprises or consists of the nucleotide sequence of SEQ ID NO: 14.

In one embodiment, RNA is formulated as a liquid, a solid, or a combination thereof.

In one embodiment, RNA is administered by injection.

In one embodiment, RNA is administered by intramuscular administration.

In one embodiment, RNA is formulated as particles.

In one embodiment, the particles are lipid nanoparticles (LNP) or lipoplex (LPX) particles.

In one embodiment, LNPs comprise ((4-hydroxybutyl) azanediyl)bis(hexane-6,1-diyl)bis(2-hexyldecanoate), 2-[(polyethylene glycol)-2000]-N,N-ditetradecylacetamide, 1,2-Distearoyl-sn-glycero-3-phosphocholine, and cholesterol.

In one embodiment, RNA lipoplex particles are obtainable by mixing RNA with liposomes. In one embodiment, RNA lipoplex particles are obtainable by mixing RNA with lipids.

In one embodiment, RNA is formulated as colloid. In one embodiment, RNA is formulated as particles, forming the dispersed phase of a colloid. In one embodiment, 50% or more, 75% or more, or 85% or more of RNA are present in the dispersed phase. In one embodiment, RNA is formulated as particles comprising RNA and lipids. In one embodiment, particles are formed by exposing RNA, dissolved in an aqueous phase, with lipids, dissolved in an organic phase. In one embodiment, the organic phase comprises ethanol. In one embodiment, particles are formed by exposing RNA, dissolved in an aqueous phase, with lipids, dispersed in an aqueous phase. In one embodiment, the lipids dispersed in an aqueous phase form liposomes.

In one embodiment, RNA is mRNA or saRNA.

In one embodiment, a method disclosed herein is a method for vaccination against coronavirus.

In one embodiment, a method disclosed herein is a method for therapeutic or prophylactic treatment of a coronavirus infection.

In one embodiment, a subject is a human.

In one embodiment, the coronavirus is a betacoronavirus.

In one embodiment, the coronavirus is a sarbecovirus.

In one embodiment, the coronavirus is SARS-CoV-2.

In one embodiment of methods described herein, a composition described herein is administered to a subject.

In one aspect, the present disclosure relates to a composition or medical preparation described herein for use in a method described herein.

Among other things, the present disclosure teaches that a composition comprising a lipid nanoparticle encapsulated RNA encoding at least a portion (e.g., that is or comprises an epitope) of a SARS-CoV-2-encoded polypeptide (e.g., of a SARS-CoV-2-encoded S protein) can achieve detectable antibody titer against an epitope in serum within 7 days after administration to a population of adult human subjects according to a regimen that includes administration of at least one dose of the composition. Moreover, the present disclosure teaches persistence of such antibody titer. In some embodiments, such antibody titer is increased when a modified mRNA is used, as compared with titer achieved with a corresponding unmodified mRNA.

In some embodiments, a provided regimen includes at least one dose. In some embodiments, a provided regimen includes a first dose and at least one subsequent dose. In some embodiments, the first dose is the same amount as at least one subsequent dose. In some embodiments, the first dose is the same amount as all subsequent doses. In some embodiments, the first dose is a different amount as at least one subsequent dose. In some embodiments, the first dose is a different amount than all subsequent doses. In some embodiments, a provided regimen comprises two doses. In some embodiments, a provided regimen consists of two doses.

In particular embodiments, an immunogenic composition is formulated as a single-dose in a container, e.g., a vial. In some embodiments, an immunogenic composition is formulated as a multi-dose formulation in a vial. In some embodiments, the multi-dose formulation includes at least 2 doses per vial. In some embodiments, the multi-dose formulation includes a total of 2-20 doses per vial, such as, for example, 2, 3, 4, 5, 6, 7, 8, 9, 10, 11, or 12 doses per vial. In some embodiments, each dose in the vial is equal in volume. In some embodiments, a first dose is a different volume than a subsequent dose.

A "stable" multi-dose formulation exhibits no unacceptable levels of microbial growth, and substantially no or no breakdown or degradation of the active biological molecule component(s). As used herein, a "stable" immunogenic composition includes a formulation that remains capable of eliciting a desired immunologic response when administered to a subject.

In some embodiments, a multi-dose formulation remains stable for a specified time with multiple or repeated inoculations/insertions into the multi-dose container. For example, in some embodiments a multi-dose formulation may be stable for at least three days with up to ten usages, when contained within a multi-dose container. In some embodiments, multi-dose formulations remain stable with 2-20 inoculations/insertions.

In some embodiments, administration of a composition comprising a lipid nanoparticle encapsulated RNA (e.g., in some embodiments mRNA) encoding at least a portion (e.g., that is or comprises an epitope) of a SARS-CoV-2-encoded polypeptide (e.g., of a SARS-CoV-2-encoded S protein), e.g., according to a regimen as described herein, may result in lymphopenia in some subjects (e.g., in all subjects, in most subjects, in about 50% or fewer, in about 40% or fewer, in about 40% or fewer, in about 25% or fewer, in about 20% or fewer, in about 15% or fewer, in about 10% or fewer, in about 5% or fewer, etc). Among other things, the present disclosure teaches that such lymphopenia can resolve over time. For example, in some embodiments, lymphopenia resolves within about 14, about 10, about 9, about 8, about 7 days or less. In some embodiments, lymphopenia is Grade 3, Grade 2, or less.

Thus, among other things, the present disclosure provides compositions comprising a lipid nanoparticle encapsulated RNA (e.g., in some embodiments mRNA) encoding at least a portion (e.g., that is or comprises an epitope) of a SARS-CoV-2-encoded polypeptide (e.g., of a SARS-CoV-2-encoded S protein) that are characterized, when administered to a relevant population of adults, to display certain characteristics (e.g., achieve certain effects) as described herein. In some embodiments, provided compositions may have been prepared, stored, transported, characterized, and/or used under conditions where temperature does not exceed a particular threshold. Alternatively or additionally, in some embodiments, provided compositions may have been protected from light (e.g., from certain wavelengths) during some or all of their preparation, storage, transport, characterization, and/or use. In some embodiments, one or more features of provided compositions (e.g., RNA stability, as may be assessed, for example, by one or more of size, presence of particular moiety or modification, etc; lipid nanoparticle stability or aggregation, pH, etc) may be or have been assessed at one or more points during preparation, storage, transport, and/or use prior to administration.

Among other things, the present disclosure documents that certain provided compositions in which nucleotides within an RNA (e.g., in some embodiments mRNA) are not modified (e.g., are naturally-occurring A, U, C, G), and/or provided methods relating to such compositions, are characterized (e.g., when administered to a relevant population, which may in some embodiments be or comprise an adult population), by an intrinsic adjuvant effect. In some embodiments, such a composition and/or method can induce an antibody and/or a T cell response. In some embodiments, such a composition and/or method can induce a higher T cell response, as compared to conventional vaccines (e.g., non-RNA vaccines such as protein vaccines).

Alternatively or additionally, the present disclosure documents that provided compositions (e.g., compositions comprising a lipid nanoparticle encapsulated RNA encoding at least a portion (e.g., that is or comprises an epitope) of a SARS-CoV-2-encoded polypeptide (e.g., of a SARS-CoV-2-encoded S protein)) in which nucleotides within an RNA are modified, and/or provided methods relating to such compositions, are characterized (e.g., when administered to a relevant population, which may in some embodiments be or comprise an adult population), by absence of an intrinsic adjuvant effect, or by a reduced intrinsic adjuvant effect as compared with an otherwise comparable composition (or method) with unmodified results. Alternatively or additionally, in some embodiments, such compositions (or methods) are characterized in that they (e.g., when administered to a relevant population, which may in some embodiments be or comprise an adult population) induce an antibody response and/or a CD4+ T cell response. Still further alternatively or additionally, in some embodiments, such compositions (or methods) are characterized in that they (e.g., when administered to a relevant population, which may in some embodiments be or comprise an adult population) induce a higher CD4+ T cell response than that observed with an alternative vaccine format (e.g., a peptide vaccine). In some embodiments involving modified nucleotides, such modified nucleotides may be present, for example, in a 3' UTR sequence, an antigen-encoding sequence, and/or a 5'UTR sequence. In some embodiments, modified nucleotides are or include one or more modified uracil residues and/or one or more modified cytosine residues.

Among other things, the present disclosure documents that provided (e.g., compositions comprising a lipid nanoparticle encapsulated RNA encoding at least a portion (e.g., that is or comprises an epitope) of a SARS-CoV-2-encoded polypeptide (e.g., of a SARS-CoV-2-encoded S protein)) and/or methods are characterized by (e.g., when administered to a relevant population, which may in some embodiments be or comprise an adult population) sustained expression of an encoded polypeptide (e.g., of a SARS-CoV-2-encoded protein [such as an S protein] or portion thereof, which portion, in some embodiments, may be or comprise an epitope thereof). For example, in some embodiments, such compositions and/or methods are characterized in that, when administered to a human, they achieve detectable polypeptide expression in a biological sample (e.g., serum) from such human and, in some embodiments, such expression persists for a period of time that is at least at least 36 hours or longer, including, e.g., at least 48 hours, at least 60 hours, at least 72 hours, at least 96 hours, at least 120 hours, at least 148 hours, or longer.

Those skilled in the art, reading the present disclosure, will appreciate that it describes various RNA constructs (e.g., in some embodiments mRNA constructs) encoding at least a portion (e.g., that is or comprises an epitope) of a SARS-CoV-2-encoded polypeptide (e.g., of a SARS-CoV-2-encoded S protein)). Such person of ordinary skill, reading the present disclosure, will particularly appreciate that it describes various RNA constructs (e.g., in some embodiments mRNA constructs) encoding at least a portion of a SARS-CoV-2 S protein, for example at least an RBD portion of a SARS-CoV-2 S protein. Still further, such a person of ordinary skill, reading the present disclosure, will appreciate that it describes particular characteristics and/or advantages of RNA constructs (e.g., in some embodiments mRNA constructs) encoding at least a portion (e.g., that is or comprises an epitope) of a SARS-CoV-2-encoded polypeptide (e.g., of a SARS-CoV-2-encoded S protein). In some embodiments, an RNA construct (e.g., in some embodiments, an mRNA construct) may encode at least one domain of a SARS-CoV-2 encoded polypeptide (e.g., one or more domains of a SARS-CoV-2 encoded polypeptide as described in WO 2021/159040, including, e.g., an N-terminal domain (NTD) of a SARS-CoV-2 Spike protein, a receptor binding domain (RBD) of a SARS-CoV-2 Spike protein, Heptapeptide repeat sequence 1 (HR1) of a SARS-CoV-2 Spike protein, Heptapeptide repeat sequence 2 (HR1) of a SARS-CoV-2 Spike protein, and/or combinations thereof). Among other things, the present disclosure particularly documents surprising and useful characteristics and/or advantages of certain RNA constructs (e.g., in some embodiments mRNA constructs) encoding a SARS-CoV-2 RBD portion and, in some embodiments, not encoding a full length SARS-CoV-2 S protein.

Without wishing to be bound by any particular theory, the present disclosure suggests that provided RNA constructs (e.g., in some embodiments mRNA constructs) that encode less than a full-length SARS-CoV-2 S protein, and particularly those that encode at least an RBD portion of such SARS-CoV-2 S protein may be particularly useful and/or effective for use as or in an immunogenic composition (e.g., a vaccine), and/or for achieving immunological effects as described herein (e.g., generation of SARS-CoV-2 neutralizing antibodies, and/or T cell responses (e.g., CD4+ and/or CD8+ T cell responses)).

In some embodiments, the present disclosure provides an RNA (e.g., mRNA) comprising an open reading frame encoding a polypeptide that comprises a receptor-binding portion of a SARS-CoV-2 S protein, which RNA is suitable for intracellular expression of the polypeptide. In some embodiments, such an encoded polypeptide does not comprise the complete S protein. In some embodiments, an encoded polypeptide comprises the receptor binding domain (RBD), for example, as shown in SEQ ID NO: 5. In some embodiments, the encoded polypeptide comprises the peptide according to SEQ ID NO: 29 or 31. In some embodiments, such an RNA (e.g., mRNA) may be complexed by a (poly)cationic polymer, polyplex(es), protein(s) or peptide(s). In some embodiments, such an RNA may be formulated in a lipid nanoparticle (e.g., ones described herein). In some embodiments, such an RNA (e.g., mRNA) may be particularly useful and/or effective for use as or in an immunogenic composition (e.g., a vaccine), and/or for achieving immunological effects as described herein (e.g., generation of SARS-CoV-2 neutralizing antibodies, and/or T cell responses (e.g., CD4+ and/or CD8+ T cell responses)). In some embodiments, such an RNA (e.g., mRNA) may be useful for vaccinating humans (including, e.g., humans known to have been exposed and/or infected by SARS-CoV-2, and/or humans not known to have been exposed to SARS-CoV-2).

Those skilled in the art, reading the present disclosure, will further appreciate that it describes various mRNA constructs comprising a nucleic acid sequence that encodes a full-length SARS-CoV-2 Spike protein (e.g., including embodiments in which such encoded SARS-CoV-2 Spike protein may comprise at least one or more amino acid substitutions, e.g., proline substitutions as described herein, and/or embodiments in which the mRNA sequence is codon-optimized e.g., for mammalian, e.g., human, subjects). In some embodiments, such a full-length SARS-CoV-2 Spike protein may have an amino acid sequence that is or comprises that set forth in SEQ ID NO: 7. Still further, such a person of ordinary skill, reading the present disclosure, will appreciate, among other things, that it describes particular characteristics and/or advantages of certain mRNA constructs comprising a nucleic acid sequence that encodes a full-length SARS-CoV-2 Spike protein. Without wishing to be bound by any particular theory, the present disclosure suggests that provided mRNA constructs that encode a full-length SARS-CoV-2 S protein may be particularly useful and/or effective for use as or in an immunogenic composition (e.g., a vaccine) in particular subject population (e.g., particular age populations).

For example, in some embodiments, such an mRNA composition may be particularly useful in younger (e.g., less than 25 years old, 20 years old, 18 years old, 15 years, 10 years old, or lower) subjects; alternatively or additionally, in some embodiments, such an mRNA composition may be particularly useful in elderly subjects (e.g., over 55 years old, 60 years old, 65 years old, 70 years old, 75 years old, 80 years old, 85 years old, or higher). In particular embodiments, an immunogenic composition comprising such an mRNA construct provided herein exhibits a minimal to modest increase (e.g., no more than 30% increase, no more than 20% increase, or no more than 10% increase, or lower) in dose level and/or dose number-dependent systemic reactogenicity (e.g., fever, fatigue, headache, chills, diarrhea, muscle pain, and/or joint pain, etc.) and/or local tolerability (e.g., pain, redness, and/or swelling, etc.), at least in some subjects (e.g., in some subject age groups); in some embodiments, such reactogenicity and/or local tolerability is observed particularly, in in younger age group (e.g., less than 25 years old, 20 years old, 18 years old or lower) subjects, and/or in older (e.g., elderly) age group (e.g., 65-85 years old). In some embodiments, provided mRNA constructs that encode a full-length SARS-CoV-2 S protein may be particularly useful and/or effective for use as or in an immunogenic composition (e.g., a vaccine) for inducing SARS-CoV-2 neutralizing antibody response level in a population of subjects that are at high risk for severe diseases associated with SARS-CoV-2 infection (e.g., an elderly population, for example, 65-85 year-old group). In some embodiments, a person of ordinary skill, reading the present disclosure, will appreciate, among other things, that provided mRNA constructs that encode a full-length SARS-CoV-2 S protein, which exhibit a favorable reactogenicity profile (e.g., as described herein) in younger and elderly age populations, may be particularly useful and/or effective for use as or in an immunogenic composition (e.g., a vaccine) for achieving immunological effects as described herein (e.g., generation of SARS-CoV-2 neutralizing antibodies, and/or T cell responses (e.g., CD4+ and/or CD8+ T cell responses)). In some embodiments, the present disclosure also suggests that provided mRNA constructs that encode a full-length SARS-CoV-2 S protein may be particularly effective to protect against SARS-CoV-2 infection, as characterized by earlier clearance of SARS-CoV-2 viral RNA in non-human mammalian subjects (e.g., rhesus macaques) that were immunized with immunogenic compositions comprising such mRNA constructs and subsequently challenged by SARS-CoV-2 strain. In some embodiments, such earlier clearance of SARS-CoV-2 viral RNA may be observed in the nose of non-human mammalian subjects (e.g., rhesus macaques) that were immunized with immunogenic compositions comprising such mRNA constructs and subsequently challenged by SARS-CoV-2 strain.

In some embodiments, the present disclosure provides an RNA (e.g., mRNA) comprising an open reading frame encoding a full-length SARS-CoV-2 S protein (e.g., a full-length SARS-CoV-2 S protein with one or more amino acid substitutions), which RNA is suitable for intracellular expression of the polypeptide. In some embodiments, the encoded polypeptide comprises the amino acid sequence of SEQ ID NO:7. In some embodiments, such an RNA (e.g., mRNA) may be complexed by a (poly)cationic polymer, polyplex(es), protein(s) or peptide(s). In some embodiments, such an RNA may be formulated in a lipid nanoparticle (e.g., ones described herein).

In some embodiments, an immunogenic composition provided herein may comprise a plurality of (e.g., at least two or more, including, e.g., at least three, at least four, at least five, at least six, at least seven, at least eight, at least nine, at least ten, etc.) immunoreactive epitopes of a SARS-CoV-2 polypeptide or variants thereof. In some such embodiments, such a plurality of immunoreactive epitopes may be encoded by a plurality of RNAs (e.g., mRNAs). In some such embodiments, such a plurality of immunoreactive epitopes may be encoded by a single RNA (e.g., mRNA). In some embodiments, nucleic acid sequences encoding a plurality of immunoreactive epitopes may be separated from each other in a single RNA (e.g., mRNA) by a linker (e.g., a peptide linker in some embodiments). Without wishing to be bound by any particular theory, in some embodiments, provided polyepitope immunogenic compositions (including, e.g., those that encode a full-length SARS-CoV-2 spike protein) may be particularly useful, when considering the genetic diversity of SARS-CoV-2 variants, to provide protection against numerous viral variants and/or may offer a greater opportunity for development of a diverse and/or otherwise robust (e.g., persistent, e.g., detectable about 5, 10, 15, 20, 25, 30, 35, 40, 45, 50, 55, 60 or more days after administration of one or more doses) neutralizing antibody and/or T cell response, and in particular a particularly robust $T_H1$-type T cell (e.g., CD4+ and/or CD8+ T cell) response.

In some embodiments, the present disclosure documents that provided compositions and/or methods are characterized by (e.g., when administered to a relevant population, which may in some embodiments be or comprise an adult population) in that they achieve one or more particular therapeutic outcomes (e.g., effective immune responses as described herein and/or detectable expression of encoded SARS-CoV-2 S protein or an immunogenic fragment thereof) with a single administration; in some such embodiments, an outcome may be assessed, for example, as compared to that observed in absence of RNA vaccines (e.g., mRNA vaccines) described herein. In some embodiments, a particular outcome may be achieved at a lower dose than required for one or more alternative strategies.

In some embodiments, the present disclosure provides an immunogenic composition comprising an isolated messenger ribonucleic acid (mRNA) polynucleotide, wherein the isolated mRNA polynucleotide comprises an open reading frame encoding a polypeptide that comprises a receptor-binding portion of a SARs-CoV-2 S protein, and wherein the isolated mRNA polynucleotide is formulated in at least one lipid nanoparticle. For example, in some embodiments, such a lipid nanoparticle may comprise a molar ratio of 20-60% ionizable cationic lipid, 5-25% non-cationic lipid (e.g., neutral lipid), 25-55% sterol or steroid, and 0.5-15% polymer-conjugated lipid (e.g., PEG-modified lipid). In some embodiments, a sterol or steroid included in a lipid nanoparticle may be or comprise cholesterol. In some embodiments, a neutral lipid may be or comprise 1,2-distearoyl-sn-glycero-3-phosphocholine (DSPC). In some embodiments, a polymer-conjugated lipid may be or comprise PEG2000 DMG. In some embodiments, such an immunogenic composition may comprise a total lipid content of about 1 mg to 10 mg, or 3 mg to 8 mg, or 4 mg to 6 mg. In some embodiments, such an immunogenic composition may comprise a total lipid content of about 5 mg/mL-15 mg/mL or 7.5 mg/mL-12.5 mg/mL or 9-11 mg/mL. In some embodiments, such an isolated mRNA polynucleotide is provided in an effective amount to induce an immune response in a subject administered at least one dose of the immunogenic composition. In some embodiments, a polypeptide encoded by a provided isolated mRNA polynucleotide does not comprise the complete S protein. In some embodiments, such an isolated mRNA polynucleotide provided in an immunogenic composition is not self-replicating RNA.

In some embodiments, an immune response may comprise generation of a binding antibody titer against SARS-CoV-2 protein (including, e.g., a stabilized prefusion spike trimer in some embodiments) or a fragment thereof. In some embodiments, an immune response may comprise generation of a binding antibody titer against the receptor binding domain (RBD) of the SARS-CoV-2 spike protein. In some embodiments, a provided immunogenic composition has been established to achieve a detectable binding antibody titer after administration of a first dose, with seroconversion in at least 70% (including, e.g., at least 80%, at least 90%, at least 95% and up to 100%) of a population of subjects receiving such a provided immunogenic composition, for example, by about 2 weeks.

In some embodiments, an immune response may comprise generation of a neutralizing antibody titer against SARS-CoV-2 protein (including, e.g., a stabilized prefusion spike trimer in some embodiments) or a fragment thereof. In some embodiments, an immune response may comprise generation of a neutralizing antibody titer against the receptor binding domain (RBD) of the SARS-CoV-2 spike protein. In some embodiments, a provided immunogenic composition has been established to achieve a neutralizing antibody titer in an appropriate system (e.g., in a human infected with SARS-CoV-2 and/or a population thereof, and/or in a model system therefor). For example, in some embodiments, such neutralizing antibody titer may have been demonstrated in one or more of a population of humans, a non-human primate model (e.g., rhesus macaques), and/or a mouse model.

In some embodiments, a neutralizing antibody titer is a titer that is (e.g., that has been established to be) sufficient to reduce viral infection of B cells relative to that observed for an appropriate control (e.g., an unvaccinated control subject, or a subject vaccinated with a live attenuated viral vaccine, an inactivated viral vaccine, or a protein subunit viral vaccine, or a combination thereof). In some such embodiments, such reduction is of at least 30%, 35%, 40%, 45%, 50%, 55%, 60%, 65%, 70%, 75%, 80%, 85%, 90%, 95%, or more.

In some embodiments, a neutralizing antibody titer is a titer that is (e.g., that has been established to be) sufficient to reduce the rate of asymptomatic viral infection relative to that observed for an appropriate control (e.g., an unvaccinated control subject, or a subject vaccinated with a live attenuated viral vaccine, an inactivated viral vaccine, or a protein subunit viral vaccine, or a combination thereof). In some such embodiments, such reduction is of at least 30%, 35%, 40%, 45%, 50%, 55%, 60%, 65%, 70%, 75%, 80%, 85%, 90%, 95%, or more. In some embodiments, such reduction can be characterized by assessment of SARS-CoV-2 N protein serology. Significant protection against asymptomatic infection was also confirmed by real life observations (see also: Dagan N. et al., N Engl J Med. 2021, doi: 10.1056/NEJMoa2101765. Epub ahead of print. PMID: 33626250) In some embodiments, a neutralizing antibody titer is a titer that is (e.g., that has been established to be) sufficient to reduce or block fusion of virus with epithelial cells and/or B cells of a vaccinated subject relative to that observed for an appropriate control (e.g., an unvaccinated control subject, or a subject vaccinated with a live attenuated viral vaccine, an inactivated viral vaccine, or a protein subunit viral vaccine, or a combination thereof). In some such embodiments, such reduction is of at least 30%, 35%, 40%, 45%, 50%, 55%, 60%, 65%, 70%, 75%, 80%, 85%, 90%, 95%, or more.

In some embodiments, induction of a neutralizing antibody titer may be characterized by an elevation in the number of B cells, which in some embodiments may include plasma cells, class-switched IgG1- and IgG2-positive B cells, and/or germinal center B cells. In some embodiments, a provided immunogenic composition has been established to achieve such an elevation in the number of B cells in an appropriate system (e.g., in a human infected with SARS-CoV-2 and/or a population thereof, and/or in a model system therefor). For example, in some embodiments, such an elevation in the number of B cells may have been demonstrated in one or more of a population of humans, a non-human primate model (e.g., rhesus macaques), and/or a mouse model. In some embodiments, such an elevation in the number of B cells may have been demonstrated in draining lymph nodes and/or spleen of a mouse model after (e.g., at least 7 days, at least 8 days, at least 9 days, at least 10 days, at least 11 days, at least 12 days, at least 13 days, at least 14 days, after) immunization of such a mouse model with a provided immunogenic composition.

In some embodiments, induction of a neutralizing antibody titer may be characterized by a reduction in the number of circulating B cells in blood. In some embodiments, a provided immunogenic composition has been established to achieve such a reduction in the number of circulating B cells in blood of an appropriate system (e.g., in a human infected with SARS-CoV-2 and/or a population thereof, and/or in a model system therefor). For example, in some embodiments, such a reduction in the number of circulating B cells in blood may have been demonstrated in one or more of a population of humans, a non-human primate model (e.g., rhesus macaques), and/or a mouse model. In some embodiments, such a reduction in the number of circulating B cells in blood may have been demonstrated in a mouse model after (e.g., at least 4 days, at least 5 days, at least 6 days, at least 7 days, at least 8 days, at least 9 days, at least 10 days, after) immunization of such a mouse model with a provided immunogenic composition. Without wishing to be bound by theory, a reduction in circulating B cells in blood may be due to B cell homing to lymphoid compartments.

In some embodiments, an immune response induced by a provided immunogenic composition may comprise an elevation in the number of T cells. In some embodiments, such an elevation in the number of T cells may include an elevation in the number of T follicular helper (TFH) cells, which in some embodiments may comprise one or more subsets with ICOS upregulation. One of skilled in the art will understand that proliferation of $T_{FH}$ in germinal centres is integral for generation of an adaptive B-cell response, and also that in humans, $T_{FH}$ occurring in the circulation after vaccination is typically correlated with a high frequency of antigen-specific antibodies. In some embodiments, a provided immunogenic composition has been established to achieve such an elevation in the number of T cells (e.g., $T_{FH}$ cells) in an appropriate system (e.g., in a human infected with SARS-CoV-2 and/or a population thereof, and/or in a model system therefor). For example, in some embodiments, such an elevation in the number of T cells (e.g., $T_{FH}$ cells) may have been demonstrated in one or more of a population of humans, a non-human primate model (e.g., rhesus macaques), and/or a mouse model. In some embodiments, such an elevation in the number of T cells (e.g., e.g., $T_{FH}$ cells) may have been demonstrated in draining lymph nodes, spleen, and/or blood of a mouse model after (e.g., at least 4 days, at least 5 days, at least 6 days, at least 7 days, at least 8 days, at least 9 days, at least 10 days, at least 11 days, at least 12 days, at least 13 days, at least 14 days, after) immunization of such a mouse model with a provided immunogenic composition.

In some embodiments, a protective response against SARS-CoV-2 induced by a provided immunogenic composition has been established in an appropriate model system for SARS-CoV-2. For example, in some embodiments, such a protective response may have been demonstrated in an animal model, e.g., a non-human primate model (e.g., rhesus macaques) and/or a mouse model. In some embodiments, a non-human primate (e.g., rhesus macaque) or a population thereof that has/have received at least one immunization with a provided immunogenic composition is/are challenged with SARS-CoV-2, e.g., through intranasal and/or intratracheal route. In some embodiments, such a challenge may be performed several weeks (e.g., 5-10 weeks) after at least one immunization (including, e.g., at least two immunizations) with a provided immunogenic composition. In some embodiments, such a challenge may be performed when a detectable level of a SARS-CoV-2 neutralizing titer (e.g., antibody response to SARS-CoV-2 spike protein and/or a fragment thereof, including, e.g., but not limited to a stabilized prefusion spike trimer, S-2P, and/or antibody response to receptor-binding portion of SARS-CoV-2) is achieved in non-human primate(s) (e.g., rhesus macaque(s)) that has received at least one immunization (including, e.g., at least two immunizations) with a provided immunogenic composition. In some embodiments, a protective response is characterized by absence of or reduction in detectable viral RNA in bronchoalveolar lavage (BAL) and/or nasal swabs of challenged non-human primate(s) (e.g., rhesus macaque(s)). In some embodiments, immunogenic compositions described herein may have been characterized in that a larger percent of challenged animals, for example, non-human primates in a population (e.g., rhesus macaques), that have received at least one immunization (including, e.g., at least two immunizations) with a provided immunogenic composition display absence of detectable RNA in their BAL and/or nasal swab, as compared to a population of non-immunized animals, for example, non-human primates (e.g., rhesus macaques). In some embodiments, immunogenic compositions described herein may have been characterized in that challenged animals, for example, non-human in a population (e.g., rhesus macaques), that have received at least one immunization (including, e.g., at least two immunizations) with a provided immunogenic composition may show clearance of viral RNA in nasal swab no later than 10 days, including, e.g., no later than 8 days, no later than 6 days, no later than 4 days, etc., as compared to a population of non-immunized animals, for example, non-human primates (e.g., rhesus macaques).

In some embodiments, immunogenic compositions described herein when administered to subjects in need thereof do not substantially increase the risk of vaccine-associated enhanced respiratory disease. In some embodiments, such vaccine-associated enhanced respiratory disease may be associated with antibody-dependent enhancement of replication and/or with vaccine antigens that induced antibodies with poor neutralizing activity and Th2-biased responses. In some embodiments, immunogenic compositions described herein when administered to subjects in need thereof do not substantially increase the risk of antibody-dependent enhancement of replication.

In some embodiments, a single dose of an RNA composition (e.g., mRNA formulated in lipid nanoparticles) can induce a therapeutic antibody response in less than 10 days of vaccination. In some embodiments, such a therapeutic antibody response may be characterized in that when such an RNA vaccine can induce production of about 10-100 μg/mL IgG measured at 10 days after vaccination at a dose of 0.1 to 10 μg or 0.2-5 μg in an animal model. In some embodiments, such a therapeutic antibody response may be characterized in that such an RNA vaccine induces about 100-1000 μg/mL IgG measured at 20 days of vaccination at a dose of 0.1 to 10 μg or 0.2-5 μg in an animal model. In some embodiments, a single dose may induce a pseudovirus-neutralization titer, as measured in an animal model, of 10-200 pVN50 titer 15 days after vaccination. In some embodiments, a single dose may induce a pseudovirus-neutralization titer, as measured in an animal model, of 50-500 pVN50 titer 15 days after vaccination.

In some embodiments, a single dose of an RNA composition (e.g., mRNA composition) can expand antigen-specific CD8 and/or CD4 T cell response by at least at 50% or more (including, e.g., at least 60%, at least 70%, at least 80%, at least 90%, at least 95%, or more), as compared to that observed in absence of such an RNA construct encoding a SARS-COV2 immunogenic protein or fragment thereof (e.g., spike protein and/or receptor binding domain). In some embodiments, a single dose of an RNA composition can expand antigen-specific CD8 and/or CD4 T cell response by at least at 1.5-fold or more (including, e.g., at least 2-fold, at least 3-fold, at least 5-fold, at least 10-fold, at least 50-fold, at least 100-fold, at least 500-fold, at least 1000-fold, or more), as compared to that observed in absence of such an RNA construct encoding a SARS-COV2 immunogenic protein or fragment thereof (e.g., spike protein and/or receptor binding domain).

In some embodiments, a regimen (e.g., a single dose of an mRNA composition) can expand T cells that exhibit a Th1 phenotype (e.g., as characterized by expression of IFN-gamma, IL-2, IL-4, and/or IL-5) by at least at 50% or more (including, e.g., at least 60%, at least 70%, at least 80%, at least 90%, at least 95%, or more), as compared to that observed in absence of such an mRNA construct encoding a SARS-COV2 immunogenic protein or fragment thereof (e.g., spike protein and/or receptor binding domain). In some embodiments, a regimen (e.g., a single dose of an mRNA composition) can expand T cells that exhibit a Th1 phenotype (e.g., as characterized by expression of IFN-gamma, IL-2, IL-4, and/or IL-5), for example by at least at 1.5-fold or more (including, e.g., at least 2-fold, at least 3-fold, at least 5-fold, at least 10-fold, at least 50-fold, at least 100-fold, at least 500-fold, at least 1000-fold, or more), as compared to that observed in absence of such an mRNA construct encoding a SARS-COV2 immunogenic protein or fragment thereof (e.g., spike protein and/or receptor binding domain). In some embodiments, a T-cell phenotype may be or comprise a Th1-dominant cytokine profile (e.g., as characterized by INF-gamma positive and/or IL-2 positive), and/or no by or biologically insignificant IL-4 secretion.

In some embodiments, a regimen as described herein (e.g., one or more doses of an mRNA composition) induces and/or achieves production of RBD-specific CD4+ T cells. Among other things, the present disclosure documents that mRNA compositions encoding an RBD-containing portion of a SARS-CoV-2 spike protein (e.g., and not encoding a full-length SARS-CoV-2 spike protein) may be particularly useful and/or effective in such induction and/or production of RBD-specific CD4+ T cells. In some embodiments, RBD-specific CD4+ T-cells induced by an mRNA composition described herein (e.g., by an mRNA composition that encodings an RBD-containing-portion of a SARS-CoV-2 spike protein and, in some embodiments not encoding a full-length SARS-CoV-2 spike protein) demonstrate a Th1-dominant cytokine profile (e.g., as characterized by INF-gamma positive and/or IL-2 positive), and/or by no or biologically insignificant IL-4 secretion.

In some embodiments, characterization of CD4+ and/or CD8+ T cell responses (e.g., described herein) in subjects receiving RNA compositions (e.g., as described herein) may be performed using ex vivo assays using PBMCs collected from the subjects.

In some embodiments, immunogenicity of RNA (e.g., mRNA) compositions described herein may be assessed by one of or more of the following serological immunogenicity assays: detection of IgG, IgM, and/or IgA to SARS-CoV-2 S protein present in blood samples of a subject receiving a provided RNA composition, and/or neutralization assays using SARS-CoV-2 pseudovirus and/or a wild-type SARS-CoV-2 virus.

In some embodiments, an RNA composition (e.g., as described herein) provide a relatively low adverse effect (e.g., Grade 1-Grade 2 pain, redness and/or swelling) within 7 days after vaccinations at a dose of 10 ug-100 ug or 1 ug-50 ug. In some embodiments, RNA compositions (e.g., as described herein) provide a relatively low observation of systemic events (e.g., Grade 1-Grade 2 fever, fatigue, headache, chills, vomiting, diarrhea, muscle pain, joint pain, medication, and combinations thereof) within 7 days after vaccinations at a dose of 10 ug-100 ug.

In some embodiments, RNA (e.g., mRNA) compositions are characterized in that when administered to subjects at 10-100 ug dose or 1 ug-50 ug, IgG directed to a SARS-CoV2 immunogenic protein or fragment thereof (e.g., spike protein and/or receptor binding domain) may be produced at a level of 100-100,000 U/mL or 500-50,000 U/mL 21 days after vaccination.

In some embodiments, an RNA (e.g., mRNA) encodes a natively-folded trimeric receptor binding protein of SARS-CoV-2. In some embodiments, an RNA (e.g., mRNA) encodes a variant of such receptor binding protein such that the encoded variant binds to ACE2 at a Kd of 10 pM or lower, including, e.g., at a Kd of 9 pM, 8 pM, 7 pM, 6 pM, 5 pM, 4 pM, or lower. In some embodiments, an RNA (e.g., mRNA) encodes a variant of such receptor binding protein such that the encoded variant binds to ACE2 at a Kd of 5 pM. In some embodiments, an RNA (e.g., mRNA) encodes a trimeric receptor binding portion of SARS-CoV-2 that comprises an ACE2 receptor binding site. In some embodiments, an RNA (e.g., mRNA) comprises a coding sequence for a receptor-binding portion of SARS-CoV-2 and a trimerization domain (e.g., a natural trimerization domain (foldon) of T4 fibritin) such that the coding sequence directs expression of a trimeric protein that has an ACE2 receptor binding site and binds ACE2. In some embodiments, an RNA (e.g., mRNA) encodes a trimeric receptor binding portion of SARS-CoV-2 or a variant thereof such that its Kd is smaller than that for a monomeric receptor-binding domain (RBD) of SARS-CoV-2. For example, in some embodiments, an RNA (e.g., mRNA) encodes a trimeric receptor binding portion of SARS-CoV-2 or a variant thereof such that its Kd is at least 10-fold (including, e.g., at least 50-fold, at least 100-fold, at least 500-fold, at least 1000-fold, etc.) smaller than that for a RBD of SARS-CoV-2.

In some embodiments, a trimer receptor binding portion of SARS-CoV-2 encoded by an RNA (e.g., as described herein) may be determined to have a size of about 3-4 angstroms when it is complexed with ACE2 and $B^0AT1$ neutral amino acid transporter in a closed conformation, as characterized by electron cryomicroscopy (cryoEM). In some embodiments, geometric mean SARS-CoV-2 neutralizing titer that characterizes and/or is achieved by an RNA composition or method as described herein can reach at least 1.5-fold, including, at least 2-fold, at least 2.5-fold, at least 3-fold, or higher, that of a COVID-19 convalescent human panel (e.g., a panel of sera from COVID-19 convalescing humans obtained 20-40 days after the onset of symptoms and at least 14 days after the start of asymptomatic convalescence.

In some embodiments, RNA compositions as provided herein may be characterized in that subjects who have been treated with such compositions (e.g., with at least one dose, at least two doses, etc) may show reduced and/or more transient presence of viral RNA in relevant site(s) (e.g., nose and/or lungs, etc, and/or any other tissue susceptible to infection) as compared with an appropriate control (e.g., an established expected level for a comparable subject or population not having been so treated and having been exposed to virus under reasonably comparable exposure conditions)

In some embodiments, the RBD antigen expressed by an mRNA construct (e.g., as described herein) can be modified by addition of a T4-fibritin-derived “foldon” trimerization domain, for example, to increase its immunogenicity.

In some embodiments, RNA (e.g., mRNA) compositions and/or methods described herein are characterized in that certain local reactions (e.g., pain, redness, and/or swelling, etc.) and/or systemic events (e.g., fever, fatigue, headache, etc.) may appear and/or peak at Day 2 after vaccination. In some embodiments, RNA (e.g., mRNA) compositions described herein are characterized in that certain local reactions (e.g., pain, redness, and/or swelling, etc.) and/or systemic events (e.g., fever, fatigue, headache, etc.) may resolve by Day 7 after vaccination. In some embodiments, RNA compositions (e.g., mRNA) and/or methods described herein are characterized in that no Grade 1 or greater change in routine clinical laboratory values or laboratory abnormalities are observed in subjects receiving RNA compositions (e.g., as described herein). Examples of such clinical laboratory assays may include lymphocyte count, hematological changes, etc.

In some embodiments, RNA (e.g., mRNA) compositions and/or methods described herein are characterized in that by 21 days after a first dose (e.g., 10-100 ug inclusive or 1 ug-50 ug inclusive), geometric mean concentrations (GMCs) of IgG directed to a SARS-CoV-2 S polypeptide or an immunogenic fragment thereof (e.g., RBD) may reach 200-3000 units/mL or 500-3000 units/mL or 500-2000 units/mL, compared to 602 units/mL for a panel of COVID-19 convalescent human sera. In some embodiments, RNA (e.g., mRNA) compositions described herein are characterized in that by 7 days after a second dose (e.g., 10-30 ug inclusive; or 1 ug-50 ug inclusive), geometric mean concentrations (GMCs) of IgG directed to a SARS-CoV-2 spike polypeptide or an immunogenic fragment thereof (e.g., RBD) may increase by at least 8-fold or higher, including, e.g., at least 9-fold, at least 10-fold, at least 15-fold, at least 20-fold, at least 25-fold, at least 30-fold, at least 35-fold, at least 40-fold, or higher. In some embodiments, RNA (e.g., mRNA) compositions described herein are characterized in that by 7 days after a second dose (e.g., 10-30 ug inclusive; or 1 ug-50 ug inclusive), geometric mean concentrations (GMCs) of IgG directed to a SARS-CoV-2 S polypeptide or an immunogenic fragment thereof (e.g., RBD) may increase to 1500 units/mL to 40,000 units/mL or 4000 units/mL to 40,000 units/mL. In some embodiments, antibody concentrations described herein can persist to at least 20 days or longer, including, e.g., at least 25 days, at least 30 days, at least 35 days, at least 40 days, at least 45 days, at least 50 days, after a first dose, or at least 10 days or longer, including, e.g., at least 15 days, at least 20 days, at least 25 days, or longer, after a second dose. In some embodiments, antibody concentrations can persist to 35 days after a first dose, or at least 14 days after a second dose.

In some embodiments, RNA (e.g., mRNA) compositions described herein are characterized in that when measured at 7 days after a second dose (e.g., 1-50 ug inclusive), GMC of IgG directed to a SARS-CoV-2 S polypeptide or an immunogenic fragment thereof (e.g., RBD) is at least 30% higher (including, e.g., at least 40% higher, at least 50% higher, at least 60%, higher, at least 70% higher, at least 80% higher, at least 90% higher, at least 95% higher, as compared to antibody concentrations observed in a panel of COVID-19 convalescent human serum. In many embodiments, geometric mean concentration (GMC) of IgG described herein is GMCs of RBD-binding IgG.

In some embodiments, RNA (e.g., mRNA) compositions described herein are characterized in that when measured at 7 days after a second dose (e.g., 10-50 ug inclusive), GMC of IgG directed to a SARS-CoV-2 S polypeptide or an immunogenic fragment thereof (e.g., RBD) is at least 1.1-fold higher (including, e.g., at least 1.5-fold, at least 2-fold, at least 3-fold, at least 4-fold, at least 5-fold, at least 6-fold higher, at least 7-fold higher, at least 8-fold higher, at least 9-fold higher, at least 10-fold higher, at least 15-fold higher, at least 20-fold higher, at least 25-fold higher, at least 30-fold higher), as compared to antibody concentrations observed in a panel of COVID-19 convalescent human serum, In many embodiments, geometric mean concentration (GMC) of IgG described herein is GMCs of RBD-binding IgG.

In some embodiments, RNA (e.g., mRNA) compositions described herein are characterized in that when measured at 21 days after a second dose, GMC of IgG directed to a SARS-CoV-2 S polypeptide or an immunogenic fragment thereof (e.g., RBD) is at least 5-fold higher (including, e.g., at least 6-fold higher, at least 7-fold higher, at least 8-fold higher, at least 9-fold higher, at least 10-fold higher, at least 15-fold higher, at least 20-fold higher, at least 25-fold higher, at least 30-fold higher), as compared to antibody concentrations observed in a panel of COVID-19 convalescent human serum, In many embodiments, geometric mean concentration (GMC) of IgG described herein is GMCs of RBD-binding IgG.

In some embodiments, RNA (e.g., mRNA) compositions and/or methods described herein are characterized in that an increase (e.g., at least 30%, at least 40%, at least 50%, or more) in SARS-CoV-2 neutralizing geometric mean titers (GMTs) is observed 21 days after a first dose. In some embodiments, RNA (e.g., mRNA) compositions described herein are characterized in that a substantially greater serum neutralizing GMTs are achieved 7 days after subjects receive a second dose (e.g., 10 pg-30 pg inclusive), reaching 150-300, compared to 94 for a COVID-19 convalescent serum panel.

In some embodiments, RNA (e.g., mRNA) compositions and/or methods described herein are characterized in that 7 days after administration of the second dose, the protective efficacy is at least 60%, e.g., at least 70%, at least 80%, at least 90, or at least 95%. In one embodiment, RNA (e.g., mRNA) compositions and/or methods described herein are characterized in that 7 days after administration of the second dose, the protective efficacy is at least 70%. In one embodiment, RNA (e.g., mRNA) compositions and/or methods described herein are characterized in that 7 days after administration of the second dose, the protective efficacy is at least 80%. In one embodiment, RNA (e.g., mRNA) compositions and/or methods described herein are characterized in that 7 days after administration of the second dose, the protective efficacy is at least 90%. In one embodiment, RNA (e.g., mRNA) compositions and/or methods described herein are characterized in that 7 days after administration of the second dose, the protective efficacy is at least 95%.

In some embodiments, an RNA composition provided herein is characterized in that it induces an immune response against SARS-CoV-2 after at least 7 days after a dose (e.g., after a second dose). In some embodiments, an RNA composition provided herein is characterized in that it induces an immune response against SARS-CoV-2 in less than 14 days after a dose (e.g., after a second dose). In some embodiments, an RNA composition provided herein is characterized in that it induces an immune response against SARS-CoV-2 after at least 7 days after a vaccination regimen. In some embodiments, a vaccination regimen comprises a first dose and a second dose. In some embodiments, a first dose and a second dose are administered by at least 21 days apart. In some such embodiments, an immune response against SARS-CoV-2 is induced at least after 28 days after a first dose.

In some embodiments, RNA (e.g., mRNA) compositions and/or methods described herein are characterized in that geometric mean concentration (GMCs) of antibodies directed to a SARS-CoV-2 spike polypeptide or an immunogenic fragment thereof (e.g., RBD), as measured in serum from subjects receiving RNA (e.g., mRNA) compositions of the present disclosure (e.g., at a dose of 10-30 ug inclusive), is substantially higher than in a convalescent serum panel (e.g., as described herein). In some embodiments where a subject may receive a second dose (e.g., 21 days after 1 first dose), geometric mean concentration (GMCs) of antibodies directed to a SARS-CoV-2 spike polypeptide or an immunogenic fragment thereof (e.g., RBD), as measured in serum from the subject, may be 8.0-fold to 50-fold higher than a convalescent serum panel GMC. In some embodiments where a subject may receive a second dose (e.g., 21 days after 1 first dose), geometric mean concentration (GMCs) of antibodies directed to a SARS-CoV-2 spike polypeptide or an immunogenic fragment thereof (e.g., RBD), as measured in serum from the subject, may be at least 8.0-fold or higher, including, e.g., at least 10-fold, at least 20-fold, at least 30-fold, at least 40-fold, at least 50-fold, at least 60-fold or higher, as compared to a convalescent serum panel GMC.

In some embodiments, RNA (e.g., mRNA) compositions and/or methods described herein are characterized in that the SARS-CoV-2 neutralizing geometric mean titer, as measured at 28 days after a first dose or 7 days after a second dose, may be at least 1.5-fold or higher (including, e.g., at least 2-fold, at least 2.5-fold, at least 3-fold, at least 3.5-fold or higher), as compared to a neutralizing GMT of a convalescent serum panel.

In some embodiments, a regimen administered to a subject may be or comprise a single dose. In some embodiments, a regimen administered to a subject may comprise a plurality of doses (e.g., at least two doses, at least three doses, or more). In some embodiments, a regimen administered to a subject may comprise a first dose and a second dose, which are given at least 2 weeks apart, at least 3 weeks apart, at least 4 weeks apart, or more. In some embodiments, such doses may be at least 1 month, at least 2 months, at least 3 months, at least 4 months, at least 5 months, at least 6 months, at least 7 months, at least 8 months, at least 9 months, at least 10 months, at least 11 months, at least 12 months, or more apart. In some embodiments, doses may be administered days apart, such as 1, 2, 3, 4, 5, 6, 7, 8, 9,10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more days apart. In some embodiments, doses may be administered about 1 to about 3 weeks apart, or about 1 to about 4 weeks apart, or about 1 to about 5 weeks apart, or about 1 to about 6 weeks apart, or about 1 to more than 6 weeks apart. In some embodiments, doses may be separated by a period of about 7 to about 60 days, such as for example about 14 to about 48 days, etc. In some embodiments, a minimum number of days between doses may be about 1, 2, 3, 4, 5, 6, 7, 8, 9, 10, 11, 12, 13, 14, 15, 16, 17, 18, 19, 20, 21 or more. In some embodiments, a maximum number of days between doses may be about 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or fewer. In some embodiments, doses may be about 21 to about 28 days apart. In some embodiments, doses may be about 19 to about 42 days apart. In some embodiments, doses may be about 7 to about 28 days apart. In some embodiments, doses may be about 14 to about 24 days. In some embodiments, doses may be about 21 to about 42 days.

In some embodiments, particularly for compositions established to achieve elevated antibody and/or T-cell titres for a period of time longer than about 3 weeks—e.g., in some embodiments, a provided composition is established to achieve elevated antibody and/or T-cell titres (e.g., specific for a relevant portion of a SARS-CoV-2 spike protein) for a period of time longer than about 3 weeks; in some such embodiments, a dosing regimen may involve only a single dose, or may involve two or more doses, which may, in some embodiments, be separated from one another by a period of time that is longer than about 21 days or three weeks. For example, in some such embodiments, such period of time may be about 4 weeks, 5 weeks, 6 weeks 7 weeks, 8 weeks, 9 weeks, 10 weeks, 11 weeks, 12 weeks, 13 weeks, 14 weeks, 15 wees, 16 weeks, 17 weeks, 18 weeks, 19 weeks, 20 weeks or more, or about 1 month, 2 months, 3 months, 4 months, 5 months, 6 months, 7 months, 8 months, 9 months, 10, months, 11 months, 12 months or more, or in some embodiments about a year or more. In some embodiments, a first dose and a second dose (and/or other subsequent dose) may be administered by intramuscular injection. In some embodiments, a first dose and a second dose may be administered in the deltoid muscle. In some embodiments, a first dose and a second dose may be administered in the same arm. In some embodiments, an RNA (e.g., mRNA) composition described herein is administered (e.g., by intramuscular injection) as a series of two doses (e.g., 0.3 mL each) 21 days part. In some embodiments, each dose is about 30 ug. In some embodiments, each dose may be higher than 30 ug, e.g., about 40 ug, about 50 ug, about 60 ug. In some embodiments, each dose may be lower than 30 ug, e.g., about 20 ug, about 10 ug, about 5 ug, etc. In some embodiments, each dose is about 3 μg or lower, e.g., about 1 ug. In some such embodiments, an RNA (e.g., mRNA) composition described herein is administered to subjects of age 16 or older (including, e.g., 16-85 years). In some such embodiments, an RNA composition (e.g., mRNA) described herein is administered to subjects of age 18-55. In some such embodiments, an RNA composition (e.g., mRNA) described herein is administered to subjects of age 56-85. In some embodiments, an RNA (e.g., mRNA) composition described herein is administered (e.g., by intramuscular injection) as a single dose.

In some embodiments, RNA (e.g., mRNA) compositions and/or methods described herein are characterized in that RBD-specific IgG (e.g., polyclonal response) induced by such RNA compositions and/or methods exhibit a higher binding affinity to RBD, as compared to a reference human monoclonal antibody with SARS-CoV-2 RBD-binding affinity (e.g., CR3022 as described in J. ter Meulen et al., PLOS Med. 3, e237 (2006).)

In some embodiments, RNA (e.g., mRNA) compositions and/or methods described herein are characterized in that sera of vaccinated subjects display neutralizing activity across a panel (e.g., at least 10, at least 15, or more) of SARs-CoV-2 spike variants (e.g., across a panel of variants described herein). In some embodiments, such SARs-CoV-2 spike variants include mutations in RBD (e.g., but not limited to Q321L, V341I, A348T, N354D, S359N, V367F, K378R, R408I, Q409E, A435S, N439K, K458R, I472V, G476S, S477N, V483A, Y508H, H519P, etc., as compared to SEQ ID NO: 1), and/or mutations in spike protein (e.g., but not limited to D614G, etc., as compared to SEQ ID NO: 1). Those skilled in the art are aware of various spike variants, and/or resources that document them (e.g., the Table of mutating sites in Spike maintained by the COVID-19 Viral Genome Analysis Pipeline and found at cov_lanl_gov/components/sequence/COV/int_sites_tbls_comp) (last accessed 24 Aug. 2020), and, reading the present specification, will appreciate that RNA (e.g, mRNA) compositions and/or methods described herein can be characterized for their ability to induce sera in vaccinated subject that display neutralizing activity with respect to any or all of such variants and/or combinations thereof.

In particular embodiments, RNA (e.g., mRNA) compositions encoding RBD of a SARS-CoV-2 spike protein are characterized in that sera of vaccinated subjects display neutralizing activity across a panel (e.g., at least 10, at least 15, or more) of SARs-CoV-2 spike variants including RBD variants (e.g., but not limited to Q321L, V341I, A348T, N354D, S359N, V367F, K378R, R408I, Q409E, A435S, N439K, K458R, I472V, G476S, S477N, V483A, Y508H, H519P, etc., as compared to SEQ ID NO: 1) and spike protein variants (e.g., but not limited to D614G, as compared to SEQ ID NO: 1).

In particular embodiments, RNA (e.g., mRNA) compositions encoding a SARS-CoV-2 spike protein variant that includes two consecutive proline substitutions at amino acid positions 986 and 987, at the top of the central helix in the S2 subunit, are characterized in that sera of vaccinated subjects display neutralizing activity across a panel (e.g., at least 10, at least 15, or more) of SARs-CoV-2 spike variants including RBD variants (e.g., but not limited to Q321L, V341I, A348T, N354D, S359N, V367F, K378R, R408I, Q409E, A435S, N439K, K458R, I472V, G476S, S477N, V483A, Y508H, H519P, etc., as compared to SEQ ID NO: 1) and spike protein variants (e.g., but not limited to D614G, as compared to SEQ ID NO: 1). For example, in some embodiments, an RNA (e.g., mRNA) composition encoding SEQ ID NO: 7 (S P2) elicits an immune response against any one of a SARs-CoV-2 spike variant including RBD variants (e.g., but not limited to Q321L, V341I, A348T, N354D, S359N, V367F, K378R, R408I, Q409E, A435S, N439K, K458R, I472V, G476S, S477N, V483A, Y508H, H519P, etc., as compared to SEQ ID NO: 1) and spike protein variants (e.g., but not limited to D614G, as compared to SEQ ID NO: 1).

In some embodiments, RNA (e.g., mRNA) compositions and/or methods described herein are characterized in that sera of vaccinated subjects display neutralizing activity against one or more SARs-CoV-2 spike variants including a mutation at position 501 in spike protein as compared to SEQ ID NO: 1. In some embodiments, RNA (e.g., mRNA) compositions and/or methods described herein are characterized in that sera of vaccinated subjects display neutralizing activity against one or more SARs-CoV-2 spike variants including a N501Y mutation in spike protein as compared to SEQ ID NO: 1.

Said one or more SARs-CoV-2 spike variants including a mutation at position 501 in spike protein as compared to SEQ ID NO: 1 or said one or more SARs-CoV-2 spike variants including a N501Y mutation in spike protein as compared to SEQ ID NO: 1 may include one or more further mutations as compared to SEQ ID NO: 1 (e.g., but not limited to H69/V70 deletion, Y144 deletion, A570D, D614G, P681H, T716I, S982A, D1118H, D80A, D215G, E484K, A701V, L18F, R246I, K417N, L242/A243/L244 deletion etc., as compared to SEQ ID NO: 1).

In particular embodiments, RNA (e.g., mRNA) compositions and/or methods described herein are characterized in that sera of vaccinated subjects display neutralizing activity against SARs-CoV-2 spike variant "Variant of Concern 202012/01" (VOC-202012/01; also known as lineage B.1.1.7). The variant had previously been named the first Variant Under Investigation in December 2020 (VUI-202012/01) by Public Health England, but was reclassified to a Variant of Concern (VOC-202012/01). VOC-202012/01 is a variant of SARS-CoV-2 which was first detected in October 2020 during the COVID-19 pandemic in the United Kingdom from a sample taken the previous month, and it quickly began to spread by mid-December. It is correlated with a significant increase in the rate of COVID-19 infection in United Kingdom; this increase is thought to be at least partly because of change N501Y inside the spike glycoprotein's receptor-binding domain, which is needed for binding to ACE2 in human cells. The VOC-202012/01 variant is defined by 23 mutations: 13 non-synonymous mutations, 4 deletions, and 6 synonymous mutations (i.e., there are 17 mutations that change proteins and six that do not). The spike protein changes in VOC 202012/01 include deletion 69-70, deletion 144, N501Y, A570D, D614G, P681H, T716I, S982A, and D1118H. One of the most important changes in VOC-202012/01 seems to be N501Y, a change from asparagine (N) to tyrosine (Y) at amino-acid site 501. This mutation alone or in combination with the deletion at positions 69/70 in the N terminal domain (NTD) may enhance the transmissibility of the virus.

In particular embodiments, RNA (e.g., mRNA) compositions and/or methods described herein are characterized in that sera of vaccinated subjects display neutralizing activity against SARs-CoV-2 spike variant including the following mutations: deletion 69-70, deletion 144, N501Y, A570D, D614G, P681H, T716I, S982A, and D1118H as compared to SEQ ID NO: 1.

In particular embodiments, RNA (e.g., mRNA) compositions and/or methods described herein are characterized in that sera of vaccinated subjects display neutralizing activity against SARs-CoV-2 spike variant "501.V2". This variant was first observed in samples from October 2020, and since then more than 300 cases with the 501.V2 variant have been confirmed by whole genome sequencing (WGS) in South Africa, where in December 2020 it was the dominant form of the virus. Preliminary results indicate that this variant may have an increased transmissibility. The 501.V2 variant is defined by multiple spike protein changes including: D80A, D215G, E484K, N501Y and A701V, and more recently collected viruses have additional changes: L18F, R246I, K417N, and deletion 242-244.

In particular embodiments, RNA (e.g., mRNA) compositions and/or methods described herein are characterized in that sera of vaccinated subjects display neutralizing activity against SARs-CoV-2 spike variant including the following mutations: D80A, D215G, E484K, N501Y and A701V as compared to SEQ ID NO: 1, and optionally: L18F, R246I, K417N, and deletion 242-244 as compared to SEQ ID NO: 1. Said SARs-CoV-2 spike variant may also include a D614G mutation as compared to SEQ ID NO: 1.

In some embodiments, RNA (e.g., mRNA) compositions and/or methods described herein are characterized in that sera of vaccinated subjects display neutralizing activity against one or more SARs-CoV-2 spike variants including a H69/V70 deletion in spike protein as compared to SEQ ID NO: 1.

In some embodiments, one or more SARs-CoV-2 spike variants including a H69/V70 deletion in spike protein as compared to SEQ ID NO: 1 may include one or more further mutations as compared to SEQ ID NO: 1 (e.g., but not limited to Y144 deletion, N501Y, A570D, D614G, P681H, T716I, S982A, D1118H, D80A, D215G, E484K, A701V, L18F, R246I, K417N, L242/A243/L244 deletion, Y453F, I692V, S1147L, M1229I etc., as compared to SEQ ID NO: 1), In particular embodiments, RNA (e.g., mRNA) compositions and/or methods described herein are characterized in that sera of vaccinated subjects display neutralizing activity against SARs-CoV-2 spike variant “Variant of Concern 202012/01” (VOC-202012/01; also known as lineage B.1.1.7).

In particular embodiments, RNA (e.g., mRNA) compositions and/or methods described herein are characterized in that sera of vaccinated subjects display neutralizing activity against SARs-CoV-2 spike variant including the following mutations: deletion 69-70, deletion 144, N501Y, A570D, D614G, P681H, T716I, S982A, and D1118H as compared to SEQ ID NO: 1.

In particular embodiments, RNA (e.g., mRNA) compositions and/or methods described herein are characterized in that sera of vaccinated subjects display neutralizing activity against SARs-CoV-2 spike variant “Cluster 5”, also referred to as ΔFVI-spike by the Danish State Serum Institute (SSI). It was discovered in North Jutland, Denmark, and is believed to have been spread from minks to humans via mink farms. In cluster 5, several different mutations in the spike protein of the virus have been confirmed. The specific mutations include 69-70deltaHV (a deletion of the histidine and valine residues at the 69th and 70th position in the protein), Y453F (a change from tyrosine to phenylalanine at position 453), I692V (isoleucine to valine at position 692), M1229I (methionine to isoleucine at position 1229), and optionally S1147L (serine to leucine at position 1147).

In particular embodiments, RNA (e.g., mRNA) compositions and/or methods described herein are characterized in that sera of vaccinated subjects display neutralizing activity against SARs-CoV-2 spike variant including the following mutations: deletion 69-70, Y453F, I692V, M1229I, and optionally S1147L, as compared to SEQ ID NO: 1.

In some embodiments, RNA (e.g., mRNA) compositions and/or methods described herein are characterized in that sera of vaccinated subjects display neutralizing activity against one or more SARs-CoV-2 spike variants including a mutation at position 614 in spike protein as compared to SEQ ID NO: 1. In some embodiments, RNA (e.g., mRNA) compositions and/or methods described herein are characterized in that sera of vaccinated subjects display neutralizing activity against one or more SARs-CoV-2 spike variants including a D614G mutation in spike protein as compared to SEQ ID NO: 1.

In some embodiments, one or more SARs-CoV-2 spike variants including a mutation at position 614 in spike protein as compared to SEQ ID NO: 1 or said one or more SARs-CoV-2 spike variants including a D614G mutation in spike protein as compared to SEQ ID NO: 1 may include one or more further mutations as compared to SEQ ID NO: 1 (e.g., but not limited to H69/V70 deletion, Y144 deletion, N501Y, A570D, P681H, T716I, S982A, D1118H, D80A, D215G, E484K, A701V, L18F, R246I, K417N, L242/A243/L244 deletion, Y453F, I692V, S1147L, M1229I etc., as compared to SEQ ID NO: 1).

In particular embodiments, RNA (e.g., mRNA) compositions and/or methods described herein are characterized in that sera of vaccinated subjects display neutralizing activity against SARs-CoV-2 spike variant “Variant of Concern 202012/01” (VOC-202012/01; also known as lineage B.1.1.7).

In particular embodiments, RNA (e.g., mRNA) compositions and/or methods described herein are characterized in that sera of vaccinated subjects display neutralizing activity against SARs-CoV-2 spike variant including the following mutations: deletion 69-70, deletion 144, N501Y, A570D, D614G, P681H, T716I, S982A, and D1118H as compared to SEQ ID NO: 1.

In particular embodiments, RNA (e.g., mRNA) compositions and/or methods described herein are characterized in that sera of vaccinated subjects display neutralizing activity against SARs-CoV-2 spike variant including the following mutations: D80A, D215G, E484K, N501Y, A701V, and D614G as compared to SEQ ID NO: 1, and optionally: L18F, R246I, K417N, and deletion 242-244 as compared to SEQ ID NO: 1.

In some embodiments, RNA (e.g., mRNA) compositions and/or methods described herein are characterized in that sera of vaccinated subjects display neutralizing activity against one or more SARs-CoV-2 spike variants including a mutation at positions 501 and 614 in spike protein as compared to SEQ ID NO: 1. In some embodiments, RNA (e.g., mRNA) compositions and/or methods described herein are characterized in that sera of vaccinated subjects display neutralizing activity against one or more SARs-CoV-2 spike variants including a N501Y mutation and a D614G mutation in spike protein as compared to SEQ ID NO: 1.

In some embodiments, one or more SARS-CoV-2 spike variants including a mutation at positions 501 and 614 in spike protein as compared to SEQ ID NO: 1 or said one or more SARs-CoV-2 spike variants including a N501Y mutation and a D614G mutation in spike protein as compared to SEQ ID NO: 1 may include one or more further mutations as compared to SEQ ID NO: 1 (e.g., but not limited to H69/V70 deletion, Y144 deletion, A570D, P681H, T716I, S982A, D1118H, D80A, D215G, E484K, A701V, L18F, R246I, K417N, L242/A243/L244 deletion, Y453F, I692V, S1147L, M1229I etc., as compared to SEQ ID NO: 1).

In particular embodiments, RNA (e.g., mRNA) compositions and/or methods described herein are characterized in that sera of vaccinated subjects display neutralizing activity against SARs-CoV-2 spike variant “Variant of Concern 202012/01” (VOC-202012/01; also known as lineage B.1.1.7).

In particular embodiments, RNA (e.g., mRNA) compositions and/or methods described herein are characterized in that sera of vaccinated subjects display neutralizing activity against SARs-CoV-2 spike variant including the following mutations: deletion 69-70, deletion 144, N501Y, A570D, D614G, P681H, T716I, S982A, and D1118H as compared to SEQ ID NO: 1.

In particular embodiments, RNA (e.g., mRNA) compositions and/or methods described herein are characterized in that sera of vaccinated subjects display neutralizing activity against SARs-CoV-2 spike variant including the following mutations: D80A, D215G, E484K, N501Y, A701V, and D614G as compared to SEQ ID NO: 1, and optionally: L18F, R246I, K417N, and deletion 242-244 as compared to SEQ ID NO: 1.

In some embodiments, RNA (e.g., mRNA) compositions and/or methods described herein are characterized in that sera of vaccinated subjects display neutralizing activity against one or more SARs-CoV-2 spike variants including a mutation at position 484 in spike protein as compared to SEQ ID NO: 1. In some embodiments, RNA (e.g., mRNA) compositions and/or methods described herein are characterized in that sera of vaccinated subjects display neutralizing activity against one or more SARs-CoV-2 spike variants including a E484K mutation in spike protein as compared to SEQ ID NO: 1.

In some embodiments, one or more SARs-CoV-2 spike variants including a mutation at position 484 in spike protein as compared to SEQ ID NO: 1 or said one or more SARs-CoV-2 spike variants including a E484K mutation in spike protein as compared to SEQ ID NO: 1 may include one or more further mutations as compared to SEQ ID NO: 1 (e.g., but not limited to H69/V70 deletion, Y144 deletion, N501Y, A570D, D614G, P681H, T716I, S982A, D1118H, D80A, D215G, A701V, L18F, R246I, K417N, L242/A243/L244 deletion, Y453F, I692V, S1147L, M1229I, T20N, P26S, D138Y, R190S, K417T, H655Y, T1027I, V1176F etc., as compared to SEQ ID NO: 1).

In particular embodiments, RNA (e.g., mRNA) compositions and/or methods described herein are characterized in that sera of vaccinated subjects display neutralizing activity against SARs-CoV-2 spike variant "501.V2".

In particular embodiments, RNA (e.g., mRNA) compositions and/or methods described herein are characterized in that sera of vaccinated subjects display neutralizing activity against SARs-CoV-2 spike variant including the following mutations: D80A, D215G, E484K, N501Y, and A701V, as compared to SEQ ID NO: 1, and optionally: L18F, R246I, K417N, and deletion 242-244 as compared to SEQ ID NO: 1. Said SARs-CoV-2 spike variant may also include a D614G mutation as compared to SEQ ID NO: 1.

Lineage B.1.1.248, known as the Brazil(ian) variant, is one of the variants of SARS-CoV-2 which has been named P.1 lineage and has 17 unique amino acid changes, 10 of which in its spike protein, including N501Y and E484K. B.1.1.248 originated from B.1.1.28. E484K is present in both B.1.1.28 and B.1.1.248. B.1.1.248 has a number of S-protein polymorphisms [L18F, T20N, P26S, D138Y, R190S, K417T, E484K, N501Y, H655Y, T1027I, V1176F] and is similar in certain key RBD positions (K417, E484, N501) to variant described from South Africa.

In particular embodiments, RNA (e.g., mRNA) compositions and/or methods described herein are characterized in that sera of vaccinated subjects display neutralizing activity against SARs-CoV-2 spike variant "B.1.1.28".

In particular embodiments, RNA (e.g., mRNA) compositions and/or methods described herein are characterized in that sera of vaccinated subjects display neutralizing activity against SARs-CoV-2 spike variant "B.1.1.248".

In particular embodiments, RNA (e.g., mRNA) compositions and/or methods described herein are characterized in that sera of vaccinated subjects display neutralizing activity against SARs-CoV-2 spike variant including the following mutations: L18F, T20N, P26S, D138Y, R190S, K417T, E484K, N501Y, H655Y, T1027I, and V1176F as compared to SEQ ID NO: 1.

In some embodiments, RNA (e.g., mRNA) compositions and/or methods described herein are characterized in that sera of vaccinated subjects display neutralizing activity against one or more SARs-CoV-2 spike variants including a mutation at positions 501 and 484 in spike protein as compared to SEQ ID NO: 1. In some embodiments, RNA (e.g., mRNA) compositions and/or methods described herein are characterized in that sera of vaccinated subjects display neutralizing activity against one or more SARs-CoV-2 spike variants including a N501Y mutation and a E484K mutation in spike protein as compared to SEQ ID NO: 1.

In some embodiments, one or more SARs-CoV-2 spike variants including a mutation at positions 501 and 484 in spike protein as compared to SEQ ID NO: 1 or said one or more SARs-CoV-2 spike variants including a N501Y mutation and a E484K mutation in spike protein as compared to SEQ ID NO: 1 may include one or more further mutations as compared to SEQ ID NO: 1 (e.g., but not limited to H69/V70 deletion, Y144 deletion, A570D, D614G, P681H, T716I, S982A, D1118H, D80A, D215G, A701V, L18F, R246I, K417N, L242/A243/L244 deletion, Y453F, I692V, S1147L, M1229I, T20N, P26S, D138Y, R190S, K417T, H655Y, T1027I, V1176F etc., as compared to SEQ ID NO: 1).

In particular embodiments, RNA (e.g., mRNA) compositions and/or methods described herein are characterized in that sera of vaccinated subjects display neutralizing activity against SARs-CoV-2 spike variant "501.V2".

In particular embodiments, RNA (e.g., mRNA) compositions and/or methods described herein are characterized in that sera of vaccinated subjects display neutralizing activity against SARs-CoV-2 spike variant including the following mutations: D80A, D215G, E484K, N501Y and A701V as compared to SEQ ID NO: 1, and optionally: L18F, R246I, K417N, and deletion 242-244 as compared to SEQ ID NO: 1. Said SARs-CoV-2 spike variant may also include a D614G mutation as compared to SEQ ID NO: 1.

In particular embodiments, RNA (e.g., mRNA) compositions and/or methods described herein are characterized in that sera of vaccinated subjects display neutralizing activity against SARs-CoV-2 spike variant "B.1.1.248".

In particular embodiments, RNA (e.g., mRNA) compositions and/or methods described herein are characterized in that sera of vaccinated subjects display neutralizing activity against SARs-CoV-2 spike variant including the following mutations: L18F, T20N, P26S, D138Y, R190S, K417T, E484K, N501Y, H655Y, T1027I, and V1176F as compared to SEQ ID NO: 1.

In some embodiments, RNA (e.g., mRNA) compositions and/or methods described herein are characterized in that sera of vaccinated subjects display neutralizing activity against one or more SARs-CoV-2 spike variants including a mutation at positions 501, 484 and 614 in spike protein as compared to SEQ ID NO: 1. In some embodiments, RNA (e.g., mRNA) compositions and/or methods described herein are characterized in that sera of vaccinated subjects display neutralizing activity against one or more SARs-CoV-2 spike variants including a N501Y mutation, a E484K mutation and a D614G mutation in spike protein as compared to SEQ ID NO: 1.

In some embodiments, one or more SARs-CoV-2 spike variants including a mutation at positions 501, 484 and 614 in spike protein as compared to SEQ ID NO: 1 or said one or more SARs-CoV-2 spike variants including a N501Y mutation, a E484K mutation and a D614G mutation in spike protein as compared to SEQ ID NO: 1 may include one or more further mutations as compared to SEQ ID NO: 1 (e.g., but not limited to H69/V70 deletion, Y144 deletion, A570D, P681H, T716I, S982A, D1118H, D80A, D215G, A701V, L18F, R246I, K417N, L242/A243/L244 deletion, Y453F, I692V, S1147L, M1229I, T20N, P26S, D138Y, R190S, K417T, H655Y, T1027I, V1176F etc., as compared to SEQ ID NO: 1).

In particular embodiments, RNA (e.g., mRNA) compositions and/or methods described herein are characterized in that sera of vaccinated subjects display neutralizing activity against SARs-CoV-2 spike variant including the following mutations: D80A, D215G, E484K, N501Y, A701V, and D614G as compared to SEQ ID NO: 1, and optionally: L18F, R246I, K417N, and deletion 242-244 as compared to SEQ ID NO: 1.

In some embodiments, RNA (e.g., mRNA) compositions and/or methods described herein are characterized in that sera of vaccinated subjects display neutralizing activity against one or more SARs-CoV-2 spike variants including a L242/A243/L244 deletion in spike protein as compared to SEQ ID NO: 1.

In some embodiments, one or more SARs-CoV-2 spike variants including a L242/A243/L244 deletion in spike protein as compared to SEQ ID NO: 1 may include one or more further mutations as compared to SEQ ID NO: 1 (e.g., but not limited to H69/V70 deletion, Y144 deletion, N501Y, A570D, D614G, P681H, T716I, S982A, D1118H, D80A, D215G, E484K, A701V, L18F, R246I, K417N, Y453F, I692V, S1147L, M1229I, T20N, P265, D138Y, R190S, K417T, H655Y, T1027I, V1176F etc., as compared to SEQ ID NO: 1).

In particular embodiments, RNA (e.g., mRNA) compositions and/or methods described herein are characterized in that sera of vaccinated subjects display neutralizing activity against SARs-CoV-2 spike variant "501.V2".

In particular embodiments, RNA (e.g., mRNA) compositions and/or methods described herein are characterized in that sera of vaccinated subjects display neutralizing activity against SARs-CoV-2 spike variant including the following mutations: D80A, D215G, E484K, N501Y, A701V and deletion 242-244 as compared to SEQ ID NO: 1, and optionally: L18F, R246I, and K417N, as compared to SEQ ID NO: 1. Said SARs-CoV-2 spike variant may also include a D614G mutation as compared to SEQ ID NO: 1.

In some embodiments, RNA (e.g., mRNA) compositions and/or methods described herein are characterized in that sera of vaccinated subjects display neutralizing activity against one or more SARs-CoV-2 spike variants including a mutation at position 417 in spike protein as compared to SEQ ID NO: 1. In some embodiments, RNA (e.g., mRNA) compositions and/or methods described herein are characterized in that sera of vaccinated subjects display neutralizing activity against one or more SARs-CoV-2 spike variants including a K417N or K417T mutation in spike protein as compared to SEQ ID NO: 1.

In some embodiments, one or more SARs-CoV-2 spike variants including a mutation at position 417 in spike protein as compared to SEQ ID NO: 1 or said one or more SARs-CoV-2 spike variants including a K417N or K417T mutation in spike protein as compared to SEQ ID NO: 1 may include one or more further mutations as compared to SEQ ID NO: 1 (e.g., but not limited to H69/V70 deletion, Y144 deletion, N501Y, A570D, D614G, P681H, T716I, S982A, D1118H, D80A, D215G, E484K, A701V, L18F, R246I, L242/A243/L244 deletion, Y453F, I692V, S1147L, M1229I, T20N, P26S, D138Y, R190S, H655Y, T1027I, V1176F etc., as compared to SEQ ID NO: 1).

In particular embodiments, RNA (e.g., mRNA) compositions and/or methods described herein are characterized in that sera of vaccinated subjects display neutralizing activity against SARs-CoV-2 spike variant "501.V2".

In particular embodiments, RNA (e.g., mRNA) compositions and/or methods described herein are characterized in that sera of vaccinated subjects display neutralizing activity against SARs-CoV-2 spike variant including the following mutations: D80A, D215G, E484K, N501Y, A701V and K417N, as compared to SEQ ID NO: 1, and optionally: L18F, R246I, and deletion 242-244 as compared to SEQ ID NO: 1. Said SARs-CoV-2 spike variant may also include a D614G mutation as compared to SEQ ID NO: 1.

In particular embodiments, RNA (e.g., mRNA) compositions and/or methods described herein are characterized in that sera of vaccinated subjects display neutralizing activity against SARs-CoV-2 spike variant "B.1.1.248".

In particular embodiments, RNA (e.g., mRNA) compositions and/or methods described herein are characterized in that sera of vaccinated subjects display neutralizing activity against SARs-CoV-2 spike variant including the following mutations: L18F, T20N, P26S, D138Y, R190S, K417T, E484K, N501Y, H655Y, T1027I, and V1176F as compared to SEQ ID NO: 1.

In some embodiments, RNA (e.g., mRNA) compositions and/or methods described herein are characterized in that sera of vaccinated subjects display neutralizing activity against one or more SARs-CoV-2 spike variants including a mutation at positions 417 and 484 and/or 501 in spike protein as compared to SEQ ID NO: 1. In some embodiments, RNA (e.g., mRNA) compositions and/or methods described herein are characterized in that sera of vaccinated subjects display neutralizing activity against one or more SARs-CoV-2 spike variants including a K417N or K417T mutation and a E484K and/or N501Y mutation in spike protein as compared to SEQ ID NO: 1.

In some embodiments, one or more SARs-CoV-2 spike variants including a mutation at positions 417 and 484 and/or 501 in spike protein as compared to SEQ ID NO: 1 or said one or more SARs-CoV-2 spike variants including a K417N or K417T mutation and a E484K and/or N501Y mutation in spike protein as compared to SEQ ID NO: 1 may include one or more further mutations as compared to SEQ ID NO: 1 (e.g., but not limited to H69/V70 deletion, Y144 deletion, A570D, D614G, P681H, T716I, S982A, D1118H, D80A, D215G, A701V, L18F, R246I, L242/A243/L244 deletion, Y453F, I692V, S1147L, M1229I, T20N, P26S, D138Y, R190S, H655Y, T1027I, V1176F etc., as compared to SEQ ID NO: 1).

In particular embodiments, RNA (e.g., mRNA) compositions and/or methods described herein are characterized in that sera of vaccinated subjects display neutralizing activity against SARs-CoV-2 spike variant "501.V2".

In particular embodiments, RNA (e.g., mRNA) compositions and/or methods described herein are characterized in that sera of vaccinated subjects display neutralizing activity against SARs-CoV-2 spike variant including the following mutations: D80A, D215G, E484K, N501Y, A701V and K417N, as compared to SEQ ID NO: 1, and optionally: L18F, R246I, and deletion 242-244 as compared to SEQ ID NO: 1. Said SARs-CoV-2 spike variant may also include a D614G mutation as compared to SEQ ID NO: 1.

In particular embodiments, RNA (e.g., mRNA) compositions and/or methods described herein are characterized in that sera of vaccinated subjects display neutralizing activity against SARs-CoV-2 spike variant "B.1.1.248".

In particular embodiments, RNA (e.g., mRNA) compositions and/or methods described herein are characterized in that sera of vaccinated subjects display neutralizing activity against SARs-CoV-2 spike variant including the following mutations: L18F, T20N, P26S, D138Y, R190S, K417T, E484K, N501Y, H655Y, T1027I, and V1176F as compared to SEQ ID NO: 1.

In some embodiments, RNA (e.g., mRNA) compositions and/or methods described herein are characterized in that sera of vaccinated subjects display neutralizing activity against SARs-CoV-2 spike variant of the Omicron (B.1.1.529) variant. Omicron (B.1.1.529) variant is a variant of SARS-CoV-2 which was detected in South Africa. Multiple Omicron variants or sublineages have arisen, including e.g., the BA.1, BA.2, BA.2.12.1, BA.3, BA.4, BA.5, and BA.2.75 sublineages. As used herein, unless otherwise specified, "Omicron variant" refers to the first disclosed Omicron variant (BA.1) or any variant thereof that has since arisen (e.g., Omicron variants described herein). In some embodiments, the spike protein changes in Omicron (B.1.1.529) BA.1 variant include A67V, Δ69-70, T95I, G142D, Δ143-145, Δ211, L212I, ins214EPE (insertion of EPE following amino acid 214), G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, and L981F. In some embodiments, the spike protein changes in Omicron (B.1.1.529) variant include A67V, Δ69-70, T95I, G142D, Δ143-145, Δ211, L212I, ins214EPE (insertion of EPE following amino acid 214), G339D, S371L, S373P, S375F, S477N, T478K, E484A, Q493R, G496S, Q498R, N501Y, Y505H, T547K, D614G, H655Y, N679K, P681H, N764K, D796Y, N856K, Q954H, N969K, and L981F. In some embodiments, the spike changes in Omicron BA.2 variant include T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K. In some embodiments BA.4 and BA.5 have the same Spike protein amino acid sequence, in which case "BA.4/5" is used to either Omicron variant. In some embodiments, the spike changes in Omicron BA.4/5 include: T19I, Δ24-26, Δ275, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, and N969K. In some embodiments, the spike changes in Omicron BA.2.75 include T19I, Δ24-26, A27S, G142D, K147E, W152R, F157L, I210V, V213G, G257S, G339H, N354D, S371F, S373P, S375F, T376A, D405N, R408S, K417N, N440K, G446S, N460K, S477N, T478K, E484A, Q498R, N501Y, Y505H D614G, H655Y, N679K, P681H, N764K, D796Y, Q954H, and N969K.

In some embodiments, RNA (e.g., mRNA) compositions and/or methods described herein are characterized in that sera of vaccinated subjects display neutralizing activity against SARs-CoV-2 spike variant including at least 10, at least 15, at least 20, at least 21, at least 22, at least 23, at least 24, at least 25, at least 26, at least 27, at least 28, at least 29, at least 30, at least 31, at least 32, at least 33, at least 34, at least 35, at least 36, or at least 37 of the following mutations: T547K, H655Y, D614G, N679K, P681H, N969K, S373P, S371L, N440K, G339D, G446S, N856K, N764K, K417N, D796Y, Q954H, T95I, A67V, L981F, S477N, G496S, T478K, Q498R, Q493R, E484A, N501Y, S375F, Y505H, V143del, H69del, V70del, N211del, L212I, ins214EPE, G142D, Y144del, Y145del, L141del, Y144F, Y145D, G142del, as compared to SEQ ID NO: 1.

In some embodiments, RNA (e.g., mRNA) compositions and/or methods described herein are characterized in that sera of vaccinated subjects display neutralizing activity against SARs-CoV-2 spike variant including at least 10, at least 15, at least 20, at least 21, at least 22, at least 23, at least 24, or all of the following mutations: T547K, H655Y, D614G, N679K, P681H, N969K, S373P, S371L, N440K, G339D, G446S, N856K, N764K, K417N, D796Y, Q954H, T95I, A67V, L981F, S477N, G496S, T478K, Q498R, Q493R, E484A, as compared to SEQ ID NO: 1. Said SARs-CoV-2 spike variant may include at least 1, at least 2, at least 3, at least 4, at least 5, or all of the following mutations: N501Y, S375F, Y505H, V143del, H69del, V70del, as compared to SEQ ID NO: 1, and/or may include at least 1, at least 2, at least 3, at least 4, at least 5, or all of the following mutations: N211del, L212I, ins214EPE, G142D, Y144del, Y145del, as compared to SEQ ID NO: 1. In some embodiments, said SARs-CoV-2 spike variant may include at least 1, at least 2, at least 3, or all of the following mutations: L141del, Y144F, Y145D, G142del, as compared to SEQ ID NO: 1.

In some embodiments, RNA (e.g., mRNA) compositions and/or methods described herein are characterized in that sera of vaccinated subjects display neutralizing activity against a SARs-CoV-2 spike variant including at least 10, at least 15, at least 20, at least 21, at least 22, at least 23, at least 24, at least 25, at least 26, at least 27, at least 28, at least 29, at least 30, at least 31, at least 32, at least 33 of the following mutations: A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, and L981F, as compared to SEQ ID NO: 1.

In some embodiments, RNA (e.g., mRNA) compositions and/or methods described herein are characterized in that sera of vaccinated subjects display neutralizing activity against a SARS-CoV-2 spike variant including at least 10, at least 15, at least 20, at least 21, at least 22, at least 23, at least 24, at least 25, at least 26, at least 27, at least 28, at least 29, at least 30, or at least 31, of the following mutations: T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K, as compared to SEQ ID NO: 1.

In some embodiments, RNA (e.g., mRNA) compositions and/or methods described herein are characterized in that sera of vaccinated subjects display neutralizing activity against a SARS-CoV-2 spike variant including at least 10, at least 15, at least 20, at least 21, at least 22, at least 23, at least 24, at least 25, at least 26, at least 27, at least 28, at least 29, at least 30, at least 31, at least 32, at least 33, or at least 34 of the following mutations: T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, and N969K, as compared to SEQ ID NO: 1.

In some embodiments, RNA (e.g., mRNA) compositions and/or methods described herein are characterized in that sera of vaccinated subjects display neutralizing activity against a SARs-CoV-2 spike variant including the following mutations: A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, and L981F, as compared to SEQ ID NO: 1.

In some embodiments, RNA (e.g., mRNA) compositions and/or methods described herein are characterized in that sera of vaccinated subjects display neutralizating against a SARS-CoV-2 spike variant including the following mutations: T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K. In some embodiments, RNA (e.g., mRNA) compositions and/or methods described herein are charcterized in that sera of vaccinated subjects display neutralizating against SARS-CoV2 spike variant including the following mutations: T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, and N969K, as compared to SEQ ID NO: 1.

In some embodiments, RNA (e.g., mRNA) compositions and/or methods described herein are characterized in that sera of vaccinated subjects display neutralizing activity against SARs-CoV-2 spike variant including the following mutations: A67V, Δ69-70, T95I, G142D, Δ143-145, Δ211, L212I, ins214EPE, G339D, S371L, S373P, S375F, S477N, T478K, E484A, Q493R, G496S, Q498R, N501Y, Y505H, T547K, D614G, H655Y, N679K, P681H, N764K, D796Y, N856K, Q954H, N969K, and L981F, as compared to SEQ ID NO: 1.

In some embodiments, RNA (e.g., mRNA) compositions and/or methods described herein are characterized in that sera of vaccinated subjects display neutralizing activity against SARs-CoV-2 spike variant including the following mutations: T19I, Δ24-26, A27S, G142D, K147E, W152R, F157L, I210V, V213G, G257S, G339H, N354D, S371F, S373P, S375F, T376A, D405N, R408S, K417N, N440K, G446S, N460K, S477N, T478K, E484A, Q498R, N501Y, Y505H D614G, H655Y, N679K, P681H, N764K, D796Y, Q954H, and N969K, as compared to SEQ ID NO: 1.

SARs-CoV-2 spike proteins encoded by RNA described herein may or may not include a D614G mutation as compared to SEQ ID NO: 1.

In some embodiments, SARS-CoV-2 spike proteins encoded by RNA described herein comprise a mutation in a furin cleavage site (e.g., in some embodiments residues 682-685 of SEQ ID NO: 1). In some embodiments, SARS-CoV-2 spike proteins encoded by RNA described herein comprise a mutation in the furin cleavage site that prevents cleavage by a furin protease (e.g., a human furin protease). In some embodiments, a SARS-CoV-2 protein described herein comprises a furin mutation disclosed in WO2021163365 or WO2021243122 (e.g., a GSAS mutation), the contents of both of which are incorporated by reference herein in their entirety.

In some embodiments, RNA (e.g., mRNA) compositions and/or methods described herein can provide protection against SARS-CoV-2 and/or decrease severity of SARS-CoV-2 infection in at least 50% of subjects receiving such RNA compositions and/or methods.

In some embodiments, populations to be treated with RNA (e.g., mRNA) compositions described herein include subjects of age 18-55. In some embodiments, populations to be treated with RNA (e.g., mRNA) compositions described herein include subjects of age 56-85.

In some embodiments, populations to be treated with RNA (e.g., mRNA) compositions described herein include older subjects (e.g., over age 60, 65, 70, 75, 80, 85, etc, for example subjects of age 65-85). In some embodiments, populations to be treated with RNA (e.g., mRNA) compositions described herein include subjects of age 18-85. In some embodiments, populations to be treated with RNA (e.g., mRNA) compositions described herein include subjects of age 18 or younger. In some embodiments, populations to be treated with RNA (e.g., mRNA) compositions described herein include subjects of age 12 or younger. In some embodiments, populations to be treated with RNA (e.g., mRNA) compositions described herein include subjects of age 10 or younger. In some embodiments, populations to be treated with RNA (e.g., mRNA) compositions described herein may include adolescent populations (e.g., individuals approximately 12 to approximately 17 years of age). In some embodiments, populations to be treated with RNA (e.g., mRNA) compositions described herein may include pediatric populations (e.g., as described herein). In some embodiments, populations to be treated with RNA (e.g., mRNA) compositions described herein include infants (e.g., less than 1 year old). In some embodiments, populations to be treated with RNA (e.g., mRNA) compositions described herein do not include infants (e.g., less than 1 year) whose mothers have received such RNA (e.g., mRNA) compositions described herein during pregnancy. Without wishing to be bound by any particular theory, a rat study has suggested that a SARS-CoV-2 neutralizing antibody response induced in female rats given such RNA compositions during pregnancy can pass onto fetuses. In some embodiments, populations to be treated with RNA (e.g., mRNA) compositions described herein include infants (e.g., less than 1 year) whose mothers did not receive such RNA compositions described herein during pregnancy. In some embodiments, populations to be treated with RNA (e.g., mRNA) compositions described herein may include pregnant women; in some embodiments, infants whose mothers were vaccinated during pregnancy (e.g., who received at least one dose, or alternatively only who received both doses), are not vaccinated during the first weeks, months, or even years (e.g., 1, 2, 3, 4, 5, 6, 7, 8 weeks or more, or 1, 2, 3, 4, 5, 6, 7, 8, 9, 10, 11, 12, 13, 14, 15, 16, 17, 18, 19, 20, 21, 22, 23, 24 months or more, or 1, 2, 3, 4, 5 years or more) post-birth. Alternatively or additionally, in some embodiments, infants whose mothers were vaccinated during pregnancy (e.g., who received at least one dose, or alternatively only who received both doses), receive reduced vaccination (e.g., lower doses and/or smaller numbers of administrations—e.g., boosters—and/or lower total exposure over a given period of time) after birth, for example during the first weeks, months, or even years (e.g., 1, 2, 3, 4, 5, 6, 7, 8 weeks or more, or 1, 2, 3, 4, 5, 6, 7, 8, 9, 10, 11, 12, 13, 14, 15, 16, 17, 18, 19, 20, 21, 22, 23, 24 months or more, or 1, 2, 3, 4, 5 years or more) post-birth or may need reduced vaccination (e.g., lower doses and/or smaller numbers of administrations—e.g., boosters—over a given period of time), In some embodiments, compositions as provided herein are administered to populations that do not include pregnant women.

In some particular embodiments, compositions as provided herein are administered to pregnant women according to a regimen that includes a first dose administered after about 24 weeks of gestation (e.g., after about 22, 23, 24, 25, 26, 27, 28 or more weeks of gestation); in some embodiments, compositions as provided herein are administered to pregnant women according to a regimen that includes a first dose administered before about 34 weeks of gestation (e.g., before about 30, 31, 32, 33, 34, 35, 36, 37, 38 weeks of gestation). In some embodiments, compositions as provided herein are administered to pregnant women according to a regimen that includes a first dose administered after about 24 weeks (e.g., after about 27 weeks of gestation, e.g., between about 24 weeks and 34 weeks, or between about 27 weeks and 34 weeks) of gestation and a second dose administered about 21 days later; in some embodiments both doses are administered prior to delivery. Without wishing to be bound by any particular theory, it is proposed that such a regimen (e.g., involving administration of a first dose after about 24 weeks, or 27 weeks of gestation and optionally before about 34 weeks of gestation), and optionally a second dose within about 21 days, ideally before delivery, may have certain advantages in terms of safety (e.g., reduced risk of premature delivery or of fetal morbidity or mortality) and/or efficacy (e.g., carryover vaccination imparted to the infant) relative to alternative dosing regimens (e.g., dosing at any time during pregnancy, refraining from dosing during pregnancy, and/or dosing later in pregnancy for example so that only one dose is administered during gestation. In some embodiments, infants born of mothers vaccinated during pregnancy, e.g., according to a particular regimen as described herein, may not need further vaccination, or may need reduced vaccination (e.g., lower doses and/or smaller numbers of administrations—e.g., boosters—, and/or lower overall exposure over a given period of time), for a period of time (e.g., as noted herein) after birth.

In some embodiments, compositions as provided herein are administered to populations in which women are advised against becoming pregnant for a period of time after receipt of the vaccine (e.g., after receipt of a first dose of the vaccine, after receipt of a final dose of the vaccine, etc.); in some such embodiments, the period of time may be at least 1 week, at least 2 weeks, at least 3 weeks, at least 4 weeks, at least 5 weeks, at least 6 weeks, at least 7 weeks, at least 8 weeks, at least 9 weeks, at least 10 weeks or more, or may be at least 1 month, at least 2 months, at least 3 months, at least 4 months, at least 5 months, at least 6 months, or more.

In some embodiments, populations to be treated with RNA (e.g., mRNA) compositions described herein may include one or more populations with one or more particularly high risk conditions or history, e.g., as noted herein. For example, in some embodiments, populations to be treated with RNA compositions described herein may include subjects whose profession and/or environmental exposure may dramatically increase their risk of getting SARS-CoV-2 infection (including, e.g., but not limited to mass transportation, prisoners, grocery store workers, residents in long-term care facilities, butchers or other meat processing workers, healthcare workers, and/or first responders, e.g., emergency responders). In particular embodiments, populations to be treated with RNA (e.g., mRNA) compositions described herein may include healthcare workers and/or first responders, e.g., emergency responders.

In some embodiments, populations to be treated with RNA (e.g., mRNA) compositions described herein may include those with a history of smoking or vaping (e.g., within 6 months, 12 months or more, including a history of chronic smoking or vaping). In some embodiments, populations to be treated with RNA (e.g., mRNA) compositions described herein may include certain ethnic groups that have been determined to be more susceptible to SARS-CoV-2 infection.

In some embodiments, populations to be treated with RNA (e.g., mRNA) compositions described herein may include certain populations with a blood type that may have been determined to more susceptible to SARS-CoV-2 infection. In some embodiments, populations to be treated with RNA (e.g., mRNA) compositions described herein may include immunocompromised subjects (e.g., those with HIV/AIDS; cancer patients (e.g., receiving antitumor treatment); patients who are taking certain immunosuppressive drugs (e.g., transplant patients, cancer patients, etc.); autoimmune diseases or other physiological conditions expected to warrant immunosuppressive therapy (e.g., within 3 months, within 6 months, or more); and those with inherited diseases that affect the immune system (e.g., congenital agammaglobulinemia, congenital IgA deficiency)). In some embodiments, populations to be treated with RNA (e.g., mRNA) compositions described herein may include those with an infectious disease. For example, in some embodiments, populations to be treated with RNA (e.g., mRNA) compositions described herein may include those infected with human immunodeficiency virus (HIV) and/or a hepatitis virus (e.g., HBV, HCV). In some embodiments, populations to be treated with RNA (e.g., mRNA) compositions described herein may include those with underlying medical conditions. Examples of such underlying medical conditions may include, but are not limited to hypertension, cardiovascular disease, diabetes, chronic respiratory disease, e.g., chronic pulmonary disease, asthma, etc., cancer, and other chronic diseases such as, e.g., lupus, rheumatoid arthritis, chronic liver diseases, chronic kidney diseases (e.g., Stage 3 or worse such as in some embodiments as characterized by a glomerular filtration rate (GFR) of less than 60 mL/min/1.73 $m^2$). In some embodiments, populations to be treated with RNA (e.g., mRNA) compositions described herein may include overweight or obese subjects, e.g., specifically including those with a body mass index (BMI) above about 30 $kg/m^2$. In some embodiments, populations to be treated with RNA (e.g., mRNA) compositions described herein may include subjects who have prior diagnosis of COVID-19 or evidence of current or prior SARS-CoV-2 infection, e.g., based on serology or nasal swab. In some embodiments, populations to be treated include white and/or non-Hispanic/non-Latino.

In some embodiments, certain RNA (e.g., mRNA) compositions described herein may be selected for administration to Asian populations (e.g., Chinese populations), or in particular embodiments to older Asian populations (e.g., 60 years old or over, e.g., 60-85 or 65-85 years old).

In some embodiments, an RNA (e.g., mRNA) composition as provided herein is administered to and/or assessed in subject(s) who have been determined not to show evidence of prior infection, and/or of present infection, before administration; in some embodiments, evidence of prior infection and/or of present infection, may be or include evidence of intact virus, or any viral nucleic acid, protein, lipid etc. present in the subject (e.g., in a biological sample thereof, such as blood, cells, mucus, and/or tissue), and/or evidence of a subject's immune response to the same. In some embodiments, an RNA (e.g., mRNA) composition as provided herein is administered to and/or assessed in subject(s) who have been determined to show evidence of prior infection, and/or of present infection, before administration; in some embodiments, evidence of prior infection and/or of present infection, may be or include evidence of intact virus, or any viral nucleic acid, protein, lipid etc. present in the subject (e.g., in a biological sample thereof, such as blood, cells, mucus, and/or tissue), and/or evidence of a subject's immune response to the same. In some embodiments, a subject is considered to have a prior infection based on having a positive N-binding antibody test result or positive nucleic acid amplification test (NAAT) result on the day of Dose 1.

In some embodiments, an RNA (e.g., mRNA) composition as provided herein is administered to a subject who has been informed of a risk of side effects that may include one or more of, for example: chills, fever, headache, injection site pain, muscle pain, tiredness; in some embodiments, an RNA (e.g., mRNA) composition is administered to a subject who has been invited to notify a healthcare provider if one or more such side effects occurs, is experienced as more than mild or moderate, persists for a period of more than a day or a few days, or if any serious or unexpected event is experienced that the subject reasonably considers may be associated with receipt of the composition. In some embodiments, an RNA (e.g., mRNA) composition as provided herein is administered to a subject who has been invited to notify a healthcare provider of particular medical conditions which may include, for example, one or more of allergies, bleeding disorder or taking a blood thinner medication, breastfeeding, fever, immunocompromised state or taking medication that affects the immune system, pregnancy or plan to become pregnant, etc. In some embodiments, an RNA (e.g., mRNA) composition as provided herein is administered to a subject who has been invited to notify a healthcare provider of having received another COVID-19 vaccine. In some embodiments, an RNA (e.g., mRNA) composition as provided herein is administered to a subject not having one of the following medical conditions: experiencing febrile illness, receiving immunosuppressant therapy, receiving anticoagulant therapy, suffering from a bleeding disorder (e.g., one that would contraindicate intramuscular injection), or pregnancy and/or breastfeeding/lactation.

In some embodiments, an RNA (e.g., mRNA) composition as provided herein is administered to a subject not having received another COVID-19 vaccine. In some embodiments, an RNA (e.g., mRNA) composition as provided herein is administered to a subject who has not had an allergic reaction to any component of the RNA (e.g., mRNA) composition. Examples of such allergic reaction may include, but are not limited to difficulty breathing, swelling of fact and/or throat, fast heartbeat, rash, dizziness and/or weakness. In some embodiments, an RNA (e.g., mRNA) composition as provided herein is administered to a subject who received a first dose and did not have an allergic reaction (e.g., as described herein) to the first dose. In some embodiments where allergic reaction occurs in subject(s) after receiving a dose of an RNA (e.g., mRNA) composition as provided herein, such subject(s) may be administered one or more interventions such as treatment to manage and/or reduce symptom(s) of such allergic reactions, for example, fever-reducing and/or anti-inflammatory agents.

In some embodiments, a subject who has received at least one dose of an RNA (e.g., mRNA) composition as provided herein is informed of avoiding being exposed to a coronavirus (e.g., SARS-CoV-2) unless and until several days (e.g., at least 7 days, at least 8 days, 9 days, at least 10 days, at least 11 days, at least 12 days, at least 13 days, at least 14 days, etc.) have passed since administration of a second dose. For example, a subject who has received at least one dose of an RNA (e.g., mRNA) composition as provided herein is informed of taking precautionary measures against SARS-CoV-2 infection (e.g., remaining socially distant, wearing masks, frequent hand-washing, etc.) unless and until several days (e.g., at least 7 days, at least 8 days, 9 days, at least 10 days, at least 11 days, at least 12 days, at least 13 days, at least 14 days, etc.) have passed since administration of a second dose. Accordingly, in some embodiments, methods of administering an RNA (e.g., mRNA) composition as provided herein comprise administering a second dose of such an RNA (e.g., mRNA) composition as provided herein to a subject who received a first dose and took precautionary measures to avoid being exposed to a coronavirus (e.g., SARS-CoV-2).

In some embodiments, RNA (e.g., mRNA) compositions described herein may be delivered to a draining lymph node of a subject in need thereof, for example, for vaccine priming. In some embodiments, such delivery may be performed by intramuscular administration of a provided RNA (e.g., mRNA) composition.

In some embodiments, different particular RNA (e.g., mRNA) compositions may be administered to different subject population(s); alternatively or additionally, in some embodiments, different dosing regimens may be administered to different subject populations. For example, in some embodiments, RNA (e.g., mRNA) compositions administered to particular subject population(s) may be characterized by one or more particular effects (e.g., incidence and/or degree of effect) in those subject populations. In some embodiments, such effect(s) may be or comprise, for example titer and/or persistence of neutralizing antibodies and/or T cells (e.g., $T_H1$-type T cells such as $CD4^+$ and/or CD8+ T cells), protection against challenge (e.g., via injection and/or nasal exposure, etc), incidence, severity, and/or persistence of side effects (e.g., reactogenicity), etc.

In some embodiments, one or more RNA (e.g., mRNA) compositions described herein may be administered according to a regimen established to reduce COVID-19 incidence per 1000 person-years, e.g., based on a laboratory test such as nucleic acid amplification test (NAAT). In some embodiments, one or more RNA (e.g., mRNA) compositions described herein may be administered according to a regimen established to reduce COVID-19 incidence per 1000 person-years based on a laboratory test such as nucleic acid amplification test (NAAT) in subjects receiving at least one dose of a provided RNA (e.g., mRNA) composition with no serological or virological evidence (e.g., up to 7 days after receipt of the last dose) of past SARS-CoV-2 infection. In some embodiments, one or more RNA (e.g., mRNA) compositions described herein may be administered according to a regimen established to reduce confirmed severe COVID-19 incidence per 1000 person-years. In some embodiments, one or more RNA (e.g., mRNA) compositions described herein may be administered according to a regimen established to reduce confirmed severe COVID-19 incidence per 1000 person-years in subjects receiving at least one dose of a provided RNA (e.g., mRNA) composition with no serological or virological evidence of past SARS-CoV-2 infection.

In some embodiments, one or more RNA (e.g., mRNA) compositions described herein may be administered according to a regimen established to produce neutralizing antibodies directed to a SARS-CoV-2 spike polypeptide and/or an immunogenic fragment thereof (e.g., RBD) as measured in serum from a subject that achieves or exceeds a reference level (e.g., a reference level determined based on human SARS-CoV-2 infection/COVID-19 convalescent sera) for a period of time and/or induction of cell-mediated immune response (e.g., a T cell response against SARS-CoV-2), including, e.g., in some embodiments induction of T cells that recognize at least one or more MHC-restricted (e.g., MHC class I-restricted) epitopes within a SARS-CoV-2 spike polypeptide and/or an immunogenic fragment thereof (e.g., RBD) for a period of time.

In some such embodiments, the period of time may be at least 2 months, 3 months, at least 4 months, at least 5 months, at least 6 months, at least 7 months, at least 8 months, at least 9 months, at least 10 months, at least 11 months, at least 12 months or longer. In some embodiments, one or more epitopes recognized by vaccine-induced T cells (e.g., CD8+ T cells) may be presented on a MHC class I allele that is present in at least 50% of subjects in a population, including, e.g., at least 60%, at least 70%, at least 80%, at least 90%, or more; in some such embodiments, the MHC class I allele may be HLA-B*0702, HLA-A*2402, HLA-B*3501, HLA-B*4401, or HLA-A*0201. In some embodiments, an epitope may comprise HLA-A*0201 YLQPRTFLL (SEQ ID NO: 138); HLA-A*0201 RLQSLQTYV (SEQ ID NO: 139); HLA-A*2402 QYIKWPWYI (SEQ ID NO: 140); HLA-A*2402 NYNYLYRLF (SEQ ID NO: 141); HLA-A*2402 KWPWYIWLGF (SEQ ID NO: 142); HLA-B*3501 QPTE- SIVRF (SEQ ID NO: 143); HLA-B*3501 IPFAMQMAY (SEQ ID NO: 144); or HLA-B*3501 LPFNDGVYF (SEQ ID NO: 145).

In some embodiments, efficacy is assessed as COVID-19 incidence per 1000 person-years in individuals without serological or virological evidence of past SARS-CoV-2 infection before and during vaccination regimen; alternatively or additionally, in some embodiments, efficacy is assessed as COVID-19 incidence per 1000 person-years in subjects with and without evidence of past SARS-CoV-2 infection before and during vaccination regimen. In some such embodiments, such incidence is of COVID-19 cases confirmed within a specific time period after the final vaccination dose (e.g., a first dose in a single-dose regimen; a second dose in a two-dose regimen, etc); in some embodiments, such time period may be within (i.e., up to and including 7 days) a particular number of days (e.g., 3, 4, 5, 6, 7, 8, 9, 10, 11, 12, 13, 14, 15, 16, 17, 18, 19, 20, 21, 22, 23, 24, 25, 26, 27, 28, 29, 30 days or more). In some embodiments, such time period may be within 7 days or within 14 days or within 21 days or within 28 days.

In some embodiments, such time period may be within 7 days. In some embodiments, such time period may be within 14 days.

In some embodiments (e.g., in some embodiments of assessing efficacy), a subject is determined to have experienced COVID-19 infection if one or more of the following is established: detection of SARS-CoV-2 nucleic acid in a sample from the subject, detection of antibodies that specifically recognize SARS-CoV-2 (e.g., a SARS-Co-V-2 spike protein), one or more symptoms of COVID-19 infection, and combinations thereof. In some such embodiments, detection of SARS-CoV-2 nucleic acid may involve, for example, NAAT testing on a mid-turbinate swap sample. In some such embodiments, detection of relevant antibodies may involve serological testing of a blood sample or portion thereof. In some such embodiments, symptoms of COVID-19 infection may be or include: fever, new or increased cough, new or increased shortness of breath, chills, new or increased muscle pain, new loss of taste or smell, sore throat, diarrhea, vomiting and combinations thereof. In some such embodiments, symptoms of COVID-19 infection may be or include: fever, new or increased cough, new or increased shortness of breath, chills, new or increased muscle pain, new loss of taste or smell, sore throat, diarrhea, vomiting, fatigue, headache, nasal congestion or runny nose, nausea, and combinations thereof. In some such embodiments, a subject is determined to have experienced COVID-19 infection if such subject both has experienced one such symptom and also has received a positive test for SARS-CoV-2 nucleic acid or antibodies, or both. In some such embodiments, a subject is determined to have experienced COVID-19 infection if such subject both has experienced one such symptom and also has received a positive test for SARS-CoV-2 nucleic acid. In some such embodiments, a subject is determined to have experienced COVID-19 infection if such subject both has experienced one such symptom and also has received a positive test for SARS-CoV-2 antibodies.

In some embodiments (e.g., in some embodiments of assessing efficacy), a subject is determined to have experienced severe COVID-19 infection if such subject has experienced one or more of: clinical signs at rest indicative or severe systemic illness (e.g., one or more of respiratory rate at greater than or equal to 30 breaths per minute, heart rate at or above 125 beats per minute, $SpO_2$ less than or equal to 93% on room air at sea level or a $PaO_2/FiO_2$ below 300 m Hg), respiratory failure (e.g., one or more of needing high-flow oxygen, noninvasive ventilation, mechanical ventilation, ECMO), evidence of shock (systolic blood pressure below 90 mm Hg, diastolic blood pressure below 60 mm Hg, requiring vasopressors), significant acute renal, hepatic, or neurologic dysfunction, admission to an intensive care unit, death, and combinations thereof.

In some embodiments, one or more RNA (e.g., mRNA) compositions described herein may be administered according to a regimen established to reduce the percentage of subjects reporting at least one of the following: (i) one or more local reactions (e.g., as described herein) for up to 7 days following each dose; (ii) one or more systemic events for up to 7 days following each dose; (iii) adverse events (e.g., as described herein) from a first dose to 1 month after the last dose; and/or (iv) serious adverse events (e.g., as described herein) from a first dose to 6 months after the last dose.

In some embodiments, one or more subjects who have received an RNA (e.g., mRNA) composition as described herein may be monitored (e.g., for a period of at least 1, 2, 3, 4, 5, 6, 7, 8, 9, 10 days or more, including, for example, 1, 2, 3, 4, 5, 6, 7, 8, 9, 10, 11, 12 weeks or more, including for example 1, 2, 3, 4, 5, 6, 7, 8, 9, 10, 11, 12, 13, 14, 15, 16, 17, 18, 19, 20, 21, 22, 23, 24 months or more, including for example 1, 2, 3, 4, 5, 6, 7, 8, 9, 10 years or more) to assess, for example, presence of an immune response to component(s) of the administered composition, evidence of exposure to and/or immune response to SARS-CoV-2 or another coronavirus, evidence of any adverse event, etc. In some embodiments, monitoring may be via tele-visit. Alternatively or additionally, in some embodiments, monitoring may be in-person.

In some embodiments, a treatment effect conferred by one or more RNA (e.g., mRNA) compositions described herein may be characterized by (i) a SARS-CoV-2 anti-S1 binding antibody level above a pre-determined threshold; (ii) a SARS-CoV-2 anti-RBD binding antibody level above a pre-determined threshold; and/or (iii) a SARS-CoV-2 serum neutralizing titer above a threshold level, e.g., at baseline, 1 month, 3 months, 6 months, 9 months, 12 months, 18 months, and/or 24 months after completion of vaccination. In some embodiments, anti-S1 binding antibody and/or anti-RBD binding antibody levels and/or serum neutralizing titers may be characterized by geometric mean concentration (GMC), geometric mean titer (GMT), or geometric mean fold-rise (GMFR).

In some embodiments, a treatment effect conferred by one or more RNA (e.g., mRNA) compositions described herein may be characterized in that percentage of treated subjects showing a SARS-CoV-2 serum neutralizing titer above a pre-determined threshold, e.g., at baseline, 1 month, 3 months, 6 months, 9 months, 12 months, 18 months, and/or 24 months after completion of vaccination, is higher than the percentage of non-treated subjects showing a SARS-CoV-2 serum neutralizing titer above such a pre-determined threshold (e.g., as described herein). In some embodiments, a serum neutralizing titer may be characterized by geometric mean concentration (GMC), geometric mean titer (GMT), or geometric mean fold-rise (GMFR).

In some embodiments, a treatment effect conferred by one or more RNA (e.g., mRNA) compositions described herein may be characterized by detection of SARS-CoV-2 NVA-specific binding antibody.

In some embodiments, a treatment effect conferred by one or more RNA (e.g., mRNA) compositions described herein may be characterized by SARS-CoV-2 detection by nucleic acid amplification test.

In some embodiments, a treatment effect conferred by one or more RNA (e.g., mRNA) compositions described herein may be characterized by induction of cell-mediated immune response (e.g., a T cell response against SARS-CoV-2), including, e.g., in some embodiments induction of T cells that recognize at least one or more MHC-restricted (e.g., MHC class I-restricted) epitopes within a SARS-CoV-2 spike polypeptide and/or an immunogenic fragment thereof (e.g., RBD). In some embodiments, one or more epitopes recognized by vaccine-induced T cells (e.g., CD8+ T cells) may be presented on a MHC class I allele that is present in at least 50% of subjects in a population, including, e.g., at least 60%, at least 70%, at least 80%, at least 90%, or more; in some such embodiments, the MHC class I allele may be HLA-B*0702, HLA-A*2402, HLA-B*3501, HLA-B*4401, or HLA-A*0201. In some embodiments, an epitope may comprise HLA-A*0201 YLQPRTFLL (SEQ ID NO: 138); HLA-A*0201 RLQSLQTYV (SEQ ID NO: 139); HLA-A*2402 QYIKWPWYI (SEQ ID NO: 140); HLA-A*2402 NYNYLYRLF (SEQ ID NO: 141); HLA-A*2402 KWPWYIWLGF (SEQ ID NO: 142); HLA-B*3501 QPTESIVRF (SEQ ID NO: 143); HLA-B*3501 IPFAMQMAY (SEQ ID NO: 144); or HLA-B*3501 LPFNDGVYF (SEQ ID NO: 145).

In some embodiments, primary vaccine efficacy (VE) of one or more RNA (e.g., mRNA) compositions described herein may be established when there is sufficient evidence (posterior probability) that either primary VE1 or both primary VE1 and primary VE2 are >30% or higher (including, e.g., greater than 40%, greater than 50%, greater than 60%, greater than 70%, greater than 80%, greater than 90%, greater than 95%, greater than 96%, greater than 97%, greater than 98%, or higher), wherein primary VE is defined as primary VE=100×(1-IRR); and IRR is calculated as the ratio of COVID-19 illness rate in the vaccine group to the corresponding illness rate in the placebo group. Primary VE1 represents VE for prophylactic RNA (e.g., mRNA) compositions described herein against confirmed COVID-19 in participants without evidence of infection before vaccination, and primary VE2 represents VE for prophylactic RNA (e.g., mRNA) compositions described herein against confirmed COVID-19 in all participants after vaccination. In some embodiments, primary VE1 and VE2 can be evaluated sequentially to control the overall type I error of 2.5% (hierarchical testing). In some embodiments where one or more RNA (e.g., mRNA) compositions described herein are demonstrated to achieve primary VE endpoints as discussed above, secondary VE endpoints (e.g., confirmed severe COVID-19 in participants without evidence of infection before vaccination and confirmed severe COVID-19 in all participants) can be evaluated sequentially, e.g., by the same method used for the primary VE endpoint evaluation (hierarchical testing) as discussed above. In some embodiments, evaluation of primary and/or secondary VE endpoints may be based on at least 20,000 or more subjects (e.g., at least 25,000 or more subjects) randomized in a 1:1 ratio to the vaccine or placebo group, e.g., based on the following assumptions: (i) 1.0% illness rate per year in the placebo group, and (ii) 20% of the participants being non-evaluable or having serological evidence of prior infection with SARS-CoV-2, potentially making them immune to further infection.

In some embodiments, one or more RNA (e.g., mRNA) compositions described herein may be administered according to a regimen established to achieve maintenance and/or continued enhancement of an immune response. For example, in some embodiments, an administration regimen may include a first dose optionally followed by one or more subsequent doses; in some embodiments, need for, timing of, and/or magnitude of any such subsequent dose(s) may be selected to maintain, enhance, and/or modify one or more immune responses or features thereof. In some embodiments, number, timing, and/or amount(s) of dose(s) have been established to be effective when administered to a relevant population. In some embodiments, number, timing and/or amount(s) of dose(s) may be adjusted for an individual subject; for example, in some embodiments, one or more features of an immune response in an individual subject may be assessed at least once (and optionally more than once, for example multiple times, typically spaced apart, often at pre-selected intervals) after receipt of a first dose. For example, presence of antibodies, B cells, and/or T cells (e.g., CD4' and/or $CD8^+$ T cells), and/or of cytokines secreted thereby and/or identity of and/or extent of responses to particular antigen(s) and/or epitope(s) may be assessed. In some embodiments, need for, timing of, and/or amount of a subsequent dose may be determined in light of such assessments.

As noted hereinabove, in some embodiments, one or more subjects who have received an RNA (e.g., mRNA) composition as described herein may be monitored (e.g., for a period of at least 1, 2, 3, 4, 5, 6, 7, 8, 9, 10 days or more, including, for example, 1, 2, 3, 4, 5, 6, 7, 8, 9, 10, 11, 12 weeks or more, including for example 1, 2, 3, 4, 5, 6, 7, 8, 9, 10, 11, 12, 13, 14, 15, 16, 17, 18, 19, 20, 21, 22, 23, 24 months or more, including for example 1, 2, 3, 4, 5, 6, 7, 8, 9, 10 years or more) from receipt of any particular dose to assess, for example, presence of an immune response to component(s) of the administered composition, evidence of exposure to and/or immune response to SARS-CoV-2 or another coronavirus, evidence of any adverse event, etc, including to perform assessment of one or more of presence of antibodies, B cells, and/or T cells (e.g., $CD4^+$ and/or $CD8^+$ T cells), and/or of cytokines secreted thereby and/or identity of and/or extent of responses to particular antigen(s) and/or epitope(s) may be assessed. Administration of a composition as described herein may be in accordance with a regimen that includes one or more such monitoring steps.

For example, in some embodiments, need for, timing of, and/or amount of a second dose relative to a first dose (and/or of a subsequent dose relative to a prior dose) is assessed, determined, and/or selected such that administration of such second (or subsequent) dose achieves amplification or modification of an immune response (e.g., as described herein) observed after the first (or other prior) dose. In some embodiments, such amplification of an immune response (e.g., ones described herein) may be at least 30%, at least 40%, at least 50%, at least 60%, at least 70%, at least 80%, at least 90%, at least 95%, or higher, as compared to the level of an immune response observed after the first dose. In some embodiments, such amplification of an immune response may be at least 1.5 fold, at least 2-fold, at least 3-fold, at least 4-fold, at least 5-fold, at least 6-fold, at least 7-fold, at least 8-fold, at least 9-fold, at least 10-fold, at least 20-fold, at least 30-fold, or higher, as compared to the level of an immune response observed after the first dose.

In some embodiments, need for, timing of, and/or amount of a second (or subsequent) dose relative to a first (or other prior) dose is assessed, determined, and/or selected such that administration of the later dose extends the durability of an immune response (e.g., as described herein) observed after the earlier dose; in some such embodiments, the durability may be extended by at least 1 week, at least 2 weeks, at least 3 weeks, at least 1 month, at least 2 months, at least 3 months, at least 4 months, at least 5 months, at least 6 months, at least 7 months, at least 8 months, at least 9 months, or longer. In some embodiments, an immune response observed after the first dose may be characterized by production of neutralizing antibodies directed to a SARS-CoV-2 spike polypeptide and/or an immunogenic fragment thereof (e.g., RBD) as measured in serum from a subject and/or induction of cell-mediated immune response (e.g., a T cell response against SARS-CoV-2), including, e.g., in some embodiments induction of T cells that recognize at least one or more MHC-restricted (e.g., MHC class I-restricted) epitopes within a SARS-CoV-2 spike polypeptide and/or an immunogenic fragment thereof (e.g., RBD). In some embodiments, one or more epitopes recognized by vaccine-induced T cells (e.g., CD8+ T cells) may be presented on a MHC class I allele that is present in at least 50% of subjects in a population, including, e.g., at least 60%, at least 70%, at least 80%, at least 90%, or more; in some such embodiments, the MHC class I allele may be HLA-B*0702, HLA-A*2402, HLA-B*3501, HLA-B*4401, or HLA-A*0201. In some embodiments, an epitope may comprise HLA-A*0201 YLQPRTFLL (SEQ ID NO: 138); HLA-A*0201 RLQSLQTYV (SEQ ID NO: 139); HLA-A*2402 QYIKWPWYI (SEQ ID NO: 140); HLA-A*2402 NYNYLYRLF (SEQ ID NO: 141); HLA-A*2402 KWPWYIWLGF (SEQ ID NO: 142); HLA-B*3501 QPTESIVRF (SEQ ID NO: 143); HLA-B*3501 IPFAMQMAY (SEQ ID NO: 144); or HLA-B*3501 LPFNDGVYF (SEQ ID NO: 145).

In some embodiments, need for, timing of, and/or amount of a second dose relative to a first dose (or other subsequent dose relative to a prior dose) is assessed, determined and/or selected such that administration of such second (or subsequent) dose maintains or exceeds a reference level of an immune response; in some such embodiments, the reference level is determined based on human SARS-CoV-2 infection/COVID-19 convalescent sera and/or PBMC samples drawn from subjects (e.g., at least a period of time such as at least 14 days or longer, including, e.g., 15 days, 16 days, 17 days, 18 days, 19 days, 20 days, 25 days, 30 days, 35 days, 40 days, 45 days, 50 days, 55 days, 60 days, or longer, after PCR-confirmed diagnosis when the subjects were asymptomatic. In some embodiments, an immune response may be characterized by production of neutralizing antibodies directed to a SARS-CoV-2 spike polypeptide and/or an immunogenic fragment thereof (e.g., RBD) as measured in serum from a subject and/or induction of cell-mediated immune response (e.g., a T cell response against SARS-CoV-2), including, e.g., in some embodiments induction of T cells that recognize at least one or more MHC-restricted (e.g., MHC class I-restricted) epitopes within a SARS-CoV-2 spike polypeptide and/or an immunogenic fragment thereof (e.g., RBD). In some embodiments, one or more epitopes recognized by vaccine-induced T cells (e.g., CD8+ T cells) may be presented on a MHC class I allele that is present in at least 50% of subjects in a population, including, e.g., at least 60%, at least 70%, at least 80%, at least 90%, or more; in some such embodiments, the MHC class I allele may be HLA-B*0702, HLA-A*2402, HLA-B*3501, HLA-B*4401, or HLA-A*0201. In some embodiments, an epitope may comprise HLA-A*0201 YLQPRTFLL(SEQ ID NO: 138); HLA-A*0201 RLQSLQTYV(SEQ ID NO: 139); HLA-A*2402 QYIKWPWYI(SEQ ID NO: 140); HLA-A*2402 NYNYLYRLF(SEQ ID NO: 141); HLA-A*2402 KWPWYIWLGF(SEQ ID NO: 142); HLA-B*3501 QPTESIVRF(SEQ ID NO: 143); HLA-B*3501 IPFAMQMAY (SEQ ID NO: 144); or HLA-B*3501 LPFNDGVYF(SEQ ID NO: 145).

In some embodiments, determination of need for, timing of, and/or amount of a second (or subsequent) dose may include one or more steps of assessing, after (e.g., 7, 8, 9, 10, 11, 12, 13, 14, 15, 16, 17, 18, 19, 20, 21 days or longer after) a first (or other prior) dose, presence and/or expression levels of neutralizing antibodies directed to a SARS-CoV-2 spike polypeptide and/or an immunogenic fragment thereof (e.g., RBD) as measured in serum from a subject and/or induction of cell-mediated immune response (e.g., a T cell response against SARS-CoV-2), including, e.g., in some embodiments induction of T cells that recognize at least one or more MHC-restricted (e.g., MHC class I-restricted) epitopes within a SARS-CoV-2 spike polypeptide and/or an immunogenic fragment thereof (e.g., RBD). In some embodiments, one or more epitopes recognized by vaccine-induced T cells (e.g., CD8+ T cells) may be presented on a MHC class I allele that is present in at least 50% of subjects in a population, including, e.g., at least 60%, at least 70%, at least 80%, at least 90%, or more; in some such embodiments, the MHC class I allele may be HLA-B*0702, HLA-A*2402, HLA-B*3501, HLA-B*4401, or HLA-A*0201. In some embodiments, an epitope may comprise HLA-A*0201 YLQPRTFLL (SEQ ID NO: 138); HLA-A*0201 RLQSLQTYV (SEQ ID NO: 139); HLA-A*2402 QYIKWPWYI (SEQ ID NO: 140); HLA-A*2402 NYNYLYRLF (SEQ ID NO: 141); HLA-A*2402 KWPWYIWLGF (SEQ ID NO: 142); HLA-B*3501 QPTESIVRF (SEQ ID NO: 143); HLA-B*3501 IPFAMQMAY (SEQ ID NO: 144); or HLA-B*3501 LPFNDGVYF (SEQ ID NO: 145).

In some embodiments, a kit as provided herein may comprise a real-time monitoring logging device, which, for example in some embodiments, is capable of providing shipment temperatures, shipment time and/or location.

In some embodiments, an RNA (e.g., mRNA) composition as described herein may be shipped, stored, and/or utilized, in a container (such as a vial or syringe), e.g., a glass container (such as a glass vial or syringe), which, in some embodiments, may be a single-dose container or a multi-dose container (e.g., may be arranged and constructed to hold, and/or in some embodiments may hold, a single dose, or multiple doses of a product for administration). In some embodiments, a multi-dose container (such as a multi-dose vial or syringe) may be arranged and constructed to hold, and/or may hold 2, 3, 4, 5, 6, 7, 8, 9, 10 or more doses; in some particular embodiments, it may be designed to hold and/or may hold 5 doses. In some embodiments, a single-dose or multi-dose container (such as a single-dose or multi-dose vial or syringe) may be arranged and constructed to hold and/or may hold a volume or amount greater than the indicated number of doses, e.g., in order to permit some loss in transfer and/or administration. In some embodiments, an RNA (e.g., mRNA) composition as described herein may be shipped, stored, and/or utilized, in a preservative-free glass container (e.g., a preservative-free glass vial or syringe, e.g., a single-dose or multi-dose preservative-free glass vial or syringe). In some embodiments, an RNA (e.g., mRNA) composition as described herein may be shipped, stored, and/or utilized, in a preservative-free glass container (e.g., a preservative-free glass vial or syringe, e.g., a single-dose or multi-dose preservative-free glass vial or syringe) that contains a frozen liquid, e.g., in some embodiments 0.45 ml of frozen liquid (e.g., including 5 doses). In some embodiments, an RNA (e.g., mRNA) composition as described herein and/or a container (e.g., a vial or syringe) in which it is disposed, is shipped, stored, and/or utilized may be maintained at a temperature below room temperature, at or below 4° C., at or below 0° C., at or below −20° C., at or below −60° C., at or below −70° C., at or below −80° C., at or below −90° C., etc. In some embodiments, an RNA (e.g., mRNA) composition as described herein and/or a container (e.g., a viral or syringe) in which it is disposed, is shipped, stored, and/or utilized may be maintained at a temperature between −80° C. and −60° C. and in some embodiments protected from light. In some embodiments, an RNA (e.g., mRNA) composition as described herein and/or a container (e.g., a viral or syringe) in which it is disposed, is shipped, stored, and/or utilized may be maintained at a temperature below about 25° C., and in some embodiments protected from light. In some embodiments, an RNA (e.g., mRNA) composition as described herein and/or a container (e.g., a viral or syringe) in which it is disposed, is shipped, stored, and/or utilized may be maintained at a temperature below about 5° C. (e.g., below about 4° C.), and in some embodiments protected from light. In some embodiments, an RNA (e.g., mRNA) composition as described herein and/or a container (e.g., a viral or syringe) in which it is disposed, is shipped, stored, and/or utilized may be maintained at a temperature below about −20° C., and in some embodiments protected from light. In some embodiments, an RNA (e.g., mRNA) composition as described herein and/or a container (e.g., a viral or syringe) in which it is disposed, is shipped, stored, and/or utilized may be maintained at a temperature above about −60° C. (e.g., in some embodiments at or above about −20° C., and in some embodiments at or above about 4-5° C., in either case optionally below about 25° C.), and in some embodiments protected from light, or otherwise without affirmative steps (e.g., cooling measures) taken to achieve a storage temperature materially below about −20° C.

In some embodiments, an RNA (e.g., mRNA) composition as described herein and/or a container (e.g., a vial or syringe) in which it is disposed is shipped, stored, and/or utilized together with and/or in the context of a thermally protective material or container and/or of a temperature adjusting material. For example, in some embodiments, an RNA (e.g., mRNA) composition as described herein and/or a container (e.g., a vial or syringe) in which it is disposed is shipped, stored, and/or utilized together with ice and/or dry ice and/or with an insulating material. In some particular embodiments, a container (e.g., a vial or syringe) in which an RNA (e.g., mRNA) composition is disposed is positioned in a tray or other retaining device and is further contacted with (or otherwise in the presence of) temperature adjusting (e.g., ice and/or dry ice) material and/or insulating material. In some embodiments, multiple containers (e.g., multiple vials or syringes such as single use or multi-use vials or syringes as described herein) in which a provided RNA (e.g., mRNA) composition is disposed are co-localized (e.g., in a common tray, rack, box, etc.) and packaged with (or otherwise in the presence of) temperature adjusting (e.g., ice and/or dry ice) material and/or insulating material. To give but one example, in some embodiments, multiple containers (e.g., multiple vials or syringes such as single use or multi-use vials or syringes as described herein) in which an RNA (e.g., mRNA) composition is disposed are positioned in a common tray or rack, and multiple such trays or racks are stacked in a carton that is surrounded by a temperature adjusting material (e.g., dry ice) in a thermal (e.g., insulated) shipper. In some embodiments, temperature adjusting material is replenished periodically (e.g., within 24 hours of arrival at a site, and/or every 2 hours, 4 hours, 6 hours, 8 hours, 10 hours, 12 hours, 14 hours, 16 hours, 18 hours, 20 hours, 22 hours, 1 day, 2 days, 3 days, 4 days, 5 days, 6 days, 7 days, 8 days, 9 days, 10 days, etc.). Preferably, re-entry into a thermal shipper should be infrequent, and desirably should not occur more than twice a day. In some embodiments, a thermal shipper is re-closed within 5, 4, 3, 2, or 1 minute, or less, of having been opened. In some embodiments, a provided RNA (e.g., mRNA) composition that has been stored within a thermal shipper for a period of time, optionally within a particular temperature range remains useful. For example, in some embodiments, if a thermal shipper as described herein containing a provided RNA (e.g., mRNA) composition is or has been maintained (e.g., stored) at a temperature within a range of about 15° C. to about 25° C., the RNA (e.g., mRNA) composition may be used for up to 10 days; that is, in some embodiments, a provided RNA (e.g., mRNA) composition that has been maintained within a thermal shipper, which thermal shipper is at a temperature within a range of about 15° C. to about 25° C., for a period of not more than 10 days is administered to a subject. Alternatively or additionally, in some embodiments, if a provided RNA (e.g., mRNA) composition is or has been maintained (e.g., stored) within a thermal shipper, which thermal shipper has been maintained (e.g., stored) at a temperature within a range of about 15° C. to about 25° C., it may be used for up to 10 days; that is, in some embodiments, a provided RNA (e.g., mRNA) composition that has been maintained within a thermal shipper, which thermal shipper has been maintained at a temperature within a range of about 15° C. to about 25° C. for a period of not more than 10 days is administered to a subject.

In some embodiments, a provided RNA (e.g., mRNA) composition is shipped and/or stored in a frozen state. In some embodiments, a provided RNA (e.g., mRNA composition is shipped and/or stored as a frozen suspension, which in some embodiments does not contain preservative. In some embodiments, a frozen RNA (e.g., mRNA) composition is thawed. In some embodiments, a thawed RNA (e.g., mRNA) composition (e.g., a suspension) may contain white to off-white opaque amorphous particles. In some embodiments, a thawed RNA (e.g., mRNA) composition may be used for up to a small number (e.g., 1, 2, 3, 4, 5, or 6) of days after thawing if maintained (e.g., stored) at a temperature at or below room temperature (e.g., below about 30° C., 25° C., 20° C., 15° C., 10° C., 8° C., 4° C., etc). In some embodiments, a thawed RNA (e.g., mRNA) composition may be used after being stored (e.g., for such small number of days) at a temperature between about 2° C. and about 8° C.; alternatively or additionally, a thawed RNA (e.g., mRNA) composition may be used within a small number (e.g., 1, 2, 3, 4, 5, 6) of hours after thawing at room temperature. Thus, in some embodiments, a provided RNA (e.g., mRNA) composition that has been thawed and maintained at a temperature at or below room temperature, and in some embodiments between about 2° C. and about 8° C., for not more than 6, 5, 4, 3, 2, or 1 days is administered to a subject. Alternatively or additionally, in some embodiments, a provided RNA (e.g., mRNA) composition that has been thawed and maintained at room temperature for not more than 6, 5, 4, 3, 2, or 1 hours is administered to a subject. In some embodiments, a provided RNA (e.g., mRNA) composition is shipped and/or stored in a concentrated state. In some embodiments, such a concentrated composition is diluted prior to administration. In some embodiments, a diluted composition is administered within a period of about 10, 9, 8, 7, 6, 5, 4, 3, 2, or 1 hour(s) post-dilution; in some embodiments, such administration is within 6 hours post-dilution. Thus, in some embodiments, diluted preparation of a provided RNA (e.g., mRNA) composition is administered to a subject within 6 hours post-dilution (e.g., as described herein after having been maintained at an appropriate temperature, e.g., at a temperature below room temperature, at or below 4° C., at or below 0° C., at or below −20° C., at or below −60° C., at or below −70° C., at or below −80° C., etc, and typically at or above about 2° C., for example between about 2° C. and about 8° C. or between about 2° C. and about 25° C.). In some embodiments, unused composition is discarded within several hours (e.g., about 10, about 9, about 8, about 7, about 6, about 5 or fewer hours) after dilution; in some embodiments, unused composition is discarded within 6 hours of dilution.

In some embodiments, an RNA (e.g., mRNA) composition that is stored, shipped or utilized (e.g., a frozen composition, a liquid concentrated composition, a diluted liquid composition, etc.) may have been maintained at a temperature materially above −60° C. for a period of time of at least 1, 2, 3, 4, 5, 6, 7 days or more, or at least 1, 2, 3, 4, 5, 6, 7, 8, 9, 10 weeks or more, or at least 1, 2, 3, 4, 5, 6, 7, 8, 9, 10, 11, 12 months or more; in some such embodiments, such composition may have been maintained at a temperature at or above about −20° C. for such period of time, and/or at a temperature up to or about 4-5° C. for such period of time, and/or may have been maintained at a temperature above about 4-5° C., and optionally about 25° C. for a period of time up that is less than two (2) months and/or optionally up to about one (1) month. In some embodiments, such composition may not have been stored, shipped or utilized (or otherwise exposed to) a temperature materially above about 4-5° C., and in particular not at or near a temperature of about 25° C. for a period of time as long as about 2 weeks, or in some embodiments 1 week. In some embodiments, such composition may not have been stored, shipped or utilized (or otherwise exposed to) a temperature materially above about −20° C., and in particular not at or near a temperature of about 4-5° C. for a period of time as long as about 12 months, 11 months, 10 months, 9 months, 8 months, 7 months, 6 months, 5 months, 4 months, 3 months, 2 months, or, in some embodiments, for a period of time as long as about 8 weeks or 6 weeks or materially more than about 2 months or, in some embodiments, 3 months or, in some embodiments 4 months.

In some embodiments, an RNA (e.g., mRNA) composition that is stored, shipped or utilized (e.g., a frozen composition, a liquid concentrated composition, a diluted liquid composition, etc.) may be protected from light. In some embodiments, one or more steps may be taken to reduce or minimize exposure to light for such compositions (e.g., which may be disposed within a container such as a vial or a syringe). In some embodiments, exposure to direct sunlight and/or to ultraviolent light is avoided. In some embodiments, a diluted solution may be handled and/or utilized under normal room light conditions (e.g., without particular steps taken to minimize or reduce exposure to room light). It should be understood that strict adherence to aseptic techniques is desirable during handling (e.g., diluting and/or administration) of an RNA (e.g., mRNA) composition as described herein. In some embodiments, an RNA (e.g., mRNA) composition as described herein is not administered (e.g., is not injected) intravenously. In some embodiments, an RNA (e.g., mRNA) composition as described herein is not administered (e.g., is not injected) intradermally. In some embodiments, an RNA (e.g., mRNA) composition as described herein is not administered (e.g., is not injected) subcutaneously. In some embodiments, an RNA (e.g., mRNA) composition as described herein is not administered (e.g., is not injected) any of intravenously, intradermally, or subcutaneously. In some embodiments, an RNA (e.g., mRNA) composition as described herein is not administered to a subject with a known hypersensitivity to any ingredient thereof. In some embodiments, a subject to whom an RNA (e.g., mRNA) composition has been administered is monitored for one or more signs of anaphylaxis. In some embodiments, a subject to whom an RNA (e.g., mRNA) composition is administered had previously received at least one dose of a different vaccine for SARS-CoV-2; in some embodiments, a subject to whom an RNA (e.g., mRNA) composition is administered had not previously received a different vaccine for SARS-CoV-2. In some embodiments, a subject's temperature is taken promptly prior to administration of an RNA (e.g., mRNA) composition (e.g., shortly before or after thawing, dilution, and/or administration of such composition); in some embodiments, if such subject is determined to be febrile, administration is delayed or canceled. In some embodiments, an RNA (e.g., mRNA) composition as described herein is not administered to a subject who is receiving anticoagulant therapy or is suffering from or susceptible to a bleeding disorder or condition that would contraindicate intramuscular injection. In some embodiments, an RNA (e.g., mRNA) composition as described herein is administered by a healthcare professional who has communicated with the subject receiving the composition information relating to side effects and risks. In some embodiments, an RNA (e.g., mRNA) composition as described herein is administered by a healthcare professional who has agreed to submit an adverse event report for any serious adverse events, which may include for example one or more of death, development of a disability or congenital anomaly/birth defect (e.g., in a child of the subject), in-patient hospitalization (including prolongation of an existing hospitalization), a life-threatening event, a medical or surgical intervention to prevent death, a persistent or significant or substantial disruption of the ability to conduct normal life functions; or another important medical event that may jeopardize the individual and may require medical or surgical intervention (treatment) to prevent one of the other outcomes.

In some embodiments, provided RNA compositions are administered to a population of individuals under 18 years of age, or under 17 years of age, or under 16 years of age, or under 15 years of age, or under 14 years of age, or under 13 years of age, for example according to a regimen established to have a rate of incidence for one or more of the local reaction events indicated below that does not exceed the rate of incidence indicated below:

- pain at the injection site (75% after a first dose and/or a second dose, and/or a lower incidence after a second dose, e.g., 65% after a second dose);
- redness at the injection site (less than 5% after a first dose and/or a second dose); and/or
- swelling at the injection site (less than 5% after a first dose and/or a second dose).

In some embodiments, provided RNA compositions are administered to a population of individuals under 18 years of age, or under 17 years of age, or under 16 years of age, or under 15 years of age, or under 14 years of age, or under 13 years of age, for example according to a regimen established to have a rate of incidence for one or more of the systemic reaction events indicated below that does not exceed the rate of incidence indicated below:

fatigue (55% after a first dose and/or a second dose);
headache (50% after a first dose and/or a second dose);
muscle pain (40% after a first dose and/or a second dose);
chills (40% after a first dose and/or a second dose);
joint pain (20% after a first dose and/or a second dose);
fever (25% after a first dose and/or a second dose);
vomiting (10% after a first dose and/or a second dose); and/or
diarrhea (10% after a first dose and/or a second dose).

In some embodiments, medication that alleviates one or more symptoms of one or more local reaction and/or systemic reaction events (e.g., described herein) are administered to individuals under 18 years of age, or under 17 years of age, or under 16 years of age, or under 15 years of age, or under 14 years of age, or under 13 years of age who have been administered with provided RNA compositions and have experienced one or more of the local and/or systemic reaction events (e.g., described herein). In some embodiments, antipyretic and/or pain medication can be administered to such individuals.

The sequence within the S1 subunit consists of the signal sequence (SS) and the receptor binding domain (RBD) which is the key subunit within the S protein which is relevant for binding to the human cellular receptor ACE2. The S2 subunit contains the S2 protease cleavage site (S2') followed by a fusion peptide (FP) for membrane fusion, heptad repeats (HR1 and HR2) with a central helix (CH) domain, the transmembrane domain (TM) and a cytoplasmic tail (CT).

Figure 1:
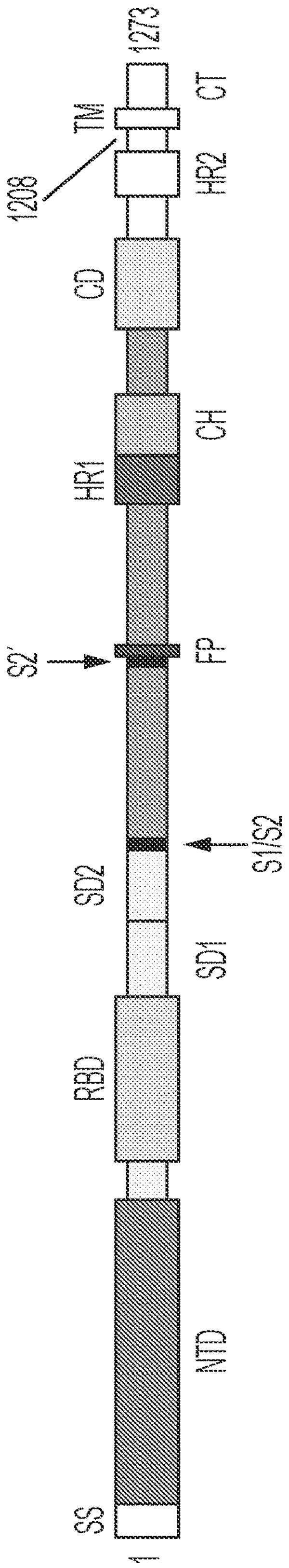
FIG. 1. Schematic overview of the S protein organization of the SARS-CoV-2 S protein.
Figure 2:
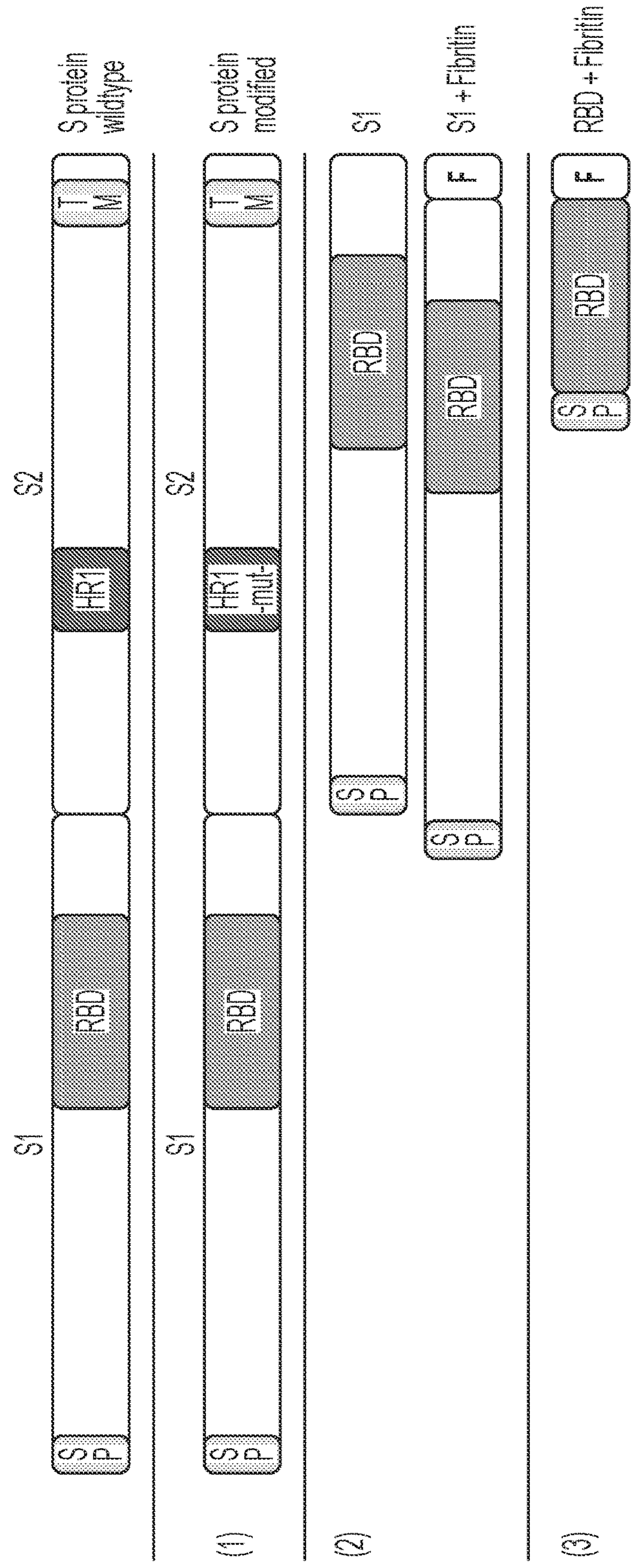

FIG. 2. Exemplary SARS-CoV-2 vaccine constructs.

Based on the full and wildtype S protein, we have designed different constructs encoding the (1) full protein with mutations in close distance to the first heptad repeat (HRP1) that include stabilizing mutations preserving neutralisation sensitive sites, the (2) S1 domain or the (3) RB domain (RBD) only. Furthermore, to stabilize the protein fragments a fibritin domain (F) was fused to the C-terminus. All constructs start with the signal peptide (SP) to ensure Golgi transport to the cell membrane.

Figure 3:
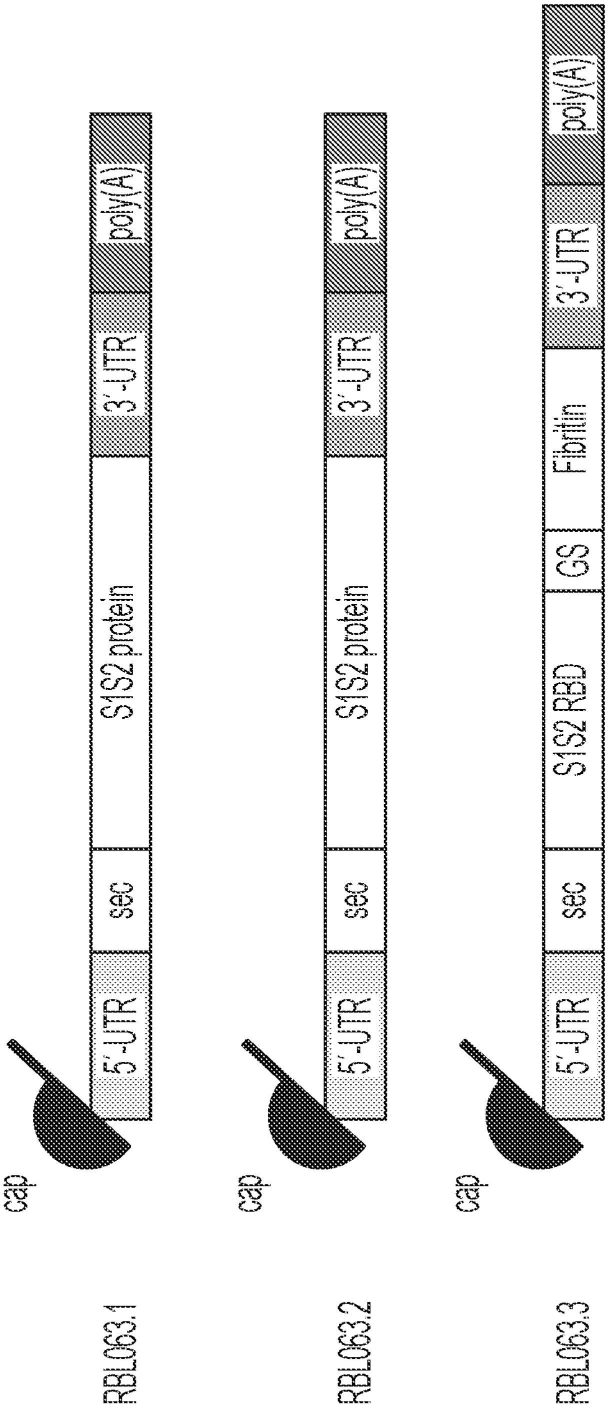

FIG. 3. General structure of the RNA.

Schematic illustration of the general structure of the RNA vaccines with 5'-cap, 5'- and 3'-untranslated regions, coding sequences with intrinsic secretory signal peptide as well as GS-linker, and poly(A)-tail. Please note that the individual elements are not drawn exactly true to scale compared to their respective sequence lengths.

UTR=Untranslated region; sec=Secretory signal peptide; RBD=Receptor Binding Domain; GS=Glycine-serine linker.

Figure 4:
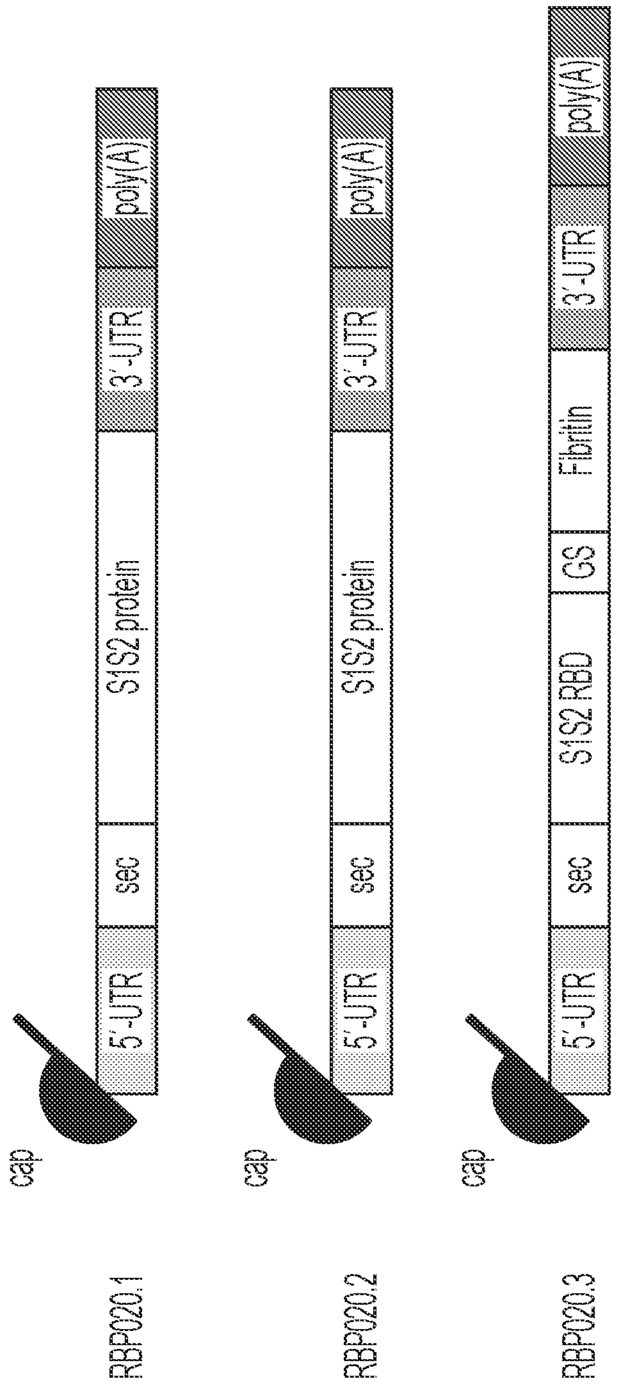

FIG. 4. General structure of the RNA.

Schematic illustration of the general structure of RNA drug substances with 5'-cap, 5'- and 3'-untranslated regions, coding sequences with intrinsic secretory signal peptide as well as GS-linker, and poly(A)-tail. Please note that the individual elements are not drawn exactly true to scale compared to their respective sequence lengths.

GS=Glycine-serine linker; UTR=Untranslated region; Sec=Secretory signal peptide; RBD=Receptor Binding Domain.

Figure 5:
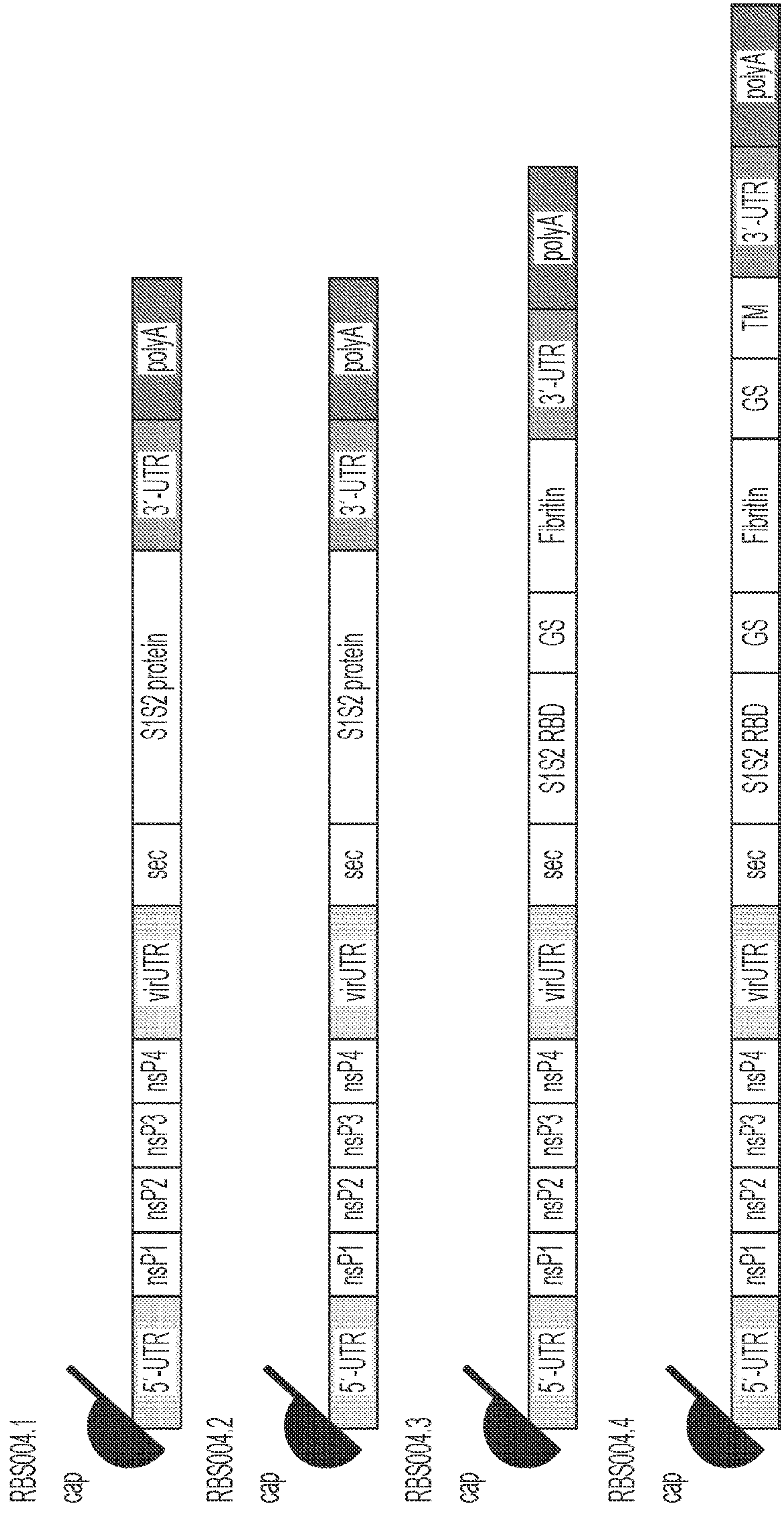

FIG. 5. General structure of the RNA.

Schematic illustration of the general structure of RNA vaccines with 5'-cap, 5'- and 3'-untranslated regions, coding sequences of the Venezuelan equine encephalitis virus (VEEV) RNA-dependent RNA polymerase replicase and the SARS-CoV-2 antigen with intrinsic secretory signal peptide as well as GS-linker, and poly(A)-tail. Please note that the individual elements are not drawn exactly true to scale compared to their respective sequence lengths.

UTR=Untranslated region; Sec=Secretory signal peptide; RBD=Receptor Binding Domain; GS=Glycine-serine linker.

Figure 6:
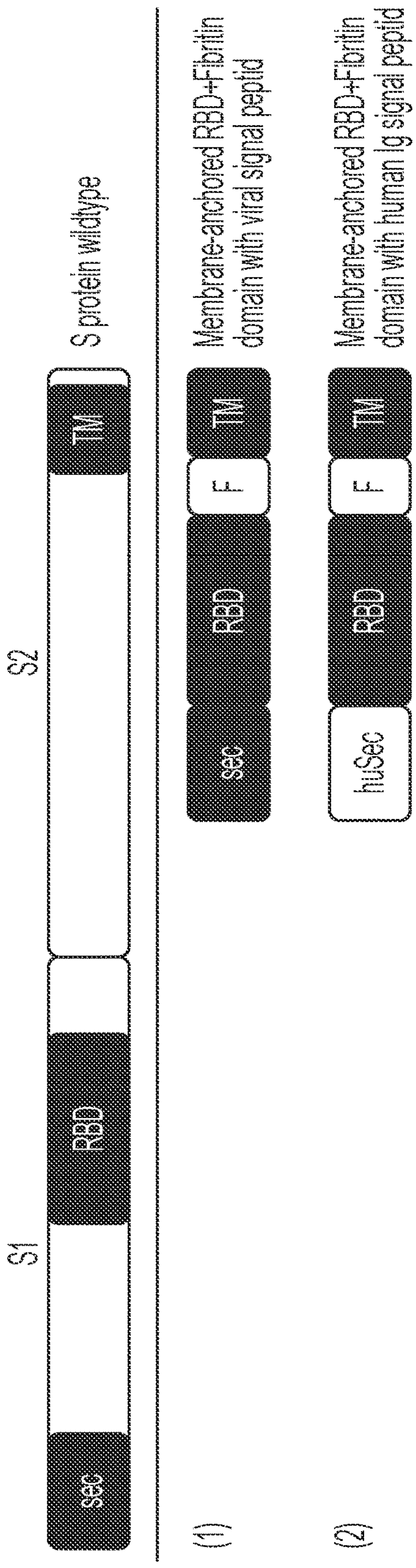

FIG. 6. Schematic overview of the S protein organization of the SARS-CoV-2 S protein and constructs for the development of a SARS-CoV-2 vaccine.

Based on the wildtype S protein, we have designed two different transmembrane-anchored RBD-based vaccine constructs encoding the RBD fragment fused to the T4 fibritin trimerization domain (F) and the autochthonus transmembrane domain (TM). Construct (1) starts with the SARS-CoV-2-S signal peptide (SP; AA 1-19 of the S protein) whereas construct (2) starts with the human Ig heavy chain signal peptide (huSec) to ensure Golgi transport to the cell membrane.

Figure 7:
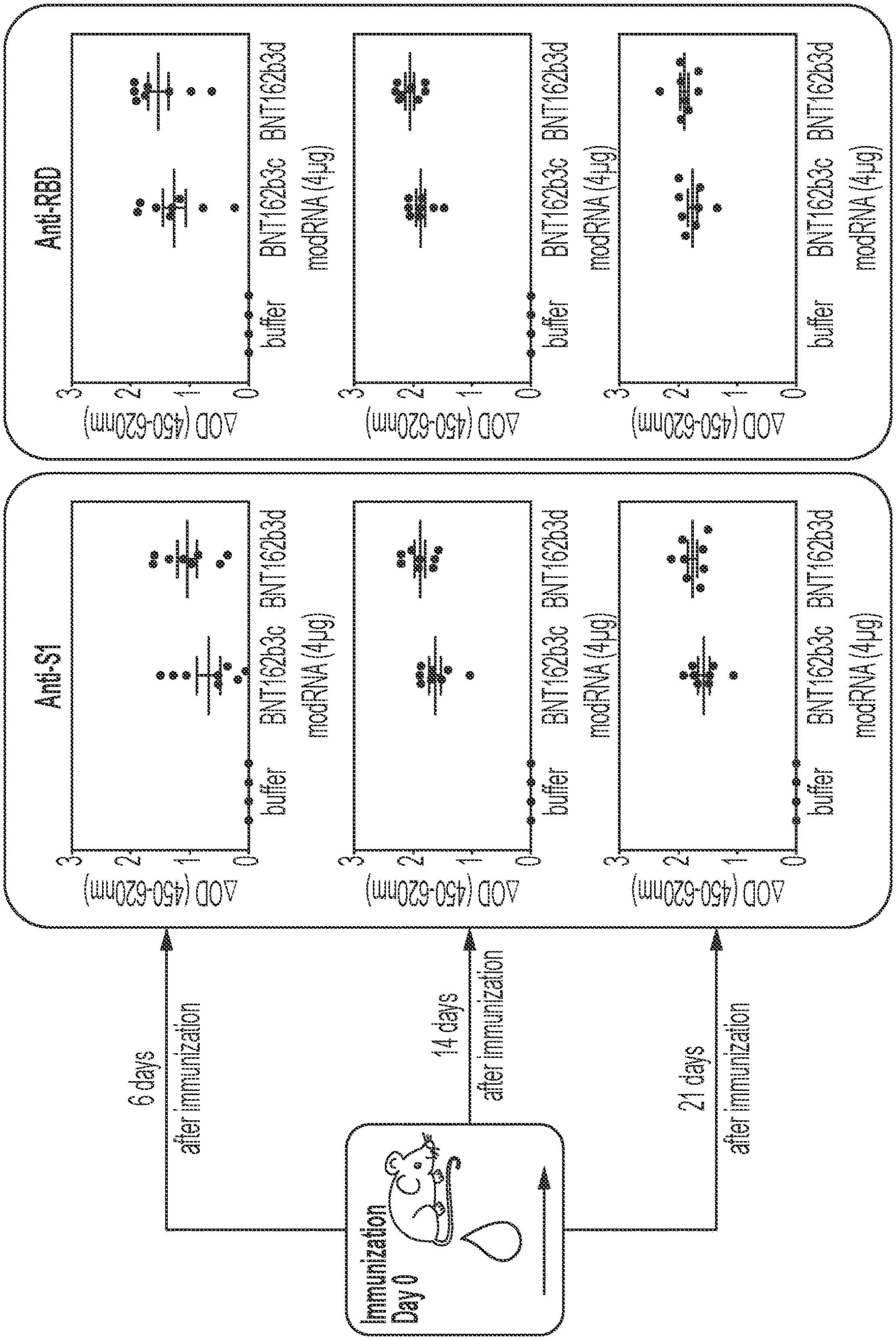

FIG. 7. Anti-S protein IgG response 6, 14 and 21 d after immunization with LNP-C12 formulated modRNA coding for transmembrane-anchored RBD-based vaccine constructs.

BALB/c mice were immunized IM once with 4 μg of LNP-C12-formulated transmembrane-anchored RBD-based vaccine constructs (surrogate to BNT162b3c/BNT162b3d). On day 6, 14 and 21 after immunization, animals were bled and the serum samples were analyzed for total amount of anti-S1 (left) and anti-RBD (right) antigen specific immunoglobulin G (IgG) measured via ELISA. For day 6 (1:50), day 14 (1:300) and day 21 (1:900) different serum dilution were included in the graph. One point in the graph stands for one mouse, every mouse sample was measured in duplicates (group size n=8; mean+SEM is included for the groups).

Figure 8:
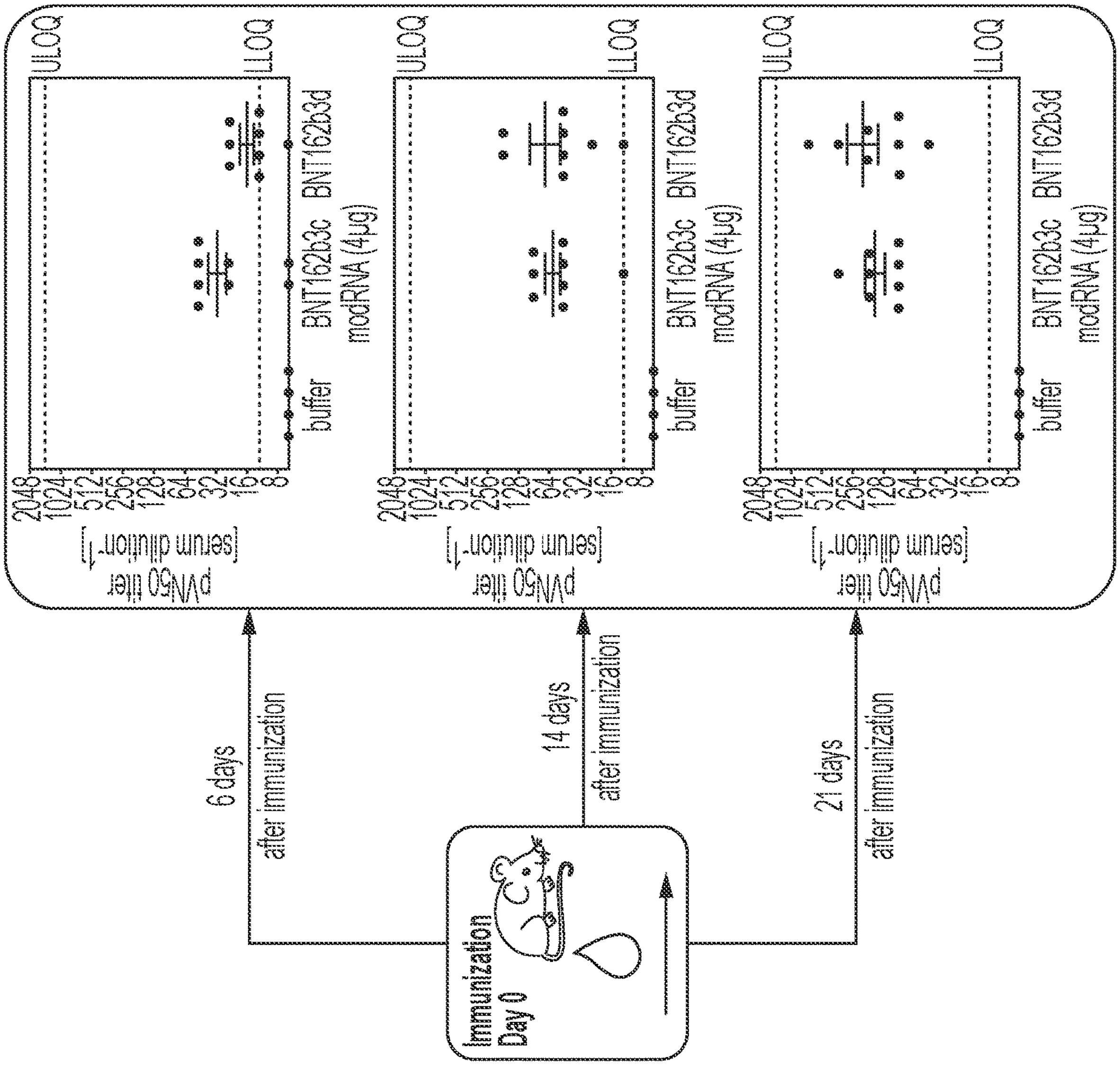

FIG. 8. Neutralization of SARS-CoV-2 pseudovirus 6, 14 and 21 d after immunization with LNP-C12 formulated modRNA coding for transmembrane-anchored RBD-based vaccine constructs.

BALB/c mice were immunized IM once with 4 μg of LNP-C12-formulated transmembrane-anchored RBD-based vaccine constructs (surrogate to BNT162b3c/BNT162b3d). On day 6, 14 and 21 after immunization, animals were bled and the sera were tested for SARS CoV-2 pseudovirus neutralization. Graphs depict $pVN_{50}$ serum dilutions (50% reduction of infectious events, compared to positive controls without serum). One point in the graphs stands for one mouse. Every mouse sample was measured in duplicate. Group size n=8. Mean+SEM is shown by horizontal bars with whiskers for each group. LLOQ, lower limit of quantification. ULOQ, upper limit of quantification.

Figure 9:
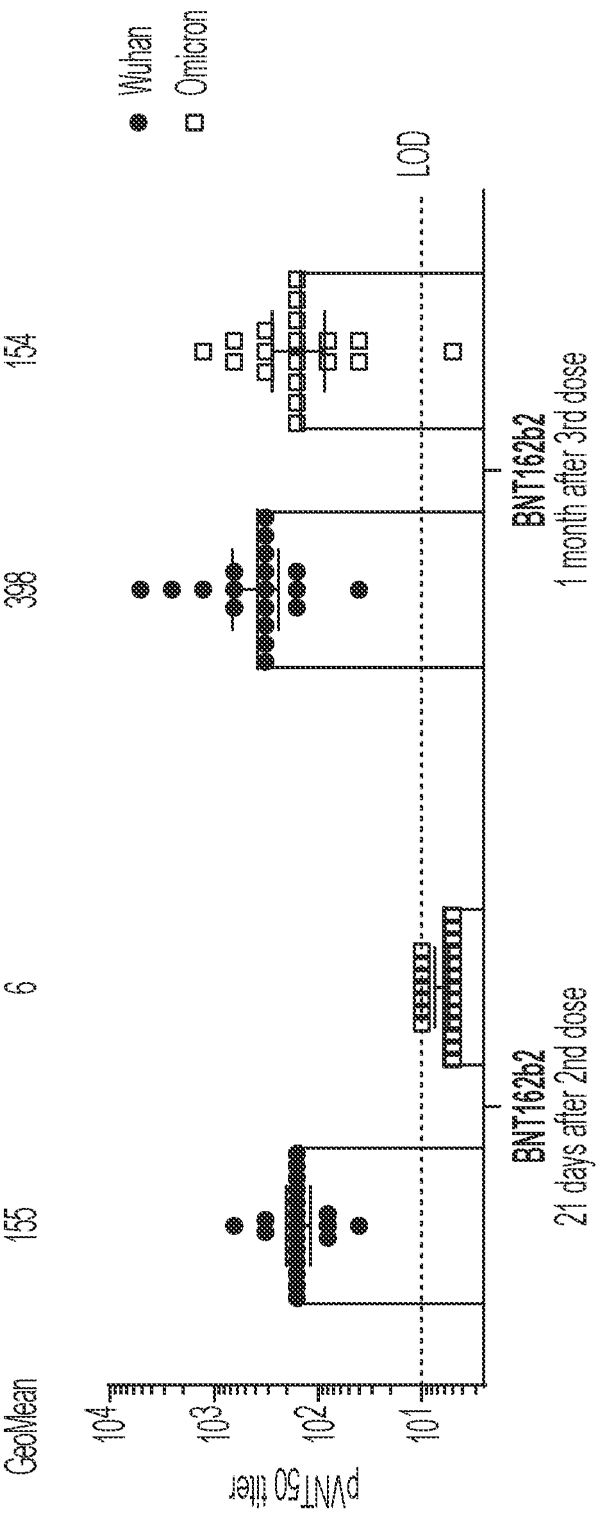

FIG. 9. 50% pseudovirus neutralization titers ($pVNT_{50}$) of sera collected 21 days after the second dose and 1 month after the third dose of BNT162b2 against VSV-SARS-CoV-2-S pseudovirus bearing the Wuhan Hu-1 reference or Omicron lineage spike protein. N=19-20 sera from immunized subjects collected either 21 days after the second BNT162b2 dose or 1 months after the third BNT162b2 dose were tested. For values below the limit of detection (LOD; 10), LOD/2 values are plotted. Group GMTs (values above bars) with 95% confidence intervals are shown.

FIG. 10. CD8+ T cell epitopes in BNT162b2 vaccine remain largely unaffected by Omicron BA.1 variant mutations. Shown is the number of previously identified MHC-1 epitopes affected in various variants of concern (VOCs). Approximately 80% of previously identified CD8+ epitopes are not affected by the mutations in the BA.1 Omicron variant, suggesting that two doses of BNT162b2 may still induce protection against severe disease.

Figure 11:
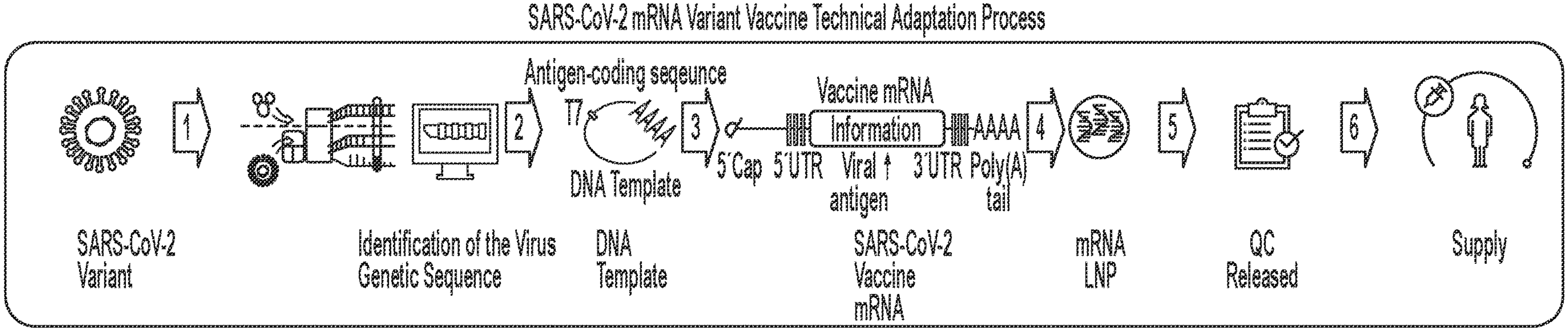

FIG. 11. Neutralization of Omicron BA.1 after two doses of BNT162b2 and variant specific booster. Shown is neutralization of the Omicron BA.1 variant from sera of patients administered two doses of BNT162b2 and (i) a third booster dose of BNT162b2, or (ii) a third booster dose of an RNA encoding a Spike protein with alpha or delta variant mutations, or a third booster dose of both a Spike protein comprising alpha mutations and a Spike protein comprising delta mutations. The values are derived from separate neutralization GMTs from the pseudovirus testing. Also shown is a schematic depicting a process for developing new SARS-CoV-2 variant specific vaccines.

Figure 12:
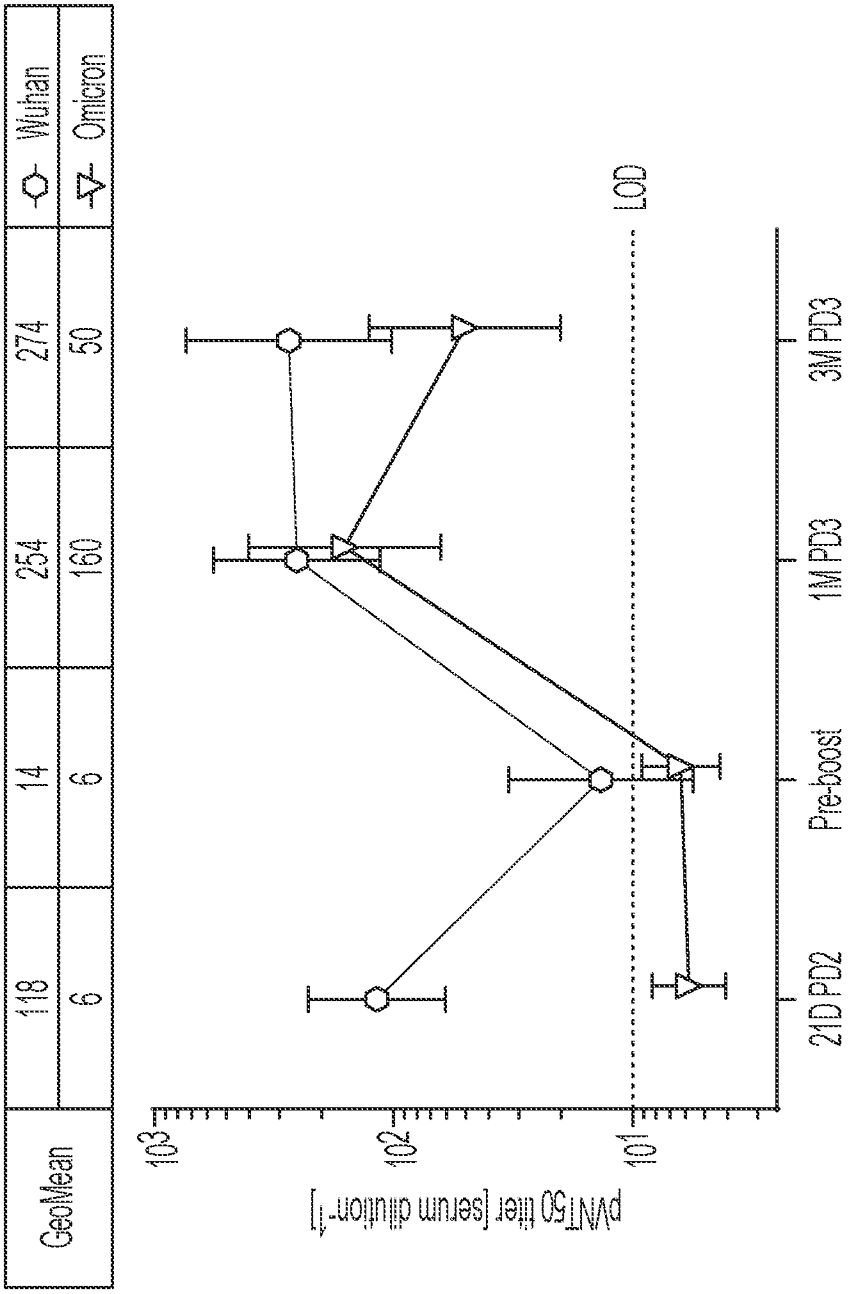

FIG. 12. Longitudinal analysis of neutralizing antibody responses against VSV-SARS-CoV-2-S pseudovirus bearing the Wuhan or Omicron BA.1 variant spike protein in a subset of study participants. Sera from n=9 participants drawn at 21 days after dose 2, prior to dose 3, 1 month after dose 3 and 3 months after dose 3 were tested. Each serum was tested in duplicate and individual geometric mean 50% pseudovirus neutralizing titers (GMTs) were calculated. For values below the limit of detection (LOD), LOD/2 values were assigned. Group GMTs (values in table) and 95% confidence intervals per timepoint are indicated.

Figure 13:
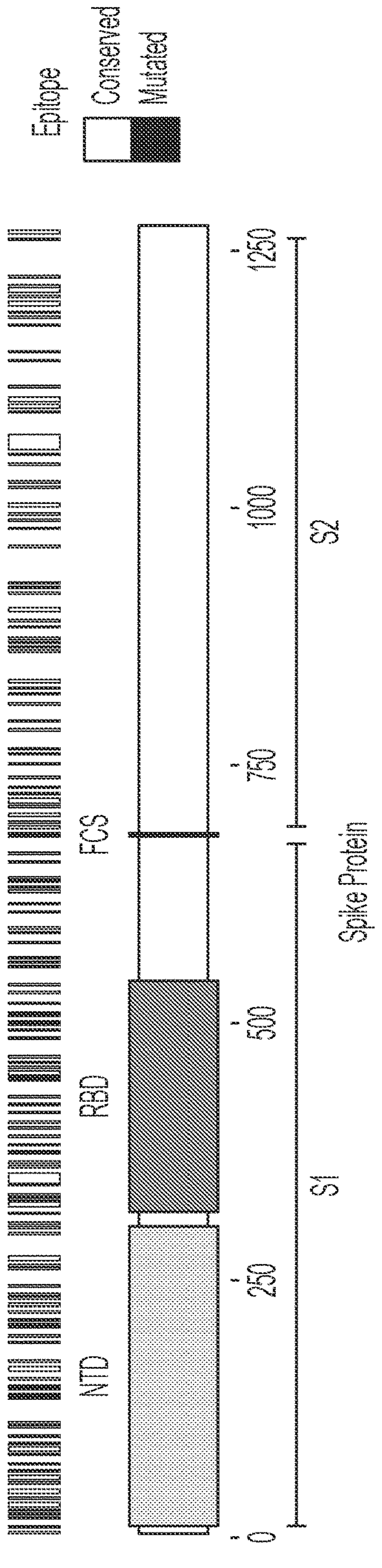

FIG. 13. Analysis of HLA class I T cell epitopes conservation between the Wuhan and Omicron BA.1 variants. HLA class I restricted Spike protein epitopes with T cell reactivity identified based on their recognition by CD8+ T cells and reported in IEDB (n=244) are plotted by their position (top row) along the Spike protein (bottom row). Epitope indications are positioned by the amino acid position of the center of the epitope; epitopes conserved in both variants are marked in light grey (n=208); while epitopes spanning an Omicron BA.1 mutation site are marked dark grey (n=36). NTD=N-terminal domain; RBD=Receptor-binding domain; FCS=Furin cleavage site. The S1 and S2 regions of the Spike protein are indicated.

Figure 14:
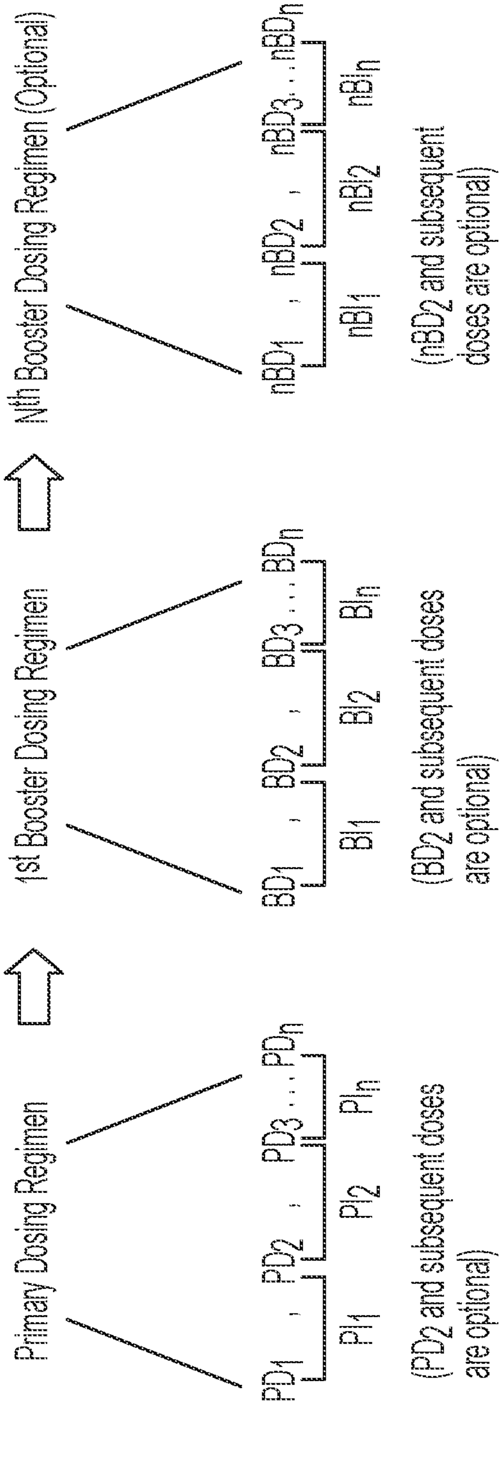

FIG. 14. Schematics of an exemplary vaccination regimen.

Figure 15:
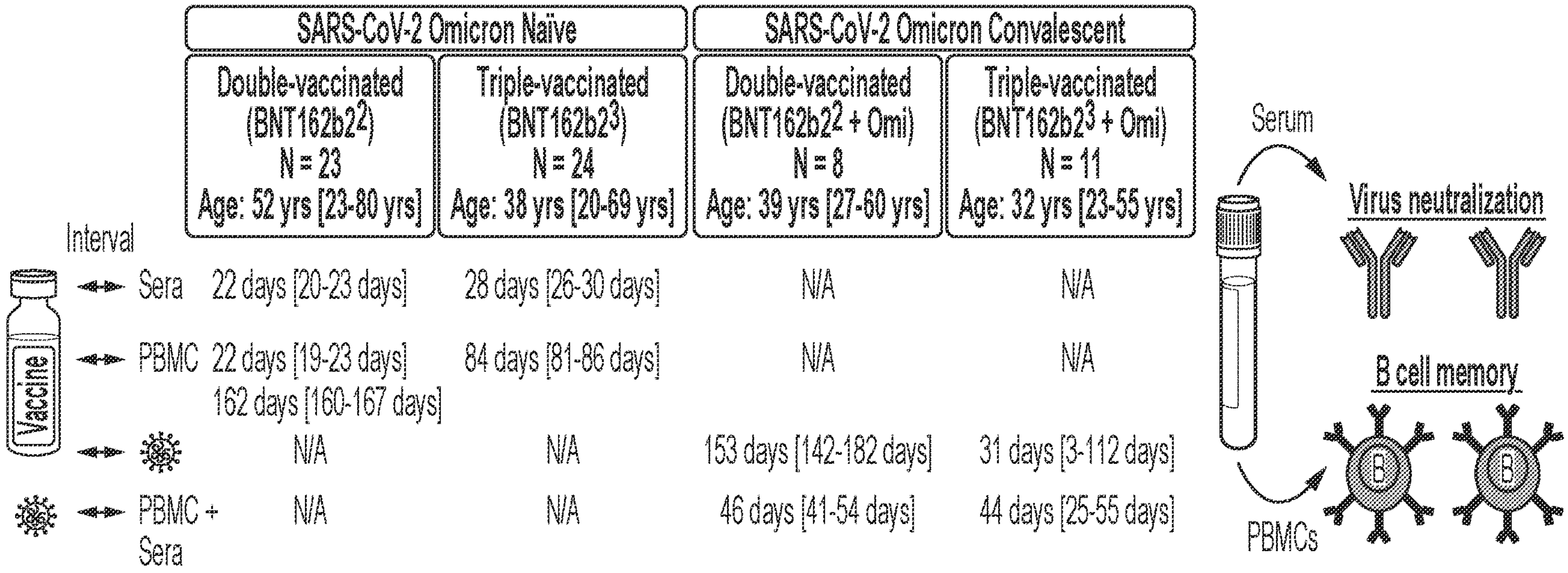

FIG. 15. Cohorts, sampling and experimental setup for characterization of immune response in Omicron breakthrough cases. Blood samples were drawn from four cohorts: Omicron-naïve individuals double- or triple-vaccinated with BNT162b2, and individuals double- or triple-vaccinated with BNT162b2 that subsequently had a breakthrough infection with Omicron BA.1. PBMCs and sera were isolated in the Omicron-naïve cohorts at the timepoints indicated following their most recent vaccination; for convalescent cohorts, the time from their most recent vaccination to Omicron BA.1 infection, and infection to PBMC and serum isolation are indicated (all values specified as median-range). Serum neutralizing capacity was assessed using a pseudovirus and live virus neutralization test; SARS-CoV-2 spike-specific $B_{MEM}$ cells were assessed via a flow cytometry-based B cell phenotyping assay using bulk PBMCs. N/A, not applicable.

Figure 16:
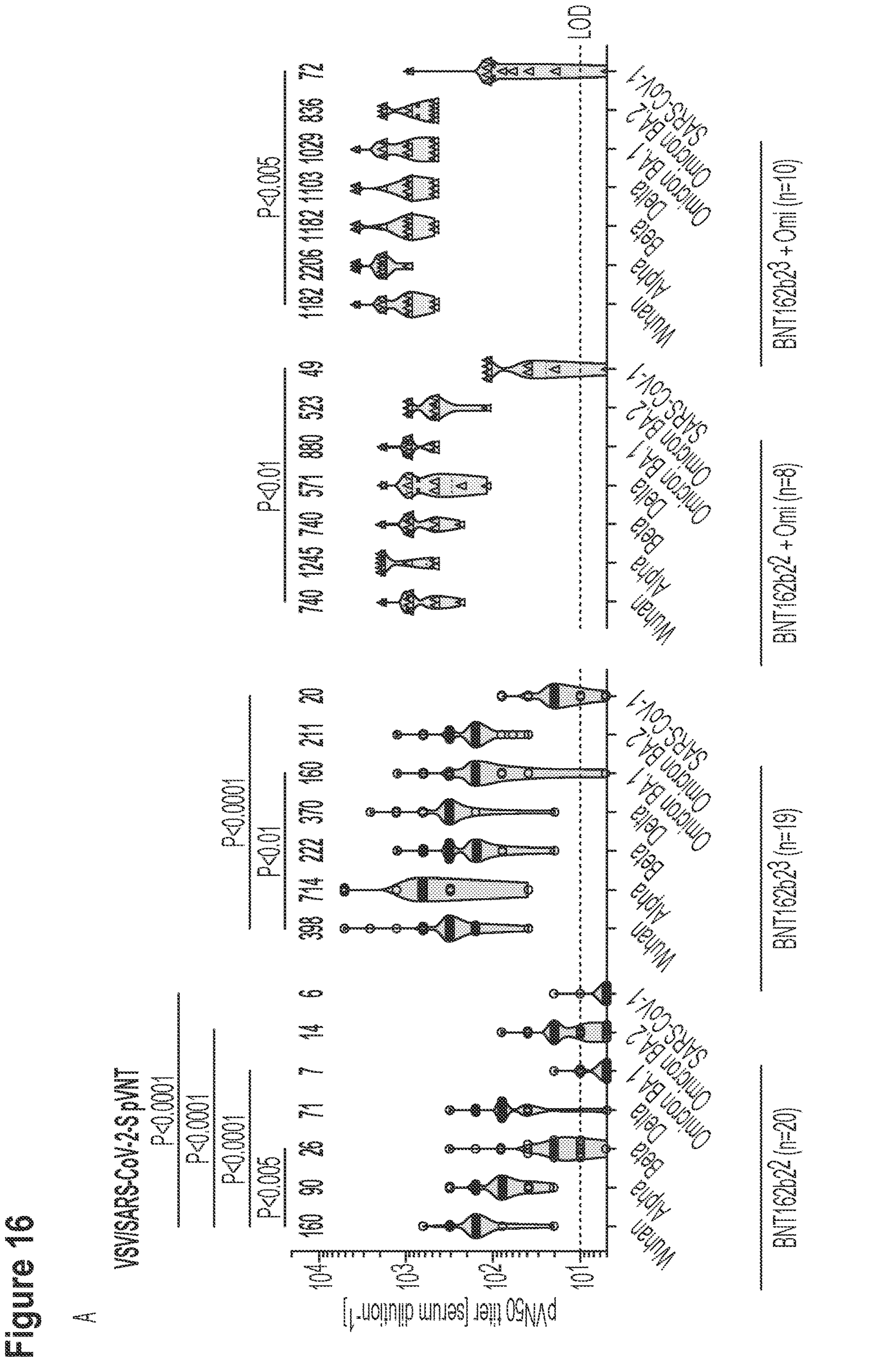
Figure 16:
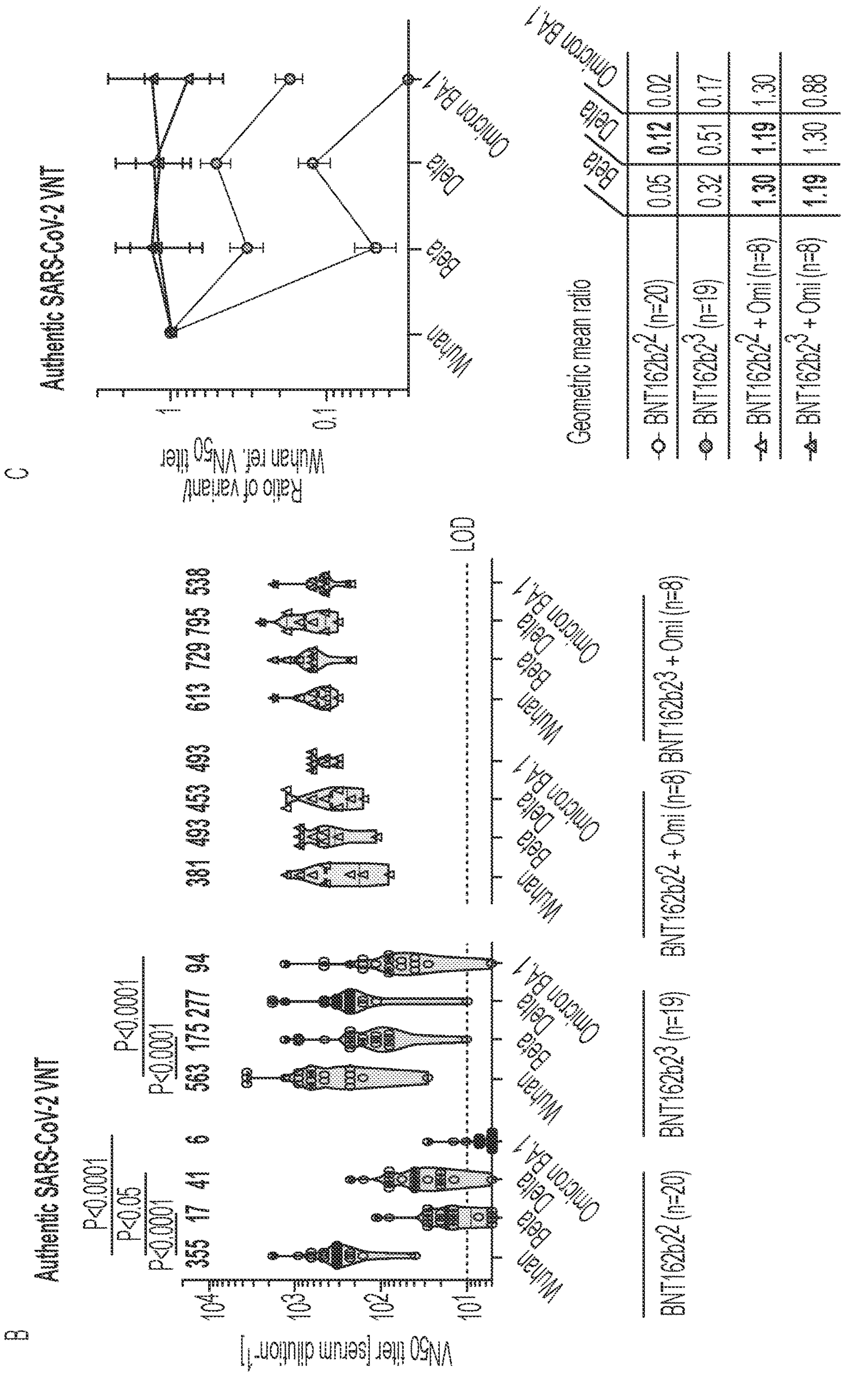

FIG. 16. Omicron breakthrough infection in BNT162b2 double- and triple-vaccinated individuals induces broad neutralization of Omicron BA.1, BA.2 and other VOCs.

Serum was drawn from double-vaccinated individuals ($BNT162b2^2$) at 22 days after the second dose (open circles), from triple-vaccinated individuals ($BNT162b2^3$) at 28 days after the third dose (closed circles), from double-vaccinated individuals with an Omicron breakthrough infection ($BNT162b2^2$+Omi) at 46 days post-infection (open triangles), and from triple-vaccinated individuals and Omicron breakthrough infection ($BNT162b2^3$+Omi) at 44 days post-infection (closed triangles). Serum was tested in duplicate; (A) shows 50% pseudovirus neutralization ($pVN_{50}$) geometric mean titers (GMTs), (B) shows 50% virus neutralization ($VN_{50}$) GMTs, and (C) shows the geometric mean ratio of SARS-CoV-2 variant of concern (VOC) and Wuhan $VN_{50}$ GMTs. For titer values below the limit of detection (LOD), LOD/2 values were plotted. Values above violin plots represent group GMTs. The non-parametric Friedman test with Dunn's multiple comparisons correction was used to compare Wuhan neutralizing group GMTs with titers against the indicated variants and SARS-CoV-1. Multiplicity-adjusted p values are shown. (A) $pVN_{50}$ GMTs against Wuhan, VOC and SARS-CoV-1 pseudovirus. (B) $VN_{50}$ GMTs against live SARS-CoV-2 Wuhan, Beta, Delta and Omicron BA.1. (C) Group geometric mean ratios with 95% confidence intervals for all cohorts shown in (B).

Figure 17:
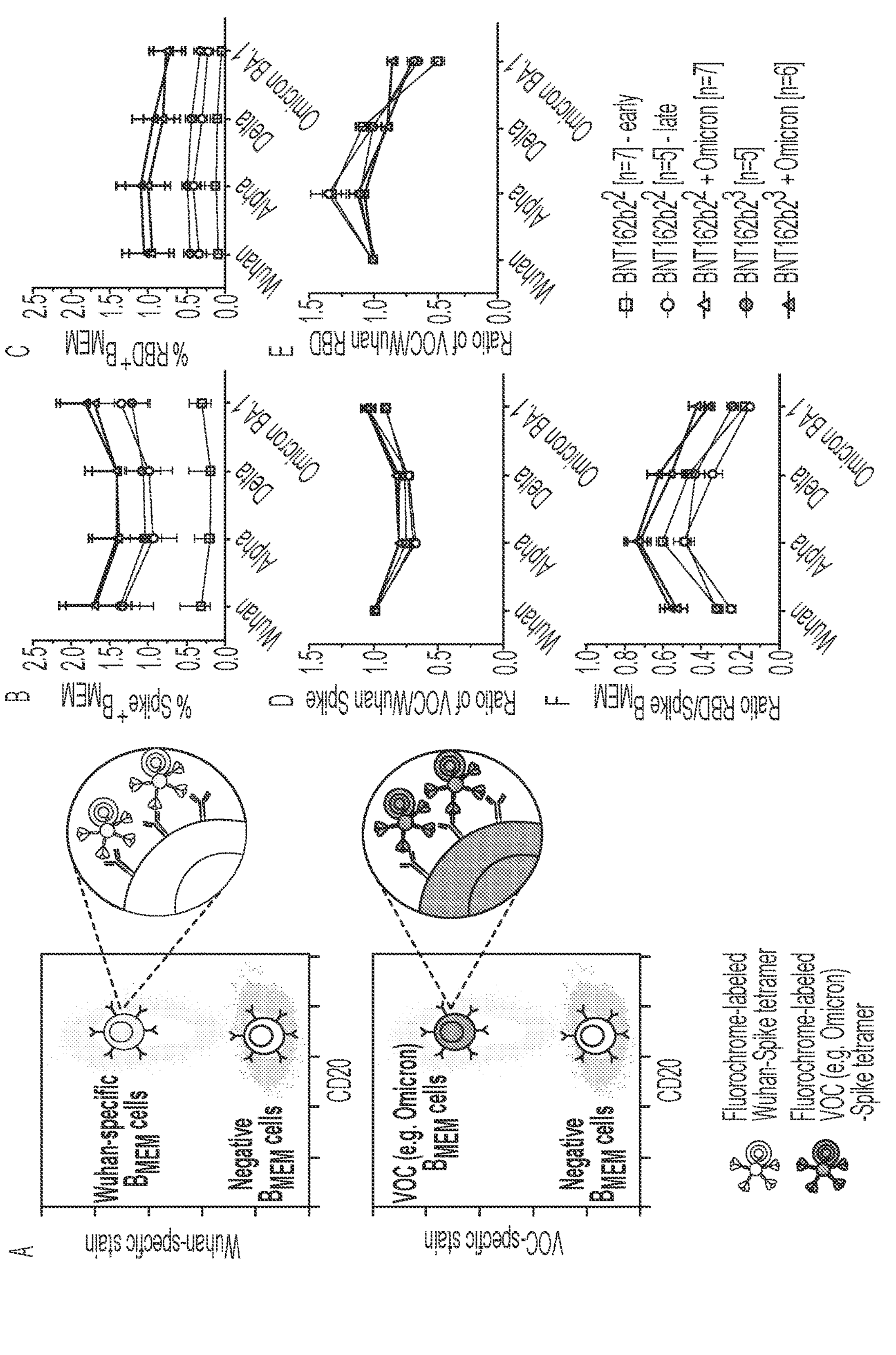

FIG. 17. $B_{MEM}$ cells of individuals double- and triple-vaccinated with BNT162b2 broadly recognize VOCs and are further boosted by Omicron breakthrough infection. PBMC samples from double-vaccinated individuals ($BNT162b2^2$) at 22 days after the second dose (open squares) and 5 months after the second dose (open circles), from triple-vaccinated individuals ($BNT162b2^3$) at 84 days after the third dose (closed circles), from double-vaccinated individuals with Omicron breakthrough infection ($BNT162b2^2$+Omi) at 46 days post-infection (open triangles), and from triple-vaccinated individuals with Omicron breakthrough infection (BNT162b23+Omi) at 44 days post-infection (closed triangles) were analyzed via flow cytometry for SARS-CoV-2-specific $B_{MEM}$ cell ($B_{MEM}$-CD3−CD19+CD20+IgD−$CD38^{int/low}$) frequencies via B cell bait staining. (A) Schematic of one-dimensional staining of $B_{MEM}$ cells with fluorochrome-labeled SARS-CoV-2 S protein tetramer bait allowing discrimination of variant recognition. Frequencies of Wuhan or VOC full-length S protein-(B) and RBD-(C) specific $B_{MEM}$ cells for the four groups of individuals were analyzed. Variant-specific $B_{MEM}$ cell frequencies were normalized to Wuhan frequencies for S protein (D) and RBD-(E) binding. (F) Depicts the frequency ratios of RBD protein specific $B_{MEM}$ cells over full-length S protein-specific BMEM cells.

Figure 18:
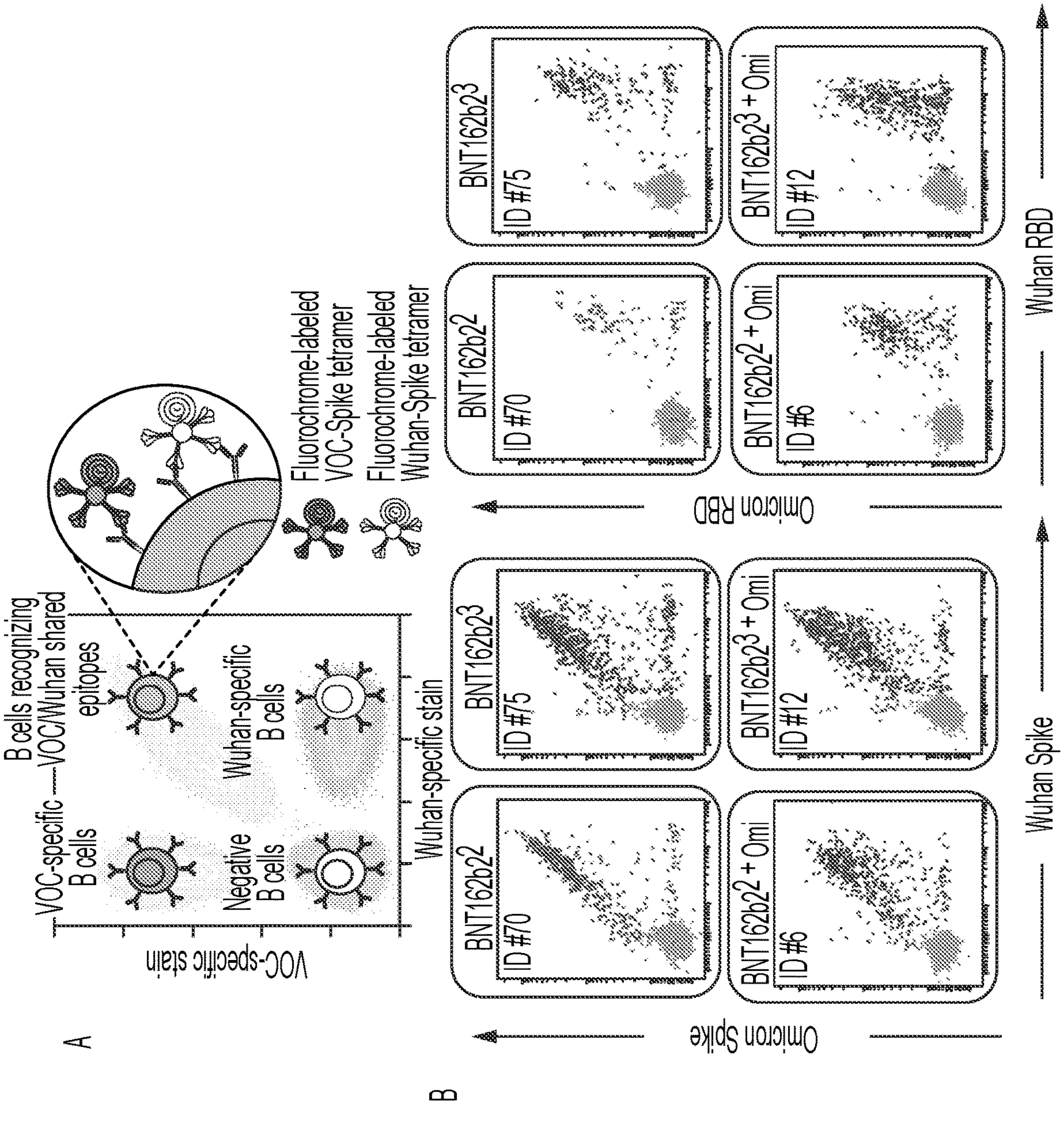
Figure 18:
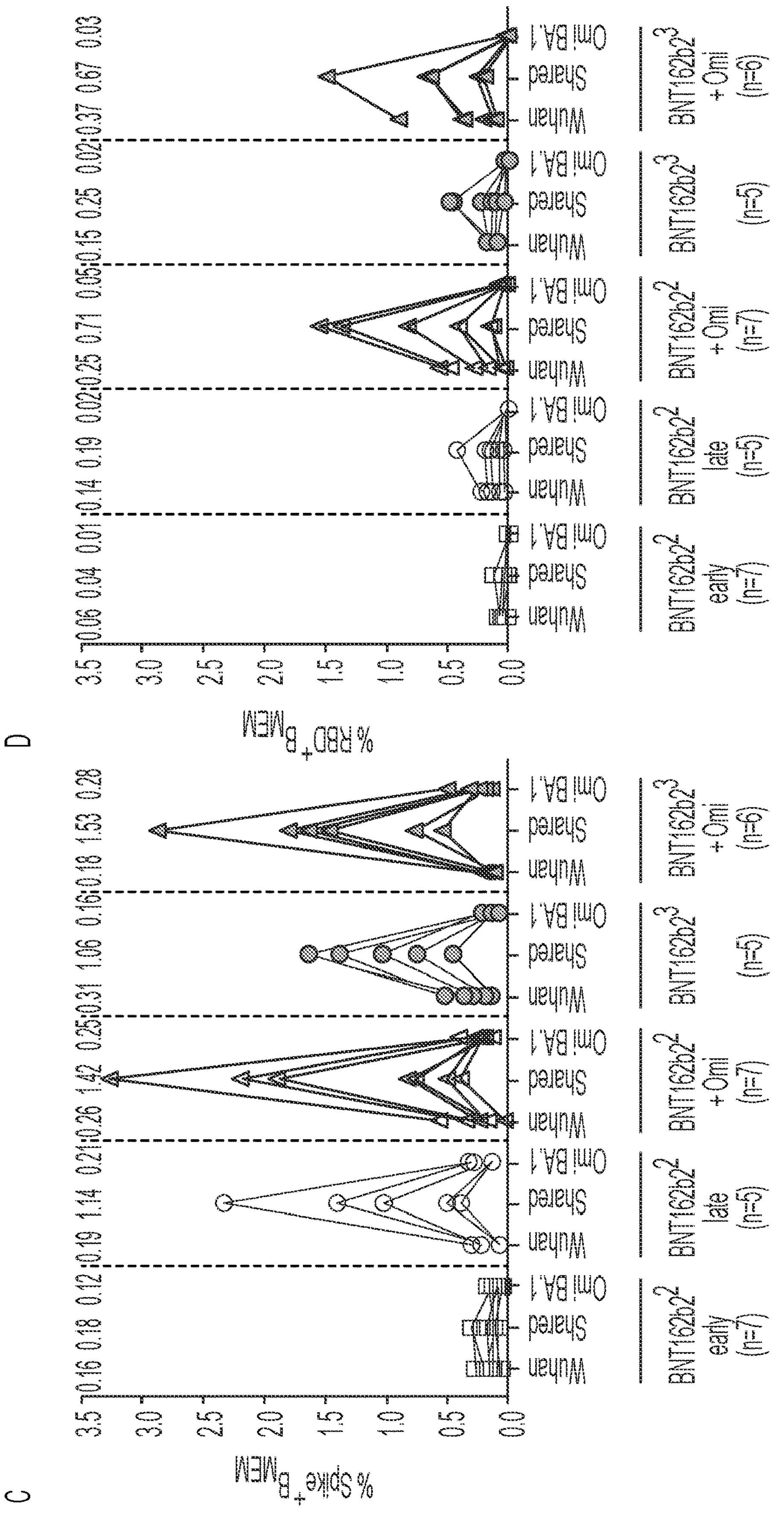
Figure 18:
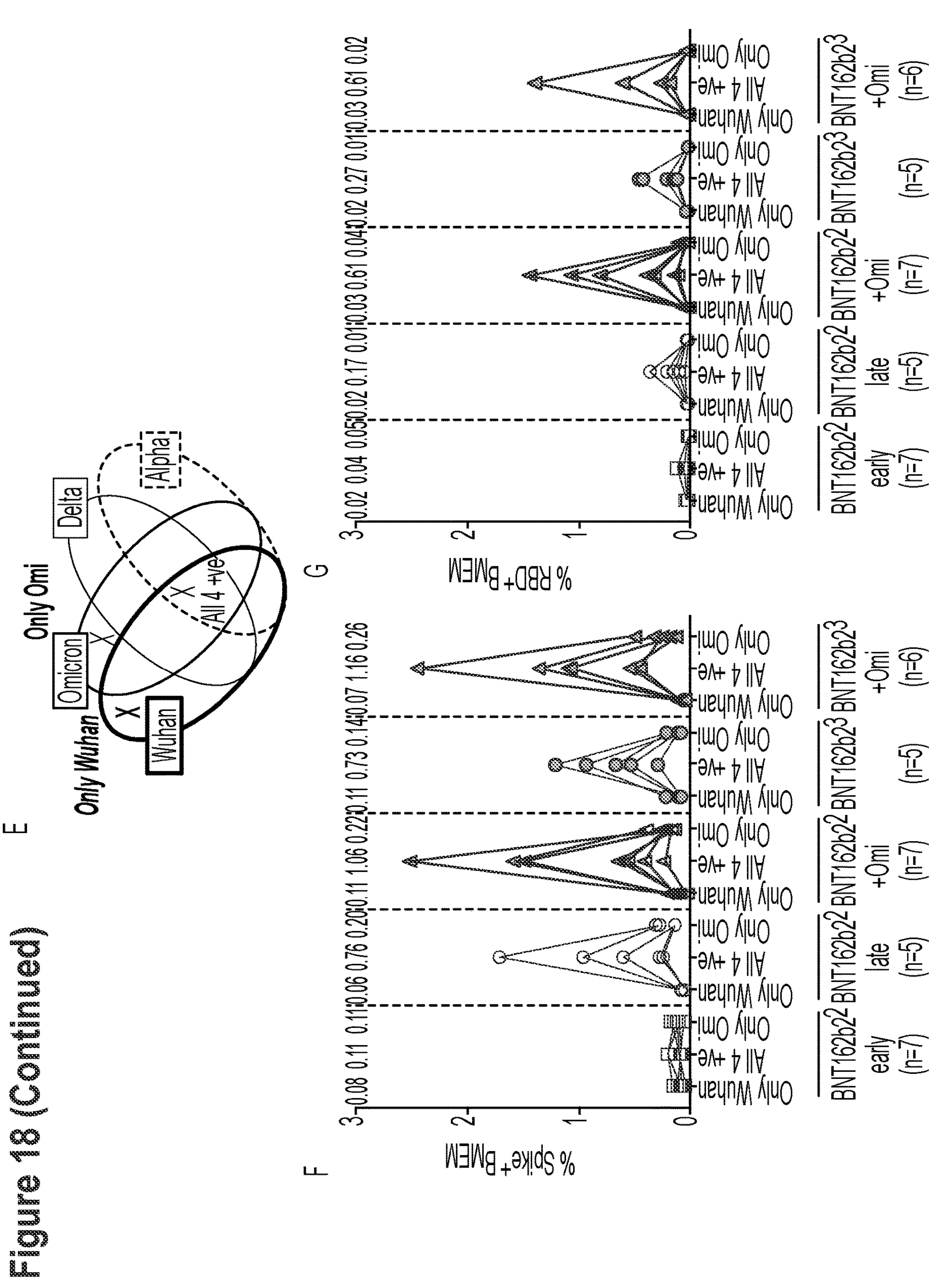
Figure 18:
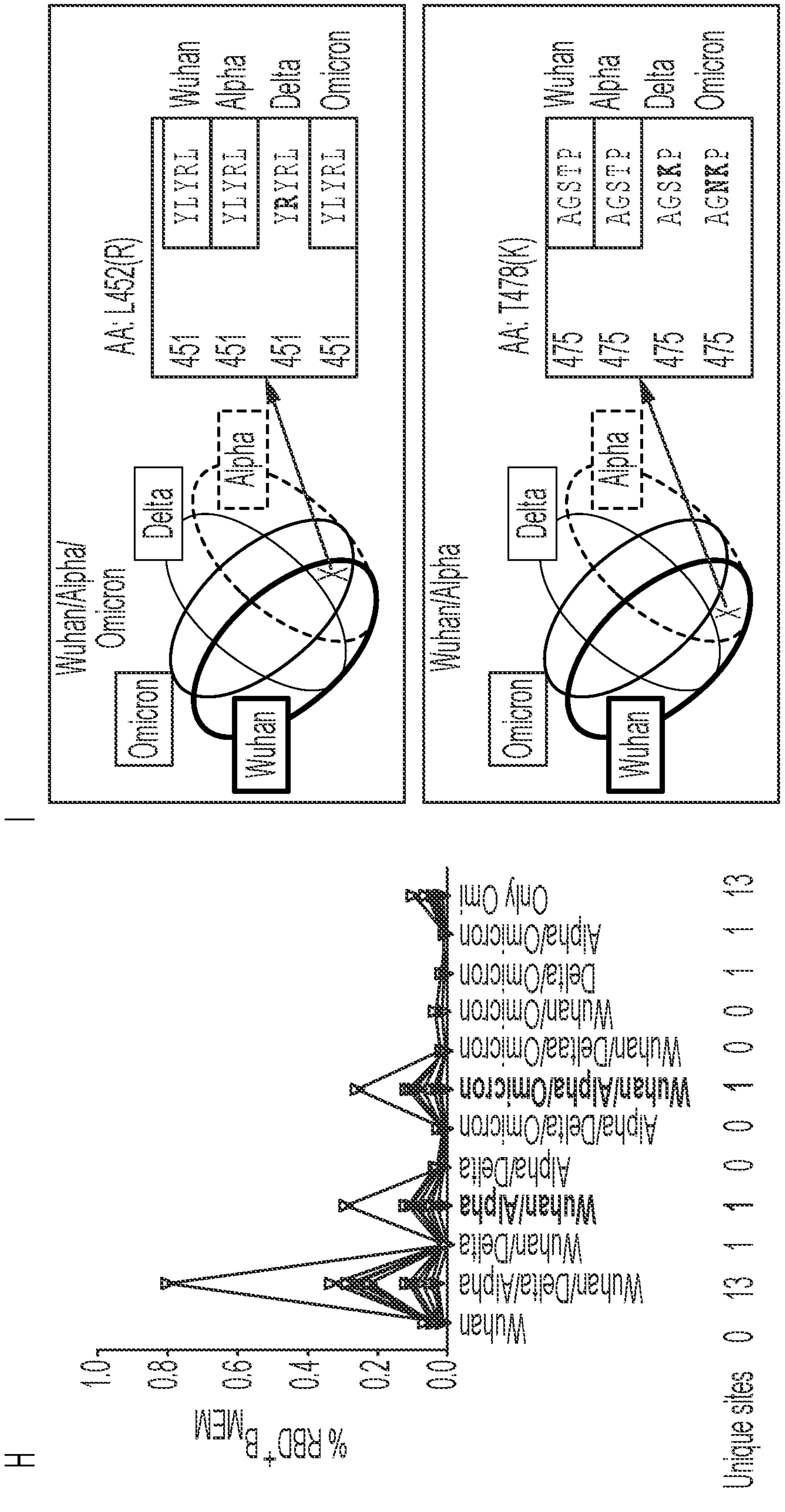

FIG. 18. (SEQ ID NO: 124-128) Omicron breakthrough infection of BNT162b2 double- and triple-vaccinated individuals primarily boosts $B_{MEM}$ against conserved epitopes shared broadly between S proteins of Wuhan and other VOCs rather than strictly Omicron S-specific epitopes. PBMC samples from double-vaccinated individuals ($BNT162b2^2$) at 22 days after the second dose (open squares) and 5 months after the second dose (open circles), from triple-vaccinated individuals ($BNT162b2^3$) at 84 days after the third dose (closed circles), from double-vaccinated individuals with Omicron breakthrough infection ($BNT162b2^2$+Omi) at 46 days post-infection (open triangles), and from triple-vaccinated individuals with Omicron breakthrough infection ($BNT162b2^3$+Omi) at 44 days post-infection (closed triangle) were analyzed via flow cytometry for SARS-CoV-2-specific memory B cell ($B_{MEM}$-CD3−CD19+CD20+IgD−$CD38^{int/low}$) frequencies via B cell bait staining (schematic shown in (A)). (B) shows representative flow plots of Omicron and Wuhan S protein- and RBD-binding for each of the four groups of individuals investigated. Frequencies of $B_{MEM}$ binding Omicron, Wuhan, or both (shared) shown for full-length S protein in (C) and RBD shown in (D) for Omicron-experienced and naïve BNT162b2 double and triple vaccinees. (E) Venn diagrams visualizing the combinatorial (Boolean) gating strategy to identify cross-reactive $B_{MEM}$ recognizing all four variants simultaneously (All 4+ve) and $B_{MEM}$ recognizing only Omicron (only Omi) or only Wuhan (only Wuhan) S proteins. Frequencies for these three $B_{MEM}$ sub-groups were compared for full-length S protein (F) and RBD (G) in the four different groups of individuals investigated. RBD variant recognition pattern by $B_{MEM}$ was assessed through Boolean flow cytometric gating strategy and frequencies recognizing combinations of Wuhan and/or variant RBDs are displayed in (H), for all Omicron convalescent subjects (double and triple vaccinees pooled, n=13). (1) Conserved site within the RBD domain recognized by RBD-specific $B_{MEM}$ after Omicron break-through infection. Mean values are indicated in C, D, F, and G. n=number of individuals per group.

Figure 19:
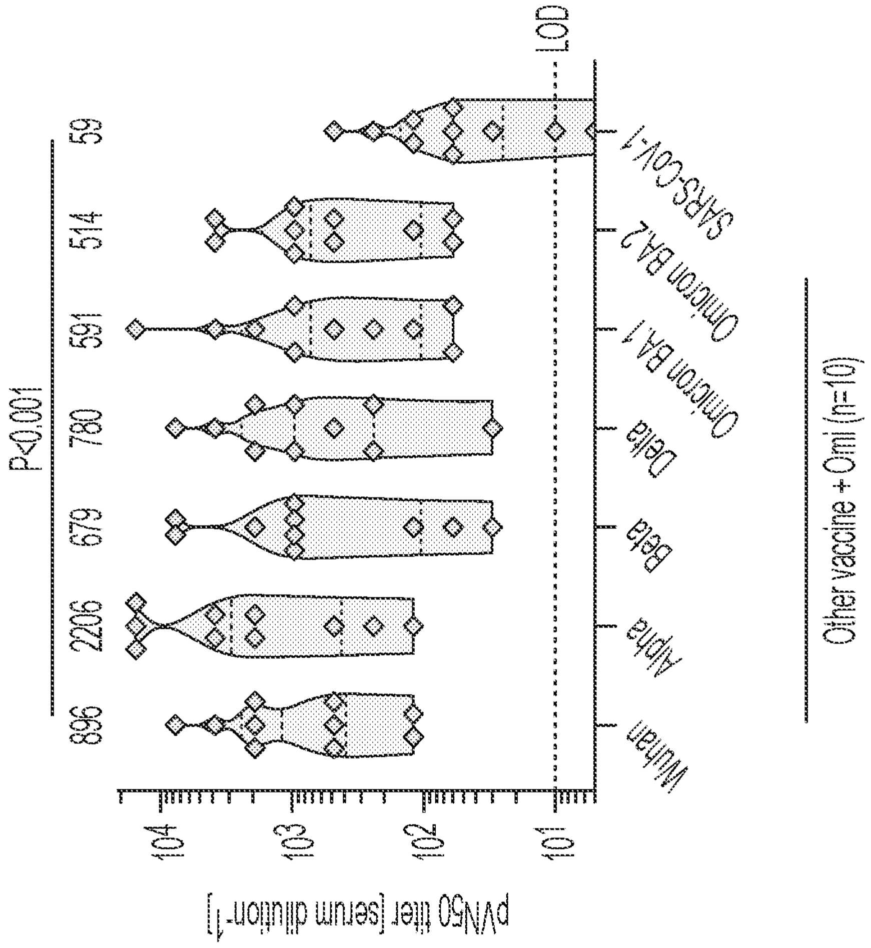

FIG. 19. Omicron breakthrough infection of individuals vaccinated with other approved COVID-19 vaccines or mixed regimens results in immune sera that broadly neutralize Omicron BA.1, BA.2 and other VOCs plus SARS-CoV-1. Serum was drawn from 10 individuals vaccinated with other approved COVID-19 vaccines or mixed regimens at a median of 43 days after infection (diamonds). Serum was tested in duplicate; individual 50% pseudovirus neutralization ($pVN_{50}$) geometric mean titers (GMTs) against SARS-CoV-2 Wuhan, Alpha, Beta, Delta and Omicron BA.1 and BA.2 variants, plus SARS-CoV-1 were plotted. For titer values below the limit of detection (LOD), LOD/2 values were plotted. Values above violin plots represent group GMTs. The non-parametric Friedman test with Dunn's multiple comparisons correction was used to compare Wuhan neutralizing group GMTs with titers against the indicated variants and SARS-CoV-1. Multiplicity-adjusted p values are shown. Approved vaccines included AZD1222, BNT162b2 (in some embodiments as part of a 4-dose series), Ad26.COV2.S, mRNA-1273 (administered as a two-dose or three-dose series), and combinations thereof.

Figure 20:
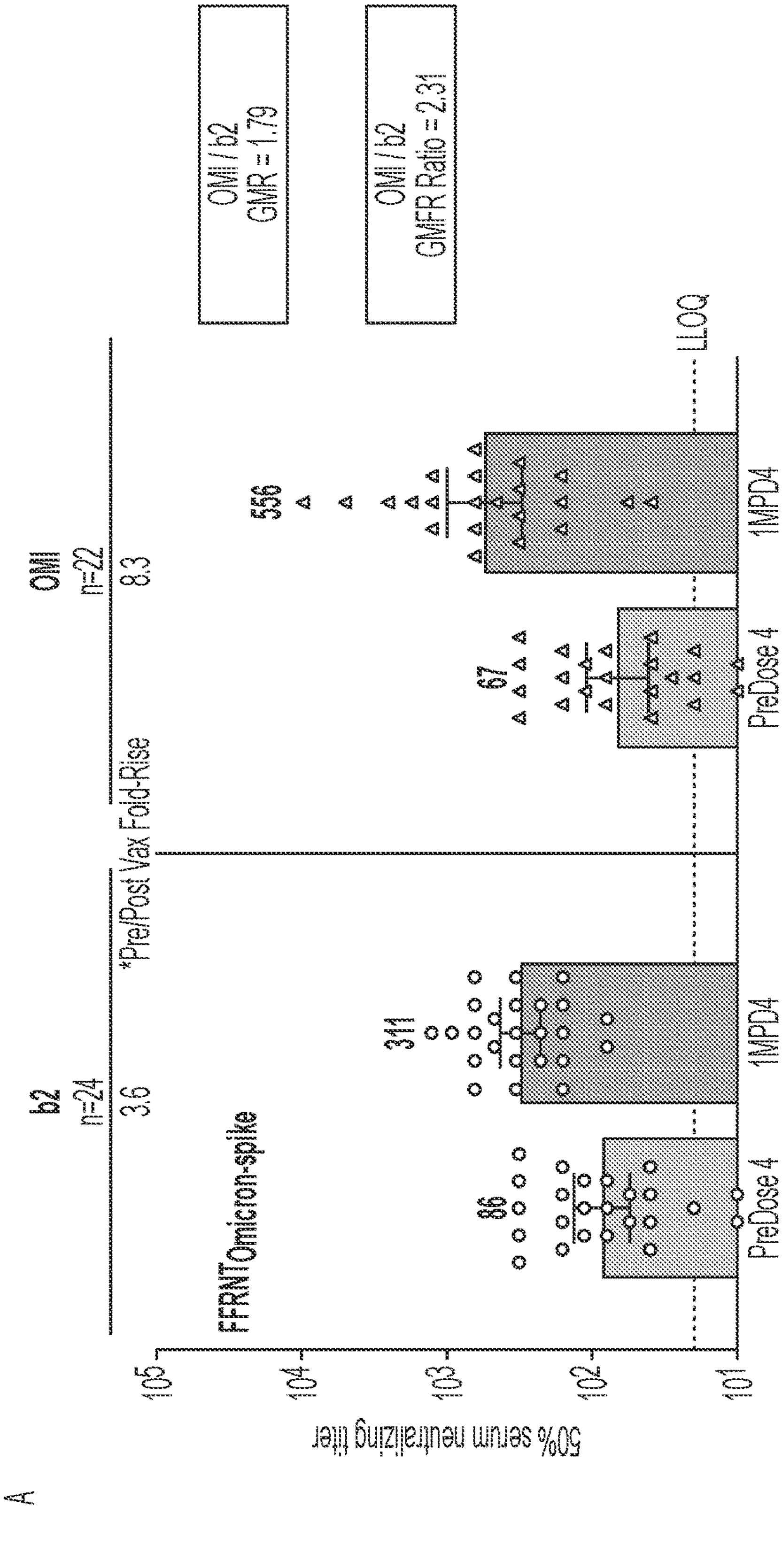
Figure 20:
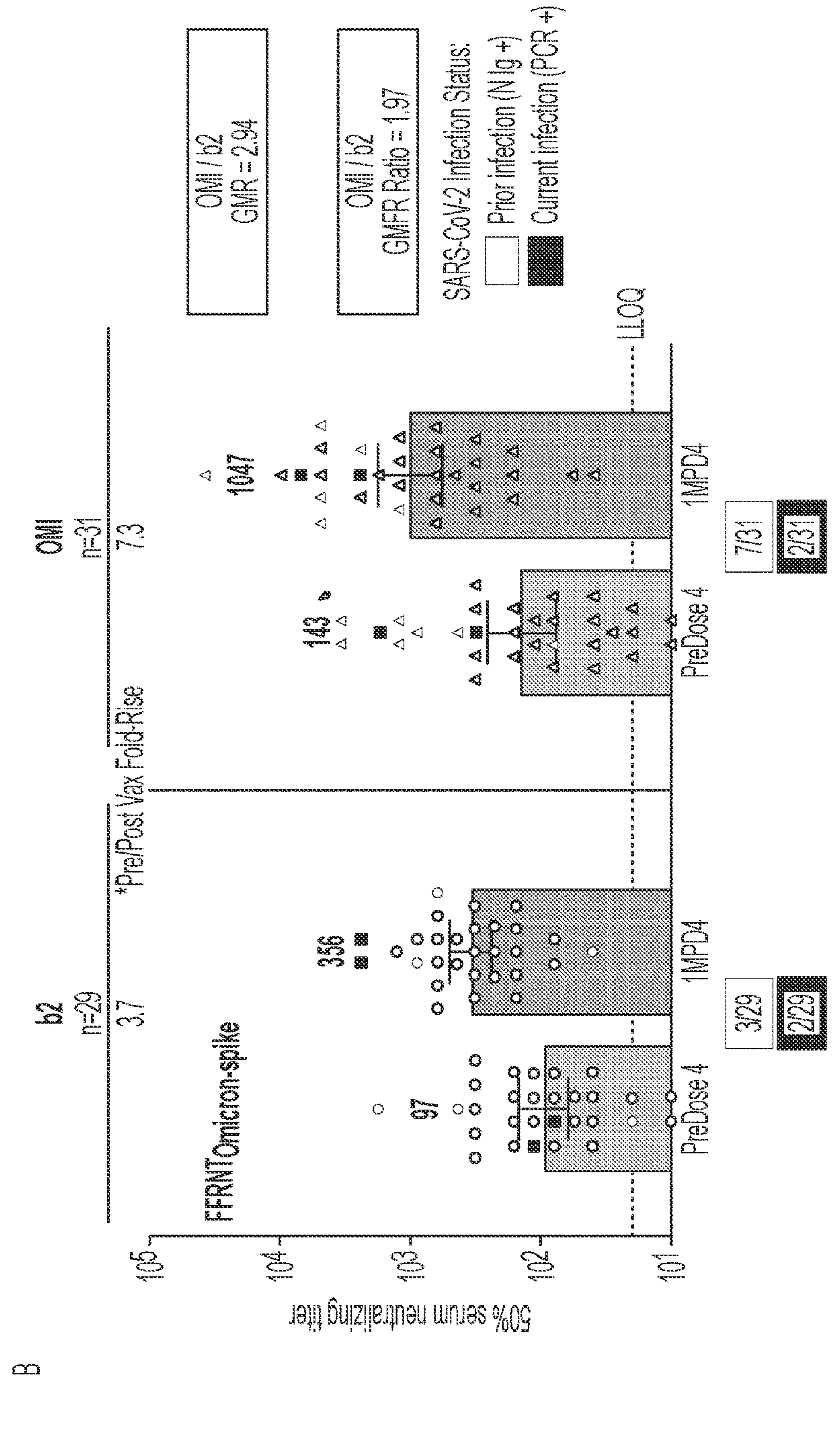
Figure 20:
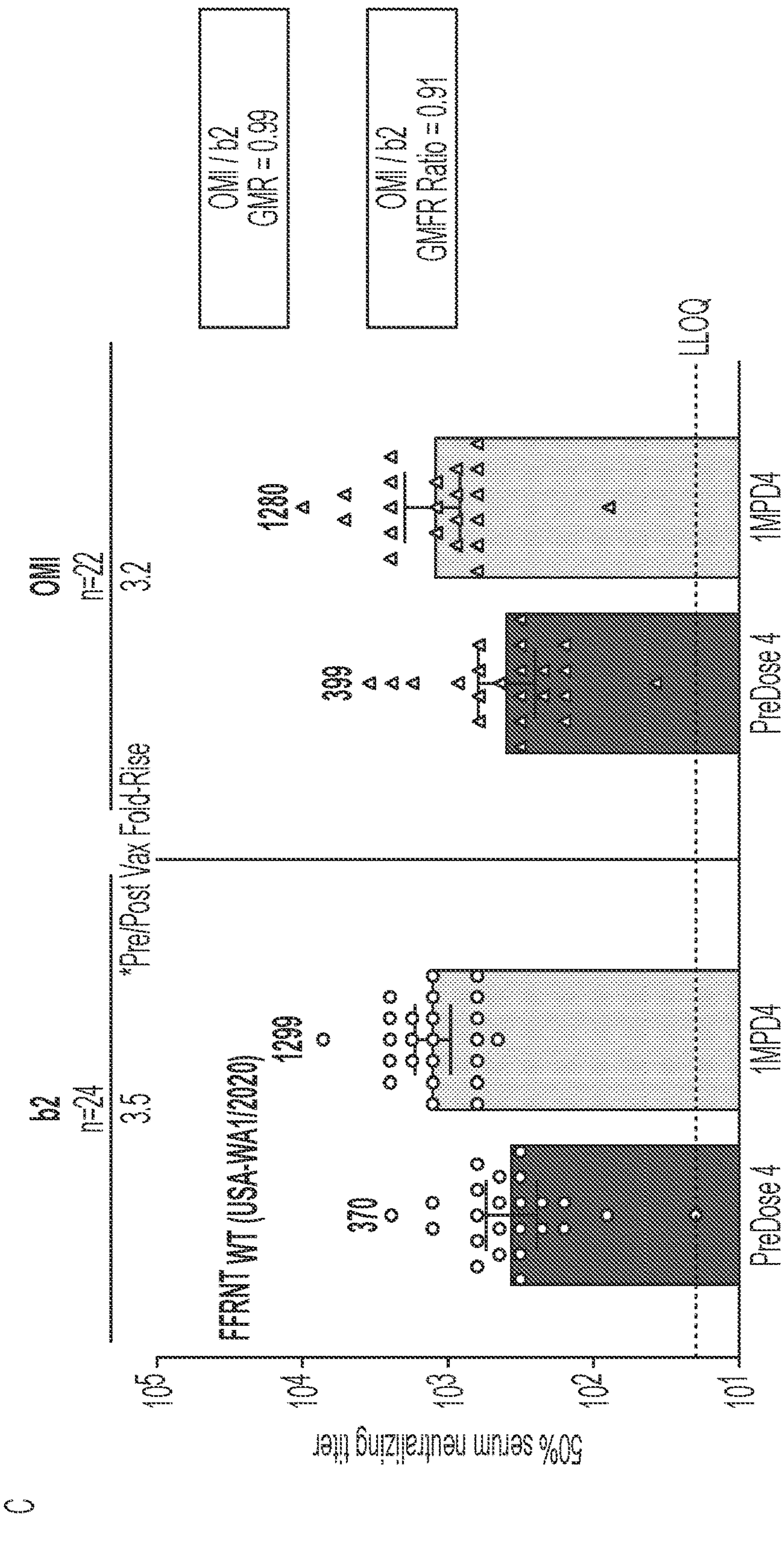
Figure 20:
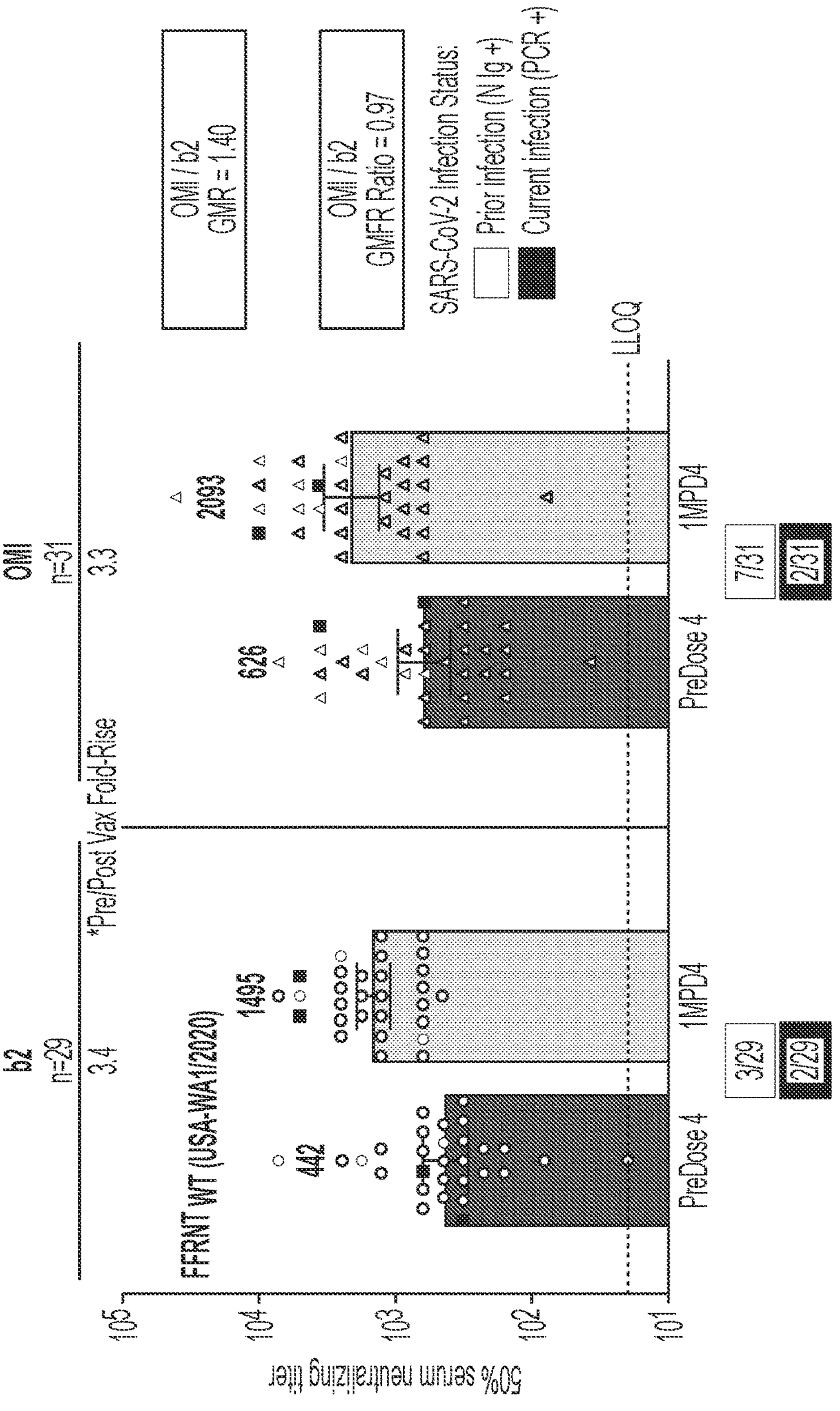
Figure 20:
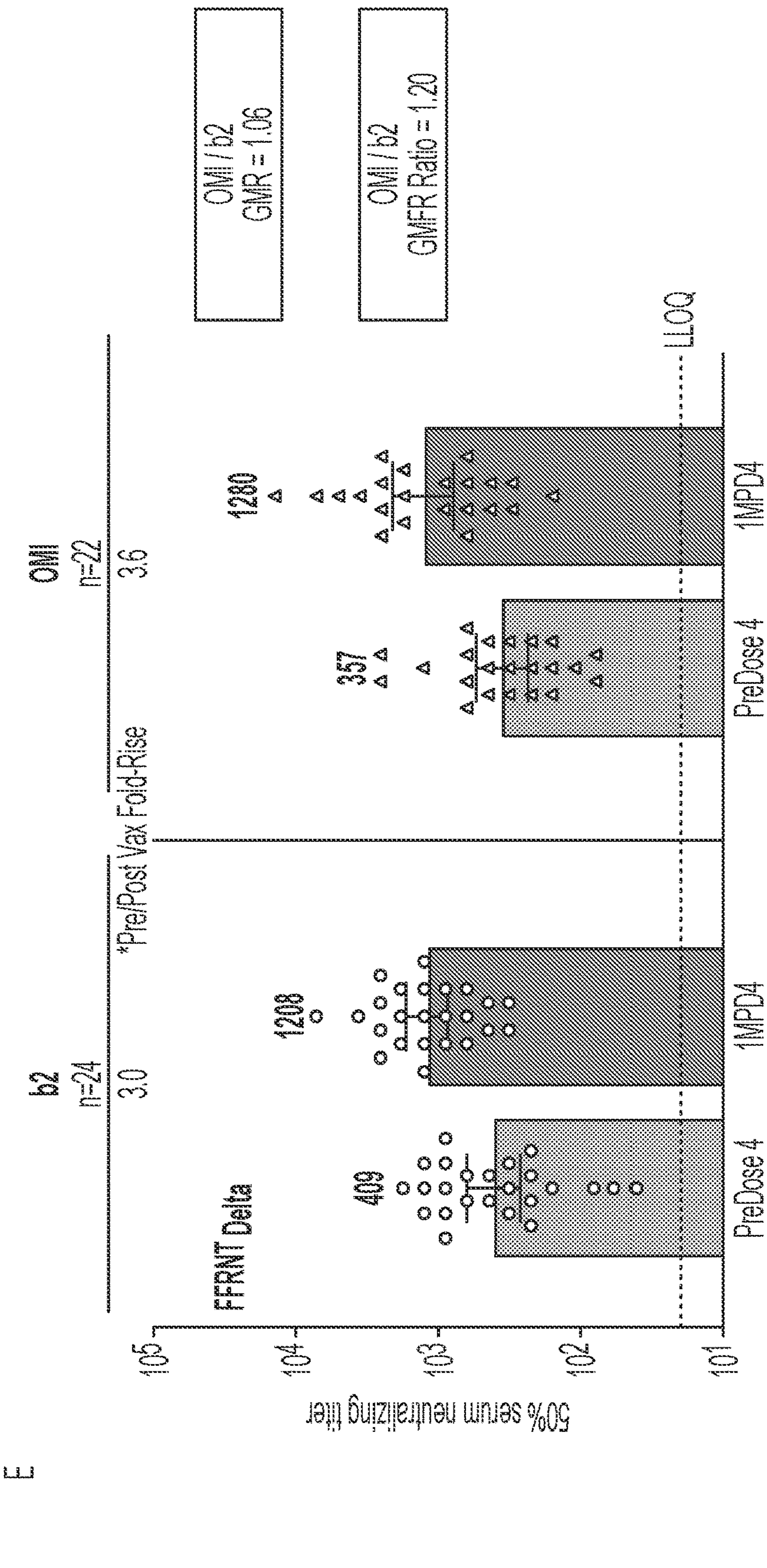
Figure 20:
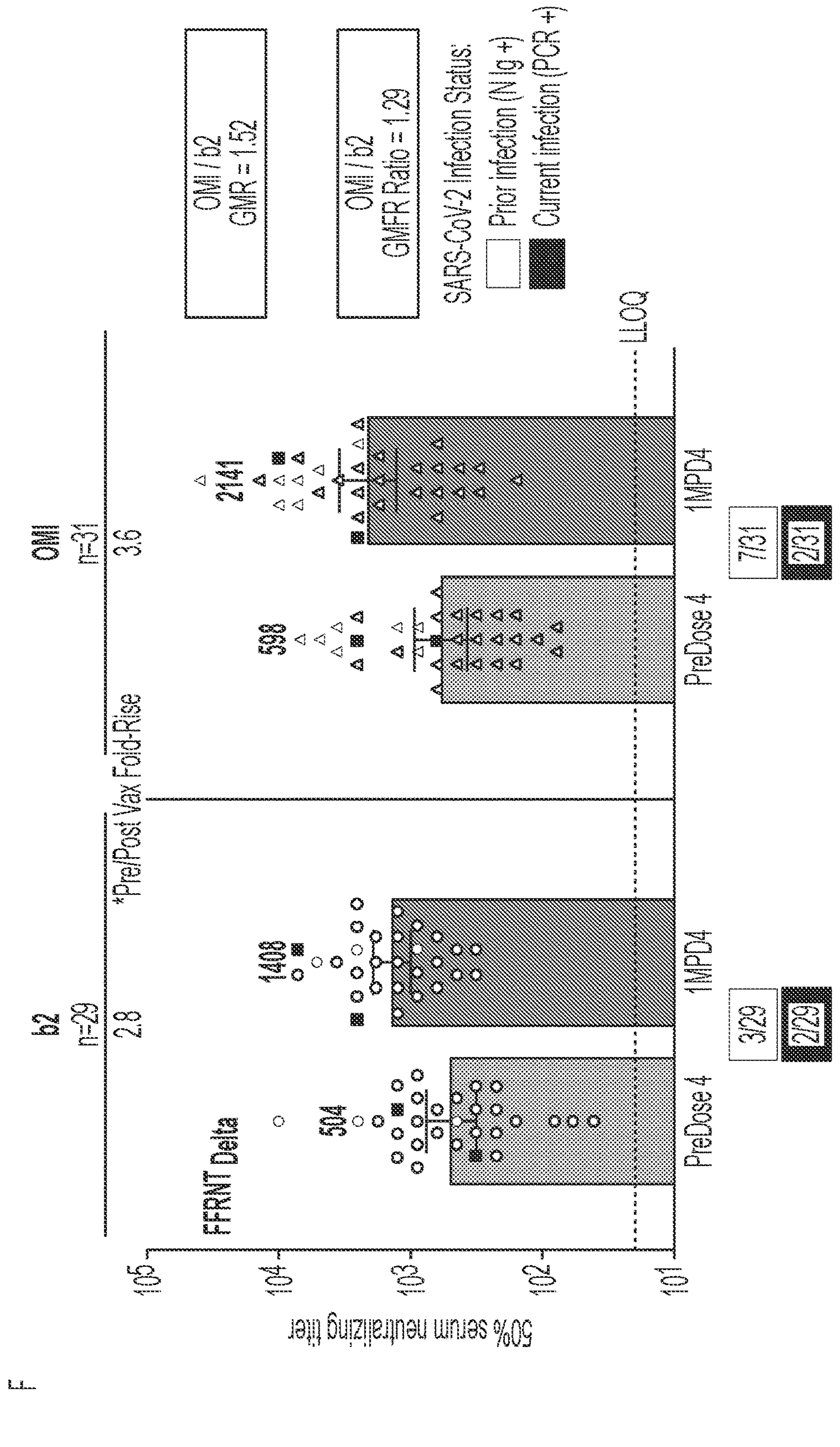

FIG. 20. 50% neutralization titers of sera collected 1 month after a fourth dose of BNT162b2 or an Omicron BA.1-specific booster. Subjects who were previously administered two doses of BNT162b2, and a third (booster) dose of BNT162b2 (30 ug) received a dose (30 ug) of (i) an RNA encoding a SARS-CoV-2 S protein from an Omicron BA.1 variant (e.g., as described herein (referred to herein as "Omicron BA.1-specific RNA vaccine"), or (ii) BNT162b2, as a fourth (booster) dose. Serum from the subjects were collected one month after administration of the 4th (booster) dose. Group GMTs (values above bars) with 95% confidence intervals are shown. "b2" refers to sera from subjects administered Wuhan-specific RNA vaccine as the $4^{th}$ (booster) dose of BNT162b2. "OMI" refers to sera from subjects administered an Omicron BA.1-specific $4^{th}$ (booster) dose. Also shown is the fold-change in titer from before administration of the $4^{th}$ dose to after administration of the $4^{th}$ dose (Pre/Post Vax Fold-Rise), and the ratio of geometric mean ratio (GMR) and geometric mean fold rise (GMFR) observed in subjects administered a $4^{th}$ dose of an Omicron BA.1-specific RNA vaccine as the $4^{th}$ dose, as compared to subjects administered BNT162b2 as the $4^{th}$ dose. "FFRNT" refers to fluorescent focus reduction neutralization test. Neutralization data was obtained using an FFRNT assay, with a viral particle containing a SARS-CoV-2 S protein from the variant indicated in the figures. (A) Comparison of titers of neutralizing antibodies against a SARS-CoV-2-S pseudovirus comprising a SARS-CoV-2 S protein having mutations characteristics of an Omicron BA.1 variant. Sera from subjects previously or currently infected with SARS-CoV-2 excluded. (B) Comparison of titers of neutralizing antibodies against a SARS-CoV-2 pseudovirus comprising a SARS-CoV-2 S protein having mutations characteristics of an Omicron BA.1 variant in sera from a population that includes subjects previously or currently infected with SARS-CoV-2 (as determined by an antigen assay or a PCR assay respectively). (C) Comparison of titers of neutralizing antibodies against a SARS-CoV-2 pseudovirus comprising a SARS-CoV-2 S protein from a Wuhan strain. Sera from subjects previously or currently infected with SARS-CoV-2 excluded. (D) Comparison of titers of neutralizing antibodies against a SARS-CoV-2 pseudovirus comprising a SARS-CoV-2 S protein from a Wuhan strain, in sera from a population comprising individuals previously or currently infected with SARS-CoV-2 (as determined by an antigen assay or a PCR assay, respectively. (E) Comparison of titers of neutralizing antibodies against a SARS-CoV-2 pseudovirus comprising a SARS-CoV-2 S protein having mutations characteristics of a delta variant. Sera from subjects previously or currently infected with SARS-CoV-2 excluded. (F) Comparison of titers of neutralization antibodies against a SARS-CoV-2 pseudovirus comprising a SARS-CoV-2 protein having mutations characteristic of a delta variant, in sera from a population including subjects previously or currently infected with SARS-CoV-2 (as determined by an antigen assay or a PCR assay, respectively).

Figure 21:
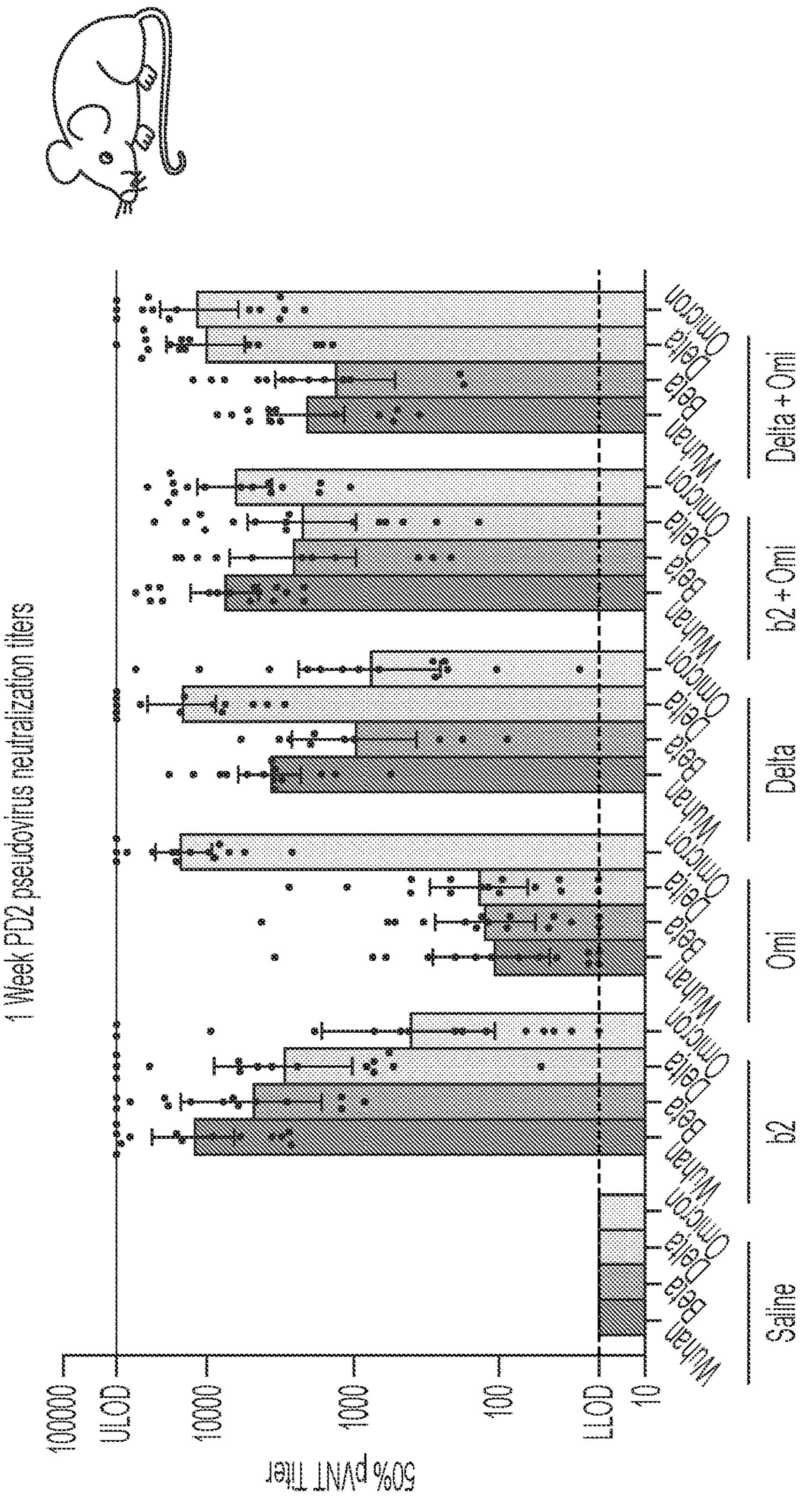

FIG. 21. Neutralization of SARS-CoV-2 pseudovirus 7 days after immunization with modRNA coding for variant specific S proteins. Mice were immunized twice with LNP-formulated vaccine comprising (i) BNT162b2 (encoding a SARS-CoV-2 S protein from a Wuhan strain), (ii) RNA encoding a SARS-CoV-2 S protein having mutations characteristic of an Omicron BA.1 variant (Omi), (iii) RNA encoding an S protein having mutations characteristic of a delta variant, (iv) a combination of BNT162b2 and an RNA encoding an protein having mutations characteristic of an Omicron BA.1 variant (B2+Omi), or (v) RNA encoding a SARS-CoV-2 S protein having mutations characteristic of a delta variant and RNA encoding a SARS-CoV-2 S protein having mutations characteristic of an Omicron BA.1 variant (Delta+Omi). 7 days after the second immunization, animals were bled and sera was tested for neutralization of a SARS-CoV-2-S pseudovirus comprising a SARS-CoV-2 S protein from a Wuhan strain, or a SARS-CoV-2 S protein having mutations characteristic of a beta, delta, or Omicron BA.1 variant. Graphs depict $pVN_{50}$ serum dilutions (50% reduction of infectious events, compared to positive controls without serum). One point in the graphs stands for one mouse. Every mouse sample was measured in duplicate. Mean+SEM is shown by horizontal bars with whiskers for each group. LLOD, lower limit of detection. ULOD, upper limit of detection.

Figure 22:
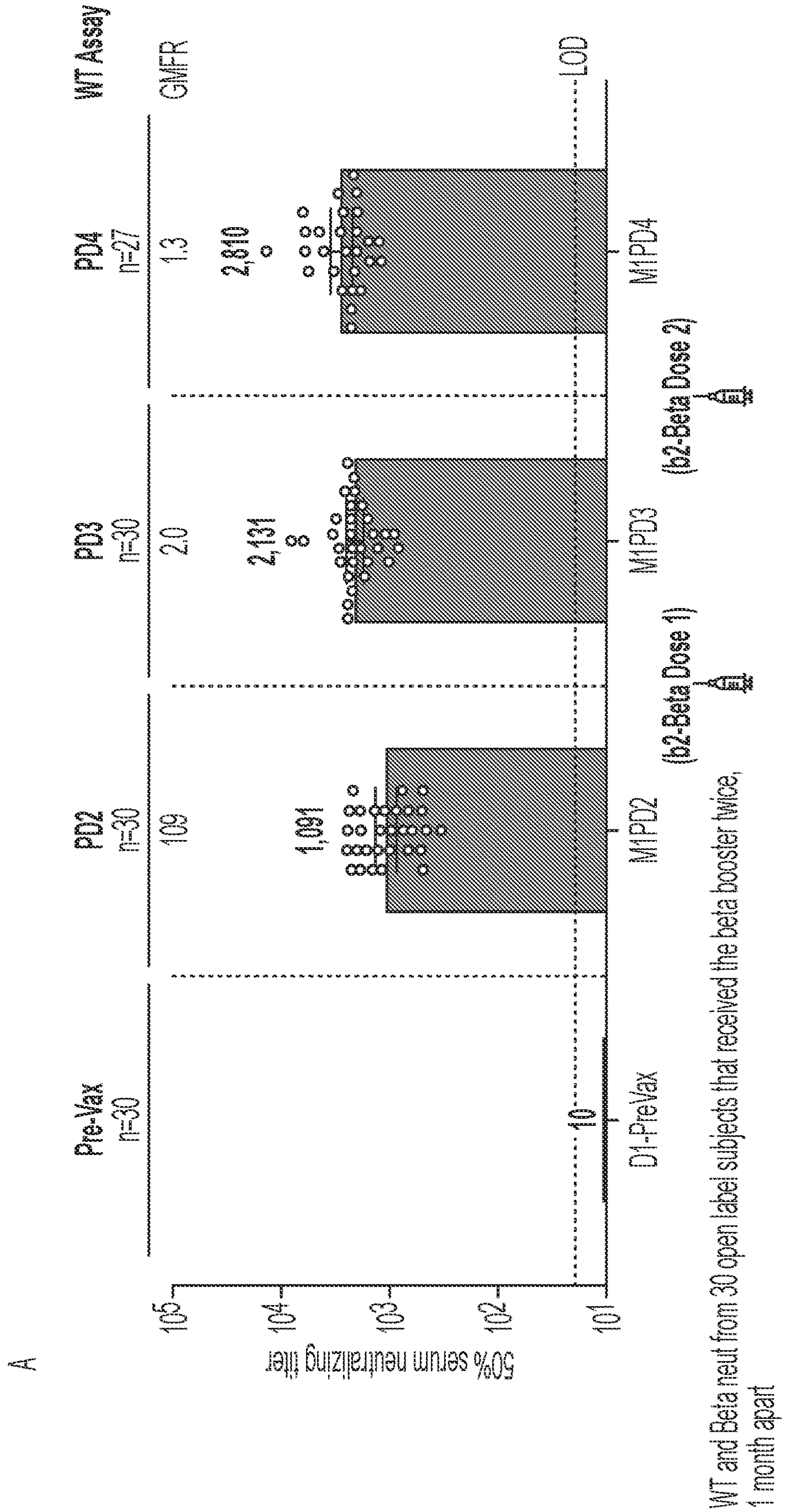
Figure 22:
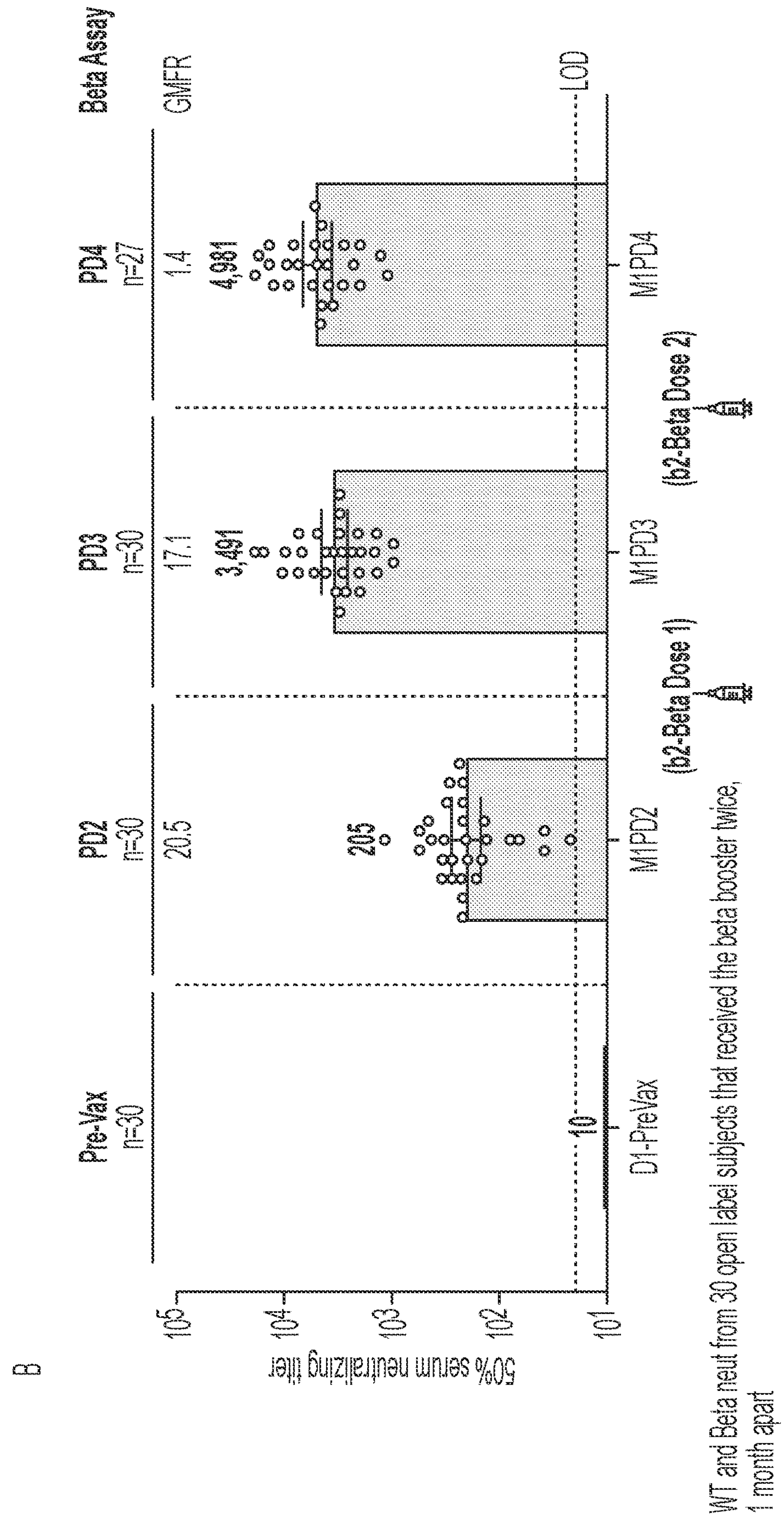

FIG. 22. RNA encoding a SARS-CoV-2 S protein having mutations characteristic of a Beta variant increases neutralization antibody titers against SARS-CoV-2 when administered to patients previously administered two doses of a vaccine encoding a SARS-CoV-2 S protein of a Wuhan strain. Subjects previously administered two doses of an RNA vaccine encoding a SARS-CoV-2 S protein of a Wuhan strain were administered a third and a fourth dose of an RNA vaccine encoding a SARS-CoV-2 S protein having mutations characteristic of a Beta variant. Neutralization antibody titers were measured before administration of an RNA vaccine encoding a SARS-CoV-2 S protein of a Wuhan strain (D1-PreVax), one month after administration of a second dose of an RNA vaccine encoding a SARS-CoV-2 S protein of a Wuhan strain (M1PD2), one-month after administration of a third dose of an RNA vaccine encoding a SARS-CoV-2 S protein having mutations characteristic of a SARS-CoV-2 Beta variant, and one month after administration of a fourth dose of an RNA vaccine encoding a SARS-CoV-2 S protein having mutations characteristic of a SARS-CoV-2 Beta variant. The third and fourth doses were administered 1 month apart from one another. GMFR refers to the geometric mean fold rise, and is a measure of the increase in neutralization antibody titers since the previous vaccine dose (e.g., the GMFR for Post-Dose2 (PD2) is a measure of the increase in neutralization antibody titers relative to before administration of any vaccine (pre-vax)). (A) Neutralization antibody titers measured in a viral neutralization assay that uses a viral particle comprising a SARS-CoV-2 S protein of a Wuhan strain. (B) Neutralization antibody titers measured in a viral neutralization assay that uses a viral particle comprising a SARS-CoV-2 S protein having mutations characteristic of a Beta variant.

Figure 23:
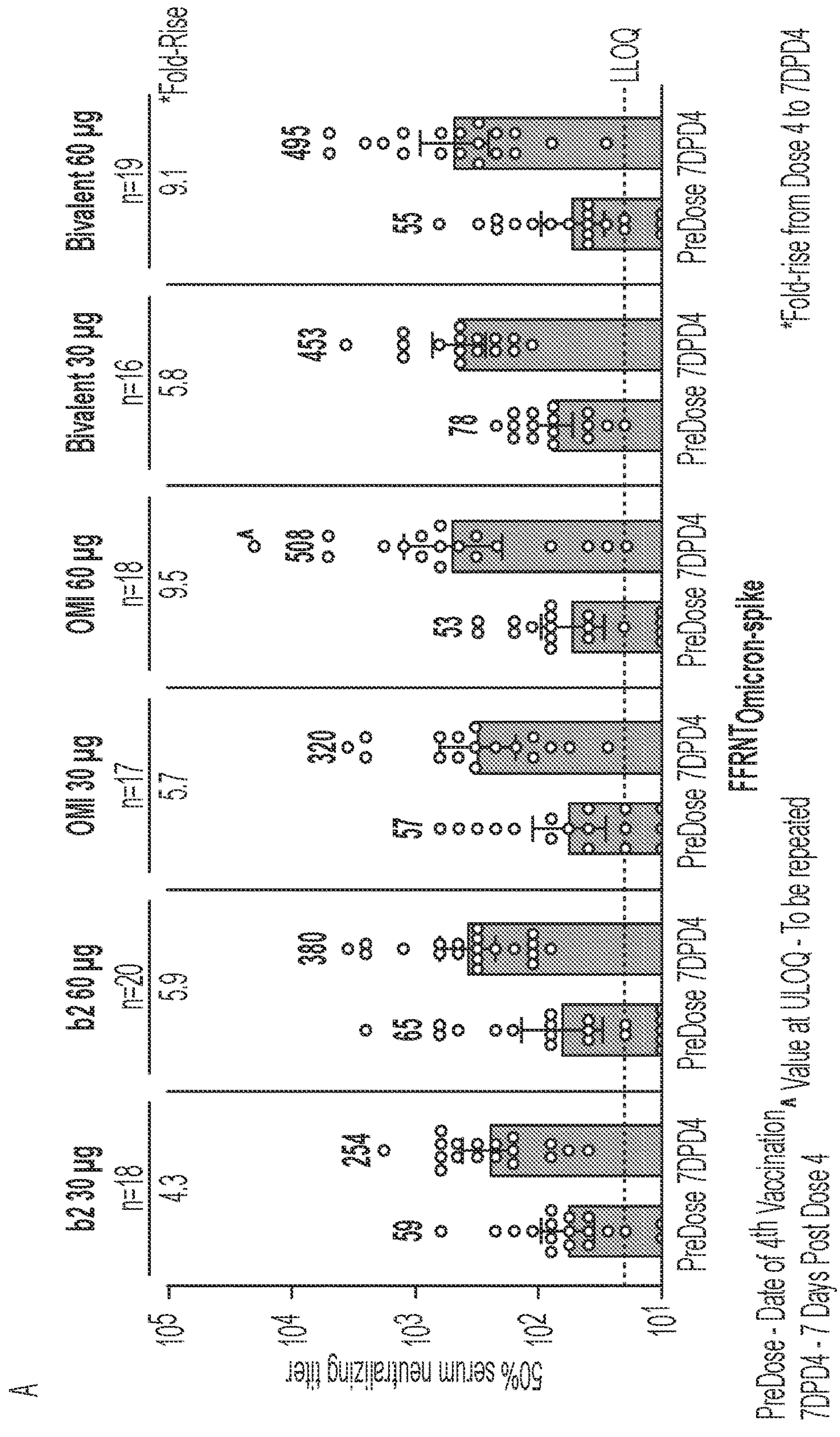
Figure 23:
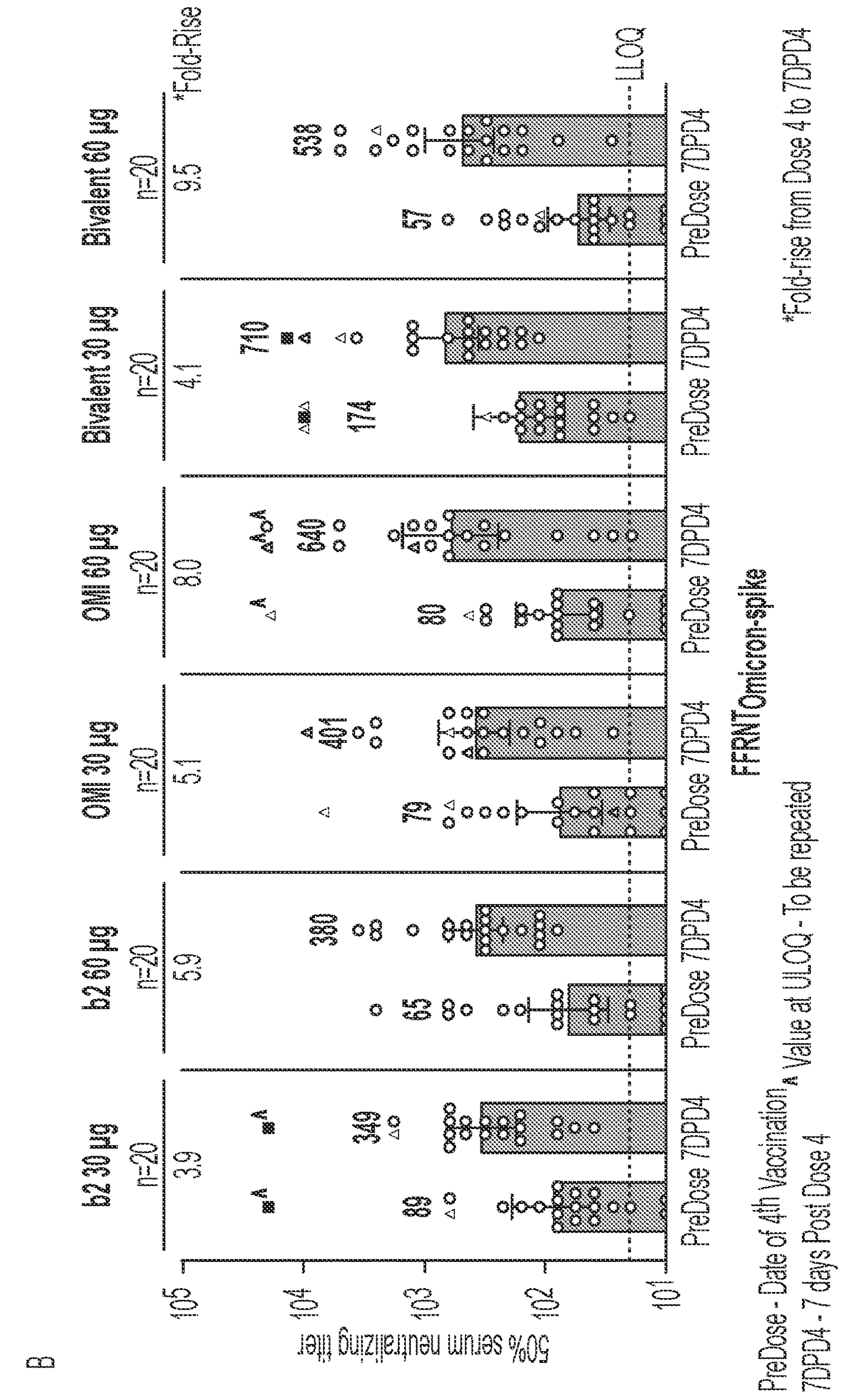
Figure 23:
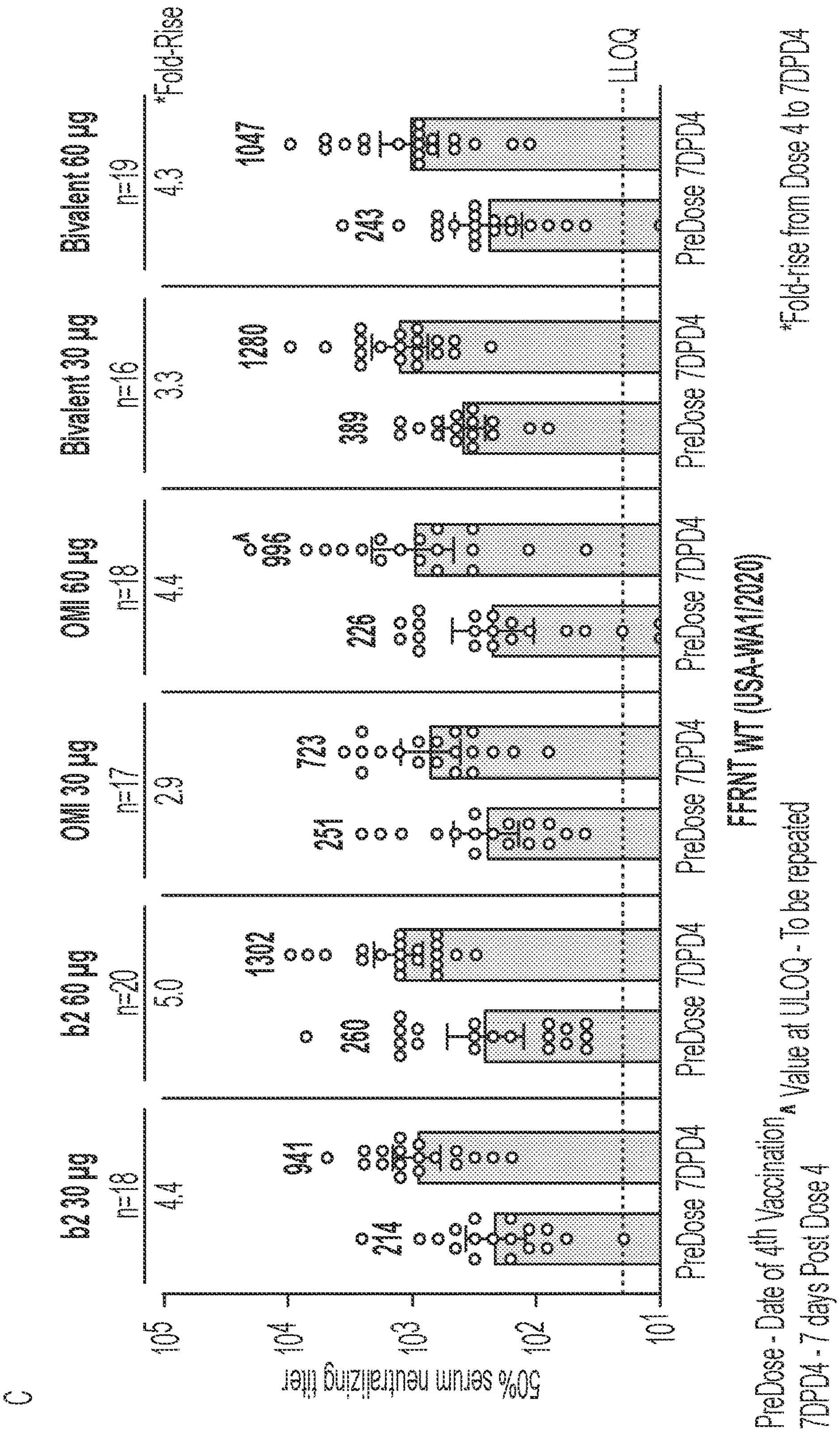
Figure 23:
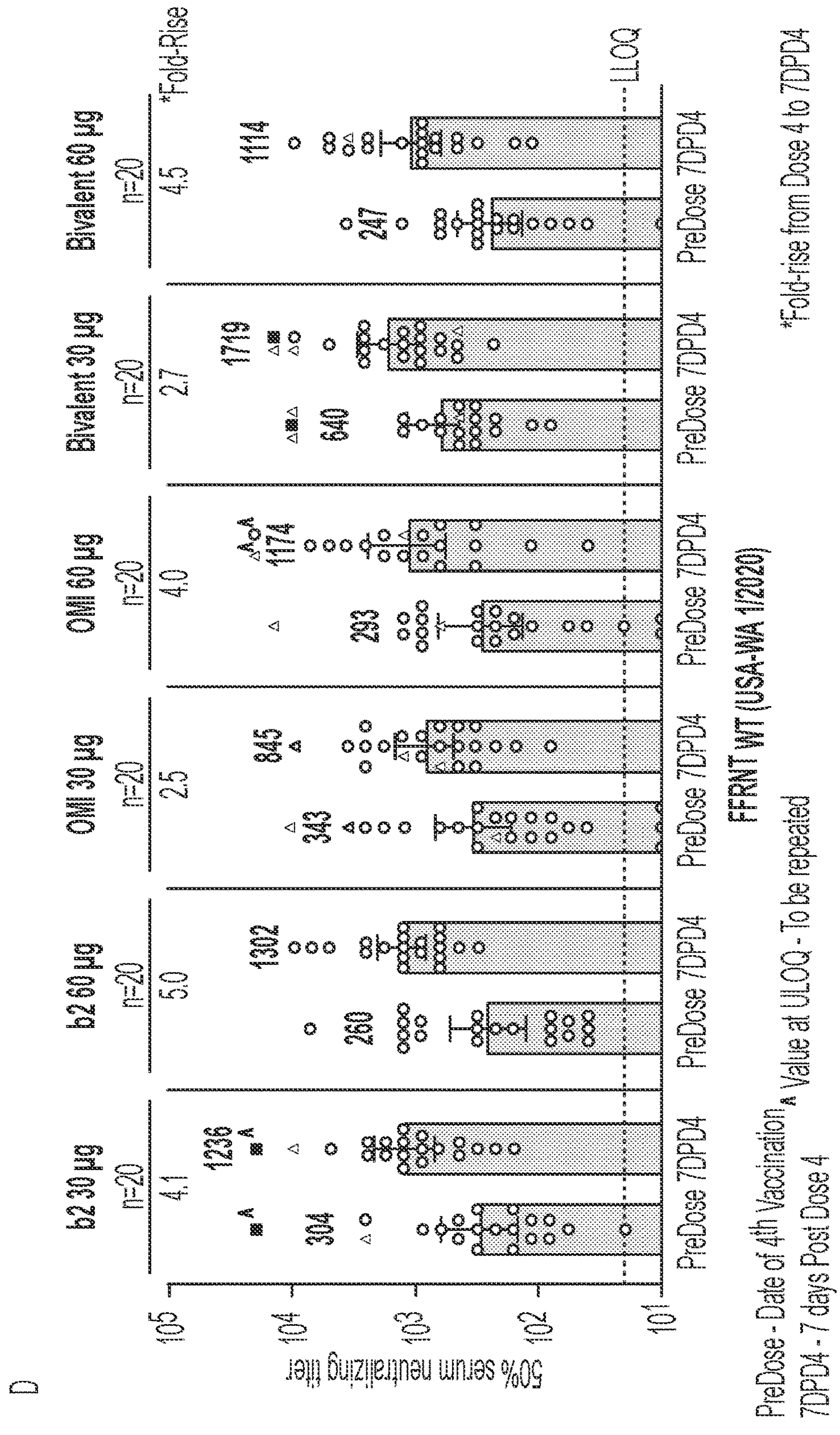
Figure 23:
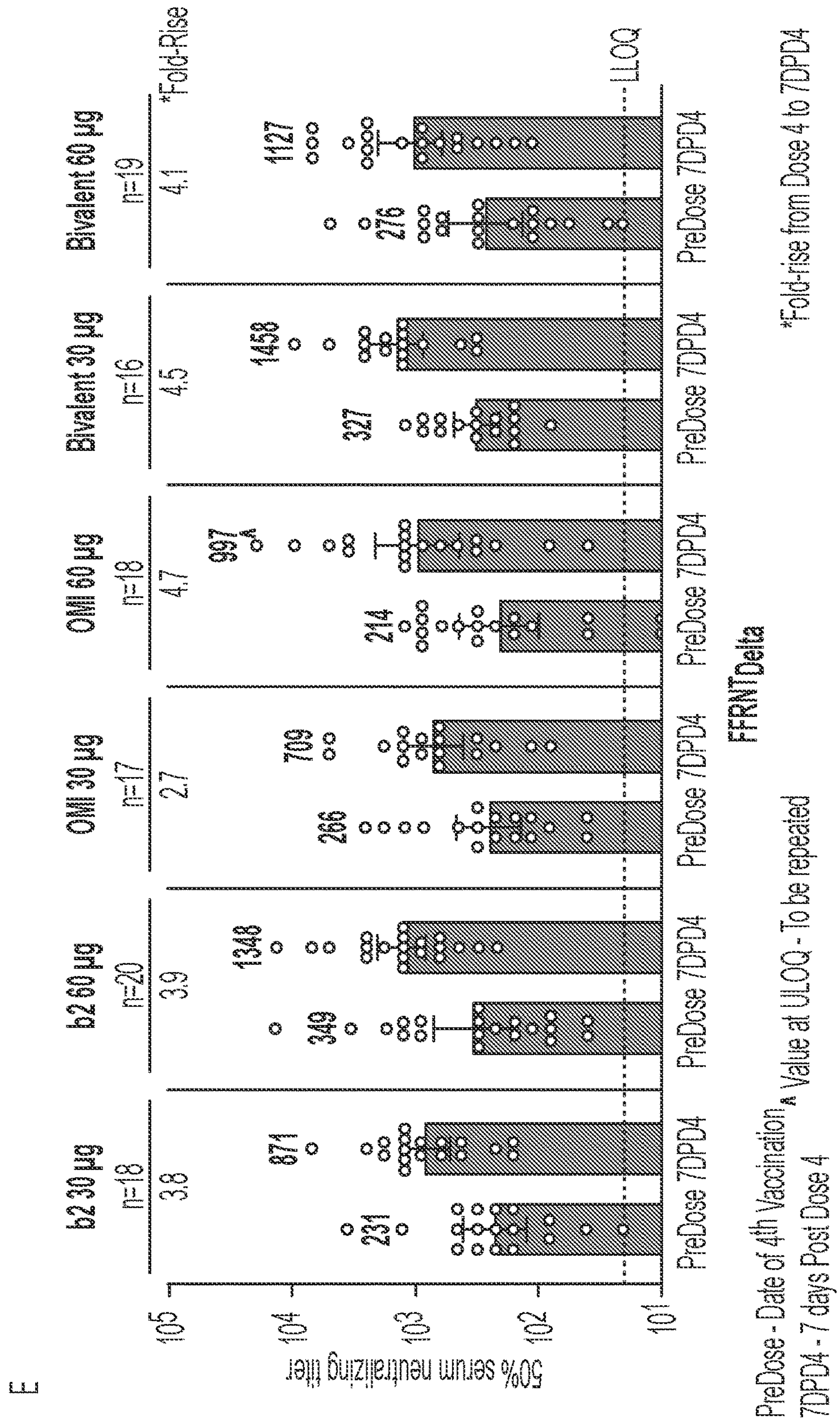
Figure 23:
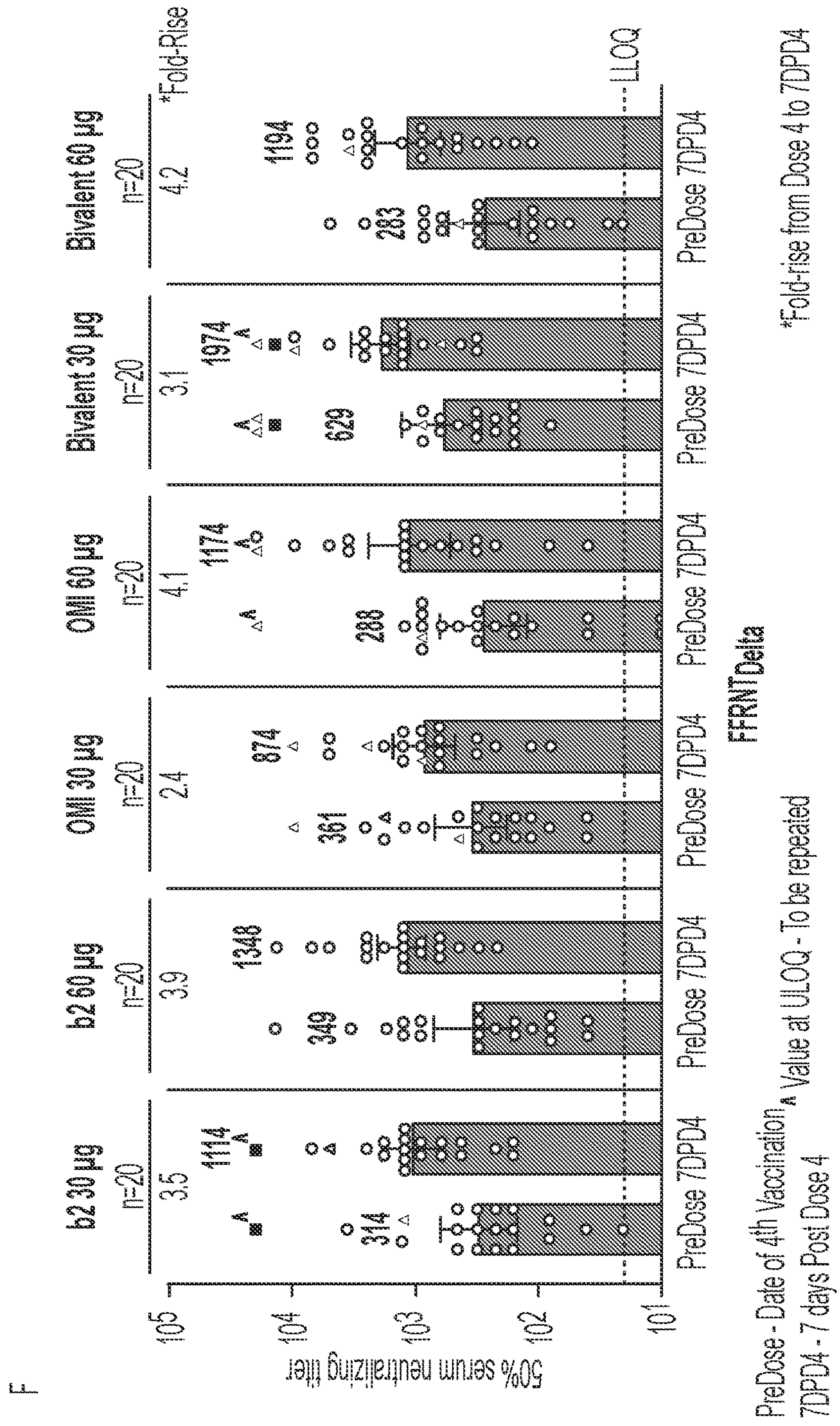

FIG. 23. 50% neutralization titers of sera collected 7 days after a fourth dose of BNT162b2, an Omicron BA.1-specific booster, or a bivalent vaccine. Subjects who were previously administered two doses of BNT162b2 (30 ug), and a third (booster) dose of BNT162b2 (30 ug) received (i) a 30 ug dose of BNT162b2 (encoding a SARS-CoV-2 S protein from a Wuhan strain), (ii) a 60 ug dose of BNT162b2, (iii) a 30 ug dose of RNA encoding a SARS-CoV-2 S protein having mutations characteristic of an Omicron BA.1 variant (e.g., as described herein (referred to herein as "Omicron BA.1-specific RNA vaccine")), (iii) a 60 ug dose of RNA encoding a SARS-CoV-2 S protein having mutations characteristic of an Omicron BA.1 variant, (iv) a 30 ug dose of a bivalent vaccine, comprising 15 μg of BNT162b2 and 15 μg of RNA encoding a SARS-CoV-2 S protein comprising mutations characteristic of an Omicron BA.1 variant, or (v) a 60 ug dose of a bivalent vaccine, comprising 30 μg of BNT162b2 and 30 μg of RNA encoding a SARS-CoV-2 S protein comprising mutations characteristic of an Omicron BA.1 variant. Geometric mean ratio (GMR) of titers in serum from subjects were collected 7 days after administration of a 4th dose. "b2" refers to sera from subjects administered a Wuhan-specific RNA vaccine as a $4^{th}$ dose of BNT162b2. "OMI" refers to sera from subjects administered an Omicron BA.1-specific $4^{th}$ dose. "Bivalent" refers to sera from subjects administered a composition comprising BNT162b2 and an RNA encoding a SARS-CoV-2 S protein comprising mutations that are characteristic of an Omicron BA.1 variant as a $4^{th}$ dose. Also shown is the fold-rise in titer from before administration of a 4th dose to 7 days after administration of a $4^{th}$ dose (*Fold-Rise). "FFRNT" refers to fluorescent focus reduction neutralization test. Neutralization data was obtained using an FFRNT assay, with a viral particle containing a SARS-CoV-2 S protein having mutations characteristic of the variant indicated in the figures. LLOQ refers to Lower Limit of Quantification and ULOQ refers to Upper Limit of Quantification. (A) Comparison of titers of neutralizing antibodies against a SARS-CoV-2 pseudovirus comprising a SARS-CoV-2 S protein having mutations characteristics of an Omicron BA.1 variant. Sera from subjects previously or currently infected with SARS-CoV-2 excluded. (B) Comparison of titers of neutralizing antibodies against a SARS-CoV-2 pseudovirus comprising a SARS-CoV-2 S protein having mutations characteristics of an Omicron BA.1 variant in sera from a population that includes subjects previously or currently infected with SARS-CoV-2 (e.g., as determined by an antibody test or a PCR assay respectively). (C) Comparison of titers of neutralizing antibodies against a SARS-CoV-2 pseudovirus comprising a SARS-CoV-2 S protein of a Wuhan strain. Sera from subjects previously or currently infected with SARS-CoV-2 excluded. (D) Comparison of titers of neutralizing antibodies against a SARS-CoV-2 pseudovirus comprising a SARS-CoV-2 S protein of a Wuhan strain, in sera from a population that includes individuals previously or currently infected with SARS-CoV-2. (E) Comparison of titers of neutralizing antibodies against a SARS-CoV-2 pseudovirus comprising a SARS-CoV-2 S protein having mutations characteristics of a Delta variant. Sera from subjects previously or currently infected with SARS-CoV-2 excluded. (F) Comparison of titers of neutralization antibodies against a SARS-CoV-2 pseudovirus comprising a SARS-CoV-2 S protein having mutations characteristic of a Delta variant, in sera from a population including subjects previously or currently infected with SARS-CoV-2. (G) Geometric mean rise (GMR) of neutralization antibodies observed in subjects administered 60 μg of BNT162b2, 30 μg of RNA encoding a SARS-CoV-2 S protein having mutations characteristic of an Omicron BA.1 variant (OMI 30 ug), 60 μg of RNA encoding a SARS-CoV-2 S protein having mutations characteristic of an Omicron BA.1 variant (OMI 60 ug), 30 μg of a bivalent vaccine comprising 15 μg of BNT162b2 and 15 μg of RNA encoding a SARS-CoV-2 S protein having mutations characteristic of an Omicron BA.1 variant (Bivalent 30 ug), or 60 μg of a bivalent vaccine comprising 30 μg of BNT162b2 and 30 μg of RNA encoding a SARS-CoV-2 S protein having mutations characteristic of an Omicron BA.1 variant (Bivalent 60 ug), as compared to subjects administered 30 μg of BNT162b2 as a $4^{th}$ dose. Results are shown both for a population pool that excludes subjects previously or currently infected with SARS-CoV-2 and a population pool that includes these subjects.

Figure 24A:
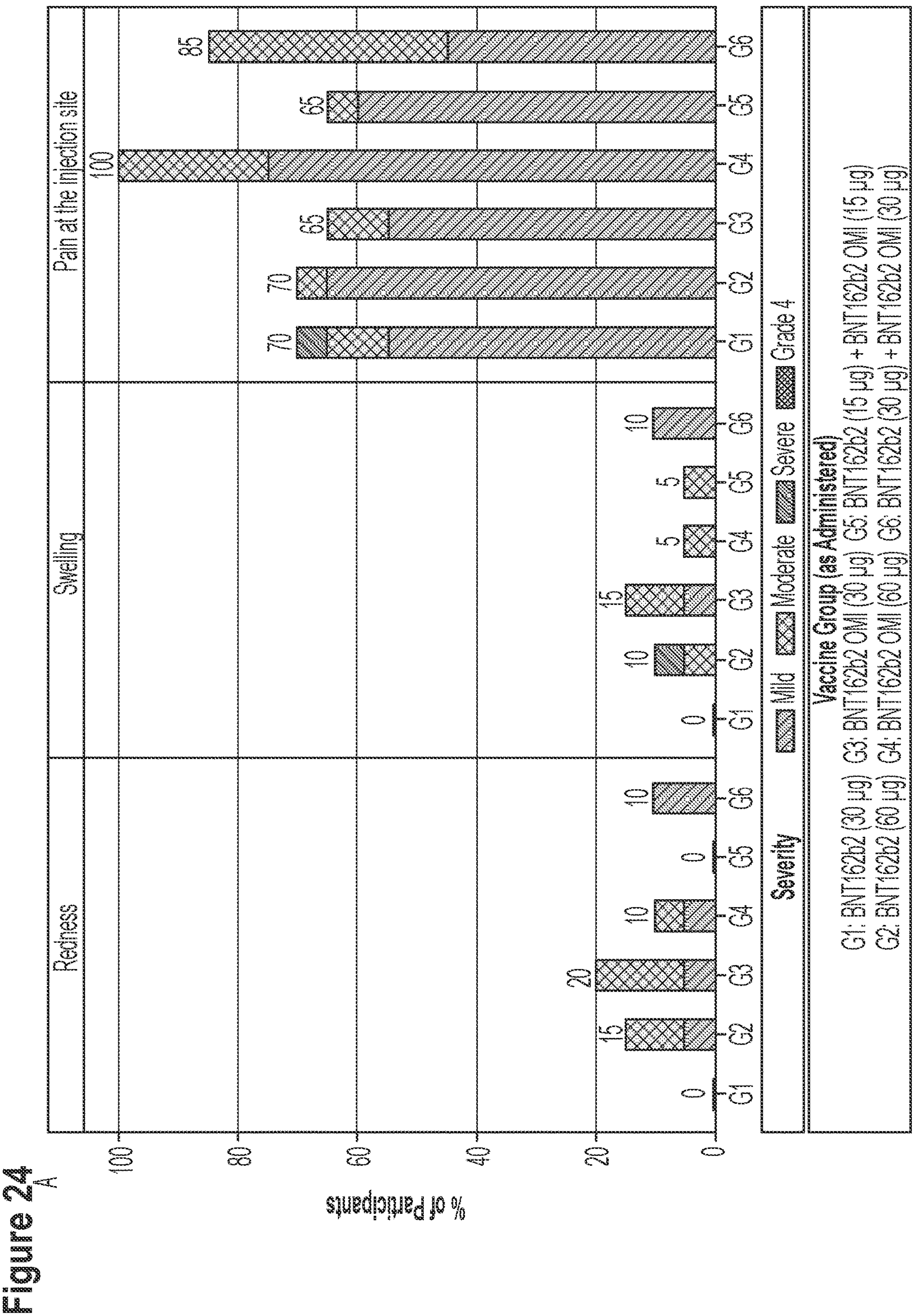
Figure 24:
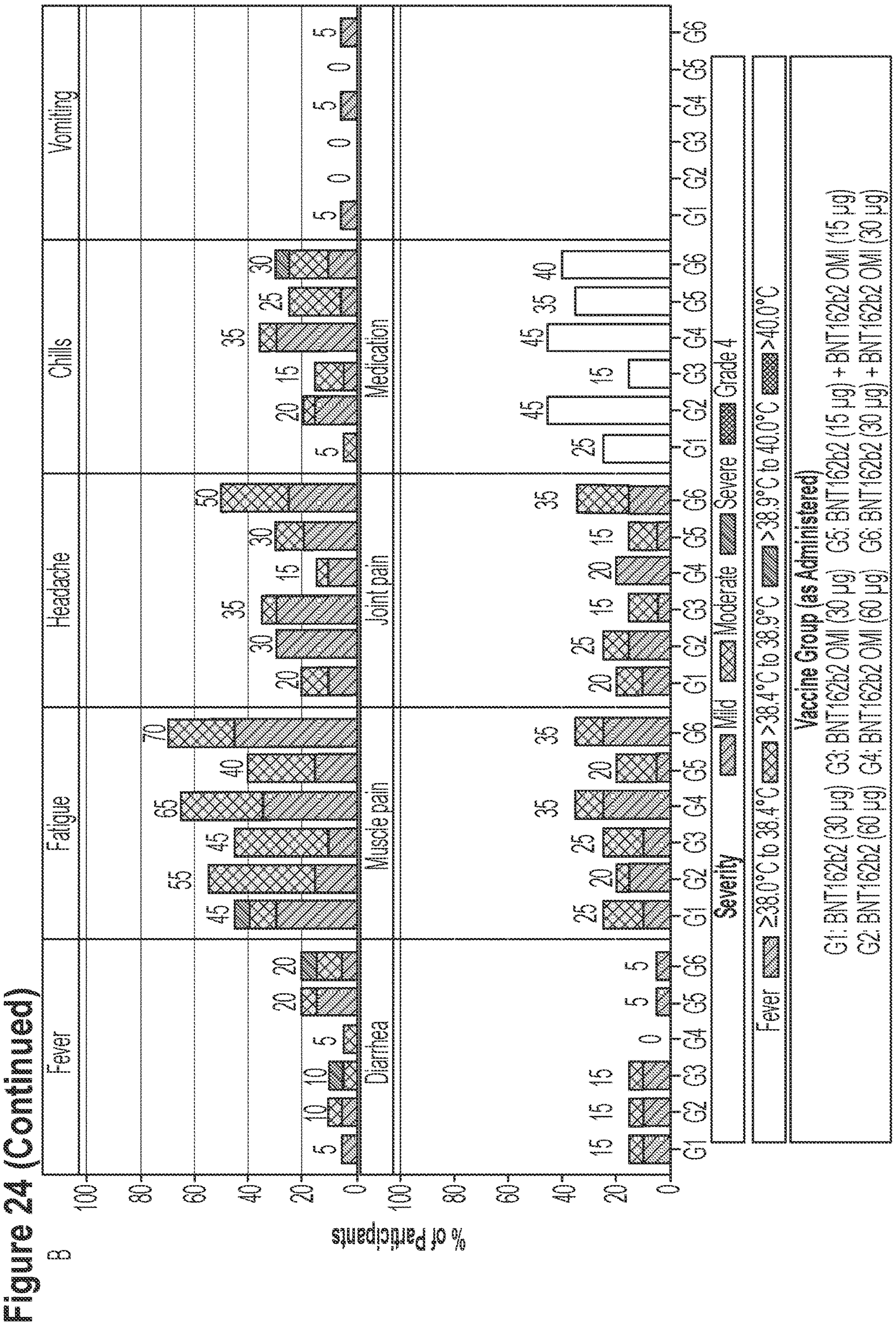

FIG. 24. Reactogenicity of certain exemplary RNA (formulated in LNP) at a given dose: subjects administered a 60 ug dose of RNA encoding a SARS-CoV-2 S protein are more likely to exhibit a higher injection site pain and exhibit similar systemic reactions as subjects administered a 30 ug dose of RNA. Subjects were administered 30 μg or 60 μg of RNA encoding a SARS-CoV-2 S protein from a Wuhan strain (BNT162b2, corresponding to groups G1 and G2, respectively), 30 μg or 60 μg of RNA encoding a SARS-CoV-2 S protein having mutations characteristic of an Omicron BA.1 variant (BNT162b2 OMI, corresponding to groups G3 and G4, respectively), 30 μg of a bivalent vaccine comprising 15 μg of RNA encoding a SARS-CoV-2 S protein from a Wuhan strain and 15 μg of RNA encoding a SARS-CoV-2 S protein having mutations characteristic of an Omicron BA.1 variant (BNT162b2 (15 ug)+BNT162b2 OMI (15 ug), corresponding to group G5), or 60 μg of a bivalent vaccine comprising 30 μg of RNA encoding a SARS-CoV-2 S protein from a Wuhan strain and 30 μg of RNA encoding a SARS-CoV-2 S protein having mutations characteristic of an Omicron BA.1 variant (BNT162b2 (30 ug)+BNT162b2 OMI (30 ug), corresponding to group G6). (A) Local reactions, including redness, swelling, and pain at the injection site, observed within 7 days of injection. Injection site pain was found to be increased in subjects administered 60 μg of RNA encoding a SARS-CoV-2 S protein comprising mutations characteristic an Omicron BA.1 variant or a bivalent vaccine, as compared to other doses tested. (B) Systemic reactions, including fever, fatigue, headache, chills, vomiting, diarrhea, muscle pain, joint pain, and use of medication, observed within 7 days of injection. Systemic reactions through 7 days were observed to be broadly similar across different groups. Fatigue was found to trend higher after administration of 60 ug doses, as compared to 30 ug doses.

Figure 25:
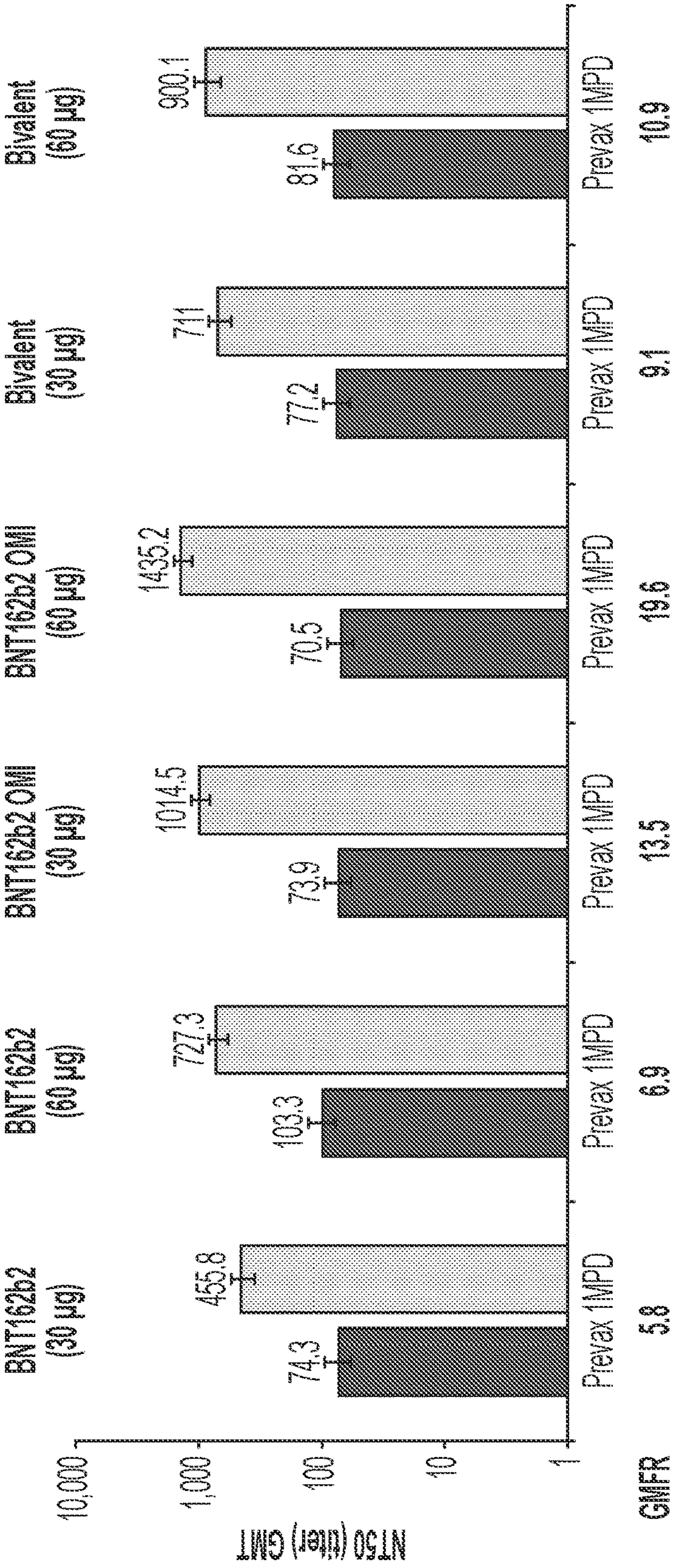

FIG. 25. 50% neutralization titers of sera collected 1 month after a fourth dose of BNT162b2, an Omicron BA.1-specific booster, or a bivalent vaccine against an Omicron BA.1 variant. Subjects who were previously administered two doses of BNT162b2 (30 ug), and a third (booster) dose of BNT162b2 (30 ug) were administered (i) a 30 ug dose of BNT162b2 (encoding a SARS-CoV-2 S protein from a Wuhan strain), (ii) a 60 ug dose of BNT162b2, (iii) a 30 ug dose of RNA encoding a SARS-CoV-2 S protein having mutations characteristic of an Omicron BA.1 variant ("BNT162b2 OMI"), (iii) a 60 ug dose of BNT162b2 OMI, (iv) a 30 ug dose of a bivalent vaccine, comprising 15 μg of BNT162b2 and 15 μg of BNT162b2 OMI ("Bivalent"), or (v) a 60 ug dose of a bivalent vaccine, comprising 30 μg of BNT162b2 and 30 μg of BNT162b2 OMI. Geometric mean titer (GMT) of neutralization antibodies were measured in serum from subjects collected 1 month after administration of a 4th dose (GMT indicated above each bar). Shown below the x-axis is the geometric fold rise (GMFR) in titer from before administration of a $4^{th}$ dose (pre-vax) to 1 month after administration of a $4^{th}$ dose (1MPD) for each patient group. Neutralization data was obtained using a neutralization assay, with a viral particle containing a SARS-CoV-2 S protein having mutations characteristic of a Omicron BA.1 variant.

Figure 26:
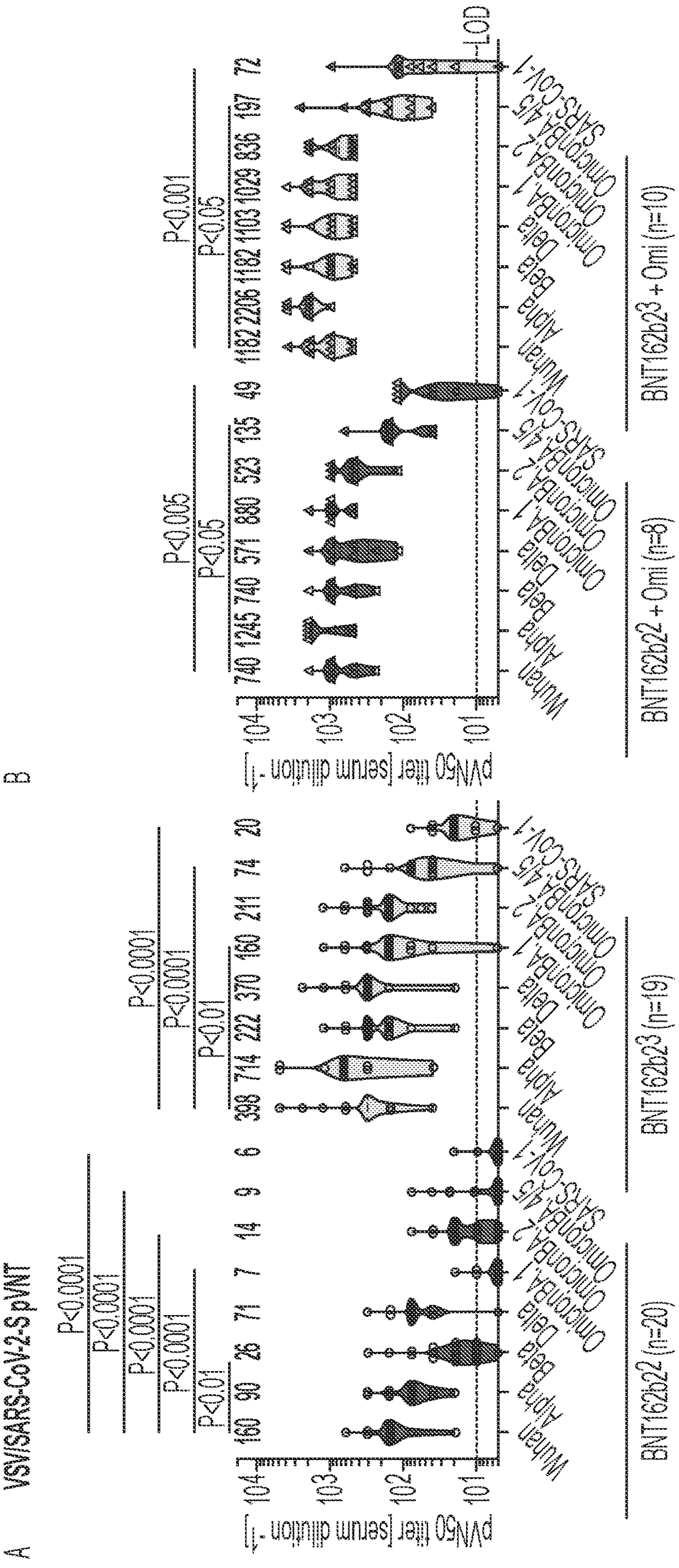
Figure 26:
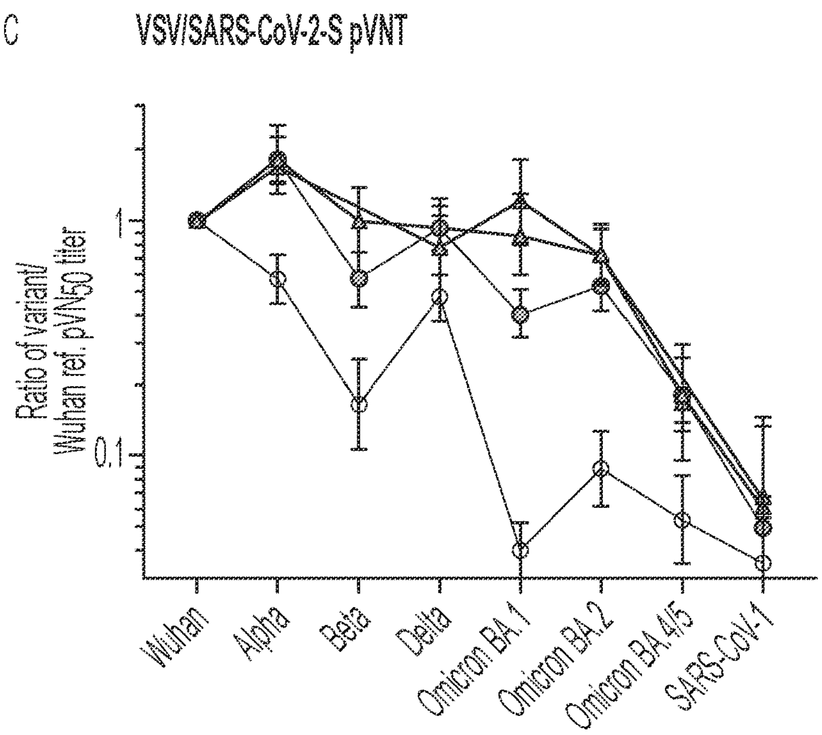

FIG. 26. Omicron BA.1 breakthrough infection of BNT162b2 double- and triple-vaccinated individuals induces broad neutralization of Omicron BA.1, BA.2 and other VOCs, but to a lesser extent against BA.4 and BA.5. This figure is an extension of FIG. 16, including data neutralizing activity against Omicron BA.4 and BA.5. As described in FIG. 16, serum was tested in duplicate; 50% pseudovirus neutralization ($pVN_{50}$) geometric mean titers (GMTs) (in A and B), and the geometric mean ratio of SARS-CoV-2 variants of concern (VOCs) and SARS-CoV-1 $pVN_{50}$ GMTs normalized against Wuhan $pVN_{50}$ GMTs (in C) were plotted. For titer values below the limit of detection (LOD), LOD/2 values were plotted. Values above violin plots represent the group GMTs. The nonparametric Friedman test with Dunn's multiple comparisons correction was used to compare Wuhan neutralizing group GMTs with titers against the indicated variants and SARS-CoV-1. Multiplicity adjusted p values are shown. (A) $pVN_{50}$ GMTs against Wuhan, VOC and SARS-CoV-1 pseudovirus in patients who received two doses or three doses of BNT162b2. (B) $pVN_{50}$ GMTs against Wuhan, VOC and SARS-CoV-1 pseudovirus in patients who received two doses or three doses of BNT162b2 and who have been previously infected with an Omicron BA.1 variant of SARS-CoV-2. (C) Group geometric mean ratios with 95% confidence intervals for all cohorts shown in (A) and (B).

Figure 27:
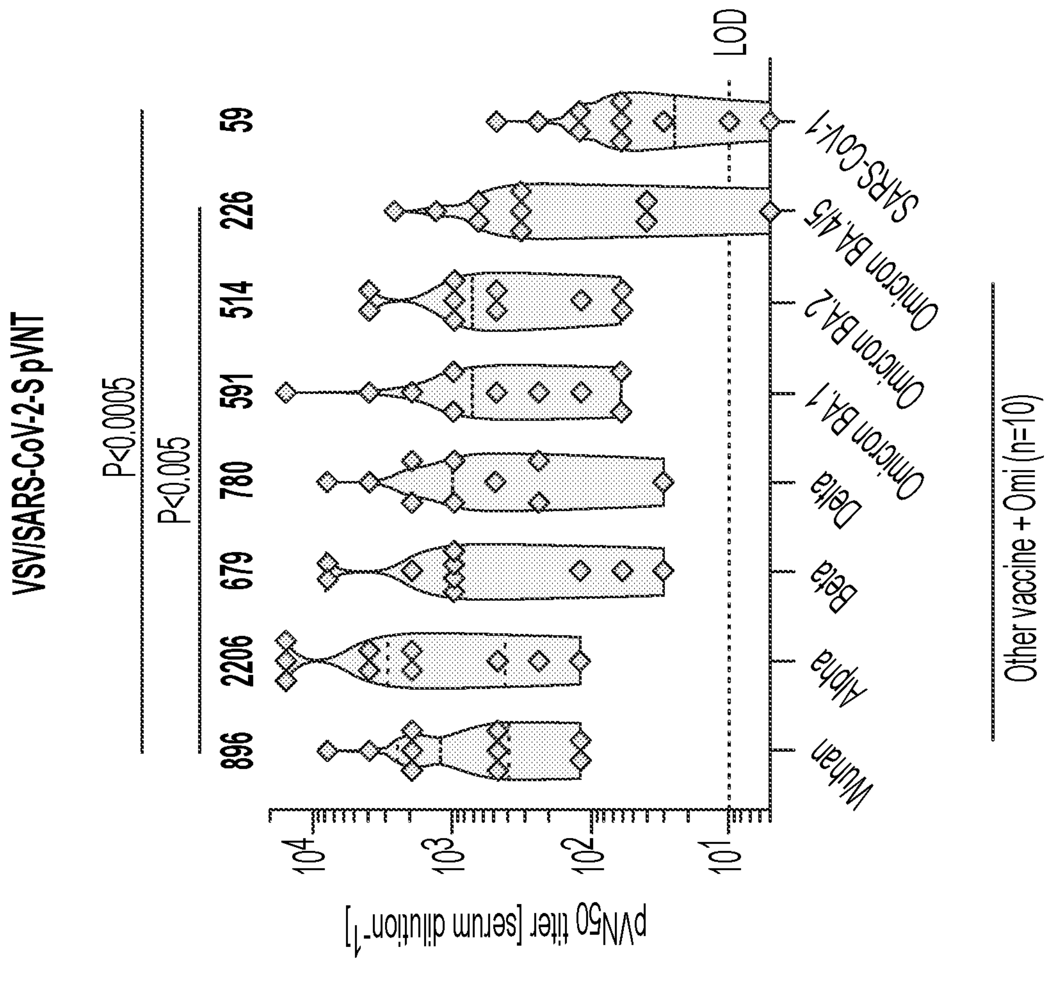

FIG. 27. Omicron BA.1 breakthrough infection of individuals vaccinated with other approved COVID-19 vaccines or mixed regimens results in immune sera that broadly neutralize Omicron BA.1, BA.2 and other VOCs, but to a lesser extent against BA.4 and BA.5. This figure is an extension of FIG. 19, including data neutralizing activity against Omicron BA.4 and BA.5. As described in FIG. 19, serum was tested in duplicate; individual 50% pseudovirus neutralization ($pVN_{50}$) geometric mean titers (GMTs) against SARS-CoV-2 Wuhan, Alpha, Beta, Delta and Omicron BA.1, BA.2 and BA.4/5 variants, plus SARS-CoV-1 were plotted. For titer values below the limit of detection (LOD), LOD/2 values were plotted. Values above violin plots represent group GMTs. The nonparametric Friedman test with Dunn's multiple comparisons correction was used to compare Wuhan neutralizing group GMTs with titers against the indicated variants and SARS-CoV-1. Multiplicity-adjusted p values are shown.

FIG. 28. (SEQ ID NO: 129-133) Sequences of RBDs of SARS-COV-2 Wuhan strain and variants thereof. Variant-specific amino acid alterations are indicated in bold font, with the original Wuhan amino acid highlighted in bold and italicized font.

Figure 29:
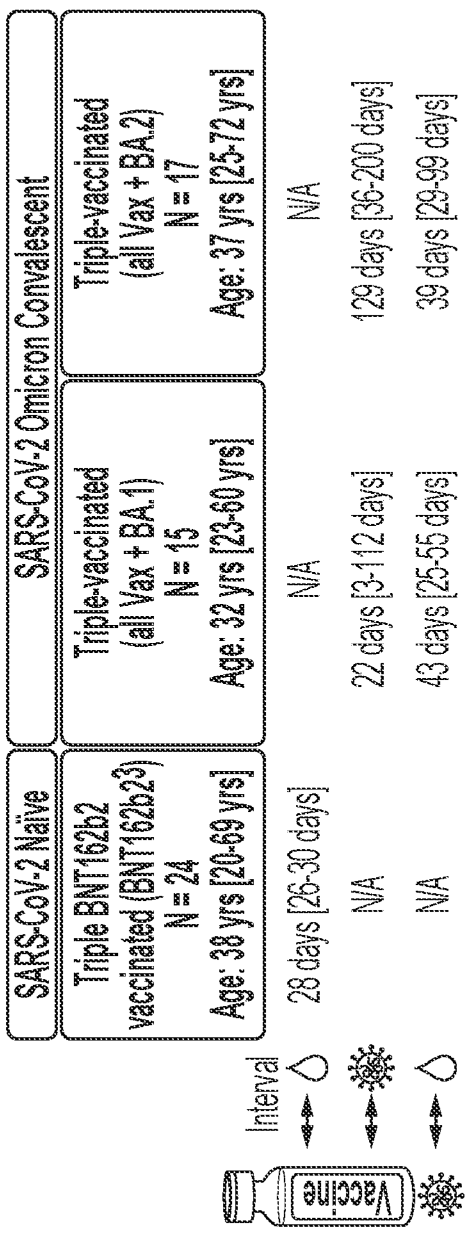

FIG. 29. Cohorts and sampling for the study described in Example 14. A schematic is shown for testing immune responses in triple-vaccinated patients who are (i) Omicron naïve, (ii) have been infected with an Omicron BA.1 variant, or (iii) have been infected with an Omicron BA.2 variant. Blood samples were drawn from three cohorts: Omicron-naïve individuals triple-vaccinated with BNT162b2 ($BNT162b2^3$), and individuals vaccinated with homologous or heterologous three doses regimens that subsequently had either a breakthrough infection with Omicron at a time of BA.1 dominance (November 2021 to January 2022; all Vax+BA.1) or at a time of BA.2 dominance (March to May 2022; all Vax+BA.2) in Germany. Sera (droplet) were isolated in the Omicron-naïve cohort at the time-point indicated following their most recent vaccination; for convalescent cohorts, the time from their most recent vaccination to Omicron infection, and infection to serum isolation are indicated. All values specified as median-range. Serum neutralizing capacity was assessed using a pseudovirus neutralization test.

Figure 30:
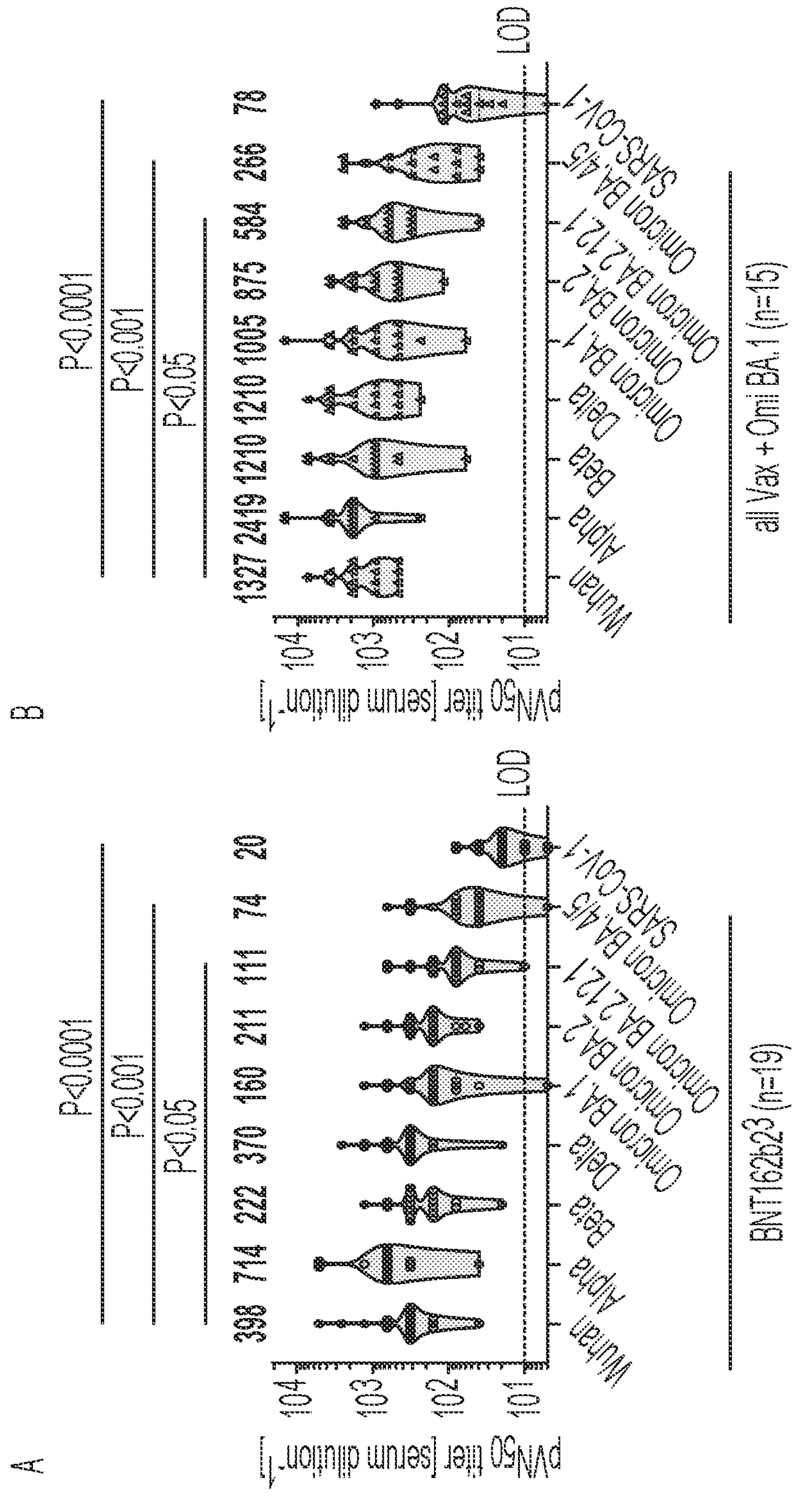

FIG. 30. 50% pseudovirus neutralization ($pVN_{50}$) geometric mean titers (GMTs) from the $BNT162b2^3$ and All Vax+Omi BA.1 breakthrough infection cohorts. Serum was drawn from Omicron-naïve BNT162b2 triple-vaccinated individuals ($BNT162b2^3$, circles) at 28 days after the third dose, and from vaccinated individuals with subsequent Omicron BA.1 breakthrough infection (all Vax+Omi BA.1, triangles) at a median 43 days post-infection. 50% pseudovirus neutralization ($pVN_{50}$) geometric mean titers (GMTs) for Omicron-naive individuals are plotted in (A) and for BA.1 breakthrough infected individuals in (B). This data was previously published in Quandt et al. (Omicron BA.1 breakthrough infection drives cross-variant neutralization and memory B cell formation against conserved epitopes." Science immunology, eabq2427 (2022), doi:10.1126/sciimmunol.abq2427), except for BA.2.12.1 neutralization data. Serum was tested in duplicate. For titer values below the limit of detection (LOD), LOD/2 values were plotted. Values above violin plots represent group GMTs. The non-parametric Friedman test with Dunn's multiple comparisons correction was used to compare Wuhan neutralizing group GMTs with titers against the indicated variants and SARS-CoV-1. Multiplicity-adjusted p values are shown.

Figure 31:
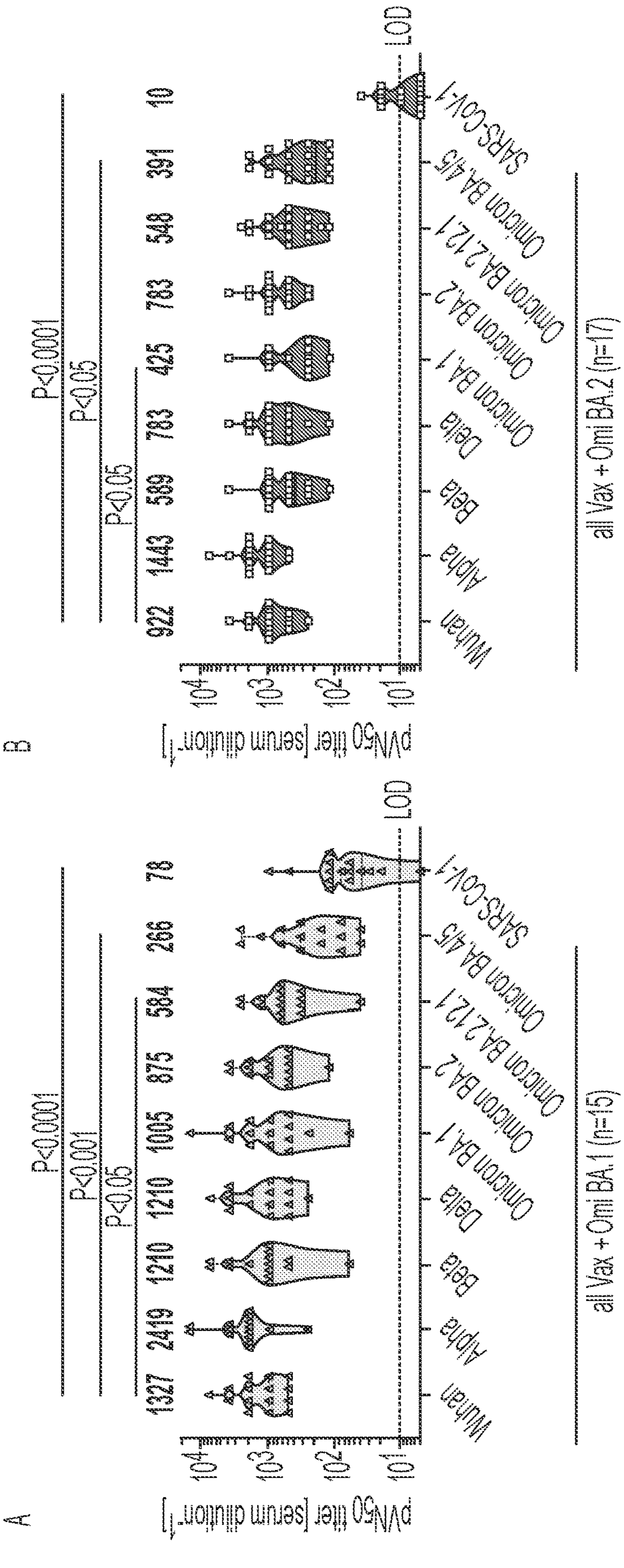
Figure 31:
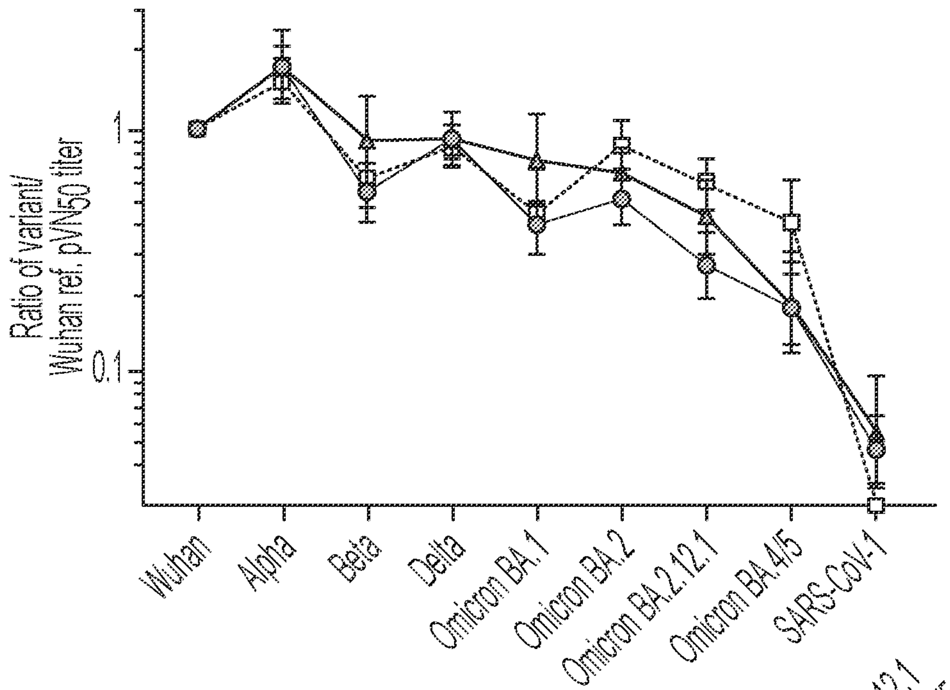

FIG. 31. Omicron BA.2 breakthrough infection of previously vaccinated individuals refocuses neutralization against Omicron BA.2 and the BA.2-derived subvariants BA.2.12.1 and BA.4/BA.5. Serum was drawn from BNT162b2 triple-vaccinated individuals with subsequent Omicron BA.1 breakthrough infection at a median 44 days post-infection ($BNT162b2^3$+Omi BA.1, triangles), and from BNT162b2 triple-vaccinated individuals with subsequent Omicron BA.2 breakthrough infection at 38 days post-infection ($BNT162b2^3$+Omi BA.2, squares). 50% pseudovirus neutralization ($pVN_{50}$) geometric mean titers (GMTs) (in A, B), and the geometric mean ratio of SARS-CoV-2 variants of concern (VOCs) and SARS-CoV-1 $pVN_{50}$ GMTs normalized against Wuhan pVN50 GMTs (in C) were plotted.

$pVN_{50}$ GMT and geometric mean ratio data for Omicron-naïve BNT162b2 triple-vaccinated individuals ($BNT162b2^3$, circles) and BNT162b2 triple-vaccinated individuals with Omicron BA.1 breakthrough infection was previously published in Quandt et al. ("Omicron BA.1 breakthrough infection drives cross-variant neutralization and memory B cell formation against conserved epitopes." Science immunology, eabq2427 (2022), doi:10.1126/sciimmunol.abq2427), except for BA.2.12.1 neutralization data. Serum was tested in duplicate. For titer values below the limit of detection (LOD), LOD/2 values were plotted. Values above violin plots represent group GMTs. The non-parametric Friedman test with Dunn's multiple comparisons correction was used to compare Wuhan neutralizing group GMTs with titers against the indicated variants and SARS-CoV-1. Multiplicity-adjusted p values are shown. (A, B) $pVN_{50}$ GMTs against Wuhan, VOC and SARS-CoV-1 pseudovirus. (C) Group geometric mean ratios with 95% confidence intervals.

Figure 32:
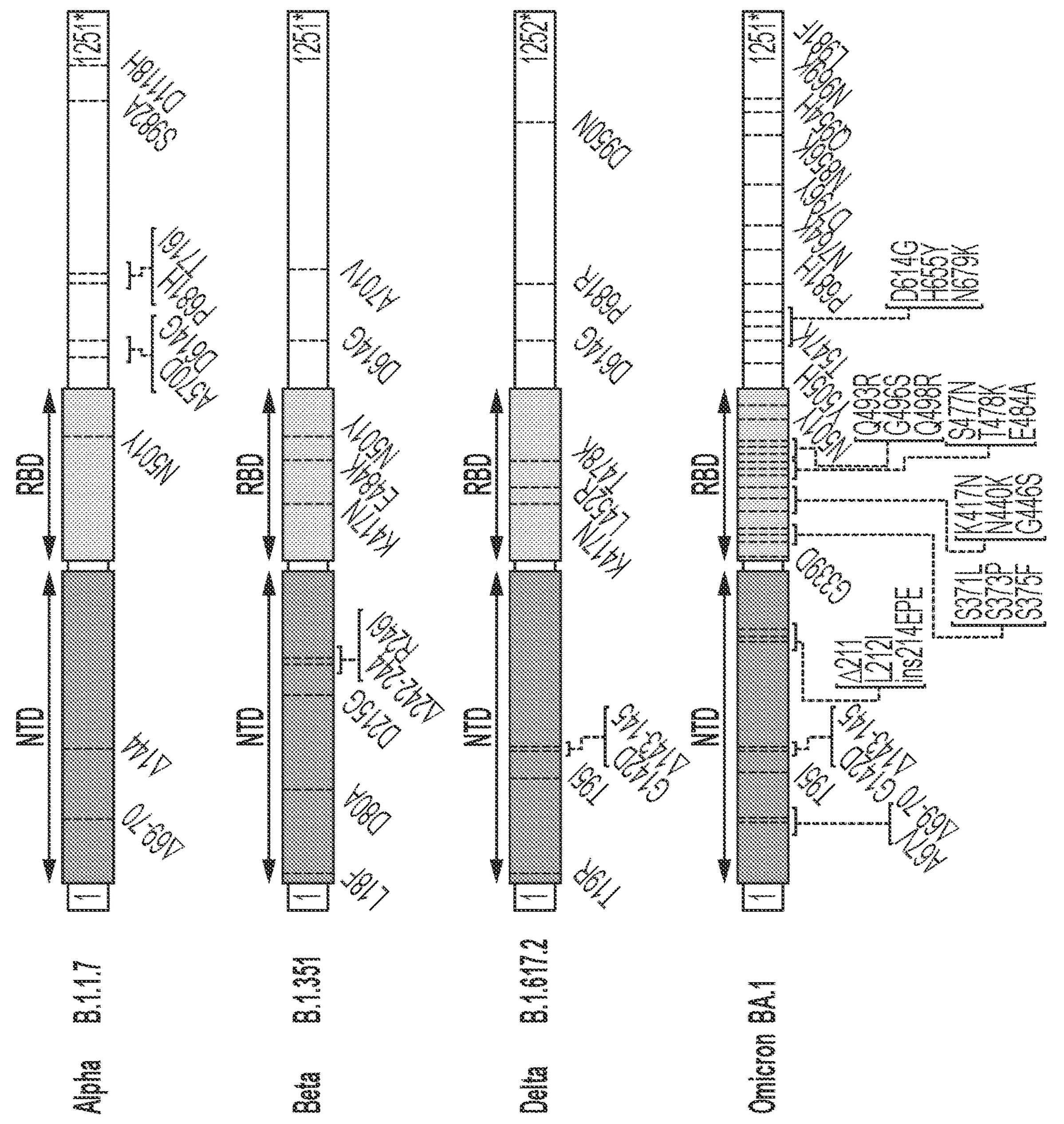
Figure 32:
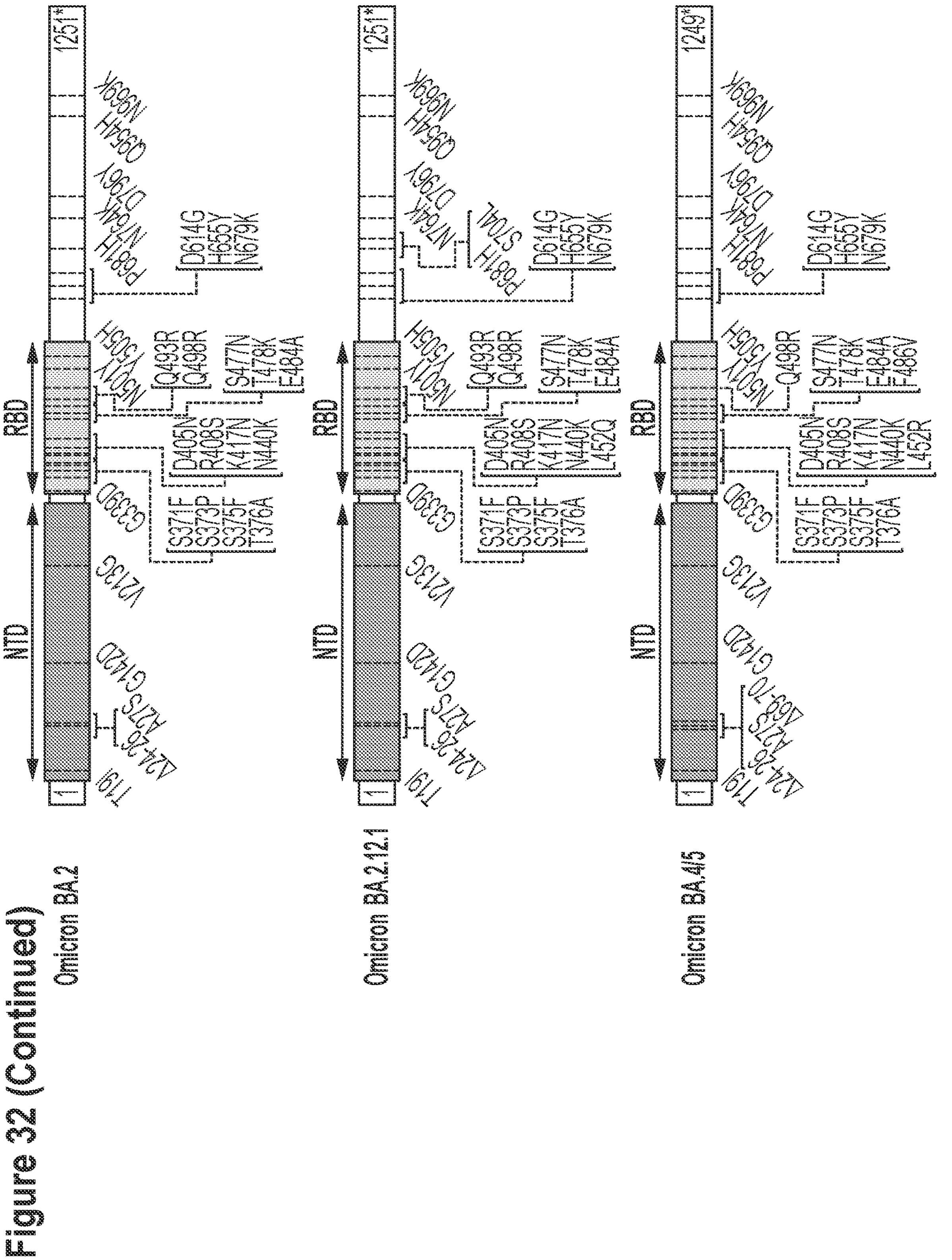

FIG. 32. Characteristics of SARS-CoV-2 S glycoproteins used in the VSV-SARS-CoV-2 pseudovirus based neutralization assays. The sequence of the Wuhan-Hu-1 isolate SARS-CoV-2 S glycoprotein (GenBank: QHD43416.1) was used as reference. Amino acid positions, amino acid descriptions (one letter code) and kind of mutations (substitutions, deletions, insertions) are indicated. NTD, N-terminal domain; RBD, Receptor-binding domain, A, deletion; ins, insertion; *, Cytoplasmic domain truncated for the C-terminal 19 amino acids.

Figure 33:
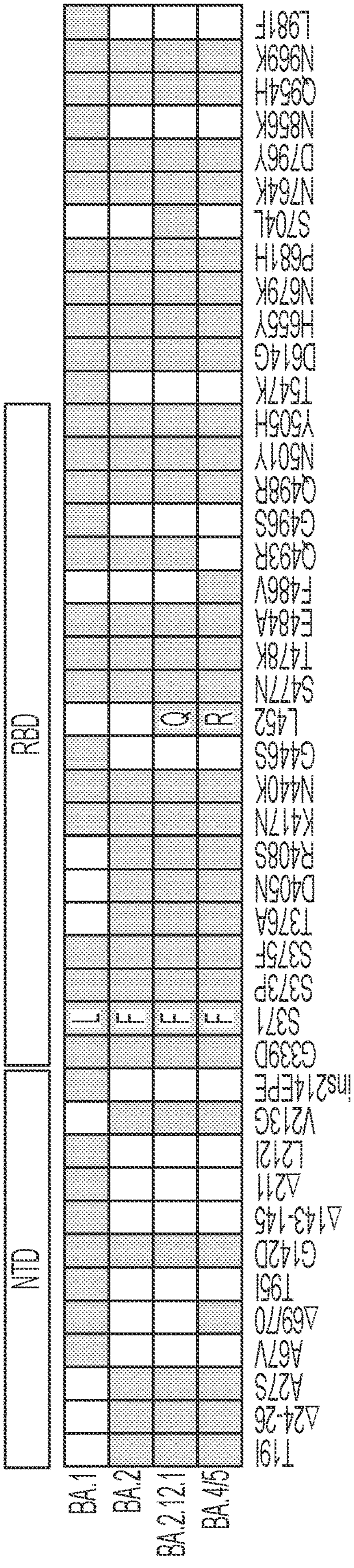

FIG. 33. Alterations on the spike glycoprotein amino acid sequence of SARS-CoV-2 Omicron sub-lineages. Amino acid positions, amino acid descriptions (one letter code) and kind of mutations substitutions, deletions, insertions) are indicated. White letters in boxes indicate the amino acid substitution per sub-lineage; A, deletion; ins, insertion; NTD, N-terminal domain; RBD, receptor-binding domain.

Figure 34:
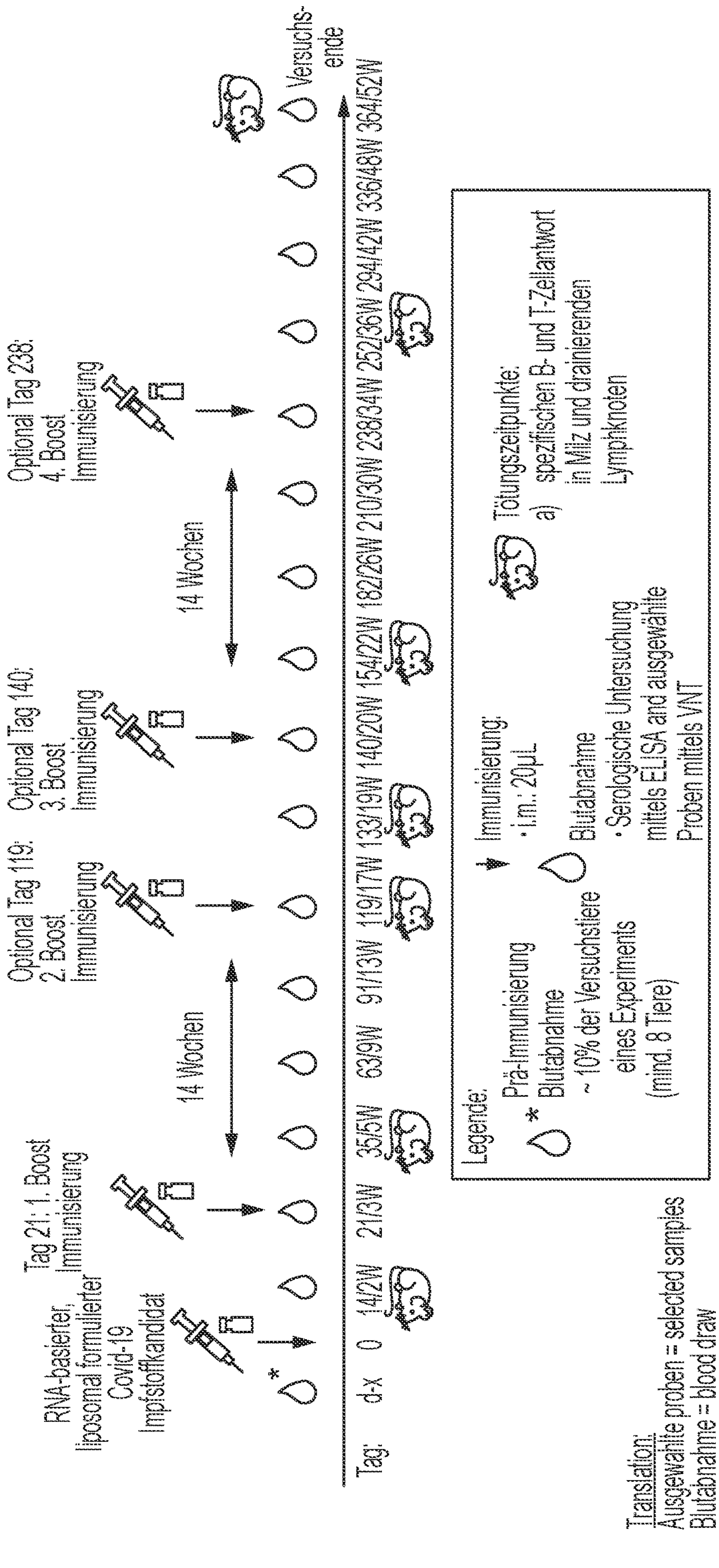

FIG. 34. Immunization protocol for studies with VOC boosters. BALB/c mice were immunized according to the indicated schedule with two doses (1 ug each) of the original BNT162b2 vaccine, followed by at least one dose (1 ug total) of a monovalent, bivalent, or trivalent booster dose of either: (a) the original BNT162b2 ("BNT162b2"); (b) BNT162b2 OMI BA.1 ("OMI BA.1"); (c) BNT162b2 OMI BA.4/5 ("OMI BA.4/5"); or a combination thereof.

Figure 35:
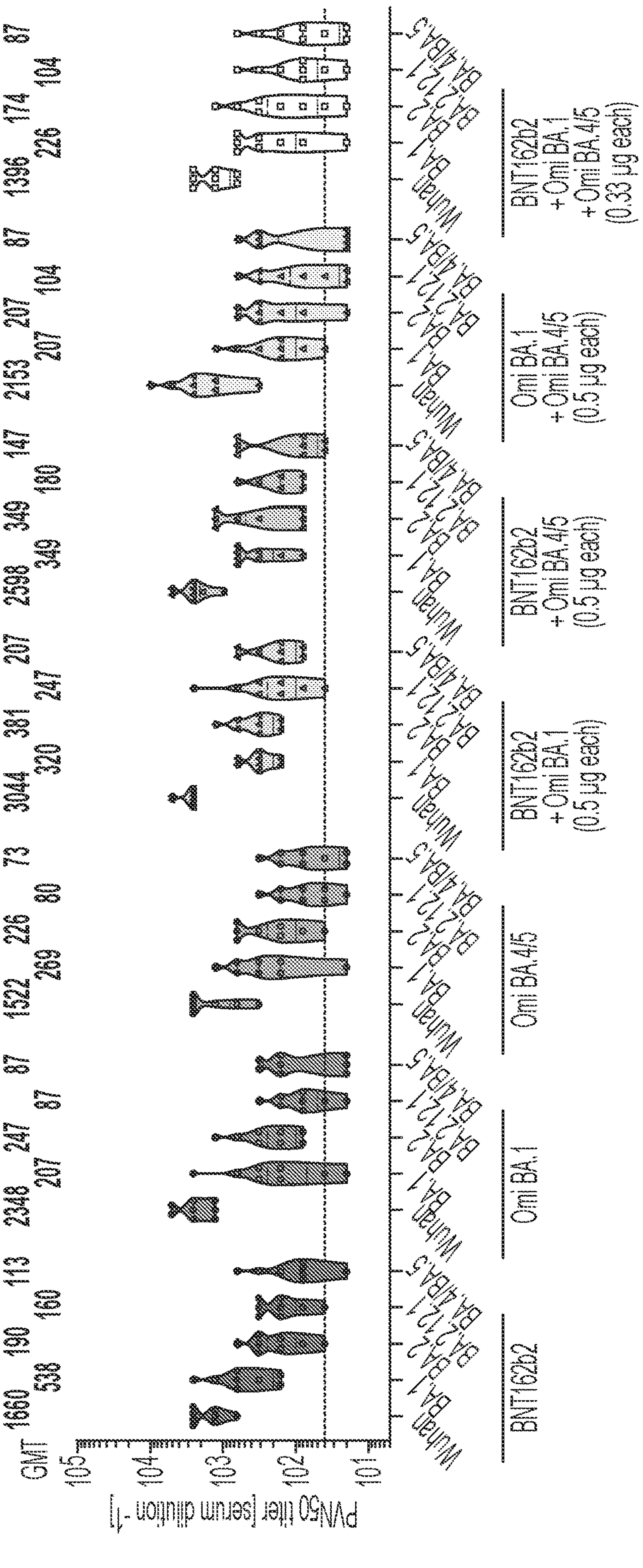

FIG. 35. Baseline grouped neutralizing GMTs. Sera drawn from mice immunized as depicted in FIG. 34 (day 104, pre-boost) were assessed for geometric mean titers of neutralizing antibodies against various strains. Data are presented grouped by cohort.

Figure 36:
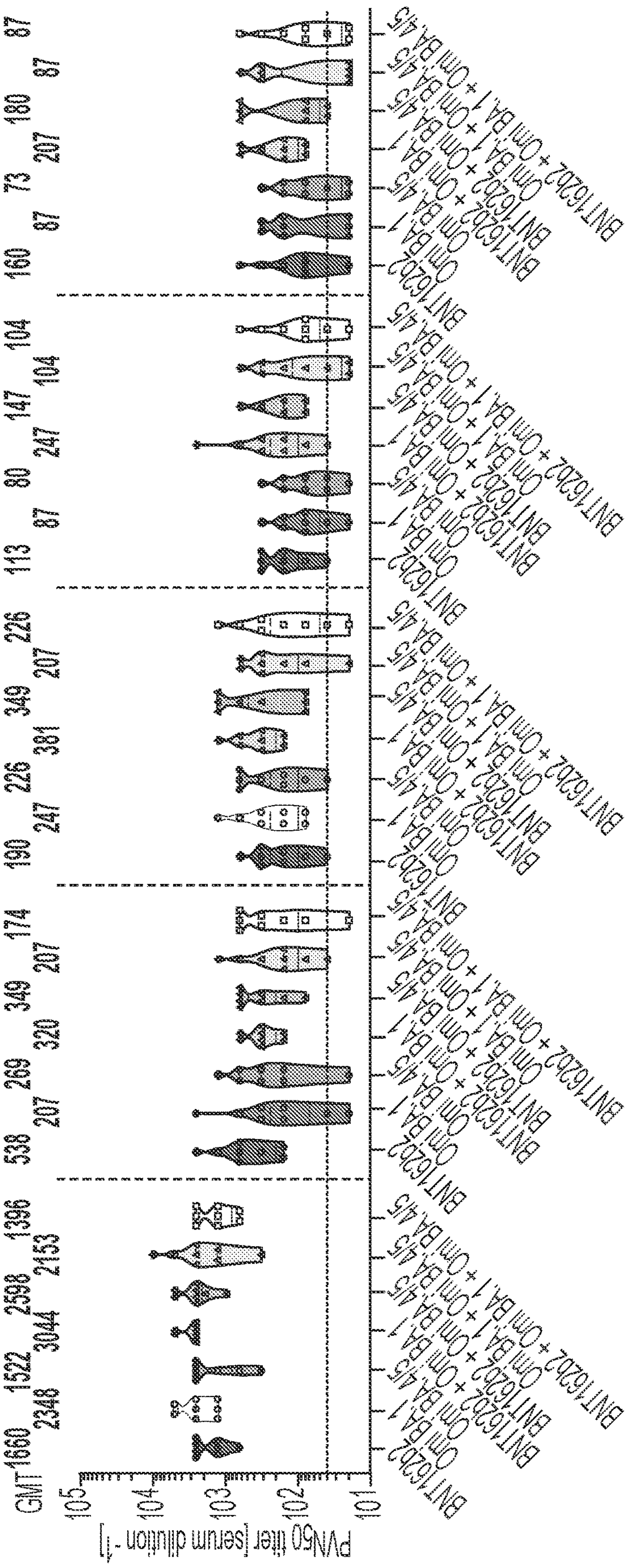

FIG. 36. Baseline staggered neutralizing GMTs. Sera drawn from mice immunized as depicted in FIG. 34 (day 104, pre-boost) were assessed for geometric mean titers of neutralizing antibodies against various strains. Data are presented in staggered format (i.e., by strain against which neutralization was assessed).

Figure 37:
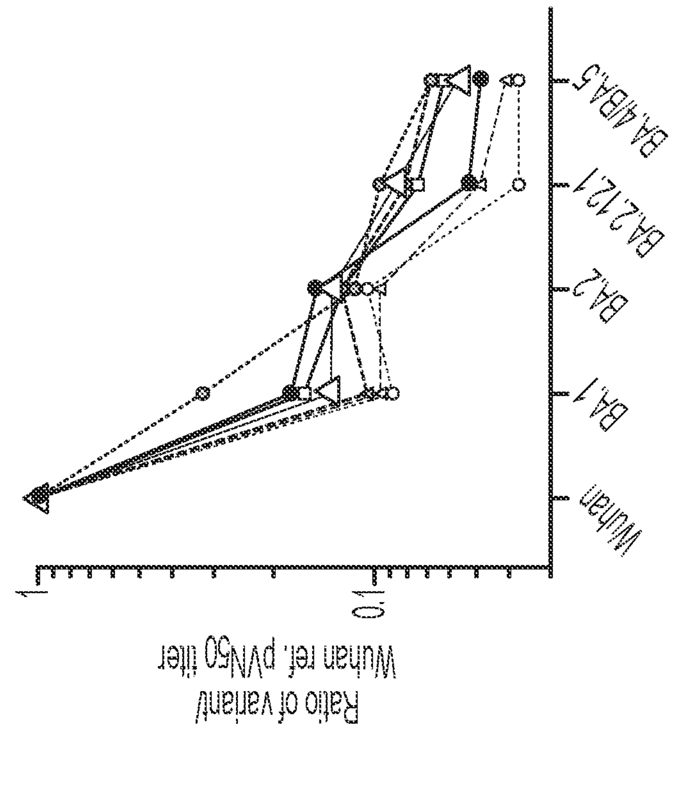

FIG. 37. Baseline cross-neutralization. Sera drawn from mice immunized as depicted in FIG. 34 (day 104, pre-boost) were assessed for geometric mean titers of neutralizing antibodies against various strains. Cross-neutralization results are presented as calculated variant/Wuhan reference GMT Ratios.

Figure 38:
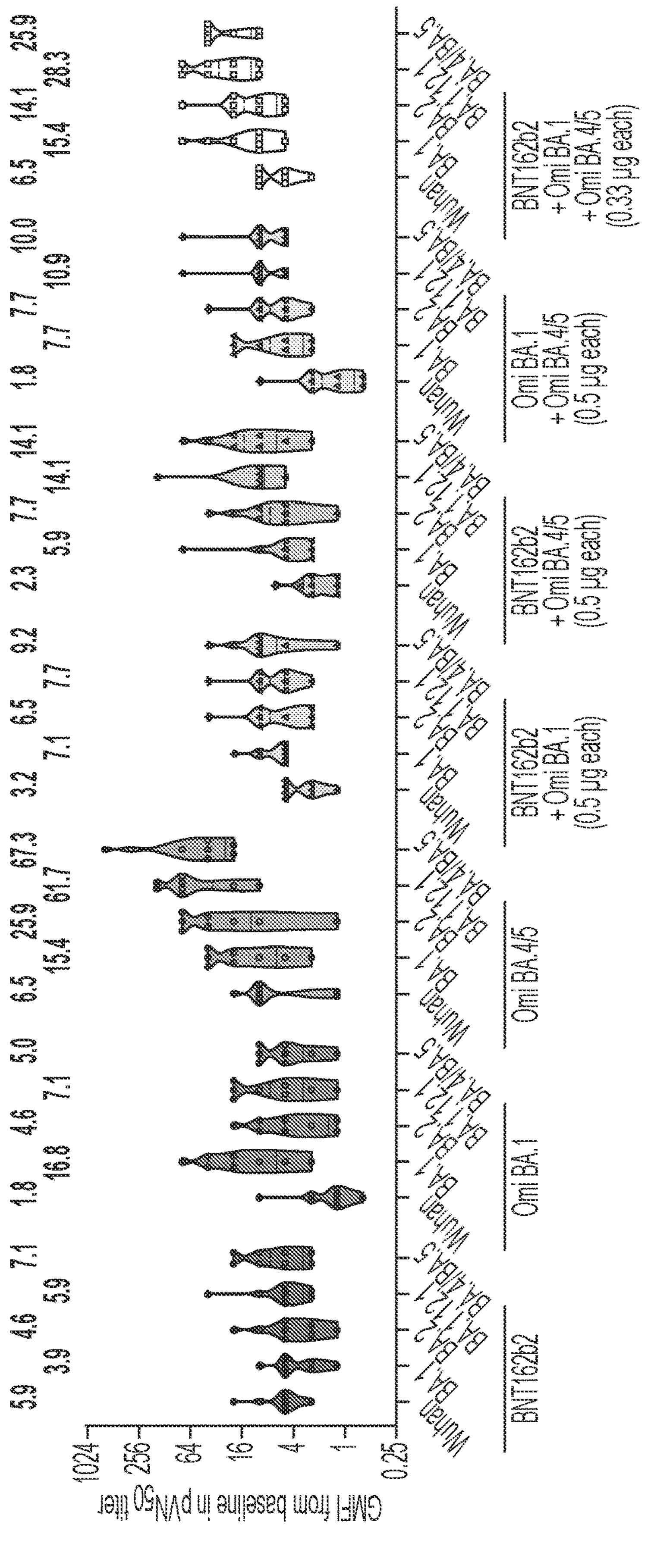

FIG. 38. Post-boost geometric mean fold increase in GMTs. Sera drawn from mice immunized as depicted in FIG. 34 (day 111, 7-days post-boost) were assessed for geometric mean fold increase in GMT of neutralizing antibodies against various strains.

Figure 39:
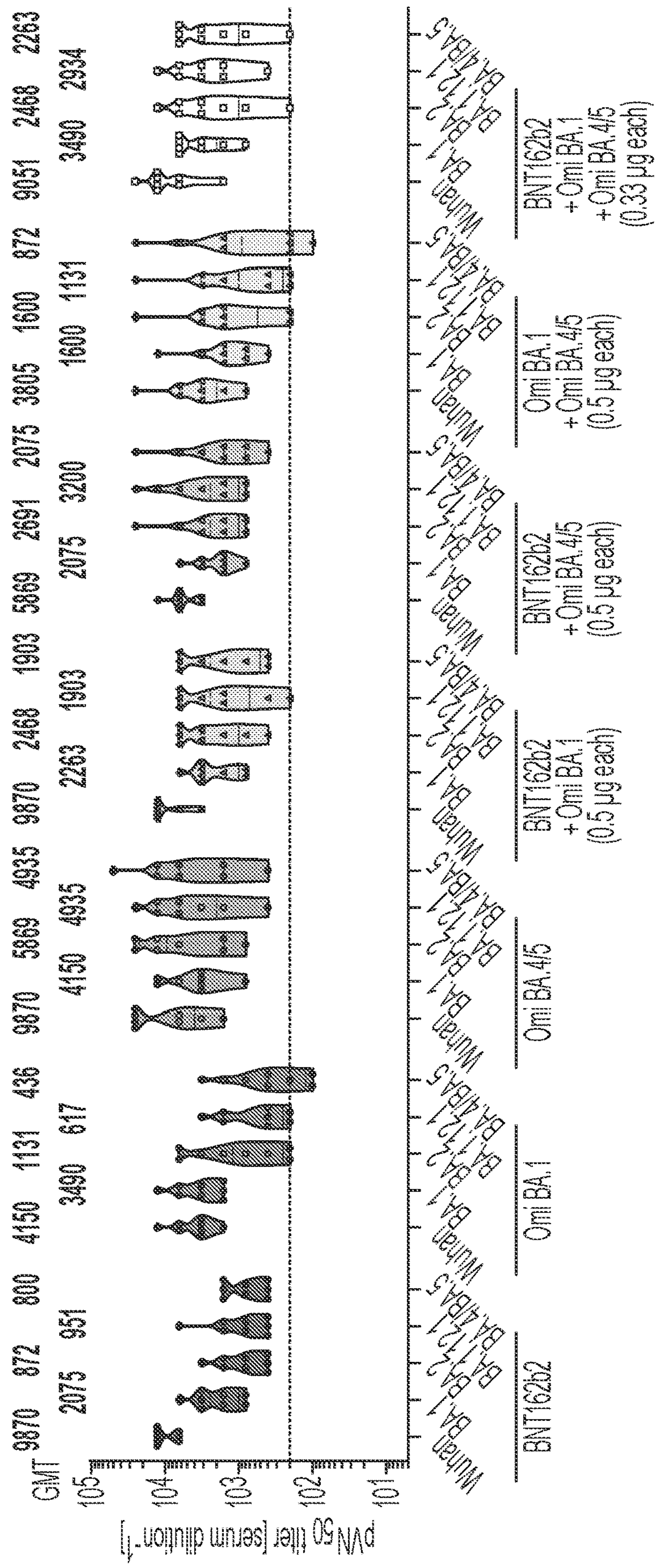

FIG. 39. Post-boost grouped neutralizing GMTs. Sera drawn from mice immunized as depicted in FIG. 34 (day 111, 7-days post-boost) were assessed for geometric mean fold increase in GMT of neutralizing antibodies against various strains. Data are presented grouped by cohort.

Figure 40:
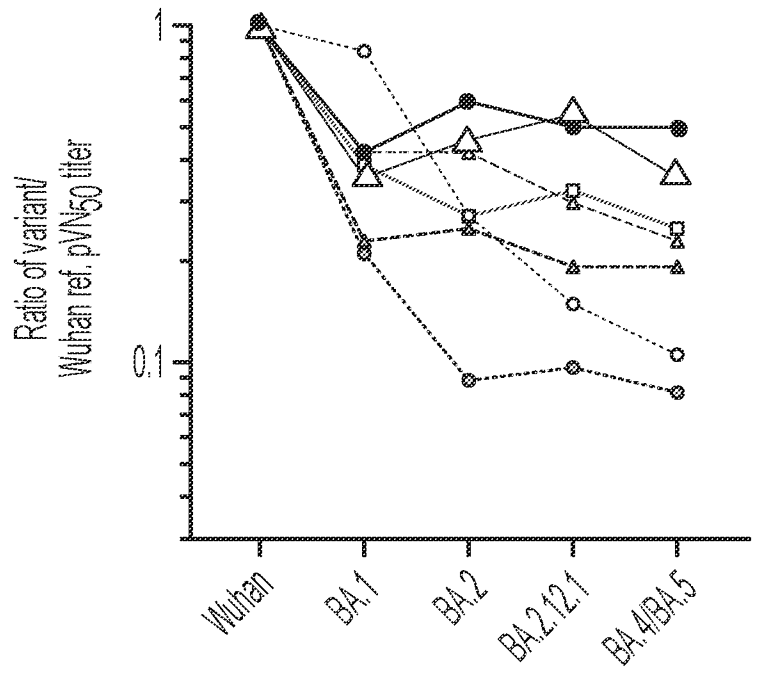

FIG. 40. Post-boost cross-neutralization. Sera drawn from mice immunized as depicted in FIG. 34 (day 111, 7-days post-boost) were assessed for geometric mean fold increase in GMT of neutralizing antibodies against various strains. Cross-neutralization results are presented as calculated variant/Wuhan reference GMT Ratios.

Figure 41:
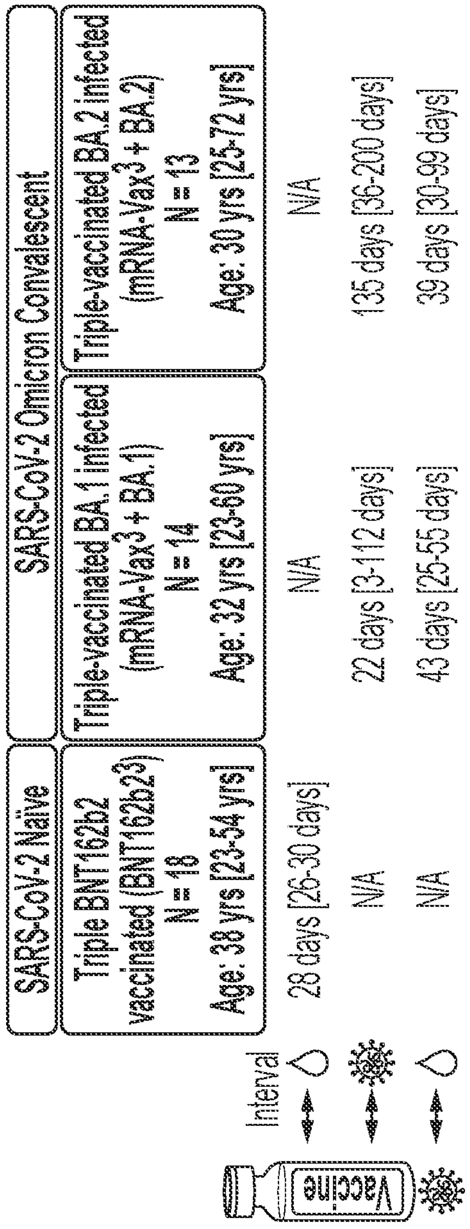

FIG. 41. Cohorts and sampling. Serum samples (droplet) were drawn from three cohorts: individuals triple-vaccinated with BNT162b2 that were SARS-CoV-2-naïve at the time of sampling ($BNT162b2^3$), and from individuals vaccinated with three doses of mRNA COVID-19 vaccine (BNT162b2/mRNA-1273 homologous or heterologous regimens) who subsequently had a breakthrough infection with Omicron either at a time of BA.1 dominance (November 2021 to January 2022; $mRNA\text{-}Vax^3$+BA.1) or at a time of BA.2 dominance (March to May 2022; $mRNA\text{-}Vax^3$+BA.2). For convalescent cohorts, relevant intervals between key events such as the most recent vaccination, SARS-CoV-2 infection, and serum isolation are indicated. All values specified as median-range. N/A, not applicable.

Figure 42:
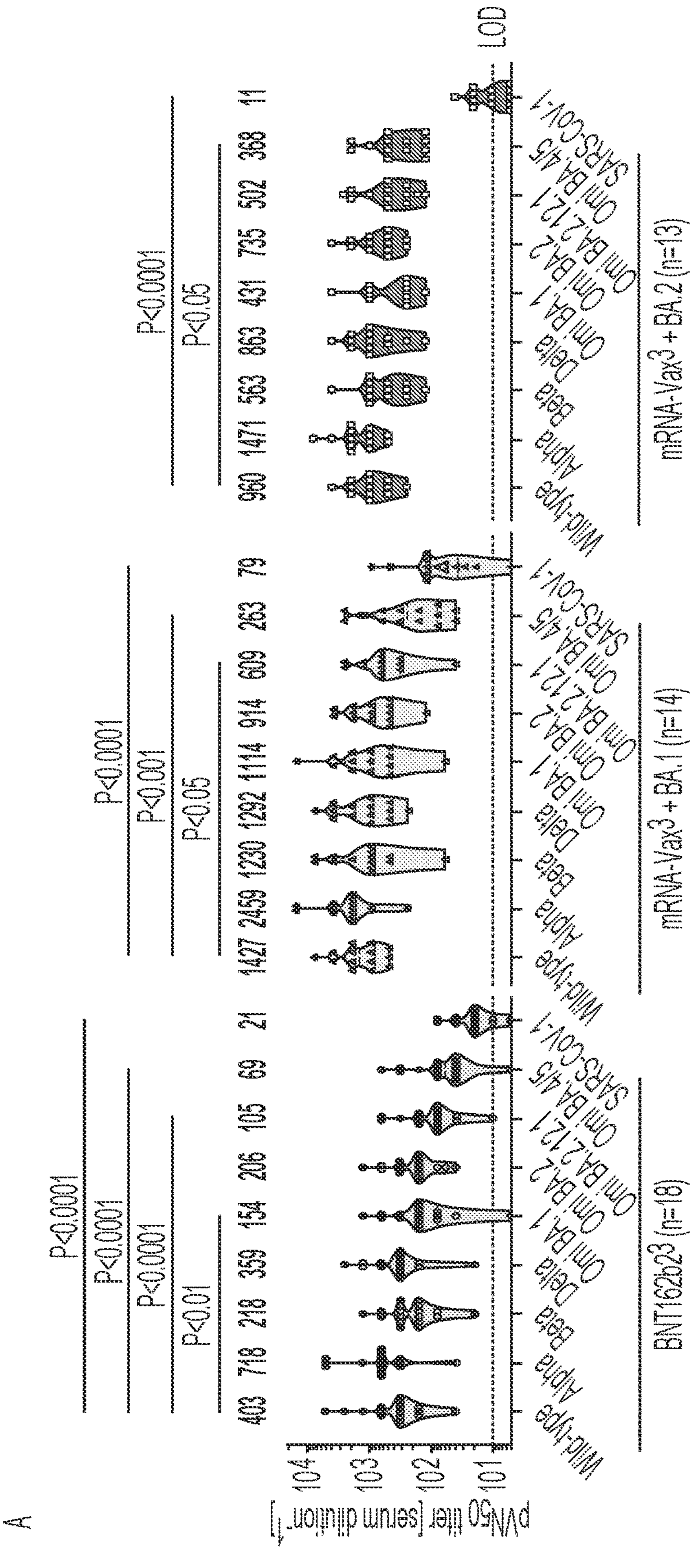
Figure 42:
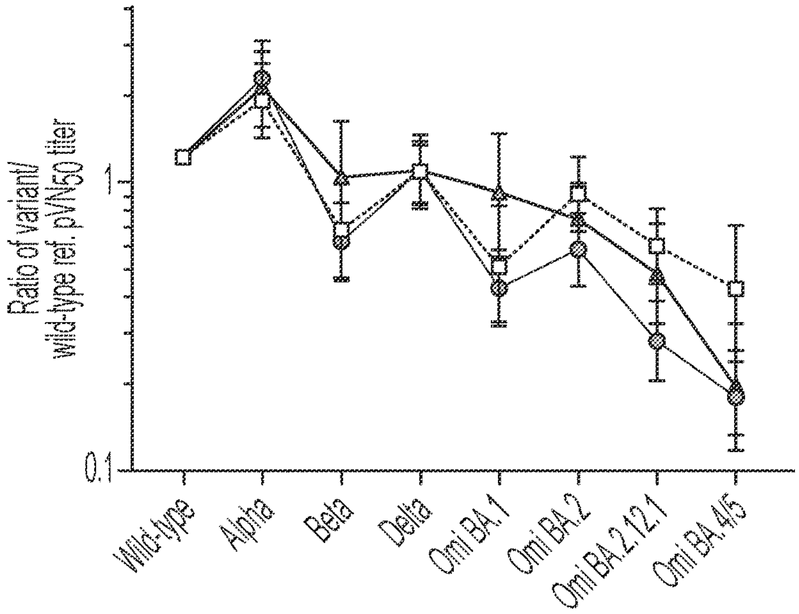

FIG. 42. Omicron BA.2 breakthrough infection of triple mRNA vaccinated individuals induces broad neutralization of SARS-CoV-2 variant pseudoviruses including Omicron BA.4/5. Cohorts and serum sampling as described in FIG. 41. (A) 50% pseudovirus neutralization ($pVN_{50}$) geometric mean titers (GMTs) against the indicated SARS-CoV-2 variants of concern (VOCs) or SARS-CoV-1 pseudoviruses. Values above violin plots represent group geometric mean titers (GMTs). $BNT162b2^3$ indicates triple vaccinated, SARS-CoV-2-naïve individuals; $mRNA\text{-}Vax^3$+BA.1 indicates triple-vaccinated individuals who subsequently had a breakthrough infection with a Omicron BA.1 variant; and $mRNA\text{-}Vax^3$+BA.2 indicates triple vaccinated individuals who subsequently had a breakthrough infection with an Omicron BA.2 variant. (B) SARS-CoV-2 variant of concern (VOC) $pVN_{50}$ GMTs normalized against the wild-type strain $pVN_{50}$ GMT (ratio VOC to wild-type). Group geometric mean ratios with 95% confidence intervals are shown in the graph and listed in the table. Serum was tested in duplicate. For titer values below the limit of detection (LOD), LOD/2 values were plotted. The non-parametric Friedman test with Dunn's multiple comparisons correction was used to compare the wild-type strain neutralizing group GMTs with titers against the indicated variants and SARS-CoV-1. Multiplicity-adjusted p values are shown.

Figure 43:
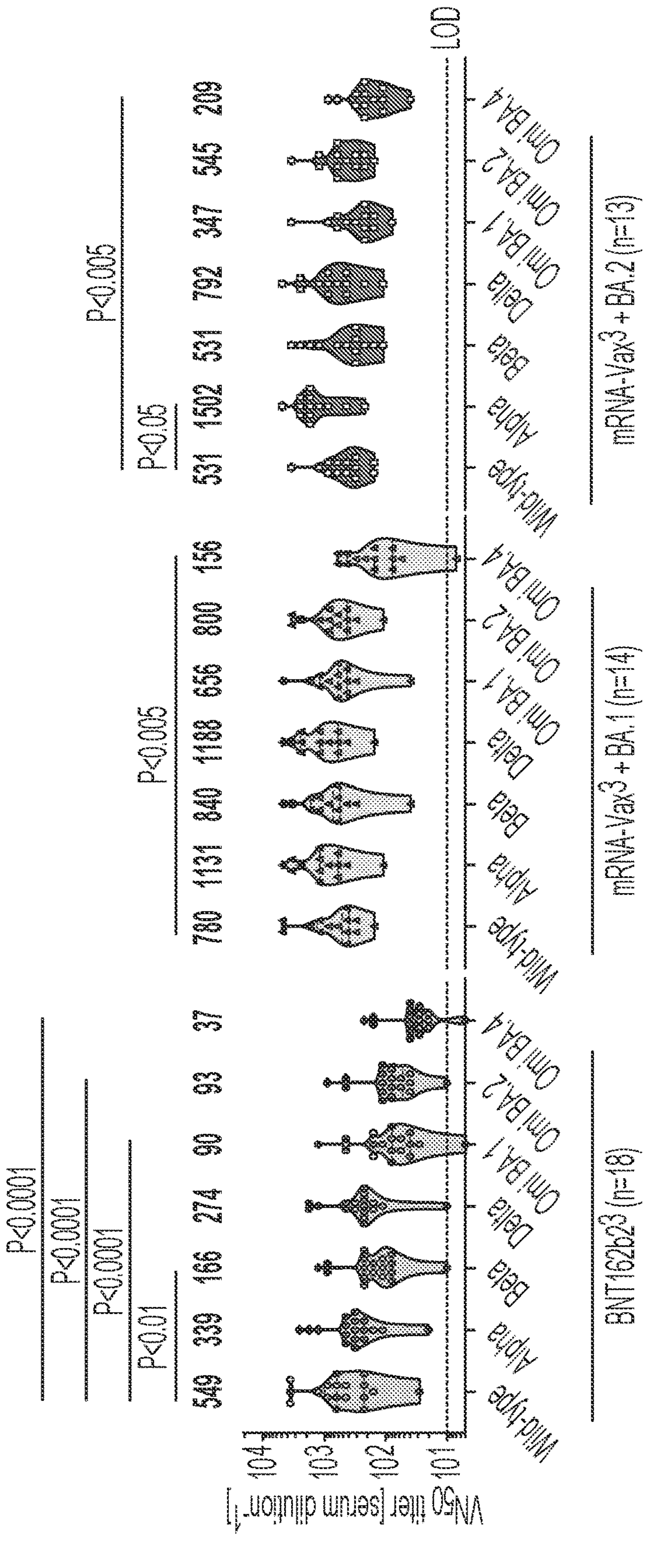
Figure 43:
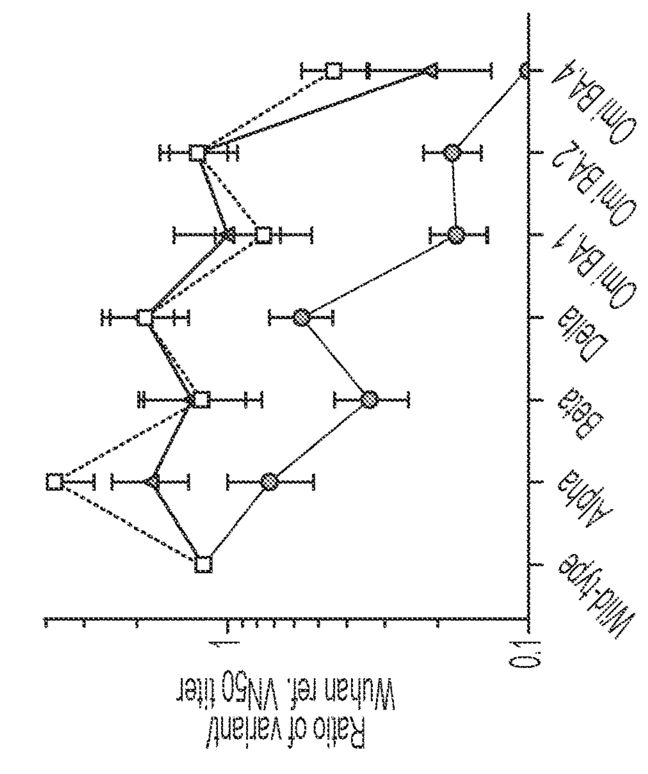

FIG. 43. Omicron BA.2 breakthrough infection of previously vaccinated individuals induces broad neutralization of authentic live SARS-CoV-2 variants including Omicron BA.4/5. Cohorts and serum sampling as described in FIG. 41. (A) 50% virus neutralization ($VN_{50}$) geometric mean titers (GMTs) against the indicated SARS-CoV-2 variants of concern (VOCs). Values listed above violin plots represent group GMTs. (B) SARS-CoV-2 VOC $VN_{50}$ GMTs normalized against the wild-type strain $VN_{50}$ GMT (ratio VOC to wild-type). Group geometric mean ratios with 95% confidence intervals are shown in the graph and listed in the table. Serum was tested in duplicate. For titer values below the limit of detection (LOD), LOD/2 values were plotted. The non-parametric Friedman test with Dunn's multiple comparisons correction was used to compare the wild-type strain neutralizing group GMTs with titers against the indicated variants and SARS-CoV-1. Multiplicity-adjusted p values are shown.

Figure 44:
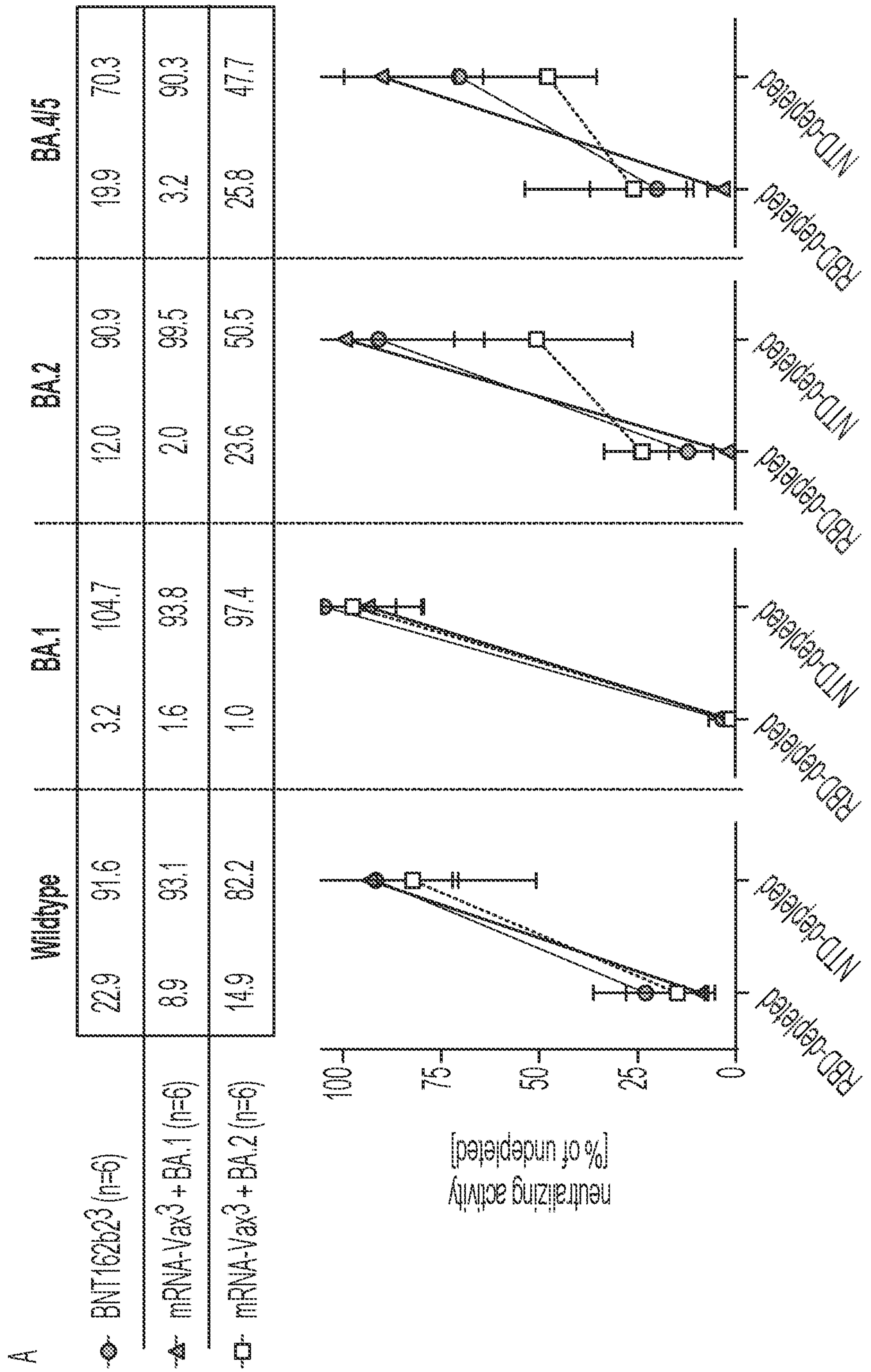
Figure 44:
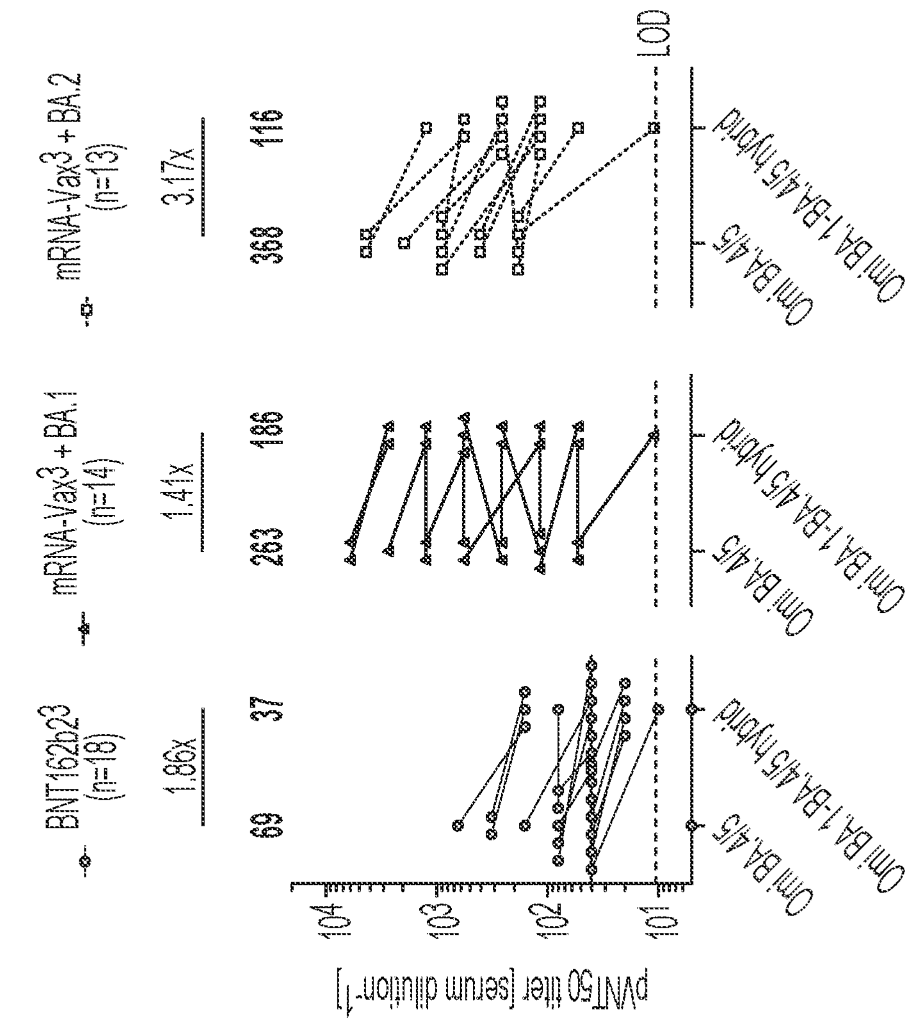

FIG. 44. Neutralization of Omicron BA.2 and BA.4/5 by sera of triple mRNA vaccinated BA.2 convalescent individuals is mediated to a large extent by NTD-targeting antibodies. Cohorts and serum sampling as described in FIG. 41. (A) Serum samples (n=6 per cohort) were depleted of RBD- or NTD-binding antibodies. Relative neutralizing activity of RBD- and NTD-depleted sera ($pVN_{50}$ titers of undepleted control sera were set to 100%) against the wild-type strain, BA.1, BA.2, and BA.4/5 was calculated and group geometric mean with 95% confidence intervals are shown. (B) 50% pseudovirus neutralization ($pVN_{50}$) geometric mean titers (GMTs) against Omicron BA.4/5 and Omicron BA.1-BA.4/5 hybrid pseudoviruses. Numbers above plots indicate group geometric mean titers (GMTs) and fold-change in GMTs between BA.4/5 and the hybrid pseudovirus. For titer values below the limit of detection (LOD), LOD/2 values are plotted.

Figure 45:
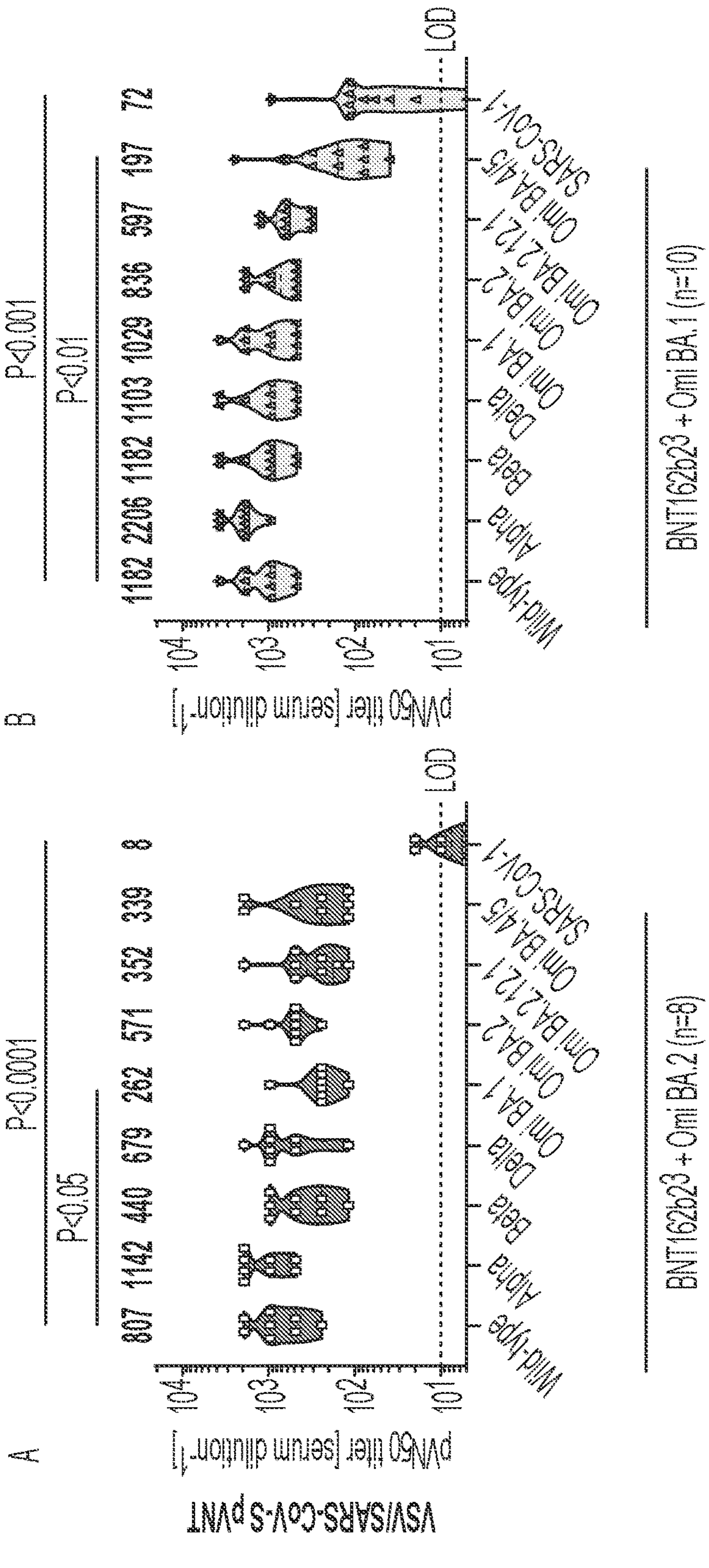
Figure 45:
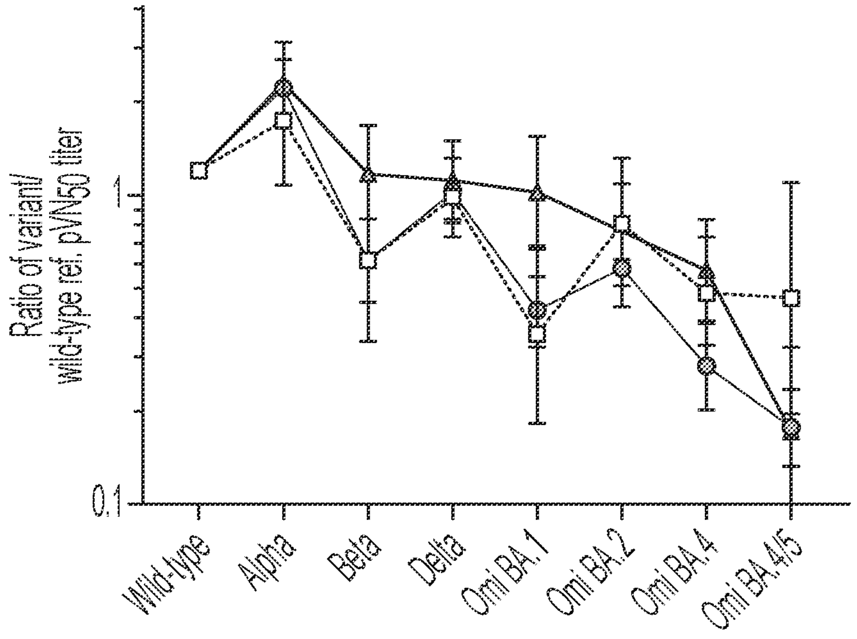
Figure 45:
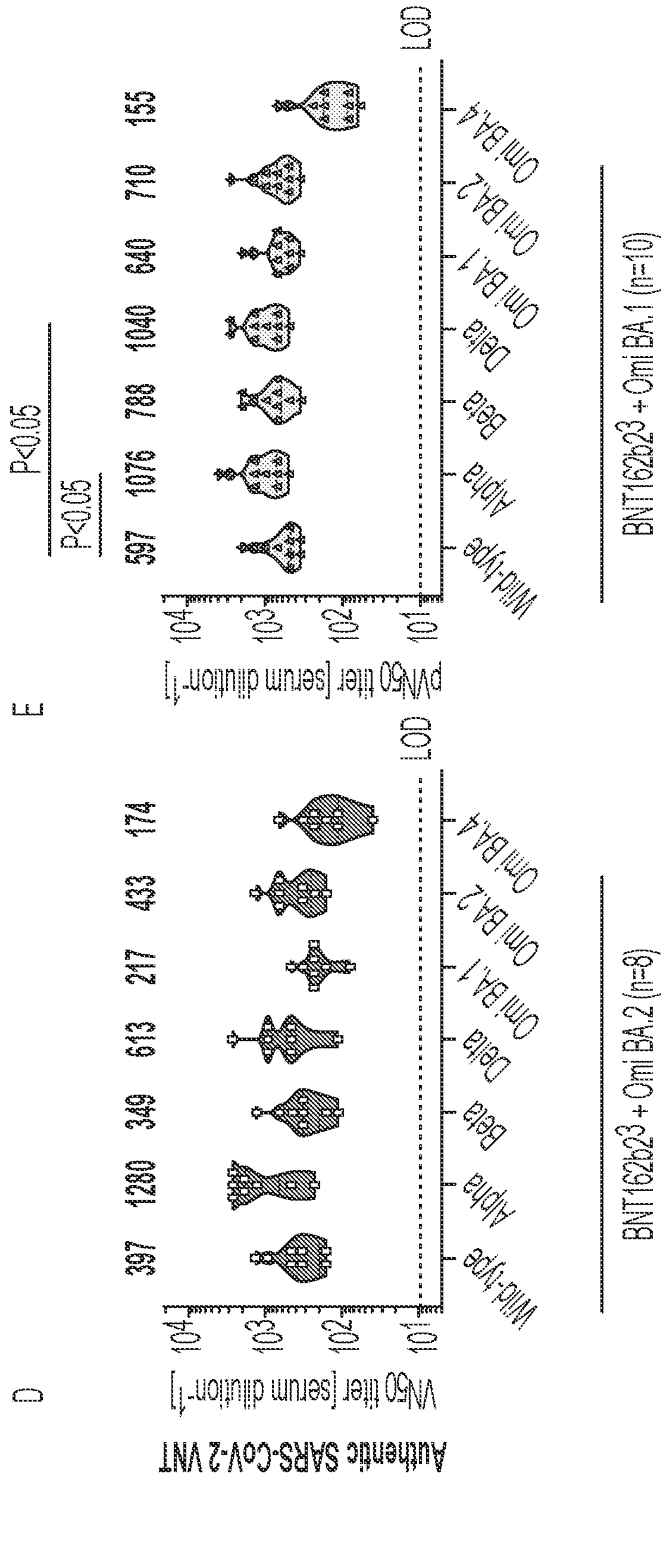
Figure 45:
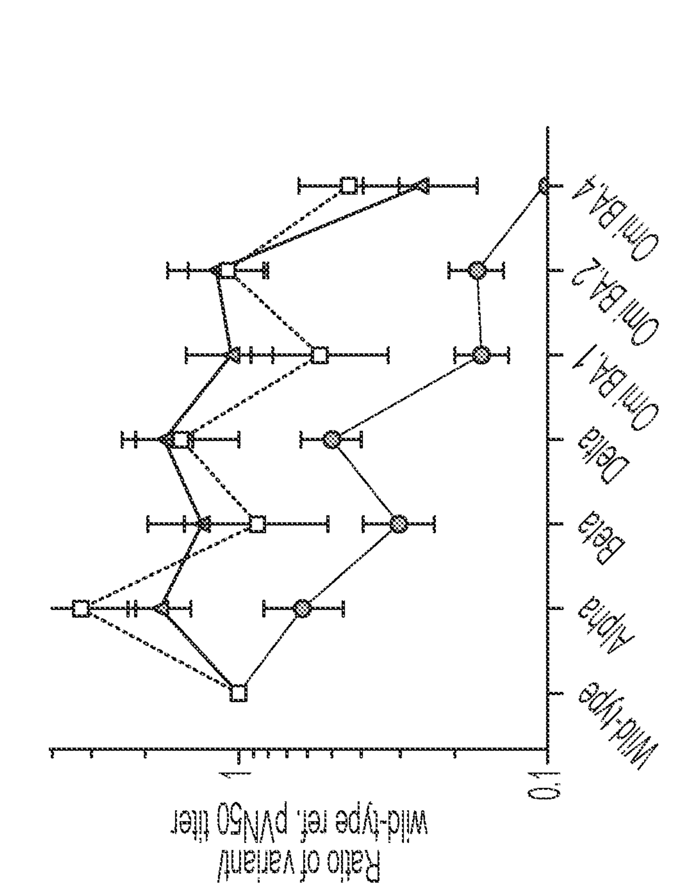

FIG. 45. Omicron BA.2 breakthrough infection of BNT162b2 triple-vaccinated individuals induces broad neutralization of VOCs including Omicron BA.4/BA.5. Cohorts and serum sampling as described in FIG. 41. (A)-(B) 50% pseudovirus neutralization ($pVN_{50}$) geometric mean titers (GMTs) against the indicated SARS-CoV-2 variants of concern (VOCs) or SARS-CoV-1 pseudoviruses. Values listed above violin plots represent group GMTs. (C) The ratio of SARS-CoV-2 VOC $pVN_{50}$ GMTs normalized against the wild-type strain $pVN_{50}$ GMT. Geometric mean ratios for the Omicron BA.2 breakthrough infected cohort were compared to $BNT162b2^3$ and $BNT162b2^3$+BA.1. Group geometric mean ratios with 95% confidence intervals are shown. (D)-(E) 50% virus neutralization ($VN_{50}$) GMTs for $BNT162b2^3$+BA.2 and $BNT162b2^3$+BA.1. Values listed above violin plots represent group GMTs. (F) The ratio of SARS-CoV-2 VOC GMTs normalized against the wild-type strain $VN_{50}$ GMT. Serum was tested in duplicate. For titer values below the limit of detection (LOD), LOD/2 values are plotted. The non-parametric Friedman test with Dunn's multiple comparisons correction was used to compare the group GMT against the wild-type strain with group GMTs against the indicated variants and SARS-CoV-1. Multiplicity-adjusted p values are shown.

Figure 46:
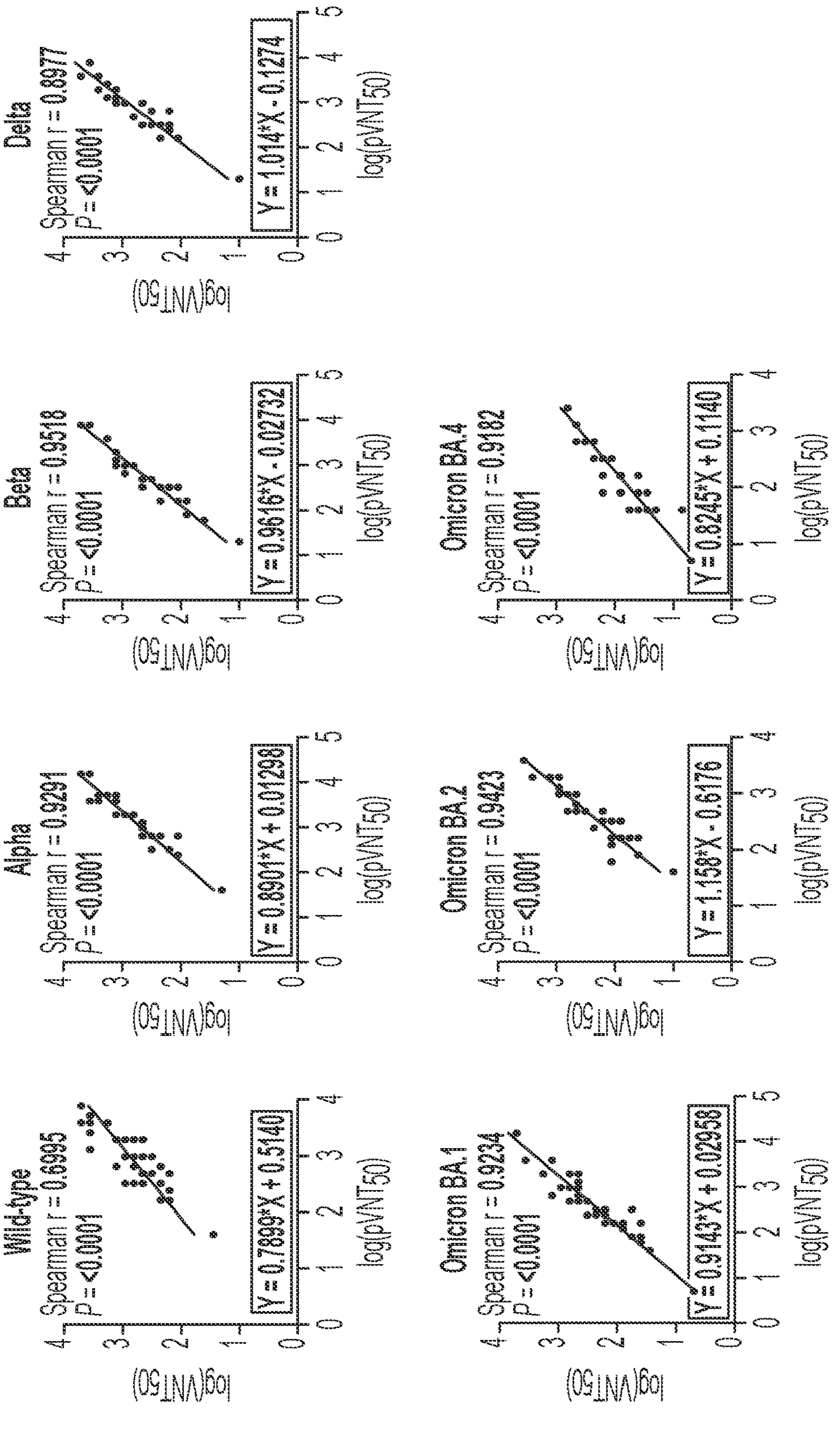

FIG. 46. 50% pseudovirus neutralization ($pVN_{50}$) correlates with 50% live SARS-CoV-2 neutralization ($VN_{50}$) titer data. Nonparametric Spearman correlation of VSV-SARS-CoV-2 $pVN_{50}$ with live SARS-CoV-2 $VN_{50}$ titers for n=45 serum samples drawn from SARS-CoV-2-naïve BNT162b2 triple-vaccinated individuals ($BNT162b2^3$; n=18) after the third dose, from triple mRNA vaccinated individuals with subsequent Omicron BA.1 breakthrough infection (mRNA-$Vax^3$+BA.1; n=14) post-infection, and from triple mRNA vaccinated individuals with subsequent Omicron BA.2 breakthrough infection (mRNA-$Vax^3$+BA.2; n=13) post-infection. Correlations are plotted per SARS-CoV-2 variant. Correlation coefficient r, two-tailed P values and the linear equation are given.

Figure 47:
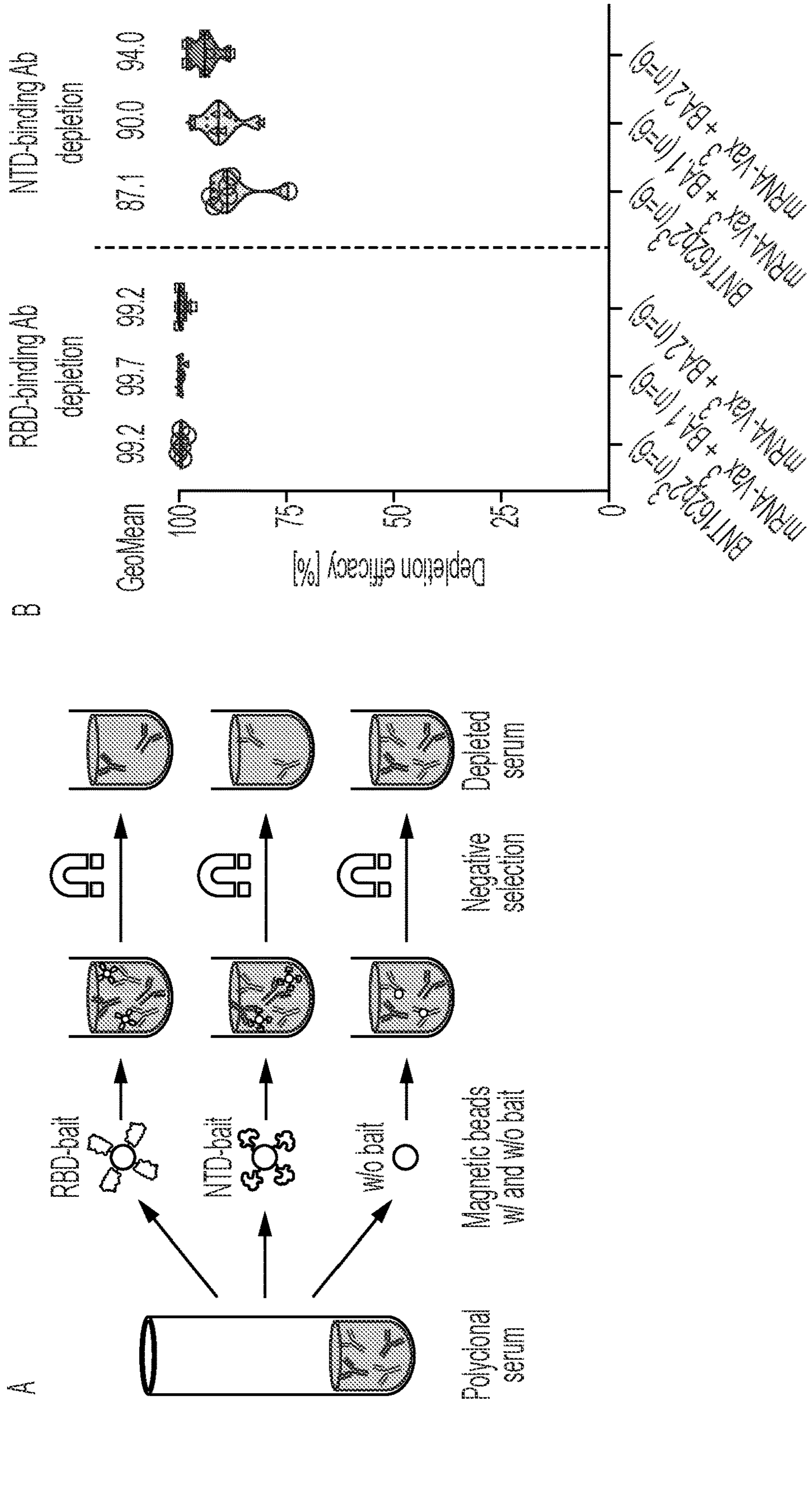

FIG. 47. RBD-binding and NTD-binding antibodies can be depleted from human serum. Serum was drawn from SARS-CoV-2-naïve BNT162b2 triple-vaccinated individuals ($BNT162b2^3$; n=6), and from triple RNA vaccinated individuals with Omicron BA.1 (mRNA-$Vax^3$+BA.1; n=6) or Omicron BA.2 breakthrough infection (mRNA-$Vax^3$+BA.2; n=6). Magnetic bead technology was used for depleting serum of RBD- or NTD-binding antibodies, or for mock depleting. (A) Schematic of antibody depletion from serum. (B) The relative concentration of RBD-binding and NTD-binding antibodies was determined by a multiplexed electrochemiluminescence immunoassay. The relative decrease in antibody concentrations in depleted compared to mock-depleted sera are shown. Numbers above graph depict geometric mean reduction within groups.

Figure 48:
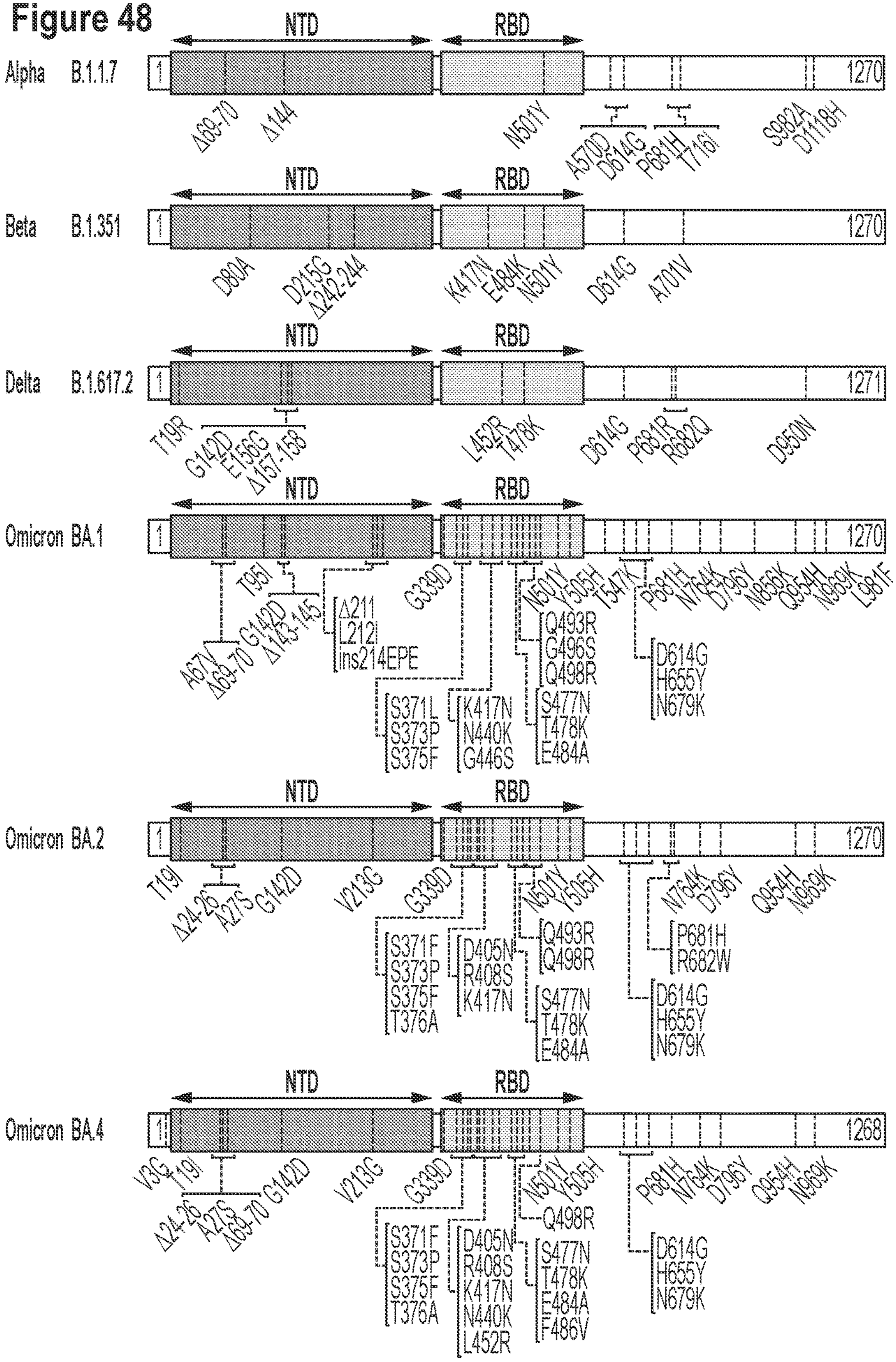

FIG. 48. Characterization of SARS-CoV-2 S glycoproteins used in the assays based on live authentic SARS-CoV-2. The sequence of the Wuhan-Hu-1 isolate SARS-CoV-2 S glycoprotein (GenBank: QHD43416.1) was used as reference. Amino acid positions, amino acid descriptions (one letter code) and kind of alterations (substitutions, deletions, insertions) are indicated. NTD, N-terminal domain; RBD, Receptor-binding domain, A, deletion; ins, insertion; *, Cytoplasmic domain truncated for the C-terminal 19 amino acids.

Figure 49:
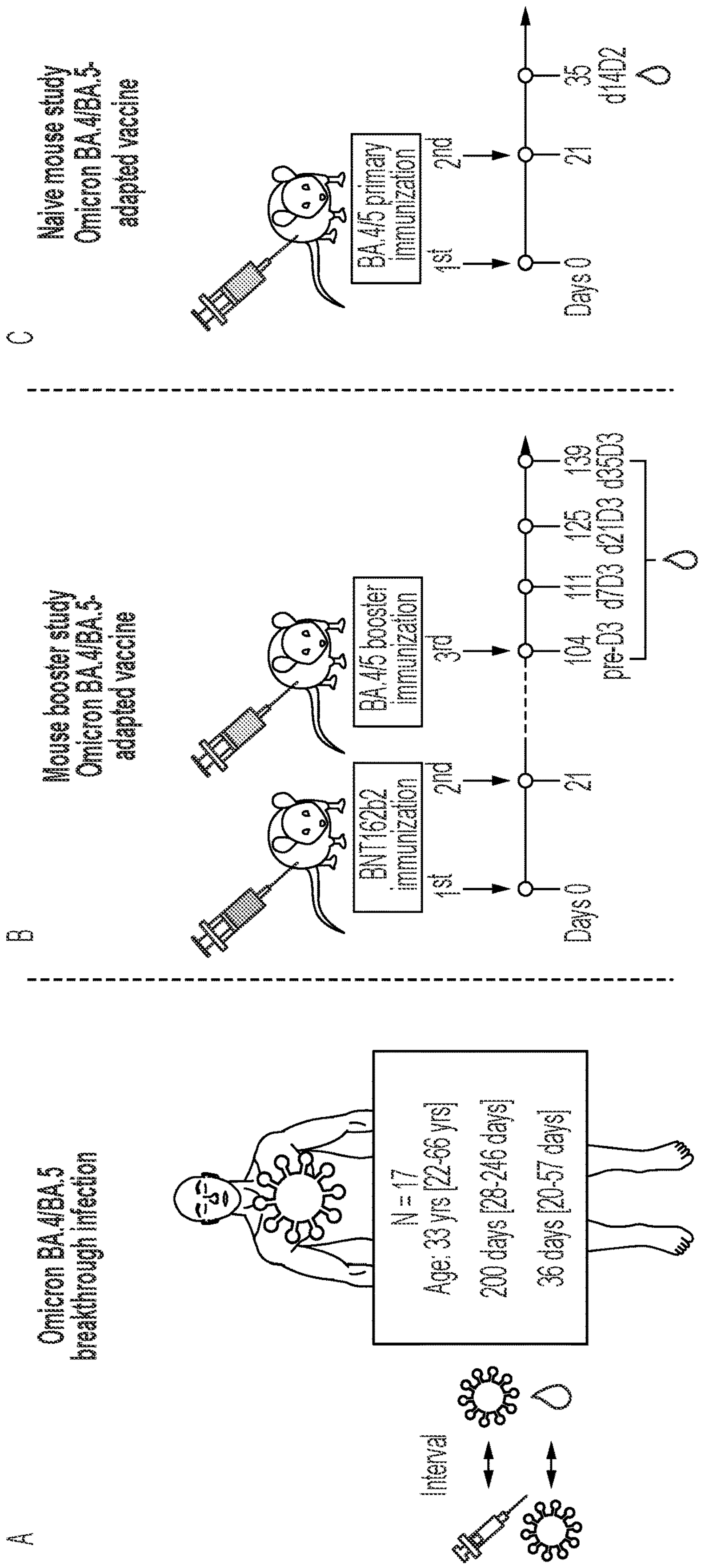

FIG. 49. BA.4/5-Breakthrough Infection and BA.4/5-Booster Study Design. (a) The effect of Omicron BA.4/BA.5 breakthrough infection on serum neutralizing activity was evaluated in individuals vaccinated with three doses of mRNA COVID-19 vaccine (BNT162b2/mRNA-1273 homologous or heterologous regimens) who subsequently experienced an infection with Omicron BA.4 or BA.5. The intervals between vaccination, breakthrough infection and sampling are indicated as median/range. (b) Effects of Omicron BA.4/BA.5-adapted booster vaccines on serum neutralizing activity was investigated in mice vaccinated twice (with the two vaccines administered 21-days apart) with BNT162b2, followed by a booster dose of BA.4/BA.5-adapted vaccines 3.5 months later. Neutralizing activity was assessed before (pre-D3) and 7, 21, and 35 days after the booster dose (d7D3, d21D3, d35D3, respectively). (c) The effects of Omicron BA.4/BA.5-adapted vaccines on serum neutralizing activity were investigated in vaccine-naïve mice vaccinated twice (with the two vaccines administered 21-days apart) with BA.4/BA.5-adapted vaccines. Neutralizing activity was assessed 14 days after administration of the second dose (d14D2).

Figure 50:
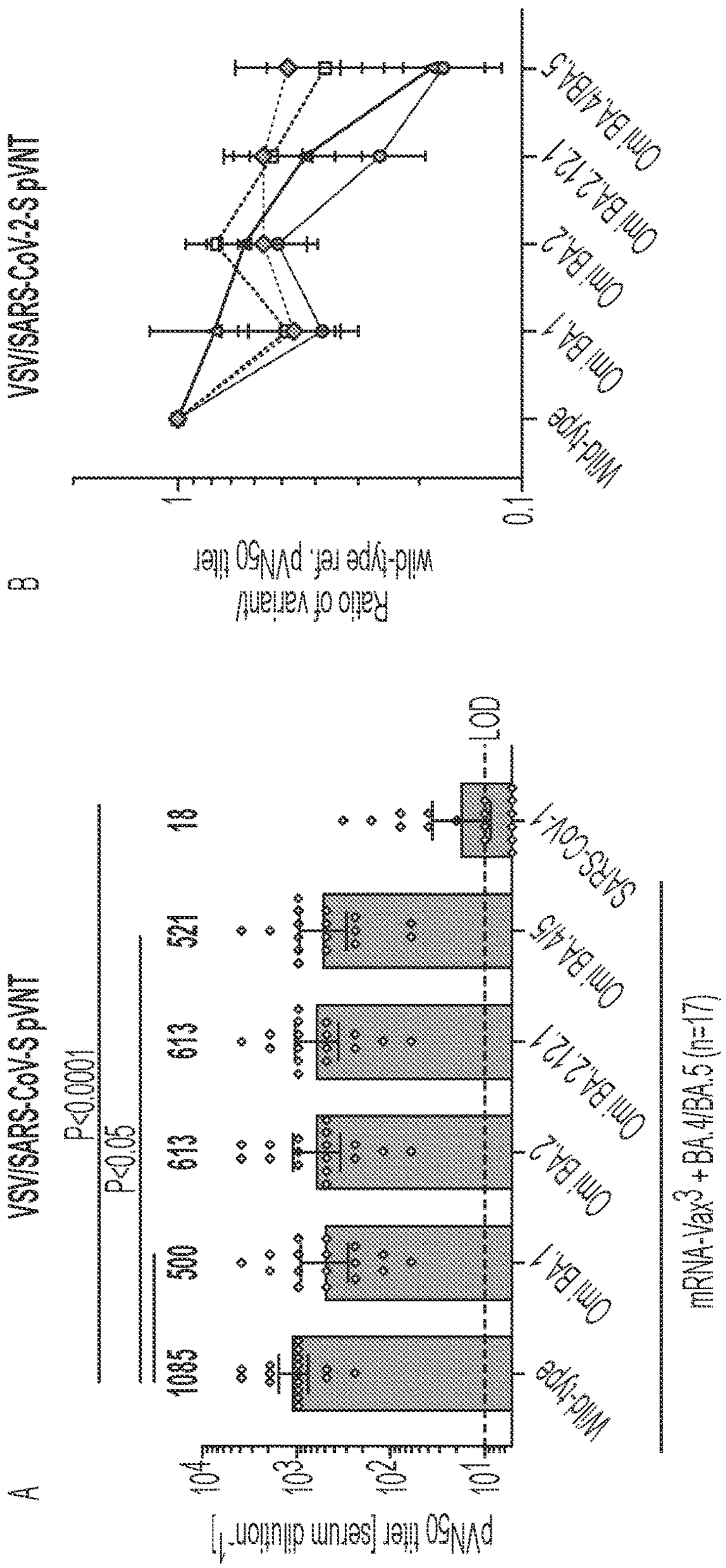
Figure 50:
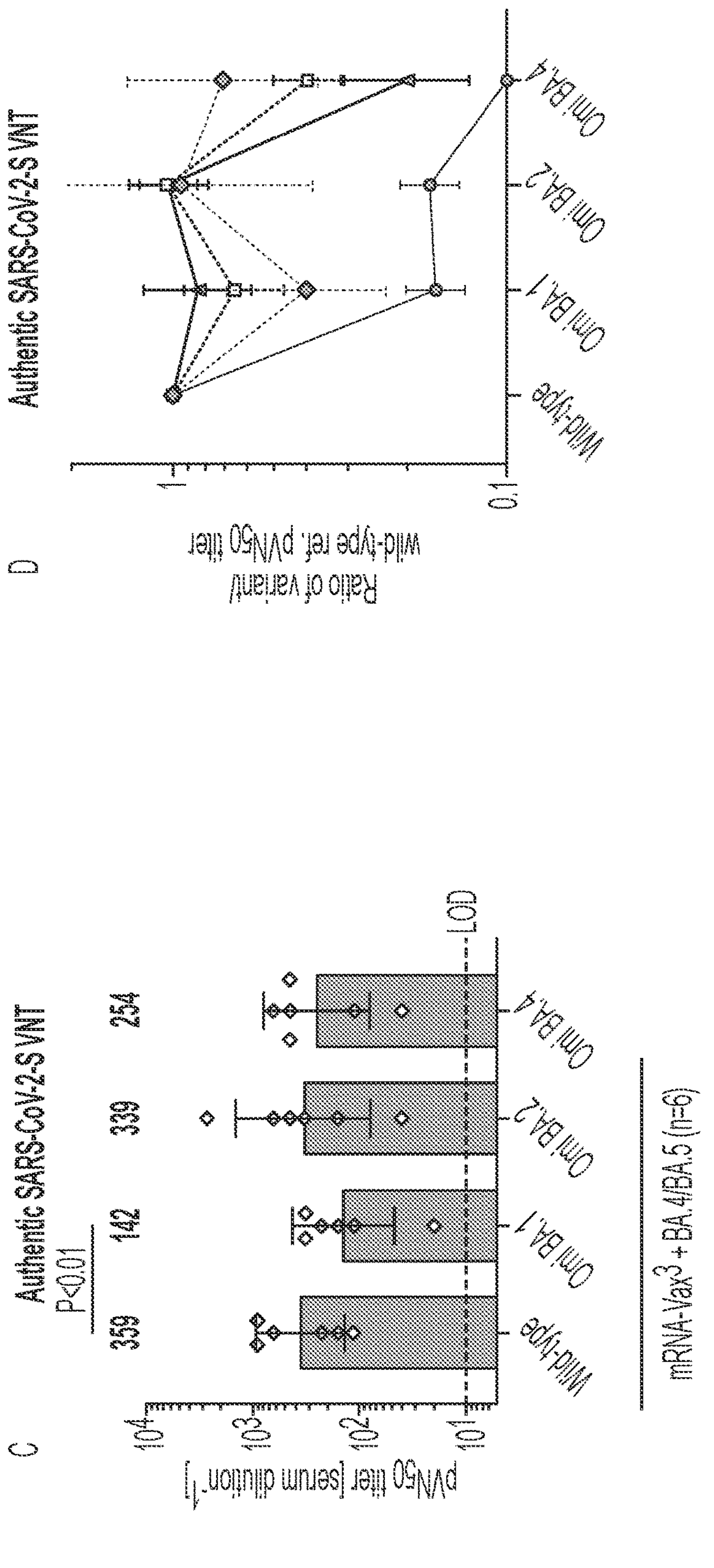

FIG. 50. Omicron BA.4/BA.5 breakthrough infection of triple mRNA vaccinated individuals mediates pan-Omicron neutralization. Cohorts and serum sampling as described in FIG. 53. (a) 50% pseudovirus neutralization ($pVN_{50}$) geometric mean titers (GMTs) in sera of mRNA-$Vax^3$+BA.4/BA.5 against the indicated SARS-CoV-2 variants of concern (VOCs) or SARS-CoV-1 pseudoviruses. Values above bars represent group GMTs. (b) SARS-CoV-2 VOC $pVN_{50}$ GMTs normalized against the wild-type strain $pVN_{50}$ GMT (ratio VOC to wild-type) of mRNA-$Vax^3$+BA.4/BA.5 and the reference cohorts as outlined in FIG. 53. Group geometric mean ratios with 95% confidence intervals are shown. (c) 50% virus neutralization ($VN_{50}$) GMTs in sera of mRNA-$Vax^3$+BA.4/BA.5 against the indicated SARS-CoV-2 VOCs. (d) SARS-CoV-2 VOC $VN_{50}$ GMTs normalized against the wild-type strain $VN_{50}$ GMT (ratio VOC to wild-type). Serum was tested in duplicate. For titer values below the limit of detection (LOD), LOD/2 values were plotted. The non-parametric Friedman test with Dunn's multiple comparisons correction was used to compare the wild-type strain neutralizing group GMTs with titers against the indicated variants and SARS-CoV-1. Multiplicity-adjusted p values are shown.

Figure 51:
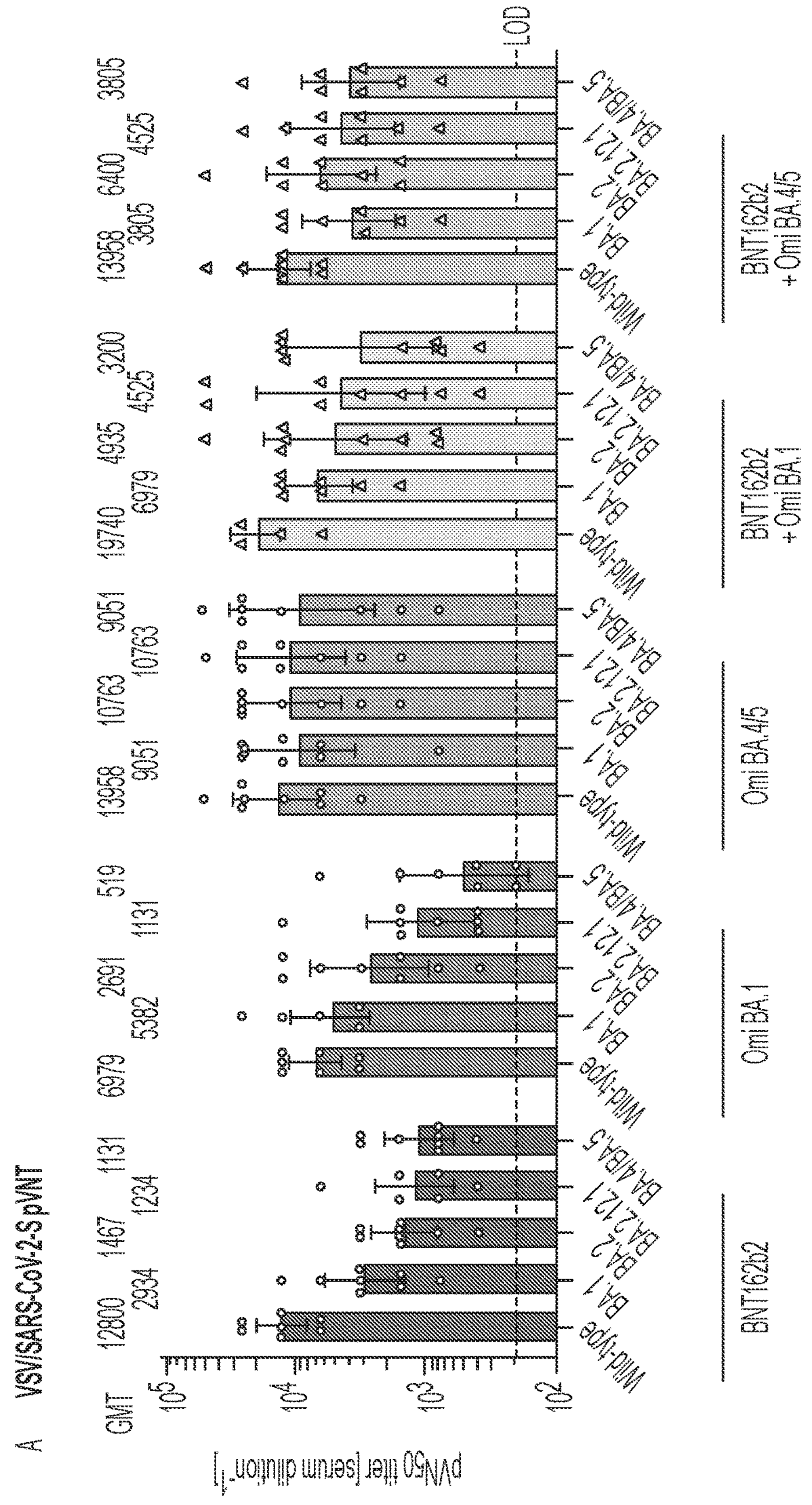
Figure 51:
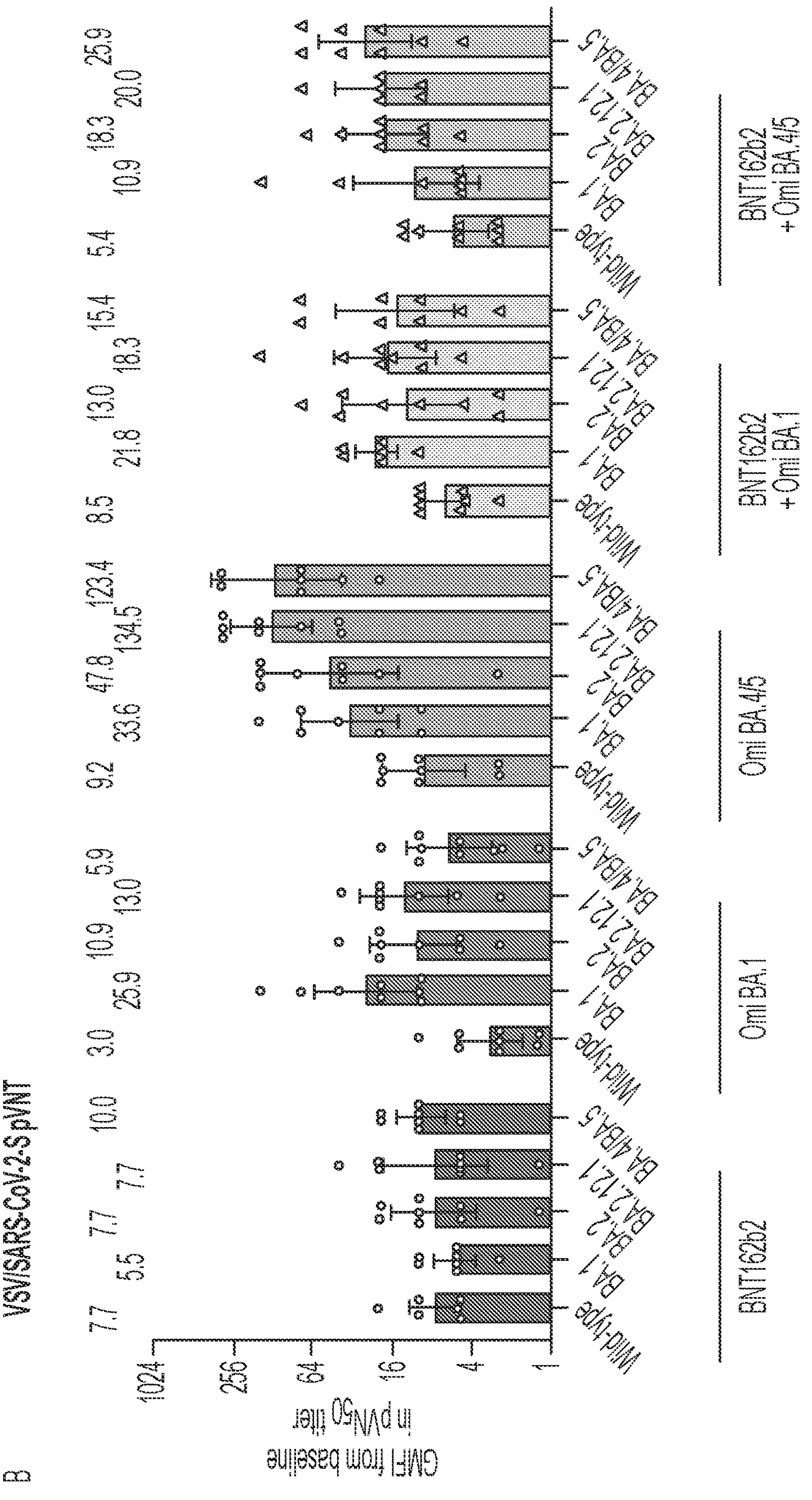
Figure 51:
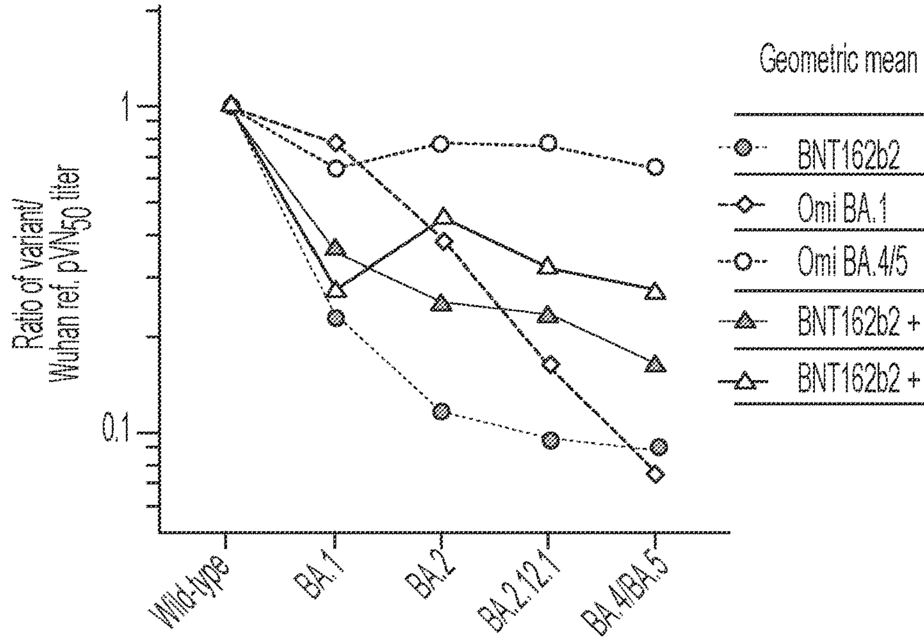
Figure 51:
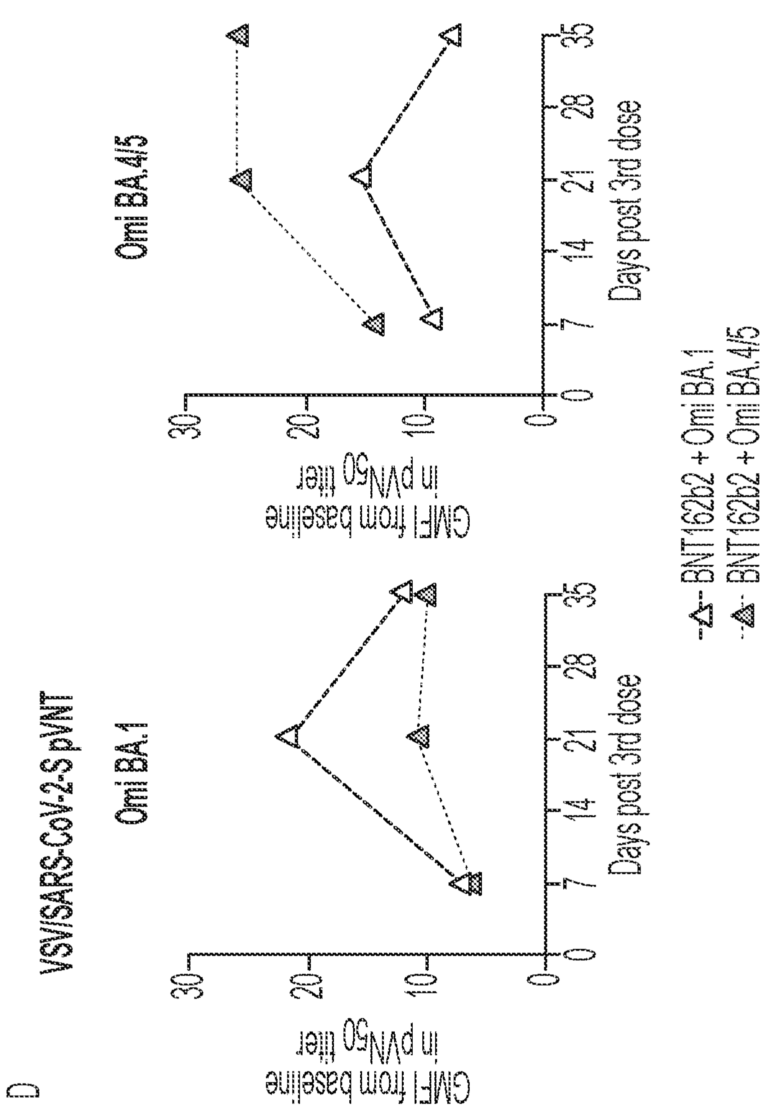
Figure 51:
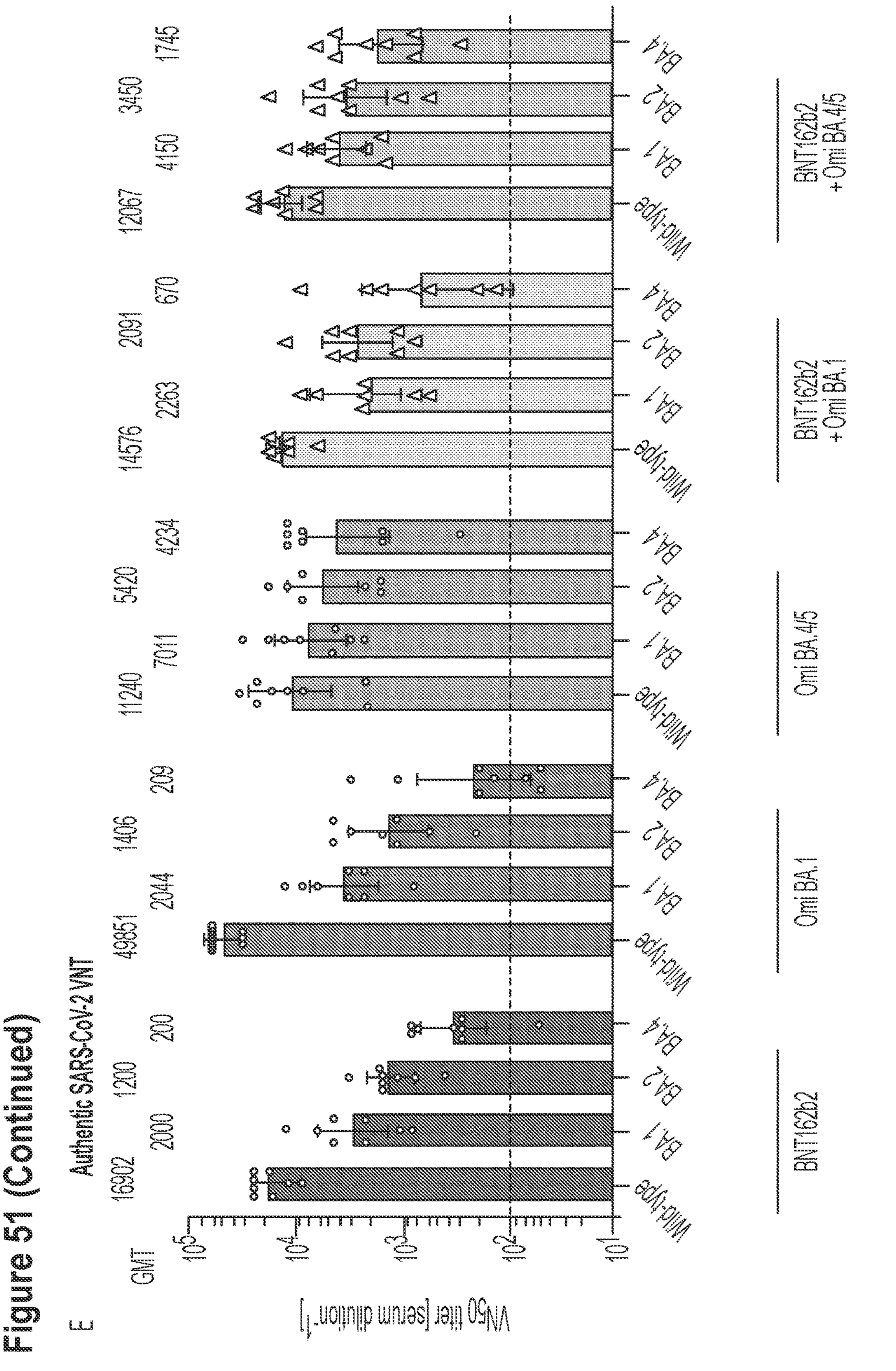
Figure 51:
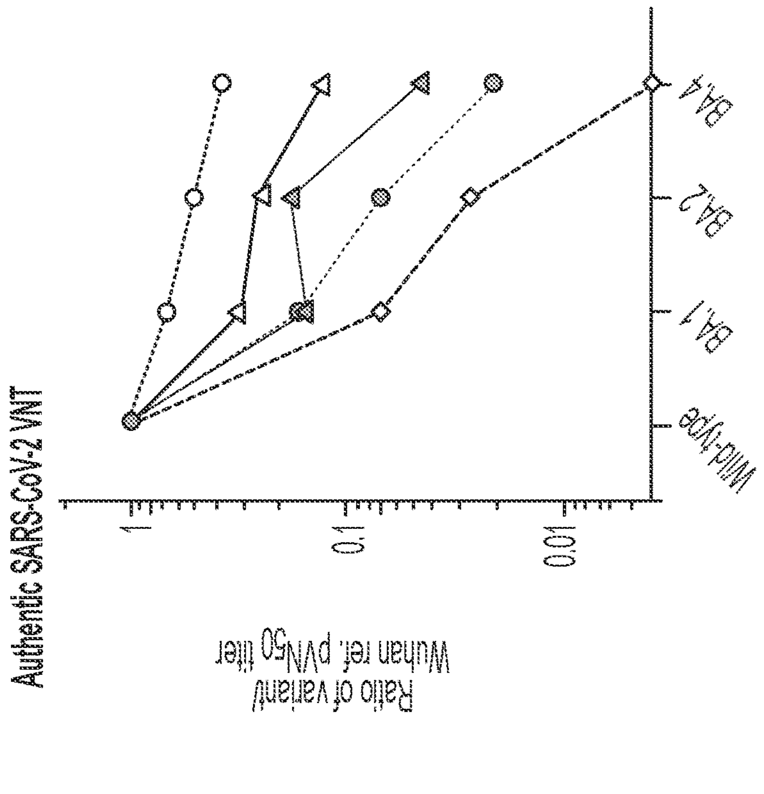

FIG. 51. Booster immunization with an Omicron BA.4/BA.5 S glycoprotein adapted RNA-vaccine mediates pan-Omicron neutralization in double-vaccinated mice. BALB/c mice (n=8) were injected intramuscularly with two doses of 1 pg BNT162b2 21 days apart, and a third dose of either BNT162b2 (1 pg) or the indicated monovalent (1 pg) or bivalent (0.5 pg each) Omicron BA.1 or BA.4/5-adapted vaccines 104 days after the first vaccination. (a) 50% pseudovirus neutralization ($pVN_{50}$) geometric mean titers (GMTs) against the indicated SARS-CoV-2 variants of concern (VOCs) in sera collected 21 days after the third vaccination (d21D3). Values above bars represent group GMTs. (b) Geometric mean fold-increase (GMFI) of $pVN_{50}$ titers on d21D3 relative to baseline titers before the third vaccination. Values above bars represent group GMFIs. (c) SARS-CoV-2 VOC $pVN_{50}$ GMTs normalized against the wild-type strain $pVN_{50}$ GMT (ratio VOC to wild-type). Group geometric mean ratios are shown. (d) GMFI of $pVN_{50}$ titers against BA.1 and BA.4/5 over time relative to baseline titers before the booster vaccination with BNT162b2/BA.1 or BNT162b2/BA.4/5 bivalent vaccines. For titer values below the limit of detection (LOD), LOD/2 values were plotted. Error bars represent 95% confidence intervals (e) 50% virus neutralization ($VN_{50}$) GMTs against the indicated SARS-CoV-2 VOCs on d21D3. Values above bars represent group GMTs. Error bars represent 95% confidence interval. (f) SARS-CoV-2 VOC $VN_{50}$ GMTs normalized against the wild-type strain $VN_{50}$ GMT (ratio VOC to wild-type). Group geometric mean ratios are shown. Serum was tested in duplicate. For titer values below the limit of detection (LOD), LOD/2 values were plotted. Error bars represent 95% confidence intervals.

Figure 52:
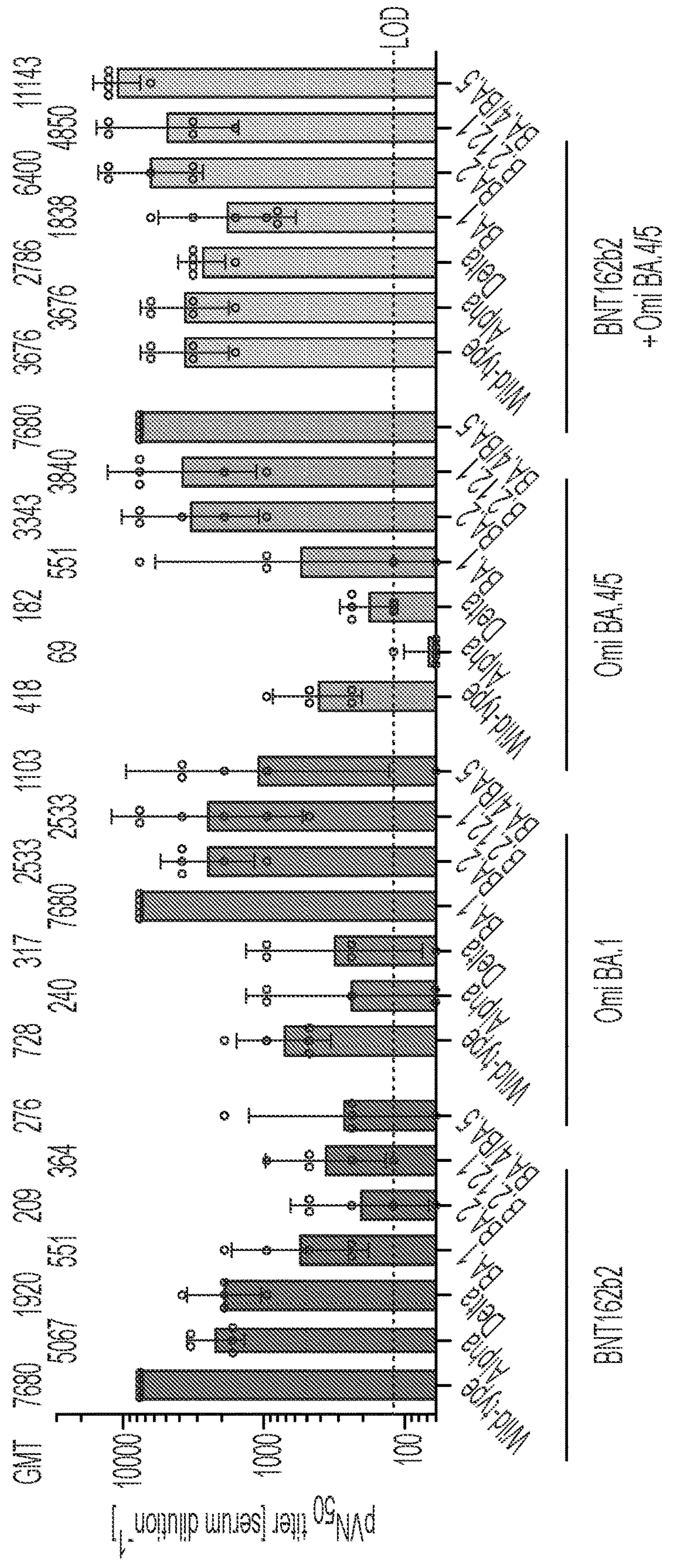

FIG. 52. Immunization with an Omicron BA.4/BA.5 S glycoprotein supplemented BNT162b2 mRNA vaccine drives pan-Omicron neutralization in previously unvaccinated mice. Vaccine-naïve BALB/c mice (n=5) were injected intramuscularly with two doses of either BNT162b2 (1 pg) or the indicated monovalent (1 pg) or bivalent (0.5 pg each) Omicron BA.1 or BA.4/5-adapted vaccines, 21 days apart. (a) 50% pseudovirus neutralization ($pVN_{50}$) geometric mean titers (GMTs) against the indicated SARS-CoV-2 variants of concern (VOCs) in sera collected 14 days after the second vaccination (d14D2). Values above bars represent group GMTs. Error bars represent 95% confidence interval. Serum was tested in duplicate. For titer values below the limit of detection (LOD), LOD/2 values were plotted. “Wild-type” refers to neutralization titers against a pseudovirus comprising a SARS-CoV-2 S protein of the original Wuhan variant.

Figure 53:
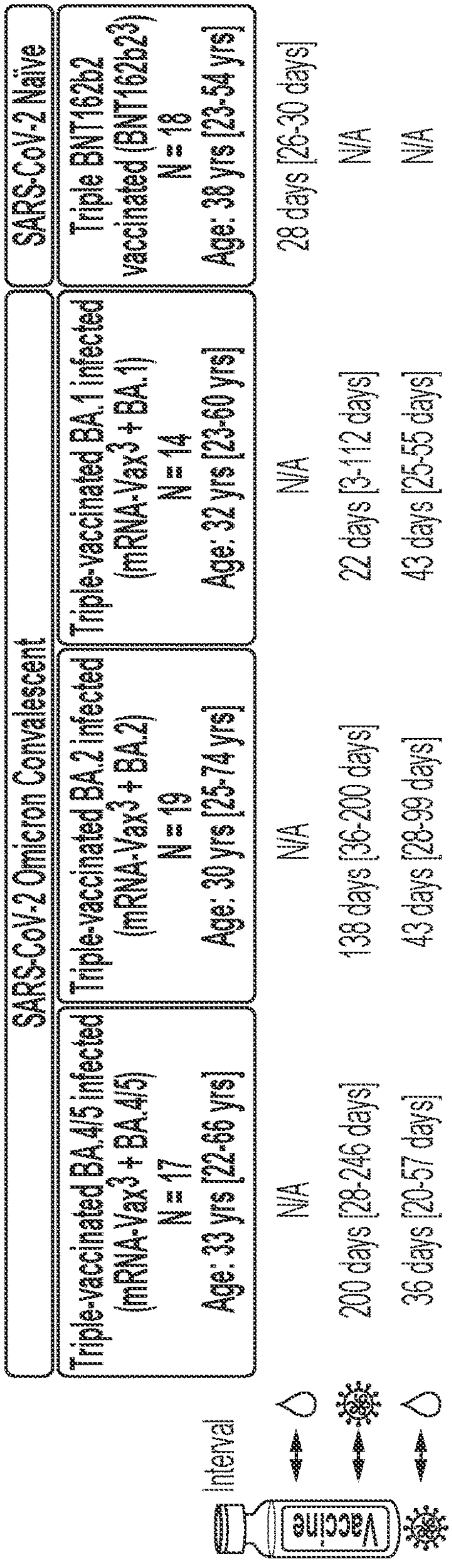

FIG. 53. Cohorts and sampling. Serum samples (droplet) were drawn from four cohorts: individuals vaccinated with three doses of mRNA COVID-19 vaccine (BNT162b2/mRNA-1273 homologous or heterologous regimens) who subsequently had a breakthrough infection with Omicron BA.4/BA.5 (mRNA-$Vax^3$+BA.4/BA.5). The breakthrough infections occurred at a time of BA.4/BA.5 dominance and/or were variant-confirmed by genome sequencing. Three cohorts were included in the study as references: triple-mRNA vaccinated individuals who experienced breakthrough infection at a time of either BA.2 dominance (March to May 2022; mRNA-$Vax^3$+BA.2), or BA.1 dominance (November 2021 to January 2022; mRNA-$Vax^3$+BA.1), or individuals triple-vaccinated with BNT162b2 that were SARS-CoV-2-naTve at the time of sampling ($BNT162b2^3$). For convalescent cohorts, relevant intervals between key events such as the most recent vaccination, SARS-CoV-2 infection, and serum isolation are indicated. All values specified as median-range. N/A, not applicable.

Figure 54:
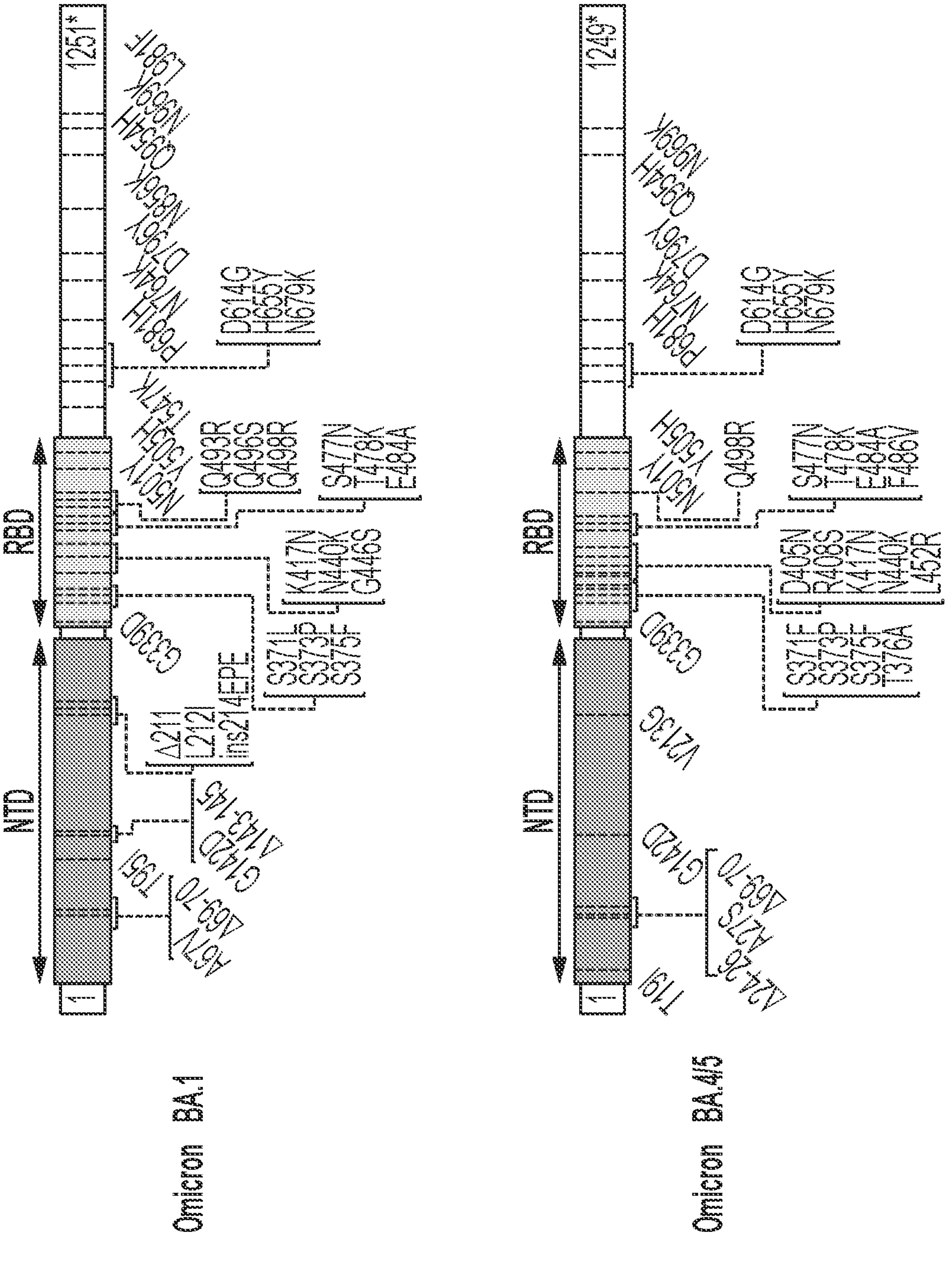

FIG. 54. Design of Omicron-adapted vaccines. Characterization of SARS-CoV-2 S glycoproteins encoded by variant-specific RNA vaccines (e.g., in some embodiments mRNA vaccines). The sequence of the Wuhan-Hu-1 isolate SARS-CoV-2 S glycoprotein (GenBank: QHD43416.1) was used as reference. Amino acid positions, amino acid descriptions (one letter code) and type of alterations (substitutions, deletions, insertions) are indicated. NTD, N-terminal domain; RBD, Receptor-binding domain, 0, deletion; ins, insertion. In some embodiments, variant specific vaccines further comprise mutations that stabilize a pre-fusion conformation (e.g., proline mutations at positions corresponding to residues 986 and 987 of SEQ ID NO: 1) and/or do not comprise a C-terminal truncation.

Figure 55:
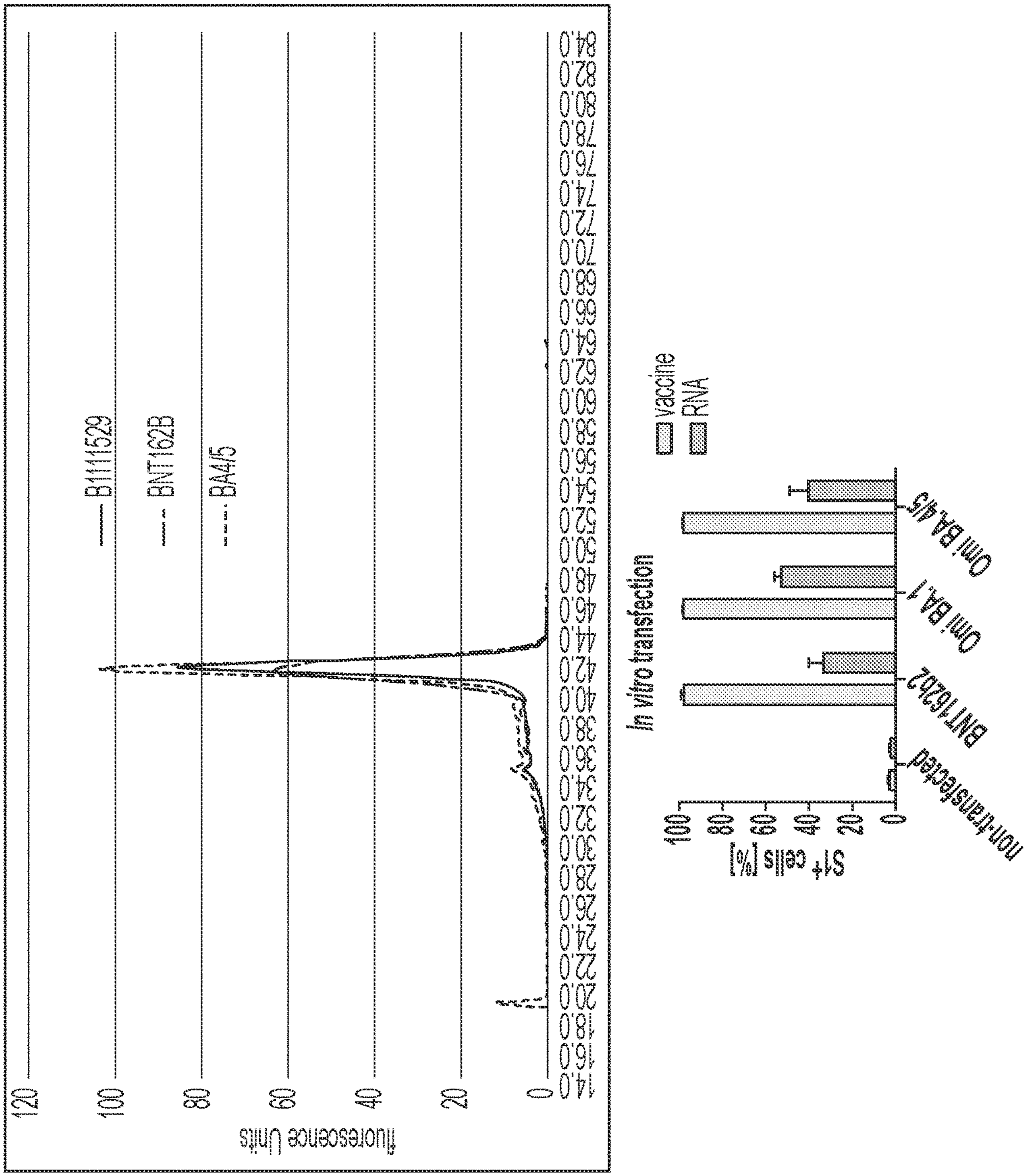

FIG. 55. Omicron-specific vaccines exhibit comparable RNA purity and integrity, and in vitro expression of antigens. (a) Liquid capillary electropherograms of in vitro transcribed samples. (b) Surface expression of BNT162b2 and Omicron-adapted vaccines in HEK293T cells measured using mFc-tagged human ACE-2 as a detection reagent with subsequent analysis in flow cytometry. HEK293T cells were transfected with BNT162b2 or Omicron-adapted vaccines formulated as lipid nanoparticles or vaccine RNAs mixed with a commercial transfection reagent, or no vaccine/RNA (non-transfected). Heights of bars indicate the means of technical replicates.

Figure 56:
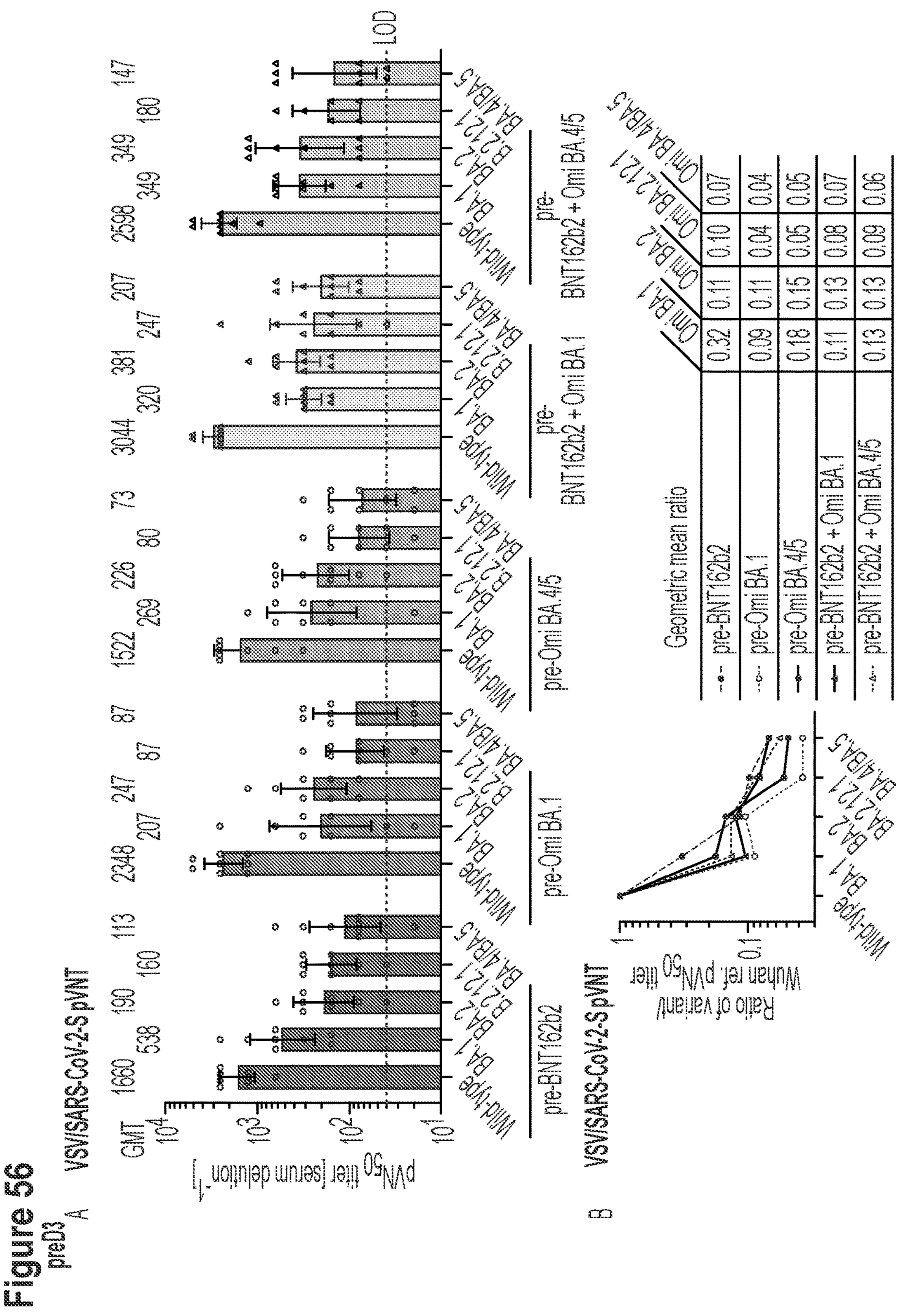

FIG. 56. Breadth and magnitude of neutralizing activity against SARS-CoV-2 variants are comparable in BNT162b2-vaccinated mice prior to booster vaccination. BALB/c mice were injected intramuscularly with two doses of 1 pg BNT162b2, administered 21 days apart. Mice were allocated to groups (n=8) prior to administration with a booster dose of the indicated vaccines. Serum was collected from mice on day 104 after the first vaccination, before booster vaccines were injected. (a) 50% pseudovirus neutralization ($pVN_{50}$) geometric mean titers (GMTs) against the indicated SARS-CoV-2 variants of concern (VOCs). Values above bars represent group GMTs. Error bars represent 95% confidence intervals. (b) SARS-CoV-2 VOC $pVN_{50}$ GMTs normalized against the wild-type strain $pVN_{50}$ GMT (ratio VOC to wild-type). Group geometric mean ratios are shown. Serum was tested in duplicate. For titer values below the limit of detection (LOD), LOD/2 values were plotted.

Figure 57:
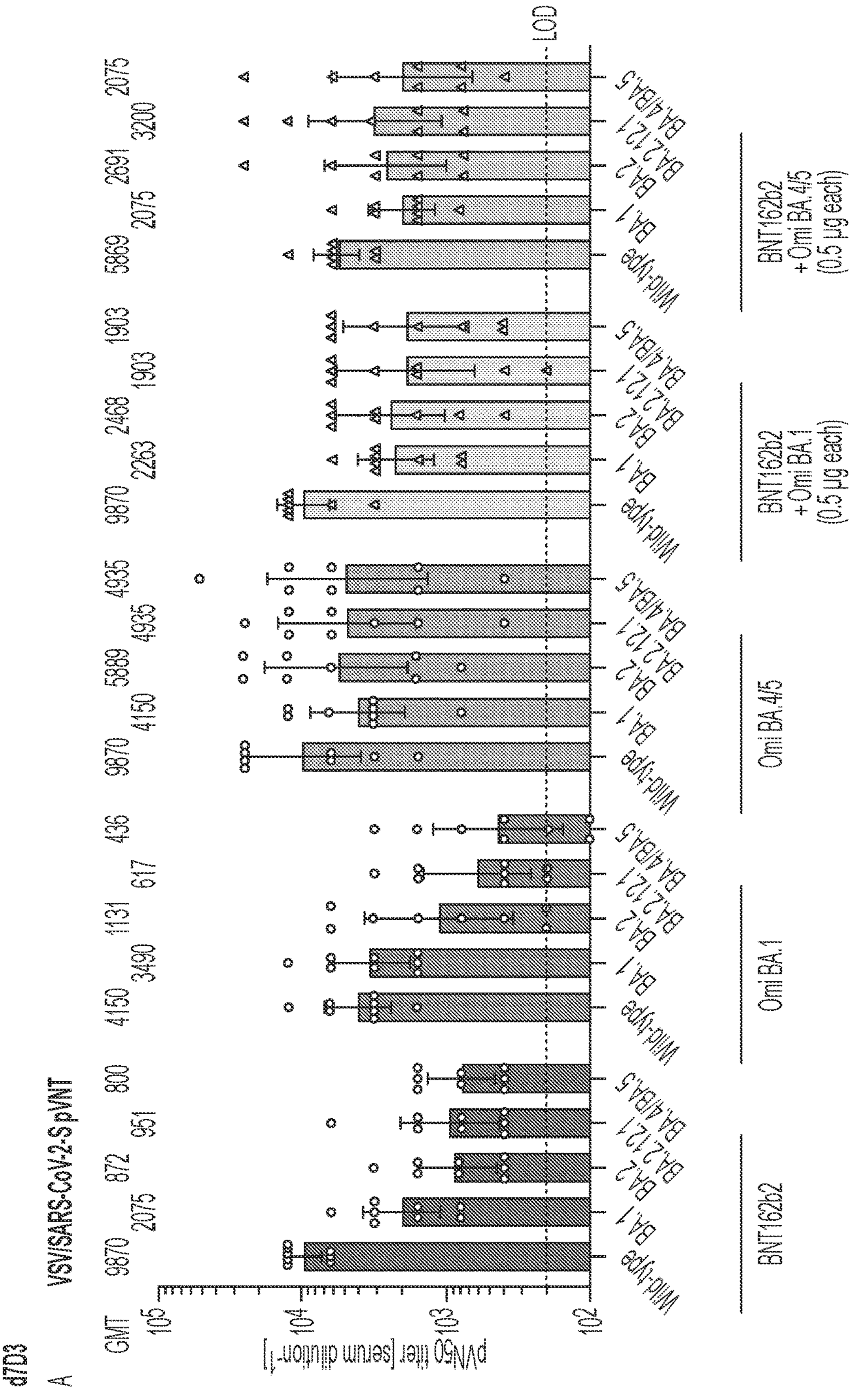
Figure 57:
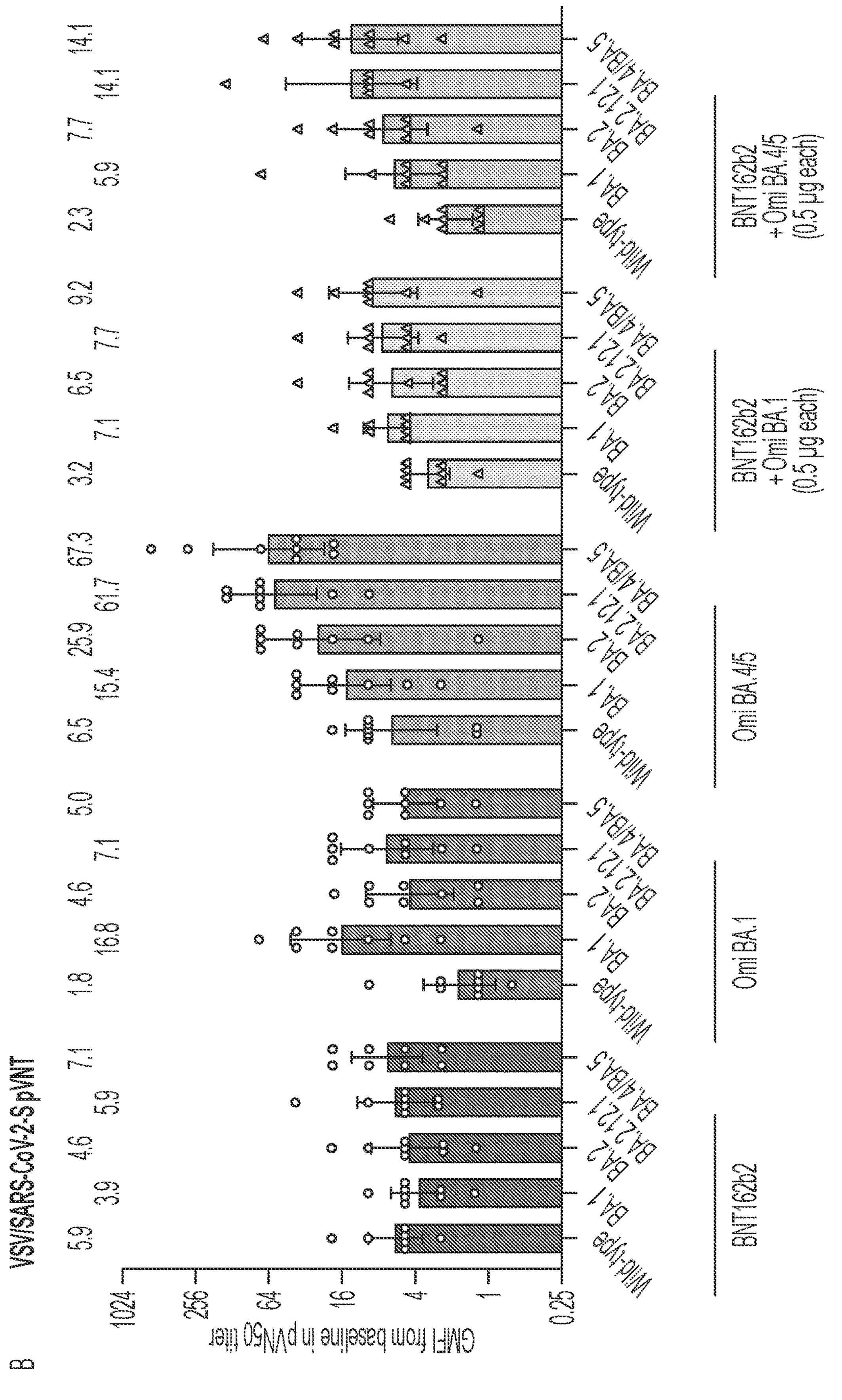
Figure 57:
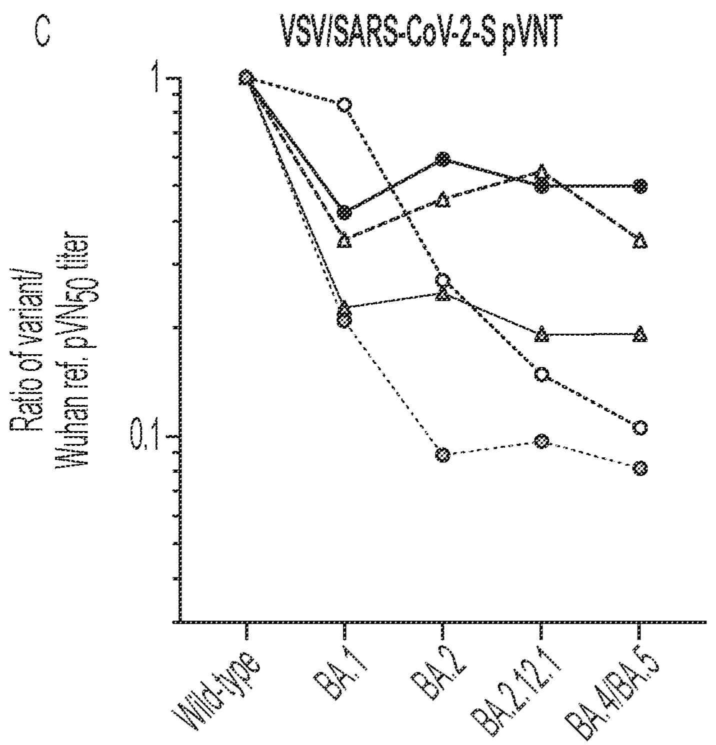

FIG. 57. Booster immunization with an Omicron BA.4/BA.5 S glycoprotein adapted mRNA vaccine mediates pan-Omicron neutralization in mice 7 days after administering the booster. BALB/c mice (n=8) were injected intramuscularly with two doses of 1 pg BNT162b2 (with a 21-day interval between the two doses), and a third dose of either BNT162b2 (1 pg) or the indicated monovalent (1 pg) or bivalent (0.5 pg each) Omicron BA.1 or BA.4/5-adapted vaccines 104 days after the first vaccination. (a) 50% pseudovirus neutralization ($pVN_{50}$) geometric mean titers (GMTs) against the indicated SARS-CoV-2 variants of concern (VOCs) in sera collected 7 days after the third vaccination (d7D3). Values above bars represent group GMTs. (b) Geometric mean fold-increase (GMFI) of $pVN_{50}$ titers on d7D3 relative to baseline titers before the third vaccination. Values above bars represent group GMFIs. (c) SARS-CoV-2 VOC $pVN_{50}$ GMTs normalized against the wild-type strain $pVN_{50}$ GMT (ratio VOC to wild-type). Group geometric mean ratios are shown. Serum was tested in duplicate. For titer values below the limit of detection (LOD), LOD/2 values were plotted. Error bars represent 95% confidence intervals.

Figure 58:
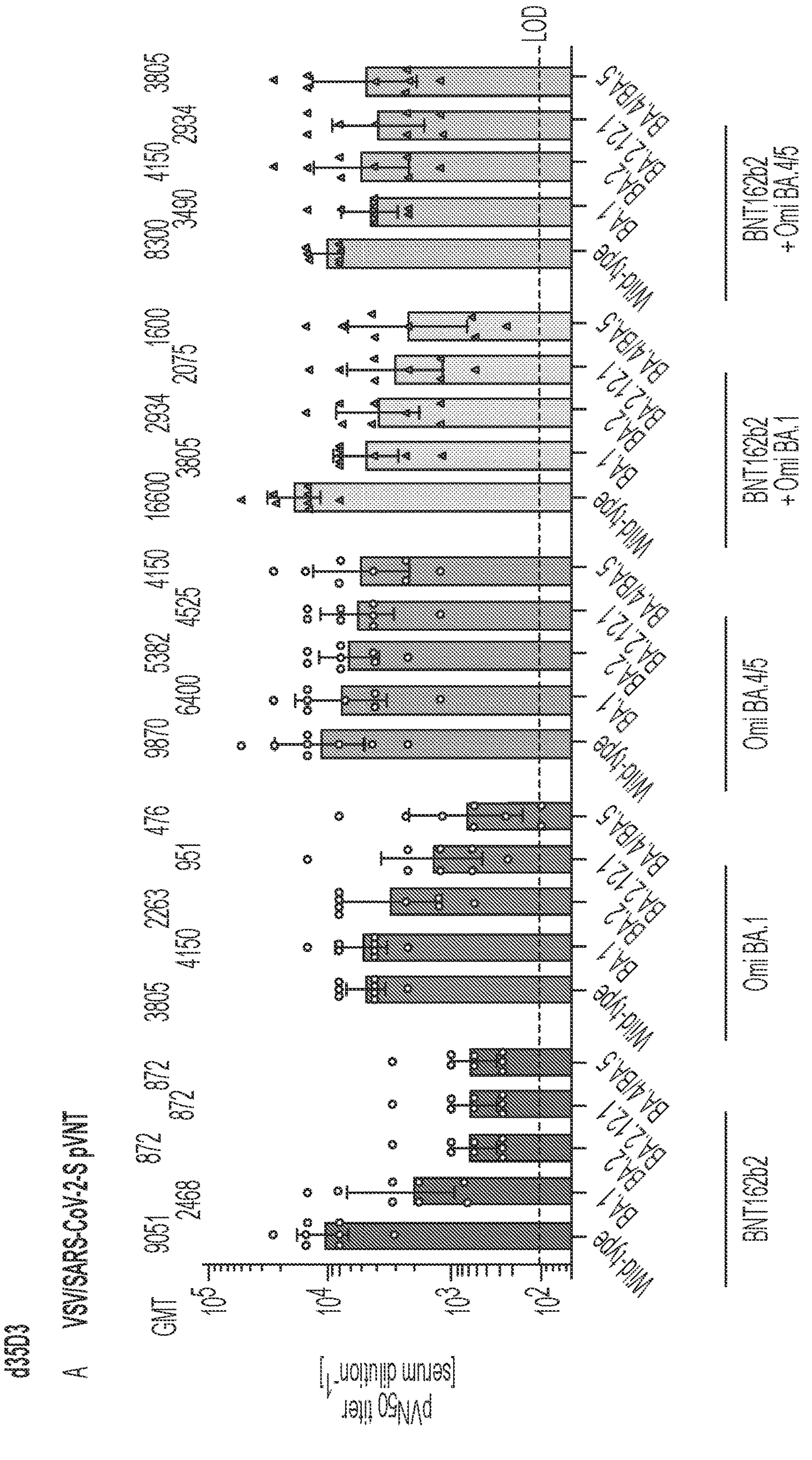
Figure 58:
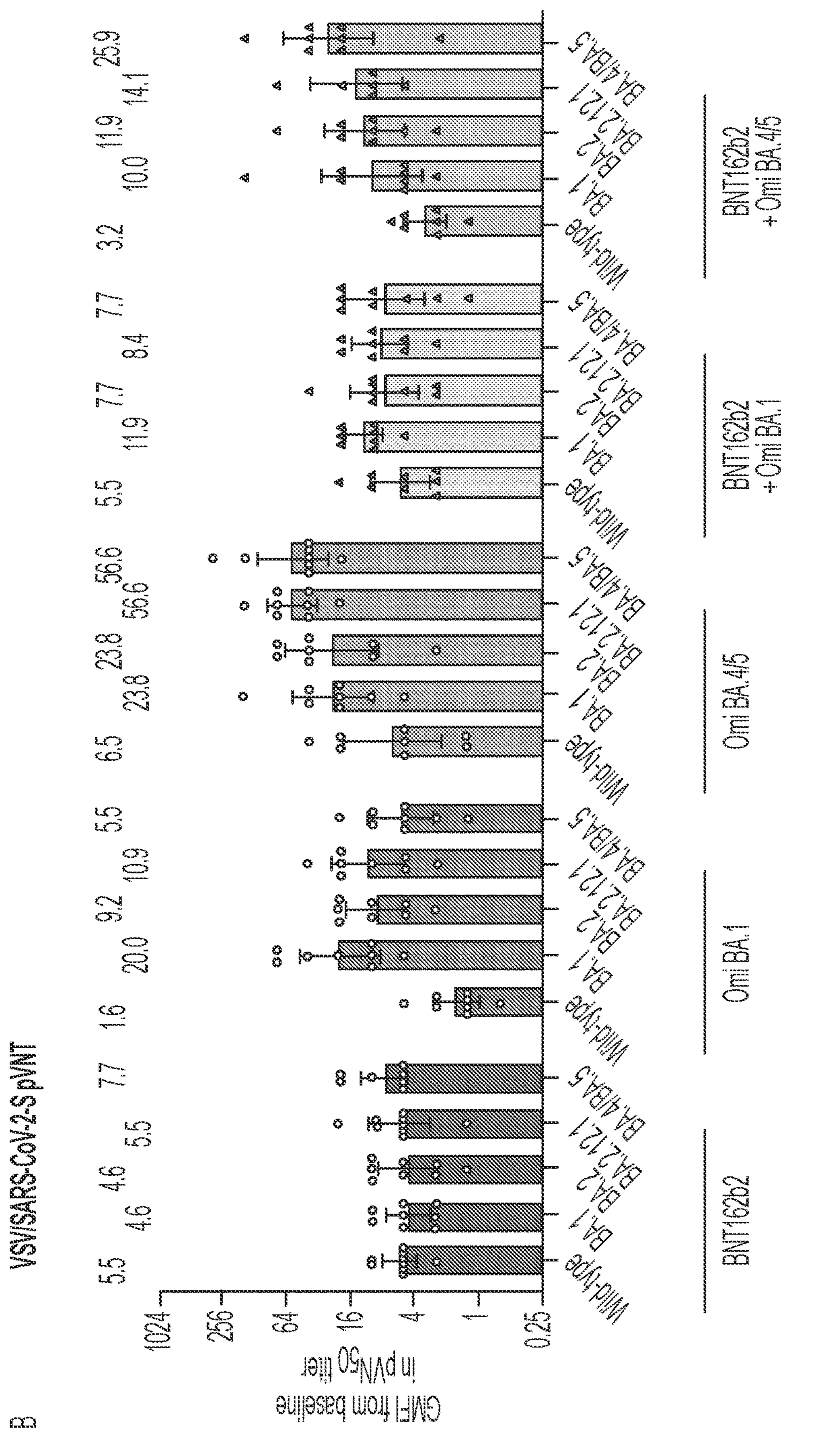
Figure 58:
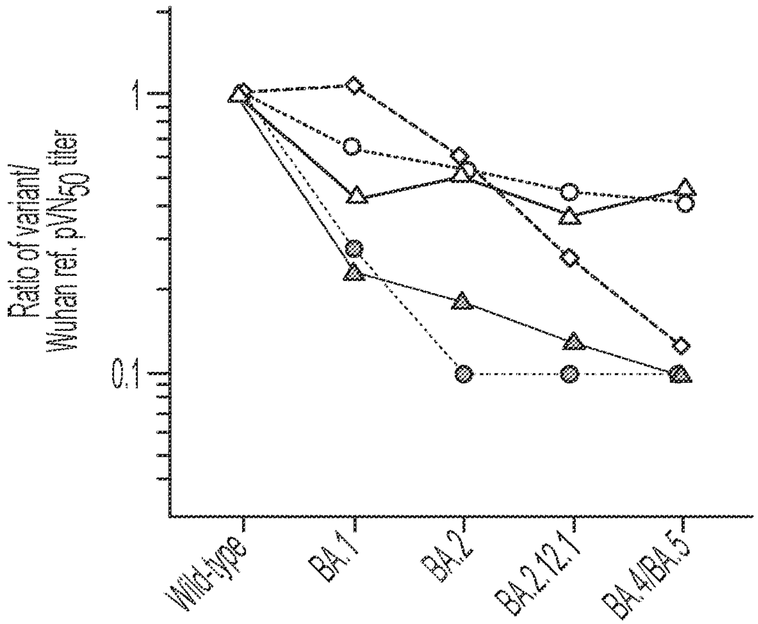
Figure 58:
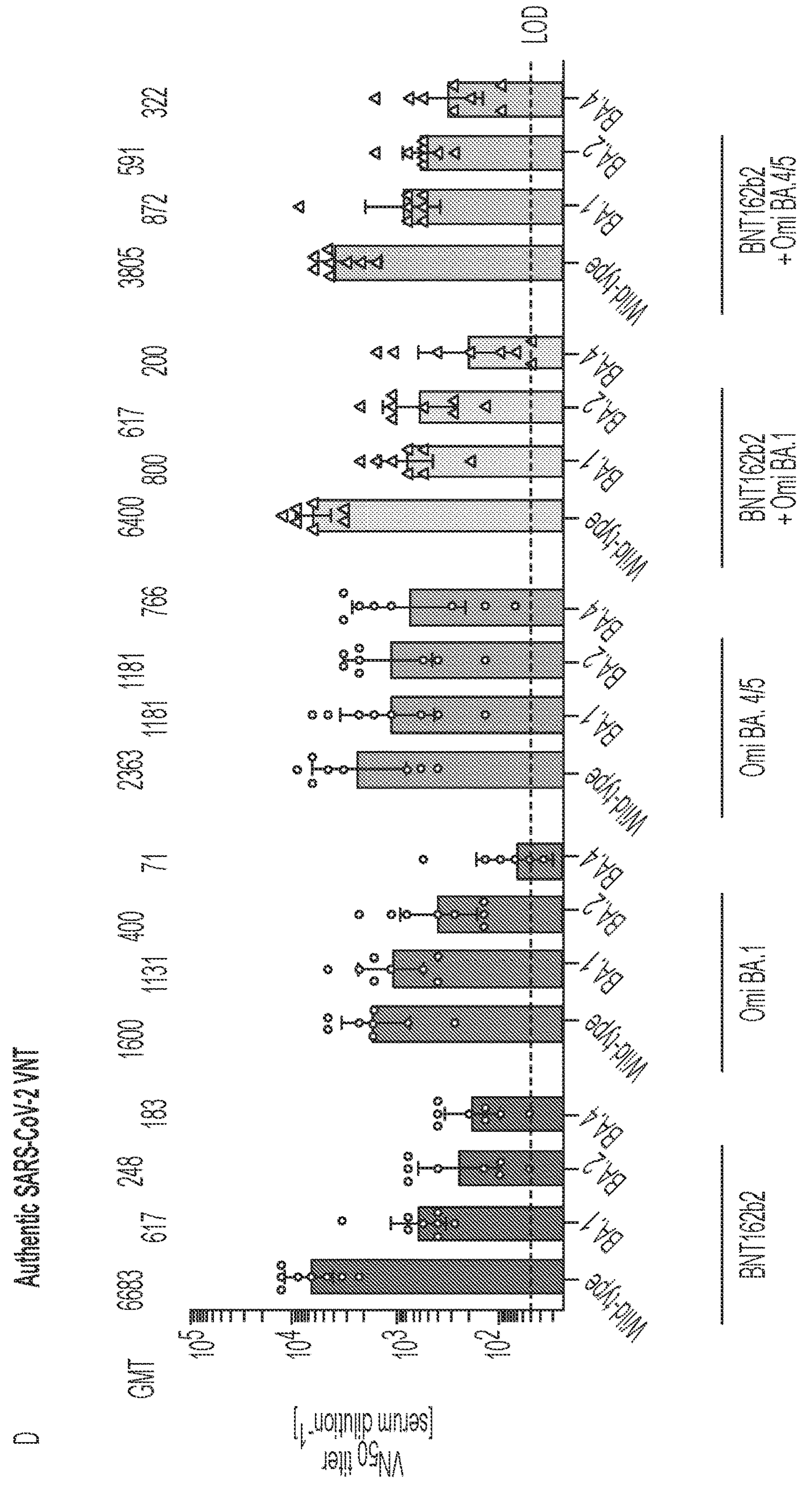
Figure 58:
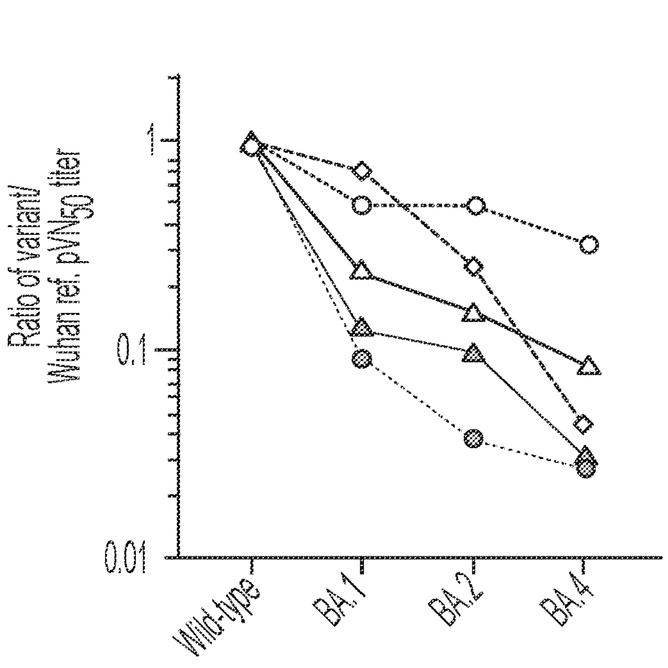

FIG. 58. Booster immunization with an Omicron BA.4/BA.5 S glycoprotein adapted vaccine mediates pan-Omicron neutralization in mice 35 days after the booster. BALB/c mice (n=8) were injected intramuscularly with two doses of 1 pg BNT162b2 (with a 21-day interval between the two doses), and a third dose of either BNT162b2 (1 pg) or the indicated monovalent (1 pg) or bivalent (0.5 pg each) Omicron BA.1 or BA.4/5-adapted vaccines 104 days after the first vaccination. (a) 50% pseudovirus neutralization ($pVN_{50}$) geometric mean titers (GMTs) against the indicated SARS-CoV-2 variants of concern (VOCs) in sera collected 35 days after the third vaccination (d35D3). Values above bars represent group GMTs. (b) Geometric mean fold-increase (GMFI) of $pVN_{50}$ titers on d35D3 relative to baseline titers before the third vaccination. Values above bars represent group GMFIs. (c) SARS-CoV-2 VOC $pVN_{50}$ GMTs normalized against the wild-type strain $pVN_{50}$ GMT (ratio VOC to wild-type). Group geometric mean ratios are shown. (d) 50% virus neutralization ($VN_{50}$) GMTs against the indicated SARS-CoV-2 VOCs on d35D3. Values above bars represent group GMTs. Error bars represent 95% confidence interval. (e) SARS-CoV-2 VOC $VN_{50}$ GMTs normalized against the wild-type strain $VN_{50}$ GMT (ratio VOC to wild-type). Group geometric mean ratios are shown. Serum was tested in duplicate. For titer values below the limit of detection (LOD), LOD/2 values were plotted. Error bars represent 95% confidence intervals.

Figure 59:
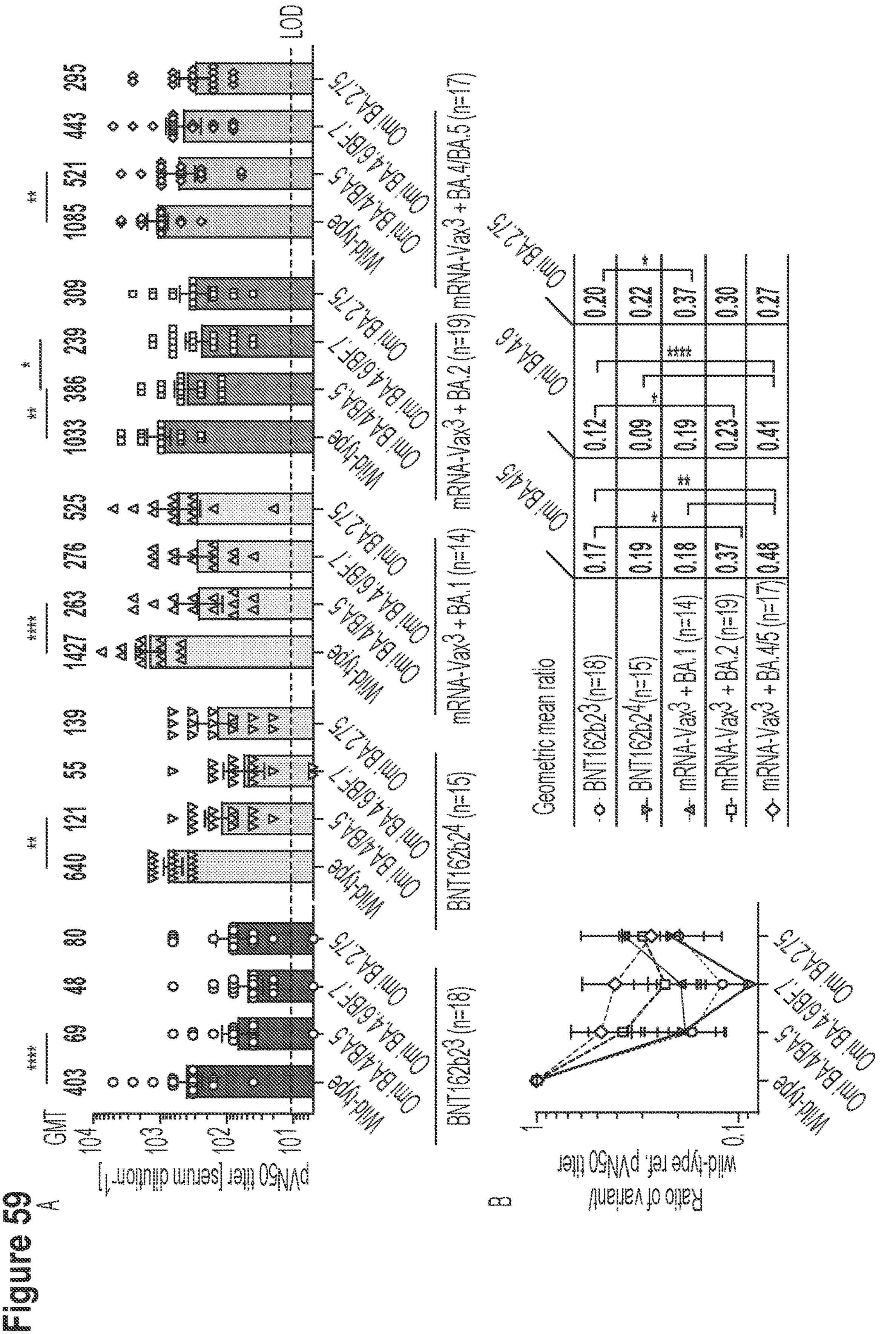

FIG. 59. Omicron BA.4/BA.5 breakthrough infection of triple mRNA vaccinated individuals induces cross-neutralization of Omicron BA.4.6 and BA.2.75. Cohorts and serum sampling as described in FIG. 61. (a) 50% pseudovirus neutralization ($pVN_{50}$) geometric mean titers (GMTs) against the indicated SARS-CoV-2 wild-type strain or Omicron variants of concern (VOCs). Values above bar graphs represent group GMTs. For titer values below the limit of detection (LOD), LOD/2 values were plotted. The non-parametric Friedman test with Dunn's multiple comparisons correction was used to compare neutralizing titers against the Omicron BA.4/BA.5 pseudovirus (which represents currently dominating BA.5) with titers against the other pseudoviruses. Multiplicity-adjusted p values are shown. (b) SARS-CoV-2 VOC $pVN_{50}$ GMTs normalized against the wild-type strain $pVN_{50}$ GMT (ratio VOC to wild-type). Group geometric mean ratios with 95% confidence intervals are shown. The non-parametric Kruskal-Wallis test with Dunn's multiple comparisons correction was used to compare the VOC GMT ratios between cohorts. **, P<0.0001; , P<0.01; *, P<0.05. Serum was tested in duplicate.

Figure 60:
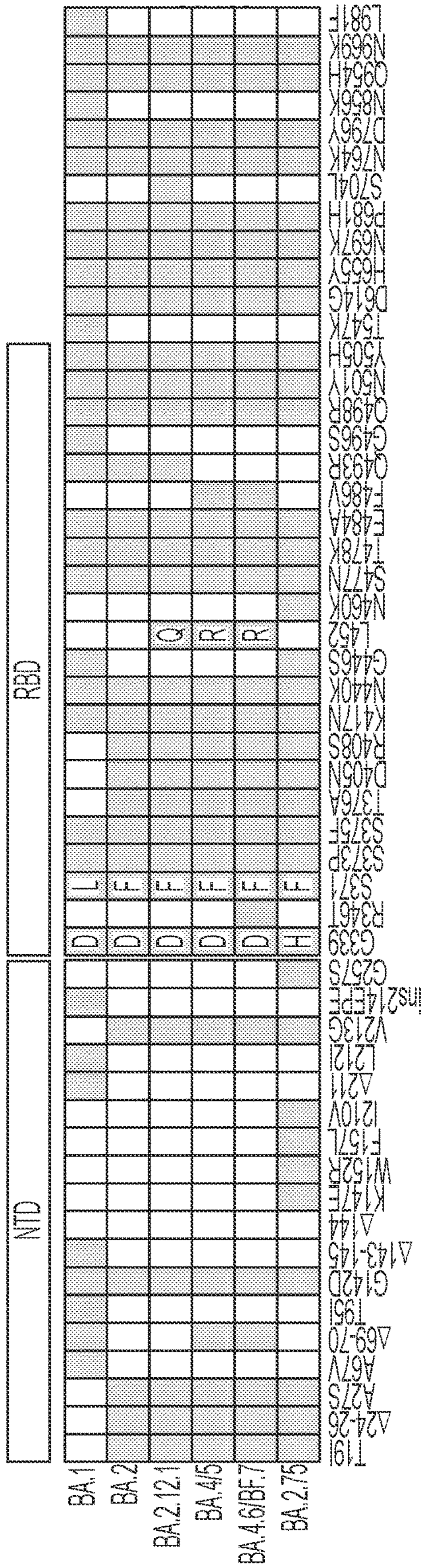

FIG. 60. Alterations of the spike glycoprotein amino acid sequence of SARS-CoV-2 Omicron sub-lineages. White letters in boxes indicate the amino acid substitution per sub-lineage; A, deletion; ins, insertion; NTD, N-terminal domain; RBD, receptor-binding domain.

Figure 61:
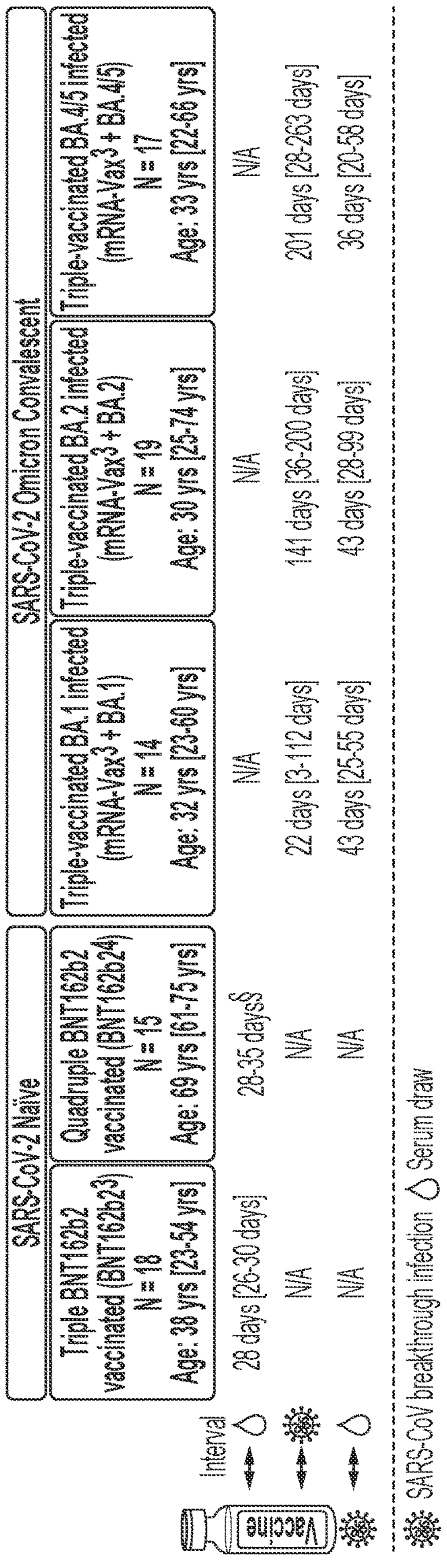

FIG. 61. Cohorts and sampling. Serum samples were drawn from five cohorts: SARS-CoV-2-naïve individuals triple-vaccinated with BNT162b2 ($BNT162b2^3$) or quadruple-vaccinated with BNT162b2 ($BNT162b2^4$), and individuals with three doses of mRNA COVID-19 vaccine (BNT162b2/mRNA-1273 homologous or heterologous regimens) who subsequently had a breakthrough infection with Omicron BA.1($mRNA\text{-}Vax^3$+BA.1), with BA.2 ($mRNA\text{-}Vax^3$+BA.2) or with BA.4/BA.5 ($mRNA\text{-}Vax^3$+BA.4/5). Breakthrough infections occurred at a time of respective VOC dominance (BA.1: November 2021 to January 2021, BA.2: March to May 2022, BA.4/5: mid-June to mid-July 2022) and/or were variant confirmed by genome sequencing. For convalescent cohorts, relevant intervals between key events such as the most recent vaccination, SARS-CoV-2 infection, and serum isolation are indicated. All values specified as median-range. N/A, not applicable; §, Serum draw was performed between 28 to 35 Days after vaccination as per protocol.

Figure 62:
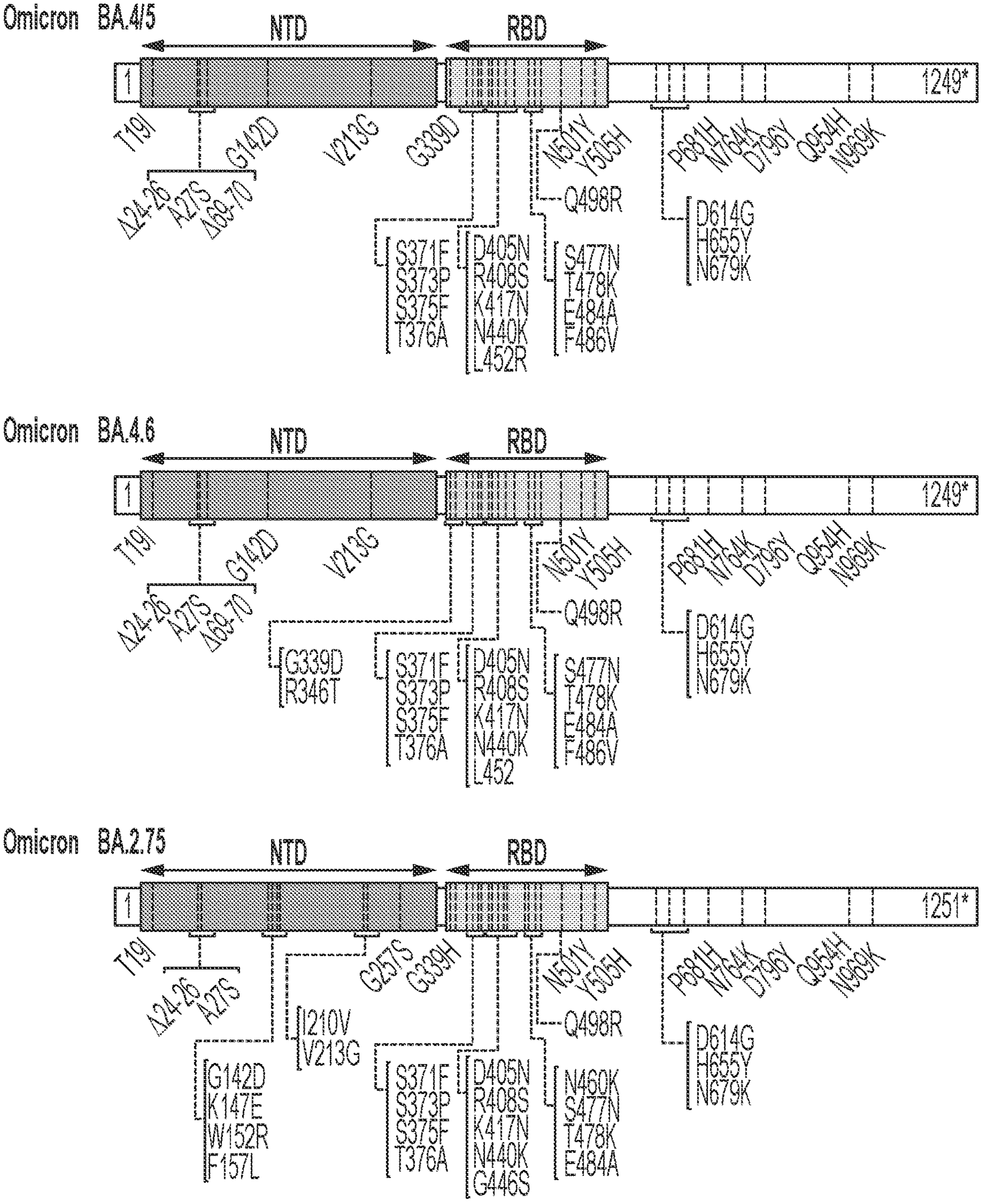

FIG. 62. Characterization of SARS-CoV-2 S glycoproteins used in VSV-SARS-CoV-2 variant pseudovirus neutralization assays. Mutation positions shown in reference to the sequence of the Wuhan-Hu-1 isolate SARS-CoV-2 S glycoprotein (GenBank: QHD43416.1). Amino acid positions, amino acid descriptions (one letter code) and kind of alterations (substitutions, deletions, insertions) are indicated. NTD, N-terminal domain; RBD, Receptor-binding domain, A, deletion; ins, insertion; *, Cytoplasmic domain truncated for the C-terminal 19 amino acids.

Figure 63:
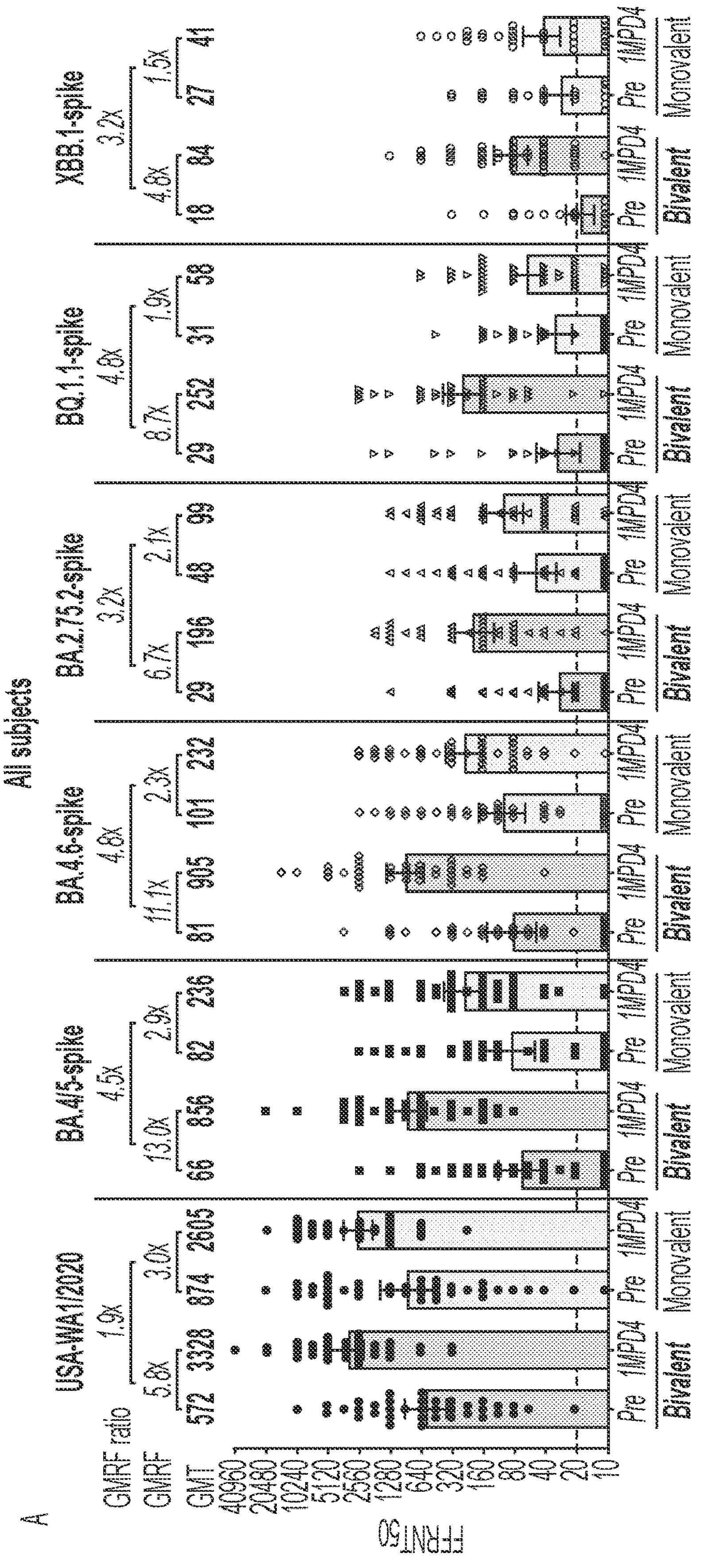
Figure 63:
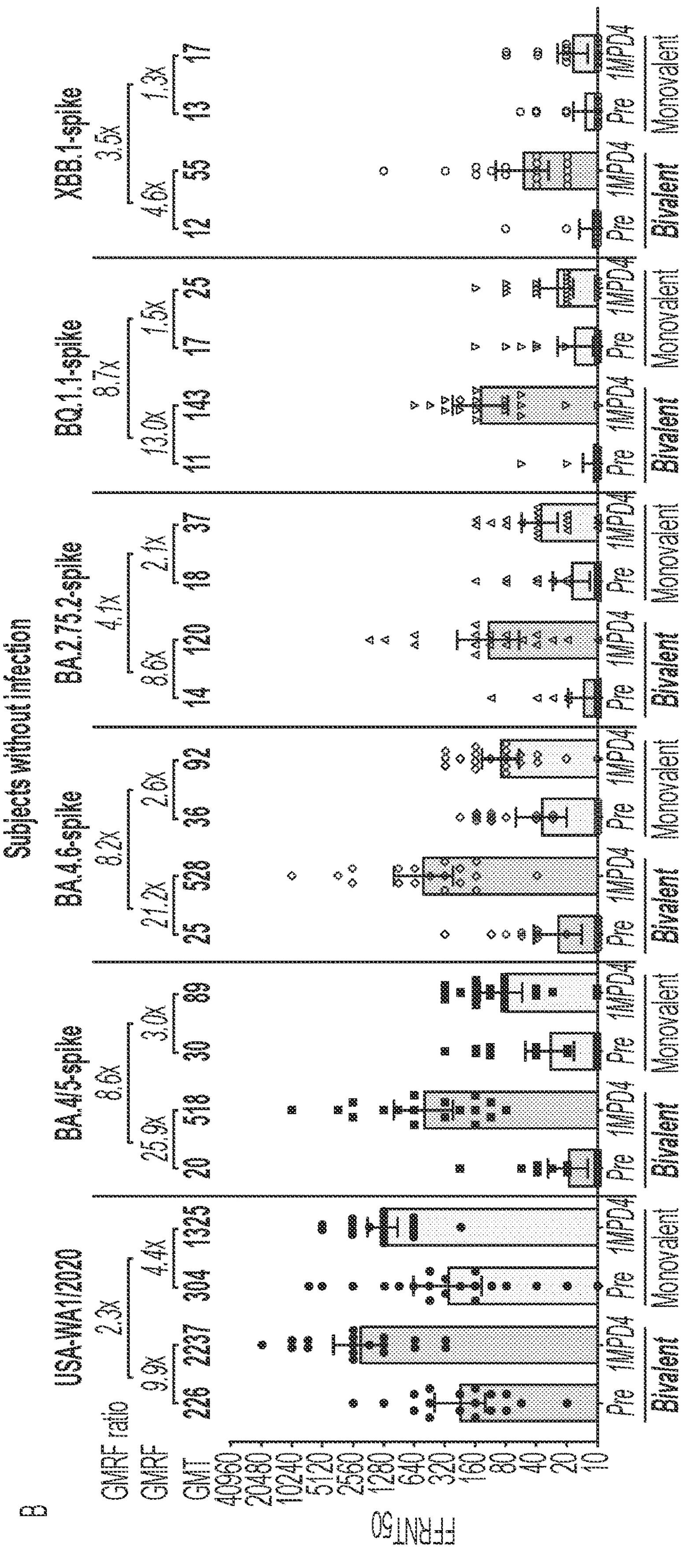
Figure 63:
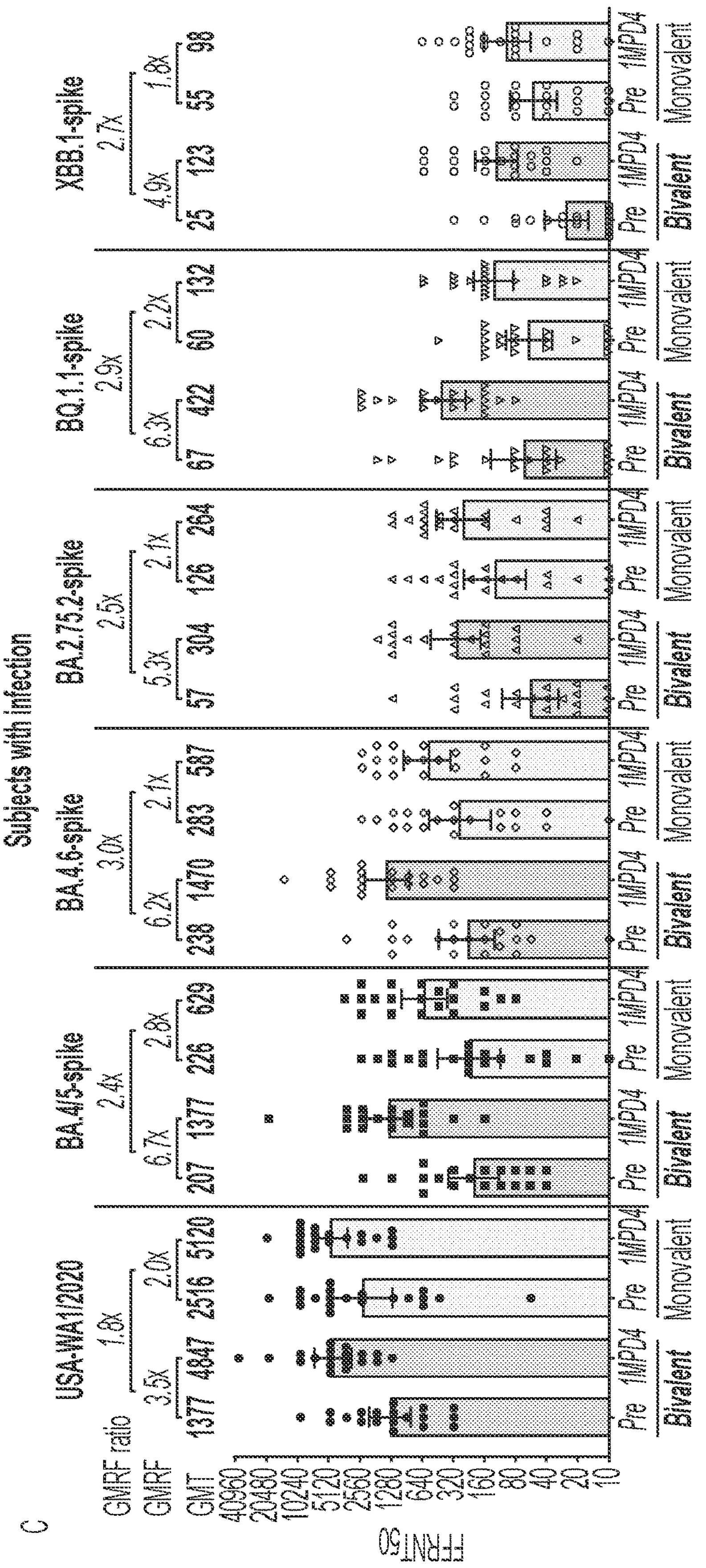

FIG. 63. Omicron BA.4/5, BA.4.6, BA.2.75.2, BQ.1.1, and XBB.1 neutralizing response with a bivalent (BA.4/5-adapted RNA+BNT162b2) or BNT16b2 monovalent booster. Bar heights and numbers immediately above bars indicate geometric means of neutralization titers (GMTs). Whiskers indicate 95% CI. Bars labeled as "Bivalent" indicate neutralization titers from subjects administered as a 4th dose a bivalent vaccine (comprising RNA encoding a SARS-CoV-2 S protein of a Wuhan strain and RNA encoding a SARS-CoV-2 S protein comprising one or more mutations characteristic of a BA.4/5 Omicron variant); bars labeled as "Monovalent" indicate neutralization titers from subjects administered as a 4th dose a monovalent vaccine (comprising RNA encoding a SARS-CoV-2 S protein of a Wuhan strain). $FFRNT_{50}$s against USA-WA1/2020 spike, BA.4/5-spike, BA.4.6-spike, BA.2.75.2-spike, BQ.1.1-spike, XBB.1-spike are shown for the bivalent or monovalent booster. "Pre" samples correspond to serum samples collected on the day of booster administration; "1MPD4" samples correspond to serum samples collected one month post dose 4 (i.e., one month post booster administration). GMFR corresponds to GMT fold rise, and was calculated as a ratio of 1MPD4 GMTs to Pre GMTs. Numbers above GMFRs indicate ratios between GMFRs of bivalent and GMFRs of monovalent. (A) $FFRNT_{50}$s of all subjects regardless of infection status. p values (two-tailed, Wilcoxon matched-pairs signed-rank test) for GMFR of bivalent or monovalent booster against USA-WA1/2020, BA.4/5-spike, BA.4.6-spike, BA.2.75.2-spike, BQ.1.1-spike, XBB.1-spike: all <0.0001. p values (two-tailed, Mann-Whitney test) for GMFR ratios of bivalent to monovalent booster against USA-WA1/2020, BA.4/5-spike, BA.4.6-spike, BA.2.75.2-spike, BQ.1.1-spike, XBB.1-spike: 0.0061, <0.0001, <0.0001, <0.0001, <0.0001, <0.0001. (B) $FFRNT_{50}$s of all subjects without evidence of prior SARS-CoV-2 infection. p values (two-tailed, Wilcoxon matched-pairs signed-rank test) for GMFR of bivalent booster against USA-WA1/2020, BA.4/5-spike, BA.4.6-spike, BA.2.75.2-spike, BQ.1.1-spike, XBB.1-spike: all <0.0001. p values (two-tailed, Wilcoxon matched-pairs signed-rank test) for GMFR of monovalent booster against USA-WA1/2020, BA.4/5-spike, BA.4.6-spike, BA.2.75.2-spike, BQ.1.1-spike, XBB.1-spike: 0.013, 0.0006, <0.0001, <0.0001, 0.013, 0.016. p values (two-tailed, Mann-Whitney test) for GMFR ratios of bivalent to monovalent booster against USA-WA1/2020, BA.4/5-spike, BA.4.6-spike, BA.2.75.2-spike, BQ.1.1-spike, XBB.1-spike: 0.035, <0.0001, <0.0001, <0.0001, <0.0001, <0.0001. (C) $FFRNT_{50}$s of all subjects with evidence of prior SARS-CoV-2 infection. p values (two-tailed, Wilcoxon matched-pairs signed-rank test) for GMFR of bivalent booster against USA-WA1/2020, BA.4/5-spike, BA.4.6-spike, BA.2.75.2-spike, BQ.1.1-spike, XBB.1-spike: all <0.0001. p values (two-tailed, Wilcoxon matched-pairs signed-rank test) for GMFR of monovalent booster against USA-WA1/2020, BA.4/5-spike, BA.4.6-spike, BA.2.75.2-spike, BQ.1.1-spike, XBB.1-spike: 0.0016, 0.0003, 0.0026, 0.0011, <0.0001, <0.0001. p values (two-tailed, Mann-Whitney test) for GMFR ratios of bivalent to monovalent booster against USA-WA1/2020, BA.4/5-spike, BA.4.6-spike, BA.2.75.2-spike, BQ.1.1-spike, XBB.1-spike: 0.065, 0.025, 0.0032, 0.0086, 0.0064, 0.0006.

Figure 64:
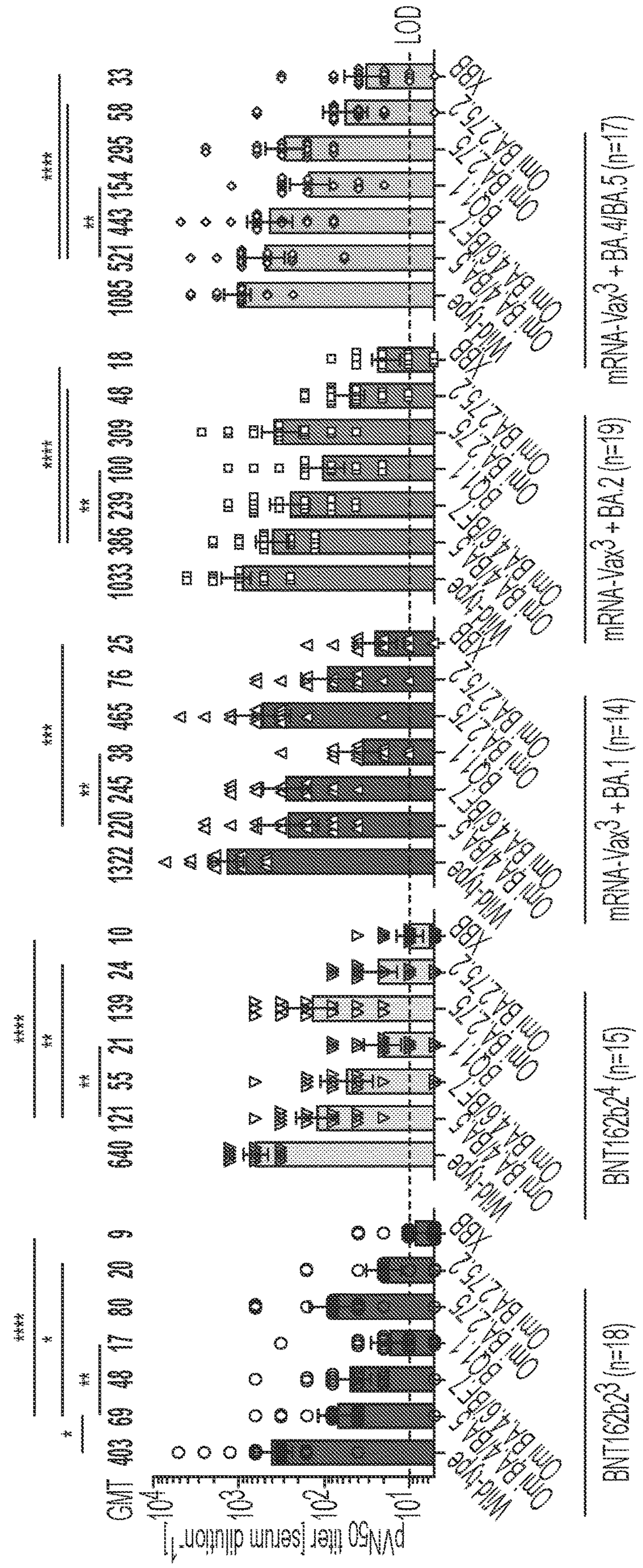
Figure 64:
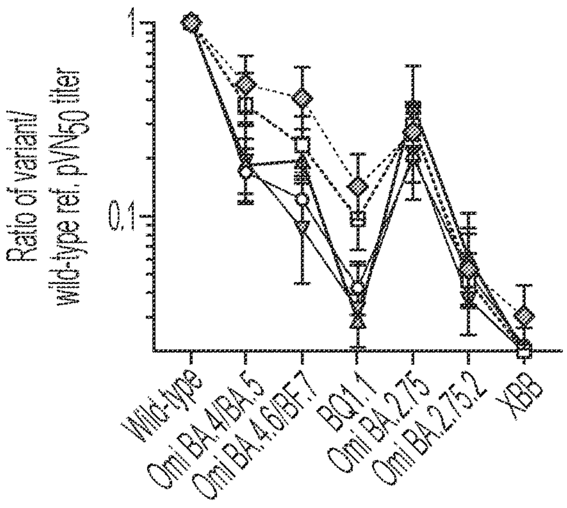

FIG. 64. Distinct cross-neutralization of Omicron sublineages by vaccine-elicited and convalescent immune sera. (A) 50% pseudovirus neutralization ($pVN_{50}$) geometric mean titers (GMTs) against the indicated SARS-CoV-2 wild-type strain or Omicron variants of concern (VOCs) in individuals (i) triple- or (ii) quadruple-vaccinated with BNT162b2 that were SARS-CoV-2-naïve at the time of sampling, and from individuals vaccinated with three doses of mRNA COVID-19 vaccine (BNT162b2/mRNA-1273 homologous or heterologous regimens) who subsequently had a breakthrough infection with Omicron at a time of (iii) BA.1 dominance, (iv) BA.2 dominance or (v) BA.4/5 dominance. Values above bar graphs represent group GMTs. For titer values below the limit of detection (LOD), LOD/2 values were plotted. The non-parametric Friedman test with Dunn's multiple comparisons correction was used to compare neutralizing titers against the Omicron BA.4/BA.5 pseudovirus (which represents currently dominating BA.5) with titers against the other pseudoviruses. Multiplicity-adjusted p values are shown. (B) SARS-CoV-2 VOC $pVN_{50}$ GMTs normalized against the wild-type strain $pVN_{50}$ GMT (ratio VOC to wild-type). Group geometric mean ratios with 95% confidence intervals are shown. The non-parametric Kruskal-Wallis test with Dunn's multiple comparisons correction was used to compare the VOC GMT ratios between cohorts. **, $P<0.0001$; *, $p<0.001$; **, $P<0.01$; *, $P<0.05$. Serum was tested in duplicate.

FIG. 65. Alterations on the spike glycoprotein amino acid sequence of SARS-CoV-2 Omicron sub-lineages. Amino acid positions, amino acid descriptions (one letter code) and types of mutations (substitutions, deletions, insertions) are indicated. White letters in boxes indicate the amino acid substitution per sub-lineage; Δ, deletion; ins, insertion; NTD, N-terminal domain; RBD, receptor-binding domain FIG. 66. T cell epitope and B cell epitope retention in the S protein of certain SARS-CoV-2 variants of concern. All potential T cell epitopes were retrieved from the Immune Epitope Database (IEDB) on Nov. 11, 2022, and the percentages of unaltered S protein linear T cell epitopes (as compared to epitopes present in BNT162b2—100%) present in each variant strain were calculated. Percentages of unaltered B cell neutralization epitopes (NTD and RBD) present in each variant strain compared to BNT162b2 were estimated by an automated Early Warning System (described in Beguir, Karim, et al., "Early computational detection of potential high risk SARS-CoV-2 variants," bioRxiv (2021)). (A) Radar chart and (B) line plot analysis of T-cell and neutralizing B cell epitope conservedness in the S protein across SARS-CoV-2 variants of concern. Percent unaltered T cell epitopes andpercent unaltered B cell neutralization epitopes are shown. In (B) numbers on top corresponding to each variant represent number of mutations in spike protein comparing to Wuhan strain. Variants are ranked in ascending order in terms of mutation number.

DETAILED DESCRIPTION

Although the present disclosure is described in detail below, it is to be understood that this disclosure is not limited to the particular methodologies, protocols and reagents described herein as these may vary. It is also to be understood that the terminology used herein is for the purpose of describing particular embodiments only, and is not intended to limit the scope of the present disclosure which will be limited only by the appended claims. Unless defined otherwise, all technical and scientific terms used herein have the same meanings as commonly understood by one of ordinary skill in the art.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present disclosure will employ, unless otherwise indicated, conventional methods of chemistry, biochemistry, cell biology, immunology, and recombinant DNA techniques which are explained in the literature in the field (cf., e.g., Molecular Cloning: A Laboratory Manual, 2nd Edition, J. Sambrook et al. eds., Cold Spring Harbor Laboratory Press, Cold Spring Harbor 1989).

In the following, the elements of the present disclosure will be described. These elements are listed with specific embodiments, however, it should be understood that they may be combined in any manner and in any number to create additional embodiments. The variously described examples and embodiments should not be construed to limit the present disclosure to only the explicitly described embodiments. This description should be understood to disclose and encompass embodiments which combine the explicitly described embodiments with any number of the disclosed elements. Furthermore, any permutations and combinations of all described elements should be considered disclosed by this description unless the context indicates otherwise.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the present disclosure was not entitled to antedate such disclosure.

Definitions

In the following, definitions will be provided which apply to all aspects of the present disclosure. The following terms have the following meanings unless otherwise indicated. Any undefined terms have their art recognized meanings.

The term "about" means approximately or nearly, and in the context of a numerical value or range set forth herein in one embodiment means±20%, ±10%, ±5%, or ±3% of the numerical value or range recited or claimed.

The terms "a" and "an" and "the" and similar reference used in the context of describing the present disclosure (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it was individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the disclosure and does not pose a limitation on the scope of the claims. No language in the specification should be construed as indicating any non-claimed element essential to the practice of the disclosure.

Unless expressly specified otherwise, the term "comprising" is used in the context of the present document to indicate that further members may optionally be present in addition to the members of the list introduced by "comprising". It is, however, contemplated as a specific embodiment of the present disclosure that the term "comprising" encompasses the possibility of no further members being present, i.e., for the purpose of this embodiment "comprising" is to be understood as having the meaning of "consisting of" or "consisting essentially of".

Terms such as "reduce", "decrease", "inhibit" or "impair" as used herein relate to an overall reduction or the ability to cause an overall reduction, preferably of at least 5%, at least 10%, at least 20%, at least 50%, at least 75% or even more, in the level. These terms include a complete or essentially complete inhibition, i.e., a reduction to zero or essentially to zero.

Terms such as "increase", "enhance" or "exceed" preferably relate to an increase or enhancement by at least 10%, at least 20%, at least 30%, at least 40%, at least 50%, at least 80%, at least 100%, at least 200%, at least 500%, or even more.

According to the present disclosure, the term "peptide" comprises oligo- and polypeptides and refers to substances which comprise about two or more, about 3 or more, about 4 or more, about 6 or more, about 8 or more, about 10 or more, about 13 or more, about 16 or more, about 20 or more, and up to about 50, about 100 or about 150, consecutive amino acids linked to one another via peptide bonds. The term "protein" or "polypeptide" refers to large peptides, in particular peptides having at least about 150 amino acids, but the terms "peptide", "protein" and "polypeptide" are used herein usually as synonyms.

A "therapeutic protein" has a positive or advantageous effect on a condition or disease state of a subject when provided to the subject in a therapeutically effective amount. In one embodiment, a therapeutic protein has curative or palliative properties and may be administered to ameliorate, relieve, alleviate, reverse, delay onset of or lessen the severity of one or more symptoms of a disease or disorder. A therapeutic protein may have prophylactic properties and may be used to delay the onset of a disease or to lessen the severity of such disease or pathological condition. The term "therapeutic protein" includes entire proteins or peptides, and can also refer to therapeutically active fragments thereof. It can also include therapeutically active variants of a protein. Examples of therapeutically active proteins include, but are not limited to, antigens for vaccination and immunostimulants such as cytokines.

"Fragment", with reference to an amino acid sequence (peptide or protein), relates to a part of an amino acid sequence, i.e. a sequence which represents the amino acid sequence shortened at the N-terminus and/or C-terminus. A fragment shortened at the C-terminus (N-terminal fragment) is obtainable e.g. by translation of a truncated open reading frame that lacks the 3'-end of the open reading frame. A fragment shortened at the N-terminus (C-terminal fragment) is obtainable e.g. by translation of a truncated open reading frame that lacks the 5'-end of the open reading frame, as long as the truncated open reading frame comprises a start codon that serves to initiate translation. A fragment of an amino acid sequence comprises e.g. at least 50%, at least 60%, at least 70%, at least 80%, at least 90% of the amino acid residues from an amino acid sequence. A fragment of an amino acid sequence preferably comprises at least 6, in particular at least 8, at least 12, at least 15, at least 20, at least 30, at least 50, or at least 100 consecutive amino acids from an amino acid sequence.

By "variant" herein is meant an amino acid sequence that differs from a parent amino acid sequence by virtue of at least one amino acid modification. The parent amino acid sequence may be a naturally occurring or wild type (WT) amino acid sequence, or may be a modified version of a wild type amino acid sequence. Preferably, the variant amino acid sequence has at least one amino acid modification compared to the parent amino acid sequence, e.g., from 1 to about 20 amino acid modifications, and preferably from 1 to about 10 or from 1 to about 5 amino acid modifications compared to the parent.

By "wild type" or "WT" or "native" herein is meant an amino acid sequence that is found in nature, including allelic variations. A wild type amino acid sequence, peptide or protein has an amino acid sequence that has not been intentionally modified.

In some embodiments, the present disclosure refers to a SARS-CoV-2 variant that is prevalent and/or rapidly spreading in a relevant jurisdiction. In some embodiments, such variants may be identified based on publicly available data (e.g., data provided in the GISAID Initiative database: www_gisaid_org, and/or data provided by the World Health Organization WHO (e.g., as provided at www_who_int/activities/tracking-SARS-CoV-2-variants). In some embodiments, such a variant refers to a variant disclosed herein.

For the purposes of the present disclosure, "variants" of an amino acid sequence (peptide, protein or polypeptide) comprise amino acid insertion variants, amino acid addition variants, amino acid deletion variants and/or amino acid substitution variants. The term "variant" includes all mutants, splice variants, posttranslationally modified variants, conformations, isoforms, allelic variants, species variants, and species homologs, in particular those which are naturally occurring. The term "variant" includes, in particular, fragments of an amino acid sequence.

Amino acid insertion variants comprise insertions of single or two or more amino acids in a particular amino acid sequence. In the case of amino acid sequence variants having an insertion, one or more amino acid residues are inserted into a particular site in an amino acid sequence, although random insertion with appropriate screening of the resulting product is also possible. Amino acid addition variants comprise amino- and/or carboxy-terminal fusions of one or more amino acids, such as 1, 2, 3, 5, 10, 20, 30, 50, or more amino acids. Amino acid deletion variants are characterized by the removal of one or more amino acids from the sequence, such as by removal of 1, 2, 3, 5, 10, 20, 30, 50, or more amino acids. The deletions may be in any position of the protein. Amino acid deletion variants that comprise the deletion at the N-terminal and/or C-terminal end of the protein are also called N-terminal and/or C-terminal truncation variants. Amino acid substitution variants are characterized by at least one residue in the sequence being removed and another residue being inserted in its place. Preference is given to the modifications being in positions in the amino acid sequence which are not conserved between homologous proteins or peptides and/or to replacing amino acids with other ones having similar properties. Preferably, amino acid changes in peptide and protein variants are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In one embodiment, conservative amino acid substitutions include substitutions within the following groups:

glycine, alanine;
valine, isoleucine, leucine;
aspartic acid, glutamic acid;
asparagine, glutamine;
serine, threonine;
lysine, arginine; and
phenylalanine, tyrosine.

Preferably the degree of similarity, preferably identity between a given amino acid sequence and an amino acid sequence which is a variant of said given amino acid sequence will be at least about 60%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, in some embodiments continuous amino acids. In some embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5. "Sequence similarity" indicates the percentage of amino acids that either are identical or that represent conservative amino acid substitutions. "Sequence identity" between two amino acid sequences indicates the percentage of amino acids that are identical between the sequences. "Sequence identity" between two nucleic acid sequences indicates the percentage of nucleotides that are identical between the sequences.

The terms "% identical", "% identity" or similar terms are intended to refer, in particular, to the percentage of nucleotides or amino acids which are identical in an optimal alignment between the sequences to be compared. Said percentage is purely statistical, and the differences between the two sequences may be but are not necessarily randomly distributed over the entire length of the sequences to be compared. Comparisons of two sequences are usually carried out by comparing the sequences, after optimal alignment, with respect to a segment or "window of comparison", in order to identify local regions of corresponding sequences. The optimal alignment for a comparison may be carried out manually or with the aid of the local homology algorithm by Smith and Waterman, 1981, Ads App. Math. 2, 482, with the aid of the local homology algorithm by Neddleman and Wunsch, 1970, J. Mol. Biol. 48, 443, with the aid of the similarity search algorithm by Pearson and Lipman, 1988, Proc. Natl Acad. Sci. USA 88, 2444, or with the aid of computer programs using said algorithms (GAP, BESTFIT, FASTA, BLAST P, BLAST N and TFASTA in Wisconsin Genetics Software Package, Genetics Computer Group, 575 Science Drive, Madison, Wis.). In some embodiments, percent identity of two sequences is determined using the BLASTN or BLASTP algorithm, as available on the United States National Center for Biotechnology Information (NCBI) website (e.g., at blast.ncbi.nlm.nih.gov/Blast.cgi?PAGE_TYPE=BlastSearch&BLAST_SPEC=blast2-seq&LINK_LOC=align2seq). In some embodiments, the algorithm parameters used for BLASTN algorithm on the NCBI website include: (i) Expect Threshold set to 10; (ii) Word Size set to 28; (iii) Max matches in a query range set to 0; (iv) Match/Mismatch Scores set to 1, −2; (v) Gap Costs set to Linear; and (vi) the filter for low complexity regions being used. In some embodiments, the algorithm parameters used for BLASTP algorithm on the NCBI website include: (i) Expect Threshold set to 10; (ii) Word Size set to 3; (iii) Max matches in a query range set to 0; (iv) Matrix set to BLOSUM62; (v) Gap Costs set to Existence: 11 Extension: 1; and (vi) conditional compositional score matrix adjustment.

Percentage identity is obtained by determining the number of identical positions at which the sequences to be compared correspond, dividing this number by the number of positions compared (e.g., the number of positions in the reference sequence) and multiplying this result by 100.

In some embodiments, the degree of similarity or identity is given for a region which is at least about 50%, at least about 60%, at least about 70%, at least about 80%, at least about 90% or about 100% of the entire length of the reference sequence. For example, if the reference nucleic acid sequence consists of 200 nucleotides, the degree of identity is given for at least about 100, at least about 120, at least about 140, at least about 160, at least about 180, or about 200 nucleotides, in some embodiments continuous nucleotides. In some embodiments, the degree of similarity or identity is given for the entire length of the reference sequence.

Homologous amino acid sequences exhibit according to the present disclosure at least 40%, in particular at least 50%, at least 60%, at least 70%, at least 80%, at least 90% and preferably at least 95%, at least 98 or at least 99% identity of the amino acid residues.

The amino acid sequence variants described herein may readily be prepared by the skilled person, for example, by recombinant DNA manipulation. The manipulation of DNA sequences for preparing peptides or proteins having substitutions, additions, insertions or deletions, is described in detail in Sambrook et al. (1989), for example. Furthermore, the peptides and amino acid variants described herein may be readily prepared with the aid of known peptide synthesis techniques such as, for example, by solid phase synthesis and similar methods.

In one embodiment, a fragment or variant of an amino acid sequence (peptide or protein) is preferably a "functional fragment" or "functional variant". The term "functional fragment" or "functional variant" of an amino acid sequence relates to any fragment or variant exhibiting one or more functional properties identical or similar to those of the amino acid sequence from which it is derived, i.e., it is functionally equivalent. With respect to antigens or antigenic sequences, one particular function is one or more immunogenic activities displayed by the amino acid sequence from which the fragment or variant is derived. The term "functional fragment" or "functional variant", as used herein, in particular refers to a variant molecule or sequence that comprises an amino acid sequence that is altered by one or more amino acids compared to the amino acid sequence of the parent molecule or sequence and that is still capable of fulfilling one or more of the functions of the parent molecule or sequence, e.g., inducing an immune response. In one embodiment, the modifications in the amino acid sequence of the parent molecule or sequence do not significantly affect or alter the characteristics of the molecule or sequence. In different embodiments, the function of the functional fragment or functional variant may be reduced but still significantly present, e.g., immunogenicity of the functional variant may be at least 50%, at least 60%, at least 70%, at least 80%, or at least 90% of the parent molecule or sequence. However, in other embodiments, immunogenicity of the functional fragment or functional variant may be enhanced compared to the parent molecule or sequence.

An amino acid sequence (peptide, protein or polypeptide) “derived from” a designated amino acid sequence (peptide, protein or polypeptide) refers to the origin of the first amino acid sequence. Preferably, the amino acid sequence which is derived from a particular amino acid sequence has an amino acid sequence that is identical, essentially identical or homologous to that particular sequence or a fragment thereof. Amino acid sequences derived from a particular amino acid sequence may be variants of that particular sequence or a fragment thereof. For example, it will be understood by one of ordinary skill in the art that the antigens suitable for use herein may be altered such that they vary in sequence from the naturally occurring or native sequences from which they were derived, while retaining the desirable activity of the native sequences.

As used herein, an “instructional material” or “instructions” includes a publication, a recording, a diagram, or any other medium of expression which can be used to communicate the usefulness of the compositions and methods of the present disclosure. The instructional material of the kit of the present disclosure may, for example, be affixed to a container which contains the compositions of the present disclosure or be shipped together with a container which contains the compositions. Alternatively, the instructional material may be shipped separately from the container with the intention that the instructional material and the compositions be used cooperatively by the recipient.

“Isolated” means altered or removed from the natural state. For example, a nucleic acid or a peptide naturally present in a living animal is not “isolated”, but the same nucleic acid or peptide partially or completely separated from the coexisting materials of its natural state is “isolated”. An isolated nucleic acid or protein can exist in substantially purified form, or can exist in a non-native environment such as, for example, a host cell.

The term “recombinant” in the context of the present disclosure means “made through genetic engineering”. Preferably, a “recombinant object” such as a recombinant nucleic acid in the context of the present disclosure is not occurring naturally.

The term “naturally occurring” as used herein refers to the fact that an object can be found in nature. For example, a peptide or nucleic acid that is present in an organism (including viruses) and can be isolated from a source in nature and which has not been intentionally modified by man in the laboratory is naturally occurring.

“Physiological pH” as used herein refers to a pH of about 7.5.

The term “genetic modification” or simply “modification” includes the transfection of cells with nucleic acid. The term “transfection” relates to the introduction of nucleic acids, in particular RNA, into a cell. For purposes of the present disclosure, the term “transfection” also includes the introduction of a nucleic acid into a cell or the uptake of a nucleic acid by such cell, wherein the cell may be present in a subject, e.g., a patient. Thus, according to the present disclosure, a cell for transfection of a nucleic acid described herein can be present in vitro or in vivo, e.g. the cell can form part of an organ, a tissue and/or an organism of a patient. According to the disclosure, transfection can be transient or stable. For some applications of transfection, it is sufficient if the transfected genetic material is only transiently expressed. RNA can be transfected into cells to transiently express its coded protein. Since the nucleic acid introduced in the transfection process is usually not integrated into the nuclear genome, the foreign nucleic acid will be diluted through mitosis or degraded. Cells allowing episomal amplification of nucleic acids greatly reduce the rate of dilution. If it is desired that the transfected nucleic acid actually remains in the genome of the cell and its daughter cells, a stable transfection must occur. Such stable transfection can be achieved by using virus-based systems or transposon-based systems for transfection. Generally, nucleic acid encoding antigen is transiently transfected into cells. RNA can be transfected into cells to transiently express its coded protein.

The term “seroconversion” includes a ≥4-fold rise from before vaccination to 1-month post Dose 2.

Coronavirus

Coronaviruses are enveloped, positive-sense, single-stranded RNA ((+) ssRNA) viruses. They have the largest genomes (26-32 kb) among known RNA viruses and are phylogenetically divided into four genera (α, β, γ, and δ), with betacoronaviruses further subdivided into four lineages (A, B, C, and D). Coronaviruses infect a wide range of avian and mammalian species, including humans. Some human coronaviruses generally cause mild respiratory diseases, although severity can be greater in infants, the elderly, and the immunocompromised. Middle East respiratory syndrome coronavirus (MERS-CoV) and severe acute respiratory syndrome coronavirus (SARS-CoV), belonging to betacoronavirus lineages C and B, respectively, are highly pathogenic. Both viruses emerged into the human population from animal reservoirs within the last 15 years and caused outbreaks with high case-fatality rates. The outbreak of severe acute respiratory syndrome coronavirus-2 (SARS-CoV-2) that causes atypical pneumonia (coronavirus disease 2019; COVID-19) has raged in China since mid-December 2019, and has developed to be a public health emergency of international concern. SARS-CoV-2 (MN908947.3) belongs to betacoronavirus lineage B. It has at least 70% sequence similarity to SARS-CoV.

In general, coronaviruses have four structural proteins, namely, envelope (E), membrane (M), nucleocapsid (N), and spike (S). The E and M proteins have important functions in the viral assembly, and the N protein is necessary for viral RNA synthesis. The critical glycoprotein S is responsible for virus binding and entry into target cells. The S protein is synthesized as a single-chain inactive precursor that is cleaved by furin-like host proteases in the producing cell into two noncovalently associated subunits, S1 and S2. The S1 subunit contains the receptor-binding domain (RBD), which recognizes the host-cell receptor. The S2 subunit contains the fusion peptide, two heptad repeats, and a transmembrane domain, all of which are required to mediate fusion of the viral and host-cell membranes by undergoing a large conformational rearrangement. The S1 and S2 subunits trimerize to form a large prefusion spike.

The S precursor protein of SARS-CoV-2 can be proteolytically cleaved into S1 (685 aa) and S2 (588 aa) subunits. The S1 subunit comprises the receptor-binding domain (RBD), which mediates virus entry into sensitive cells through the host angiotensin-converting enzyme 2 (ACE2) receptor.

Antigen

The present disclosure comprises the use of RNA encoding an amino acid sequence comprising SARS-CoV-2 S protein, an immunogenic variant thereof, or an immunogenic fragment of the SARS-CoV-2 S protein or the immunogenic variant thereof. Thus, the RNA encodes a peptide or protein comprising at least an epitope SARS-CoV-2 S protein or an immunogenic variant thereof for inducing an immune response against coronavirus S protein, in particular SARS-CoV-2 S protein in a subject. The amino acid sequence comprising SARS-CoV-2 S protein, an immunogenic variant thereof, or an immunogenic fragment of the SARS-CoV-2 S protein or the immunogenic variant thereof (i.e., the antigenic peptide or protein) is also designated herein as "vaccine antigen", "peptide and protein antigen", "antigen molecule" or simply "antigen". The SARS-CoV-2 S protein, an immunogenic variant thereof, or an immunogenic fragment of the SARS-CoV-2 S protein or the immunogenic variant thereof is also designated herein as "antigenic peptide or protein" or "antigenic sequence".

The SARS-CoV-2 coronavirus full length spike (S) protein from the first detected SARS-CoV-2 strain (referred to as the Wuhan strain herein) consists of 1273 amino acids and has the amino acid sequence according to SEQ ID NO: 1:

(SEQ ID NO: 1)

```
MFVFLVLLPLVSSQCVNLTTRTQLPPAYTNSFTRGVYYPDKVFRSS
VLHSTQDLFLPFFSNVTWFHAIHVSGTNGTKRFDNPVLPFNDGVY
FASTEKSNIIRGWIFGTTLDSKTQSLLIVNNATNVVIKVCEFQFC
NDPFLGVYYHKNNKSWMESEFRVYSSANNCTFEYVSQPFLMDLEG
KQGNFKNLREFVFKNIDGYFKIYSKHTPINLVRDLPQGFSALEPL
VDLPIGINITRFQTLLALHRSYLTPGDSSSGWTAGAAAYYVGYLQ
PRTFLLKYNENGTITDAVDCALDPLSETKCTLKSFTVEKGIYQTS
NFRVQPTESIVRFPNITNLCPFGEVFNATRFASVYAWNRKRISNC
VADYSVLYNSASFSTEKCYGVSPTKLNDLCFTNVYADSFVIRGDE
VRQIAPGQTGKIADYNYKLPDDFTGCVIAWNSNNLDSKVGGNYNY
LYRLFRKSNLKPFERDISTEIYQAGSTPCNGVEGFNCYFPLQSYG
FQPTNGVGYQPYRVVVLSFELLHAPATVCGPKKSTNLVKNKCVNF
NFNGLTGTGVLTESNKKFLPFQQFGRDIADTTDAVRDPQTLEILD
ITPCSFGGVSVITPGTNTSNQVAVLYQDVNCTEVPVAIHADQLTP
TWRVYSTGSNVFQTRAGCLIGAEHVNNSYECDIPIGAGICASYQT
QTNSPRRARSVASQSIIAYTMSLGAENSVAYSNNSIAIPTNFTIS
VTTEILPVSMTKTSVDCTMYICGDSTECSNLLLQYGSFCTQLNRA
LTGIAVEQDKNTQEVFAQVKQIYKTPPIKDFGGFNFSQILPDPSK
PSKRSFIEDLLFNKVTLADAGFIKQYGDCLGDIAARDLICAQKFN
GLTVLPPLLTDEMIAQYTSALLAGTITSGWTFGAGAALQIPFAMQ
```

-continued

```
MAYRFNGIGVTQNVLYENQKLIANQFNSAIGKIQDSLSSTASALG
KLQDVVNQNAQALNTLVKQLSSNFGAISSVLNDILSRLDKVEAEV
QIDRLITGRLQSLQTYVTQQLIRAAEIRASANLAATKMSECVLGQ
SKRVDFCGKGYHLMSFPQSAPHGVVFLHVTYVPAQEKNFTTAPAI
CHDGKAHFPREGVFVSNGTHWFVTQRNFYEPQIITTDNTFVSGNC
DVVIGIVNNTVYDPLQPELDSFKEELDKYFKNHTSPDVDLGDISG
INASVVNIQKEIDRLNEVAKNLNESLIDLQELGKYEQYIKWPWYI
WLGFIAGLIAIVMVTIMLCCMTSCCSCLKGCCSCGSCCKFDEDDS
EPVLKGVKLHYT
```

For purposes of the present disclosure, the above sequence is considered the wildtype or Wuhan SARS-CoV-2 S protein amino acid sequence. Unless otherwise indicated, position numberings in a SARS-CoV-2 S protein given herein are in relation to the amino acid sequence according to SEQ ID NO: 1. One of skill in the art reading the present disclosure will understand the corresponding positions in SARS-CoV-2 S protein variants based on the position numbering relative to the amino acid sequence of SEQ ID NO: 1.

In specific embodiments, full length spike (S) protein encoded by an RNA described herein can be modified in such a way that the prototypical prefusion conformation is stabilized. Certain mutations that stabilize a prefusion confirmation are known in the art, e.g., as disclosed in WO 2021243122 Δ2 and Hsieh, Ching-Lin, et al. ("Structure-based design of prefusion-stabilized SARS-CoV-2 spikes," Science 369.6510 (2020): 1501-1505), the contents of each which are incorporated by reference herein in their entirety. In some embodiments, a SARS-CoV-2 S protein may be stabilized by introducing one or more proline mutations. In some embodiments, a SARS-CoV-2 S protein comprises a proline substitution at positions corresponding to residues 986 and/or 987 of SEQ ID NO: 1. In some embodiments, a SARS-CoV-2 S protein comprises a proline substitution at one or more positions corresponding to residues 817, 892, 899, and 942 of SEQ ID NO: 1. In some embodiments, a SARS-CoV-2 S protein comprises a proline substitution at positions corresponding to each of residues 817, 892, 899, and 942 of SEQ ID NO: 1. In some embodiments, a SARS-CoV-2 S protein comprises a proline substitution at positions corresponding to each of residues 817, 892, 899, 942, 986, and 987 of SEQ ID NO:1.

In some embodiments, stabilization of the prefusion conformation may be obtained by introducing two consecutive proline substitutions at residues 986 and 987 in the full length spike protein. Specifically, spike (S) protein stabilized protein variants are obtained in a way that the amino acid residue at position 986 is exchanged to proline and the amino acid residue at position 987 is also exchanged to proline. In one embodiment, a SARS-CoV-2 S protein variant wherein the prototypical prefusion conformation is stabilized comprises the amino acid sequence shown in SEQ ID NO: 7:

(SEQ ID NO: 7)

```
MFVFLVLLPLVSSQCVNLTTRTQLPPAYTNSFTRGVYYPDKVFRSS
VLHSTQDLFLPFFSNVTWFHAIHVSGINGTKRFDNPVLPFNDGVY
```

-continued

```
FASTEKSNIIRGWIFGTTLDSKTQSLLIVNNATNVVIKVCEFQFC

NDPFLGVYYHKNNKSWMESEFRVYSSANNCTFEYVSQPFLMDLEG

KQGNFKNLREFVFKNIDGYFKIYSKHTPINLVRDLPQGFSALEPL

VDLPIGINITRFQTLLALHRSYLTPGDSSSGWTAGAAAYYVGYLQ

PRTFLLKYNENGTITDAVDCALDPLSETKCTLKSFTVEKGIYQTS

NFRVQPTESIVRFPNITNLCPFGEVFNATRFASVYAWNRKRISNC

VADYSVLYNSASFSTFKCYGVSPTKLNDLCFTNVYADSFVIRGDE

VRQIAPGQTGKIADYNYKLPDDFTGCVIAWNSNNLDSKVGGNYNY

LYRLFRKSNLKPFERDISTEIYQAGSTPCNGVEGFNCYFPLQSYG

FQPTNGVGYQPYRVVVLSFELLHAPATVCGPKKSTNLVKNKCVNF

NFNGLTGTGVLTESNKKFLPFQQFGRDIADTTDAVRDPQTLEILD

ITPCSFGGVSVITPGTNTSNQVAVLYQDVNCTEVPVAIHADQLTP

TWRVYSTGSNVFQTRAGCLIGAEHVNNSYECDIPIGAGICASYQT

QTNSPRRARSVASQSIIAYTMSLGAENSVAYSNNSIAIPTNFTIS

VTTEILPVSMTKTSVDCTMYICGDSTECSNLLLQYGSFCTQLNRA

LTGIAVEQDKNTQEVFAQVKQIYKTPPIKDFGGFNFSQILPDPSK

PSKRSFIEDLLFNKVTLADAGFIKQYGDCLGDIAARDLICAQKFN

GLTVLPPLLTDEMIAQYTSALLAGTITSGWTFGAGAALQIPFAMQ

MAYRFNGIGVTQNVLYENQKLIANQFNSAIGKIQDSLSSTASALG

KLQDVVNQNAQALNTLVKQLSSNFGAISSVLNDILSRLDPPEAEV

QIDRLITGRLQSLQTYVTQQLIRAAEIRASANLAATKMSECVLGQ

SKRVDFCGKGYHLMSFPQSAPHGVVFLHVTYVPAQEKNFTTAPAI

CHDGKAHFPREGVFVSNGTHWFVTQRNFYEPQIITTDNTFVSGNC

DVVIGIVNNTVYDPLQPELDSFKEELDKYFKNHTSPDVDLGDISG

INASVVNIQKEIDRLNEVAKNLNESLIDLQELGKYEQYIKWPWYI

WLGFIAGLIAIVMVTIMLCCMTSCCSCLKGCCSCGSCCKFDEDDS

EPVLKGVKLHYT
```

Those skilled in the art are aware of various spike variants, and/or resources that document them. For example, the following strains, their SARS-CoV-2 S protein amino acid sequences and, in particular, modifications thereof compared to wildtype SARS-CoV-2 S protein amino acid sequence, e.g., as compared to SEQ ID NO: 1, are useful herein.

B.1.1.7 ("Variant of Concern 202012/01" (VOC-202012/01)

B.1.1.7 (the "alpha variant") is a variant of SARS-CoV-2 which was first detected in October 2020 during the COVID-19 pandemic in the United Kingdom from a sample taken the previous month, and it quickly began to spread by mid-December. It is correlated with a significant increase in the rate of COVID-19 infection in United Kingdom; this increase is thought to be at least partly because of change N501Y inside the spike glycoprotein's receptor-binding domain, which is needed for binding to ACE2 in human cells. The B.1.1.7 variant is defined by 23 mutations: 13 non-synonymous mutations, 4 deletions, and 6 synonymous mutations (i.e., there are 17 mutations that change proteins and six that do not). The spike protein changes in B.1.1.7 include deletion 69-70, deletion 144, N501Y, A570D, D614G, P681H, T716I, S982A, and D1118H.

B.1.351 (501.V2)

B.1.351 lineage (the "Beta variant") and colloquially known as South African COVID-19 variant, is a variant of SARS-CoV-2. Preliminary results indicate that this variant may have an increased transmissibility. The B.1.351 variant is defined by multiple spike protein changes including: L18F, D80A, D215G, deletion 242-244, R246I, K417N, E484K, N501Y, D614G and A701V. There are three mutations of particular interest in the spike region of the B.1.351 genome: K417N, E484K, N501Y.

B.1.1.298 (Cluster 5)

B.1.1.298 was discovered in North Jutland, Denmark, and is believed to have been spread from minks to humans via mink farms. Several different mutations in the spike protein of the virus have been confirmed. The specific mutations include deletion 69-70, Y453F, D614G, I692V, M1229I, and optionally S1147L.

P.1 (B.1.1.248)

Lineage B.1.1.248 (the "gamma variant"), known as the Brazil(ian) variant, is one of the variants of SARS-CoV-2 which has been named P.1 lineage. P.1 has a number of S-protein modifications [L18F, T20N, P26S, D138Y, R190S, K417T, E484K, N501Y, D614G, H655Y, T1027I, V1176F] and is similar in certain key RBD positions (K417, E484, N501) to variant B.1.351 from South Africa.

B.1.427/B.1.429 (CAL.20C)

Lineage B.1.427/B.1.429 (the "epsilon variant"), also known as CAL.20C, is defined by the following modifications in the S-protein: 5131, W152C, L452R, and D614G of which the L452R modification is of particular concern. CDC has listed B.1.427/B.1.429 as "variant of concern".

B.1.525

B.1.525 (the "eta variant") carries the same E484K modification as found in the P.1, and B.1.351 variants, and also carries the same ΔH69/ΔV70 deletion as found in B.1.1.7, and B.1.1.298. It also carries the modifications D614G, Q677H and F888L.

B.1.526

B.1.526 (the "iota variant") was detected as an emerging lineage of viral isolates in the New York region that shares mutations with previously reported variants. The most common sets of spike mutations in this lineage are L5F, T95I, D253G, E484K, D614G, and A701V.

The following table shows an overview of circulating SARS-CoV-2 strains which are VOI/VOC.

TABLE 1

Overview of certain circulating SARS-CoV-2 strains which have been/are VOI/VOC

| Lineage | Amino acid substitution | | | | | | | | |
|---|---|---|---|---|---|---|---|---|---|
| P.1 (BRA) | L18F | T20N | P26S | | | D138Y | | R190S | |
| B.1.1.7 (UK) | | | | ΔH69/V70 | | | ΔY144 | | |
| B.1.351 (SA) | L18F | | | | D80A | | | | D215G |

TABLE 1-continued

Overview of certain circulating SARS-CoV-2 strains which have been/are VOI/VOC

| | | | | | |
|---|---|---|---|---|---|
| B.1.1.298 (DK) | | | ΔH69/V70 | | |
| B.1.427/B.1.429 (CAL) | | S13I | | | W152C |
| B.1.525 | | | ΔH69/V70 | | |
| B.1.526 (NY) | L5F | | | T95I | |

| Lineage | Amino acid substitution | | | | | | | | | | |
|---|---|---|---|---|---|---|---|---|---|---|---|
| P.1 (BRA) | | | | K417T | | | E484K | N501Y | | D614G | H655Y |
| B.1.1.7 (UK) | | | | | | | | N501Y | A570D | D614G | |
| B.1.351 (SA) | Δ242/243 | R246I | | K417N | | | E484K | N501Y | | D614G | |
| B.1.1.298 (DK) | | | | | | Y453F | | | | D614G | |
| B.1.427/B.1.429 (CAL) | | | | | L452R | | | | | D614G | |
| B.1.525 | | | | | | | E484K | | | D614G | |
| B.1.526 (NY) | | | D253G | | | | E484K | | | D614G | |

| Lineage | Amino acid substitution | | | | | | | | | | |
|---|---|---|---|---|---|---|---|---|---|---|---|
| P.1 (BRA) | | | | | | | | T1027I | | V1176F | |
| B.1.1.7 (UK) | | P681H | | | T716I | | S982A | | D1118H | | |
| B.1.351 (SA) | | | | A701V | | | | | | | |
| B.1.1.298 (DK) | | | I692V | | | | | | | | M1229I |
| B.1.427/B.1.429 (CAL) | | | | | | | | | | | |
| B.1.525 | Q677H | | | | | F888L | | | | | |
| B.1.526 (NY) | | | | A701V | | | | | | | |

B.1.1.529

B.1.529 ("Omicron variant") was first detected in South Africa in November 2021. Omicron multiplies around 70 times faster than Delta variants, and quickly became the dominant strain of SARS-CoV-2 worldwide. Since its initial detection, a number of Omicron sublineages have arisen. Listed below are the current Omicron variants of concern, along with certain characteristic mutations associated with the S protein of each. The S protein of BA.4 and BA.5 have the same set of characteristic mutations, which is why the below table has a single row for "BA.4 or BA.5", and why the present disclosure refers to a "BA.4/5" S protein in some embodiments. Similarly, the S proteins of the BA.4.6 and BF.7 Omicron variants have the same set of characteristic mutations, which is why the below table has a single row for "BA.4.6 or BF.7").

TABLE 2

Omicron Variants of Concern and Characteristic mutations

| Subvariant | Common mutations |
|---|---|
| BA.1 | A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F |
| BA.2 | T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K |
| BA.2.12.1 | T19I, Δ24-26, A27S, G142D, V213G, G339D, S371F, S373P, S375F, T376A, D405N, R408S, K417N, N440K, L452Q, S477N, T478K, E484A, Q493R, Q498R, N501Y, Y505H, D614G, H655Y, N679K, P681H, S704L, N764K, D796Y, Q954H, N969K |
| BA.4 or BA.5 | T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K |
| BA.2.75 | T19I, Δ24-26, A27S, G142D, K147E, W152R, F157L, I210V, V213G, G257S, G339H, N354D, S371F, S373P, S375F, T376A, |

TABLE 2-continued

| Omicron Variants of Concern and Characteristic mutations | |
|---|---|
| Subvariant | Common mutations |
| | D405N, R408S, K417N, N440K, G446S, N460K, S477N, T478K, E484A, Q498R, N501Y, Y505H D614G, H655Y, N679K, P681H, N764K, D796Y, Q954H, and N969K |
| BA.2.75.2 | T19I, Δ24-26, A27S, G142D, K147E, W152R, F157L, I210V, V213G, G257S, G339H, R346T, N354D, S371F, S373P, S375F, T376A, D405N, R408S, K417N, N440K, G446S, N460K, S477N, T478K, E484A, F486S, Q498R, N501Y, Y505H, D614G, H655Y, N679K, P681H, N764K, D796Y, Q954H, N969K, and D1199N |
| BJ.1 | T19I, Δ24-26, A27S, V83A, G142D, Δ144, H146Q, Q183E, V213E, G339H, R346T, L368I, S371F, S373P, S375F, T376A, D405N, R408S, K417N, N440K, V445P, G446S, S477N, T478K, V483A, E484A, F490V, Q493R, Q498R, N501Y, Y505H, D614G, H655Y, N679K, P681H, N764K, D796Y, G798D, Q954H, N969K, and S1003I |
| BA.4.6 or BF.7 | T19I, Δ24-26, A27S, Δ69/70, G142D, V213G, G339D, R346T, S371F, S373P, S375F, T376A, D405N, R408S, K417N, N440K, L452R, S477N, T478K, E484A, F486V, Q498R, N501Y, Y505H, D614G, H655Y, N658S, N679K, P681H, N764K, D796Y, Q954H, and N969K |
| XBB | T19I, Δ24-26, A27S, V83A, G142D, Δ144, H146Q, Q183E, V213E, G339H, R346T, L368I, S371F, S373P, S375F, T376A, D405N, R408S, K417N, N440K, V445P, G446S, N460K, S477N, T478K, E484A, F486S, F490S, Q493R, Q498R, N501Y, Y505H, D614G, H655Y, N679K, P681H, N764K, D796Y, Q954H, and N969K |
| XBB.1 | T19I, Δ24-26, A27S, V83A, G142D, Δ144, H146Q, Q183E, V213E, G252V, G339H, R346T, L368I, S371F, S373P, S375F, T376A, D405N, R408S, K417N, N440K, V445P, G446S, N460K, S477N, T478K, E484A, F486S, F490S, Q493R, Q498R, N501Y, Y505H, D614G, H655Y, N679K, P681H, N764K, D796Y, Q954H, and N969K |
| XBB.2 | T19I, Δ24-26, A27S, V83A, G142D, Δ144, H146Q, Q183E, V213E, D253G, G339H, R346T, L368I, S371F, S373P, S375F, T376A, D405N, R408S, K417N, N440K, V445P, G446S, N460K, S477N, T478K, E484A, F486S, F490S, Q493R, Q498R, N501Y, Y505H, D614G, H655Y, N679K, P681H, N764K, D796Y, Q954H, and N969K |
| XBB.1.3 | T19I, Δ24-26, A27S, V83A, G142D, Δ144, H146Q, Q183E, V213E, G252V, G339H, R346T, L368I, S371F, S373P, S375F, T376A, D405N, R408S, K417N, N440K, V445P, G446S, N460K, S477N, T478K, A484T, F486S, F490S, Q493R, Q498R, N501Y, Y505H, D614G, H655Y, N679K, P681H, N764K, D796Y, Q954H, and N969K |
| BA.2.3.20 | T19I, Δ24-26, A27S, G142D, M153T, N164K, V213G, H245N, G257D, G339D, S371F, S373P, S375F, T376A, D405N, R408S, K417N, N440K, K444R, E484R N450D, L452M, N460K, S477N, T478K, E484A, Q493R, Q498R, N501Y, Y505H, D614G, H655Y, N679K, P681H, N764K, D796Y, Q954H, and N969K |
| BQ.1.1 | T19I, Δ24-26, A27S, Δ69/70, G142D, V213G, G339D, R346T, S371F, S373P, S375F, T376A, D405N, R408S, K417N, N440K, K444T, L452R, N460K, S477N, T478K, E484A, F486V, Q498R, N501Y, Y505H, D614G, H655Y, N679K, P681H, N764K, D796Y, Q954H, N969K |

In some embodiments, RNA described herein comprises a nucleotide sequence encoding a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) that are characteristic of an Omicron variant (e.g., one or more mutations of an Omicron variant listed in Table 2). In some embodiments, such RNA further comprises one or more mutations that stabilize the S protein in a pre-fusion confirmation (e.g., in some embodiments, such RNA further comprises proline residues at positions corresponding to residues 986 and 987 of SEQ ID NO: 1). In some embodiments, an RNA comprises a nucleotide sequence encoding a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) listed in Table 2. In some such embodiments, one or more mutations may come from two or more variants as listed in Table 2. In some embodiments, an RNA comprises a nucleotide sequence encoding a SARS-CoV-2 S protein comprising each of the mutations identified in Table 2 as being characteristic of a certain Omicron variant (e.g., in some embodiments, an RNA comprises a nucleotide sequence encoding a SARS-CoV-2 S protein comprising each of the mutations listed in Table 2 as being characteristic of an Omicron BA.1, BA.2, BA.2.12.1, BA.4/5, BA.2.75, BA.2.75.1, BA.4.6, BQ.1.1, XBB, XBB.1, XBB.2, or XBB.1.3 variant).

In some embodiments, an RNA disclosed herein comprises a nucleotide sequence that encodes an immunogenic fragment of the SARS-Cov-2 S protein (e.g., the RBD) and which comprises one or more mutations that are characteristic of a SARS-CoV-2 variant (e.g., an Omicron variant described herein). For example, in some embodiments, an RNA comprises a nucleotide sequence encoding the RBD of an S protein of a SARS-CoV-2 variant (e.g., a region of the S protein corresponding to amino acids 327 to 528 of SEQ ID NO: 1, and comprising one or more mutations that are characteristic of a variant of concern that lie within this region of the S protein).

In some embodiments, an RNA encodes a SARS-CoV-2 S protein comprising a subset of the mutations listed in Table 2. In some embodiments, an RNA encodes a SARS-CoV-2 S protein comprising the mutations listed in Table 2 that are most prevalent in a certain variant (e.g., mutations that have been detected in at least 30%, at least 40%, at least 50%, at least 60%, at least 70%, at least 80%, at least 90%, at least 95%, at least 96%, at least 97%, at least 98%, at least 99%, or 100% of sequences collected to date for a given variant sequenced). Mutation prevalence can be determined, e.g., based on published sequences (e.g., sequences that are collected and made available to the public by GISAID).

In some embodiments, RNA described herein encodes a SARS-CoV-2 S protein comprising one or more mutations that are characteristic of a BA.4/5 variant. In some embodiments, the one or more mutations characteristic of a BA.4/5 variant include T19I, Δ24-26, A27S, Δ69/70, G142D, V213G, G339D, S371F, S373P, S375F, T376A, D405N, K417N, N440K, L452R, S477N, T478K, E484A, F486V, Q498R, N501Y, Y505H, D614G, H655Y, N679K, P681H, N764K, D796Y, Q954H, and N969K. In some embodiments, RNA described herein encodes a SARS-CoV-2 S protein comprising one or more mutations that are characteristic of a BA.4/5 variant and excludes R408S. In some embodiments, RNA described herein encodes a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) that are characteristic of a BA.4/5 variant and excludes R408S.

In some embodiments, RNA described herein encodes a SARS-CoV-2 S protein comprising one or more (including, e.g., 2, 3, 4, 5, 6, 7, 8, 9, 10, 11, 12, 13, 14, 15, 16, 17, 18, 19, 20, or more) mutations characteristic of a BA.2.75 variant. In some embodiments, the one or more mutations characteristic of a BA.2.75 variant include T19I, Δ24-26, A27S, G142D, K147E, W152R, F157L, I210V, V213G, G257S, G339H, S371F, S373P, S375F, T376A, D405N, R408S, K417N, N440K, G446S, N460K, S477N, T478K, E484A, Q498R, N501Y, Y505H D614G, H655Y, N679K, P681H, N764K, Q954H, and N969K. In some embodiments, RNA described herein encodes a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) that are characteristic of a BA.2.75 variant, and which excludes N354D. In some embodiments, RNA described herein encodes a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) that are characteristic of a BA.2.75 variant, and which excludes D796Y. In some embodiments, RNA described herein encodes a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) that are characteristic of a BA.2.75 variant, and which excludes D796Y and N354D.

In some embodiments, RNA described herein encodes a SARS-CoV-2 S protein comprising one or more mutations characteristic of a BA.2.75.2 variant. In some embodiments, the one or more mutations characteristic of a BA.2.75.2 variant include T19I, Δ24-26, A27S, G142D, K147E, W152R, F157L, I210V, V213G, G257S, G339H, R346T, N354D, S371F, S373P, S375F, T376A, D405N, R408S, K417N, N440K, G446S, N460K, S477N, T478K, E484A, F486S, Q498R, N501Y, Y505H, D614G, H655Y, N679K, P681H, N764K, D796Y, Q954H, N969K, and D1199N. In some embodiments, RNA described herein encodes a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) that are characteristic of a BA.2.75.2 variant, and which excludes R346T.

In some embodiments, RNA described herein encodes a SARS-CoV-2 S protein comprising one or more mutations characteristic of a BA.4.6 or BF.7 variant. In some embodiments, the one or more mutations characteristic of a BA.4.6 or BF.7 variant include T19I, Δ24-26, A27S, Δ69/70, G142D, V213G, G339D, R346T, S371F, S373P, S375F, T376A, D405N, K417N, N440K, L452R, S477N, T478K, E484A, F486V, Q498R, N501Y, Y505H, D614G, H655Y, N679K, P681H, N764K, D796Y, Q954H, and N969K. In some embodiments, RNA described herein encodes a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) that are characteristic of a BA.4.6 or BF.7 variant, and which exclude R408S. In some embodiments, RNA described herein encodes a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) that are characteristic of a BA.4.6 or BF.7 variant, and which exclude N658S. In some embodiments, RNA described herein encodes a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) that are characteristic of a BA.4.6 or BF.7 variant, and which exclude N658S and R408S.

In some embodiments, RNA described herein encodes a SARS-CoV-2 S protein comprising one or more mutations characteristic of an Omicron XBB variant. In some embodiments, the one or more mutations characteristic of an Omicron XBB variant include T19I, Δ24-26, A27S, V83A, G142D, Δ144, H146Q, Q183E, V213E, G339H, R346T, L368I, S371F, S373P, S375F, T376A, D405N, R408S, K417N, N440K, V445P, G446S, N460K, S477N, T478K, E484A, F486S, F490S, Q498R, N501Y, Y505H, D614G, H655Y, N679K, P681H, N764K, D796Y, Q954H, and N969K.

In some embodiments, RNA described herein encodes a SARS-CoV-2 S protein comprising one or more mutations characteristic of an Omicron XBB.1 variant. In some embodiments, the one or more mutations characteristic of an Omicron XBB.1 variant include G252V. In some embodiments, the one or more mutations characteristic of an Omicron XBB.1 variant include T19I, Δ24-26, A27S, V83A, G142D, Δ144, H146Q, Q183E, V213E, G252V, G339H, R346T, L368I, S371F, S373P, S375F, T376A, D405N, R408S, K417N, N440K, V445P, G446S, N460K, S477N, T478K, E484A, F486S, F490S, Q498R, N501Y, Y505H, D614G, H655Y, N679K, P681H, N764K, D796Y, Q954H, and N969K. In some embodiments, RNA described herein encodes a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) that are characteristic of an Omicron XBB.1 variant and which exclude Q493R. In some embodiments, RNA described herein encodes a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) that are characteristic of an Omicron XBB variant and which exclude Q493R and G252V.

In some embodiments, RNA described herein encodes a SARS-CoV-2 S protein comprising one or more mutations characteristic of an Omicron XBB.2 variant. In some embodiments, the one or more mutations characteristic of an Omicron XBB.2 variant include D253G. In some embodiments, the one or more mutations characteristic of an Omicron-XBB.2 variant include T19I, Δ24-26, A27S, V83A, G142D, Δ144, H146Q, Q183E, V213E, D253G, G339H, R346T, L368I, S371F, S373P, S375F, T376A, D405N, R408S, K417N, N440K, V445P, G446S, N460K, S477N, T478K, E484A, F486S, F490S, Q493R, Q498R, N501Y, Y505H, D614G, H655Y, N679K, P681H, N764K, D796Y, Q954H, and N969K.

In some embodiments, RNA described herein encodes a SARS-CoV-2 S protein comprising one or more mutations characteristic of an Omicron XBB.1.3 variant. In some embodiments, the one or more mutations characteristic of an Omicron XBB.1.3 variant include G252V and Δ484T. In some embodiments, the one or more mutations characteristic of an Omicron XBB.1.3 variant include T19I, Δ24-26, A27S, V83A, G142D, Δ144, H146Q, Q183E, V213E, G252V, G339H, R346T, L368I, S371F, S373P, S375F, T376A, D405N, R408S, K417N, N440K, V445P, G446S, N460K, S477N, T478K, Δ484T, F486S, F490S, Q493R, Q498R, N501Y, Y505H, D614G, H655Y, N679K, P681H, N764K, D796Y, Q954H, and N969K.

In some embodiments, RNA described herein encodes a SARS-CoV-2 S protein comprising one or more mutations that are characteristic of a BQ.1.1 variant. In some embodiments, the one or more mutations characteristic of a BQ.1.1 variant include T19I, Δ24-26, A27S, Δ69/70, G142D, V213G, G339D, S371F, S373P, S375F, T376A, D405N, R408S, K417N, N440K, K444T, L452R, N463K, S477N, T478K, E484A, F486V, Q498R, N501Y, Y505H, D614G, H655Y, N679K, P681H, N764K, D796Y, Q954H, and N969K. In some embodiments, RNA described herein encodes a SARS-CoV-2 S protein comprising one or more mutations (including, e.g., 2, 3, 4, 5, 6, 7, 8, 9, 10, 11, 12, 13, 14, 15, 16, 17, 18, 19, 20, or more) that are characteristic of a BQ.1.1 variant.

In one embodiment, the vaccine antigen described herein comprises, consists essentially of or consists of a spike protein (S) of SARS-CoV-2, a variant thereof, or an immunogenic fragment thereof (e.g., but not limited to RBD).

In one embodiment, a vaccine antigen comprises the amino acid sequence of amino acids 17 to 1273 of SEQ ID NO: 1 or 7, an amino acid sequence having at least 99%, 98%, 97%, 96%, 95%, 90%, 85%, or 80% identity to the amino acid sequence of amino acids 17 to 1273 of SEQ ID NO: 1 or 7, or an immunogenic fragment of the amino acid sequence of amino acids 17 to 1273 of SEQ ID NO: 1 or 7, or the amino acid sequence having at least 99%, 98%, 97%, 96%, 95%, 90%, 85%, or 80% identity to the amino acid sequence of amino acids 17 to 1273 of SEQ ID NO: 1 or 7. In one embodiment, a vaccine antigen comprises the amino acid sequence of amino acids 17 to 1273 of SEQ ID NO: 1 or 7.

In one embodiment, RNA encoding a vaccine antigen (i) comprises the nucleotide sequence of nucleotides 49 to 3819 of SEQ ID NO: 2, 8 or 9, a nucleotide sequence having at least 99%, 98%, 97%, 96%, 95%, 90%, 85%, or 80% identity to the nucleotide sequence of nucleotides 49 to 3819 of SEQ ID NO: 2, 8 or 9, or a fragment of the nucleotide sequence of nucleotides 49 to 3819 of SEQ ID NO: 2, 8 or 9, or the nucleotide sequence having at least 99%, 98%, 97%, 96%, 95%, 90%, 85%, or 80% identity to the nucleotide sequence of nucleotides 49 to 3819 of SEQ ID NO: 2, 8 or 9; and/or (ii) encodes an amino acid sequence comprising the amino acid sequence of amino acids 17 to 1273 of SEQ ID NO: 1 or 7, an amino acid sequence having at least 99%, 98%, 97%, 96%, 95%, 90%, 85%, or 80% identity to the amino acid sequence of amino acids 17 to 1273 of SEQ ID NO: 1 or 7, or an immunogenic fragment of the amino acid sequence of amino acids 17 to 1273 of SEQ ID NO: 1 or 7, or the amino acid sequence having at least 99%, 98%, 97%, 96%, 95%, 90%, 85%, or 80% identity to the amino acid sequence of amino acids 17 to 1273 of SEQ ID NO: 1 or 7. In one embodiment, RNA encoding a vaccine antigen (i) comprises the nucleotide sequence of nucleotides 49 to 3819 of SEQ ID NO: 2, 8 or 9; and/or (ii) encodes an amino acid sequence comprising the amino acid sequence of amino acids 17 to 1273 of SEQ ID NO: 1 or 7.

In one embodiment, the vaccine antigen comprises, consists essentially of or consists of SARS-CoV-2 spike S1 fragment (S1) (the S1 subunit of a spike protein (S) of SARS-CoV-2), a variant thereof, or a fragment thereof.

In one embodiment, a vaccine antigen comprises the amino acid sequence of amino acids 17 to 683 of SEQ ID NO: 1, an amino acid sequence having at least 99%, 98%, 97%, 96%, 95%, 90%, 85%, or 80% identity to the amino acid sequence of amino acids 17 to 683 of SEQ ID NO: 1, or an immunogenic fragment of the amino acid sequence of amino acids 17 to 683 of SEQ ID NO: 1, or the amino acid sequence having at least 99%, 98%, 97%, 96%, 95%, 90%, 85%, or 80% identity to the amino acid sequence of amino acids 17 to 683 of SEQ ID NO: 1. In one embodiment, a vaccine antigen comprises the amino acid sequence of amino acids 17 to 683 of SEQ ID NO: 1.

In one embodiment, RNA encoding a vaccine antigen (i) comprises the nucleotide sequence of nucleotides 49 to 2049 of SEQ ID NO: 2, 8 or 9, a nucleotide sequence having at least 99%, 98%, 97%, 96%, 95%, 90%, 85%, or 80% identity to the nucleotide sequence of nucleotides 49 to 2049 of SEQ ID NO: 2, 8 or 9, or a fragment of the nucleotide sequence of nucleotides 49 to 2049 of SEQ ID NO: 2, 8 or 9, or the nucleotide sequence having at least 99%, 98%, 97%, 96%, 95%, 90%, 85%, or 80% identity to the nucleotide sequence of nucleotides 49 to 2049 of SEQ ID NO: 2, 8 or 9; and/or (ii) encodes an amino acid sequence comprising the amino acid sequence of amino acids 17 to 683 of SEQ ID NO: 1, an amino acid sequence having at least 99%, 98%, 97%, 96%, 95%, 90%, 85%, or 80% identity to the amino acid sequence of amino acids 17 to 683 of SEQ ID NO: 1, or an immunogenic fragment of the amino acid sequence of amino acids 17 to 683 of SEQ ID NO: 1, or the amino acid sequence having at least 99%, 98%, 97%, 96%, 95%, 90%, 85%, or 80% identity to the amino acid sequence of amino acids 17 to 683 of SEQ ID NO: 1. In one embodiment, RNA encoding a vaccine antigen (i) comprises the nucleotide sequence of nucleotides 49 to 2049 of SEQ ID NO: 2, 8 or 9; and/or (ii) encodes an amino acid sequence comprising the amino acid sequence of amino acids 17 to 683 of SEQ ID NO: 1.

In one embodiment, a vaccine antigen comprises the amino acid sequence of amino acids 17 to 685 of SEQ ID NO: 1, an amino acid sequence having at least 99%, 98%, 97%, 96%, 95%, 90%, 85%, or 80% identity to the amino acid sequence of amino acids 17 to 685 of SEQ ID NO: 1, or an immunogenic fragment of the amino acid sequence of amino acids 17 to 685 of SEQ ID NO: 1, or the amino acid sequence having at least 99%, 98%, 97%, 96%, 95%, 90%, 85%, or 80% identity to the amino acid sequence of amino acids 17 to 685 of SEQ ID NO: 1. In one embodiment, a vaccine antigen comprises the amino acid sequence of amino acids 17 to 685 of SEQ ID NO: 1.

In one embodiment, RNA encoding a vaccine antigen (i) comprises the nucleotide sequence of nucleotides 49 to 2055 of SEQ ID NO: 2, 8 or 9, a nucleotide sequence having at least 99%, 98%, 97%, 96%, 95%, 90%, 85%, or 80% identity to the nucleotide sequence of nucleotides 49 to 2055 of SEQ ID NO: 2, 8 or 9, or a fragment of the nucleotide sequence of nucleotides 49 to 2055 of SEQ ID NO: 2, 8 or 9, or the nucleotide sequence having at least 99%, 98%, 97%, 96%, 95%, 90%, 85%, or 80% identity to the nucleotide sequence of nucleotides 49 to 2055 of SEQ ID NO: 2, 8 or 9; and/or (ii) encodes an amino acid sequence comprising the amino acid sequence of amino acids 17 to 685 of SEQ ID NO: 1, an amino acid sequence having at least 99%, 98%, 97%, 96%, 95%, 90%, 85%, or 80% identity to the amino acid sequence of amino acids 17 to 685 of SEQ ID NO: 1, or an immunogenic fragment of the amino acid sequence of amino acids 17 to 685 of SEQ ID NO: 1, or the amino acid sequence having at least 99%, 98%, 97%, 96%, 95%, 90%, 85%, or 80% identity to the amino acid sequence of amino acids 17 to 685 of SEQ ID NO: 1. In one embodiment, RNA encoding a vaccine antigen (i) comprises the nucleotide sequence of nucleotides 49 to 2055 of SEQ ID NO: 2, 8 or 9; and/or (ii) encodes an amino acid sequence comprising the amino acid sequence of amino acids 17 to 685 of SEQ ID NO: 1.

In one embodiment, a vaccine antigen comprises, consists essentially of or consists of the receptor binding domain (RBD) of the S1 subunit of a spike protein (S) of SARS-CoV-2, a variant thereof, or a fragment thereof. The amino acid sequence of amino acids 327 to 528 of SEQ ID NO: 1, a variant thereof, or a fragment thereof is also referred to herein as "RBD" or "RBD domain".

In one embodiment, a vaccine antigen comprises the amino acid sequence of amino acids 327 to 528 of SEQ ID NO: 1, an amino acid sequence having at least 99%, 98%, 97%, 96%, 95%, 90%, 85%, or 80% identity to the amino acid sequence of amino acids 327 to 528 of SEQ ID NO: 1, or an immunogenic fragment of the amino acid sequence of amino acids 327 to 528 of SEQ ID NO: 1, or the amino acid sequence having at least 99%, 98%, 97%, 96%, 95%, 90%, 85%, or 80% identity to the amino acid sequence of amino acids 327 to 528 of SEQ ID NO: 1. In one embodiment, a vaccine antigen comprises the amino acid sequence of amino acids 327 to 528 of SEQ ID NO: 1.

In one embodiment, RNA encoding a vaccine antigen (i) comprises the nucleotide sequence of nucleotides 979 to 1584 of SEQ ID NO: 2, 8 or 9, a nucleotide sequence having at least 99%, 98%, 97%, 96%, 95%, 90%, 85%, or 80% identity to the nucleotide sequence of nucleotides 979 to 1584 of SEQ ID NO: 2, 8 or 9, or a fragment of the nucleotide sequence of nucleotides 979 to 1584 of SEQ ID NO: 2, 8 or 9, or the nucleotide sequence having at least 99%, 98%, 97%, 96%, 95%, 90%, 85%, or 80% identity to the nucleotide sequence of nucleotides 979 to 1584 of SEQ ID NO: 2, 8 or 9; and/or (ii) encodes an amino acid sequence comprising the amino acid sequence of amino acids 327 to 528 of SEQ ID NO: 1, an amino acid sequence having at least 99%, 98%, 97%, 96%, 95%, 90%, 85%, or 80% identity to the amino acid sequence of amino acids 327 to 528 of SEQ ID NO: 1, or an immunogenic fragment of the amino acid sequence of amino acids 327 to 528 of SEQ ID NO: 1, or the amino acid sequence having at least 99%, 98%, 97%, 96%, 95%, 90%, 85%, or 80% identity to the amino acid sequence of amino acids 327 to 528 of SEQ ID NO: 1. In one embodiment, RNA encoding a vaccine antigen (i) comprises the nucleotide sequence of nucleotides 979 to 1584 of SEQ ID NO: 2, 8 or 9; and/or (ii) encodes an amino acid sequence comprising the amino acid sequence of amino acids 327 to 528 of SEQ ID NO: 1.

According to certain embodiments, a signal peptide is fused, either directly or through a linker, to a SARS-CoV-2 S protein, a variant thereof, or a fragment thereof, i.e., the antigenic peptide or protein. Accordingly, in one embodiment, a signal peptide is fused to the above described amino acid sequences derived from SARS-CoV-2 S protein or immunogenic fragments thereof (antigenic peptides or proteins) comprised by the vaccine antigens described above.

Such signal peptides are sequences, which typically exhibit a length of about 15 to 30 amino acids and are preferably located at the N-terminus of the antigenic peptide or protein, without being limited thereto. Signal peptides as defined herein preferably allow the transport of the antigenic peptide or protein as encoded by the RNA into a defined cellular compartment, preferably the cell surface, the endoplasmic reticulum (ER) or the endosomal-lysosomal compartment. In one embodiment, the signal peptide sequence as defined herein includes, without being limited thereto, the signal peptide sequence of SARS-CoV-2 S protein, in particular a sequence comprising the amino acid sequence of amino acids 1 to 16 or 1 to 19 of SEQ ID NO: 1 or a functional variant thereof.

In one embodiment, a signal sequence comprises the amino acid sequence of amino acids 1 to 16 of SEQ ID NO: 1, an amino acid sequence having at least 99%, 98%, 97%, 96%, 95%, 90%, 85%, or 80% identity to the amino acid sequence of amino acids 1 to 16 of SEQ ID NO: 1, or a functional fragment of the amino acid sequence of amino acids 1 to 16 of SEQ ID NO: 1, or the amino acid sequence having at least 99%, 98%, 97%, 96%, 95%, 90%, 85%, or 80% identity to the amino acid sequence of amino acids 1 to 16 of SEQ ID NO: 1. In one embodiment, a signal sequence comprises the amino acid sequence of amino acids 1 to 16 of SEQ ID NO: 1.

In one embodiment, RNA encoding a signal sequence (i) comprises the nucleotide sequence of nucleotides 1 to 48 of SEQ ID NO: 2, 8 or 9, a nucleotide sequence having at least 99%, 98%, 97%, 96%, 95%, 90%, 85%, or 80% identity to the nucleotide sequence of nucleotides 1 to 48 of SEQ ID NO: 2, 8 or 9, or a fragment of the nucleotide sequence of nucleotides 1 to 48 of SEQ ID NO: 2, 8 or 9, or the nucleotide sequence having at least 99%, 98%, 97%, 96%, 95%, 90%, 85%, or 80% identity to the nucleotide sequence of nucleotides 1 to 48 of SEQ ID NO: 2, 8 or 9; and/or (ii) encodes an amino acid sequence comprising the amino acid sequence of amino acids 1 to 16 of SEQ ID NO: 1, an amino acid sequence having at least 99%, 98%, 97%, 96%, 95%, 90%, 85%, or 80% identity to the amino acid sequence of amino acids 1 to 16 of SEQ ID NO: 1, or a functional fragment of the amino acid sequence of amino acids 1 to 16 of SEQ ID NO: 1, or the amino acid sequence having at least 99%, 98%, 97%, 96%, 95%, 90%, 85%, or 80% identity to the amino acid sequence of amino acids 1 to 16 of SEQ ID NO: 1. In one embodiment, RNA encoding a signal sequence (i) comprises the nucleotide sequence of nucleotides 1 to 48 of SEQ ID NO: 2, 8 or 9; and/or (ii) encodes an amino acid sequence comprising the amino acid sequence of amino acids 1 to 16 of SEQ ID NO: 1.

In one embodiment, a signal sequence comprises the amino acid sequence of amino acids 1 to 19 of SEQ ID NO: 1, an amino acid sequence having at least 99%, 98%, 97%, 96%, 95%, 90%, 85%, or 80% identity to the amino acid sequence of amino acids 1 to 19 of SEQ ID NO: 1, or a functional fragment of the amino acid sequence of amino acids 1 to 19 of SEQ ID NO: 1, or the amino acid sequence having at least 99%, 98%, 97%, 96%, 95%, 90%, 85%, or 80% identity to the amino acid sequence of amino acids 1 to 19 of SEQ ID NO: 1. In one embodiment, a signal sequence comprises the amino acid sequence of amino acids 1 to 19 of SEQ ID NO: 1.

In one embodiment, RNA encoding a signal sequence (i) comprises the nucleotide sequence of nucleotides 1 to 57 of SEQ ID NO: 2, 8 or 9, a nucleotide sequence having at least 99%, 98%, 97%, 96%, 95%, 90%, 85%, or 80% identity to the nucleotide sequence of nucleotides 1 to 57 of SEQ ID NO: 2, 8 or 9, or a fragment of the nucleotide sequence of nucleotides 1 to 57 of SEQ ID NO: 2, 8 or 9, or the nucleotide sequence having at least 99%, 98%, 97%, 96%, 95%, 90%, 85%, or 80% identity to the nucleotide sequence of nucleotides 1 to 57 of SEQ ID NO: 2, 8 or 9; and/or (ii) encodes an amino acid sequence comprising the amino acid sequence of amino acids 1 to 19 of SEQ ID NO: 1, an amino acid sequence having at least 99%, 98%, 97%, 96%, 95%, 90%, 85%, or 80% identity to the amino acid sequence of amino acids 1 to 19 of SEQ ID NO: 1, or a functional fragment of the amino acid sequence of amino acids 1 to 19 of SEQ ID NO: 1, or the amino acid sequence having at least 99%, 98%, 97%, 96%, 95%, 90%, 85%, or 80% identity to the amino acid sequence of amino acids 1 to 19 of SEQ ID NO: 1. In one embodiment, RNA encoding a signal sequence (i) comprises the nucleotide sequence of nucleotides 1 to 57 of SEQ ID NO: 2, 8 or 9; and/or (ii) encodes an amino acid sequence comprising the amino acid sequence of amino acids 1 to 19 of SEQ ID NO: 1.

In some embodiments, a signal peptide sequence as defined herein includes, without being limited thereto, the signal peptide sequence of an immunoglobulin, e.g., the signal peptide sequence of an immunoglobulin heavy chain variable region, wherein the immunoglobulin may be human immunoglobulin. In particular, in some embodiments the signal peptide sequence as defined herein includes a sequence comprising the amino acid sequence of amino acids 1 to 22 of SEQ ID NO: 31 or a functional variant thereof.

In some embodiments, a signal peptide sequence is functional in mammalian cells.

In some embodiments, a utilized signal sequence is "intrinsic" in that it is, in nature, it is associated with (e.g., linked to) the encoded polypeptide.

In some embodiments, a utilized signal sequence is heterologous to the encoded polypeptide—e.g., is not naturally part of a polypeptide (e.g., protein) whose sequences are included in the encoded polypeptide.

In some embodiments, signal peptides are sequences, which are typically characterized by a length of about 15 to 30 amino acids.

In many embodiments, signal peptides are positioned at the N-terminus of an encoded polypeptide as described herein, without being limited thereto. In some embodiments, signal peptides preferably allow the transport of the polypeptide encoded by RNAs of the present disclosure with which they are associated into a defined cellular compartment, preferably the cell surface, the endoplasmic reticulum (ER) or the endosomal-lysosomal compartment.

In some embodiments, a signal sequence is selected from an 5152 signal peptide (aa 1-19), an immunoglobulin secretory signal peptide (aa 1-22), an HSV-1 gD signal peptide (MGGAAARLGAVILFVVIVGLHGVRSKY (SEQ ID NO: 105)), an HSV-2 gD signal peptide (MGRLTSGVGTAALLVVAVGLRVVCA (SEQ ID NO: 106)); a human SPARC signal peptide, a human insulin isoform 1 signal peptide, a human albumin signal peptide, etc. Those skilled in the art will be aware of other secretory signal peptides such as, for example, as disclosed in WO2017/081082 (e.g., SEQ ID NOs: 1-1115 and 1728, or fragments variants thereof) and WO2019008001.

In some embodiments, an RNA sequence encodes an epitope that may comprise or otherwise be linked to a signal sequence (e.g., secretory sequence), such as those listed in Table A, or at least a sequence having 1, 2, 3, 4, or 5 amino acid differences relative thereto. In some embodiments, a signal sequence such as MFVFLVLLPLVSSQCVNLT (SEQ ID NO: 108), or at least a sequence having 1, 2, 3, 4, or at the most 5 amino acid differences relative thereto is utilized. In some embodiments, a sequence such as MFVFLVLLPLVSSQCVNLT (SEQ ID NO: 108), or a sequence having 1, 2, 3, 4, or at the most 5 amino acid differences relative thereto, is utilized. In some embodiments, a signal sequence is selected from those included in the Table A below and/or those encoded by the sequences in Table B below:

TABLE A

Exemplary signal sequences

| SEQ ID NO: | Signal | Sequence (Amino Acid) |
|---|---|---|
| 105 | HSV-1 gD SP | MGGAAARLGAVILFVVIVGLHGVRSKY |
| 106 | HSV-2 gD SP | MGRLTSGVGTAALLVVAVGLRVVCA |
| 107 | HSV-2 | MGRLTSGVGTAALLVVAVGLRVVCAKYA |
| 108 | SARS-COV-2-S | MFVFLVLLPLVSSQCVNLT |
| 109 | human Ig heavy chain signal peptide (huSec) | MDWIWRILFLVGAATGAHSQM |
| 110 | HuIgGk signal peptide | METPAQLLFLLLLWLPDTTG |
| 111 | IgE heavy chain epsilon-1signal peptide | MDWTWILFLVAAATRVHS |
| 112 | Japanese encephalitis PRM signal sequence | MLGSNSGQRVVFTILLLLVAPAYS |
| 113 | VSVg protein signal sequence | MKCLLYLAFLFIGVNCA |
| 114 | | MDWTWILFLVAAATRVHS |
| 115 | | ETPAQLLFLLLLWLPDTTG |
| 116 | | MLGSNSGQRVVFTILLLLVAPAYS |
| 117 | | MKCLLYLAFLFIGVNCA |
| 118 | | MWLVSLAIVTACAGA |
| 119 | | MFVFLVLLPLVSSQC |

TABLE B

| Exemplary nucleotide sequences encoding signal sequences | | |
|---|---|---|
| SEQ ID NO: | Signal | Sequence (Nucleotide) |
| 120 | HSV-1 gD SP wild-type | ATGGGGGGGGCTGCCGCCAGGTTGGG GGCCGTGATTTTGTTTGTCGTCATAG TGGGCCTCCATGGGGTCCGCAGCAAA TAT |
| 121 | HSV-1 gD SP optimized nucleotide sequence | ATGggaggagccGCCGCCagactgggaGC CGTGatcctgttcgtggtgatcGTGgga ctgCATggagtgagaAGCaagtac |
| 122 | SARS-COV-2-S | ATGTTTGTGTTTCTTGTGCTGCTGCCTCT TGTGTCTTCTCAGTGTGTGAATTTGACA |
| 123 | human Ig heavy chain signal peptide (huSec) | ATGGATTGGATTTGGAGAATCCTGTTCCTC GTGGGAGCCGCTACAGGAGCCCACTCCCAG ATG |

In some embodiments, an RNA utilized as described herein encodes a multimerization element (e.g., a heterologous multimerization element). In some embodiments, a heterologous multimerization element comprises a dimerization, trimerization or tetramerization element.

In some embodiments, a multimerization element is one described in WO2017/081082 (e.g., SEQ ID NOs: 1116-1167, or fragments or variants thereof).

Exemplary trimerization and tetramerization elements include, but are not limited to, engineered leucine zippers, fibritin foldon domain from enterobacteria phage T4, GCN4pll, GCN4-pll, and p53.

In some embodiments, a provided encoded polypeptide(s) is able to form a trimeric complex. For example, a utilized encoded polypeptide(s) may comprise a domain allowing formation of a multimeric complex, such as for example particular a trimeric complex of an amino acid sequence comprising an encoded polypeptide(s) as described herein. In some embodiments, a domain allowing formation of a multimeric complex comprises a trimerization domain, for example, a trimerization domain as described herein.

In some embodiments, an encoded polypeptide(s) can be modified by addition of a T4-fibritin-derived "foldon" trimerization domain, for example, to increase its immunogenicity.

In some embodiments, an RNAs described herein encodes a membrane association element (e.g., a heterologous membrane association element), such as a transmembrane domain.

A transmembrane domain can be N-terminal, C-terminal, or internal to an encoded polypeptide. A coding sequence of a transmembrane element is typically placed in frame (i.e., in the same reading frame), 5', 3', or internal to coding sequences of sequences (e.g., sequences encoding polypeptide(s)) with which it is to be linked.

In some embodiments, a transmembrane domain comprises or is a transmembrane domain of Hemagglutinin (HA) of Influenza virus, Env of HIV-1, equine infectious anaemia virus (EIAV), murine leukaemia virus (MLV), mouse mammary tumor virus, G protein of vesicular stomatitis virus (VSV), Rabies virus, or a seven transmembrane domain receptor.

In one embodiment, a signal sequence comprises the amino acid sequence of amino acids 1 to 22 of SEQ ID NO: 31, an amino acid sequence having at least 99%, 98%, 97%, 96%, 95%, 90%, 85%, or 80% identity to the amino acid sequence of amino acids 1 to 22 of SEQ ID NO: 31, or a functional fragment of the amino acid sequence of amino acids 1 to 22 of SEQ ID NO: 31, or the amino acid sequence having at least 99%, 98%, 97%, 96%, 95%, 90%, 85%, or 80% identity to the amino acid sequence of amino acids 1 to 22 of SEQ ID NO: 31. In one embodiment, a signal sequence comprises the amino acid sequence of amino acids 1 to 22 of SEQ ID NO: 31.

In one embodiment, RNA encoding a signal sequence (i) comprises the nucleotide sequence of nucleotides 54 to 119 of SEQ ID NO: 32, a nucleotide sequence having at least 99%, 98%, 97%, 96%, 95%, 90%, 85%, or 80% identity to the nucleotide sequence of nucleotides 54 to 119 of SEQ ID NO: 32, or a fragment of the nucleotide sequence of nucleotides 54 to 119 of SEQ ID NO: 32, or the nucleotide sequence having at least 99%, 98%, 97%, 96%, 95%, 90%, 85%, or 80% identity to the nucleotide sequence of nucleotides 54 to 119 of SEQ ID NO: 32; and/or (ii) encodes an amino acid sequence comprising the amino acid sequence of amino acids 1 to 22 of SEQ ID NO: 31, an amino acid sequence having at least 99%, 98%, 97%, 96%, 95%, 90%, 85%, or 80% identity to the amino acid sequence of amino acids 1 to 22 of SEQ ID NO: 31, or a functional fragment of the amino acid sequence of amino acids 1 to 22 of SEQ ID NO: 31, or the amino acid sequence having at least 99%, 98%, 97%, 96%, 95%, 90%, 85%, or 80% identity to the amino acid sequence of amino acids 1 to 22 of SEQ ID NO: 31. In one embodiment, RNA encoding a signal sequence (i) comprises the nucleotide sequence of nucleotides 54 to 119 of SEQ ID NO: 32; and/or (ii) encodes an amino acid sequence comprising the amino acid sequence of amino acids 1 to 22 of SEQ ID NO: 31.

Such signal peptides are preferably used in order to promote secretion of the encoded antigenic peptide or protein. More preferably, a signal peptide as defined herein is fused to an encoded antigenic peptide or protein as defined herein.

Accordingly, in particularly preferred embodiments, the RNA described herein comprises at least one coding region encoding an antigenic peptide or protein and a signal peptide, said signal peptide preferably being fused to the antigenic peptide or protein, more preferably to the N-terminus of the antigenic peptide or protein as described herein.

In one embodiment, a vaccine antigen comprises the amino acid sequence of SEQ ID NO: 1 or 7, an amino acid sequence having at least 99%, 98%, 97%, 96%, 95%, 90%, 85%, or 80% identity to the amino acid sequence of SEQ ID NO: 1 or 7, or an immunogenic fragment of the amino acid sequence of SEQ ID NO: 1 or 7, or the amino acid sequence having at least 99%, 98%, 97%, 96%, 95%, 90%, 85%, or 80% identity to the amino acid sequence of SEQ ID NO: 1 or 7. In one embodiment, a vaccine antigen comprises the amino acid sequence of SEQ ID NO: 1 or 7.

In one embodiment, RNA encoding a vaccine antigen (i) comprises the nucleotide sequence of SEQ ID NO: 2, 8 or 9, a nucleotide sequence having at least 99%, 98%, 97%, 96%, 95%, 90%, 85%, or 80% identity to the nucleotide sequence of SEQ ID NO: 2, 8 or 9, or a fragment of the nucleotide sequence of SEQ ID NO: 2, 8 or 9, or the nucleotide sequence having at least 99%, 98%, 97%, 96%, 95%, 90%, 85%, or 80% identity to the nucleotide sequence of SEQ ID NO: 2, 8 or 9; and/or (ii) encodes an amino acid sequence comprising the amino acid sequence of SEQ ID NO: 1 or 7, an amino acid sequence having at least 99%, 98%, 97%, 96%, 95%, 90%, 85%, or 80% identity to the amino acid sequence of SEQ ID NO: 1 or 7, or an immunogenic fragment of the amino acid sequence of SEQ ID NO: 1 or 7, or the amino acid sequence having at least 99%, 98%, 97%, 96%, 95%, 90%, 85%, or 80% identity to the amino acid sequence of SEQ ID NO: 1 or 7. In one embodiment, RNA encoding a vaccine antigen (i) comprises the nucleotide sequence of SEQ ID NO: 2, 8 or 9; and/or (ii) encodes an amino acid sequence comprising the amino acid sequence of SEQ ID NO: 1 or 7.

In one embodiment, a vaccine antigen comprises the amino acid sequence of SEQ ID NO: 7, an amino acid sequence having at least 99%, 98%, 97%, 96%, 95%, 90%, 85%, or 80% identity to the amino acid sequence of SEQ ID NO: 7, or an immunogenic fragment of the amino acid sequence of SEQ ID NO: 7, or the amino acid sequence having at least 99%, 98%, 97%, 96%, 95%, 90%, 85%, or 80% identity to the amino acid sequence of SEQ ID NO: 7. In one embodiment, a vaccine antigen comprises the amino acid sequence of SEQ ID NO: 7.

In one embodiment, RNA encoding a vaccine antigen (i) comprises the nucleotide sequence of SEQ ID NO: 15, 16, 19, 20, 24, or 25, a nucleotide sequence having at least 99%, 98%, 97%, 96%, 95%, 90%, 85%, or 80% identity to the nucleotide sequence of SEQ ID NO: 15, 16, 19, 20, 24, or 25, or a fragment of the nucleotide sequence of SEQ ID NO: 15, 16, 19, 20, 24, or 25, or the nucleotide sequence having at least 99%, 98%, 97%, 96%, 95%, 90%, 85%, or 80% identity to the nucleotide sequence of SEQ ID NO: 15, 16, 19, 20, 24, or 25; and/or (ii) encodes an amino acid sequence comprising the amino acid sequence of SEQ ID NO: 7, an amino acid sequence having at least 99%, 98%, 97%, 96%, 95%, 90%, 85%, or 80% identity to the amino acid sequence of SEQ ID NO: 7, or an immunogenic fragment of the amino acid sequence of SEQ ID NO: 7, or the amino acid sequence having at least 99%, 98%, 97%, 96%, 95%, 90%, 85%, or 80% identity to the amino acid sequence of SEQ ID NO: 7. In one embodiment, RNA encoding a vaccine antigen (i) comprises the nucleotide sequence of SEQ ID NO: 15, 16, 19, 20, 24, or 25; and/or (ii) encodes an amino acid sequence comprising the amino acid sequence of SEQ ID NO: 7.

In one embodiment, a vaccine antigen comprises the amino acid sequence of amino acids 1 to 683 of SEQ ID NO: 1, an amino acid sequence having at least 99%, 98%, 97%, 96%, 95%, 90%, 85%, or 80% identity to the amino acid sequence of amino acids 1 to 683 of SEQ ID NO: 1, or an immunogenic fragment of the amino acid sequence of amino acids 1 to 683 of SEQ ID NO: 1, or the amino acid sequence having at least 99%, 98%, 97%, 96%, 95%, 90%, 85%, or 80% identity to the amino acid sequence of amino acids 1 to 683 of SEQ ID NO: 1. In one embodiment, a vaccine antigen comprises the amino acid sequence of amino acids 1 to 683 of SEQ ID NO: 1.

In one embodiment, RNA encoding a vaccine antigen (i) comprises the nucleotide sequence of nucleotides 1 to 2049 of SEQ ID NO: 2, 8 or 9, a nucleotide sequence having at least 99%, 98%, 97%, 96%, 95%, 90%, 85%, or 80% identity to the nucleotide sequence of nucleotides 1 to 2049 of SEQ ID NO: 2, 8 or 9, or a fragment of the nucleotide sequence of nucleotides 1 to 2049 of SEQ ID NO: 2, 8 or 9, or the nucleotide sequence having at least 99%, 98%, 97%, 96%, 95%, 90%, 85%, or 80% identity to the nucleotide sequence of nucleotides 1 to 2049 of SEQ ID NO: 2, 8 or 9; and/or (ii) encodes an amino acid sequence comprising the amino acid sequence of amino acids 1 to 683 of SEQ ID NO: 1, an amino acid sequence having at least 99%, 98%, 97%, 96%, 95%, 90%, 85%, or 80% identity to the amino acid sequence of amino acids 1 to 683 of SEQ ID NO: 1, or an immunogenic fragment of the amino acid sequence of amino acids 1 to 683 of SEQ ID NO: 1, or the amino acid sequence having at least 99%, 98%, 97%, 96%, 95%, 90%, 85%, or 80% identity to the amino acid sequence of amino acids 1 to 683 of SEQ ID NO: 1. In one embodiment, RNA encoding a vaccine antigen (i) comprises the nucleotide sequence of nucleotides 1 to 2049 of SEQ ID NO: 2, 8 or 9; and/or (ii) encodes an amino acid sequence comprising the amino acid sequence of amino acids 1 to 683 of SEQ ID NO: 1.

In one embodiment, a vaccine antigen comprises the amino acid sequence of amino acids 1 to 685 of SEQ ID NO: 1, an amino acid sequence having at least 99%, 98%, 97%, 96%, 95%, 90%, 85%, or 80% identity to the amino acid sequence of amino acids 1 to 685 of SEQ ID NO: 1, or an immunogenic fragment of the amino acid sequence of amino acids 1 to 685 of SEQ ID NO: 1, or the amino acid sequence having at least 99%, 98%, 97%, 96%, 95%, 90%, 85%, or 80% identity to the amino acid sequence of amino acids 1 to 685 of SEQ ID NO: 1. In one embodiment, a vaccine antigen comprises the amino acid sequence of amino acids 1 to 685 of SEQ ID NO: 1.

In one embodiment, RNA encoding a vaccine antigen (i) comprises the nucleotide sequence of nucleotides 1 to 2055 of SEQ ID NO: 2, 8 or 9, a nucleotide sequence having at least 99%, 98%, 97%, 96%, 95%, 90%, 85%, or 80% identity to the nucleotide sequence of nucleotides 1 to 2055 of SEQ ID NO: 2, 8 or 9, or a fragment of the nucleotide sequence of nucleotides 1 to 2055 of SEQ ID NO: 2, 8 or 9, or the nucleotide sequence having at least 99%, 98%, 97%, 96%, 95%, 90%, 85%, or 80% identity to the nucleotide sequence of nucleotides 1 to 2055 of SEQ ID NO: 2, 8 or 9; and/or (ii) encodes an amino acid sequence comprising the amino acid sequence of amino acids 1 to 685 of SEQ ID NO: 1, an amino acid sequence having at least 99%, 98%, 97%, 96%, 95%, 90%, 85%, or 80% identity to the amino acid sequence of amino acids 1 to 685 of SEQ ID NO: 1, or an immunogenic fragment of the amino acid sequence of amino acids 1 to 685 of SEQ ID NO: 1, or the amino acid sequence having at least 99%, 98%, 97%, 96%, 95%, 90%, 85%, or 80% identity to the amino acid sequence of amino acids 1 to 685 of SEQ ID NO: 1. In one embodiment, RNA encoding a vaccine antigen (i) comprises the nucleotide sequence of nucleotides 1 to 2055 of SEQ ID NO: 2, 8 or 9; and/or (ii) encodes an amino acid sequence comprising the amino acid sequence of amino acids 1 to 685 of SEQ ID NO: 1.

In one embodiment, a vaccine antigen comprises the amino acid sequence of SEQ ID NO: 3, an amino acid sequence having at least 99%, 98%, 97%, 96%, 95%, 90%, 85%, or 80% identity to the amino acid sequence of SEQ ID NO: 3, or an immunogenic fragment of the amino acid sequence of SEQ ID NO: 3, or the amino acid sequence having at least 99%, 98%, 97%, 96%, 95%, 90%, 85%, or 80% identity to the amino acid sequence of SEQ ID NO: 3. In one embodiment, a vaccine antigen comprises the amino acid sequence of SEQ ID NO: 3.

In one embodiment, RNA encoding a vaccine antigen (i) comprises the nucleotide sequence of SEQ ID NO: 4, a nucleotide sequence having at least 99%, 98%, 97%, 96%, 95%, 90%, 85%, or 80% identity to the nucleotide sequence of SEQ ID NO: 4, or a fragment of the nucleotide sequence of SEQ ID NO: 4, or the nucleotide sequence having at least 99%, 98%, 97%, 96%, 95%, 90%, 85%, or 80% identity to the nucleotide sequence of SEQ ID NO: 4; and/or (ii) encodes an amino acid sequence comprising the amino acid sequence of SEQ ID NO: 3, an amino acid sequence having at least 99%, 98%, 97%, 96%, 95%, 90%, 85%, or 80% identity to the amino acid sequence of SEQ ID NO: 3, or an immunogenic fragment of the amino acid sequence of SEQ ID NO: 3, or the amino acid sequence having at least 99%, 98%, 97%, 96%, 95%, 90%, 85%, or 80% identity to the amino acid sequence of SEQ ID NO: 3. In one embodiment, RNA encoding a vaccine antigen (i) comprises the nucleotide sequence of SEQ ID NO: 4; and/or (ii) encodes an amino acid sequence comprising the amino acid sequence of SEQ ID NO: 3.

In one embodiment, a vaccine antigen comprises the amino acid sequence of amino acids 1 to 221 of SEQ ID NO: 29, an amino acid sequence having at least 99%, 98%, 97%, 96%, 95%, 90%, 85%, or 80% identity to the amino acid sequence of amino acids 1 to 221 of SEQ ID NO: 29, or an immunogenic fragment of the amino acid sequence of amino acids 1 to 221 of SEQ ID NO: 29, or the amino acid sequence having at least 99%, 98%, 97%, 96%, 95%, 90%, 85%, or 80% identity to the amino acid sequence of amino acids 1 to 221 of SEQ ID NO: 29. In one embodiment, a vaccine antigen comprises the amino acid sequence of amino acids 1 to 221 of SEQ ID NO: 29.

In one embodiment, RNA encoding a vaccine antigen (i) comprises the nucleotide sequence of nucleotides 54 to 716 of SEQ ID NO: 30, a nucleotide sequence having at least 99%, 98%, 97%, 96%, 95%, 90%, 85%, or 80% identity to the nucleotide sequence of nucleotides 54 to 716 of SEQ ID NO: 30, or a fragment of the nucleotide sequence of nucleotides 54 to 716 of SEQ ID NO: 30, or the nucleotide sequence having at least 99%, 98%, 97%, 96%, 95%, 90%, 85%, or 80% identity to the nucleotide sequence of nucleotides 54 to 716 of SEQ ID NO: 30; and/or (ii) encodes an amino acid sequence comprising the amino acid sequence of amino acids 1 to 221 of SEQ ID NO: 29, an amino acid sequence having at least 99%, 98%, 97%, 96%, 95%, 90%, 85%, or 80% identity to the amino acid sequence of amino acids 1 to 221 of SEQ ID NO: 29, or an immunogenic fragment of the amino acid sequence of amino acids 1 to 221 of SEQ ID NO: 29, or the amino acid sequence having at least 99%, 98%, 97%, 96%, 95%, 90%, 85%, or 80% identity to the amino acid sequence of amino acids 1 to 221 of SEQ ID NO: 29. In one embodiment, RNA encoding a vaccine antigen (i) comprises the nucleotide sequence of nucleotides 54 to 716 of SEQ ID NO: 30; and/or (ii) encodes an amino acid sequence comprising the amino acid sequence of amino acids 1 to 221 of SEQ ID NO: 29.

In one embodiment, a vaccine antigen comprises the amino acid sequence of amino acids 1 to 224 of SEQ ID NO: 31, an amino acid sequence having at least 99%, 98%, 97%, 96%, 95%, 90%, 85%, or 80% identity to the amino acid sequence of amino acids 1 to 224 of SEQ ID NO: 31, or an immunogenic fragment of the amino acid sequence of amino acids 1 to 224 of SEQ ID NO: 31, or the amino acid sequence having at least 99%, 98%, 97%, 96%, 95%, 90%, 85%, or 80% identity to the amino acid sequence of amino acids 1 to 224 of SEQ ID NO: 31. In one embodiment, a vaccine antigen comprises the amino acid sequence of amino acids 1 to 224 of SEQ ID NO: 31.

In one embodiment, RNA encoding a vaccine antigen (i) comprises the nucleotide sequence of nucleotides 54 to 725 of SEQ ID NO: 32, a nucleotide sequence having at least 99%, 98%, 97%, 96%, 95%, 90%, 85%, or 80% identity to the nucleotide sequence of nucleotides 54 to 725 of SEQ ID NO: 32, or a fragment of the nucleotide sequence of nucleotides 54 to 725 of SEQ ID NO: 32, or the nucleotide sequence having at least 99%, 98%, 97%, 96%, 95%, 90%, 85%, or 80% identity to the nucleotide sequence of nucleotides 54 to 725 of SEQ ID NO: 32; and/or (ii) encodes an amino acid sequence comprising the amino acid sequence of amino acids 1 to 224 of SEQ ID NO: 31, an amino acid sequence having at least 99%, 98%, 97%, 96%, 95%, 90%, 85%, or 80% identity to the amino acid sequence of amino acids 1 to 224 of SEQ ID NO: 31, or an immunogenic fragment of the amino acid sequence of amino acids 1 to 224 of SEQ ID NO: 31, or the amino acid sequence having at least 99%, 98%, 97%, 96%, 95%, 90%, 85%, or 80% identity to the amino acid sequence of amino acids 1 to 224 of SEQ ID NO: 31. In one embodiment, RNA encoding a vaccine antigen (i) comprises the nucleotide sequence of nucleotides 54 to 725 of SEQ ID NO: 32; and/or (ii) encodes an amino acid sequence comprising the amino acid sequence of amino acids 1 to 224 of SEQ ID NO: 31.

According to certain embodiments, a trimerization domain is fused, either directly or through a linker, e.g., a glycine/serine linker, to a SARS-CoV-2 S protein, a variant thereof, or a fragment thereof, i.e., the antigenic peptide or protein. Accordingly, in one embodiment, a trimerization domain is fused to the above described amino acid sequences derived from SARS-CoV-2 S protein or immunogenic fragments thereof (antigenic peptides or proteins) comprised by the vaccine antigens described above (which may optionally be fused to a signal peptide as described above).

Such trimerization domains are preferably located at the C-terminus of the antigenic peptide or protein, without being limited thereto. Trimerization domains as defined herein preferably allow the trimerization of the antigenic peptide or protein as encoded by the RNA. Examples of trimerization domains as defined herein include, without being limited thereto, foldon, the natural trimerization domain of T4 fibritin. The C-terminal domain of T4 fibritin (foldon) is obligatory for the formation of the fibritin trimer structure and can be used as an artificial trimerization domain. In one embodiment, the trimerization domain as defined herein includes, without being limited thereto, a sequence comprising the amino acid sequence of amino acids 3 to 29 of SEQ ID NO: 10 or a functional variant thereof. In one embodiment, the trimerization domain as defined herein includes, without being limited thereto, a sequence comprising the amino acid sequence of SEQ ID NO: 10 or a functional variant thereof.

In one embodiment, a trimerization domain comprises the amino acid sequence of amino acids 3 to 29 of SEQ ID NO: 10, an amino acid sequence having at least 99%, 98%, 97%, 96%, 95%, 90%, 85%, or 80% identity to the amino acid sequence of amino acids 3 to 29 of SEQ ID NO: 10, or a functional fragment of the amino acid sequence of amino acids 3 to 29 of SEQ ID NO: 10, or the amino acid sequence having at least 99%, 98%, 97%, 96%, 95%, 90%, 85%, or 80% identity to the amino acid sequence of amino acids 3 to 29 of SEQ ID NO: 10. In one embodiment, a trimerization domain comprises the amino acid sequence of amino acids 3 to 29 of SEQ ID NO: 10.

In one embodiment, RNA encoding a trimerization domain (i) comprises the nucleotide sequence of nucleotides 7 to 87 of SEQ ID NO: 11, a nucleotide sequence having at least 99%, 98%, 97%, 96%, 95%, 90%, 85%, or 80% identity to the nucleotide sequence of nucleotides 7 to 87 of SEQ ID NO: 11, or a fragment of the nucleotide sequence of nucleotides 7 to 87 of SEQ ID NO: 11, or the nucleotide sequence having at least 99%, 98%, 97%, 96%, 95%, 90%, 85%, or 80% identity to the nucleotide sequence of nucleotides 7 to 87 of SEQ ID NO: 11; and/or (ii) encodes an amino acid sequence comprising the amino acid sequence of amino acids 3 to 29 of SEQ ID NO: 10, an amino acid sequence having at least 99%, 98%, 97%, 96%, 95%, 90%, 85%, or 80% identity to the amino acid sequence of amino acids 3 to 29 of SEQ ID NO: 10, or a functional fragment of the amino acid sequence of amino acids 3 to 29 of SEQ ID NO: 10, or the amino acid sequence having at least 99%, 98%, 97%, 96%, 95%, 90%, 85%, or 80% identity to the amino acid sequence of amino acids 3 to 29 of SEQ ID NO: 10. In one embodiment, RNA encoding a trimerization domain (i) comprises the nucleotide sequence of nucleotides 7 to 87 of SEQ ID NO: 11; and/or (ii) encodes an amino acid sequence comprising the amino acid sequence of amino acids 3 to 29 of SEQ ID NO: 10.

In one embodiment, a trimerization domain comprises the amino acid sequence SEQ ID NO: 10, an amino acid sequence having at least 99%, 98%, 97%, 96%, 95%, 90%, 85%, or 80% identity to the amino acid sequence of SEQ ID NO: 10, or a functional fragment of the amino acid sequence of SEQ ID NO: 10, or the amino acid sequence having at least 99%, 98%, 97%, 96%, 95%, 90%, 85%, or 80% identity to the amino acid sequence of SEQ ID NO: 10. In one embodiment, a trimerization domain comprises the amino acid sequence of SEQ ID NO: 10.

In one embodiment, RNA encoding a trimerization domain (i) comprises the nucleotide sequence of SEQ ID NO: 11, a nucleotide sequence having at least 99%, 98%, 97%, 96%, 95%, 90%, 85%, or 80% identity to the nucleotide sequence of SEQ ID NO: 11, or a fragment of the nucleotide sequence of SEQ ID NO: 11, or the nucleotide sequence having at least 99%, 98%, 97%, 96%, 95%, 90%, 85%, or 80% identity to the nucleotide sequence of SEQ ID NO: 11; and/or (ii) encodes an amino acid sequence comprising the amino acid sequence of SEQ ID NO: 10, an amino acid sequence having at least 99%, 98%, 97%, 96%, 95%, 90%, 85%, or 80% identity to the amino acid sequence of SEQ ID NO: 10, or a functional fragment of the amino acid sequence of SEQ ID NO: 10, or the amino acid sequence having at least 99%, 98%, 97%, 96%, 95%, 90%, 85%, or 80% identity to the amino acid sequence of SEQ ID NO: 10. In one embodiment, RNA encoding a trimerization domain (i) comprises the nucleotide sequence of SEQ ID NO: 11; and/or (ii) encodes an amino acid sequence comprising the amino acid sequence of SEQ ID NO: 10.

Such trimerization domains are preferably used in order to promote trimerization of the encoded antigenic peptide or protein. More preferably, a trimerization domain as defined herein is fused to an antigenic peptide or protein as defined herein.

Accordingly, in particularly preferred embodiments, the RNA described herein comprises at least one coding region encoding an antigenic peptide or protein and a trimerization domain as defined herein, said trimerization domain preferably being fused to the antigenic peptide or protein, more preferably to the C-terminus of the antigenic peptide or protein.

In one embodiment, a vaccine antigen comprises the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5. In one embodiment, a vaccine antigen comprises the amino acid sequence of SEQ ID NO: 5.

In one embodiment, RNA encoding a vaccine antigen (i) comprises the nucleotide sequence of SEQ ID NO: 6, a nucleotide sequence having at least 99%, 98%, 97%, 96%, 95%, 90%, 85%, or 80% identity to the nucleotide sequence of SEQ ID NO: 6, or a fragment of the nucleotide sequence of SEQ ID NO: 6, or the nucleotide sequence having at least 99%, 98%, 97%, 96%, 95%, 90%, 85%, or 80% identity to the nucleotide sequence of SEQ ID NO: 6; and/or (ii) encodes an amino acid sequence comprising the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5. In one embodiment, RNA encoding a vaccine antigen (i) comprises the nucleotide sequence of SEQ ID NO: 6; and/or (ii) encodes an amino acid sequence comprising the amino acid sequence of SEQ ID NO: 5.

In one embodiment, RNA encoding a vaccine antigen (i) comprises the nucleotide sequence of SEQ ID NO: 17, 21, or 26, a nucleotide sequence having at least 99%, 98%, 97%, 96%, 95%, 90%, 85%, or 80% identity to the nucleotide sequence of SEQ ID NO: 17, 21, or 26, or a fragment of the nucleotide sequence of SEQ ID NO: 17, 21, or 26, or the nucleotide sequence having at least 99%, 98%, 97%, 96%, 95%, 90%, 85%, or 80% identity to the nucleotide sequence of SEQ ID NO: 17, 21, or 26; and/or (ii) encodes an amino acid sequence comprising the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5. In one embodiment, RNA encoding a vaccine antigen (i) comprises the nucleotide sequence of SEQ ID NO: 17, 21, or 26; and/or (ii) encodes an amino acid sequence comprising the amino acid sequence of SEQ ID NO: 5.

In one embodiment, a vaccine antigen comprises the amino acid sequence of SEQ ID NO: 18, an amino acid sequence having at least 99%, 98%, 97%, 96%, 95%, 90%, 85%, or 80% identity to the amino acid sequence of SEQ ID NO: 18, or an immunogenic fragment of the amino acid sequence of SEQ ID NO: 18, or the amino acid sequence having at least 99%, 98%, 97%, 96%, 95%, 90%, 85%, or 80% identity to the amino acid sequence of SEQ ID NO: 18. In one embodiment, a vaccine antigen comprises the amino acid sequence of SEQ ID NO: 18.

In one embodiment, a vaccine antigen comprises the amino acid sequence of amino acids 1 to 257 of SEQ ID NO: 29, an amino acid sequence having at least 99%, 98%, 97%, 96%, 95%, 90%, 85%, or 80% identity to the amino acid sequence of amino acids 1 to 257 of SEQ ID NO: 29, or an immunogenic fragment of the amino acid sequence of amino acids 1 to 257 of SEQ ID NO: 29, or the amino acid sequence having at least 99%, 98%, 97%, 96%, 95%, 90%, 85%, or 80% identity to the amino acid sequence of amino acids 1 to 257 of SEQ ID NO: 29. In one embodiment, a vaccine antigen comprises the amino acid sequence of amino acids 1 to 257 of SEQ ID NO: 29.

In one embodiment, RNA encoding a vaccine antigen (i) comprises the nucleotide sequence of nucleotides 54 to 824 of SEQ ID NO: 30, a nucleotide sequence having at least 99%, 98%, 97%, 96%, 95%, 90%, 85%, or 80% identity to the nucleotide sequence of nucleotides 54 to 824 of SEQ ID NO: 30, or a fragment of the nucleotide sequence of nucleotides 54 to 824 of SEQ ID NO: 30, or the nucleotide sequence having at least 99%, 98%, 97%, 96%, 95%, 90%, 85%, or 80% identity to the nucleotide sequence of nucleotides 54 to 824 of SEQ ID NO: 30; and/or (ii) encodes an amino acid sequence comprising the amino acid sequence of amino acids 1 to 257 of SEQ ID NO: 29, an amino acid sequence having at least 99%, 98%, 97%, 96%, 95%, 90%, 85%, or 80% identity to the amino acid sequence of amino acids 1 to 257 of SEQ ID NO: 29, or an immunogenic fragment of the amino acid sequence of amino acids 1 to 257 of SEQ ID NO: 29, or the amino acid sequence having at least 99%, 98%, 97%, 96%, 95%, 90%, 85%, or 80% identity to the amino acid sequence of amino acids 1 to 257 of SEQ ID NO: 29. In one embodiment, RNA encoding a vaccine antigen (i) comprises the nucleotide sequence of nucleotides 54 to 824 of SEQ ID NO: 30; and/or (ii) encodes an amino acid sequence comprising the amino acid sequence of amino acids 1 to 257 of SEQ ID NO: 29.

In one embodiment, a vaccine antigen comprises the amino acid sequence of amino acids 1 to 260 of SEQ ID NO: 31, an amino acid sequence having at least 99%, 98%, 97%, 96%, 95%, 90%, 85%, or 80% identity to the amino acid sequence of amino acids 1 to 260 of SEQ ID NO: 31, or an immunogenic fragment of the amino acid sequence of amino acids 1 to 260 of SEQ ID NO: 31, or the amino acid sequence having at least 99%, 98%, 97%, 96%, 95%, 90%, 85%, or 80% identity to the amino acid sequence of amino acids 1 to 260 of SEQ ID NO: 31. In one embodiment, a vaccine antigen comprises the amino acid sequence of amino acids 1 to 260 of SEQ ID NO: 31.

In one embodiment, RNA encoding a vaccine antigen (i) comprises the nucleotide sequence of nucleotides 54 to 833 of SEQ ID NO: 32, a nucleotide sequence having at least 99%, 98%, 97%, 96%, 95%, 90%, 85%, or 80% identity to the nucleotide sequence of nucleotides 54 to 833 of SEQ ID NO: 32, or a fragment of the nucleotide sequence of nucleotides 54 to 833 of SEQ ID NO: 32, or the nucleotide sequence having at least 99%, 98%, 97%, 96%, 95%, 90%, 85%, or 80% identity to the nucleotide sequence of nucleotides 54 to 833 of SEQ ID NO: 32; and/or (ii) encodes an amino acid sequence comprising the amino acid sequence of amino acids 1 to 260 of SEQ ID NO: 31, an amino acid sequence having at least 99%, 98%, 97%, 96%, 95%, 90%, 85%, or 80% identity to the amino acid sequence of amino acids 1 to 260 of SEQ ID NO: 31, or an immunogenic fragment of the amino acid sequence of amino acids 1 to 260 of SEQ ID NO: 31, or the amino acid sequence having at least 99%, 98%, 97%, 96%, 95%, 90%, 85%, or 80% identity to the amino acid sequence of amino acids 1 to 260 of SEQ ID NO: 31. In one embodiment, RNA encoding a vaccine antigen (i) comprises the nucleotide sequence of nucleotides 54 to 833 of SEQ ID NO: 32; and/or (ii) encodes an amino acid sequence comprising the amino acid sequence of amino acids 1 to 260 of SEQ ID NO: 31.

In one embodiment, a vaccine antigen comprises the amino acid sequence of amino acids 20 to 257 of SEQ ID NO: 29, an amino acid sequence having at least 99%, 98%, 97%, 96%, 95%, 90%, 85%, or 80% identity to the amino acid sequence of amino acids 20 to 257 of SEQ ID NO: 29, or an immunogenic fragment of the amino acid sequence of amino acids 20 to 257 of SEQ ID NO: 29, or the amino acid sequence having at least 99%, 98%, 97%, 96%, 95%, 90%, 85%, or 80% identity to the amino acid sequence of amino acids 20 to 257 of SEQ ID NO: 29. In one embodiment, a vaccine antigen comprises the amino acid sequence of amino acids 20 to 257 of SEQ ID NO: 29.

In one embodiment, RNA encoding a vaccine antigen (i) comprises the nucleotide sequence of nucleotides 111 to 824 of SEQ ID NO: 30, a nucleotide sequence having at least 99%, 98%, 97%, 96%, 95%, 90%, 85%, or 80% identity to the nucleotide sequence of nucleotides 111 to 824 of SEQ ID NO: 30, or a fragment of the nucleotide sequence of nucleotides 111 to 824 of SEQ ID NO: 30, or the nucleotide sequence having at least 99%, 98%, 97%, 96%, 95%, 90%, 85%, or 80% identity to the nucleotide sequence of nucleotides 111 to 824 of SEQ ID NO: 30; and/or (ii) encodes an amino acid sequence comprising the amino acid sequence of amino acids 20 to 257 of SEQ ID NO: 29, an amino acid sequence having at least 99%, 98%, 97%, 96%, 95%, 90%, 85%, or 80% identity to the amino acid sequence of amino acids 20 to 257 of SEQ ID NO: 29, or an immunogenic fragment of the amino acid sequence of amino acids 20 to 257 of SEQ ID NO: 29, or the amino acid sequence having at least 99%, 98%, 97%, 96%, 95%, 90%, 85%, or 80% identity to the amino acid sequence of amino acids 20 to 257 of SEQ ID NO: 29. In one embodiment, RNA encoding a vaccine antigen (i) comprises the nucleotide sequence of nucleotides 111 to 824 of SEQ ID NO: 30; and/or (ii) encodes an amino acid sequence comprising the amino acid sequence of amino acids 20 to 257 of SEQ ID NO: 29.

In one embodiment, a vaccine antigen comprises the amino acid sequence of amino acids 23 to 260 of SEQ ID NO: 31, an amino acid sequence having at least 99%, 98%, 97%, 96%, 95%, 90%, 85%, or 80% identity to the amino acid sequence of amino acids 23 to 260 of SEQ ID NO: 31, or an immunogenic fragment of the amino acid sequence of amino acids 23 to 260 of SEQ ID NO: 31, or the amino acid sequence having at least 99%, 98%, 97%, 96%, 95%, 90%, 85%, or 80% identity to the amino acid sequence of amino acids 23 to 260 of SEQ ID NO: 31. In one embodiment, a vaccine antigen comprises the amino acid sequence of amino acids 23 to 260 of SEQ ID NO: 31.

In one embodiment, RNA encoding a vaccine antigen (i) comprises the nucleotide sequence of nucleotides 120 to 833 of SEQ ID NO: 32, a nucleotide sequence having at least 99%, 98%, 97%, 96%, 95%, 90%, 85%, or 80% identity to the nucleotide sequence of nucleotides 120 to 833 of SEQ ID NO: 32, or a fragment of the nucleotide sequence of nucleotides 120 to 833 of SEQ ID NO: 32, or the nucleotide sequence having at least 99%, 98%, 97%, 96%, 95%, 90%, 85%, or 80% identity to the nucleotide sequence of nucleotides 120 to 833 of SEQ ID NO: 32; and/or (ii) encodes an amino acid sequence comprising the amino acid sequence of amino acids 23 to 260 of SEQ ID NO: 31, an amino acid sequence having at least 99%, 98%, 97%, 96%, 95%, 90%, 85%, or 80% identity to the amino acid sequence of amino acids 23 to 260 of SEQ ID NO: 31, or an immunogenic fragment of the amino acid sequence of amino acids 23 to 260 of SEQ ID NO: 31, or the amino acid sequence having at least 99%, 98%, 97%, 96%, 95%, 90%, 85%, or 80% identity to the amino acid sequence of amino acids 23 to 260 of SEQ ID NO: 31. In one embodiment, RNA encoding a vaccine antigen (i) comprises the nucleotide sequence of nucleotides 120 to 833 of SEQ ID NO: 32; and/or (ii) encodes an amino acid sequence comprising the amino acid sequence of amino acids 23 to 260 of SEQ ID NO: 31.

According to certain embodiments, a transmembrane domain is fused, either directly or through a linker, e.g., a glycine/serine linker, to a SARS-CoV-2 S protein, a variant thereof, or a fragment thereof, i.e., the antigenic peptide or protein. Accordingly, in one embodiment, a transmembrane domain is fused to the above described amino acid sequences derived from SARS-CoV-2 S protein or immunogenic fragments thereof (antigenic peptides or proteins) comprised by the vaccine antigens described above (which may optionally be fused to a signal peptide and/or trimerization domain as described above).

Such transmembrane domains are preferably located at the C-terminus of the antigenic peptide or protein, without being limited thereto. Preferably, such transmembrane domains are located at the C-terminus of the trimerization domain, if present, without being limited thereto. In one embodiment, a trimerization domain is present between the SARS-CoV-2 S protein, a variant thereof, or a fragment thereof, i.e., the antigenic peptide or protein, and the transmembrane domain.

Transmembrane domains as defined herein preferably allow the anchoring into a cellular membrane of the antigenic peptide or protein as encoded by the RNA.

In one embodiment, the transmembrane domain sequence as defined herein includes, without being limited thereto, the transmembrane domain sequence of SARS-CoV-2 S protein, in particular a sequence comprising the amino acid sequence of amino acids 1207 to 1254 of SEQ ID NO: 1 or a functional variant thereof.

In one embodiment, a transmembrane domain sequence comprises the amino acid sequence of amino acids 1207 to 1254 of SEQ ID NO: 1, an amino acid sequence having at least 99%, 98%, 97%, 96%, 95%, 90%, 85%, or 80% identity to the amino acid sequence of amino acids 1207 to 1254 of SEQ ID NO: 1, or a functional fragment of the amino acid sequence of amino acids 1207 to 1254 of SEQ ID NO: 1, or the amino acid sequence having at least 99%, 98%, 97%, 96%, 95%, 90%, 85%, or 80% identity to the amino acid sequence of amino acids 1207 to 1254 of SEQ ID NO: 1. In one embodiment, a transmembrane domain sequence comprises the amino acid sequence of amino acids 1207 to 1254 of SEQ ID NO: 1.

In one embodiment, RNA encoding a transmembrane domain sequence (i) comprises the nucleotide sequence of nucleotides 3619 to 3762 of SEQ ID NO: 2, 8 or 9, a nucleotide sequence having at least 99%, 98%, 97%, 96%, 95%, 90%, 85%, or 80% identity to the nucleotide sequence of nucleotides 3619 to 3762 of SEQ ID NO: 2, 8 or 9, or a fragment of the nucleotide sequence of nucleotides 3619 to 3762 of SEQ ID NO: 2, 8 or 9, or the nucleotide sequence having at least 99%, 98%, 97%, 96%, 95%, 90%, 85%, or 80% identity to the nucleotide sequence of nucleotides 3619 to 3762 of SEQ ID NO: 2, 8 or 9; and/or (ii) encodes an amino acid sequence comprising the amino acid sequence of amino acids 1207 to 1254 of SEQ ID NO: 1, an amino acid sequence having at least 99%, 98%, 97%, 96%, 95%, 90%, 85%, or 80% identity to the amino acid sequence of amino acids 1207 to 1254 of SEQ ID NO: 1, or a functional fragment of the amino acid sequence of amino acids 1207 to 1254 of SEQ ID NO: 1, or the amino acid sequence having at least 99%, 98%, 97%, 96%, 95%, 90%, 85%, or 80% identity to the amino acid sequence of amino acids 1207 to 1254 of SEQ ID NO: 1. In one embodiment, RNA encoding a transmembrane domain sequence (i) comprises the nucleotide sequence of nucleotides 3619 to 3762 of SEQ ID NO: 2, 8 or 9; and/or (ii) encodes an amino acid sequence comprising the amino acid sequence of amino acids 1207 to 1254 of SEQ ID NO: 1.

In one embodiment, a vaccine antigen comprises the amino acid sequence of amino acids 1 to 311 of SEQ ID NO: 29, an amino acid sequence having at least 99%, 98%, 97%, 96%, 95%, 90%, 85%, or 80% identity to the amino acid sequence of amino acids 1 to 311 of SEQ ID NO: 29, or an immunogenic fragment of the amino acid sequence of amino acids 1 to 311 of SEQ ID NO: 29, or the amino acid sequence having at least 99%, 98%, 97%, 96%, 95%, 90%, 85%, or 80% identity to the amino acid sequence of amino acids 1 to 311 of SEQ ID NO: 29. In one embodiment, a vaccine antigen comprises the amino acid sequence of amino acids 1 to 311 of SEQ ID NO: 29.

In one embodiment, RNA encoding a vaccine antigen (i) comprises the nucleotide sequence of nucleotides 54 to 986 of SEQ ID NO: 30, a nucleotide sequence having at least 99%, 98%, 97%, 96%, 95%, 90%, 85%, or 80% identity to the nucleotide sequence of nucleotides 54 to 986 of SEQ ID NO: 30, or a fragment of the nucleotide sequence of nucleotides 54 to 986 of SEQ ID NO: 30, or the nucleotide sequence having at least 99%, 98%, 97%, 96%, 95%, 90%, 85%, or 80% identity to the nucleotide sequence of nucleotides 54 to 986 of SEQ ID NO: 30; and/or (ii) encodes an amino acid sequence comprising the amino acid sequence of amino acids 1 to 311 of SEQ ID NO: 29, an amino acid sequence having at least 99%, 98%, 97%, 96%, 95%, 90%, 85%, or 80% identity to the amino acid sequence of amino acids 1 to 311 of SEQ ID NO: 29, or an immunogenic fragment of the amino acid sequence of amino acids 1 to 311 of SEQ ID NO: 29, or the amino acid sequence having at least 99%, 98%, 97%, 96%, 95%, 90%, 85%, or 80% identity to the amino acid sequence of amino acids 1 to 311 of SEQ ID NO: 29. In one embodiment, RNA encoding a vaccine antigen (i) comprises the nucleotide sequence of nucleotides 54 to 986 of SEQ ID NO: 30; and/or (ii) encodes an amino acid sequence comprising the amino acid sequence of amino acids 1 to 311 of SEQ ID NO: 29.

In one embodiment, a vaccine antigen comprises the amino acid sequence of amino acids 1 to 314 of SEQ ID NO: 31, an amino acid sequence having at least 99%, 98%, 97%, 96%, 95%, 90%, 85%, or 80% identity to the amino acid sequence of amino acids 1 to 314 of SEQ ID NO: 31, or an immunogenic fragment of the amino acid sequence of amino acids 1 to 314 of SEQ ID NO: 31, or the amino acid sequence having at least 99%, 98%, 97%, 96%, 95%, 90%, 85%, or 80% identity to the amino acid sequence of amino acids 1 to 314 of SEQ ID NO: 31. In one embodiment, a vaccine antigen comprises the amino acid sequence of amino acids 1 to 314 of SEQ ID NO: 31.

In one embodiment, RNA encoding a vaccine antigen (i) comprises the nucleotide sequence of nucleotides 54 to 995 of SEQ ID NO: 32, a nucleotide sequence having at least 99%, 98%, 97%, 96%, 95%, 90%, 85%, or 80% identity to the nucleotide sequence of nucleotides 54 to 995 of SEQ ID NO: 32, or a fragment of the nucleotide sequence of nucleotides 54 to 995 of SEQ ID NO: 32, or the nucleotide sequence having at least 99%, 98%, 97%, 96%, 95%, 90%, 85%, or 80% identity to the nucleotide sequence of nucleotides 54 to 995 of SEQ ID NO: 32; and/or (ii) encodes an amino acid sequence comprising the amino acid sequence of amino acids 1 to 314 of SEQ ID NO: 31, an amino acid sequence having at least 99%, 98%, 97%, 96%, 95%, 90%, 85%, or 80% identity to the amino acid sequence of amino acids 1 to 314 of SEQ ID NO: 31, or an immunogenic fragment of the amino acid sequence of amino acids 1 to 314 of SEQ ID NO: 31, or the amino acid sequence having at least 99%, 98%, 97%, 96%, 95%, 90%, 85%, or 80% identity to the amino acid sequence of amino acids 1 to 314 of SEQ ID NO: 31. In one embodiment, RNA encoding a vaccine antigen (i) comprises the nucleotide sequence of nucleotides 54 to 995 of SEQ ID NO: 32; and/or (ii) encodes an amino acid sequence comprising the amino acid sequence of amino acids 1 to 314 of SEQ ID NO: 31.

In one embodiment, a vaccine antigen comprises the amino acid sequence of amino acids 20 to 311 of SEQ ID NO: 29, an amino acid sequence having at least 99%, 98%, 97%, 96%, 95%, 90%, 85%, or 80% identity to the amino acid sequence of amino acids 20 to 311 of SEQ ID NO: 29, or an immunogenic fragment of the amino acid sequence of amino acids 20 to 311 of SEQ ID NO: 29, or the amino acid sequence having at least 99%, 98%, 97%, 96%, 95%, 90%, 85%, or 80% identity to the amino acid sequence of amino acids 20 to 311 of SEQ ID NO: 29. In one embodiment, a vaccine antigen comprises the amino acid sequence of amino acids 20 to 311 of SEQ ID NO: 29.

In one embodiment, RNA encoding a vaccine antigen (i) comprises the nucleotide sequence of nucleotides 111 to 986 of SEQ ID NO: 30, a nucleotide sequence having at least 99%, 98%, 97%, 96%, 95%, 90%, 85%, or 80% identity to the nucleotide sequence of nucleotides 111 to 986 of SEQ ID NO: 30, or a fragment of the nucleotide sequence of nucleotides 111 to 986 of SEQ ID NO: 30, or the nucleotide sequence having at least 99%, 98%, 97%, 96%, 95%, 90%, 85%, or 80% identity to the nucleotide sequence of nucleotides 111 to 986 of SEQ ID NO: 30; and/or (ii) encodes an amino acid sequence comprising the amino acid sequence of amino acids 20 to 311 of SEQ ID NO: 29, an amino acid sequence having at least 99%, 98%, 97%, 96%, 95%, 90%, 85%, or 80% identity to the amino acid sequence of amino acids 20 to 311 of SEQ ID NO: 29, or an immunogenic fragment of the amino acid sequence of amino acids 20 to 311 of SEQ ID NO: 29, or the amino acid sequence having at least 99%, 98%, 97%, 96%, 95%, 90%, 85%, or 80% identity to the amino acid sequence of amino acids 20 to 311 of SEQ ID NO: 29. In one embodiment, RNA encoding a vaccine antigen (i) comprises the nucleotide sequence of nucleotides 111 to 986 of SEQ ID NO: 30; and/or (ii) encodes an amino acid sequence comprising the amino acid sequence of amino acids 20 to 311 of SEQ ID NO: 29.

In one embodiment, a vaccine antigen comprises the amino acid sequence of amino acids 23 to 314 of SEQ ID NO: 31, an amino acid sequence having at least 99%, 98%, 97%, 96%, 95%, 90%, 85%, or 80% identity to the amino acid sequence of amino acids 23 to 314 of SEQ ID NO: 31, or an immunogenic fragment of the amino acid sequence of amino acids 23 to 314 of SEQ ID NO: 31, or the amino acid sequence having at least 99%, 98%, 97%, 96%, 95%, 90%, 85%, or 80% identity to the amino acid sequence of amino acids 23 to 314 of SEQ ID NO: 31. In one embodiment, a vaccine antigen comprises the amino acid sequence of amino acids 23 to 314 of SEQ ID NO: 31.

In one embodiment, RNA encoding a vaccine antigen (i) comprises the nucleotide sequence of nucleotides 120 to 995 of SEQ ID NO: 32, a nucleotide sequence having at least 99%, 98%, 97%, 96%, 95%, 90%, 85%, or 80% identity to the nucleotide sequence of nucleotides 120 to 995 of SEQ ID NO: 32, or a fragment of the nucleotide sequence of nucleotides 120 to 995 of SEQ ID NO: 32, or the nucleotide sequence having at least 99%, 98%, 97%, 96%, 95%, 90%, 85%, or 80% identity to the nucleotide sequence of nucleotides 120 to 995 of SEQ ID NO: 32; and/or (ii) encodes an amino acid sequence comprising the amino acid sequence of amino acids 23 to 314 of SEQ ID NO: 31, an amino acid sequence having at least 99%, 98%, 97%, 96%, 95%, 90%, 85%, or 80% identity to the amino acid sequence of amino acids 23 to 314 of SEQ ID NO: 31, or an immunogenic fragment of the amino acid sequence of amino acids 23 to 314 of SEQ ID NO: 31, or the amino acid sequence having at least 99%, 98%, 97%, 96%, 95%, 90%, 85%, or 80% identity to the amino acid sequence of amino acids 23 to 314 of SEQ ID NO: 31. In one embodiment, RNA encoding a vaccine antigen (i) comprises the nucleotide sequence of nucleotides 120 to 995 of SEQ ID NO: 32; and/or (ii) encodes an amino acid sequence comprising the amino acid sequence of amino acids 23 to 314 of SEQ ID NO: 31.

In one embodiment, RNA encoding a vaccine antigen (i) comprises the nucleotide sequence of SEQ ID NO: 30, a nucleotide sequence having at least 99%, 98%, 97%, 96%, 95%, 90%, 85%, or 80% identity to the nucleotide sequence of SEQ ID NO: 30, or a fragment of the nucleotide sequence of SEQ ID NO: 30, or the nucleotide sequence having at least 99%, 98%, 97%, 96%, 95%, 90%, 85%, or 80% identity to the nucleotide sequence of SEQ ID NO: 30; and/or (ii) encodes an amino acid sequence comprising the amino acid sequence of SEQ ID NO: 29, an amino acid sequence having at least 99%, 98%, 97%, 96%, 95%, 90%, 85%, or 80% identity to the amino acid sequence of SEQ ID NO: 29, or an immunogenic fragment of the amino acid sequence of SEQ ID NO: 29, or the amino acid sequence having at least 99%, 98%, 97%, 96%, 95%, 90%, 85%, or 80% identity to the amino acid sequence of SEQ ID NO: 29. In one embodiment, RNA encoding a vaccine antigen (i) comprises the nucleotide sequence of SEQ ID NO: 30; and/or (ii) encodes an amino acid sequence comprising the amino acid sequence of SEQ ID NO: 29.

In one embodiment, RNA encoding a vaccine antigen (i) comprises the nucleotide sequence of SEQ ID NO: 32, a nucleotide sequence having at least 99%, 98%, 97%, 96%, 95%, 90%, 85%, or 80% identity to the nucleotide sequence of SEQ ID NO: 32, or a fragment of the nucleotide sequence of SEQ ID NO: 32, or the nucleotide sequence having at least 99%, 98%, 97%, 96%, 95%, 90%, 85%, or 80% identity to the nucleotide sequence of SEQ ID NO: 32; and/or (ii) encodes an amino acid sequence comprising the amino acid sequence of SEQ ID NO: 31, an amino acid sequence having at least 99%, 98%, 97%, 96%, 95%, 90%, 85%, or 80% identity to the amino acid sequence of SEQ ID NO: 31, or an immunogenic fragment of the amino acid sequence of SEQ ID NO: 31, or the amino acid sequence having at least 99%, 98%, 97%, 96%, 95%, 90%, 85%, or 80% identity to the amino acid sequence of SEQ ID NO: 31. In one embodiment, RNA encoding a vaccine antigen (i) comprises the nucleotide sequence of SEQ ID NO: 32; and/or (ii) encodes an amino acid sequence comprising the amino acid sequence of SEQ ID NO: 31.

In one embodiment, a vaccine antigen comprises the amino acid sequence of SEQ ID NO: 28, an amino acid sequence having at least 99%, 98%, 97%, 96%, 95%, 90%, 85%, or 80% identity to the amino acid sequence of SEQ ID NO: 28, or an immunogenic fragment of the amino acid sequence of SEQ ID NO: 28, or the amino acid sequence having at least 99%, 98%, 97%, 96%, 95%, 90%, 85%, or 80% identity to the amino acid sequence of SEQ ID NO: 28. In one embodiment, a vaccine antigen comprises the amino acid sequence of SEQ ID NO: 28.

In one embodiment, RNA encoding a vaccine antigen (i) comprises the nucleotide sequence of SEQ ID NO: 27, a nucleotide sequence having at least 99%, 98%, 97%, 96%, 95%, 90%, 85%, or 80% identity to the nucleotide sequence of SEQ ID NO: 27, or a fragment of the nucleotide sequence of SEQ ID NO: 27, or the nucleotide sequence having at least 99%, 98%, 97%, 96%, 95%, 90%, 85%, or 80% identity to the nucleotide sequence of SEQ ID NO: 27; and/or (ii) encodes an amino acid sequence comprising the amino acid sequence of SEQ ID NO: 28, an amino acid sequence having at least 99%, 98%, 97%, 96%, 95%, 90%, 85%, or 80% identity to the amino acid sequence of SEQ ID NO: 28, or an immunogenic fragment of the amino acid sequence of SEQ ID NO: 28, or the amino acid sequence having at least 99%, 98%, 97%, 96%, 95%, 90%, 85%, or 80% identity to the amino acid sequence of SEQ ID NO: 28. In one embodiment, RNA encoding a vaccine antigen (i) comprises the nucleotide sequence of SEQ ID NO: 27; and/or (ii) encodes an amino acid sequence comprising the amino acid sequence of SEQ ID NO: 28.

In one embodiment, a vaccine antigen comprises the amino acid sequence of SEQ ID NO: 49, an amino acid sequence having at least 99.5%, 99%, 98.5%, 98%, 98.5% or 97% identity to the amino acid sequence of SEQ ID NO: 49, or an immunogenic fragment of the amino acid sequence of SEQ ID NO: 49, or the amino acid sequence having at least 99.5%, 99%, 98.5%, 98%, 98.5% or 97% identity to the amino acid sequence of SEQ ID NO: 49. In one embodiment, a vaccine antigen comprises the amino acid sequence of SEQ ID NO: 49. The amino acid sequence of SEQ ID NO: 49 corresponds to the amino acid sequence of the full-length S protein from Omicron BA.1, which includes proline residues at positions corresponding to residues 986 and 987 of SEQ ID NO: 1 (residues 983 and 984 of SEQ ID NO: 49).

In one embodiment, RNA encoding a vaccine antigen (i) comprises the nucleotide sequence of SEQ ID NO: 50, a nucleotide sequence having at least 99.5%, 99%, 98.5%, 98%, 98.5% or 97% identity to the nucleotide sequence of SEQ ID NO: 50, or a fragment of the nucleotide sequence of SEQ ID NO: 50, or the nucleotide sequence having at least 99.5%, 99%, 98.5%, 98%, 98.5% or 97% identity to the nucleotide sequence of SEQ ID NO: 50; and/or (ii) encodes an amino acid sequence comprising the amino acid sequence of SEQ ID NO: 49, an amino acid sequence having at least 99.5%, 99%, 98.5%, 98%, 98.5% or 97% identity to the amino acid sequence of SEQ ID NO: 49, or an immunogenic fragment of the amino acid sequence of SEQ ID NO: 49, or the amino acid sequence having at least 99.5%, 99%, 98.5%, 98%, 98.5% or 97% identity to the amino acid sequence of SEQ ID NO: 49. In one embodiment, RNA encoding a vaccine antigen (i) comprises the nucleotide sequence of SEQ ID NO: 50; and/or (ii) encodes an amino acid sequence comprising the amino acid sequence of SEQ ID NO: 49. The nucleotide sequence of SEQ ID NO: 50 is a nucleotide sequence designed to encode the amino acid sequence of the full-length S protein from Omicron BA.1 with proline residues at positions corresponding to residues 986 and 987 of SEQ ID NO: 1 (residues 983 and 984 of SEQ ID NO: 49).

In one embodiment, RNA encoding a vaccine antigen (i) comprises the nucleotide sequence of SEQ ID NO: 51, a nucleotide sequence having at least 99.5%, 99%, 98.5%, 98%, 98.5% or 97% identity to the nucleotide sequence of SEQ ID NO: 51, or a fragment of the nucleotide sequence of SEQ ID NO: 51, or the nucleotide sequence having at least 99.5%, 99%, 98.5%, 98%, 98.5% or 97% identity to the nucleotide sequence of SEQ ID NO: 51; and/or (ii) encodes an amino acid sequence comprising the amino acid sequence of SEQ ID NO: 49, an amino acid sequence having at least 99.5%, 99%, 98.5%, 98%, 98.5% or 97% identity to the amino acid sequence of SEQ ID NO: 49, or an immunogenic fragment of the amino acid sequence of SEQ ID NO: 49, or the amino acid sequence having at least 99.5%, 99%, 98.5%, 98%, 98.5% or 97% identity to the amino acid sequence of SEQ ID NO: 49. In one embodiment, RNA encoding a vaccine antigen (i) comprises the nucleotide sequence of SEQ ID NO: 51; and/or (ii) encodes an amino acid sequence comprising the amino acid sequence of SEQ ID NO: 49. The nucleotide sequence of SEQ ID NO: 51 corresponds to an RNA construct (e.g., comprising a 5' UTR, a S-protein-encoding sequence, a 3' UTR, and a poly-A tail), which encodes the amino acid sequence of the full-length S protein from Omicron BA.1 with proline residues at positions corresponding to residues 986 and 987 of SEQ ID NO: 1 (corresponding to residues 983 and 984 of SEQ ID NO: 49).

In one embodiment, a vaccine antigen comprises the amino acid sequence of SEQ ID NO: 55, an amino acid sequence having at least 99.5%, 99%, 98.5%, 98%, 98.5% or 97% identity to the amino acid sequence of SEQ ID NO: 55, or an immunogenic fragment of the amino acid sequence of SEQ ID NO: 55, or the amino acid sequence having at least 99.5%, 99%, 98.5%, 98%, 98.5% or 97% identity to the amino acid sequence of SEQ ID NO: 55. In one embodiment, a vaccine antigen comprises the amino acid sequence of SEQ ID NO: 55.

In one embodiment, RNA encoding a vaccine antigen (i) comprises the nucleotide sequence of SEQ ID NO: 56, a nucleotide sequence having at least 99.5%, 99%, 98.5%, 98%, 98.5% or 97% identity to the nucleotide sequence of SEQ ID NO: 56, or a fragment of the nucleotide sequence of SEQ ID NO: 56, or the nucleotide sequence having at least 99.5%, 99%, 98.5%, 98%, 98.5% or 97% identity to the nucleotide sequence of SEQ ID NO: 56; and/or (ii) encodes an amino acid sequence comprising the amino acid sequence of SEQ ID NO: 55, an amino acid sequence having at least 99.5%, 99%, 98.5%, 98%, 98.5% or 97% identity to the amino acid sequence of SEQ ID NO: 55, or an immunogenic fragment of the amino acid sequence of SEQ ID NO: 55, or the amino acid sequence having at least 99.5%, 99%, 98.5%, 98%, 98.5% or 97% identity to the amino acid sequence of SEQ ID NO: 55. In one embodiment, RNA encoding a vaccine antigen (i) comprises the nucleotide sequence of SEQ ID NO: 56; and/or (ii) encodes an amino acid sequence comprising the amino acid sequence of SEQ ID NO: 55.

In one embodiment, RNA encoding a vaccine antigen (i) comprises the nucleotide sequence of SEQ ID NO: 57, a nucleotide sequence having at least 99.5%, 99%, 98.5%, 98%, 98.5% or 97% identity to the nucleotide sequence of SEQ ID NO: 57, or a fragment of the nucleotide sequence of SEQ ID NO: 57, or the nucleotide sequence having at least 99.5%, 99%, 98.5%, 98%, 98.5% or 97% identity to the nucleotide sequence of SEQ ID NO: 57; and/or (ii) encodes an amino acid sequence comprising the amino acid sequence of SEQ ID NO: 55, an amino acid sequence having at least 99.5%, 99%, 98.5%, 98%, 98.5% or 97% identity to the amino acid sequence of SEQ ID NO: 55, or an immunogenic fragment of the amino acid sequence of SEQ ID NO: 55, or the amino acid sequence having at least 99.5%, 99%, 98.5%, 98%, 98.5% or 97% identity to the amino acid sequence of SEQ ID NO: 55. In one embodiment, RNA encoding a vaccine antigen (i) comprises the nucleotide sequence of SEQ ID NO: 57; and/or (ii) encodes an amino acid sequence comprising the amino acid sequence of SEQ ID NO: 55.

In one embodiment, a vaccine antigen comprises the amino acid sequence of SEQ ID NO: 58, an amino acid sequence having at least 99.5%, 99%, 98.5%, 98%, 98.5% or 97% identity to the amino acid sequence of SEQ ID NO: 58, or an immunogenic fragment of the amino acid sequence of SEQ ID NO: 58, or the amino acid sequence having at least 99.5%, 99%, 98.5%, 98%, 98.5% or 97% identity to the amino acid sequence of SEQ ID NO: 58. In one embodiment, a vaccine antigen comprises the amino acid sequence of SEQ ID NO: 58.

In one embodiment, RNA encoding a vaccine antigen (i) comprises the nucleotide sequence of SEQ ID NO: 59, a nucleotide sequence having at least 99.5%, 99%, 98.5%, 98%, 98.5% or 97% identity to the nucleotide sequence of SEQ ID NO: 59, or a fragment of the nucleotide sequence of SEQ ID NO: 59, or the nucleotide sequence having at least 99.5%, 99%, 98.5%, 98%, 98.5% or 97% identity to the nucleotide sequence of SEQ ID NO: 59; and/or (ii) encodes an amino acid sequence comprising the amino acid sequence of SEQ ID NO: 58, an amino acid sequence having at least 99.5%, 99%, 98.5%, 98%, 98.5% or 97% identity to the amino acid sequence of SEQ ID NO: 58, or an immunogenic fragment of the amino acid sequence of SEQ ID NO: 58, or the amino acid sequence having at least 99.5%, 99%, 98.5%, 98%, 98.5% or 97% identity to the amino acid sequence of SEQ ID NO: 58. In one embodiment, RNA encoding a vaccine antigen (i) comprises the nucleotide sequence of SEQ ID NO: 59; and/or (ii) encodes an amino acid sequence comprising the amino acid sequence of SEQ ID NO: 58.

In one embodiment, RNA encoding a vaccine antigen (i) comprises the nucleotide sequence of SEQ ID NO: 60, a nucleotide sequence having at least 99.5%, 99%, 98.5%, 98%, 98.5% or 97% identity to the nucleotide sequence of SEQ ID NO: 60, or a fragment of the nucleotide sequence of SEQ ID NO: 60, or the nucleotide sequence having at least 99.5%, 99%, 98.5%, 98%, 98.5% or 97% identity to the nucleotide sequence of SEQ ID NO: 60; and/or (ii) encodes an amino acid sequence comprising the amino acid sequence of SEQ ID NO: 58, an amino acid sequence having at least 99.5%, 99%, 98.5%, 98%, 98.5% or 97% identity to the amino acid sequence of SEQ ID NO: 58, or an immunogenic fragment of the amino acid sequence of SEQ ID NO: 58, or the amino acid sequence having at least 99.5%, 99%, 98.5%, 98%, 98.5% or 97% identity to the amino acid sequence of SEQ ID NO: 58. In one embodiment, RNA encoding a vaccine antigen (i) comprises the nucleotide sequence of SEQ ID NO: 60; and/or (ii) encodes an amino acid sequence comprising the amino acid sequence of SEQ ID NO: 58.

In one embodiment, a vaccine antigen comprises the amino acid sequence of SEQ ID NO: 61, an amino acid sequence having at least 99.5%, 99%, 98.5%, 98%, 98.5% or 97% identity to the amino acid sequence of SEQ ID NO: 61, or an immunogenic fragment of the amino acid sequence of SEQ ID NO: 61, or the amino acid sequence having at least 99.5%, 99%, 98.5%, 98%, 98.5% or 97% identity to the amino acid sequence of SEQ ID NO: 61. In one embodiment, a vaccine antigen comprises the amino acid sequence of SEQ ID NO: 61.

In one embodiment, RNA encoding a vaccine antigen (i) comprises the nucleotide sequence of SEQ ID NO: 62a, a nucleotide sequence having at least 99.5%, 99%, 98.5%, 98%, 98.5% or 97% identity to the nucleotide sequence of SEQ ID NO: 62a, or a fragment of the nucleotide sequence of SEQ ID NO: 62a, or the nucleotide sequence having at least 99.5%, 99%, 98.5%, 98%, 98.5% or 97% identity to the nucleotide sequence of SEQ ID NO: 62a; and/or (ii) encodes an amino acid sequence comprising the amino acid sequence of SEQ ID NO: 61, an amino acid sequence having at least 99.5%, 99%, 98.5%, 98%, 98.5% or 97% identity to the amino acid sequence of SEQ ID NO: 61, or an immunogenic fragment of the amino acid sequence of SEQ ID NO: 61, or the amino acid sequence having at least 99.5%, 99%, 98.5%, 98%, 98.5% or 97% identity to the amino acid sequence of SEQ ID NO: 61. In one embodiment, RNA encoding a vaccine antigen (i) comprises the nucleotide sequence of SEQ ID NO: 62a; and/or (ii) encodes an amino acid sequence comprising the amino acid sequence of SEQ ID NO: 61.

In one embodiment, RNA encoding a vaccine antigen (i) comprises the nucleotide sequence of SEQ ID NO: 63a, a nucleotide sequence having at least 99.5%, 99%, 98.5%, 98%, 98.5% or 97% identity to the nucleotide sequence of SEQ ID NO: 63a, or a fragment of the nucleotide sequence of SEQ ID NO: 63a, or the nucleotide sequence having at least 99.5%, 99%, 98.5%, 98%, 98.5% or 97% identity to the nucleotide sequence of SEQ ID NO: 63a; and/or (ii) encodes an amino acid sequence comprising the amino acid sequence of SEQ ID NO: 61, an amino acid sequence having at least 99.5%, 99%, 98.5%, 98%, 98.5% or 97% identity to the amino acid sequence of SEQ ID NO: 61, or an immunogenic fragment of the amino acid sequence of SEQ ID NO: 61, or the amino acid sequence having at least 99.5%, 99%, 98.5%, 98%, 98.5% or 97% identity to the amino acid sequence of SEQ ID NO: 61. In one embodiment, RNA encoding a vaccine antigen (i) comprises the nucleotide sequence of SEQ ID NO: 63a; and/or (ii) encodes an amino acid sequence comprising the amino acid sequence of SEQ ID NO: 61.

In one embodiment, a vaccine antigen comprises the amino acid sequence of SEQ ID NO: 52, an amino acid sequence having at least 99.5%, 99%, 98.5%, 98%, 98.5% or 97% identity to the amino acid sequence of SEQ ID NO: 52, or an immunogenic fragment of the amino acid sequence of SEQ ID NO: 52, or the amino acid sequence having at least 99.5%, 99%, 98.5%, 98%, 98.5% or 97% identity to the amino acid sequence of SEQ ID NO: 52. In one embodiment, a vaccine antigen comprises the amino acid sequence of SEQ ID NO: 52.

In one embodiment, RNA encoding a vaccine antigen (i) comprises the nucleotide sequence of SEQ ID NO: 53, a nucleotide sequence having at least 99.5%, 99%, 98.5%, 98%, 98.5% or 97% identity to the nucleotide sequence of SEQ ID NO: 53, or a fragment of the nucleotide sequence of SEQ ID NO: 53, or the nucleotide sequence having at least 99.5%, 99%, 98.5%, 98%, 98.5% or 97% identity to the nucleotide sequence of SEQ ID NO: 53; and/or (ii) encodes an amino acid sequence comprising the amino acid sequence of SEQ ID NO: 52, an amino acid sequence having at least 99.5%, 99%, 98.5%, 98%, 98.5% or 97% identity to the amino acid sequence of SEQ ID NO: 52, or an immunogenic fragment of the amino acid sequence of SEQ ID NO: 52, or the amino acid sequence having at least 99.5%, 99%, 98.5%, 98%, 98.5% or 97% identity to the amino acid sequence of SEQ ID NO: 52. In one embodiment, RNA encoding a vaccine antigen (i) comprises the nucleotide sequence of SEQ ID NO: 53; and/or (ii) encodes an amino acid sequence comprising the amino acid sequence of SEQ ID NO: 52.

In one embodiment, RNA encoding a vaccine antigen (i) comprises the nucleotide sequence of SEQ ID NO: 54, a nucleotide sequence having at least 99.5%, 99%, 98.5%, 98%, 98.5% or 97% identity to the nucleotide sequence of SEQ ID NO: 54, or a fragment of the nucleotide sequence of SEQ ID NO: 54, or the nucleotide sequence having at least 99.5%, 99%, 98.5%, 98%, 98.5% or 97% identity to the nucleotide sequence of SEQ ID NO: 54; and/or (ii) encodes an amino acid sequence comprising the amino acid sequence of SEQ ID NO: 52, an amino acid sequence having at least 99.5%, 99%, 98.5%, 98%, 98.5% or 97% identity to the amino acid sequence of SEQ ID NO: 52, or an immunogenic fragment of the amino acid sequence of SEQ ID NO: 52, or the amino acid sequence having at least 99.5%, 99%, 98.5%, 98%, 98.5% or 97% identity to the amino acid sequence of SEQ ID NO: 52. In one embodiment, RNA encoding a vaccine antigen (i) comprises the nucleotide sequence of SEQ ID NO: 54; and/or (ii) encodes an amino acid sequence comprising the amino acid sequence of SEQ ID NO: 52.

In one embodiment, the vaccine antigens described above comprise a contiguous sequence of SARS-CoV-2 coronavirus spike (S) protein that consists of or essentially consists of the above described amino acid sequences derived from SARS-CoV-2 S protein or immunogenic fragments thereof (antigenic peptides or proteins) comprised by the vaccine antigens described above. In one embodiment, the vaccine antigens described above comprise a contiguous sequence of SARS-CoV-2 coronavirus spike (S) protein of no more than 220 amino acids, 215 amino acids, 210 amino acids, or 205 amino acids.

In one embodiment, RNA encoding a vaccine antigen is nucleoside modified messenger RNA (modRNA) described herein as BNT162b1 (RBP020.3), BNT162b2 (RBP020.1 or RBP020.2), or BNT162b3 (e.g., BNT162b3c). In one embodiment, RNA encoding a vaccine antigen is nucleoside modified messenger RNA (modRNA) described herein as RBP020.2. In one embodiment, RNA encoding a vaccine antigen is nucleoside modified messenger RNA (modRNA) described herein as BNT162b3 (e.g., BNT162b3c).

In one embodiment, RNA encoding a vaccine antigen is nucleoside modified messenger RNA (modRNA) and (i) comprises the nucleotide sequence of SEQ ID NO: 21, a nucleotide sequence having at least 99%, 98%, 97%, 96%, 95%, 90%, 85%, or 80% identity to the nucleotide sequence of SEQ ID NO: 21, and/or (ii) encodes an amino acid sequence comprising the amino acid sequence of SEQ ID NO: 5, or an amino acid sequence having at least 99%, 98%, 97%, 96%, 95%, 90%, 85%, or 80% identity to the amino acid sequence of SEQ ID NO: 5. In one embodiment, RNA encoding a vaccine antigen is nucleoside modified messenger RNA (modRNA) and (i) comprises the nucleotide sequence of SEQ ID NO: 21; and/or (ii) encodes an amino acid sequence comprising the amino acid sequence of SEQ ID NO: 5.

In one embodiment, RNA encoding a vaccine antigen is nucleoside modified messenger RNA (modRNA) and (i) comprises the nucleotide sequence of SEQ ID NO: 19, or 20, a nucleotide sequence having at least 99%, 98%, 97%, 96%, 95%, 90%, 85%, or 80% identity to the nucleotide sequence of SEQ ID NO: 19, or 20, and/or (ii) encodes an amino acid sequence comprising the amino acid sequence of SEQ ID NO: 7, or an amino acid sequence having at least 99%, 98%, 97%, 96%, 95%, 90%, 85%, or 80% identity to the amino acid sequence of SEQ ID NO: 7. In one embodiment, RNA encoding a vaccine antigen is nucleoside modified messenger RNA (modRNA) and (i) comprises the nucleotide sequence of SEQ ID NO: 19, or 20; and/or (ii) encodes an amino acid sequence comprising the amino acid sequence of SEQ ID NO: 7.

In one embodiment, RNA encoding a vaccine antigen is nucleoside modified messenger RNA (modRNA) and (i) comprises the nucleotide sequence of SEQ ID NO: 20, a nucleotide sequence having at least 99%, 98%, 97%, 96%, 95%, 90%, 85%, or 80% identity to the nucleotide sequence of SEQ ID NO: 20, and/or (ii) encodes an amino acid sequence comprising the amino acid sequence of SEQ ID NO: 7, or an amino acid sequence having at least 99%, 98%, 97%, 96%, 95%, 90%, 85%, or 80% identity to the amino acid sequence of SEQ ID NO: 7. In one embodiment, RNA encoding a vaccine antigen is nucleoside modified messenger RNA (modRNA) and (i) comprises the nucleotide sequence of SEQ ID NO: 20; and/or (ii) encodes an amino acid sequence comprising the amino acid sequence of SEQ ID NO: 7.

In one embodiment, RNA encoding a vaccine antigen is nucleoside modified messenger RNA (modRNA) and (i) comprises the nucleotide sequence of SEQ ID NO: 30, a nucleotide sequence having at least 99%, 98%, 97%, 96%, 95%, 90%, 85%, or 80% identity to the nucleotide sequence of SEQ ID NO: 30, and/or (ii) encodes an amino acid sequence comprising the amino acid sequence of SEQ ID NO: 29, or an amino acid sequence having at least 99%, 98%, 97%, 96%, 95%, 90%, 85%, or 80% identity to the amino acid sequence of SEQ ID NO: 29. In one embodiment, RNA encoding a vaccine antigen is nucleoside modified messenger RNA (modRNA) and (i) comprises the nucleotide sequence of SEQ ID NO: 30; and/or (ii) encodes an amino acid sequence comprising the amino acid sequence of SEQ ID NO: 29.

In one embodiment, RNA encoding a vaccine antigen is nucleoside modified messenger RNA (modRNA) and (i) comprises the nucleotide sequence of SEQ ID NO: 50, a nucleotide sequence having at least 99.5%, 99%, 98.5%, 98%, 98.5% or 97% identity to the nucleotide sequence of SEQ ID NO: 50, and/or (ii) encodes an amino acid sequence comprising the amino acid sequence of SEQ ID NO: 49, or an amino acid sequence having at least 99.5%, 99%, 98.5%, 98%, 98.5% or 97% identity to the amino acid sequence of SEQ ID NO: 49. In one embodiment, RNA encoding a vaccine antigen is nucleoside modified messenger RNA (modRNA) and (i) comprises the nucleotide sequence of SEQ ID NO: 50; and/or (ii) encodes an amino acid sequence comprising the amino acid sequence of SEQ ID NO: 49.

In one embodiment, RNA encoding a vaccine antigen is nucleoside modified messenger RNA (modRNA) and (i) comprises the nucleotide sequence of SEQ ID NO: 51, a nucleotide sequence having at least 99.5%, 99%, 98.5%, 98%, 98.5% or 97% identity to the nucleotide sequence of SEQ ID NO: 51, and/or (ii) encodes an amino acid sequence comprising the amino acid sequence of SEQ ID NO: 49, or an amino acid sequence having at least 99.5%, 99%, 98.5%, 98%, 98.5% or 97% identity to the amino acid sequence of SEQ ID NO: 49. In one embodiment, RNA encoding a vaccine antigen is nucleoside modified messenger RNA (modRNA) and (i) comprises the nucleotide sequence of SEQ ID NO: 51; and/or (ii) encodes an amino acid sequence comprising the amino acid sequence of SEQ ID NO: 49.

In one embodiment, RNA encoding a vaccine antigen is nucleoside modified messenger RNA (modRNA) and (i) comprises the nucleotide sequence of SEQ ID NO: 57, a nucleotide sequence having at least 99.5%, 99%, 98.5%, 98%, 98.5% or 97% identity to the nucleotide sequence of SEQ ID NO: 57, and/or (ii) encodes an amino acid sequence comprising the amino acid sequence of SEQ ID NO: 55, or an amino acid sequence having at least 99.5%, 99%, 98.5%, 98%, 98.5% or 97% identity to the amino acid sequence of SEQ ID NO: 55. In one embodiment, RNA encoding a vaccine antigen is nucleoside modified messenger RNA (modRNA) and (i) comprises the nucleotide sequence of SEQ ID NO: 57; and/or (ii) encodes an amino acid sequence comprising the amino acid sequence of SEQ ID NO: 55.

In one embodiment, RNA encoding a vaccine antigen is nucleoside modified messenger RNA (modRNA) and (i) comprises the nucleotide sequence of SEQ ID NO: 60, a nucleotide sequence having at least 99.5%, 99%, 98.5%, 98%, 98.5% or 97% identity to the nucleotide sequence of SEQ ID NO: 60, and/or (ii) encodes an amino acid sequence comprising the amino acid sequence of SEQ ID NO: 58, or an amino acid sequence having at least 99.5%, 99%, 98.5%, 98%, 98.5% or 97% identity to the amino acid sequence of SEQ ID NO: 58. In one embodiment, RNA encoding a vaccine antigen is nucleoside modified messenger RNA (modRNA) and (i) comprises the nucleotide sequence of SEQ ID NO: 60; and/or (ii) encodes an amino acid sequence comprising the amino acid sequence of SEQ ID NO: 58.

In one embodiment, RNA encoding a vaccine antigen is nucleoside modified messenger RNA (modRNA) and (i) comprises the nucleotide sequence of SEQ ID NO: 63a, a nucleotide sequence having at least 99.5%, 99%, 98.5%, 98%, 98.5% or 97% identity to the nucleotide sequence of SEQ ID NO: 63a, and/or (ii) encodes an amino acid sequence comprising the amino acid sequence of SEQ ID NO: 61, or an amino acid sequence having at least 99.5%, 99%, 98.5%, 98%, 98.5% or 97% identity to the amino acid sequence of SEQ ID NO: 61. In one embodiment, RNA encoding a vaccine antigen is nucleoside modified messenger RNA (modRNA) and (i) comprises the nucleotide sequence of SEQ ID NO: 63a; and/or (ii) encodes an amino acid sequence comprising the amino acid sequence of SEQ ID NO: 61.

In one embodiment, RNA encoding a vaccine antigen is nucleoside modified messenger RNA (modRNA) and (i) comprises the nucleotide sequence of SEQ ID NO: 53, a nucleotide sequence having at least 99.5%, 99%, 98.5%, 98%, 98.5% or 97% identity to the nucleotide sequence of SEQ ID NO: 53, and/or (ii) encodes an amino acid sequence comprising the amino acid sequence of SEQ ID NO: 52, or an amino acid sequence having at least 99.5%, 99%, 98.5%, 98%, 98.5% or 97% identity to the amino acid sequence of SEQ ID NO: 52. In one embodiment, RNA encoding a vaccine antigen is nucleoside modified messenger RNA (modRNA) and (i) comprises the nucleotide sequence of SEQ ID NO: 53; and/or (ii) encodes an amino acid sequence comprising the amino acid sequence of SEQ ID NO: 52.

In one embodiment, RNA encoding a vaccine antigen is nucleoside modified messenger RNA (modRNA) and (i) comprises the nucleotide sequence of SEQ ID NO: 54, a nucleotide sequence having at least 99.5%, 99%, 98.5%, 98%, 98.5% or 97% identity to the nucleotide sequence of SEQ ID NO: 54, and/or (ii) encodes an amino acid sequence comprising the amino acid sequence of SEQ ID NO: 52, or an amino acid sequence having at least 99.5%, 99%, 98.5%, 98%, 98.5% or 97% identity to the amino acid sequence of SEQ ID NO: 52. In one embodiment, RNA encoding a vaccine antigen is nucleoside modified messenger RNA (modRNA) and (i) comprises the nucleotide sequence of SEQ ID NO: 54; and/or (ii) encodes an amino acid sequence comprising the amino acid sequence of SEQ ID NO: 52.

As used herein, the term "vaccine" refers to a composition that induces an immune response upon inoculation into a subject. In some embodiments, the induced immune response provides protective immunity.

In one embodiment, the RNA encoding the antigen molecule is expressed in cells of the subject to provide the antigen molecule. In one embodiment, expression of the antigen molecule is at the cell surface or into the extracellular space. In one embodiment, the antigen molecule is presented in the context of MHC. In one embodiment, the RNA encoding the antigen molecule is transiently expressed in cells of the subject. In one embodiment, after administration of the RNA encoding the antigen molecule, in particular after intramuscular administration of the RNA encoding the antigen molecule, expression of the RNA encoding the antigen molecule in muscle occurs. In one embodiment, after administration of the RNA encoding the antigen molecule, expression of the RNA encoding the antigen molecule in spleen occurs. In one embodiment, after administration of the RNA encoding the antigen molecule, expression of the RNA encoding the antigen molecule in antigen presenting cells, preferably professional antigen presenting cells occurs. In one embodiment, the antigen presenting cells are selected from the group consisting of dendritic cells, macrophages and B cells. In one embodiment, after administration of the RNA encoding the antigen molecule, no or essentially no expression of the RNA encoding the antigen molecule in lung and/or liver occurs. In one embodiment, after administration of the RNA encoding the antigen molecule, expression of the RNA encoding the antigen molecule in spleen is at least 5-fold the amount of expression in lung. In some embodiments, the methods and agents, e.g., RNA compositions, described herein following administration, in particular following intramuscular administration, to a subject result in delivery of the RNA encoding a vaccine antigen to lymph nodes and/or spleen. In some embodiments, RNA encoding a vaccine antigen is detectable in lymph nodes and/or spleen 6 hours or later following administration and preferably up to 6 days or longer.

In some embodiments, the methods and agents, e.g., mRNA compositions, described herein following administration, in particular following intramuscular administration, to a subject result in delivery of the RNA encoding a vaccine antigen to B cell follicles, subcapsular sinus, and/or T cell zone, in particular B cell follicles and/or subcapsular sinus of lymph nodes.

In some embodiments, the methods and agents, e.g., mRNA compositions, described herein following administration, in particular following intramuscular administration, to a subject result in delivery of the RNA encoding a vaccine antigen to B cells (CD19+), subcapsular sinus macrophages (CD169+) and/or dendritic cells (CD11c+) in the T cell zone and intermediary sinus of lymph nodes, in particular to B cells (CD19+) and/or subcapsular sinus macrophages (CD169+) of lymph nodes.

In some embodiments, the methods and agents, e.g., mRNA compositions, described herein following administration, in particular following intramuscular administration, to a subject result in delivery of the RNA encoding a vaccine antigen to white pulp of spleen.

In some embodiments, the methods and agents, e.g., mRNA compositions, described herein following administration, in particular following intramuscular administration, to a subject result in delivery of the RNA encoding a vaccine antigen to B cells, DCs (CD11c+), in particular those surrounding the B cells, and/or macrophages of spleen, in particular to B cells and/or DCs (CD11c+).

In one embodiment, the vaccine antigen is expressed in lymph node and/or spleen, in particular in the cells of lymph node and/or spleen described above.

The peptide and protein antigens suitable for use according to the present disclosure typically include a peptide or protein comprising an epitope of SARS-CoV-2 S protein or a functional variant thereof for inducing an immune response. The peptide or protein or epitope may be derived from a target antigen, i.e. the antigen against which an immune response is to be elicited. For example, the peptide or protein antigen or the epitope contained within the peptide or protein antigen may be a target antigen or a fragment or variant of a target antigen. The target antigen may be a coronavirus S protein, in particular SARS-CoV-2 S protein.

The antigen molecule or a procession product thereof, e.g., a fragment thereof, may bind to an antigen receptor such as a BCR or TCR carried by immune effector cells, or to antibodies.

A peptide and protein antigen which is provided to a subject according to the present disclosure by administering RNA encoding the peptide and protein antigen, i.e., a vaccine antigen, preferably results in the induction of an immune response, e.g., a humoral and/or cellular immune response in the subject being provided the peptide or protein antigen. Said immune response is preferably directed against a target antigen, in particular coronavirus S protein, in particular SARS-CoV-2 S protein. Thus, a vaccine antigen may comprise the target antigen, a variant thereof, or a fragment thereof. In one embodiment, such fragment or variant is immunologically equivalent to the target antigen. In the context of the present disclosure, the term "fragment of an antigen" or "variant of an antigen" means an agent which results in the induction of an immune response which immune response targets the antigen, i.e. a target antigen. Thus, the vaccine antigen may correspond to or may comprise the target antigen, may correspond to or may comprise a fragment of the target antigen or may correspond to or may comprise an antigen which is homologous to the target antigen or a fragment thereof. Thus, according to the present disclosure, a vaccine antigen may comprise an immunogenic fragment of a target antigen or an amino acid sequence being homologous to an immunogenic fragment of a target antigen. An "immunogenic fragment of an antigen" according to the present disclosure preferably relates to a fragment of an antigen which is capable of inducing an immune response against the target antigen. The vaccine antigen may be a recombinant antigen.

The term "immunologically equivalent" means that the immunologically equivalent molecule such as the immunologically equivalent amino acid sequence exhibits the same or essentially the same immunological properties and/or exerts the same or essentially the same immunological effects, e.g., with respect to the type of the immunological effect. In the context of the present disclosure, the term "immunologically equivalent" is preferably used with respect to the immunological effects or properties of antigens or antigen variants used for immunization. For example, an amino acid sequence is immunologically equivalent to a reference amino acid sequence if said amino acid sequence when exposed to the immune system of a subject induces an immune reaction having a specificity of reacting with the reference amino acid sequence.

"Activation" or "stimulation", as used herein, refers to the state of an immune effector cell such as T cell that has been sufficiently stimulated to induce detectable cellular proliferation.

Activation can also be associated with initiation of signaling pathways, induced cytokine production, and detectable effector functions. The term "activated immune effector cells" refers to, among other things, immune effector cells that are undergoing cell division.

The term "priming" refers to a process wherein an immune effector cell such as a T cell has its first contact with its specific antigen and causes differentiation into effector cells such as effector T cells.

The term "clonal expansion" or "expansion" refers to a process wherein a specific entity is multiplied. In the context of the present disclosure, the term is preferably used in the context of an immunological response in which immune effector cells are stimulated by an antigen, proliferate, and the specific immune effector cell recognizing said antigen is amplified.

Preferably, clonal expansion leads to differentiation of the immune effector cells.

The term "antigen" relates to an agent comprising an epitope against which an immune response can be generated. The term "antigen" includes, in particular, proteins and peptides.

In one embodiment, an antigen is presented by cells of the immune system such as antigen presenting cells like dendritic cells or macrophages. An antigen or a procession product thereof such as a T-cell epitope is in one embodiment bound by a T- or B-cell receptor, or by an immunoglobulin molecule such as an antibody. Accordingly, an antigen or a procession product thereof may react specifically with antibodies or T lymphocytes (T cells). In one embodiment, an antigen is a viral antigen, such as a coronavirus S protein, e.g., SARS-CoV-2 S protein, and an epitope is derived from such antigen.

The term "viral antigen" refers to any viral component having antigenic properties, i.e. being able to provoke an immune response in an individual. The viral antigen may be coronavirus S protein, e.g., SARS-CoV-2 S protein.

The term "expressed on the cell surface" or "associated with the cell surface" means that a molecule such as an antigen is associated with and located at the plasma membrane of a cell, wherein at least a part of the molecule faces the extracellular space of said cell and is accessible from the outside of said cell, e.g., by antibodies located outside the cell. In this context, a part is preferably at least 4, preferably at least 8, preferably at least 12, more preferably at least 20 amino acids. The association may be direct or indirect. For example, the association may be by one or more transmembrane domains, one or more lipid anchors, or by the interaction with any other protein, lipid, saccharide, or other structure that can be found on the outer leaflet of the plasma membrane of a cell. For example, a molecule associated with the surface of a cell may be a transmembrane protein having an extracellular portion or may be a protein associated with the surface of a cell by interacting with another protein that is a transmembrane protein.

"Cell surface" or "surface of a cell" is used in accordance with its normal meaning in the art, and thus includes the outside of the cell which is accessible to binding by proteins and other molecules. An antigen is expressed on the surface of cells if it is located at the surface of said cells and is accessible to binding by e.g. antigen-specific antibodies added to the cells.

The term "extracellular portion" or "exodomain" in the context of the present disclosure refers to a part of a molecule such as a protein that is facing the extracellular space of a cell and preferably is accessible from the outside of said cell, e.g., by binding molecules such as antibodies located outside the cell. Preferably, the term refers to one or more extracellular loops or domains or a fragment thereof.

The term "epitope" refers to a part or fragment of a molecule such as an antigen that is recognized by the immune system. For example, the epitope may be recognized by T cells, B cells or antibodies. An epitope of an antigen may include a continuous or discontinuous portion of the antigen and may be between about 5 and about 100, such as between about 5 and about 50, more preferably between about 8 and about 30, most preferably between about 8 and about 25 amino acids in length, for example, the epitope may be preferably 9, 10, 11, 12, 13, 14, 15, 16, 17, 18, 19, 20, 21, 22, 23, 24, or 25 amino acids in length. In one embodiment, an epitope is between about 10 and about 25 amino acids in length. The term "epitope" includes T cell epitopes.

The term "T cell epitope" refers to a part or fragment of a protein that is recognized by a T cell when presented in the context of MHC molecules. The term "major histocompatibility complex" and the abbreviation "MHC" includes MHC class I and MHC class II molecules and relates to a complex of genes which is present in all vertebrates. MHC proteins or molecules are important for signaling between lymphocytes and antigen presenting cells or diseased cells in immune reactions, wherein the MHC proteins or molecules bind peptide epitopes and present them for recognition by T cell receptors on T cells. The proteins encoded by the MHC are expressed on the surface of cells, and display both self-antigens (peptide fragments from the cell itself) and non-self-antigens (e.g., fragments of invading microorganisms) to a T cell. In the case of class I MHC/peptide complexes, the binding peptides are typically about 8 to about 10 amino acids long although longer or shorter peptides may be effective. In the case of class Il MHC/peptide complexes, the binding peptides are typically about 10 to about 25 amino acids long and are in particular about 13 to about 18 amino acids long, whereas longer and shorter peptides may be effective.

The peptide and protein antigen can be 2-100 amino acids, including for example, 5 amino acids, 10 amino acids, 15 amino acids, 20 amino acids, 25 amino acids, 30 amino acids, 35 amino acids, 40 amino acids, 45 amino acids, or 50 amino acids in length. In some embodiments, a peptide can be greater than 50 amino acids. In some embodiments, the peptide can be greater than 100 amino acids.

The peptide or protein antigen can be any peptide or protein that can induce or increase the ability of the immune system to develop antibodies and T cell responses to the peptide or protein.

In one embodiment, vaccine antigen is recognized by an immune effector cell. Preferably, the vaccine antigen if recognized by an immune effector cell is able to induce in the presence of appropriate co-stimulatory signals, stimulation, priming and/or expansion of the immune effector cell carrying an antigen receptor recognizing the vaccine antigen. In the context of the embodiments of the present disclosure, the vaccine antigen is preferably presented or present on the surface of a cell, preferably an antigen presenting cell. In one embodiment, an antigen is presented by a diseased cell such as a virus-infected cell. In one embodiment, an antigen receptor is a TCR which binds to an epitope of an antigen presented in the context of MHC. In one embodiment, binding of a TCR when expressed by T cells and/or present on T cells to an antigen presented by cells such as antigen presenting cells results in stimulation, priming and/or expansion of said T cells. In one embodiment, binding of a TCR when expressed by T cells and/or present on T cells to an antigen presented on diseased cells results in cytolysis and/or apoptosis of the diseased cells, wherein said T cells preferably release cytotoxic factors, e.g. perforins and granzymes.

In one embodiment, an antigen receptor is an antibody or B cell receptor which binds to an epitope in an antigen. In one embodiment, an antibody or B cell receptor binds to native epitopes of an antigen.

Nucleic Acids

The term "polynucleotide" or "nucleic acid", as used herein, is intended to include DNA and RNA such as genomic DNA, cDNA, mRNA, recombinantly produced and chemically synthesized molecules. A nucleic acid may be single-stranded or double-stranded. RNA includes in vitro transcribed RNA (IVT RNA) or synthetic RNA. According to the present disclosure, a polynucleotide is preferably isolated.

Nucleic acids may be comprised in a vector. The term "vector" as used herein includes any vectors known to the skilled person including plasmid vectors, cosmid vectors, phage vectors such as lambda phage, viral vectors such as retroviral, adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

In one embodiment of all aspects of the present disclosure, the RNA encoding the vaccine antigen is expressed in cells such as antigen presenting cells of the subject treated to provide the vaccine antigen.

The nucleic acids described herein may be recombinant and/or isolated molecules.

In the present disclosure, the term "RNA" relates to a nucleic acid molecule which includes ribonucleotide residues. In preferred embodiments, the RNA contains all or a majority of ribonucleotide residues. As used herein, "ribonucleotide" refers to a nucleotide with a hydroxyl group at the 2'-position of a @-D-ribofuranosyl group. RNA encompasses without limitation, double stranded RNA, single stranded RNA, isolated RNA such as partially purified RNA, essentially pure RNA, synthetic RNA, recombinantly produced RNA, as well as modified RNA that differs from naturally occurring RNA by the addition, deletion, substitution and/or alteration of one or more nucleotides. Such alterations may refer to addition of non-nucleotide material to internal RNA nucleotides or to the end(s) of RNA. It is also contemplated herein that nucleotides in RNA may be non-standard nucleotides, such as chemically synthesized nucleotides or deoxynucleotides. For the present disclosure, these altered RNAs are considered analogs of naturally-occurring RNA.

In certain embodiments of the present disclosure, the RNA is messenger RNA (mRNA) that relates to a RNA transcript which encodes a peptide or protein. As established in the art, mRNA generally contains a 5' untranslated region (5'-UTR), a peptide coding region and a 3' untranslated region (3'-UTR). In some embodiments, the RNA is produced by in vitro transcription or chemical synthesis. In one embodiment, the mRNA is produced by in vitro transcription using a DNA template where DNA refers to a nucleic acid that contains deoxyribonucleotides.

In one embodiment, RNA is in vitro transcribed RNA (IVT-RNA) and may be obtained by in vitro transcription of an appropriate DNA template. The promoter for controlling transcription can be any promoter for any RNA polymerase. A DNA template for in vitro transcription may be obtained by cloning of a nucleic acid, in particular cDNA, and introducing it into an appropriate vector for in vitro transcription. The cDNA may be obtained by reverse transcription of RNA.

In certain embodiments of the present disclosure, the RNA is "replicon RNA" or simply a "replicon", in particular "self-replicating RNA" or "self-amplifying RNA". In one particularly preferred embodiment, the replicon or self-replicating RNA is derived from or comprises elements derived from a ssRNA virus, in particular a positive-stranded ssRNA virus such as an alphavirus. Alphaviruses are typical representatives of positive-stranded RNA viruses.

Alphaviruses replicate in the cytoplasm of infected cells (for review of the alphaviral life cycle see Josd et al., Future Microbiol., 2009, vol. 4, pp. 837-856). The total genome length of many alphaviruses typically ranges between 11,000 and 12,000 nucleotides, and the genomic RNA typically has a 5'-cap, and a 3' poly(A) tail. The genome of alphaviruses encodes non-structural proteins (involved in transcription, modification and replication of viral RNA and in protein modification) and structural proteins (forming the virus particle). There are typically two open reading frames (ORFs) in the genome. The four non-structural proteins (nsP1-nsP4) are typically encoded together by a first ORF beginning near the 5' terminus of the genome, while alphavirus structural proteins are encoded together by a second ORF which is found downstream of the first ORF and extends near the 3' terminus of the genome. Typically, the first ORF is larger than the second ORF, the ratio being roughly 2:1. In cells infected by an alphavirus, only the nucleic acid sequence encoding non-structural proteins is translated from the genomic RNA, while the genetic information encoding structural proteins is translatable from a subgenomic transcript, which is an RNA molecule that resembles eukaryotic messenger RNA (mRNA; Gould et al., 2010, Antiviral Res., vol. 87 pp. 111-124). Following infection, i.e. at early stages of the viral life cycle, the (+) stranded genomic RNA directly acts like a messenger RNA for the translation of the open reading frame encoding the non-structural poly-protein (nsP1234). Alphavirus-derived vectors have been proposed for delivery of foreign genetic information into target cells or target organisms. In simple approaches, the open reading frame encoding alphaviral structural proteins is replaced by an open reading frame encoding a protein of interest. Alphavirus-based trans-replication systems rely on alphavirus nucleotide sequence elements on two separate nucleic acid molecules: one nucleic acid molecule encodes a viral replicase, and the other nucleic acid molecule is capable of being replicated by said replicase in trans (hence the designation trans-replication system). Trans-replication requires the presence of both these nucleic acid molecules in a given host cell. The nucleic acid molecule capable of being replicated by the replicase in trans must comprise certain alphaviral sequence elements to allow recognition and RNA synthesis by the alphaviral replicase.

In one embodiment, the RNA described herein may have modified nucleosides. In some embodiments, the RNA comprises a modified nucleoside in place of at least one (e.g., every) uridine.

The term "uracil," as used herein, describes one of the nucleobases that can occur in the nucleic acid of RNA. The structure of uracil is:

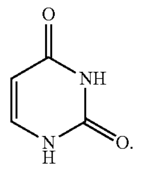

The term "uridine," as used herein, describes one of the nucleosides that can occur in RNA. The structure of uridine is:

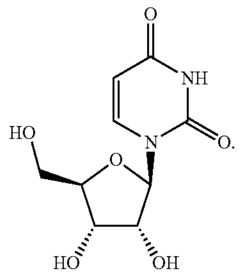 [SMILES: O=c1ccn([C@@H]2O[C@H](CO)[C@@H](O)[C@H]2O)c(=O)[nH]1]

UTP (uridine 5'-triphosphate) has the following structure:

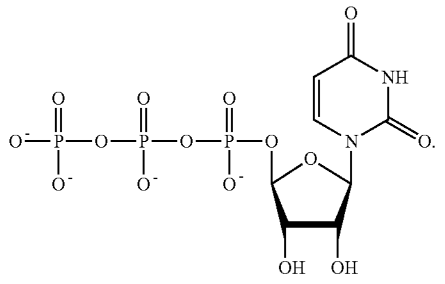

Pseudo-UTP (pseudouridine 5'-triphosphate) has the following structure:

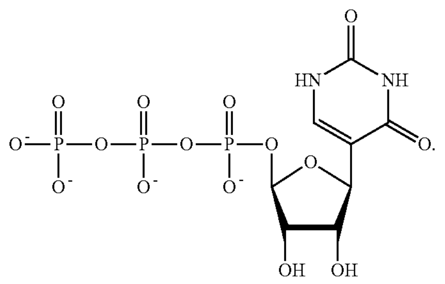

"Pseudouridine" is one example of a modified nucleoside that is an isomer of uridine, where the uracil is attached to the pentose ring via a carbon-carbon bond instead of a nitrogen-carbon glycosidic bond.

Another exemplary modified nucleoside is N1-methyl-pseudouridine (m1ψ), which has the structure:

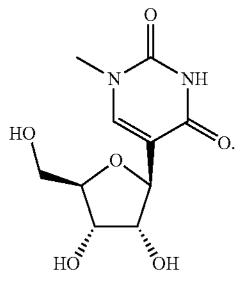 [SMILES: Cn1cc([C@@H]2O[C@H](CO)[C@@H](O)[C@H]2O)c(=O)[nH]c1=O]

N1-methyl-pseudo-UTP has the following structure:

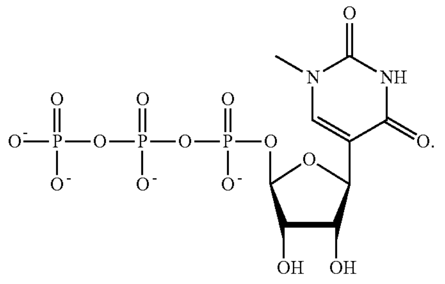

Another exemplary modified nucleoside is 5-methyl-uridine (m5U), which has the structure:

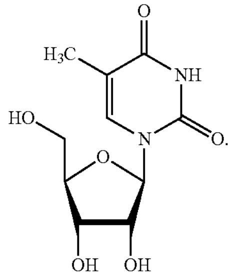

In some embodiments, one or more uridine in the RNA described herein is replaced by a modified nucleoside. In some embodiments, the modified nucleoside is a modified uridine.

In some embodiments, RNA comprises a modified nucleoside in place of at least one uridine.

In some embodiments, RNA comprises a modified nucleoside in place of each uridine.

In some embodiments, the modified nucleoside is independently selected from pseudouridine (ψ), N1-methyl-pseudouridine (m1ψ), and 5-methyl-uridine (m5U). In some embodiments, the modified nucleoside comprises pseudouridine (ψ). In some embodiments, the modified nucleoside comprises N1-methyl-pseudouridine (m1ψ). In some embodiments, the modified nucleoside comprises 5-methyl-uridine (m5U). In some embodiments, RNA may comprise more than one type of modified nucleoside, and the modified nucleosides are independently selected from pseudouridine (ψ), N1-methyl-pseudouridine (m1ψ), and 5-methyl-uridine (m5U). In some embodiments, the modified nucleosides comprise pseudouridine (ψ) and N1-methyl-pseudouridine (m1ψ). In some embodiments, the modified nucleosides comprise pseudouridine (ψ) and 5-methyl-uridine (m5U). In some embodiments, the modified nucleosides comprise N1-methyl-pseudouridine (m1ψ) and 5-methyl-uridine (m5U). In some embodiments, the modified nucleosides comprise pseudouridine (ψ), N1-methyl-pseudouridine (m1ψ), and 5-methyl-uridine (m5U).

In some embodiments, the modified nucleoside replacing one or more, e.g., all, uridine in the RNA may be any one or more of 3-methyl-uridine ($m^3U$), 5-methoxy-uridine ($mo^5U$), 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), uridine 5-oxyacetic acid ($cmo^5U$), uridine 5-oxyacetic acid methyl ester (mcmoSU), 5-carboxymethyl-uridine ($cm^1U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxycarbonylmethyl-2-thio-uridine ($mcm^5s^2U$), 5-aminomethyl-2-thio-uridine ($nm^5s^2U$), 5-methylaminomethyl-uridine ($mnm^5U$), 1-ethyl-pseudouridine, 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine (τm5s2U), 1-taurinomethyl-4-thio-pseudouridine), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$)), 5-(isopentenylaminomethyl)uridine ($inm^5U$), 5-(isopentenylaminomethyl)-2-thio-uridine ($inm^5s^2U$), α-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, 5-[3-(1-E-propenylamino)uridine, or any other modified uridine known in the art.

In one embodiment, the RNA comprises other modified nucleosides or comprises further modified nucleosides, e.g., modified cytidine. For example, in one embodiment, in the RNA 5-methylcytidine is substituted partially or completely, preferably completely, for cytidine. In one embodiment, the RNA comprises 5-methylcytidine and one or more selected from pseudouridine (ψ), N1-methyl-pseudouridine (m1ψ), and 5-methyl-uridine (m5U). In one embodiment, the RNA comprises 5-methylcytidine and N1-methyl-pseudouridine (m1ψ). In some embodiments, the RNA comprises 5-methylcytidine in place of each cytidine and N1-methyl-pseudouridine (m1ψ) in place of each uridine.

In some embodiments, the RNA according to the present disclosure comprises a 5'-cap. In one embodiment, the RNA of the present disclosure does not have uncapped 5'-triphosphates. In one embodiment, the RNA may be modified by a 5'-cap analog. The term "5'-cap" refers to a structure found on the 5'-end of an mRNA molecule and generally consists of a guanosine nucleotide connected to the mRNA via a 5'- to 5'-triphosphate linkage. In one embodiment, this guanosine is methylated at the 7-position. Providing an RNA with a 5'-cap or 5'-cap analog may be achieved by in vitro transcription, in which the 5'-cap is co-transcriptionally expressed into the RNA strand, or may be attached to RNA post-transcriptionally using capping enzymes. In some embodiments, the RNA (e.g., mRNA) comprises a cap0, cap1, or cap2, preferably cap1 or cap2, more preferably cap1. According to the present disclosure, the term "cap0" comprises the structure "$m^7GpppN$", wherein N is any nucleoside bearing an OH moiety at position 2'. According to the present disclosure, the term "cap1" comprises the structure "$m^7GpppNm$", wherein Nm is any nucleoside bearing an $OCH_3$ moiety at position 2'. According to the present disclosure, the term "cap2" comprises the structure "$m^7GpppNmNm$", wherein each Nm is independently any nucleoside bearing an $OCH_3$ moiety at position 2'.

In some embodiments, the building block cap for RNA is $m_2^{7,3'-O}Gppp(m_1^{2'-O})ApG$ (also sometimes referred to as $m_2^{7,3'O}G(5')ppp(5')m^{2'-O}ApG$), which has the following structure:
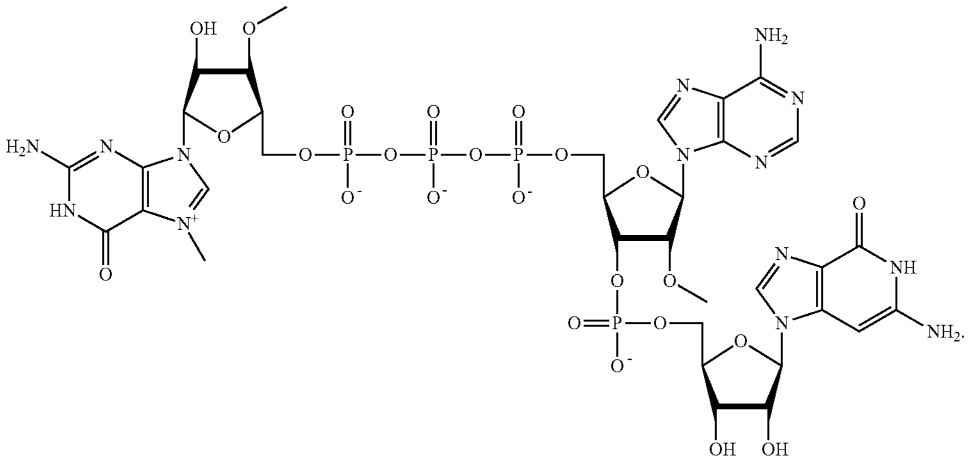
Below is an exemplary Cap1 RNA, which comprises RNA and $m2^{7,3'O}G(5')ppp(5')m^{2'-O}ApG$:
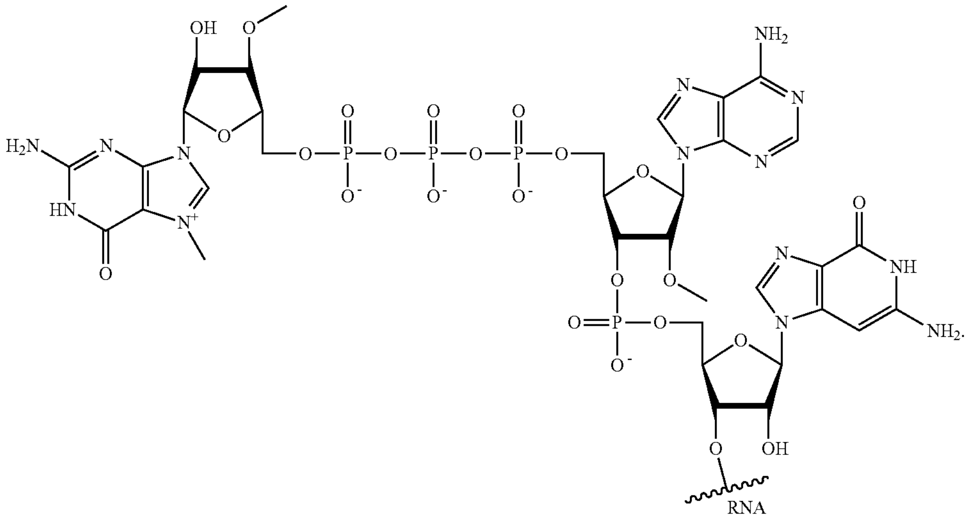

Below is another exemplary Cap1 RNA (no cap analog):
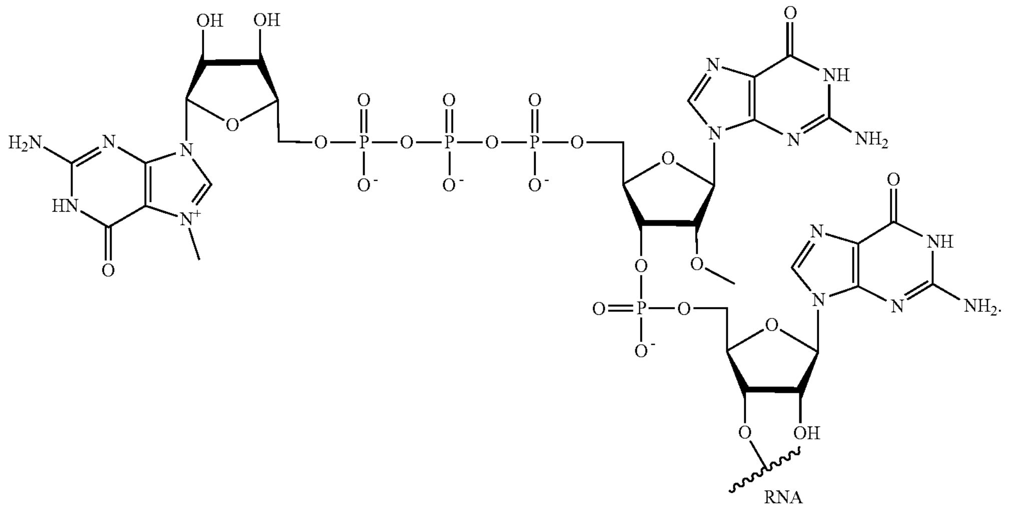
In some embodiments, the RNA is modified with "Cap0" structures using, in one embodiment, the cap analog anti-reverse cap (ARCA Cap ($m_2^{7,3'O}G(5')ppp(5')G$)) with the structure:
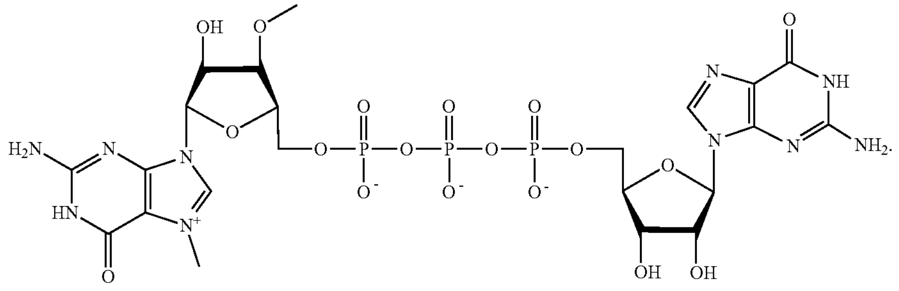
Below is an exemplary Cap0 RNA comprising RNA and $m_2^{7,3'O}G(5')ppp(5')G$:
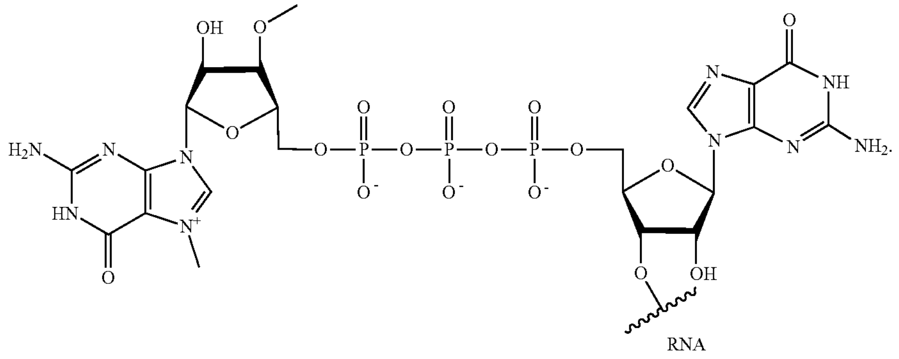

In some embodiments, the "Cap0" structures are generated using the cap analog Beta-S-ARCA ($m_2^{7,2'O}G(5')ppSp(5')G$) with the structure:

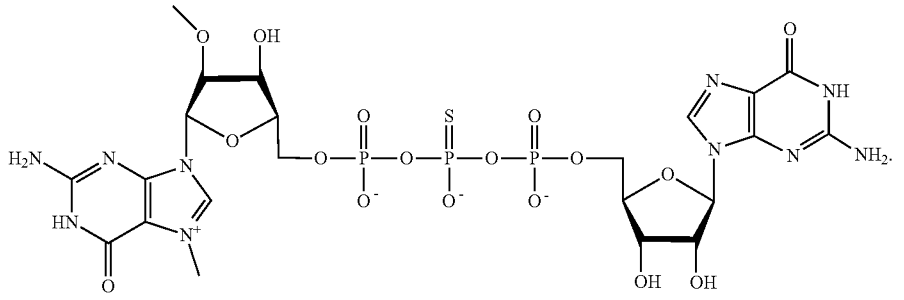

Below is an exemplary Cap0 RNA comprising Beta-S-ARCA ($m_2^{7,2'O}G(5')ppSp(5')G$) and RNA:

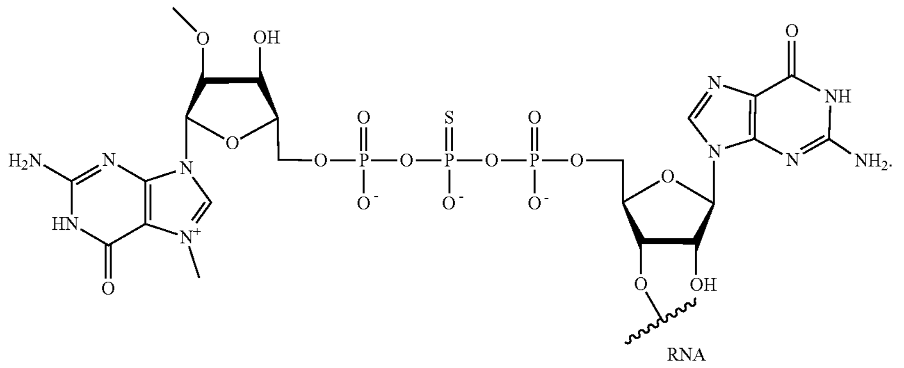

The "D1" diastereomer of beta-S-ARCA or "beta-S-ARCA(D1)" is the diastereomer of beta-S-ARCA which elutes first on an HPLC column compared to the D2 diastereomer of beta-S-ARCA (beta-S-ARCA(D2)) and thus exhibits a shorter retention time (cf., WO 2011/015347, herein incorporated by reference).

A particularly preferred cap is beta-S-ARCA(D1) ($m_2^{7,2'-O}GppSpG$) or $m_2^{7,3'-O}Gppp(m_1^{2'-O})ApG$.

In some embodiments, RNA according to the present disclosure comprises a 5'-UTR and/or a 3'-UTR. The term "untranslated region" or "UTR" relates to a region in a DNA molecule which is transcribed but is not translated into an amino acid sequence, or to the corresponding region in an RNA molecule, such as an mRNA molecule. An untranslated region (UTR) can be present 5' (upstream) of an open reading frame (5'-UTR) and/or 3' (downstream) of an open reading frame (3'-UTR). A 5'-UTR, if present, is located at the 5' end, upstream of the start codon of a protein-encoding region. A 5'-UTR is downstream of the 5'-cap (if present), e.g. directly adjacent to the 5'-cap. A 3'-UTR, if present, is located at the 3' end, downstream of the termination codon of a protein-encoding region, but the term "3'-UTR" does preferably not include the poly(A) sequence. Thus, the 3'-UTR is upstream of the poly(A) sequence (if present), e.g. directly adjacent to the poly(A) sequence.

In some embodiments, RNA comprises a 5'-UTR comprising the nucleotide sequence of SEQ ID NO: 12, or a nucleotide sequence having at least 99%, 98%, 97%, 96%, 95%, 90%, 85%, or 80% identity to the nucleotide sequence of SEQ ID NO: 12.

In some embodiments, RNA comprises a 3'-UTR comprising the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

A particularly preferred 5'-UTR comprises the nucleotide sequence of SEQ ID NO: 12. A particularly preferred 3'-UTR comprises the nucleotide sequence of SEQ ID NO: 13.

In some embodiments, the RNA according to the present disclosure comprises a 3'-poly(A) sequence.

As used herein, the term "poly(A) sequence" or "poly-A tail" refers to an uninterrupted or interrupted sequence of adenylate residues which is typically located at the 3'-end of an RNA molecule. Poly(A) sequences are known to those of skill in the art and may follow the 3'-UTR in the RNAs described herein. An uninterrupted poly(A) sequence is characterized by consecutive adenylate residues. In nature, an uninterrupted poly(A) sequence is typical. RNAs disclosed herein can have a poly(A) sequence attached to the free 3'-end of the RNA by a template-independent RNA polymerase after transcription or a poly(A) sequence encoded by DNA and transcribed by a template-dependent RNA polymerase.

It has been demonstrated that a poly(A) sequence of about 120 A nucleotides has a beneficial influence on the levels of RNA in transfected eukaryotic cells, as well as on the levels of protein that is translated from an open reading frame that is present upstream (5') of the poly(A) sequence (Holtkamp et al., 2006, Blood, vol. 108, pp. 4009-4017).

The poly(A) sequence may be of any length. In some embodiments, a poly(A) sequence comprises, essentially consists of, or consists of at least 20, at least 30, at least 40, at least 80, or at least 100 and up to 500, up to 400, up to 300, up to 200, or up to 150 A nucleotides, and, in particular, about 120 A nucleotides. In this context, "essentially consists of" means that most nucleotides in the poly(A) sequence, typically at least 75%, at least 80%, at least 85%, at least 90%, at least 95%, at least 96%, at least 97%, at least 98%, or at least 99% by number of nucleotides in the poly(A) sequence are A nucleotides, but permits that remaining nucleotides are nucleotides other than A nucleotides, such as U nucleotides (uridylate), G nucleotides (guanylate), or C nucleotides (cytidylate). In this context, "consists of" means that all nucleotides in the poly(A) sequence, i.e., 100% by number of nucleotides in the poly(A) sequence, are A nucleotides. The term "A nucleotide" or "A" refers to adenylate.

In some embodiments, a poly(A) sequence is attached during RNA transcription, e.g., during preparation of in vitro transcribed RNA, based on a DNA template comprising repeated dT nucleotides (deoxythymidylate) in the strand complementary to the coding strand. The DNA sequence encoding a poly(A) sequence (coding strand) is referred to as poly(A) cassette.

In some embodiments, the poly(A) cassette present in the coding strand of DNA essentially consists of dA nucleotides, but is interrupted by a random sequence of the four nucleotides (dA, dC, dG, and dT). Such random sequence may be 5 to 50, 10 to 30, or 10 to 20 nucleotides in length. Such a cassette is disclosed in WO 2016/005324 A1, hereby incorporated by reference. Any poly(A) cassette disclosed in WO 2016/005324 A1 may be used in the present disclosure. A poly(A) cassette that essentially consists of dA nucleotides, but is interrupted by a random sequence having an equal distribution of the four nucleotides (dA, dC, dG, dT) and having a length of e.g., 5 to 50 nucleotides shows, on DNA level, constant propagation of plasmid DNA in *E. coli* and is still associated, on RNA level, with the beneficial properties with respect to supporting RNA stability and translational efficiency is encompassed. Consequently, in some embodiments, the poly(A) sequence contained in an RNA molecule described herein essentially consists of A nucleotides, but is interrupted by a random sequence of the four nucleotides (A, C, G, U). Such random sequence may be 5 to 50, 10 to 30, or 10 to 20 nucleotides in length.

In some embodiments, no nucleotides other than A nucleotides flank a poly(A) sequence at its 3'-end, i.e., the poly(A) sequence is not masked or followed at its 3-end by a nucleotide other than A.

In some embodiments, the poly(A) sequence may comprise at least 20, at least 30, at least 40, at least 80, or at least 100 and up to 500, up to 400, up to 300, up to 200, or up to 150 nucleotides. In some embodiments, the poly(A) sequence may essentially consist of at least 20, at least 30, at least 40, at least 80, or at least 100 and up to 500, up to 400, up to 300, up to 200, or up to 150 nucleotides. In some embodiments, the poly(A) sequence may consist of at least 20, at least 30, at least 40, at least 80, or at least 100 and up to 500, up to 400, up to 300, up to 200, or up to 150 nucleotides. In some embodiments, the poly(A) sequence comprises at least 100 nucleotides. In some embodiments, the poly(A) sequence comprises about 150 nucleotides. In some embodiments, the poly(A) sequence comprises about 120 nucleotides.

In some embodiments, a poly(A) sequence included in an RNA described herein is a interrupted poly(A) sequence, e.g., as described in WO2016/005324, the entire content of which is incorporated herein by reference for purposes described herein. In some embodiments, a poly(A) sequence comprises a stretch of at least 20 adenosine residues (including, e.g., at least 30, at least 40, at least 50, at least 60, at least 70, or more adenosine residues), followed by a linker sequence (e.g., in some embodiments comprising non-A nucleotides) and another stretch of at least 20 adenosine residues (including, e.g., at least 30, at least 40, at least 50, at least 60, at least 70, or more adenosine residues). In some embodiments, such a linker sequence may be 3-50 nucleotides in length, or 5-25 nucleotides in length, or 10-15 nucleotides in length. In some embodiments, a poly(A) sequence comprises a stretch of about 30 adenosine residues, followed by a linker sequence having a length of about 5-15 nucleotides (e.g., in some embodiments comprising non-A nucleotides) and another stretch of about 70 adenosine residues.

In some embodiments, RNA comprises a poly(A) sequence comprising the nucleotide sequence of SEQ ID NO: 14, or a nucleotide sequence having at least 99%, 98%, 97%, 96%, 95%, 90%, 85%, or 80% identity to the nucleotide sequence of SEQ ID NO: 14.

A particularly preferred poly(A) sequence comprises the nucleotide sequence of SEQ ID NO: 14.

According to the present disclosure, vaccine antigen is preferably administered as single-stranded, 5'-capped RNA (e.g., mRNA) that is translated into the respective protein upon entering cells of a subject being administered the RNA. Preferably, the RNA contains structural elements optimized for maximal efficacy of the RNA with respect to stability and translational efficiency (5'-cap, 5'-UTR, 3'-UTR, poly(A) sequence).

In one embodiment, beta-S-ARCA(D1) is utilized as specific capping structure at the 5'-end of the RNA. In one embodiment, $m_2^{7,3'-O}$Gppp($m_1{}_2$'-O)ApG is utilized as specific capping structure at the 5'-end of the RNA. In one embodiment, the 5'-UTR sequence is derived from the human alpha-globin mRNA and optionally has an optimized 'Kozak sequence' to increase translational efficiency. In one embodiment, a combination of two sequence elements (FI element) derived from the "amino terminal enhancer of split" (AES) mRNA (called F) and the mitochondrial encoded 12S ribosomal RNA (called I) are placed between the coding sequence and the poly(A) sequence to assure higher maximum protein levels and prolonged persistence of the RNA (e.g., mRNA). In one embodiment, two re-iterated 3'-UTRs derived from the human beta-globin mRNA are placed between the coding sequence and the poly(A) sequence to assure higher maximum protein levels and prolonged persistence of the RNA (e.g., mRNA). In one embodiment, a poly(A) sequence measuring 110 nucleotides in length, consisting of a stretch of 30 adenosine residues, followed by a linker sequence (e.g., 10 nucleotide linker sequence) and another 70 adenosine residues is used. This poly(A) sequence was designed to enhance RNA stability and translational efficiency.

In one embodiment of all aspects of the present disclosure, RNA encoding a vaccine antigen is expressed in cells of the subject treated to provide the vaccine antigen. In one embodiment of all aspects of the present disclosure, the RNA is transiently expressed in cells of the subject.

In one embodiment of all aspects of the present disclosure, the RNA is in vitro transcribed RNA. In one embodiment of all aspects of the present disclosure, expression of the vaccine antigen is at the cell surface. In one embodiment of all aspects of the present disclosure, the vaccine antigen is expressed and presented in the context of MHC. In one embodiment of all aspects of the present disclosure, expression of the vaccine antigen is into the extracellular space, i.e., the vaccine antigen is secreted.

In the context of the present disclosure, the term "transcription" relates to a process, wherein the genetic code in a DNA sequence is transcribed into RNA. Subsequently, the RNA may be translated into peptide or protein.

According to the present disclosure, the term "transcription" comprises "in vitro transcription", wherein the term "in vitro transcription" relates to a process wherein RNA, in particular mRNA, is in vitro synthesized in a cell-free system, preferably using appropriate cell extracts. Preferably, cloning vectors are applied for the generation of transcripts. These cloning vectors are generally designated as transcription vectors and are according to the present disclosure encompassed by the term "vector". According to the present disclosure, the RNA used in the present disclosure preferably is in vitro transcribed RNA (IVT-RNA) and may be obtained by in vitro transcription of an appropriate DNA template. The promoter for controlling transcription can be any promoter for any RNA polymerase. Particular examples of RNA polymerases are the T7, T3, and SP6 RNA polymerases. Preferably, the in vitro transcription according to the disclosure is controlled by a T7 or SP6 promoter. A DNA template for in vitro transcription may be obtained by cloning of a nucleic acid, in particular cDNA, and introducing it into an appropriate vector for in vitro transcription. The cDNA may be obtained by reverse transcription of RNA.

With respect to RNA, the term "expression" or "translation" relates to the process in the ribosomes of a cell by which a strand of mRNA directs the assembly of a sequence of amino acids to make a peptide or protein.

In one embodiment, after administration of the RNA described herein, e.g., formulated as RNA lipid particles, at least a portion of the RNA is delivered to a target cell. In one embodiment, at least a portion of the RNA is delivered to the cytosol of the target cell. In one embodiment, the RNA is translated by the target cell to produce the peptide or protein it encodes. In one embodiment, the target cell is a spleen cell. In one embodiment, the target cell is an antigen presenting cell such as a professional antigen presenting cell in the spleen. In one embodiment, the target cell is a dendritic cell or macrophage. RNA particles such as RNA lipid particles described herein may be used for delivering RNA to such target cell. Accordingly, the present disclosure also relates to a method for delivering RNA to a target cell in a subject comprising the administration of the RNA particles described herein to the subject. In one embodiment, the RNA is delivered to the cytosol of the target cell. In one embodiment, the RNA is translated by the target cell to produce the peptide or protein encoded by the RNA.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

In one embodiment, the RNA encoding vaccine antigen to be administered according to the present disclosure is non-immunogenic. RNA encoding immunostimulant may be administered according to the present disclosure to provide an adjuvant effect. The RNA encoding immunostimulant may be standard RNA or non-immunogenic RNA.

The term "non-immunogenic RNA" as used herein refers to RNA that does not induce a response by the immune system upon administration, e.g., to a mammal, or induces a weaker response than would have been induced by the same RNA that differs only in that it has not been subjected to the modifications and treatments that render the non-immunogenic RNA non-immunogenic, i.e., than would have been induced by standard RNA (stdRNA). In one preferred embodiment, non-immunogenic RNA, which is also termed modified RNA (modRNA) herein, is rendered non-immunogenic by incorporating modified nucleosides suppressing RNA-mediated activation of innate immune receptors into the RNA and removing double-stranded RNA (dsRNA).

For rendering the non-immunogenic RNA non-immunogenic by the incorporation of modified nucleosides, any modified nucleoside may be used as long as it lowers or suppresses immunogenicity of the RNA. Particularly preferred are modified nucleosides that suppress RNA-mediated activation of innate immune receptors. In one embodiment, the modified nucleosides comprises a replacement of one or more uridines with a nucleoside comprising a modified nucleobase. In one embodiment, the modified nucleobase is a modified uracil. In one embodiment, the nucleoside comprising a modified nucleobase is selected from the group consisting of 3-methyl-uridine ($m^3U$), 5-methoxy-uridine ($mo^1U$), 5-aza-uridine, 6-aza-uridine, 2-thio-5-aza-uridine, 2-thio-uridine ($s^2U$), 4-thio-uridine ($s^4U$), 4-thio-pseudouridine, 2-thio-pseudouridine, 5-hydroxy-uridine ($ho^5U$), 5-aminoallyl-uridine, 5-halo-uridine (e.g., 5-iodo-uridine or 5-bromo-uridine), uridine 5-oxyacetic acid ($cmo^5U$), uridine 5-oxyacetic acid methyl ester ($mcmo^5U$), 5-carboxymethyl-uridine ($cm^5U$), 1-carboxymethyl-pseudouridine, 5-carboxyhydroxymethyl-uridine ($chm^5U$), 5-carboxyhydroxymethyl-uridine methyl ester ($mchm^5U$), 5-methoxycarbonylmethyl-uridine ($mcm^5U$), 5-methoxy-carbonylmethyl-2-thio-uridine ($mcm^5s^2U$), 5-aminomethyl-2-thio-uridine ($nm^5s^2U$), 5-methylaminomethyl-uridine ($mnm^5U$), 1-ethyl-pseudouridine, 5-methylaminomethyl-2-thio-uridine ($mnm^5s^2U$), 5-methylaminomethyl-2-seleno-uridine ($mnm^5se^2U$), 5-carbamoylmethyl-uridine ($ncm^5U$), 5-carboxymethylaminomethyl-uridine ($cmnm^5U$), 5-carboxymethylaminomethyl-2-thio-uridine ($cmnm^5s^2U$), 5-propynyl-uridine, 1-propynyl-pseudouridine, 5-taurinomethyl-uridine ($\tau m^5U$), 1-taurinomethyl-pseudouridine, 5-taurinomethyl-2-thio-uridine($\tau m^5s^2U$), 1-taurinomethyl-4-thio-pseudouridine), 5-methyl-2-thio-uridine ($m^5s^2U$), 1-methyl-4-thio-pseudouridine ($m^1s^4\psi$), 4-thio-1-methyl-pseudouridine, 3-methyl-pseudouridine ($m^3\psi$), 2-thio-1-methyl-pseudouridine, 1-methyl-1-deaza-pseudouridine, 2-thio-1-methyl-1-deaza-pseudouridine, dihydrouridine (D), dihydropseudouridine, 5,6-dihydrouridine, 5-methyl-dihydrouridine ($m^5D$), 2-thio-dihydrouridine, 2-thio-dihydropseudouridine, 2-methoxy-uridine, 2-methoxy-4-thio-uridine, 4-methoxy-pseudouridine, 4-methoxy-2-thio-pseudouridine, N1-methyl-pseudouridine, 3-(3-amino-3-carboxypropyl)uridine ($acp^3U$), 1-methyl-3-(3-amino-3-carboxypropyl)pseudouridine ($acp^3\psi$), 5-(isopentenylaminomethyl)uridine ($inm^5U$), 5-(isopentenylaminomethyl)-2-thio-uridine ($inm^5s^2U$), $\alpha$-thio-uridine, 2'-O-methyl-uridine (Um), 5,2'-O-dimethyl-uridine ($m^5Um$), 2'-O-methyl-pseudouridine (ψm), 2-thio-2'-O-methyl-uridine ($s^2Um$), 5-methoxycarbonylmethyl-2'-O-methyl-uridine ($mcm^5Um$), 5-carbamoylmethyl-2'-O-methyl-uridine ($ncm^5Um$), 5-carboxymethylaminomethyl-2'-O-methyl-uridine ($cmnm^5Um$), 3,2'-O-dimethyl-uridine ($m^3Um$), 5-(isopentenylaminomethyl)-2'-O-methyl-uridine ($inm^5Um$), 1-thio-uridine, deoxythymidine, 2'-F-ara-uridine, 2'-F-uridine, 2'-OH-ara-uridine, 5-(2-carbomethoxyvinyl) uridine, and 5-[3-(1-E-propenylamino)uridine. In one particularly preferred embodiment, the nucleoside comprising a modified nucleobase is pseudouridine (ψ), N1-methyl-pseudouridine (m1ψ) or 5-methyl-uridine (m5U), in particular N1-methyl-pseudouridine.

In one embodiment, the replacement of one or more uridines with a nucleoside comprising a modified nucleobase comprises a replacement of at least 1%, at least 2%, at least 3%, at least 4%, at least 5%, at least 10%, at least 25%, at least 50%, at least 75%, at least 90%, at least 95%, at least 96%, at least 97%, at least 98%, at least 99% or 100% of the uridines.

During synthesis of RNA (e.g., mRNA) by in vitro transcription (IVT) using T7 RNA polymerase significant amounts of aberrant products, including double-stranded RNA (dsRNA) are produced due to unconventional activity of the enzyme. dsRNA induces inflammatory cytokines and activates effector enzymes leading to protein synthesis inhibition. dsRNA can be removed from RNA such as IVT RNA, for example, by ion-pair reversed phase HPLC using a non-porous or porous C-18 polystyrene-divinylbenzene (PS-DVB) matrix. Alternatively, an enzymatic based method using *E. coli* RNaseIII that specifically hydrolyzes dsRNA but not ssRNA, thereby eliminating dsRNA contaminants from IVT RNA preparations can be used.

Furthermore, dsRNA can be separated from ssRNA by using a cellulose material. In one embodiment, an RNA preparation is contacted with a cellulose material and the ssRNA is separated from the cellulose material under conditions which allow binding of dsRNA to the cellulose material and do not allow binding of ssRNA to the cellulose material.

As the term is used herein, "remove" or "removal" refers to the characteristic of a population of first substances, such as non-immunogenic RNA, being separated from the proximity of a population of second substances, such as dsRNA, wherein the population of first substances is not necessarily devoid of the second substance, and the population of second substances is not necessarily devoid of the first substance. However, a population of first substances characterized by the removal of a population of second substances has a measurably lower content of second substances as compared to the non-separated mixture of first and second substances.

In one embodiment, the removal of dsRNA from non-immunogenic RNA comprises a removal of dsRNA such that less than 10%, less than 5%, less than 4%, less than 3%, less than 2%, less than 1%, less than 0.5%, less than 0.3%, or less than 0.1% of the RNA in the non-immunogenic RNA composition is dsRNA. In one embodiment, the non-immunogenic RNA is free or essentially free of dsRNA. In some embodiments, the non-immunogenic RNA composition comprises a purified preparation of single-stranded nucleoside modified RNA. For example, in some embodiments, the purified preparation of single-stranded nucleoside modified RNA is substantially free of double stranded RNA (dsRNA). In some embodiments, the purified preparation is at least 90%, at least 91%, at least 92%, at least 93%, at least 94%, at least 95%, at least 96%, at least 97%, at least 98%, at least 99%, at least 99.5%, or at least 99.9% single stranded nucleoside modified RNA, relative to all other nucleic acid molecules (DNA, dsRNA, etc.).

In one embodiment, the non-immunogenic RNA is translated in a cell more efficiently than standard RNA with the same sequence. In one embodiment, translation is enhanced by a factor of 2-fold relative to its unmodified counterpart. In one embodiment, translation is enhanced by a 3-fold factor. In one embodiment, translation is enhanced by a 4-fold factor. In one embodiment, translation is enhanced by a 5-fold factor. In one embodiment, translation is enhanced by a 6-fold factor. In one embodiment, translation is enhanced by a 7-fold factor. In one embodiment, translation is enhanced by an 8-fold factor. In one embodiment, translation is enhanced by a 9-fold factor. In one embodiment, translation is enhanced by a 10-fold factor. In one embodiment, translation is enhanced by a 15-fold factor. In one embodiment, translation is enhanced by a 20-fold factor. In one embodiment, translation is enhanced by a 50-fold factor. In one embodiment, translation is enhanced by a 100-fold factor. In one embodiment, translation is enhanced by a 200-fold factor. In one embodiment, translation is enhanced by a 500-fold factor. In one embodiment, translation is enhanced by a 1000-fold factor. In one embodiment, translation is enhanced by a 2000-fold factor. In one embodiment, the factor is 10-1000-fold. In one embodiment, the factor is 10-100-fold. In one embodiment, the factor is 10-200-fold. In one embodiment, the factor is 10-300-fold. In one embodiment, the factor is 10-500-fold. In one embodiment, the factor is 20-1000-fold. In one embodiment, the factor is 30-1000-fold. In one embodiment, the factor is 50-1000-fold. In one embodiment, the factor is 100-1000-fold. In one embodiment, the factor is 200-1000-fold. In one embodiment, translation is enhanced by any other significant amount or range of amounts.

In one embodiment, the non-immunogenic RNA exhibits significantly less innate immunogenicity than standard RNA with the same sequence. In one embodiment, the non-immunogenic RNA exhibits an innate immune response that is 2-fold less than its unmodified counterpart. In one embodiment, innate immunogenicity is reduced by a 3-fold factor. In one embodiment, innate immunogenicity is reduced by a 4-fold factor. In one embodiment, innate immunogenicity is reduced by a 5-fold factor. In one embodiment, innate immunogenicity is reduced by a 6-fold factor. In one embodiment, innate immunogenicity is reduced by a 7-fold factor. In one embodiment, innate immunogenicity is reduced by a 8-fold factor. In one embodiment, innate immunogenicity is reduced by a 9-fold factor. In one embodiment, innate immunogenicity is reduced by a 10-fold factor. In one embodiment, innate immunogenicity is reduced by a 15-fold factor. In one embodiment, innate immunogenicity is reduced by a 20-fold factor. In one embodiment, innate immunogenicity is reduced by a 50-fold factor. In one embodiment, innate immunogenicity is reduced by a 100-fold factor. In one embodiment, innate immunogenicity is reduced by a 200-fold factor. In one embodiment, innate immunogenicity is reduced by a 500-fold factor. In one embodiment, innate immunogenicity is reduced by a 1000-fold factor. In one embodiment, innate immunogenicity is reduced by a 2000-fold factor.

The term "exhibits significantly less innate immunogenicity" refers to a detectable decrease in innate immunogenicity. In one embodiment, the term refers to a decrease such that an effective amount of the non-immunogenic RNA can be administered without triggering a detectable innate immune response. In one embodiment, the term refers to a decrease such that the non-immunogenic RNA can be repeatedly administered without eliciting an innate immune response sufficient to detectably reduce production of the protein encoded by the non-immunogenic RNA. In one embodiment, the decrease is such that the non-immunogenic RNA can be repeatedly administered without eliciting an innate immune response sufficient to eliminate detectable production of the protein encoded by the non-immunogenic RNA.

"Immunogenicity" is the ability of a foreign substance, such as RNA, to provoke an immune response in the body of a human or other animal. The innate immune system is the component of the immune system that is relatively unspecific and immediate. It is one of two main components of the vertebrate immune system, along with the adaptive immune system.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence.

As used herein, the terms "linked," "fused", or "fusion" are used interchangeably. These terms refer to the joining together of two or more elements or components or domains.

Codon-Optimization/Increase in G/C Content

In some embodiment, the amino acid sequence comprising a SARS-CoV-2 S protein, an immunogenic variant thereof, or an immunogenic fragment of the SARS-CoV-2 S protein or the immunogenic variant thereof described herein is encoded by a coding sequence which is codon-optimized and/or the G/C content of which is increased compared to wild type coding sequence. This also includes embodiments, wherein one or more sequence regions of the coding sequence are codon-optimized and/or increased in the G/C content compared to the corresponding sequence regions of the wild type coding sequence. In one embodiment, the codon-optimization and/or the increase in the G/C content preferably does not change the sequence of the encoded amino acid sequence.

The term "codon-optimized" refers to the alteration of codons in the coding region of a nucleic acid molecule to reflect the typical codon usage of a host organism without preferably altering the amino acid sequence encoded by the nucleic acid molecule. Within the context of the present disclosure, coding regions are preferably codon-optimized for optimal expression in a subject to be treated using the RNA molecules described herein. Codon-optimization is based on the finding that the translation efficiency is also determined by a different frequency in the occurrence of tRNAs in cells. Thus, the sequence of RNA may be modified such that codons for which frequently occurring tRNAs are available are inserted in place of "rare codons".

In some embodiments of the present disclosure, the guanosine/cytosine (G/C) content of the coding region of the RNA described herein is increased compared to the G/C content of the corresponding coding sequence of the wild type RNA, wherein the amino acid sequence encoded by the RNA is preferably not modified compared to the amino acid sequence encoded by the wild type RNA. This modification of the RNA sequence is based on the fact that the sequence of any RNA region to be translated is important for efficient translation of that mRNA. Sequences having an increased G (guanosine)/C (cytosine) content are more stable than sequences having an increased A (adenosine)/U (uracil) content. In respect to the fact that several codons code for one and the same amino acid (so-called degeneration of the genetic code), the most favourable codons for the stability can be determined (so-called alternative codon usage). Depending on the amino acid to be encoded by the RNA, there are various possibilities for modification of the RNA sequence, compared to its wild type sequence. In particular, codons which contain A and/or U nucleotides can be modified by substituting these codons by other codons, which code for the same amino acids but contain no A and/or U or contain a lower content of A and/or U nucleotides.

In various embodiments, the G/C content of the coding region of the RNA described herein is increased by at least 10%, at least 20%, at least 30%, at least 40%, at least 50%, at least 55%, or even more compared to the G/C content of the coding region of the wild type RNA. In some embodiments, G/C content of a coding region is increased by about 10% to about 60% (e.g., by about 20% to about 60%, about 30% to about 60%, about 40% to about 60%, about 50% to about 60%, or by about 51%, about 52%, about 53%, about 54%, about 55%, about 56%, about 57%, about 58%, about 59%, or about 60%) compared to the G/C content of the coding region of the wild type RNA.

In some embodiments, RNA disclosed herein comprises a sequence disclosed herein (e.g., SEQ ID NO: 9), that has been modified to encode one or more mutations characteristic of a SARS-CoV-2 variant (e.g., ones described herein including but not limited to a BA.2 or a BA.4/5 Omicron variant). In some embodiments, RNA can be modified to encode one or more mutations characteristic of a SARS-CoV-2 variant by making as few nucleotide changes as possible. In some embodiments, RNA can be modified to encode one or more mutations that are characteristic of a SARS-CoV-2 variant by introducing mutations that result in high codon-optimization and/or increased G/C content.

In some embodiments, one or more mutations characteristic of a SARS-CoV-2 variant are introduced onto a full-length S protein (e.g., an S protein comprising SEQ ID NO: 1). In some embodiments one or more mutations characteristic of a SARS-CoV-2 variant are introduced onto a full-length S protein having one or more proline mutations that increase stability of a prefusion confirmation. For example, in some embodiments, proline substitutions are made at positions corresponding to positions 986 and 987 of SEQ ID NO: 1. In some embodiments, at least 4 proline substitutions are made. In some embodiments, at least four of such proline mutations include mutations at positions corresponding to residues 817, 892, 899, and 942 of SEQ ID NO: 1, e.g., as described in WO 2021243122 Δ2, the entire contents of which are incorporated herein by reference in its entirety. In some embodiments, such a SARS-CoV-2 S protein comprising proline substitutions at positions corresponding to residues 817, 892, 899, and 942 of SEQ ID NO: 1, may further comprise proline substitutions at positions corresponding to residues 986 and 987 of SEQ ID NO: 1. In some embodiments, one or more mutations characteristic of a SARS-CoV-2 variant are introduced onto an immunogenic fragment of an S protein (e.g., the RBD of SEQ ID NO: 1).

Embodiments of Administered RNAs

In some embodiments, the present disclosure provides an RNA (e.g., mRNA) comprising an open reading frame encoding a polypeptide that comprises at least a portion of a SARS-CoV-2 S protein. The RNA is suitable for intracellular expression of the polypeptide. In some embodiments, such an encoded polypeptide comprises a sequence corresponding to the complete S protein. In some embodiments, such an encoded polypeptide does not comprise a sequence corresponding to the complete S protein. In some embodiments, the encoded polypeptide comprises a sequence that corresponds to the receptor binding domain (RBD). In some embodiments, the encoded polypeptide comprises a sequence that corresponds to the RBD, and further comprises a trimerization domain (e.g., a trimerization domain as disclosed herein, such as a fibritin domain). In some embodiments an RBD comprises a signaling domain (e.g., a signaling domain as disclosed herein). In some embodiments an RBD comprises a transmembrane domain (e.g., a transmembrane domain as disclosed herein). In some embodiments, an RBD comprises a signaling domain and a trimerization domain. In some embodiments, an RBD comprises a signaling domain, a trimerization domain, and transmembrane domain.

In some embodiments, the encoded polypeptide comprises a sequence that corresponds to two receptor binding domains. In some embodiments, the encoded polypeptide comprises a sequence that corresponds to two receptor binding domains in tandem in an amino acid chain, e.g., as disclosed in Dai, Lianpan, et al. "A universal design of betacoronavirus vaccines against COVID-19, MERS, and SARS," Cell 182.3 (2020): 722-733, the contents of which are incorporated by reference herein in their entirety.

In some embodiments, a SARS-CoV-2 S protein, or an immunogenic fragment thereof comprises one or more mutations to alter or remove a glycosylation site, e.g., as described in WO2022221835Δ2, US20220323574Δ1, or WO2022195351Δ1.

In some embodiments, compositions or medical preparations described herein comprise RNA encoding an amino acid sequence comprising SARS-CoV-2 S protein, an immunogenic variant thereof, or an immunogenic fragment of the SARS-CoV-2 S protein or the immunogenic variant thereof. Likewise, methods described herein comprise administration of such RNA.

The active platform for use herein is based on an antigen-coding RNA vaccine to induce robust neutralising antibodies and accompanying/concomitant T cell response to achieve protective immunization with preferably minimal vaccine doses. The RNA administered is preferably in-vitro transcribed RNA.

Three different RNA platforms are particularly preferred, namely non-modified uridine containing mRNA (uRNA), nucleoside modified mRNA (modRNA) and self-amplifying RNA (saRNA). In one particularly preferred embodiment, the RNA is in vitro transcribed RNA. In some embodiments, uRNA is mRNA. In some embodiments, modRNA is mRNA.

In the following, embodiments of these three different RNA platforms are described, wherein certain terms used when describing elements thereof have the following meanings:

S1S2 protein/S1S2 RBD: Sequences encoding the respective antigen of SARS-CoV-2.

nsP1, nsP2, nsP3, and nsP4: Wildtype sequences encoding the Venezuelan equine encephalitis virus (VEEV) RNA-dependent RNA polymerase replicase and a subgenomic promotor plus conserved sequence elements supporting replication and translation.

virUTR: Viral untranslated region encoding parts of the subgenomic promotor as well as replication and translation supporting sequence elements.

hAg-Kozak: 5'-UTR sequence of the human alpha-globin mRNA with an optimized 'Kozak sequence' to increase translational efficiency.

Sec: Sec corresponds to a secretory signal peptide (sec), which guides translocation of the nascent polypeptide chain into the endoplasmatic reticulum. In some embodiments, such a secretory signal peptide includes the intrinsic S1S2 secretory signal peptide. In some embodiments, such a secretory signal peptide is a secretory signal peptide from a non-S1S2 protein. For example, an immunoglobulin secretory signal peptide (aa 1-22), an HSV-1 gD signal peptide (MGGAAARLGAVILFVVIVGLHGVRSKY(SEQ ID NO: 105)), an HSV-2 gD signal peptide (MGRLTSGVGTAALLVVAVGLRVVCA(SEQ ID NO: 106)); a human SPARC signal peptide, a human insulin isoform 1 signal peptide, a human albumin signal peptide, or any other signal peptide described herein.

Glycine-serine linker (GS): Sequences coding for short linker peptides predominantly consisting of the amino acids glycine (G) and serine (S), as commonly used for fusion proteins.

Fibritin: Partial sequence of T4 fibritin (foldon), used as artificial trimerization domain.

TM: TM sequence corresponds to the transmembrane part of a protein. A transmembrane domain can be N-terminal, C-terminal, or internal to an encoded polypeptide. A coding sequence of a transmembrane element is typically placed in frame (i.e., in the same reading frame), 5', 3', or internal to coding sequences of sequences (e.g., sequences encoding polypeptide(s)) with which it is to be linked. In some embodiments, a transmembrane domain comprises or is a transmembrane domain of Hemagglutinin (HA) of Influenza virus, Env of HIV-1, equine infectious anaemia virus (EIAV), murine leukaemia virus (MLV), mouse mammary tumor virus, G protein of vesicular stomatitis virus (VSV), Rabies virus, or a seven transmembrane domain receptor. In some embodiments, the transmembrane part of a protein is from the S1S2 protein.

FI element: The 3'-UTR is a combination of two sequence elements derived from the "amino terminal enhancer of split" (AES) mRNA (called F) and the mitochondrial encoded 12S ribosomal RNA (called 1). These were identified by an ex vivo selection process for sequences that confer RNA stability and augment total protein expression.

A30L70: A poly(A)-tail measuring 110 nucleotides in length, consisting of a stretch of 30 adenosine residues, followed by a 10 nucleotide linker sequence and another 70 adenosine residues designed to enhance RNA stability and translational efficiency in dendritic cells.

In some embodiments, vaccine RNA described herein may comprise, from 5' to 3', one of the following structures:

Cap-5'-UTR-Vaccine Antigen-Encoding Sequence-3'-UTR-Poly(A)

or

Cap-hAg-Kozak-Vaccine Antigen-Encoding Sequence-FI-A30L70.

In some embodiments, a vaccine antigen described herein may comprise a full-length S protein or an immunogenic fragment thereof (e.g., RBD). In some embodiments where a vaccine antigen comprises a full-length S protein, its secretory signal peptide and/or transmembrane domain may be replaced by a heterologous secretory signal peptide (e.g., as described herein) and/or a heterologous transmembrane domain (e.g., as described herein).

In some embodiments, a vaccine antigen described herein may comprise, from N-terminus to C-terminus, one of the following structures:

Signal Sequence-RBD-Trimerization Domain or

Signal Sequence-RBD-Trimerization Domain-Transmembrane Domain.

RBD and Trimerization Domain may be separated by a linker, in particular a GS linker such as a linker having the amino acid sequence GSPGSGSGS (SEQ ID NO: 134). Trimerization Domain and Transmembrane Domain may be separated by a linker, in particular a GS linker such as a linker having the amino acid sequence GSGSGS (SEQ ID NO: 135).

Signal Sequence may be a signal sequence as described herein. RBD may be a RBD domain as described herein. Trimerization Domain may be a trimerization domain as described herein. Transmembrane Domain may be a transmembrane domain as described herein.

In one embodiment,

Signal sequence comprises the amino acid sequence of amino acids 1 to 16 or 1 to 19 of SEQ ID NO: 1 or the amino acid sequence of amino acids 1 to 22 of SEQ ID NO: 31, or an amino acid sequence having at least 99%, 98%, 97%, 96%, 95%, 90%, 85%, or 80% identity to this amino acid sequence, RBD comprises the amino acid sequence of amino acids 327 to 528 of SEQ ID NO: 1, or an amino acid sequence having at least 99%, 98%, 97%, 96%, 95%, 90%, 85%, or 80% identity to this amino acid sequence, Trimerization Domain comprises the amino acid sequence of amino acids 3 to 29 of SEQ ID NO: 10 or the amino acid sequence of SEQ ID NO: 10, or an amino acid sequence having at least 99%, 98%, 97%, 96%, 95%, 90%, 85%, or 80% identity to this amino acid sequence; and Transmembrane Domain comprises the amino acid sequence of amino acids 1207 to 1254 of SEQ ID NO: 1, or an amino acid sequence having at least 99%, 98%, 97%, 96%, 95%, 90%, 85%, or 80% identity to this amino acid sequence.

In one embodiment,

Signal sequence comprises the amino acid sequence of amino acids 1 to 16 or 1 to 19 of SEQ ID NO: 1 or the amino acid sequence of amino acids 1 to 22 of SEQ ID NO: 31, RBD comprises the amino acid sequence of amino acids 327 to 528 of SEQ ID NO: 1, Trimerization Domain comprises the amino acid sequence of amino acids 3 to 29 of SEQ ID NO: 10 or the amino acid sequence of SEQ ID NO: 10; and Transmembrane Domain comprises the amino acid sequence of amino acids 1207 to 1254 of SEQ ID NO: 1.

In some embodiments, an RNA polynucleotide comprising a sequence encoding a vaccine antigen (e.g., a SARS-CoV-2 S protein, an immunogenic variant thereof, or an immunogenic fragment of the SARS-CoV-2 S protein or the immunogenic variant thereof) or comprising an open reading frame encoding a vaccine antigen (e.g., a SARS-CoV-2 S protein, an immunogenic variant thereof, or an immunogenic fragment of the SARS-CoV-2 S protein or the immunogenic variant thereof) such as the nucleotide sequence of SEQ ID NO: 50 or the nucleotide sequence of SEQ ID NO: 53, a variant or fragment thereof, further comprises a 5' cap, e.g., a 5' cap comprising a Cap1 structure, a 5' UTR sequence, e.g., a 5' UTR sequence comprising the nucleotide sequence of SEQ ID NO: 12, a 3' UTR sequence, e.g., a 3' UTR sequence comprising the nucleotide sequence of SEQ ID NO: 13, and polyA sequence, e.g., a polyA sequence comprising the nucleotide sequence of SEQ ID NO: 14. In some embodiments, RNA is formulated in a composition comprising ((4-hydroxybutyl)azanediyl)bis(hexane-6,1-diyl)bis(2-hexyldecanoate), cholesterol, distearoylphosphatidylcholine, and (2-[(polyethylene glycol)-2000]-N,N-ditetradecylacetamide).

RNA described herein or RNA encoding the vaccine antigen described herein may be non-modified uridine containing RNA (uRNA), nucleoside modified RNA (modRNA) or self-amplifying RNA (saRNA). In some embodiments, uRNA is mRNA. In some embodiments, modRNA is mRNA. In one embodiment, RNA described herein or RNA encoding the vaccine antigen described herein is nucleoside modified RNA (modRNA).

Variant Specific Vaccines

In some embodiments, RNA disclosed herein encodes an S protein comprising one or more mutations that are characteristic of a SARS-CoV-2 variant. In some embodiments, RNA encodes a SARS-CoV-2 S protein comprising one or more mutations characteristic of an Alpha variant. In some embodiments, RNA encodes a SARS-CoV-2 S protein comprising one or more mutations characteristic of a Beta variant. In some embodiments, RNA encodes a SARS-CoV-2 S protein comprising one or more mutations characteristic of a Delta variant. In some embodiments, RNA encodes a SARS-CoV-2 S protein comprising one or more mutations characteristic of an Omicron variant (e.g., an S protein comprising one or more mutations characteristic of a BA.1, BA.2, or BA.4/5 Omicron variant). In some embodiments, RNA encodes a SARS-CoV-2 S protein comprising one or more mutations characteristic of an BA.1 Omicron variant. In some embodiments, RNA encodes a SARS-CoV-2 S protein comprising one or more mutations characteristic of an BA.2 Omicron variant. In some embodiments, RNA encodes a SARS-CoV-2 S protein comprising one or more mutations characteristic of an BA.2.12.1 Omicron variant. In some embodiments, RNA encodes a SARS-CoV-2 S protein comprising one or more mutations characteristic of a BA.3 Omicron variant. In some embodiments, RNA encodes a SARS-CoV-2 S protein comprising one or more mutations characteristic of a BA.4 or BA.5 Omicron variant.

Non-Modified Uridine RNA (uRNA)

In some embodiments, a non-modified uridine RNA is a messenger RNA. In some embodiments, the active principle of non-modified messenger RNA drug substance is a single-stranded mRNA that is translated upon entering a cell. In addition to the sequence encoding the coronavirus vaccine antigen (i.e. open reading frame), each uRNA preferably contains common structural elements optimized for maximal efficacy of the RNA with respect to stability and translational efficiency (including, e.g., 5'-cap, 5'-UTR, 3'-UTR, poly(A)-tail as described herein). The preferred 5' cap structure is beta-S-ARCA(D1) ($m_2^{7,2'-O}$GppSpG). The preferred 5'-UTR and 3'-UTR comprise the nucleotide sequence of SEQ ID NO: 12 and the nucleotide sequence of SEQ ID NO: 13, respectively. The preferred poly(A)-tail comprises the sequence of SEQ ID NO: 14.

Different embodiments of this platform are as follows:

RBL063.1 (SEQ ID NO: 15; SEQ ID NO: 7)

Structure beta-S-ARCA(D1)-hAg-Kozak-S1S2-PP-FI-A30L70

Encoded antigen Viral spike protein (S1S2 protein) of the SARS-CoV-2 (S1S2 full-length protein, sequence variant)

RBL063.2 (SEQ ID NO: 16; SEQ ID NO: 7)

Structure beta-S-ARCA(D1)-hAg-Kozak-S1S2-PP-FI-A30L70

Encoded antigen Viral spike protein (S1S2 protein) of the SARS-CoV-2 (S1S2 full-length protein, sequence variant)

BNT162a1; RBL063.3 (SEQ ID NO: 17; SEQ ID NO: 5)

Structure beta-S-ARCA(D1)-hAg-Kozak-RBD-GS-Fibritin-FI-A30L70

Encoded antigen Viral spike protein (S protein) of the SARS-CoV-2 (partial sequence, Receptor Binding Domain (RBD) of S1S2 protein)

FIG. 3 schematizes the general structure of the antigen-encoding RNAs.

Nucleoside modified RNA (modRNA)

In some embodiments, nucleoside modified RNA is mRNA. In some embodiments, the active principle of nucleoside modified RNA (modRNA) drug substance is a single-stranded RNA (e.g., mRNA) that can be translated upon entering a cell. In addition to a sequence encoding a coronavirus vaccine antigen (i.e., open reading frame), each modRNA contains common structural elements optimized for maximal efficacy of the RNA as the uRNA (5'-cap, 5'-UTR, 3'-UTR, poly(A)-tail). Compared to uRNA, modRNA comprises at least one nucleotide modification (e.g., as described herein). In some embodiments, modRNA contains 1-methyl-pseudouridine instead of uridine. The preferred 5' cap structure is $m_2^{7,3'-O}$Gppp($m_1^{2'-O}$)ApG. The preferred 5'-UTR and 3'-UTR comprise the nucleotide sequence of SEQ ID NO: 12 and the nucleotide sequence of SEQ ID NO: 13, respectively. The preferred poly(A)-tail comprises the sequence of SEQ ID NO: 14. An additional purification step is applied for modRNA to reduce dsRNA contaminants generated during the in vitro transcription reaction.

Different embodiment of this platform are as follows:

BNT162b2; RBP020.1 (SEQ ID NO: 19; SEQ ID NO: 7)

Structure $m_2^{7,3'-O}$Gppp($m_1^{2'-O}$)ApG)-hAg-Kozak-S1S2-PP-FI-A30L70

Encoded antigen Viral spike protein (S1S2 protein) of the SARS-CoV-2 (S1S2 full-length protein, sequence variant)

BNT162b2; RBP020.2 (SEQ ID NO: 20; SEQ ID NO: 7)

Structure $m_2^{7,3'-O}$Gppp($m_1^{2'-0}$)ApG)-hAg-Kozak-S1S2-PP-FI-A30L70

Encoded antigen Viral spike protein (S1S2 protein) of the SARS-CoV-2 (S1S2 full-length protein, sequence variant)

BNT162b1; RBP020.3 (SEQ ID NO: 21; SEQ ID NO: 5)

Structure $m_2^{7,3'-O}$Gppp($m_1^{2'-O}$)ApG-hAg-Kozak-RBD-GS-Fibritin-FI-A30L70

Encoded antigen Viral spike protein (S1S2 protein) of the SARS-CoV-2 (partial sequence, Receptor Binding Domain (RBD) of S1S2 protein fused to fibritin)

FIG. 4 schematizes the general structure of the antigen-encoding RNAs.

BNT162b3c (SEQ ID NO: 29; SEQ ID NO: 30)

Structure $m_2^{7,3'-O}$Gppp($m_1^{2'-O}$)ApG-hAg-Kozak-RBD-GS-Fibritin-GS-TM-FI-A30L70

Encoded antigen Viral spike protein (5152 protein) of the SARS-CoV-2 (partial sequence, Receptor Binding Domain (RBD) of S1S2 protein fused to Fibritin fused to Transmembrane Domain (TM) of S1S2 protein); intrinsic S1S2 protein secretory signal peptide (aa 1-19) at the N-terminus of the antigen sequence BNT162b3d (SEQ ID NO: 31; SEQ ID NO: 32)

Structure $m_2^{7,3'-O}$Gppp($m_1^{2'-O}$)ApG-hAg-Kozak-RBD-GS-Fibritin-GS-TM-FI-A30L70

Encoded antigen Viral spike protein (S152 protein) of the SARS-CoV-2 (partial sequence, Receptor Binding Domain (RBD) of S1S2 protein fused to Fibritin fused to Transmembrane Domain (TM) of S1S2 protein); immunoglobulin secretory signal peptide (aa 1-22) at the N-terminus of the antigen sequence.

BNT162b2-Beta variant; RBP020.11 (SEQ ID NO: 57; SEQ ID NO: 55)

Structure $m_2^{7,3'-O}$Gppp($m_1^{2'-O}$)ApG)-hAg-Kozak-S1S2-PP-FI-A30L70

Encoded antigen Viral spike protein (5152 protein) of the SARS-CoV-2 (S1S2 full-length protein, sequence variant), comprising mutations characteristic of the Beta variant of SARS-CoV-2

BNT162b2-Alpha variant; RBP020.14 (SEQ ID NO: 60; SEQ ID NO: 58)

Structure $m_2^{7,3'-O}$Gppp($m_1^{2'-O}$)ApG)-hAg-Kozak-S1S2-PP-FI-A30L70

Encoded antigen Viral spike protein (5152 protein) of the SARS-CoV-2 (S1S2 full-length protein, sequence variant), comprising mutations characteristic of the Alpha variant of SARS-CoV-2

BNT162b2-Delta variant; RBP020.16 (SEQ ID NO: 63a; SEQ ID NO: 61)

Structure $m_2^{7,3'O}$Gppp($m_1^{2'-O}$)ApG)-hAg-Kozak-S1S2-PP-FI-A30L70

Encoded antigen Viral spike protein (5152 protein) of the SARS-CoV-2 (S152 full-length protein, sequence variant), comprising mutations characteristic of the Delta variant of SARS-CoV-2

Nucleotide Sequence of RBP020.11 (Beta-Specific Vaccine)

Nucleotide sequence is shown with individual sequence elements as indicated in bold letters. In addition, the sequence of the translated protein is shown in italic letters below the coding nucleotide sequence (*=stop codon). Red text indicates point mutations in the nucleotide and amino acid sequences.

```
        10         20         30         40         50  53
AGAATAAACT AGTATTCTTC TGGTCCCCAC AGACTCAGAG AGAACCCGCC ACC
                         hAg-Kozak

        63         73         83         93        103        313
ATGTTCGTGT TCCTGGTGCT GCRGCCTCTG GTGTCCAGCC AGTGTGTGAA CTTCACCACC
   H  F  V   F  L  V   L  L  P  L   V  S  S   Q  C  V   N  F  T  T
                         S Protein mut

       123        133        143        153        163        173
AGAACACAGC TGCCTCCAGC CTACACCAAC AGCTTTACCA GAGGCGTGTA CTACCCCGAC
   R  T  Q   L  P  P   A  Y  T  N   S  F  T   R  G  V   Y  Y  P  D
                         S Protein mut
```

-continued

```
       183        193        203        213        223        233
AAGGTGTTCA GATCCAGCGT GCTGCACTCT ACCCAGGACC TGTTCCTGCC TTTCTTCAGC
 K  V  F   R  S  S   C  L  H  S   T  Q  D   L  F  L   F  F  F  S
                          S Protein mut

       243        253        263        273        283        293
AACGTGACCT GGTTCCACGC CATCCACGTG TCCGGCACCA ATGGCACCAA GAGATTCGCC
 N  V  T   W  F  H   A  I  H  V   S  G  T   N  G  T   K  R  F  A
                          S Protein mut

       303        313        323        333        343        353
AACCCCGTGC TGCCCTTCAA CGACGGGGTG TACTTTGCCA GCACCGAGAA GTCCAACATC
 N  P  V   L  P  F   N  D  G  V   Y  F  A   S  T  E   K  S  N  I
                          S Protein mut

       383        373        383        383        403        433
ATCAGAGGCT GGATCTTCGG CACCACACTG GACAGCAAGA CCCAGAGCCT GCTGATCGTG
 I  R  G   W  I  F   G  T  T  L   D  S  K   T  Q  S   L  L  I  V
                          S Protein mut

       423        433        443        453        463        473
AACAACGCCA CCAACGTGGT CATCAAAGTG TGCGAGTTCC AGTTCTGCAA CGACCCCTTC
 N  N  A   T  N  V   V  I  K  V   C  E  F   Q  F  C   N  D  P  F
                          S Protein mut

       483        493        503        513        523        533
CTGGGCGTCT ACTACCACAA GAACAACAAG AGCTGGATGG AAAGCGAGTT CCGGGTGTAC
 L  G  V   Y  Y  H   K  N  N  K   S  W  M   E  S  E   F  R  V  Y
                          S Protein mut

       543        553        563        573        583        593
AGCAGCGCCA ACAACTGCAC CTTCGAGTAC GTGTCCCAGC CTTTCCTGAT GGACCTGGAA
 S  S  A   N  N  C   T  F  E  Y   V  S  Q   F  F  L   M  D  L  E
                          S Protein mut

       603        613        623        633        643        653
GGCAAGCAGG GCAACTTCAA GAACCTGCGC GAGTTCGTGT TTAACAACAT CGACGGCTAC
 G  K  Q   K  N  F   K  N  L  R   E  F  V   F  K  N   T  D  G  Y
                          S Protein mut

       663        673        683        693        703        713
TTCAAGATCT ACAGCAAGCA CACCCCTATC AACCTCGTGC GGGGCCTGCC TCAGGGCTTC
 F  K  I   Y  S  K   H  T  P  I   N  L  V   R  G  L   F  Q  G  F
                          S Protein mut

       723        733        743        753        763        773
TCTGCTCTGG AACCCCTGGT GGATCTGCCC ATCGGCATCA ACATCACCCG GTTTCAGACA
 S  A  L   E  P  L   V  D  L  P   I  G  I   N  I  T   R  F  Q  T
                          S Protein mut

       783        793        803        813        823        833
CTGCACATCA GCTACCTGAC ACCTGGCGAT AGCAGCAGCG GATGGACAGC TGGTGCCGCC
 L  H  Y  S  Y  L  T  P  G  D  S  D  D  G  W  T  A  G  A  A
                          S Protein mut

       843        353        853        873        883        893
GCTTAGTATG TGGGCTACCT GCAGCCTAGA ACCTTCCTGC TGAAGTACAA CGAGAACGGC
 A  Y  Y   V  G  Y   L  Q  P  R   T  F  L   L  K  Y   N  E  N  G
                          S Protein mut

       903        913        923        933        943        953
ACCATCACCG ACGCCGTGGA TTGTGCTCTG GATCCTCTGA GCGAGACAAA GTGCACCCTG
 T  I  T   D  A  V   D  C  A  L   D  F  L   D  E  T   K  C  T  L
                          S Protein mut

       963        973        983        993       1003       1013
AAGTCCTTCA CCGTGGAAAA GGGCATCTAC CAGACCAGCA ACTTCCGGGT GCAGCCCACC
 K  G  F   T  V  E   K  G  I  Y   Q  T  S   N  F  R   V  Q  P  T
                          S Protein mut

      1023       1033       1043       1053       1063       1073
GAATCCATCG TGCGGTTCCC CAATATCACC AATCTGTGCC CCTTCGGCGA GGTGTTCAAT
 E  S  I   V  R  F   P  N  I  T   N  L  C   P  F  G   E  V  F  N
                          S Protein mut

      1033       1093       1103       1113       1123       1133
GCCACGAGAT TCGCCTCTGT GTACGCCTGG AACCGGAAGC GGATCAGCAA TTGCGTGGCC
 A  T  R   F  A  S   V  Y  A  W   N  R  K   R  I  S   N  C  V  A
                          S Protein mut
```

-continued

```
      1143        1153        1163        1173        1183        1193
GACTACTCCG TGCTGTACAA CTCCGCCAGC TTCAGCACCT TCAAGTGCTA CGGCGTGTCC
  D  Y  S   V  L  Y   N  S  A  S   F  S  F   F  K  C   Y  G  V  S
                            S Protein mut

      1203        1213        1223        1233        2243        1253
CCTACCAAGC IGAACGACCT GTGCTTCACA AACGTGTACG CCGACAGCTT CGTGATCCGG
  P  T  K   L  N  D   L  C  F  T   N  V  Y   A  D  S   F  V  I  R
                            S Protein mut

      1268        1273        1283        1293        1303        1313
GGAGATGAAG TGCGGCAGAT TGCCCCTGGA CAGACAGGCA ACATCGCCGA CTACAACTAC
  G  D  E   V  R  Q   I  A  F  G   Q  T  G   N  I  A   D  Y  N  Y
                            S Protein mut

      1323        1333        1343        1353        1363        1373
AAGCTGCCCG ACGACTTCAC CGGCTGTGTG ATTGCCTGGA ACAGCAACAA CCTGGACTCC
  K  L  F   D  D  F   T  G  C  V   I  A  W   N  S  N   N  L  D  S
                            S Protein mut

      1383        1393        1403        1413        1423        1433
AAAGTCGGCG GCAACTACAA TTACCTGTAC CGGCTGTTCC GGAAGTCCAA TCTGAAGCCC
  K  V  G   G  N  Y   N  Y  L  Y   R  L  F   R  K  S   N  L  K  P
                            S Protein mut

      1443        1453        1463        1473        1483        1493
TTCGAGCGGG ACATCTCCAC CGAGATCTAT CAGGCCGCCA GCACCCCTTG TAACGGCGTG
  F  E  R   D  I  S   T  E  I  Y   Q  A  G   S  T  P   C  N  G  V
                            S Protein mut

      1503        1513        1523        1533        1543        1553
AAGGGCTTCA ACTGCTACTT CCCACTGCAG TCCTACGGCT TTCAGCCCAC ATACGGCGTG
  K  G  F   N  C  Y   E  P  L  Q   S  Y  G   F  Q  P   T  T  G  V
                            S Protein mut

      1563        1573        1583        1593        1603        1613
GGCTATCAGC CCTACAGAGT GGTGGTGCTG AGCTTCGAAC TGCTGCATGC CCCTGCCACA
  G  Y  Q   P  Y  R   V  V  V  L   S  F  E   L  L  N   A  P  A  T
                            S Protein mut

      1623        1633        1643        1653        1673
GTGTGCGGCC CTAAGAAAAG CACCAATCTC CTGAAGAACA AATGCGTGAA CTTCAACTTC
  V  C  G   P  K  K   S  T  N  L   V  K  N   K  C  V   N  F  N  F
                            S Protein mut

      1683        1693        1703        1713        1723        1733
AACGGCCTCA CCGGCACCGG CGTGCTGACA GAGAGCAACA AGAAGTTCCT GCCATTCCAG
  N  G  L   T  G  T   G  V  L  T   E  G  N   K  K  F   L  P  F  Q
                            S Protein mut

      1743        1753        1763        1773        1783        1793
CAGTTTGGCC GGGATATCGC CGATACCACA GACGCCGTTA GAGATCCCCA GACACTGGAA
  Q  F  G   R  D  I   A  D  T  T   D  A  V   R  D  F   Q  T  L  E
                            S Protein mut

      1803        1813        1823        1833        1843        1853
ATCCTGGACA TCACCCCTTG CAGCTTCGGC GGAGTGTCTG TGATCACCCC TGGCACCAAC
  I  L  D   I  R  P   C  S  F  G   G  V  S   V  I  F   P  G  T  N
                            S Protein mut

      1863        1873        1883        1893        1903        1913
ACCAGCAATC AGGTGGCAGT GCTGTACCAG CGCGTGAACT GTACCGAAGT GCCCGTGGCC
  T  S  N   Q  V  A   V  L  Y  Q   G  V  N   C  T  E   V  P  V  A
                            S Protein mut

      1923        1933        1943        1953        1963        1973
ATTCACGCCG ATCAGCTGAC ACCTACATGG CGGGTGTACT CCACCGGCAG CAATGTGTTT
  I  H  A   D  Q  L   T  P  T  W   R  V  Y   S  T  G   S  N  V  F
                            S Protein mut

      1983        1993        2003        2013        2023        2033
CAGACCAGAG CCGGCTGTCT GATCGGAGCC GAGCACGTGA ACAATAGCTA CGAGTGCGAC
  Q  T  R   A  G  C   L  I  G  A   E  K  V   N  N  S   Y  E  C  D
                            S Protein mut

      2043        2053        2063        2073        2083        2093
ATCCCCATCG GCGCTGGAAT CTGCGCCAGC TACCAGACAG AGACAAACAG CCCTCGGAGA
  I  P  I   G  A  G   I  C  A  S   Y  Q  T   Q  T  N   S  F  R  R
                            S Protein mut
```

-continued

```
      2103       2113       2123       2133       2143       2153
GCCAGAAGCG TGGCCAGCCA GAGCATCATT GCCTACACAA TGTCTCTGGG CGTCGAGAAC
  A  R  S   V  A  S   Q  S  I  I   A  Y  T   M  S  L   G  V  E  N
                          S Protein mut

      2163       2173       2183       2193       2203       2213
AGCGTGGCCT ACTCCAACAA CTCTATCGCT ATCCCCACCA ACTTCACCAT CAGCGTGACC
  S  V  A   Y  S  N   N  S  I  A   I  F  T   N  F  T   I  S  V  T
                          S Protein mut

      2223       2233       2243       2253       2263       2273
ACAGAGATCC TGCCTGTGTC CATGACCAAG ACCAGCGTGA ACTGCACCAT GTACATCTGC
  T  E  I   L  F  V   S  N  T  K   T  S  V   D  C  T   N  Y  I  C
                          S Protein mut

      2283       2293       2303       2313       2323       2333
GGCGATTCCA CCGAGAGCTC CAACCTGCTG CTGCAGTACG GCAGCTTCTG CACCCAGCTG
  G  D  S   T  E  C   S  N  L  L   L  Q  T   G  S  F   C  T  Q  L
                          S Protein mut

      2343       2353       2363       2373       2383       2393
AATAGAGCCC TGACAGGGAT CGCCGTGGAA CAGGACAAGA ACACCCAAGA GGTGTTCGCC
  N  R  A  L  T  G  I  A  V  E  Q  D  K  N  T  Q  S  V  F  A
                          S Protein mut

      2403       2413       2423       2433       2443       2453
CAAGTGAAGC AGATCTACAA GACCCCTCCT ATCAAGGACT TCGGCGGCTT CAATTTCAGC
  Q  V  K   Q  I  Y   K  T  T  P   I  K  D   F  G  G   F  N  F  S
                          S Protein mut

      2463       2473       2483       2493       2503       2513
CAGATTCTGC CCGATCCTAG CAACCCCAGC AAGCGGAGCT TCATCGAGGA CCTGCTGTTC
  Q  I  L   F  D  F   S  K  F  D   K  R  D   F  I  E   D  L  L  F
                          S Protein mut

      2523       2533       2543       2553       2563       2573
AACAAAGTGA CACTGGCCGA CGCCGGCTTC ATCAAGCAGT ATGGCGATTG TCTGGGCGAC
  N  K  V   T  L  A   D  A  G  F   I  K  Q   Y  G  D   C  L  G  D
S Protein mout
      2583       2593       2603       2613       2623       2633
ATTGCGGCCA GGGATCTGAT TTGCGCCCAG AAGTTTAACG GACTGACAGT GCTGCCTCCT
  I  A  A   R  D  L   I  C  A  Q   K  F  N   G  L  T   V  L  F  F
                          S Protein mut

      2643       2653       2663       2673       2683       2693
CTGCTGACCG ATGAGATGAT CGCCCAGTAC ACATCTGCCC TGCTGGCCGG CACAATCACA
  L  L  T   D  E  M   I  A  Q  Y   T  S  A   L  L  A   G  T  I  T
                          S Protein mut

      2703       2713       2723       2733       2743       2753
AGCGGCTGGA CATTTGGAGC AGGCGCCGCT CTGCAGATCC CCTTTGCTAT GCAGATGGCC
  S  G  W   T  G  A   A  G  A  A   L  Q  I   P  F  A   N  Q  N  A
                          S Protein mut

      2763       2773       2783       2793       2803       2813
TACCGGTTCA ACGGCATCGG AGTGACCCAG AATGTGCTGT ACGAGAACCA GAAGCTGATC
  Y  R  F   N  G  I   G  V  T  Q   N  V  L   Y  E  N   Q  K  L  I
                          S Protein mut

      2823       2833       2843       2853       2863       2873
GCCAACCAGT TCAACAGCGC CATCGGCAAG ATCCAGGACA GCCTGAGCAG CACAGCAAGC
  A  N  Q   F  N  S   A  I  G  K   I  Q  D   S  L  S   S  T  A  S
                          S Protein mut

      2883       2893       2903       2913       2923       2933
GCCCTGGGAA AGCTGCAGGA CGTGGTCAAC CAGAATGGCC AGGCACTGAA CACCCTGGTC
  A  L  G   K  L  Q   D  V  V  N   Q  N  A   Q  A  L   N  T  L  V
                          S Protein mut

      2943       2953       2963       2973       2983       2993
AAGCAGCTGT CCTCCAACTT CGGCGCCATC AGCTCTGTGC TGAACGATAT CCTGAGCACA
  K  Q  L   S  S  N   F  G  A  I   S  S  V   L  N  D   I  L  S  R
                          S Protein mut

      3003       3013       3023       3033       3043       3053
CTGGACCCTC CTGAGGCCGA GGTGCAGATC GACAGACTGA TCACAGGCAG ACTGCAGAGC
  L  D  P   P  E  A   E  V  Q  I   D  R  L   I  T  G   R  L  Q  S
                          S Protein mut
```

-continued

```
     3063       3073       3083       3093       3103       3113
CTCCAGACAT ACGTGACCCA GCAGCTGATC AGAGCCGCCG AGATTAGAGC CTCTGCCAAT
  L  Q  T   Y  V  T   Q  Q  L  I   R  A  A   E  I  R   A  S  A  N
                          S Protein mut

     3123       3133       3143       3153       3163       3173
CTGGCCGCCA CCAAGATGTC TGAGTGTGTG CTGGGCCAGA GCAAGAGAGT GGACTTTTGC
  L  A  A   T  K  N   S  E  C  V   L  G  Q   S  K  R   V  D  F  C
                          S Protein mut

     3183       3193       3203       3213       3223       3233
GGCAAGGGCT ACCACCTGAT GAGCTTCCCT CAGTCTGCCC CTCACGGCGT GGTGTTTCTG
  G  K  G   Y  H  L   M  S  F  P   Q  S  A   P  H  G   V  V  F  L
                          S Protein mut

     3243       3253       3263       3273       3283       3293
CACGTGACAT ATGTGCCCGC TCAAGAGAAG AATTTCACCA CCGCTCCAGC CATCTGCCAC
  H  V  T   Y  V  P   A  Q  E  K   N  F  T   T  A  P   A  I  C  H
                          S Protein mut

     3303       3313       3323       3333       3343       3353
GACGGCAAAG CCCACTTTCC TAGAGAAGGC GTGTTCGTGT CCAACGGCAC CCATTGGTTC
  D  G  K   A  H  F   P  R  E  G   V  F  V   S  N  G   T  H  W  F
                          S Protein mut

     3363       3373       3383       3393       3403       3413
GTGACACAGG GGAACTTCTA CGAGCCCCAG ATCATCACCA CCGACAACAC CTTCGTGTCT
  V  T  Q   R  N  F   Y  E  P  Q   I  I  T   T  D  N   T  F  V  S
                          S Protein mut

     3423       3433       3443       3453       3463       3473
GGCAACTGCG ACGTCGTGAT CGGCATTGTG AACAATACCG TGTACGACCC TCTGCAGCCC
  G  N  C   D  V  V   I  G  I  V   N  N  T   V  Y  D   P  L  Q  F
                          S Protein mut

     3483       3493       3503       3513       3523       3533
GAGCTGGACA GCTTCAAAGA GGAACTGGAC AAGTACTTTA AGAACCACAC AAGCCCCGAC
  E  L  D   S  F  K   E  E  L  D   K  Y  F   K  N  K   T  S  F  D
                          S Protein mut

     3543       3553       3563       3573       3583       3593
GTGGACCTGG GCGATATCAG CGGAATCAAT GCCAGCGTCG TGAACATCCA GAAAGAGATC
  V  D  L   G  D  I   S  G  I  N   A  S  V   V  N  I   Q  R  E  I
                          S Protein mut

     3603       3613       3623       3633       3643       3653
GACCGGCTGA ACGAGGTGGC CAAGAATCTG AACGAGAGCC TGATCGACCT GCAAGAACTG
  D  R  L   N  E  V   A  K  N  L   N  E  S   L  I  D   L  Q  E  L
                          S Protein mut

     3663       3673       3683       3893       3703       3713
GGGAAGTACG AGCAGTACAT CAAGTGGCCC TGGTACATCT GGCTGGGCTT TATCGCCGGA
  G  K  Y   E  Q  Y   I  K  F  P   W  Y  I   W  L  G   F  I  A  G
                          S Protein mut

     3723       3733       3743       3753       3763       3773
CTGATTGCCA TCGTGATGGT CACAATCATG CTGTGTTGCA TGACCAGCTG CTGTAGCTGC
  L  I  A   I  V  N   V  T  I  N   L  C  C   N  T  S   C  C  S  C
                          S Protein mut

     3783       3793       3803       3813       3823       3833
CTGAAGGGCT GTTGTAGCTG TGGCAGCTGC TGCAAGTTCG ACGAGGACGA TTCTGAGCCC
  L  K  G   C  C  S   S  G  S  C   C  K  F   D  E  D   D  S  E  P
                          S Protein mut

     3843       3853       3863    3670
GTGCTGAAGG GCGTGAAACT GCACTACACA TGATGAC
  V  L  K   G  V  K   L  H  Y  T   *  *
                          S Protein mut

     3880       3890       3900       3910       3920       3930
TCGAGCTGGT ACTGCATGCA CGCAATGCTA GCTGCCCCTT TCCCGTCCTG GGTACCCCGA
                          FI Element

     3940       3850       3960       3970       3980       3990
GTCTCCCCCG ACCTCGGGTC CCAGGTATGC TCCCACCTCC ACCTGCCCCA CTCACCACCT
                          FI Element

     4000       4010       4020       4030       4040       4050
CTGCTAGTTC CAGACACCTC CCAAGCACGC AGCAATGCAG CTCAAAACGC TTAGCCTAGC
                          FI Element
```

-continued

```
     4060       4070       4080       4090       4100       4110
CACACCCCCA CGGGAAACAG CAGTGATTAA CCTTTAGCAA TAAACGAAAG TTTAACTAAG
                          FI Element

     4120       4130       4140       4150       4160       4164
CTATACTAAC CCCAGGGTTG GTCAATTTCG TGCCAGCCAC ACCCTGGAGC TAGC
                          FI Element

     4174       4184       4194       4204       4214       4224
AAAAAAAAAA AAAAAAAAAA AAAAAAAAAA GCATATGACT AAAAAAAAAA AAAAAAAAAA
                          A30L70

     4234       4244       4254       4264       4274
AAAAAAAAAA AAAAAAAAAA AAAAAAAAAA AAAAAAAAAA AAAAAAAAAA
                          A30L70
```

Sequences of RBP020.11 are also shown in Table 3 (SEQ ID NO: 157) (SEQ ID NO:55).

TABLE 3

Sequences of RBP020.11 (a Beta-specific RNA vaccine)

| SEQ ID NO. | Brief Description | Sequence |
|---|---|---|
| 55 | Amino acid sequence of RNA-encoded SARS-CoV-2 S protein from a Beta variant (with PRO mutations at positions corresponding to K986P and V987P of SEQ ID NO: 1; i.e., PRO mutations at positions 983 and 984 of SEQ ID NO: 55) | MFVFLVLLPLVSSQCVNFTTRTQLPPAYTNSFTRGVYYPDKVFRSSVLHSTQDLFLPFFSNVTWFH<br>AIHVSGTNGTKRFANPVLPFNDGVYFASTEKSNIIRGWIFGTTLDSKTQSLLIVNNATNVVIKVCE<br>FQFCNDPFLGVYYHKNNKSWMESEFRVYSSANNCTFEYVSQPFLMDLEGKQGNFKNLREFVFKNID<br>GYFRIYSKHTPINDVRGLPQGFSALEPLVDLPIGINITRFQTLHISYLTPGDSSSGWTAGAAAYYV<br>GYLQPRTFLLKYNENGTITDAVDCALDPLSETKCTLKSFTVEKGIYQTSNFRVQPTESIVRFPNIT<br>NLCPFGEVFNATRFASVYAWNRKRISNCVADYSVLYNSASFSTFKCYGVSPTKLNDLCFTNVYADS<br>FVIRGDEVRQIAPGQTGNIADYNYKLPDDFTGCVIAWNSNNLDSKVGGNYNYLYRLFRKSNLKPFE<br>RDISTEIYQAGSTPCNGVKGFNCYFPLQSYGFQPTYGVGYQPYRVVVLSFELLHAPATVCGPKKST<br>NLVKNKCVNFNFNGLTGTGVLTESNKKFLPFQQFGRDIADTTDAVRDPQTLEILDITPCSFGGVSV<br>ITPGTNTSNQVAVLYQGVNCTEVPVAIHADQLTPTWRVYSTGSNVFQTRAGCLIGAEHVNNSYECD<br>IPIGAGICASYQTQTNSPRRARSVASQSIIAYTMSLGVENSVAYSNNSIAIPTNFTISVTTEILPV<br>SMTKTSVDCTMYICGDSTECSNLLLQYGSFCTQLNRALTGIAVEQDKNTQEVFAQVKQIYKTPPIK<br>DFGGFNFSQILPDPSKPSKRSFIEDLLFNKVTLADAGFIKQYGDCLGDIAARDLICAQKFNGLTVL<br>PPLLTDEMIAQYTSALLAGTITSGWTFGAGAALQIPFAMQMAYRFNGIGVTQNVLYENQKLIANQE<br>NSAIGKIQDSLSSTASALGKLQDVVNQNAQALNTLVKQLSSNFGAISSVLNDILSRLDPPEAEVQI<br>DRLITGRLQSLQTYVTQQLIRAAEIRASANLAATKMSECVLGQSKRVDFCGKGYHLMSFPQSAPHG<br>VVFLHVTYVPAQEKNFTTAPAICHDGKAHFPREGVFVSNGTHWFVTQRNFYEPQIITTDNTFVSGN<br>CDVVIGIVNNTVYDPLQPELDSFKEELDKYFKNHTSPDVDLGDISGINASVVNIQKEIDRLNEVAK<br>NLNESLIDLQELGKYEQYIKWPWYIWLGFIAGLIAIVMVTIMLCCMTSCCSCLKGCCSCGSCCKFD<br>EDDSEPVLKGVKLHYT** |
| 56 | RNA sequence encoding a SARS-CoV-2 S protein from a Beta variant | auguucgugu uccuggugcu gcugccucug guguccagcc agugugugaa cuucaccacc<br>agaacacagc ugccuccagc cuacaccaac agcuuuacca gaggcgugua cuaccccgac<br>aagguguuca gauccagcgu gcugcacucu acccaggacc uguuccugcs uuucuucagc<br>aacgugaccu gguuccacgc cauccacgug uccggcacca auggcaccaa gagauucgcc<br>aaccccgugc ugcccuucaa cgacggggug uacuuugcca gcaccgagas guccaacauc<br>aucagaggcu ggaucuucgg caccacacug gacagcaaga cccagagccu gcugaucgug<br>aacaacgcca ccaacguggu caucaaagug ugcgaguucc aguucugcas cgaccccuuc<br>cugggcgucu acuaccacaa gaacaacaag agcuggaugg aaagcgaguu ccggguguac<br>agcagcgcca acaacugcac cuucgaguac gugucccagc cuuuccugau ggaccuggaa<br>ggcaagcagg gcaacuucaa gaaccugcgc gaguucgugu uusagaacau cgacggcuac<br>uucaagaucu acagcaagca caccccuauc aaccucgugc ggggccugcc ucagggcuuc<br>ucugcucugg aaccccuggu ggaucugccc aucggcauca acaucacccg guuucagaca<br>cugcacauca gcuaccugac accuggcgau agcagcagcg gauggacagc uggugccgcc<br>gcuuacuaug ugggcuaccu gcagccuaga accuuccugc ugaaguacaa cgagaacggc<br>accaucaccg acgccgugga uugugcucug gauccucuga gcgagacaaa gugcacccug<br>aaguccuuca ccguggaaaa gcgcaucuac cagaccagca acuuccgggu gcagcccacc<br>gaauccaucg ugcgguuccc caauaucacc aaucugugcc ccuucggcga gguguucaau<br>gccaccagau ucgccucugu guacgccugg aaccggaagc ggaucagcaa uugcguggcc<br>gacuacuccg ugcuguacaa cuccgccagc uucagcaccu ucaagugcua cggcgugucc<br>ccuaccaagc ugaacgaccu gugcuucaca aacguguacg ccgacagcuu cgugauccgg<br>ggagaugaag ugcggcagau ugccccugga cagacaggca acaucgccga cuacaacuac<br>aagcugcccg acgacuucac cggcugugug auugccugga acagcaacaa ccuggacucc<br>aaagucggcg gcaacuacaa uuaccuguac cggcuguucc ggaaguccaa ucugaagccc<br>uucgagcggg acaucuccac cgagaucuau caggccggca gcaccccuug uaacggcgug<br>aagggcuuca acugcuacuu cccacugcag uccuacggcu uucagcccac auacggcgug<br>ggcuaucagc ccuacagagu gguggugcug agcuucgaac ugcugcaugc cccugccaca<br>gugugcggcc cuaagaaaag caccaaucuc gugaagaaca aaugcgugaa cuucaacuuc<br>aacggccuga ccggcaccgg cgugcugaca gagagcaaca agaaguuccu gccauuccag<br>caguuuggcr gggauaucgc cgauaccaca gacgccguua gagaucccca gacacuggaa<br>auccuggaca ucaccccuug cagcuucggc ggagugucug ugaucacccc uggcaccaac |

TABLE 3-continued

Sequences of RBP020.11 (a Beta-specific RNA vaccine)

| SEQ ID NO. | Brief Description | Sequence |
| --- | --- | --- |
| | | accagcaauc agguggcagu gcuguaccag ggcgugaacu guaccgaagu gcccguggcc |
| | | auucacgccg aucagcugac accuacaugg cggguguacu ccaccggcag caauguguuu |
| | | cagaccagag ccggcugucu gaucggagcc gagcacguga acaauagcua cgagugcgac |
| | | auccccaucg gcgcuggaau cugcgccagc uaccagacac agacaaacag cccucggaga |
| | | gccagaagcg uggccagcca gagcaucauu gccuacacaa ugucucuggg cgucgagaac |
| | | agcguggccu acuccaacaa cucuaucgcu auccccacca acuucaccau cagcgugacc |
| | | acagagaucc ugccuguguc caugaccaag accagcgugg acugcaccau guacaucugc |
| | | ggcgauucca ccgagugcuc caaccugcug cugcaguacg gcagcuucug cacccagcug |
| | | aauagagccc ugacagggau ccccguggaa caggacaaga acacccaaga gguguucgcc |
| | | caagugaagc agaucuacaa gaccccuccu aucaaggacu ucggcggcuu caauuucagc |
| | | cagauucugc ccgauccuag caagcccagc aagcggagcu ucaucgagga ccugcuguuc |
| | | aacaaaguga cacuggccga ccccggcuuc aucaagcagu auggcgauug ucugggcgac |
| | | auugccgcca gggaucugau uugcgcccag aaguuuaacg gacugacagu gcugccuccu |
| | | cugcugaccg augagaugau cgcccaquac acaucugccc ugcuggccgg cacaaucaca |
| | | agcggcugga cauuuggagc aggcgccgcu cugcagaucc ccuuugcuau gcagauggcc |
| | | uaccgguuca acggcaucgg agugacccag aaugugcugu acgagaacca gaagcugauc |
| | | gccaaccagu ucaacagcgc caucggcaag auccaggaca gccugagcag cacagcaagc |
| | | gcccugggaa agcugcagga ccuggucaac cagaaugccc aggcacugaa cacccugguc |
| | | aagcagcugu ccuccaacuu cggcgccauc agcucugugc ugaacgauau ccugagcaga |
| | | cuggacccuc cugaggccga ggugcagauc gacagacuga ucacaggcag acugcagagc |
| | | cuccagacau acgugaccca gcagcugauc agagccgccg agauuagagc cucugccaau |
| | | cuggccgcca ccaagauguc ugagugugug cugggccaga gcaagagagu ggacuuuugc |
| | | ggcaagggcu accaccugau gagcuucccu cagucugccc cucacggcgu gguguuucug |
| | | cacgugacau augugcccgc ucaagagaag aauuucacca ccgcuccagc caucugccad |
| | | gacggcaaag cccacuuucc uagagaaggc guguucgugu ccaacggcac ccauugguuc |
| | | gugacacagc ggaacuucua cgagccccag aucaucacca ccgacaacac cuucgugucu |
| | | ggcaacugcg acqucgugau ccgcauugug aacaauaccg uquacgaccc ucugcagccc |
| | | gagcuggaca gcuucaaaga ggaacuggac aaguacuuua agaaccacac aagccccgac |
| | | guggaccugg gcgauaucag ccgaaucaau gccagcgucg ugaacaucca gaaagagauc |
| | | gaccggcuga acgagguggc caagaaucug aacgagagcc ugaucgaccu gcaagaacug |
| | | gggaaguacg agcaguacau caaguggccc ugguacaucu ggcugggcuu uaucgccgga |
| | | cugauugcca ucgugauggu cacaaucaug cuguguugca ugaccagcug cuguagcugc |
| | | cugaagggcu guuguagcug uggcagcugc ugcaaguucg acgaggacga uucugagccc |
| | | gugcugaagg gcgugaaacu gcacuacaca ugaugac |
| 152 | DNA sequence | atgttcgtgt tcctggtgct gctgcctctg gtgtccagcc agtgtgtgaa cttcaccacc |
| | encoding a SARS- | agaacacagc tgcctccagc ctacaccaac agctttacca gaggcgtgta ctaccccgac |
| | CoV-2 S protein | aaggtqttca gatccagcgt gctgcactct acccaggacc tcttcctgcc tttcttcagc |
| | from a Beta | aacgtgacct ggttccacgc catccacgtq tccggcacca atqqcaccaa gagattcqcc |
| | variant | aaccccgtgc tgcccttcaa cgacggggtg tactttgcca gcaccgagaa gtccaacatc |
| | | atcagaggct ggatcttcgg caccacactg gacagcaaga cccagagcct gctgatcgtg |
| | | aacaacgcca ccaacgtggt catcaaagtg tgcgagttcc agttctgcaa cgaccccttc |
| | | ctgggcgtct actaccacaa gaacaacaag agctggatgg aaagcgagtt ccgggtgtac |
| | | agcagcgcca acaactgcac cttcgagtac gigtcccagc ctttcctgat ggacctggaa |
| | | ggcaagcagg gcaacttcaa gaacctgcgc gagttcgtgt ttaagaacat cgacggctac |
| | | ttcaagatct acagcaagca cacccctatc aacctcgtgc ggggcctgcc tcagggcttc |
| | | tctgctctgg aacccctggt ggatctgccc atcggcatca acatcacccg gtttcagaca |
| | | ctgcacatca gctacctgac acctggcgat agcagcagcg gatggacagc tcgtgccgcc |
| | | gcttactatg tgggctacct gcagcctaga accttcctgc tgaagtacaa cgagaacggc |
| | | accatcaccg acgccgtgga ttgtgctctg gatcctctga gcgagacaaa gtgcaccctg |
| | | aagtccttca ccgtggaaaa gggcatctac cagaccagca acttccgggt gcagcccacc |
| | | gaatccatcg tgcggttccc caatatcacc aatctgtgcc ccttcggcgc ggtgttcaat |
| | | gccaccagat tcgcctctgt gtacgcctgg aaccggaagc ggatcagcaa ttgcgtggcc |
| | | gactactccg tgctgtacaa ctccgccagc ttcagcacct tcaagtgcta cggcgtgtcc |
| | | cctaccaagc tgaacgacct gtgcttcaca aacgtgtacg ccgacagctt cgtgatccgg |
| | | ggagatgaag tgcggcagat tgcccctgga cagacaggca acatcgccga ctacaactac |
| | | aagctgcccg acgacttcac ccgctgtgtg attgcctgga acagcaacaa cctggactcc |
| | | aaagtcggcg gcaactacaa ttacctgtac ccgctgttcc ggaagtccaa tctgaagccc |
| | | ttcgagcggg acatctccac cgagatctat caggccggca gcaccccttg taacggcgtg |
| | | aagggcttca actgctactt cccactgcag tcctacggct ttcagcccac atacggcgtg |
| | | ggctatcagc cctacagagt ggtggtgctg agcttcgaac tgctgcatgc ccctgccaca |
| | | gtgtgcggcc ctaagaaaag caccaatctc gtgaagaaca aatgcgtgaa cttcaacttc |
| | | aacggcctga ccggcaccgg cgtgctgaca gagagcaaca agaagttcct gccattccag |
| | | cagtttggcc gggatatcgc cgataccaca gacgccgtta gagatcccca gacactggaa |
| | | atcctggaca tcaccccttg cagcttcggc ggagtgtctg tgatcacccc tggcaccaac |
| | | accagcaatc aggtggcagt gctgtaccag ggcgtgaact gtaccgaagt gcccgtggcc |
| | | attcacgccg atcagctgac acctacatgg cgggtqtact ccaccggcag caatgtgttt |
| | | cagaccagag ccggctgtct gatcggagcc gagcacgtga acaatagcta cgagtgcgac |
| | | atccccatcg gcgctggaat ctgcgccagc taccagacac agacaaacag ccctcggaga |
| | | gccagaagcg tcgccagcca gagcatcatt gcctacacaa tctctctggg cgtcgagaac |
| | | agcgtggcct actccaacaa ctctatcgct atccccacca acttcaccat cagcgtgacc |
| | | acagagatcc tgcctgtgtc catgaccaag accagcgtyg actgcaccat gtacatctgc |
| | | ggcgattcca ccgagtgctc caacctgctg ctgcagtacg gcagcttctg cacccagctg |
| | | aatagagccc tgacagggat cgccgtggaa caggacaaga acacccaaga ggtgttcgcc |

TABLE 3-continued

Sequences of RBP020.11 (a Beta-specific RNA vaccine)

| SEQ ID NO. | Brief Description | Sequence |
|---|---|---|
| | | caagtgaagc agatctacaa gacccctcct atcaaggact tcggcggctt caatttcagc<br>cagattctgc ccgatcctag caagcccagc aagcggagct tcatcgagga cctgctgttc<br>aacaaagtga cactggccga ccccggcttc atcaagcagt atggcgattg tctgggcgac<br>attgccgcca gggatctgat ttgcgcccag aagtttaacg gactgacagt gctgcctcct<br>ctgctgaccg atgagatgat cgcccagtac acatctgccc tgctggccgg cacaatcaca<br>agcggctgga catttggagc aggcgccgct ctgcagatcc cctttgctat gcagatggcc<br>taccggttca acggcatcgg agtgacccag aatgtgctgt acgagaacca gaagctgatc<br>gccaaccagt tcaacagcgc catcggcaag atccaggaca gcctgagcag cacagcaagc<br>gccctgggaa agctgcagga cgtggtcaac cagaatgccc aggcactgaa caccctggtc<br>aagcagctgt cctccaactt cggcgccatc agctctgtgc tgaacgatat cctgagcaga<br>ctggaccctc ctgaggccga ggtgcagatc gacagactga tcacaggcag actgcagagc<br>ctccagacat acqtgaccca gcagctgatc agagccgccg agattagagc ctctgccaat<br>ctggccgcca ccaagatgtc tgagtgtgtg ctgggccaga gcaagagagt ggacttttgc<br>ggcaagggct accacctgat gagcttccct cagtctgccc ctcacggcgt ggtgtttctg<br>cacgtgacat atgtgcccgc tcaagagaag aatttcacca ccgctccagc catctgccac<br>gacggcaaag cccactttcc tagagaaggc gtgttcgtgt ccaacggcac ccattggttc<br>gtgacacagc ggaacttcta cgagccccag atcatcacca ccgacaacac cttcgtgtct<br>ggcaactgcg acgtcgtgat cggcattgtg aacaataccg tgtacgaccc tctgcagccc<br>gagctggaca gcttcaaaga ggaactggac aagtacttta agaaccacac aagccccgac<br>gtggacctgg gcgatatcag cggaatcaat gccagcgtcg tgaacatcca gaaagagatc<br>gaccggctga acgaggtggc caagaatctg aacgagagcc tgatcgacct gcaagaactg<br>gggaagtacg agcagtacat caagtggccc tcgtacatct ggctgggctt tatcgccgga<br>ctgattgcca tcgtgatggt cacaatcaty ctgtgttgca tgaccagctg ctgtagctgc<br>ctgaagggct gttgtagctg tygcagctgc tgcaagttcg acgaggacga ttctgagccc<br>gtgctgaagg gcgtgaaact gcactacaca tgatgac |
| 57 | Full length RNA sequence of RBP020.11 | agaauaaacu aguauucuuc ugguccccac agacucagag agaacccgcc acc<br>auguucgugu uccuggugcu cgacggggug guguccagcc agugugugaa cuucaccacc<br>agaacacagc ugccuccagc gcugccucug agcuuuacca gaggcgugua cuaccccgac<br>aagguguuca gauccagcgu cuacaccaac acccaggacc uguuccugcc uuucuucagc<br>aacgugaccu gguuccacgc gcugcacucu uccggcacca auggcaccaa gagauucgcc<br>aaccccgugc ugcccuucaa cauccacgug uacuuugcca gcaccgagaa guccaacauc<br>aucagaggcu ggaucuucgg caccacacug gacagcaaga cccagagccu gcugaucgug<br>aacaacgcca ccaacguggu caucaaagug ugcgaguucc aguucugcaa cgaccccuuc<br>cugggcgucu acuaccacaa gaacaacaag agcuggaugg aaagcgaguu ccggguguac<br>agcagcgcca acaacugcac cuucgaguac gugucccagc cuuuccugau ggaccuggaa<br>ggcaagcagg gcaacuucaa gaaccugcgc gaguucgugu uusagaacau cgacggcuac<br>uucaagaucu acagcaagca caccccuauc aaccucgugc ggggccugcc ucagggcuuc<br>ucugcucugg aaccccuggu ggaucugccc aucggcauca acaucacccg guuucagaca<br>cugcacauca gcuaccugac accuggcgau agcagcagcg gauggacagc uggugccgcc<br>gcuuacuaug ugggcuaccu gcagccuaga accuuccugc ugaaguacaa cgagaacggc<br>accaucaccg acgccgugga uugugcucug gauccucuga gcgagacaaa gugcacccug<br>aaguccuuca ccguggaaaa gggcaucuac cagaccagca acuuccgggu gcagcccacc<br>gaauccaucg ugcgguuccc caauaucacc aaucugugcc ccuucggcga gguguucaau<br>gccaccagau ucgccucugu guacgccugg aaccggaagc ggaucagcaa uugcguggcc<br>gacuacuccg ugcuguacaa cuccgccagc uucagcaccu ucaagugcua cggcgugucc<br>ccuaccaagc ugaacgaccu gugcuucaca aacguguacg ccgacagcuu cgugauccgg<br>ggagaugaag ugcggcagau ugccccugga cagacaggca acaucgccga cuacaacuac<br>aagcugcccg acgacuucac ccgcugugug auugccugga acagcaacaa ccuggacucc<br>aaaguccgcg gcaacuacaa uuaccuquac ccgcuguucc ggaaguccaa ucugaagccc<br>uucgagcggg acaucuccac cgagaucuau caggccggca gcaccccuug uaacggcgug<br>aagggcuuca acugcuacuu cccacugcag uccuacggcu uucagcccac auacggcgug<br>ggcuaucagc ccuacagagu gguggugcug agcuucgaac ugcugcaugc cccugccaca<br>gugugcggcc cuaagaaaag caccaaucuc gugaagaaca aaugcgugas cuucaacuuc<br>aacggccuga ccggcaccgg cgugcugaca gagagcaaca agaaguuccu gccauuccag<br>caguuuggcc gggauaucgc cgauaccaca gacgccguua gagaucccca gacacuggaa<br>auccuggaca ucaccccuug cagcuucggc ggagugucug ugaucacccc uggcaccaac<br>accagcaauc agguggcagu gcuguaccag ggcgugaacu guaccgaagu gcccguggcc<br>cagaccagag ccggcugucu gaucggagcc gagcacguga acaauagcua cgagugcgac<br>auccccaucg gcgcuggaau cugcgccagc uaccagacac agacaaacag cccucggaga<br>gccagaagcg uggccagcca gagcaucauu gccuacacaa ugucucuggg cgucgagaac<br>agcguggccu acuccaacaa cucuaucgcu auccccacca acuucaccau cagcgugacc<br>acagagaucc ugccuguguc caugacccag accagcgugg acugcaccau guacaucugc<br>ggcgauucca ccgagugcuc caaccugcug cugcaguacg gcagcuucug cacccagcug<br>aauagagccc ugacagggau ccccguggaa caggacaaga acacccaaga gguguucgcc<br>caagugaagc agaucuacaa gaccccuccu aucaaggacu ucggcggcuu caauuucagc<br>cagauucugc ccgauccuag caagcccagc aagcggagcu ucaucgagga ccugcuguuc<br>aacaaaguga cacuggccga cgccggcuuc aucaagcagu auggcgauug ucugggcgac<br>auugccgcca gggaucugau uugcgcccag aaguuuaacg gacugacagu gcugccuccu<br>cugcugaccg augagaugau cgcccaguac acaucugccc ugcuggccgg cacaaucaca<br>agcggcugga cauuuggagc aggcgccgcu cugcagaucc ccuuugcuau gcagauggcc<br>uaccgguuca acggcaucgg agugacccag aaugugcugu acgagaacca gaagcugauc<br>gccaaccagu ucaacagcgc caucggcaag auccaggaca gccugagcag cacagcaagc<br>gcccugggaa agcugcagga cguggucaac cagaaugccc aggcacugaa cacccugguc |

TABLE 3-continued

Sequences of RBP020.11 (a Beta-specific RNA vaccine)

| SEQ ID NO. | Brief Description | Sequence |
|---|---|---|
| | | aagcagcugu ccuccaacuu cggcgccauc agcucugugc ugaacgauau ccugagcaga |
| | | cuggacccuc cugaggccga ggugcagauc gacagacuga ucacaggcag acugcagagc |
| | | cuccagacau acgugaccca gcagcugauc agagccgccg agauuagagc cucugccaau |
| | | ggcaagggcu accaccugau gagcuucccu cagucugccc cucacggcgu gguguuucug |
| | | cacgugacau augugcccgc ucaagagaag aauuucacca ccgcuccagc caucugccac |
| | | gacggcaaag cccacuuucc uagagaaggc guguucgugu ccaacggcac ccauugguuc |
| | | gugacacagc ggaacuucua cgagccccag aucaucacca ccgacaacac cuucgugucu |
| | | ggcaacugcg acgucgugau cggcauugug aacaauaccg uguacgaccc ucugcagccc |
| | | gagcuggaca gcuucaaaga ggaacuggac aaguacuuua agaaccacac aagccccgac |
| | | guggaccugg gcgauaucag cggaaucaau gccagcgucg ugaacaucca gaaagagauc |
| | | gaccggcuga acgagguggc caagaaucug aacgagagcc ugaucgaccu gcaagaacug |
| | | gggaaguacg agcaguacau caaguggccc ugguacaucu ggcugggcuu uaucgccgga |
| | | cugauugcca ucgugauggu cacaaucaug cuguguugca ugaccagcug cuguagcugc |
| | | cugaagggcu guuguagcug uggcagcugc ugcaaguucg acgaggacga uucugagccc |
| | | gugcugaagg gcgugaaacu gcacuacaca ugaugac |
| | | ucgagcuggu acugcaugca cgcaaugcua gcugccccuu ucccguccug gguaccccga |
| | | gucuccccccg accucggguc ccagguaugc ucccaccucc accugcccca cucaccaccu |
| | | cugcuaguuc cagacaccuc ccaagcacgc agcaaugcag cucaaaacgc uuagccuagc |
| | | cacaccccca ccggaaacag cagugauuaa ccuuuagcaa uaaacgaaag uuuaacuaag |
| | | cuauacuaac cccaggguug gucaauuucg ugccagccac acccuggagc uagc |
| | | aaaaaaaaaa aaaaaaaaaa Aaaaaaaaaa Gcauaugacu aaaaaaaaaa aaaaaaaaaa |
| | | aaaaaaaaaa aaaaaaaaaa aaaaaaaaaa aaaaaaaaaa aaaaaaaaaa |
| 153 | Full length DNA sequence of RBP020.11 | agaataaact agtattcttc tcgtccccac agactcagag agaacccgcc acc |
| | | atgttcgtgt tcctggtgct gctgcctctg gtgtccagcc agtgtgtgaa cttcaccacc |
| | | agaacacagc tccctccagc ctacaccaac agctttacca gaggcgtgta ctaccccgac |
| | | aaggtgttca gatccagcgt gctgcactct acccaggacc tcttcctgcc tttcttcagc |
| | | aacgtgacct ggttccacgc catccacgtg tccggcacca atggcaccaa gagattcgcc |
| | | aaccccgtgc tgcccttcaa cgacggggtg tactttgcca gcaccgagaa gtccaacatc |
| | | atcagaggct ggatcttcgg caccacactg gacagcaaga cccagagcct gctgatcgtg |
| | | aacaacgcca ccaacgtggt catcaaagtg tgcgagttcc agttctgcaa cgaccccttc |
| | | ctgggcgtct actaccacaa gaacaacaag agctggatgg aaagcgagtt ccgggtgtac |
| | | agcagcgcca acaactgcac cttcgagtac gtgtcccagc ctttcctgat ggacctggaa |
| | | ggcaagcagg gcaacttcaa gaacctgcgc gagttcgtgt ttaagaacat cgacggctac |
| | | ttcaagatct acagcaagca cacccctatc aacctcgtgc ggggcctgcc tcagggcttc |
| | | tctgctctgg aacccctggt ggatctgccc atcggcatca acatcacccg gtttcagaca |
| | | ctgcacatca gctacctgac acctggcgat agcagcagcg gatggacagc tggtgccgcc |
| | | gcttactatg tgggctacct gcagcctaga accttcctgc tgaagtacaa cgagaacggc |
| | | accatcaccg acgccgtgga ttgtgctctg gatcctctga gcgagacaaa gtgcaccctg |
| | | aagtccttca ccgtcgaaaa gggcatctac cagaccagca acttccgggt gcagcccacc |
| | | gaatccatcg tgcggttccc caatatcacc aatctgtgcc ccttcggcga ggtgttcaat |
| | | gccaccagat tcgcctctgt gtacgcctgg aaccggaagc ggatcagcaa ttgcgtggcc |
| | | gactactccg tgctgtacaa ctccgccagc ttcagcacct tcaagtgcta cggcgtgtcc |
| | | cctaccaagc tgaacgacct gtgcttcaca aacgtgtacg ccgacagctt cgtgatccgg |
| | | ggagatgaag tgcggcagat tgcccctgga cagacaggca acatcgccgc ctacaactac |
| | | aagctgcccg acgacttcac cggctgtgtg attgcctgga acagcaacaa cctggactcc |
| | | aaagtcggcg gcaactacaa ttacctgtac cggctgttcc ggaagtccaa tctgaagccc |
| | | ttcgagcggg acatctccac cgagatctat caggccggca gcaccccttg taacggcgtg |
| | | aagggcttca actgctactt cccactgcag tcctacggct ttcagcccac atacggcgtg |
| | | ggctatcagc cctacagagt gctggtgctg agcttcgaac tgctgcatgc ccctgccaca |
| | | gtgtgcggcc ctaagaaaag caccaatctc gtgaagaaca aatgcgtgaa cttcaacttc |
| | | aacggcctga ccggcaccgg cgtgctgaca gagagcaaca agaagttcct gccattccag |
| | | cagtttggcc gggatatcgc cgataccaca gacgccgtta gagatcccca gacactggaa |
| | | atcctggaca tcaccccttg cagcttcggc ggagtgtcty tgatcacccc tygcaccaac |
| | | accagcaatc aggtygcagt gctgtaccag ggcgtgaact gtaccgaagt gcccgtggcc |
| | | attcacgccg atcagctgac acctacatgg cgggtgtact ccaccggcag caatgtgttt |
| | | cagaccagag ccggctgtct gatcggagcc gagcacgtga acaatagcta cgagtgcgac |
| | | atccccatcg gcgctggaat ctgcgccagc taccagacac agacaaacag ccctcggaga |
| | | gccagaagcg tcgccagcca gagcatcatt gcctacacaa tctctctggg cgtcgagaac |
| | | agcgtggcct actccaacaa ctctatcgct atccccacca acttcaccat cagcgtgacc |
| | | acagagatcc tgcctgtgtc catgaccaag accagcgtgg actgcaccat gtacatctgc |
| | | ggcgattcca ccgagtgctc caacctgcty ctgcagtacg gcagcttctg cacccagctg |
| | | aatagagccc tgacagggat cgccgtggaa caggacaaga acacccaaga ggtgttcgcc |
| | | caagtgaagc agatctacaa gacccctcct atcaaggact tcggcggctt caatttcagc |
| | | cagattctgc ccgatcctag caagcccagc aagcggagct tcatcgagga cctgctgttc |
| | | aacaaagtga cactggccga cgccggcttc atcaagcagt atggcgattg tctgggcgac |
| | | attgccgcca gggatctgat ttgcgcccag aagtttaacg gactgacagt gctgcctcct |
| | | ctgctgaccg atgagatgat cccccagtac acatctgccc tgctggccgg cacaatcaca |
| | | agcggctgga catttggagc aggcgccgct ctgcagatcc cctttgctat gcagatggcc |
| | | taccggttca acggcatcgg agtgacccag aatgtgctgt acgagaacca gaagctgatc |
| | | gccaaccagt tcaacagcgc catcggcaag atccaggaca gcctgagcag cacagcaagc |
| | | gccctgggaa agctgcagga cgtggtcaac cagaatgccc aggcactgaa caccctggtc |
| | | aagcagctgt cctccaactt cggcgccatc agctctgtgc tgaacgatat cctgagcaga |
| | | ctggaccctc ctgaggccga ggtgcagatc gacagactga tcacaggcag actgcagagc |

TABLE 3-continued

Sequences of RBP020.11 (a Beta-specific RNA vaccine)

| SEQ ID NO. | Brief Description | Sequence |
|---|---|---|
| | | ctccagacat acgtgaccca gcagctgatc agagccgccg agattagagc ctctgccaat<br>ctggccgcca ccaagatgtc tgagtgtgtg ctgggccaga gcaagagagt ggacttttgc<br>ggcaagggct accacctgat gagcttccct cagtctgccc ctcacggcgt ggtgtttctg<br>cacgtgacat atgtgcccgc tcaagagaag aatttcacca ccgctccagc catctgccac<br>gacggcaaag cccactttcc tagagaaggc gtgttcgtgt ccaacggcac ccattggttc<br>gtgacacagc ggaacttcta cgagccccag atcatcacca ccgacaacac cttcgtgtct<br>ggcaactgcg acgtcgtgat cggcattgtg aacaataccg tctacgaccc tctgcagccc<br>gagctggaca gcttcaaaga ggaactggac aagtacttta agaaccacac aagccccgac<br>gtggacctgg gcgatatcag cggaatcaat gccagcgtcg tgaacatcca gaaagagatc<br>gaccggctga acgaggtggc caagaatctg aacgagagcc tgatcgacct gcaagaactg<br>gggaagtacg agcagtacat caagtggccc tggtacatct ggctgggctt tatcgccgga<br>ctgattgcca tcgtgatggt cacaatcatg ctgtgttgca tgaccagctg ctgtagctgc<br>ctgaagggct gttgtagctg tcgcagctgc tccaagttcg acgaggacga ttctgagccc<br>gtgctgaagg gcgtgaaact gcactacaca tgatgac<br>tcgagctggt actgcatgca cgcaatgcta gctgcccctt tcccgtcctg ggtaccccga<br>gtctcccccg acctcgggtc ccaggtatgc tcccacctcc acctgcccca ctcaccacct<br>ctgctagttc cagacacctc ccaagcacgc agcaatgcag ctcaaaacgc ttagcctagc<br>cacaccccca ccqqaaacag cagtgattaa cctttagcaa taaacgaaag tttaactaag<br>ctatactaac cccagggttg gtcaatttcg tgccagccac accctggagc tagc<br>aaaaaaaaaa aaaaaaaaaa aaaaaaaaaa aaaaaaaaaa gcatatcact aaaaaaaaaa<br>aaaaaaaaaa aaaaaaaaaa aaaaaaaaaa aaaaaaaaaa aaaaaaaaaa |

Nucleotide Sequence of RBP020.14 (Alpha-Specific Vaccine)

Nucleotide sequence is shown with individual sequence elements as indicated in bold letters. In addition, the sequence of the translated protein is shown in italic letters below the coding nucleotide sequence (*=stop codon). Red text indicates point mutations in both the nucleotide and amino acid sequences.

```
        10         20         30         40         50  53
AGAAUAAACU AGUAUUCUUC UGGUCCCCAC AGACUCAGAG AGAACCCGCC ACC
                         hAg-Kozak

        63         73         83         93        103        113
AUGUUCGUGU UCCUGGUGCU GCUGCCUCUG GUGUCCAGCC AGUGUGUGAA CCUGACCACC
  M  F  V   F  L  V   L  L  P  L   V  S  S   Q  C  V   N  L  T  T
                          S protein mut4

       123        133        143        153        163        173
AGAACACAGC UGCCUCCAGC CUACACCAAC AGCUUUACCA GAGGCGUGUA CUACCCCGAC
  R  T  Q   L  P  P   A  Y  T  N   S  F  T   R  G  V   Y  Y  P  D
                          S protein mut3

       183        193        203        213        223        233
AAGGUGUUCA GAUCCAGCGU GCUGCACUCU ACCCAGGACC UGUUCCUGCC UUUCUUCAGC
  K  V  F   R  S  S   V  L  H  S   T  Q  D   L  F  L   P  F  F  S
                          S protein mut3

       243        253        263        273        283        293
AACGUGACCU GGUUCCACGC CAUCUCCGGC ACCAAUGGCA CCAAGAGAUU CGACAACCCC
  N  V  T   W  F  H   A  I  S  G   T  N  G   T  K  R   F  D  N  P
                          S protein mut3

       303        313        323        333        343        353
GUGCUGCCCU UCAACGACGG GGUGUACUUU GCCAGCACCG AGAAGUCCAA CAUCAUCAGA
  V  L  P   F  N  D   G  V  Y  F   A  S  T   E  K  S   N  I  I  R
                          S protein mut3

       363        373        383        393        403        413
GGCUGGAUCU UCGGCACCAC ACUGGACAGC AAGACCCAGA GCCUGCUGAU CGUGAACAAC
  G  W  I   F  G  T   T  L  D  S   K  T  Q   S  L  L   I  V  N  N
                          S protein mut3

       423        433        443        453        463        473
GCCACCAACG UGGUCAUCAA AGUGUGCGAG UUCCAGUUCU GCAACGACCC CUUCCUGGGC
  A  T  N   V  V  I   K  V  C  E   F  Q  F   C  N  D   P  F  L  G
                          S protein mut3

       483        493        503        513        523        533
GUCUACCACA AGAACAACAA GAGCUGGAUG GAAAGCGAGU UCCGGGUGUA CAGCAGCGCC
  V  Y  H   K  N  N   K  S  W  M   E  S  E   F  R  V   Y  S  S  A
                          S protein mut3
```

-continued

```
        543        553        563        573        583        593
AACAACUGCA CCUUCGAGUA CGUGUCCCAG CCUUUCCUGA UGGACCUGGA AGGCAAGCAG
  N  N  C   T  F  E   Y  V  S  Q   P  F  L   M  D  L   E  G  K  Q
                           S protein mut3

        603        613        623        633        643        653
GGCAACUUCA AGAACCUGCG CGAGUUCGUG UUUAAGAACA UCGACGGCUA CUUCAAGAUC
  G  N  F   K  N  L   R  E  F  V   F  K  N   I  D  G   Y  F  K  I
                           S protein mut3

        663        673        683        693        703        713
UACAGCAAGC ACACCCCUAU CAACCUCGUG CGGGAUCUGC CUCAGGGCUU CUCUGCUCUG
  Y  S  K   H  T  P   I  N  L  V   R  D  L   P  Q  G   F  S  A  L
                           S protein mut3

        723        733        743        753        763        773
GAACCCCUGG UGGAUCUGCC CAUCGGCAUC AACAUCACCC GGUUUCAGAC ACUGCUGGCC
  E  P  L   V  D  L   P  I  G  I   N  I  T   R  F  Q   T  L  L  A
                           S protein mut3

        783        793        803        813        823        833
CUGCACAGAA GCUACCUGAC ACCUGGCGAU AGCAGCAGCG GAUGGACAGC UGGUGCCGCC
  L  H  R   S  Y  L   T  P  G  D   S  S  S   G  W  T   A  G  A  A
                           S protein mut3

        843        853        863        873        883        893
GCUUACUAUG UGGGCUACCU GCAGCCUAGA ACCUUCCUGC UGAAGUACAA CGAGAACGGC
  A  Y  Y   V  G  Y   L  Q  P  R   T  F  L   L  K  Y   N  E  N  G
                           S protein mut3

        903        913        923        933        943        953
ACCAUCACCG ACGCCGUGGA UUGUGCUCUG GAUCCUCUGA GCGAGACAAA GUGCACCCUG
  T  I  T   D  A  V   D  C  A  L   D  P  L   S  E  T   K  C  T  L
                           S protein mut3

        963        973        983        993       1003       1013
AAGUCCUUCA CCGUGGAAAA GGGCAUCUAC CAGACCAGCA ACUUCCGGGU GCAGCCCACC
  K  S  F   T  V  E   K  G  I  Y   Q  T  S   N  F  R   V  Q  P  T
                           S protein mut3

       1023       1033       1043       1053       1063       1073
GAAUCCAUCG UGCGGUUCCC CAAUAUCACC AAUCUGUGCC CCUUCGGCGA GGUGUUCAAU
  E  S  I   V  R  F   P  N  I  T   N  L  C   P  F  G   E  V  F  N
                           S protein mut3

       1083       1093       1103       1113       1123       1133
GCCACCAGAU UCGCCUCUGU GUACGCCUGG AACCGGAAGC GGAUCAGCAA UUGCGUGGCC
  A  T  R   F  A  S   V  Y  A  W   N  R  K   R  I  S   N  C  V  A
                           S protein mut3

       1143       1153       1163       1173       1183       1193
GACUACUCCG UGCUGUACAA CUCCGCCAGC UUCAGCACCU UCAAGUGCUA CGGCGUGUCC
  D  Y  S   V  L  Y   N  S  A  S   F  S  T   F  K  C   Y  G  V  S
                           S protein mut3

       1203       1213       1223       1233       1243       1253
CCUACCAAGC UGAACGACCU GUGCUUCACA AACGUGUACG CCGACAGCUU CGUGAUCCGG
  P  T  K   L  N  D   L  C  F  T   N  V  Y   A  D  S   F  V  I  R
                           S protein mut3

       1263       1273       1283       1293       1303       1313
GGAGAUGAAG UGCGGCAGAU UGCCCCUGGA CAGACAGGCA AGAUCGCCGA CUACAACUAC
  G  D  E   V  R  Q   I  A  P  G   Q  T  G   K  I  A   D  Y  N  Y
                           S protein mut3

       1323       1333       1343       1353       1363       1373
AAGCUGCCCG ACGACUUCAC CGGCUGUGUG AUUGCCUGGA ACAGCAACAA CCUGGACUCC
  K  L  P   D  D  F   T  G  C  V   I  A  W   N  S  N   N  L  D  S
                           S protein mut3

       1383       1393       1403       1413       1423       1433
AAAGUCGGCG GCAACUACAA UUACCUGUAC CGGCUGUUCC GGAAGUCCAA UCUGAAGCCC
  K  V  G   G  N  Y   N  Y  L  Y   R  L  F   R  K  S   N  L  K  P
                           S protein mut3

       1443       1453       1463       1473       1483       1493
UUCGAGCGGG ACAUCUCCAC CGAGAUCUAU CAGGCCGGCA GCACCCCUUG UAACGGCGUG
  F  E  R   D  I  S   T  E  I  Y   Q  A  G   S  T  P   C  N  G  V
                           S protein mut3
```

-continued

```
     1503       1513       1523       1533       1543       1553
GAAGGCUUCA ACUGCUACUU CCCACUGCAG UCCUACGGCU UUCAGCCCAC AUACGGCGUG
  E  G  F   N  C  Y   F  P  L  Q   S  Y  G   F  Q  P   T  Y  G  V
                          S protein mut3

     1563       1573       1583       1593       1603       1613
GGCUAUCAGC CCUACAGAGU GGUGGUGCUG AGCUUCGAAC UGCUGCAUGC CCCUGCCACA
  G  Y  Q   P  Y  R   V  V  V  L   S  F  E   L  L  H   A  P  A  T
                          S protein mut3

     1623       1633       1643       1653       1663       1673
GUGUGCGGCC CUAAGAAAAG CACCAAUCUC GUGAAGAACA AAUGCGUGAA CUUCAACUUC
  V  C  G   P  K  K   S  T  N  L   V  K  N   K  C  V   N  F  N  F
                          S protein mut3

     1683       1693       1703       1713       1723       1733
AACGGCCUGA CCGGCACCGG CGUGCUGACA GAGAGCAACA AGAAGUUCCU GCCAUUCCAG
  N  G  L   T  G  T   G  V  L  T   E  S  N   K  K  F   L  P  F  Q
                          S protein mut3

     1743       1753       1763       1773       1783       1793
CAGUUUGGCC GGGAUAUCGA CGAUACCACA GACGCCGUUA GAGAUCCCCA GACACUGGAA
  Q  F  G   R  D  I   D  D  T  T   D  A  V   R  D  P   Q  T  L  E
                          S protein mut3

     1803       1813       1823       1833       1843       1853
AUCCUGGACA UCACCCCUUG CAGCUUCGGC GGAGUGUCUG UGAUCACCCC UGGCACCAAC
  I  L  D   I  T  P   C  S  F  G   G  V  S   V  I  T   P  G  T  N
                          S protein mut3

     1863       1873       1883       1893       1903       1913
ACCAGCAAUC AGGUGGCAGU GCUGUACCAG GGCGUGAACU GUACCGAAGU GCCCGUGGCC
  T  S  N   Q  V  A   V  L  Y  Q   G  V  N   C  T  E   V  P  V  A
                          S protein mut3

     1923       1933       1943       1953       1963       1973
AUUCACGCCG AUCAGCUGAC ACCUACAUGG CGGGUGUACU CCACCGGCAG CAAUGUGUUU
  I  H  A   D  Q  L   T  P  T  W   R  V  Y   S  T  G   S  N  V  F
                          S protein mut3

     1983       1993       2003       2013       2023       2033
CAGACCAGAG CCGGCUGUCU GAUCGGAGCC GAGCACGUGA ACAAUAGCUA CGAGUGCGAC
  Q  T  R   A  G  C   L  I  G  A   E  H  V   N  N  S   Y  E  C  D
                          S protein mut3

     2043       2053       2063       2073       2083       2093
AUCCCCAUCG GCGCUGGAAU CUGCGCCAGC UACCAGACAC AGACAAACAG CCACCGGAGA
  I  P  I   G  A  G   I  C  A  S   Y  Q  T   Q  T  N   S  H  R  R
                          S protein mut3

     2103       2113       2123       2133       2143       2153
GCCAGAAGCG UGGCCAGCCA GAGCAUCAUU GCCUACACAA UGUCUCUGGG CGCCGAGAAC
  A  R  S   V  A  S   Q  S  I  I   A  Y  T   M  S  L   G  A  E  N
                          S protein mut3

     2163       2173       2183       2193       2203       2213
AGCGUGGCCU ACUCCAACAA CUCUAUCGCU AUCCCCAUCA ACUUCACCAU CAGCGUGACC
  S  V  A   Y  S  N   N  S  I  A   I  P  I   N  F  T   I  S  V  T
                          S protein mut3

     2223       2233       2243       2253       2263       2273
ACAGAGAUCC UGCCUGUGUC CAUGACCAAG ACCAGCGUGG ACUGCACCAU GUACAUCUGC
  T  E  I   L  P  V   S  M  T  K   T  S  V   D  C  T   M  Y  I  C
                          S protein mut3

     2283       2293       2303       2313       2323       2333
GGCGAUUCCA CCGAGUGCUC CAACCUGCUG CUGCAGUACG GCAGCUUCUG CACCCAGCUG
  G  D  S   T  E  C   S  N  L  L   L  Q  Y   G  S  F   C  T  Q  L
                          S protein mut3

     2343       2353       2363       2373       2383       2393
AAUAGAGCCC UGACAGGGAU CGCCGUGGAA CAGGACAAGA ACACCCAAGA GGUGUUCGCC
  N  R  A   L  T  G   I  A  V  E   Q  D  K   N  T  Q   E  V  F  A
                          S protein mut3

     2403       2413       2423       2433       2443       2453
CAAGUGAAGC AGAUCUACAA GACCCCUCCU AUCAAGGACU UCGGCGGCUU CAAUUUCAGC
  Q  V  K   Q  I  Y   K  T  P  P   I  K  D   F  G  G   F  N  F  S
                          S protein mut3
```

-continued

```
     2463       2473       2483       2493       2503       2513
CAGAUUCUGC CCGAUCCUAG CAAGCCCAGC AAGCGGAGCU UCAUCGAGGA CCUGCUGUUC
  Q  I  L   P  D  P   S  K  P  S   K  R  S   F  I  E   D  L  L  F
                          S protein mut3

     2523       2533       2543       2553       2563       2573
AACAAAGUGA CACUGGCCGA CGCCGGCUUC AUCAAGCAGU AUGGCGAUUG UCUGGGCGAC
  N  K  V   T  L  A   D  A  G  F   I  K  Q   Y  G  D   C  L  G  D
                          S protein mut3

     2583       2593       2603       2613       2623       2633
AUUGCCGCCA GGGAUCUGAU UUGCGCCCAG AAGUUUAACG GACUGACAGU GCUGCCUCCU
  I  A  A   R  D  L   I  C  A  Q   K  F  N   G  L  T   V  L  P  P
                          S protein mut3

     2643       2653       2663       2673       2683       2693
CUGCUGACCG AUGAGAUGAU CGCCCAGUAC ACAUCUGCCC UGCUGGCCGG CACAAUCACA
  L  L  T   D  E  M   I  A  Q  Y   T  S  A   L  L  A   G  T  I  T
                          S protein mut3

     2703       2713       2723       2733       2743       2753
AGCGGCUGGA CAUUUGGAGC AGGCGCCGCU CUGCAGAUCC CCUUUGCUAU GCAGAUGGCC
  S  G  W   T  F  G   A  G  A  A   L  Q  I   P  F  A   M  Q  M  A
                          S protein mut3

     2763       2773       2783       2793       2803       2813
UACCGGUUCA ACGGCAUCGG AGUGACCCAG AAUGUGCUGU ACGAGAACCA GAAGCUGAUC
  Y  R  F   N  G  I   G  V  T  Q   N  V  L   Y  E  N   Q  K  L  I
                          S protein mut3

     2823       2833       2843       2853       2863       2873
GCCAACCAGU UCAACAGCGC CAUCGGCAAG AUCCAGGACA GCCUGAGCAG CACAGCAAGC
  A  N  Q   F  N  S   A  I  G  K   I  Q  D   S  L  S   S  T  A  S
                          S protein mut3

     2883       2893       2903       2913       2923       2933
GCCCUGGGAA AGCUGCAGGA CGUGGUCAAC CAGAAUGCCC AGGCACUGAA CACCCUGGUC
  A  L  G   K  L  Q   D  V  V  N   Q  N  A   Q  A  L   N  T  L  V
                          S protein mut3

     2943       2953       2963       2973       2983       2993
AAGCAGCUGU CCUCCAACUU CGGCGCCAUC AGCUCUGUGC UGAACGAUAU CCUGGCCAGA
  K  Q  L   S  S  N   F  G  A  I   S  S  V   L  N  D   I  L  A  R
                          S protein mut3

     3003       3013       3023       3033       3043       3053
CUGGACCCUC CUGAGGCCGA GGUGCAGAUC GACAGACUGA UCACAGGCAG ACUGCAGAGC
  L  D  P   P  E  A   E  V  Q  I   D  R  L   I  T  G   R  L  Q  S
                          S protein mut3

     3063       3073       3083       3093       3103       3113
CUCCAGACAU ACGUGACCCA GCAGCUGAUC AGAGCCGCCG AGAUUAGAGC CUCUGCCAAU
  L  Q  T   Y  V  T   Q  Q  L  I   R  A  A   E  I  R   A  S  A  N
                          S protein mut3

     3123       3133       3143       3153       3163       3173
CUGGCCGCCA CCAAGAUGUC UGAGUGUGUG CUGGGCCAGA GCAAGAGAGU GGACUUUUGC
  L  A  A   T  K  M   S  E  C  V   L  G  Q   S  K  R   V  D  F  C
                          S protein mut3

     3183       3193       3203       3213       3223       3233
GGCAAGGGCU ACCACCUGAU GAGCUUCCCU CAGUCUGCCC CUCACGGCGU GGUGUUUCUG
  G  K  G   Y  H  L   M  S  F  P   Q  S  A   P  H  G   V  V  F  L
                          S protein mut3

     3243       3253       3263       3273       3283       3293
CACGUGACAU AUGUGCCCGC UCAAGAGAAG AAUUUCACCA CCGCUCCAGC CAUCUGCCAC
  H  V  T   Y  V  P   A  Q  E  K   N  F  T   T  A  P   A  I  C  H
                          S protein mut3

     3303       3313       3323       3333       3343       3353
GACGGCAAAG CCCACUUUCC UAGAGAAGGC GUGUUCGUGU CCAACGGCAC CCAUUGGUUC
  D  G  K   A  H  F   P  R  E  G   V  F  V   S  N  G   T  H  W  F
                          S protein mut3

     3363       3373       3383       3393       3403       3413
GUGACACAGC GGAACUUCUA CGAGCCCCAG AUCAUCACCA CCCACAACAC CUUCGUGUCU
  V  T  Q   R  N  F   Y  E  P  Q   I  I  T   T  H  N   T  F  V  S
                          S protein mut3
```

-continued

```
     3423       3433       3443       3453       3463       3473
GGCAACUGCG ACGUCGUGAU CGGCAUUGUG AACAAUACCG UGUACGACCC UCUGCAGCCC
  G  N  C   D  V  V   I  G  I  V   N  N  T   V  Y  D   P  L  Q  P
                          S protein mut3

     3483       3493       3503       3513       3523       3533
GAGCUGGACA GCUUCAAAGA GGAACUGGAC AAGUACUUUA AGAACCACAC AAGCCCCGAC
  E  L  D   S  F  K   E  E  L  D   K  Y  F   K  N  H   T  S  P  D
                          S protein mut3

     3543       3553       3563       3573       3583       3593
GUGGACCUGG GCGAUAUCAG CGGAAUCAAU GCCAGCGUCG UGAACAUCCA GAAAGAGAUC
  V  D  L   G  D  I   S  G  I  N   A  S  V   V  N  I   Q  K  E  I
                          S protein mut3

     3603       3613       3623       3633       3643       3653
GACCGGCUGA ACGAGGUGGC CAAGAAUCUG AACGAGAGCC UGAUCGACCU GCAAGAACUG
  D  R  L   N  E  V   A  K  N  L   N  E  S   L  I  D   L  Q  E  L
                          S protein mut3

     3663       3673       3683       3693       3703       3713
GGGAAGUACG AGCAGUACAU CAAGUGGCCC UGGUACAUCU GGCUGGGCUU UAUCGCCGGA
  G  K  Y   E  Q  Y   I  K  W  P   W  Y  I   W  L  G   F  I  A  G
                          S protein mut3

     3723       3733       3743       3753       3763       3773
CUGAUUGCCA UCGUGAUGGU CACAAUCAUG CUGUGUUGCA UGACCAGCUG CUGUAGCUGC
  L  I  A   I  V  M   V  T  I  M   L  C  C   M  T  S   C  C  S  C
                          S protein mut3

     3783       3793       3803       3813       3823       3833
CUGAAGGGCU GUUGUAGCUG UGGCAGCUGC UGCAAGUUCG ACGAGGACGA UUCUGAGCCC
  L  K  G   C  C  S   C  G  S  C   C  K  F   D  E  D   D  S  E  P
                          S protein mut3

     3843       3853       3863    3869
GUGCUGAAGG GCGUGAAACU GCACUACACA UGAUGA
  V  L  K   G  V  K   L  H  Y  T   *  *
                          S protein mut3

     3879       3889       3899       3909       3919       3929
GAUCUGCUGG UACUGCAUGC ACGCAAUGCU AGCUGCCCCU UUCCCGUCCU GGGUACCCCG
                          FI element

     3939       3949       3959       3969       3979       3989
AGUCUCCCCC GACCUCGGGU CCCAGGUAUG CUCCCACCUC CACCUGCCCC ACUCACCACC
                          FI element

     3999       4009       4019       4029       4039       4049
UCUGCUAGUU CCAGACACCU CCCAAGCACG CAGCAAUGCA GCUCAAAACG CUUAGCCUAG
                          FI element

     4059       4069       4079       4089       4099       4109
CCACACCCCC ACGGGAAACA GCAGUGAUUA ACCUUUAGCA AUAAACGAAA GUUUAACUAA
                          FI element

     4119       4129       4139       4149       4159  4164
GCUAUACUAA CCCCAGGGUU GGUCAAUUUC GUGCCAGCCA CACCCUGGAG CUAGC
                          FI element

     4174       4184       4194       4204       4214       4224
AAAAAAAAAA AAAAAAAAAA AAAAAAAAAA GCAUAUGACU AAAAAAAAAA AAAAAAAAAA
                             Poly(A)

     4234       4244       4254       4264       4274
AAAAAAAAAA AAAAAAAAAA AAAAAAAAAA AAAAAAAAAA AAAAAAAAAA
                             Poly(A)
```

Sequences of RBP020.14 are also shown in Table 4. (SEQ ID NO: 58 and 59)

TABLE 4

Sequences of RBP020.14 (Alpha-specific RNA vaccine)

| SEQ ID NO. | Brief Description | Sequence |
|---|---|---|
| 58 | Amino acid sequence of RNA-encoded SARS-Cov-2 S protein from an Alpha variant (with PRO mutations at positions corresponding to K986P and V987P of SEQ ID NO: 1; i.e., PRO mutations at positions 983 and 984 of SEQ ID NO: 58) | MFVFLVLLPLVSSQCVNLTTRTQLPPAYTNSFTRGVYYPDKVFRSSVLHSTQDLFLPFFSNVTWF<br>HAISGTNGTKRFDNPVLPFNDGVYFASTEKSNIIRGWIFGTTLDSKTQSLLIVNNATNVVIKVCE<br>FQFCNDPFLGVYHKNNKSWMESEFRVYSSANNCTFEYVSQPFLMDLEGKQGNFKNLREFVFKNID<br>GYFKIYSKHTPINLVRDLPQGFSALEPLVDLPIGINITRFQTLLALHRSYLTPGDSSSGWTAGAA<br>AYYVGYLQPRTFLLKYNENGTITDAVDCALDPLSETKCTLKSFTVEKGIYQTSNFRVQPTESIVR<br>FPNITNLCPFGEVFNATRFASVYAWNRKRISNCVADYSVLYNSASFSTFKCYGVSPTKLNDLCFT<br>NVYADSFVIRGDEVRQIAPGQTGKIADYNYKLPDDFTGCVIAWNSNNLDSKVGGNYNYLYRLFRK<br>SNLKPFERDISTEIYQAGSTPCNGVEGFNCYFPLQSYGFQPTYGVGYQPYRVVVLSFELLHAPAT<br>VCGPKKSTNLVKNKCVNFNFNGLTGTGVLTESNKKFLPFQQFGRDIDDTTDAVRDPQTLEILDIT<br>PCSFGGVSVITPGTNTSNQVAVLYQGVNCTEVPVAIHADQLTPTWRVYSTGSNVFQTRAGCLIGA<br>EHVNNSYECDIPIGAGICASYQTQTNSHRRARSVASQSIIAYTMSLGAENSVAYSNNSIAIPINF<br>TISVTTEILPVSMTKTSVDCTMYICGDSTECSNLLLQYGSFCTQLNRALTGIAVEQDKNTQEVFA<br>QVKQIYKTPPIKDFGGFNFSQILPDPSKPSKRSFIEDLLFNKVTLADAGFIKQYGDCLGDIAARD<br>LICAQKFNGLTVLPPLLTDEMIAQYTSALLAGTITSGWTFGAGAALQIPFAMQMAYRFNGIGVTQ<br>NVLYENQKLIANQFNSAIGKIQDSLSSTASALGKLQDVVNQNAQALNTLVKQLSSNFGAISSVLN<br>DILARLDPPEAEVQIDRLITGRLQSLQTYVTQQLIRAAEIRASANLAATKMSECVLGQSKRVDFC<br>GKGYHLMSFPQSAPHGVVFLHVTYVPAQEKNFTTAPAICHDGKAHFPREGVFVSNGTHWFVTQRN<br>FYEPQIITTHNTFVSGNCDVVIGIVNNTVYDPLQPELDSFKEELDKYFKNHTSPDVDLGDISGIN<br>ASVVNIQKEIDRLNEVAKNLNESLIDLQELGKYEQYIKWPWYIWLGFIAGLIAIVMVTIMLCCMT<br>SCCSCLKGCCSCGSCCKFDEDDSEPVLKGVKLHYT** |
| 59 | RNA sequence encoding a SARS-CoV-2 S protein from a Alpha variant | AUGUUCGUGU UCCUGGUGCU GCUGCCUCUG GUGUCCAGCC AGUGUGUGAA CCUGACCACC<br>AGAACACAGC UGCCUCCAGC CUACACCAAC AGCUUUACCA GAGGCGUGUA CUACCCCGAC<br>AAGGUGUUCA GAUCCAGCGU GCUGCACUCU ACCCAGGACC UGUUCCUGCC UUUCUUCAGC<br>AACGUGACCU GGUUCCACGC CAUCUCCGGC ACCAAUGGCA CCAAGAGAUU CGACAACCCC<br>GUGCUGCCCU UCAACGACGG GGUGUACUUU GCCAGCACCG AGAAGUCCAA CAUCAUCAGA<br>GGCUGGAUCU UCGGCACCAC ACUGGACAGC AAGACCCAGA GCCUGCUGAU CGUGAACAAC<br>GCCACCAACG UGGUCAUCAA AGUGUGCGAG UUCCAGUUCU GCAACGACCC CUUCCUGGGC<br>GUCUACCACA AGAACAACAA GAGCUGGAUG GAAAGCGAGU UCCGGGUGUA CAGCAGCGCC<br>AACAACUGCA CCUUCGAGUA CGUGUCCCAG CCUUUCCUGA UGGACCUGGA AGGCAAGCAG<br>GGCAACUUCA AGAACCUGCG CGAGUUCGUG UUUAAGAACA UCGACGGCUA CUUCAAGAUC<br>UACAGCAAGC ACACCCCUAU CAACCUCGUG CGGGAUCUGC CUCAGGGCUU CUCUGCUCUG<br>GAACCCCUGG UGGAUCUGCC CAUCGGCAUC AACAUCACCC GGUUUCAGAC ACUGCUGGCC<br>CUGCACAGAA GCUACCUGAC ACCUGGCGAU AGCAGCAGCG GAUGGACAGC UGGUGCCGCC<br>GCUUACUAUG UGGGCUACCU GCAGCCUAGA ACCUUCCUGC UGAAGUACAA CGAGAACGGC<br>ACCAUCACCG ACGCCGUGGA UUGUGCUCUG GAUCCUCUGA GCGAGACAAA GUGCACCCUG<br>AAGUCCUUCA CCGUGGAAAA GGGCAUCUAC CAGACCAGCA ACUUCCGGGU GCAGCCCACC<br>GAAUCCAUCG UGCGGUUCCC CAAUAUCACC AAUCUGUGCC CCUUCGGCGA GGUGUUCAAU<br>GCCACCAGAU UCGCCUCUGU GUACGCCUGG AACCGGAAGC GGAUCAGCAA UUGCGUGGCC<br>GACUACUCCG UGCUGUACAA CUCCGCCAGC UUCAGCACCU UCAAGUGCUA CGGCGUGUCC<br>CCUACCAAGC UGAACGACCU GUGCUUCACA AACGUGUACG CCGACAGCUU CGUGAUCCGG<br>GGAGAUGAAG UGCGGCAGAU UGCCCCUGGA CAGACAGGCA AGAUCGCCGA CUACAACUAC<br>AAGCUGCCCG ACGACUUCAC CGGCUGUGUG AUUGCCUGGA ACAGCAACAA CCUGGACUCC<br>AAAGUCGGCG GCAACUACAA UUACCUGUAC CGGCUGUUCC GGAAGUCCAA UCUGAAGCCC<br>UUCGAGCGGG ACAUCUCCAC CGAGAUCUAU CAGGCCGGCA GCACCCCUUG UAACGGCGUG<br>GAAGGCUUCA ACUGCUACUU CCCACUGCAG UCCUACGGCU UUCAGCCCAC AUACGGCGUG<br>GGCUAUCAGC CCUACAGAGU GGUGGUGCUG AGCUUCGAAC UGCUGCAUGC CCCUGCCACA<br>GUGUGCGGCC CUAAGAAAAG CACCAAUCUC GUGAAGAACA AAUGCGUGAA CUUCAACUUC<br>AACGGCCUGA CCGGCACCGG CGUGCUGACA GAGAGCAACA AGAAGUUCCU GCCAUUCCAG<br>CAGUUUGGCC GGGAUAUCGA CGAUACCACA GACGCCGUUA GAGAUCCCCA GACACUGGAA<br>AUCCUGGACA UCACCCCUUG CAGCUUCGGC GGAGUGUCUG UGAUCACCCC UGGCACCAAC<br>ACCAGCAAUC AGGUGGCAGU GCUGUACCAG GGCGUGAACU GUACCGAAGU GCCCGUGGCC<br>AUUCACGCCG AUCAGCUGAC ACCUACAUGG CGGGUGUACU CCACCGGCAG CAAUGUGUUU<br>CAGACCAGAG CCGGCUGUCU GAUCGGAGCC CUGCGCCAGC ACAAUAGCUA CGAGUGCGAC<br>AUCCCCAUCG GCGCUGGAAU GAGCAUCAUU GAGCACGUGA AGACAAACAG CCACCGGAGA<br>GCCAGAAGCG UGGCCAGCCA UACCAGACAC GCCUACACAA UGUCUCUGGG CGCCGAGAAC<br>AGCGUGGCCU ACUCCAACAA CUCUAUCGCU AUCCCCAUCA ACUUCACCAU CAGCGUGACC<br>ACAGAGAUCC UGCCUGUGUC CAUGACCAAG ACCAGCGUGG ACUGCACCAU GUACAUCUGC<br>GGCGAUUCCA CCGAGUGCUC CAACCUGCUG CUGCAGUACG GCAGCUUCUG CACCCAGCUG<br>AAUAGAGCCC UGACAGGGAU CGCCGUGGAA CAGGACAAGA ACACCCAAGA GGUGUUCGCC<br>CAAGUGAAGC AGAUCUACAA GACCCCUCCU AUCAAGGACU UCGGCGGCUU CAAUUUCAGC<br>CAGAUUCUGC CCGAUCCUAG CAAGCCCAGC AAGCGGAGCU UCAUCGAGGA CCUGCUGUUC<br>AACAAAGUGA CACUGGCCGA CGCCGGCUUC AUCAAGCAGU AUGGCGAUUG UCUGGGCGAC<br>AUUGCCGCCA GGGAUCUGAU UUGCGCCCAG AAGUUUAACG GACUGACAGU GCUGCCUCCU<br>CUGCUGACCG AUGAGAUGAU CGCCCAGUAC ACAUCUGCCC UGCUGGCCGG CACAAUCACA<br>AGCGGCUGGA CAUUUGGAGC AGGCGCCGCU CUGCAGAUCC CCUUUGCUAU GCAGAUGGCC<br>UACCGGUUCA ACGGCAUCGG AGUGACCCAG AAUGUGCUGU ACGAGAACCA GAAGCUGAUC<br>GCCAACCAGU UCAACAGCGC CAUCGGCAAG AUCCAGGACA GCCUGAGCAG CACAGCAAGC<br>GCCCUGGGAA AGCUGCAGGA CGUGGUCAAC CAGAAUGCCC AGGCACUGAA CACCCUGGUC<br>AAGCAGCUGU CCUCCAACUU CGGCGCCAUC AGCUCUGUGC UGAACGAUAU CCUGGCCAGA<br>CUGGACCCUC CUGAGGCCGA GGUGCAGAUC GACAGACUGA UCACAGGCAG ACUGCAGAGC<br>CUCCAGACAU ACGUGACCCA GCAGCUGAUC AGAGCCGCCG AGAUUAGAGC CUCUGCCAAU |

TABLE 4-continued

Sequences of RBP020.14 (Alpha-specific RNA vaccine)

| SEQ ID NO. | Brief Description | Sequence |
|---|---|---|
| | | CUGGCCGCCA CCAAGAUGUC UGAGUGUGUG CUGGGCCAGA GCAAGAGAGU GGACUUUUGC<br>GGCAAGGGCU ACCACCUGAU GAGCUUCCCU CAGUCUGCCC CUCACGGCGU GGUGUUUCUG<br>CACGUGACAU AUGUGCCCGC UCAAGAGAAG AAUUUCACCA CCGCUCCAGC CAUCUGCCAC<br>GACGGCAAAG CCCACUUUCC UAGAGAAGGC GUGUUCGUGU CCAACGGCAC CCAUUGGUUC<br>GUGACACAGC GGAACUUCUA CGAGCCCCAG AUCAUCACCA CCCACAACAC CUUCGUGUCU<br>GGCAACUGCG ACGUCGUGAU CGGCAUUGUG AACAAUACCG UGUACGACCC UCUGCAGCCC<br>GAGCUGGACA GCUUCAAAGA GGAACUGGAC AAGUACUUUA AGAACCACAC AAGCCCCGAC<br>GUGGACCUGG GCGAUAUCAG CGGAAUCAAU GCCAGCGUCG UGAACAUCCA GAAAGAGAUC<br>GACCGGCUGA ACGAGGUGGC CAAGAAUCUG AACGAGAGCC UGAUCGACCU GCAAGAACUG<br>GGGAAGUACG AGCAGUACAU CAAGUGGCCC UGGUACAUCU GGCUGGGCUU UAUCGCCGGA<br>CUGAUUGCCA UCGUGAUGGU CACAAUCAUG CUGUGUUGCA UGACCAGCUG CUGUAGCUGC<br>CUGAAGGGCU GUUGUAGCUG UGGCAGCUGC UGCAAGUUCG ACGAGGACGA UUCUGAGCCC<br>GUGCUGAAGG GCGUGAAACU GCACUACACA UGAUGA |
| 154 | Sequence encoding a SARS-COV-2 S protein from a Alpha variant | ATGTTCGTGT TCCTGGTGCT GCTGCCTCTG GTGTCCAGCC AGTGTGTGAA CCTGACCACC<br>AGAACACAGC TGCCTCCAGC CTACACCAAC AGCTTTACCA GAGGCGTGTA CTACCCCGAC<br>AAGGTGTTCA GATCCAGCGT GCTGCACTCT ACCCAGGACC TGTTCCTGCC TTTCTTCAGC<br>AACGTGACCT GGTTCCACGC CATCTCCGGC ACCAATGGCA CCAAGAGATT CGACAACCCC<br>GTGCTGCCCT TCAACGACGG GGTGTACTTT GCCAGCACCG AGAAGTCCAA CATCATCAGA<br>GGCTGGATCT TCGGCACCAC ACTGGACAGC AAGACCCAGA GCCTGCTGAT CGTGAACAAC<br>GCCACCAACG TGGTCATCAA AGTGTGCGAG TTCCAGTTCT GCAACGACCC CTTCCTGGGC<br>GTCTACCACA AGAACAACAA GAGCTGGATG GAAAGCGAGT TCCGGGTGTA CAGCAGCGCC<br>AACAACTGCA CCTTCGAGTA CGTGTCCCAG CCTTTCCTGA TGGACCTGGA AGGCAAGCAG<br>GGCAACTTCA AGAACCTGCG CGAGTTCGTG TTTAAGAACA TCGACGGCTA CTTCAAGATC<br>TACAGCAAGC ACACCCCTAT CAACCTCGTG CGGGATCTGC CTCAGGGCTT CTCTGCTCTG<br>GAACCCCTGG TGGATCTGCC CATCGGCATC AACATCACCC GGTTTCAGAC ACTGCTGGCC<br>CTGCACAGAA GCTACCTGAC ACCTGGCGAT AGCAGCAGCG GATGGACAGC TGGTGCCGCC<br>GCTTACTATG TGGGCTACCT GCAGCCTAGA ACCTTCCTGC TGAAGTACAA CGAGAACGGC<br>ACCATCACCG ACGCCGTGGA TTGTGCTCTG GATCCTCTGA GCGAGACAAA GTGCACCCTG<br>AAGTCCTTCA CCGTGGAAAA GGGCATCTAC CAGACCAGCA ACTTCCGGGT GCAGCCCACC<br>GAATCCATCG TGCGGTTCCC CAATATCACC AATCTGTGCC CCTTCGGCGA GGTGTTCAAT<br>GCCACCAGAT TCGCCTCTGT GTACGCCTGG AACCGGAAGC GGATCAGCAA TTGCGTGGCC<br>GACTACTCCG TGCTGTACAA CTCCGCCAGC TTCAGCACCT TCAAGTGCTA CGGCGTGTCC<br>CCTACCAAGC TGAACGACCT GTGCTTCACA AACGTGTACG CCGACAGCTT CGTGATCCGG<br>GGAGATGAAG TGCGGCAGAT TGCCCCTGGA CAGACAGGCA AGATCGCCGA CTACAACTAC<br>AAGCTGCCCG ACGACTTCAC CGGCTGTGTG ATTGCCTGGA ACAGCAACAA CCTGGACTCC<br>AAAGTCGGCG GCAACTACAA TTACCTGTAC CGGCTGTTCC GGAAGTCCAA TCTGAAGCCC<br>TTCGAGCGGG ACATCTCCAC CGAGATCTAT CAGGCCGGCA GCACCCCTTG TAACGGCGTG<br>GAAGGCTTCA ACTGCTACTT CCCACTGCAG TCCTACGGCT TTCAGCCCAC ATACGGCGTG<br>GGCTATCAGC CCTACAGAGT GGTGGTGCTG AGCTTCGAAC TGCTGCATGC CCCTGCCACA<br>GTGTGCGGCC CTAAGAAAAG CACCAATCTC GTGAAGAACA AATGCGTGAA CTTCAACTTC<br>AACGGCCTGA CCGGCACCGG CGTGCTGACA GAGAGCAACA AGAAGTTCCT GCCATTCCAG<br>CAGTTTGGCC GGGATATCGA CGATACCACA GACGCCGTTA GAGATCCCCA GACACTGGAA<br>ATCCTGGACA TCACCCCTTG CAGCTTCGGC GGAGTGTCTG TGATCACCCC TGGCACCAAC<br>ACCAGCAATC AGGTGGCAGT GCTGTACCAG GGCGTGAACT GTACCGAAGT GCCCGTGGCC<br>ATTCACGCCG ATCAGCTGAC ACCTACATGG CGGGTGTACT CCACCGGCAG CAATGTGTTT<br>CAGACCAGAG CCGGCTGTCT GATCGGAGCC GAGCACGTGA ACAATAGCTA CGAGTGCGAC<br>ATCCCCATCG GCGCTGGAAT CTGCGCCAGC TACCAGACAC AGACAAACAG CCACCGGAGA<br>GCCAGAAGCG TGGCCAGCCA GAGCATCATT GCCTACACAA TGTCTCTGGG CGCCGAGAAC<br>AGCGTGGCCT ACTCCAACAA CTCTATCGCT ATCCCCATCA ACTTCACCAT CAGCGTGACC<br>ACAGAGATCC TGCCTGTGTC CATGACCAAG ACCAGCGTGG ACTGCACCAT GTACATCTGC<br>GGCGATTCCA CCGAGTGCTC CAACCTGCTG CTGCAGTACG GCAGCTTCTG CACCCAGCTG<br>AATAGAGCCC TGACAGGGAT CGCCGTGGAA CAGGACAAGA ACACCCAAGA GGTGTTCGCC<br>CAAGTGAAGC AGATCTACAA GACCCCTCCT ATCAAGGACT TCGGCGGCTT CAATTTCAGC<br>CAGATTCTGC CCGATCCTAG CAAGCCCAGC AAGCGGAGCT TCATCGAGGA CCTGCTGTTC<br>AACAAAGTGA CACTGGCCGA CGCCGGCTTC ATCAAGCAGT ATGGCGATTG TCTGGGCGAC<br>ATTGCCGCCA GGGATCTGAT TTGCGCCCAG AAGTTTAACG GACTGACAGT GCTGCCTCCT<br>CTGCTGACCG ATGAGATGAT CGCCCAGTAC ACATCTGCCC TGCTGGCCGG CACAATCACA<br>AGCGGCTGGA CATTTGGAGC AGGCGCCGCT CTGCAGATCC CCTTTGCTAT GCAGATGGCC<br>TACCGGTTCA ACGGCATCGG AGTGACCCAG AATGTGCTGT ACGAGAACCA GAAGCTGATC<br>GCCAACCAGT TCAACAGCGC CATCGGCAAG ATCCAGGACA GCCTGAGCAG CACAGCAAGC<br>GCCCTGGGAA AGCTGCAGGA CGTGGTCAAC CAGAATGCCC AGGCACTGAA CACCCTGGTC<br>AAGCAGCTGT CCTCCAACTT CGGCGCCATC AGCTCTGTGC TGAACGATAT CCTGGCCAGA<br>CTGGACCCTC CTGAGGCCGA GGTGCAGATC GACAGACTGA TCACAGGCAG ACTGCAGAGC<br>CTCCAGACAT ACGTGACCCA GCAGCTGATC AGAGCCGCCG AGATTAGAGC CTCTGCCAAT<br>CTGGCCGCCA CCAAGATGTC TGAGTGTGTG CTGGGCCAGA GCAAGAGAGT GGACTTTTGC<br>GGCAAGGGCT ACCACCTGAT GAGCTTCCCT CAGTCTGCCC CTCACGGCGT GGTGTTTCTG<br>CACGTGACAT ATGTGCCCGC TCAAGAGAAG AATTTCACCA CCGCTCCAGC CATCTGCCAC<br>GACGGCAAAG CCCACTTTCC TAGAGAAGGC GTGTTCGTGT CCAACGGCAC CCATTGGTTC<br>GTGACACAGC GGAACTTCTA CGAGCCCCAG ATCATCACCA CCCACAACAC CTTCGTGTCT<br>GGCAACTGCG ACGTCGTGAT CGGCATTGTG AACAATACCG TGTACGACCC TCTGCAGCCC<br>GAGCTGGACA GCTTCAAAGA GGAACTGGAC AAGTACTTTA AGAACCACAC AAGCCCCGAC<br>GTGGACCTGG GCGATATCAG CGGAATCAAT GCCAGCGTCG TGAACATCCA GAAAGAGATC<br>GACCGGCTGA ACGAGGTGGC CAAGAATCTG AACGAGAGCC TGATCGACCT GCAAGAACTG<br>GGGAAGTACG AGCAGTACAT CAAGTGGCCC TGGTACATCT GGCTGGGCTT TATCGCCGGA |

TABLE 4-continued

Sequences of RBP020.14 (Alpha-specific RNA vaccine)

| SEQ ID NO. | Brief Description | Sequence |
|---|---|---|
| | | CTGATTGCCA TCGTGATGGT CACAATCATG CTGTGTTGCA TGACCAGCTG CTGTAGCTGC<br>CTGAAGGGCT GTTGTAGCTG TGGCAGCTGC TGCAAGTTCG ACGAGGACGA TTCTGAGCCC<br>GTGCTGAAGG GCGTGAAACT GCACTACACA TGATGA |
| 60 | Full length sequence of RBP020.14 (RNA) | AGAAUAAACU AGUAUUCUUC UGGUCCCCAC AGACUCAGAG AGAACCCGCC ACC<br>AUGUUCGUGU UCCUGGUGCU GCUGCCUCUG GUGUCCAGCC AGUGUGUGAA CCUGACCACC<br>AGAACACAGC UGCCUCCAGC CUACACCAAC AGCUUUACCA GAGGCGUGUA CUACCCCGAC<br>AAGGUGUUCA GAUCCAGCGU GCUGCACUCU ACCCAGGACC UGUUCCUGCC UUUCUUCAGC<br>AACGUGACCU GGUUCCACGC CAUCUCCGGC ACCAAUGGCA CCAAGAGAUU CGACAACCCC<br>GUGCUGCCCU UCAACGACGG GGUGUACUUU GCCAGCACCG AGAAGUCCAA CAUCAUCAGA<br>GGCUGGAUCU UCGGCACCAC ACUGGACAGC AAGACCCAGA GCCUGCUGAU CGUGAACAAC<br>GCCACCAACG UGGUCAUCAA AGUGUGCGAG UUCCAGUUCU GCAACGACCC CUUCCUGGGC<br>GUCUACCACA AGAACAACAA GAGCUGGAUG GAAAGCGAGU UCCGGGUGUA CAGCAGCGCC<br>AACAACUGCA CCUUCGAGUA CGUGUCCCAG CCUUUCCUGA UGGACCUGGA AGGCAAGCAG<br>GGCAACUUCA AGAACCUGCG CGAGUUCGUG UUUAAGAACA UCGACGGCUA CUUCAAGAUC<br>UACAGCAAGC ACACCCCUAU CAACCUCGUG CGGGAUCUGC CUCAGGGCUU CUCUGCUCUG<br>GAACCCCUGG UGGAUCUGCC CAUCGGCAUC AACAUCACCC GGUUUCAGAC ACUGCUGGCC<br>CUGCACAGAA GCUACCUGAC ACCUGGCGAU AGCAGCAGCG GAUGGACAGC UGGUGCCGCC<br>GCUUACUAUG UGGGCUACCU GCAGCCUAGA ACCUUCCUGC UGAAGUACAA CGAGAACGGC<br>ACCAUCACCG ACGCCGUGGA UUGUGCUCUG GAUCCUCUGA GCGAGACAAA GUGCACCCUG<br>AAGUCCUUCA CCGUGGAAAA GGGCAUCUAC CAGACCAGCA ACUUCCGGGU GCAGCCCACC<br>GAAUCCAUCG UGCGGUUCCC CAAUAUCACC AAUCUGUGCC CCUUCGGCGA GGUGUUCAAU<br>GCCACCAGAU UCGCCUCUGU GUACGCCUGG AACCGGAAGC GGAUCAGCAA UUGCGUGGCC<br>GACUACUCCG UGCUGUACAA CUCCGCCAGC UUCAGCACCU UCAAGUGCUA CGGCGUGUCC<br>CCUACCAAGC UGAACGACCU GUGCUUCACA AACGUGUACG CCGACAGCUU CGUGAUCCGG<br>GGAGAUGAAG UGCGGCAGAU UGCCCCUGGA CAGACAGGCA AGAUCGCCGA CUACAACUAC<br>AAGCUGCCCG ACGACUUCAC CGGCUGUGUG AUUGCCUGGA ACAGCAACAA CCUGGACUCC<br>AAAGUCGGCG GCAACUACAA UUACCUGUAC CGGCUGUUCC GGAAGUCCAA UCUGAAGCCC<br>UUCGAGCGGG ACAUCUCCAC CGAGAUCUAU CAGGCCGGCA GCACCCCUUG UAACGGCGUG<br>GAAGGCUUCA ACUGCUACUU CCCACUGCAG UCCUACGGCU UUCAGCCCAC AUACGGCGUG<br>GGCUAUCAGC CCUACAGAGU GGUGGUGCUG AGCUUCGAAC UGCUGCAUGC CCCUGCCACA<br>GUGUGCGGCC CUAAGAAAAG CACCAAUCUC GUGAAGAACA AAUGCGUGAA CUUCAACUUC<br>AACGGCCUGA CCGGCACCGG CGUGCUGACA GAGAGCAACA AGAAGUUCCU GCCAUUCCAG<br>CAGUUUGGCC GGGAUAUCGA CGAUACCACA GACGCCGUUA GAGAUCCCCA GACACUGGAA<br>AUCCUGGACA UCACCCCUUG CAGCUUCGGC GGAGUGUCUG UGAUCACCCC UGGCACCAAC<br>ACCAGCAAUC AGGUGGCAGU GCUGUACCAG GGCGUGAACU GUACCGAAGU GCCCGUGGCC<br>AUUCACGCCG AUCAGCUGAC ACCUACAUGG CGGGUGUACU CCACCGGCAG CAAUGUGUUU<br>CAGACCAGAG CCGGCUGUCU GAUCGGAGCC GAGCACGUGA ACAAUAGCUA CGAGUGCGAC<br>AUCCCCAUCG GCGCUGGAAU CUGCGCCAGC UACCAGACAC AGACAAACAG CCACCGGAGA<br>GCCAGAAGCG UGGCCAGCCA GAGCAUCAUU GCCUACACAA UGUCUCUGGG CGCCGAGAAC<br>AGCGUGGCCU ACUCCAACAA CUCUAUCGCU AUCCCCAUCA ACUUCACCAU CAGCGUGACC<br>ACAGAGAUCC UGCCUGUGUC CAUGACCAAG ACCAGCGUGG ACUGCACCAU GUACAUCUGC<br>GGCGAUUCCA CCGAGUGCUC CAACCUGCUG CUGCAGUACG GCAGCUUCUG CACCCAGCUG<br>AAUAGAGCCC UGACAGGGAU CGCCGUGGAA CAGGACAAGA ACACCCAAGA GGUGUUCGCC<br>CAAGUGAAGC AGAUCUACAA GACCCCUCCU AUCAAGGACU UCGGCGGCUU CAAUUUCAGC<br>CAGAUUCUGC CCGAUCCUAG CAAGCCCAGC AAGCGGAGCU UCAUCGAGGA CCUGCUGUUC<br>AACAAAGUGA CACUGGCCGA CGCCGGCUUC AUCAAGCAGU AUGGCGAUUG UCUGGGCGAC<br>AUUGCCGCCA GGGAUCUGAU UUGCGCCCAG AAGUUUAACG GACUGACAGU GCUGCCUCCU<br>CUGCUGACCG AUGAGAUGAU CGCCCAGUAC ACAUCUGCCC UGCUGGCCGG CACAAUCACA<br>AGCGGCUGGA CAUUUGGAGC AGGCGCCGCU CUGCAGAUCC CCUUUGCUAU GCAGAUGGCC<br>UACCGGUUCA ACGGCAUCGG AGUGACCCAG AAUGUGCUGU ACGAGAACCA GAAGCUGAUC<br>GCCAACCAGU UCAACAGCGC CAUCGGCAAG AUCCAGGACA GCCUGAGCAG CACAGCAAGC<br>GCCCUGGGAA AGCUGCAGGA CGUGGUCAAC CAGAAUGCCC AGGCACUGAA CACCCUGGUC<br>AAGCAGCUGU CCUCCAACUU CGGCGCCAUC AGCUCUGUGC UGAACGAUAU CCUGGCCAGA<br>CUGGACCCUC CUGAGGCCGA GGUGCAGAUC GACAGACUGA UCACAGGCAG ACUGCAGAGC<br>CUCCAGACAU ACGUGACCCA GCAGCUGAUC AGAGCCGCCG AGAUUAGAGC CUCUGCCAAU<br>CUGGCCGCCA CCAAGAUGUC UGAGUGUGUG CUGGGCCAGA GCAAGAGAGU GGACUUUUGC<br>GGCAAGGGCU ACCACCUGAU GAGCUUCCCU CAGUCUGCCC CUCACGGCGU GGUGUUUCUG<br>CACGUGACAU AUGUGCCCGC UCAAGAGAAG AAUUUCACCA CCGCUCCAGC CAUCUGCCAC<br>GACGGCAAAG CCCACUUUCC UAGAGAAGGC GUGUUCGUGU CCAACGGCAC CCAUUGGUUC<br>GUGACACAGC GGAACUUCUA CGAGCCCCAG AUCAUCACCA CCCACAACAC CUUCGUGUCU<br>GGCAACUGCG ACGUCGUGAU CGGCAUUGUG AACAAUACCG UGUACGACCC UCUGCAGCCC<br>GAGCUGGACA GCUUCAAAGA GGAACUGGAC AAGUACUUUA AGAACCACAC AAGCCCCGAC<br>GUGGACCUGG GCGAUAUCAG CGGAAUCAAU GCCAGCGUCG UGAACAUCCA GAAAGAGAUC<br>GACCGGCUGA ACGAGGUGGC CAAGAAUCUG AACGAGAGCC UGAUCGACCU GCAAGAACUG<br>GGGAAGUACG AGCAGUACAU CAAGUGGCCC UGGUACAUCU GGCUGGGCUU UAUCGCCGGA<br>CUGAUUGCCA UCGUGAUGGU CACAAUCAUG CUGUGUUGCA UGACCAGCUG CUGUAGCUGC<br>CUGAAGGGCU GUUGUAGCUG UGGCAGCUGC UGCAAGUUCG ACGAGGACGA UUCUGAGCCC<br>GUGCUGAAGG GCGUGAAACU GCACUACACA UGAUGA<br>GAUCUGCUGG UACUGCAUGC ACGCAAUGCU AGCUGCCCCU UUCCCGUCCU GGGUACCCCG<br>AGUCUCCCCC GACCUCGGGU CCCAGGUAUG CUCCCACCUC CACCUGCCCC ACUCACCACC<br>UCUGCUAGUU CCAGACACCU CCCAAGCACG CAGCAAUGCA GCUCAAAACG CUUAGCCUAG<br>CCACACCCCC ACGGGAAACA GCAGUGAUUA ACCUUUAGCA AUAAACGAAA GUUUAACUAA<br>GCUAUACUAA CCCCAGGGUU GGUCAAUUUC GUGCCAGCCA CACCCUGGAG CUAGC<br>AAAAAAAAAA AAAAAAAAAA AAAAAAAAAA GCAUAUGACU AAAAAAAAAA AAAAAAAAAA |

TABLE 4-continued

Sequences of RBP020.14 (Alpha-specific RNA vaccine)

| SEQ ID NO. | Brief Description | Sequence |
|---|---|---|
| | | AAAAAAAAAA AAAAAAAAAA AAAAAAAAAA AAAAAAAAAA AAAAAAAAAA |
| 155 | Full length | AGAATAAACT AGTATTCTTC TGGTCCCCAC AGACTCAGAG AGAACCCGCC ACC |
| | sequence of | ATGTTCGTGT TCCTGGTGCT GCTGCCTCTG GTGTCCAGCC AGTGTGTGAA CCTGACCACC |
| | RBP020.14 (DNA) | AGAACACAGC TGCCTCCAGC CTACACCAAC AGCTTTACCA GAGGCGTGTA CTACCCCGAC |
| | | AAGGTGTTCA GATCCAGCGT GCTGCACTCT ACCCAGGACC TGTTCCTGCC TTTCTTCAGC |
| | | AACGTGACCT GGTTCCACGC CATCTCCGGC ACCAATGGCA CCAAGAGATT CGACAACCCC |
| | | GTGCTGCCCT TCAACGACGG GGTGTACTTT GCCAGCACCG AGAAGTCCAA CATCATCAGA |
| | | GGCTGGATCT TCGGCACCAC ACTGGACAGC AAGACCCAGA GCCTGCTGAT CGTGAACAAC |
| | | GCCACCAACG TCGTCATCAA AGTGTGCGAG TTCCAGTTCT GCAACGACCC CTTCCTGGGC |
| | | GTCTACCACA AGAACAACAA GAGCTGGATG GAAAGCGAGT TCCGGGTGTA CAGCAGCGCC |
| | | AACAACTGCA CCTTCGAGTA CGTGTCCCAG CCTTTCCTGA TGGACCTGGA AGGCAAGCAG |
| | | GGCAACTTCA AGAACCTGCG CGAGTTCGTG TTTAAGAACA TCGACGGCTA CTTCAAGATC |
| | | TACAGCAAGC ACACCCCTAT CAACCTCGTG CGGGATCTGC CTCAGGGCTT CTCTGCTCTG |
| | | GAACCCCTGG TGGATCTGCC CATCGGCATC AACATCACCC GGTTTCAGAC ACTGCTGGCC |
| | | CTGCACAGAA GCTACCTGAC ACCTGGCGAT AGCAGCAGCG GATGGACAGC TGGTGCCGCC |
| | | GCTTACTATG TGGGCTACCT GCAGCCTAGA ACCTTCCTGC TGAAGTACAA CGAGAACGGC |
| | | ACCATCACCG ACGCCGTGGA TTGTGCTCTG GATCCTCTGA GCGAGACAAA GTGCACCCTG |
| | | AAGTCCTTCA CCGTGGAAAA GGGCATCTAC CAGACCAGCA ACTTCCGGGT GCAGCCCACC |
| | | GAATCCATCG TGCGGTTCCC CAATATCACC AATCTGTGCC CCTTCGGCGA GGTGTTCAAT |
| | | GCCACCAGAT TCGCCTCTGT GTACGCCTGG AACCGGAAGC GGATCAGCAA TTGCGTGGCC |
| | | GACTACTCCG TGCTGTACAA CTCCGCCAGC TTCAGCACCT TCAAGTGCTA CGGCGTGTCC |
| | | CCTACCAAGC TGAACGACCT GTGCTTCACA AACGTGTACG CCGACAGCTT CGTGATCCGG |
| | | GGAGATGAAG TGCGGCAGAT TGCCCCTGGA CAGACAGGCA AGATCGCCGA CTACAACTAC |
| | | AAGCTGCCCG ACGACTTCAC CGGCTGTGTG ATTGCCTGGA ACAGCAACAA CCTGGACTCC |
| | | AAAGTCGGCG GCAACTACAA TTACCTGTAC CGGCTGTTCC GGAAGTCCAA TCTGAAGCCC |
| | | TTCGAGCGGG ACATCTCCAC CGAGATCTAT CAGGCCGGCA GCACCCCTTG TAACGGCGTG |
| | | GAAGGCTTCA ACTGCTACTT CCCACTGCAG TCCTACGGCT TTCAGCCCAC ATACGGCGTG |
| | | GGCTATCAGC CCTACAGAGT GGTGGTGCTG AGCTTCGAAC TGCTGCATGC CCCTGCCACA |
| | | GTGTGCGGCC CTAAGAAAAG CACCAATCTC GTGAAGAACA AATGCGTGAA CTTCAACTTC |
| | | AACGGCCTGA CCGGCACCGG CGTGCTGACA GAGAGCAACA AGAAGTTCCT GCCATTCCAG |
| | | CAGTTTGGCC GGGATATCGA CGATACCACA GACGCCGTTA GAGATCCCCA GACACTGGAA |
| | | ATCCTGGACA TCACCCCTTG CAGCTTCGGG GGAGTGTCTG TGATCACCCC TGGCACCAAC |
| | | ACCAGCAATC AGGTGGCAGT GCTGTACCAG GGCGTGAACT GTACCGAAGT GCCCGTGGCC |
| | | ATTCACGCCG ATCAGCTGAC ACCTACATGG CGGGTGTACT CCACCGGCAG CAATGTGTTT |
| | | CAGACCAGAG CCGGCTGTCT GATCGGAGCC GAGCACGTGA ACAATAGCTA CGAGTGCGAC |
| | | ATCCCCATCG GCGCTGGAAT CTGCGCCAGC TACCAGACAC AGACAAACAG CCACCGGAGA |
| | | GCCAGAAGCG TGGCCAGCCA GAGCATCATT GCCTACACAA TGTCTCTGGG CGCCGAGAAC |
| | | AGCGTGGCCT ACTCCAACAA CTCTATCGCT ATCCCCATCA ACTTCACCAT CAGCGTGACC |
| | | ACAGAGATCC TGCCTGTGTC CATGACCAAG ACCAGCGTGG ACTGCACCAT GTACATCTGC |
| | | GGCGATTCCA CCGAGTGCTC CAACCTGCTG CTGCAGTACG GCAGCTTCTG CACCCAGCTG |
| | | AATAGAGCCC TGACAGGGAT CGCCGTGGAA CAGGACAAGA ACACCCAAGA GGTGTTCGCC |
| | | CAAGTGAAGC AGATCTACAA GACCCCTCCT ATCAAGGACT TCGGCGGCTT CAATTTCAGC |
| | | CAGATTCTGC CCGATCCTAG CAAGCCCAGC AAGCGGAGCT TCATCGAGGA CCTGCTGTTC |
| | | AACAAAGTGA CACTGGCCGA CGCCGGCTTC ATCAAGCAGT ATGGCGATTG TCTGGGCGAC |
| | | ATTGCCGCCA GGGATCTGAT TTGCGCCCAG AAGTTTAACG GACTGACAGT GCTGCCTCCT |
| | | CTGCTGACCG ATGAGATGAT CGCCCAGTAC ACATCTGCCC TGCTGGCCGG CACAATCACA |
| | | AGCGGCTGGA CATTTGGAGC AGGCGCCGCT CTGCAGATCC CCTTTGCTAT GCAGATGGCC |
| | | TACCGGTTCA ACGGCATCGG AGTGACCCAG AATGTGCTGT ACGAGAACCA GAAGCTGATC |
| | | GCCAACCAGT TCAACAGCGC CATCGGCAAG ATCCAGGACA GCCTGAGCAG CACAGCAAGC |
| | | GCCCTGGGAA AGCTGCAGGA CGTGGTCAAC CAGAATGCCC AGGCACTGAA CACCCTGGTC |
| | | AAGCAGCTGT CCTCCAACTT CGGCGCCATC AGCTCTGTGC TGAACGATAT CCTGGCCAGA |
| | | CTGGACCCTC CTGAGGCCGA GGTGCAGATC GACAGACTGA TCACAGGCAG ACTGCAGAGC |
| | | CTCCAGACAT ACGTGACCCA GCAGCTGATC AGAGCCGCCG AGATTAGAGC CTCTGCCAAT |
| | | CTGGCCGCCA CCAAGATGTC TGAGTGTGTG CTGGGCCAGA GCAAGAGAGT GGACTTTTGC |
| | | GGCAAGGGCT ACCACCTGAT GAGCTTCCCT CAGTCTGCCC CTCACGGCGT GGTGTTTCTG |
| | | CACGTGACAT ATGTGCCCGC TCAAGAGAAG AATTTCACCA CCGCTCCAGC CATCTGCCAC |
| | | GACGGCAAAG CCCACTTTCC TAGAGAAGGC GTGTTCGTGT CCAACGGCAC CCATTGGTTC |
| | | GTGACACAGC GGAACTTCTA CGAGCCCCAG ATCATCACCA CCCACAACAC CTTCGTGTCT |
| | | GGCAACTGCG ACGTCGTGAT CGGCATTGTG AACAATACCG TGTACGACCC TCTGCAGCCC |
| | | GAGCTGGACA GCTTCAAAGA GGAACTGGAC AAGTACTTTA AGAACCACAC AAGCCCCGAC |
| | | GTGGACCTGG GCGATATCAG CGGAATCAAT GCCAGCGTCG TGAACATCCA GAAAGAGATC |
| | | GACCGGCTGA ACGAGGTGGC CAAGAATCTG AACGAGAGCC TGATCGACCT GCAAGAACTG |
| | | GGGAAGTACG AGCAGTACAT CAAGTGGCCC TGGTACATCT GGCTGGGCTT TATCGCCGGA |
| | | CTGATTGCCA TCGTGATGGT CACAATCATG CTGTGTTGCA TGACCAGCTG CTGTAGCTGC |
| | | CTGAAGGGCT GTTGTAGCTG TGGCAGCTGC TGCAAGTTCG ACGAGGACGA TTCTGAGCCC |
| | | GTGCTGAAGG GCGTGAAACT GCACTACACA TGATGA |
| | | GATCTGCTGG TACTGCATGC ACGCAATGCT AGCTGCCCCT TTCCCGTCCT GGGTACCCCG |
| | | AGTCTCCCCC GACCTCGGGT CCCAGGTATG CTCCCACCTC CACCTGCCCC ACTCACCACC |
| | | TCTGCTAGTT CCAGACACCT CCCAAGCACG CAGCAATGCA GCTCAAAACG CTTAGCCTAG |
| | | CCACACCCCC ACGGGAAACA GCAGTGATTA ACCTTTAGCA ATAAACGAAA GTTTAACTAA |
| | | GCTATACTAA CCCCAGGGTT GGTCAATTTC GTGCCAGCCA CACCCTGGAG CTAGC |
| | | AAAAAAAAAA AAAAAAAAAA AAAAAAAAAA GCATATGACT AAAAAAAAAA AAAAAAAAAA |
| | | AAAAAAAAAA AAAAAAAAAA AAAAAAAAAA AAAAAAAAAA AAAAAAAAAA |

Nucleotide Sequence of RBP020.16 (Delta-Specific Vaccine)

Nucleotide sequence is shown with individual sequence elements as indicated in bold letters. In addition, the sequence of the translated protein is shown in italic letters below the coding nucleotide sequence (*=stop codon). Red text indicates point mutations in both the nucleotide and amino acid sequences.

```
        10         20         30         40         50  53
AGAATAAACT AGTATTCTTC TGGTCCCCAC AGACTCAGAG AGAACCCGCC ACC
                      hAg-Kozak

        63         73         83         93        103        113
ATGTTCGTGT TCCTGGTGCT GCTGCCTCTG GTGTCCAGCC AGTGTGTGAA CCTGAGAACC
 M  F  V   F  L  V   L  L  P  L   V  S  S   Q  C  V   N  L  R  T
                      S protein mut4

       123        133        143        153        163        173
AGAACACAGC TGCCTCCAGC CTACACCAAC AGCTTTACCA GAGGCGTGTA CTACCCCGAC
 R  T  Q   L  P  P   A  Y  T  N   S  F  T   R  G  V   Y  Y  P  D
                      S protein mut4

       183        193        203        213        223        233
AAGGTGTTCA GATCCAGCGT GCTGCACTCT ACCCAGGACC TGTTCCTGCC TTTCTTCAGC
 K  V  F   R  S  S   V  L  H  S   T  Q  D   L  F  L   P  F  F  S
                      S protein mut4

       243        253        263        273        283        293
AACGTGACCT GGTTCCACGC CATCCACGTG TCCGGCACCA ATGGCACCAA GAGATTCGAC
 N  V  T   W  F  H   A  I  H  V   S  G  T   N  G  T   K  R  F  D
                      S protein mut4

       303        313        323        333        343        353
AACCCCGTGC TGCCCTTCAA CGACGGGGTG TACTTTGCCA GCACCGAGAA GTCCAACATC
 N  P  V   L  P  F   N  D  G  V   Y  F  A   S  T  E   K  S  N  I
                      S protein mut4

       363        373        383        393        403        413
ATCAGAGGCT GGATCTTCGG CACCACACTG GACAGCAAGA CCCAGAGCCT GCTGATCGTG
 I  R  G   W  I  F   G  T  T  L   D  S  K   T  Q  S   L  L  I  V
                      S protein mut4

       423        433        443        453        463        473
AACAACGCCA CCAACGTGGT CATCAAAGTG TGCGAGTTCC AGTTCTGCAA CGACCCCTTC
 N  N  A   T  N  V   V  I  K  V   C  E  F   Q  F  C   N  D  P  F
                      S protein mut4

       483        493        503        513        523        533
CTGGACGTCT ACTACCACAA GAACAACAAG AGCTGGATGG AAAGCGGCGT GTACAGCAGC
 L  D  V   Y  Y  H   K  N  N  K   S  W  M   E  S  G   V  Y  S  S
                      S protein mut4

       543        553        563        573        583        593
GCCAACAACT GCACCTTCGA GTACGTGTCC CAGCCTTTCC TGATGGACCT GGAAGGCAAG
 A  N  N   C  T  F   E  Y  V  S   Q  P  F   L  M  D   L  E  G  K
                      S protein mut4

       603        613        623        633        643        653
CAGGGCAACT TCAAGAACCT GCGCGAGTTC GTGTTTAAGA ACATCGACGG CTACTTCAAG
 Q  G  N   F  K  N   L  R  E  F   V  F  K   N  I  D   G  Y  F  K
                      S protein mut4

       663        673        683        693        703        713
ATCTACAGCA AGCACACCCC TATCAACCTC GTGCGGGATC TGCCTCAGGG CTTCTCTGCT
 I  Y  S   K  H  T   P  I  N  L   V  R  D   L  P  Q   G  F  S  A
                      S protein mut4

       723        733        743        753        763        773
CTGGAACCCC TGGTGGATCT GCCCATCGGC ATCAACATCA CCCGGTTTCA GACACTGCTG
 L  E  P   L  V  D   L  P  I  G   I  N  I   T  R  F   Q  T  L  L
                      S protein mut4

       783        793        803        813        823        833
GCCCTGCACA GAAGCTACCT GACACCTGGC GATAGCAGCA GCGGATGGAC AGCTGGTGCC
 A  L  H   R  S  Y   L  T  P  G   D  S  S   S  G  W   T  A  G  A
                      S protein mut4

       843        853        863        873        883        893
GCCGCTTACT ATGTGGGCTA CCTGCAGCCT AGAACCTTCC TGCTGAAGTA CAACGAGAAC
 A  A  Y   Y  V  G   Y  L  Q  P   R  T  F   L  L  K   Y  N  E  N
                      S protein mut4
```

-continued

```
       903        913        923        933        943        953
GGCACCATCA CCGACGCCGT GGATTGTGCT CTGGATCCTC TGAGCGAGAC AAAGTGCACC
  G  T  I   T  D  A   V  D  C  A   L  D  P   L  S  E   T  K  C  T
                         S protein mut4

       963        973        983        993       1003       1013
CTGAAGTCCT TCACCGTGGA AAAGGGCATC TACCAGACCA GCAACTTCCG GGTGCAGCCC
  L  K  S   F  T  V   E  K  G  I   Y  Q  T   S  N  F   R  V  Q  P
                         S protein mut4

      1023       1033       1043       1053       1063       1073
ACCGAATCCA TCGTGCGGTT CCCCAATATC ACCAATCTGT GCCCCTTCGG CGAGGTGTTC
  T  E  S   I  V  R   F  P  N  I   T  N  L   C  P  F   G  E  V  F
                         S protein mut4

      1083       1093       1103       1113       1123       1133
AATGCCACCA GATTCGCCTC TGTGTACGCC TGGAACCGGA AGCGGATCAG CAATTGCGTG
  N  A  T   R  F  A   S  V  Y  A   W  N  R   K  R  I   S  N  C  V
                         S protein mut4

      1143       1153       1163       1173       1183       1193
GCCGACTACT CCGTGCTGTA CAACTCCGCC AGCTTCAGCA CCTTCAAGTG CTACGGCGTG
  A  D  Y   S  V  L   Y  N  S  A   S  F  S   T  F  K   C  Y  G  V
                         S protein mut4

      1203       1213       1223       1233       1243       1253
TCCCCTACCA AGCTGAACGA CCTGTGCTTC ACAAACGTGT ACGCCGACAG CTTCGTGATC
  S  P  T   K  L  N   D  L  C  F   T  N  V   Y  A  D   S  F  V  I
                         S protein mut4

      1263       1273       1283       1293       1303       1313
CGGGGAGATG AAGTGCGGCA GATTGCCCCT GGACAGACAG GCAAGATCGC CGACTACAAC
  R  G  D   E  V  R   Q  I  A  P   G  Q  T   G  K  I   A  D  Y  N
                         S protein mut4

      1323       1333       1343       1353       1363       1373
TACAAGCTGC CCGACGACTT CACCGGCTGT GTGATTGCCT GGAACAGCAA CAACCTGGAC
  Y  K  L   P  D  D   F  T  G  C   V  I  A   W  N  S   N  N  L  D
                         S protein mut4

      1383       1393       1403       1413       1423       1433
TCCAAAGTCG GCGGCAACTA CAATTACAGG TACCGGCTGT TCCGGAAGTC CAATCTGAAG
  S  K  V   G  G  N   Y  N  Y  R   Y  R  L   F  R  K   S  N  L  K
                         S protein mut4

      1443       1453       1463       1473       1483       1493
CCCTTCGAGC GGGACATCTC CACCGAGATC TATCAGGCCG GCAGCAAGCC TTGTAACGGC
  P  F  E   R  D  I   S  T  E  I   Y  Q  A   G  S  K   P  C  N  G
                         S protein mut4

      1503       1513       1523       1533       1543       1553
GTGGAAGGCT TCAACTGCTA CTTCCCACTG CAGTCCTACG GCTTTCAGCC CACAAATGGC
  V  E  G   F  N  C   Y  F  P  L   Q  S  Y   G  F  Q   P  T  N  G
                         S protein mut4

      1563       1573       1583       1593       1603       1613
GTGGGCTATC AGCCCTACAG AGTGGTGGTG CTGAGCTTCG AACTGCTGCA TGCCCCTGCC
  V  G  Y   Q  P  Y   R  V  V  V   L  S  F   E  L  L   H  A  P  A
                         S protein mut4

      1623       1633       1643       1653       1663       1673
ACAGTGTGCG GCCCTAAGAA AAGCACCAAT CTCGTGAAGA ACAAATGCGT GAACTTCAAC
  T  V  C   G  P  K   K  S  T  N   L  V  K   N  K  C   V  N  F  N
                         S protein mut4

      1683       1693       1703       1713       1723       1733
TTCAACGGCC TGACCGGCAC CGGCGTGCTG ACAGAGAGCA ACAAGAAGTT CCTGCCATTC
  F  N  G   L  T  G   T  G  V  L   T  E  S   N  K  K   F  L  P  F
                         S protein mut4

      1743       1753       1763       1773       1783       1793
CAGCAGTTTG GCCGGGATAT CGCCGATACC ACAGACGCCG TTAGAGATCC CCAGACACTG
  Q  Q  F   G  R  D   I  A  D  T   T  D  A   V  R  D   P  Q  T  L
                         S protein mut4

      1803       1813       1823       1833       1843       1853
GAAATCCTGG ACATCACCCC TTGCAGCTTC GGCGGAGTGT CTGTGATCAC CCCTGGCACC
  E  I  L   D  I  T   P  C  S  F   G  G  V   S  V  I   T  P  G  T
                         S protein mut4
```

-continued

```
      1863       1873       1883       1893       1903       1913
AACACCAGCA ATCAGGTGGC AGTGCTGTAC CAGGGCGTGA ACTGTACCGA AGTGCCCGTG
  N  T  S   N  Q  V   A  V  L  Y   Q  G  V   N  C  T   E  V  P  V
                         S protein mut4

      1923       1933       1943       1953       1963       1973
GCCATTCACG CCGATCAGCT GACACCTACA TGGCGGGTGT ACTCCACCGG CAGCAATGTG
  A  I  H   A  D  Q   L  T  P  T   W  R  V   Y  S  T   G  S  N  V
                         S protein mut4

      1983       1993       2003       2013       2023       2033
TTTCAGACCA GAGCCGGCTG TCTGATCGGA GCCGAGCACG TGAACAATAG CTACGAGTGC
  F  Q  T   R  A  G   C  L  I  G   A  E  H   V  N  N   S  Y  E  C
                         S protein mut4

      2043       2053       2063       2073       2083       2093
GACATCCCCA TCGGCGCTGG AATCTGCGCC AGCTACCAGA CACAGACAAA CAGCAGGCGG
  D  I  P   I  G  A   G  I  C  A   S  Y  Q   T  Q  T   N  S  P  R
                         S protein mut4

      2103       2113       2123       2133       2143       2153
AGAGCCAGAA GCGTGGCCAG CCAGAGCATC ATTGCCTACA CAATGTCTCT GGGCGCCGAG
  R  A  R   S  V  A   S  Q  S  I   I  A  Y   T  M  S   L  G  A  E
                         S protein mut4

      2163       2173       2183       2193       2203       2213
AACAGCGTGG CCTACTCCAA CAACTCTATC GCTATCCCCA CCAACTTCAC CATCAGCGTG
  N  S  V   A  Y  S   N  N  S  I   A  I  P   T  N  F   T  I  S  V
                         S protein mut4

      2223       2233       2243       2253       2263       2273
ACCACAGAGA TCCTGCCTGT GTCCATGACC AAGACCAGCG TGGACTGCAC CATGTACATC
  T  T  E   I  L  P   V  S  M  T   K  T  S   V  D  C   T  M  Y  I
                         S protein mut4

      2283       2293       2303       2313       2323       2333
TGCGGCGATT CCACCGAGTG CTCCAACCTG CTGCTGCAGT ACGGCAGCTT CTGCACCCAG
  C  G  D   S  T  E   C  S  N  L   L  L  Q   Y  G  S   F  C  T  Q
                         S protein mut4

      2343       2353       2363       2373       2383       2393
CTGAATAGAG CCCTGACAGG GATCGCCGTG GAACAGGACA AGAACACCCA AGAGGTGTTC
  L  N  R   A  L  T   G  I  A  V   E  Q  D   K  N  T   Q  E  V  F
                         S protein mut4

      2403       2413       2423       2433       2443       2453
GCCCAAGTGA AGCAGATCTA CAAGACCCCT CCTATCAAGG ACTTCGGCGG CTTCAATTTC
  A  Q  V   K  Q  I   Y  K  T  P   P  I  K   D  F  G   G  F  N  F
                         S protein mut4

      2463       2473       2483       2493       2503       2513
AGCCAGATTC TGCCCGATCC TAGCAAGCCC AGCAAGCGGA GCTTCATCGA GGACCTGCTG
  S  Q  I   L  P  D   P  S  K  P   S  K  R   S  F  I   E  D  L  L
                         S protein mut4

      2523       2533       2543       2553       2563       2573
TTCAACAAAG TGACACTGGC CGACGCCGGC TTCATCAAGC AGTATGGCGA TTGTCTGGGC
  F  N  K   V  T  L   A  D  A  G   F  I  K   Q  Y  G   D  C  L  G
                         S protein mut4

      2583       2593       2603       2613       2623       2633
GACATTGCCG CCAGGGATCT GATTTGCGCC CAGAAGTTTA ACGGACTGAC AGTGCTGCCT
  D  I  A   A  R  D   L  I  C  A   Q  K  F   N  G  L   T  V  L  P
                         S protein mut4

      2643       2653       2663       2673       2683       2693
CCTCTGCTGA CCGATGAGAT GATCGCCCAG TACACATCTG CCCTGCTGGC CGGCACAATC
  P  L  L   T  D  E   M  I  A  Q   Y  T  S   A  L  L   A  G  T  I
                         S protein mut4

      2703       2713       2723       2733       2743       2753
ACAAGCGGCT GGACATTTGG AGCAGGCGCC GCTCTGCAGA TCCCCTTTGC TATGCAGATG
  T  S  G   W  T  F   G  A  G  A   A  L  Q   I  P  F   A  M  Q  M
                         S protein mut4

      2763       2773       2783       2793       2803       2813
GCCTACCGGT TCAACGGCAT CGGAGTGACC CAGAATGTGC TGTACGAGAA CCAGAAGCTG
  A  Y  R   F  N  G   I  G  V  T   Q  N  V   L  Y  E   N  Q  K  L
                         S protein mut4
```

-continued

```
      2823       2833       2843       2853       2863       2873
ATCGCCAACC AGTTCAACAG CGCCATCGGC AAGATCCAGG ACAGCCTGAG CAGCACAGCA
 I  A  N   Q  F  N   S  A  I  G   K  I  Q   D  S  L   S  S  T  A
                         S protein mut4

      2883       2893       2903       2913       2923       2933
AGCGCCCTGG GAAAGCTGCA GAACGTGGTC AACCAGAATG CCCAGGCACT GAACACCCTG
 S  A  L   G  K  L   Q  H  V  V   N  Q  N   A  Q  A   L  N  T  L
                         S protein mut4

      2943       2953       2963       2973       2983       2993
GTCAAGCAGC TGTCCTCCAA CTTCGGCGCC ATCAGCTCTG TGCTGAACGA TATCCTGAGC
 V  K  Q   L  S  S   N  F  G  A   I  S  S   V  L  N   D  I  L  S
                         S protein mut4

      3003       3013       3023       3033       3043       3053
AGACTGGACC CTCCTGAGGC CGAGGTGCAG ATCGACAGAC TGATCACAGG CAGACTGCAG
 R  L  D   P  P  E   A  E  V  Q   I  D  R   L  I  T   G  R  L  Q
                         S protein mut4

      3063       3073       3083       3093       3103       3113
AGCCTCCAGA CATACGTGAC CCAGCAGCTG ATCAGAGCCG CCGAGATTAG AGCCTCTGCC
 S  L  Q   T  Y  V   T  Q  Q  L   I  R  A   A  E  I   R  A  S  A
                         S protein mut4

      3123       3133       3143       3153       3163       3173
AATCTGGCCG CCACCAAGAT GTCTGAGTGT GTGCTGGGCC AGAGCAAGAG AGTGGACTTT
 N  L  A   A  T  K   M  S  E  C   V  L  G   Q  S  K   R  V  D  F
                         S protein mut4

      3183       3193       3203       3213       3223       3233
TGCGGCAAGG GCTACCACCT GATGAGCTTC CCTCAGTCTG CCCCTCACGG CGTGGTGTTT
 C  G  K   G  Y  H   L  M  S  F   P  Q  S   A  P  H   G  V  V  F
                         S protein mut4

      3243       3253       3263       3273       3283       3293
CTGCACGTGA CATATGTGCC CGCTCAAGAG AAGAATTTCA CCACCGCTCC AGCCATCTGC
 L  H  V   T  Y  V   P  A  Q  E   K  N  F   T  T  A   P  A  I  C
                         S protein mut4

      3303       3313       3323       3333       3343       3353
CACGACGGCA AAGCCCACTT TCCTAGAGAA GGCGTGTTCG TGTCCAACGG CACCCATTGG
 H  D  G   K  A  H   F  P  R  E   G  V  F   V  S  N   G  T  H  W
                         S protein mut4

      3363       3373       3383       3393       3403       3413
TTCGTGACAC AGCGGAACTT CTACGAGCCC CAGATCATCA CCACCGACAA CACCTTCGTG
 F  V  T   Q  R  N   F  Y  E  P   Q  I  I   T  T  D   N  T  F  V
                         S protein mut4

      3423       3433       3443       3453       3463       3473
TCTGGCAACT GCGACGTCGT GATCGGCATT GTGAACAATA CCGTGTACGA CCCTCTGCAG
 S  G  N   C  D  V   V  I  G  I   V  N  N   T  V  Y   D  P  L  Q
                         S protein mut4

      3483       3493       3503       3513       3523       3533
CCCGAGCTGG ACAGCTTCAA AGAGGAACTG GACAAGTACT TTAAGAACCA CACAAGCCCC
 P  E  L   D  S  F   K  E  E  L   D  K  Y   F  K  N   H  T  S  P
                         S protein mut4

      3543       3553       3563       3573       3583       3593
GACGTGGACC TGGGCGATAT CAGCGGAATC AATGCCAGCG TCGTGAACAT CCAGAAAGAG
 D  V  D   L  G  D   I  S  G  I   N  A  S   V  V  N   I  Q  K  E
                         S protein mut4

      3603       3613       3623       3633       3643       3653
ATCGACCGGC TGAACGAGGT GGCCAAGAAT CTGAACGAGA GCCTGATCGA CCTGCAAGAA
 I  D  R   L  N  E   V  A  K  N   L  N  E   S  L  I   D  L  Q  E
                         S protein mut4

      3663       3673       3683       3693       3703       3713
CTGGGGAAGT ACGAGCAGTA CATCAAGTGG CCCTGGTACA TCTGGCTGGG CTTTATCGCC
 L  G  K   Y  E  Q   Y  I  K  W   P  W  Y   I  W  L   G  F  I  A
                         S protein mut4

      3723       3733       3743       3753       3763       3773
GGACTGATTG CCATCGTGAT GGTCACAATC ATGCTGTGTT GCATGACCAG CTGCTGTAGC
 G  L  I   A  I  V   M  V  T  I   M  L  C   C  M  T   S  C  C  S
                         S protein mut4
```

-continued

```
     3783       3793       3803       3813       3823       3833
TGCCTGAAGG GCTGTTGTAG CTGTGGCAGC TGCTGCAAGT TCGACGAGGA CGATTCTGAG
  C  L  K   G  C  C   S  C  G  S   C  C  K   F  D  E   D  D  S  E
                         S protein mut4

     3843       3853       3863      3872
CCCGTGCTGA AGGGCGTGAA ACTGCACTAC ACATGATGA
  P  V  L   K  G  V   K  L  H  Y   T  *  *
                         S protein mut4

     3882       3892       3902       3912       3922       3932
TTTCACCTGG TACTGCATGC ACGCAATGCT AGCTGCCCCT TTCCCGTCCT GGGTACCCCG
                         FI element

     3942       3952       3962       3972       3982       3992
AGTCTCCCCC GACCTCGGGT CCCAGGTATG CTCCCACCTC CACCTGCCCC ACTCACCACC
                         FI element

     4002       4012       4022       4032       4042       4052
TCTGCTAGTT CCAGACACCT CCCAAGCACG CAGCAATGCA GCTCAAAACG CTTAGCCTAG
                         FI element

     4062       4072       4082       4092       4102       4112
CCACACCCCC ACGGGAAACA GCAGTGATTA ACCTTTAGCA ATAAACGAAA GTTTAACTAA
                         FI element

     4122       4132       4142       4152       4162  4167
GCTATACTAA CCCCAGGGTT GGTCAATTTC GTGCCAGCCA CACCCTGGAG CTAGC
                         FI element

     4177       4187       4197       4207       4217       4227
AAAAAAAAAA AAAAAAAAAA AAAAAAAAAA GCATATGACT AAAAAAAAAA AAAAAAAAAA
                           Poly(A)

     4237       4247       4257       4267       4277
AAAAAAAAAA AAAAAAAAAA AAAAAAAAAA AAAAAAAAAA AAAAAAAAAA
                           Poly(A)
```

Sequences of RBP020.14 are also shown in Table 5. (SEQ ID NO: 61). (SEQ ID NO: 62)

TABLE 5

Sequences of RBP020.16 (Delta-specific RNA vaccine)

| SEQ ID NO. | Brief Description | Sequence |
|---|---|---|
| 61 | Amino acid sequence of RNA-encoded SARS-CoV-2 S protein from a Delta variant (with PRO mutations at positions corresponding to K986P and V987P of SEQ ID NO: 1; i.e., PRO mutations at positions 984 and 985 of SEQ ID NO: 61) | MFVFLVLLPLVSSQCVNLRTRTQLPPAYTNSFTRGVYYPDKVFRSSVLHSTQDLFLPFFSNVTWF HAIHVSGTNGTKRFDNPVLPFNDGVYFASTEKSNIIRGWIFGTTLDSKTQSLLIVNNATNVVIKV CEFQFCNDPFLDVYYHKNNKSWMESGVYSSANNCTFEYVSQPFLMDLEGKQGNFKNLREFVFKNI DGYFKIYSKHTPINLVRDLPQGFSALEPLVDLPIGINITRFQTLLALHRSYLTPGDSSSGWTAGA AAYYVGYLQPRTFLLKYNENGTITDAVDCALDPLSETKCTLKSFTVEKGIYQTSNFRVQPTESIV RFPNITNLCPFGEVFNATRFASVYAWNRKRISNCVADYSVLYNSASFSTFKCYGVSPTKLNDLCF TNVYADSFVIRGDEVRQIAPGQTGKIADYNYKLPDDFTGCVIAWNSNNLDSKVGGNYNYRYRLFR KSNLKPFERDISTEIYQAGSKPCNGVEGFNCYFPLQSYGFQPTNGVGYQPYRVVVLSFELLHAPA TVCGPKKSTNLVKNKCVNFNFNGLTGTGVLTESNKKFLPFQQFGRDIADTTDAVRDPQTLEILDI TPCSFGGVSVITPGTNTSNQVAVLYQGVNCTEVPVAIHADQLTPTWRVYSTGSNVFQTRAGCLIG AEHVNNSYECDIPIGAGICASYQTQTNSRRRARSVASQSIIAYTMSLGAENSVAYSNNSIAIPTN FTISVTTEILPVSMTKTSVDCTMYICGDSTECSNLLLQYGSFCTQLNRALTGIAVEQDKNTQEVF AQVKQIYKTPPIKDFGGFNFSQILPDPSKPSKRSFIEDLLFNKVTLADAGFIKQYGDCLGDIAAR DLICAQKFNGLTVLPPLLTDEMIAQYTSALLAGTITSGWTFGAGAALQIPFAMQMAYRFNGIGVT QNVLYENQKLIANQFNSAIGKIQDSLSSTASALGKLQNVVNQNAQALNTLVKQLSSNFGAISSVL NDILSRLDPPEAEVQIDRLITGRLQSLQTYVTQQLIRAAEIRASANLAATKMSECVLGQSKRVDF CGKGYHLMSFPQSAPHGVVFLHVTYVPAQEKNFTTAPAICHDGKAHFPREGVFVSNGTHWFVTQR NFYEPQIITTDNTFVSGNCDVVIGIVNNTVYDPLQPELDSFKEELDKYFKNHTSPDVDLGDISGI NASVVNIQKEIDRLNEVAKNLNESLIDLQELGKYEQYIKWPWYIWLGFIAGLIAIVMVTIMLCCM TSCCSCLKGCCSCGSCCKFDEDDSEPVLKGVKLHYT-- |
| 62 | Sequence encoding a SARS-CoV-2 S protein from a Delta variant | ATGTTCGTGT TCCTGGTGCT GCTGCCTCTG GTGTCCAGCC AGTGTGTGAA CCTGAGAACC AGAACACAGC TGCCTCCAGC CTACACCAAC AGCTTTACCA GAGGCGTGTA CTACCCCGAC AAGGTGTTCA GATCCAGCGT GCTGCACTCT ACCCAGGACC TGTTCCTGCC TTTCTTCAGC AACGTGACCT GGTTCCACGC CATCCACGTG TCCGGCACCA ATGGCACCAA GAGATTCGAC AACCCCGTGC TGCCCTTCAA CGACGGGGTG TACTTTGCCA GCACCGAGAA GTCCAACATC ATCAGAGGCT GGATCTTCGG CACCACACTG GACAGCAAGA CCCAGAGCCT GCTGATCGTG AACAACGCCA CCAACGTGGT CATCAAAGTG TGCGAGTTCC AGTTCTGCAA CGACCCCTTC CTGGACGTCT ACTACCACAA GAACAACAAG AGCTGGATGG AAAGCGGCGT GTACAGCAGC GCCAACAACT GCACCTTCGA GTACGTGTCC CAGCCTTTCC TGATGGACCT GGAAGGCAAG CAGGGCAACT TCAAGAACCT GCGCGAGTTC GTGTTTAAGA ACATCGACGG CTACTTCAAG |

TABLE 5-continued

| SEQ ID NO. | Brief Description | Sequence |
|---|---|---|
| | Sequences of RBP020.16 (Delta-specific RNA vaccine) | |
| | | ATCTACAGCA AGCACACCCC TATCAACCTC GTGCGGGATC TGCCTCAGGG CTTCTCTGCT CTGGAACCCC TGGTGGATCT GCCCATCGGC ATCAACATCA CCCGGTTTCA GACACTGCTG GCCCTGCACA GAAGCTACCT GACACCTGGC GATAGCAGCA GCGGATGGAC AGCTGGTGCC GCCGCTTACT ATGTGGGCTA CCTGCAGCCT AGAACCTTCC TGCTGAAGTA CAACGAGAAC GGCACCATCA CCGACGCCGT GGATTGTGCT CTGGATCCTC TGAGCGAGAC AAAGTGCACC CTGAAGTCCT TCACCGTGGA AAAGGGCATC TACCAGACCA GCAACTTCCG GGTGCAGCCC ACCGAATCCA TCGTGCGGTT CCCCAATATC ACCAATCTGT GCCCCTTCGG CGAGGTGTTC AATGCCACCA GATTCGCCTC TGTGTACGCC TGGAACCGGA AGCGGATCAG CAATTGCGTG GCCGACTACT CCGTGCTGTA CAACTCCGCC AGCTTCAGCA CCTTCAAGTG CTACGGCGTG TCCCCTACCA AGCTGAACGA CCTGTGCTTC ACAAACGTGT ACGCCGACAG CTTCGTGATC CGGGGAGATG AAGTGCGGCA GATTGCCCCT GGACAGACAG GCAAGATCGC CGACTACAAC TACAAGCTGC CCGACGACTT CACCGGCTGT GTGATTGCCT GGAACAGCAA CAACCTGGAC TCCAAAGTCG GCGGCAACTA CAATTACAGG TACCGGCTGT TCCGGAAGTC CAATCTGAAG CCCTTCGAGC GGGACATCTC CACCGAGATC TATCAGGCCG GCAGCAAGCC TTGTAACGGC GTGGAAGGCT TCAACTGCTA CTTCCCACTG CAGTCCTACG GCTTTCAGCC CACAAATGGC GTGGGCTATC AGCCCTACAG AGTGGTGGTG CTGAGCTTCG AACTGCTGCA TGCCCCTGCC ACAGTGTGCG GCCCTAAGAA AAGCACCAAT CTCGTGAAGA ACAAATGCGT GAACTTCAAC TTCAACGGCC TGACCGGCAC CGGCGTGCTG ACAGAGAGCA ACAAGAAGTT CCTGCCATTC CAGCAGTTTG GCCGGGATAT CGCCGATACC ACAGACGCCG TTAGAGATCC CCAGACACTG GAAATCCTGG ACATCACCCC TTGCAGCTTC GGCGGAGTGT CTGTGATCAC CCCTGGCACC AACACCAGCA ATCAGGTGGC AGTGCTGTAC CAGGGCGTGA ACTGTACCGA AGTGCCCGTG GCCATTCACG CCGATCAGCT GACACCTACA TGGCGGGTGT ACTCCACCGG CAGCAATGTG TTTCAGACCA GAGCCGGCTG TCTGATCGGA GCCGAGCACG TGAACAATAG CTACGAGTGC GACATCCCCA TCGGCGCTGG AATCTGCGCC AGCTACCAGA CACAGACAAA CAGCAGCCGG AGAGCCAGAA GCGTGGCCAG CCAGAGCATC ATTGCCTACA CAATGTCTCT GGGCGCCGAG AACAGCGTGG CCTACTCCAA CAACTCTATC GCTATCCCCA CCAACTTCAC CATCAGCGTG ACCACAGAGA TCCTGCCTGT GTCCATGACC AAGACCAGCG TGGACTGCAC CATGTACATC TGCGGCGATT CCACCGAGTG CTCCAACCTG CTGCTGCAGT ACGGCAGCTT CTGCACCCAG CTGAATAGAG CCCTGACAGG GATCGCCGTG GAACAGGACA AGAACACCCA AGAGGTGTTC GCCCAAGTGA AGCAGATCTA CAAGACCCCT CCTATCAAGG ACTTCGGCGG CTTCAATTTC AGCCAGATTC TGCCCGATCC TAGCAAGCCC AGCAAGCGGA GCTTCATCGA GGACCTGCTG TTCAACAAAG TGACACTGGC CGACGCCGGC TTCATCAAGC AGTATGGCGA TTGTCTGGGC GACATTGCCG CCAGGGATCT GATTTGCGCC CAGAAGTTTA ACGGACTGAC AGTGCTGCCT CCTCTGCTGA CCGATGAGAT GATCGCCCAG TACACATCTG CCCTGCTGGC CGGCACAATC ACAAGCGGCT GGACATTTGG AGCAGGCGCC GCTCTGCAGA TCCCCTTTGC TATGCAGATG GCCTACCGGT TCAACGGCAT CGGAGTGACC CAGAATGTGC TGTACGAGAA CCAGAAGCTG ATCGCCAACC AGTTCAACAG CGCCATCGGC AAGATCCAGG ACAGCCTGAG CAGCACAGCA AGCGCCCTGG GAAAGCTGCA GAACGTGGTC AACCAGAATG CCCAGGCACT GAACACCCTG GTCAAGCAGC TGTCCTCCAA CTTCGGCGCC ATCAGCTCTG TGCTGAACGA TATCCTGAGC AGACTGGACC CTCCTGAGGC CGAGGTGCAG ATCGACAGAC TGATCACAGG CAGACTGCAG AGCCTCCAGA CATACGTGAC CCAGCAGCTG ATCAGAGCCG CCGAGATTAG AGCCTCTGCC AATCTGGCCG CCACCAAGAT GTCTGAGTGT GTGCTGGGCC AGAGCAAGAG AGTGGACTTT TGCGGCAAGG GCTACCACCT GATGAGCTTC CCTCAGTCTG CCCCTCACGG CGTGGTGTTT CTGCACGTGA CATATGTGCC CGCTCAAGAG AAGAATTTCA CCACCGCTCC AGCCATCTGC CACGACGGCA AAGCCCACTT TCCTAGAGAA GGCGTGTTCG TGTCCAACGG CACCCATTGG TTCGTGACAC AGCGGAACTT CTACGAGCCC CAGATCATCA CCACCGACAA CACCTTCGTG TCTGGCAACT GCGACGTCGT GATCGGCATT GTGAACAATA CCGTGTACGA CCCTCTGCAG CCCGAGCTGG ACAGCTTCAA AGAGGAACTG GACAAGTACT TTAAGAACCA CACAAGCCCC GACGTGGACC TGGGCGATAT CAGCGGAATC AATGCCAGCG TCGTGAACAT CCAGAAAGAG ATCGACCGGC TGAACGAGGT GGCCAAGAAT CTGAACGAGA GCCTGATCGA CCTGCAAGAA CTGGGGAAGT ACGAGCAGTA CATCAAGTGG CCCTGGTACA TCTGGCTGGG CTTTATCGCC GGACTGATTG CCATCGTGAT GGTCACAATC ATGCTGTGTT GCATGACCAG CTGCTGTAGC TGCCTGAAGG GCTGTTGTAG CTGTGGCAGC TGCTGCAAGT TCGACGAGGA CGATTCTGAG CCCGTGCTGA AGGGCGTGAA ACTGCACTAC ACATGATGA |
| 156 | RNA sequence encoding a SARS-CoV-2 S protein from a Delta variant | AUGUUCGUGU UCCUGGUGCU GCUGCCUCUG GUGUCCAGCC AGUGUGUGAA CCUGAGAACC AGAACACAGC UGCCUCCAGC CUACACCAAC AGCUUUACCA GAGGCGUGUA CUACCCCGAC AAGGUGUUCA GAUCCAGCGU GCUGCACUCU ACCCAGGACC UGUUCCUGCC UUUCUUCAGC AACGUGACCU GGUUCCACGC CAUCCACGUG UCCGGCACCA AUGGCACCAA GAGAUUCGAC AACCCCGUGC UGCCCUUCAA CGACGGGGUG UACUUUGCCA GCACCGAGAA GUCCAACAUC AUCAGAGGCU GGAUCUUCGG CACCACACUG GACAGCAAGA CCCAGAGCCU GCUGAUCGUG AACAACGCCA CCAACGUGGU CAUCAAAGUG UGCGAGUUCC AGUUCUGCAA CGACCCCUUC CUGGACGUCU ACUACCACAA GAACAACAAG AGCUGGAUGG AAAGCGGCGU GUACAGCAGC GCCAACAACU GCACCUUCGA GUACGUGUCC CAGCCUUUCC UGAUGGACCU GGAAGGCAAG CAGGGCAACU UCAAGAACCU GCGCGAGUUC GUGUUUAAGA ACAUCGACGG CUACUUCAAG AUCUACAGCA AGCACACCCC UAUCAACCUC GUGCGGGAUC UGCCUCAGGG CUUCUCUGCU CUGGAACCCC UGGUGGAUCU GCCCAUCGGC AUCAACAUCA CCCGGUUUCA GACACUGCUG GCCCUGCACA GAAGCUACCU GACACCUGGC GAUAGCAGCA GCGGAUGGAC AGCUGGUGCC GCCGCUUACU AUGUGGGCUA CCUGCAGCCU AGAACCUUCC UGCUGAAGUA CAACGAGAAC GGCACCAUCA CCGACGCCGU GGAUUGUGCU CUGGAUCCUC UGAGCGAGAC AAAGUGCACC CUGAAGUCCU UCACCGUGGA AAAGGGCAUC UACCAGACCA GCAACUUCCG GGUGCAGCCC ACCGAAUCCA UCGUGCGGUU CCCCAAUAUC ACCAAUCUGU GCCCCUUCGG CGAGGUGUUC AAUGCCACCA GAUUCGCCUC UGUGUACGCC UGGAACCGGA AGCGGAUCAG CAAUUGCGUG GCCGACUACU CCGUGCUGUA CAACUCCGCC AGCUUCAGCA CCUUCAAGUG CUACGGCGUG UCCCCUACCA AGCUGAACGA CCUGUGCUUC ACAAACGUGU ACGCCGACAG CUUCGUGAUC |

TABLE 5-continued

Sequences of RBP020.16 (Delta-specific RNA vaccine)

| SEQ ID NO. | Brief Description | Sequence |
|---|---|---|
| | | CGGGGAGAUG AAGUGCGGCA GAUUGCCCCU GGACAGACAG GCAAGAUCGC CGACUACAAC |
| | | UACAAGCUGC CCGACGACUU CACCGGCUGU GUGAUUGCCU GGAACAGCAA CAACCUGGAC |
| | | UCCAAAGUCG GCGGCAACUA CAAUUACAGG UACCGGCUGU UCCGGAAGUC CAAUCUGAAG |
| | | CCCUUCGAGC GGGACAUCUC CACCGAGAUC UAUCAGGCCG GCAGCAAGCC UUGUAACGGC |
| | | GUGGAAGGCU UCAACUGCUA CUUCCCACUG CAGUCCUACG GCUUUCAGCC CACAAAUGGC |
| | | GUGGGCUAUC AGCCCUACAG AGUGGUGGUG CUGAGCUUCG AACUGCUGCA UGCCCCUGCC |
| | | ACAGUGUGCG GCCCUAAGAA AAGCACCAAU CUCGUGAAGA ACAAAUGCGU GAACUUCAAC |
| | | UUCAACGGCC UGACCGGCAC CGGCGUGCUG ACAGAGAGCA ACAAGAAGUU CCUGCCAUUC |
| | | CAGCAGUUUG GCCGGGAUAU CGCCGAUACC ACAGACGCCG UUAGAGAUCC CCAGACACUG |
| | | GAAAUCCUGG ACAUCACCCC UUGCAGCUUC GGCGGAGUGU CUGUGAUCAC CCCUGGCACC |
| | | AACACCAGCA AUCAGGUGGC AGUGCUGUAC CAGGGCGUGA ACUGUACCGA AGUGCCCGUG |
| | | GCCAUUCACG CCGAUCAGCU GACACCUACA UGGCGGGUGU ACUCCACCGG CAGCAAUGUG |
| | | UUUCAGACCA GAGCCGGCUG UCUGAUCGGA GCCGAGCACG UGAACAAUAG CUACGAGUGC |
| | | GACAUCCCCA UCGGCGCUGG AAUCUGCGCC AGCUACCAGA CACAGACAAA CAGCAGGCGG |
| | | AGAGCCAGAA GCGUGGCCAG CCAGAGCAUC AUUGCCUACA CAAUGUCUCU GGGCGCCGAG |
| | | AACAGCGUGG CCUACUCCAA CAACUCUAUC GCUAUCCCCA CCAACUUCAC CAUCAGCGUG |
| | | ACCACAGAGA UCCUGCCUGU GUCCAUGACC AAGACCAGCG UGGACUGCAC CAUGUACAUC |
| | | UGCGGCGAUU CCACCGAGUG CUCCAACCUG CUGCUGCAGU ACGGCAGCUU CUGCACCCAG |
| | | CUGAAUAGAG CCCUGACAGG GAUCGCCGUG GAACAGGACA AGAACACCCA AGAGGUGUUC |
| | | GCCCAAGUGA AGCAGAUCUA CAAGACCCCU CCUAUCAAGG ACUUCGGCGG CUUCAAUUUC |
| | | AGCCAGAUUC UGCCCGAUCC UAGCAAGCCC AGCAAGCGGA GCUUCAUCGA GGACCUGCUG |
| | | UUCAACAAAG UGACACUGGC CGACGCCGGC UUCAUCAAGC AGUAUGGCGA UUGUCUGGGC |
| | | GACAUUGCCG CCAGGGAUCU GAUUUGCGCC CAGAAGUUUA ACGGACUGAC AGUGCUGCCU |
| | | CCUCUGCUGA CCGAUGAGAU GAUCGCCCAG UACACAUCUG CCCUGCUGGC CGGCACAAUC |
| | | ACAAGCGGCU GGACAUUUGG AGCAGGCGCC GCUCUGCAGA UCCCCUUUGC UAUGCAGAUG |
| | | GCCUACCGGU UCAACGGCAU CGGAGUGACC CAGAAUGUGC UGUACGAGAA CCAGAAGCUG |
| | | AUCGCCAACC AGUUCAACAG CGCCAUCGGC AAGAUCCAGG ACAGCCUGAG CAGCACAGCA |
| | | AGCGCCCUGG GAAAGCUGCA GAACGUGGUC AACCAGAAUG CCCAGGCACU GAACACCCUG |
| | | GUCAACCACC UCUCCUCCAA CUUCCCCCCC AUCACCUCUC UCCUCAACCA UAUCCUCACC |
| | | AGACUGGACC CUCCUGAGGC CGAGGUGCAG AUCGACAGAC UGAUCACAGG CAGACUGCAG |
| | | AGCCUCCAGA CAUACGUGAC CCAGCAGCUG AUCAGAGCCG CCGAGAUUAG AGCCUCUGCC |
| | | AAUCUGGCCG CCACCAAGAU GUCUGAGUGU GUGCUGGGCC AGAGCAAGAG AGUGGACUUU |
| | | UGCGGCAAGG GCUACCACCU GAUGAGCUUC CCUCAGUCUG CCCCUCACGG CGUGGUGUUU |
| | | CUGCACGUGA CAUAUGUGCC CGCUCAAGAG AAGAAUUUCA CCACCGCUCC AGCCAUCUGC |
| | | CACGACGGCA AAGCCCACUU UCCUAGAGAA GGCGUGUUCG UGUCCAACGG CACCCAUUGG |
| | | UUCGUGACAC AGCGGAACUU CUACGAGCCC CAGAUCAUCA CCACCGACAA CACCUUCGUG |
| | | UCUGGCAACU GCGACGUCGU GAUCGGCAUU GUGAACAAUA CCGUGUACGA CCCUCUGCAG |
| | | CCCGAGCUGG ACAGCUUCAA AGAGGAACUG GACAAGUACU UUAAGAACCA CACAAGCCCC |
| | | GACGUGGACC UGGGCGAUAU CAGCGGAAUC AAUGCCAGCG UCGUGAACAU CCAGAAAGAG |
| | | AUCGACCGGC UGAACGAGGU GGCCAAGAAU CUGAACGAGA GCCUGAUCGA CCUGCAAGAA |
| | | CUGGGGAAGU ACGAGCAGUA CAUCAAGUGG CCCUGGUACA UCUGGCUGGG CUUUAUCGCC |
| | | GGACUGAUUG CCAUCGUGAU GGUCACAAUC AUGCUGUGUU GCAUGACCAG CUGCUGUAGC |
| | | UGCCUGAAGG GCUGUUGUAG CUGUGGCAGC UGCUGCAAGU UCGACGAGGA CGAUUCUGAG |
| | | CCCGUGCUGA AGGGCGUGAA ACUGCACUAC ACAUGAUGA |
| 63 | Full length sequence of RBP020.14 | AGAATAAACT AGTATTCTTC TGGTCCCCAC AGACTCAGAG AGAACCCGCC ACC |
| | | ATGTTCGTGT TCCTGGTGCT GCTGCCTCTG GTGTCCAGCC AGTGTGTGAA CCTGAGAACC |
| | | AGAACACAGC TGCCTCCAGC CTACACCAAC AGCTTTACCA GAGGCGTGTA CTACCCCGAC |
| | | AAGGTGTTCA GATCCAGCGT GCTGCACTCT ACCCAGGACC TGTTCCTGCC TTTCTTCAGC |
| | | AACGTGACCT GGTTCCACGC CATCCACGTG TCCGGCACCA ATGGCACCAA GAGATTCGAC |
| | | AACCCCGTGC TGCCCTTCAA CGACGGGGTG TACTTTGCCA GCACCGAGAA GTCCAACATC |
| | | ATCAGAGGCT GGATCTTCGG CACCACACTG GACAGCAAGA CCCAGAGCCT GCTGATCGTG |
| | | AACAACGCCA CCAACGTGGT CATCAAAGTG TGCGAGTTCC AGTTCTGCAA CGACCCCTTC |
| | | CTGGACGTCT ACTACCACAA GAACAACAAG AGCTGGATGG AAAGCGSCGT GTACAGCAGC |
| | | GCCAACAACT GCACCTTCGA GTACGTGTCC CAGCCTTTCC TGATGGACCT GGAAGGCAAG |
| | | CAGGGCAACT TCAAGAACCT GCGCGAGTTC GTGTTTAAGA ACATCGACGG CTACTTCAAG |
| | | ATCTACAGCA AGCACACCCC TATCAACCTC GTGCGGGATC TGCCTCAGGG CTTCTCTGCT |
| | | CTGGAACCCC TGGTGGATCT GCCCATCGGC ATCAACATCA CCCGGTTTCA GACACTGCTG |
| | | GCCCTGCACA GAAGCTACCT GACACCTGGC GATAGCAGCA GCGGATGGAC AGCTGGTGCC |
| | | GCCGCTTACT ATGTGGGCTA CCTGCAGCCT AGAACCTTCC TGCTGAAGTA CAACGAGAAC |
| | | GGCACCATCA CCGACGCCGT GGATTGTGCT CTGGATCCTC TGAGCGAGAC AAAGTGCACC |
| | | CTGAAGTCCT TCACCGTGGA AAAGGGCATC TACCAGACCA GCAACTTCCG GGTGCAGCCC |
| | | ACCGAATCCA TCGTGCGGTT CCCCAATATC ACCAATCTGT GCCCCTTCGG CGAGGTGTTC |
| | | AATGCCACCA GATTCGCCTC TGTGTACGCC TGGAACCGGA AGCGGATCAG CAATTGCGTG |
| | | GCCGACTACT CCGTGCTGTA CAACTCCGCC AGCTTCAGCA CCTTCAAGTG CTACGGCGTG |
| | | TCCCCTACCA AGCTGAACGA CCTGTGCTTC ACAAACGTGT ACGCCGACAG CTTCGTGATC |
| | | CGGGGAGATG AAGTGCGGCA GATTGCCCCT GGACAGACAG GCAAGATCGC CGACTACAAC |
| | | TACAAGCTGC CCGACGACTT CACCGGCTGT GTGATTGCCT GGAACAGCAA CAACCTGGAC |
| | | TCCAAAGTCG GCGGCAACTA CAATTACAGG TACCGGCTGT TCCGGAAGTC CAATCTGAAG |
| | | CCCTTCGAGC GGGACATCTC CACCGAGATC TATCAGGCCG GCAGCAAGCC TTGTAACGGC |
| | | GTGGAAGGCT TCAACTGCTA CTTTCCCACTG CAGTCCTACG GCTTTCAGCC CACAAATGGC |
| | | GTGGGCTATC AGCCCTACAG AGTGGTGGTG CTGAGCTTCG AACTGCTGCA TGCCCCTGCC |
| | | ACAGTGTGCG GCCCTAAGAA AAGCACCAAT CTCGTGAAGA ACAAATGCGT GAACTTCAAC |
| | | TTCAACGGCC TGACCGGCAC CGGCGTGCTG ACAGAGAGCA ACAAGAAGTT CCTGCCATTC |
| | | CAGCAGTTTG GCCGGGATAT CGCCGATACC ACAGACGCCG TTAGAGATCC CCAGACACTG |

TABLE 5-continued

Sequences of RBP020.16 (Delta-specific RNA vaccine)

| SEQ ID NO. | Brief Description | Sequence |
|---|---|---|
| | | GAAATCCTGG ACATCACCCC TTGCAGCTTC GGCGGAGTGT CTGTGATCAC CCCTGGCACC<br>AACACCAGCA ATCAGGTGGC AGTGCTGTAC CAGGGCGTGA ACTGTACCGA AGTGCCCGTG<br>GCCATTCACG CCGATCAGCT GACACCTACA TGGCGGGTGT ACTCCACCGG CAGCAATGTG<br>TTTCAGACCA GAGCCGGCTG TCTGATCGGA GCCGAGCACG TGAACAATAG CTACGAGTGC<br>GACATCCCCA TCGGCGCTGG AATCTGCGCC AGCTACCAGA CACAGACAAA CAGCAGGCGG<br>AGAGCCAGAA GCGTGGCCAG CCAGAGCATC ATTGCCTACA CAATGTCTCT GGGCGCCGAG<br>AACAGCGTGG CCTACTCCAA CAACTCTATC GCTATCCCCA CCAACTTCAC CATCAGCGTG<br>ACCACAGAGA TCCTGCCTGT GTCCATGACC AAGACCAGCG TGGACTGCAC CATGTACATC<br>TGCGGCGATT CCACCGAGTG CTCCAACCTG CTGCTGCAGT ACGGCAGCTT CTGCACCCAG<br>CTGAATAGAG CCCTGACAGG GATCGCCGTG GAACAGGACA AGAACACCCA AGAGGTGTTC<br>GCCCAAGTGA AGCAGATCTA CAAGACCCCT CCTATCAAGG ACTTCGGCGG CTTCAATTTC<br>AGCCAGATTC TGCCCGATCC TAGCAAGCCC AGCAAGCGGA GCTTCATCGA GGACCTGCTG<br>TTCAACAAAG TGACACTGGC CGACGCCGGC TTCATCAAGC AGTATGGCGA TTGTCTGGGC<br>GACATTGCCG CCAGGGATCT GATTTGCGCC CAGAAGTTTA ACGGACTGAC AGTGCTGCCT<br>CCTCTGCTGA CCGATGAGAT GATCGCCCAG TACACATCTG CCCTGCTGGC CGGCACAATC<br>ACAAGCGGCT GGACATTTGG AGCAGGCGCC GCTCTGCAGA TCCCCTTTGC TATGCAGATG<br>GCCTACCGGT TCAACGGCAT CGGAGTGACC CAGAATGTGC TGTACGAGAA CCAGAAGCTG<br>ATCGCCAACC AGTTCAACAG CGCCATCGGC AAGATCCAGG ACAGCCTGAG CAGCACAGCA<br>AGCGCCCTGG GAAAGCTGCA GAACGTGGTC AACCAGAATG CCCAGGCACT GAACACCCTG<br>GTCAAGCAGC TGTCCTCCAA CTTCGGCGCC ATCAGCTCTG TGCTGAACGA TATCCTGAGC<br>AGACTGGACC CTCCTGAGGC CGAGGTGCAG ATCGACAGAC TGATCACAGG CAGACTGCAG<br>AGCCTCCAGA CATACGTGAC CCAGCAGCTG ATCAGAGCCG CCGAGATTAG AGCCTCTGCC<br>AATCTGGCCG CCACCAAGAT GTCTGAGTGT GTGCTGGGCC AGAGCAAGAG AGTGGACTTT<br>TGCGGCAAGG GCTACCACCT GATGAGCTTC CCTCAGTCTG CCCCTCACGG CGTGGTGTTT<br>CTGCACGTGA CATATGTGCC CGCTCAAGAG AAGAATTTCA CCACCGCTCC AGCCATCTGC<br>CACGACGGCA AAGCCCACTT TCCTAGAGAA GGCGTGTTCG TGTCCAACGG CACCCATTGG<br>TTCGTGACAC AGCGGAACTT CTACGAGCCC CAGATCATCA CCACCGACAA CACCTTCGTG<br>TCTGGCAACT GCGACGTCGT GATCGGCATT GTGAACAATA CCGTGTACGA CCCTCTGCAG<br>CCCGAGCTGG ACAGCTTCAA AGAGGAACTG GACAAGTACT TTAAGAACCA CACAAGCCCC<br>GACGTGGACC TGGGCGATAT CAGCGGAATC AATGCCAGCG TCGTGAACAT CCAGAAAGAG<br>ATCGACCGGC TGAACGAGGT GGCCAAGAAT CTGAACGAGA GCCTGATCGA CCTGCAAGAA<br>CTGGGGAAGT ACGAGCAGTA CATCAAGTGG CCCTGGTACA TCTGGCTGGG CTTTATCGCC<br>GGACTGATTG CCATCGTGAT GGTCACAATC ATGCTGTGTT GCATGACCAG CTGCTGTAGC<br>TGCCTGAAGG GCTGTTGTAG CTGTGGCAGC TGCTGCAAGT TCGACGAGGA CGATTCTGAG<br>CCCGTGCTGA AGGGCGTGAA ACTGCACTAC ACATGATGA<br>TTTCACCTGG TACTGCATGC ACGCAATGCT AGCTGCCCCT TTCCCGTCCT GGGTACCCCG<br>AGTCTCCCCC GACCTCGGGT CCCAGGTATG CTCCCACCTC CACCTGCCCC ACTCACCACC<br>TCTGCTAGTT CCAGACACCT CCCAAGCACG CAGCAATGCA GCTCAAAACG CTTAGCCTAG<br>CCACACCCCC ACGGGAAACA GCAGTGATTA ACCTTTAGCA ATAAACGAAA GTTTAACTAA<br>GCTATACTAA CCCCAGGGTT GGTCAATTTC GTGCCAGCCA CACCCTGGAG CTAGC<br>AAAAAAAAAA AAAAAAAAAA AAAAAAAAAA GCATATGACT AAAAAAAAAA AAAAAAAAAA<br>AAAAAAAAAA AAAAAAAAAA AAAAAAAAAA AAAAAAAAAA AAAAAAAAAA |
| 157 | Full length sequence of RBP020.14 (RNA) | AGAAUAAACU AGUAUUCUUC UGGUCCCCAC AGACUCAGAG AGAACCCGCC ACC<br>AUGUUCGUGU UCCUGGUGCU GCUGCCUCUG GUGUCCAGCC AGUGUGUGAA CCUGAGAACC<br>AGAACACAGC UGCCUCCAGC CUACACCAAC AGCUUUACCA GAGGCGUGUA CUACCCCGAC<br>AAGGUGUUCA GAUCCAGCGU GCUGCACUCU ACCCAGGACC UGUUCCUGCC UUUCUUCAGC<br>AACGUGACCU GGUUCCACGC CAUCCACGUG UCCGGCACCA AUGGCACCAA GAGAUUCGAC<br>AACCCCGUGC UGCCCUUCAA CGACGGGGUG UACUUUGCCA GCACCGAGAA GUCCAACAUC<br>AUCAGAGGCU GGAUCUUCGG CACCACACUG GACAGCAAGA CCCAGAGCCU GCUGAUCGUG<br>AACAACGCCA CCAACGUGGU CAUCAAAGUG UGCGAGUUCC AGUUCUGCAA CGACCCCUUC<br>CUGGACGUCU ACUACCACAA GAACAACAAG AGCUGGAUGG AAAGCGGCGU GUACAGCAGC<br>GCCAACAACU GCACCUUCGA GUACGUGUCC CAGCCUUUCC UGAUGGACCU GGAAGGCAAG<br>CAGGGCAACU UCAAGAACCU GCGCGAGUUC GUGUUUAAGA ACAUCGACGG CUACUUCAAG<br>AUCUACAGCA AGCACACCCC UAUCAACCUC GUGCGGGAUC UGCCUCAGGG CUUCUCUGCU<br>CUGGAACCCC UGGUGGAUCU GCCCAUCGGC AUCAACAUCA CCCGGUUUCA GACACUGCUG<br>GCCCUGCACA GAAGCUACCU GACACCUGGC GAUAGCAGCA GCGGAUGGAC AGCUGGUGCC<br>GCCGCUUACU AUGUGGGCUA CCUGCAGCCU AGAACCUUCC UGCUGAAGUA CAACGAGAAC<br>GGCACCAUCA CCGACGCCGU GGAUUGUGCU CUGGAUCCUC UGAGCGAGAC AAAGUGCACC<br>CUGAAGUCCU UCACCGUGGA AAAGGGCAUC UACCAGACCA GCAACUUCCG GGUGCAGCCC<br>ACCGAAUCCA UCGUGCGGUU CCCCAAUAUC ACCAAUCUGU GCCCCUUCGG CGAGGUGUUC<br>AAUGCCACCA GAUUCGCCUC UGUGUACGCC UGGAACCGGA AGCGGAUCAG CAAUUGCGUG<br>GCCGACUACU CCGUGCUGUA CAACUCCGCC AGCUUCAGCA CCUUCAAGUG CUACGGCGUG<br>UCCCCUACCA AGCUGAACGA CCUGUGCUUC ACAAACGUGU ACGCCGACAG CUUCGUGAUC<br>CGGGGAGAUG AAGUGCGGCA GAUUGCCCCU GGACAGACAG GCAAGAUCGC CGACUACAAC<br>UACAAGCUGC CCGACGACUU CACCGGCUGU GUGAUUGCCU GGAACAGCAA CAACCUGGAC<br>UCCAAAGUCG GCGGCAACUA CAAUUACAGG UACCGGCUGU UCCGGAAGUC CAAUCUGAAG<br>CCCUUCGAGC GGGACAUCUC CACCGAGAUC UAUCAGGCCG GCAGCAAGCC UUGUAACGGC<br>GUGGAAGGCU UCAACUGCUA CUUCCCACUG CAGUCCUACG GCUUUCAGCC CACAAAUGGC<br>GUGGGCUAUC AGCCCUACAG AGUGGUGGUG CUGAGCUUCG AACUGCUGCA UGCCCCUGCC<br>ACAGUGUGCG GCCCUAAGAA AAGCACCAAU CUCGUGAAGA ACAAAUGCGU GAACUUCAAC<br>UUCAACGGCC UGACCGGCAC CGGCGUGCUG ACAGAGAGCA ACAAGAAGUU CCUGCCAUUC<br>CAGCAGUUUG GCCGGGAUAU CGCCGAUACC ACAGACGCCG UUAGAGAUCC CCAGACACUG<br>GAAAUCCUGG ACAUCACCCC UUGCAGCUUC GGCGGAGUGU CUGUGAUCAC CCCUGGCACC<br>AACACCAGCA AUCAGGUGGC AGUGCUGUAC CAGGGCGUGA ACUGUACCGA AGUGCCCGUG |

TABLE 5-continued

| Sequences of RBP020.16 (Delta-specific RNA vaccine) | | |
|---|---|---|
| SEQ ID NO. | Brief Description | Sequence |
| | | GCCAUUCACG CCGAUCAGCU GACACCUACA UGGCGGGUGU ACUCCACCGG CAGCAAUGUG UUUCAGACCA GAGCCGGCUG UCUGAUCGGA GCCGAGCACG UGAACAAUAG CUACGAGUGC GACAUCCCCA UCGGCGCUGG AAUCUGCGCC AGCUACCAGA CACAGACAAA CAGCAGGCGG AGAGCCAGAA GCGUGGCCAG CCAGAGCAUC AUUGCCUACA CAAUGUCUCU GGGCGCCGAG AACAGCGUGG CCUACUCCAA CAACUCUAUC GCUAUCCCCA CCAACUUCAC CAUCAGCGUG ACCACAGAGA UCCUGCCUGU GUCCAUGACC AAGACCAGCG UGGACUGCAC CAUGUACAUC UGCGGCGAUU CCACCGAGUG CUCCAACCUG CUGCUGCAGU ACGGCAGCUU CUGCACCCAG CUGAAUAGAG CCCUGACAGG GAUCGCCGUG GAACAGGACA AGAACACCCA AGAGGUGUUC GCCCAAGUGA AGCAGAUCUA CAAGACCCCU CCUAUCAAGG ACUUCGGCGG CUUCAAUUUC AGCCAGAUUC UGCCCGAUCC UAGCAAGCCC AGCAAGCGGA GCUUCAUCGA GGACCUGCUG UUCAACAAAG UGACACUGGC CGACGCCGGC UUCAUCAAGC AGUAUGGCGA UUGUCUGGGC GACAUUGCCG CCAGGGAUCU GAUUUGCGCC CAGAAGUUUA ACGGACUGAC AGUGCUGCCU CCUCUGCUGA CCGAUGAGAU GAUCGCCCAG UACACAUCUG CCCUGCUGGC CGGCACAAUC ACAAGCGGCU GGACAUUUGG AGCAGGCGCC GCUCUGCAGA UCCCCUUUGC UAUGCAGAUG GCCUACCGGU UCAACGGCAU CGGAGUGACC CAGAAUGUGC UGUACGAGAA CCAGAAGCUG AUCGCCAACC AGUUCAACAG CGCCAUCGGC AAGAUCCAGG ACAGCCUGAG CAGCACAGCA AGCGCCCUGG GAAAGCUGCA GAACGUGGUC AACCAGAAUG CCCAGGCACU GAACACCCUG GUCAAGCAGC UGUCCUCCAA CUUCGGCGCC AUCAGCUCUG UGCUGAACGA UAUCCUGAGC AGACUGGACC CUCCUGAGGC CGAGGUGCAG AUCGACAGAC UGAUCACAGG CAGACUGCAG AGCCUCCAGA CAUACGUGAC CCAGCAGCUG AUCAGAGCCG CCGAGAUUAG AGCCUCUGCC AAUCUGGCCG CCACCAAGAU GUCUGAGUGU GUGCUGGGCC AGAGCAAGAG AGUGGACUUU UGCGGCAAGG GCUACCACCU GAUGAGCUUC CCUCAGUCUG CCCCUCACGG CGUGGUGUUU CUGCACGUGA CAUAUGUGCC CGCUCAAGAG AAGAAUUUCA CCACCGCUCC AGCCAUCUGC CACGACGGCA AAGCCCACUU UCCUAGAGAA GGCGUGUUCG UGUCCAACGG CACCCAUUGG UUCGUGACAC AGCGGAACUU CUACGAGCCC CAGAUCAUCA CCACCGACAA CACCUUCGUG UCUGGCAACU GCGACGUCGU GAUCGGCAUU GUGAACAAUA CCGUGUACGA CCCUCUGCAG CCCGAGCUGG ACAGCUUCAA AGAGGAACUG GACAAGUACU UUAAGAACCA CACAAGCCCC GACGUGGACC UGGGCGAUAU CAGCGGAAUC AAUGCCAGCG UCGUGAACAU CCAGAAAGAG AUCGACCGGC UGAACGAGGU GGCCAAGAAU CUGAACGAGA GCCUGAUCGA CCUGCAAGAA CUGGGGAAGU ACGAGCAGUA CAUCAAGUGG CCCUGGUACA UCUGGCUGGG CUUUAUCGCC GGACUGAUUG CCAUCGUGAU GGUCACAAUC AUGCUGUGUU GCAUGACCAG CUGCUGUAGC UGCCUGAAGG GCUGUUGUAG CUGUGGCAGC UGCUGCAAGU UCGACGAGGA CGAUUCUGAG CCCGUGCUGA AGGGCGUGAA ACUGCACUAC ACAUGAUGA<br>UUUCACCUGG UACUGCAUGC ACGCAAUGCU AGCUGCCCCU UUCCCGUCCU GGGUACCCCG AGUCUCCCCC GACCUCGGGU CCCAGGUAUG CUCCCACCUC CACCUGCCCC ACUCACCACC UCUGCUAGUU CCAGACACCU CCCAAGCACG CAGCAAUGCA GCUCAAAACG CUUAGCCUAG CCACACCCCC ACGGGAAACA GCAGUGAUUA ACCUUUAGCA AUAAACGAAA GUUUAACUAA GCUAUACUAA CCCCAGGGUU GGUCAAUUUC GUGCCAGCCA CACCCUGGAG CUAGC<br>AAAAAAAAAA AAAAAAAAAA AAAAAAAAAA GCAUAUGACU AAAAAAAAAA AAAAAAAAAA AAAAAAAAAA AAAAAAAAAA AAAAAAAAAA AAAAAAAAAA AAAAAAAAAA |

TABLE 6

| Sequences of RBP020.18 (Omicron BA.2-specific RNA vaccine) | | |
|---|---|---|
| SEQ ID NO. | Brief Description | Sequence |
| 64 | Amino acid sequence of RNA-encoded SARS-CoV-2 S protein from an Omicron BA.2 variant (with PRO mutations at positions corresponding to K986P and V987P of SEQ ID NO: 1; i.e., PRO mutations at positions 983 and 984 of SEQ ID NO: 64) | MFVFLVLLPLVSSQCVNLITRTQSYTNSFTRGVYYPDKVFRSSVLHSTQDLFLPFFSNVTWFHAIHVSGTNGTKRFDNPVLPFNDGVYFASTEKSNIIRGWIFGTTLDSKTQSLLIVNNATNVVIKVCEFQFCNDPFLDVYYHKNNKSWMESEFRVYSSANNCTFEYVSQPFLMDLEGKQGNFKNLREFVFKNIDGYFKIYSKHTPINLGRDLPQGFSALEPLVDLPIGINITRFQTLLALHRSYLTPGDSSSGWTAGAAAYYVGYLQPRTELLKYNENGTITDAVDCALDPLSETKCTLKSFTVEKGIYQTSNFRVQPTESIVRFPNITNLCPFDEVFNATRFASVYAWNRKRISNCVADYSVLYNFAPFFAFKCYGVSPTKLNDLCFTNVYADSFVIRGNEVSQIAPGQTGNIADYNYKLPDDFTGCVIAWNSNKLDSKVGGNYNYLYRLFRKSNLKPFERDISTEIYQAGNKPCNGVAGFNCYFPLRSYGFRPTYGVGHQPYRVVVLSFELLHAPATVCGPKKSTNLVKNKCVNFNFNGLTGTGVLTESNKKFLPFQQFGRDIADTTDAVRDPQTLEILDITPCSFGGVSVITPGTNTSNQVAVLYQGVNCTEVPVAIHADQLTPTWRVYSTGSNVFQTRAGCLIGAEYVNNSYECDIPIGAGICASYQTQTKSHRRARSVASQSIIAYTMSLGAENSVAYSNNSIAIPTNFTISVTTEILPVSMTKTSVDCTMYICGDSTECSNLLLQYGSFCTQLKRALTGIAVEQDKNTQEVFAQVKQIYKTPPIKYFGGFNFSQILPDPSKPSKRSFIEDLLENKVTLADAGFIKQYGDCLGDIAARDLICAQKFNGLTVLPPLLTDEMIAQYTSALLAGTITSGWTFGAGAALQIPFAMQMAYRENGIGVTQNVLYENQKLIANQFNSAIGKIQDSLSSTASALGKLQDVVNHNAQALNTLVKQLSSKFGAISSVLNDILSRLDPPEAEVQIDRLITGRLQSLQTYVTQQLIRAAEIRASANLAATKMSECVLGQSKRVDFCGKGYHLMSFPQSAPHGVVFLHVTYVPAQEKNFTTAPAICHDGKAHFPREGVFVSNGTHWEVTQRNFYEPQIITTDNTFVSGNCDVVIGIVNNTVYDPLQPELDSFKEELDKYFKNHTSPDVDLGDISGINASVVNIQKEIDRLNEVAKNLNESLIDLQELGKYEQYIKWPWYIWLGFIAGLIAIVMVTIMLCCMTSCCSCLKGCCSCGSCCKFDEDDSEPVLKGVKLHYT** |
| 65 | RNA sequence encoding a SARS-CoV-2 S protein from an Omicron BA.2 variant | AUGUUCGUGUUCCUGGUGCUGCUGCCUCUGGUGUCCAGCCAGUGUGUGAACCUGAUCACCAGAACACAGUCAUACACCAACAGCUUUACCAGAGGCGUGUACUACCCCGACAAGGUGUUCAGAUCCAGCGUGCUGCACUCUACCCAGGACCUGUUCCUGCCUUUCUUCAGCAACGUGACCUGGUUCCACGCCAUCCAC |

TABLE 6-continued

Sequences of RBP020.18 (Omicron BA.2-specific RNA vaccine)

| SEQ ID NO. | Brief Description | Sequence |
|---|---|---|
| | | GUGUCCGGCACCAAUGGCACCAAGAGAUUCGACAACCCCGUGCUGCCCUUCAACGACGGGGUGUAC<br>UUUGCCAGCACCGAGAAGUCCAACAUCAUCAGAGGCUGGAUCUUCGGCACCACACUGGACAGCAAG<br>ACCCAGAGCCUGCUGAUCGUGAACAACGCCACCAACGUGGUCAUCAAAGUGUGCGAGUUCCAGUUC<br>UGCAACGACCCCUUCCUGGACGUCUACUACCACAAGAACAACAAGAGCUGGAUGGAAAGCGAGUUC<br>CGGGUGUACAGCAGCGCCAACAACUGCACCUUCGAGUACGUGUCCCAGCCUUUCCUGAUGGACCUG<br>GAAGGCAAGCAGGGCAACUUCAAGAACCUGCGCGAGUUCGUGUUUAAGAACAUCGACGGCUACUUC<br>AAGAUCUACAGCAAGCACACCCCUAUCAACCUCGGCCGGGAUCUGCCUCAGGGCUUCUCUGCUCUG<br>GAACCCCUGGUGGAUCUGCCCAUCGGCAUCAACAUCACCCGGUUUCAGACACUGCUGGCCCUGCAC<br>AGAAGCUACCUGACACCUGGCGAUAGCAGCAGCGGAUGGACAGCUGGUGCCGCCGCUUACUAUGUG<br>GGCUACCUGCAGCCUAGAACCUUCCUGCUGAAGUACAACGAGAACGGCACCAUCACCGACGCCGUG<br>GAUUGUGCUCUGGAUCCUCUGAGCGAGACAAAGUGCACCCUGAAGUCCUUCACCGUGGAAAAGGGC<br>AUCUACCAGACCAGCAACUUCCGGGUGCAGCCCACCGAAUCCAUCGUGCGGUUCCCCAAUAUCACC<br>AAUCUGUGCCCCUUCGACGAGGUGUUCAAUGCCACCAGAUUCGCCUCUGUGUACGCCUGGAACCGG<br>AAGCGGAUCAGCAAUUGCGUGGCCGACUACUCCGUGCUGUACAACUUCGCCCCCUUCUUCGCAUUC<br>AAGUGCUACGGCGUGUCCCCUACCAAGCUGAACGACCUGUGCUUCACAAACGUGUACGCCGACAGC<br>UUCGUGAUCCGGGGAAACGAAGUGUCACAGAUUGCCCCUGGACAGACAGGCAACAUCGCCGACUAC<br>AACUACAAGCUGCCCGACGACUUCACCGGCUGUGUGAUUGCCUGGAACAGCAACAAGCUGGACUCC<br>AAAGUCGGCGGCAACUACAAUUACCUGUACCGGCUGUUCCGGAAGUCCAAUCUGAAGCCCUUCGAG<br>CGGGACAUCUCCACCGAGAUCUAUCAGGCCGGCAACAAGCCUUGUAACGGCGUGGCAGGCUUCAAC<br>UGCUACUUCCCACUGAGGUCCUACGGCUUUAGGCCCACAUACGGCGUGGGCCACCAGCCCUACAGA<br>GUGGUGGUGCUGAGCUUCGAACUGCUGCAUGCCCCUGCCACAGUGUGCGGCCCUAAGAAAAGCACC<br>AAUCUCGUGAAGAACAAAUGCGUGAACUUCAACUUCAACGGCCUGACCGGCACCGGCGUGCUGACA<br>GAGAGCAACAAGAAGUUCCUGCCAUUCCAGCAGUUUGGCCGGGAUAUCGCCGAUACCACAGACGCC<br>GUUAGAGAUCCCCAGACACUGGAAAUCCUGGACAUCACCCCUUGCAGCUUCGGCGGAGUGUCUGUG<br>AUCACCCCUGGCACCAACACCAGCAAUCAGGUGGCAGUGCUGUACCAGGGCGUGAACUGUACCGAA<br>GUGCCCGUGGCCAUUCACGCCGAUCAGCUGACACCUACAUGGCGGGUGUACUCCACCGGCAGCAAU<br>GUGUUUCAGACCAGAGCCGGCUGUCUGAUCGGAGCCGAGUACGUGAACAAUAGCUACGAGUGCGAC<br>AUCCCCAUCGGCGCUGGAAUCUGCGCCAGCUACCAGACACAGACAAAGAGCCACCGGAGAGCCAGA<br>AGCGUGGCCAGCCAGAGCAUCAUUGCCUACACAAUGUCUCUGGGCGCCGAGAACAGCGUGGCCUAC<br>UCCAACAACUCUAUCGCUAUCCCCACCAACUUCACCAUCAGCGUGACCACAGAGAUCCUGCCUGUG<br>UCCAUGACCAAGACCAGCGUGGACUGCACCAUGUACAUCUGCGGCGAUUCCACCGAGUGCUCCAAC<br>CUGCUGCUGCAGUACGGCAGCUUCUGCACCCAGCUGAAAAGAGCCCUGACAGGGAUCGCCGUGGAA<br>CAGGACAAGAACACCCAAGAGGUGUUCGCCCAAGUGAAGCAGAUCUACAAGACCCCUCCUAUCAAG<br>UACUUCGGCGGCUUCAAUUUCAGCCAGAUUCUGCCCGAUCCUAGCAAGCCCAGCAAGCGGAGCUUC<br>AUCGAGGACCUGCUGUUCAACAAAGUGACACUGGCCGACGCCGGCUUCAUCAAGCAGUAUGGCGAU<br>UGUCUGGGCGACAUUGCCGCCAGGGAUCUGAUUUGCGCCCAGAAGUUUAACGGACUGACAGUGCUG<br>CCUCCUCUGCUGACCGAUGAGAUGAUCGCCCAGUACACAUCUGCCCUGCUGGCCGGCACAAUCACA<br>AGCGGCUGGACAUUUGGAGCAGGCGCCGCUCUGCAGAUCCCCUUUGCUAUGCAGAUGGCCUACCGG<br>UUCAACGGCAUCGGAGUGACCCAGAAUGUGCUGUACGAGAACCAGAAGCUGAUCGCCAACCAGUUC<br>AACAGCGCCAUCGGCAAGAUCCAGGACAGCCUGAGCAGCACAGCAAGCGCCCUGGGAAAGCUGCAG<br>GACGUGGUCAACCACAAUGCCCAGGCACUGAACACCCUGGUCAAGCAGCUGUCCUCCAAGUUCGGC<br>GCCAUCAGCUCUGUGCUGAACGAUAUCCUGAGCAGACUGGACCCUCCUGAGGCCGAGGUGCAGAUC<br>GACAGACUGAUCACAGGCAGACUGCAGAGCCUCCAGACAUACGUGACCCAGCAGCUGAUCAGAGCC<br>GCCGAGAUUAGAGCCUCUGCCAAUCUGGCCGCCACCAAGAUGUCUGAGUGUGUGCUGGGCCAGAGC<br>AAGAGAGUGGACUUUUGCGGCAAGGGCUACCACCUGAUGAGCUUCCCUCAGUCUGCCCCUCACGGC<br>GUGGUGUUUCUGCACGUGACAUAUGUGCCCGCUCAAGAGAAGAAUUUCACCACCGCUCCAGCCAUC<br>UGCCACGACGGCAAAGCCCACUUUCCUAGAGAAGGCGUGUUCGUGUCCAACGGCACCCAUUGGUUC<br>GUGACACAGCGGAACUUCUACGAGCCCCAGAUCAUCACCACCGACAACACCUUCGUGUCUGGCAAC<br>UGCGACGUCGUGAUCGGCAUUGUGAACAAUACCGUGUACGACCCUCUGCAGCCCGAGCUGGACAGC<br>UUCAAAGAGGAACUGGACAAGUACUUUAAGAACCACACAAGCCCCGACGUGGACCUGGGCGAUAUC<br>AGCGGAAUCAAUGCCAGCGUCGUGAACAUCCAGAAAGAGAUCGACCGGCUGAACGAGGUGGCCAAG<br>AAUCUGAACGAGAGCCUGAUCGACCUGCAAGAACUGGGGAAGUACGAGCAGUACAUCAAGUGGCCC<br>UGGUACAUCUGGCUGGGCUUUAUCGCCGGACUGAUUGCCAUCGUGAUGGUCACAAUCAUGCUGUGU<br>UGCAUGACCAGCUGCUGUAGCUGCCUGAAGGGCUGUUGUAGCUGUGGCAGCUGCUCCAAGUUCGAC<br>GAGGACGAUUCUGAGCCCGUGCUGAAGGGCGUGAAACUGCACUACACAUGAUGA |
| 66 | DNA sequence encoding a SARS-CoV-2 S protein from an Omicron BA.2 variant | ATGTTCGTGTTCCTGGTGCTGCTGCCTCTGGTGTCCAGCCAGTGTGTGAACCTGATCACCAGAACA<br>CAGTCATACACCAACAGCTTTACCAGAGGCGTGTACTACCCCGACAAGGTGTTCAGATCCAGCGTG<br>CTGCACTCTACCCAGGACCTGTTCCTGCCTTTCTTCAGCAACGTGACCTGGTTCCACGCCATCCAC<br>GTGTCCGGCACCAATGGCACCAAGAGATTCGACAACCCCGTGCTGCCCTTCAACGACGGGGTGTAC<br>TTTGCCAGCACCGAGAAGTCCAACATCATCAGAGGCTGGATCTTCGGCACCACACTGGACAGCAAG<br>ACCCAGAGCCTGCTGATCGTGAACAACGCCACCAACGTGGTCATCAAAGTGTGCGAGTTCCAGTTC<br>TGCAACGACCCCTTCCTGGACGTCTACTACCACAAGAACAACAAGAGCTGGATGGAAAGCGAGTTC<br>CGGGTGTACAGCAGCGCCAACAACTGCACCTTCGAGTACGTGTCCCAGCCTTTCCTGATGGACCTG<br>GAAGGCAAGCAGGGCAACTTCAAGAACCTGCGCGAGTTCGTGTTTAAGAACATCGACGGCTACTTC<br>AAGATCTACAGCAAGCACACCCCTATCAACCTCGGCCGGGATCTGCCTCAGGGCTTCTCTGCTCTG<br>GAACCCCTGGTGGATCTGCCCATCGGCATCAACATCACCCGGTTTCAGACACTGCTGGCCCTGCAC<br>AGAAGCTACCTGACACCTGGCGATAGCAGCAGCGGATGGACAGCTGGTGCCGCCGCTTACTATGTG<br>GGCTACCTGCAGCCTAGAACCTTCCTGCTGAAGTACAACGAGAACGGCACCATCACCGACGCCGTG<br>GATTGTGCTCTGGATCCTCTGAGCGAGACAAAGTGCACCCTGAAGTCCTTCACCGTGGAAAAGGGC<br>ATCTACCAGACCAGCAACTTCCGGGTGCAGCCCACCGAATCCATCGTGCGGTTCCCCAATATCACC<br>AATCTGTGCCCCTTCGACGAGGTGTTCAATGCCACCAGATTCGCCTCTGTGTACGCCTGGAACCGG<br>AAGCGGATCAGCAATTGCGTGGCCGACTACTCCGTGCTGTACAACTTCGCCCCCTTCTTCGCATTC<br>AAGTGCTACGGCGTGTCCCCTACCAAGCTGAACGACCTGTGCTTCACAAACGTGTACGCCGACAGC<br>TTCGTGATCCGGGGAAACGAAGTGTCACAGATTGCCCCTGGACAGACAGGCAACATCGCCGACTAC |

TABLE 6-continued

| Sequences of RBP020.18 (Omicron BA.2-specific RNA vaccine) | | |
|---|---|---|
| SEQ ID NO. | Brief Description | Sequence |
| | | AACTACAAGCTGCCCGACGACTTCACCGGCTGTGTGATTGCCTGGAACAGCAACAAGCTGGACTCC<br>AAAGTCGGCGGCAACTACAATTACCTGTACCGGCTGTTCCGGAAGTCCAATCTGAAGCCCTTCGAG<br>CGGGACATCTCCACCGAGATCTATCAGGCCGGCAACAAGCCTTGTAACGGCGTGGCAGGCTTCAAC<br>TGCTACTTCCCACTGAGGTCCTACGGCTTTAGGCCCACATACGGCGTGGGCCACCAGCCCTACAGA<br>GTGGTGGTGCTGAGCTTCGAACTGCTGCATGCCCCTGCCACAGTGTGCGGCCCTAAGAAAAGCACC<br>AATCTCGTGAAGAACAAATGCGTGAACTTCAACTTCAACGGCCTGACCGGCACCGGCGTGCTGACA<br>GAGAGCAACAAGAAGTTCCTGCCATTCCAGCAGTTTGGCCGGGATATCGCCGATACCACAGACGCC<br>GTTAGAGATCCCCAGACACTGGAAATCCTGGACATCACCCCTTGCAGCTTCGGCGGAGTGTCTGTG<br>ATCACCCCTGGCACCAACACCAGCAATCAGGTGGCAGTGCTGTACCAGGGCGTGAACTGTACCGAA<br>GTGCCCGTGGCCATTCACGCCGATCAGCTGACACCTACATGGCGGGTGTACTCCACCGGCAGCAAT<br>GTGTTTCAGACCAGAGCCGGCTGTCTGATCGGAGCCGAGTACGTGAACAATAGCTACGAGTGCGAC<br>ATCCCCATCGGCGCTGGAATCTGCGCCAGCTACCAGACACAGACAAAGAGCCACCGGAGAGCCAGA<br>AGCGTGGCCAGCCAGAGCATCATTGCCTACACAATGTCTCTGGGCGCCGAGAACAGCGTGGCCTAC<br>TCCAACAACTCTATCGCTATCCCCACCAACTTCACCATCAGCGTGACCACAGAGATCCTGCCTGTG<br>TCCATGACCAAGACCAGCGTGGACTGCACCATGTACATCTGCGGCGATTCCACCGAGTGCTCCAAC<br>CTGCTGCTGCAGTACGGCAGCTTCTGCACCCAGCTGAAAAGAGCCCTGACAGGGATCGCCGTGGAA<br>CAGGACAAGAACACCCAAGAGGTGTTCGCCCAAGTGAAGCAGATCTACAAGACCCCTCCTATCAAG<br>TACTTCGGCGGCTTCAATTTCAGCCAGATTCTGCCCGATCCTAGCAAGCCCAGCAAGCGGAGCTTC<br>ATCGAGGACCTGCTGTTCAACAAAGTGACACTGGCCGACGCCGGCTTCATCAAGCAGTATGGCGAT<br>TGTCTGGGCGACATTGCCGCCAGGGATCTGATTTGCGCCCAGAAGTTTAACGGACTGACAGTGCTG<br>CCTCCTCTGCTGACCGATGAGATGATCGCCCAGTACACATCTGCCCTGCTGGCCGGCACAATCACA<br>AGCGGCTGGACATTTGGAGCAGGCGCCGCTCTGCAGATCCCCTTTGCTATGCAGATGGCCTACCGG<br>TTCAACGGCATCGGAGTGACCCAGAATGTGCTGTACGAGAACCAGAAGCTGATCGCCAACCAGTTC<br>AACAGCGCCATCGGCAAGATCCAGGACAGCCTGAGCAGCACAGCAAGCGCCCTGGGAAAGCTGCAG<br>GACGTGGTCAACCACAATGCCCAGGCACTGAACACCCTGGTCAAGCAGCTGTCCTCCAAGTTCGGC<br>GCCATCAGCTCTGTGCTGAACGATATCCTGAGCAGACTGGACCCTCCTGAGGCCGAGGTGCAGATC<br>GACAGACTGATCACAGGCAGACTGCAGAGCCTCCAGACATACGTGACCCAGCAGCTGATCAGAGCC<br>GCCGAGATTAGAGCCTCTGCCAATCTGGCCGCCACCAAGATGTCTGAGTGTGTGCTGGGCCAGAGC<br>AAGAGAGTGGACTTTTGCGGCAAGGGCTACCACCTGATGAGCTTCCCTCAGTCTGCCCCTCACGGC<br>GTGGTGTTTCTGCACGTGACATATGTGCCCGCTCAAGAGAAGAATTTCACCACCGCTCCAGCCATC<br>TGCCACGACGGCAAAGCCCACTTTCCTAGAGAAGGCGTGTTCGTGTCCAACGGCACCCATTGGTTC<br>GTGACACAGCGGAACTTCTACGAGCCCCAGATCATCACCACCGACAACACCTTCGTGTCTGGCAAC<br>TGCGACGTCGTGATCGGCATTGTGAACAATACCGTGTACGACCCTCTGCAGCCCGAGCTGGACAGC<br>TTCAAAGAGGAACTGGACAAGTACTTTAAGAACCACACAAGCCCCGACGTGGACCTGGGCGATATC<br>AGCGGAATCAATGCCAGCGTCGTGAACATCCAGAAAGAGATCGACCGGCTGAACGAGGTGGCCAAG<br>AATCTGAACGAGAGCCTGATCGACCTGCAAGAACTGGGGAAGTACGAGCAGTACATCAAGTGGCCC<br>TGGTACATCIGGCTGGGCTTTATCGCCGGACTGATTGCCATCGTGATGGTCACAATCATGCTGTGT<br>TGCATGACCAGCTGCTGTAGCTGCCTGAAGGGCTGTTGTAGCTGTGGCAGCTGCTGCAAGTTCGAC<br>GAGGACGATTCTGAGCCCGTGCTGAAGGGCGTGAAACTGCACTACACATGATGA |
| 67 | Full length RNA construct sequence of RBP020.18 | AGAAUAAACUAGUAUUCUUCUGGUCCCCACAGACUCAGAGAGAACCCGCCACCAUGUUCGUGUUCC<br>UGGUGCUGCUGCCUCUGGUGUCCAGCCAGUGUGUGAACCUGAUCACCAGAACACAGUCAUACACCA<br>ACAGCUUUACCAGAGGCGUGUACUACCCCGACAAGGUGUUCAGAUCCAGCGUGCUGCACUCUACCC<br>AGGACCUGUUCCUGCCUUUCUUCAGCAACGUGACCUGGUUCCACGCCAUCCACGUGUCCGGCACCA<br>AUGGCACCAAGAGAUUCGACAACCCCGUGCUGCCCUUCAACGACGGGGUGUACUUUGCCAGCACCG<br>AGAAGUCCAACAUCAUCAGAGGCUGGAUCUUCGGCACCACACUGGACAGCAAGACCCAGAGCCUGC<br>UGAUCGUGAACAACGCCACCAACGUGGUCAUCAAAGUGUGCGAGUUCCAGUUCUGCAACGACCCCU<br>UCCUGGACGUCUACUACCACAAGAACAACAAGAGCUGGAUGGAAAGCGAGUUCCGGGUGUACAGCA<br>GCGCCAACAACUGCACCUUCGAGUACGUGUCCCAGCCUUUCCUGAUGGACCUGGAAGGCAAGCAGG<br>GCAACUUCAAGAACCUGCGCGAGUUCGUGUUUAAGAACAUCGACGGCUACUUCAAGAUCUACAGCA<br>AGCACACCCCUAUCAACCUCGGCCGGGAUCUGCCUCAGGGCUUCUCUGCUCUGGAACCCCUGGUGG<br>AUCUGCCCAUCGGCAUCAACAUCACCCGGUUUCAGACACUGCUGGCCCUGCACAGAAGCUACCUGA<br>CACCUGGCGAUAGCAGCAGCGGAUGGACAGCUGGUGCCGCCGCUUACUAUGUGGGCUACCUGCAGC<br>CUAGAACCUUCCUGCUGAAGUACAACGAGAACGGCACCAUCACCGACGCCGUGGAUUGUGCUCUGG<br>AUCCUCUGAGCGAGACAAAGUGCACCCUGAAGUCCUUCACCGUGGAAAAGGGCAUCUACCAGACCA<br>GCAACUUCCGGGUGCAGCCCACCGAAUCCAUCGUGCGGUUCCCCAAUAUCACCAAUCUGUGCCCCU<br>UCGACGAGGUGUUCAAUGCCACCAGAUUCGCCUCUGUGUACGCCUGGAACCGGAAGCGGAUCAGCA<br>AUUGCGUGGCCGACUACUCCGUGCUGUACAACUUCGCCCCCUUCUUCGCAUUCAAGUGCUACGGCG<br>UGUCCCCUACCAAGCUGAACGACCUGUGCUUCACAAACGUGUACGCCGACAGCUUCGUGAUCCGGG<br>GAAACGAAGUGUCACAGAUUGCCCCUGGACAGACAGGCAACAUCGCCGACUACAACUACAAGCUGC<br>CCGACGACUUCACCGGCUGUGUGAUUGCCUGGAACAGCAACAAGCUGGACUCCAAAGUCGGCGGCA<br>ACUACAAUUACCUGUACCGGCUGUUCCGGAAGUCCAAUCUGAAGCCCUUCGAGCGGGACAUCUCCA<br>CCGAGAUCUAUCAGGCCGGCAACAAGCCUUGUAACGGCGUGGCAGGCUUCAACUGCUACUUCCCAC<br>UGAGGUCCUACGGCUUUAGGCCCACAUACGGCGUGGGCCACCAGCCCUACAGAGUGGUGGUGCUGA<br>GCUUCGAACUGCUGCAUGCCCCUGCCACAGUGUGCGGCCCUAAGAAAAGCACCAAUCUCGUGAAGA<br>ACAAAUGCGUGAACUUCAACUUCAACGGCCUGACCGGCACCGGCGUGCUGACAGAGAGCAACAAGA<br>AGUUCCUGCCAUUCCAGCAGUUUGGCCGGGAUAUCGCCGAUACCACAGACGCCGUUAGAGAUCCCC<br>AGACACUGGAAAUCCUGGACAUCACCCCUUGCAGCUUCGGCGGAGUGUCUGUGAUCACCCCUGGCA<br>CCAACACCAGCAAUCAGGUGGCAGUGCUGUACCAGGGCGUGAACUGUACCGAAGUGCCCGUGGCCA<br>UUCACGCCGAUCAGCUGACACCUACAUGGCGGGUGUACUCCACCGGCAGCAAUGUGUUUCAGACCA<br>GAGCCGGCUGUCUGAUCGGAGCCGAGUACGUGAACAAUAGCUACGAGUGCGACAUCCCCAUCGGCG<br>CUGGAAUCUGCGCCAGCUACCAGACACAGACAAAGAGCCACCGGAGAGCCAGAAGCGUGGCCAGCC<br>AGAGCAUCAUUGCCUACACAAUGUCUCUGGGCGCCGAGAACAGCGUGGCCUACUCCAACAACUCUA<br>UCGCUAUCCCCACCAACUUCACCAUCAGCGUGACCACAGAGAUCCUGCCUGUGUCCAUGACCAAGA<br>CCAGCGUGGACUGCACCAUGUACAUCUGCGGCGAUUCCACCGAGUGCUCCAACCUGCUGCUGCAGU |

TABLE 6-continued

Sequences of RBP020.18 (Omicron BA.2-specific RNA vaccine)

| SEQ ID NO. | Brief Description | Sequence |
|---|---|---|
| | | ACGGCAGCUUCUGCACCCAGCUGAAAAGAGCCCUGACAGGGAUCGCCGUGGAACAGGACAAGAACA<br>CCCAAGAGGUGUUCGCCCAAGUGAAGCAGAUCUACAAGACCCCUCCUAUCAAGUACUUCGGCGGCU<br>UCAAUUUCAGCCAGAUUCUGCCCGAUCCUAGCAAGCCCAGCAAGCGGAGCUUCAUCGAGGACCUGC<br>UGUUCAACAAAGUGACACUGGCCGACGCCGGCUUCAUCAAGCAGUAUGGCGAUUGUCUGGGCGACA<br>UUGCCGCCAGGGAUCUGAUUUGCGCCCAGAAGUUUAACGGACUGACAGUGCUGCCUCCUCUGCUGA<br>CCGAUGAGAUGAUCGCCCAGUACACAUCUGCCCUGCUGGCCGGCACAAUCACAAGCGGCUGGACAU<br>UUGGAGCAGGCGCCGCUCUGCAGAUCCCCUUUGCUAUGCAGAUGGCCUACCGGUUCAACGGCAUCG<br>GAGUGACCCAGAAUGUGCUGUACGAGAACCAGAAGCUGAUCGCCAACCAGUUCAACAGCGCCAUCG<br>GCAAGAUCCAGGACAGCCUGAGCAGCACAGCAAGCGCCCUGGGAAAGCUGCAGGACGUGGUCAACC<br>ACAAUGCCCAGGCACUGAACACCCUGGUCAAGCAGCUGUCCUCCAAGUUCGGCGCCAUCAGCUCUG<br>UGCUGAACGAUAUCCUGAGCAGACUGGACCCUCCUGAGGCCGAGGUGCAGAUCGACAGACUGAUCA<br>CAGGCAGACUGCAGAGCCUCCAGACAUACGUGACCCAGCAGCUGAUCAGAGCCGCCGAGAUUAGAG<br>CCUCUGCCAAUCUGGCCGCCACCAAGAUGUCUGAGUGUGUGCUGGGCCAGAGCAAGAGAGUGGACU<br>UUUGCGGCAAGGGCUACCACCUGAUGAGCUUCCCUCAGUCUGCCCCUCACGGCGUGGUGUUUCUGC<br>ACGUGACAUAUGUGCCCGCUCAAGAGAAGAAUUUCACCACCGCUCCAGCCAUCUGCCACGACGGCA<br>AAGCCCACUUUCCUAGAGAAGGCGUGUUCGUGUCCAACGGCACCCAUUGGUUCGUGACACAGCGGA<br>ACUUCUACGAGCCCCAGAUCAUCACCACCGACAACACCUUCGUGUCUGGCAACUGCGACGUCGUGA<br>UCGGCAUUGUGAACAAUACCGUGUACGACCCUCUGCAGCCCGAGCUGGACAGCUUCAAAGAGGAAC<br>UGGACAAGUACUUUAAGAACCACACAAGCCCCGACGUGGACCUGGGCGAUAUCAGCGGAAUCAAUG<br>CCAGCGUCGUGAACAUCCAGAAAGAGAUCGACCGGCUGAACGAGGUGGCCAAGAAUCUGAACGAGA<br>GCCUGAUCGACCUGCAAGAACUGGGGAAGUACGAGCAGUACAUCAAGUGGCCCUGGUACAUCUGGC<br>UGGGCUUUAUCGCCGGACUGAUUGCCAUCGUGAUGGUCACAAUCAUGCUGUGUUGCAUGACCAGCU<br>GCUGUAGCUGCCUGAAGGGCUGUUGUAGCUGUGGCAGCUGCUGCAAGUUCGACGAGGACGAUUCUG<br>AGCCCGUGCUGAAGGGCGUGAAACUGCACUACACAUGAUGACUCGAGCUGGUACUGCAUGCACGCA<br>AUGCUAGCUGCCCCUUUCCCGUCCUGGGUACCCCGAGUCUCCCCCGACCUCGGGUCCCAGGUAUGC<br>UCCCACCUCCACCUGCCCCACUCACCACCUCUGCUAGUUCCAGACACCUCCCAAGCACGCAGCAAU<br>GCAGCUCAAAACGCUUAGCCUAGCCACACCCCCACGGGAAACAGCAGUGAUUAACCUUUAGCAAUA<br>AACGAAAGUUUAACUAAGCUAUACUAACCCCAGGGUUGGUCAAUUUCGUGCCAGCCACACCCUGGA<br>GCUAGCAAAAAAAAAAAAAAAAAAAAAAAAAAAAAAGCAUAUGACUAAAAAAAAAAAAAAAAAAAA<br>AAAAAAAAAAAAAAAAAAAAAAAAAAAAAAAAAAAAAAAAAAAAAAAAAA |
| 68 | Full length DNA construct sequence of RBP020.18 | AGAATAAACTAGTATTCTTCTGGTCCCCACAGACTCAGAGAGAACCCGCCACCATGTTCGTGTTCC<br>TGGTGCTGCTGCCTCTGGTGTCCAGCCAGTGTGTGAACCTGATCACCAGAACACAGTCATACACCA<br>ACAGCTTTACCAGAGGCGTGTACTACCCCGACAAGGTGTTCAGATCCAGCGTGCTGCACTCTACCC<br>AGGACCTGTTCCTGCCTTTCTTCAGCAACGTGACCTGGTTCCACGCCATCCACGTGTCCGGCACCA<br>ATGGCACCAAGAGATTCGACAACCCCGTGCTGCCCTTCAACGACGGGGTGTACTTTGCCAGCACCG<br>AGAAGTCCAACATCATCAGAGGCTGGATCTTCGGCACCACACTGGACAGCAAGACCCAGAGCCTGC<br>TGATCGTGAACAACGCCACCAACGTGGTCATCAAAGTGTGCGAGTTCCAGTTCTGCAACGACCCCT<br>TCCTGGACGTCTACTACCACAAGAACAACAAGAGCTGGATGGAAAGCGAGTTCCGGGTGTACAGCA<br>GCGCCAACAACTGCACCTTCGAGTACGTGTCCCAGCCTTTCCTGATGGACCTGGAAGGCAAGCAGG<br>GCAACTTCAAGAACCTGCGCGAGTTCGTGTTTAAGAACATCGACGGCTACTTCAAGATCTACAGCA<br>AGCACACCCCTATCAACCTCGGCCGGGATCTGCCTCAGGGCTTCTCTGCTCTGGAACCCCTGGTGG<br>ATCTGCCCATCGGCATCAACATCACCCGGTTTCAGACACTGCTGGCCCTGCACAGAAGCTACCTGA<br>CACCTGGCGATAGCAGCAGCGGATGGACAGCTGGTGCCGCCGCTTACTATGTGGGCTACCTGCAGC<br>CTAGAACCTTCCTGCTGAAGTACAACGAGAACGGCACCATCACCGACGCCGTGGATTGTGCTCTGG<br>ATCCTCTGAGCGAGACAAAGTGCACCCTGAAGTCCTTCACCGTGGAAAAGGGCATCTACCAGACCA<br>GCAACTTCCGGGTGCAGCCCACCGAATCCATCGTGCGGTTCCCCAATATCACCAATCTGTGCCCCT<br>TCGACGAGGTGTTCAATGCCACCAGATTCGCCTCTGTGTACGCCTGGAACCGGAAGCGGATCAGCA<br>ATTGCGTGGCCGACTACTCCGTGCTGTACAACTTCGCCCCCTTCTTCGCATTCAAGTGCTACGGCG<br>TGTCCCCTACCAAGCTGAACGACCTGTGCTTCACAAACGTGTACGCCGACAGCTTCGTGATCCGGG<br>GAAACGAAGTGTCACAGATTGCCCCTGGACAGACAGGCAACATCGCCGACTACAACTACAAGCTGC<br>CCGACGACTTCACCGGCTGTGTGATTGCCTGGAACAGCAACAAGCTGGACTCCAAAGTCGGCGGCA<br>ACTACAATTACCTGTACCGGCTGTTCCGGAAGTCCAATCTGAAGCCCTTCGAGCGGGACATCTCCA<br>CCGAGATCTATCAGGCCGGCAACAAGCCTTGTAACGGCGTGGCAGGCTTCAACTGCTACTTCCCAC<br>TGAGGTCCTACGGCTTTAGGCCCACATACGGCGTGGGCCACCAGCCCTACAGAGTGGTGGTGCTGA<br>GCTTCGAACTGCTGCATGCCCCTGCCACAGTGTGCGGCCCTAAGAAAAGCACCAATCTCGTGAAGA<br>ACAAATGCGTGAACTTCAACTTCAACGGCCTGACCGGCACCGGCGTGCTGACAGAGAGCAACAAGA<br>AGTTCCTGCCATTCCAGCAGTTIGGCCGGGATATCGCCGATACCACAGACGCCGTTAGAGATCCCC<br>AGACACTGGAAATCCTGGACATCACCCCTTGCAGCTTCGGCGGAGTGTCTGTGATCACCCCIGGCA<br>CCAACACCAGCAATCAGGTGGCAGTGCTGTACCAGGGCGTGAACTGTACCGAAGTGCCCGTGGCCA<br>TTCACGCCGATCAGCTGACACCTACATGGCGGGTGTACTCCACCGGCAGCAATGTGTTTCAGACCA<br>GAGCCGGCTGTCTGATCGGAGCCGAGTACGTGAACAATAGCTACGAGTGCGACATCCCCATCGGCG<br>CTGGAATCTGCGCCAGCTACCAGACACAGACAAAGAGCCACCGGAGAGCCAGAAGCGTGGCCAGCC<br>AGAGCATCATTGCCTACACAATGTCTCTGGGCGCCGAGAACAGCGTGGCCTACTCCAACAACTCTA<br>TCGCTATCCCCACCAACTTCACCATCAGCGTGACCACAGAGATCCTGCCTGTGTCCATGACCAAGA<br>CCAGCGTGGACTGCACCATGTACATCTGCGGCGATTCCACCGAGTGCTCCAACCTGCTGCTGCAGT<br>ACGGCAGCTTCTGCACCCAGCTGAAAAGAGCCCTGACAGGGATCGCCGTGGAACAGGACAAGAACA<br>CCCAAGAGGTGTTCGCCCAAGTGAAGCAGATCTACAAGACCCCTCCTATCAAGTACTTCGGCGGCT<br>TCAATTTCAGCCAGATTCTGCCCGATCCTAGCAAGCCCAGCAAGCGGAGCTTCATCGAGGACCTGC<br>TGTTCAACAAAGTGACACTGGCCGACGCCGGCTTCATCAAGCAGTATGGCGATTGTCTGGGCGACA<br>TTGCCGCCAGGGATCTGATTTGCGCCCAGAAGTTTAACGGACTGACAGTGCTGCCTCCTCTGCTGA<br>CCGATGAGATGATCGCCCAGTACACATCTGCCCTGCTGGCCGGCACAATCACAAGCGGCTGGACAT<br>TTGGAGCAGGCGCCGCTCTGCAGATCCCCTTTGCTATGCAGATGGCCTACCGGTTCAACGGCATCG<br>GAGTGACCCAGAATGTGCTGTACGAGAACCAGAAGCTGATCGCCAACCAGTTCAACAGCGCCATCG<br>GCAAGATCCAGGACAGCCTGAGCAGCACAGCAAGCGCCCTGGGAAAGCTGCAGGACGTGGTCAACC |

TABLE 6-continued

Sequences of RBP020.18 (Omicron BA.2-specific RNA vaccine)

| SEQ ID NO. | Brief Description | Sequence |
|---|---|---|
| | | ACAATGCCCAGGCACTGAACACCCTGGTCAAGCAGCTGTCCTCCAAGTTCGGCGCCATCAGCTCTG<br>TGCTGAACGATATCCTGAGCAGACTGGACCCTCCTGAGGCCGAGGTGCAGATCGACAGACTGATCA<br>CAGGCAGACTGCAGAGCCTCCAGACATACGTGACCCAGCAGCTGATCAGAGCCGCCGAGATTAGAG<br>CCTCTGCCAATCTGGCCGCCACCAAGATGTCTGAGTGTGTGCTGGGCCAGAGCAAGAGAGTGGACT<br>TTTGCGGCAAGGGCTACCACCTGATGAGCTTCCCTCAGTCTGCCCCTCACGGCGTGGTGTTTCTGC<br>ACGTGACATATGTGCCCGCTCAAGAGAAGAATTTCACCACCGCTCCAGCCATCTGCCACGACGGCA<br>AAGCCCACTTTCCTAGAGAAGGCGTGTTCGTGTCCAACGGCACCCATTGGTTCGTGACACAGCGGA<br>ACTTCTACGAGCCCCAGATCATCACCACCGACAACACCTTCGTGTCTGGCAACTGCGACGTCGTGA<br>TCGGCATTGTGAACAATACCGTGTACGACCCTCTGCAGCCCGAGCTGGACAGCTTCAAAGAGGAAC<br>TGGACAAGTACTTTAAGAACCACACAAGCCCCGACGTGGACCTGGGCGATATCAGCGGAATCAATG<br>CCAGCGTCGTGAACATCCAGAAAGAGATCGACCGGCTGAACGAGGTGGCCAAGAATCTGAACGAGA<br>GCCTGATCGACCTGCAAGAACTGGGGAAGTACGAGCAGTACATCAAGTGGCCCTGGTACATCTGGC<br>TGGGCTTTATCGCCGGACTGATTGCCATCGTGATGGTCACAATCATGCTGTGTTGCATGACCAGCT<br>GCTGTAGCTGCCTGAAGGGCTGTTGTAGCTGTGGCAGCTGCTGCAAGTTCGACGAGGACGATTCTG<br>AGCCCGTGCTGAAGGGCGTGAAACTGCACTACACATGATGACTCGAGCTGGTACTGCATGCACGCA<br>ATGCTAGCTGCCCCTTTCCCGTCCTGGGTACCCCGAGTCTCCCCCGACCTCGGGTCCCAGGTATGC<br>TCCCACCTCCACCTGCCCCACTCACCACCTCTGCTAGTTCCAGACACCTCCCAAGCACGCAGCAAT<br>GCAGCTCAAAACGCTTAGCCTAGCCACACCCCCACGGGAAACAGCAGTGATTAACCTTTAGCAATA<br>AACGAAAGTTTAACTAAGCTATACTAACCCCAGGGTTGGTCAATTTCGTGCCAGCCACACCCTGGA<br>GCTAGCAAAAAAAAAAAAAAAAAAAAAAAAAAAAAAGCATATGACTAAAAAAAAAAAAAAAAAAAA<br>AAAAAAAAAAAAAAAAAAAAAAAAAAAAAAAAAAAAAAAAAAAAAAAAAA |

TABLE 7

Description of sequences of RBP020.18 (Omicron BA.2-specific RNA vaccine) as described in Table 6 above (amino acid mutation positioning shown relative to SEQ ID NO: 1)

| Construct | Omicron BA.2 P2 | |
|---|---|---|
| Antigen | P2-mutated full spike protein | |
| Changes | Amino Acid[a] | mRNA Nucleotides (location) |
| Furin site | RRAR (SEQ ID NO: 136) | CGGAGAGCCAGA (SEQ ID NO: 137) (2088-2099) |
| Proline | K986P | CCU (3000-3002) |
| | V987P | CCU (3003-3005) |
| Lineage | T19I | AUC (108-110) |
| | L24del | / |
| | P25del | / |
| | P26del | / |
| | A27S | UCA (123-125) |
| | G142D | GAC (468-470) |
| | V213G | GGC (681-683) |
| | G339D | GAC (1059-1061) |
| | S371F | UUC (1155-1157) |
| | S373P | CCC (1161-1163) |

TABLE 7-continued

Description of sequences of RBP020.18 (Omicron BA.2-specific RNA vaccine) as described in Table 6 above (amino acid mutation positioning shown relative to SEQ ID NO: 1)

| Construct | Omicron BA.2 P2 | |
|---|---|---|
| | S375F | UUC (1167-1169) |
| | T376A | GCA (1170-1172) |
| | D405N | AAC (1257-1259) |
| | R408S | UCA (1266-1268) |
| | K417N | AAC (1293-1295) |
| | N440K | AAG (1362-1364) |
| | S477N | AAC (1473-1475) |
| | T478K | AAG (1476-1478) |
| | E484A | GCA (1494-1496) |
| | Q493R | AGG (1521-1523) |
| | Q498R | AGG (1536-1538) |
| | N501Y | UAC (1545-1547) |
| | Y505H | CAC (1557-1559) |
| | D614G | GGC (1884-1886) |
| | H655Y | UAC (2007-2009) |
| | N679K | AAG (2079-2081) |
| | P681H | CAC (2085-2087) |
| | N764K | AAA (2334-2336) |
| | D796Y | UAC (2430-2432) |
| | Q954H | CAC (2904-2906) |
| | N969K | AAG (2949-2951) |

TABLE 8

Sequences of RBP020.22 (Omicron BA.4/BA.5-specific RNA vaccine)

| SEQ ID NO. | Brief Description | Sequence |
|---|---|---|
| 69 | Amino acid sequence of RNA-encoded SARS-CoV-2 S protein from an Omicron BA.4/BA.5 variant (with PRO mutations at positions corresponding to positions K986P and V987P of SEQ ID NO: 7, i.e., at residues 981 and 982 of SEQ ID NO: 69) | MEVELVLLPLVSSQCVNLITRTQSYTNSFTRGVYYPDKVFRSSVLHSTQDLFLPFFSNVTWFHAIS<br>GTNGTKRFDNPVLPFNDGVYFASTEKSNIIRGWIFGTTLDSKTQSLLIVNNATNVVIKVCEFQFCN<br>DPFLDVYYHKNNKSWMESEFRVYSSANNCTFEYVSQPFLMDLEGKQGNFKNLREFVFKNIDGYFKI<br>YSKHTPINLGRDLPQGFSALEPLVDLPIGINITRFQTLLALHRSYLTPGDSSSGWTAGAAAYYVGY<br>LQPRTFLLKYNENGTITDAVDCALDPLSETKCTLKSFTVEKGIYQTSNFRVQPTESIVRFPNITNL<br>CPFDEVENATRFASVYAWNRKRISNCVADYSVLYNFAPFFAFKCYGVSPTKLNDLCFTNVYADSFV<br>IRGNEVRQIAPGQTGNIADYNYKLPDDFTGCVIAWNSNKLDSKVGGNYNYRYRLFRKSNLKPFERD<br>ISTEIYQAGNKPCNGVAGVNCYFPLQSYGFRPTYGVGHQPYRVVVLSFELLHAPATVCGPKKSTNL<br>VKNKCVNFNFNGLTGTGVLTESNKKELPFQQFGRDIADTTDAVRDPQTLEILDITPCSFGGVSVIT<br>PGTNTSNQVAVLYQGVNCTEVPVAIHADQLTPTWRVYSTGSNVFQTRAGCLIGAEYVNNSYECDIP |

TABLE 8-continued

Sequences of RBP020.22 (Omicron BA.4/BA.5-specific RNA vaccine)

| SEQ ID NO. | Brief Description | Sequence |
| --- | --- | --- |
| | | IGAGICASYQTQTKSHRRARSVASQSIIAYTMSLGAENSVAYSNNSIAIPTNFTISVTTEILPVSM<br>TKTSVDCTMYICGDSTECSNLLLQYGSFCTQLKRALTGIAVEQDKNTQEVFAQVKQLYKTPPIKYF<br>GGFNFSQILPDPSKPSKRSFIEDLLENKVTLADAGFIKQYGDCLGDIAARDLICAQKENGLTVLPP<br>LLTDEMIAQYTSALLAGTITSGWTFGAGAALQIPFAMQMAYRENGIGVTQNVLYENQKLIANQENS<br>AIGKIQDSLSSTASALGKLQDVVNHNAQALNTLVKQLSSKFGAISSVLNDILSRLDPPEAEVQIDR<br>LITGRLQSLQTYVTQQLIRAAEIRASANLAATKMSECVLGQSKRVDFCGKGYHLMSFPQSAPHGVV<br>FLHVTYVPAQEKNFTTAPAICHDGKAHFPREGVFVSNGTHWFVTQRNFYEPQIITTDNTFVSGNCD<br>VVIGIVNNTVYDPLQPELDSFKEELDKYFKNHTSPDVDLGDISGINASVVNIQKEIDRLNEVAKNL<br>NESLIDLQELGKYEQYIKWPWYIWLGFIAGLIAIVMVTIMLCCMTSCCSCLKGCCSCGSCCKEDED<br>DSEPVLKGVKLHYT** |
| 70 | RNA sequence encoding a SARS-CoV-2 S protein from an Omicron BA.4/BA.5 variant | AUGUUCGUGUUCCUGGUGCUGCUGCCUCUGGUGUCCAGCCAGUGUGUGAACCUGAUCACCAGAACA<br>CAGUCAUACACCAACAGCUUUACCAGAGGCGUGUACUACCCCGACAAGGUGUUCAGAUCCAGCGUG<br>CUGCACUCUACCCAGGACCUGUUCCUGCCUUUCUUCAGCAACGUGACCUGGUUCCACGCCAUCUCC<br>GGCACCAAUGGCACCAAGAGAUUCGACAACCCCGUGCUGCCCUUCAACGACGGGGUGUACUUUGCC<br>AGCACCGAGAAGUCCAACAUCAUCAGAGGCUGGAUCUUCGGCACCACACUGGACAGCAAGACCCAG<br>AGCCUGCUGAUCGUGAACAACGCCACCAACGUGGUCAUCAAAGUGUGCGAGUUCCAGUUCUGCAAC<br>GACCCCUUCCUGGACGUCUACUACCACAAGAACAACAAGAGCUGGAUGGAAAGCGAGUUCCGGGUG<br>UACAGCAGCGCCAACAACUGCACCUUCGAGUACGUGUCCCAGCCUCUCCUGAUGGACCUGGAAGGC<br>AAGCAGGGCAACUUCAAGAACCUGCGCGAGUUCGUGUUUAAGAACAUCGACGGCUACUUCAAGAUC<br>UACAGCAAGCACACCCCUAUCAACCUCGGCCGGGAUCUGCCUCAGGGCUUCUCUGCUCUGGAACCC<br>CUGGUGGAUCUGCCCAUCGGCAUCAACAUCACCCGGUUUCAGACACUGCUGGCCCUGCACAGAAGC<br>UACCUGACACCUGGCGAUAGCAGCAGCGGAUGGACAGCUGGUGCCGCCGCUUACUAUGUGGGCUAC<br>CUGCAGCCUAGAACCUUCCUGCUGAAGUACAACGAGAACGGCACCAUCACCGACGCCGUGGAUUGU<br>GCUCUGGAUCCUCUGAGCGAGACAAAGUGCACCCUGAAGUCCUUCACCGUGGAAAAGGGCAUCUAC<br>CAGACCAGCAACUUCCGGGUGCAGCCCACCGAAUCCAUCGUGCGGUUCCCCAAUAUCACCAAUCUG<br>UGCCCCUUCGACGAGGUGUUCAAUGCCACCAGAUUCGCCUCUGUGUACGCCUGGAACCGGAAGCGG<br>AUCAGCAAUUGCGUGGCCGACUACUCCGUGCUGUACAACUUCGCCCCCUUCUUCGCAUUCAAGUGC<br>UACGGCGUGUCCCCUACCAAGCUGAACGACCUGUGCUUCACAAACGUGUACGCCGACAGCUUCGUG<br>AUCCGGGGAAACGAAGUGCGGCAGAUUGCCCCUGGACAGACAGGCAACAUCGCCGACUACAACUAC<br>AAGCUGCCCGACGACUUCACCGGCUGUGUGAUUGCCUGGAACAGCAACAAGCUGGACUCCAAAGUC<br>GGCGGCAACUACAAUUACAGGUACCGGCUGUUCCGGAAGUCCAAUCUGAAGCCCUUCGAGCGGGAC<br>AUCUCCACCGAGAUCUAUCAGGCCGGCAACAAGCCUUGUAACGGCGUGGCAGGCGUGAACUGCUAC<br>UUCCCACUGCAGUCCUACGGCUUUAGGCCCACAUACGGCGUGGGCCACCAGCCCUACAGAGUGGUG<br>GUGCUGAGCUUCGAACUGCUGCAUGCCCCUGCCACAGUGUGCGGCCCUAAGAAAAGCACCAAUCUC<br>GUGAAGAACAAAUGCGUGAACUUCAACUUCAACGGCCUGACCGGCACCGGCGUGCUGACAGAGAGC<br>AACAAGAAGUUCCUGCCAUUCCAGCAGUUUGGCCGGGAUAUCGCCGAUACCACAGACGCCGUUAGA<br>GAUCCCCAGACACUGGAAAUCCUGGACAUCACCCCUUGCAGCUUCGGCGGAGUGUCUGUGAUCACC<br>CCUGGCACCAACACCAGCAAUCAGGUGGCAGUGCUGUACCAGGGCGUGAACUGUACCGAAGUGCCC<br>GUGGCCAUUCACGCCGAUCAGCUGACACCUACAUGGCGGGUGUACUCCACCGGCAGCAAUGUGUUU<br>CAGACCAGAGCCGGCUGUCUGAUCGGAGCCGAGUACGUGAACAAUAGCUACGAGUGCGACAUCCCC<br>AUCGGCGCUGGAAUCUGCGCCAGCUACCAGACACAGACAAAGAGCCACCGGAGAGCCAGAAGCGUG<br>GCCAGCCAGAGCAUCAUUGCCUACACAAUGUCUCUGGGCGCCGAGAACAGCGUGGCCUACUCCAAC<br>AACUCUAUCGCUAUCCCCACCAACUUCACCAUCAGCGUGACCACAGAGAUCCUGCCUGUGUCCAUG<br>ACCAAGACCAGCGUGGACUGCACCAUGUACAUCUGCGGCGAUUCCACCGAGUGCUCCAACCUGCUG<br>CUGCAGUACGGCAGCUUCUGCACCCAGCUGAAAAGAGCCCUGACAGGGAUCGCCGUGGAACAGGAC<br>AAGAACACCCAAGAGGUGUUCGCCCAAGUGAAGCAGAUCUACAAGACCCCUCCUAUCAAGUACUUC<br>GGCGGCUUCAAUUUCAGCCAGAUUCUGCCCGAUCCUAGCAAGCCCAGCAAGCGGAGCUUCAUCGAG<br>GACCUGCUGUUCAACAAAGUGACACUGGCCGACGCCGGCUUCAUCAAGCAGUAUGGCGAUUGUCUG<br>GGCGACAUUGCCGCCAGGGAUCUGAUUUGCGCCCAGAAGUUUAACGGACUGACAGUGCUGCCUCCU<br>CUGCUGACCGAUGAGAUGAUCGCCCAGUACACAUCUGCCCUGCUGGCCGGCACAAUCACAAGCGGC<br>UGGACAUUUGGAGCAGGCGCCGCUCUGCAGAUCCCCUUUGCUAUGCAGAUGGCCUACCGGUUCAAC<br>GGCAUCGGAGUGACCCAGAAUGUGCUGUACGAGAACCAGAAGCUGAUCGCCAACCAGUUCAACAGC<br>GCCAUCGGCAAGAUCCAGGACAGCCUGAGCAGCACAGCAAGCGCCCUGGGAAAGCUGCAGGACGUG<br>GUCAACCACAAUGCCCAGGCACUGAACACCCUGGUCAAGCAGCUGUCCUCCAAGUUCGGCGCCAUC<br>AGCUCUGUGCUGAACGAUAUCCUGAGCAGACUGGACCCUCCUGAGGCCGAGGUGCAGAUCGACAGA<br>CUGAUCACAGGCAGACUGCAGAGCCUCCAGACAUACGUGACCCAGCAGCUGAUCAGAGCCGCCGAG<br>AUUAGAGCCUCUGCCAAUCUGGCCGCCACCAAGAUGUCUGAGUGUGUGCUGGGCCAGAGCAAGAGA<br>GUGGACUUUUGCGGCAAGGGCUACCACCUGAUGAGCUUCCCUCAGUCUGCCCCUCACGGCGUGGUG<br>UUUCUGCACGUGACAUAUGUGCCCGCUCAAGAGAAGAAUUUCACCACCGCUCCAGCCAUCUGCCAC<br>GACGGCAAAGCCCACUUUCCUAGAGAAGGCGUGUUCGUGUCCAACGGCACCCAUUGGUUCGUGACA<br>CAGCGGAACUUCUACGAGCCCCAGAUCAUCACCACCGACAACACCUUCGUGUCUGGCAACUGCGAC<br>GUCGUGAUCGGCAUUGUGAACAAUACCGUGUACGACCCUCUGCAGCCCGAGCUGGACAGCUUCAAA<br>GAGGAACUGGACAAGUACUUUAAGAACCACACAAGCCCCGACGUGGACCUGGGCGAUAUCAGCGGA<br>AUCAAUGCCAGCGUCGUGAACAUCCAGAAAGAGAUCGACCGGCUGAACGAGGUGGCCAAGAAUCUG<br>AACGAGAGCCUGAUCGACCUGCAAGAACUGGGGAAGUACGAGCAGUACAUCAAGUGGCCCUGGUAC<br>AUCUGGCUGGGCUUUAUCGCCGGACUGAUUGCCAUCGUGAUGGUCACAAUCAUGCUGUGUUGCAUG<br>ACCAGCUGCUGUAGCUGCCUGAAGGGCUGUUGUAGCUGUGGCAGCUGCUGCAAGUUCGACGAGGAC<br>GAUUCUGAGCCCGUGCUGAAGGGCGUGAAACUGCACUACACAUGAUGA |
| 71 | DNA sequence encoding a SARS-CoV-2 S protein from an Omicron BA.4/BA.5 variant | ATGTTCGTGTTCCTGGTGCTGCTGCCTCTGGTGTCCAGCCAGTGTGTGAACCTGATCACCAGAACA<br>CAGTCATACACCAACAGCITTACCAGAGGCGTGTACTACCCCGACAAGGTGTTCAGATCCAGCGTG<br>CTGCACTCTACCCAGGACCTGTTCCTGCCTTTCTTCAGCAACGTGACCTGGTTCCACGCCATCTCC<br>GGCACCAATGGCACCAAGAGATTCGACAACCCCGTGCTGCCCTTCAACGACGGGGTGTACTTTGCC<br>AGCACCGAGAAGTCCAACATCATCAGAGGCTGGATCTTCGGCACCACACTGGACAGCAAGACCCAG |

TABLE 8-continued

Sequences of RBP020.22 (Omicron BA.4/BA.5-specific RNA vaccine)

| SEQ ID NO. | Brief Description | Sequence |
|---|---|---|
| | | AGCCTGCTGATCGTGAACAACGCCACCAACGTGGTCATCAAAGTGTGCGAGTTCCAGTTCTGCAAC<br>GACCCCTTCCTGGACGTCTACTACCACAAGAACAACAAGAGCTGGATGGAAAGCGAGTTCCGGGTG<br>TACAGCAGCGCCAACAACTGCACCTTCGAGTACGTGTCCCAGCCTTTCCTGATGGACCTGGAAGGC<br>AAGCAGGGCAACTTCAAGAACCTGCGCGAGTTCGTGTTTAAGAACATCGACGGCTACTTCAAGATC<br>TACAGCAAGCACACCCCTATCAACCTCGGCCGGGATCTGCCTCAGGGCTTCTCTGCTCTGGAACCC<br>CTGGTGGATCTGCCCATCGGCATCAACATCACCCGGTTTCAGACACTGCTGGCCCTGCACAGAAGC<br>TACCTGACACCTGGCGATAGCAGCAGCGGATGGACAGCTGGTGCCGCCGCTTACTATGTGGGCTAC<br>CTGCAGCCTAGAACCTTCCTGCTGAAGTACAACGAGAACGGCACCATCACCGACGCCGTGGATTGT<br>GCTCTGGATCCTCTGAGCGAGACAAAGTGCACCCTGAAGTCCTTCACCGTGGAAAAGGGCATCTAC<br>CAGACCAGCAACTTCCGGGTGCAGCCCACCGAATCCATCGTGCGGTTCCCCAATATCACCAATCTG<br>TGCCCCTTCGACGAGGTGTTCAATGCCACCAGATTCGCCTCTGTGTACGCCTGGAACCGGAAGCGG<br>ATCAGCAATTGCGTGGCCGACTACTCCGTGCTGTACAACTTCGCCCCCTTCTTCGCATTCAAGTGC<br>TACGGCGTGTCCCCTACCAAGCTGAACGACCTGTGCTTCACAAACGTGTACGCCGACAGCTTCGTG<br>ATCCGGGGAAACGAAGTGCGGCAGATTGCCCCTGGACAGACAGGCAACATCGCCGACTACAACTAC<br>AAGCTGCCCGACGACTTCACCGGCTGTGTGATTGCCTGGAACAGCAACAAGCTGGACTCCAAAGTC<br>GGCGGCAACTACAATTACAGGTACCGGCTGTTCCGGAAGTCCAATCTGAAGCCCTTCGAGCGGGAC<br>ATCTCCACCGAGATCTATCAGGCCGGCAACAAGCCTTGTAACGGCGTGGCAGGCGTGAACTGCTAC<br>TTCCCACTGCAGTCCTACGGCTTTAGGCCCACATACGGCGTGGGCCACCAGCCCTACAGAGTGGTG<br>GTGCTGAGCTTCGAACTGCTGCATGCCCCTGCCACAGTGTGCGGCCCTAAGAAAAGCACCAATCTC<br>GTGAAGAACAAATGCGTGAACTTCAACTTCAACGGCCTGACCGGCACCGGCGTGCTGACAGAGAGC<br>AACAAGAAGTTCCTGCCATTCCAGCAGTTTGGCCGGGATATCGCCGATACCACAGACGCCGTTAGA<br>GATCCCCAGACACTGGAAATCCTGGACATCACCCCTTGCAGCTTCGGCGGAGTGTCTGTGATCACC<br>CCTGGCACCAACACCAGCAATCAGGTGGCAGTGCTGTACCAGGGCGTGAACTGTACCGAAGTGCCC<br>GTGGCCATTCACGCCGATCAGCTGACACCTACATGGGGGTGTACTCCACCGGCAGCAATGTGITT<br>CAGACCAGAGCCGGCTGTCTGATCGGAGCCGAGTACGTGAACAATAGCTACGAGTGCGACATCCCC<br>ATCGGCGCTGGAATCTGCGCCAGCTACCAGACACAGACAAAGAGCCACCGGAGAGCCAGAAGCGTG<br>GCCAGCCAGAGCATCATTGCCTACACAATGTCTCTGGGCGCCGAGAACAGCGTGGCCTACTCCAAC<br>AACTCTATCGCTATCCCCACCAACTTCACCATCAGCGTGACCACAGAGATCCTGCCTGTGTCCATG<br>ACCAAGACCAGCGTGGACTGCACCATGTACATCTGCGGCGATTCCACCGAGTGCTCCAACCTGCTG<br>CTGCAGTACGGCAGCTTCTGCACCCAGCTGAAAAGAGCCCTGACAGGGATCGCCGTGGAACAGGAC<br>AAGAACACCCAAGAGGTGTTCGCCCAAGTGAAGCAGATCTACAAGACCCCTCCTATCAAGTACTTC<br>GGCGGCTTCAATTTCAGCCAGATTCTGCCCGATCCTAGCAAGCCCAGCAAGCGGAGCTTCATCGAG<br>GACCTGCTGTTCAACAAAGTGACACTGGCCGACGCCGGCTTCATCAAGCAGTATGGCGATTGTCTG<br>GGCGACATTGCCGCCAGGGATCTGATTTGCGCCCAGAAGTTTAACGGACTGACAGTGCTGCCTCCT<br>CTGCTGACCGATGAGATGATCGCCCAGTACACATCTGCCCTGCTGGCCGGCACAATCACAAGCGGC<br>TGGACATTTGGAGCAGGCGCCGCTCTGCAGATCCCCTTTGCTATGCAGATGGCCTACCGGTTCAAC<br>GGCATCGGAGTGACCCAGAATGTGCTGTACGAGAACCAGAAGCTGATCGCCAACCAGTTCAACAGC<br>GCCATCGGCAAGATCCAGGACAGCCTGAGCAGCACAGCAAGCGCCCTGGGAAAGCTGCAGGACGTG<br>GTCAACCACAATGCCCAGGCACTGAACACCCTGGTCAAGCAGCTGTCCTCCAAGTTCGGCGCCATC<br>AGCTCTGTGCTGAACGATATCCTGAGCAGACTGGACCCTCCTGAGGCCGAGGTGCAGATCGACAGA<br>CTGATCACAGGCAGACTGCAGAGCCTCCAGACATACGTGACCCAGCAGCTGATCAGAGCCGCCGAG<br>ATTAGAGCCTCTGCCAATCTGGCCGCCACCAAGATGTCTGAGTGTGTGCTGGGCCAGAGCAAGAGA<br>GTGGACTTTTGCGGCAAGGGCTACCACCTGATGAGCTTCCCTCAGTCTGCCCCTCACGGCGTGGTG<br>TTTCTGCACGTGACATATGTGCCCGCTCAAGAGAAGAATTTCACCACCGCTCCAGCCATCTGCCAC<br>GACGGCAAAGCCCACTTTCCTAGAGAAGGCGTGTTCGTGTCCAACGGCACCCATTGGTTCGTGACA<br>CAGCGGAACTTCTACGAGCCCCAGATCATCACCACCGACAACACCTTCGTGTCTGGCAACTGCGAC<br>GTCGTGATCGGCATTGTGAACAATACCGTGTACGACCCTCTGCAGCCCGAGCTGGACAGCTTCAAA<br>GAGGAACTGGACAAGTACTTTAAGAACCACACAAGCCCCGACGTGGACCTGGGCGATATCAGCGGA<br>ATCAATGCCAGCGTCGTGAACATCCAGAAAGAGATCGACCGGCTGAACGAGGTGGCCAAGAATCTG<br>AACGAGAGCCTGATCGACCTGCAAGAACTGGGGAAGTACGAGCAGTACATCAAGTGGCCCTGGTAC<br>ATCTGGCTGGGCTTTATCGCCGGACTGATTGCCATCGTGATGGTCACAATCATGCTGTGTTGCATG<br>ACCAGCTGCTGTAGCTGCCTGAAGGGCTGTTGTAGCTGTGGCAGCTGCTGCAAGTTCGACGAGGAC<br>GATTCTGAGCCCGTGCTGAAGGGCGTGAAACTGCACTACACATGATGA |
| 72 | Full length RNA construct sequence of RBP020.22 | AGAAUAAACUAGUAUUCUUCUGGUCCCCACAGACUCAGAGAGAACCCGCCACCAUGUUCGUGUUCC<br>UGGUGCUGCUGCCUCUGGUGUCCAGCCAGUGUGUGAACCUGAUCACCAGAACACAGUCAUACACCA<br>ACAGCUUUACCAGAGGCGUGUACUACCCCGACAAGGUGUUCAGAUCCAGCGUGCUGCACUCUACCC<br>AGGACCUGUUCCUGCCUUUCUUCAGCAACGUGACCUGGUUCCACGCCAUCUCCGGCACCAAUGGCA<br>CCAAGAGAUUCGACAACCCCGUGCUGCCCUUCAACGACGGGGUGUACUUUGCCAGCACCGAGAAGU<br>CCAACAUCAUCAGAGGCUGGAUCUUCGGCACCACACUGGACAGCAAGACCCAGAGCCUGCUGAUCG<br>UGAACAACGCCACCAACGUGGUCAUCAAAGUGUGCGAGUUCCAGUUCUGCAACGACCCCUUCCUGG<br>ACGUCUACUACCACAAGAACAACAAGAGCUGGAUGGAAAGCGAGUUCCGGGUGUACAGCAGCGCCA<br>ACAACUGCACCUUCGAGUACGUGUCCCAGCCUUUCCUGAUGGACCUGGAAGGCAAGCAGGGCAACU<br>UCAAGAACCUGCGCGAGUUCGUGUUUAAGAACAUCGACGGCUACUUCAAGAUCUACAGCAAGCACA<br>CCCCUAUCAACCUCGGCCGGGAUCUGCCUCAGGGCUUCUCUGCUCUGGAACCCCUGGUGGAUCUGC<br>CCAUCGGCAUCAACAUCACCCGGUUUCAGACACUGCUGGCCCUGCACAGAAGCUACCUGACACCUG<br>GCGAUAGCAGCAGCGGAUGGACAGCUGGUGCCGCCGCUUACUAUGUGGGCUACCUGCAGCCUAGAA<br>CCUUCCUGCUGAAGUACAACGAGAACGGCACCAUCACCGACGCCGUGGAUUGUGCUCUGGAUCCUC<br>UGAGCGAGACAAAGUGCACCCUGAAGUCCUUCACCGUGGAAAAGGGCAUCUACCAGACCAGCAACU<br>UCCGGGUGCAGCCCACCGAAUCCAUCGUGCGGUUCCCCAAUAUCACCAAUCUGUGCCCCUUCGACG<br>AGGUGUUCAAUGCCACCAGAUUCGCCUCUGUGUACGCCUGGAACCGGAAGCGGAUCAGCAAUUGCG<br>UGGCCGACUACUCCGUGCUGUACAACUUCGCCCCCUUCUUCGCAUUCAAGUGCUACGGCGUGUCCC<br>CUACCAAGCUGAACGACCUGUGCUUCACAAACGUGUACGCCGACAGCUUCGUGAUCCGGGGAAACG<br>AAGUGCGGCAGAUUGCCCCUGGACAGACAGGCAACAUCGCCGACUACAACUACAAGCUGCCCGACG<br>ACUUCACCGGCUGUGUGAUUGCCUGGAACAGCAACAAGCUGGACUCCAAAGUCGGCGGCAACUACA |

TABLE 8-continued

| Sequences of RBP020.22 (Omicron BA.4/BA.5-specific RNA vaccine) | | |
|---|---|---|
| SEQ ID NO. | Brief Description | Sequence |
| | | AUUACAGGUACCGGCUGUUCCGGAAGUCCAAUCUGAAGCCCUUCGAGCGGGACAUCUCCACCGAGA<br>UCUAUCAGGCCGGCAACAAGCCUUGUAACGGCGUGGCAGGCGUGAACUGCUACUUCCCACUGCAGU<br>CCUACGGCUUUAGGCCCACAUACGGCGUGGGCCACCAGCCCUACAGAGUGGUGGUGCUGAGCUUCG<br>AACUGCUGCAUGCCCCUGCCACAGUGUGCGGCCCUAAGAAAAGCACCAAUCUCGUGAAGAACAAAU<br>GCGUGAACUUCAACUUCAACGGCCUGACCGGCACCGGCGUGCUGACAGAGAGCAACAAGAAGUUCC<br>UGCCAUUCCAGCAGUUUGGCCGGGAUAUCGCCGAUACCACAGACGCCGUUAGAGAUCCCCAGACAC<br>UGGAAAUCCUGGACAUCACCCCUUGCAGCUUCGGCGGAGUGUCUGUGAUCACCCCUGGCACCAACA<br>CCAGCAAUCAGGUGGCAGUGCUGUACCAGGGCGUGAACUGUACCGAAGUGCCCGUGGCCAUUCACG<br>CCGAUCAGCUGACACCUACAUGGCGGGUGUACUCCACCGGCAGCAAUGUGUUUCAGACCAGAGCCG<br>GCUGUCUGAUCGGAGCCGAGUACGUGAACAAUAGCUACGAGUGCGACAUCCCCAUCGGCGCUGGAA<br>UCUGCGCCAGCUACCAGACACAGACAAAGAGCCACCGGAGAGCCAGAAGCGUGGCCAGCCAGAGCA<br>UCAUUGCCUACACAAUGUCUCUGGGCGCCGAGAACAGCGUGGCCUACUCCAACAACUCUAUCGCUA<br>UCCCCACCAACUUCACCAUCAGCGUGACCACAGAGAUCCUGCCUGUGUCCAUGACCAAGACCAGCG<br>UGGACUGCACCAUGUACAUCUGCGGCGAUUCCACCGAGUGCUCCAACCUGCUGCUGCAGUACGGCA<br>GCUUCUGCACCCAGCUGAAAAGAGCCCUGACAGGGAUCGCCGUGGAACAGGACAAGAACACCCAAG<br>AGGUGUUCGCCCAAGUGAAGCAGAUCUACAAGACCCCUCCUAUCAAGUACUUCGGCGGCUUCAAUU<br>UCAGCCAGAUUCUGCCCGAUCCUAGCAAGCCCAGCAAGCGGAGCUUCAUCGAGGACCUGCUGUUCA<br>ACAAAGUGACACUGGCCGACGCCGGCUUCAUCAAGCAGUAUGGCGAUUGUCUGGGCGACAUUGCCG<br>CCAGGGAUCUGAUUUGCGCCCAGAAGUUUAACGGACUGACAGUGCUGCCUCCUCUGCUGACCGAUG<br>AGAUGAUCGCCCAGUACACAUCUGCCCUGCUGGCCGGCACAAUCACAAGCGGCUGGACAUUUGGAG<br>CAGGCGCCGCUCUGCAGAUCCCCUUUGCUAUGCAGAUGGCCUACCGGUUCAACGGCAUCGGAGUGA<br>CCCAGAAUGUGCUGUACGAGAACCAGAAGCUGAUCGCCAACCAGUUCAACAGCGCCAUCGGCAAGA<br>UCCAGGACAGCCUGAGCAGCACAGCAAGCGCCCUGGGAAAGCUGCAGGACGUGGUCAACCACAAUG<br>CCCAGGCACUGAACACCCUGGUCAAGCAGCUGUCCUCCAAGUUCGGCGCCAUCAGCUCUGUGCUGA<br>ACGAUAUCCUGAGCAGACUGGACCCUCCUGAGGCCGAGGUGCAGAUCGACAGACUGAUCACAGGCA<br>GACUGCAGAGCCUCCAGACAUACGUGACCCAGCAGCUGAUCAGAGCCGCCGAGAUUAGAGCCUCUG<br>CCAAUCUGGCCGCCACCAAGAUGUCUGAGUGUGUGCUGGGCCAGAGCAAGAGAGUGGACUUUUGCG<br>GCAAGGGCUACCACCUGAUGAGCUUCCCUCAGUCUGCCCCUCACGGCGUGGUGUUUCUGCACGUGA<br>CAUAUGUGCCCGCUCAAGAGAAGAAUUUCACCACCGCUCCAGCCAUCUGCCACGACGGCAAAGCCC<br>ACUUUCCUAGAGAAGGCGUGUUCGUGUCCAACGGCACCCAUUGGUUCGUGACACAGCGGAACUUCU<br>ACGAGCCCCAGAUCAUCACCACCGACAACACCUUCGUGUCUGGCAACUGCGACGUCGUGAUCGGCA<br>UUGUGAACAAUACCGUGUACGACCCUCUGCAGCCCGAGCUGGACAGCUUCAAAGAGGAACUGGACA<br>AGUACUUUAAGAACCACACAAGCCCCGACGUGGACCUGGGCGAUAUCAGCGGAAUCAAUGCCAGCG<br>UCGUGAACAUCCAGAAAGAGAUCGACCGGCUGAACGAGGUGGCCAAGAAUCUGAACGAGAGCCUGA<br>UCGACCUGCAAGAACUGGGGAAGUACGAGCAGUACAUCAAGUGGCCCUGGUACAUCUGGCUGGGCU<br>UUAUCGCCGGACUGAUUGCCAUCGUGAUGGUCACAAUCAUGCUGUGUUGCAUGACCAGCUGCUGUA<br>GCUGCCUGAAGGGCUGUUGUAGCUGUGGCAGCUGCUGCAAGUUCGACGAGGACGAUUCUGAGCCCG<br>UGCUGAAGGGCGUGAAACUGCACUACACAUGAUGACUCGAGCUGGUACUGCAUGCACGCAAUGCUA<br>GCUGCCCCUUUCCCGUCCUGGGUACCCCGAGUCUCCCCCGACCUCGGGUCCCAGGUAUGCUCCCAC<br>CUCCACCUGCCCCACUCACCACCUCUGCUAGUUCCAGACACCUCCCAAGCACGCAGCAAUGCAGCU<br>CAAAACGCUUAGCCUAGCCACACCCCCACGGGAAACAGCAGUGAUUAACCUUUAGCAAUAAACGAA<br>AGUUUAACUAAGCUAUACUAACCCCAGGGUUGGUCAAUUUCGUGCCAGCCACACCCUGGAGCUAGC<br>AAAAAAAAAAAAAAAAAAAAAAAAAAAAAAGCAUAUGACUAAAAAAAAAAAAAAAAAAAAAAAAAA<br>AAAAAAAAAAAAAAAAAAAAAAAAAAAAAAAAAAAAAAAAAAAA |
| 73 | Full length DNA construct sequence of RBP020.22 | AGAATAAACTAGTATTCTTCTGGTCCCCACAGACTCAGAGAGAACCCGCCACCATGTTCGTGTTCC<br>TGGTGCTGCTGCCTCTGGTGTCCAGCCAGTGTGTGAACCTGATCACCAGAACACAGTCATACACCA<br>ACAGCTTTACCAGAGGCGTGTACTACCCCGACAAGGTGTTCAGATCCAGCGTGCTGCACTCTACCC<br>AGGACCTGTTCCTGCCTTTCTTCAGCAACGTGACCTGGTTCCACGCCATCTCCGGCACCAATGGCA<br>CCAAGAGATTCGACAACCCCGTGCTGCCCTTCAACGACGGGGTGTACTTTGCCAGCACCGAGAAGT<br>CCAACATCATCAGAGGCTGGATCTTCGGCACCACACTGGACAGCAAGACCCAGAGCCTGCTGATCG<br>TGAACAACGCCACCAACGTGGTCATCAAAGTGTGCGAGTTCCAGTTCTGCAACGACCCCTTCCTGG<br>ACGTCTACTACCACAAGAACAACAAGAGCTGGATGGAAAGCGAGTTCCGGGTGTACAGCAGCGCCA<br>ACAACTGCACCTTCGAGTACGTGTCCCAGCCTTTCCTGATGGACCTGGAAGGCAAGCAGGGCAACT<br>TCAAGAACCTGCGCGAGTTCGTGTTTAAGAACATCGACGGCTACTTCAAGATCTACAGCAAGCACA<br>CCCCTATCAACCTCGGCCGGGATCTGCCTCAGGGCTTCTCTGCTCTGGAACCCCTGGTGGATCTGC<br>CCATCGGCATCAACATCACCCGGTTTCAGACACTGCTGGCCCTGCACAGAAGCTACCTGACACCTG<br>GCGATAGCAGCAGCGGATGGACAGCTGGTGCCGCCGCTTACTATGTGGGCTACCTGCAGCCTAGAA<br>CCTTCCTGCTGAAGTACAACGAGAACGGCACCATCACCGACGCCGTGGATTGTGCTCTGGATCCTC<br>TGAGCGAGACAAAGTGCACCCTGAAGTCCTTCACCGTGGAAAAGGGCATCTACCAGACCAGCAACT<br>TCCGGGTGCAGCCCACCGAATCCATCGTGCGGTTCCCCAATATCACCAATCTGTGCCCCTTCGACG<br>AGGTGTTCAATGCCACCAGATTCGCCTCTGTGTACGCCTGGAACCGGAAGCGGATCAGCAATTGCG<br>TGGCCGACTACTCCGTGCTGTACAACTTCGCCCCCTTCTTCGCATTCAAGTGCTACGGCGTGTCCC<br>CTACCAAGCTGAACGACCTGTGCTTCACAAACGTGTACGCCGACAGCTTCGTGATCCGGGGAAACG<br>AAGTGCGGCAGATTGCCCCTGGACAGACAGGCAACATCGCCGACTACAACTACAAGCTGCCCGACG<br>ACTTCACCGGCTGTGTGATTGCCTGGAACAGCAACAAGCTGGACTCCAAAGTCGGCGGCAACTACA<br>ATTACAGGTACCGGCTGTTCCGGAAGTCCAATCTGAAGCCCTTCGAGCGGGACATCTCCACCGAGA<br>TCTATCAGGCCGGCAACAAGCCTTGTAACGGCGTGGCAGGCGTGAACTGCTACTTCCCACTGCAGT<br>CCTACGGCTTTAGGCCCACATACGGCGTGGGCCACCAGCCCTACAGAGTGGTGGTGCTGAGCTTCG<br>AACTGCTGCATGCCCCTGCCACAGTGTGCGGCCCTAAGAAAAGCACCAATCTCGTGAAGAACAAAT<br>GCGTGAACTTCAACTTCAACGGCCTGACCGGCACCGGCGTGCTGACAGAGAGCAACAAGAAGTTCC<br>TGCCATTCCAGCAGTTTGGCCGGGATATCGCCGATACCACAGACGCCGTTAGAGATCCCCAGACAC<br>TGGAAATCCTGGACATCACCCCTTGCAGCTTCGGCGGAGTGTCTGTGATCACCCCTGGCACCAACA<br>CCAGCAATCAGGTGGCAGTGCTGTACCAGGGCGTGAACTGTACCGAAGTGCCCGTGGCCATTCACG<br>CCGATCAGCTGACACCTACATGGCGGGTGTACTCCACCGGCAGCAATGTGTTTCAGACCAGAGCCG |

TABLE 8-continued

| Sequences of RBP020.22 (Omicron BA.4/BA.5-specific RNA vaccine) | | |
|---|---|---|
| SEQ ID NO. | Brief Description | Sequence |
| | | GCTGTCTGATCGGAGCCGAGTACGTGAACAATAGCTACGAGTGCGACATCCCCATCGGCGCTGGAA<br>TCTGCGCCAGCTACCAGACACAGACAAAGAGCCACCGGAGAGCCAGAAGCGTGGCCAGCCAGAGCA<br>TCATTGCCTACACAATGTCTCTGGGCGCCGAGAACAGCGTGGCCTACTCCAACAACTCTATCGCTA<br>TCCCCACCAACTTCACCATCAGCGTGACCACAGAGATCCTGCCTGTGTCCATGACCAAGACCAGCG<br>TGGACTGCACCATGTACATCTGCGGCGATTCCACCGAGTGCTCCAACCTGCTGCTGCAGTACGGCA<br>GCTTCTGCACCCAGCTGAAAAGAGCCCTGACAGGGATCGCCGTGGAACAGGACAAGAACACCCAAG<br>AGGTGTTCGCCCAAGTGAAGCAGATCTACAAGACCCCTCCTATCAAGTACTTCGGCGGCTTCAATT<br>TCAGCCAGATTCTGCCCGATCCTAGCAAGCCCAGCAAGCGGAGCTTCATCGAGGACCTGCTGTTCA<br>ACAAAGTGACACTGGCCGACGCCGGCTTCATCAAGCAGTATGGCGATTGTCTGGGCGACATTGCCG<br>CCAGGGATCTGATTTGCGCCCAGAAGTTTAACGGACTGACAGTGCTGCCTCCTCTGCTGACCGATG<br>AGATGATCGCCCAGTACACATCTGCCCTGCTGGCCGGCACAATCACAAGCGGCTGGACATTTGGAG<br>CAGGCGCCGCTCTGCAGATCCCCTTTGCTATGCAGATGGCCTACCGGTTCAACGGCATCGGAGTGA<br>CCCAGAATGTGCTGTACGAGAACCAGAAGCTGATCGCCAACCAGTTCAACAGCGCCATCGGCAAGA<br>TCCAGGACAGCCTGAGCAGCACAGCAAGCGCCCTGGGAAAGCTGCAGGACGTGGTCAACCACAATG<br>CCCAGGCACTGAACACCCTGGTCAAGCAGCTGTCCTCCAAGTTCGGCGCCATCAGCTCTGTGCTGA<br>ACGATATCCTGAGCAGACTGGACCCTCCTGAGGCCGAGGTGCAGATCGACAGACTGATCACAGGCA<br>GACTGCAGAGCCTCCAGACATACGTGACCCAGCAGCTGATCAGAGCCGCCGAGATTAGAGCCTCTG<br>CCAATCTGGCCGCCACCAAGATGTCTGAGTGTGTGCTGGGCCAGAGCAAGAGAGTGGACTTTTGCG<br>GCAAGGGCTACCACCTGATGAGCTTCCCTCAGTCTGCCCCTCACGGCGTGGTGTTTCTGCACGTGA<br>CATATGTGCCCGCTCAAGAGAAGAATTTCACCACCGCTCCAGCCATCTGCCACGACGGCAAAGCCC<br>ACTTTCCTAGAGAAGGCGTGTTCGTGTCCAACGGCACCCATTGGTTCGTGACACAGCGGAACTTCT<br>ACGAGCCCCAGATCATCACCACCGACAACACCTTCGTGTCTGGCAACTGCGACGTCGTGATCGGCA<br>TTGTGAACAATACCGTGTACGACCCTCTGCAGCCCGAGCTGGACAGCTTCAAAGAGGAACTGGACA<br>AGTACTTTAAGAACCACACAAGCCCCGACGTGGACCTGGGCGATATCAGCGGAATCAATGCCAGCG<br>TCGTGAACATCCAGAAAGAGATCGACCGGCTGAACGAGGTGGCCAAGAATCTGAACGAGAGCCTGA<br>TCGACCTGCAAGAACTGGGGAAGTACGAGCAGTACATCAAGTGGCCCTGGTACATCTGGCTGGGCT<br>TTATCGCCGGACTGATTGCCATCGTGATGGTCACAATCATGCTGTGTTGCATGACCAGCTGCTGTA<br>GCTGCCTGAAGGGCTGTTGTAGCTGTGGCAGCTGCTGCAAGTTCGACGAGGACGATTCTGAGCCCG<br>TGCTGAAGGGCGTGAAACTGCACTACACATGATGACTCGAGCTGGTACTGCATGCACGCAATGCTA<br>GCTGCCCCTTTCCCGTCCTGGGTACCCCGAGTCTCCCCCGACCTCGGGTCCCAGGTATGCTCCCAC<br>CTCCACCTGCCCCACTCACCACCTCTGCTAGTTCCAGACACCTCCCAAGCACGCAGCAATGCAGCT<br>CAAAACGCTTAGCCTAGCCACACCCCCACGGGAAACAGCAGTGATTAACCTTTAGCAATAAACGAA<br>AGTTTAACTAAGCTATACTAACCCCAGGGTTGGTCAATTTCGTGCCAGCCACACCCTGGAGCTAGC<br>AAAAAAAAAAAAAAAAAAAAAAAAAAAAAAGCATATGACTAAAAAAAAAAAAAAAAAAAAAAAAAA<br>AAAAAAAAAAAAAAAAAAAAAAAAAAAAAAAAAAAAAAAAAAAA |

TABLE 9

| Description of RBP020.22 (Omicron BA.4/BA.5-specific RNA vaccine) as shown in Table 8 above (positioning of amino acid mutations shown relative to SEQ ID NO: 1) | | |
|---|---|---|
| Construct Antigen | Omicron BA.4/BA.5 P2 P2-mutated full spike protein | |
| Changes | Amino Acid[a] | mRNA Nucleotides (location) |
| Furin site | RRAR(SEQ ID NO: 136) | CGGAGAGCCAGA (SEQ ID NO: 137) (2082-2093) |
| Proline | K986P | CCU (3000-3002) |
| | V987P | CCU (3003-3005) |
| Lineage | T191 | AUC (108-110) |
| | L24del | / |
| | P25del | / |
| | P26del | / |
| | A27S | UCA (123-125) |
| | H69del | / |
| | V70del | / |
| | G142D | GAC (462-464) |
| | V213G | GGC (675-677) |
| | G339D | GAC (1053-1055) |
| | S371F | UUC (1149-1151) |
| | S373P | CCC (1155-1157) |
| | S375F | UUC (1161-1163) |
| | T376A | GCA (1164-1166) |
| | D405N | AAC (1251-1253) |
| | K417N | AAC (1287-1289) |
| | N440K | AAG (1356-1358) |

TABLE 9-continued

Description of RBP020.22 (Omicron BA.4/BA.5-specific RNA vaccine) as shown in Table 8 above (positioning of amino acid mutations shown relative to SEQ ID NO: 1)

| Construct Antigen | Omicron BA.4/BA.5 P2 P2-mutated full spike protein | |
|---|---|---|
| Changes | Amino Acid[a] | mRNA Nucleotides (location) |
| | L452R | AGG (1392-1394) |
| | S477N | AAC (1467-1469) |
| | T478K | AAG (1470-1472) |
| | E484A | GCA (1488-1490) |
| | F486V | GUG (1494-1496) |
| | Q498R | AGG (1530-1532) |
| | N501Y | UAC (1539-1541) |
| | Y505H | CAC (1551-1553) |
| | D614G | GGC (1878-1880) |
| | H655Y | UAC (2001-2003) |
| | N679K | AAG (2073-2075) |
| | P681H | CAC (2079-2081) |
| | N764K | AAA (2328-2330) |
| | D796Y | UAC (2424-2426) |
| | Q954H | CAC (2898-2900) |
| | N969K | AAG (2943-2945) |

TABLE 10

Sequence of one embodiment of Omicron BA.4/BA.5-specific RNA vaccine

| SEQ ID NO. | Brief Description | Sequence |
|---|---|---|
| 74 | Amino acid sequence of RNA-encoded SARS-CoV-2 S protein from an Omicron BA.4/BA.5 variant (with PRO mutations at positions corresponding to K986P and V987P of SEQ ID NO: 1; i.e., PRO mutations at positions 981 and 982 of SEQ ID NO: 74) | MFVFLVLLPLVSSQCVNLITRTQSYTNSFTRGVYYPDKVFRSSVLHSTQDLFLPFFSNVTWFHAIS<br>GTNGTKRFDNPVLPFNDGVYFASTEKSNIIRGWIFGTTLDSKTQSLLIVNNATNVVIKVCEFQFCN<br>DPFLDVYYHKNNKSWMESEFRVYSSANNCTFEYVSQPFLMDLEGKQGNFKNLREFVFKNIDGYFKI<br>YSKHTPINLGRDLPQGFSALEPLVDLPIGINITRFQTLLALHRSYLTPGDSSSGWTAGAAAYYVGY<br>LQPRTFLLKYNENGTITDAVDCALDPLSETKCTLKSFTVEKGIYQTSNFRVQPTESIVRFPNITNL<br>CPFDEVENATRFASVYAWNRKRISNCVADYSVLYNFAPFFAFKCYGVSPTKLNDLCFTNVYADSFV<br>IRGNEVSQIAPGQTGNIADYNYKLPDDFTGCVIAWNSNKLDSKVGGNYNYRYRLFRKSNLKPFERD<br>ISTEIYQAGNKPCNGVAGVNCYFPLQSYGFRPTYGVGHQPYRVVVLSFELLHAPATVCGPKKSTNL<br>VKNKCVNFNFNGLTGTGVLTESNKKELPFQQFGRDIADTTDAVRDPQTLEILDITPCSFGGVSVIT<br>PGTNTSNQVAVLYQGVNCTEVPVAIHADQLTPTWRVYSTGSNVFQTRAGCLIGAEYVNNSYECDIP<br>IGAGICASYQTQTKSHRRARSVASQSIIAYTMSLGAENSVAYSNNSIAIPTNETISVTTEILPVSM<br>TKTSVDCTMYICGDSTECSNELLQYGSFCTQLKRALTGIAVEQDKNTQEVFAQVKQLYKTPPIKYF<br>GGFNFSQILPDPSKPSKRSFIEDLLENKVTLADAGFIKQYGDCLGDIAARDLICAQKENGLTVLPP<br>LLTDEMIAQYTSALLAGTITSGWTFGAGAALQIPFAMQMAYRENGIGVTQNVLYENQKLIANQFNS<br>AIGKIQDSLSSTASALGKLQDVVNHNAQALNTLVKQLSSKFGAISSVLNDILSRLDPPEAEVQIDR<br>LITGRLQSLQTYVTQQLIRAAEIRASANLAATKMSECVLGQSKRVDFCGKGYHLMSFPQSAPHGVV<br>FLHVTYVPAQEKNETTAPAICHDGKAHFPREGVEVSNGTHWFVTQRNFYEPQIITTDNTFVSGNCD<br>VVIGIVNNTVYDPLQPELDSFKEELDKYFKNHTSPDVDLGDISGINASVVNIQKEIDRLNEVAKNL<br>NESLIDLQELGKYEQYIKWPWYIWLGFIAGLIAIVMVTIMLCCMTSCCSCLKGCCSCGSCCKFDED<br>DSEPVLKGVKLHYT |
| 75 | RNA sequence encoding a SARS-CoV-2 S protein from an Omicron BA.4/BA.5 variant (with proline residues at positions corresponding to K986P and V987P of SEQ ID NO: 1) | AUGUUCGUGUUCCUGGUGCUGCUGCCUCUGGUGUCCAGCCAGUGUGUGAACCUGAUCACCAGAACA<br>CAGAGCUACACCAACAGCUUUACCAGAGGCGUGUACUACCCCGACAAGGUGUUCAGAUCCAGCGUG<br>CUGCACUCUACCCAGGACCUGUUCCUGCCUUUCUUCAGCAACGUGACCUGGUUCCACGCCAUCUCC<br>GGCACCAAUGGCACCAAGAGAUUCGACAACCCCGUGCUGCCCUUCAACGACGGGGUGUACUUUGCC<br>AGCACCGAGAAGUCCAACAUCAUCAGAGGCUGGAUCUUCGGCACCACACUGGACAGCAAGACCCAG<br>AGCCUGCUGAUCGUGAACAACGCCACCAACGUGGUCAUCAAAGUGUGCGAGUUCCAGUUCUGCAAC<br>GACCCCUUCCUGGACGUGUACUACCACAAGAACAACAAGAGCUGGAUGGAAAGCGAGUUCCGGGUG<br>UACAGCAGCGCCAACAACUGCACCUUCGAGUACGUGUCCCAGCCUUUCCUGAUGGACCUGGAAGGC<br>AAGCAGGGCAACUUCAAGAACCUGCGCGAGUUCGUGUUUAAGAACAUCGACGGCUACUUCAAGAUC<br>UACAGCAAGCACACCCCUAUCAACCUCGGCCGGGAUCUGCCUCAGGGCUUCUCUGCUCUGGAACCC<br>CUGGUGGAUCUGCCCAUCGGCAUCAACAUCACCCGGUUUCAGACACUGCUGGCCCUGCACAGAAGC<br>UACCUGACACCUGGCGAUAGCAGCAGCGGAUGGACAGCUGGUGCCGCCGCUUACUAUGUGGGCUAC<br>CUGCAGCCUAGAACCUUCCUGCUGAAGUACAACGAGAACGGCACCAUCACCGACGCCGUGGAUUGU<br>GCUCUGGAUCCUCUGAGCGAGACAAAGUGCACCCUGAAGUCCUUCACCGUGGAAAAGGGCAUCUAC<br>CAGACCAGCAACUUCCGGGUGCAGCCCACCGAAUCCAUCGUGCGGUUCCCCAAUAUCACCAAUCUG<br>UGCCCCUUCGACGAGGUGUUCAAUGCCACCAGAUUCGCCUCUGUGUACGCCUGGAACCGGAAGCGG<br>AUCAGCAAUUGCGUGGCCGACUACUCCGUGCUGUACAACUUCGCCCCCUUCUUCGCCUUCAAGUGC<br>UACGGCGUGUCCCCUACCAAGCUGAACGACCUGUGCUUCACAAACGUGUACGCCGACAGCUUCGUG<br>AUCCGGGGAAACGAAGUGAGCCAGAUUGCCCCUGGACAGACAGGCAACAUCGCCGACUACAACUAC<br>AAGCUGCCCGACGACUUCACCGGCUGUGUGAUUGCCUGGAACAGCAACAAGCUGGACUCCAAAGUC<br>GGCGGCAACUACAAUUACAGGUACCGGCUGUUCCGGAAGUCCAAUCUGAAGCCCUUCGAGCGGGAC<br>AUCUCCACCGAGAUCUAUCAGGCCGGCAACAAGCCUUGUAACGGCGUGGCCGGCGUGAACUGCUAC |

TABLE 10-continued

| Sequence of one embodiment of Omicron BA.4/BA.5-specific RNA vaccine | | |
|---|---|---|
| SEQ ID NO. | Brief Description | Sequence |
| | | UUCCCACUGCAGUCCUACGGCUUUAGGCCCACAUAUGGCGUGGGCCAUCAGCCCUACAGAGUGGUG<br>GUGCUGAGCUUCGAACUGCUGCAUGCCCCUGCCACAGUGUGCGGCCCUAAGAAAAGCACCAAUCUC<br>GUGAAGAACAAAUGCGUGAACUUCAACUUCAACGGCCUGACCGGCACCGGCGUGCUGACAGAGAGC<br>AACAAGAAGUUCCUGCCAUUCCAGCAGUUUGGCCGGGAUAUCGCCGAUACCACAGACGCCGUUAGA<br>GAUCCCCAGACACUGGAAAUCCUGGACAUCACCCCUUGCAGCUUCGGCGGAGUGUCUGUGAUCACC<br>CCUGGCACCAACACCAGCAAUCAGGUGGCAGUGCUGUACCAGGGCGUGAACUGUACCGAAGUGCCC<br>GUGGCCAUUCACGCCGAUCAGCUGACACCUACAUGGCGGGUGUACUCCACCGGCAGCAAUGUGUUU<br>CAGACCAGAGCCGGCUGUCUGAUCGGAGCCGAGUACGUGAACAAUAGCUACGAGUGCGACAUCCCC<br>AUCGGCGCUGGAAUCUGCGCCAGCUACCAGACACAGACAAAGAGCCACCGGAGAGCCAGAAGCGUG<br>GCCAGCCAGAGCAUCAUUGCCUACACAAUGUCUCUGGGCGCCGAGAACAGCGUGGCCUACUCCAAC<br>AACUCUAUCGCUAUCCCCACCAACUUCACCAUCAGCGUGACCACAGAGAUCCUGCCUGUGUCCAUG<br>ACCAAGACCAGCGUGGACUGCACCAUGUACAUCUGCGGCGAUUCCACCGAGUGCUCCAACCUGCUG<br>CUGCAGUACGGCAGCUUCUGCACCCAGCUGAAGAGAGCCCUGACAGGGAUCGCCGUGGAACAGGAC<br>AAGAACACCCAAGAGGUGUUCGCCCAAGUGAAGCAGAUCUACAAGACCCCUCCUAUCAAGUACUUC<br>GGCGGCUUCAAUUUCAGCCAGAUUCUGCCCGAUCCUAGCAAGCCCAGCAAGCGGAGCUUCAUCGAG<br>GACCUGCUGUUCAACAAAGUGACACUGGCCGACGCCGGCUUCAUCAAGCAGUAUGGCGAUUGUCUG<br>GGCGACAUUGCCGCCAGGGAUCUGAUUUGCGCCCAGAAGUUUAACGGACUGACAGUGCUGCCUCCU<br>CUGCUGACCGAUGAGAUGAUCGCCCAGUACACAUCUGCCCUGCUGGCCGGCACAAUCACAAGCGGC<br>UGGACAUUUGGAGCAGGCGCCGCUCUGCAGAUCCCCUUUGCUAUGCAGAUGGCCUACCGGUUCAAC<br>GGCAUCGGAGUGACCCAGAAUGUGCUGUACGAGAACCAGAAGCUGAUCGCCAACCAGUUCAACAGC<br>GCCAUCGGCAAGAUCCAGGACAGCCUGAGCAGCACAGCAAGCGCCCUGGGAAAGCUGCAGGACGUG<br>GUCAACCACAAUGCCCAGGCACUGAACACCCUGGUCAAGCAGCUGUCCUCCAAGUUCGGCGCCAUC<br>AGCUCUGUGCUGAACGAUAUCCUGAGCAGACUGGACCCUCCUGAGGCCGAGGUGCAGAUCGACAGA<br>CUGAUCACAGGCAGACUGCAGAGCCUCCAGACAUACGUGACCCAGCAGCUGAUCAGAGCCGCCGAG<br>AUUAGAGCCUCUGCCAAUCUGGCCGCCACCAAGAUGUCUGAGUGUGUGCUGGGCCAGAGCAAGAGA<br>GUGGACUUUUGCGGCAAGGGCUACCACCUGAUGAGCUUCCCUCAGUCUGCCCCUCACGGCGUGGUG<br>UUUCUGCACGUGACAUAUGUGCCCGCUCAAGAGAAGAAUUUCACCACCGCUCCAGCCAUCUGCCAC<br>GACGGCAAAGCCCACUUUCCUAGAGAAGGCGUGUUCGUGUCCAACGGCACCCAUUGGUUCGUGACA<br>CAGCGGAACUUCUACGAGCCCCAGAUCAUCACCACCGACAACACCUUCGUGUCUGGCAACUGCGAC<br>GUCGUGAUCGGCAUUGUGAACAAUACCGUGUACGACCCUCUGCAGCCCGAGCUGGACAGCUUCAAA<br>GAGGAACUGGACAAGUACUUUAAGAACCACACAAGCCCCGACGUGGACCUGGGCGAUAUCAGCGGA<br>AUCAAUGCCAGCGUCGUGAACAUCCAGAAAGAGAUCGACCGGCUGAACGAGGUGGCCAAGAAUCUG<br>AACGAGAGCCUGAUCGACCUGCAAGAACUGGGGAAGUACGAGCAGUACAUCAAGUGGCCCUGGUAC<br>AUCUGGCUGGGCUUUAUCGCCGGACUGAUUGCCAUCGUGAUGGUCACAAUCAUGCUGUGUUGCAUG<br>ACCAGCUGCUGUAGCUGCCUGAAGGGCUGUUGUAGCUGUGGCAGCUGCUGCAAGUUCGACGAGGAC<br>GAUUCUGAGCCCGUGCUGAAGGGCGUGAAACUGCACUACACAUGAUGA |
| 76 | DNA sequence encoding a SARS-CoV-2 S protein from an Omicron BA.4/BA.5 variant (with proline residues at positions corresponding to K986P and V987P of SEQ ID NO: 1) | ATGTTCGTGTTCCTGGTGCTGCTGCCTCTGGTGTCCAGCCAGTGTGTGAACCTGATCACCAGAACA<br>CAGAGCTACACCAACAGCTTTACCAGAGGCGTGTACTACCCCGACAAGGTGTTCAGATCCAGCGTG<br>CTGCACTCTACCCAGGACCTGTTCCTGCCTTTCTTCAGCAACGTGACCTGGTTCCACGCCATCTCC<br>GGCACCAATGGCACCAAGAGATTCGACAACCCCGTGCTGCCCTTCAACGACGGGGTGTACTTTGCC<br>AGCACCGAGAAGTCCAACATCATCAGAGGCTGGATCTTCGGCACCACACTGGACAGCAAGACCCAG<br>AGCCTGCTGATCGTGAACAACGCCACCAACGTGGTCATCAAAGTGTGCGAGTTCCAGTTCTGCAAC<br>GACCCCTTCCTGGACGTGTACTACCACAAGAACAACAAGAGCTGGATGGAAAGCGAGTTCCGGGTG<br>TACAGCAGCGCCAACAACTGCACCTTCGAGTACGTGTCCCAGCCTTTCCTGATGGACCTGGAAGGC<br>AAGCAGGGCAACTTCAAGAACCTGCGCGAGTTCGTGTTTAAGAACATCGACGGCTACTTCAAGATC<br>TACAGCAAGCACACCCCTATCAACCTCGGCCGGGATCTGCCTCAGGGCTTCTCTGCTCTGGAACCC<br>CTGGTGGATCTGCCCATCGGCATCAACATCACCCGGTTTCAGACACTGCTGGCCCTGCACAGAAGC<br>TACCTGACACCTGGCGATAGCAGCAGCGGATGGACAGCTGGTGCCGCCGCTTACTATGTGGGCTAC<br>CTGCAGCCTAGAACCTTCCTGCTGAAGTACAACGAGAACGGCACCATCACCGACGCCGTGGATTGT<br>GCTCTGGATCCTCTGAGCGAGACAAAGTGCACCCTGAAGTCCTTCACCGTGGAAAAGGGCATCTAC<br>CAGACCAGCAACTTCCGGGTGCAGCCCACCGAATCCATCGTGCGGTTCCCCAATATCACCAATCTG<br>TGCCCCTTCGACGAGGTGTTCAATGCCACCAGATTCGCCTCTGTGTACGCCTGGAACCGGAAGCGG<br>ATCAGCAATTGCGTGGCCGACTACTCCGTGCTGTACAACTTCGCCCCCTTCTTCGCCTTCAAGTGC<br>TACGGCGTGTCCCCTACCAAGCTGAACGACCTGTGCTTCACAAACGTGTACGCCGACAGCTTCGTG<br>ATCCGGGGAAACGAAGTGAGCCAGATTGCCCCTGGACAGACAGGCAACATCGCCGACTACAACTAC<br>AAGCTGCCCGACGACTTCACCGGCTGTGTGATTGCCTGGAACAGCAACAAGCTGGACTCCAAAGTC<br>GGCGGCAACTACAATTACAGGTACCGGCTGTTCCGGAAGTCCAATCTGAAGCCCTTCGAGCGGGAC<br>ATCTCCACCGAGATCTATCAGGCCGGCAACAAGCCTTGTAACGGCGTGGCCGGCGTGAACTGCTAC<br>TTCCCACTGCAGTCCTACGGCTTTAGGCCCACATATGGCGTGGGCCATCAGCCCTACAGAGTGGTG<br>GTGCTGAGCTTCGAACTGCTGCATGCCCCTGCCACAGTGTGCGGCCCTAAGAAAAGCACCAATCTC<br>GTGAAGAACAAATGCGTGAACTTCAACTTCAACGGCCTGACCGGCACCGGCGTGCTGACAGAGAGC<br>AACAAGAAGTTCCTGCCATTCCAGCAGTTTGGCCGGGATATCGCCGATACCACAGACGCCGTTAGA<br>GATCCCCAGACACTGGAAATCCTGGACATCACCCCTTGCAGCTTCGGCGGAGTGTCTGTGATCACC<br>CCTGGCACCAACACCAGCAATCAGGTGGCAGTGCTGTACCAGGGCGTGAACTGTACCGAAGTGCCC<br>GTGGCCATTCACGCCGATCAGCTGACACCTACATGGCGGGTGTACTCCACCGGCAGCAATGTGTTT<br>CAGACCAGAGCCGGCTGTCTGATCGGAGCCGAGTACGTGAACAATAGCTACGAGTGCGACATCCCC<br>ATCGGCGCTGGAATCTGCGCCAGCTACCAGACACAGACAAAGAGCCACCGGAGAGCCAGAAGCGTG<br>GCCAGCCAGAGCATCATTGCCTACACAATGTCTCTGGGCGCCGAGAACAGCGTGGCCTACTCCAAC<br>AACTCTATCGCTATCCCCACCAACTTCACCATCAGCGTGACCACAGAGATCCTGCCTGTGTCCATG<br>ACCAAGACCAGCGTGGACTGCACCATGTACATCTGCGGCGATTCCACCGAGTGCTCCAACCTGCTG<br>CTGCAGTACGGCAGCTTCTGCACCCAGCTGAAGAGAGCCCTGACAGGGATCGCCGTGGAACAGGAC<br>AAGAACACCCAAGAGGTGTTCGCCCAAGTGAAGCAGATCTACAAGACCCCTCCTATCAAGTACTTC<br>GGCGGCTTCAATTTCAGCCAGATTCTGCCCGATCCTAGCAAGCCCAGCAAGCGGAGCTTCATCGAG |

TABLE 10-continued

| Sequence of one embodiment of Omicron BA.4/BA.5-specific RNA vaccine | | |
|---|---|---|
| SEQ ID NO. | Brief Description | Sequence |
| | | GACCTGCTGTTCAACAAAGTGACACTGGCCGACGCCGGCTTCATCAAGCAGTATGGCGATTGTCTG GGCGACATTGCCGCCAGGGATCTGATTTGCGCCCAGAAGTTTAACGGACTGACAGTGCTGCCTCCT CTGCTGACCGATGAGATGATCGCCCAGTACACATCTGCCCTGCTGGCCGGCACAATCACAAGCGGC TGGACATTTGGAGCAGGCGCCGCTCTGCAGATCCCCTTTGCTATGCAGATGGCCTACCGGTTCAAC GGCATCGGAGTGACCCAGAATGTGCTGTACGAGAACCAGAAGCTGATCGCCAACCAGTTCAACAGC GCCATCGGCAAGATCCAGGACAGCCTGAGCAGCACAGCAAGCGCCCTGGGAAAGCTGCAGGACGTG GTCAACCACAATGCCCAGGCACTGAACACCCTGGTCAAGCAGCTGTCCTCCAAGTTCGGCGCCATC AGCTCTGTGCTGAACGATATCCTGAGCAGACTGGACCCTCCTGAGGCCGAGGTGCAGATCGACAGA CTGATCACAGGCAGACTGCAGAGCCTCCAGACATACGTGACCCAGCAGCTGATCAGAGCCGCCGAG ATTAGAGCCTCTGCCAATCTGGCCGCCACCAAGATGTCTGAGTGTGTGCTGGGCCAGAGCAAGAGA GTGGACTTTTGCGGCAAGGGCTACCACCTGATGAGCTTCCCTCAGTCTGCCCCTCACGGCGTGGTG TTTCTGCACGTGACATATGTGCCCGCTCAAGAGAAGAATTTCACCACCGCTCCAGCCATCTGCCAC GACGGCAAAGCCCACTTTCCTAGAGAAGGCGTGTTCGTGTCCAACGGCACCCATTGGTTCGTGACA CAGCGGAACTTCTACGAGCCCCAGATCATCACCACCGACAACACCTTCGTGTCTGGCAACTGCGAC GTCGTGATCGGCATTGTGAACAATACCGTGTACGACCCTCTGCAGCCCGAGCTGGACAGCTTCAAA GAGGAACTGGACAAGTACTTTAAGAACCACACAAGCCCCGACGTGGACCTGGGCGATATCAGCGGA ATCAATGCCAGCGTCGTGAACATCCAGAAAGAGATCGACCGGCTGAACGAGGTGGCCAAGAATCTG AACGAGAGCCTGATCGACCTGCAAGAACTGGGGAAGTACGAGCAGTACATCAAGTGGCCCTGGTAC ATCTGGCTGGGCTTTATCGCCGGACTGATTGCCATCGTGATGGTCACAATCATGCTGTGTTGCATG ACCAGCTGCTGTAGCTGCCTGAAGGGCTGTTGTAGCTGTGGCAGCTGCTGCAAGTTCGACGAGGAC GATTCTGAGCCCGTGCTGAAGGGCGTGAAACTGCACTACACATGATGA |

TABLE 11

| Sequence of one embodiment of Omicron BA.4/BA.5-specific RNA vaccine | | |
|---|---|---|
| SEQ ID NO. | Brief Description | Sequence |
| 77 | Amino acid sequence of RNA-encoded SARS-CoV-2 S protein from an Omicron BA.4/BA.5 variant (with PRO mutations at positions corresponding to K986P and V987P of SEQ ID NO: 1; i.e., PRO mutations at positions 981 and 982 of SEQ ID NO: 77) | MFVFLVLLPLVSSQCVNLITRTQSYTNSFTRGVYYPDKVFRSSVLHSTQDLFLPFFSNVTWFHAIS GTNGTKRFDNPVLPFNDGVYFASTEKSNIIRGWIFGTTLDSKTQSLLIVNNATNVVIKVCEFQFCN DPFLDVYYHKNNKSWMESEFRVYSSANNCTFEYVSQPFLMDLEGKQGNFKNLREFVFKNIDGYFKI YSKHTPINLGRDLPQGFSALEPLVDLPIGINITREQTLLALHRSYLTPGDSSSGWTAGAAAYYVGY LQPRTFLLKYNENGTITDAVDCALDPLSETKCTLKSFTVEKGIYQTSNERVQPTESIVRFPNITNL CPFDEVFNATRFASVYAWNRKRISNCVADYSVLYNFAPFFAFKCYGVSPTKLNDLCFTNVYADSFV IRGNEVRQIAPGQTGNIADYNYKLPDDFTGCVIAWNSNKLDSKVGGNYNYRYRLFRKSNLKPFERD ISTEIYQAGNKPCNGVAGVNCYFPLQSYGFRPTYGVGHQPYRVVVLSFELLHAPATVCGPKKSTNL VKNKCVNFNFNGLTGTGVLTESNKKFLPFQQFGRDIADTTDAVRDPQTLEILDITPCSFGGVSVIT PGTNTSNQVAVLYQGVNCTEVPVAIHADQLTPTWRVYSTGSNVFQTRAGCLIGAEYVNNSYECDIP IGAGICASYQTQTKSHRRARSVASQSIIAYTMSLGAENSVAYSNNSIAIPTNFTISVTTEILPVSM TKTSVDCTMYICGDSTECSNLLLQYGSFCTQLKRALTGIAVEQDKNTQEVFAQVKQIYKTPPIKYF GGFNFSQILPDPSKPSKRSFIEDLLFNKVTLADAGFIKQYGDCLGDIAARDLICAQKENGLTVLPP LLTDEMIAQYTSALLAGTITSGWTFGAGAALQIPFAMQMAYRENGIGVTQNVLYENQKLIANQFNS AIGKIQDSLSSTASALGKLQDVVNHNAQALNTLVKQLSSKFGAISSVLNDILSRLDPPEAEVQIDR LITGRLQSLQTYVTQQLIRAAEIRASANLAATKMSECVLGQSKRVDFCGKGYHLMSFPQSAPHGVV FLHVTYVPAQEKNETTAPAICHDGKAHFPREGVEVSNGTHWFVTQRNFYEPQIITTDNTFVSGNCD VVIGIVNNTVYDPLQPELDSFKEELDKYFKNHTSPDVDLGDISGINASVVNIQKEIDRLNEVAKNL NESLIDLQELGKYEQYIKWPWYIWLGFIAGLIAIVMVTIMLCCMTSCCSCLKGCCSCGSCCKEDED DSEPVLKGVKLHYT |
| 78 | RNA sequence encoding a SARS-CoV-2 S protein from an Omicron BA.4/BA.5 variant | AUGUUCGUGUUCCUGGUGCUGCUGCCUCUGGUGUCCAGCCAGUGUGUGAACCUGAUCACCAGAACA CAGUCAUACACCAACAGCUUUACCAGAGGCGUGUACUACCCCGACAAGGUGUUCAGAUCCAGCGUG CUGCACUCUACCCAGGACCUGUUCCUGCCUUUCUUCAGCAACGUGACCUGGUUCCACGCCAUCUCC GGCACCAAUGGCACCAAGAGAUUCGACAACCCCGUGCUGCCCUUCAACGACGGGGUGUACUUUGCC AGCACCGAGAAGUCCAACAUCAUCAGAGGCUGGAUCUUCGGCACCACACUGGACAGCAAGACCCAG AGCCUGCUGAUCGUGAACAACGCCACCAACGUGGUCAUCAAAGUGUGCGAGUUCCAGUUCUGCAAC GACCCCUUCCUGGACGUCUACUACCACAAGAACAACAAGAGCUGGAUGGAAAGCGAGUUCCGGGUG UACAGCAGCGCCAACAACUGCACCUUCGAGUACGUGUCCCAGCCUUUCCUGAUGGACCUGGAAGGC AAGCAGGGCAACUUCAAGAACCUGCGCGAGUUCGUGUUUAAGAACAUCGACGGCUACUUCAAGAUC UACAGCAAGCACACCCCUAUCAACCUCGGCCGGGAUCUGCCUCAGGGCUUCUCUGCUCUGGAACCC CUGGUGGAUCUGCCCAUCGGCAUCAACAUCACCCGGUUUCAGACACUGCUGGCCCUGCACAGAAGC UACCUGACACCUGGCGAUAGCAGCAGCGGAUGGACAGCUGGUGCCGCCGCUUACUAUGUGGGCUAC CUGCAGCCUAGAACCUUCCUGCUGAAGUACAACGAGAACGGCACCAUCACCGACGCCGUGGAUUGU GCUCUGGAUCCUCUGAGCGAGACAAAGUGCACCCUGAAGUCCUUCACCGUGGAAAAGGGCAUCUAC CAGACCAGCAACUUCCGGGUGCAGCCCACCGAAUCCAUCGUGCGGUUCCCCAAUAUCACCAAUCUG UGCCCCUUCGACGAGGUGUUCAAUGCCACCAGAUUCGCCUCUGUGUACGCCUGGAACCGGAAGCGG AUCAGCAAUUGCGUGGCCGACUACUCCGUGCUGUACAACUUCGCCCCCUUCUUCGCAUUCAAGUGC UACGGCGUGUCCCCUACCAAGCUGAACGACCUGUGCUUCACAAACGUGUACGCCGACAGCUUCGUG AUCCGGGGAAACGAAGUGCGGCAGAUUGCCCCUGGACAGACAGGCAACAUCGCCGACUACAACUAC AAGCUGCCCGACGACUUCACCGGCUGUGUGAUUGCCUGGAACAGCAACAAGCUGGACUCCAAAGUC |

TABLE 11-continued

Sequence of one embodiment of Omicron BA.4/BA.5-specific RNA vaccine

| SEQ ID NO. | Brief Description | Sequence |
| --- | --- | --- |
| | | GGCGGCAACUACAAUUACAGGUACCGGCUGUUCCGGAAGUCCAAUCUGAAGCCCUUCGAGCGGGAC<br>AUCUCCACCGAGAUCUAUCAGGCCGGCAACAAGCCUUGUAACGGCGUGGCAGGCGUGAACUGCUAC<br>UUCCCACUGCAGUCCUACGGCUUUAGGCCCACAUACGGCGUGGGCCACCAGCCCUACAGAGUGGUG<br>GUGCUGAGCUUCGAACUGCUGCAUGCCCCUGCCACAGUGUGCGGCCCUAAGAAAAGCACCAAUCUC<br>GUGAAGAACAAAUGCGUGAACUUCAACUUCAACGGCCUGACCGGCACCGGCGUGCUGACAGAGAGC<br>AACAAGAAGUUCCUGCCAUUCCAGCAGUUUGGCCGGGAUAUCGCCGAUACCACAGACGCCGUUAGA<br>GAUCCCCAGACACUGGAAAUCCUGGACAUCACCCCUUGCAGCUUCGGCGGAGUGUCUGUGAUCACC<br>CCUGGCACCAACACCAGCAAUCAGGUGGCAGUGCUGUACCAGGGCGUGAACUGUACCGAAGUGCCC<br>GUGGCCAUUCACGCCGAUCAGCUGACACCUACAUGGCGGGUGUACUCCACCGGCAGCAAUGUGUUU<br>CAGACCAGAGCCGGCUGUCUGAUCGGAGCCGAGUACGUGAACAAUAGCUACGAGUGCGACAUCCCC<br>AUCGGCGCUGGAAUCUGCGCCAGCUACCAGACACAGACAAAGAGCCACCGGAGAGCCAGAAGCGUG<br>GCCAGCCAGAGCAUCAUUGCCUACACAAUGUCUCUGGGCGCCGAGAACAGCGUGGCCUACUCCAAC<br>AACUCUAUCGCUAUCCCCACCAACUUCACCAUCAGCGUGACCACAGAGAUCCUGCCUGUGUCCAUG<br>ACCAAGACCAGCGUGGACUGCACCAUGUACAUCUGCGGCGAUUCCACCGAGUGCUCCAACCUGCUG<br>CUGCAGUACGGCAGCUUCUGCACCCAGCUGAAAAGAGCCCUGACAGGGAUCGCCGUGGAACAGGAC<br>AAGAACACCCAAGAGGUGUUCGCCCAAGUGAAGCAGAUCUACAAGACCCCUCCUAUCAAGUACUUC<br>GGCGGCUUCAAUUUCAGCCAGAUUCUGCCCGAUCCUAGCAAGCCCAGCAAGCGGAGCUUCAUCGAG<br>GACCUGCUGUUCAACAAAGUGACACUGGCCGACGCCGGCUUCAUCAAGCAGUAUGGCGAUUGUCUG<br>GGCGACAUUGCCGCCAGGGAUCUGAUUUGCGCCCAGAAGUUUAACGGACUGACAGUGCUGCCUCCU<br>CUGCUGACCGAUGAGAUGAUCGCCCAGUACACAUCUGCCCUGCUGGCCGGCACAAUCACAAGCGGC<br>UGGACAUUUGGAGCAGGCGCCGCUCUGCAGAUCCCCUUUGCUAUGCAGAUGGCCUACCGGUUCAAC<br>GGCAUCGGAGUGACCCAGAAUGUGCUGUACGAGAACCAGAAGCUGAUCGCCAACCAGUUCAACAGC<br>GCCAUCGGCAAGAUCCAGGACAGCCUGAGCAGCACAGCAAGCGCCCUGGGAAAGCUGCAGGACGUG<br>GUCAACCACAAUGCCCAGGCACUGAACACCCUGGUCAAGCAGCUGUCCUCCAAGUUCGGCGCCAUC<br>AGCUCUGUGCUGAACGAUAUCCUGAGCAGACUGGACCCUCCUGAGGCCGAGGUGCAGAUCGACAGA<br>CUGAUCACAGGCAGACUGCAGAGCCUCCAGACAUACGUGACCCAGCAGCUGAUCAGAGCCGCCGAG<br>AUUAGAGCCUCUGCCAAUCUGGCCGCCACCAAGAUGUCUGAGUGUGUGCUGGGCCAGAGCAAGAGA<br>GUGGACUUUUGCGGCAAGGGCUACCACCUGAUGAGCUUCCCUCAGUCUGCCCCUCACGGCGUGGUG<br>UUUCUGCACGUGACAUAUGUGCCCGCUCAAGAGAAGAAUUUCACCACCGCUCCAGCCAUCUGCCAC<br>GACGGCAAAGCCCACUUUCCUAGAGAAGGCGUGUUCGUGUCCAACGGCACCCAUUGGUUCGUGACA<br>CAGCGGAACUUCUACGAGCCCCAGAUCAUCACCACCGACAACACCUUCGUGUCUGGCAACUGCGAC<br>GUCGUGAUCGGCAUUGUGAACAAUACCGUGUACGACCCUCUGCAGCCCGAGCUGGACAGCUUCAAA<br>GAGGAACUGGACAAGUACUUUAAGAACCACACAAGCCCCGACGUGGACCUGGGCGAUAUCAGCGGA<br>AUCAAUGCCAGCGUCGUGAACAUCCAGAAAGAGAUCGACCGGCUGAACGAGGUGGCCAAGAAUCUG<br>AACGAGAGCCUGAUCGACCUGCAAGAACUGGGGAAGUACGAGCAGUACAUCAAGUGGCCCUGGUAC<br>AUCUGGCUGGGCUUUAUCGCCGGACUGAUUGCCAUCGUGAUGGUCACAAUCAUGCUGUGUUGCAUG<br>ACCAGCUGCUGUAGCUGCCUGAAGGGCUGUUGUAGCUGUGGCAGCUGCUGCAAGUUCGACGAGGAC<br>GAUUCUGAGCCCGUGCUGAAGGGCGUGAAACUGCACUACACAUGAUGA |
| 79 | DNA sequence encoding a SARS-CoV-2 S protein from an Omicron BA.4/BA.5 variant | ATGTTCGTGTTCCTGGTGCTGCTGCCTCTGGTGTCCAGCCAGTGTGTGAACCTGATCACCAGAACA<br>CAGTCATACACCAACAGCTTTACCAGAGGCGTGTACTACCCCGACAAGGTGTTCAGATCCAGCGTG<br>CTGCACTCTACCCAGGACCTGTTCCTGCCTTTCTTCAGCAACGTGACCTGGTTCCACGCCATCTCC<br>GGCACCAATGGCACCAAGAGATTCGACAACCCCGTGCTGCCCTTCAACGACGGGGTGTACTTTGCC<br>AGCACCGAGAAGTCCAACATCATCAGAGGCTGGATCTTCGGCACCACACTGGACAGCAAGACCCAG<br>AGCCTGCTGATCGTGAACAACGCCACCAACGTGGTCATCAAAGTGTGCGAGTTCCAGTTCTGCAAC<br>GACCCCTTCCTGGACGTCTACTACCACAAGAACAACAAGAGCTGGATGGAAAGCGAGTTCCGGGTG<br>TACAGCAGCGCCAACAACTGCACCTTCGAGTACGTGTCCCAGCCTTTCCTGATGGACCTGGAAGGC<br>AAGCAGGGCAACTTCAAGAACCTGCGCGAGTTCGTGTTTAAGAACATCGACGGCTACTTCAAGATC<br>TACAGCAAGCACACCCCTATCAACCTCGGCCGGGATCTGCCTCAGGGCTTCTCTGCTCTGGAACCC<br>CTGGTGGATCTGCCCATCGGCATCAACATCACCCGGTTTCAGACACTGCTGGCCCTGCACAGAAGC<br>TACCTGACACCTGGCGATAGCAGCAGCGGATGGACAGCTGGTGCCGCCGCTTACTATGTGGGCTAC<br>CTGCAGCCTAGAACCTTCCTGCTGAAGTACAACGAGAACGGCACCATCACCGACGCCGTGGATTGT<br>GCTCTGGATCCTCTGAGCGAGACAAAGTGCACCCTGAAGTCCTTCACCGTGGAAAAGGGCATCTAC<br>CAGACCAGCAACTTCCGGGTGCAGCCCACCGAATCCATCGTGCGGTTCCCCAATATCACCAATCTG<br>TGCCCCTTCGACGAGGTGTTCAATGCCACCAGATTCGCCTCTGTGTACGCCTGGAACCGGAAGCGG<br>ATCAGCAATTGCGTGGCCGACTACTCCGTGCTGTACAACTTCGCCCCCTTCTTCGCATTCAAGTGC<br>TACGGCGTGTCCCCTACCAAGCTGAACGACCTGTGCTTCACAAACGTGTACGCCGACAGCTTCGTG<br>ATCCGGGGAAACGAAGTGCGGCAGATTGCCCCTGGACAGACAGGCAACATCGCCGACTACAACTAC<br>AAGCTGCCCGACGACTTCACCGGCTGTGTGATTGCCTGGAACAGCAACAAGCTGGACTCCAAAGTC<br>GGCGGCAACTACAATTACAGGTACCGGCTGTTCCGGAAGTCCAATCTGAAGCCCTTCGAGCGGGAC<br>ATCTCCACCGAGATCTATCAGGCCGGCAACAAGCCTTGTAACGGCGTGGCAGGCGTGAACTGCTAC<br>TTCCCACTGCAGTCCTACGGCTTTAGGCCCACATACGGCGTGGGCCACCAGCCCTACAGAGTGGTG<br>GTGCTGAGCTTCGAACTGCTGCATGCCCCTGCCACAGTGTGCGGCCCTAAGAAAAGCACCAATCTC<br>GTGAAGAACAAATGCGTGAACTTCAACTTCAACGGCCTGACCGGCACCGGCGTGCTGACAGAGAGC<br>AACAAGAAGTTCCTGCCATTCCAGCAGTTTGGCCGGGATATCGCCGATACCACAGACGCCGTTAGA<br>GATCCCCAGACACTGGAAATCCTGGACATCACCCCTTGCAGCTTCGGCGGAGTGTCTGTGATCACC<br>CCTGGCACCAACACCAGCAATCAGGTGGCAGTGCTGTACCAGGGCGTGAACTGTACCGAAGTGCCC<br>GTGGCCATTCACGCCGATCAGCTGACACCTACATGGCGGGTGTACTCCACCGGCAGCAATGTGTTT<br>CAGACCAGAGCCGGCTGTCTGATCGGAGCCGAGTACGTGAACAATAGCTACGAGTGCGACATCCCC<br>ATCGGCGCTGGAATCTGCGCCAGCTACCAGACACAGACAAAGAGCCACCGGAGAGCCAGAAGCGTG<br>GCCAGCCAGAGCATCATTGCCTACACAATGTCTCTGGGCGCCGAGAACAGCGTGGCCTACTCCAAC<br>AACTCTATCGCTATCCCCACCAACTTCACCATCAGCGTGACCACAGAGATCCTGCCTGTGTCCATG<br>ACCAAGACCAGCGTGGACTGCACCATGTACATCTGCGGCGATTCCACCGAGTGCTCCAACCTGCTG<br>CTGCAGTACGGCAGCTTCTGCACCCAGCTGAAAAGAGCCCTGACAGGGATCGCCGTGGAACAGGAC |

TABLE 11-continued

| Sequence of one embodiment of Omicron BA.4/BA.5-specific RNA vaccine | | |
|---|---|---|
| SEQ ID NO. | Brief Description | Sequence |
| | | AAGAACACCCAAGAGGTGTTCGCCCAAGTGAAGCAGATCTACAAGACCCCTCCTATCAAGTACTTC<br>GGCGGCTTCAATTTCAGCCAGATTCTGCCCGATCCTAGCAAGCCCAGCAAGCGGAGCTTCATCGAG<br>GACCTGCTGTTCAACAAAGTGACACTGGCCGACGCCGGCTTCATCAAGCAGTATGGCGATTGTCTG<br>GGCGACATTGCCGCCAGGGATCTGATTTGCGCCCAGAAGTTTAACGGACTGACAGTGCTGCCTCCT<br>CTGCTGACCGATGAGATGATCGCCCAGTACACATCTGCCCTGCTGGCCGGCACAATCACAAGCGGC<br>TGGACATTTGGAGCAGGCGCCGCTCTGCAGATCCCCTTTGCTATGCAGATGGCCTACCGGTTCAAC<br>GGCATCGGAGTGACCCAGAATGTGCTGTACGAGAACCAGAAGCTGATCGCCAACCAGTTCAACAGC<br>GCCATCGGCAAGATCCAGGACAGCCTGAGCAGCACAGCAAGCGCCCTGGGAAAGCTGCAGGACGTG<br>GTCAACCACAATGCCCAGGCACTGAACACCCTGGTCAAGCAGCTGTCCTCCAAGTTCGGCGCCATC<br>AGCTCTGTGCTGAACGATATCCTGAGCAGACTGGACCCTCCTGAGGCCGAGGTGCAGATCGACAGA<br>CTGATCACAGGCAGACTGCAGAGCCTCCAGACATACGTGACCCAGCAGCTGATCAGAGCCGCCGAG<br>ATTAGAGCCTCTGCCAATCTGGCCGCCACCAAGATGTCTGAGTGTGTGCTGGGCCAGAGCAAGAGA<br>GTGGACTTTTGCGGCAAGGGCTACCACCTGATGAGCTTCCCTCAGTCTGCCCCTCACGGCGTGGTG<br>TTTCTGCACGTGACATATGTGCCCGCTCAAGAGAAGAATTTCACCACCGCTCCAGCCATCTGCCAC<br>GACGGCAAAGCCCACTTTCCTAGAGAAGGCGTGTTCGTGTCCAACGGCACCCATTGGTTCGTGACA<br>CAGCGGAACTTCTACGAGCCCCAGATCATCACCACCGACAACACCTTCGTGTCTGGCAACTGCGAC<br>GTCGTGATCGGCATTGTGAACAATACCGTGTACGACCCTCTGCAGCCCGAGCTGGACAGCTTCAAA<br>GAGGAACTGGACAAGTACITTAAGAACCACACAAGCCCCGACGTGGACCTGGGCGATATCAGCGGA<br>ATCAATGCCAGCGTCGTGAACATCCAGAAAGAGATCGACCGGCTGAACGAGGTGGCCAAGAATCTG<br>AACGAGAGCCTGATCGACCTGCAAGAACTGGGGAAGTACGAGCAGTACATCAAGTGGCCCTGGTAC<br>ATCTGGCTGGGCTTTATCGCCGGACTGATTGCCATCGTGATGGTCACAATCATGCTGTGTTGCATG<br>ACCAGCTGCTGTAGCTGCCTGAAGGGCTGTTGTAGCTGTGGCAGCTGCTGCAAGTTCGACGAGGAC<br>GATTCTGAGCCCGTGCTGAAGGGCGTGAAACTGCACTACACATGATGA |

TABLE 12

| Sequence of one embodiment of an exemplary Omicron BA.2.75-specific RNA vaccine | | |
|---|---|---|
| SEQ ID NO. | Brief Description | Sequence |
| 80 | Amino acid sequence of RNA-encoded SARS-CoV-2 S protein from an Omicron BA.2.75 variant (with PRO mutations at positions corresponding to positions K986P and V987P of SEQ ID NO: 1; i.e., PRO mutations at positions 983 and 984 of SEQ ID NO: 80) | MFVFLVLLPLVSSQCVNLITRTQSYTNSFTRGVYYPDKVFRSSVLHSTQDLFLPFFSNVTWFHAIH<br>VSGTNGTKRFDNPVLPFNDGVYFASTEKSNIIRGWIEGTTLDSKTQSLLIVNNATNVVIKVCEFQF<br>CNDPFLDVYYHENNKSRMESELRVYSSANNCTFEYVSQPFLMDLEGKQGNFKNLREFVFKNIDGYE<br>KIYSKHTPVNLGRDLPQGFSALEPLVDLPIGINITRFQTLLALHRSYLTPGDSSSSWTAGAAAYYV<br>GYLQPRTFLLKYNENGTITDAVDCALDPLSETKCTLKSFRVEKFIYQTSNFRVQPTESIVRFPNIT<br>NLCPFHEVFNATRFASVYAWNRKRISNCVADYSVLYNFAPFFAFKCYGVSPTKLNDLCFTNVYADS<br>FVIRGNEVSQIAPGQTGNIADYNYKLPDDFTGCVIAWNSNKLDSKVSGNYNYLYRLFRKSKLKPFE<br>RDISTEIYQAGNKPCNGVAGENCYFPLQSYGFRPTYGVGHQPYRVVVLSFELLHAPATVCGPKKST<br>NLVKNKCVNFNFNGLTGTGVLTESNKKFLPFQQFGRDIADTTDAVRDPQTLEILDITPCSFGGVSV<br>ITPGTNTSNQVAVLYQGVNCTEVPVAIHADQLTPTWRVYSTGSNVFQTRAGCLIGAEYVNNSYECD<br>IPIGAGICASYQTQTKSHRRARSVASQSIIAYTMSLGAENSVAYSNNSIAIPTNETISVTTEILPV<br>SMTKTSVDCTMYICGDSTECSNLLLQYGSFCTQLKRALTGIAVEQDKNTQEVFAQVKQIYKTPPIK<br>YFGGFNFSQILPDPSKPSKRSFIEDLLENKVTLADAGFIKQYGDCLGDIAARDLICAQKENGLTVL<br>PPLLTDEMIAQYTSALLAGTITSGWTFGAGAALQIPFAMQMAYRFNGIGVTQNVLYENQKLIANQF<br>NSAIGKIQDSLSSTASALGKLQDVVNHNAQALNTLVKQLSSKFGAISSVLNDILSRLDPPEAEVQI<br>DRLITGRLQSLQTYVTQQLIRAAEIRASANLAATKMSECVLGQSKRVDFCGKGYHLMSFPQSAPHG<br>VVFLHVTYVPAQEKNFTTAPAICHDGKAHFPREGVEVSNGTHWFVTQRNFYEPQIITTDNTFVSGN<br>CDVVIGIVNNTVYDPLQPELDSFKEELDKYFKNHTSPDVDLGDISGINASVVNIQKEIDRLNEVAK<br>NLNESLIDLQELGKYEQYIKWPWYIWLGFIAGLIAIVMVTIMLCCMTSCCSCLKGCCSCGSCCKFD<br>EDDSEPVLKGVKLHYT |
| 81 | RNA sequence encoding a SARS-CoV-2 S protein from an Omicron BA.2.75 variant | auguucguguuccuggugcugcugccucuggugguccagccagugugugaaccugaucaccagaaca<br>cagucauacaccaacagcuuuaccagaggcguguacuaccccgacaagguguucagauccagcgug<br>cugcacucuacccaggaccuguuccugccuuucuucagcaacgugaccugguuccacgccauccac<br>guguccggcaccaauggcaccaagagauucgacaaccccgugcugcccuucaacgacgggguguac<br>uuugccagcaccgagaaguccaacaucaucagaggcuggaucuucggcaccacacuggacagcaag<br>acccagagccugcugaucgugaacaacgccaccaacguggucaucaaagugugcgaguuccaguuc<br>ugcaacgaccccuuccuggacgucuacuaccacgagaacaacaagagcaggauggaaagcgagcuc<br>cggguguacagcagcgccaacaacugcaccuucgaguacgugucccagccuuuccugauggaccug<br>gaaggcaagcagggcaacuucaagaaccugcgcgaguucguguuuaagaacaucgacggcuacuuc<br>aagaucuacagcaagcacaccccugugaaccucggccgggaucugccucagggcuucucugcucug<br>gaaccccugguggaucugcccaucggcaucaacaucacccgguuucagacacugcuggcccugcac<br>agaagcuaccugacaccuggcgauagcagcagcagcuggacagcuggugccgccgcuuacuaugug<br>ggcuaccugcagccuagaaccuuccugcugaaquacaacgagaacggcaccaucaccgacgccgug<br>gauugugcucuggaucccucugagcgagacaaagugcacccugaaguccuucaccguggaaaagggc<br>aucuaccagaccagcaacuuccgggugcagcccaccgaauccaucgugcgguuccccaauaucacc<br>aaucugugccccuuccacgagguguucaaugccaccagauucgccucuguguacgccuggaaccgg<br>aagcggaucagcaauugcguggccgacuacuccgugcuguacaacuucgccccuucuucgcauuc<br>aagugcuacggcguguccccuaccaagcugaacgaccugugcuucacaaacguguacgccgacagc |

TABLE 12-continued

Sequence of one embodiment of an exemplary Omicron BA.2.75-specific RNA vaccine

| SEQ ID NO. | Brief Description | Sequence |
|---|---|---|
| | | uucgugauccggggaaacgaagugucacagauugccccuggacagacaggcaacaucgccgacuac<br>aacuacaagcugcccgacgacuucaccggcugugugauugccuggaacagcaacaagcuggacucc<br>aaagucagcggcaacuacaauuaccuguaccggcuguuccggaaguccaagcugaagcccuucgag<br>cgggacaucuccaccgagaucuaucaggccggcaacaagccuuguaacggcguggcaggcuucaac<br>ugcuacuucccacugcaguccuacggcuuuaggcccacauacggcguggccaccagcccuacaga<br>gugguggugcugagcuucgaacugcugcaugccccugccacagugugcggcccuaagaaaagcacc<br>aaucucgugaagaacaaaugcgugaacuucaacuucaacggccugaccggcaccggcgugcugaca<br>gagagcaacaagaaguuccugccauuccagcaguuuggccgggauaucgccgauaccacagacgcc<br>guuagagaucccagacacuggaaauccuggacaucaccccuugcagcuucggcggagugucugug<br>aucaccccuggcaccaacaccagcaaucagguggcagugcuguaccagggcgugaacuguaccgaa<br>gugcccguggccauucacgccgaucagcugacaccuacauggcggguguacuccaccggcagcaau<br>guguuucagaccagagccggcugucugaucggagccgaguacgugaacaauagcuacgagugcgac<br>auccccaucggcgcuggaaucugcgccagcuaccagacacagacaaagagccaccggagagccaga<br>agcguggccagccagagcaucauugccuacacaaugucucugggcgccgagaacagcguggccuac<br>uccaacaacucuaucgcuauccccaccaacuucaccaucagcgugaccacagagauccugccugug<br>uccaugaccaagaccagcguggacugcaccauguacaucugcggcgauuccaccgagugcuccaac<br>cugcugcugcaguacggcagcuucugcacccagcugaaaagagcccugacagggaucgccguggaa<br>caggacaagaacacccaagagguguucgcccaagugaagcagaucuacaagaccccuccuaucaag<br>uacuucggcggcuucaauuucagccagauucugcccgauccuagcaagcccagcaagcggagcuuc<br>aucgaggaccugcuguucaacaaagugacacuggccgacgccggcuucaucaagcaguauggcgau<br>ugucugggcgacauugccgccagggaucugauuugcgcccagaaguuuaacggacugacagugcug<br>ccuccucugcugaccgaugagaugaucgcccaguacacaucugcccugcuggccggcacaaucaca<br>agcggcuggacauuuggagcaggcgccgcucugcagauccccuuugcuaugcagauggccuaccgg<br>uucaacggcaucggagugacccagaaugugcuguacgagaaccagaagcugaucgccaaccaguuc<br>aacagcgccaucggcaagauccaggacagccugagcagcacagcaagcgcccugggaaagcugcag<br>gacguggucaaccacaaugcccaggcacugaacacccuggucaagcagcuguccuccaaguucggc<br>gccaucagcucugugcugaacgauauccugagcagacuggacccuccugaggccgaggugcagauc<br>gacagacugaucacaggcagacugcagagccuccagacauacgugacccagcagcugaucagagcc<br>gccgagauuagagccucugccaaucuggccgccaccaagaugucugagugugugcugggccagagc<br>aagagaguggacuuuugcggcaagggcuaccaccugaugagcuucccucagucugccccucacggc<br>gugguguuucugcacgugacauaugugcccgcucaagagaagaauuucaccaccgcuccagccauc<br>ugccacgacggcaaagcccacuuuccuagagaaggcguguucguguccaacggcacccauugguuc<br>gugacacagcggaacuucuacgagccccagaucaucaccaccgacaacaccuucgugucuggcaac<br>ugcgacqucgugaucggcauugugaacaauaccguguacgacccucugcagcccgagcuggacagc<br>uucaaagaggaacuggacaaguacuuuaagaaccacacaagccccgacguggaccugggcgauauc<br>agcggaaucaaugccagcgucgugaacauccagaaagagaucgaccggcugaacgagguggccaag<br>aaucugaacgagagccugaucgaccugcaagaacuggggaaguacgagcaguacaucaaguggccc<br>ugguacaucuggcugggcuuuaucgccggacugauugccaucgugauggucacaaucaugcugugu<br>ugcaugaccagcugcuguagcugccugaagggcuguuguagcuguggcagcugcugcaaguucgac<br>gaggacgauucugagcccgugcugaagggcgugaaacugcacuacacaugauga |
| 82 | DNA sequence encoding a SARS-CoV-2 S protein from an Omicron BA.2.75 variant | atgttcgtgttcctggtgctgctgcctctggtgtccagccagtgtgtgaacctgatcaccagaaca<br>cagtcatacaccaacagctttaccagaggcgtgtactaccccgacaaggtgttcagatccagcgtg<br>ctgcactgtacccaggacctgttcctgcctttcttcagcaacgtgacctggttccacgccatccac<br>gtgtccggcaccaatggcaccaagagattcgacaaccccgtgctgcccttcaacgacggggtgtac<br>tttgccagcaccgagaagtccaacatcatcagaggctggatcttcggcaccacactggacagcaag<br>acccagagcctgctgatcgtgaacaacgccaccaacgtggtcatcaaagtgtgcgagttccagttc<br>tgcaacgaccccttcctggacgtctactaccacgagaacaacaagagcaggatggaaagcgagctc<br>cgggtgtacagcagcgccaacaactgcaccttcgagtacgtgtcccagcctttcctgatggacctg<br>gaaggcaagcagggcaacttcaagaacctgcgcgagttcgtgtttaagaacatcgacggctacttc<br>aagatctacagcaagcacacccctgtgaacctcggccgggatctgcctcagggcttctctgctctg<br>gaacccctggtggatctgcccatcggcatcaacatcacccggtttcagacactgctggccctgcac<br>agaagctacctgacacctggcgatagcagcagcagctggacagctggtgccgccgcttactatgtg<br>ggctacctgcagcctagaaccttcctgctgaagtacaacgagaacggcaccatcaccgacgccgtg<br>gattgtgctctggatcctctgagcgagacaaagtgcaccctgaagtccttcaccgtggaaaagggc<br>atctaccagaccagcaacttccgggtgcagcccaccgaatccatcgtgcggttccccaatatcacc<br>aatctgtgccccttccacgaggtgttcaatgccaccagattcgcctctgtgtacgcctggaaccgg<br>aagcggatcagcaattgcgtggccgactactccgtgctgtacaacttcgcccccttcttcgcattc<br>aagtgctacggcgtgtcccctaccaagctgaacgacctgtgcttcacaaacgtgtacgccgacagc<br>ttcgtgatccggggaaacgaagtgtcacagattgcccctggacagacaggcaacatcgccgactac<br>aactacaagctgcccgacgacttcaccggctgtgtgattgcctggaacagcaacaagctggactcc<br>aaagtcagcggcaactacaattacctgtaccggctgttccggaagtccaagctgaagcccttcgag<br>cgggacatctccaccgagatctatcaggccggcaacaagccttgtaacggcgtggcaggcttcaac<br>tgctacttcccactgcagtcctacggctttaggcccacatacggcgtgggccaccagccctacaga<br>gtggtggtgctgagcttcgaactgctgcatgcccctgccacagtgtgcggccctaagaaaagcacc<br>aatctcgtgaagaacaaatgcgtgaacttcaacttcaacggcctgaccggcaccggcgtgctgaca<br>gagagcaacaagaagttcctgccattccagcagtttggccgggatatcgccgataccacagacgcc<br>gttagagatccccagacactggaaatcctggacatcaccccttgcagcttcggcggagtgtctgtg<br>atcacccctggcaccaacaccagcaatcaggtggcagtgctgtaccagggcgtgaactgtaccgaa<br>gtgcccgtggccattcacgccgatcagctgacacctacatggcgggtgtactccaccggcagcaat<br>gtgtttcagaccagagccggctgtctgatcggagccgagtacgtgaacaatagctacgagtgcgac<br>atccccatcggcgctggaatctgcgccagctaccagacacagacaaagagccaccggagagccaga<br>agcgtggccagccagagcatcattgcctacacaatgtctctgggcgccgagaacagcgtggcctac<br>tccaacaactctatcgctatccccaccaacttcaccatcagcgtgaccacagagatcctgcctgtg |

TABLE 12-continued

Sequence of one embodiment of an exemplary Omicron BA.2.75-specific RNA vaccine

| SEQ ID NO. | Brief Description | Sequence |
|---|---|---|
| | | tccatgaccaagaccagcgtggactgcaccatgtacatctgcggcgattccaccgagtgctccaac<br>ctgctgctgcagtacggcagcttctgcacccagctgaaaagagccctgacagggatcgccgtggaa<br>caggacaagaacacccaagaggtgttcgcccaagtgaagcagatctacaagacccctcctatcaag<br>tacttcggcggcttcaatttcagccagattctgcccgatcctagcaagcccagcaagcggagcttc<br>atcgaggacctgctgttcaacaaagtgacactggccgacgccggcttcatcaagcagtatggcgat<br>tgtctgggcgacattgccgccagggatctgatttgcgcccagaagtttaacggactgacagtgctg<br>cctcctctgctgaccgatgagatgatcgcccagtacacatctgccctgctggccggcacaatcaca<br>agcggctggacatttggagcaggcgccgctctgcagatcccctttgctatgcagatggcctaccgg<br>ttcaacggcatcggagtgacccagaatgtgctgtacgagaaccagaagctgatcgccaaccagttc<br>aacagcgccatcggcaagatccaggacagcctgagcagcacagcaagcgccctgggaaagctgcag<br>gacgtggtcaaccacaatgcccaggcactgaacaccctggtcaagcagctgtcctccaagttcggc<br>gccatcagctctgtgctgaacgatatcctgagcagactggaccctcctgaggccgaggtgcagatc<br>gacagactgatcacaggcagactgcagagcctccagacatacgtgacccagcagctgatcagagcc<br>gccgagattagagcctctgccaatctggccgccaccaagatgtctgagtgtgtgctgggccagagc<br>aagagagtggacttttgcggcaagggctaccacctgatgagcttccctcagtctgcccctcacggc<br>gtggtgtttctgcacgtgacatatgtgcccgctcaagagaagaatttcaccaccgctccagccatc<br>tgccacgacggcaaagcccactttcctagagaaggcgtgttcgtgtccaacggcacccattggttc<br>gtgacacagcggaacttctacgagccccagatcatcaccaccgacaacaccttcgtgtctggcaac<br>tgcgacgtcgtgatcggcattgtgaacaataccgtgtacgaccctctqcagcccgagctggacagc<br>ttcaaagaggaactggacaagtactttaagaaccacacaagccccgacgtggacctgggcgatatc<br>agcggaatcaatgccagcgtcgtgaacatccagaaagagatcgaccggctgaacgaggtggccaag<br>aatctgaacgagagcctgatcgacctgcaagaactggggaagtacgagcagtacatcaagtggccc<br>tggtacatctggctgggctttatcgccggactgattgccatcgtgatggtcacaatcatgctgtgt<br>tgcatgaccagctgctgtagctgcctgaagggctgttgtagctgtggcagctgctgcaagttcgac<br>gaggacgattctgagcccgtgctgaagggcgtgaaactgcactacacatgatga |
| 83 | Full length RNA construct encoding a SARS-Cov-2 S protein from an Omicron BA.2.75 variant | agaauaaacuaguauucuucuggucccacagacucagagagaacccgccaccauguucguguucc<br>uggugcugcugccucugguguccagccagugugugaaccugaucaccagaacacagucauacacca<br>acagcuuuaccagaggcguguacuaccccgacaagguguucagauccagcgugcugcacucuaccc<br>aggaccuguuccugccuuucuucagcaacgugaccugguuccacgccauccacguguccggcacca<br>auggcaccaagagauucgacaaccccgugcugcccuucaacgacgggguguacuuugccagcaccg<br>agaaguccaacaucaucagaggcuggaucuucggcaccacacuggacagcaagacccagagccugc<br>ugaucgugaacaacgccaccaacguggucaucaaagugugcgaguuccaguucugcaacgaccccu<br>uccuggacgucuacuaccacgagaacaacaagagcaggauggaaagcgagcuccggguguacagca<br>gcgccaacaacugcaccuucgaguacgugucccagccuuuccugauggaccuggaaggcaagcagg<br>gcaacuucaagaaccugcgcgaguucguguuuaagaacaucgacggcuacuucaagaucuacagca<br>agcacaccccugugaaccucggccgggaucugccucagggcuucucugcucuggaaccccuggugg<br>aucugcccaucggcaucaacaucacccgguuucagacacugcuggcccugcacagaagcuaccuga<br>caccuggcgauagcagcagcagcuggacagcuggugccgccgcuuacuaugugggcuaccugcagc<br>cuagaaccuuccugcugaaguacaacgagaacggcaccaucaccgacgccguggauugugcucugg<br>aucccucugagcgagacaaagugcacccugaaguccuucaccguggaaaagggcaucuaccagacca<br>gcaacuuccgggugcagcccaccgaauccaucgugcgguuccccaauaucaccaaucugugccccu<br>uccacgagguguucaaugccaccagauucgccucuguguacgccuggaaccggaagcggaucagca<br>auugcguggccgacuacuccgugcuguacaacuucgccccuucuucgcauucaagugcuacggcg<br>uguccccuaccaagcugaacgaccugugcuucacaaacguguacgccgacagcuucgugauccggg<br>gaaacgaagugucacagauugccccuggacagacaggcaacaucgccgacuacaacuacaagcugc<br>ccgacgacuucaccggcugugugauugccuggaacagcaacaagcuggacuccaaagucagcggca<br>acuacaauuaccuguaccggcuguuccggaaguccaagcugaagcccuucgagcgggacaucucca<br>ccgagaucuaucaggccggcaacaagccuuguaacggcguggcaggcuucaacugcuacuucccac<br>ugcaguccuacggcuuuaggcccacauacggcgugggccaccagcccuacagagugguggugcuga<br>gcuucgaacugcugcaugccccugccacagugugcggcccuaagaaaagcaccaaucucgugaaga<br>acaaaugcgugaacuucaacuucaacggccugaccggcaccggcgugcugacagagagcaacaaga<br>aguuccugccauuccagcaguuuggccgggauaucgccgauaccacagacgccguuagagaucccc<br>agacacuggaaauccuggacaucaccccuugcagcuucggcggagugucugugaucaccccuggca<br>ccaacaccagcaaucagguggcagugcuguaccagggcgugaacuguaccgaagugcccguggcca<br>uucacgccgaucagcugacaccuacauggcggguguacuccaccggcagcaauguguuucagacca<br>gagccggcugucugaucggagccgaguacgugaacaauagcuacgagugcgacauccccaucggcg<br>cuggaaucugcgccagcuaccagacacagacaaagagccaccggagagccagaagcguggccagcc<br>agagcaucauugccuacacaaugucucugggcgccgagaacagcguggccuacuccaacaacucua<br>ucgcuagccccaccaacuucaccaucagcgugaccacagagauccugccuguguccaugaccaaga<br>ccagcguggacugcaccauguacaucugcggcgauuccaccgagugcuccaaccugcugcugcagu<br>acggcagcuucugcacccagcugaaaagagcccugacagggaucgccguggaacaggacaagaaca<br>cccaagagguguucgcccaagugaagcagaucuacaagaccccuccuaucaaguacuucggcggcu<br>ucaauuucagccagauucugcccgauccuagcsagcccagcaagcggagcuucaucgaggaccugc<br>uguucaacaaagugacacuggccgacgccggcuucaucaagcaguauggcgauugucugggcgaca<br>uugccgccagggaucugauuugcgcccagaaguuuaacggacugacagugcugccuccucugcuga<br>ccgaugagaugaucgcccaguacacaucugcccugcuggccggcacaaucacaagcggcuggacau<br>uuggagcaggcgccgcucugcagauccccuuugcuaugcagauggccuaccgguucaacggcaucg<br>gagugacccagaaugugcuguacgagaaccagaagcugaucgccaaccaguucaacagcgccaucg<br>gcaagauccaggacagccugagcagcacagcaagcgcccugggaaagcugcaggacguggucaacc<br>acaaugcccaggcacugaacacccuggucaagcagcuguccuccaaguucggcgccaucagcucug<br>ugcugaacgauauccugagcagacuggacccuccugaggccgaggugcagaucgacagacugauca<br>caggcagacugcagagccuccagacauacgugacccagcagcugaucagagccgccgagauuagag<br>ccucugccaaucuggccgccaccaagaugucugagugugugcugggccagagcaagagaguggacu |

TABLE 12-continued

| Sequence of one embodiment of an exemplary Omicron BA.2.75-specific RNA vaccine | | |
|---|---|---|
| SEQ ID NO. | Brief Description | Sequence |
| | | uuugcggcaagggcuaccaccugaugagcuucccucagucugccccucacggcgugguguuucugc acgugacauaugugcccgcucaagagaagaauuucaccaccgcuccagccaucugccacgacggca aagcccacuuuccuagagaaggcguguucguguccaacggcacccauugguucgugacacagcgga acuucuacgagccccagaucaucaccaccgacaacaccuucgugucuggcaacugcgacgucguga ucggcauugugaacaauaccguguacgacccucugcagcccgagcuggacagcuucaaagaggaac uggacaaquacuuuaagaaccacacaagccccgacguggaccugggcgauaucagcggaaucaaug ccagcgucgugaacauccagaaagagaucgaccggcugaacgagguggccaagaaucugaacgaga gccugaucgaccugcaagaacuggggaaguacgagcaguacaucaaguggcccugguacaucuggc ugggcuuuaucgccggacugauugccaucgugauggucacaaucaugcuguguugcaugaccagcu gcuguagcugccugaagggcuguuguagcuguggcagcugcugcaaguucgacgaggacgauucug agcccgugcugaagggcgugaaacugcacuacacaugaugacucgagcugguacugcaugcacgca augcuagcugcccuuucccguccugggguaccccgagucuccccgaccucgggucccagguaugc ucccaccuccaccugccccacucaccaccucugcuaguuccagacaccucccaagcacgcagcaau gcagcucaaaacgcuuagccuagccacacccccacgggaaacagcagugauuaaccuuuagcaaua aacgaaaguuuaacuaagcuauacuaaccccaggguuggucaauuucgugccagccacacccugga gcuagcaaaaaaaaaaaaaaaaaaaaaaaaaaaaaagcauaugacuaaaaaaaaaaaaaaaaaaaa aaaaaaaaaaaaaaaaaaaaaaaaaaaaaaaaaaaaaaaaaaaaaaaaaa |
| 84 | Full length DNA construct encoding a SARS-CoV-2 S protein from an Omicron BA.2.75 variant | agaataaactagtattcttctggtccccacagactcagagagaacccgccaccatgttcgtgttcc tggtgctgctgcctctggtgtccagccagtgtgtgaacctgatcaccagaacacagtcatacacca acagctttaccagaggcgtgtactaccccgacaaggtgttcagatccagcgtgctgcactctaccc aggacctgttcctgcctttcttcagcaacgtgacctggttccacgccatccacgtgtccggcacca atggcaccaagagattcgacaaccccgtgctgcccttcaacgacggggtgtactttgccagcaccg agaagtccaacatcatcagaggctggatcttcggcaccacactggacagcaagacccagagcctgc tgatcgtgaacaacgccaccaacgtggtcatcaaagtgtgcgagttccagttctgcaacgacccct tcctggacgtctactaccacgagaacaacaagagcaggatggaaagcgagctccgggtgtacagca gcgccaacaactgcaccttcgagtacgtgtcccagcctttcctgatggacctggaaggcaagcagg gcaacttcaagaacctgcgcgagttcgtgtttaagaacatcgacggctacttcaagatctacagca agcacacccctgtgaacctcggccgggatctgcctcagggcttctctgctctggaacccctggtgg atctgcccatcggcatcaacatcacccggtttcagacactgctggccctgcacagaagctacctga cacctggcgatagcagcagcagctggacagctggtgccgccgcttactatgtgggctacctgcagc ctagaaccttcctgctgaagtacaacgagaacggcaccatcaccgacgccgtggattgtgctctgg atcctctgagcgagacaaagtgcaccctgaagtccttcaccgtggaaaagggcatctaccagacca gcaacttccgggtgcagcccaccgaatccatcgtgcggttccccaatatcaccaatctgtgcccct tccacgaggtgttcaatgccaccagattcgcctctgtgtacgcctggaaccggaagcggatcagca attgcgtggccgactactccgtgctgtacaacttcgcccccttcttcgcattcaagtgctacggcg tgtcccctaccaagctgaacgacctgtgcttcacaaacgtgtacgccgacagcttcgtgatccggg gaaacgaagtgtcacagattgcccctggacagacaggcaacatcgccgactacaactacaagctgc ccgacgacttcaccggctgtgtgattgcctggaacagcaacaagctggactccaaagtcagcggca actacaattacctgtaccggctgttccggaagtccaagctgaagcccttcgagcgggacatctcca ccgagatctatcaggccggcaacaagccttgtaacggcgtggcaggcttcaactgctacttcccac tgcagtcctacggctttaggcccacatacggcgtgggccaccagccctacagagtggtggtgctga gcttcgaactgctgcatgcccctgccacagtgtgcggccctaagaaaagcaccaatctcgtgaaga acaaatgcgtgaacttcaacttcaacggcctgaccggcaccggcgtgctgacagagagcaacaaga agttcctgccattccagcagtttggccgggatatcgccgataccacagacgccgttagagatcccc agacactggaaatcctggacatcaccccttgcagcttcggcggagtgtctgtgatcacccctggca ccaacaccagcaatcaggtggcagtgctgtaccagggcgtgaactgtaccgaagtgcccgtggcca ttcacgccgatcagctgacacctacatggcgggtgtactccaccggcagcaatgtgtttcagacca gagccggctgtctgatcggagccgagtacgtgaacaatagctacgagtgcgacatccccatcggcg ctggaatctgcgccagctaccagacacagacaaagagccaccggagagccagaagcgtggccagcc agagcatcattgcctacacaatgtctctgggcgccgagaacagcgtggcctactccaacaactcta tcgctatccccaccaacttcaccatcagcgtgaccacagagatcctgcctgtgtccatgaccaaga ccagcgtggactgcaccatgtacatctgcggcgattccaccgagtgctccaacctgctgctgcagt acggcagcttctgcacccagctgaaaagagccctgacagggatcgccgtggaacaggacaagaaca cccaagaggtgttcgcccaagtgaagcagatctacaagacccctcctatcaagtacttcggcggct tcaatttcagccagattctgcccgatcctagcaagcccagcaagcggagcttcatcgaggacctqc tgttcaacaaagtgacactggccgacgccggcttcatcaagcagtatggcgattgtctgggcgaca ttgccgccagggatctgatttgcgcccagaagtttaacggactgacagtgctgcctcctctgctga ccgatgagatgatcgcccagtacacatctgccctgctggccggcacaatcacaagcggctggacat ttggagcaggcgccgctctgcagatcccctttgctatgcagatggcctaccggttcaacggcatcg gagtgacccagaatgtgctgtacgagaaccagaagctgatcgccaaccagttcaacagcgccatcg gcaagatccaggacagcctgagcagcacagcaagcgccctgggaaagctgcaggacgtggtcaacc acaatgcccaggcactgaacaccctggtcaagcagctgtcctccaagttcggcgccatcagctctg tgctgaacgatatcctgagcagactggaccctcctgaggccgaggtgcagatcgacagactgatca caggcagactgcagagcctccagacatacgtgacccagcagctgatcagagccgccgagattagag cctctgccaatctggccgccaccaagatgtctgagtgtgtgctgggccagagcaagagagtggact tttgcggcaagggctaccacctgatgagcttccctcagtctgcccctcacggcgtggtgtttctgc acgtgacatatgtgcccgctcaagagaagaatttcaccaccgctccagccatctgccacgacggca aagcccactttcctagagaaggcgtgttcgtgtccaacggcacccattggttcgtgacacagcgga acttctacgagccccagatcatcaccaccgacaacaccttcgtgtctggcaactgcgacgtcgtga tcggcattgtgaacaataccgtgtacgaccctctgcagcccgagctggacagcttcaaagaggaac tggacaagtactttaagaaccacacaagccccgacgtggacctgggcgatatcagcggaatcaatg ccagcgtcgtgaacatccagaaagagatcgaccggctgaacgaggtggccaagaatctgaacgaga gcctgatcgacctgcaagaactggggaagtacgagcagtacatcaagtggccctggtacatctggc |

TABLE 12-continued

| SEQ ID NO. | Brief Description | Sequence |
|---|---|---|
| | | tgggctttatcgccggactgattaccatcgtgatggtcacaatcatgctgtgttgcatgaccagct<br>gctgtagctgcctgaagggctgttgtagctgtggcagctgctgcaagttcgacgaggacgattctg<br>agcccgtgctgaagggcgtgaaactgcactacacatgatgactcgagctggtactgcatgcacgca<br>atgctagctgcccctttcccgtcctgggtaccccgagtctcccccgacctcgggtcccaggtatgc<br>tcccacctccacctgccccactcaccacctctgctagttccagacacctcccaagcacgcagcaat<br>gcagctcaaaacgcttagcctagccacacccccacgggaaacagcagtgattaacctttagcaata<br>aacgaaagtttaactaagctatactaaccccagggttggtcaatttcgtgccagccacaccctgga<br>gctagcaaaaaaaaaaaaaaaaaaaaaaaaaaaaaagcatatgactaaaaaaaaaaaaaaaaaaaa<br>aaaaaaaaaaaaaaaaaaaaaaaaaaaaaaaaaaaaaaaaaaaaaaaaaa |

TABLE 13

Sequence of one embodiment of an exemplary Omicron BA.2.75.2-specific RNA vaccine

| SEQ ID NO. | Brief Description | Sequence |
|---|---|---|
| 85 | Amino acid sequence of RNA-encoded SARS-CoV-2 S protein from an Omicron BA.2.75.2 variant (with PRO mutations at positions corresponding to K986P and V987P of SEQ ID NO: 1; i.e., PRO mutations at positions 983 and 984 of SEQ ID NO: 85) | MFVFLVLLPLVSSQCVNLITRTQSYTNSFTRGVYYPDKVFRSSVLHSTQDLFLPFFSNVTWFHAIH<br>VSGTNGTKRFDNPVLPENDGVYFASTEKSNIIRGWIFGTTLDSKTQSLLIVNNATNVVIKVCEFQF<br>CNDPFLDVYYHENNKSRMESELRVYSSANNCTFEYVSQPFLMDLEGKQGNFKNLREFVFKNIDGYF<br>KIYSKHTPVNLGRDLPQGFSALEPLVDLPIGINITREQTLLALHRSYLTPGDSSSSWTAGAAAYYV<br>GYLQPRTELLKYNENGTITDAVDCALDPLSETKCTLKSFTVEKGIYQTSNFRVQPTESIVRFPNIT<br>NLCPFHEVFNATTFASVYAWNRKRISNCVADYSVLYNFAPFFAFKCYGVSPTKLNDLCFTNVYADS<br>FVIRGNEVSQIAPGQTGNIADYNYKLPDDFTGCVIAWNSNKLDSKVSGNYNYLYRLFRKSKLKPFE<br>RDISTELYQAGNKPCNGVAGSNCYFPLQSYGFRPTYGVGHQPYRVVVLSFELLHAPATVCGPKKST<br>NLVKNKCVNFNFNGLTGTGVLTESNKKFLPFQQFGRDIADTTDAVRDPQTLEILDITPCSFGGVSV<br>ITPGTNTSNQVAVLYQGVNCTEVPVAIHADQLTPTWRVYSTGSNVFQTRAGCLIGAEYVNNSYECD<br>IPIGAGICASYQTQTKSHRRARSVASQSIIAYTMSLGAENSVAYSNNSIAIPTNFTISVTTEILPV<br>SMTKTSVDCTMYICGDSTECSNLLLQYGSFCTQLKRALTGIAVEQDKNTQEVFAQVKQTYKTPPIK<br>YFGGFNFSQILPDPSKPSKRSFIEDLLENKVTLADAGFIKQYGDCLGDIAARDLICAQKENGLTVL<br>PPLLTDEMIAQYTSALLAGTITSGWTFGAGAALQIPFAMQMAYRENGIGVTQNVLYENQKLIANQF<br>NSAIGKIQDSLSSTASALGKLQDVVNHNAQALNTLVKQLSSKFGAISSVLNDILSRLDPPEAEVQI<br>DRLITGRLQSLQTYVTQQLIRAAEIRASANLAATKMSECVLGQSKRVDFCGKGYHLMSFPQSAPHG<br>VVFLHVTYVPAQEKNFTTAPAICHDGKAHFPREGVEVSNGTHWFVTQRNFYEPQIITTDNTFVSGN<br>CDVVIGIVNNTVYDPLQPELDSFKEELDKYFKNHTSPDVDLGDISGINASVVNIQKEIDRLNEVAK<br>NLNESLINLQELGKYEQYIKWPWYIWLGFIAGLIAIVMVTIMLCCMTSCCSCLKGCCSCGSCCKFD<br>EDDSEPVLKGVKLHYT |
| 86 | RNA sequence encoding a SARS-CoV-2 S protein from an Omicron BA.2.75.2 variant | auguucguguuccuggugcugcugccuguggugucca gccagugugugaaccugaucaccagaaca<br>cagucauacaccaacagcuuuaccagaggcguguacuaccccgacaagguguucagauccagcgug<br>cugcacucuacccaggaccuguuccugccuuucuucagcaacgugaccugguuccacgccauccac<br>guguccggcaccaauggcaccaagagauucgacaaccccgugcugcccuucaacgacgggguguac<br>uuugccagcaccgagaaguccaacaucaucagaggcuggaucuucggcaccacacuggacagcaag<br>acccagagccugcugaucgugaacaacgccaccaacguggucaucaaagugugcgaguuccaguuc<br>ugcaacgaccccuuccuggacqucuacuaccacgagaacaacaagagcaggauggaaagcgagcuc<br>cggguguacagcagcgccaacaacugcaccuucgaguacgugucccagccuuuccugauggaccug<br>gaaggcaagcagggcaacuucaagaaccugcgcgaguucguguuuaagaacaucgacggcuacuuc<br>aagaucuacagcaagcacaccccugugaaccucggccgggaucugccucagggcuucucugcucug<br>gaaccccugguggaucugcccaucggcaucaacaucacccgguuucagacacugcuggcccugcac<br>agaagcuaccugacaccuggcgauagcagcagcagcuggacagcuggugccgccgcuuacuaugug<br>ggcuaccugcagccuagaaccuuccugcugaaguacaacgagaacggcaccaucaccgacgccgug<br>gauugugcucuggaucccucugagcgagacaaagugcacccugaaguccuucaccguggaaaagggc<br>aucuaccagaccagcaacuuccgggugcagcccaccgaauccaucgugcgguuccccaauaucacc<br>aaucugugccccuuccacgagguguucaaugccaccaccuucgccucuguguacgccuggaaccgg<br>aagcggaucagcaauugcguggccgacuacuccgugcuguacaacuucgccccuucuucgcauuc<br>aagugcuacggcguguccccuaccaagcugaacgaccugugcuucacaaacguguacgccgacagc<br>uucgugauccggggaaacgaagugucacagauugccccuggacagacaggcaacaucgccgacuac<br>aacuacaagcugcccgacgacuucaccggcugugugauugccuggaacagcaacaagcuggacucc<br>aaagucagcggcaacuacaauuaccuguaccggcuguuccggaaguccaagcugaagcccuucgag<br>cgggacaucuccaccgagaucuaucaggccggcaacaagccuuguaacggcguggcaggcagcaac<br>ugcuacuucccacugcaguccuacggcuuuaggcccacauacggcgugggccaccagcccuacaga<br>gugguggugcugagcuucgaacugcugcaugccccugccacagugugcggcccuaagaaaagcacc<br>aaucucgugaagaacaaaugcgugaacuucaacuucaacggccugaccggcaccggcgugcugaca<br>gagagcaacaagaaguuccugccauuccagcaguuuggccgggauaucgccgauaccacagacgcc<br>guuagagaucccagacacuggaaauccuggacaucaccccuugcagcuucggcggagugucugug<br>aucaccccuggcaccaacaccagcaaucagguggcagugcuguaccagggcgugaacuguaccgaa<br>gugcccguggccauucacgccgaucagcugacaccuacauggcgguguacucccaccggcagcaau<br>guguuucagaccagagccggcugucugaucggagccgaguacgugaacaauagcuacgagugcgac<br>auccccaucggcgcuggaaucugcgccagcuaccagacacagacaaagagccaccggagagccaga<br>agcguggccagccagagcaucauugccuacacaaugucucugggcgccgagaacgacguggccuac |

TABLE 13-continued

Sequence of one embodiment of an exemplary Omicron BA.2.75.2-specific RNA vaccine

| SEQ ID NO. | Brief Description | Sequence |
|---|---|---|
| | | uccaacaacucuaucgcuauccccaccaacuucaccaucagcgugaccacagagauccugccugug<br>uccaugaccaagaccagcguggacugcaccauguacaucugcggcgauuccaccgagugcuccaac<br>cugcugcugcaguacggcagcuucugcacccagcugaaaagagcccugacagggaucgccguggaa<br>caggacaagaacacccaagagguguucgcccaagugaagcagaucuacaagaccccuccuaucaag<br>uacuucggcggcuucaauuucagccagauucugcccgauccuagcaagcccagcaagcggagcuuc<br>aucgaggaccugcuguucaacaaagugacacuggccgacgccggcuucaucaagcaguauggcgau<br>ugucugggcgacauugccgccagggaucugauuugcgcccagaaguuuaacggacugacagugcug<br>ccuccucugcugaccgaugagaugaucgcccaguacacaucugcccugcuggccggcacaaucaca<br>agcggcuggacauuuggagcaggcgccgcucugcagauccccuuugcuaugcagauggccuaccgg<br>uucaacggcaucggagugacccagaaugugcuguacgagaaccagaagcugaucgccaaccaguuc<br>aacagcgccaucggcaagauccaggacagccugagcagcacagcaagcgcccugggaaagcugcag<br>gacguggucaaccacaaugcccaggcacugaacacccuggucaagcagcuguccuccaaguucggc<br>gccaucagcucugugcugaacgauauccugagcagacuggacccuccugaggccgaggugcagauc<br>gacagacugaucacaggcagacugcagagccuccagacauacgugacccagcagcugaucagagcc<br>gccgagauuagagccucugccaaucuggccgccaccaagaugucugagugugugcugggccagagc<br>aagagaguggacuuuugcggcaagggcuaccaccugaugagcuucccucagucugccccucacggc<br>gugguguuucugcacgugacauaugugcccgcucaagagaagaauuucaccaccgcuccagccauc<br>ugccacgacggcaaagcccacuuuccuagagaaggcguguucguguccaacggcacccauugguuc<br>gugacacagcggaacuucuacgagccccagaucaucaccaccgacaacaccuucgugucuggcaac<br>ugcgacgucgugaucggcauugugaacaauaccguguacgacccucugcagcccgagcuggacagc<br>uucaaagaggaacuggacaaguacuuuaagaaccacacaagccccgacguggaccugggcgauauc<br>agcggaaucaaugccagcgucgugaacauccagaaagagaucgaccggcugaacgagguggccaag<br>aaucugaacgagagccugaucaaccugcaagaacuggggaaquacgagcaguacaucaaguggccc<br>ugguacaucuggcugggcuuuaucgccggacugauugccaucgugauggucacaaucaugcugugu<br>ugcaugaccagcugcuguagcugccugaagggcuguuguagcuguggcagcugcugcaaguucgac<br>gaggacgauucugagcccgugcugaagggcgugaaacugcacuacacaugauga |
| 87 | DNA sequence encoding a SARS-CoV-2 S protein from an Omicron BA.2.75.2 variant | atgttcgtgttcctggtgctgctgcctctggtgtccagccagtgtgtgaacctgatcaccagaaca<br>cagtcatacaccaacagctttaccagaggcgtgtactaccccgacaaggtgttcagatccagcgtg<br>ctgcactctacccaggacctgttcctgcctttcttcagcaacgtgacctggttccacgccatccac<br>gtgtccggcaccaatggcaccaagagattcgacaaccccgtgctgcccttcaacgacggggtgtac<br>tttgccagcaccgagaagtccaacatcatcagaggctggatcttcggcaccacactggacagcaag<br>acccagagcctgctgatcgtgaacaacgccaccaacgtggtcatcaaagtgtgcgagttccagttc<br>tgcaacgaccccttcctggacgtctactaccacgagaacaacaagagcaggatggaaagcgagctc<br>cgggtgtacagcagcgccaacaactgcaccttcgagtacgtgtcccagcctttcctgatggacctg<br>gaaggcaagcagggcaacttcaagaacctgcgcgagttcgtgtttaagaacatcgacggctacttc<br>aagatctacagcaagcacacccctgtgaacctcggccgggatctgcctcagggcttctctgctctg<br>gaacccctggtggatctgcccatcggcatcaacatcacccggtttcagacactgctggccctgcac<br>agaagctacctgacacctggcgatagcagcagcagctggacagctggtgccgccgcctactatgtg<br>ggctacctgcagcctagaaccttcctgctgaagtacaacgagaacggcaccatcaccgacgccgtg<br>gattgtgctctggatcctctgagcgagacaaagtgcaccctgaagtccttcaccgtggaaaagggc<br>atctaccagaccagcaacttccgggtgcagcccaccgaatccatcgtgcggttccccaatatcacc<br>aatctgtgccccttccacgaggtgttcaatgccaccaccttcgcctctgtgtacgcctggaaccgg<br>aagcggatcagcaattgcgtggccgactactccgtgctgtacaacttcgccccttcttcgcattc<br>aagtgctacggcgtgtcccctaccaagctgaacgacctgtgcttcacasacgtgtacgccgacagc<br>ttcgtgatccggggaaacgaagtgtcacagattgcccctggacagacaggcaacatcgccgactac<br>aactacaagctgcccgacgacttcaccggctgtgtgattgcctggaacagcaacaagctggactcc<br>aaagtcagcggcaactacaattacctgtaccggctgttccggaagtccaagctgaagcccttcgag<br>cgggacatctccaccgagatctatcaggccggcaacaagccttgtaacggcgtggcaggcagcaac<br>tgctacttcccactgcagtcctacggctttaggcccacatacggcgtgggccaccagccctacaga<br>gtggtggtgctgagcttcgaactgctgcatgcccctgccacagtgtgcggccctaagaaaagcacc<br>aatctcgtgaagaacaaatgcgtgaacttcaacttcaacggcctgaccggcaccggcgtgctgaca<br>gagagcaacaagaagttcctgccattccagcagtttggccgggatatcgccgataccacagacgcc<br>gttagagatccccagacactggaaatcctggacatcaccccttgcagcttcggcggagtgtctgtg<br>atcacccctggcaccaacaccagcaatcaggtggcagtgctgtaccagggcgtgaactgtaccgaa<br>gtgcccgtggccattcacgccgatcagctgacacctacatggcgggtgtactccaccggcagcaat<br>gtgtttcagaccagagccggctgtctgatcggagccgagtacgtgaacaatagctacgagtgcgac<br>atccccatcggcgctggaatctgcgccagctaccagacacagacaaagagccaccggagagccaga<br>agcgtggccagccagagcatcattgcctacacaatgtctctgggcgccgagaacagcgtggcctac<br>tccaacaactctatcgctatccccaccaacttcaccatcagcgtgaccacagagatcctgcctgtg<br>tccatgaccaagaccagcgtggactgcaccatgtacatctgcggcgattccaccgagtgctccaac<br>ctgctgctgcagtacggcagcttctgcacccagctgaaaagagccctgacagggatcgccgtggaa<br>caggacaagaacacccaagaggtcttcgcccaagtgaagcagatctacaagacccctcctatcaag<br>tacttcggcggcttcaatttcagccagattctgcccgatcctagcaagcccagcaagcggagcttc<br>atcgaggacctgctgttcaacaaagtgacactggccgacgccggcttcatcaagcagtatggcgat<br>tgtctgggcgacattgccgccagggatctgatttgcgcccagaagtttaacggactgacagtgctg<br>cctcctctgctgaccgatgagatgatcgcccagtacacatctgccctgctggccggcacaatcaca<br>agcggctggacatttggagcaggcgccgctctgcagatcccctttgctatgcagatggcctaccgg<br>ttcaacggcatcggagtgacccagaatgtgctgtacgagaaccagaagctgatcgccaaccagttc<br>aacagcgccatcggcaagatccaggacagcctgagcagcacagcaagcgccctgggaaagctgcag<br>gacgtggtcaaccacaatgcccaggcactgaacaccctggtcaagcagctgtcctccaagttcggc<br>gccatcagctctgtgctgaacgatatcctgagcagactggaccctcctgaggccgaggtgcagatc<br>gacagactgatcacaggcagactgcagagcctccagacatacgtgacccagcagctgatcagagcc<br>gccgagattagagcctctgccaatctggccgccaccaagatgtctgagtgtgtgctgggccagagc |

TABLE 13-continued

Sequence of one embodiment of an exemplary Omicron BA.2.75.2-specific RNA vaccine

| SEQ ID NO. | Brief Description | Sequence |
| --- | --- | --- |
| | | aagagagtggacttttgcggcaagggctaccacctgatgagcttccctcagtctgcccctcacggc<br>gtggtgtttctgcacgtgacatatgtgcccgctcaagagaagaatttcaccaccgctccagccatc<br>tgccacgacggcaaagcccactttcctagagaaggcgtgttcgtgtccaacggcacccattggttc<br>gtgacacagcggaacttctacgagccccagatcatcaccaccgacaacaccttcgtgtctggcaac<br>tgcgacgtcgtgatcggcattgtgaacaataccgtgtacgaccctctgcagcccgagctggacagc<br>ttcaaagaggaactggacaagtactttaagaaccacacaagccccgacgtggacctgggcgatatc<br>agcggaatcaatgccagcgtcgtgaacatccagaaagagatcgaccggctgaacgaggtggccaag<br>aatctgaacgagagcctgatcaacctgcaagaactggggaagtacgagcagtacatcaagtggccc<br>tggtacatctggctgggctttatcgccggactgattgccatcgtgatggtcacaatcatgctgtgt<br>tgcatgaccagctgctgtagctgcctgaagggctgttgtagctgtggcagctgctgcaagttcgac<br>gaggacgattctgagcccgtgctgaagggcgtgaaactgcactacacatgatga |
| 88 | Full length RNA construct encoding a *SARS-CoV-2 S* protein from an Omicron BA.2.75.2 variant | agaauaaacuaguauucuucugguccccacagacucagagagaacccgccaccauguucguguucc<br>uggugcugcugccucugguguccagccagugugugaaccugaucaccagaacacagucauacacca<br>acagcuuuaccagaggcguguacuaccccgacaagguguucagauccagcgugcugcacucuaccc<br>aggaccuquuccugccuuucuucagcaacgugaccugguuccacgccauccacguguccggcacca<br>auggcaccaagagauucgacaaccccgugcugcccuucaacgacgggguguacuuugccagcaccg<br>agaaguccaacaucaucagaggcuggaucuucggcaccacacuggacagcaagacccagagccugc<br>ugaucgugaacaacgccaccaacguggucaucaaagugugcgaguuccaguucugcaacgaccccu<br>uccuggacgucuacuaccacgagaacaacaagagcaggauggaaagcgagcuccggguguacagca<br>gcgccascaacugcaccuucgaquacgugucccagccuuuccugauggaccuggaaggcaagcagg<br>gcaacuucaagaaccugcgcgaguucguguuusagaacaucgacggcuacuucaagaucuacagca<br>agcacaccccugugaaccucggccgggaucugccucagggcuucucugcucuggaaccccuggugg<br>aucugcccaucggcaucaacaucacccgguuucagacacugcuggcccugcacagaagcuaccuga<br>caccuggcgauagcagcagcagcuggacagcuggugccgccgcuuacuaugugggcuaccugcagc<br>cuagaaccuuccugcugaaguacaacgagaacggcaccaucaccgacgccguggauugugcucugg<br>aucccucugagcgagacaaagugcacccugaaguccuucaccguggaaaagggcaucuaccagacca<br>gcaacuuccgggugcagcccaccgaauccaucgugcgguuccccaauaucaccaaucugugccccu<br>uccacgagguguucaaugccaccaccuucgccucuguguacgccuggaaccggaagcggaucagca<br>auugcguggccgacuacuccgugcuguacaacuucgccccuucuucgcauucaagugcuacggcg<br>uguccccuaccaagcugaacgaccugugcuucacaaacguguacgccgacagcuucgugauccggg<br>gaaacgaagugucacagauugccccuggacagacaggcaacaucgccgacuacaacuacaagcugc<br>ccgacgacuucaccggcugugugauugccuggaacagcaacaagcuggacuccaaagucagcggca<br>acuacaauuaccuguaccggcuguuccggaaguccaagcugaagcccuucgagcgggacaucucca<br>ccgagaucuaucaggccggcaacaagccuuguaacggcguggcaggcagcaacugcuacuucccac<br>ugcaguccuacggcuuuaggcccacauacggcgugggccaccagcccuacagagugguggugcuga<br>gcuucgaacugcugcaugccccugccacagugugcggcccuaagaaaagcaccaaucucgugaaga<br>acaaaugcgugaacuucaacuucaacggccugaccggcaccggcgugcugacagagagcaacaaga<br>aguuccugccauuccagcaguuuggccgggauaucgccgauaccacagacgccguuagagaucccc<br>agacacuggaaauccuggacaucaccccuugcagcuucggcggagugucugugaucaccccuggca<br>ccaacaccagcaaucagguggcagugcuguaccagggcgugaacuguaccgaagugcccguggcca<br>uucacgccgaucagcugacaccuacauggcggguguacuccaccggcagcaauguguuucagacca<br>gagccggcugucugaucggagccgaguacgugaacaauagcuacgagugcgacauccccaucggcg<br>cuggaaucugcgccagcuaccagacacagacaaagagccaccggagagccagaagcguggccagcc<br>agagcaucauugccuacacaaugucucugggcgccgagaacagcguggccuacuccaacaacucua<br>ucgcuauccccaccaacuucaccaucagcgugaccacagagauccugccuguguccaugaccaaga<br>ccagcguggacugcaccauguacaucugcggcgauuccaccgagugcuccaaccugcugcugcagu<br>acggcagcuucugcacccagcugaaaagagcccugacagggaucgccguggaacaggacaagaaca<br>cccaagagguguucgcccaagugaagcagaucuacaagaccccuccuaucaaguacuucggcggcu<br>ucaauuucagccagauucugcccgauccuagcaagcccagcaagcggagcaucaucgaggaccugc<br>uguucaacaaagugacacuggccgacgccggcuucaucaagcaguauggcgauugucugggcgaca<br>uugccgccagggaucugauuugcgcccagaaguuuaacggacugacagugcugccuccucugcuga<br>ccgaugagaugaucgcccaguacacaucugcccugcuggccggcacaaucacaagcggcuggacau<br>uuggagcaggcgccgcucugcagauccccuuugcuaugcagauggccuaccgguucaacggcaucg<br>gagugacccagaaugugcuguacgagaaccagaagcugaucgccaaccaguucaacagcgccaucg<br>gcaagauccaggacagccugagcagcacagcaagcgcccugggaaagcugcaggacguggucaacc<br>acaaugcccaggcacugaacacccuggucaagcagcuguccuccaaguucggcgccaucagcucug<br>ugcugaacgauauccugagcagacuggacccuccugaggccgaggugcagaucgacagacugauca<br>caggcagacugcagagccuccagacauacgugacccagcagcugaucagagccgccgagauuagag<br>ccucugccaaucuggccgccaccaagaugucugagugugugcugggccagagcaagagaguggacu<br>uuugcggcaagggcuaccaccugaugagcuucccucagucugccccucacggcgugguguuucugc<br>acgugacauaugugcccgcucaagagaagaauuucaccaccgcuccagccaucugccacgacggca<br>aagcccacuuuccuagagaaggcguguucguguccaacggcacccauugguucgugacacagcgga<br>acuucuacgagccccagaucaucaccaccgacaacaccuucgugucuggcaacugcgacgucguga<br>ucggcauugugaacaauaccguguacgacccucugcagcccgagcuggacagcuucaaagaggaac<br>uggacaaquacuuuaagaaccacacaagccccgacguggaccugggcgauaucagcggaaucaaug<br>ccagcgucgugaacauccagaaagagaucgaccggcugaacgagguggccaagaaucugaacgaga<br>gccugaucaaccugcaagaacuggggaaguacgagcaguacaucaaguggcccugquacaucuggc<br>ugggcuuuaucgccggacugauugccaucgugauggucacaaucaugcuguguugcaugaccagcu<br>gcuguagcugccugaagggcuguuguagcuguggcagcugcugcaaguucgacgaggacgauucug<br>agcccgugcugaagggcgugaaacugcacuacacaugaugacucgagcugguacugcaugcacgca<br>augcuagcugccccuuucccguccugggguaccccgagucucccccgaccucggguccagguaugc<br>ucccaccuccaccugccccacucaccaccucugcuaguuccagacaccucccaagcacgcagcaau<br>gcagcucaaaacgcuuagccuagccacacccccacgggaaacagcagugauuaaccuuuagcaaua |

TABLE 13-continued

| Sequence of one embodiment of an exemplary Omicron BA.2.75.2-specific RNA vaccine | | |
|---|---|---|
| SEQ ID NO. | Brief Description | Sequence |
| | | aacgaaaguuuaacuaagcuauacuaaccccagggguuggucaauuucgugccagccacacccugga<br>gcuagcaaaaaaaaaaaaaaaaaaaaaaaaaaaaaagcauaugacuaaaaaaaaaaaaaaaaaaaa<br>aaaaaaaaaaaaaaaaaaaaaaaaaaaaaaaaaaaaaaaaaaaaaaaaaa |
| 89 | Full length DNA construct encoding a SARS-CoV-2 S protein from an Omicron BA.2.75.2 variant | agaataaactagtattcttctggtccccacagactcagagagaacccgccaccatgttcgtgttcc<br>tggtgctgctgcctctggtgtccagccagtgtgtgaacctgatcaccagaacacagtcatacacca<br>acagctttaccagaggcgtgtactaccccgacaaggtgttcagatccagcgtgctgcactctaccc<br>aggacctgttcctgcctttcttcagcaacgtgacctggttccacgccatccacgtgtccggcacca<br>atggcaccaagagattcgacaaccccgtgctgcccttcaacgacggggtgtactttgccagcaccg<br>agaagtccaacatcatcagaggctggatcttcggcaccacactggacagcaagacccagagcctgc<br>tgatcgtgaacaacgccaccaacgtggtcatcaaagtgtgcgagttccagttctgcaacgacccct<br>tcctggacgtctactaccacgagaacaacaagagcaggatggaaagcgagctccgggtgtacagca<br>gcgccaacaactgcaccttcgagtacgtgtcccagcctttcctgatggacctggaaggcaagcagg<br>gcaacttcaagaacctgcgcgagttcgtgtttaagaacatcgacggctacttcaagatctacagca<br>agcacacccctgtgaacctcggccgggatctgcctcagggcttctctgctctggaacccctggtgg<br>atctgcccatcggcatcaacatcacccggtttcagacactgctggccctgcacagaagctacctga<br>cacctggcgatagcagcagcagctggacagctggtgccgccgcttactatgtgggctacctgcagc<br>ctagaaccttcctgctgaagtacaacgagaacggcaccatcaccgacgccgtggattgtgctctgg<br>atcctctgagcgagacaaagtgcaccctgaagtccttcaccgtggaaaagggcatctaccagacca<br>gcaacttccgggtgcagcccaccgaatccatcgtgcggttccccaatatcaccaatctgtgcccct<br>tccacgaggtgttcaatgccaccaccttcgcctctgtgtacgcctggaaccggaagcggatcagca<br>attgcgtggccgactactccgtgctgtacaacttcgccccctttcttcgcattcaagtgctacggcg<br>tgtcccctaccaagctgaacgacctgtgcttcacaaacgtgtacgccgacagcttcgtgatccggg<br>gaaacgaagtgtcacagattgcccctggacagacaggcaacatcgccgactacaactacaagctgc<br>ccgacgacttcaccggctgtgtgattgcctggaacagcaacaagctggactccaaagtcagcggca<br>actacaattacctgtaccggctgttccggaagtccaagctgaagcccttcgagcgggacatctcca<br>ccgagatctatcaggccggcaacaagccttgtaacggcgtggcaggcagcaactgctacttcccac<br>tgcagtcctacggctttaggcccacatacggcgtgggccaccagccctacagagtggtggtgctga<br>gcttcgaactgctgcatgcccctgccacagtgtgcggccctaagaaaagcaccaatctcgtgaaga<br>acaaatgcgtgaacttcaacttcaacggcctgaccggcaccggcgtgctgacagagagcaacaaga<br>agttcctgccattccagcagtttggccgggatatcgccgataccacagacgccgttagagatcccc<br>agacactggaaatcctggacatcaccccttgcagcttcggcggagtgtctgtgatcacccctggca<br>ccaacaccagcaatcaggtggcagtgctgtaccagggcgtgaactgtaccgaagtgcccgtggcca<br>ttcacgccgatcagctgacacctacatggcgggtgtactccaccggcagcaatgtgtttcagacca<br>gagccggctgtctgatcggagccgagtacgtgaacaatagctacgagtgcgacatccccatcggcg<br>ctggaatctgcgccagctaccagacacagacaaagagccaccggagagccagaagcgtggccagcc<br>agagcatcattgcctacacaatgtctctgggcgccgagaacagcgtggcctactccaacaactcta<br>tcgctatccccaccaacttcaccatcagcgtgaccacagagatcctgcctgtgtccatgaccaaga<br>ccagcgtggactgcaccatgtacatctgcggcgattccaccgagtgctccaacctgctgctgcagt<br>acggcagcttctgcacccagctgaaaagagccctgacagggatcgccgtggaacaggacaagaaca<br>cccaagaggtgttcgcccaagtgaagcagatctacaagacccctcctatcaagtacttcggcggct<br>tcaatttcagccagattctgcccgatcctagcaagcccagcaagcggagcttcatcgaggacctgc<br>tgttcaacaaagtgacactggccgacgccggcttcatcaagcagtatggcgattgtctgggcgaca<br>ttgccgccagggatctgatttgcgcccagaagtttaacggactgacagtgctgcctcctctgctga<br>ccgatgagatgatcgcccagtacacatctgccctgctggccggcacaatcacaagcggctggacat<br>ttggagcaggcgccgctctgcagatcccctttgctatgcagatggcctaccggttcaacggcatcg<br>gagtgacccagaatgtgctgtacgagaaccagaagctgatcgccaaccagttcaacagcgccatcg<br>gcaagatccaggacagcctgagcagcacagcaagcgccctgggaaagctgcaggacgtggtcaacc<br>acaatgcccaggcactgaacaccctggtcaagcagctgtcctccaagttcggcgccatcagctctg<br>tgctgaacgatatcctgagcagactggaccctcctgaggccgaggtgcagatcgacagactgatca<br>caggcagactgcagagcctccagacatacgtgacccagcagctgatcagagccgccgagattagag<br>cctctgccaatctggccgccaccaagatgtctgagtgtgtgctgggccagagcaagagagtggact<br>tttgcggcaagggctaccacctgatgagcttccctcagtctgcccctcacggcgtggtgtttctgc<br>acgtgacatatgtgcccgctcaagagaagaatttcaccaccgctccagccatctgccacgacggca<br>aagcccactttcctagagaaggcgtgttcgtgtccaacggcacccattggttcgtgacacagcgga<br>acttctacgagccccagatcatcaccaccgacaacaccttcgtgtctggcaactgcgacgtcgtga<br>tcggcattgtgaacaataccgtgtacgaccctctgcagcccgagctggacagcttcaaagaggaac<br>tggacaagtactttaagaaccacacaagccccgacgtggacctgggcgatatcagcggaatcaatg<br>ccagcgtcgtgaacatccagaaagagatcgaccggctgaacgaggtggccaagaatctgaacgaga<br>gcctgatcaacctgcaagaactggggaagtacgagcagtacatcaagtggccctggtacatctggc<br>tgggctttatcgccggactgattgccatcgtgatggtcacaatcatgctgtgttgcatgaccagct<br>gctgtagctgcctgaagggctgttgtagctgtggcagctgctgcaagttcgacgaggacgattctg<br>agcccgtgctgaagggcgtgaaactgcactacacatgatgactcgagctggtactgcatgcacgca<br>atgctagctgcccctttcccgtcctgggtaccccgagtctcccccgacctcgggtcccaggtatgc<br>tcccacctccacctgccccactcaccacctctgctagttccagacacctcccaagcacgcagcaat<br>gcagctcaaaacgcttagcctagccacacccccacgggaaacagcagtgattaacctttagcaata<br>aacgaaagtttaactaagctatactaaccccagggttggtcaatttcgtgccagccacaccctgga<br>gctagcaaaaaaaaaaaaaaaaaaaaaaaaaaaaaagcatatgactaaaaaaaaaaaaaaaaaaaa<br>aaaaaaaaaaaaaaaaaaaaaaaaaaaaaaaaaaaaaaaaaaaaaaaaaa |

TABLE 14

Sequence of one embodiment of an exemplary Omicron BA.4.6/BF.7-specific RNA vaccine

| SEQ ID NO. | Brief Description | Sequence |
| --- | --- | --- |
| 90 | Amino acid sequence of RNA-encoded SARS-Cov-2 S protein from an Omicron BA.4.6/BF.7 variant (with PRO mutations at positions corresponding to K986P and V987P of SEQ ID NO: 1; i.e., PRO mutations at positions 981 and 982 of SEQ ID NO: 90) | MFVFLVLLPLVSSQCVNLITRTQSYTNSFTRGVYYPDKVFRSSVLHSTQDLFLPFFSNVTWFHAIS<br>GTNGTKRFDNPVLPENDGVYFASTEKSNIIRGWIFGTTLDSKTQSLLIVNNATNVVIKVCEFQFCN<br>DPFLDVYYHKNNKSWMESEFRVYSSANNCTFEYVSQPFLMDLEGKQGNFKNLREFVFKNIDGYFKI<br>YSKHTPINLGRDLPQGFSALEPLVDLPIGINITRFQTLLALHRSYLTPGDSSSGWTAGAAAYYVGY<br>CPFDEVFNATTFASVYAWNRKRISNCVADYSVLYNFAPFFAFKCYGVSPTKLNDLCFTNVYADSFV<br>IRGNEVRQIAPGQTGNIADYNYKLPDDFTGCVIAWNSNKLDSKVGGNYNYRYRLFRKSNLKPFERD<br>ISTEIYQAGNKPCNGVAGVNCYFPLQSYGFRPTYGVGHQPYRVVVLSFELLHAPATVCGPKKSTNL<br>VKNKCVNFNFNGLTGTGVLTESNKKELPFQQFGRDIADTTDAVRDPQTLEILDITPCSFGGVSVIT<br>PGTNTSNQVAVLYQGVNCTEVPVAIHADQLTPTWRVYSTGSNVFQTRAGCLIGAEYVNNSYECDIP<br>IGAGICASYQTQTKSHRRARSVASQSIIAYTMSLGAENSVAYSNNSIAIPTNFTISVTTEILPVSM<br>TKTSVDCTMYICGDSTECSNLLLQYGSFCTQLKRALTGIAVEQDKNTQEVFAQVKQIYKTPPIKYF<br>GGFNFSQILPDPSKPSKRSFIEDLLFNKVTLADAGFIKQYGDCLGDIAARDLICAQKFNGLTVLPP<br>LLTDEMIAQYTSALLAGTITSGWTFGAGAALQIPFAMQMAYRENGIGVTQNVLYENQKLIANQFNS<br>AIGKIQDSLSSTASALGKLQDVVNHNAQALNTLVKQLSSKFGAISSVLNDILSRLDPPEAEVQIDR<br>LITGRLQSLQTYVTQQLIRAAEIRASANLAATKMSECVLGQSKRVDFCGKGYHLMSFPQSAPHGVV<br>FLHVTYVPAQEKNETTAPAICHDGKAHFPREGVFVSNGTHWFVTQRNFYEPQIITTDNTFVSGNCD<br>VVIGIVNNTVYDPLQPELDSFKEELDKYFKNHTSPDVDLGDISGINASVVNIQKEIDRLNEVAKNL<br>NESLIDLQELGKYEQYIKWPWYIWLGFIAGLIAIVMVTIMLCCMTSCCSCLKGCCSCGSCCKFDED<br>DSEPVLKGVKLHYT |
| 91 | RNA sequence encoding a SARS-CoV-2 S protein from an Omicron BA.4.6/BF.7 variant | auguucguguuccuggugcugcugccucugguguccagccagugugugaaccugaucaccagaaca<br>cagucauacaccaacagcuuuaccagaggcguguacuaccccgacaagguguucagauccagcgug<br>cugcacucuacccaggaccuguuccugccuuucuucagcaacgugaccugguuccacgccaucucc<br>ggcaccaauggcaccaagagauucgacaaccccgugcugcccuucaacgacgggguguacuuugcc<br>agcaccgagaaguccaacaucaucagaggcuggaucuucggcaccacacuggacagcaagacccag<br>agccugcugaucgugaacaacgccaccaacguggucaucaaagugugcgaguuccaguucugcaac<br>gaccccuuccuggacgucuacuaccacaagaacaacaagagcuggauggaaagcgaguuccgggug<br>uacagcagcgccaacaacugcaccuucgaguacgugucccagccuuuccugauggaccuggaaggc<br>aagcagggcaacuucaagaaccugcgcgaguucguguuuaagaacaucgacggcuacuucaagauc<br>uacagcaagcacaccccuaucaaccucggccgggaucugccucagggcuucucugcucuggaaccc<br>cugguggaucugcccaucggcaucaacaucacccgguuucagacacugcuggcccugcacagaagc<br>uaccugacaccuggcgauagcagcagcggauggacagcuggugccgccgcuuacuaugugggcuac<br>cugcagccuagaaccuuccugcugaaguacaacgagaacggcaccaucaccgacgccguggauugu<br>gcucuggaucccucugagcgagacaaagugcacccugaaguccuucaccguggaaaagggcaucuac<br>cagaccagcaacuuccgggugcagcccaccgaauccaucgugcgguuccccaauaucaccaaucug<br>ugccccuucgacgagguguucaaugccaccaccuucgccucuguguacgccuggaaccggaagcgg<br>aucagcaauugcguggccgacuacuccgugcuguacaacuucgccccuucuucgcauucaagugc<br>uacggcguguccccuaccaagcugaacgaccugugcuucacaaacguguacgccgacagcuucgug<br>auccggggaaacgaagugcggcagauugccccuggacagacaggcaacaucgccgacuacaacuac<br>aagcugcccgacgacuucaccggcugugugauugccuggaacagcaacaagcuggacuccaaaguc<br>ggcggcaacuacaauuacagguaccggcuguuccggaaguccaaucugaagcccuucgagcgggac<br>aucuccaccgagaucuaucaggccggcaacaagccuuguaacggcguggcaggcgugaacugcuac<br>uucccacugcaguccuacggcuuuaggcccacauacggcgugggccaccagcccuacagaguggug<br>gugcugagcuucgaacugcugcaugccccugccacagugugcggcccuaagaaaagcaccaaucuc<br>gugaagaacaaaugcgugaacuucaacuucaacggccugaccggcaccggcgugcugacagagagc<br>aacaagaaguuccugccauuccagcaguuuggccgggauaucgccgauaccacagacgccguuaga<br>gauccccagacacuggaaauccuggacaucaccccuugcagcuucggcggagugucugugaucacc<br>ccuggcaccaacaccagcaaucagguggcagugcuguaccagggcgugaacuguaccgaagugccc<br>guggccauucacgccgaucagcugacaccuacauggcggguguacuccaccggcagcaauguguuu<br>cagaccagagccggcugucugaucggagccgaguacgugaacaauagcuacgagugcgacaucccc<br>aucggcgcuggaaucugcgccagcuaccagacacagacaaagagccaccggagagccagaagcgug<br>gccagccagagcaucauugccuacacaaugucucugggcgccgagaacagcguggccuacuccaac<br>aacucuaucgcuauccccaccaacuucaccaucagcgugaccacagagauccugccuguguccaug<br>accaagaccagcguggacugcaccauguacaucugcggcgauuccaccgagugcuccaaccugcug<br>cugcaguacggcagcuucugcacccagcugaaaagagcccugacagggaucgccguggaacaggac<br>aagaacacccaagagguguucgcccaagugaagcagaucuacaagaccccuccuaucaaguacuuc<br>ggcggcuucaauuucagccagauucugcccgauccuagcaagcccagcaagcggagcuucaucgag<br>gaccugcuguucaacaaagugacacuggccgacgccggcuucaucaagcaguauggcgauugucug<br>ggcgacauugccgccagggaucugauuugcgcccagaaguuuaacggacugacagugcugccuccu<br>cugcugaccgaugagaugaucgcccaguacacaucugcccugcuggccggcacaaucacaagcggc<br>uggacauuuggagcaggcgccgcucugcagaucccuuugcuaugcagauggccuaccgguucaac<br>ggcaucggagugacccagaaugugcuguacgagaaccagaagcugaucgccaaccaguucaacagc<br>gccaucggcaagauccaggacagccugagcagcacagcaagcgcccugggaaagcugcaggacgug<br>gucaaccacaaugcccaggcacugaacacccuggucaagcagcuguccuccaaguucggcgccauc<br>agcucugugcugaacgauauccugagcagacuggacccuccugaggccgaggugcagaucgacaga<br>cugaucacaggcagacugcagagccuccagacauacgugacccagcagcugaucagagccgccgag<br>auuagagccucugccaaucuggccgccaccaagaugucugagugugugcugggccagagcaagaga<br>guggacuuuugcggcaagggcuaccaccugaugagcuucccucagucugccccucacggcguggug<br>uuucugcacgugacauaugugcccgcucaagagaagaauuucaccaccgcuccagccaucugccac<br>gacggcaaagcccacuuuccuagagaaggcguguucguguccaacggcacccauugguucgugaca<br>cagcggaacuucuacgagccccagaucaucaccaccgacaacaccuucgugucuggcaacugcgac<br>gucgugaucggcauugugaacaauaccguguacgacccucugcagcccgagcuggacagcuucaaa<br>gaggaacuggacaaguacuuuaagaaccacacaagccccgacguggaccugggcgauaucagcgga<br>aucaaugccagcgucgugaacauccagaaagagaucgaccggcugaacgagguggccaagaaucug |

TABLE 14-continued

| Sequence of one embodiment of an exemplary Omicron BA.4.6/BF.7-specific RNA vaccine | | |
|---|---|---|
| SEQ ID NO. | Brief Description | Sequence |
| | | aacgagagccugaucgaccugcaagaacuggggaaguacgagcaguacaucaaguggcccugguac<br>aucuggcugggcuuuaucgccggacugauugccaucgugauggucacaaucaugcuguguugcaug<br>accagcugcuguagcugccugaagggcuguuguagcuguggcagcugcugcaaguucgacgaggac<br>gauucugagcccgugcugaagggcgugaaacugcacuacacaugauga |
| 92 | DNA sequence encoding a SARS-CoV-2 S protein from an Omicron BA.4.6/BF.7 variant | atgttcgtgttcctggtgctgctgcctctggtgtccagccagtgtgtgaacctgatcaccagaaca<br>cagtcatacaccaacagctttaccagaggcgtgtactaccccgacaaggtgttcagatccagcgtg<br>ctgcactctacccaggacctgttcctgcctttcttcagcaacgtgacctggttccacgccatctcc<br>ggcaccaatggcaccaagagattcgacaaccccgtgctgcccttcaacgacggggtgtactttgcc<br>agcaccgagaagtccaacatcatcagaggctggatcttcggcaccacactggacagcaagacccag<br>agcctgctgatcgtgsacaacgccaccaacgtggtcatcaaagtgtgcgagttccagttctgcaac<br>gaccccttcctggacgtctactaccacaagaacaacaagagctggatggaaagcgagttccgggtg<br>tacagcagcgccaacaactgcaccttcgagtacgtgtcccagcctttcctgatggacctggaaggc<br>aagcagggcaacttcaagaacctgcgcgagttcgtgtttaagaacatcgacggctacttcaagatc<br>tacagcaagcacacccctatcaacctcggccgggatctgcctcagggcttctctgctctggaaccc<br>ctggtggatctgcccatcggcatcaacatcacccggtttcagacactgctggccctgcacagaagc<br>tacctgacacctggcgatagcagcagcggatggacagctggtgccgccgcttactatgtgggctac<br>ctgcagcctagaaccttcctgctgaagtacaacgagaacggcaccatcaccgacgccgtggattgt<br>gctctggatcctctgagcgagacaaagtgcaccctgaagtccttcaccgtggaaaagggcatctac<br>cagaccagcaacttccgggtgcagcccaccgaatccatcgtgcggttccccaatatcaccaatctg<br>tgccccttcgacgaggtgttcaatgccaccaccttcgcctctgtgtacgcctggaaccggaagcgg<br>atcagcaattgcgtggccgactactccgtgctgtacaacttcgcccccttcttcgcattcaagtgc<br>tacggcgtgtcccctaccaagctgaacgacctgtgcttcacaaacgtgtacgccgacagcttcgtg<br>atccggggaaacgaagtgcggcagattgcccctggacagacaggcaacatcgccgactacaactac<br>aagctgcccgacgacttcaccggctgtgtgattgcctggaacagcaacaagctggactccaaagtc<br>ggcggcaactacaattacaggtaccggctgttccggaagtccaatctgaagcccttcgagcgggac<br>atctccaccgagatctatcaggccggcaacaagccttgtaacggcgtggcaggcgtgaactgctac<br>ttcccactgcagtcctacggctttaggcccacatacggcgtgggccaccagccctacagagtggtg<br>gtgctgagcttcgaactgctgcatgcccctgccacagtgtgcggccctaagaaaagcaccaatctc<br>gtgaagaacaaatgcgtgaacttcaacttcaacggcctgaccggcaccggcgtgctgacagagagc<br>aacaagaagttcctgccattccagcagtttggccgggatatcgccgataccacagacgccgttaga<br>gatccccagacactggaaatcctggacatcaccccttgcagcttcggcggagtgtctgtgatcacc<br>cctggcaccaacaccagcaatcaggtggcagtgctgtaccagggcgtgaactgtaccgaagtgccc<br>gtggccattcacgccgatcagctgacacctacatggcgggtgtactccaccggcagcaatgtgttt<br>cagaccagagccggctgtctgatcggagccgagtacgtgaacaatagctacgagtgcgacatcccc<br>atcggcgctggaatctgcgccagctaccagacacagacaaagagccaccggagagccagaagcgtg<br>gccagccagagcatcattgcctacacaatgtctctgggcgccgagaacagcgtggcctactccaac<br>aactctatcgctatccccaccaacttcaccatcagcgtgaccacagagatcctgcctgtgtccatg<br>accaagaccagcgtggactgcaccatgtacatctgcggcgattccaccgagtgctccaacctgctg<br>ctgcagtacggcagcttctgcacccagctgassagagccctgacagggatcgccgtggaacaggac<br>aagaacacccaagaggtgttcgcccaagtgaagcagatctacaagacccctcctatcaagtacttc<br>ggcggcttcaatttcagccagattctgcccgatcctagcaagcccagcaagcggagcttcatcgag<br>gacctgctgttcaacaaagtgacactggccgacgccggcttcatcaagcagtatggcgattgtctg<br>ggcgacattgccgccagggatctgatttgcgcccagaagtttaacggactgacagtgctgcctcct<br>ctgctgaccgatgagatgatcgcccagtacacatctgccctgctggccggcacaatcacaagcggc<br>tggacatttggagcaggcgccgctctgcagatcccctttgctatgcagatggcctaccggttcaac<br>ggcatcggagtgacccagaatgtgctgtacgagaaccagaagctgatcgccaaccagttcaacagc<br>gccatcggcaagatccaggacagcctgagcagcacagcaagcgccctgggaaagctgcaggacgtg<br>gtcaaccacaatgcccaggcactgaacaccctggtcaagcagctgtcctccaagttcggcgccatc<br>agctctgtgctgaacgatatcctgagcagactggaccctcctgaggccgaggtgcagatcgacaga<br>ctgatcacaggcagactgcagagcctccagacatacgtgacccagcagctgatcagagccgccgag<br>attagagcctctgccaatctggccgccaccaagatgtctgagtgtgtgctgggccagagcaagaga<br>gtggacttttgcggcaagggctaccacctgatgagcttccctcagtctgcccctcacggcgtggtg<br>tttctgcacgtgacatatgtgcccgctcaagagaagaatttcaccaccgctccagccatctgccac<br>gacggcaaagcccactttcctagagaaggcgtgttcgtgtccaacggcacccattggttcgtgaca<br>cagcggaacttctacgagccccagatcatcaccaccgacaacaccttcgtgtctggcaactgcgac<br>gtcgtgatcggcattgtgaacaataccgtgtacgaccctctgcagcccgagctggacagcttcaaa<br>gaggaactggacaagtactttaagaaccacacaagccccgacgtggacctgggcgatatcagcgga<br>atcaatgccagcgtcgtgaacatccagaaagagatcgaccggctgaacgaggtggccaagaatctg<br>aacgagagcctgatcgacctgcaagaactggggaagtacgagcagtacatcaagtggccctggtac<br>atctggctgggctttatcgccggactgattgccatcgtgatggtcacaatcatgctgtgttgcatg<br>accagctgctgtagctgcctgaagggctgttgtagctgtggcagctgctgcaagttcgacgaggac<br>gattctgagcccgtgctgaagggcgtgaaactgcactacacatgatga |
| 93 | Full length RNA construct encoding a SARS-COV-2 S protein from an Omicron BA.4.6/BF.7 variant | agaauaaacuaguauucuucugguccccacagacucagagagaacccgccaccauguucguguucc<br>uggugcugcugccucugguguccagccagugugugaaccugaucaccagaacacagucauacacca<br>acagcuuuaccagaggcguguacuaccccgacaagguguucagauccagcgugcugcacucuaccc<br>aggaccuguuccugccuuucuucagcaacgugaccugguuccacgccaucuccggcaccaauggca<br>ccaagagauucgacaaccccgugcugcccuucaacgacgggguguacuuugccagcaccgagaagu<br>ccaacaucaucagaggcuggaucuucggcaccacacuggacagcaagacccagagccugcugaucg<br>ugaacaacgccaccaacquggucaucaaagugugcgaguuccaguucugcaacgaccccuuccugg<br>acgucuacuaccacaagaacaacaagagcuggauggaaagcgaguuccggguguacagcagcgcca<br>acaacugcaccuucgaguacgugucccagccuuuccugauggaccuggaaggcaagcagggcaacu<br>ucaagaaccugcgcgaguucguguuuaagaacaucgacggcuacuucaagaucuacagcaagcaca |

TABLE 14-continued

| Sequence of one embodiment of an exemplary Omicron BA.4.6/BF.7-specific RNA vaccine | | |
|---|---|---|
| SEQ ID NO. | Brief Description | Sequence |
| | | ccccuaucaaccucggccgggaucugccucagggcuucucugcucuggaaccccugguggaucugc<br>ccaucggcaucaacaucacccgguuucagacacugcuggcccugcacagaagcuaccugacaccug<br>gcgauagcagcagcggauggacagcuggugccgccgcuuacuaugugggcuaccugcagccuagaa<br>ccuuccugcugaaguacaacgagaacggcaccaucaccgacgccguggauugugcucuggauccuc<br>ugagcgagacaaagugcacccugaaguccuucaccguggaaagggcaucuaccagaccagcaacu<br>uccgggugcagcccaccgaauccaucgugcgguuccccaauaucaccaaucugugccccuucgacg<br>agguguucaaugccaccaccuucgccucuguguacgccuggaaccggaagcggaucagcaauugcg<br>uggccgacuacuccgugcuguacaacuucgccccuucuucgcauucaagugcuacggcgugucc c<br>cuaccaagcugaacgaccugugcuucacaaacguguacgccgacagcuucgugauccggggaaacg<br>aagugcggcagauugccccuggacagacaggcaacaucgccgacuacaacuacaagcugcccgacg<br>acuucaccggcugugugauugccuggaacagcaacaagcuggacuccaaagucggcggcaacuaca<br>auuacagguaccggcuguuccggaaguccaaucugaagcccuucgagcgggacaucuccaccgaga<br>ucuaucaggccggcaacaagccuuguaacggcguggcaggcgugaacugcuacuucccacugcagu<br>ccuacggcuuuaggcccacauacggcgugggccaccagcccuacagagugguggugcugagcuucg<br>aacugcugcaugccccugccacagugugcggcccuaagaaaagcaccaaucucgugaagaacaaau<br>gcgugaacuucaacuucaacggccugaccggcaccggcgugcugacagagagcaacaagaaguucc<br>ugccauuccagcaguuuggccgggauaucgccgauaccacagacgccguuagagauccccagacac<br>uggaaauccuggacaucaccccuugcagcuucggcggagugucugugaucaccccuggcaccaaca<br>ccagcaaucagguggcagugcuguaccagggcgugaacuguaccgaagugcccguggccauucacg<br>ccgaucagcugacaccuacauggcggguguacuccaccggcagcaauguguuucagaccagagccg<br>gcugucugaucggagccgaguacgugaacaauagcuacgagugcgacauccccaucggcgcuggaa<br>ucugcgccagcuaccagacacagacaaagagccaccggagagccagaagcguggccagccagagca<br>ucauugccuacacaaugucucugggcgccgagaacagcguggccuacuccaacaacucuaucgcua<br>ucccccaccaacuucaccaucagcgugaccacagagauccugccuguguccaugaccaagaccagcg<br>uggacugcaccauguacaucugcggcgauuccaccgagugcuccaaccugcugcugcaguacggca<br>gcuucugcacccagcugaaaagagcccugacagggaucgccguggaacaggacaagaacacccaag<br>agguguucgcccaagugaagcagaucuacaagaccccuccuaucaaguacuucggcggcuucaauu<br>ucagccagauucugcccgauccuagcaagcccagcaagcggagcuucaucgaggaccugcuguuca<br>acaaagugacacuggccgacgccggcuucaucaagcaguauggcgauugucugggcgacauugccg<br>ccagggaucugauuugcgcccagaaguuuaacggacugacagugcugccuccucugcugaccgaug<br>agaugaucgcccaguacacaucugcccugcuggccggcacaaucacaagcggcuggacauuuggag<br>caggcgccgcucugcagauccccuuugcuaugcagauggccuaccgguucaacggcaucggaguga<br>cccagaaugugcuguacgagaaccagaagcugaucgccaaccaguucaacagcgccaucggcaaga<br>uccaggacagccugagcagcacagcaagcgcccugggaaagcugcaggacguggucaaccacaaug<br>cccaggcacugaacacccuggucaagcagcuguccuccaaguucggcgccaucagcucugugcuga<br>acgauauccugagcagacuggacccuccugaggccgaggugcagaucgacagacugaucacaggca<br>gacugcagagccuccagacauacgugacccagcagcugaucagagccgccgagauuagagccucug<br>ccaaucuggccgccaccaagaugucugagugugugcugggccagagcaagagaguggacuuuugcg<br>gcaagggcuaccaccugaugagcuucccucagucugccccucacggcgugguguuucugcacguga<br>cauaugugcccgcucaagagaagaauuucaccaccgcuccagccaucugccacgacggcaaagccc<br>acuuuccuagagaaggcguguucguguccaacggcacccauugguucgugacacagcggaacuucu<br>acgagccccagaucaucaccaccgacaacaccuucgugucuggcaacugcgacgucgugaucggca<br>uugugaacaauaccguguacgacccucugcagcccgagcuggacagcuucaaagaggaacuggaca<br>aguacuuuaagaaccacacaagccccgacguggaccugggcgauaucagcggaaucaaugccagcg<br>ucgugaacauccagaaagagaucgaccggcugaacgagguggccaagaaucugaacgagagccuga<br>ucgaccugcaagaacuggggaaguacgagcaguacaucaaguggcccugguacaucuggcugggcu<br>uuaucgccggacugauugccaucgugauggucacaaucaugcuguguugcaugaccagcugcugua<br>gcugccugaagggcuguuguagcuguggcagcugcugcaaguucgacgaggacgauucugagcccg<br>ugcugaagggcgugaaacugcacuacacaugaugacucgagcugguacugcaugcacgcaaugcua<br>gcugccccuuucccguccugguaccccgagucucccccgaccucgggucccagguaugcucccac<br>cuccaccugccccacucaccaccucugcuaguuccagacaccucccaagcacgcagcaaugcagcu<br>caaaacgcuuagccuagccacacccccacgggaaacagcagugauuaaccuuuagcaauaaacgaa<br>aguuuaacuaagcuauacuaaccccaggguuggucaauuucgugccagccacacccuggagcuagc<br>aaaaaaaaaaaaaaaaaaaaaaaagcauaugacuaaaaaaaaaaaaaaaaaaaaaaaaaa<br>aaaaaaaaaaaaaaaaaaaaaaaaaaaaaaaaaaaaaaa |
| 94 | Full length DNA construct encoding a SARS-COV-2 S protein from an Omicron BA.4.6/BF.7 variant | agaataaactagtattcttctggtccccacagactcagagagaacccgccaccatqttcgtgttcc<br>tggtgctgctgcctctggtgtccagccagtqtqtgaacctgatcaccagaacacagtcatacacca<br>acagctttaccagaggcgtgtactaccccgacaaggtgttcagatccagcgtgctgcactctaccc<br>aggacctgttcctgcctttcttcagcaacgtgacctggttccacgccatctccggcaccaatggca<br>ccaagagattcgacaaccccgtgctgcccttcaacgacggggtgtactttgccagcaccgagaagt<br>ccaacatcatcagaggctggatcttcggcaccacactggacagcaagacccagagcctgctgatcg<br>tgaacaacgccaccaacgtggtcatcaaagtgtgcgagttccagttctgcaacgaccccttcctgg<br>acgtctactaccacaagaacaacaagagctggatggaaagcgagttccgggtgtacagcagcgcca<br>acaactgcaccttcgagtacgtgtcccagcctttcctgatggacctggaaggcaagcagggcaact<br>tcaagaacctgcgcgagttcgtgtttaagaacatcgacggctacttcaagatctacagcaagcaca<br>cccctatcaacctcggccgggatctgcctcagggcttctctgctctggaacccctggtggatctgc<br>ccatcggcatcaacatcacccggtttcagacactgctggccctgcacagaagctacctgacacctg<br>gcgatagcagcagcggatggacagctggtgccgccgcttactatgtgggctacctgcagcctagaa<br>ccttcctgctgaagtacaacgagaacggcaccatcaccgacgccgtggattgtgctctggatcctc<br>tgagcgagacaaagtgcaccctgaagtccttcaccgtggaaagggcatctaccagaccagcaact<br>tccgggtgcagcccaccgaatccatcgtgcggttccccaatatcaccaatctgtgccccttcgacg<br>aggtgttcaatgccaccaccttcgcctctgtgtacgcctggaaccggaagcggatcagcaattgcg<br>tggccgactactccgtgctgtacaacttcgccccttcttcgcattcaagtgctacggcgtgtccc |

TABLE 14-continued

Sequence of one embodiment of an exemplary Omicron BA.4.6/BF.7-specific RNA vaccine

| SEQ ID NO. | Brief Description | Sequence |
| --- | --- | --- |
| | | ctaccaagctgaacgacctgtgcttcacaaacgtgtacgccgacagcttcgtgatccggggaaacg<br>aagtgcggcagattgcccctggacagacaggcaacatcgccgactacaactacaagctgcccgacg<br>acttcaccggctgtgtgattgcctggaacagcaacaagctggactccaaagtcggcggcaactaca<br>attacaggtaccggctgttccggaagtccaatctgaagcccttcgagcgggacatctccaccgaga<br>tctatcaggccggcaacaagccttgtaacggcgtggcaggcgtgaactgctacttcccactgcagt<br>cctacggctttaggcccacatacggcgtgggccaccagccctacagagtggtggtgctgagcttcg<br>aactgctgcatgcccctgccacagtgtgcggccctaagaaaagcaccaatctcgtgaagaacaaat<br>gcgtgaacttcaacttcaacggcctgaccggcaccggcgtgctgacagagagcaacaagaagttcc<br>tgccattccagcagtttggccgggatatcgccgataccacagacgccgttagagatccccagacac<br>tggaaatcctggacatcacccttgcagcttcggcggagtgtctgtgatcacccctggcaccaaca<br>ccagcaatcaggtggcagtgctgtaccagggcgtgaactgtaccgaagtgcccgtggccattcacg<br>ccgatcagctgacacctacatggcgggtgtactccaccggcagcaatgtgtttcagaccagagccg<br>gctgtctgatcggagccgagtacgtgaacaatagctacgagtgcgacatccccatcggcgctggaa<br>tctgcgccagctaccagacacagacaaagagccaccggagagccagaagcgtggccagccagagca<br>tcattgcctacacaatgtctctgggcgccgagaacagcgtggcctactccaacaactctatcgcta<br>tccccaccaacttcaccatcagcgtgaccacagagatcctgcctgtgtccatgaccaagaccagcg<br>tggactgcaccatgtacatctgcggcgattccaccgagtgctccaacctgctgctgcagtacggca<br>gcttctgcacccagctgaaaagagccctgacagggatcgccgtggaacaggacaagaacacccaag<br>aggtgttcgcccaagtgaagcagatctacaagacccctcctatcaagtacttcggcggcttcaatt<br>tcagccagattctgcccgatcctagcaagcccagcaagcggagcttcatcgaggacctgctgttca<br>acaaagtgacactggccgacgccggcttcatcaagcagtatggcgattgtctgggcgacattgccg<br>ccagggatctgatttgcgcccagaagtttaacggactgacagtgctgcctcctctgctgaccgatg<br>agatgatcgcccagtacacatctgccctgctggccggcacaatcacaagcggctggacatttggag<br>caggcgccgctctgcagatcccctttgctatgcagatggcctaccggttcaacggcatcggagtga<br>cccagaatgtgctgtacgagaaccagaagctgatcgccaaccagttcaacagcgccatcggcaaga<br>tccaggacagcctgagcagcacagcaagcgccctgggaaagctgcaggacgtggtcaaccacaatg<br>cccaggcactgaacaccctggtcaagcagctqtcctccaagttcggcgccatcagctctgtgctga<br>acgatatcctgagcagactggaccctcctgaggccgaggtgcagatcgacagactgatcacaggca<br>gactgcagagcctccagacatacgtgacccagcagctgatcagagccgccgagattagagcctctg<br>ccaatctggccgccaccaagatgtctgagtgtgtgctgggccagagcaagagagtggacttttgcg<br>gcaagggctaccacctgatgagcttccctcagtctgcccctcacggcgtggtgtttctgcacgtga<br>catatgtgcccgctcaagagaagaatttcaccaccgctccagccatctgccacgacggcaaagccc<br>actttcctagagaaggcgtgttcgtgtccaacggcacccattggttcgtgacacagcggaacttct<br>acgagccccagatcatcaccaccgacaacaccttcgtgtctggcaactgcgacgtcgtgatcggca<br>ttgtgaacaataccgtgtacgaccctctgcagcccgagctggacagcttcaaagaggaactggaca<br>agtactttaagaaccacacaagccccgacgtggacctgggcgatatcagcggaatcaatgccagcg<br>tcgtgaacatccagaaagagatcgaccggctgaacgaggtggccaagaatctgaacgagagcctga<br>tcgacctgcaagaactggggaagtacgagcagtacatcaagtggccctggtacatctggctgggct<br>ttatcgccggactgattgccatcgtgatggtcacaatcatgctgtgttgcatgaccagctgctgta<br>gctgcctgaagggctgttgtagctgtggcagctgctgcaagttcgacgaggacgattctgagcccg<br>ctccacctgccccactcaccacctctgctagttccagacacctcccaagcacgcagcaatgcagct<br>tgctgaagggcgtgaaactgcactacacatgatgactcgagctggtactgcatgcacgcaatgcta<br>gctgcccctttcccgtcctgggtaccccgagtctcccccgacctcgggtcccaggtatgctcccac<br>ctccacctgccccactcaccacctctgctagttccagacacctcccaagcacgcagcaatgcagct<br>caaaacgcttagcctagccacacccccacgggaaacagcagtgattaacctttagcaataaacgaa<br>agtttaactaagctatactaaccccagggttggtcaatttcgtgccagccacaccctggagctagc<br>aaaaaaaaaaaaaaaaaaaaaaaaaaaaaagcatatgactaaaaaaaaaaaaaaaaaaaaaaaaaa<br>aaaaaaaaaaaaaaaaaaaaaaaaaaaaaaaaaaaaaaaaaaaa |

TABLE 15

Sequence of one embodiment of an exemplary Omicron XBB-specific RNA vaccine

| SEQ ID NO. | Brief Description | Sequence |
| --- | --- | --- |
| 95 | Amino acid sequence of RNA-encoded SARS-Cov-2 S protein from an Omicron XBB variant (with PRO mutations at positions corresponding to K986P and V987P of SEQ ID NO: 1; i.e., PRO mutations at positions 981 and 982 of SEQ ID NO: 95) | MFVFLVLLPLVSSQCVNLITRTQSYTNSFTRGVYYPDKVFRSSVLHSTQDLFLPFFSNVTWFHAIH<br>VSGTNGTKRFDNPALPFNDGVYFASTEKSNIIRGWIFGTTLDSKTQSLLIVNNATNVVIKVCEFQF<br>CNDPFLDVYQKNNKSWMESEFRVYSSANNCTFEYVSQPFLMDLEGKEGNFKNLREFVFKNIDGYFK<br>IYSKHTPINLERDLPQGFSALEPLVDLPIGINITRFQTLLALHRSYLTPGDSSSGWTAGAAAYYVG<br>YLQPRTFLLKYNENGTITDAVDCALDPLSETKCTLKSFTVEKGIYQTSNFRVQPTESIVRFPNITN<br>LCPFHEVFNATTFASVYAWNRKRISNCVADYSVIYNFAPFFAFKCYGVSPTKLNDLCFTNVYADSF<br>VIRGNEVSQIAPGQTGNIADYNYKLPDDFTGCVIAWNSNKLDSKPSGNYNYLYRLFRKSKLKPFER<br>DISTEIYQAGNKPCNGVAGSNCYSPLQSYGFRPTYGVGHQPYRVVVLSFELLHAPATVCGPKKSTN<br>LVKNKCVNFNFNGLTGTGVLTESNKKFLPFQQFGRDIADTTDAVRDPQTLEILDITPCSFGGVSVI<br>TPGTNTSNQVAVLYQGVNCTEVPVAIHADQLTPTWRVYSTGSNVFQTRAGCLIGAEYVNNSYECDI<br>PIGAGICASYQTQTKSHRRARSVASQSIIAYTMSLGAENSVAYSNNSIAIPTNFTISVTTEILPVS<br>MTKTSVDCTMYICGDSTECSNLLLQYGSFCTQLKRALTGIAVEQDKNTQEVFAQVKQIYKTPPIKY<br>FGGFNFSQILPDPSKPSKRSFIEDLLFNKVTLADAGFIKQYGDCLGDIAARDLICAQKENGLTVLP<br>PLLTDEMIAQYTSALLAGTITSGWTFGAGAALQIPFAMQMAYRFNGIGVTQNVLYENQKLIANQFN |

TABLE 15-continued

Sequence of one embodiment of an exemplary Omicron XBB-specific RNA vaccine

| SEQ ID NO. | Brief Description | Sequence |
|---|---|---|
| | | SAIGKIQDSLSSTASALGKLQDVVNHNAQALNTLVKQLSSKFGAISSVLNDILSRLDPPEAEVQID<br>RLITGRLQSLQTYVTQQLIRAAEIRASANLAATKMSECVLGQSKRVDFCGKGYHLMSFPQSAPHGV<br>VFLHVTYVPAQEKNFTTAPAICHDGKAHFPREGVFVSNGTHWFVTQRNFYEPQIITTDNTFVSGNC<br>DVVIGIVNNTVYDPLQPELDSFKEELDKYFKNHTSPDVDLGDISGINASVVNIQKEIDRLNEVAKN<br>LNESLIDLQELGKYEQYIKWPWYIWLGFIAGLIAIVMVTIMLCCMTSCCSCLKGCCSCGSCCKFDE<br>DDSEPVLKGVKLHYT |
| 96 | RNA sequence encoding a SARS-COV-2 S protein from an Omicron XBB variant | auguucguguuccuggugcugcugccucuggugguccagccagugugugaaccugaucaccagaaca<br>cagUCAuacaccaacagouuuaccagaggcguguacuaccccgacaagguguucagauccagcgug<br>cugcacucuacccaggaccuguuccugccuuucuucagcaacgugaccugguuccacgccauccac<br>guguccggcaccaauggcaccaagagauucgacaaccccgcccugcccuucaacgacgggguguac<br>uuugccagcaccgagaaguccaacaucaucagaggcuggaucuucggcaccacacuggacagcaag<br>acccagagccugcugaucgugaacaacgccaccaacguggucaucaaagugugcgaguuccaguuc<br>ugcaacgaccccuuccuggacgucuaccagaagaacaacaagagcuggauggaaagcgaguuccgg<br>guguacagcagcgccaacaacugcaccuucgaguacgugucccagccuuuccugauggaccuggaa<br>ggcaaggagggcaacuucaagaaccugcgcgaguucguguuuaagaacaucgacggcuacuucaag<br>aucuacagcaagcacaccccuaucaaccucgagcgggaucugccucagggcuucucugcucuggaa<br>ccccugguggaucugcccaucggcaucaacaucacccgguuucagacacugcuggcccugcacaga<br>agcuaccugacaccuggcgauagcagcagcggauggacagouggugccgccgcuuacuaugugggc<br>uaccugcagccuagaaccuuccugcugaaguacaacgagaacggcaccaucaccgacgccguggau<br>ugugcucuggauccucugagcgagacaaagugcacccugaaguccuucaccguggaaaagggcauc<br>uaccagaccagcaacuuccgggugcagcccaccgaauccaucgugcgguuccccaauaucaccaau<br>cugugccccuuccacgagguguucaaugccaccaccuucgccucuguguacgccuggaaccggaag<br>cggaucagcaauugcguggccgacuacuccgugaucuacaacuucgccccuucuucgcauucaag<br>ugcuacggcguguccccuaccaagcugaacgaccugugcuucacaaacguguacgccgacagcuuc<br>gugauccggggaaacgaagugucacagauugccccuggacagacaggcaacaucgccgacuacaac<br>uacaagcugcccgacgacuucaccgocugugugauugccuggaacagcaacaagcuggacuccaaa<br>cccagcggcaacuacaauuaccuguaccggcuguuccggaaguccaagcugaagcccuucgagcgg<br>gacaucuccaccgagaucuaucaggccggcaacaagccuuguaacggcguggcaggcagcaacugc<br>uacagcccacugcaguccuacggcuuuaggcccacauacggcgugggccaccagcccuacagagug<br>guggugcugagcuucgaacugcugcaugccccugccacagugugcggcccuaagassagcaccaau<br>cucgugaagaacaaaugcgugaacuucaacuucaacggccugaccggcaccggcgugcugacagag<br>agcaacaagaaguuccugccauuccagcaguuuggccgggauaucgccgauaccacagacgccguu<br>agagaucccagacacuggaaauccuggacaucaccccuugcagcuucggcggagugucugugauc<br>accccuggcaccaacaccagcaaucagguggcagugcuguaccagggcgugaacuguaccgaagug<br>cccguggccauucacgccgaucagcugacaccuacauggcggguguacuccaccggcagcaaugug<br>uuucagaccagagcoggcugucugaucggagccgaguacgugaacaauagcuacgagugcgacauc<br>cccaucggcgcuggaaucugcgccagcuaccagacacagacaaagagccaccggagagccagaagc<br>guggccagccagagcaucauugccuacacaaugucucugggcgccgagaacagcguggccuacucc<br>aacaacucuaucgcuauccccaccaacuucaccaucagcgugaccacagagauccugccuguguccc<br>augaccaagaccagoguggacugcaccauguacaucugcggcgauuccaccgagugcuccaaccug<br>cugcugcaguacggcagouucugcacccagcugaaaagagcccugacagggaucgccguggaacag<br>gacaagaacacccaagagguguucgcccaagugaagcagaucuacaagaccccuccuaucaaguac<br>uucggcggcuucaauuucagccagauucugcccgauccuagcaagcccagcaagcggagcuucauc<br>gaggaccugcuguucaacaaagugacacuggccgacgccggcuucaucaagcaguauggcgauugu<br>cugggcgacauugccgccagggaucugauuugcgcccagaaguuuaacggacugacagugcugccu<br>ccucugcugaccgaugagaugaucgcccaguacacaucugcccugcuggccggcacaaucacaagc<br>ggcuggacauuuggagcaggcgccgcucugcagauccccuuugcuaugcagauggccuaccgguuc<br>aacggcaucggagugacccagaaugugcuguacgagaaccagaagcugaucgccaaccaguucaac<br>agcgccaucggcaagauccaggacagccugagcagcacagcaagcgcccugggaaagcugcaggac<br>guggucaaccacaaugcccaggcacugaacacccuggucaagcagcuguccuccaaguucggcgcc<br>aucagcucugugougaacgauauccugagcagacuggacccuccugaggccgaggugcagaucgac<br>agacugaucacaggcagacugcagagccuccagacauacgugacccagcagcugaucagagccgcc<br>gagauuagagccucugccaaucuggccgccaccaagaugucugagugugugcugggccagagcaag<br>agaguggacuuuugcggcaagggcuaccaccugaugagcuucccucagucugccccucacggcgug<br>guguuucugcacgugacauaugugcccgcucaagagaagaauuucaccaccgcuccagccaucugc<br>cacgacggcaaagcccacuuuccuagagaaggcguguucguguccaacggcacccauugguucgug<br>acacagcggaacuucuacgagccccagaucaucaccaccgacaacaccuucgugucuggcaacugc<br>gacgucgugaucggcauugugaacaauaccguguacgacccucugcagcccgagcuggacagcuuc<br>aaagaggaacuggacaaguacuuuaagaaccacacaagccccgacguggaccugggcgauaucagc<br>ggaaucaaugccagcgucgugaacauccagaaagagaucgaccggcugaacgagguggccaagaau<br>cugaacgagagccugaucgaccugcaagaacuggggaaguacgagcaguacaucaaguggcccugg<br>uacaucuggcugggcuuuaucgccggacugauugccaucgugauggucacaaucaugcuguguugc<br>augaccagougouguagcugccugaagggcuguuguagcuguggcagcugcugcaaguucgacgag<br>gacgauucugagcccgugougaagggcgugaaacugcacuacacaugauga |
| 97 | DNA sequence encoding a SARS-CoV-2 S protein from an Omicron XBB variant | atgttcgtgttcctggtgctgctgcctctggtgtccagccagtgtgtgaacctgatcaccagaaca<br>cagTCAtacaccaacagctttaccagaggcgtgtactaccccgacaaggtgttcagatccagcgtg<br>ctgcactctacccaggacctgttcctgcctttcttcagcaacgtgacctggttccacgccatccac<br>gtgtccggcaccaatggcaccaagagattcgacaaccccgccctgcccttcaacgacggggtgtac<br>tttgccagcaccgagaagtccaacatcatcagaggctggatcttcggcaccacactggacagcaag<br>acccagagcctgctgatcgtgaacaacgccaccaacgtggtcatcaaagtgtgcgagttccagttc<br>tgcaacgaccccttcctggacgtctaccagaagaacaacaagagctggatggaaagcgagttccgg<br>gtgtacagcagcgccaacaactgcaccttcgagtacgtgtcccagcctttcctgatggacctggaa |

TABLE 15-continued

Sequence of one embodiment of an exemplary Omicron XBB-specific RNA vaccine

| SEQ ID NO. | Brief Description | Sequence |
|---|---|---|
| | | ggcaaggagggcaacttcaagaacctgcgcgagttcgtgtttaagaacatcgacggctacttcaag<br>atctacagcaagcacacccctatcaacctcgagcgggatctgcctcagggcttctctgctctggaa<br>cccctggtggatctgcccatcggcatcaacatcacccggtttcagacactgctggccctgcacaga<br>agctacctgacacctggcgatagcagcagcggatggacagctggtgccgccgcttactatgtgggc<br>tacctgcagcctagaaccttcctgctgaagtacaacgagaacggcaccatcaccgacgccgtggat<br>tgtgctctggatcctctgagcgagacaaagtgcaccctgaagtccttcaccgtggaaaagggcatc<br>taccagaccagcaacttccgggtgcagcccaccgaatccatcgtgcggttccccaatatcaccaat<br>ctgtgccccttccacgaggtgttcaatgccaccaccttcgcctctgtgtacgcctggaaccggaag<br>cggatcagcaattgcgtggccgactactccgtgatctacaacttcgcccccttcttcgcattcaag<br>tgctacggcgtgtcccctaccaagctgaacgacctgtgcttcacaaacgtgtacgccgacagcttc<br>gtgatccggggaaacgaagtgtcacagattgcccctggacagacaggcaacatcgccgactacaac<br>tacaagctgcccgacgacttcaccggctgtgtgattgcctggaacagcaacaagctggactccaaa<br>cccagcggcaactacaattacctgtaccggctgttccggaagtccaagctgaagcccttcgagcgg<br>gacatctccaccgagatctatcaggccggcaacaagccttgtaacggcgtggcaggcagcaactgc<br>tacagcccactgcagtcctacggctttaggcccacatacggcgtgggccaccagccctacagagtg<br>gtggtgctgagcttcgaactgctgcatgcccctgccacagtgtgcggccctaagaaaagcaccaat<br>ctcgtgaagaacaaatgcgtgaacttcaacttcaacggcctgaccggcaccggcgtgctgacagag<br>agcaacaagaagttcctgccattccagcagtttggccgggatatcgccgataccacagacgccgtt<br>agagatccccagacactggaaatcctggacatcaccccttgcagcttcggcggagtgtctgtgatc<br>acccctggcaccaacaccagcaatcaggtggcagtgctgtaccagggcgtgaactgtaccgaagtg<br>cccgtggccattcacgccgatcagctgacacctacatggcgggtgtactccaccggcagcaatgtg<br>tttcagaccagagccggctgtctgatcggagccgagtacgtgaacaatagctacgagtgcgacatc<br>cccatcggcgctggaatctgcgccagctaccagacacagacaaagagccaccggagagccagaagc<br>gtggccagccagagcatcattgcctacacaatgtctctgggcgccgagaacagcgtggcctactcc<br>aacaactctatcgctatccccaccaacttcaccatcagcgtgaccacagagatcctgcctgtgtcc<br>atgaccaagaccagcgtggactgcaccatgtacatctgcggcgattccaccgagtgctccaacctg<br>ctgctgcagtacggcagcttctgcacccagctgaaaagagccctgacagggatcgccgtggaacag<br>gacaagaacacccaagaggtgttcgcccaagtgaagcagatctacaagacccctcctatcaagtac<br>ttcggcggcttcaatttcagccagattctgcccgatcctagcaagcccagcaagcggagcttcatc<br>gaggacctgctgttcaacaaagtgacactggccgacgccggcttcatcaagcagtatggcgattgt<br>ctgggcgacattgccgccagggatctgatttgcgcccagaagtttaacggactgacagtgctgcct<br>cctctgctgaccgatgagatgatcgcccagtacacatctgccctgctggccggcacaatcacaagc<br>ggctggacatttggagcaggcgccgctctgcagatcccctttgctatgcagatggcctaccggttc<br>aacggcatcggagtgacccagaatgtgctgtacgagaaccagaagctgatcgccaaccagttcaac<br>agcgccatcggcaagatccaggacagcctgagcagcacagcaagcgccctgggaaagctgcaggac<br>gtggtcaaccacaatgcccaggcactgaacaccctggtcaagcagctgtcctccaagttcggcgcc<br>atcagctctgtgctgaacgatatcctgagcagactggaccctcctgaggccgaggtqcagatcgac<br>agactgatcacaggcagactgcagagcctccagacatacgtgacccagcagctgatcagagccgcc<br>gagattagagcctctgccaatctggccgccaccaagatgtctgagtgtgtgctgggccagagcaag<br>agagtggacttttgcggcaagggctaccacctgatgagcttccctcagtctgcccctcacggcgtg<br>gtgtttctgcacgtgacatatgtgcccgctcaagagaagaatttcaccaccgctccagccatctgc<br>cacgacggcaaagcccactttcctagagaaggcgtgttcgtgtccaacggcacccattggttcgtg<br>acacagcggaacttctacgagccccagatcatcaccaccgacaacaccttcgtgtctggcaactgc<br>gacgtcgtgatcggcattgtgaacaataccgtgtacgaccctctgcagcccgagctggacagcttc<br>aaagaggaactggacaagtactttaagaaccacacaagccccgacgtggacctgggcgatatcagc<br>ggaatcaatgccagcgtcgtgaacatccagaaagagatcgaccggctgaacgaggtggccaagaat<br>ctgaacgagagcctgatcgacctgcaagaactggggaagtacgagcagtacatcaagtggccctgg<br>tacatctggctgggctttatcgccggactgattgccatcgtgatggtcacaatcatgctgtgttgc<br>atgaccagctgctgtagctgcctgaagggctgttgtagctgtggcagctgctgcaagttcgacgag<br>gacgattctgagcccgtgctgaagggcgtgaaactgcactacacatgatga |
| 98 | Full length RNA construct encoding a SARS-COV-2 S protein from an Omicron XBB variant | agaauaaacuaguauucuucugguccccacagacucagagagaacccgccaccauguucguguucc<br>uggugcugcugccucugguguccagccagugugugaaccugaucaccagaacacagUCAuacacca<br>acagcuuuaccagaggcguguacuaccccgacaagguguucagauccagcgugcugcacucuaccc<br>aggaccuguuccugccuuucuucagcaacgugaccugguuccacgccauccacguguccggcacca<br>auggcaccaagagauucgacaaccccgcccugcccuucaacgacgggguguacuuugccagcaccg<br>agaaguccaacaucaucagaggcuggaucuucggcaccacacuggacagcaagacccagagccugc<br>ugaucgugaacaacgccaccaacguggucaucaaagugugcgaguuccaguucugcaacgaccccu<br>uccuggacgucuaccagaagaacascaagagcuggauggaaagcgaguuccggguguacagcagcg<br>ccaacaacugcaccuucgaguacgugucccagccuuuccugauggaccuggaaggcaaggagggca<br>acuucaagaaccugcgcgaguucguguuuaagaacaucgacggcuacuucaagaucuacagcaagc<br>acaccccuaucaaccucgagcgggaucugccucagggcuucucugcucuggaaccccugguggauc<br>ugcccaucggcaucaacaucacccgguuucagacacugcuggcccugcacagaagcuaccugacac<br>cuggcgauagcagcagcggauggacagcuggugccgccgcuuacuaugugggcuaccugcagccua<br>gaaccuuccugcugaaguacaacgagaacggcaccaucaccgacgccguggauugugcucuggauc<br>cucugagcgagacaaagugcacccugaaguccuucaccguggaaaagggcaucuaccagaccagca<br>acuuccgggugcagcccaccgaauccaucgugcgguuccccaauaucaccaaucugugccccuucc<br>acgagguguucaaugccaccaccuucgccucuguguacgccuggaaccggaagcggaucagcaauu<br>gcguggccgacuacuccgugaucuacaacuucgcccccuucuucgcauucaagugcuacggcgugu<br>ccccuaccaagcugaacgaccugugcuucacaaacguguacgccgacagcuucgugauccggggaa<br>acgaagugucacagauugccccuggacagacaggcaacaucgccgacuacaacuacaagcugcccg<br>acgacuucaccggcugugugauugccuggaacagcaacaagcuggacuccaaacccagcggcaacu<br>acaauuaccuguaccggcuguuccggaaguccaagcugaagcccuucgagcgggacaucuccaccg<br>agaucuaucaggccggcaacaagccuuguaacggcguggcaggcagcaacugcuacagcccacugc |

TABLE 15-continued

Sequence of one embodiment of an exemplary Omicron XBB-specific RNA vaccine

| SEQ ID NO. | Brief Description | Sequence |
|---|---|---|
| | | aguccuacggcuuuaggcccacauacggcgugggccaccagcccuacagagugguggugcugagcu<br>ucgaacugcugcaugccccugccacagugugcggcccuaagaaaagcaccaaucucgugaagaaca<br>aaugcgugaacuucaacuucaacggccugaccggcaccggcgugcugacagagagcaacaagaagu<br>uccugccauuccagcaguuuggccgggauaucgccgauaccacagacgccguuagagauccccaga<br>cacuggaaauccuggacaucaccccuugcagcuucggcggagugucugugaucaccccuggcacca<br>acaccagcaaucagguggcagugcuguaccagggcgugaacuguaccgaagugcccguggccauuc<br>acgccgaucagcugacaccuacauggcggguguacuccaccggcagcaauguguuucagaccagag<br>ccggcugucugaucggagccgaquacgugaacaauagcuacgagugcgacauccccaucggcgcug<br>gaaucugcgccagcuaccagacacagacaaagagccaccggagagccagaagcguggccagccaga<br>gcaucauugccuacacaaugucucuggggcgcgagaacagcguggccuacuccaacaacucuaucg<br>cuauccccaccaacuucaccaucagcgugaccacagagauccugccuguguccaugaccaagacca<br>gcguggacugcaccauguacaucugcggcgauuccaccgagugcuccaaccugcugcugcaguacg<br>gcagcuucugcacccagcugaaaagagcccugacagggaucgccguggaacaggacaagaacaccc<br>aagagguguucgcccaagugaagcagaucuacaagaccccuccuaucaaguacuucggcggcuuca<br>auuucagccagauucugcccgauccuagcaagcccagcaagcggagcuucaucgaggaccugcugu<br>ucaacaaagugacacuggccgacgccggcuucaucaagcaguauggcgauugucugggcgacauug<br>ccgccagggaucugauuugcgcccagaaguuuaacggacugacagugcugccuccucugcugaccg<br>augagaugaucgcccaguacacaucugcccugcuggccggcacaaucacaagcggcuggacauuug<br>gagcaggcgccgcucugcagauccccuuugcuaugcagauggccuaccgguucaacggcaucggag<br>ugacccagaaugugcuguacgagaaccagaagcugaucgccaaccaguucaacagcgccaucggca<br>agauccaggacagccugagcagcacagcaagcgcccugggaaagcugcaggacguggucaaccaca<br>augcccaggcacugaacacccuggucaagcagcuguccuccaaguucggcgccaucagcucugugc<br>ugaacgauauccugagcagacuggacccuccugaggccgaggugcagaucgacagacugaucacag<br>gcagacugcagagccuccagacauacgugacccagcagcugaucagagccgccgagauuagagccu<br>cugccaaucuggccgccaccaagaugucugagugugugcugggccagagcaagagaguggacuuuu<br>gcggcaagggcuaccaccugaugagcuucccucagucugccccucacggcgugguguuucugcacg<br>ugacauaugugcccgcucaagagaagaauuucaccaccgcuccagccaucugccacgacggcaaag<br>cccacuuuccuagagaaggcguguucguguccaacggcacccauugguucgugacacagcggaacu<br>ucuacgagccccagaucaucaccaccgacaacaccuucgugucuggcaacugcgacgucgugaucg<br>gcauugugaacaauaccguguacgacccucugcagcccgagcuggacagcuucaaagaggaacugg<br>acaaguacuuuaagaaccacacaagccccgacguggaccugggcgauaucagcggaaucaaugcca<br>gcgucgugaacauccagaaagagaucgaccggcugaacgagguggccaagaaucugaacgagagcc<br>ugaucgaccugcaagaacuggggaaguacgagcaguacaucaaguggcccugguacaucuggcugg<br>gcuuuaucgccggacugauugccaucgugauggucacaaucaugcuguguugcaugaccagcugcu<br>guagcugccugaagggcuguuguagcuguggcagcugcugcaaguucgacgaggacgauucugagc<br>ccgugcugaagggcgugaaacugcacuacacaugaugacucgagcugguacugcaugcacgcaaug<br>cuagcugccccuuucccguccuggguaccccgagucucccccgaccucggucccagguaugcucc<br>caccuccaccugccccacucaccaccucugcuaguuccagacaccucccaagcacgcagcaaugca<br>gcucaaaacgcuuagccuagccacacccccacgggaaacagcagugauuaaccuuuagcaauaaac<br>gaaaguuuaacuaagcuauacuaaccccaggguuggucaauuucgugccagccacacccuggagcu<br>agcaaaaaaaaaaaaaaaaaaaaaaaaaaaaaagcauaugacuaaaaaaaaaaaaaaaaaaaaaa<br>aaaaaaaaaaaaaaaaaaaaaaaaaaaaaaaaaaaaaaaaaaaa |
| 99 | Full length DNA construct encoding a SARS-COV-2 S protein from an Omicron XBB variant | agaataaactagtattcttctggtccccacagactcagagagaacccqccaccatgttcgtgttcc<br>tggtgctgctgcctctggtgtccagccagtgtgtgaacctgatcaccagaacacagTCAtacacca<br>acagctttaccagaggcgtgtactaccccgacaaggtgttcagatccagcgtgctgcactctaccc<br>aggacctgttcctgcctttcttcagcaacgtgacctggttccacgccatccacgtgtccggcacca<br>atggcaccaagagattcgacaaccccgccctgcccttcaacgacggggtgtactttgccagcaccg<br>agaagtccaacatcatcagaggctggatcttcggcaccacactggacagcaagacccagagcctgc<br>tgatcgtgaacaacgccaccaacgtggtcatcaaagtgtgcgagttccagttctgcaacgacccct<br>tcctggacgtctaccagaagaacaacaagagctggatggaaagcgagttccgggtgtacagcagcg<br>ccaacaactgcaccttcgagtacgtgtcccagcctttcctgatggacctggaaggcaaggagggca<br>acttcaagaacctgcgcgagttcgtgtttaagaacatcgacggctacttcaagatctacagcaagc<br>acacccctatcaacctcgagcgggatctgcctcagggcttctctgctctggaacccctggtggatc<br>tgcccatcggcatcaacatcacccggtttcagacactgctggccctgcacagaagctacctgacac<br>ctggcgatagcagcagcggatggacagctggtgccgccgcttactatgtgggctacctgcagccta<br>gaaccttcctgctgaagtacaacgagaacggcaccatcaccgacgccgtggattgtgctctggatc<br>ctctgagcgagacasagtgcaccctgaagtccttcaccgtggaaaagggcatctaccagaccagca<br>acttccgggtgcagcccaccgaatccatcgtgcggttccccaatatcaccaatctgtgccccttcc<br>acgaggtgttcaatgccaccaccttcgcctctgtgtacgcctggaaccggaagcggatcagcaatt<br>gcgtggccgactactccgtgatctacaacttcgccccctcttcgcattcaagtgctacggcgtgt<br>cccctaccaagctgaacgacctgtgcttcacaaacgtgtacgccgacagcttcgtgatccggggaa<br>acgaagtgtcacagattccccctggacagacaggcaacatcgccgactacaactacaagctgcccg<br>acgacttcaccggctgtgtgattgcctggaacagcaacaagctggactccaaacccagcggcaact<br>acaattacctgtaccggctgttccggaagtccaagctgaagcccttcgagcgggacatctccaccg<br>agatctatcaggccggcaacaagccttgtaacggcgtggcaggcagcaactgctacagcccactgc<br>agtcctacggctttaggcccacatacggcgtgggccaccagccctacagagtggtggtgctgagct<br>tcgaactgctgcatgcccctgccacagtgtgcggccctaagaaaagcaccaatctcgtgaagaaca<br>aatgcgtgaacttcaacttcaacggcctgaccggcaccggcgtgctgacagagagcaacaagaagt<br>tcctgccattccagcagtttggccgggatatcgccgataccacagacgccgttagagatccccaga<br>cactggaaatcctggacatcaccccttgcagcttcggcggagtgtctgtgatcacccctggcacca<br>acaccagcaatcaggtcgcagtgctgtaccagggcgtgaactgtaccgaagtgcccgtggccattc<br>acgccgatcagctgacacctacatggcgggtgtactccaccggcagcaatgtgtttcagaccagag<br>ccggctgtctgatcggagccgagtacgtgaacaatagctacgagtgcgacatccccatcggcgctg |

TABLE 15-continued

Sequence of one embodiment of an exemplary Omicron XBB-specific RNA vaccine

| SEQ ID NO. | Brief Description | Sequence |
|---|---|---|
| | | gaatctgcgccagctaccagacacagacaaagagccaccggagagccagaagcgtggccagccaga gcatcattgcctacacaatgtctctgggcgccgagaacagcgtggcctactccaacaactctatcg ctatccccaccaacttcaccatcagcgtgaccacagagatcctgcctgtgtccatgaccaagacca gcgtggactgcaccatgtacatctgcggcgattccaccgagtgctccaacctgctgctgcagtacg gcagcttctgcacccagctgaaaagagccctgacagggatcgccgtggaacaggacaagaacaccc aagaggtgttcgcccaagtgaagcagatctacaagacccctcctatcaagtacttcggcggcttca atttcagccagattctgcccgatcctagcaagcccagcaagcggagcttcatcgaggacctgctgt tcaacaaagtgacactggccgacgccggcttcatcaagcagtatggcgattgtctgggcgacattg ccgccagggatctgatttccgcccagaagtttaacggactgacagtgctgcctcctctgctgaccg atgagatgatcgcccagtacacatctgccctgctggccggcacaatcacaagcggctggacatttg gagcaggcgccgctctgcagatcccctttgctatgcagatggcctaccggttcaacggcatcggag tgacccagaatgtgctgtacgagaaccagaagctgatcgccaaccagttcaacagcgccatcggca agatccaggacagcctgagcagcacagcaagcgccctgggaaagctgcaggacgtggtcaaccaca atgcccaggcactgaacaccctggtcaagcagctgtcctccaagttcggcgccatcagctctgtgc tgaacgatatcctgagcagactggaccctcctgaggccgagggtgcagatcgacagactgatcacag gcagactgcagagcctccagacatacgtgacccagcagctgatcagagccgccgagattagagcct ctgccaatctggccgccaccaagatgtctgagtgtgtgctgggccagagcaagagagtggacttttt gcggcaagggctaccacctgatgagcttccctcagtctgccctcacggcgtggtgtttctgcacg tgacatatgtgcccgctcaagagaagaatttcaccaccgctccagccatctgccacgacggcaaag cccactttcctagagaaggcgtgttcgtgtccaacggcacccattggttcgtgacacagcggaact tctacgagccccagatcatcaccaccgacaacaccttcgtgtctggcaactgcgacgtcgtgatcg gcattgtgaacaataccgtgtacgaccctctgcagcccgagctggacagcttcaaagaggaactgg acaagtacttcaagaaccacacaagccccgacgtggacctgggcgatatcagcggaatcaatgcca gcgtcgtgaacatccagaaagagatcgaccggctgaacgaggtggccaagaatctgaacgagagcc tgatcgacctgcaagaactggggsagtacgagcagtacatcaagtggccctggtacatctggctgg gctttatcgccggactgattgccatcgtgatggtcacaatcatgctgtgttgcatgaccagctgct gtagctgcctgaagggctgttgtagctgtggcagctgctgcaagttcgacgaggacgattctgagc ccgcgctgaagggcgtgaaactgcactacacatgatgactcgagctggtactgcatgcacgcaatg ctagctgccccctttcccgtcctgggtaccccgagtctcccccgacctcgggtcccaggtatgctcc cacctccacctgccccactcaccacctctgctagttccagacacctcccaagcacgcagcaatgca gctcaaaacgcttagcctagccacaccccacgggaaacagcagtgattaacctttagcaataaac gaaagtttaactaagctatactaaccccagggttggtcaatttcgtgccagccacaccctggagct agcaaaaaaaaaaaaaaaaaaaaaaaaaaaaaagcatatgactaaaaaaaaaaaaaaaaaaaaaaa aaaaaaaaaaaaaaaaaaaaaaaaaaaaaaaaaaaaaaaaaaaaaaaa |

TABLE 16

Sequence of one embodiment of an exemplary Omicron BQ.1.1-specific RNA vaccine

| SEQ ID NO. | Brief Description | Sequence |
|---|---|---|
| 100 | Amino acid sequence of RNA-encoded SARS-CoV-2 S protein from an Omicron BQ.1.1 variant (with PRO mutations at positions corresponding to K986P and V987P of SEQ ID NO: 1; i.e., PRO mutations at positions 981 and 982 of SEQ ID NO: 100) | MFVFLVLLPLVSSQCVNLITRTQSYTNSFTRGVYYPDKVFRSSVLHSTQDLFLPFFSNVTWFHAIS GTNGTKRFDNPVLPFNDGVYFASTEKSNIIRGWIFGTTLDSKTQSLLIVNNATNVVIKVCEFQFCN DPFLDVYYHKNNKSWMESEFRVYSSANNCTFEYVSQPFLMDLEGKQGNFKNLREFVFKNIDGYFKI YSKHTPINLGRDLPQGFSALEPLVDLPIGINITRFQTLLALHRSYLTPGDSSSGWTAGAAAYYVGY LQPRTFLLKYNENGTITDAVDCALDPLSETKCTLKSFTVEKGIYQTSNFRVQPTESIVRFPNITNL CPFDEVENATTFASVYAWNRKRISNCVADYSVLYNFAPFFAFKCYGVSPTKLNDLCFTNVYADSFV IRGNEVSQIAPGQTGNIADYNYKLPDDFTGCVIAWNSNKLDSTVGGNYNYRYRLFRKSKLKPFERD ISTEIYQAGNKPCNGVAGVNCYFPLQSYGFRPTYGVGHQPYRVVVLSFELLHAPATVCGPKKSTNL VKNKCVNFNFNGLTGTGVLTESNKKFLPFQQFGRDIADTTDAVRDPQTLEILDITPCSFGGVSVIT PGTNTSNQVAVLYQGVNCTEVPVAIHADQLTPTWRVYSTGSNVFQTRAGCLIGAEYVNNSYECDIP IGAGICASYQTQTKSHRRARSVASQSIIAYTMSLGAENSVAYSNNSIAIPTNFTISVTTEILPVSM TKTSVDCTMYICGDSTECSNLLLQYGSFCTQLKRALTGIAVEQDKNTQEVFAQVKQIYKTPPIKYF GGFNFSQILPDPSKPSKRSFIEDLLENKVTLADAGFIKQYGDCLGDIAARDLICAQKFNGLTVLPP LLTDEMIAQYTSALLAGTITSGWTFGAGAALQIPFAMQMAYRENGIGVTQNVLYENQKLIANQFNS AIGKIQDSLSSTASALGKLQDVVNHNAQALNTLVKQLSSKFGAISSVLNDILSRLDPPEAEVQIDR LITGRLQSLQTYVTQQLIRAAEIRASANLAATKMSECVLGQSKRVDFCGKGYHLMSFPQSAPHGVV FLHVTYVPAQEKNETTAPAICHDGKAHFPREGVEVSNGTHWEVTQRNFYEPQIITTDNTFVSGNCD VVIGIVNNTVYDPLQPELDSFKEELDKYFKNHTSPDVDLGDISGINASVVNIQKEIDRLNEVAKNL NESLIDLQELGKYEQYIKWPWYIWLGFIAGLIAIVMVTIMLCCMTSCCSCLKGCCSCGSCCKFDED DSEPVLKGVKLHYT |
| 101 | RNA sequence encoding a SARS-COV-2 S protein from an Omicron BQ.1.1 variant | AUGUUCGUGUUCCUGGUGCUGCUGCCUCUGGUGUCCAGCCAGUGUGUGAACCUGAUCACCAGAACA CAGUCAUACACCAACAGCUUUACCAGAGGCGUGUACUACCCCGACAAGGUGUUCAGAUCCAGCGUG CUGCACUCUACCCAGGACUGUUCCUGCCUUUCUUUCAGCAACGUGACCUGGUUCCACGCCAUCUCC GGCACCAAUGGCACCAAGAGAUUCGACAACCCCGUGCUGCCCUUCAACGACGGGGUGUACUUUGCC AGCACCGAGAAGUCCAACAUCAUCAGAGGCUGGAUCUUCGGCACCACACUGGACAGCAAGACCCAG AGCCUGCUGAUCGUGAACAACGCCACCAACGUGGUCAUCAAAGUGUGCGAGUUCCAGUUCUGCAAC GACCCCUUCCUGGACGUCUACUACCACAAGAACAACAAGAGCUGGAUGGAAAGCGAGUUCCGGGUG |

TABLE 16-continued

| SEQ ID NO. | Brief Description | Sequence |
| --- | --- | --- |
| Sequence of one embodiment of an exemplary Omicron BQ.1.1-specific RNA vaccine | | |
| | | UACAGCAGCGCCAACAACUGCACCUUCGAGUACGUGUCCCAGCCUUUCCUGAUGGACCUGGAAGGC<br>AAGCAGGGCAACUUCAAGAACCUGCGCGAGUUCGUGUUUAAGAACAUCGACGGCUACUUCAAGAUC<br>UACAGCAAGCACACCCCUAUCAACCUCGGCCGGGAUCUGCCUCAGGGCUUCUCUGCUCUGGAACCC<br>CUGGUGGAUCUGCCCAUCGGCAUCAACAUCACCCGGUUUCAGACACUGCUGGCCCUGCACAGAAGC<br>UACCUGACACCUGGCGAUAGCAGCAGCGGAUGGACAGCUGGUGCCGCCGCUUACUAUGUGGGCUAC<br>CUGCAGCCUAGAACCUUCCUGCUGAAGUACAACGAGAACGGCACCAUCACCGACGCCGUGGAUUGU<br>GCUCUGGAUCCUCUGAGCGAGACAAAGUGCACCCUGAAGUCCUUCACCGUGGAAAAGGGCAUCUAC<br>CAGACCAGCAACUUCCGGGUGCAGCCCACCGAAUCCAUCGUGCGGUUCCCCAAUAUCACCAAUCUG<br>UGCCCCUUCGACGAGGUGUUCAAUGCCACCACCUUCGCCUCUGUGUACGCCUGGAACCGGAAGCGG<br>AUCAGCAAUUGCGUGGCCGACUACUCCGUGCUGUACAACUUCGCCCCCUUCUUCGCAUUCAAGUGC<br>UACGGCGUGUCCCCUACCAAGCUGAACGACCUGUGCUUCACAAACGUGUACGCCGACAGCUUCGUG<br>AUCCGGGGAAACGAAGUGUCACAGAUUGCCCCUGGACAGACAGGCAACAUCGCCGACUACAACUAC<br>AAGCUGCCCGACGACUUCACCGGCUGUGUGAUUGCCUGGAACAGCAACAAGCUGGACUCCACCGUC<br>GGCGGCAACUACAAUUACAGGUACCGGCUGUUCCGGAAGUCCAAGCUGAAGCCCUUCGAGCGGGAC<br>AUCUCCACCGAGAUCUAUCAGGCCGGCAACAAGCCUUGUAACGGCGUGGCAGGCGUGAACUGCUAC<br>UUCCCACUGCAGUCCUACGGCCUUAGGCCCACAUACGGCGUGGGCCACCAGCCCUACAGAGUGGUG<br>GUGCUGAGCUUCGAACUGCUGCAUGCCCCUGCCACAGUGUGCGGCCCUAAGAAAAGCACCAAUCUC<br>GUGAAGAACAAAUGCGUGAACUUCAACUUCAACGGCCUGACCGGCACCGGCGUGCUGACAGAGAGC<br>AACAAGAAGUUCCUGCCAUUCCAGCAGUUUGGCCGGGAUAUCGCCGAUACCACAGACGCCGUUAGA<br>GAUCCCCAGACACUGGAAAUCCUGGACAUCACCCCUUGCAGCUUCGGCGGAGUGUCUGUGAUCACC<br>CCUGGCACCAACACCAGCAAUCAGGUGGCAGUGCUGUACCAGGGCGUGAACUGUACCGAAGUGCCC<br>GUGGCCAUUCACGCCGAUCAGCUGACACCUACAUGGCGGGUGUACUCCACCGGCAGCAAUGUGUUU<br>CAGACCAGAGCCGGCUGUCUGAUCGGAGCCGAGUACGUGAACAAUAGCUACGAGUGCGACAUCCCC<br>AUCGGCGCUGGAAUCUGCGCCAGCUACCAGACACAGACAAAGAGCCACCGGAGAGCCAGAAGCGUG<br>GCCAGCCAGAGCAUCAUUGCCUACACAAUGUCUCUGGGCGCCGAGAACAGCGUGGCCUACUCCAAC<br>AACUCUAUCGCUAUCCCCACCAACUUCACCAUCAGCGUGACCACAGAGAUCCUGCCUGUGUCCAUG<br>ACCAAGACCAGCGUGGACUGCACCAUGUACAUCUGCGGCGAUUCCACCGAGUGCUCCAACCUGCUG<br>CUGCAGUACGGCAGCUUCUGCACCCAGCUGAAAAGAGCCCUGACAGGGAUCGCCGUGGAACAGGAC<br>AAGAACACCCAAGAGGUGUUCGCCCAAGUGAAGCAGAUCUACAAGACCCCUCCUAUCAAGUACUUC<br>GGCGGCUUCAAUUUCAGCCAGAUUCUGCCCGAUCCUAGCAAGCCCAGCAAGCGGAGCUUCAUCGAG<br>GACCUGCUGUUCAACAAAGUGACACUGGCCGACGCCGGCUUCAUCAAGCAGUAUGGCGAUUGUCUG<br>GGCGACAUUGCCGCCAGGGAUCUGAUUUGCGCCCAGAAGUUUAACGGACUGACAGUGCUGCCUCCU<br>CUGCUGACCGAUGAGAUGAUCGCCCAGUACACAUCUGCCCUGCUGGCCGGCACAAUCACAAGCGGC<br>UGGACAUUUGGAGCAGGCGCCGCUCUGCAGAUCCCCUUUGCUAUGCAGAUGGCCUACCGGUUCAAC<br>GGCAUCGGAGUGACCCAGAAUGUGCUGUACGAGAACCAGAAGCUGAUCGCCAACCAGUUCAACAGC<br>GCCAUCGGCAAGAUCCAGGACAGCCUGAGCAGCACAGCAAGCGCCCUGGGAAAGCUGCAGGACGUG<br>GUCAACCACAAUGCCCAGGCACUGAACACCCUGGUCAAGCAGCUGUCCUCCAAGUUCGGCGCCAUC<br>AGCUCUGUGCUGAACGAUAUCCUGAGCAGACUGGACCCUCCUGAGGCCGAGGUGCAGAUCGACAGA<br>CUGAUCACAGGCAGACUGCAGAGCCUCCAGACAUACGUGACCCAGCAGCUGAUCAGAGCCGCCGAG<br>AUUAGAGCCUCUGCCAAUCUGGCCGCCACCAAGAUGUCUGAGUGUGUGCUGGGCCAGAGCAAGAGA<br>GUGGACUUUUGCGGCAAGGGCUACCACCUGAUGAGCUUCCCUCAGUCUGCCCCUCACGGCGUGGUG<br>UUUCUGCACGUGACAUAUGUGCCCGCUCAAGAGAAGAAUUUCACCACCGCUCCAGCCAUCUGCCAC<br>GACGGCAAAGCCCACUUUCCUAGAGAAGGCGUGUUCGUGUCCAACGGCACCCAUUGGUUCGUGACA<br>CAGCGGAACUUCUACGAGCCCCAGAUCAUCACCACCGACAACACCUUCGUGUCUGGCAACUGCGAC<br>GUCGUGAUCGGCAUUGUGAACAAUACCGUGUACGACCCUCUGCAGCCCGAGCUGGACAGCUUCAAA<br>GAGGAACUGGACAAGUACUUUAAGAACCACACAAGCCCCGACGUGGACCUGGGCGAUAUCAGCGGA<br>AUCAAUGCCAGCGUCGUGAACAUCCAGAAAGAGAUCGACCGGCUGAACGAGGUGGCCAAGAAUCUG<br>AACGAGAGCCUGAUCGACCUGCAAGAACUGGGGAAGUACGAGCAGUACAUCAAGUGGCCCUGGUAC<br>AUCUGGCUGGGCUUUAUCGCCGGACUGAUUGCCAUCGUGAUGGUCACAAUCAUGCUGUGUUGCAUG<br>ACCAGCUGCUGUAGCUGCCUGAAGGGCUGUUGUAGCUGUGGCAGCUGCUGCAAGUUCGACGAGGAC<br>GAUUCUGAGCCCGUGCUGAAGGGCGUGAAACUGCACUACACAUGAUGA |
| 102 | DNA sequence encoding a SARS-CoV-2 S protein from an Omicron BQ.1.1 variant | ATGTTCGTGTTCCTGGTGCTGCTGCCTCTGGTGTCCAGCCAGTGTGTGAACCTGATCACCAGAACA<br>CAGTCATACACCAACAGCTTTACCAGAGGCGTGTACTACCCCGACAAGGTGTTCAGATCCAGCGTG<br>CTGCACTCTACCCAGGACCTGTTCCTGCCTTTCTTCAGCAACGTGACCTGGTTCCACGCCATCTCC<br>GGCACCAATGGCACCAAGAGATTCGACAACCCCGTGCTGCCCTTCAACGACGGGGTGTACTTTGCC<br>AGCACCGAGAAGTCCAACATCATCAGAGGCTGGATCTTCGGCACCACACTGGACAGCAAGACCCAG<br>AGCCTGCTGATCGTGAACAACGCCACCAACGTGGTCATCAAAGTGTGCGAGTTCCAGTTCTGCAAC<br>GACCCCTTCCTGGACGTCTACTACCACAAGAACAACAAGAGCTGGATGGAAAGCGAGTTCCGGGTG<br>TACAGCAGCGCCAACAACTGCACCTTCGAGTACGTGTCCCAGCCTTTCCTGATGGACCTGGAAGGC<br>AAGCAGGGCAACTTCAAGAACCTGCGCGAGTTCGTGTTTAAGAACATCGACGGCTACTTCAAGATC<br>TACAGCAAGCACACCCCTATCAACCTCGGCCGGGATCTGCCTCAGGGCTTCTCTGCTCTGGAACCC<br>CTGGTGGATCTGCCCATCGGCATCAACATCACCCGGTTTCAGACACTGCTGGCCCTGCACAGAAGC<br>TACCTGACACCTGGCGATAGCAGCAGCGGATGGACAGCTGGTGCCGCCGCTTACTATGTGGGCTAC<br>CTGCAGCCTAGAACCTTCCTGCTGAAGTACAACGAGAACGGCACCATCACCGACGCCGTGGATTGT<br>GCTCTGGATCCTCTGAGCGAGACAAAGTGCACCCTGAAGTCCTTCACCGTGGAAAAGGGCATCTAC<br>CAGACCAGCAACTTCCGGGTGCAGCCCACCGAATCCATCGTGCGGTTCCCCAATATCACCAATCTG<br>TGCCCCTTCGACGAGGTGTTCAATGCCACCACCTTCGCCTCTGTGTACGCCTGGAACCGGAAGCGG<br>ATCAGCAATTGCGTGGCCGACTACTCCGTGCTGTACAACTTCGCCCCCTTCTTCGCATTCAAGTGC<br>TACGGCGTGTCCCCTACCAAGCTGAACGACCTGTGCTTCACAAACGTGTACGCCGACAGCTTCGTG<br>ATCCGGGGAAACGAAGTGTCACAGATTGCCCCTGGACAGACAGGCAACATCGCCGACTACAACTAC<br>AAGCTGCCCGACGACTTCACCGGCTGTGTGATTGCCTGGAACAGCAACAAGCTGGACTCCACCGTC<br>GGCGGCAACTACAATTACAGGTACCGGCTGTTCCGGAAGTCCAAGCTGAAGCCCTTCGAGCGGGAC<br>ATCTCCACCGAGATCTATCAGGCCGGCAACAAGCCTTGTAACGGCGTGGCAGGCGTGAACTGCTAC |

TABLE 16-continued

Sequence of one embodiment of an exemplary Omicron BQ.1.1-specific RNA vaccine

| SEQ ID NO. | Brief Description | Sequence |
|---|---|---|
| | | TTCCCACTGCAGTCCTACGGCTTTAGGCCCACATACGGCGTGGGCCACCAGCCCTACAGAGTGGTG<br>GTGCTGAGCTTCGAACTGCTGCATGCCCCTGCCACAGTGTGCGGCCCTAAGAAAAGCACCAATCTC<br>GTGAAGAACAAATGCGTGAACTTCAACTTCAACGGCCTGACCGGCACCGGCGTGCTGACAGAGAGC<br>AACAAGAAGTTCCTGCCATTCCAGCAGTTTGGCCGGGATATCGCCGATACCACAGACGCCGTTAGA<br>GATCCCCAGACACTGGAAATCCTGGACATCACCCCTTGCAGCTTCGGCGGAGTGTCTGTGATCACC<br>CCTGGCACCAACACCAGCAATCAGGTGGCAGTGCTGTACCAGGGCGTGAACTGTACCGAAGTGCCC<br>GTGGCCATTCACGCCGATCAGCTGACACCTACATGGGGGTGTACTCCACCGGCAGCAATGTGTTT<br>CAGACCAGAGCCGGCTGTCTGATCGGAGCCGAGTACGTGAACAATAGCTACGAGTGCGACATCCCC<br>ATCGGCGCTGGAATCTGCGCCAGCTACCAGACACAGACAAAGAGCCACCGGAGAGCCAGAAGCGTG<br>GCCAGCCAGAGCATCATTGCCTACACAATGTCTCTGGGCGCCGAGAACAGCGTGGCCTACTCCAAC<br>AACTCTATCGCTATCCCCACCAACTTCACCATCAGCGTGACCACAGAGATCCTGCCTGTGTCCATG<br>ACCAAGACCAGCGTGGACTGCACCATGTACATCTGCGGCGATTCCACCGAGTGCTCCAACCTGCTG<br>CTGCAGTACGGCAGCTTCTGCACCCAGCTGAAAAGAGCCCTGACAGGGATCGCCGTGGAACAGGAC<br>AAGAACACCCAAGAGGTGTTCGCCCAAGTGAAGCAGATCTACAAGACCCCTCCTATCAAGTACTTC<br>GGCGGCTTCAATTTCAGCCAGATTCTGCCCGATCCTAGCAAGCCCAGCAAGCGGAGCTTCATCGAG<br>GACCTGCTGTTCAACAAAGTGACACTGGCCGACGCCGGCTTCATCAAGCAGTATGGCGATTGTCTG<br>GGCGACATTGCCGCCAGGGATCTGATTTGCGCCCAGAAGTTTAACGGACTGACAGTGCTGCCTCCT<br>CTGCTGACCGATGAGATGATCGCCCAGTACACATCTGCCCTGCTGGCCGGCACAATCACAAGCGGC<br>TGGACATTTGGAGCAGGCGCCGCTCTGCAGATCCCCTTTGCTATGCAGATGGCCTACCGGTTCAAC<br>GGCATCGGAGTGACCCAGAATGTGCTGTACGAGAACCAGAAGCTGATCGCCAACCAGTTCAACAGC<br>GCCATCGGCAAGATCCAGGACAGCCTGAGCAGCACAGCAAGCGCCCTGGGAAAGCTGCAGGACGTG<br>GTCAACCACAATGCCCAGGCACTGAACACCCTGGTCAAGCAGCTGTCCTCCAAGTTCGGCGCCATC<br>AGCTCTGTGCTGAACGATATCCTGAGCAGACTGGACCCTCCTGAGGCCGAGGTGCAGATCGACAGA<br>CTGATCACAGGCAGACTGCAGAGCCTCCAGACATACGTGACCCAGCAGCTGATCAGAGCCGCCGAG<br>ATTAGAGCCTCTGCCAATCTGGCCGCCACCAAGATGTCTGAGTGTGTGCTGGGCCAGAGCAAGAGA<br>GTGGACTTTTGCGGCAAGGGCTACCACCTGATGAGCTTCCCTCAGTCTGCCCCTCACGGCGTGGTG<br>TTTCTGCACGTGACATATGTGCCCGCTCAAGAGAAGAATTTCACCACCGCTCCAGCCATCTGCCAC<br>GACGGCAAAGCCCACTTTCCTAGAGAAGGCGTGTTCGTGTCCAACGGCACCCATTGGTTCGTGACA<br>CAGCGGAACTTCTACGAGCCCCAGATCATCACCACCGACAACACCTTCGTGTCTGGCAACTGCGAC<br>GTCGTGATCGGCATTGTGAACAATACCGTGTACGACCCTCTGCAGCCCGAGCTGGACAGCTTCAAA<br>GAGGAACTGGACAAGTACTTTAAGAACCACACAAGCCCCGACGTGGACCTGGGCGATATCAGCGGA<br>ATCAATGCCAGCGTCGTGAACATCCAGAAAGAGATCGACCGGCTGAACGAGGTGGCCAAGAATCTG<br>AACGAGAGCCTGATCGACCTGCAAGAACTGGGGAAGTACGAGCAGTACATCAAGTGGCCCTGGTAC<br>ATCTGGCTGGGCTTTATCGCCGGACTGATTGCCATCGTGATGGTCACAATCATGCTGTGTTGCATG<br>ACCAGCTGCTGTAGCTGCCTGAAGGGCTGTTGTAGCTGTGGCAGCTGCTGCAAGTTCGACGAGGAC<br>GATTCTGAGCCCGTGCTGAAGGGCGTGAAACTGCACTACACATGATGA |
| 103 | Full length RNA construct encoding a SARS-COV-2 S protein from an Omicron BQ.1.1 variant | AgaauaaacuaguauucuucugguccccacagacucagagagaacccgccaccAUGUUCGUGUUCC<br>UGGUGCUGCUGCCUCUGGUGUCCAGCCAGUGUGUGAACCUGAUCACCAGAACACAGUCAUACACCA<br>ACAGCUUUACCAGAGGCGUGUACUACCCCGACAAGGUGUUCAGAUCCAGCGUGCUGCACUCUACCC<br>AGGACCUGUUCCUGCCUUUCUUCAGCAACGUGACCUGGUUCCACGCCAUCUCCGGCACCAAUGGCA<br>CCAAGAGAUUCGACAACCCCGUGCUGCCCUUCAACGACGGGGUGUACUUUGCCAGCACCGAGAAGU<br>CCAACAUCAUCAGAGGCUGGAUCUUCGGCACCACACUGGACAGCAAGACCCAGAGCCUGCUGAUCG<br>UGAACAACGCCACCAACGUGGUCAUCAAAGUGUGCGAGUUCCAGUUCUGCAACGACCCCUUCCUGG<br>ACGUCUACUACCACAAGAACAACAAGAGCUGGAUGGAAAGCGAGUUCCGGGUGUACAGCAGCGCCA<br>ACAACUGCACCUUCGAGUACGUGUCCCAGCCUUUCCUGAUGGACCUGGAAGGCAAGCAGGGCAACU<br>UCAAGAACCUGCGCGAGUUCGUGUUUAAGAACAUCGACGGCUACUUCAAGAUCUACAGCAAGCACA<br>CCCCUAUCAACCUCGGCCGGGAUCUGCCUCAGGGCUUCUCUGCUCUGGAACCCCUGGUGGAUCUGC<br>CCAUCGGCAUCAACAUCACCCGGUUUCAGACACUGCUGGCCCUGCACAGAAGCUACCUGACACCUG<br>GCGAUAGCAGCAGCGGAUGGACAGCUGGUGCCGCCGCUUACUAUGUGGGCUACCUGCAGCCUAGAA<br>CCUUCCUGCUGAAGUACAACGAGAACGGCACCAUCACCGACGCCGUGGAUUGUGCUCUGGAUCCUC<br>UGAGCGAGACAAAGUGCACCCUGAAGUCCCUCACCGUGGAAAAGGGCAUCUACCAGACCAGCAACU<br>UCCGGGUGCAGCCCACCGAAUCCAUCGUGCGGUUCCCCAAUAUCACCAAUCUGUGCCCCUUCGACG<br>AGGUGUUCAAUGCCACCACCUUCGCCUCUGUGUACGCCUGGAACCGGAAGCGGAUCAGCAAUUGCG<br>UGGCCGACUACUCCGUGCUGUACAACUUCGCCCCCUUCUUCGCAUUCAAGUGCUACGGCGUGUCCC<br>CUACCAAGCUGAACGACCUGUGCUUCACAAACGUGUACGCCGACAGCUUCGUGAUCCGGGGAAACG<br>AAGUGUCACAGAUUGCCCCUGGACAGACAGGCAACAUCGCCGACUACAACUACAAGCUGCCCGACG<br>ACUUCACCGGCUGUGUGAUUGCCUGGAACAGCAACAAGCUGGACUCCACCGUCGGCGGCAACUACA<br>AUUACAGGUACCGGCUGUUCCGGAAGUCCAAGCUGAAGCCCUUCGAGCGGGACAUCUCCACCGAGA<br>UCUAUCAGGCCGGCAACAAGCCUUGUAACGGCGUGGCAGGCGUGAACUGCUACUUCCCACUGCAGU<br>CCUACGGCUUUAGGCCCACAUACGGCGUGGGCCACCAGCCCUACAGAGUGGUGGUGCUGAGCUUCG<br>AACUGCUGCAUGCCCCUGCCACAGUGUGCGGCCCUAAGAAAAGCACCAAUCUCGUGAAGAACAAAU<br>GCGUGAACUUCAACUUCAACGGCCUGACCGGCACCGGCGUGCUGACAGAGAGCAACAAGAAGUUCC<br>UGCCAUUCCAGCAGUUUGGCCGGGAUAUCGCCGAUACCACAGACGCCGUUAGAGAUCCCCAGACAC<br>UGGAAAUCCUGGACAUCACCCCUUGCAGCUUCGGCGGAGUGUCUGUGAUCACCCCUGGCACCAACA<br>CCAGCAAUCAGGUGGCAGUGCUGUACCAGGGCGUGAACUGUACCGAAGUGCCCGUGGCCAUUCACG<br>CCGAUCAGCUGACACCUACAUGGCGGGUGUACUCCACCGGCAGCAAUGUGUUUCAGACCAGAGCCG<br>GCUGUCUGAUCGGAGCCGAGUACGUGAACAAUAGCUACGAGUGCGACAUCCCCAUCGGCGCUGGAA<br>UCUGCGCCAGCUACCAGACACAGACAAAGAGCCACCGGAGAGCCAGAAGCGUGGCCAGCCAGAGCA<br>UCAUUGCCUACACAAUGUCUCUGGGCGCCGAGAACAGCGUGGCCUACUCCAACAACUCUAUCGCUA<br>UCCCCACCAACUUCACCAUCAGCGUGACCACAGAGAUCCUGCCUGUGUCCAUGACCAAGACCAGCG<br>UGGACUGCACCAUGUACAUCUGCGGCGAUUCCACCGAGUGCUCCAACCUGCUGCUGCAGUACGGCA<br>GCUUCUGCACCCAGCUGAAAAGAGCCCUGACAGGGAUCGCCGUGGAACAGGACAAGAACACCCAAG<br>AGGUGUUCGCCCAAGUGAAGCAGAUCUACAAGACCCCUCCUAUCAAGUACUUCGGCGGCUUCAAUU |

TABLE 16-continued

Sequence of one embodiment of an exemplary Omicron BQ.1.1-specific RNA vaccine

| SEQ ID NO. | Brief Description | Sequence |
|---|---|---|
| | | UCAGCCAGAUUCUGCCCGAUCCUAGCAAGCCCAGCAAGCGGAGCUUCAUCGAGGACCUGCUGUUCA<br>ACAAAGUGACACUGGCCGACGCCGGCUUCAUCAAGCAGUAUGGCGAUUGUCUGGGCGACAUUGCCG<br>CCAGGGAUCUGAUUUGCGCCCAGAAGUUUAACGGACUGACAGUGCUCCCUCCUCUGCUGACCGAUG<br>AGAUGAUCGCCCAGUACACAUCUGCCCUGCUGGCCGGCACAAUCACAAGCGGCUGGACAUUUGGAG<br>CAGGCGCCGCUCUGCAGAUCCCCUUUGCUAUGCAGAUGGCCUACCGGUUCAACGGCAUCGGAGUGA<br>CCCAGAAUGUGCUGUACGAGAACCAGAAGCUGAUCGCCAACCAGUUCAACAGCGCCAUCGGCAAGA<br>UCCAGGACAGCCUGAGCAGCACAGCAAGCGCCCUGGGAAAGCUGCAGGACGUGGUCAACCACAAUG<br>CCCAGGCACUGAACACCCUGGUCAAGCAGCUGUCCUCCAAGUUCGGCGCCAUCAGCUCUGUGCUGA<br>ACGAUAUCCUGAGCAGACUGGACCCUCCUGAGGCCGAGGUGCAGAUCGACAGACUGAUCACAGGCA<br>GACUGCAGAGCCUCCAGACAUACGUGACCCAGCAGCUGAUCAGAGCCGCCGAGAUUAGAGCCUCUG<br>CCAAUCUGGCCGCCACCAAGAUGUCUGAGUGUGUGCUGGGCCAGAGCAAGAGAGUGGACUUUUGCG<br>GCAAGGGCUACCACCUGAUGAGCUUCCCUCAGUCUGCCCCUCACGGCGUGGUGUUUCUGCACGUGA<br>CAUAUGUGCCCGCUCAAGAGAAGAAUUUCACCACCGCUCCAGCCAUCUGCCACGACGGCAAAGCCC<br>ACUUUCCUAGAGAAGGCGUGUUCGUGUCCAACGGCACCCAUUGGUUCGUGACACAGCGGAACUUCU<br>ACGAGCCCCAGAUCAUCACCACCGACAACACCUUCGUGUCUGGCAACUGCGACGUCGUGAUCGGCA<br>UUGUGAACAAUACCGUGUACGACCCUCUGCAGCCCGAGCUGGACAGCUUCAAAGAGGAACUGGACA<br>AGUACUUUAAGAACCACACAAGCCCCGACGUGGACCUGGGCGAUAUCAGCGGAAUCAAUGCCAGCG<br>UCGUGAACAUCCAGAAAGAGAUCGACCGGCUGAACGAGGUGGCCAAGAAUCUGAACGAGAGCCUGA<br>UCGACCUGCAAGAACUGGGGAAGUACGAGCAGUACAUCAAGUGGCCCUGGUACAUCUGGCUGGGCU<br>UUAUCGCCGGACUGAUUGCCAUCGUGAUGGUCACAAUCAUGCUGUGUUGCAUGACCAGCUGCUGUA<br>GCUGCCUGAAGGGCUGUUGUAGCUGUGGCAGCUGCUGCAAGUUCGACGAGGACGAUUCUGAGCCCG<br>UGCUGAAGGGCGUGAAACUGCACUACACAUGAUGAcucgagcugguacugcaugcacgcaaugcua<br>gcugccccuuucccguccuggguaccccgagucucccccgaccucgggucccagguaugcucccac<br>cuccaccugccccacucaccaccucugcuaguuccagacaccucccaagcacgcagcaaugcagcu<br>caaaacgcuuagccuagccacacccccacgggaaacagcagugauuaaccuuuagcaauaaacgaa<br>aguuuaacuaagcuauacuaaccccaggguuggucaauuucgugccagccacacccuggagcuagc<br>aaaaaaaaaaaaaaaaaaaaaaaaaaaaaagcauaugacuaaaaaaaaaaaaaaaaaaaaaaaaaaaaaa<br>aaaaaaaaaaaaaaaaaaaaaaaaaaaaaaaaaaaaaaaa |
| 104 | Full length DNA construct encoding a SARS-COV-2 S protein from an Omicron BQ.1.1 variant | AgaataaactagtattottctggtccccacagactcagagagaacccqccaccATGTTCGTGTTCC<br>TGGTGCTGCTGCCTCTGGTGTCCAGCCAGTGTGTGAACCTGATCACCAGAACACAGTCATACACCA<br>ACAGCTTTACCAGAGGCGTGTACTACCCCGACAAGGTGTTCAGATCCAGCGTGCTGCACTCTACCC<br>AGGACCTGTTCCTGCCTTTCTTCAGCAACGTGACCTGGTTCCACGCCATCTCCGGCACCAATGGCA<br>CCAAGAGATTCGACAACCCCGTGCTGCCCTTCAACGACGGGGTGTACTTTGCCAGCACCGAGAAGT<br>CCAACATCATCAGAGGCTGGATCTTCGGCACCACACTGGACAGCAAGACCCAGAGCCTGCTGATCG<br>TGAACAACGCCACCAACGTGGTCATCAAAGTGTGCGAGTTCCAGTTCTGCAACGACCCCTTCCTGG<br>ACGTCTACTACCACAAGAACAACAAGAGCTGGATGGAAAGCGAGTTCCGGGTGTACAGCAGCGCCA<br>ACAACTGCACCTTCGAGTACGTGTCCCAGCCTTTCCTGATGGACCTGGAAGGCAAGCAGGGCAACT<br>TCAAGAACCTGCGCGAGTTCGTGTTTAAGAACATCGACGGCTACTTCAAGATCTACAGCAAGCACA<br>CCCCTATCAACCTCGGCCGGGATCTGCCTCAGGGCTTCTCTGCTCTGGAACCCCTGGTGGATCTGC<br>CCATCGGCATCAACATCACCCGGTTTCAGACACTGCTGGCCCTGCACAGAAGCTACCTGACACCTG<br>GCGATAGCAGCAGCGGATGGACAGCTGGTGCCGCCGCTTACTATGTGGGCTACCTGCAGCCTAGAA<br>CCTTCCTGCTGAAGTACAACGAGAACGGCACCATCACCGACGCCGTGGATTGTGCTCTGGATCCTC<br>TGAGCGAGACAAAGTGCACCCTGAAGTCCTTCACCGTGGAAAAGGGCATCTACCAGACCAGCAACT<br>TCCGGGTGCAGCCCACCGAATCCATCGTGCGGTTCCCCAATATCACCAATCTGTGCCCCTTCGACG<br>AGGTGTTCAATGCCACCACCTTCGCCTCTGTGTACGCCTGGAACCGGAAGCGGATCAGCAATTGCG<br>TGGCCGACTACTCCGTGCTGTACAACTTCGCCCCCTTCTTCGCATTCAAGTGCTACGGCGTGTCCC<br>CTACCAAGCTGAACGACCTGTGCTTCACAAACGTGTACGCCGACAGCTTCGTGATCCGGGGAAACG<br>AAGTGTCACAGATTGCCCCTGGACAGACAGGCAACATCGCCGACTACAACTACAAGCTGCCCGACG<br>ACTTCACCGGCTGTGTGATTGCCTGGAACAGCAACAAGCTGGACTCCACCGTCGGCGGCAACTACA<br>ATTACAGGTACCGGCTGTTCCGGAAGTCCAAGCTGAAGCCCTTCGAGCGGGACATCTCCACCGAGA<br>TCTATCAGGCCGGCAACAAGCCTTGTAACGGCGTGGCAGGCGTGAACTGCTACTTCCCACTGCAGT<br>CCTACGGCTTTAGGCCCACATACGGCGTGGGCCACCAGCCCTACAGAGTGGTGGTGCTGAGCTTCG<br>AACTGCTGCATGCCCCTGCCACAGTGTGCGGCCCTAAGAAAAGCACCAATCTCGTGAAGAACAAAT<br>GCGTGAACTTCAACTTCAACGGCCTGACCGGCACCGGCGTGCTGACAGAGAGCAACAAGAAGTTCC<br>TGCCATTCCAGCAGTTTGGCCGGGATATCGCCGATACCACAGACGCCGTTAGAGATCCCCAGACAC<br>TGGAAATCCTGGACATCACCCCTTGCAGCTTCGGCGGAGTGTCTGTGATCACCCCTGGCACCAACA<br>CCAGCAATCAGGTGGCAGTGCTGTACCAGGGCGTGAACTGTACCGAAGTGCCCGTGGCCATTCACG<br>CCGATCAGCTGACACCTACATGGCGGGTGTACTCCACCGGCAGCAATGTGTTTCAGACCAGAGCCG<br>GCTGTCTGATCGGAGCCGAGTACGTGAACAATAGCTACGAGTGCGACATCCCCATCGGCGCTGGAA<br>TCTGCGCCAGCTACCAGACACAGACAAAGAGCCACCGGAGAGCCAGAAGCGTGGCCAGCCAGAGCA<br>TCATTGCCTACACAATGTCTCTGGGCGCCGAGAACAGCGTGGCCTACTCCAACAACTCTATCGCTA<br>TCCCCACCAACTTCACCATCAGCGTGACCACAGAGATCCTGCCTGTGTCCATGACCAAGACCAGCG<br>TGGACTGCACCATGTACATCTGCGGCGATTCCACCGAGTGCTCCAACCTGCTGCTGCAGTACGGCA<br>GCTTCTGCACCCAGCTGAAAAGAGCCCTGACAGGGATCGCCGTGGAACAGGACAAGAACACCCAAG<br>AGGTGTTCGCCCAAGTGAAGCAGATCTACAAGACCCCTCCTATCAAGTACTTCGGCGGCTTCAATT<br>TCAGCCAGATTCTGCCCGATCCTAGCAAGCCCAGCAAGCGGAGCTTCATCGAGGACCTGCTGTTCA<br>ACAAAGTGACACTGGCCGACGCCGGCTTCATCAAGCAGTATGGCGATTGTCTGGGCGACATTGCCG<br>CCAGGGATCTGATTTGCGCCCAGAAGTTTAACGGACTGACAGTGCTGCCTCCTCTGCTGACCGATG<br>AGATGATCGCCCAGTACACATCTGCCCTGCTGGCCGGCACAATCACAAGCGGCTGGACATTTGGAG<br>CAGGCGCCGCTCTGCAGATCCCCTTTGCTATGCAGATGGCCTACCGGTTCAACGGCATCGGAGTGA<br>CCCAGAATGTGCTGTACGAGAACCAGAAGCTGATCGCCAACCAGTTCAACAGCGCCATCGGCAAGA<br>TCCAGGACAGCCTGAGCAGCACAGCAAGCGCCCTGGGAAAGCTGCAGGACGTGGTCAACCACAATG<br>CCCAGGCACTGAACACCCTGGTCAAGCAGCTGTCCTCCAAGTTCGGCGCCATCAGCTCTGTGCTGA |

TABLE 16-continued

Sequence of one embodiment of an exemplary Omicron BQ.1.1-specific RNA vaccine

| SEQ ID NO. | Brief Description | Sequence |
|---|---|---|
| | | ACGATATCCTGAGCAGACTGGACCCTCCTGAGGCCGAGGTGCAGATCGACAGACTGATCACAGGCA GACTGCAGAGCCTCCAGACATACGTGACCCAGCAGCTGATCAGAGCCGCCGAGATTAGAGCCTCTG CCAATCTGGCCGCCACCAAGATGTCTGAGTGTGTGCTGGGCCAGAGCAAGAGAGTGGACTTTTGCG GCAAGGGCTACCACCTGATGAGCTTCCCTCAGTCTGCCCCTCACGGCGTGGTGTTTCTGCACGTGA CATATGTGCCCGCTCAAGAGAAGAATTTCACCACCGCTCCAGCCATCTGCCACGACGGCAAAGCCC ACTTTCCTAGAGAAGGCGTGTTCGTGTCCAACGGCACCCATTGGTTCGTGACACAGCGGAACTTCT ACGAGCCCCAGATCATCACCACCGACAACACCTTCGTGTCTGGCAACTGCGACGTCGTGATCGGCA TTGTGAACAATACCGTGTACGACCCTCTGCAGCCCGAGCTGGACAGCTTCAAAGAGGAACTGGACA AGTACTTTAAGAACCACACAAGCCCCGACGTGGACCTGGGCGATATCAGCGGAATCAATGCCAGCG TCGTGAACATCCAGAAAGAGATCGACCGGCTGAACGAGGTGGCCAAGAATCTGAACGAGAGCCTGA TCGACCTGCAAGAACTGGGGAAGTACGAGCAGTACATCAAGTGGCCCTGGTACATCTGGCTGGGCT TTATCGCCGGACTGATTGCCATCGTGATGGTCACAATCATGCTGTGTTGCATGACCAGCTGCTGTA GCTGCCTGAAGGGCTGTTGTAGCTGTGGCAGCTGCTGCAAGTTCGACGAGGACGATTCTGAGCCCG TGCTGAAGGGCGTGAAACTGCACTACACATGATGActcgagctggtactgcatgcacgcaatgcta gctgcccctttcccgtcctgggtaccccgagtctcccccgacctcgggtcccaggtatgctcccac ctccacctgccccactcaccacctctgctagttccagacacctcccaagcacgcagcaatgcagct caaaacgcttagcctagccacacccccacgggaaacagcagtgattaacctttagcaataaacgaa agtttaactaagctatactaaccccagggttggtcaatttcgtgccagccacaccctggagctagc aaaaaaaaaaaaaaaaaaaaaaaaaaaaaagcatatgactaaaaaaaaaaaaaaaaaaaaaaaaaaaaaa aaaaaaaaaaaaaaaaaaaaaaaaaaaaaaaaaaaaaaaaaaa |

Tables 3-16 show amino acid sequences of SARS-CoV-2 S proteins encoded by RNAs described herein from different variants with 2 proline substitutions at positions corresponding to K986P and V987P of SEQ ID NO: 1. In some embodiments, an RNA described herein encodes a SARS-CoV-2 S protein as described herein, for example, in some embodiments, as described in Tables 3-16, without the 2 proline substitutions at positions corresponding to K986P and V987P of SEQ ID NO: 1. In some embodiments, such an RNA described herein encodes a SARS-CoV-2 S protein comprising one or more mutations characteristic of a variant described herein, and further comprising at least four (including, e.g., at least five, at least six, or more) proline mutations. In some embodiments, at least four of such proline mutations include mutations at positions corresponding to residues 817, 892, 899, and 942 of SEQ ID NO: 1, e.g., as described in WO 2021243122 Δ2, the entire contents of which are incorporated herein by reference in its entirety. In some embodiments, such a SARS-CoV-2 S protein comprising proline substitutions at positions corresponding to residues 817, 892, 899, and 942 of SEQ ID NO: 1, may further comprise proline substitutions at positions corresponding to residues 986 and 987 of SEQ ID NO:1.

Self-Amplifying RNA (saRNA)

The active principle of a self-amplifying RNA (saRNA) drug substance is a single-stranded RNA, which self-amplifies upon entering a cell, and a coronavirus vaccine antigen is translated thereafter. In contrast to uRNA and modRNA that preferably code for a single protein, the coding region of saRNA contains two open reading frames (ORFs). The 5'-ORF encodes an RNA-dependent RNA polymerase such as Venezuelan equine encephalitis virus (VEEV) RNA-dependent RNA polymerase (replicase). The replicase ORF is followed 3' by a subgenomic promoter and a second ORF encoding an antigen. Furthermore, saRNA UTRs contain 5' and 3' conserved sequence elements (CSEs) required for self-amplification. The saRNA contains common structural elements optimized for maximal efficacy of the RNA as the uRNA (including, e.g., 5'-cap, 5'-UTR, 3'-UTR, poly(A)-tail). In some embodiments, the saRNA preferably contains uridine. In some embodiments, the saRNA comprises one or more nucleoside modifications as described herein. The preferred 5' cap structure is beta-S-ARCA(D1) ($m_2^{7,2'-}$*o*GppSpG).

Cytoplasmic delivery of saRNA initiates an alphavirus-like life cycle. However, saRNA does not encode for alphaviral structural proteins required for genome packaging or cell entry, therefore generation of replication competent viral particles is very unlikely or not possible. Replication does not involve any intermediate steps that generate DNA. The use/uptake of saRNA therefore poses no risk of genomic integration or other permanent genetic modification within the target cell. Furthermore, the saRNA itself prevents its persistent replication by effectively activating innate immune response via recognition of dsRNA intermediates.

Different embodiments of this platform are as follows:

RBS004.1 (SEQ ID NO: 24; SEQ ID NO: 7)
- Structure beta-S-ARCA(D1)-replicase-S1S2-PP-FI-A30L70
- Encoded antigen Viral spike protein (S protein) of the SARS-CoV-2 (S1S2 full-length protein, sequence variant)

RBS004.2 (SEQ ID NO: 25; SEQ ID NO: 7)
- Structure beta-S-ARCA(D1)-replicase-S1S2-PP-FI-A30L70
- Encoded antigen Viral spike protein (S protein) of the SARS-CoV-2 (5152 full-length protein, sequence variant)

BNT162c1; RBS004.3 (SEQ ID NO: 26; SEQ ID NO: 5)
- Structure beta-S-ARCA(D1)-replicase-RBD-GS-Fibritin-FI-A30L70
- Encoded antigen Viral spike protein (S protein) of the SARS-CoV-2 (partial sequence, Receptor Binding Domain (RBD) of S1S2 protein)

RBS004.4 (SEQ ID NO: 27; SEQ ID NO: 28)
- Structure beta-S-ARCA(D1)-replicase-RBD-GS-Fibritin-TM-FI-A30L70
- Encoded antigen Viral spike protein (S protein) of the SARS-CoV-2 (partial sequence, Receptor Binding Domain (RBD) of S1S2 protein)

FIG. 5 schematizes the general structure of the antigen-encoding RNAs.

In some embodiments, vaccine RNA described herein comprises a nucleotide sequence selected from the group consisting of SEQ ID NO: 15, 16, 17, 19, 20, 21, 24, 25, 26, 27, 30, and 32. A particularly preferred vaccine RNA described herein comprises a nucleotide sequence selected from the group consisting of SEQ ID NO: 15, 17, 19, 21, 25, 26, 30, and 32 such as selected from the group consisting of SEQ ID NO: 17, 19, 21, 26, 30, and 32.

In some embodiments, RNA described herein is formulated in lipid nanoparticles, lipoplex, polyplexes (PLX), lipidated polyplexes (LPLX), liposomes, or polysaccharide nanoparticles. In some embodiments, RNA described herein is preferably formulated in lipid nanoparticles (LNP). In one embodiment, LNP comprise a cationic lipid, a neutral lipid, a steroid, a polymer conjugated lipid; and RNA. In one embodiment, the cationic lipid is ALC-0315, the neutral lipid is DSPC, the steroid is cholesterol, and the polymer conjugated lipid is ALC-0159. The preferred mode of administration is intramuscular administration, more preferably in aqueous cryoprotectant buffer for intramuscular administration. Drug product is a preferably a preservative-free, sterile dispersion of RNA formulated in lipid nanoparticles (LNP) in aqueous cryoprotectant buffer for intramuscular administration.

In different embodiments, drug product comprises the components shown below, preferably at the proportions or concentrations shown below:

| Component | Function | Proportion (mol %) |
|---|---|---|
| ALC-0315 [1] | Functional lipid | 47.5 |
| ALC-0159 [2] | Functional lipid | 1.8 |
| DSPC [3] | Structural lipid | 10.0 |
| Cholesterol, synthetic | Structural lipid | 40.7 |

| Component | Function | Concentration (mg/mL) |
|---|---|---|
| Drug Substance | Active | 0.5 |
| ALC-0315 [1] | Functional lipid | 7.17 |
| ALC-0159 [2] | Functional lipid | 0.89 |
| DSPC [3] | Structural lipid | 1.56 |
| Cholesterol, synthetic | Structural lipid | 3.1 |
| Sucrose | Cryoprotectant | 102.69 |
| NaCl | Buffer | 6.0 |
| KCl | Buffer | 0.15 |
| $Na_2HPO_4$ | Buffer | 1.08 |
| $KH_2PO_4$ | Buffer | 0.18 |
| Water for injection | Solvent/Vehicle | q.s. |
| Drug Substance | Active | 1.0 |
| ALC-0315 [1] | Functional lipid | 13.56 |
| ALC-0159 [2] | Functional lipid | 1.77 |
| DSPC [3] | Structural lipid | 3.11 |
| Cholesterol, synthetic | Structural lipid | 6.20 |
| Sucrose | Cryoprotectant | 102.69 |
| NaCl | Buffer | 6.0 |
| KCl | Buffer | 0.15 |
| $Na_2HPO_4$ | Buffer | 1.08 |
| $KH_2PO_4$ | Buffer | 0.15 |
| Water for injection | Solvent/Vehicle | q.s. |

[1] ALC-0315 = ((4-hydroxybutyl)azanediyl)bis(hexane-6,1-diyl)bis(2-hexyldecanoate)/6-[N-6-(2-hexyldecanoyloxy)hexyl-N-(4-hydroxybutyl)amino]hexyl 2-hexyldecanoate
[2] ALC-0159 = 2-[(polyethylene glycol)-2000]-N,N-ditetradecylacetamide/2-[2-(ω-methoxy(polyethyleneglycol2000)ethoxy]-N,N-ditetradecylacetamide
[3] DSPC = 1,2-Distearoyl-sn-glycero-3-phosphocholine
q.s. = quantum satis (as much as may suffice)

ALC-0315

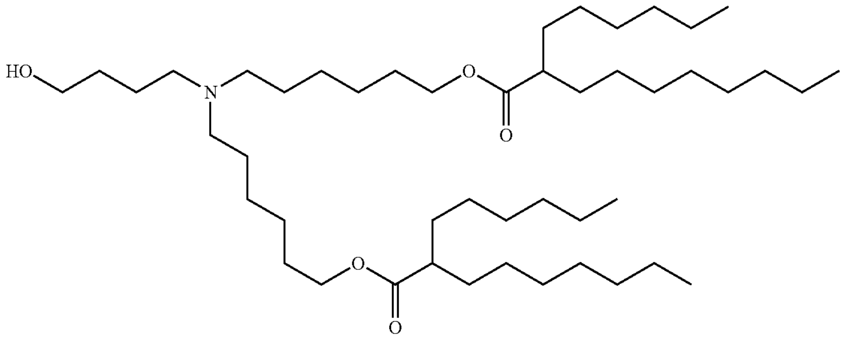

ALC-0159

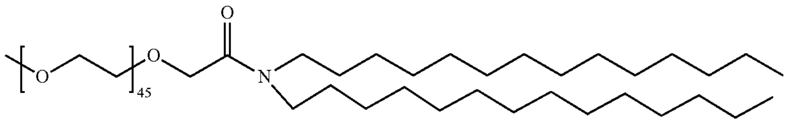

DSPC

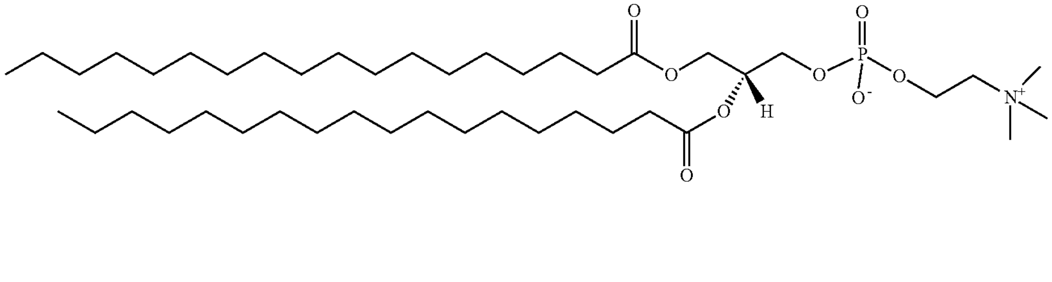

-continued

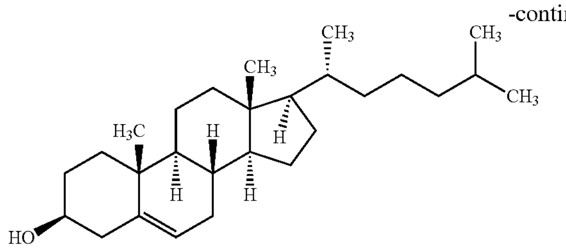

Cholesterol

In some embodiments, particles disclosed herein are formulated in a solution comprising 10 mM Tris and 10% sucrose, and optionally having a pH of about 7.4. In some embodiments, particles disclosed herein are formulated in a solution comprising about 103 mg/ml sucrose, about 0.20 mg/ml tromethamine (Tris base), and about 1.32 mg/ml Tris.

In some embodiments, a composition comprises:

(a) about 0.1 mg/mL RNA comprising an open reading frame encoding a polypeptide that comprises a SARS-CoV-2 protein or an immunogenic fragment or variant thereof,
(b) about 1.43 mg/ml ALC-0315,
(c) about 0.18 mg/ml ALC-0159,
(d) about 0.31 mg/ml DSPC,
(e) about 0.62 mg/ml cholesterol,
(f) about 103 mg/ml sucrose,
(g) about 0.20 mg/ml tromethamine (Tris base),
(h) about 1.32 mg/ml Tris (hydroxymethyl) aminomethane hydrochloride (Tris HCl), and (i) q.s. water.

In one embodiment, the ratio of RNA (e.g., mRNA) to total lipid (N/P) is between 6.0 and 6.5 such as about 6.0 or about 6.3.

Nucleic Acid Containing Particles

Nucleic acids described herein such as RNA encoding a vaccine antigen may be administered formulated as particles.

In the context of the present disclosure, the term "particle" relates to a structured entity formed by molecules or molecule complexes. In one embodiment, the term "particle" relates to a micro- or nano-sized structure, such as a micro- or nano-sized compact structure dispersed in a medium. In one embodiment, a particle is a nucleic acid containing particle such as a particle comprising DNA, RNA or a mixture thereof.

Electrostatic interactions between positively charged molecules such as polymers and lipids and negatively charged nucleic acid are involved in particle formation. This results in complexation and spontaneous formation of nucleic acid particles. In one embodiment, a nucleic acid particle is a nanoparticle.

As used in the present disclosure, "nanoparticle" refers to a particle having an average diameter suitable for parenteral administration.

A "nucleic acid particle" can be used to deliver nucleic acid to a target site of interest (e.g., cell, tissue, organ, and the like). A nucleic acid particle may be formed from at least one cationic or cationically ionizable lipid or lipid-like material, at least one cationic polymer such as protamine, or a mixture thereof and nucleic acid. In some embodiments, exemplary nanoparticles include lipid nanoparticles, polyplexes (PLX), lipidated polyplexes (LPLX), liposomes, or polysaccharide nanoparticles.

In some embodiments, the RNA encoding an amino acid sequence comprising a SARS-CoV-2 S protein, an immunogenic variant thereof, or an immunogenic fragment of the SARS-CoV-2 S protein or the immunogenic variant thereof is formulated as LNPs. In some embodiments, the LNPs comprise one or more cationically ionizable lipids; one or more neutral lipids (e.g., in some embodiments sterol such as, e.g., cholesterol; and/or phospholipids), and one or more polymer-conjugated lipids. In some embodiments, the formulation comprises ALC-0315 (4-hydroxybutyl)azanediyl) bis(hexane-6,1-diyl)bis(2-hexyldecanoate), ALC-0159 (2-[(polyethylene glycol)-20001-N,N-ditetradecylacetamide), DSPC (1,2-distearoyl-sn-glycero-3-phosphocholine), cholesterol, sucrose, trometamol (Tris), trometamol hydrochloride and water.

RNA particles described herein include nanoparticles. In some embodiments, exemplary nanoparticles include lipid nanoparticles, lipoplex, polyplexes (PLX), lipidated polyplexes (LPLX), liposomes, or polysaccharide nanoparticles.

Polyplexes (PLX), polysaccharide nanoparticles, and liposomes, are all delivery technologies that are well known to a person of skill in the art. See, e.g., Lächelt, Ulrich, and Ernst Wagner. "Nucleic acid therapeutics using polyplexes: a journey of 50 years (and beyond)" Chemical reviews 115.19 (2015): 11043-11078; Plucinski, Alexander, Zan Lyu, and Bernhard V K J Schmidt, "Polysaccharide nanoparticles: from fabrication to applications." Journal of Materials Chemistry B (2021); and Tenchov, Rumiana, et al. "Lipid Nanoparticles—From Liposomes to mRNA Vaccine Delivery, a Landscape of Research Diversity and Advancement," ACS nano 15.11 (2021): 16982-17015, respectively, the contents of each of which are hereby incorporated by reference herein in their entirety.

In some embodiments, the concentration of the RNA in the pharmaceutical RNA preparation is about 0.1 mg/ml. In some embodiments, the concentration of the RNA in the pharmaceutical RNA preparation is about 30 μg/ml to about 100 μg/ml. In some embodiments, the concentration of the RNA in the pharmaceutical RNA preparation is about 50 μg/ml to about 100 μg/ml.

Without intending to be bound by any theory, it is believed that the cationic or cationically ionizable lipid or lipid-like material and/or the cationic polymer combine together with the nucleic acid to form aggregates, and this aggregation results in colloidally stable particles.

In one embodiment, particles described herein further comprise at least one lipid or lipid-like material other than a cationic or cationically ionizable lipid or lipid-like material, at least one polymer other than a cationic polymer, or a mixture thereof In some embodiments, nucleic acid particles comprise more than one type of nucleic acid molecules, where the molecular parameters of the nucleic acid molecules may be similar or different from each other, like with respect to molar mass or fundamental structural elements such as molecular architecture, capping, coding regions or other features.

Nucleic acid particles described herein may have an average diameter that in one embodiment ranges from about 30 nm to about 1000 nm, from about 50 nm to about 800 nm, from about 70 nm to about 600 nm, from about 90 nm to about 400 nm, or from about 100 nm to about 300 nm.

Nucleic acid particles described herein may exhibit a polydispersity index less than about 0.5, less than about 0.4, less than about 0.3, or about 0.2 or less. By way of example, the nucleic acid particles can exhibit a polydispersity index in a range of about 0.1 to about 0.3 or about 0.2 to about 0.3.

With respect to RNA lipid particles, the N/P ratio gives the ratio of the nitrogen groups in the lipid to the number of phosphate groups in the RNA. It is correlated to the charge ratio, as the nitrogen atoms (depending on the pH) are usually positively charged and the phosphate groups are negatively charged. The N/P ratio, where a charge equilibrium exists, depends on the pH. Lipid formulations are frequently formed at N/P ratios larger than four up to twelve, because positively charged nanoparticles are considered favorable for transfection. In that case, RNA is considered to be completely bound to nanoparticles.

Nucleic acid particles described herein can be prepared using a wide range of methods that may involve obtaining a colloid from at least one cationic or cationically ionizable lipid or lipid-like material and/or at least one cationic polymer and mixing the colloid with nucleic acid to obtain nucleic acid particles.

The term "colloid" as used herein relates to a type of homogeneous mixture in which dispersed particles do not settle out. The insoluble particles in the mixture are microscopic, with particle sizes between 1 and 1000 nanometers. The mixture may be termed a colloid or a colloidal suspension. Sometimes the term "colloid" only refers to the particles in the mixture and not the entire suspension.

For the preparation of colloids comprising at least one cationic or cationically ionizable lipid or lipid-like material and/or at least one cationic polymer methods are applicable herein that are conventionally used for preparing liposomal vesicles and are appropriately adapted. The most commonly used methods for preparing liposomal vesicles share the following fundamental stages: (i) lipids dissolution in organic solvents, (ii) drying of the resultant solution, and (iii) hydration of dried lipid (using various aqueous media).

In the film hydration method, lipids are firstly dissolved in a suitable organic solvent, and dried down to yield a thin film at the bottom of the flask. The obtained lipid film is hydrated using an appropriate aqueous medium to produce a liposomal dispersion. Furthermore, an additional downsizing step may be included.

Reverse phase evaporation is an alternative method to the film hydration for preparing liposomal vesicles that involves formation of a water-in-oil emulsion between an aqueous phase and an organic phase containing lipids. A brief sonication of this mixture is required for system homogenization. The removal of the organic phase under reduced pressure yields a milky gel that turns subsequently into a liposomal suspension.

The term "ethanol injection technique" refers to a process, in which an ethanol solution comprising lipids is rapidly injected into an aqueous solution through a needle. This action disperses the lipids throughout the solution and promotes lipid structure formation, for example lipid vesicle formation such as liposome formation. Generally, the RNA lipoplex particles described herein are obtainable by adding RNA to a colloidal liposome dispersion.

Using the ethanol injection technique, such colloidal liposome dispersion is, in one embodiment, formed as follows: an ethanol solution comprising lipids, such as cationic lipids and additional lipids, is injected into an aqueous solution under stirring. In one embodiment, the RNA lipoplex particles described herein are obtainable without a step of extrusion.

The term "extruding" or "extrusion" refers to the creation of particles having a fixed, cross-sectional profile. In particular, it refers to the downsizing of a particle, whereby the particle is forced through filters with defined pores.

Other methods having organic solvent free characteristics may also be used according to the present disclosure for preparing a colloid.

LNPs typically comprise four components: ionizable cationic lipids, neutral lipids such as phospholipids, a steroid such as cholesterol, and a polymer conjugated lipid such as polyethylene glycol (PEG)-lipids. Each component is responsible for payload protection, and enables effective intracellular delivery. LNPs may be prepared by mixing lipids dissolved in ethanol rapidly with nucleic acid in an aqueous buffer.

The term "average diameter" refers to the mean hydrodynamic diameter of particles as measured by dynamic laser light scattering (DLS) with data analysis using the so-called cumulant algorithm, which provides as results the so-called $Z_{average}$ with the dimension of a length, and the polydispersity index (PI), which is dimensionless (Koppel, D., J. Chem. Phys. 57, 1972, pp 4814-4820, ISO 13321). Here "average diameter", "diameter" or "size" for particles is used synonymously with this value of the $Z_{average}$.

The "polydispersity index" is preferably calculated based on dynamic light scattering measurements by the so-called cumulant analysis as mentioned in the definition of the "average diameter". Under certain prerequisites, it can be taken as a measure of the size distribution of an ensemble of nanoparticles.

Different types of nucleic acid containing particles have been described previously to be suitable for delivery of nucleic acid in particulate form (e.g. Kaczmarek, J. C. et al., 2017, Genome Medicine 9, 60). For non-viral nucleic acid delivery vehicles, nanoparticle encapsulation of nucleic acid physically protects nucleic acid from degradation and, depending on the specific chemistry, can aid in cellular uptake and endosomal escape.

The present disclosure describes particles comprising nucleic acid, at least one cationic or cationically ionizable lipid or lipid-like material, and/or at least one cationic polymer which associate with nucleic acid to form nucleic acid particles and compositions comprising such particles. The nucleic acid particles may comprise nucleic acid which is complexed in different forms by non-covalent interactions to the particle. The particles described herein are not viral particles, in particular infectious viral particles, i.e., they are not able to virally infect cells.

Suitable cationic or cationically ionizable lipids or lipid-like materials and cationic polymers are those that form nucleic acid particles and are included by the term "particle forming components" or "particle forming agents". The term "particle forming components" or "particle forming agents" relates to any components which associate with nucleic acid to form nucleic acid particles. Such components include any component which can be part of nucleic acid particles.

In some embodiments, a nucleic acid containing particle (e.g., a lipid nanoparticle (LNP)) comprises two or more RNA molecules, each comprising a different nucleic acid sequence. In some embodiments, a nucleic acid containing particle comprises two or more RNA molecules, each encoding a different immunogenic polypeptide or immunogenic fragment thereof. In some embodiments, two or more RNA molecules present in a nucleic acid containing particle comprise: a first RNA molecule encodes an immunogenic polypeptide or immunogenic fragment thereof from a coronavirus and a second RNA molecule encodes an immunogenic polypeptide or immunogenic fragment thereof from an infectious disease pathogen (e.g., virus, bacteria, parasite, etc.). For example, in some embodiments, two or more RNA molecules present in a nucleic acid containing particle comprise: a first RNA molecule encoding an immunogenic polypeptide or immunogenic fragment thereof from a coronavirus (e.g., in some embodiments SARS-CoV-2 Wuhan strain or a variant thereof, e.g., a SARS-CoV-2 having one or more mutations characteristic of an Omicron variant) and a second RNA molecule encoding an immunogenic polypeptide or immunogenic fragment thereof from an influenza virus. In some embodiments, two or more RNA molecules present in a nucleic acid containing particle comprise: a first RNA molecule encoding an immunogenic polypeptide or immunogenic fragment thereof from a first coronavirus (e.g., as described herein) and a second RNA molecule encoding an immunogenic polypeptide or immunogenic fragment thereof from a second coronavirus (e.g., as described herein). In some embodiments, a first coronavirus is different from a second coronavirus. In some embodiments, a first and/or second coronavirus is independently from a SARS-CoV-2 Wuhan strain or a variant thereof, e.g., a SARS-CoV-2 having one or more mutations characteristic of an Omicron variant.

In some embodiments, two or more RNA molecules present in a nucleic acid containing particle each encode an immunogenic polypeptide or an immunogenic fragment thereof from the same and/or different strains and/or variants of coronavirus (e.g., in some embodiments SARS-CoV-2 strains or variants). For example, in some embodiments, two or more RNA molecules present in a nucleic acid containing particle each encode a different immunogenic polypeptide or immunogenic fragment thereof from a coronavirus membrane protein, a coronavirus nucleocapsid protein, a coronavirus spike protein, a coronavirus non-structural protein and/or a coronavirus accessory protein. In some embodiments, such immunogenic polypeptides or immunogenic fragments thereof may be from the same or a different coronavirus (e.g., in some embodiments a SARS-CoV-2 Wuhan strain or variants thereof, for example, in some embodiments a variant having one or more mutations characteristic of a prevalent variant such as an Omicron variant). In some embodiments, a nucleic acid containing particle comprises a first RNA molecule encoding a SARS-CoV-2 S protein or an immunogenic fragment thereof from a first strain or variant, and a second RNA molecule encoding a SARS-CoV-2 S protein or an immunogenic fragment thereof from a second strain or variant, wherein the second strain or variant is different from the first strain or variant.

In some embodiments, a nucleic acid containing particle (e.g., in some embodiments an LNP as described herein) comprises a first RNA molecule encoding a SARS-CoV-2 S protein from a Wuhan strain and a second RNA molecule encoding a SARS-CoV-2 S protein comprising one or more mutations that are characteristic of an Omicron variant (e.g., a BA.1, BA.2, BA.3, BA.4, or BA.5 Omicron variant).

In some embodiments, a nucleic acid containing particle comprises a first RNA molecule encoding a SARS-CoV-2 S protein from a Wuhan strain and a second RNA molecule encoding a SARS-CoV-2 S protein comprising one or more mutations that are characteristic of an Omicron BA.1 variant. In some embodiments, the ratio of the first RNA molecule encoding a SARS-CoV-2 S protein from a Wuhan strain and the second RNA molecule encoding a SARS-CoV-2 S protein comprising one or more mutations that are characteristic of an Omicron BA.1 variant is 1:1. In some embodiments, the ratio of the first RNA molecule encoding a SARS-CoV-2 S protein from a Wuhan strain and the second RNA molecule encoding a SARS-CoV-2 S protein comprising one or more mutations that are characteristic of an Omicron BA.1 variant is 1:2. In some embodiments, the ratio of the first RNA molecule encoding a SARS-CoV-2 S protein from a Wuhan strain and the second RNA molecule encoding a SARS-CoV-2 S protein comprising one or more mutations that are characteristic of an Omicron BA.1 variant is 1:3.

In some embodiments, a nucleic acid containing particle comprises a first RNA molecule encoding a SARS-CoV-2 S protein from a Wuhan strain and a second RNA molecule encoding a SARS-CoV-2 S protein comprising one or more mutations that are characteristic of an Omicron BA.2 variant. In some embodiments, the ratio of the first RNA molecule encoding a SARS-CoV-2 S protein from a Wuhan strain and the second RNA molecule encoding a SARS-CoV-2 S protein comprising one or more mutations that are characteristic of an Omicron BA.2 variant is 1:1. In some embodiments, the ratio of the first RNA molecule encoding a SARS-CoV-2 S protein from a Wuhan strain and the second RNA molecule encoding a SARS-CoV-2 S protein comprising one or more mutations that are characteristic of an Omicron BA.2 variant is 1:2. In some embodiments, the ratio of the first RNA molecule encoding a SARS-CoV-2 S protein from a Wuhan strain and the second RNA molecule encoding a SARS-CoV-2 S protein comprising one or more mutations that are characteristic of an Omicron BA.2 variant is 1:3.

In some embodiments, a nucleic acid containing particle comprises a first RNA molecule encoding a SARS-CoV-2 S protein from a Wuhan strain and a second RNA molecule encoding a SARS-CoV-2 S protein comprising one or more mutations that are characteristic of an Omicron BA.3 variant. In some embodiments, a nucleic acid containing particle comprises a first RNA molecule encoding a SARS-CoV-2 S protein from a Wuhan strain and a second RNA molecule encoding a SARS-CoV-2 S protein comprising one or more mutations that are characteristic of an Omicron BA.4 or BA.5 variant. In some embodiments, the ratio of the first RNA molecule encoding a SARS-CoV-2 S protein from a Wuhan strain and the second RNA molecule encoding a SARS-CoV-2 S protein comprising one or more mutations that are characteristic of an Omicron BA.4 or BA.5 variant is 1:1. In some embodiments, the ratio of the first RNA molecule encoding a SARS-CoV-2 S protein from a Wuhan strain and the second RNA molecule encoding a SARS-CoV-2 S protein comprising one or more mutations that are characteristic of an Omicron BA.4 or BA.5 variant is 1:2. In some embodiments, the ratio of the first RNA molecule encoding a SARS-CoV-2 S protein from a Wuhan strain and the second RNA molecule encoding a SARS-CoV-2 S protein comprising one or more mutations that are characteristic of an Omicron BA.4 or BA.5 variant is 1:3.

In some embodiments, a nucleic acid containing particle comprises a first RNA molecule encoding a SARS-CoV-2 S protein from a first Omicron variant and a second RNA molecule encoding a SARS-CoV-2 S protein comprising one or more mutations that are characteristic of a second Omicron variant.

In some embodiments, a nucleic acid containing particle comprises a first RNA molecule encoding a SARS-CoV-2 S protein from a BA.1 Omicron variant and a second RNA molecule encoding a SARS-CoV-2 S protein comprising one or more mutations that are characteristic of a BA.2 Omicron variant. In some embodiments, the ratio of the first RNA molecule encoding a SARS-CoV-2 S protein comprising one or more mutations characteristic of a BA.1 Omicron variant strain and the second RNA molecule encoding a SARS-CoV-2 S protein comprising one or more mutations that are characteristic of an Omicron BA.2 variant is 1:1. In some embodiments, the ratio of the first RNA molecule encoding a SARS-CoV-2 S protein comprising one or more mutations characteristic of a BA.1 Omicron variant strain and the second RNA molecule encoding a SARS-CoV-2 S protein comprising one or more mutations that are characteristic of an Omicron BA.2 variant is 1:2. In some embodiments, the ratio of the first RNA molecule encoding a SARS-CoV-2 S protein comprising one or more mutations characteristic of a BA.1 Omicron variant strain and the second RNA molecule encoding a SARS-CoV-2 S protein comprising one or more mutations that are characteristic of an Omicron BA.2 variant is 1:3.

In some embodiments, a nucleic acid containing particle comprises a first RNA molecule encoding a SARS-CoV-2 S protein from a BA.1 Omicron variant and a second RNA molecule encoding a SARS-CoV-2 S protein comprising one or more mutations that are characteristic of a BA.3 Omicron variant. In some embodiments, the ratio of the first RNA molecule encoding a SARS-CoV-2 S protein comprising one or more mutations characteristic of a BA.1 Omicron variant strain and the second RNA molecule encoding a SARS-CoV-2 S protein comprising one or more mutations that are characteristic of an Omicron BA.3 variant is 1:1. In some embodiments, the ratio of the first RNA molecule encoding a SARS-CoV-2 S protein comprising one or more mutations characteristic of a BA.1 Omicron variant strain and the second RNA molecule encoding a SARS-CoV-2 S protein comprising one or more mutations that are characteristic of an Omicron BA.3 variant is 1:2. In some embodiments, the ratio of the first RNA molecule encoding a SARS-CoV-2 S protein comprising one or more mutations characteristic of a BA.1 Omicron variant strain and the second RNA molecule encoding a SARS-CoV-2 S protein comprising one or more mutations that are characteristic of an Omicron BA.3 variant is 1:3.

In some embodiments, a nucleic acid containing particle comprises a first RNA molecule encoding a SARS-CoV-2 S protein from a BA.1 Omicron variant and a second RNA molecule encoding a SARS-CoV-2 S protein comprising one or more mutations that are characteristic of a BA.4 or BA.5 Omicron variant. In some embodiments, the ratio of the first RNA molecule encoding a SARS-CoV-2 S protein comprising one or more mutations characteristic of a BA.1 Omicron variant strain and the second RNA molecule encoding a SARS-CoV-2 S protein comprising one or more mutations that are characteristic of an Omicron BA.4 or BA.5 variant is 1:1. In some embodiments, the ratio of the first RNA molecule encoding a SARS-CoV-2 S protein comprising one or more mutations characteristic of a BA.1 Omicron variant strain and the second RNA molecule encoding a SARS-CoV-2 S protein comprising one or more mutations that are characteristic of an Omicron BA.4 or BA.5 variant is 1:2. In some embodiments, the ratio of the first RNA molecule encoding a SARS-CoV-2 S protein comprising one or more mutations characteristic of a BA.1 Omicron variant strain and the second RNA molecule encoding a SARS-CoV-2 S protein comprising one or more mutations that are characteristic of an Omicron BA.4 or BA.5 variant is 1:3.

In some embodiments, a nucleic acid containing particle comprises a first RNA molecule encoding a SARS-CoV-2 S protein from a BA.2 Omicron variant and a second RNA molecule encoding a SARS-CoV-2 S protein comprising one or more mutations that are characteristic of a BA.3 Omicron variant. In some embodiments, the ratio of the first RNA molecule encoding a SARS-CoV-2 S protein comprising one or more mutations characteristic of a BA.2 Omicron variant strain and the second RNA molecule encoding a SARS-CoV-2 S protein comprising one or more mutations that are characteristic of an Omicron BA.3 variant is 1:1. In some embodiments, the ratio of the first RNA molecule encoding a SARS-CoV-2 S protein comprising one or more mutations characteristic of a BA.2 Omicron variant strain and the second RNA molecule encoding a SARS-CoV-2 S protein comprising one or more mutations that are characteristic of an Omicron BA.3 variant is 1:2. In some embodiments, the ratio of the first RNA molecule encoding a SARS-CoV-2 S protein comprising one or more mutations characteristic of a BA.2 Omicron variant strain and the second RNA molecule encoding a SARS-CoV-2 S protein comprising one or more mutations that are characteristic of an Omicron BA.3 variant is 1:3.

In some embodiments, a nucleic acid containing particle comprises a first RNA molecule encoding a SARS-CoV-2 S protein from a BA.2 Omicron variant and a second RNA molecule encoding a SARS-CoV-2 S protein comprising one or more mutations that are characteristic of a BA.4 or BA.5 Omicron variant. In some embodiments, the ratio of the first RNA molecule encoding a SARS-CoV-2 S protein comprising one or more mutations characteristic of a BA.2 Omicron variant strain and the second RNA molecule encoding a SARS-CoV-2 S protein comprising one or more mutations that are characteristic of an Omicron BA.4 or BA.5 variant is 1:1. In some embodiments, the ratio of the first RNA molecule encoding a SARS-CoV-2 S protein comprising one or more mutations characteristic of a BA.2 Omicron variant strain and the second RNA molecule encoding a SARS-CoV-2 S protein comprising one or more mutations that are characteristic of an Omicron BA.4 or BA.5 variant is 1:2. In some embodiments, the ratio of the first RNA molecule encoding a SARS-CoV-2 S protein comprising one or more mutations characteristic of a BA.2 Omicron variant strain and the second RNA molecule encoding a SARS-CoV-2 S protein comprising one or more mutations that are characteristic of an Omicron BA.4 or BA.5 variant is 1:3.

In some embodiments, a nucleic acid containing particle comprises a first RNA molecule encoding a SARS-CoV-2 S protein from a BA.3 Omicron variant and a second RNA molecule encoding a SARS-CoV-2 S protein comprising one or more mutations that are characteristic of a BA.4 or BA.5 Omicron variant. In some embodiments, the ratio of the first RNA molecule encoding a SARS-CoV-2 S protein comprising one or more mutations characteristic of a BA.3 Omicron variant strain and the second RNA molecule encoding a SARS-CoV-2 S protein comprising one or more mutations that are characteristic of an Omicron BA.4 or BA.5 variant is 1:1. In some embodiments, the ratio of the first RNA molecule encoding a SARS-CoV-2 S protein comprising one or more mutations characteristic of a BA.3 Omicron variant strain and the second RNA molecule encoding a SARS- CoV-2 S protein comprising one or more mutations that are characteristic of an Omicron BA.4 or BA.5 variant is 1:2. In some embodiments, the ratio of the first RNA molecule encoding a SARS-CoV-2 S protein comprising one or more mutations characteristic of a BA.3 Omicron variant strain and the second RNA molecule encoding a SARS-CoV-2 S protein comprising one or more mutations that are characteristic of an Omicron BA.4 or BA.5 variant is 1:3.

In some embodiments, a nucleic acid containing particle (e.g., in some embodiments an LNP as described herein) comprises three or more RNA molecules, each encoding a SARS-CoV-2 S protein comprising mutations of a different SARS-CoV-2 variant. In some embodiments, a nucleic acid containing particle comprises a first RNA molecule encoding a SARS-CoV-2 S protein from a Wuhan strain, a second RNA molecule encoding a SARS-CoV-2 S protein comprising one or more mutations that are characteristic of an Omicron variant (e.g., a BA.1, BA.2, BA.3, BA.4, or BA.5 Omicron variant), and a third RNA molecule encoding a SARS-CoV-2 S protein comprising one or more mutations that are characteristic of an Omicron variant (e.g., a BA.1, BA.2, BA.3, BA.4, or BA.5 Omicron variant), wherein the second and third RNA molecules encode a SARS-CoV-2 S protein comprising one or mutations characteristic of different Omicron subvariants. In some embodiments, a nucleic acid containing particle comprises a first RNA molecule encoding a SARS-CoV-2 S protein from a Wuhan strain, a second RNA molecule encoding a SARS-CoV-2 S protein comprising one or more mutations that are characteristic of a BA.1 Omicron variant, and a third RNA molecule encoding a SARS-CoV-2 S protein comprising one or more mutations that are characteristic of a BA.2 Omicron variant. In some embodiments, a nucleic acid containing particle comprises a first RNA molecule encoding a SARS-CoV-2 S protein from a Wuhan strain, a second RNA molecule encoding a SARS-CoV-2 S protein comprising one or more mutations that are characteristic of a BA.1 Omicron variant, and a third RNA molecule encoding a SARS-CoV-2 S protein comprising one or more mutations that are characteristic of a BA.2 Omicron variant. In some embodiments, a nucleic acid containing particle comprises a first RNA molecule encoding a SARS-CoV-2 S protein from a Wuhan strain, a second RNA molecule encoding a SARS-CoV-2 S protein comprising one or more mutations that are characteristic of a BA.1 Omicron variant, and a third RNA molecule encoding a SARS-CoV-2 S protein comprising one or more mutations that are characteristic of a BA.4/5 Omicron variant. In some embodiments, a nucleic acid containing particle comprises a first RNA molecule encoding a SARS-CoV-2 S protein from a Wuhan strain, a second RNA molecule encoding a SARS-CoV-2 S protein comprising one or more mutations that are characteristic of a BA.2 Omicron variant, and a third RNA molecule encoding a SARS-CoV-2 S protein comprising one or more mutations that are characteristic of a BA.4/5 Omicron variant. In some embodiments, a nucleic acid containing particle comprises a first RNA molecule encoding a SARS-CoV-2 S protein comprising one or more mutations that are characteristic of a BA.1 Omicron variant, a second RNA molecule encoding a SARS-CoV-2 S protein comprising one or more mutations that are characteristic of a BA.2 Omicron variant, and a third RNA molecule encoding a SARS-CoV-2 S protein comprising one or more mutations that are characteristic of a BA.4/5 Omicron variant.

In some embodiments, a nucleic acid containing particle (e.g., in some embodiments an LNP as described herein) comprising two or more RNA molecules, comprises each RNA molecule in the same amount (i.e., at a 1:1 ratio).

In some embodiments, a nucleic acid containing particle (e.g., in some embodiments an LNP as described herein) comprising two or more RNA molecules, comprises a different amount of each RNA molecule. For example, in some embodiments, a nucleic acid containing particle comprises a first RNA molecule and a second RNA molecule, where the first RNA molecule is present in an amount that is 0.01 to 100 times that of the second RNA molecule (e.g., wherein the amount of the first RNA molecule is 0.01 to 50, 0.01 to 4, 0.01 to 30, 0.01 to 25, 0.01 to 20, 0.01 to 15, 0.01 to 10, 0.01 to 9, 0.01 to 8, 0.01 to 7, 0.01 to 6, 0.01 to 5, 0.01 to 4, 0.01 to 3, 0.01 to 2, 0.01 to 1.5, 1 to 50, 1 to 4, 1 to 30, 1 to 25, 1 to 20, 1 to 15, 1 to 10, 1 to 9, 1 to 8, 1 to 7, 1 to 6, 1 to 5, 1 to 4, 1 to 3, 1 to 2, or 1 to 1.5 times higher than the second RNA molecule). In some embodiments, a nucleic acid containing particle comprises a first RNA molecule and a second RNA molecule, wherein the concentration of the first RNA molecule is 1 to 10 times that of the second RNA molecule. In some embodiments, a nucleic acid containing particle comprises a first RNA molecule and a second RNA molecule, wherein the concentration of the first RNA molecule is 1 to 5 times that of the second RNA molecule. In some embodiments, a nucleic acid containing particle comprises a first RNA molecule and a second RNA molecule, wherein the concentration of the first RNA molecule is 1 to 3 times that of the second RNA molecule. In some embodiments, a nucleic acid containing particle comprises a first RNA molecule and a second RNA molecule, wherein the concentration of the first RNA molecule is 2 times that of the second RNA molecule. In some embodiments, a nucleic acid containing particle comprises a first RNA molecule and a second RNA molecule, wherein the concentration of the first RNA molecule is 3 times that of the second RNA molecule.

In some embodiments, a nucleic acid containing particle (e.g., in some embodiments an LNP as described herein) comprising three RNA molecules, comprises each RNA molecule in the same amount (i.e., at a 1:1:1 ratio).

In some embodiments, a nucleic acid containing particle (e.g., in some embodiments an LNP as described herein) comprising three RNA molecules, comprises a different amount of each RNA molecule. For example, in some embodiments, the ratio of first RNA molecule:second RNA molecule:third RNA molecule is 1:0.01-100:0.01-100 (e.g., 1:0.01-50:0.01-50; 1:0.01-40:0.01-40; 1:0.01-30:0.01-25; 1:0.01-25:0.01-25; 1:0.01-20:0.01-20; 1:0.01-15:0.01-15; 1:0.01-10:0.01-9; 1:0.01-9:0.01-9; 1:0.01-8:0.01-8; 1:0.01-7:0.01-7; 1:0.01-6:0.01-6; 1:0.01-5:0.01-5; 1:0.01-4:0.01-4; 1:0.01-3:0.01-3; 1:0.01-2:0.01-2; or 1:0.01-1.5:0.01-1.5). In some embodiments, the ratio of first RNA molecule:second RNA molecule:third RNA molecule is 1:1:3. In some embodiments, the ratio of first RNA molecule:second RNA molecule:third RNA molecule is 1:3:3.

In some embodiments, a first RNA molecule encoding a SARS-CoV-2 S protein from a Wuhan strain comprises a nucleotide sequence that encodes the amino acid sequence of SEQ ID NO: 7. In some embodiments, a first RNA molecule encoding a SARS-CoV-2 S protein from a Wuhan strain comprises a nucleotide sequence that is at least 80% identical (e.g., at least 85%, at least 90%, at least 91%, at least 92%, at least 93%, at least 94%, at least 95%, at least 96%, at least 97%, at least 98%, or at least 99% identical) to SEQ ID NO: 9. In some embodiments, a first RNA molecule encoding a SARS-COV-2 S protein from a Wuhan strain comprises a nucleotide sequence that is at least 80% identical to (e.g., at least 85%, at least 90%, at least 91%, at least 92%, at least 93%, at least 94%, at least 95%, at least 96%, at least 97%, at least 98%, or at least 99% identical to) SEQ ID NO: 20. In some embodiments, a first RNA molecule encoding a SARS-COV-2 S protein from a Wuhan strain comprises a nucleotide sequence that encodes an amino acid sequence that is at least 80% identical to (e.g., at least 85%, at least 90%, at least 91%, at least 92%, at least 93%, at least 94%, at least 95%, at least 96%, at least 97%, at least 98%, or at least 99% identical to) SEQ ID NO: 7. In some embodiments, a second RNA molecule encoding a SARS-CoV-2 S protein having one or more mutations that are characteristic of an Omicron variant comprises a nucleotide sequence that encodes the amino acid sequence of SEQ ID NO: 49. In some embodiments, a second RNA molecule encoding a SARS-CoV-2 S protein comprising one or more mutations characteristic of an Omicron variant comprises a nucleotide sequence that is at least 80% identical (e.g., at least 85%, at least 90%, at least 91%, at least 92%, at least 93%, at least 94%, at least 95%, at least 96%, at least 97%, at least 98%, or at least 99% identical) to SEQ ID NO: 50. In some embodiments, a second RNA molecule encoding a SARS-COV-2 S protein comprising one or more mutations characteristic of an Omicron variant comprises a nucleotide sequence that is at least 80% identical to (e.g., at least 85%, at least 90%, at least 91%, at least 92%, at least 93%, at least 94%, at least 95%, at least 96%, at least 97%, at least 98%, or at least 99% identical to) SEQ ID NO: 51. In some embodiments, a second RNA molecule encoding a SARS-COV-2 S protein comprising one or more mutations characteristic of an Omicron variant comprises a nucleotide sequence that encodes an amino acid sequence that is at least 80% identical to (e.g., at least 85%, at least 90%, at least 91%, at least 92%, at least 93%, at least 94%, at least 95%, at least 96%, at least 97%, at least 98%, or at least 99% identical to) SEQ ID NO: 49.

In some embodiments, a second RNA molecule encoding a SARS-CoV-2 S protein having one or more mutations that are characteristic of an Omicron variant comprises a nucleotide sequence that encodes the amino acid sequence of SEQ ID NO: 64. In some embodiments, a second RNA molecule encoding a SARS-CoV-2 S protein comprising one or more mutations characteristic of an Omicron variant comprises a nucleotide sequence that is at least 80% identical (e.g., at least 85%, at least 90%, at least 91%, at least 92%, at least 93%, at least 94%, at least 95%, at least 96%, at least 97%, at least 98%, or at least 99% identical) to SEQ ID NO: 65. In some embodiments, a second RNA molecule encoding a SARS-COV-2 S protein comprising one or more mutations characteristic of an Omicron variant comprises a nucleotide sequence that is at least 80% identical to (e.g., at least 85%, at least 90%, at least 91%, at least 92%, at least 93%, at least 94%, at least 95%, at least 96%, at least 97%, at least 98%, or at least 99% identical to) SEQ ID NO: 67. In some embodiments, a second RNA molecule encoding a SARS-COV-2 S protein comprising one or more mutations characteristic of an Omicron variant comprises a nucleotide sequence that encodes an amino acid sequence that is at least 80% identical to (e.g., at least 85%, at least 90%, at least 91%, at least 92%, at least 93%, at least 94%, at least 95%, at least 96%, at least 97%, at least 98%, or at least 99% identical to) SEQ ID NO: 64.

In some embodiments, a second RNA molecule encoding a SARS-CoV-2 S protein having one or more mutations that are characteristic of an Omicron variant comprises a nucleotide sequence that encodes the amino acid sequence of SEQ ID NO: 69. In some embodiments, a second RNA molecule encoding a SARS-CoV-2 S protein comprising one or more mutations characteristic of an Omicron variant comprises a nucleotide sequence that is at least 80% identical (e.g., at least 85%, at least 90%, at least 91%, at least 92%, at least 93%, at least 94%, at least 95%, at least 96%, at least 97%, at least 98%, or at least 99% identical) to SEQ ID NO: 70. In some embodiments, a second RNA molecule encoding a SARS-COV-2 S protein comprising one or more mutations characteristic of an Omicron variant comprises a nucleotide sequence that is at least 80% identical to (e.g., at least 85%, at least 90%, at least 91%, at least 92%, at least 93%, at least 94%, at least 95%, at least 96%, at least 97%, at least 98%, or at least 99% identical to) SEQ ID NO: 72. In some embodiments, a second RNA molecule encoding a SARS-COV-2 S protein comprising one or more mutations characteristic of an Omicron variant comprises a nucleotide sequence that encodes an amino acid sequence that is at least 80% identical to (e.g., at least 85%, at least 90%, at least 91%, at least 92%, at least 93%, at least 94%, at least 95%, at least 96%, at least 97%, at least 98%, or at least 99% identical to) SEQ ID NO: 69.

In some embodiments, a second RNA molecule encoding a SARS-CoV-2 S protein having one or more mutations that are characteristic of an Omicron variant comprises a nucleotide sequence that encodes the amino acid sequence of SEQ ID NO: 74. In some embodiments, a second RNA molecule encoding a SARS-CoV-2 S protein comprising one or more mutations characteristic of an Omicron variant comprises a nucleotide sequence that is at least 80% identical (e.g., at least 85%, at least 90%, at least 91%, at least 92%, at least 93%, at least 94%, at least 95%, at least 96%, at least 97%, at least 98%, or at least 99% identical) to SEQ ID NO: 75. In some embodiments, a second RNA molecule encoding a SARS-COV-2 S protein comprising one or more mutations characteristic of an Omicron variant comprises a nucleotide sequence that is at least 80% identical to (e.g., at least 85%, at least 90%, at least 91%, at least 92%, at least 93%, at least 94%, at least 95%, at least 96%, at least 97%, at least 98%, or at least 99% identical to) SEQ ID NO: 77. In some embodiments, a second RNA molecule encoding a SARS-COV-2 S protein comprising one or more mutations characteristic of an Omicron variant comprises a nucleotide sequence that encodes an amino acid sequence that is at least 80% identical to (e.g., at least 85%, at least 90%, at least 91%, at least 92%, at least 93%, at least 94%, at least 95%, at least 96%, at least 97%, at least 98%, or at least 99% identical to) SEQ ID NO: 74.

In some embodiments, a nucleic acid containing particle (e.g., in some embodiments an LNP as described herein) comprises: a first RNA molecule comprising a nucleotide sequence that encodes the amino acid sequence of SEQ ID NO: 7 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 7); and a second RNA molecule comprising a nucleotide sequence that encodes the amino acid sequence of SEQ ID NO: 49 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 49. In some embodiments, the ratio of the first RNA molecule that encodes the amino acid sequence of SEQ ID NO: 7 or a sequence that is at least 80% identical to SEQ ID NO: 7 to the second RNA molecule that encodes the amino acid sequence of SEQ ID NO: 49 or a sequence that is at least 80% identical to SEQ ID NO: 49 is 1:1. In some embodiments, the ratio of the first RNA molecule that encodes the amino acid sequence of SEQ ID NO: 7 or a sequence that is at least 80% identical to SEQ ID NO: 7 to the second RNA molecule that encodes the amino acid sequence of SEQ ID NO: 49 or a sequence that is at least 80% identical to SEQ ID NO: 49 is 1:2. In some embodiments, the ratio of the first RNA molecule that encodes the amino acid sequence of SEQ ID NO: 7 or a sequence that is at least 80% identical to SEQ ID NO: 7 to the second RNA molecule that encodes the amino acid sequence of SEQ ID NO: 49 or a sequence that is at least 80% identical to SEQ ID NO: 49 is 1:3.

In some embodiments, a nucleic acid containing particle (e.g., in some embodiments an LNP as described herein) comprises: a first RNA molecule comprising a nucleotide sequence of SEQ ID NO: 9 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 9); and a second RNA molecule comprising a nucleotide sequence of SEQ ID NO: 50 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 50. In some embodiments, the ratio of the first RNA molecule comprising the nucleotide sequence of SEQ ID NO: 9 or a sequence that is at least 80% identical to SEQ ID NO: 9 to the second RNA molecule that comprises a nucleotide sequence of SEQ ID NO: 50 or a sequence that is at least 80% identical to SEQ ID NO: 50 is 1:1. In some embodiments, the ratio of the first RNA molecule comprising the nucleotide sequence of SEQ ID NO: 9 or a sequence that is at least 80% identical to SEQ ID NO: 9 to the second RNA molecule that comprises a nucleotide sequence of SEQ ID NO: 50 or a sequence that is at least 80% identical to SEQ ID NO: 50 is 1:2. In some embodiments, the ratio of the first RNA molecule comprising the nucleotide sequence of SEQ ID NO: 9 or a sequence that is at least 80% identical to SEQ ID NO: 9 to the second RNA molecule that comprises a nucleotide sequence of SEQ ID NO: 50 or a sequence that is at least 80% identical to SEQ ID NO: 50 is 1:3.

In some embodiments, a nucleic acid containing particle (e.g., in some embodiments an LNP as described herein) comprises: a first RNA molecule comprising a nucleotide sequence of SEQ ID NO: 20 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 20; and a second RNA molecule comprising a nucleotide sequence of SEQ ID NO: 51 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 51. In some embodiments, the ratio of the first RNA molecule comprising the nucleotide sequence of SEQ ID NO: 20 or a sequence that is at least 80% identical to SEQ ID NO: 20 to the second RNA molecule that comprises a nucleotide sequence of SEQ ID NO: 51 or a sequence that is at least 80% identical to SEQ ID NO: 51 is 1:1. In some embodiments, the ratio of the first RNA molecule comprising the nucleotide sequence of SEQ ID NO: 20 or a sequence that is at least 80% identical to SEQ ID NO: 20 to the second RNA molecule that comprises a nucleotide sequence of SEQ ID NO: 51 or a sequence that is at least 80% identical to SEQ ID NO: 51 is 1:2. In some embodiments, the ratio of the first RNA molecule comprising the nucleotide sequence of SEQ ID NO: 20 or a sequence that is at least 80% identical to SEQ ID NO: 20 to the second RNA molecule that comprises a nucleotide sequence of SEQ ID NO: 51 or a sequence that is at least 80% identical to SEQ ID NO: 51 is 1:3.

In some embodiments, a nucleic acid containing particle (e.g., in some embodiments an LNP as described herein) comprises: a first RNA molecule comprising a nucleotide sequence that encodes the amino acid sequence of SEQ ID NO: 7 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 7); and a second RNA molecule comprising a nucleotide sequence that encodes the amino acid sequence of SEQ ID NO: 64 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 64. In some embodiments, the ratio of the first RNA molecule that encodes the amino acid sequence of SEQ ID NO: 7 or a sequence that is at least 80% identical to SEQ ID NO: 7 to the second RNA molecule that encodes the amino acid sequence of SEQ ID NO: 49 or a sequence that is at least 80% identical to SEQ ID NO: 64 is 1:1. In some embodiments, the ratio of the first RNA molecule that encodes the amino acid sequence of SEQ ID NO: 7 or a sequence that is at least 80% identical to SEQ ID NO: 7 to the second RNA molecule that encodes the amino acid sequence of SEQ ID NO: 64 or a sequence that is at least 80% identical to SEQ ID NO: 64 is 1:2. In some embodiments, the ratio of the first RNA molecule that encodes the amino acid sequence of SEQ ID NO: 7 or a sequence that is at least 80% identical to SEQ ID NO: 7 to the second RNA molecule that encodes the amino acid sequence of SEQ ID NO: 64 or a sequence that is at least 80% identical to SEQ ID NO: 64 is 1:3.

In some embodiments, a nucleic acid containing particle (e.g., in some embodiments an LNP as described herein) comprises: a first RNA molecule comprising a nucleotide sequence of SEQ ID NO: 9 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 9); and a second RNA molecule comprising a nucleotide sequence of SEQ ID NO: 65 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 65. In some embodiments, the ratio of the first RNA molecule comprising the nucleotide sequence of SEQ ID NO: 9 or a sequence that is at least 80% identical to SEQ ID NO: 9 to the second RNA molecule that comprises a nucleotide sequence of SEQ ID NO: 65 or a sequence that is at least 80% identical to SEQ ID NO: 65 is 1:1. In some embodiments, the ratio of the first RNA molecule comprising the nucleotide sequence of SEQ ID NO: 9 or a sequence that is at least 80% identical to SEQ ID NO: 9 to the second RNA molecule that comprises a nucleotide sequence of SEQ ID NO: 65 or a sequence that is at least 80% identical to SEQ ID NO: 65 is 1:2. In some embodiments, the ratio of the first RNA molecule comprising the nucleotide sequence of SEQ ID NO: 9 or a sequence that is at least 80% identical to SEQ ID NO: 9 to the second RNA molecule that comprises a nucleotide sequence of SEQ ID NO: 65 or a sequence that is at least 80% identical to SEQ ID NO: 65 is 1:3.

In some embodiments, a nucleic acid containing particle (e.g., in some embodiments an LNP as described herein) comprises: a first RNA molecule comprising a nucleotide sequence of SEQ ID NO: 20 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 20; and a second RNA molecule comprising a nucleotide sequence of SEQ ID NO: 51 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 67. In some embodiments, the ratio of the first RNA molecule comprising the nucleotide sequence of SEQ ID NO: 20 or a sequence that is at least 80% identical to SEQ ID NO: 20 to the second RNA molecule that comprises a nucleotide sequence of SEQ ID NO: 67 or a sequence that is at least 80% identical to SEQ ID NO: 67 is 1:1. In some embodiments, the ratio of the first RNA molecule comprising the nucleotide sequence of SEQ ID NO: 20 or a sequence that is at least 80% identical to SEQ ID NO: 20 to the second RNA molecule that comprises a nucleotide sequence of SEQ ID NO: 67 or a sequence that is at least 80% identical to SEQ ID NO: 67 is 1:2. In some embodiments, the ratio of the first RNA molecule comprising the nucleotide sequence of SEQ ID NO: 20 or a sequence that is at least 80% identical to SEQ ID NO: 20 to the second RNA molecule that comprises a nucleotide sequence of SEQ ID NO: 67 or a sequence that is at least 80% identical to SEQ ID NO: 67 is 1:3.

In some embodiments, a nucleic acid containing particle (e.g., in some embodiments an LNP as described herein) comprises: a first RNA molecule comprising a nucleotide sequence that encodes the amino acid sequence of SEQ ID NO: 7 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 7); and a second RNA molecule comprising a nucleotide sequence that encodes the amino acid sequence of SEQ ID NO: 69 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 69. In some embodiments, the ratio of the first RNA molecule that encodes the amino acid sequence of SEQ ID NO: 7 or a sequence that is at least 80% identical to SEQ ID NO: 7 to the second RNA molecule that encodes the amino acid sequence of SEQ ID NO: 69 or a sequence that is at least 80% identical to SEQ ID NO: 69 is 1:1. In some embodiments, the ratio of the first RNA molecule that encodes the amino acid sequence of SEQ ID NO: 7 or a sequence that is at least 80% identical to SEQ ID NO: 7 to the second RNA molecule that encodes the amino acid sequence of SEQ ID NO: 69 or a sequence that is at least 80% identical to SEQ ID NO: 69 is 1:2. In some embodiments, the ratio of the first RNA molecule that encodes the amino acid sequence of SEQ ID NO: 7 or a sequence that is at least 80% identical to SEQ ID NO: 7 to the second RNA molecule that encodes the amino acid sequence of SEQ ID NO: 69 or a sequence that is at least 80% identical to SEQ ID NO: 69 is 1:3.

In some embodiments, a nucleic acid containing particle (e.g., in some embodiments an LNP as described herein) comprises: a first RNA molecule comprising a nucleotide sequence of SEQ ID NO: 9 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 9); and a second RNA molecule comprising a nucleotide sequence of SEQ ID NO: 70 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 70. In some embodiments, the ratio of the first RNA molecule comprising the nucleotide sequence of SEQ ID NO: 9 or a sequence that is at least 80% identical to SEQ ID NO: 9 to the second RNA molecule that comprises a nucleotide sequence of SEQ ID NO: 70 or a sequence that is at least 80% identical to SEQ ID NO: 70 is 1:1. In some embodiments, the ratio of the first RNA molecule comprising the nucleotide sequence of SEQ ID NO: 9 or a sequence that is at least 80% identical to SEQ ID NO: 9 to the second RNA molecule that comprises a nucleotide sequence of SEQ ID NO: 70 or a sequence that is at least 80% identical to SEQ ID NO: 70 is 1:2. In some embodiments, the ratio of the first RNA molecule comprising the nucleotide sequence of SEQ ID NO: 9 or a sequence that is at least 80% identical to SEQ ID NO: 9 to the second RNA molecule that comprises a nucleotide sequence of SEQ ID NO: 50 or a sequence that is at least 80% identical to SEQ ID NO: 70 is 1:3.

In some embodiments, a nucleic acid containing particle (e.g., in some embodiments an LNP as described herein) comprises: a first RNA molecule comprising a nucleotide sequence of SEQ ID NO: 20 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 20; and a second RNA molecule comprising a nucleotide sequence of SEQ ID NO: 72 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 72. In some embodiments, the ratio of the first RNA molecule comprising the nucleotide sequence of SEQ ID NO: 20 or a sequence that is at least 80% identical to SEQ ID NO: 20 to the second RNA molecule that comprises a nucleotide sequence of SEQ ID NO: 72 or a sequence that is at least 80% identical to SEQ ID NO: 72 is 1:1. In some embodiments, the ratio of the first RNA molecule comprising the nucleotide sequence of SEQ ID NO: 20 or a sequence that is at least 80% identical to SEQ ID NO: 20 to the second RNA molecule that comprises a nucleotide sequence of SEQ ID NO: 72 or a sequence that is at least 80% identical to SEQ ID NO: 72 is 1:2. In some embodiments, the ratio of the first RNA molecule comprising the nucleotide sequence of SEQ ID NO: 20 or a sequence that is at least 80% identical to SEQ ID NO: 20 to the second RNA molecule that comprises a nucleotide sequence of SEQ ID NO: 72 or a sequence that is at least 80% identical to SEQ ID NO: 72 is 1:3.

In some embodiments, a nucleic acid containing particle (e.g., in some embodiments an LNP as described herein) comprises: a first RNA molecule comprising a nucleotide sequence that encodes the amino acid sequence of SEQ ID NO: 7 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 7); and a second RNA molecule comprising a nucleotide sequence that encodes the amino acid sequence of SEQ ID NO: 74 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 74. In some embodiments, the ratio of the first RNA molecule that encodes the amino acid sequence of SEQ ID NO: 7 or a sequence that is at least 80% identical to SEQ ID NO: 7 to the second RNA molecule that encodes the amino acid sequence of SEQ ID NO: 74 or a sequence that is at least 80% identical to SEQ ID NO: 74 is 1:1. In some embodiments, the ratio of the first RNA molecule that encodes the amino acid sequence of SEQ ID NO: 7 or a sequence that is at least 80% identical to SEQ ID NO: 7 to the second RNA molecule that encodes the amino acid sequence of SEQ ID NO: 74 or a sequence that is at least 80% identical to SEQ ID NO: 74 is 1:2. In some embodiments, the ratio of the first RNA molecule that encodes the amino acid sequence of SEQ ID NO: 7 or a sequence that is at least 80% identical to SEQ ID NO: 7 to the second RNA molecule that encodes the amino acid sequence of SEQ ID NO: 74 or a sequence that is at least 80% identical to SEQ ID NO: 74 is 1:3.

In some embodiments, a nucleic acid containing particle (e.g., in some embodiments an LNP as described herein) comprises: a first RNA molecule comprising a nucleotide sequence of SEQ ID NO: 9 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 9); and a second RNA molecule comprising a nucleotide sequence of SEQ ID NO: 75 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 75. In some embodiments, the ratio of the first RNA molecule comprising the nucleotide sequence of SEQ ID NO: 9 or a sequence that is at least 80% identical to SEQ ID NO: 9 to the second RNA molecule that comprises a nucleotide sequence of SEQ ID NO: 75 or a sequence that is at least 80% identical to SEQ ID NO: 75 is 1:1. In some embodiments, the ratio of the first RNA molecule comprising the nucleotide sequence of SEQ ID NO: 9 or a sequence that is at least 80% identical to SEQ ID NO: 9 to the second RNA molecule that comprises a nucleotide sequence of SEQ ID NO: 75 or a sequence that is at least 80% identical to SEQ ID NO: 75 is 1:2. In some embodiments, the ratio of the first RNA molecule comprising the nucleotide sequence of SEQ ID NO: 9 or a sequence that is at least 80% identical to SEQ ID NO: 9 to the second RNA molecule that comprises a nucleotide sequence of SEQ ID NO: 75 or a sequence that is at least 80% identical to SEQ ID NO: 75 is 1:3.

In some embodiments, a nucleic acid containing particle (e.g., in some embodiments an LNP as described herein) comprises: a first RNA molecule comprising a nucleotide sequence of SEQ ID NO: 20 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 20; and a second RNA molecule comprising a nucleotide sequence of SEQ ID NO: 77 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 77. In some embodiments, the ratio of the first RNA molecule comprising the nucleotide sequence of SEQ ID NO: 20 or a sequence that is at least 80% identical to SEQ ID NO: 20 to the second RNA molecule that comprises a nucleotide sequence of SEQ ID NO: 77 or a sequence that is at least 80% identical to SEQ ID NO: 77 is 1:1. In some embodiments, the ratio of the first RNA molecule comprising the nucleotide sequence of SEQ ID NO: 20 or a sequence that is at least 80% identical to SEQ ID NO: 20 to the second RNA molecule that comprises a nucleotide sequence of SEQ ID NO: 77 or a sequence that is at least 80% identical to SEQ ID NO: 77 is 1:2. In some embodiments, the ratio of the first RNA molecule comprising the nucleotide sequence of SEQ ID NO: 20 or a sequence that is at least 80% identical to SEQ ID NO: 20 to the second RNA molecule that comprises a nucleotide sequence of SEQ ID NO: 77 or a sequence that is at least 80% identical to SEQ ID NO: 77 is 1:3.

In some embodiments, a nucleic acid containing particle (e.g., in some embodiments an LNP as described herein) comprises: a first RNA molecule comprising a nucleotide sequence that encodes the amino acid sequence of SEQ ID NO: 7 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 7); and a second RNA molecule comprising a nucleotide sequence that encodes the amino acid sequence of SEQ ID NO: 55, 58, or 61 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 55, 58, or 61.

In some embodiments, a nucleic acid containing particle (e.g., in some embodiments an LNP as described herein) comprises: a first RNA molecule comprising a nucleotide sequence of SEQ ID NO: 9 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 9; and a second RNA molecule comprising a nucleotide sequence of SEQ ID NO: 56, 59, or 62a or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 56, 59, or 62a.

In some embodiments, a nucleic acid containing particle (e.g., in some embodiments an LNP as described herein) comprises: a first RNA molecule comprising a nucleotide sequence of SEQ ID NO: 20 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 20; and a second RNA molecule comprising a nucleotide sequence of SEQ ID NO: 57, 60, or 63a or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 57, 60, or 63a.

In some embodiments, a nucleic acid containing particle (e.g., in some embodiments an LNP as described herein) comprises: a first RNA molecule comprising a nucleotide sequence that encodes the amino acid sequence of SEQ ID NO: 58 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 58; and a second RNA molecule comprising a nucleotide sequence that encodes an amino acid sequence of SEQ ID NO: 49, 55, or 61 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 49, 55, or 61.

In some embodiments, a nucleic acid containing particle (e.g., in some embodiments an LNP as described herein) comprises: a first RNA molecule comprising a nucleotide sequence of SEQ ID NO: 59 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 59; and a second RNA molecule comprising a nucleotide sequence of SEQ ID NO: 50, 56, or 62a, or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 50, 56, or 62a.

In some embodiments, a nucleic acid containing particle (e.g., in some embodiments an LNP as described herein) comprises: a first RNA molecule comprising a nucleotide sequence of SEQ ID NO: 60 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 60; and a second RNA molecule comprising a nucleotide sequence of SEQ ID NO: 51, 57, or 63a, or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 51, 57, or 63a.

In some embodiments, a nucleic acid containing particle (e.g., in some embodiments an LNP as described herein) comprises: a first RNA molecule comprising a nucleotide sequence that encodes the amino acid sequence of SEQ ID NO: 49 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 49; and a second RNA molecule comprising a nucleotide sequence that encodes the amino acid sequence of SEQ ID NO: 55 or 61 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 55 or 61.

In some embodiments, a nucleic acid containing particle (e.g., in some embodiments an LNP as described herein) comprises: a first RNA molecule comprising a nucleotide sequence of SEQ ID NO: 50 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 50; and a second RNA molecule comprising a nucleotide sequence of SEQ ID NO: 56 or 62a or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 56 or 62a.

In some embodiments, a nucleic acid containing particle (e.g., in some embodiments an LNP as described herein) comprises: a first RNA molecule comprising a nucleotide sequence of SEQ ID NO: 51 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 51; and a second RNA molecule comprising a nucleotide sequence of SEQ ID NO: 57 or 63a or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 57 or 63a.

In some embodiments, a nucleic acid containing particle (e.g., in some embodiments an LNP as described herein) comprises: a first RNA molecule comprising a nucleotide sequence that encodes the amino acid sequence of SEQ ID NO: 55 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 55; and a second RNA molecule comprising a nucleotide sequence that encodes the amino acid sequence of SEQ ID NO: 61 or an amino acid sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 61.

In some embodiments, a nucleic acid containing particle (e.g., in some embodiments an LNP as described herein) comprises: a first RNA molecule comprising a nucleotide sequence of SEQ ID NO: 56 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 56; and a second RNA molecule comprising a nucleotide sequence of SEQ ID NO: 62a, or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 62a.

In some embodiments, a nucleic acid containing particle (e.g., in some embodiments an LNP as described herein) comprises: a first RNA molecule comprising a nucleotide sequence of SEQ ID NO: 57 or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 57; and a second RNA molecule comprising a nucleotide sequence of SEQ ID NO: 63a or a nucleotide sequence that is at least 80% (e.g., at least 85%, at least 90%, at least 91%, at least 92%, at least 93%, at least 94%, at least 95%, at least 96%, at least 97%, at least 98%, at least 99% or higher) identical to SEQ ID NO: 63a.

In some embodiments, a particle (e.g., in some embodiments an LNP) containing nucleic acids (e.g., RNAs) encoding different polypeptides can be formed by mixing a plurality of (e.g., at least two, at least three, or more) RNA molecules with particle-forming components (e.g., lipids). In some embodiments, nucleic acids (e.g., RNAs) encoding different polypeptides can be mixed (e.g., in some embodiments in substantially equal proportions, e.g., in some embodiments at a 1:1 ratio when two RNA molecules are present) prior to mixing with particle-forming components (e.g., lipids).

In some embodiments, two or more RNA molecules each encoding a different polypeptide (e.g., as described herein) can be mixed with particle-forming agents to form nucleic acid containing particles as described above. In alternative embodiments, two or more RNA molecules each encoding a different polypeptide (e.g., as described herein) can be formulated into separate particle compositions, which are then mixed together. For example, in some embodiments, individual populations of nucleic acid containing particles, each population comprising an RNA molecule encoding a different immunogenic polypeptide or immunogenic fragment thereof (e.g., as described herein), can be separately formed and then mixed together, for example, prior to filling into vials during a manufacturing process, or immediately prior to administration (e.g., by an administering health-care professional)). Accordingly, in some embodiments, described herein is a composition comprises two or more populations of particles (e.g., in some embodiments, lipid nanoparticles), each population comprising at least one RNA molecule encoding a different immunogenic polypeptide or immunogenic fragment thereof (e.g., a SARS-CoV-2 S protein, or fragments thereof, from a different variant). In some embodiments, each population may be provided in a composition at a desirable proportion (e.g., in some embodiments, each population may be provided in a composition in an amount that provides the same amount of RNA molecules).

Cationic Polymer

Given their high degree of chemical flexibility, polymers are commonly used materials for nanoparticle-based delivery. Typically, cationic polymers are used to electrostatically condense the negatively charged nucleic acid into nanoparticles. These positively charged groups often consist of amines that change their state of protonation in the pH range between 5.5 and 7.5, thought to lead to an ion imbalance that results in endosomal rupture. Polymers such as poly-L-lysine, polyamidoamine, protamine and polyethyleneimine, as well as naturally occurring polymers such as chitosan have all been applied to nucleic acid delivery and are suitable as cationic polymers herein. In addition, some investigators have synthesized polymers specifically for nucleic acid delivery. Poly(R-amino esters), in particular, have gained widespread use in nucleic acid delivery owing to their ease of synthesis and biodegradability. Such synthetic polymers are also suitable as cationic polymers herein.

A "polymer," as used herein, is given its ordinary meaning, i.e., a molecular structure comprising one or more repeat units (monomers), connected by covalent bonds. The repeat units can all be identical, or in some cases, there can be more than one type of repeat unit present within the polymer. In some cases, the polymer is biologically derived, i.e., a biopolymer such as a protein. In some cases, additional moieties can also be present in the polymer, for example targeting moieties such as those described herein.

If more than one type of repeat unit is present within the polymer, then the polymer is said to be a "copolymer." It is to be understood that the polymer being employed herein can be a copolymer. The repeat units forming the copolymer can be arranged in any fashion. For example, the repeat units can be arranged in a random order, in an alternating order, or as a "block" copolymer, i.e., comprising one or more regions each comprising a first repeat unit (e.g., a first block), and one or more regions each comprising a second repeat unit (e.g., a second block), etc. Block copolymers can have two (a diblock copolymer), three (a triblock copolymer), or more numbers of distinct blocks.

In certain embodiments, the polymer is biocompatible. Biocompatible polymers are polymers that typically do not result in significant cell death at moderate concentrations. In certain embodiments, the biocompatible polymer is biodegradable, i.e., the polymer is able to degrade, chemically and/or biologically, within a physiological environment, such as within the body.

In certain embodiments, polymer may be protamine or polyalkyleneimine, in particular protamine.

The term "protamine" refers to any of various strongly basic proteins of relatively low molecular weight that are rich in arginine and are found associated especially with DNA in place of somatic histones in the sperm cells of various animals (as fish). In particular, the term "protamine" refers to proteins found in fish sperm that are strongly basic, are soluble in water, are not coagulated by heat, and yield chiefly arginine upon hydrolysis. In purified form, they are used in a long-acting formulation of insulin and to neutralize the anticoagulant effects of heparin.

According to the present disclosure, the term "protamine" as used herein is meant to comprise any protamine amino acid sequence obtained or derived from natural or biological sources including fragments thereof and multimeric forms of said amino acid sequence or fragment thereof as well as (synthesized) polypeptides which are artificial and specifically designed for specific purposes and cannot be isolated from native or biological sources.

In one embodiment, the polyalkyleneimine comprises polyethylenimine and/or polypropylenimine, preferably polyethyleneimine. A preferred polyalkyleneimine is polyethyleneimine (PEI). The average molecular weight of PEI is preferably $0.75\cdot10^2$ to $10^7$ Da, preferably 1000 to $10^5$ Da, more preferably 10000 to 40000 Da, more preferably 15000 to 30000 Da, even more preferably 20000 to 25000 Da.

Preferred according to the present disclosure is linear polyalkyleneimine such as linear polyethyleneimine (PEI).

Cationic polymers (including polycationic polymers) contemplated for use herein include any cationic polymers which are able to electrostatically bind nucleic acid. In one embodiment, cationic polymers contemplated for use herein include any cationic polymers with which nucleic acid can be associated, e.g. by forming complexes with the nucleic acid or forming vesicles in which the nucleic acid is enclosed or encapsulated.

Particles described herein may also comprise polymers other than cationic polymers, i.e., non-cationic polymers and/or anionic polymers. Collectively, anionic and neutral polymers are referred to herein as non-cationic polymers.

Lipid and Lipid-Like Material

The terms "lipid" and "lipid-like material" are broadly defined herein as molecules which comprise one or more hydrophobic moieties or groups and optionally also one or more hydrophilic moieties or groups. Molecules comprising hydrophobic moieties and hydrophilic moieties are also frequently denoted as amphiphiles. Lipids are usually poorly soluble in water.

In an aqueous environment, the amphiphilic nature allows the molecules to self-assemble into organized structures and different phases. One of those phases consists of lipid bilayers, as they are present in vesicles, multilamellar/unilamellar liposomes, or membranes in an aqueous environment. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). The hydrophilic groups may comprise polar and/or charged groups and include carbohydrates, phosphate, carboxylic, sulfate, amino, sulfhydryl, nitro, hydroxyl, and other like groups.

As used herein, the term "amphiphilic" refers to a molecule having both a polar portion and a non-polar portion. Often, an amphiphilic compound has a polar head attached to a long hydrophobic tail. In some embodiments, the polar portion is soluble in water, while the non-polar portion is insoluble in water. In addition, the polar portion may have either a formal positive charge, or a formal negative charge. Alternatively, the polar portion may have both a formal positive and a negative charge, and be a zwitterion or inner salt. For purposes of the present disclosure, the amphiphilic compound can be, but is not limited to, one or a plurality of natural or non-natural lipids and lipid-like compounds.

The term "lipid-like material", "lipid-like compound" or "lipid-like molecule" relates to substances that structurally and/or functionally relate to lipids but may not be considered as lipids in a strict sense. For example, the term includes compounds that are able to form amphiphilic layers as they are present in vesicles, multilamellar/unilamellar liposomes, or membranes in an aqueous environment and includes surfactants, or synthesized compounds with both hydrophilic and hydrophobic moieties. Generally speaking, the term refers to molecules, which comprise hydrophilic and hydrophobic moieties with different structural organization, which may or may not be similar to that of lipids. As used herein, the term "lipid" is to be construed to cover both lipids and lipid-like materials unless otherwise indicated herein or clearly contradicted by context.

Specific examples of amphiphilic compounds that may be included in an amphiphilic layer include, but are not limited to, phospholipids, aminolipids and sphingolipids.

In certain embodiments, the amphiphilic compound is a lipid. The term "lipid" refers to a group of organic compounds that are characterized by being insoluble in water, but soluble in many organic solvents. Generally, lipids may be divided into eight categories: fatty acids, glycerolipids, glycerophospholipids, sphingolipids, saccharolipids, polyketides (derived from condensation of ketoacyl subunits), sterol lipids and prenol lipids (derived from condensation of isoprene subunits). Although the term "lipid" is sometimes used as a synonym for fats, fats are a subgroup of lipids called triglycerides. Lipids also encompass molecules such as fatty acids and their derivatives (including tri-, di-, monoglycerides, and phospholipids), as well as sterol-containing metabolites such as cholesterol.

Fatty acids, or fatty acid residues are a diverse group of molecules made of a hydrocarbon chain that terminates with a carboxylic acid group; this arrangement confers the molecule with a polar, hydrophilic end, and a nonpolar, hydrophobic end that is insoluble in water. The carbon chain, typically between four and 24 carbons long, may be saturated or unsaturated, and may be attached to functional groups containing oxygen, halogens, nitrogen, and sulfur. If a fatty acid contains a double bond, there is the possibility of either a cis or trans geometric isomerism, which significantly affects the molecule's configuration. Cis-double bonds cause the fatty acid chain to bend, an effect that is compounded with more double bonds in the chain. Other major lipid classes in the fatty acid category are the fatty esters and fatty amides. Glycerolipids are composed of mono-, di-, and tri-substituted glycerols, the best-known being the fatty acid triesters of glycerol, called triglycerides. The word "triacylglycerol" is sometimes used synonymously with "triglyceride". In these compounds, the three hydroxyl groups of glycerol are each esterified, typically by different fatty acids. Additional subclasses of glycerolipids are represented by glycosylglycerols, which are characterized by the presence of one or more sugar residues attached to glycerol via a glycosidic linkage.

The glycerophospholipids are amphipathic molecules (containing both hydrophobic and hydrophilic regions) that contain a glycerol core linked to two fatty acid-derived "tails" by ester linkages and to one "head" group by a phosphate ester linkage. Examples of glycerophospholipids, usually referred to as phospholipids (though sphingomyelins are also classified as phospholipids) are phosphatidylcholine (also known as PC, GPCho or lecithin), phosphatidylethanolamine (PE or GPEtn) and phosphatidylserine (PS or GPSer).

Sphingolipids are a complex family of compounds that share a common structural feature, a sphingoid base backbone. The major sphingoid base in mammals is commonly referred to as sphingosine. Ceramides (N-acyl-sphingoid bases) are a major subclass of sphingoid base derivatives with an amide-linked fatty acid. The fatty acids are typically saturated or mono-unsaturated with chain lengths from 16 to 26 carbon atoms. The major phosphosphingolipids of mammals are sphingomyelins (ceramide phosphocholines), whereas insects contain mainly ceramide phosphoethanolamines and fungi have phytoceramide phosphoinositols and mannose-containing headgroups. The glycosphingolipids are a diverse family of molecules composed of one or more sugar residues linked via a glycosidic bond to the sphingoid base. Examples of these are the simple and complex glycosphingolipids such as cerebrosides and gangliosides.

Sterol lipids, such as cholesterol and its derivatives, or tocopherol and its derivatives, are an important component of membrane lipids, along with the glycerophospholipids and sphingomyelins.

Saccharolipids describe compounds in which fatty acids are linked directly to a sugar backbone, forming structures that are compatible with membrane bilayers. In the saccharolipids, a monosaccharide substitutes for the glycerol backbone present in glycerolipids and glycerophospholipids. The most familiar saccharolipids are the acylated glucosamine precursors of the Lipid A component of the lipopolysaccharides in Gram-negative bacteria. Typical lipid A molecules are disaccharides of glucosamine, which are derivatized with as many as seven fatty-acyl chains. The minimal lipopolysaccharide required for growth in *E. coli* is Kdo2-Lipid A, a hexa-acylated disaccharide of glucosamine that is glycosylated with two 3-deoxy-D-manno-octulosonic acid (Kdo) residues.

Polyketides are synthesized by polymerization of acetyl and propionyl subunits by classic enzymes as well as iterative and multimodular enzymes that share mechanistic features with the fatty acid synthases. They comprise a large number of secondary metabolites and natural products from animal, plant, bacterial, fungal and marine sources, and have great structural diversity. Many polyketides are cyclic molecules whose backbones are often further modified by glycosylation, methylation, hydroxylation, oxidation, or other processes.

According to the present disclosure, lipids and lipid-like materials may be cationic, anionic or neutral. Neutral lipids or lipid-like materials exist in an uncharged or neutral zwitterionic form at a selected pH.

Cationic or Cationically Ionizable Lipids or Lipid-Like Materials

The nucleic acid particles described herein may comprise at least one cationic or cationically ionizable lipid or lipid-like material as particle forming agent. Cationic or cationically ionizable lipids or lipid-like materials contemplated for use herein include any cationic or cationically ionizable lipids or lipid-like materials which are able to electrostatically bind nucleic acid. In one embodiment, cationic or cationically ionizable lipids or lipid-like materials contemplated for use herein can be associated with nucleic acid, e.g.

by forming complexes with the nucleic acid or forming vesicles in which the nucleic acid is enclosed or encapsulated.

As used herein, a "cationic lipid" or "cationic lipid-like material" refers to a lipid or lipid-like material having a net positive charge. Cationic lipids or lipid-like materials bind negatively charged nucleic acid by electrostatic interaction. Generally, cationic lipids possess a lipophilic moiety, such as a sterol, an acyl chain, a diacyl or more acyl chains, and the head group of the lipid typically carries the positive charge.

In certain embodiments, a cationic lipid or lipid-like material has a net positive charge only at certain pH, in particular acidic pH, while it has preferably no net positive charge, preferably has no charge, i.e., it is neutral, at a different, preferably higher pH such as physiological pH. This ionizable behavior is thought to enhance efficacy through helping with endosomal escape and reducing toxicity as compared with particles that remain cationic at physiological pH.

For purposes of the present disclosure, such "cationically ionizable" lipids or lipid-like materials are comprised by the term "cationic lipid or lipid-like material" unless contradicted by the circumstances.

In one embodiment, the cationic or cationically ionizable lipid or lipid-like material comprises a head group which includes at least one nitrogen atom (N) which is positive charged or capable of being protonated.

Examples of cationic lipids include, but are not limited to 1,2-dioleoyl-3-trimethylammonium propane (DOTAP); N,N-dimethyl-2,3-dioleyloxypropylamine (DODMA), 1,2-di-O-octadecenyl-3-trimethylammonium propane (DOTMA), 3-(N—(N',N'-dimethylaminoethane)-carbamoyl)cholesterol (DC-Chol), dimethyldioctadecylammonium (DDAB); 1,2-dioleoyl-3-dimethylammonium-propane (DODAP); 1,2-diacyloxy-3-dimethylammonium propanes; 1,2-dialkyloxy-3-dimethylammonium propanes; dioctadecyldimethyl ammonium chloride (DODAC), 1,2-distearyloxy-N,N-dimethyl-3-aminopropane (DSDMA), 2,3-di(tetradecoxy)propyl-(2-hydroxyethyl)-dimethylazanium (DMRIE), 1,2-dimyristoyl-sn-glycero-3-ethylphosphocholine (DMEPC), I,2-dimyristoyl-3-trimethylammonium propane (DMTAP), 1,2-dioleyloxypropyl-3-dimethyl-hydroxyethyl ammonium bromide (DORIE), and 2,3-dioleoyloxy-N-[2(spermine carboxamide)ethyl]-N,N-dimethyl-I-propanamium trifluoroacetate (DOSPA), 1,2-dilinoleyloxy-N,N-dimethylaminopropane (DLinDMA), 1,2-dilinolenyloxy-N,N-dimethylaminopropane (DLenDMA), dioctadecylamidoglycyl spermine (DOGS), 3-dimethylamino-2-(cholest-5-en-3-beta-oxybutan-4-oxy)-1-(cis,cis-9, 12-oc-tadecadienoxy)propane (CLinDMA), 2-[5'-(cholest-5-en-3-beta-oxy)-3'-oxapentoxy)-3-dimethyl-1-(cis,cis-9', 12'-octadecadienoxy)propane (CpLinDMA), N,N-dimethyl-3,4-dioleyloxybenzylamine (DMOBA), 1,2-N,N'-dioleylcarbamyl-3-dimethylaminopropane (DOcarbDAP), 2,3-Dilinoleoyloxy-N,N-dimethylpropylamine (DLinDAP), 1,2-N,N'-Dilinoleylcarbamyl-3-dimethylaminopropane (DLincarbDAP), 1,2-Dilinoleoylcarbamyl-3-dimethylaminopropane (DLinCDAP), 2,2-dilinoleyl-4-dimethylaminomethyl-[1,3]-dioxolane (DLin-K-DMA), 2,2-dilinoleyl-4-dimethylaminoethyl-[1,3]-dioxolane (DLin-K-XTC2-DMA), 2,2-dilinoleyl-4-(2-dimethylaminoethyl)-[1,3]-dioxolane (DLin-KC2-DMA), heptatriaconta-6,9,28,31-tetraen-19-yl-4-(dimethylamino)butanoate (DLin-MC3-DMA), N-(2-Hydroxyethyl)-N,N-dimethyl-2,3-bis(tetradecyloxy)-1-propanaminium bromide (DMRIE), (±)-N-(3-aminopropyl)-N,N-dimethyl-2,3-bis(cis-9-tetradecenyloxy)-1-propanaminium bromide (GAP-DMORIE), (±)-N-(3-aminopropyl)-N,N-dimethyl-2,3-bis(dodecyloxy)-1-propanaminium bromide (GAP-DLRIE), (±)-N-(3-aminopropyl)-N,N-dimethyl-2,3-bis(tetradecyloxy)-1-propanaminium bromide (GAP-DMRIE), N-(2-Aminoethyl)-N,N-dimethyl-2,3-bis(tetradecyloxy)-1-propanaminium bromide (B3AE-DMRIE), N-(4-carboxybenzyl)-N,N-dimethyl-2,3-bis(oleoyloxy)propan-1-aminium (DOBAQ), 2-({8-[(3β)-cholest-5-en-3-yloxy]octyl}oxy)-N,N-dimethyl-3-[(9Z,12Z)-octadeca-9,12-dien-1-yloxy]propan-1-amine (Octyl-CLinDMA), 1,2-dimyristoyl-3-dimethylammonium-propane (DMDAP), 1,2-dipalmitoyl-3-dimethylammonium-propane (DPDAP), N1-[2-((1S)-1-[(3-aminopropyl)amino]-4-[di(3-amino-propyl)amino]butylcarboxamido)ethyl]-3,4-di[oleyloxy]-benzamide (MVLS), 1,2-dioleoyl-sn-glycero-3-ethylphosphocholine (DOEPC), 2,3-bis(dodecyloxy)-N-(2-hydroxyethyl)-N,N-dimethylpropan-1-ammonium bromide (DLRIE), N-(2-aminoethyl)-N,N-dimethyl-2,3-bis(tetradecyloxy)propan-1-aminium bromide (DMORIE), di((Z)-non-2-en-1-yl) 8,8'-((((2(dimethylamino)ethyl)thio)carbonyl)azanediyl)dioctanoate (ATX), N,N-dimethyl-2,3-bis(dodecyloxy)propan-1-amine (DLDMA), N,N-dimethyl-2,3-bis(tetradecyloxy)propan-1-amine (DMDMA), Di((Z)-non-2-en-1-yl)-9-((4-(dimethylaminobutanoyl)oxy)heptadecanedioate (L319), N-Dodecyl-3-((2-dodecylcarbamoyl-ethyl)-{2-[(2-dodecylcarbamoyl-ethyl)-2-{(2-dodecylcarbamoyl-ethyl)-[2-(2-dodecylcarbamoyl-ethylamino)-ethyl]-amino}-ethylamino)propionamide (lipidoid 98N2-5), 1-[2-[bis(2-hydroxydodecyl)amino]ethyl-[2-[4-[2-[bis(2 hydroxydodecyl)amino]ethyl]piperazin-1-yl]ethyl]amino]dodecan-2-ol (lipidoid C12-200).

In some embodiments, the cationic lipid may comprise from about 10 mol % to about 100 mol %, about 20 mol % to about 100 mol %, about 30 mol % to about 100 mol %, about 40 mol % to about 100 mol %, or about 50 mol % to about 100 mol % of the total lipid present in the particle.

Additional Lipids or Lipid-Like Materials

Particles described herein may also comprise lipids or lipid-like materials other than cationic or cationically ionizable lipids or lipid-like materials, i.e., non-cationic lipids or lipid-like materials (including non-cationically ionizable lipids or lipid-like materials). Collectively, anionic and neutral lipids or lipid-like materials are referred to herein as non-cationic lipids or lipid-like materials. Optimizing the formulation of nucleic acid particles by addition of other hydrophobic moieties, such as cholesterol and lipids, in addition to an ionizable/cationic lipid or lipid-like material may enhance particle stability and efficacy of nucleic acid delivery.

An additional lipid or lipid-like material may be incorporated which may or may not affect the overall charge of the nucleic acid particles. In certain embodiments, the additional lipid or lipid-like material is a non-cationic lipid or lipid-like material. The non-cationic lipid may comprise, e.g., one or more anionic lipids and/or neutral lipids. As used herein, an "anionic lipid" refers to any lipid that is negatively charged at a selected pH. As used herein, a "neutral lipid" refers to any of a number of lipid species that exist either in an uncharged or neutral zwitterionic form at a selected pH. In preferred embodiments, the additional lipid comprises one of the following neutral lipid components: (1) a phospholipid, (2) cholesterol or a derivative thereof; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, tocopherol and derivatives thereof, and mixtures thereof.

Specific phospholipids that can be used include, but are not limited to, phosphatidylcholines, phosphatidylethanolamines, phosphatidylglycerols, phosphatidic acids, phosphatidylserines or sphingomyelin. Such phospholipids include in particular diacylphosphatidylcholines, such as distearoylphosphatidylcholine (DSPC), dioleoylphosphatidylcholine (DOPC), dimyristoylphosphatidylcholine (DMPC), dipentadecanoylphosphatidylcholine, dilauroylphosphatidylcholine, dipalmitoylphosphatidylcholine (DPPC), diarachidoylphosphatidylcholine (DAPC), dibehenoylphosphatidylcholine (DBPC), ditricosanoylphosphatidylcholine (DTPC), dilignoceroylphatidylcholine (DLPC), palmitoyloleoyl-phosphatidylcholine (POPC), 1,2-di-O-octadecenyl-sn-glycero-3-phosphocholine (18:0 Diether PC), 1-oleoyl-2-cholesterylhemisuccinoyl-sn-glycero-3-phosphocholine (OChemsPC), 1-hexadecyl-sn-glycero-3-phosphocholine (C16 Lyso PC) and phosphatidylethanolamines, in particular diacylphosphatidylethanolamines, such as dioleoylphosphatidylethanolamine (DOPE), distearoyl-phosphatidylethanolamine (DSPE), dipalmitoyl-phosphatidylethanolamine (DPPE), dimyristoyl-phosphatidylethanolamine (DMPE), dilauroyl-phosphatidylethanolamine (DLPE), diphytanoyl-phosphatidylethanolamine (DPyPE), and further phosphatidylethanolamine lipids with different hydrophobic chains.

In certain preferred embodiments, the additional lipid is DSPC or DSPC and cholesterol.

In certain embodiments, the nucleic acid particles include both a cationic lipid and an additional lipid.

In one embodiment, particles described herein include a polymer conjugated lipid such as a pegylated lipid. The term "pegylated lipid" refers to a molecule comprising both a lipid portion and a polyethylene glycol portion. Pegylated lipids are known in the art.

Without wishing to be bound by theory, the amount of the at least one cationic lipid compared to the amount of the at least one additional lipid may affect important nucleic acid particle characteristics, such as charge, particle size, stability, tissue selectivity, and bioactivity of the nucleic acid. Accordingly, in some embodiments, the molar ratio of the at least one cationic lipid to the at least one additional lipid is from about 10:0 to about 1:9, about 4:1 to about 1:2, or about 3:1 to about 1:1.

In some embodiments, the non-cationic lipid, in particular neutral lipid, (e.g., one or more phospholipids and/or cholesterol) may comprise from about 0 mol % to about 90 mol %, from about 0 mol % to about 80 mol %, from about 0 mol % to about 70 mol %, from about 0 mol % to about 60 mol %, or from about 0 mol % to about 50 mol %, of the total lipid present in the particle.

Lipoplex Particles

In certain embodiments of the present disclosure, the RNA described herein may be present in RNA lipoplex particles.

In the context of the present disclosure, the term "RNA lipoplex particle" relates to a particle that contains lipid, in particular cationic lipid, and RNA. Electrostatic interactions between positively charged liposomes and negatively charged RNA results in complexation and spontaneous formation of RNA lipoplex particles. Positively charged liposomes may be generally synthesized using a cationic lipid, such as DOTMA, and additional lipids, such as DOPE. In one embodiment, a RNA lipoplex particle is a nanoparticle.

In certain embodiments, the RNA lipoplex particles include both a cationic lipid and an additional lipid. In an exemplary embodiment, the cationic lipid is DOTMA and the additional lipid is DOPE.

In some embodiments, the molar ratio of the at least one cationic lipid to the at least one additional lipid is from about 10:0 to about 1:9, about 4:1 to about 1:2, or about 3:1 to about 1:1. In specific embodiments, the molar ratio may be about 3:1, about 2.75:1, about 2.5:1, about 2.25:1, about 2:1, about 1.75:1, about 1.5:1, about 1.25:1, or about 1:1. In an exemplary embodiment, the molar ratio of the at least one cationic lipid to the at least one additional lipid is about 2:1.

RNA lipoplex particles described herein have an average diameter that in one embodiment ranges from about 200 nm to about 1000 nm, from about 200 nm to about 800 nm, from about 250 to about 700 nm, from about 400 to about 600 nm, from about 300 nm to about 500 nm, or from about 350 nm to about 400 nm. In specific embodiments, the RNA lipoplex particles have an average diameter of about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 700 nm, about 725 nm, about 750 nm, about 775 nm, about 800 nm, about 825 nm, about 850 nm, about 875 nm, about 900 nm, about 925 nm, about 950 nm, about 975 nm, or about 1000 nm. In an embodiment, the RNA lipoplex particles have an average diameter that ranges from about 250 nm to about 700 nm. In another embodiment, the RNA lipoplex particles have an average diameter that ranges from about 300 nm to about 500 nm. In an exemplary embodiment, the RNA lipoplex particles have an average diameter of about 400 nm.

The RNA lipoplex particles and compositions comprising RNA lipoplex particles described herein are useful for delivery of RNA to a target tissue after parenteral administration, in particular after intravenous administration. The RNA lipoplex particles may be prepared using liposomes that may be obtained by injecting a solution of the lipids in ethanol into water or a suitable aqueous phase. In one embodiment, the aqueous phase has an acidic pH. In one embodiment, the aqueous phase comprises acetic acid, e.g., in an amount of about 5 mM. Liposomes may be used for preparing RNA lipoplex particles by mixing the liposomes with RNA. In one embodiment, the liposomes and RNA lipoplex particles comprise at least one cationic lipid and at least one additional lipid. In one embodiment, the at least one cationic lipid comprises 1,2-di-O-octadecenyl-3-trimethylammonium propane (DOTMA) and/or 1,2-dioleoyl-3-trimethylammonium-propane (DOTAP). In one embodiment, the at least one additional lipid comprises 1,2-di-(9Z-octadecenoyl)-sn-glycero-3-phosphoethanolamine (DOPE), cholesterol (Chol) and/or 1,2-dioleoyl-sn-glycero-3-phosphocholine (DOPC). In one embodiment, the at least one cationic lipid comprises 1,2-di-O-octadecenyl-3-trimethylammonium propane (DOTMA) and the at least one additional lipid comprises 1,2-di-(9Z-octadecenoyl)-sn-glycero-3-phosphoethanolamine (DOPE). In one embodiment, the liposomes and RNA lipoplex particles comprise 1,2-di-O-octadecenyl-3-trimethylammonium propane (DOTMA) and 1,2-di-(9Z-octadecenoyl)-sn-glycero-3-phosphoethanolamine (DOPE). Spleen targeting RNA lipoplex particles are described in WO 2013/143683, herein incorporated by reference. It has been found that RNA lipoplex particles having a net negative charge may be used to preferentially target spleen tissue or spleen cells such as antigen-presenting cells, in particular dendritic cells. Accordingly, following administration of the RNA lipoplex particles, RNA accumulation and/or RNA expression in the spleen occurs. Thus, RNA lipoplex particles of the present disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the present disclosure may be used for expressing RNA in such antigen presenting cells. In one embodiment, the antigen presenting cells are dendritic cells and/or macrophages.

Lipid Nanoparticles (LNPs)

In one embodiment, nucleic acid such as RNA described herein is administered in the form of lipid nanoparticles (LNPs). The LNP may comprise any lipid capable of forming a particle to which the one or more nucleic acid molecules are attached, or in which the one or more nucleic acid molecules are encapsulated.

In one embodiment, the LNP comprises one or more cationic lipids, and one or more stabilizing lipids. Stabilizing lipids include neutral lipids and pegylated lipids.

In one embodiment, the LNP comprises a cationic lipid, a neutral lipid, a steroid, a polymer conjugated lipid; and the RNA, encapsulated within or associated with the lipid nanoparticle. In one embodiment, the LNP comprises from 40 to 55 mol percent, from 40 to 50 mol percent, from 41 to 49 mol percent, from 41 to 48 mol percent, from 42 to 48 mol percent, from 43 to 48 mol percent, from 44 to 48 mol percent, from 45 to 48 mol percent, from 46 to 48 mol percent, from 47 to 48 mol percent, or from 47.2 to 47.8 mol percent of the cationic lipid. In one embodiment, the LNP comprises about 47.0, 47.1, 47.2, 47.3, 47.4, 47.5, 47.6, 47.7, 47.8, 47.9 or 48.0 mol percent of the cationic lipid.

In one embodiment, the neutral lipid is present in a concentration ranging from 5 to 15 mol percent, from 7 to 13 mol percent, or from 9 to 11 mol percent. In one embodiment, the neutral lipid is present in a concentration of about 9.5, 10 or 10.5 mol percent.

In one embodiment, the steroid is present in a concentration ranging from 30 to 50 mol percent, from 35 to 45 mol percent or from 38 to 43 mol percent. In one embodiment, the steroid is present in a concentration of about 40, 41, 42, 43, 44, 45 or 46 mol percent.

In one embodiment, the LNP comprises from 1 to 10 mol percent, from 1 to 5 mol percent, or from 1 to 2.5 mol percent of the polymer conjugated lipid.

In one embodiment, the LNP comprises from 40 to 50 mol percent a cationic lipid; from 5 to 15 mol percent of a neutral lipid; from 35 to 45 mol percent of a steroid; from 1 to 10 mol percent of a polymer conjugated lipid; and the RNA, encapsulated within or associated with the lipid nanoparticle.

In one embodiment, the mol percent is determined based on total mol of lipid present in the lipid nanoparticle.

In one embodiment, the neutral lipid is selected from the group consisting of DSPC, DPPC, DMPC, DOPC, POPC, DOPE, DOPG, DPPG, POPE, DPPE, DMPE, DSPE, and SM. In one embodiment, the neutral lipid is selected from the group consisting of DSPC, DPPC, DMPC, DOPC, POPC, DOPE and SM. In one embodiment, the neutral lipid is DSPC.

In one embodiment, the steroid is cholesterol.

In one embodiment, the polymer conjugated lipid is a pegylated lipid. In one embodiment, the pegylated lipid has the following structure:

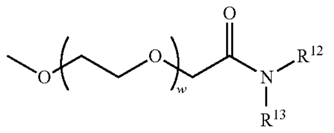

or a pharmaceutically acceptable salt, tautomer or stereoisomer thereof, wherein:

$R^{12}$ and $R^{13}$ are each independently a straight or branched, saturated or unsaturated alkyl chain containing from 10 to 30 carbon atoms, wherein the alkyl chain is optionally interrupted by one or more ester bonds; and w has a mean value ranging from 30 to 60. In one embodiment, $R^{12}$ and $R^{13}$ are each independently straight, saturated alkyl chains containing from 12 to 16 carbon atoms. In one embodiment, w has a mean value ranging from 40 to 55. In one embodiment, the average w is about 45. In one embodiment, $R^{12}$ and $R^{13}$ are each independently a straight, saturated alkyl chain containing about 14 carbon atoms, and w has a mean value of about 45.

In one embodiment, the pegylated lipid is DMG-PEG 2000, e.g., having the following structure:

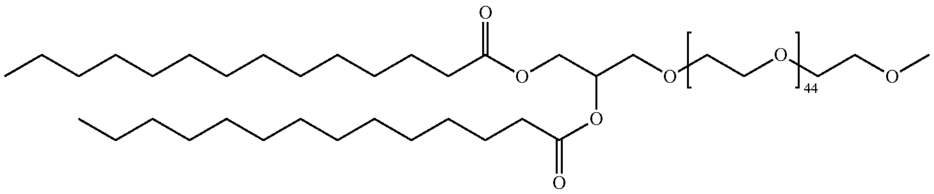

In some embodiments, the cationic lipid component of the LNPs has the structure of Formula (III):

(III)

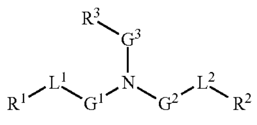

or a pharmaceutically acceptable salt, tautomer, prodrug or stereoisomer thereof, wherein:

one of $L^1$ or $L^2$ is —O(C═O)—, —(C═O)O—, —C(═O)—, —O—, —S(O)$_x$—, —S—S—,

—C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O—, and the other of $L^1$ or $L^2$ is —O(C═O)—, —(C═O)O—, —C(═O)—, —O—, —S(O)$_x$—, —S—S—, —C(═O)S—, SC(═O)—, —NR$^a$C(═O)—, —C(═O)NR$^a$—, NR$^a$C(═O)NR$^a$—, —OC(═O)NR$^a$— or —NR$^a$C(═O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, $OR^5$, CN, —C(═O)OR$^4$, —OC(═O)R$^4$ or —NR$^5$C(═O)R$^4$;

$R^4$ is $C_1$-$C_{12}$ alkyl;

$R^5$ is H or $C_1$-$C_6$ alkyl; and x is 0, 1 or 2.

In some of the foregoing embodiments of Formula (III), the lipid has one of the following structures (IIIA) or (IIIB):

(IIIA)

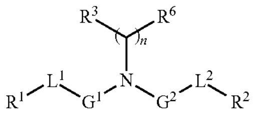

or (IIIB)

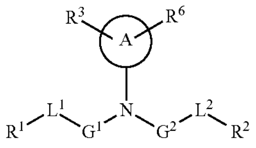

wherein:

A is a 3 to 8-membered cycloalkyl or cycloalkylene ring;

$R^6$ is, at each occurrence, independently H, OH or $C_1$-$C_{24}$ alkyl;

n is an integer ranging from 1 to 15.

In some of the foregoing embodiments of Formula (III), the lipid has structure (IIIA), and in other embodiments, the lipid has structure (IIIB).

In other embodiments of Formula (III), the lipid has one of the following structures (IIIC) or (IIID):

(IIIC)

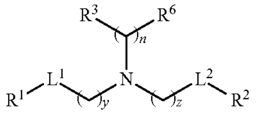

or (IIID)

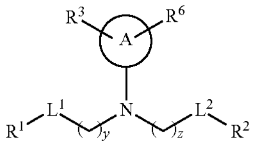

wherein y and z are each independently integers ranging from 1 to 12.

In any of the foregoing embodiments of Formula (III), one of $L^1$ or $L^2$ is —O(C═O)—. For example, in some embodiments each of L1 and $L^2$ are —O(C═O)—. In some different embodiments of any of the foregoing, $L^1$ and L2 are each independently —(C═O)O— or —O(C═O)—. For example, in some embodiments each of L1 and $L^2$ is —(C═O)O—.

In some different embodiments of Formula (III), the lipid has one of the following structures (IIIE) or (IIIF):

(IIIE)

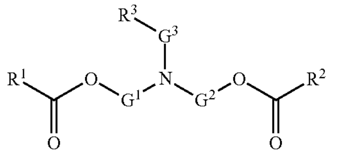

or (IIIF)

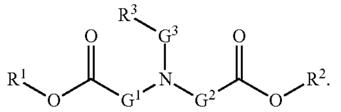

In some of the foregoing embodiments of Formula (III), the lipid has one of the following structures (IIIG), (IIIH), (IIII), or (IIIJ):

(IIIG)

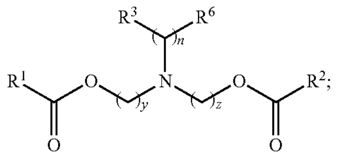

(IIIH)

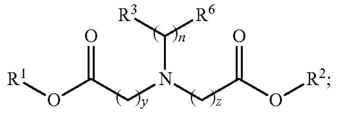

(IIII)

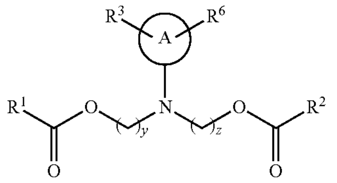

or (IIIJ)

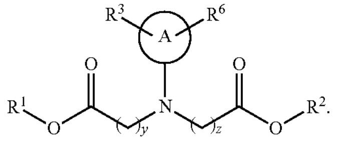

In some of the foregoing embodiments of Formula (III), n is an integer ranging from 2 to 12, for example from 2 to 8 or from 2 to 4. For example, in some embodiments, n is 3, 4, 5 or 6. In some embodiments, n is 3. In some embodiments, n is 4. In some embodiments, n is 5. In some embodiments, n is 6.

In some other of the foregoing embodiments of Formula (III), y and z are each independently an integer ranging from 2 to 10. For example, in some embodiments, y and z are each independently an integer ranging from 4 to 9 or from 4 to 6.

In some of the foregoing embodiments of Formula (III), $R^6$ is H. In other of the foregoing embodiments, $R^6$ is $C_1$-$C_{24}$ alkyl. In other embodiments, $R^6$ is OH.

In some embodiments of Formula (III), $G^3$ is unsubstituted. In other embodiments, G3 is substituted. In various different embodiments, $G^3$ is linear $C_1$-$C_{24}$ alkylene or linear $C_1$-$C_{24}$ alkenylene.

In some other foregoing embodiments of Formula (III), R1 or $R^2$, or both, is $C_6$-$C_{24}$ alkenyl. For example, in some embodiments, $R^1$ and $R^2$ each, independently have the following structure:

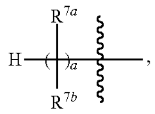

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of Formula (III), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of Formula (III), $R^1$ or $R^2$, or both, has one of the following structures:

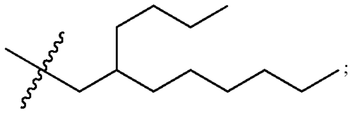

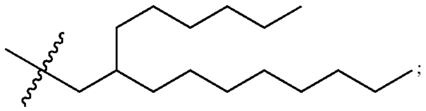

-continued

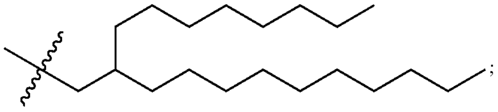

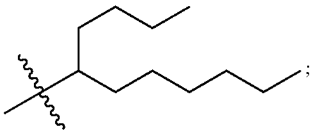

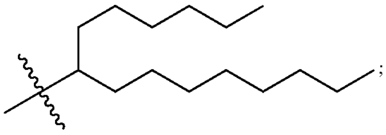

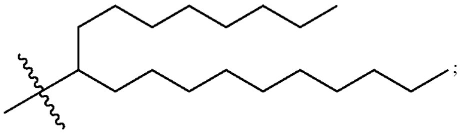

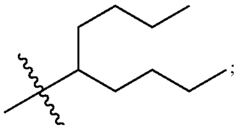

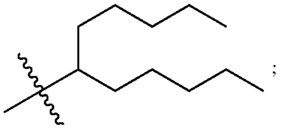

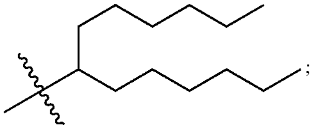

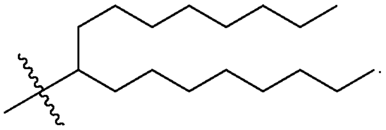

In some of the foregoing embodiments of Formula (III), $R^3$ is OH, CN, —C(=O)OR$^4$, —OC(=O)R$^4$ or —NHC(=O)R$^4$. In some embodiments, $R^4$ is methyl or ethyl.

In various different embodiments, the cationic lipid of Formula (III) has one of the structures set forth in the table below.

TABLE 17

Representative Compounds of Formula (III).

| No. | Structure |
|---|---|
| III-1 | 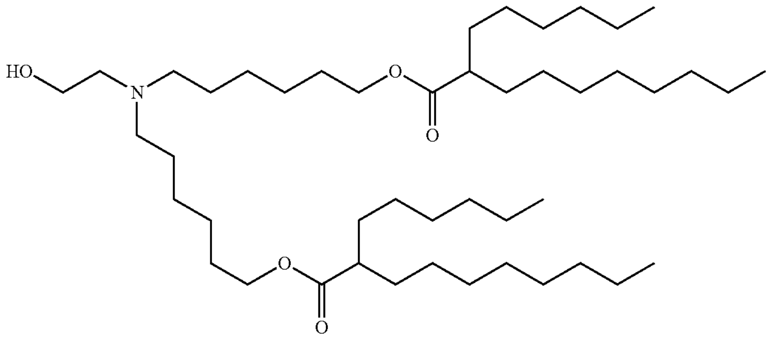 [SMILES: CCCCCCCCC(CCCCCC)C(=O)OCCCCCCN(CCO)CCCCCCOC(=O)C(CCCCCC)CCCCCCCC] |

TABLE 17-continued
| Representative Compounds of Formula (III). | |
|---|---|
| No. | Structure |
| III-2 | 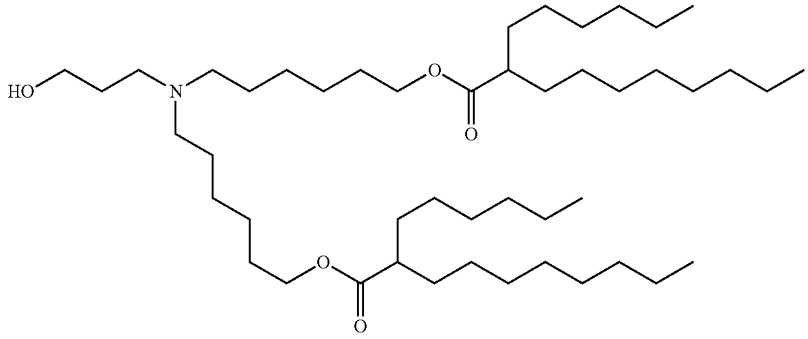 [SMILES: CCCCCCCCC(CCCCCC)C(=O)OCCCCCCN(CCCO)CCCCCCOC(=O)C(CCCCCC)CCCCCCCC] |
| III-3 | 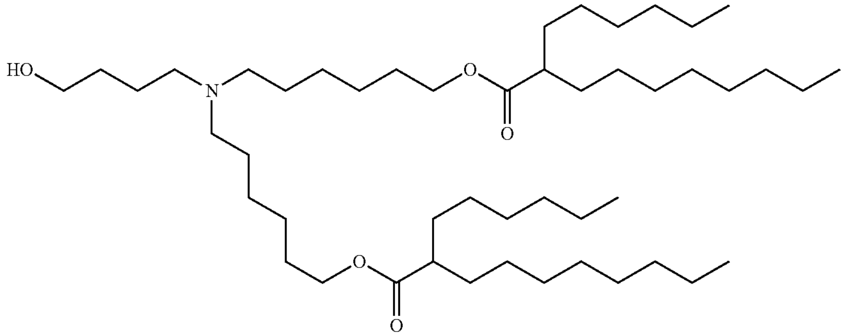 [SMILES: CCCCCCCCC(CCCCCC)C(=O)OCCCCCCN(CCCCO)CCCCCCOC(=O)C(CCCCCC)CCCCCCCC] |
| III-4 | 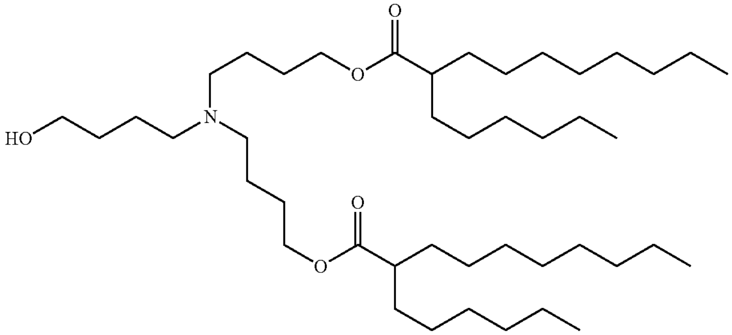 [SMILES: CCCCCCCCC(CCCCCC)C(=O)OCCCCN(CCCCO)CCCCOC(=O)C(CCCCCC)CCCCCCCC] |
| III-5 | 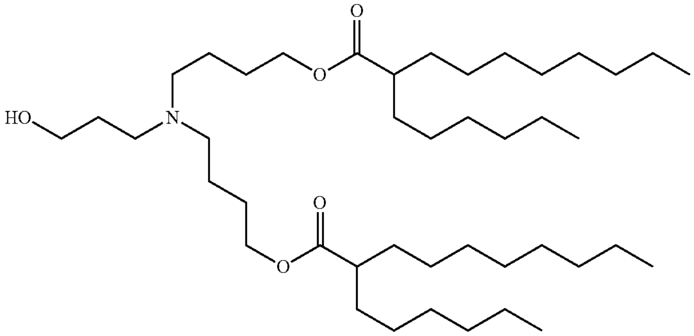 [SMILES: CCCCCCCCC(CCCCCC)C(=O)OCCCCN(CCCO)CCCCOC(=O)C(CCCCCC)CCCCCCCC] |

TABLE 17-continued
| Representative Compounds of Formula (III). | |
|---|---|
| No. | Structure |
| III-6 | 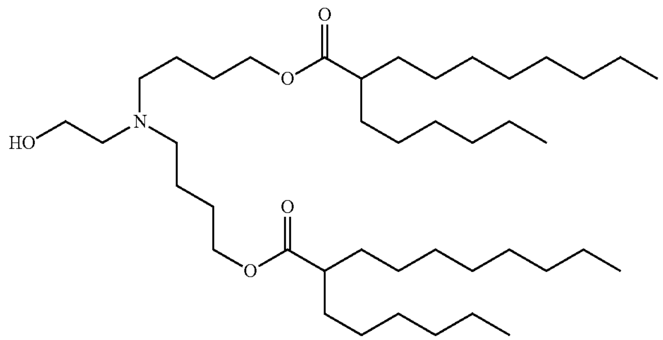 [SMILES: CCCCCCCCC(CCCCCC)C(=O)OCCCCN(CCO)CCCCOC(=O)C(CCCCCC)CCCCCCCC] |
| III-7 | 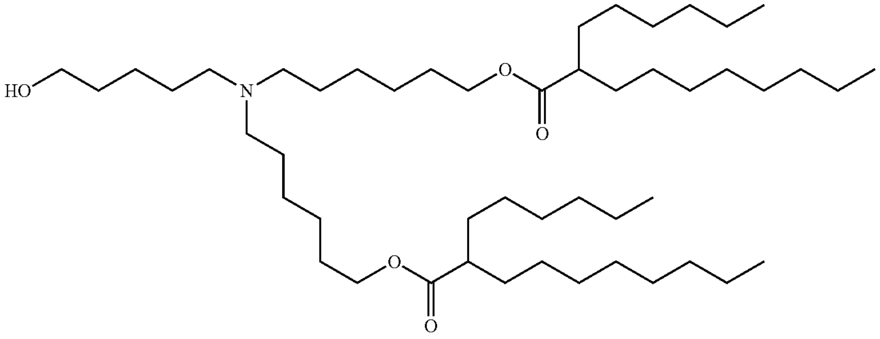 [SMILES: CCCCCCCCC(CCCCCC)C(=O)OCCCCCCN(CCCCCO)CCCCCCOC(=O)C(CCCCCC)CCCCCCCC] |
| III-8 | 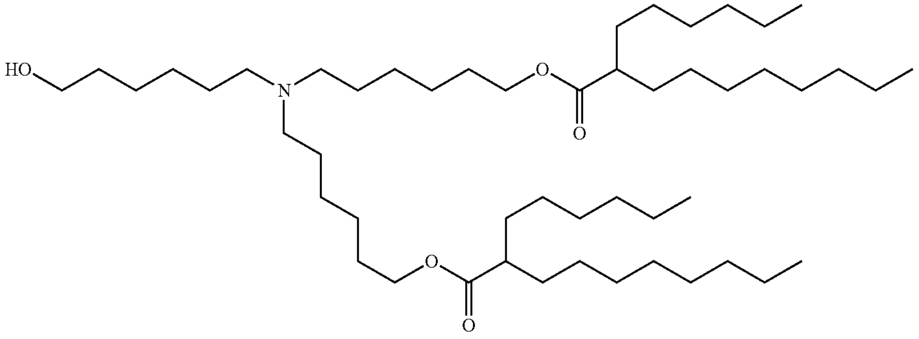 [SMILES: CCCCCCCCC(CCCCCC)C(=O)OCCCCCCN(CCCCCCO)CCCCCCOC(=O)C(CCCCCC)CCCCCCCC] |
| III-9 | 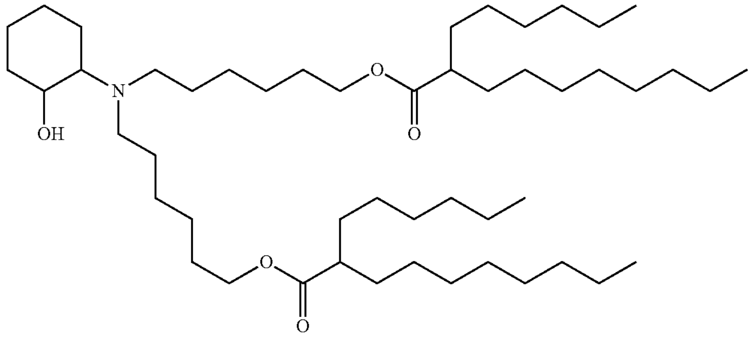 [SMILES: CCCCCCCCC(CCCCCC)C(=O)OCCCCCCN(CCCCCCOC(=O)C(CCCCCC)CCCCCCCC)C1CCCCC1O] |

TABLE 17-continued
| Representative Compounds of Formula (III). | |
|---|---|
| No. | Structure |
| III-10 | 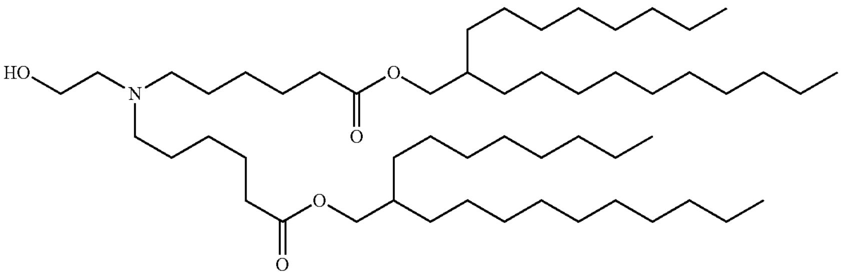 [SMILES: CCCCCCCCCCC(CCCCCCCC)COC(=O)CCCCCN(CCO)CCCCCC(=O)OCC(CCCCCCCC)CCCCCCCCCC] |
| III-11 | 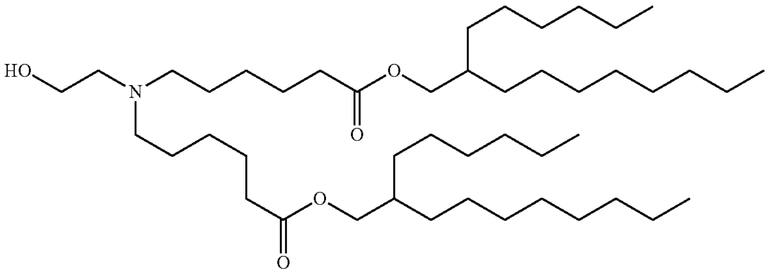 [SMILES: CCCCCCCCC(CCCCCC)COC(=O)CCCCCN(CCO)CCCCCC(=O)OCC(CCCCCC)CCCCCCCC] |
| III-12 | 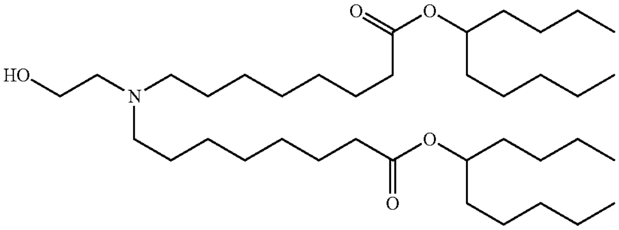 [SMILES: CCCCCC(CCCC)OC(=O)CCCCCCCN(CCO)CCCCCCCC(=O)OC(CCCC)CCCCC] |
| III-13 | 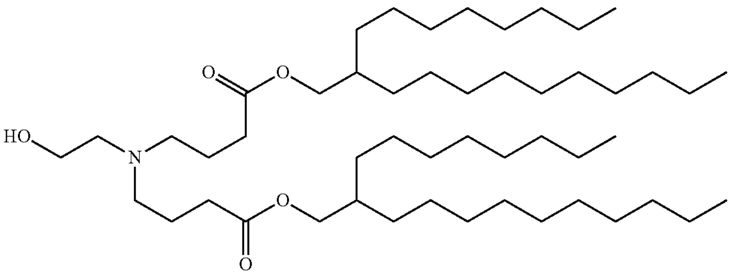 [SMILES: CCCCCCCCCCC(CCCCCCCC)COC(=O)CCCN(CCO)CCCC(=O)OCC(CCCCCCCC)CCCCCCCCCC] |
| III-14 | 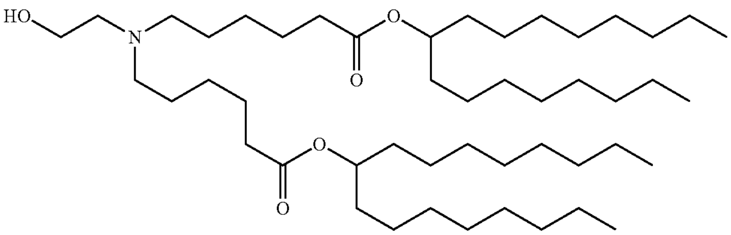 [SMILES: CCCCCCCCC(CCCCCCCC)OC(=O)CCCCCN(CCO)CCCCCC(=O)OC(CCCCCCCC)CCCCCCCC] |

TABLE 17-continued
| Representative Compounds of Formula (III). | |
|---|---|
| No. | Structure |
| III-15 | 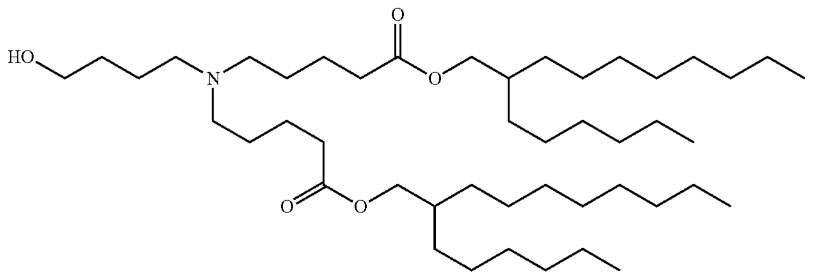 [SMILES: CCCCCCCCC(CCCCCC)COC(=O)CCCCN(CCCCO)CCCCC(=O)OCC(CCCCCC)CCCCCCCC] |
| III-16 | 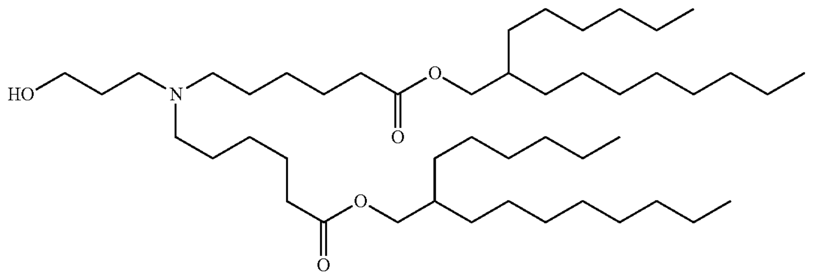 [SMILES: CCCCCCCCC(CCCCCC)COC(=O)CCCCCN(CCCO)CCCCCC(=O)OCC(CCCCCC)CCCCCCCC] |
| III-17 | 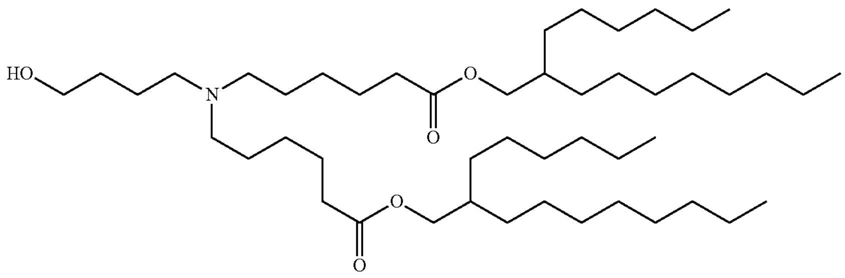 [SMILES: CCCCCCCCC(CCCCCC)COC(=O)CCCCCN(CCCCO)CCCCCC(=O)OCC(CCCCCC)CCCCCCCC] |
| III-18 | 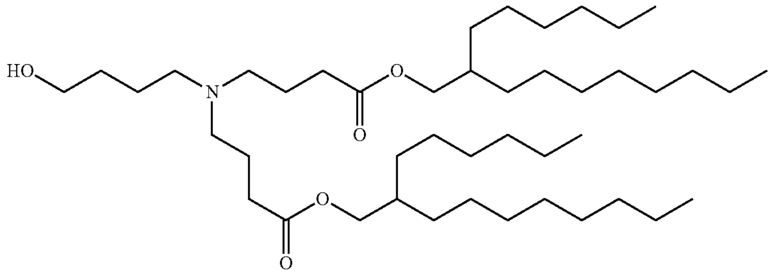 [SMILES: CCCCCCCCC(CCCCCC)COC(=O)CCCN(CCCCO)CCCC(=O)OCC(CCCCCC)CCCCCCCC] |
| III-19 | 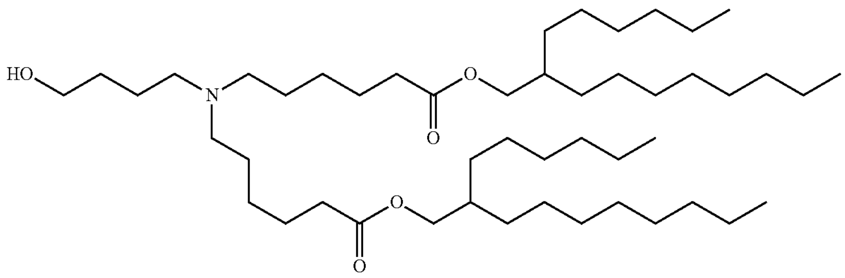 [SMILES: CCCCCCCCC(CCCCCC)COC(=O)CCCCCN(CCCCO)CCCCCC(=O)OCC(CCCCCC)CCCCCCCC] |

TABLE 17-continued
| Representative Compounds of Formula (III). | |
|---|---|
| No. | Structure |
| III-20 | 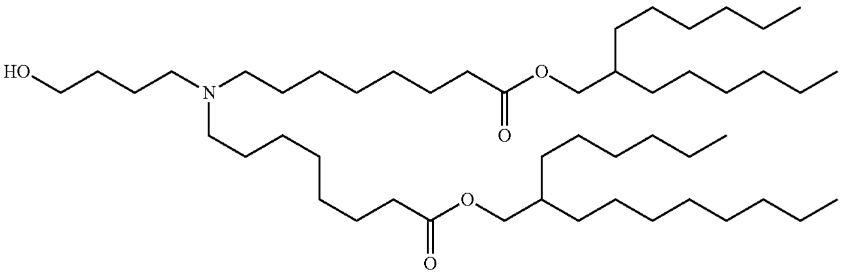 [SMILES: CCCCCCCCC(CCCCCC)COC(=O)CCCCCCCN(CCCCO)CCCCCCCC(=O)OCC(CCCCCC)CCCCCC] |
| III-21 | 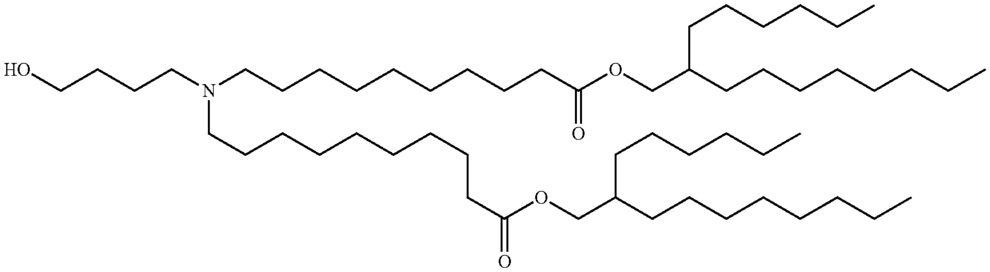 [SMILES: CCCCCCCCC(CCCCCC)COC(=O)CCCCCCCCCN(CCCCO)CCCCCCCCCC(=O)OCC(CCCCCC)CCCCCCCC] |
| III-22 | 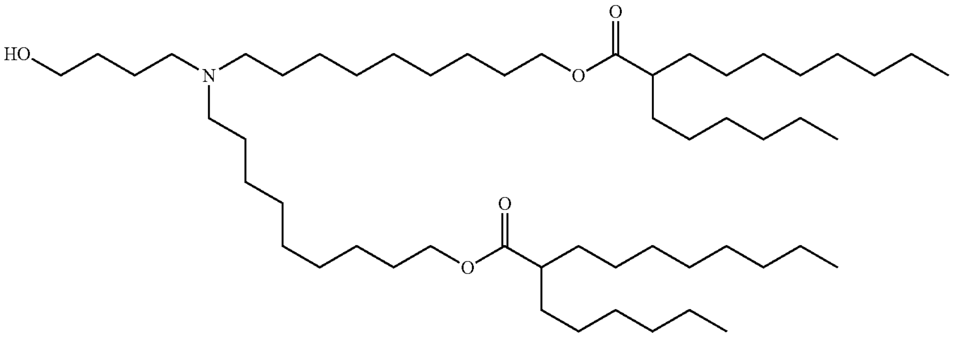 [SMILES: CCCCCCCCC(CCCCCC)C(=O)OCCCCCCCCCN(CCCCO)CCCCCCCCCOC(=O)C(CCCCCC)CCCCCCCC] |
| III-23 | 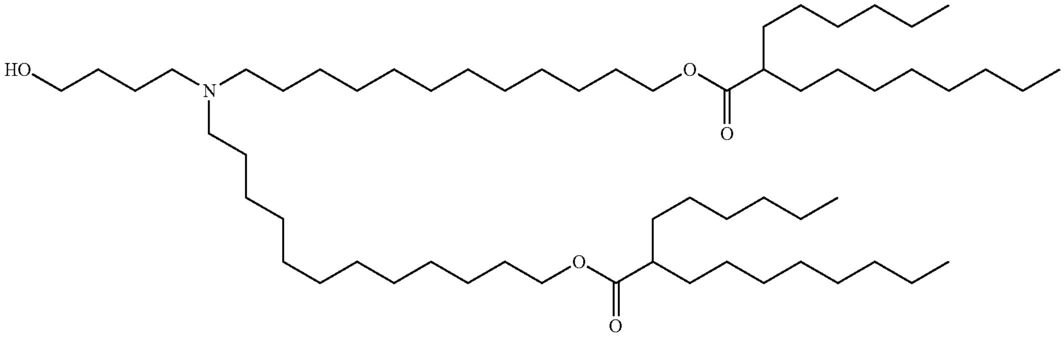 [SMILES: CCCCCCCCC(CCCCCC)C(=O)OCCCCCCCCCCCCN(CCCCO)CCCCCCCCCCCCOC(=O)C(CCCCCC)CCCCCCCC] |

TABLE 17-continued
| Representative Compounds of Formula (III). | |
|---|---|
| No. | Structure |
| III-24 | 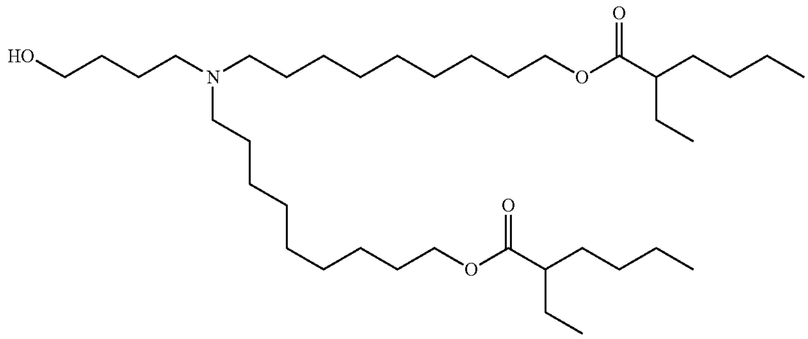 [SMILES: CCCCC(CC)C(=O)OCCCCCCCCCN(CCCCO)CCCCCCCCCOC(=O)C(CC)CCCC] |
| III-25 | 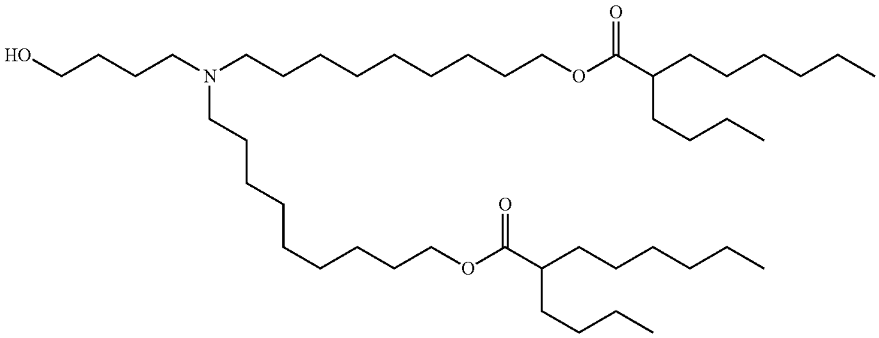 [SMILES: CCCCCCC(CCCC)C(=O)OCCCCCCCCCN(CCCCO)CCCCCCCCCOC(=O)C(CCCC)CCCCCC] |
| III-26 | 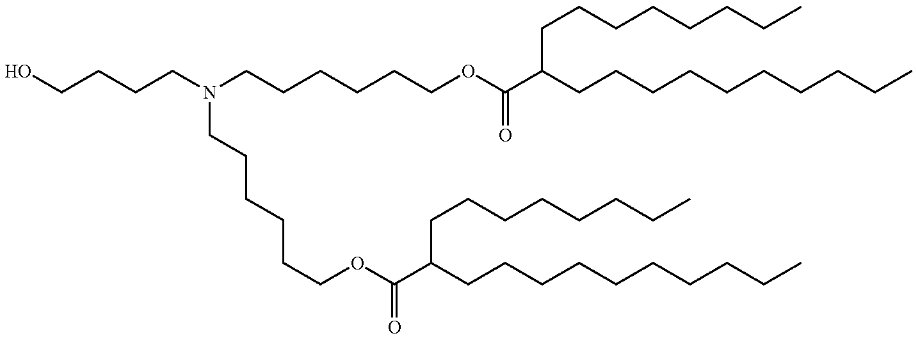 [SMILES: CCCCCCCCCCC(CCCCCCCC)C(=O)OCCCCCCN(CCCCO)CCCCCCOC(=O)C(CCCCCCCC)CCCCCCCCCC] |
| III-27 | 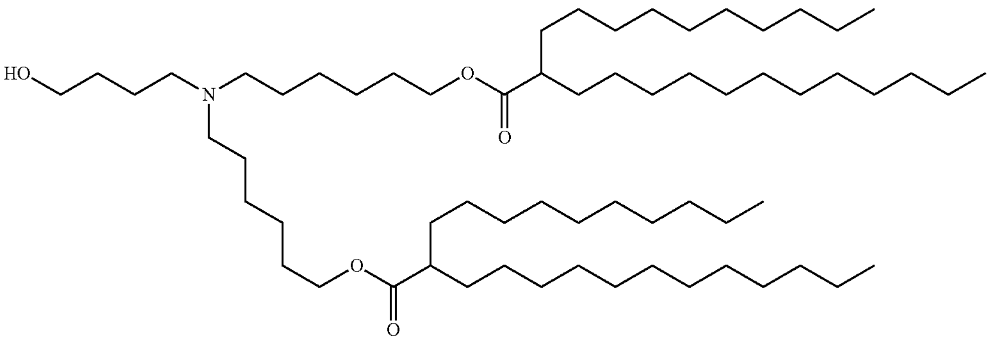 [SMILES: CCCCCCCCCCCCC(CCCCCCCCCC)C(=O)OCCCCCCN(CCCCO)CCCCCCOC(=O)C(CCCCCCCCCC)CCCCCCCCCCCC] |

TABLE 17-continued
| Representative Compounds of Formula (III). | |
|---|---|
| No. | Structure |
| III-28 | 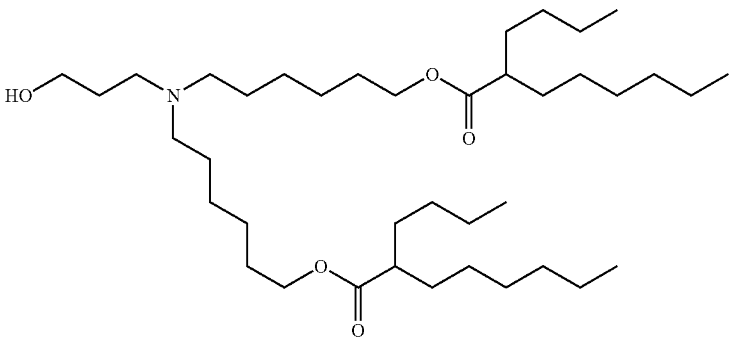 [SMILES: CCCCCCC(CCCC)C(=O)OCCCCCCN(CCCO)CCCCCCOC(=O)C(CCCC)CCCCCC] |
| III-29 | 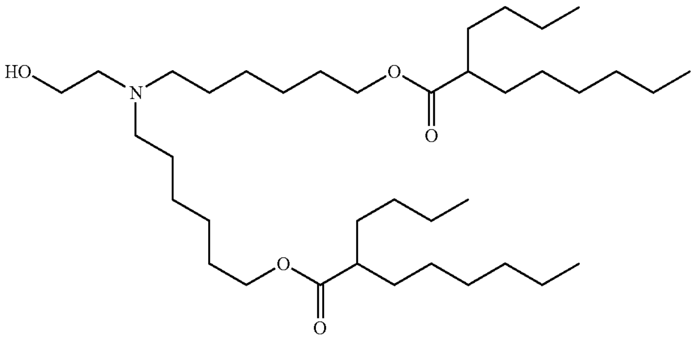 [SMILES: CCCCCCC(CCCC)C(=O)OCCCCCCN(CCO)CCCCCCOC(=O)C(CCCC)CCCCCC] |
| III-30 | 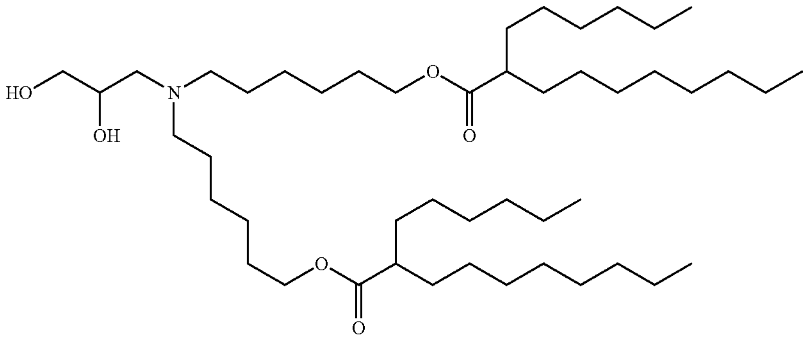 [SMILES: CCCCCCCCC(CCCCCC)C(=O)OCCCCCCN(CCCCCCOC(=O)C(CCCCCC)CCCCCCCC)CC(O)CO] |
| III-31 | 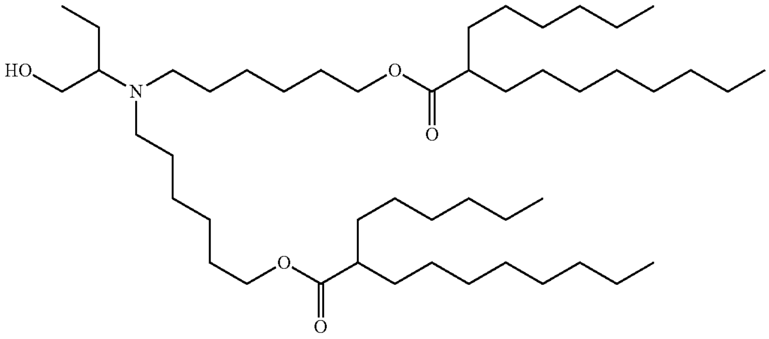 [SMILES: CCCCCCCCC(CCCCCC)C(=O)OCCCCCCN(CCCCCCOC(=O)C(CCCCCC)CCCCCCCC)C(CC)CO] |

TABLE 17-continued
| Representative Compounds of Formula (III). | |
|---|---|
| No. | Structure |
| III-32 | 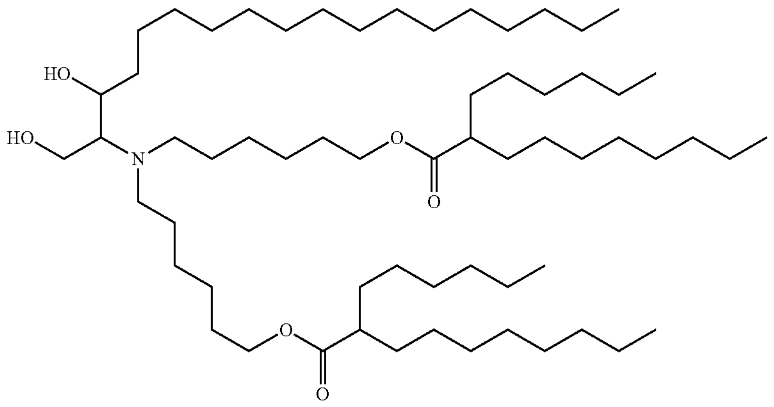 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] |
| III-33 | 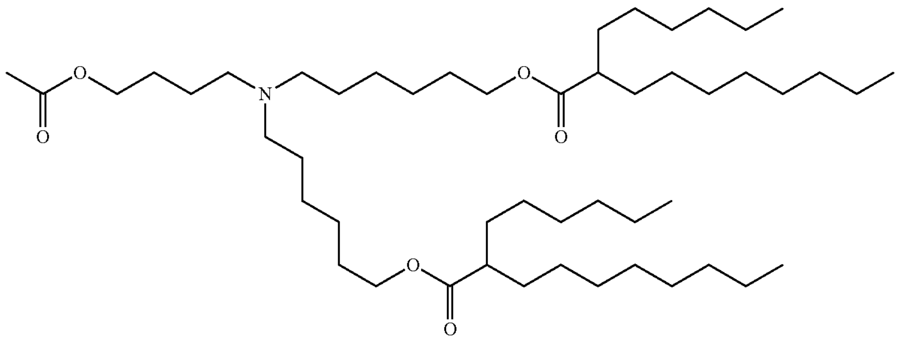 [SMILES: CCCCCCCCC(CCCCCC)C(=O)OCCCCCCN(CCCCCCOC(=O)C(CCCCCC)CCCCCCCC)CCCCOC(C)=O] |
| III-34 | 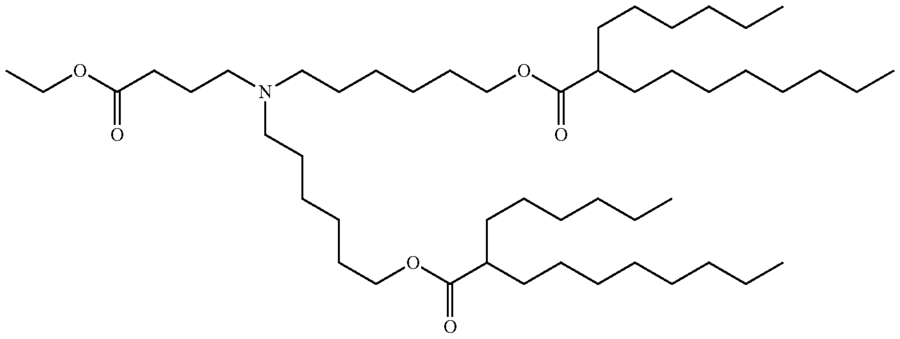 [SMILES: CCCCCCCCC(CCCCCC)C(=O)OCCCCCCN(CCCCCCOC(=O)C(CCCCCC)CCCCCCCC)CCCC(=O)OCC] |
| III-35 | 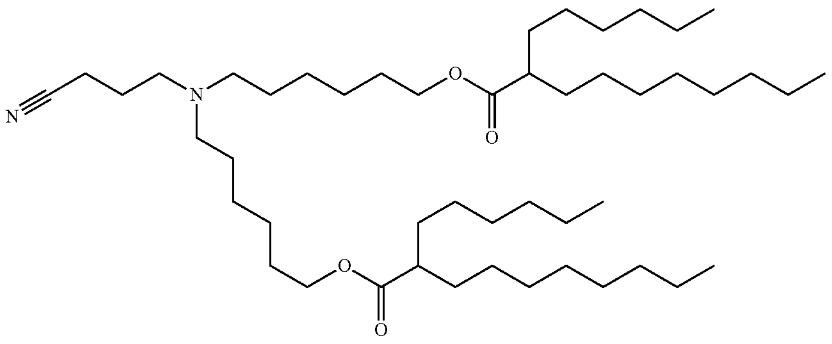 [SMILES: CCCCCCCCC(CCCCCC)C(=O)OCCCCCCN(CCCC#N)CCCCCCOC(=O)C(CCCCCC)CCCCCCCC] |

TABLE 17-continued

| Representative Compounds of Formula (III). | |
|---|---|
| No. | Structure |
| III-36 | 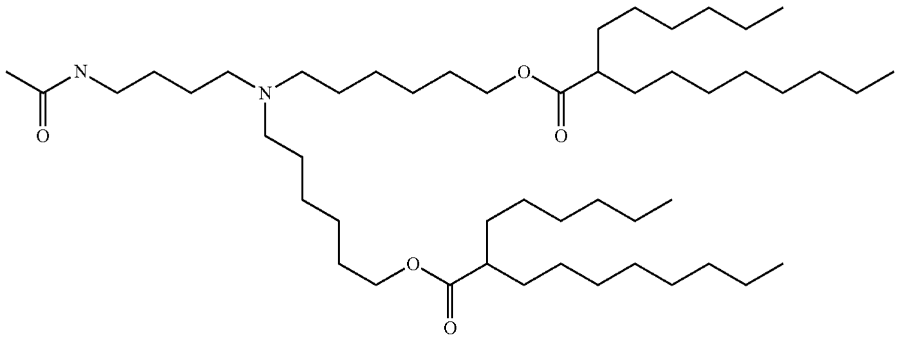 [SMILES: CCCCCCCCC(CCCCCC)C(=O)OCCCCCCN(CCCCCCOC(=O)C(CCCCCC)CCCCCCCC)CCCCNC(C)=O] |

In some embodiments, the LNP comprises a lipid of Formula (III), RNA, a neutral lipid, a steroid and a pegylated lipid. In some embodiments, the lipid of Formula (III) is compound III-3. In some embodiments, the neutral lipid is DSPC. In some embodiments, the steroid is cholesterol. In some embodiments, the pegylated lipid is ALC-0159.

In some embodiments, the cationic lipid is present in the LNP in an amount from about 40 to about 50 mole percent. In one embodiment, the neutral lipid is present in the LNP in an amount from about 5 to about 15 mole percent. In one embodiment, the steroid is present in the LNP in an amount from about 35 to about 45 mole percent. In one embodiment, the pegylated lipid is present in the LNP in an amount from about 1 to about 10 mole percent.

In some embodiments, the LNP comprises compound III-3 in an amount from about 40 to about 50 mole percent, DSPC in an amount from about 5 to about 15 mole percent, cholesterol in an amount from about 35 to about 45 mole percent, and ALC-0159 in an amount from about 1 to about 10 mole percent.

In some embodiments, the LNP comprises compound III-3 in an amount of about 47.5 mole percent, DSPC in an amount of about 10 mole percent, cholesterol in an amount of about 40.7 mole percent, and ALC-0159 in an amount of about 1.8 mole percent.

In various different embodiments, the cationic lipid has one of the structures set forth in the table below.

TABLE 18

| Representative cationic lipids. | |
|---|---|
| No. | Structure |
| A | 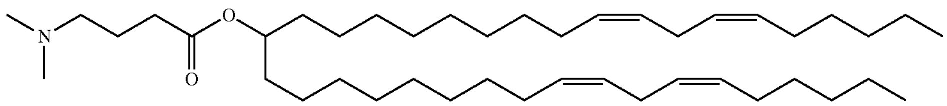 [SMILES: CCCCC/C=C\C/C=C\CCCCCCCCC(CCCCCCCC/C=C\C/C=C\CCCCC)OC(=O)CCCN(C)C] |
| B | 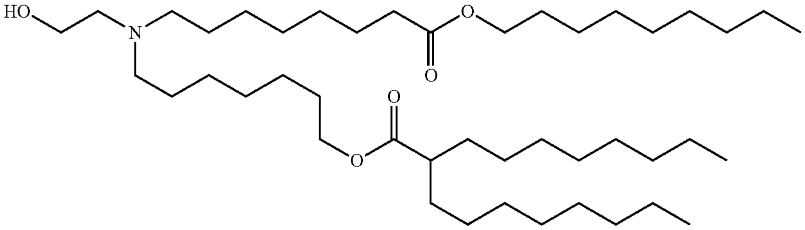 [SMILES: CCCCCCCCCOC(=O)CCCCCCCN(CCO)CCCCCCCOC(=O)C(CCCCCCCC)CCCCCCCC] |
| C | 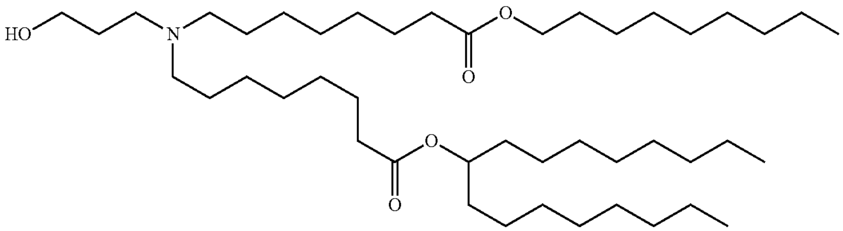 [SMILES: CCCCCCCCCOC(=O)CCCCCCCN(CCCO)CCCCCCCC(=O)OC(CCCCCCCC)CCCCCCCC] |

TABLE 18-continued

Representative cationic lipids.

| No. | Structure |
| --- | --- |
| D | 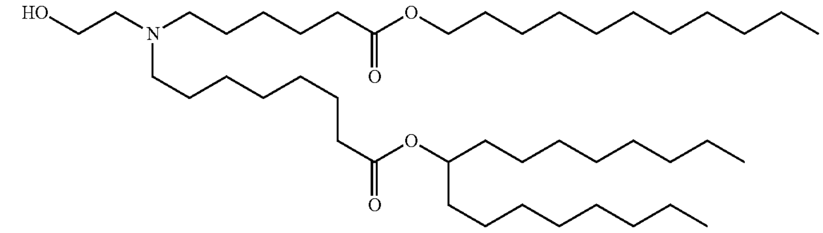 [SMILES: CCCCCCCCCCCOC(=O)CCCCCN(CCO)CCCCCCCC(=O)OC(CCCCCCCC)CCCCCCCC] |
| E | 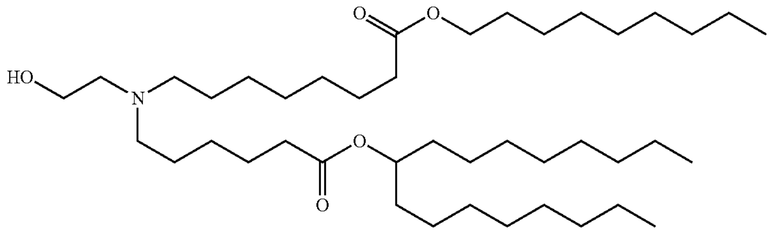 [SMILES: CCCCCCCCCOC(=O)CCCCCCCN(CCO)CCCCCC(=O)OC(CCCCCCCC)CCCCCCCC] |
| F | 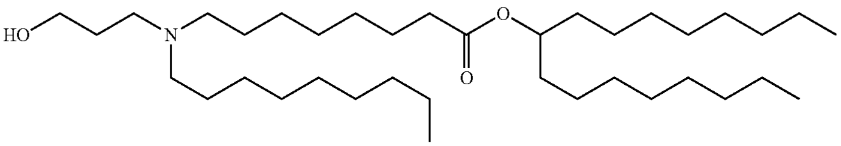 [SMILES: CCCCCCCCCN(CCCO)CCCCCCCC(=O)OC(CCCCCCCC)CCCCCCCC] |

In some embodiments, the LNP comprises a cationic lipid shown in the above table, e.g., a cationic lipid of Formula (B) or Formula (D), in particular a cationic lipid of Formula (D), RNA, a neutral lipid, a steroid and a pegylated lipid. In some embodiments, the neutral lipid is DSPC.

In some embodiments, the steroid is cholesterol. In some embodiments, the pegylated lipid is DMG-PEG 2000.

In one embodiment, the LNP comprises a cationic lipid that is an ionizable lipid-like material (lipidoid). In one embodiment, the cationic lipid has the following structure:

RNA administered is RNA encoding vaccine antigen. RNA may be delivered to lung, for example, by administering the RNA which may be formulated as particles as described herein, e.g., lipid particles, by inhalation.

In one embodiment, the present disclosure involves targeting the lymphatic system, in particular secondary lymphoid organs, more specifically spleen. Targeting the lymphatic system, in particular secondary lymphoid organs, more specifically spleen is in particular preferred if the RNA administered is RNA encoding vaccine antigen.

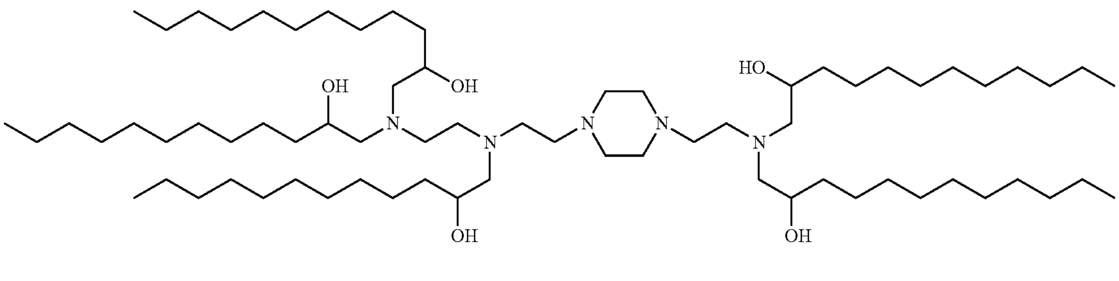 [SMILES: CCCCCCCCCCC(O)CN(CCN1CCN(CCN(CC(O)CCCCCCCCCC)CC(O)CCCCCCCCCC)CC1)CCN(CC(O)CCCCCCCCCC)CC(O)CCCCCCCCCC]

The N/P value is preferably at least about 4. In some embodiments, the N/P value ranges from 4 to 20, 4 to 12, 4 to 10, 4 to 8, or 5 to 7. In one embodiment, the N/P value is about 6.

LNP described herein may have an average diameter that in one embodiment ranges from about 30 nm to about 200 nm, or from about 60 nm to about 120 nm.

RNA Targeting

Some aspects of the present disclosure involve the targeted delivery of the RNA disclosed herein (e.g., RNA encoding vaccine antigens and/or immunostimulants).

In one embodiment, the present disclosure involves targeting lung. Targeting lung is in particular preferred if the In one embodiment, the target cell is a spleen cell. In one embodiment, the target cell is an antigen presenting cell such as a professional antigen presenting cell in the spleen. In one embodiment, the target cell is a dendritic cell in the spleen.

The "lymphatic system" is part of the circulatory system and an important part of the immune system, comprising a network of lymphatic vessels that carry lymph. The lymphatic system consists of lymphatic organs, a conducting network of lymphatic vessels, and the circulating lymph. The primary or central lymphoid organs generate lymphocytes from immature progenitor cells. The thymus and the bone marrow constitute the primary lymphoid organs. Secondary or peripheral lymphoid organs, which include lymph nodes and the spleen, maintain mature naïve lymphocytes and initiate an adaptive immune response.

RNA may be delivered to spleen by so-called lipoplex formulations, in which the RNA is bound to liposomes comprising a cationic lipid and optionally an additional or helper lipid to form injectable nanoparticle formulations. The liposomes may be obtained by injecting a solution of the lipids in ethanol into water or a suitable aqueous phase. RNA lipoplex particles may be prepared by mixing the liposomes with RNA. Spleen targeting RNA lipoplex particles are described in WO 2013/143683, herein incorporated by reference. It has been found that RNA lipoplex particles having a net negative charge may be used to preferentially target spleen tissue or spleen cells such as antigen-presenting cells, in particular dendritic cells. Accordingly, following administration of the RNA lipoplex particles, RNA accumulation and/or RNA expression in the spleen occurs. Thus, RNA lipoplex particles of the present disclosure may be used for expressing RNA in the spleen. In an embodiment, after administration of the RNA lipoplex particles, no or essentially no RNA accumulation and/or RNA expression in the lung and/or liver occurs. In one embodiment, after administration of the RNA lipoplex particles, RNA accumulation and/or RNA expression in antigen presenting cells, such as professional antigen presenting cells in the spleen occurs. Thus, RNA lipoplex particles of the present disclosure may be used for expressing RNA in such antigen presenting cells. In one embodiment, the antigen presenting cells are dendritic cells and/or macrophages.

The electric charge of the RNA lipoplex particles of the present disclosure is the sum of the electric charges present in the at least one cationic lipid and the electric charges present in the RNA. The charge ratio is the ratio of the positive charges present in the at least one cationic lipid to the negative charges present in the RNA. The charge ratio of the positive charges present in the at least one cationic lipid to the negative charges present in the RNA is calculated by the following equation: charge ratio=[(cationic lipid concentration (mol))*(the total number of positive charges in the cationic lipid)]/[(RNA concentration (mol))*(the total number of negative charges in RNA)].

The spleen targeting RNA lipoplex particles described herein at physiological pH preferably have a net negative charge such as a charge ratio of positive charges to negative charges from about 1.9:2 to about 1:2, or about 1.6:2 to about 1:2, or about 1.6:2 to about 1.1:2. In specific embodiments, the charge ratio of positive charges to negative charges in the RNA lipoplex particles at physiological pH is about 1.9:2.0, about 1.8:2.0, about 1.7:2.0, about 1.6:2.0, about 1.5:2.0, about 1.4:2.0, about 1.3:2.0, about 1.2:2.0, about 1.1:2.0, or about 1:2.0.

Immunostimulants may be provided to a subject by administering to the subject RNA encoding an immunostimulant in a formulation for preferential delivery of RNA to liver or liver tissue. The delivery of RNA to such target organ or tissue is preferred, in particular, if it is desired to express large amounts of the immunostimulant and/or if systemic presence of the immunostimulant, in particular in significant amounts, is desired or required.

RNA delivery systems have an inherent preference to the liver. This pertains to lipid-based particles, cationic and neutral nanoparticles, in particular lipid nanoparticles such as liposomes, nanomicelles and lipophilic ligands in bioconjugates. Liver accumulation is caused by the discontinuous nature of the hepatic vasculature or the lipid metabolism (liposomes and lipid or cholesterol conjugates).

For in vivo delivery of RNA to the liver, a drug delivery system may be used to transport the RNA into the liver by preventing its degradation. For example, polyplex nanomicelles consisting of a poly(ethylene glycol) (PEG)-coated surface and an RNA (e.g., mRNA)-containing core is a useful system because the nanomicelles provide excellent in vivo stability of the RNA, under physiological conditions. Furthermore, the stealth property provided by the polyplex nanomicelle surface, composed of dense PEG palisades, effectively evades host immune defenses.

Examples of suitable immunostimulants for targeting liver are cytokines involved in T cell proliferation and/or maintenance. Examples of suitable cytokines include IL2 or IL7, fragments and variants thereof, and fusion proteins of these cytokines, fragments and variants, such as extended-PK cytokines.

In another embodiment, RNA encoding an immunostimulant may be administered in a formulation for preferential delivery of RNA to the lymphatic system, in particular secondary lymphoid organs, more specifically spleen. The delivery of an immunostimulant to such target tissue is preferred, in particular, if presence of the immunostimulant in this organ or tissue is desired (e.g., for inducing an immune response, in particular in case immunostimulants such as cytokines are required during T-cell priming or for activation of resident immune cells), while it is not desired that the immunostimulant is present systemically, in particular in significant amounts (e.g., because the immunostimulant has systemic toxicity).

Examples of suitable immunostimulants are cytokines involved in T cell priming. Examples of suitable cytokines include IL12, IL15, IFN-α, or IFN-3, fragments and variants thereof, and fusion proteins of these cytokines, fragments and variants, such as extended-PK cytokines.

Immunostimulants

In one embodiment, the RNA encoding vaccine antigen may be non-immunogenic. In this and other embodiments, the RNA encoding vaccine antigen may be co-administered with an immunostimulant or RNA encoding an immunostimulant. The methods and agents described herein are particularly effective if the immunostimulant is attached to a pharmacokinetic modifying group (hereafter referred to as "extended-pharmacokinetic (PK)" immunostimulant). The methods and agents described herein are particularly effective if the immunostimulant is administered in the form of RNA encoding an immunostimulant. In one embodiment, said RNA is targeted to the liver for systemic availability. Liver cells can be efficiently transfected and are able to produce large amounts of protein.

An "immunostimulant" is any substance that stimulates the immune system by inducing activation or increasing activity of any of the immune system's components, in particular immune effector cells. The immunostimulant may be pro-inflammatory.

According to one aspect, the immunostimulant is a cytokine or a variant thereof. Examples of cytokines include interferons, such as interferon-alpha (IFN-α) or interferon-gamma (IFN-γ), interleukins, such as IL2, IL7, IL12, IL15 and IL23, colony stimulating factors, such as M-CSF and GM-CSF, and tumor necrosis factor. According to another aspect, the immunostimulant includes an adjuvant-type immunostimulatory agent such as APC Toll-like Receptor agonists or costimulatory/cell adhesion membrane proteins. Examples of Toll-like Receptor agonists include costimulatory/adhesion proteins such as CD80, CD86, and ICAM-1.

Cytokines are a category of small proteins (~5-20 kDa) that are important in cell signaling. Their release has an effect on the behavior of cells around them. Cytokines are involved in autocrine signaling, paracrine signaling and endocrine signaling as immunomodulating agents. Cytokines include chemokines, interferons, interleukins, lymphokines, and tumour necrosis factors but generally not hormones or growth factors (despite some overlap in the terminology). Cytokines are produced by a broad range of cells, including immune cells like macrophages, B lymphocytes, T lymphocytes and mast cells, as well as endothelial cells, fibroblasts, and various stromal cells. A given cytokine may be produced by more than one type of cell. Cytokines act through receptors, and are especially important in the immune system; cytokines modulate the balance between humoral and cell-based immune responses, and they regulate the maturation, growth, and responsiveness of particular cell populations. Some cytokines enhance or inhibit the action of other cytokines in complex ways.

According to the present disclosure, a cytokine may be a naturally occurring cytokine or a functional fragment or variant thereof. A cytokine may be human cytokine and may be derived from any vertebrate, especially any mammal. One particularly preferred cytokine is interferon-α.

Interferons

Interferons (IFNs) are a group of signaling proteins made and released by host cells in response to the presence of several pathogens, such as viruses, bacteria, parasites, and also tumor cells.

In a typical scenario, a virus-infected cell will release interferons causing nearby cells to heighten their anti-viral defenses.

Based on the type of receptor through which they signal, interferons are typically divided among three classes: type I interferon, type II interferon, and type Ill interferon.

All type I interferons bind to a specific cell surface receptor complex known as the IFN-α/β receptor (IFNAR) that consists of IFNAR1 and IFNAR2 chains.

The type I interferons present in humans are IFNα, IFNβ, IFNε, IFNκ and IFNω. In general, type I interferons are produced when the body recognizes a virus that has invaded it. They are produced by fibroblasts and monocytes. Once released, type I interferons bind to specific receptors on target cells, which leads to expression of proteins that will prevent the virus from producing and replicating its RNA and DNA.

The IFNα proteins are produced mainly by plasmacytoid dendritic cells (pDCs). They are mainly involved in innate immunity against viral infection. The genes responsible for their synthesis come in 13 subtypes that are called IFNA1, IFNA2, IFNA4, IFNA5, IFNA6, IFNA7, IFNA8, IFNA10, IFNA13, IFNA14, IFNA16, IFNA17, IFNA21. These genes are found together in a cluster on chromosome 9.

The IFNβ proteins are produced in large quantities by fibroblasts. They have antiviral activity that is involved mainly in innate immune response. Two types of IFNβ have been described, IFNβ1 and IFNβ3. The natural and recombinant forms of IFNβ1 have antiviral, antibacterial, and anticancer properties.

Type II interferon (IFNγ in humans) is also known as immune interferon and is activated by IL12. Furthermore, type II interferons are released by cytotoxic T cells and T helper cells. Type III interferons signal through a receptor complex consisting of IL10R2 (also called CRF2-4) and IFNLR1 (also called CRF2-12). Although discovered more recently than type I and type II IFNs, recent information demonstrates the importance of type III IFNs in some types of virus or fungal infections.

In general, type I and II interferons are responsible for regulating and activating the immune response.

According to the present disclosure, a type I interferon is preferably IFNα or IFNβ, more preferably IFNα.

According to the present disclosure, an interferon may be a naturally occurring interferon or a functional fragment or variant thereof. An interferon may be human interferon and may be derived from any vertebrate, especially any mammal.

Interleukins

Interleukins (ILs) are a group of cytokines (secreted proteins and signal molecules) that can be divided into four major groups based on distinguishing structural features. However, their amino acid sequence similarity is rather weak (typically 15-25% identity). The human genome encodes more than 50 interleukins and related proteins.

According to the present disclosure, an interleukin may be a naturally occurring interleukin or a functional fragment or variant thereof. An interleukin may be human interleukin and may be derived from any vertebrate, especially any mammal.

Extended-PK Group

Immunostimulant polypeptides described herein can be prepared as fusion or chimeric polypeptides that include an immunostimulant portion and a heterologous polypeptide (i.e., a polypeptide that is not an immunostimulant). The immunostimulant may be fused to an extended-PK group, which increases circulation half-life. Non-limiting examples of extended-PK groups are described infra. It should be understood that other PK groups that increase the circulation half-life of immunostimulants such as cytokines, or variants thereof, are also applicable to the present disclosure. In certain embodiments, the extended-PK group is a serum albumin domain (e.g., mouse serum albumin, human serum albumin).

As used herein, the term "PK" is an acronym for "pharmacokinetic" and encompasses properties of a compound including, byway of example, absorption, distribution, metabolism, and elimination by a subject. As used herein, an "extended-PK group" refers to a protein, peptide, or moiety that increases the circulation half-life of a biologically active molecule when fused to or administered together with the biologically active molecule. Examples of an extended-PK group include serum albumin (e.g., HSA), Immunoglobulin Fc or Fc fragments and variants thereof, transferrin and variants thereof, and human serum albumin (HSA) binders (as disclosed in U.S. Publication Nos. 2005/0287153 and 2007/0003549). Other exemplary extended-PK groups are disclosed in Kontermann, Expert Opin Biol Ther, 2016 July; 16(7):903-15 which is herein incorporated by reference in its entirety. As used herein, an "extended-PK" immunostimulant refers to an immunostimulant moiety in combination with an extended-PK group. In one embodiment, the extended-PK immunostimulant is a fusion protein in which an immunostimulant moiety is linked or fused to an extended-PK group.

In certain embodiments, the serum half-life of an extended-PK immunostimulant is increased relative to the immunostimulant alone (i.e., the immunostimulant not fused to an extended-PK group). In certain embodiments, the serum half-life of the extended-PK immunostimulant is at least 20, 40, 60, 80, 100, 120, 150, 180, 200, 400, 600, 800, or 1000% longer relative to the serum half-life of the immunostimulant alone. In certain embodiments, the serum half-life of the extended-PK immunostimulant is at least 1.5-fold, 2-fold, 2.5-fold, 3-fold, 3.5 fold, 4-fold, 4.5-fold, 5-fold, 6-fold, 7-fold, 8-fold, 10-fold, 12-fold, 13-fold, 15-fold, 17-fold, 20-fold, 22-fold, 25-fold, 27-fold, 30-fold, 35-fold, 40-fold, or 50-fold greater than the serum half-life of the immunostimulant alone. In certain embodiments, the serum half-life of the extended-PK immunostimulant is at least 10 hours, 15 hours, 20 hours, 25 hours, 30 hours, 35 hours, 40 hours, 50 hours, 60 hours, 70 hours, 80 hours, 90 hours, 100 hours, 110 hours, 120 hours, 130 hours, 135 hours, 140 hours, 150 hours, 160 hours, or 200 hours.

As used herein, "half-life" refers to the time taken for the serum or plasma concentration of a compound such as a peptide or protein to reduce by 50%, in vivo, for example due to degradation and/or clearance or sequestration by natural mechanisms. An extended-PK immunostimulant suitable for use herein is stabilized in vivo and its half-life increased by, e.g., fusion to serum albumin (e.g., HSA or MSA), which resist degradation and/or clearance or sequestration. The half-life can be determined in any manner known per se, such as by pharmacokinetic analysis. Suitable techniques will be clear to the person skilled in the art, and may for example generally involve the steps of suitably administering a suitable dose of the amino acid sequence or compound to a subject; collecting blood samples or other samples from said subject at regular intervals; determining the level or concentration of the amino acid sequence or compound in said blood sample; and calculating, from (a plot of) the data thus obtained, the time until the level or concentration of the amino acid sequence or compound has been reduced by 50% compared to the initial level upon dosing. Further details are provided in, e.g., standard handbooks, such as Kenneth, A. et al., Chemical Stability of Pharmaceuticals: A Handbook for Pharmacists and in Peters et al., Pharmacokinetic Analysis: A Practical Approach (1996). Reference is also made to Gibaldi, M. et al., Pharmacokinetics, 2nd Rev. Edition, Marcel Dekker (1982).

In certain embodiments, the extended-PK group includes serum albumin, or fragments thereof or variants of the serum albumin or fragments thereof (all of which for the purpose of the present disclosure are comprised by the term "albumin"). Polypeptides described herein may be fused to albumin (or a fragment or variant thereof) to form albumin fusion proteins. Such albumin fusion proteins are described in U.S. Publication No. 20070048282.

As used herein, "albumin fusion protein" refers to a protein formed by the fusion of at least one molecule of albumin (or a fragment or variant thereof) to at least one molecule of a protein such as a therapeutic protein, in particular an immunostimulant. The albumin fusion protein may be generated by translation of a nucleic acid in which a polynucleotide encoding a therapeutic protein is joined in-frame with a polynucleotide encoding an albumin. The therapeutic protein and albumin, once part of the albumin fusion protein, may each be referred to as a "portion", "region" or "moiety" of the albumin fusion protein (e.g., a "therapeutic protein portion" or an "albumin protein portion"). In a highly preferred embodiment, an albumin fusion protein comprises at least one molecule of a therapeutic protein (including, but not limited to a mature form of the therapeutic protein) and at least one molecule of albumin (including but not limited to a mature form of albumin). In one embodiment, an albumin fusion protein is processed by a host cell such as a cell of the target organ for administered RNA, e.g. a liver cell, and secreted into the circulation. Processing of the nascent albumin fusion protein that occurs in the secretory pathways of the host cell used for expression of the RNA may include, but is not limited to signal peptide cleavage; formation of disulfide bonds; proper folding; addition and processing of carbohydrates (such as for example, N- and O-linked glycosylation); specific proteolytic cleavages; and/or assembly into multimeric proteins. An albumin fusion protein is preferably encoded by RNA in a non-processed form which in particular has a signal peptide at its N-terminus and following secretion by a cell is preferably present in the processed form wherein in particular the signal peptide has been cleaved off. In a most preferred embodiment, the "processed form of an albumin fusion protein" refers to an albumin fusion protein product which has undergone N-terminal signal peptide cleavage, herein also referred to as a "mature albumin fusion protein". In preferred embodiments, albumin fusion proteins comprising a therapeutic protein have a higher plasma stability compared to the plasma stability of the same therapeutic protein when not fused to albumin. Plasma stability typically refers to the time period between when the therapeutic protein is administered in vivo and carried into the bloodstream and when the therapeutic protein is degraded and cleared from the bloodstream, into an organ, such as the kidney or liver, that ultimately clears the therapeutic protein from the body. Plasma stability is calculated in terms of the half-life of the therapeutic protein in the bloodstream. The half-life of the therapeutic protein in the bloodstream can be readily determined by common assays known in the art.

As used herein, "albumin" refers collectively to albumin protein or amino acid sequence, or an albumin fragment or variant, having one or more functional activities (e.g., biological activities) of albumin. In particular, "albumin" refers to human albumin or fragments or variants thereof especially the mature form of human albumin, or albumin from other vertebrates or fragments thereof, or variants of these molecules. The albumin may be derived from any vertebrate, especially any mammal, for example human, cow, sheep, or pig. Non-mammalian albumins include, but are not limited to, hen and salmon. The albumin portion of the albumin fusion protein may be from a different animal than the therapeutic protein portion.

In certain embodiments, the albumin is human serum albumin (HSA), or fragments or variants thereof, such as those disclosed in U.S. Pat. No. 5,876,969, WO 2011/124718, WO 2013/075066, and WO 2011/0514789.

The terms, human serum albumin (HSA) and human albumin (HA) are used interchangeably herein. The terms, "albumin and "serum albumin" are broader, and encompass human serum albumin (and fragments and variants thereof) as well as albumin from other species (and fragments and variants thereof).

As used herein, a fragment of albumin sufficient to prolong the therapeutic activity or plasma stability of the therapeutic protein refers to a fragment of albumin sufficient in length or structure to stabilize or prolong the therapeutic activity or plasma stability of the protein so that the plasma stability of the therapeutic protein portion of the albumin fusion protein is prolonged or extended compared to the plasma stability in the non-fusion state.

The albumin portion of the albumin fusion proteins may comprise the full length of the albumin sequence, or may include one or more fragments thereof that are capable of stabilizing or prolonging the therapeutic activity or plasma stability. Such fragments may be of 10 or more amino acids in length or may include about 15, 20, 25, 30, 50, or more contiguous amino acids from the albumin sequence or may include part or all of specific domains of albumin. For instance, one or more fragments of HSA spanning the first two immunoglobulin-like domains may be used. In a preferred embodiment, the HSA fragment is the mature form of HSA.

Generally speaking, an albumin fragment or variant will be at least 100 amino acids long, preferably at least 150 amino acids long.

According to the present disclosure, albumin may be naturally occurring albumin or a fragment or variant thereof. Albumin may be human albumin and may be derived from any vertebrate, especially any mammal.

Preferably, the albumin fusion protein comprises albumin as the N-terminal portion, and a therapeutic protein as the C-terminal portion. Alternatively, an albumin fusion protein comprising albumin as the C-terminal portion, and a therapeutic protein as the N-terminal portion may also be used. In other embodiments, the albumin fusion protein has a therapeutic protein fused to both the N-terminus and the C-terminus of albumin. In a preferred embodiment, the therapeutic proteins fused at the N- and C-termini are the same therapeutic proteins. In another preferred embodiment, the therapeutic proteins fused at the N- and C-termini are different therapeutic proteins. In one embodiment, the different therapeutic proteins are both cytokines.

In one embodiment, the therapeutic protein(s) is (are) joined to the albumin through (a) peptide linker(s). A linker peptide between the fused portions may provide greater physical separation between the moieties and thus maximize the accessibility of the therapeutic protein portion, for instance, for binding to its cognate receptor. The linker peptide may consist of amino acids such that it is flexible or more rigid. The linker sequence may be cleavable by a protease or chemically.

As used herein, the term “Fc region” refers to the portion of a native immunoglobulin formed by the respective Fc domains (or Fc moieties) of its two heavy chains. As used herein, the term “Fc domain” refers to a portion or fragment of a single immunoglobulin (Ig) heavy chain wherein the Fc domain does not comprise an Fv domain. In certain embodiments, an Fc domain begins in the hinge region just upstream of the papain cleavage site and ends at the C-terminus of the antibody. Accordingly, a complete Fc domain comprises at least a hinge domain, a CH2 domain, and a CH3 domain. In certain embodiments, an Fc domain comprises at least one of: a hinge (e.g., upper, middle, and/or lower hinge region) domain, a CH2 domain, a CH3 domain, a CH4 domain, or a variant, portion, or fragment thereof. In certain embodiments, an Fc domain comprises a complete Fc domain (i.e., a hinge domain, a CH2 domain, and a CH3 domain). In certain embodiments, an Fc domain comprises a hinge domain (or portion thereof) fused to a CH3 domain (or portion thereof). In certain embodiments, an Fc domain comprises a CH2 domain (or portion thereof) fused to a CH3 domain (or portion thereof). In certain embodiments, an Fc domain consists of a CH3 domain or portion thereof. In certain embodiments, an Fc domain consists of a hinge domain (or portion thereof) and a CH3 domain (or portion thereof). In certain embodiments, an Fc domain consists of a CH2 domain (or portion thereof) and a CH3 domain. In certain embodiments, an Fc domain consists of a hinge domain (or portion thereof) and a CH2 domain (or portion thereof). In certain embodiments, an Fc domain lacks at least a portion of a CH2 domain (e.g., all or part of a CH2 domain). An Fc domain herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. The Fc domain encompasses native Fc and Fc variant molecules. As set forth herein, it will be understood by one of ordinary skill in the art that any Fc domain may be modified such that it varies in amino acid sequence from the native Fc domain of a naturally occurring immunoglobulin molecule. In certain embodiments, the Fc domain has reduced effector function (e.g., FcγR binding).

The Fc domains of a polypeptide described herein may be derived from different immunoglobulin molecules. For example, an Fc domain of a polypeptide may comprise a CH2 and/or CH3 domain derived from an IgG1 molecule and a hinge region derived from an IgG3 molecule. In another example, an Fc domain can comprise a chimeric hinge region derived, in part, from an IgG1 molecule and, in part, from an IgG3 molecule. In another example, an Fc domain can comprise a chimeric hinge derived, in part, from an IgG1 molecule and, in part, from an IgG4 molecule.

In certain embodiments, an extended-PK group includes an Fc domain or fragments thereof or variants of the Fc domain or fragments thereof (all of which for the purpose of the present disclosure are comprised by the term “Fc domain”). The Fc domain does not contain a variable region that binds to antigen. Fc domains suitable for use in the present disclosure may be obtained from a number of different sources. In certain embodiments, an Fc domain is derived from a human immunoglobulin. In certain embodiments, the Fc domain is from a human IgG1 constant region. It is understood, however, that the Fc domain may be derived from an immunoglobulin of another mammalian species, including for example, a rodent (e.g. a mouse, rat, rabbit, guinea pig) or non-human primate (e.g. chimpanzee, macaque) species. Moreover, the Fc domain (or a fragment or variant thereof) may be derived from any immunoglobulin class, including IgM, IgG, IgD, IgA, and IgE, and any immunoglobulin isotype, including IgG1, IgG2, IgG3, and IgG4.

A variety of Fc domain gene sequences (e.g., mouse and human constant region gene sequences) are available in the form of publicly accessible deposits. Constant region domains comprising an Fc domain sequence can be selected lacking a particular effector function and/or with a particular modification to reduce immunogenicity. Many sequences of antibodies and antibody-encoding genes have been published and suitable Fc domain sequences (e.g. hinge, CH2, and/or CH3 sequences, or fragments or variants thereof) can be derived from these sequences using art recognized techniques.

In certain embodiments, the extended-PK group is a serum albumin binding protein such as those described in US2005/0287153, US2007/0003549, US2007/0178082, US2007/0269422, US2010/0113339, WO2009/083804, and WO2009/133208, which are herein incorporated by reference in their entirety. In certain embodiments, the extended-PK group is transferrin, as disclosed in U.S. Pat. Nos. 7,176,278 and 8,158,579, which are herein incorporated by reference in their entirety. In certain embodiments, the extended-PK group is a serum immunoglobulin binding protein such as those disclosed in US2007/0178082, US2014/0220017, and US2017/0145062, which are herein incorporated by reference in their entirety. In certain embodiments, the extended-PK group is a fibronectin (Fn)-based scaffold domain protein that binds to serum albumin, such as those disclosed in US2012/0094909, which is herein incorporated by reference in its entirety. Methods of making fibronectin-based scaffold domain proteins are also disclosed in US2012/0094909. A non-limiting example of a Fn3-based extended-PK group is Fn3(HSA), i.e., a Fn3 protein that binds to human serum albumin.

In certain aspects, the extended-PK immunostimulant, suitable for use according to the present disclosure, can employ one or more peptide linkers. As used herein, the term "peptide linker" refers to a peptide or polypeptide sequence which connects two or more domains (e.g., the extended-PK moiety and an immunostimulant moiety) in a linear amino acid sequence of a polypeptide chain. For example, peptide linkers may be used to connect an immunostimulant moiety to a HSA domain.

Linkers suitable for fusing the extended-PK group to e.g. an immunostimulant are well known in the art. Exemplary linkers include glycine-serine-polypeptide linkers, glycine-proline-polypeptide linkers, and proline-alanine polypeptide linkers. In certain embodiments, the linker is a glycine-serine-polypeptide linker, i.e., a peptide that consists of glycine and serine residues.

In addition to, or in place of, the heterologous polypeptides described above, an immunostimulant polypeptide described herein can contain sequences encoding a "marker" or "reporter". Examples of marker or reporter genes include β-lactamase, chloramphenicol acetyltransferase (CAT), adenosine deaminase (ADA), aminoglycoside phosphotransferase, dihydrofolate reductase (DHFR), hygromycin-B-hosphotransferase (HPH), thymidine kinase (TK), S-galactosidase, and xanthine guanine phosphoribosyltransferase (XGPRT).

Pharmaceutical Compositions

The agents described herein may be administered in pharmaceutical compositions or medicaments and may be administered in the form of any suitable pharmaceutical composition.

In one embodiment, the pharmaceutical composition described herein is an immunogenic composition for inducing an immune response against coronavirus in a subject. For example, in one embodiment, the immunogenic composition is a vaccine.

In one embodiment of all aspects of the present disclosure, the components described herein such as RNA encoding a vaccine antigen may be administered in a pharmaceutical composition which may comprise a pharmaceutically acceptable carrier and may optionally comprise one or more adjuvants, stabilizers etc. In one embodiment, the pharmaceutical composition is for therapeutic or prophylactic treatments, e.g., for use in treating or preventing a coronavirus infection.

The term "pharmaceutical composition" relates to a formulation comprising a therapeutically effective agent, preferably together with pharmaceutically acceptable carriers, diluents and/or excipients. Said pharmaceutical composition is useful for treating, preventing, or reducing the severity of a disease or disorder by administration of said pharmaceutical composition to a subject. A pharmaceutical composition is also known in the art as a pharmaceutical formulation.

The pharmaceutical compositions of the present disclosure may comprise one or more adjuvants or may be administered with one or more adjuvants. The term "adjuvant" relates to a compound which prolongs, enhances or accelerates an immune response. Adjuvants comprise a heterogeneous group of compounds such as oil emulsions (e.g., Freund's adjuvants), mineral compounds (such as alum), bacterial products (such as *Bordetella pertussis* toxin), or immune-stimulating complexes. Examples of adjuvants include, without limitation, LPS, GP96, CpG oligodeoxynucleotides, growth factors, and cytokines, such as monokines, lymphokines, interleukins, chemokines. The cytokines may be IL1, IL2, IL3, IL4, IL5, IL6, IL7, IL8, IL9, IL10, IL12, IFNα, IFNγ, GM-CSF, LT-a. Further known adjuvants are aluminium hydroxide, Freund's adjuvant or oil such as Montanide® ISA51. Other suitable adjuvants for use in the present disclosure include lipopeptides, such as Pam3Cys.

The pharmaceutical compositions according to the present disclosure are generally applied in a "pharmaceutically effective amount" and in "a pharmaceutically acceptable preparation".

The term "pharmaceutically acceptable" refers to the non-toxicity of a material which does not interact with the action of the active component of the pharmaceutical composition.

The term "pharmaceutically effective amount" or "therapeutically effective amount" refers to the amount which achieves a desired reaction or a desired effect alone or together with further doses. In the case of the treatment of a particular disease, the desired reaction preferably relates to inhibition of the course of the disease. This comprises slowing down the progress of the disease and, in particular, interrupting or reversing the progress of the disease. The desired reaction in a treatment of a disease may also be delay of the onset or a prevention of the onset of said disease or said condition. An effective amount of the compositions described herein will depend on the condition to be treated, the severeness of the disease, the individual parameters of the patient, including age, physiological condition, size and weight, the duration of treatment, the type of an accompanying therapy (if present), the specific route of administration and similar factors. Accordingly, the doses administered of the compositions described herein may depend on various of such parameters. In the case that a reaction in a patient is insufficient with an initial dose, higher doses (or effectively higher doses achieved by a different, more localized route of administration) may be used.

The pharmaceutical compositions of the present disclosure may contain salts, buffers, preservatives, and optionally other therapeutic agents. In one embodiment, the pharmaceutical compositions of the present disclosure comprise one or more pharmaceutically acceptable carriers, diluents and/or excipients.

Suitable preservatives for use in the pharmaceutical compositions of the present disclosure include, without limitation, benzalkonium chloride, chlorobutanol, paraben and thimerosal.

The term "excipient" as used herein refers to a substance which may be present in a pharmaceutical composition of the present disclosure but is not an active ingredient. Examples of excipients, include without limitation, carriers, binders, diluents, lubricants, thickeners, surface active agents, preservatives, stabilizers, emulsifiers, buffers, flavoring agents, or colorants.

The term "diluent" relates a diluting and/or thinning agent. Moreover, the term "diluent" includes any one or more of fluid, liquid or solid suspension and/or mixing media. Examples of suitable diluents include ethanol, glycerol and water.

The term "carrier" refers to a component which may be natural, synthetic, organic, inorganic in which the active component is combined in order to facilitate, enhance or enable administration of the pharmaceutical composition. A carrier as used herein may be one or more compatible solid or liquid fillers, diluents or encapsulating substances, which are suitable for administration to subject. Suitable carrier include, without limitation, sterile water, Ringer, Ringer lactate, sterile sodium chloride solution, isotonic saline, polyalkylene glycols, hydrogenated naphthalenes and, in particular, biocompatible lactide polymers, lactide/glycolide copolymers or polyoxyethylene/polyoxy-propylene copolymers. In one embodiment, the pharmaceutical composition of the present disclosure includes isotonic saline.

Pharmaceutically acceptable carriers, excipients or diluents for therapeutic use are well known in the pharmaceutical art, and are described, for example, in Remington's Pharmaceutical Sciences, Mack Publishing Co. (A. R Gennaro edit. 1985).

Pharmaceutical carriers, excipients or diluents can be selected with regard to the intended route of administration and standard pharmaceutical practice.

In one embodiment, pharmaceutical compositions described herein may be administered intravenously, intraarterially, subcutaneously, intradermally or intramuscularly. In certain embodiments, the pharmaceutical composition is formulated for local administration or systemic administration. Systemic administration may include enteral administration, which involves absorption through the gastrointestinal tract, or parenteral administration. As used herein, "parenteral administration" refers to the administration in any manner other than through the gastrointestinal tract, such as by intravenous injection. In a preferred embodiment, the pharmaceutical composition is formulated for intramuscular administration. In another embodiment, the pharmaceutical composition is formulated for systemic administration, e.g., for intravenous administration.

The term "co-administering" as used herein means a process whereby different compounds or compositions (e.g., RNA encoding an antigen and RNA encoding an immunostimulant) are administered to the same patient. The different compounds or compositions may be administered simultaneously, at essentially the same time, or sequentially.

The pharmaceutical compositions and products described herein may be provided as a frozen concentrate for solution for injection, e.g., at a concentration of 0.50 mg/mL. In one embodiment, for preparation of solution for injection, a drug product is thawed and diluted with isotonic sodium chloride solution (e.g., 0.9% NaCl, saline), e.g., by a one-step dilution process. In some embodiments, bacteriostatic sodium chloride solution (e.g., 0.9% NaCl, saline) cannot be used as a diluent. In some embodiments, a diluted drug product is an off-white suspension. The concentration of the final solution for injection varies depending on the respective dose level to be administered.

In one embodiment, administration is performed within 6 h after begin of preparation due to the risk of microbial contamination and considering the multiple-dose approach of the preparation process. In one embodiment, in this period of 6 h, two conditions are allowed: room temperature for preparation, handling and transfer as well as 2 to 8° C. for storage. Compositions described herein may be shipped and/or stored under temperature-controlled conditions, e.g., temperature conditions of about 4-5° C. or below, about −20° C. or below, −70° C.±10° C. (e.g., −80° C. to −60° C.), e.g., utilizing a cooling system (e.g., that may be or include dry ice) to maintain the desired temperature. In one embodiment, compositions described herein are shipped in temperature-controlled thermal shippers. Such shippers may contain a GPS-enabled thermal sensor to track the location and temperature of each shipment. The compositions can be stored by refilling with, e.g., dry ice.

Treatments

The present disclosure provides methods and agents for inducing an adaptive immune response against coronavirus in a subject comprising administering an effective amount of a composition comprising RNA encoding a coronavirus vaccine antigen described herein.

In one embodiment, the methods and agents described herein provide immunity in a subject to coronavirus, coronavirus infection, or to a disease or disorder associated with coronavirus. The present disclosure thus provides methods and agents for treating or preventing the infection, disease, or disorder associated with coronavirus.

In one embodiment, the methods and agents described herein are administered to a subject having an infection, disease, or disorder associated with coronavirus. In one embodiment, the methods and agents described herein are administered to a subject at risk for developing the infection, disease, or disorder associated with coronavirus. For example, the methods and agents described herein may be administered to a subject who is at risk for being in contact with coronavirus. In one embodiment, the methods and agents described herein are administered to a subject who lives in, traveled to, or is expected to travel to a geographic region in which coronavirus is prevalent. In one embodiment, the methods and agents described herein are administered to a subject who is in contact with or expected to be in contact with another person who lives in, traveled to, or is expected to travel to a geographic region in which coronavirus is prevalent. In one embodiment, the methods and agents described herein are administered to a subject who has knowingly been exposed to coronavirus through their occupation, or other contact. In one embodiment, a coronavirus is SARS-CoV-2. In some embodiments, methods and agents described herein are administered to a subject with evidence of prior exposure to and/or infection with SARS-CoV-2 and/or an antigen or epitope thereof or cross-reactive therewith. For example, in some embodiments, methods and agents described herein are administered to a subject in whom antibodies, B cells, and/or T cells reactive with one or more epitopes of a SARS-CoV-2 spike protein are detectable and/or have been detected.

For a composition to be useful as a vaccine, the composition must induce an immune response against the coronavirus antigen in a cell, tissue or subject (e.g., a human). In some embodiments, the composition induces an immune response against the coronavirus antigen in a cell, tissue or subject (e.g., a human). In some instances, the vaccine induces a protective immune response in a mammal. The therapeutic compounds or compositions of the present disclosure may be administered prophylactically (i.e., to prevent a disease or disorder) or therapeutically (i.e., to treat a disease or disorder) to subjects suffering from, or at risk of (or susceptible to) developing a disease or disorder. Such subjects may be identified using standard clinical methods. In the context of the present disclosure, prophylactic administration occurs prior to the manifestation of overt clinical symptoms of disease, such that a disease or disorder is prevented or alternatively delayed in its progression. In the context of the field of medicine, the term "prevent" encompasses any activity, which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

The term "dose" as used herein refers in general to a "dose amount" which relates to the amount of RNA administered per administration, i.e., per dosing.

In some embodiments, administration of an immunogenic composition or vaccine of the present disclosure may be performed by single administration or boosted by multiple administrations.

In some embodiments, a regimen described herein includes at least one dose. In some embodiments, a regimen includes a first dose and at least one subsequent dose. In some embodiments, the first dose is the same amount as at least one subsequent dose. In some embodiments, the first dose is the same amount as all subsequent doses. In some embodiments, the first dose is a different amount as at least one subsequent dose. In some embodiments, the first dose is a different amount than all subsequent doses. In some embodiments, a regimen comprises two doses. In some embodiments, a provided regimen consists of two doses. In some embodiments, a regimen comprises three doses.

In one embodiment, the present disclosure envisions administration of a single dose. In one embodiment, the present disclosure envisions administration of a priming dose followed by one or more booster doses. The booster dose or the first booster dose may be administered 7 to 28 days or 14 to 24 days following administration of the priming dose. In some embodiments, a first booster dose may be administered 1 week to 3 months (e.g., 1 week, 2 weeks, 3 weeks, 4 weeks, 5 weeks, 6 weeks, 7 weeks, 8 weeks, 9 weeks, 10 weeks, 11 weeks, 12 weeks) following administration of a priming dose. In some embodiments, a subsequent booster dose may be administered at least 1 week or longer, including, e.g., at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, or longer, following a preceding booster dose. In some embodiments, subsequent booster doses may be administered about 5-9 weeks or 6-8 weeks apart. In some embodiments, at least one subsequent booster dose (e.g., after a first booster dose) may be administered at least 3 months or longer, including, e.g., at least 4 months, at least 5 months, at least 6 months, at least 7 months, at least 8 months, at least 9 months, at least 10 months, or longer, following a preceding dose.

In some embodiments, a subsequent dose given to an individual (e.g., as part of a primary regimen or booster regimen) can have the same amount of RNA as previously given to the individual. In some embodiments, a subsequent dose given to an individual (e.g., as part of a primary regimen or booster regimen) can differ in the amount of RNA, as compared to the amount previously given to the individual. For example, in some embodiments, a subsequent dose can be higher or lower than the prior dose, for example, based on consideration of various factors, including, e.g., immunogenicity and/or reactogenicity induced by the prior dose, prevalence of the disease, etc. In some embodiments, a subsequent dose can be higher than a prior dose by at least 30%, at least 40%, at least 50%, at least 60%, at least 70%, at least 80%, at least 90%, or higher. In some embodiments, a subsequent dose can be higher than a prior dose by at least 1.5-fold, at least 2-fold, at least 2.5 fold, at least 3-fold, or higher. In some embodiments, a subsequent dose can be higher than a prior dose by at least 30%, at least 40%, at least 50%, at least 60%, at least 70%, at least 80%, at least 90%, or higher. In some embodiments, a subsequent dose can be lower than a prior dose by at least 10%, at least 20%, at least 30%, at least 40%, at least 50%, at least 60%, at least 70% or lower. In some embodiments, an amount the RNA described herein from 0.1 μg to 300 μg, 0.5 μg to 200 μg, or 1 μg to 100 μg, such as about 1 μg, about 2 μg, about 3 μg, about 10 μg, about 15 μg, about 20 μg, about 25 μg, about 30 μg, about 35 μg, about 40 μg, about 45 μg, about 50 μg, about 55 μg, about 60 μg, about 70 μg, about 80 μg, about 90 μg, or about 100 μg may be administered per dose (e.g., in a given dose).

In some embodiments, an amount of the RNA described herein of 60 μg or lower, 55 μg or lower, 50 μg or lower, 45 μg or lower, 40 μg or lower, 35 μg or lower, 30 μg or lower, 25 μg or lower, 20 μg or lower, 15 μg or lower, 10 μg or lower, 5 μg or lower, 3 ag or lower, 2.5 μg or lower, or 1 μg or lower may be administered per dose (e.g., in a given dose).

In some embodiments, an amount of the RNA described herein of at least 0.25 μg, at least 0.5 μg, at least 1 μg, at least 2 μg, at least 3 μg, at least 4 μg, at least 5 μg, at least 10 μg, at least 15 μg, at least 20 μg, at least 25 μg, at least 30 μg, at least 40 μg, at least 50 μg, or at least 60 μg may be administered per dose (e.g., in a given dose). In some embodiments, an amount of the RNA described herein of at least 3 ug may be administered in at least one of given doses. In some embodiments, an amount of the RNA described herein of at least 10 ug may be administered in at least one of given doses. In some embodiments, an amount of the RNA described herein of at least 15 ug may be administered in at least one of given doses. In some embodiments, an amount of the RNA described herein of at least 20 ug may be administered in at least one of given doses. In some embodiments, an amount of the RNA described herein of at least 25 ug may be administered in at least one of given doses. In some embodiments, an amount of the RNA described herein of at least 30 ug may be administered in at least one of given doses. In some embodiments, an amount of the RNA described herein of at least 50 ug may be administered in at least one of given doses. In some embodiments, an amount of the RNA described herein of at least 60 ug may be administered in at least one of given doses. In some embodiments, combinations of aforementioned amounts may be administered in a regimen comprising two or more doses (e.g., a prior dose and a subsequent dose can be of different amounts as described herein). In some embodiments, combinations of aforementioned amounts may be administered in a primary regimen and a booster regimen (e.g., different doses can be given in a primary regimen and a booster regimen).

In some embodiments, an amount of the RNA described herein of 0.25 μg to 60 μg, 0.5 μg to 55 μg, 1 μg to 50 μg, 5 μg to 40 μg, or 10 μg to 30 μg may be administered per dose. In some embodiments, an amount of the RNA described herein of 3 μg to 30 μg may be administered in at least one of given doses. In some embodiments, an amount of the RNA described herein of 3 μg to 20 μg may be administered in at least one of given doses. In some embodiments, an amount of the RNA described herein of 3 μg to 15 μg may be administered in at least one of given doses. In some embodiments, an amount of the RNA described herein of 3 μg to 10 μg may be administered in at least one of given doses. In some embodiments, an amount of the RNA described herein of 10 μg to 30 μg may be administered in at least one of given doses.

In some embodiments, a regimen administered to a subject may comprise a plurality of doses (e.g., at least two doses, at least three doses, or more). In some embodiments, a regimen administered to a subject may comprise a first dose and a second dose, which are given at least 2 weeks apart, at least 3 weeks apart, at least 4 weeks apart, or more. In some embodiments, such doses may be at least 1 month, at least 2 months, at least 3 months, at least 4 months, at least 5 months, at least 6 months, at least 7 months, at least 8 months, at least 9 months, at least 10 months, at least 11 months, at least 12 months, or more apart. In some embodiments, doses may be administered days apart, such as 1, 2, 3, 4, 5, 6, 7, 8, 9,10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or more days apart. In some embodiments, doses may be administered about 1 to about 3 weeks apart, or about 1 to about 4 weeks apart, or about 1 to about 5 weeks apart, or about 1 to about 6 weeks apart, or about 1 to more than 6 weeks apart. In some embodiments, doses may be separated by a period of about 7 to about 60 days, such as for example about 14 to about 48 days, etc. In some embodiments, a minimum number of days between doses may be about 1, 2, 3, 4, 5, 6, 7, 8, 9, 10, 11, 12, 13, 14, 15, 16, 17, 18, 19, 20, 21 or more. In some embodiments, a maximum number of days between doses may be about 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or fewer. In some embodiments, doses may be about 21 to about 28 days apart. In some embodiments, doses may be about 19 to about 42 days apart. In some embodiments, doses may be about 7 to about 28 days apart. In some embodiments, doses may be about 14 to about 24 days. In some embodiments, doses may be about 21 to about 42 days.

In some embodiments, a vaccination regimen comprises a first dose and a second dose. In some embodiments, a first dose and a second dose are administered by at least 21 days apart. In some embodiments, a first dose and a second dose are administered by at least 28 days apart.

In some embodiments, a vaccination regimen comprises a first dose and a second dose, wherein the amount of RNA administered in the first dose is the same as the amount of RNA administered in the second dose. In some embodiments, a vaccination regimen comprises a first dose and a second dose wherein the amount of RNA administered in the first dose differs from that administered in the second dose.

In some embodiments, a vaccination regimen comprises a first dose and a second dose, wherein the amount of RNA administered in the first dose is less than that administered in the second dose. In some embodiments, the amount of RNA administered in the first dose is 10%-90% of the second dose. In some embodiments, the amount of RNA administered in the first dose is 10%-50% of the second dose. In some embodiments, the amount of RNA administered in the first dose is 10%-20% of the second dose. In some embodiments, the first dose and the second dose are administered at least 2 weeks apart, including, at least 3 weeks apart, at least 4 weeks apart, at least 5 weeks apart, at least 6 weeks apart or longer. In some embodiments, the first dose and the second dose are administered at least 3 weeks apart.

In some embodiments, a first dose comprises less than about 30 ug of RNA and a second dose comprises at least about 30 ug of RNA. In some embodiments, a first dose comprises about 1 to less than about 30 ug of RNA (e.g., about 0.1, about 1, about 3, about 5, about 10, about 15, about 20, about 25, or less than about 30 ug of RNA) and a second dose comprises about 30 to about 100 ug of RNA (e.g., about 30, about 40, about 50, or about 60 ug of RNA). In some embodiments, a first dose comprises about 1 to about 20 ug of RNA, about 1 to about 10 ug of RNA, or about 1 to about 5 ug of RNA and a second dose comprises about 30 to about 60 ug of RNA.

In some embodiments, a first dose comprises about 1 to about 10 ug of RNA (e.g., about 1, about 2, about 3, about 4, about 5, about 6, about 7, about 8, about 9, or about 10 ug of RNA) and a second dose comprises about 30 to about 60 ug of RNA (e.g., about 30, about 35, about 40, about 45, about 50, about 55, or about 60 ug of RNA).

In some embodiments, a first dose comprises about 1 ug of RNA and a second dose comprises about 30 ug of RNA. In some embodiments, a first dose comprises about 3 ug of RNA and a second dose comprises about 30 ug of RNA. In some embodiments, a first dose comprises about 5 ug of RNA and a second dose comprises about 30 ug of RNA. In some embodiments, a first dose comprises about 10 ug of RNA and a second dose comprises about 30 ug of RNA. In some embodiments, a first dose comprises about 15 ug of RNA and a second dose comprises about 30 ug of RNA.

In some embodiments, a first dose comprises about 1 ug of RNA and a second dose comprises about 60 ug of RNA. In some embodiments, a first dose comprises about 3 ug of RNA and a second dose comprises about 60 ug of RNA. In some embodiments, a first dose comprises about 5 ug of RNA and a second dose comprises about 60 ug of RNA. In some embodiments, a first dose comprises about 6 ug of RNA and a second dose comprises about 60 ug of RNA. In some embodiments, a first dose comprises about 10 ug of RNA and a second dose comprises about 60 ug of RNA. In some embodiments, a first dose comprises about 15 ug of RNA and a second dose comprises about 60 ug of RNA. In some embodiments, a first dose comprises about 20 ug of RNA and a second dose comprises about 60 ug of RNA. In some embodiments, a first dose comprises about 25 ug of RNA and a second dose comprises about 60 ug of RNA. In some embodiments, a first dose comprises about 30 ug of RNA and a second dose comprises about 60 ug of RNA.

In some embodiments, a first dose comprises less than about 10 ug of RNA and a second dose comprises at least about 10 ug of RNA. In some embodiments, a first dose comprises about 0.1 to less than about 10 ug of RNA (e.g., about 0.1, about 0.5, about 1, about 2, about 3, about 4, about 5, about 6, about 7, about 8, or less than about 10 ug of RNA) and a second dose comprises about 10 to about 30 ug of RNA (e.g., about 10, about 15, about 20, about 25, or about 30 ug of RNA). In some embodiments, a first dose comprises about 0.1 to about 10 ug of RNA, about 1 to about 5 ug of RNA, or about 0.1 to about 3 ug of RNA and a second dose comprises about 10 to about 30 ug of RNA.

In some embodiments, a first dose comprises about 0.1 to about 5 ug of RNA (e.g., about 0.1, about 0.5, about 1, about 2, about 3, about 4, about 5ug of RNA) and a second dose comprises about 10 to about 20 ug of RNA (e.g., about 10, about 12, about 14, about 16, about 18, about 20 ug of RNA).

In some embodiments, a first dose comprises about 0.1 ug of RNA and a second dose comprises about 10 ug of RNA. In some embodiments, a first dose comprises about 0.3 ug of RNA and a second dose comprises about 10 ug of RNA. In some embodiments, a first dose comprises about 1 ug of RNA and a second dose comprises about 10 ug of RNA. In some embodiments, a first dose comprises about 3 ug of RNA and a second dose comprises about 10 ug of RNA.

In some embodiments, a first dose comprises less than about 3 ug of RNA and a second dose comprises at least about 3 ug of RNA. In some embodiments, a first dose comprises about 0.1 to less than about 3 ug of RNA (e.g., about 0.1, about 0.2, about 0.3, about 0.5, about 0.6, about 0.7, about 0.8, about 0.9, about 1.0, about 1.5, about 2.0, or about 2.5 ug of RNA) and a second dose comprises about 3 to about 10 ug of RNA (e.g., about 3, about 4, about 5, about 6, or about 7, about 8, about 9, or about 10 ug of RNA). In some embodiments, a first dose comprises about 0.1 to about 3 ug of RNA, about 0.1 to about 1 ug of RNA, or about 0.1 to about 0.5 ug of RNA and a second dose comprises about 3 to about 10 ug of RNA.

In some embodiments, a first dose comprises about 0.1 to about 1.0 ug of RNA (e.g., about 0.1, about 0.2, about 0.3, about 0.4, about 0.5, about 0.6, about 0.7, about 0.8, about 0.9, or about 1.0 ug of RNA) and a second dose comprises about 1 to about 3 ug of RNA (e.g., about 1.0, about 1.5, about 2.0, about 2.5, or about 3.0 ug of RNA).

In some embodiments, a first dose comprises about 0.1 ug of RNA and a second dose comprises about 3 ug of RNA. In some embodiments, a first dose comprises about 0.3 ug of RNA and a second dose comprises about 3 ug of RNA. In some embodiments, a first dose comprises about 0.5 ug of RNA and a second dose comprises about 3 ug of RNA. In some embodiments, a first dose comprises about 1 ug of RNA and a second dose comprises about 3 ug of RNA.

In some embodiments, a vaccination regimen comprises a first dose and a second dose, wherein the amount of RNA administered in the first dose is greater than that administered in the second dose. In some embodiments, the amount of RNA administered in the second dose is 10%-90% of the first dose. In some embodiments, the amount of RNA administered in the second dose is 10%-50% of the first dose. In some embodiments, the amount of RNA administered in the second dose is 10%-20% of the first dose. In some embodiments, the first dose and the second dose are administered at least 2 weeks apart, including, at least 3 weeks apart, at least 4 weeks apart, at least 5 weeks apart, at least 6 weeks apart or longer. In some embodiments, the first dose and the second dose are administered at least 3 weeks apart In some embodiments, a first dose comprises at least about 30 ug of RNA and a second dose comprises less than about 30 ug of RNA. In some embodiments, a first dose comprises about 30 to about 100 ug of RNA (e.g., about 30, about 40, about 50, or about 60 ug of RNA) and a second dose comprises about 1 to about 30 ug of RNA (e.g., about 0.1, about 1, about 3, about 5, about 10, about 15, about 20, about 25, or about 30 ug of RNA). In some embodiments, a second dose comprises about 1 to about 20 ug of RNA, about 1 to about 10 ug of RNA, or about 1 to 5 ug of RNA. In some embodiments, a first dose comprises about 30 to about 60 ug of RNA and a second dose comprises about 1 to about 20 ug of RNA, about 1 to about 10 ug of RNA, or about 0.1 to about 3 ug of RNA.

In some embodiments, a first dose comprises about 30 to about 60 ug of RNA (e.g., about 30, about 35, about 40, about 45, about 50, about 55, or about 60 ug of RNA) and a second dose comprises about 1 to about 10 ug of RNA (e.g., about 1, about 2, about 3, about 4, about 5, about 6, about 7, about 8, about 9, or about 10 ug of RNA).

In some embodiments, a first dose comprises about 30 ug of RNA and a second dose comprises about 1 ug of RNA. In some embodiments, a first dose comprises about 30 ug of RNA and a second dose comprises about 3 ug of RNA. In some embodiments, a first dose comprises about 30 ug of RNA and a second dose comprises about 5 ug of RNA. In some embodiments, a first dose comprises about 30 ug of RNA and a second dose comprises about 10 ug of RNA. In some embodiments, a first dose comprises about 30 ug of RNA and a second dose comprises about 15 ug of RNA.

In some embodiments, a first dose comprises about 60 ug of RNA and a second dose comprises about 1 ug of RNA. In some embodiments, a first dose comprises about 60 ug of RNA and a second dose comprises about 3 ug of RNA. In some embodiments, a first dose comprises about 60 ug of RNA and a second dose comprises about 5 ug of RNA. In some embodiments, a first dose comprises about 60 ug of RNA and a second dose comprises about 6 ug of RNA. In some embodiments, a first dose comprises about 60 ug of RNA and a second dose comprises about 10 ug of RNA. In some embodiments, a first dose comprises about 60 ug of RNA and a second dose comprises about 15 ug of RNA. In some embodiments, a first dose comprises about 60 ug of RNA and a second dose comprises about 20 ug of RNA. In some embodiments, a first dose comprises about 60 ug of RNA and a second dose comprises about 25 ug of RNA. In some embodiments, a first dose comprises about 60 ug of RNA and a second dose comprises about 30 ug of RNA.

In some embodiments, a first dose comprises at least about 10 ug of RNA and a second dose comprises less than about 10 ug of RNA. In some embodiments, a first dose comprises about 10 to about 30 ug of RNA (e.g., about 10, about 15, about 20, about 25, or about 30 ug of RNA) and a second dose comprises about 0.1 to less than about 10 ug of RNA (e.g., about 0.1, about 0.5, about 1, about 2, about 3, about 4, about 5, about 6, about 7, about 8, or less than about 10 ug of RNA). In some embodiments, a first dose comprises about 10 to about 30 ug of RNA, or about 0.1 to about 3 ug of RNA and a second dose comprises about 1 to about 10 ug of RNA, or about 1 to about 5 ug of RNA.

In some embodiments, a first dose comprises about 10 to about 20 ug of RNA (e.g., about 10, about 12, about 14, about 16, about 18, about 20 ug of RNA) and a second dose comprises about 0.1 to about 5 ug of RNA (e.g., about 0.1, about 0.5, about 1, about 2, about 3, about 4, or about 5 ug of RNA).

In some embodiments, a first dose comprises about 10 ug of RNA and a second dose comprises about 0.1 ug of RNA. In some embodiments, a first dose comprises about 10 ug of RNA and a second dose comprises about 0.3 ug of RNA. In some embodiments, a first dose comprises about 10 ug of RNA and a second dose comprises about 1 ug of RNA. In some embodiments, a first dose comprises about 10 ug of RNA and a second dose comprises about 3 ug of RNA.

In some embodiments, a first dose comprises at least about 3 ug of RNA and a second dose comprises less than about 3 ug of RNA. In some embodiments, a first dose comprises about 3 to about 10 ug of RNA (e.g., about 3, about 4, about 5, about 6, or about 7, about 8, about 9, or about 10 ug of RNA) and a second dose comprises 0.1 to less than about 3 ug of RNA (e.g., about 0.1, about 0.2, about 0.3, about 0.5, about 0.6, about 0.7, about 0.8, about 0.9, about 1.0, about 1.5 about 2.0, or about 2.5 ug of RNA). In some embodiments, a first dose comprises about 3 to about 10 ug of RNA and a second dose comprises about 0.1 to about 3 ug of RNA, about 0.1 to about 1 ug of RNA, or about 0.1 to about 0.5 ug of RNA.

In some embodiments, a first dose comprises about 1 to about 3 ug of RNA (e.g., about 1, about 1.5, about 2.0, about 2.5, or about 3.0 ug of RNA) and a second dose comprises about 0.1 to 0.3 ug of RNA (e.g., about 0.1, about 0.2, about 0.3, about 0.4, about 0.5, about 0.6, about 0.7, about 0.8, about 0.9, or about 1.0 ug of RNA).

In some embodiments, a first dose comprises about 3 ug of RNA and a second dose comprises about 0.1 ug of RNA. In some embodiments, a first dose comprises about 3 ug of RNA and a second dose comprises about 0.3 ug of RNA. In some embodiments, a first dose comprises about 3 ug of RNA and a second dose comprises about 0.6 ug of RNA. In some embodiments, a first dose comprises about 3 ug of RNA and a second dose comprises about 1 ug of RNA.

In some embodiments, a vaccination regimen comprises at least two doses, including, e.g., at least three doses, at least four doses or more. In some embodiments, a vaccination regimen comprises three doses. In some embodiments, the time interval between the first dose and the second dose can be the same as the time interval between the second dose and the third dose. In some embodiments, the time interval between the first dose and the second dose can be longer than the time interval between the second dose and the third dose, e.g., by days or weeks (including, e.g., at least 3 days, at least 4 days, at least 5 days, at least 6 days, at least 1 week, at least 2 weeks, at least 3 weeks, at least 4 weeks, at least 5 weeks, at least 6 weeks, or longer). In some embodiments, the time interval between the first dose and the second dose can be shorter than the time interval between the second dose and the third dose, e.g., by days or weeks (including, e.g., at least 3 days, at least 4 days, at least 5 days, at least 6 days, at least 1 week, at least 2 weeks, at least 3 weeks, at least 4 weeks, at least 5 weeks, at least 6 weeks, or longer). In some embodiments, the time interval between the first dose and the second dose can be shorter than the time interval between the second dose and the third dose, e.g., by at least 1 month (including, e.g., at least 2 months, at least 3 months, at least 4 months, at least 5 months, at least 6 months, at least 7 months, at least 8 months, at least 9 months, at least 10 months, at least 11 months, at least 12 months, or longer).

In some embodiments, a last dose of a primary regimen and a first dose of a booster regimen are given at least 2 months, at least 3 months, at least 4 months, at least 5 months, at least 6 months, at least 7 months, at least 8 months, at least 9 months, at least 10 months, at least 11 months, at least 12 months, or more apart. In some embodiments, a primary regimen may comprises two doses. In some embodiments, a primary regimen may comprises three doses.

In some embodiments, a first dose and a second dose (and/or other subsequent dose) may be administered by intramuscular injection. In some embodiments, a first dose and a second dose (and/or other subsequent dose) may be administered in the deltoid muscle. In some embodiments, a first dose and a second dose (and/or other subsequent dose) may be administered in the same arm.

In some embodiments, an RNA (e.g., mRNA) composition described herein is administered (e.g., by intramuscular injection) as a series of two doses (e.g., 0.3 mL each) 21 days apart. In some embodiments, an RNA (e.g., mRNA) composition described herein is administered (e.g., by intramuscular injection) as a series of two doses (e.g., 0.2 mL each) 21 days apart. In some embodiments, an RNA (e.g., mRNA) composition described herein is administered (e.g., by intramuscular injection) as a series of three doses (e.g., 0.3 mL or lower including, e.g., 0.2 mL), wherein doses are given at least 3 weeks apart. In some embodiments, the first and second doses may be administered 3 weeks apart, while the second and third doses may be administered at a longer time interval than that between the first and the second doses, e.g., at least 4 weeks apart or longer (including, at least 5 weeks, at least 6 weeks, at least 7 weeks, at least 8 weeks, at least 9 weeks, or longer). In some embodiments, each dose is about 60 ug. In some embodiments, each dose is about 50 ug. In some embodiments, each dose is about 30 ug. In some embodiments, each dose is about 25 ug. In some embodiments, each dose is about 20 ug. In some embodiments, each dose is about 15 ug. In some embodiments, each dose is about 10 ug. In some embodiments, each dose is about 3 ug.

In some embodiments, at least one dose given in a vaccination regimen (e.g., a primary vaccination regimen and/or a booster vaccination regimen) is about 60 ug. In some embodiments, at least one dose given in a vaccination regimen (e.g., a primary vaccination regimen and/or a booster vaccination regimen) is about 50 ug. In some embodiments, at least one dose given in a vaccination regimen (e.g., a primary vaccination regimen and/or a booster vaccination regimen) is about 30 ug. In some embodiments, at least one dose given in a vaccination regimen (e.g., a primary vaccination regimen and/or a booster vaccination regimen) is about 25 ug. In some embodiments, at least one dose given in a vaccination regimen (e.g., a primary vaccination regimen and/or a booster vaccination regimen) is about 20 ug. In some embodiments, at least one dose given in a vaccination regimen (e.g., a primary vaccination regimen and/or a booster vaccination regimen) is about 15 ug. In some embodiments, at least one dose given in a vaccination regimen (e.g., a primary vaccination regimen and/or a booster vaccination regimen) is about 10 ug. In some embodiments, at least one dose given in a vaccination regimen (e.g., a primary vaccination regimen and/or a booster vaccination regimen) is about 3 ug.

In one embodiment, an amount of the RNA described herein of about 60 μg is administered per dose. In one embodiment, an amount of the RNA described herein of about 50 μg is administered per dose. In one embodiment, an amount of the RNA described herein of about 30 μg is administered per dose. In one embodiment, an amount of the RNA described herein of about 25 μg is administered per dose. In one embodiment, an amount of the RNA described herein of about 20 μg is administered per dose. In one embodiment, an amount of the RNA described herein of about 15 μg is administered per dose. In one embodiment, an amount of the RNA described herein of about 10 μg is administered per dose. In one embodiment, an amount of the RNA described herein of about 5 μg is administered per dose. In one embodiment, an amount of the RNA described herein of about 3 μg is administered per dose.

In one embodiment, at least two of such doses are administered. For example, a second dose may be administered about 21 days following administration of the first dose.

In some embodiments, the efficacy of the RNA vaccine described herein (e.g., administered in two doses, wherein a second dose may be administered about 21 days following administration of the first dose, and administered, for example, in an amount of about 30 μg per dose) is at least 70%, at least 80%, at least 90, or at least 95% beginning 7 days after administration of the second dose (e.g., beginning 28 days after administration of the first dose if a second dose is administered 21 days following administration of the first dose). In some embodiments, such efficacy is observed in populations of age of at least 50, at least 55, at least 60, at least 65, at least 70, or older. In some embodiments, the efficacy of the RNA vaccine described herein (e.g., administered in two doses, wherein a second dose may be administered about 21 days following administration of the first dose, and administered, for example, in an amount of about 30 μg per dose) beginning 7 days after administration of the second dose (e.g., beginning 28 days after administration of the first dose if a second dose is administered 21 days following administration of the first dose) in populations of age of at least 65, such as 65 to 80, 65 to 75, or 65 to 70, is at least 90%, at least 91%, at least 92%, at least 93%, at least 94%, or at least 95%. Such efficacy may be observed over time periods of up to 1 month, 2 months, 3 months, 6 months or even longer.

In one embodiment, vaccine efficacy is defined as the percent reduction in the number of subjects with evidence of infection (vaccinated subjects vs. non-vaccinated subjects).

In one embodiment, efficacy is assessed through surveillance for potential cases of COVID-19. If, at any time, a patient develops acute respiratory illness, for the purposes herein, the patient can be considered to potentially have COVID-19 illness. The assessments can include a nasal (midturbinate) swab, which may be tested using a reverse transcription-polymerase chain reaction (RT-PCR) test to detect SARS-CoV-2. In addition, clinical information and results from local standard-of-care tests can be assessed.

In some embodiments, efficacy assessments may utilize a definition of SARS-CoV-2-related cases wherein:

Confirmed COVID-19: presence of at least 1 of the following symptoms and SARS-CoV-2 NAAT (nucleic acid amplification-based test) positive during, or within 4 days before or after, the symptomatic period: fever; new or increased cough; new or increased shortness of breath; chills; new or increased muscle pain; new loss of taste or smell; sore throat; diarrhea; vomiting. Alternatively or additionally, in some embodiments, efficacy assessments may utilize a definition of SARS-CoV-2-related cases wherein one or more of the following additional symptoms defined by the CDC can be considered: fatigue; headache; nasal congestion or runny nose; nausea.

In some embodiments, efficacy assessments may utilize a definition of SARS-CoV-2-related severe cases Confirmed severe COVID-19: confirmed COVID-19 and presence of at least 1 of the following: clinical signs at rest indicative of severe systemic illness (e.g., RR 30 breaths per minute, HR 2125 beats per minute, $SpO_2$593% on room air at sea level, or $PaO_2/FiO_2$<300 mm Hg); respiratory failure (which can be defined as needing high-flow oxygen, noninvasive ventilation, mechanical ventilation, or ECMO); evidence of shock (e.g., SBP <90 mm Hg, DBP <60 mm Hg, or requiring vasopressors); significant acute renal, hepatic, or neurologic dysfunction; admission to an ICU; death.

Alternatively or additionally, in some embodiments a serological definition can be used for patients without clinical presentation of COVID-19: e.g., confirmed seroconversion to SARS-CoV-2 without confirmed COVID-19: e.g., positive N-binding antibody result in a patient with a prior negative N-binding antibody result.

In some embodiments, any or all of the following assays can be performed on serum samples: SARS-CoV-2 neutralization assay; S1-binding IgG level assay; RBD-binding IgG level assay; N-binding antibody assay.

In one embodiment, methods and agents described herein are administered to a paediatric population. In various embodiments, the paediatric population comprises or consists of subjects under 18 years, e.g., 5 to less than 18 years of age, 12 to less than 18 years of age, 16 to less than 18 years of age, 12 to less than 16 years of age, 5 to less than 12 years of age, or 6 months to less than 12 years of age. In various embodiments, the paediatric population comprises or consists of subjects under 5 years, e.g., 2 to less than 5 years of age, 12 to less than 24 months of age, 7 to less than 12 months of age, or less than 6 months of age. In some such embodiments, an RNA (e.g., mRNA) composition described herein is administered to subjects of less than 2 years old, for example, 6 months to less than 2 years old. In some such embodiments, an RNA (e.g., mRNA) composition described herein is administered to subjects of less than 6 months old, for example, 1 month to less than 4 months old. In some embodiments, a dosing regimen (e.g., doses and/or dosing schedule) for a paediatric population may vary for different age groups. For example, in some embodiments, a subject 6 months through 4 years of age may be administered according to a primary regimen comprising at least three doses, in which the initial two doses are administered at least 3 weeks (including, e.g., at least 4 weeks, at least 5 weeks, at least 6 weeks, or longer) apart followed by a third dose administered at least 8 weeks (including, e.g., at least 9 weeks, at least 10 weeks, at least 11 weeks, at least 12 weeks, or longer) after the second dose. In some such embodiments, at least one dose administered is 3 ug RNA described herein. In some embodiments, a subject 5 years of age and older may be administered according to a primary regimen comprising at least two doses, in which the two doses are administered at least 3 weeks (including, e.g., at least 3 weeks, at least 4 weeks, at least 5 weeks, at least 6 weeks, or longer) apart. In some such embodiments, at least one dose administered is 10 ug RNA described herein. In some embodiments, a subject 5 years of age and older who are immunocompromised (e.g., in some embodiments subjects who have undergone solid organ transplantation, or who are diagnosed with conditions that are considered to have an equivalent of immunocompromise) may be administered according to a primary regimen comprising at least three doses, in which the initial two doses are administered at least 3 weeks (including, e.g., at least 3 weeks, at least 4 weeks, at least 5 weeks, at least 6 weeks, or longer) apart, followed by a third dose administered at least 4 weeks (including, e.g., at least 5 weeks, at least 6 weeks, at least 7 weeks, at least 8 weeks, at least 9 weeks, at least 10 weeks, at least 11 weeks, at least 12 weeks, or longer) after the second dose.

In some embodiments, an RNA (e.g., mRNA) composition described herein is administered to subjects of age 12 or older and each dose is about 30 ug. In some embodiments, an RNA (e.g., mRNA) composition described herein is administered to subjects of age 12 or older (including, e.g., age 18 or older) and each dose is higher than 30 ug, including, e.g., 35 ug, 40 ug, 45 ug, 50 ug, 55 ug, 60 ug, 65 ug, 70 ug, or higher. In some such embodiments, an RNA (e.g., mRNA) composition described herein is administered to subjects of age 12 or older and each dose is about 60 ug. In some such embodiments, an RNA (e.g., mRNA) composition described herein is administered to subjects of age 12 or older and each dose is about 50 ug. In one embodiment, the paediatric population comprises or consists of subjects 12 to less than 18 years of age including subjects 16 to less than 18 years of age and/or subjects 12 to less than 16 years of age. In this embodiment, treatments may comprise 2 vaccinations 21 days apart, wherein, in one embodiment, the vaccine is administered in an amount of 30 μg RNA per dose, e.g., by intramuscular administration. In some embodiments, higher doses are administered to older pediatric patients and adults, e.g., to patients 12 years or older, compared to younger children or infants, e.g. 2 to less than 5 years old, 6 months to less than 2 years old, or less than 6 months old. In some embodiments, higher doses are administered to children who are 2 to less than 5 years old, as compared to toddlers and/or infants, e.g., who are 6 months to less than 2 years old, or less than 6 months old.

In one embodiment, the paediatric population comprises or consists of subjects 5 to less than 18 years of age including subjects 12 to less than 18 years of age and/or subjects 5 to less than 12 years of age. In this embodiment, treatments may comprise 2 vaccinations 21 days apart, wherein, in various embodiments, the vaccine is administered in an amount of 10 μg, 20 μg, or 30 μg RNA per dose, e.g., by intramuscular administration. In some such embodiments, an RNA (e.g., mRNA) composition described herein is administered to subjects of age 5 to 11 and each dose is about 10 ug In some embodiments, each dose comprises about 5 ug of RNA encoding a SARS-CoV-2 S protein of a first variant and about 5 ug of RNA encoding a SARS-CoV-2 S protein of a second variant. In some embodiments, each dose comprises about 5 ug of RNA encoding a SARS-CoV-2 S protein of a Wuhan strain and about 5 ug of RNA encoding a SARS-CoV-2 S protein of an Omicron variant. In some embodiments, each dose comprises about 5 ug of RNA encoding a SARS-CoV-2 S protein of a Wuhan strain (e.g., RNA comprising SEQ ID NO: 20) and about 5 ug of RNA encoding a SARS-CoV-2 S protein of a BA.1 Omicron variant (e.g., RNA comprising SEQ ID NO: 51). In some embodiments, each dose comprises about 5 ug of RNA encoding a SARS-CoV-2 S protein of a Wuhan strain (e.g., RNA comprising SEQ ID NO: 20) and about 5 ug of RNA encoding a SARS-CoV-2 S protein of a BA.4/5 Omicron variant (e.g., RNA comprising SEQ ID NO: 72).

In one embodiment, the paediatric population comprises or consists of subjects less than 5 years of age including subjects 2 to less than 5 years of age, subjects 12 to less than 24 months of age, subjects 7 to less than 12 months of age, subjects 6 to less than 12 months of age and/or subjects less than 6 months of age. In this embodiment, treatments may comprise 2 vaccinations, e.g., 21 to 42 days apart, e.g., 21 days apart, wherein, in various embodiments, the vaccine is administered in an amount of 3 μg, 10 μg, 20 μg, or 30 μg RNA per dose, e.g., by intramuscular administration. In some such embodiments, an RNA (e.g., mRNA) composition described herein is administered to subjects of age 2 to less than 5 and each dose is about 3 ug. In some such embodiments, an RNA (e.g., mRNA) composition described herein is administered to subjects of about 6 months to less than about 5 years and each dose is about 3 ug.

In some embodiments, each dose comprises about 1.5 ug of RNA encoding a SARS-CoV-2 S protein of a first variant and about 1.5 ug of RNA encoding a SARS-CoV-2 S protein of a second variant. In some embodiments, each dose comprises about 1.5 ug of RNA encoding a SARS-CoV-2 S protein of a Wuhan strain and about 1.5 ug of RNA encoding a SARS-CoV-2 S protein of an Omicron variant. In some embodiments, each dose comprises about 1.5 ug of RNA encoding a SARS-CoV-2 S protein of a Wuhan strain (e.g., RNA comprising SEQ ID NO: 20) and about 1.5 ug of RNA encoding a SARS-CoV-2 S protein of a BA.1 Omicron variant (e.g., RNA comprising SEQ ID NO: 51). In some embodiments, each dose comprises about 1.5 ug of RNA encoding a SARS-CoV-2 S protein of a Wuhan strain (e.g., RNA comprising SEQ ID NO: 20) and about 1.5 ug of RNA encoding a SARS-CoV-2 S protein of a BA.4/5 Omicron variant (e.g., RNA comprising SEQ ID NO: 72).

In some embodiments, an RNA (e.g., mRNA) composition described herein is administered to subjects of age 12 or older and at least one dose given in a vaccination regimen (e.g., a primary vaccination regimen and/or a booster vaccination regimen) is about 60 ug. In some embodiments, an RNA (e.g., mRNA) composition described herein is administered to subjects of age 12 or older and at least one dose given in a vaccination regimen (e.g., a primary vaccination regimen and/or a booster vaccination regimen) is about 30 ug. In some embodiments, an RNA (e.g., mRNA) composition described herein is administered to subjects of age 12 or older and at least one dose given in a vaccination regimen (e.g., a primary vaccination regimen and/or a booster vaccination regimen) is about 15 ug. In some embodiments, an RNA (e.g., mRNA) composition described herein is administered to subjects of age 5 to less than 12 years of age and at least one dose given in a vaccination regimen (e.g., a primary vaccination regimen and/or a booster vaccination regimen) is about 10 ug. In some embodiments, an RNA (e.g., mRNA) composition described herein is administered to subjects of age 2 to less than 5 and at least one dose given in a vaccination regimen (e.g., a primary vaccination regimen and/or a booster vaccination regimen) is about 3 ug. In some embodiments, an RNA (e.g., mRNA) composition described herein is administered to subjects of 6 months to less than age 2 and at least one dose given in a vaccination regimen (e.g., a primary vaccination regimen and/or a booster vaccination regimen) is about 3 ug or lower, including, e.g., 2 ug, 1 ug, or lower). In some embodiments, an RNA (e.g., mRNA) composition described herein is administered to infants of less than 6 months and at least one dose given in a vaccination regimen (e.g., a primary vaccination regimen and/or a booster vaccination regimen) is about 3 ug or lower, including, e.g., 2 ug, 1 ug, 0.5 ug, or lower).

In some embodiments, an RNA (e.g., mRNA) composition described herein is administered (e.g., by intramuscular injection) as a single dose. In some embodiments, a single dose comprise a single RNA encoding a SARS-CoV-2 S protein or an immunogenic fragment thereof (e.g., an RBD domain). In some embodiments, a single dose comprise at least two RNAs described herein, for example, each RNA encoding a SARS-CoV-2 S protein or an immunogenic fragment thereof (e.g., an RBD domain) from different strains. In some embodiments, such at least two RNAs described herein can be administered as a single mixture. For example, in some such embodiments, two separate RNA compositions described herein can be mixed to generate a single mixture prior to injection. In some embodiments, such at least two RNAs described herein can be administered as two separate compositions, which, for example, can be administered at different injection sites (e.g., on different arms, or different sites on the same arm).

In some embodiments, a dose administered to subjects in need thereof may comprise administration of a single RNA (e.g., mRNA) composition described herein.

In some embodiments, a dose administered to subjects in need thereof may comprise administration of at least two or more (including, e.g., at least three or more) different drug products/formulations. For example, in some embodiments, at least two or more different drug products/formulations may comprise at least two different RNA (e.g., mRNA) compositions described herein (e.g., in some embodiments each comprising a different RNA construct).

In some embodiments, an RNA (e.g., mRNA) composition disclosed herein may be administered in conjunction with a vaccine targeting a different infectious agent. In some embodiments, the different infectious agent is one that increases the likelihood of a subject experiencing deleterious symptoms when coinfected with SARS-CoV-2 and the infectious agent. In some embodiments, the infectious agent is one that increases the infectivity of SARS-CoV-2 when a subject is coinfected with SARS-CoV-2 and the infectious agent. In some embodiments, at least one RNA (e.g., mRNA) composition described herein may be administered in combination with a vaccine that targets influenza. In some embodiments, at least two or more different drug products/formulations may comprise at least one RNA (e.g., mRNA)

composition described herein and a vaccine targeting a different infectious agent (e.g., an influenza vaccine). In some embodiments, different drug products/formulations are separately administered. In some embodiments, such different drug product/formulations are separately administered at the same time (e.g., at the same vaccination session) at different sites of a subject (e.g., at different arms of the subject).

In one embodiment, at least two doses are administered. For example, a second dose may be administered about 21 days following administration of the first dose.

In some embodiments, at least one single dose is administered. In some embodiments, such single dose is administered to subjects, for example, who may have previously received one or more doses of, or a complete regimen of, a SARS-CoV-2 vaccine (e.g., of a BNT162b2 vaccine [including, e.g., as described herein], an mRNA-1273 vaccine, an Ad26.CoV2.S vaccine, a ChAdxOx1 vaccine, an NVX-CoV2373 vaccine, a CvnCoV vaccine, a GAM-COVID0Vac vaccine, a CoronaVac vaccine, a BBIBP-CorV vaccine, an Ad5-nCoV vaccine, a zf2001 vaccine, a SCB-2019 vaccine, or other approved RNA (e.g., mRNA) or adenovector vaccines, etc. Alternatively or additionally, in some embodiments, a single dose is administered to subjects who have been exposed to and/or infected by SARS-CoV-2. In some embodiments, at least one single dose is administered to subjects who both have received one or more doses of, or a complete regimen of, a SARS-CoV-2 vaccine and have been exposed to and/or infected with SARS-CoV-2.

In some particular embodiments where at least one single dose is administered to subjects who have received one or more doses of a prior SARS-CoV-2 vaccine, such prior SARS-CoV-2 vaccine is a different vaccine, or a different form (e.g., formulation) and/or dose of a vaccine with the same active (e.g., BNT162b2); in some such embodiments, such subjects have not received a complete regimen of such prior vaccine and/or have experienced one or more undesirable reactions to or effects of one or more received doses of such prior vaccine. In some particular embodiments, such prior vaccine is or comprises higher dose(s) of the same active (e.g., BNT162b2). Alternatively or additionally, in some such embodiments, such subjects were exposed to and/or infected by SARS-CoV-2 prior to completion (but, in some embodiments, after initiation) of a full regimen of such prior vaccine..

In one embodiment, at least two doses are administered. For example, a second dose may be administered about 21 days following administration of the first dose.

In one embodiment, at least three doses are administered. In some embodiments, such third dose is administered a period of time after the second dose that is comparable to (e.g., the same as) the period of time between the first and second doses. For example, in some embodiments, a third dose may be administered about 21 days following administration of the second dose. In some embodiments, a third dose is administered after a longer period of time relative to the second dose than the second dose was relative to the first dose. In some embodiments, a three-dose regimen is administered to an immunocompromised patient, e.g., a cancer patient, an HIV patient, a patient who has received and/or is receiving immunosuppressant therapy (e.g., an organ transplant patient). In some embodiments, the length of time between the second and third dose (e.g., a second and third dose administered to an immunocompromised patient) is at least about 21 days (e.g., at least about 28 days).

In some embodiments, a vaccination regimen comprises administering the same amount of RNA in different doses (e.g., in first and/or second and/or third and/or subsequent doses). In some embodiments, a vaccination regimen comprises administering different amounts of RNA in different doses. In some embodiments, one or more later doses is larger than one or more earlier doses (e.g., in situations where waning of vaccine efficacy from one or more earlier doses is observed and/or immune escape by a variant (e.g., one described herein) that is prevalent or rapidly spreading is observed in a relevant jurisdiction at the time of administration is observed). In some embodiments, one or more later doses may be larger than one or more earlier doses by at least 30%, at least 40%, at least 50%, at least 60%, at least 70%, at least 80%, at least 90%, at least 95%, or higher, provided that safety and/or tolerability of such a dose is clinically acceptable. In some embodiments, one or more later doses may be larger than one or more earlier doses by at least 1.1-fold, at least 1.5-fold, at least 2-fold, at least 3-fold, at least 4-fold, or higher provided that safety and/or tolerability of such a dose is clinically acceptable. In some embodiments, one or more later doses is smaller than one or more earlier doses (e.g., in a negative reaction was experienced after one or more earlier doses and/or if exposure to and/or infection by SARS-CoV-2 between an earlier dose and a subsequent dose). In some embodiments, one or more later doses may be smaller than one or more earlier doses by at least 10%, at least 20%, at least 30%, at least 40%, at least 50%, at least 60%, or higher. In some embodiments, where different doses are utilized, they are related to one another by identity with and/or dilution of a common stock as described herein. In some embodiments, where at least two or more doses are administered (e.g., at least two doses administered in a primary regimen, at least two doses administered in a booster regimen, or at least one dose administered in a primary regimen and at least one dose in a booster regimen), the same RNA compositions described herein may be administered in such doses and each of such doses can be the same or different (as described herein). In some embodiments, where at least two or more doses are administered (e.g., at least two doses administered in a primary regimen, at least two doses administered in a booster regimen, or at least one dose administered in a primary regimen and at least one dose in a booster regimen), different RNA compositions described herein (e.g., different encoded viral polypeptides, e.g., from different coronavirus clades, or from different strains of the same coronavirus clade; different construct elements such as 5' cap, 3' UTR, 5' UTR, etc.; different formulations, e.g., different excipients and/or buffers (e.g., PBS vs. Tris); different LNP compositions; or combinations thereof) may be administered in such doses and each of such doses can be the same or different (e.g., as described herein).

In some embodiments, a subject is administered two or more RNAs (e.g., as part of either a primary regimen or a booster regimen), wherein the two or more RNAs are administered on the same day or same visit. In some embodiments, the two or more RNAs are administered in separate compositions, e.g., by administering each RNA to a separate part of the subject (e.g., by intramuscular administration to different arms of the subject or to different sites of the same arm of the subject). In some embodiments, the two or more RNAs are mixed prior to administration (e.g., mixed immediately prior to administration, e.g., by the administering practitioner). In some embodiments, the two or more RNAs are formulated together (e.g., by (a) mixing separate populations of LNPs, each population comprising a different RNA; or (b) by mixing two or more RNAs prior to LNP formulation, so that each LNP comprises two or more RNAs). In some embodiments, the two or more RNAs comprise an RNA that encode a coronavirus S protein or immunogenic fragment thereof (e.g., RBD or other relevant domains) from one strain (e.g., Wuhan strain) and a variant that is prevalent or rapidly spreading in a relevant jurisdiction at the time of administration (e.g., a variant described herein). In some embodiments, such a variant is an Omicron variant (e.g., a BA.1, BA.2, or BA.3 variant). In some embodiments, the two or more RNAs comprise a first RNA and a second RNA that have been shown to elicit a broad immune response in subject. In some embodiments the two or more RNAs comprise an RNA encoding a SARS-CoV-2 S protein from a Wuhan strain and an RNA encoding a SARS-CoV-2 S protein from a BA.1 Omicron variant. In some embodiments the two or more RNAs comprise an RNA encoding a SARS-CoV-2 S protein from a Wuhan strain and an RNA encoding a SARS-CoV-2 S protein from a BA.2 Omicron variant. In some embodiments the two or more RNAs comprise an RNA encoding a SARS-CoV-2 S protein from a Wuhan strain and an RNA encoding a SARS-CoV-2 S protein from a BA.4 or BA.5 Omicron variant. In some embodiments the two or more RNAs comprise an RNA encoding a SARS-CoV-2 S protein from a BA.1 Omicron variant and an RNA encoding a SARS-CoV-2 S protein from a BA.2 Omicron variant. In some embodiments the two or more RNAs comprise an RNA encoding a SARS-CoV-2 S protein from a BA.1 Omicron variant and an RNA encoding a SARS-CoV-2 S protein from a BA.4 or BA.5 Omicron variant. In some embodiments the two or more RNAs comprise an RNA encoding a SARS-CoV-2 S protein from a BA.2 Omicron variant and an RNA encoding a SARS-CoV-2 S protein from a BA.4 or 5 Omicron variant. In some embodiments the two or more RNAs comprise an RNA encoding a SARS-CoV-2 S protein from a Wuhan strain, an alpha variant, a beta variant, or a delta variant, or sublineages derived therefrom; and an RNA encoding a SARS-CoV-2 S protein from a BA.2, BA.4 or 5 Omicron variant, or sublineages derived therefrom.

In some embodiments, a subject may be administered any one of combinations 1 to 66, listed in the below table. In some embodiments, such combinations can be administered using an LNP formulation, where the first RNA and the second RNA are encapsulated in the same LNP or in separate LNPs. In some embodiments, such combinations can be administered as separate LNP formulations (e.g., by administering at separate sites to a subject).

| Combination | SARS-CoV-2 S protein encoded by a first RNA[1] | SARS-CoV-2 S protein encoded by a second RNA[1] |
|---|---|---|
| 1 | Wuhan | Alpha |
| 2 | Wuhan | Beta |
| 3 | Wuhan | Delta |
| 4 | Wuhan | BA.1 |
| 5 | Wuhan | BA.2 |
| 6 | Wuhan | BA.2.12.1 |
| 7 | Wuhan | BA.3 |
| 8 | Wuhan | BA.4/5 |
| 9 | Wuhan | XBB |
| 10 | Wuhan | XBB variant (e.g., XBB.1, XBB.2, XBB.1.3) |
| 11 | Wuhan | BQ.1.1 |
| 12 | Alpha | Beta |
| 13 | Alpha | Delta |
| 14 | Alpha | BA.1 |
| 15 | Alpha | BA.2 |
| 16 | Alpha | BA.2.12.1 |
| 17 | Alpha | BA.3 |
| 18 | Alpha | BA.4/5 |
| 19 | Alpha | XBB |
| 20 | Alpha | XBB variant (e.g., XBB.1, XBB.2, XBB.1.3) |
| 21 | Alpha | BQ.1.1 |
| 22 | Beta | Delta |
| 23 | Beta | BA.1 |
| 24 | Beta | BA.2 |
| 25 | Beta | BA.2.12.1 |
| 26 | Beta | BA.3 |
| 27 | Beta | BA.4/5 |
| 28 | Beta | XBB |
| 29 | Beta | XBB variant (e.g., XBB.1, XBB.2, XBB.1.3) |
| 30 | Beta | BQ.1.1 |
| 31 | Delta | BA.1 |
| 32 | Delta | BA.2 |
| 33 | Delta | BA.2.12.1 |
| 34 | Delta | BA.3 |
| 35 | Delta | BA.4/5 |
| 36 | Delta | XBB |
| 37 | Delta | XBB variant (e.g., XBB.1, XBB.2, XBB.1.3) |
| 38 | Delta | BQ.1.1 |
| 39 | BA.1 | BA.2 |
| 40 | BA.1 | BA.2.12.1 |
| 41 | BA.1 | BA.3 |
| 42 | BA.1 | BA.4/5 |
| 43 | BA.1 | XBB |
| 44 | BA.1 | XBB variant (e.g., XBB.1, XBB.2, XBB.1.3) |
| 45 | BA.1 | BQ.1.1 |
| 46 | BA.2 | BA.2.12.1 |
| 47 | BA.2 | BA.3 |
| 48 | BA.2 | BA.4/5 |
| 49 | BA.2 | XBB |
| 50 | BA.2 | XBB variant (e.g., XBB.1, XBB.2, XBB.1.3) |
| 51 | BA.2 | BQ.1.1 |
| 52 | BA.2.12.1 | BA.3 |
| 53 | BA.2.12.1 | BA.4/5 |
| 54 | BA.2.12.1 | XBB |
| 55 | BA.2.12.1 | XBB variant (e.g., XBB.1, XBB.2, XBB.1.3) |
| 56 | BA.2.12.1 | BQ.1.1 |
| 57 | BA.3 | BA.4/5 |
| 58 | BA.3 | XBB |
| 59 | BA.3 | XBB variant (e.g., XBB.1, XBB.2, XBB.3) |
| 60 | BA.3 | BQ.1.1 |
| 61 | BA.4/5 | XBB |
| 62 | BA.4/5 | XBB variant (e.g., XBB.1, XBB.2, XBB.1.3) |
| 63 | BA.4/5 | BQ.1.1 |
| 64 | XBB | XBB variant (e.g., XBB.1, XBB.2, XBB.1.3) |
| 65 | XBB | BQ.1.1 |
| 66 | XBB variant (e.g., XBB.1, XBB.2, XBB.1.3) | BQ.1.1 |

[1]Listed RNAs encode a SARS-CoV-2 S protein having mutations characteristic of the indicated SARS-CoV-2 variant.

In some embodiments, a subject is administered a first RNA and a second RNA, each in the same amount (i.e., at a 1:1 ratio).

In some embodiments, a subject is administered a first RNA and a second RNA, each in a different amount. For example, in some embodiments, a subject is administered a first RNA in an amount that is 0.01 to 100 times that of a second RNA (e.g., wherein the amount of a first RNA is 0.01 to 50, 0.01 to 4, 0.01 to 30, 0.01 to 25, 0.01 to 20, 0.01 to 15, 0.01 to 10, 0.01 to 9, 0.01 to 8, 0.01 to 7, 0.01 to 6, 0.01 to 5, 0.01 to 4, 0.01 to 3, 0.01 to 2, 0.01 to 1.5, 1 to 50, 1 to 4, 1 to 30, 1 to 25, 1 to 20, 1 to 15, 1 to 10, 1 to 9, 1 to 8, 1 to 7, 1 to 6, 1 to 5, 1 to 4, 1 to 3, 1 to 2, or 1 to 1.5 times that of a second RNA). In some embodiments, a subject is administered a first RNA and a second RNA, wherein the concentration of the first RNA is 1 to 10 times that of the second RNA. In some embodiments, a subject is administered a first RNA and a second RNA, wherein the amount of the first RNA is 1 to 5 times that of the second RNA. In some embodiments, a subject is administered a first RNA and a second RNA, wherein the concentration of the first RNA is 1 to 3 times that of the second RNA. In some embodiments, a subject is administered a first RNA and a second RNA, wherein the amount of the first RNA is 2 times that of the second RNA. In some embodiments, a subject is administered a first RNA and a second RNA, wherein the concentration of the first RNA is 3 times that of the second RNA.

In some embodiments, a subject is administered three RNAs, each encoding a SARS-CoV-2 S protein comprising one or more mutations characteristic of a different SARS-CoV-2 variant, and each in the same amount (i.e., at a 1:1:1 ratio).

In some embodiments, a subject is administered three RNAs, each encoding a SARS-CoV-2 S protein comprising one or more mutations characteristic of a different SARS-CoV-2 variant, wherein the amount of each RNA is not the same (e.g., one RNA is present in an amount that is different than the other two RNA, or all three RNAs are present in different amounts). For example, in some embodiments, the ratio of first RNA:second RNA:third RNA is 1:0.01-100:0.01-100 (e.g., 1:0.01-50:0.01-50; 1:0.01-40:0.01-40; 1:0.01-30:0.01-25; 1:0.01-25:0.01-25; 1:0.01-20:0.01-20; 1:0.01-15:0.01-15; 1:0.01-10:0.01-9; 1:0.01-9:0.01-9; 1:0.01-8: 0.01-8; 1:0.01-7:0.01-7; 1:0.01-6:0.01-6; 1:0.01-5:0.01-5; 1:0.01-4:0.01-4; 1:0.01-3:0.01-3; 1:0.01-2:0.01-2; or 1:0.01-1.5:0.01-1.5). In some embodiments, a subject is administered three RNAs at a ratio of 1:1:3. In some embodiments, a subject is administered three RNAs at a ratio of 1:3:3.

In some embodiments, a vaccination regimen comprises a first vaccination regimen (e.g., a primary regimen) that includes at least two doses of an RNA composition as described herein, e.g., wherein the second dose may be administered about 21 days following administration of the first dose, and a second vaccination (e.g., a booster regimen) that comprises a single dose or multiple doses, e.g., two doses, of an RNA composition as described herein. In some embodiments, doses of a booster regimen are related to those of a primary regimen by identity with or dilution from a common stock as described herein. In various embodiments, a booster regimen is administered (e.g., is initiated) at least 1 week, at least 2 weeks, at least 3 weeks, at least 1 month, at least 2 months, at least 3 months, at least 4 months, at least 5 months, or at least 6 months, at least 7 months, at least 8 months, at least 9 months, at least 10 months, at least 11 months, at least 12 months, or longer, after administration of a primary regimen, e.g., after completion of a primary regimen comprising at least two doses. In various embodiments, a booster regimen is administered (e.g., is initiated) 1-12 months, 2-12 months, 3-12 months, 4-12 months, 6-12 months, 1-6 months, 1-5 months, 1-4 months, 1-3 months, or 2-3 months after administration of a primary regimen, e.g., after completion of a primary regimen comprising at least two doses. In various embodiments, a booster regimen is administered (e.g., is initiated) 1 to 60 months, 2 to 48 months, 2 to 24 months, 3 to 24 months, 6 to 18 months, 6 to 12 months, or 5 to 7 months after administration of a primary regimen, e.g., after completion of a two-dose primary regimen. In some embodiments, each dose of a primary regimen is about 60 μg per dose. In some embodiments, each dose of a primary regimen is about 50 μg per dose. In some embodiments, each dose of a primary regimen is about 30 μg per dose. In some embodiments, each dose of a primary regimen is about 25 μg per dose. In some embodiments, each dose of a primary regimen is about 20 μg per dose. In some embodiments, each dose of a primary regimen is about 15 μg per dose. In some embodiments, each dose of a primary regimen is about 10 μg per dose. In some embodiments, each dose of a primary regimen is about 3 μg per dose. In some embodiments, each dose of a booster regimen is the same as that of the primary regimen. In some embodiments, each dose of a booster regimen comprises the same amount of RNA as a dose administered in a primary regimen. In some embodiments, at least one dose of a booster regimen is the same as that of the primary regimen. In some embodiments, at least one dose of a booster regimen comprises the same amount of RNA as at least one dose of a primary regimen. In some embodiments, at least one dose of a booster regimen is lower than that of the primary regimen. In some embodiments, at least one dose of a booster regimen comprises an amount of RNA that is lower than that of a primary regimen. In some embodiments, at least one dose of a booster regimen is higher than that of the primary regimen. In some embodiments, at least one dose of a booster regimen comprises an amount of RNA that is higher than that of a primary regimen.

In some embodiments, a booster regimen (e.g., as described herein) is administered to a pediatric patient (e.g., a patient aged 2 through 5 years old, a patient aged 5 through 11 years old, or a patient aged 12 through 15 years old). In some embodiments, a booster regimen is administered to a pediatric patient who is 6 months old to less than 2 years old. In some embodiments, a booster regimen is administered to a pediatric patient who is less than 6 months old. In some embodiments, a booster regimen is administered to a pediatric patient who is 6 months old to less than 5 years old. In some embodiments, a booster regimen is administered to a pediatric patient who is 2 years old to less than 5 years old. In some embodiments, a booster regimen is administered to a pediatric patient who is 5 years old to less than 12 years old. In some embodiments, a booster regimen is administered to a pediatric patient who is 12 years old to less than 16 years old. In some embodiments, each dose of a pediatric booster regimen comprises about 3 μg of RNA. In some embodiments, each dose of a pediatric booster regimen comprises about 10 μg of RNA. In some embodiments, each dose of a pediatric booster regimen comprises about 15 μg of RNA. In some embodiments, each dose of a pediatric booster regimen comprises about 20 μg of RNA. In some embodiments, each dose of a pediatric booster regimen comprises about 25 μg of RNA. In some embodiments, each dose of a pediatric booster regimen comprises about 30 μg of RNA. In some embodiments, a booster regimen is administered to a non-pediatric patient (e.g., a patient 16 years or older, a patient aged 18 through 64 years old, and/or a patient 65 years and older). In some embodiments, each dose of a non-pediatric booster regimen comprises about 3 ug of RNA, about 10 ug of RNA, about 25 μg or RNA, about 30 μg of RNA, about 40 μg of RNA, about 45 μg of RNA, about 50 μg of RNA, about 55 μg of RNA, or about 60 μg of RNA. In some embodiments, the same booster regimen may be administered to both pediatric and non-pediatric patients (e.g., to a patient 12 years or older). In some embodiments, a booster regimen that is administered to a non-pediatric patient is administered in a formulation and dose that is related to that of a primary regimen previously received by the patient by identity with or by dilution as described herein. In some embodiments, a non-pediatric patient who receives a booster regimen at a lower dose than a primary regimen may have experienced an adverse reaction to one or more doses of such primary regimen and/or may have been exposed to and/or infected by SARS-CoV-2 between such primary regimen and such booster regimen, or between doses of such primary regimen and/or of such booster regimen. In some embodiments, pediatric and non-pediatric patients may receive a booster regimen at a higher dose than a primary regimen when waning of vaccine efficacy at lower doses is observed, and/or when immune escape of a variant that is prevalent and/or spreading rapidly at a relevant jurisdiction at the time of administration is observed.

In some embodiments one or more doses of a booster regimen differs from that of a primary regimen. For example, in some embodiments, an administered dose may correspond to a subject's age and a patient may age out of one treatment age group and into a next. Alternatively or additionally, in some embodiments, an administered dose may correspond to a patient's condition (e.g., immunocompromised state) and a different dose may be selected for one or more doses of a booster regimen than for a primary regimen (e.g., due to intervening cancer treatment, infection with HIV, receipt of immunosuppressive therapy, for example associated with an organ transplant. In some embodiments, at least one dose of a booster regimen may comprise an amount of RNA that is higher than at least one dose administered in a primary regimen (e.g., in situations where waning of vaccine efficacy from one or more earlier doses is observed and/or immune escape by a variant (e.g., one described herein) that is prevalent or rapidly spreading is observed in a relevant jurisdiction at the time of administration).

In some embodiments, a primary regimen may involve one or more 3 ug doses and a booster regimen may involve one or more 10 ug doses, and/or one or more 20 ug doses, or one or more 30 ug doses. In some embodiments, a primary regimen may involve one or more 3 ug doses and a booster regimen may involve one or more 3 ug doses. In some embodiments, a primary regimen may involve two or more 3 ug doses (e.g., at least two doses, each comprising 3 ug of RNA, and administered about 21 days after one another) and a booster regimen may involve one or more 3 ug doses. In some embodiments, a primary regimen may involve one or more 10 ug doses and a booster regimen may involve one or more 20 ug doses, and/or one or more 30 ug doses. In some embodiments, a primary regimen may involve one or more 10 ug doses and a booster regimen may involve one or more 10 ug doses. In some embodiments, a primary regimen may involve two or more 10 ug doses (e.g., two doses, each comprising 10 ug of RNA, administered about 21 days apart) and a booster regimen may involve one or more 10 ug doses. In some embodiments, a primary regimen may involve one or more 20 ug doses and a booster regimen may involve one or more 30 ug doses. In some embodiments, a primary regimen may involve one or more 20 ug doses and a booster regimen may involve one or more 20 ug doses. In some embodiments, a primary regimen may involve one or more 30 ug doses, and a booster regimen may also involve one or more 30 ug doses. In some embodiments, a primary regimen may involve two or more 30 ug doses (e.g., two doses, each comprising 30 ug of RNA, administered about 21 days apart), and a booster regimen may also involve one or more 30 ug doses. In some embodiments, a primary regimen may involve two or more 30 ug doses (e.g., two doses, each comprising 30 ug of RNA, administered about 21 days apart), and a booster regimen may involve one or more 50 ug doses. In some embodiments, a primary regimen may involve two or more 30 ug doses (e.g., two doses, each comprising 30 ug of RNA, administered about 21 days apart), and a booster regimen may involve one or more 60 ug doses.

In some embodiments, a subject is administered a booster regimen comprising at least one 30 ug dose of RNA. In some embodiments, a subject is administered a booster regimen comprising at least one 30 ug dose of RNA encoding a SARS-CoV-2 S protein from a Wuhan strain of SARS-CoV-2 (e.g., BNT162b2). In some embodiments, a subject is administered a booster regimen comprising at least one dose of 30 ug of RNA encoding a SARS-CoV-2 S protein having one or more mutations that are characteristic of a SARS-CoV-2 variant (e.g., a variant described herein). In some embodiments, a subject is administered a booster regimen comprising at least one dose of 30 ug of RNA encoding a SARS-CoV-2 S protein having one or more mutations that are characteristic of an Omicron variant (e.g., a BA.1, BA.2, BA.3, or BA.4 or BA.5 Omicron variant). In some embodiments, a subject is administered a booster regimen comprising at least one dose of 30 ug of RNA, wherein the 30 ug of RNA comprises RNA encoding a SARS-CoV-2 S protein from a Wuhan strain and RNA encoding a SARS-CoV-2 S protein comprising mutations that are characteristic of a SARS-CoV-2 variant (e.g., in some embodiments, a subject is administered a booster regimen comprising at least one dose comprising 15 ug of RNA encoding a SARS-CoV-2 S protein from a Wuhan strain and 15 ug of RNA encoding a SARS-CoV-2 S protein having one or more mutations that are characteristic of an Omicron variant). In some embodiments, a subject is administered a booster regimen comprising at least one dose comprising 15 ug of RNA encoding a SARS-CoV-2 S protein from a Wuhan strain and 15 ug of RNA encoding a SARS-CoV-2 S protein having one or more mutations that are characteristic of a BA.1 Omicron variant. In some embodiments, a subject is administered a booster regimen comprising at least one dose comprising 10 ug of RNA encoding a SARS-CoV-2 S protein from a Wuhan strain and 20 ug of RNA encoding a SARS-CoV-2 S protein having one or more mutations that are characteristic of a BA.1 Omicron variant. In some embodiments, a subject is administered a booster regimen comprising at least one dose comprising 7.5 ug of RNA encoding a SARS-CoV-2 S protein from a Wuhan strain and 22.5 ug of RNA encoding a SARS-CoV-2 S protein having one or more mutations that are characteristic of a BA.1 Omicron variant. In some embodiments, a subject is administered a booster regimen comprising at least one dose comprising 15 ug of RNA encoding a SARS-CoV-2 S protein from a Wuhan strain and 15 ug of RNA encoding a SARS-CoV-2 S protein having one or more mutations that are characteristic of a BA.2 Omicron variant. In some embodiments, a subject is administered a booster regimen comprising at least one dose comprising 10 ug of RNA encoding a SARS-CoV-2 S protein from a Wuhan strain and 20 ug of RNA encoding a SARS-CoV-2 S protein having one or more mutations that are characteristic of a BA.2 Omicron variant. In some embodiments, a subject is administered a booster regimen comprising at least one dose comprising 7.5 ug of RNA encoding a SARS-CoV-2 S protein from a Wuhan strain and 22.5 ug of RNA encoding a SARS-CoV-2 S protein having one or more mutations that are characteristic of a BA.2 Omicron variant. In some embodiments, a subject is administered a booster regimen comprising at least one dose comprising 15 ug of RNA encoding a SARS-CoV-2 S protein from a Wuhan strain and 15 ug of RNA encoding a SARS-CoV-2 S protein having one or more mutations that are characteristic of a BA.3 Omicron variant. In some embodiments, a subject is administered a booster regimen comprising at least one dose comprising 10 ug of RNA encoding a SARS-CoV-2 S protein from a Wuhan strain and 20 ug of RNA encoding a SARS-CoV-2 S protein having one or more mutations that are characteristic of a BA.3 Omicron variant. In some embodiments, a subject is administered a booster regimen comprising at least one dose comprising 7.5 ug of RNA encoding a SARS-CoV-2 S protein from a Wuhan strain and 22.5 ug of RNA encoding a SARS-CoV-2 S protein having one or more mutations that are characteristic of a BA.3 Omicron variant. In some embodiments, a subject is administered a booster regimen comprising at least one dose comprising 15 ug of RNA encoding a SARS-CoV-2 S protein from a Wuhan strain and 15 ug of RNA encoding a SARS-CoV-2 S protein having one or more mutations that are characteristic of a BA.4 or BA.5 Omicron variant. In some embodiments, a subject is administered a booster regimen comprising at least one dose comprising 10 ug of RNA encoding a SARS-CoV-2 S protein from a Wuhan strain and 20 ug of RNA encoding a SARS-CoV-2 S protein having one or more mutations that are characteristic of a BA.4 or BA.5 Omicron variant. In some embodiments, a subject is administered a booster regimen comprising at least one dose comprising 7.5 ug of RNA encoding a SARS-CoV-2 S protein from a Wuhan strain and 22.5 ug of RNA encoding a SARS-CoV-2 S protein having one or more mutations that are characteristic of a BA.4 or BA.5 Omicron variant.

In some embodiments, a subject is administered a booster regimen comprising at least one dose comprising 15 ug of RNA encoding a SARS-CoV-2 S protein from a BA.1 Omicron variant and 15 ug of RNA encoding a SARS-CoV-2 S protein having one or more mutations that are characteristic of a BA.2 Omicron variant. In some embodiments, a subject is administered a booster regimen comprising at least one dose comprising 10 ug of RNA encoding a SARS-CoV-2 S protein from a BA.1 Omicron variant and 20 ug of RNA encoding a SARS-CoV-2 S protein having one or more mutations that are characteristic of a BA.2 Omicron variant. In some embodiments, a subject is administered a booster regimen comprising at least one dose comprising 7.5 ug of RNA encoding a SARS-CoV-2 S protein from a BA.1 Omicron variant and 22.5 ug of RNA encoding a SARS-CoV-2 S protein having one or more mutations that are characteristic of a BA.2 Omicron variant. In some embodiments, a subject is administered a booster regimen comprising at least one dose comprising 15 ug of RNA encoding a SARS-CoV-2 S protein from a BA.1 Omicron variant and 15 ug of RNA encoding a SARS-CoV-2 S protein having one or more mutations that are characteristic of a BA.3 Omicron variant. In some embodiments, a subject is administered a booster regimen comprising at least one dose comprising 10 ug of RNA encoding a SARS-CoV-2 S protein from a BA.1 Omicron variant and 20 ug of RNA encoding a SARS-CoV-2 S protein having one or more mutations that are characteristic of a BA.3 Omicron variant. In some embodiments, a subject is administered a booster regimen comprising at least one dose comprising 7.5 ug of RNA encoding a SARS-CoV-2 S protein from a BA.1 Omicron variant and 22.5 ug of RNA encoding a SARS-CoV-2 S protein having one or more mutations that are characteristic of a BA.3 Omicron variant. In some embodiments, a subject is administered a booster regimen comprising at least one dose comprising 15 ug of RNA encoding a SARS-CoV-2 S protein from a BA.1 Omicron variant and 15 ug of RNA encoding a SARS-CoV-2 S protein having one or more mutations that are characteristic of a BA.4 or BA.5 Omicron variant. In some embodiments, a subject is administered a booster regimen comprising at least one dose comprising 10 ug of RNA encoding a SARS-CoV-2 S protein from a BA.1 Omicron variant and 20 ug of RNA encoding a SARS-CoV-2 S protein having one or more mutations that are characteristic of a BA.4 or BA.5 Omicron variant. In some embodiments, a subject is administered a booster regimen comprising at least one dose comprising 7.5 ug of RNA encoding a SARS-CoV-2 S protein from a BA.1 Omicron variant and 22.5 ug of RNA encoding a SARS-CoV-2 S protein having one or more mutations that are characteristic of a BA.4 or BA.5 Omicron variant.

In some embodiments, a subject is administered a booster regimen comprising at least one dose comprising 15 ug of RNA encoding a SARS-CoV-2 S protein from a BA.2 Omicron variant and 15 ug of RNA encoding a SARS-CoV-2 S protein having one or more mutations that are characteristic of a BA.4 or BA.5 Omicron variant. In some embodiments, a subject is administered a booster regimen comprising at least one dose comprising 10 ug of RNA encoding a SARS-CoV-2 S protein from a BA.2 Omicron variant and 20 ug of RNA encoding a SARS-CoV-2 S protein having one or more mutations that are characteristic of a BA.4 or BA.5 Omicron variant. In some embodiments, a subject is administered a booster regimen comprising at least one dose comprising 7.5 ug of RNA encoding a SARS-CoV-2 S protein from a BA.2 Omicron variant and 22.5 ug of RNA encoding a SARS-CoV-2 S protein having one or more mutations that are characteristic of a BA.4 or BA.5 Omicron variant. In some embodiments, a subject is administered a booster regimen comprising at least one dose comprising 15 ug of RNA encoding a SARS-CoV-2 S protein from a BA.3 Omicron variant and 15 ug of RNA encoding a SARS-CoV-2 S protein having one or more mutations that are characteristic of a BA.4 or BA.5 Omicron variant. In some embodiments, a subject is administered a booster regimen comprising at least one dose comprising 10 ug of RNA encoding a SARS-CoV-2 S protein from a BA.3 Omicron variant and 20 ug of RNA encoding a SARS-CoV-2 S protein having one or more mutations that are characteristic of a BA.4 or BA.5 Omicron variant. In some embodiments, a subject is administered a booster regimen comprising at least one dose comprising 7.5 ug of RNA encoding a SARS-CoV-2 S protein from a BA.3 Omicron variant and 22.5 ug of RNA encoding a SARS-CoV-2 S protein having one or more mutations that are characteristic of a BA.4 or BA.5 Omicron variant.

In some embodiments, a subject is administered a booster regimen comprising two or more doses of 30 ug of RNA, administered at least two months apart from each other. For example, in some embodiments, subjects are administered a booster regimen comprising two doses of 30 ug of RNA encoding a SARS-CoV-2 S protein having one or more mutations that are characteristic of an Omicron variant (e.g., a BA.1, BA.2, or BA.4 or BA.5 Omicron variant).

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a dose of 30 ug of RNA encoding a SARS-CoV-2 S protein having one or mutations that are characteristic of an Omicron variant of SARS-CoV-2 (e.g., a BA.1, BA.2, BA.3, BA.4, or BA.5 Omicron variant), wherein the booster regimen is administered at least two months (including, e.g., at least three months, at least four months, at least five months, at least six months, or more) after completion of the primary regimen. In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 30 ug dose of RNA comprising 15 ug RNA encoding a SARS-CoV-2 S protein from a Wuhan strain and 15 ug of RNA encoding a SARS-CoV-2 S protein having one or more mutations that are characteristic of an Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a dose of 30 ug of RNA encoding a SARS-CoV-2 S protein having one or mutations that are characteristic of a BA.1 Omicron variant of SARS-CoV-2, wherein the booster regimen is administered at least two months (including, e.g., at least three months, at least four months, at least five months, at least six months, or more) after completion of the primary regimen. In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 30 ug dose of RNA comprising 15 ug RNA encoding a SARS-CoV-2 S protein from a Wuhan strain and 15 ug of RNA encoding a SARS-CoV-2 S protein having one or more mutations that are characteristic of a BA.1 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a dose of 30 ug of RNA encoding a SARS-CoV-2 S protein having one or mutations that are characteristic of a BA.2 Omicron variant of SARS-CoV-2, wherein the booster regimen is administered at least two months (including, e.g., at least three months, at least four months, at least five months, at least six months, or more) after completion of the primary regimen. In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 30 ug dose of RNA comprising 15 ug RNA encoding a SARS-CoV-2 S protein from a Wuhan strain and 15 ug of RNA encoding a SARS-CoV-2 S protein having one or more mutations that are characteristic of a BA.2 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a dose of 30 ug of RNA encoding a SARS-CoV-2 S protein having one or mutations that are characteristic of a BA.4 or BA.5 Omicron variant of SARS-CoV-2, wherein the booster regimen is administered at least two months (including, e.g., at least three months, at least four months, at least five months, at least six months, or more) after completion of the primary regimen. In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 30 ug dose of RNA comprising 15 ug RNA encoding a SARS-CoV-2 S protein from a Wuhan strain and 15 ug of RNA encoding a SARS-CoV-2 S protein having one or more mutations that are characteristic of a BA.4 or BA.5 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 30 ug dose of RNA comprising 15 ug RNA encoding a SARS-CoV-2 S protein from a BA.1 Omicron variant and 15 ug of RNA encoding a SARS-CoV-2 S protein having one or more mutations that are characteristic of a BA.2 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 30 ug dose of RNA comprising 15 ug RNA encoding a SARS-CoV-2 S protein from a BA.1 Omicron variant and 15 ug of RNA encoding a SARS-CoV-2 S protein having one or more mutations that are characteristic of a BA.4 or BA.5 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 30 ug dose of RNA comprising 15 ug RNA encoding a SARS-CoV-2 S protein from a BA.2 Omicron variant and 15 ug of RNA encoding a SARS-CoV-2 S protein having one or more mutations that are characteristic of a BA.4 or BA.5 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising at least one 30 ug dose of RNA encoding a SARS-CoV-2 S protein from a non-BA.1 Omicron variant.

In some embodiments, a subject is administered (i) a primary regimen comprising two 30 ug doses of RNA encoding a SARS-CoV-2 S protein from a Wuhan strain, wherein the two doses are administered at least approximately 21 days apart, and (ii) a booster regimen comprising at least two 30 ug doses of RNA encoding a SARS-CoV-2 S protein having one or more mutations characteristic of an Omicron variant, wherein the booster regimen is administered at least two months (including, e.g., at least three months, at least four months, at least five months, at least six months, or more) after completion of the primary regimen, and the two booster doses are administered at least two months apart from each other.

In some embodiments, a subject is administered a booster regimen comprising at least one 50 ug dose of RNA. In some embodiments, a subject is administered a booster regimen comprising at least one dose of 50 ug of RNA encoding a SARS-CoV-2 S protein from a Wuhan strain (e.g., BNT162b2). In some embodiments, a subject is administered a booster regimen comprising at least one dose of 50 ug of RNA encoding a SARS-CoV-2 S protein having one or more mutations that are characteristic of a SARS-CoV-2 variant (e.g., a variant described herein). In some embodiments, a subject is administered a booster regimen comprising at least one dose of 50 ug of RNA encoding a SARS-CoV-2 S protein having one or more mutations that are characteristic of an Omicron variant. In some embodiments, a subject is administered a booster regimen comprising at least one 50 ug dose of RNA, wherein the 50 ug of RNA comprises RNA encoding a SARS-CoV-2 S protein from a Wuhan strain and RNA encoding a SARS-CoV-2 S protein comprising mutations that are characteristic of a SARS-CoV-2 variant (e.g., in some embodiments, a subject is administered a booster regimen comprising a 50 ug dose of RNA comprising 25 ug of RNA encoding a SARS-CoV-2 S protein from a Wuhan strain and 25 ug of RNA encoding a SARS-CoV-2 S protein having one or more mutations that are characteristic of an Omicron variant).

In some embodiments, a subject is administered a booster regimen comprising at least one dose comprising 25 ug of RNA encoding a SARS-CoV-2 S protein from a Wuhan strain and 25 µg of RNA encoding a SARS-CoV-2 S protein having one or more mutations that are characteristic of a BA.1 Omicron variant. In some embodiments, a subject is administered a booster regimen comprising at least one dose comprising 25 ug of RNA encoding a SARS-CoV-2 S protein from a Wuhan strain and 25 ug of RNA encoding a SARS-CoV-2 S protein having one or more mutations that are characteristic of a BA.2 Omicron variant. In some embodiments, a subject is administered a booster regimen comprising at least one dose comprising 25 ug of RNA encoding a SARS-CoV-2 S protein from a Wuhan strain and 25 ug of RNA encoding a SARS-CoV-2 S protein having one or more mutations that are characteristic of a BA.3 Omicron variant. In some embodiments, a subject is administered a booster regimen comprising at least one dose comprising 25 ug of RNA encoding a SARS-CoV-2 S protein from a Wuhan strain and 25 ug of RNA encoding a SARS-CoV-2 S protein having one or more mutations that are characteristic of a BA.4 or BA.5 Omicron variant.

In some embodiments, a subject is administered a booster regimen comprising at least one dose comprising 25 ug of RNA encoding a SARS-CoV-2 S protein from a BA.1 Omicron variant and 25 ug of RNA encoding a SARS-CoV-2 S protein having one or more mutations that are characteristic of a BA.2 Omicron variant. In some embodiments, a subject is administered a booster regimen comprising at least one dose comprising 25 ug of RNA encoding a SARS-CoV-2 S protein from a BA.1 Omicron variant and 25 ug of RNA encoding a SARS-CoV-2 S protein having one or more mutations that are characteristic of a BA.3 Omicron variant. In some embodiments, a subject is administered a booster regimen comprising at least one dose comprising 25 ug of RNA encoding a SARS-CoV-2 S protein from a BA.1 Omicron variant and 25 ug of RNA encoding a SARS-CoV-2 S protein having one or more mutations that are characteristic of a BA.4 or BA.5 Omicron variant.

In some embodiments, a subject is administered a booster regimen comprising at least one dose comprising 25 ug of RNA encoding a SARS-CoV-2 S protein from a BA.2 Omicron variant and 25 ug of RNA encoding a SARS-CoV-2 S protein having one or more mutations that are characteristic of a BA.4 or BA.5 Omicron variant. In some embodiments, a subject is administered a booster regimen comprising at least one dose comprising 25 ug of RNA encoding a SARS-CoV-2 S protein from a BA.3 Omicron variant and 25 ug of RNA encoding a SARS-CoV-2 S protein having one or more mutations that are characteristic of a BA.4 or BA.5 Omicron variant.

In some embodiments, a subject is administered (i) a primary regimen comprising two 30 ug doses of RNA encoding a SARS-CoV-2 S protein from a Wuhan strain, wherein the two doses are administered approximately 21 days apart, and (ii) a booster regimen comprising at least one 50 ug dose of RNA encoding a SARS-CoV-2 S protein having one or mutations that are characteristic of an Omicron variant of SARS-CoV-2 (e.g., a BA.1, BA.2, BA.4 or BA.5 Omicron variant), wherein the booster regimen is administered at least two months (including, e.g., at least three months, at least four months, at least five months, at least six months, or more) after completion of the primary regimen. In some embodiments, a subject is administered (i) a primary regimen comprising two 30 ug doses of RNA encoding a SARS-CoV-2 S protein from a Wuhan strain, wherein the two doses are administered approximately 21 days apart, and (ii) a booster regimen comprising at least one 50 ug dose of RNA, wherein the 50 ug of RNA comprises 25 ug of RNA encoding a SARS-CoV-2 S protein of a Wuhan strain and 25 ug of RNA encoding a SARS-CoV-2 S protein having one or mutations that are characteristic of an Omicron variant (e.g., a BA.1, BA.2, BA.4, or BA.5 variant), wherein the booster regimen is administered at least two months (including, e.g., at least three months, at least four months, at least five months, at least six months, or more) after completion of a first booster regimen. In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a dose of 50 ug of RNA encoding a SARS-CoV-2 S protein having one or mutations that are characteristic of a BA.1 Omicron variant of SARS-CoV-2, wherein the booster regimen is administered at least two months (including, e.g., at least three months, at least four months, at least five months, at least six months, or more) after completion of the primary regimen. In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 50 ug dose of RNA comprising 25 ug RNA encoding a SARS-CoV-2 S protein from a Wuhan strain and 25 ug of RNA encoding a SARS-CoV-2 S protein having one or more mutations that are characteristic of a BA.1 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a dose of 50 ug of RNA encoding a SARS-CoV-2 S protein having one or mutations that are characteristic of a BA.2 Omicron variant of SARS-CoV-2, wherein the booster regimen is administered at least two months (including, e.g., at least three months, at least four months, at least five months, at least six months, or more) after completion of the primary regimen. In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 50 ug dose of RNA comprising 25 ug RNA encoding a SARS-CoV-2 S protein from a Wuhan strain and 25 ug of RNA encoding a SARS-CoV-2 S protein having one or more mutations that are characteristic of a BA.2 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a dose of 50 ug of RNA encoding a SARS-CoV-2 S protein having one or mutations that are characteristic of a BA.4 or BA.5 Omicron variant of SARS-CoV-2, wherein the booster regimen is administered at least two months (including, e.g., at least three months, at least four months, at least five months, at least six months, or more) after completion of the primary regimen. In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 50 ug dose of RNA comprising 25 ug RNA encoding a SARS-CoV-2 S protein from a Wuhan strain and 25 ug of RNA encoding a SARS-CoV-2 S protein having one or more mutations that are characteristic of a BA.4 or BA.5 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 50 ug dose of RNA comprising 25 ug RNA encoding a SARS-CoV-2 S protein from a BA.1 Omicron variant and 25 ug of RNA encoding a SARS-CoV-2 S protein having one or more mutations that are characteristic of a BA.2 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 50 ug dose of RNA comprising 25 ug RNA encoding a SARS-CoV-2 S protein from a BA.1 Omicron variant and 25 ug of RNA encoding a SARS-CoV-2 S protein having one or more mutations that are characteristic of a BA.4 or BA.5 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 50 ug dose of RNA comprising 25 ug RNA encoding a SARS-CoV-2 S protein from a BA.2 Omicron variant and 25 ug of RNA encoding a SARS-CoV-2 S protein having one or more mutations that are characteristic of a BA.4 or BA.5 Omicron variant.

In some embodiments, a subject is administered a booster regimen comprising at least one 60 ug dose of RNA. In some embodiments, a subject is administered a booster regimen comprising 60 ug of RNA encoding a SARS-CoV-2 S protein from a Wuhan variant. In some embodiments, a subject is administered 60 ug of RNA encoding a SARS-CoV-2 S protein having one or more mutations that are characteristic of a SARS-CoV-2 variant (e.g., a variant described herein). In some embodiments, a subject is administered a booster regimen comprising 60 ug of RNA encoding a SARS-CoV-2 S protein having one or more mutations that are characteristic of an Omicron variant (e.g., a BA.1, BA.2, BA.4, or BA.5 Omicron variant). In some embodiments, a subject is administered a booster regimen comprising 60 ug of RNA, wherein the RNA comprises a first RNA encoding a SARS-CoV-2 S protein from a Wuhan strain, and at least one additional RNA encoding a SARS-CoV-2 S protein comprising mutations that are characteristic of a SARS-CoV-2 variant (e.g., in some embodiments, a subject is administered a booster regimen comprising 30 ug of RNA encoding a SARS-CoV-2 S protein from a Wuhan strain and 30 ug of RNA encoding a SARS-CoV-2 S protein having one or more mutations that are characteristic of an Omicron variant (e.g., a BA.1, BA.2, BA.4, or BA.5 variant).

In some embodiments, a subject is administered a booster regimen comprising at least one dose comprising 30 ug of RNA encoding a SARS-CoV-2 S protein from a Wuhan strain and 30 μg of RNA encoding a SARS-CoV-2 S protein having one or more mutations that are characteristic of a BA.1 Omicron variant. In some embodiments, a subject is administered a booster regimen comprising at least one dose comprising 20 ug of RNA encoding a SARS-CoV-2 S protein from a Wuhan strain and 40 ug of RNA encoding a SARS-CoV-2 S protein having one or more mutations that are characteristic of a BA.1 Omicron variant. In some embodiments, a subject is administered a booster regimen comprising at least one dose comprising 15 ug of RNA encoding a SARS-CoV-2 S protein from a Wuhan strain and 45 ug of RNA encoding a SARS-CoV-2 S protein having one or more mutations that are characteristic of a BA.1 Omicron variant. In some embodiments, a subject is administered a booster regimen comprising at least one dose comprising 30 ug of RNA encoding a SARS-CoV-2 S protein from a Wuhan strain and 30 ug of RNA encoding a SARS-CoV-2 S protein having one or more mutations that are characteristic of a BA.2 Omicron variant. In some embodiments, a subject is administered a booster regimen comprising at least one dose comprising 20 ug of RNA encoding a SARS-CoV-2 S protein from a Wuhan strain and 40 ug of RNA encoding a SARS-CoV-2 S protein having one or more mutations that are characteristic of a BA.2 Omicron variant. In some embodiments, a subject is administered a booster regimen comprising at least one dose comprising 15 ug of RNA encoding a SARS-CoV-2 S protein from a Wuhan strain and 45 ug of RNA encoding a SARS-CoV-2 S protein having one or more mutations that are characteristic of a BA.2 Omicron variant. In some embodiments, a subject is administered a booster regimen comprising at least one dose comprising 30 ug of RNA encoding a SARS-CoV-2 S protein from a Wuhan strain and 30 ug of RNA encoding a SARS-CoV-2 S protein having one or more mutations that are characteristic of a BA.3 Omicron variant. In some embodiments, a subject is administered a booster regimen comprising at least one dose comprising 20 ug of RNA encoding a SARS-CoV-2 S protein from a Wuhan strain and 40 ug of RNA encoding a SARS-CoV-2 S protein having one or more mutations that are characteristic of a BA.3 Omicron variant. In some embodiments, a subject is administered a booster regimen comprising at least one dose comprising 15 ug of RNA encoding a SARS-CoV-2 S protein from a Wuhan strain and 45 ug of RNA encoding a SARS-CoV-2 S protein having one or more mutations that are characteristic of a BA.3 Omicron variant. In some embodiments, a subject is administered a booster regimen comprising at least one dose comprising 30 ug of RNA encoding a SARS-CoV-2 S protein from a Wuhan strain and 30 ug of RNA encoding a SARS-CoV-2 S protein having one or more mutations that are characteristic of a BA.4 or BA.5 Omicron variant. In some embodiments, a subject is administered a booster regimen comprising at least one dose comprising 20 ug of RNA encoding a SARS-CoV-2 S protein from a Wuhan strain and 40 ug of RNA encoding a SARS-CoV-2 S protein having one or more mutations that are characteristic of a BA.4 or BA.5 Omicron variant. In some embodiments, a subject is administered a booster regimen comprising at least one dose comprising 15 ug of RNA encoding a SARS-CoV-2 S protein from a Wuhan strain and 45 ug of RNA encoding a SARS-CoV-2 S protein having one or more mutations that are characteristic of a BA.4 or BA.5 Omicron variant.

In some embodiments, a subject is administered a booster regimen comprising at least one dose comprising 30 ug of RNA encoding a SARS-CoV-2 S protein from a BA.1 Omicron variant and 30 ug of RNA encoding a SARS-CoV-2 S protein having one or more mutations that are characteristic of a BA.2 Omicron variant. In some embodiments, a subject is administered a booster regimen comprising at least one dose comprising 20 ug of RNA encoding a SARS-CoV-2 S protein from a BA.1 Omicron variant and 40 ug of RNA encoding a SARS-CoV-2 S protein having one or more mutations that are characteristic of a BA.2 Omicron variant. In some embodiments, a subject is administered a booster regimen comprising at least one dose comprising 15 ug of RNA encoding a SARS-CoV-2 S protein from a BA.1 Omicron variant and 45 ug of RNA encoding a SARS-CoV-2 S protein having one or more mutations that are characteristic of a BA.2 Omicron variant. In some embodiments, a subject is administered a booster regimen comprising at least one dose comprising 30 ug of RNA encoding a SARS-CoV-2 S protein from a BA.1 Omicron variant and 30 ug of RNA encoding a SARS-CoV-2 S protein having one or more mutations that are characteristic of a BA.3 Omicron variant. In some embodiments, a subject is administered a booster regimen comprising at least one dose comprising 20 ug of RNA encoding a SARS-CoV-2 S protein from a BA.1 Omicron variant and 40 ug of RNA encoding a SARS-CoV-2 S protein having one or more mutations that are characteristic of a BA.3 Omicron variant. In some embodiments, a subject is administered a booster regimen comprising at least one dose comprising 15 ug of RNA encoding a SARS-CoV-2 S protein from a BA.1 Omicron variant and 45 ug of RNA encoding a SARS-CoV-2 S protein having one or more mutations that are characteristic of a BA.3 Omicron variant. In some embodiments, a subject is administered a booster regimen comprising at least one dose comprising 30 ug of RNA encoding a SARS-CoV-2 S protein from a BA.1 Omicron variant and 30 ug of RNA encoding a SARS-CoV-2 S protein having one or more mutations that are characteristic of a BA.4 or BA.5 Omicron variant. In some embodiments, a subject is administered a booster regimen comprising at least one dose comprising 20 ug of RNA encoding a SARS-CoV-2 S protein from a BA.1 Omicron variant and 40 ug of RNA encoding a SARS-CoV-2 S protein having one or more mutations that are characteristic of a BA.4 or BA.5 Omicron variant. In some embodiments, a subject is administered a booster regimen comprising at least one dose comprising 15 ug of RNA encoding a SARS-CoV-2 S protein from a BA.1 Omicron variant and 45 ug of RNA encoding a SARS-CoV-2 S protein having one or more mutations that are characteristic of a BA.4 or BA.5 Omicron variant.

In some embodiments, a subject is administered a booster regimen comprising at least one dose comprising 30 ug of RNA encoding a SARS-CoV-2 S protein from a BA.2 Omicron variant and 30 ug of RNA encoding a SARS-CoV-2 S protein having one or more mutations that are characteristic of a BA.4 or BA.5 Omicron variant. In some embodiments, a subject is administered a booster regimen comprising at least one dose comprising 20 ug of RNA encoding a SARS-CoV-2 S protein from a BA.2 Omicron variant and 40 ug of RNA encoding a SARS-CoV-2 S protein having one or more mutations that are characteristic of a BA.4 or BA.5 Omicron variant. In some embodiments, a subject is administered a booster regimen comprising at least one dose comprising 15 ug of RNA encoding a SARS-CoV-2 S protein from a BA.2 Omicron variant and 45 ug of RNA encoding a SARS-CoV-2 S protein having one or more mutations that are characteristic of a BA.4 or BA.5 Omicron variant. In some embodiments, a subject is administered a booster regimen comprising at least one dose comprising 30 ug of RNA encoding a SARS-CoV-2 S protein from a BA.3 Omicron variant and 30 ug of RNA encoding a SARS-CoV-2 S protein having one or more mutations that are characteristic of a BA.4 or BA.5 Omicron variant. In some embodiments, a subject is administered a booster regimen comprising at least one dose comprising 20 ug of RNA encoding a SARS-CoV-2 S protein from a BA.3 Omicron variant and 40 ug of RNA encoding a SARS-CoV-2 S protein having one or more mutations that are characteristic of a BA.4 or BA.5 Omicron variant. In some embodiments, a subject is administered a booster regimen comprising at least one dose comprising 15 ug of RNA encoding a SARS-CoV-2 S protein from a BA.3 Omicron variant and 45 ug of RNA encoding a SARS-CoV-2 S protein having one or more mutations that are characteristic of a BA.4 or BA.5 Omicron variant.

In some embodiments, a subject is administered (i) a primary regimen comprising two 30 ug doses of RNA encoding a SARS-CoV-2 S protein from a Wuhan strain of SARS-CoV-2, wherein the two doses are administered approximately 21 days apart, and (ii) a booster regimen comprising at least one 60 ug dose of RNA encoding a SARS-CoV-2 S protein from a Wuhan strain of SARS-CoV-2, wherein the booster regimen is administered at least two months (including, e.g., at least three months, at least four months, at least five months, at least six months, or more) after completion of the primary regimen.

In some embodiments, a subject is administered (i) a primary regimen comprising two 30 ug doses of RNA encoding a SARS-CoV-2 S protein from a Wuhan strain, wherein the two doses are administered approximately 21 days apart, and (ii) a booster regimen comprising at least one 60 ug dose of RNA encoding a SARS-CoV-2 S protein having one or mutations that are characteristic of an Omicron variant of SARS-CoV-2 (e.g., a BA.1, BA.2, BA.4 or BA.5 Omicron variant), wherein the booster regimen is administered at least two months (including, e.g., at least three months, at least four months, at least five months, at least six months, or more) after completion of the primary regimen. In some embodiments, a subject is administered (i) a primary regimen comprising two 30 ug doses of RNA encoding a SARS-CoV-2 S protein from a Wuhan strain, wherein the two doses are administered approximately 21 days apart, and (iii) a booster regimen comprising at least one 60 ug dose of RNA comprising 30 ug of RNA encoding a SARS-CoV-2 S protein having one or mutations that are characteristic of an Omicron variant of SARS-CoV-2 and 30 ug of RNA encoding a SARS-CoV-2 S protein from a Wuhan strain, wherein a second booster regimen is administered at least two months (including, e.g., at least three months, at least four months, at least five months, at least six months, or more) after completion of a first booster regimen.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a dose of 60 ug of RNA encoding a SARS-CoV-2 S protein having one or mutations that are characteristic of a BA.1 Omicron variant of SARS-CoV-2, wherein the booster regimen is administered at least two months (including, e.g., at least three months, at least four months, at least five months, at least six months, or more) after completion of the primary regimen. In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 60 ug dose of RNA comprising 30 ug RNA encoding a SARS-CoV-2 S protein from a Wuhan strain and 30 ug of RNA encoding a SARS-CoV-2 S protein having one or more mutations that are characteristic of a BA.1 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a dose of 60 ug of RNA encoding a SARS-CoV-2 S protein having one or mutations that are characteristic of a BA.2 Omicron variant of SARS-CoV-2, wherein the booster regimen is administered at least two months (including, e.g., at least three months, at least four months, at least five months, at least six months, or more) after completion of the primary regimen. In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 60 ug dose of RNA comprising 30 ug RNA encoding a SARS-CoV-2 S protein from a Wuhan strain and 30 ug of RNA encoding a SARS-CoV-2 S protein having one or more mutations that are characteristic of a BA.2 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a dose of 60 ug of RNA encoding a SARS-CoV-2 S protein having one or mutations that are characteristic of a BA.4 or BA.5 Omicron variant of SARS-CoV-2, wherein the booster regimen is administered at least two months (including, e.g., at least three months, at least four months, at least five months, at least six months, or more) after completion of the primary regimen. In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 60 ug dose of RNA comprising 30 ug RNA encoding a SARS-CoV-2 S protein from a Wuhan strain and 30 ug of RNA encoding a SARS-CoV-2 S protein having one or more mutations that are characteristic of a BA.4/5 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 60 ug dose of RNA comprising 30 ug RNA encoding a SARS-CoV-2 S protein from a BA.1 Omicron variant and 30 ug of RNA encoding a SARS-CoV-2 S protein having one or more mutations that are characteristic of a BA.2 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 60 ug dose of RNA comprising 30 ug RNA encoding a SARS-CoV-2 S protein from a BA.1 Omicron variant and 30 ug of RNA encoding a SARS-CoV-2 S protein having one or more mutations that are characteristic of a BA.4 or BA.5 Omicron variant.

In some embodiments, a subject is administered (i) a primary regimen comprising at least two 30 ug doses of RNA encoding a SARS-CoV-2 S protein from a Wuhan strain, wherein the two doses are administered at least approximately 21 days apart, and (ii) a booster regimen comprising a 60 ug dose of RNA comprising 30 ug RNA encoding a SARS-CoV-2 S protein from a BA.2 Omicron variant and 30 ug of RNA encoding a SARS-CoV-2 S protein having one or more mutations that are characteristic of a BA.4 or BA.5 Omicron variant.

In some embodiments, a patient is administered a primary regimen comprising two 30 ug doses, administered approximately 21 days apart, and a booster regimen comprising at least one 60 ug dose of RNA (e.g., 60 ug of RNA encoding a SARS-CoV-2 S protein from a Wuhan strain, 60 ug of RNA encoding a SARS-CoV-2 S protein having one or more mutations that are characteristic of an Omicron variant (e.g., a BA.1, BA.2, BA.4, or BA.5 Omicron variant), or 30 ug of RNA encoding a SARS-CoV-2 S protein from a Wuhan strain and 30 ug of RNA encoding a SARS-CoV-2 S protein having one or more mutations that are characteristic of an Omicron variant). In some embodiments, a patient is administered a primary regimen comprising two 30 ug doses, administered approximately 21 days apart, and a booster regimen comprising at least one 50 ug dose of RNA (e.g., 50 ug of RNA encoding a SARS-CoV-2 S protein from a Wuhan strain, 50 ug of RNA encoding a SARS-CoV-2 S protein having one or more mutations that are characteristic of an Omicron variant, or 25 ug of RNA encoding a SARS-CoV-2 S protein from a Wuhan strain and 25 ug of RNA encoding a SARS-CoV-2 S protein having one or more mutations that are characteristic of an Omicron variant). In some embodiments, a patient is administered a primary regimen comprising two 30 ug doses, administered approximately 21 days apart, and a booster regimen comprising at least one 30 ug dose of RNA (e.g., 30 ug of RNA encoding a SARS-CoV-2 S protein from a Wuhan strain, 30 ug of RNA encoding a SARS-CoV-2 S protein having one or more mutations that are characteristic of an Omicron variant, or 15 ug of RNA encoding a SARS-CoV-2 S protein from a Wuhan strain and 15 ug of RNA encoding a SARS-CoV-2 S protein having one or more mutations that are characteristic of an Omicron variant).

In some embodiments, a primary regimen may involve one or more 30 ug doses and a booster regimen may involve one or more 20 ug doses, one or more 10 ug doses, and/or one or more 3 ug doses. In some embodiments, a primary regimen may involve one or more 20 ug doses and a booster regimen may involve one or more 10 ug doses, and/or one or more 3 ug doses. In some embodiments, a primary regimen may involve one or more 10 ug doses and a booster regimen may involve one or more 3 ug doses. In some embodiments, a primary regimen may involve one or more 3 ug doses, and a booster regimen may also involve one or more 3 ug doses.

In some embodiments, a booster regimen comprises a single dose, e.g., for patients who experienced an adverse reaction while receiving the primary regimen.

In some embodiments, the same RNA as used in a primary regimen is used in a booster regimen. In some embodiment, an RNA used in primary and booster regimens is BNT162b2. In some embodiments, a different RNA is used in a booster regimen relative to that used in a primary regimen administered to the same subject. In some embodiments, BNT162b2 is used in a primary regimen but not in a booster regimen. In some embodiments, BNT162b2 is used in a booster regimen but not in a primary regimen. In some embodiments, a similar BNT162b2 construct can be used in a primary regimen and in a booster regimen, except that the RNA constructs used in the primary and booster regimens encode a SARS-CoV-2 S protein (or an immunogenic portion thereof) of different SARS-CoV-2 strains (e.g., as described herein).

In some embodiments, where BNT162b2 is used for a primary regimen or a booster regimen but not both, and a different RNA is used in the other, such different RNA may be an RNA encoding the same SARS-CoV-2 S protein but with different codon optimization or other different RNA sequence. In some embodiments, such different RNA may encode a SARS-CoV-2 S protein (or an immunogenic portion thereof) of a different SARS-CoV-2 strain, e.g., of a variant strain discussed herein. In some such embodiments, such variant strain that is prevalent or rapidly spreading in a relevant jurisdiction. In some embodiments, such different RNA may be an RNA encoding a SARS-CoV-2 S protein or variant thereof (or immunogenic portion of either) comprising one or more mutations described herein for S protein variants such as SARS-CoV-2 S protein variants, in particular naturally occurring S protein variants; in some such embodiments, a SARS-CoV-2 variant may be selected from the group consisting of VOC-202012/01, 501.V2, Cluster 5 and B.1.1.248. In some embodiments, a SARS-CoV-2 variant may be selected from the group consisting of VOC-202012/01, 501.V2, Cluster 5 and B.1.1.248, B.1.1.7, B.1.617.2, and B.1.1.529. In some embodiments, a booster regimen comprises at least one dose of RNA that encodes a SARS-CoV-2 S protein (or an immunogenic fragment thereof) of a variant that is spreading rapidly in a relevant jurisdiction at the time of administration. In some such embodiments, a variant that is encoded by RNA administered in a booster regimen may be different from that encoded by RNA administered in a primary regimen.

In some embodiments, a booster regimen comprises administering (i) a dose of RNA encoding the same SARS-CoV-2 S protein (or an immunogenic fragment thereof) as the RNA administered in the primary regimen (e.g., an RNA encoding a SARS-CoV-2 the S protein (or an immunogenic fragment thereof) from the SARS-CoV-2 Wuhan strain) and (ii) a dose of RNA encoding a SARS-CoV-2 S protein (or an immunogenic fragment thereof) of a variant that is spreading rapidly in a relevant jurisdiction at the time of administration (e.g., a SARS-CoV-2 S protein (or an immunogenic fragment thereof) from one of the SARS-CoV-2 variants discussed herein).

In some embodiments, a booster regimen comprises multiple doses (e.g., at least two doses, at least three doses, or more). For example, in some embodiments, a first dose of a booster regimen may comprise an RNA encoding the same SARS-CoV-2 S protein (or an immunogenic fragment thereof) administered in the primary regimen and a second dose of a booster regimen may comprise the RNA encoding a SARS-CoV-2 S protein of a variant that is spreading rapidly in a relevant jurisdiction at the time of administration. In some embodiments, a first dose of a booster regimen may comprise RNA encoding a SARS-CoV-2 S protein (or an immunogenic fragment thereof) of a variant that is spreading rapidly in a relevant jurisdiction at the time of administration and a second dose of a booster regimen may comprise RNA encoding the same SARS-CoV-2 S protein (or an immunogenic fragment thereof) administered in the primary regimen. In some embodiments, the booster regimen comprises multiple doses, and the RNA encoding the S protein of a variant that is spreading rapidly in a relevant jurisdiction is administered in a first dose and the RNA encoding the S protein administered in the primary regimen is administered in a second dose.

In some embodiments, doses (e.g., a first and a second dose or any two consecutive doses) in a booster regimen are administered at least 2 weeks apart, including, e.g., at least 3 weeks, at least 4 weeks, at least 5 weeks, at least 6 weeks, at least 7 week, at least 8 weeks, at least 9 weeks, at least 10 weeks, at least 11 weeks, at least 12 weeks, at least 13 weeks, at least 14 weeks, at least 15 weeks, at least 16 weeks, or longer, apart. In some embodiments, doses (e.g., a first and a second dose or any two consecutive doses) in a booster regimen are administered approximately 2 to 168 weeks apart. In some embodiments, doses (e.g., a first and a second dose or any two consecutive doses) in a booster regimen are administered approximately 3 to 12 weeks apart. In some embodiments, doses (e.g., a first and a second dose or any two consecutive doses) in a booster regimen are administered approximately 4 to 10 weeks apart. In some embodiments, doses (e.g., a first and a second dose or any two consecutive doses) in a booster regimen are administered approximately 6 to 8 weeks apart. (e.g., about 21 days apart, or about 6 to 8 weeks apart). In some embodiments, the first and second dose are administered on the same day (e.g., by intramuscular injection at different sites on the subject).

In such embodiments, the booster regimen can optionally further comprise a third and fourth dose, administered approximately 2 to 8 weeks after the first and second dose (e.g., about 21 days after the first and second dose, or about 6 weeks to about 8 weeks after the first and second dose), where the third and fourth dose are also administered on the same day (e.g., by intramuscular injection at different sites on the subject), and comprise the same RNAs administered in the first and second doses of the booster regimen.

In some embodiments, multiple booster regimens may be administered. In some embodiments, a booster regimen is administered to a patient who has previously been administered a booster regimen.

In some embodiments, a second booster regimen is administered to a patient who has previously received a first booster regimen, and the amount of RNA administered in at least one dose of a second booster regimen is higher than the amount of RNA administered in at least one dose of a first booster regimen.

In some embodiments, a second booster regimen comprises administering at least one dose of 3 ug of RNA. In some embodiments, a second booster regimen comprises administering at least one dose of 5 ug of RNA. In some embodiments, a second booster regimen comprises administering at least one dose of 10 ug of RNA. In some embodiments, a second booster regimen comprises administering at least one dose of 15 ug of RNA. In some embodiments, a second booster regimen comprises administering at least one dose of 20 ug of RNA. In some embodiments, a second booster regimen comprises administering at least one dose of 25 ug of RNA. In some embodiments, a second booster regimen comprises administering at least one dose of 30 ug of RNA. In some embodiments, a second booster regimen comprises administering at least one dose of 50 ug of RNA. In some embodiments, a second booster regimen comprises administering at least one dose of 60 ug of RNA.

In some embodiments, a subject is administered a primary regimen that comprises two doses of 30 ug of RNA, administered approximately 21 days apart, and a booster regimen comprising at least one dose of approximately 30 ug of RNA. In some embodiments, a subject is administered a primary regimen that comprises two doses of 30 ug of RNA, administered approximately 21 days apart, and a booster regimen comprising at least one dose of approximately 50 ug of RNA. In some embodiments, a subject is administered a primary regimen that comprises two doses of 30 ug of RNA, administered approximately 21 days apart, and a booster regimen comprising at least one dose of approximately 60 ug of RNA.

In some embodiments, a subject is administered a primary regimen that comprises two doses of 30 ug of RNA, administered approximately 21 days apart, a first booster regimen comprising at least one dose of approximately 30 ug of RNA, and a second booster regimen comprising at least one dose of approximately 30 ug of RNA. In some embodiments, a subject is administered a primary regimen that comprises two doses of 30 ug of RNA, administered approximately 21 days apart, a first booster regimen comprising at least one dose of approximately 30 ug of RNA, and a second booster regimen comprising at least one dose of approximately 50 ug of RNA. In some embodiments, a subject is administered a primary regimen that comprises two doses of 30 ug of RNA, administered approximately 21 days apart, a first booster regimen comprising at least one dose of approximately 30 ug of RNA, and a second booster regimen comprising at least one dose of approximately 60 ug of RNA. In some embodiments, a first booster regimen comprises two doses of RNA, wherein each dose comprises an RNA encoding a Spike protein from a different SARS-CoV-2 variant. In some embodiments, a first booster regimen comprises two doses of RNA, wherein each dose comprises an RNA encoding a Spike protein from a different SARS-CoV-2 variant, and wherein the two doses of RNA are administered on the same day. In some embodiments, the two doses of RNA are administered in a single composition (e.g., by mixing a first composition comprising an RNA encoding a Spike protein from a first SARS-CoV-2 variant with a second composition comprising an RNA encoding a Spike protein from a second SARS-CoV-2 variant).

In some embodiments, a subject is administered a booster regimen comprising a first dose comprising an RNA that encodes a Spike protein from a Wuhan strain of SARS-CoV-2 and a second dose comprising an RNA that encodes a Spike protein comprising mutations from a variant that is prevalent and/or rapidly spreading in a relevant jurisdiction at the time of administering the booster regimen, wherein the first dose and the second dose of RNA may be administered on the same day. In some embodiments, a subject is administered a booster regimen comprising a first dose comprising an RNA that encodes a Spike protein from a Wuhan strain of SARS-CoV-2 and a second dose comprising an RNA that encodes a Spike protein comprising mutations from an alpha variant of SARS-CoV-2, wherein the first dose and the second dose may be administered on the same day. In some embodiments, a subject is administered a booster regimen comprising a first dose comprising an RNA that encodes a Spike protein from a Wuhan strain of SARS-CoV-2 and a second dose comprising an RNA that encodes a Spike protein comprising mutations from a beta variant of SARS-CoV-2, wherein the first dose and the second dose may be administered on the same day. In some embodiments, a subject is administered a booster regimen comprising a first dose comprising an RNA that encodes a Spike protein from a Wuhan strain of SARS-CoV-2 and a second dose comprising an RNA that encodes a Spike protein comprising mutations from a delta variant of SARS-CoV-2, wherein the first dose and the second dose may be administered on the same day. In some embodiments, a subject is administered a booster regimen comprising a first dose comprising an RNA that encodes a Spike protein from a Wuhan strain of SARS-CoV-2 and a second dose comprising an RNA that encodes a Spike protein comprising mutations from an Omicron variant of SARS-CoV-2, wherein the first dose and the second dose may be administered on the same day. Such booster regimens may be administered, e.g., to a subject previously administered a primary dosing regimen and/or to a subject previously administered a primary dosing regimen and a booster regimen.

In some embodiments, a subject is administered a first booster regimen comprising a first dose of 15 ug of RNA encoding a Spike protein from a Wuhan variant and a second dose of 15 ug of RNA encoding a Spike protein from an Omicron variant of SARS-CoV-2, where the first and the second dose are administered on the same day (e.g., wherein compositions comprising the RNA are mixed prior to administration, and the mixture is then administered to a patient). In some embodiments, a subject is administered a first booster regimen comprising a first dose of 25 ug of RNA encoding a Spike protein from a Wuhan variant and a second dose of 25 ug of RNA encoding a Spike protein from an Omicron variant of SARS-CoV-2. In some embodiments, the first and the second doses are optionally administered on the same day. In some embodiments, a subject is administered a first booster regimen comprising a first dose of 25 ug of RNA encoding a Spike protein from a Wuhan variant and a second dose of 25 ug of RNA encoding a Spike protein from an Omicron variant of SARS-CoV-2. In some embodiments, the first and the second doses are administered on the same day. In some embodiments, a subject is administered a first booster regimen comprising a first dose of 30 ug of RNA encoding a Spike protein from a Wuhan variant and a second dose of 30 ug of RNA encoding a Spike protein from an Omicron variant of SARS-CoV-2, wherein the first and the second dose are optionally administered on the same day (e.g., in separate administrations or as administration of a multivalent vaccine). In some embodiments, such a first booster regimen is administered to a subject previously administered a primary regimen comprising two doses of 30 ug of RNA, administered about 21 days apart wherein the first booster regimen is administered at least 3 months (e.g., at least 4, at least 5, or at least 6 months) after administration of a primary regimen.

In some embodiments, a subject is administered a second booster regimen comprising a first dose of 15 ug of RNA encoding a Spike protein from a Wuhan variant and a second dose of 15 ug of RNA encoding a Spike protein from an Omicron variant of SARS-CoV-2, where the first and the second dose are administered on the same day (e.g., wherein compositions comprising the RNA are mixed prior to administration to form a multivalent vaccine, and the mixture is then administered to a patient). In some embodiments, a subject is administered a second booster regimen comprising a first dose of 25 ug of RNA encoding a Spike protein from a Wuhan variant and a second dose of 25 ug of RNA encoding a Spike protein from an Omicron variant of SARS-CoV-2, wherein the first dose and the second dose are optionally administered on the same day (e.g., via administration of a multivalent vaccine or via administration of separate compositions). In some embodiments, a subject is administered a second booster regimen comprising a first dose of 25 ug of RNA encoding a Spike protein from a Wuhan variant and a second dose of 25 ug of RNA encoding a Spike protein from an Omicron variant of SARS-CoV-2. In some embodiments, a subject is administered a second booster regimen comprising a first dose of 30 ug of RNA encoding a Spike protein from a Wuhan variant and a second dose of 30 ug of RNA encoding a Spike protein from an Omicron variant of SARS-CoV-2, wherein the first dose and the second dose are optionally administered on the same day (e.g., via administration of a multivalent vaccine or via administration of separate compositions). In some embodiments, such a second booster regimen is administered to a subject previously administered a primary regimen comprising two doses of 30 ug of RNA, administered about 21 days apart. In some embodiments, such a second booster regimen is administered to a subject previously administered a primary regimen comprising two doses of 30 ug of RNA, administered about 21 days apart, and a first booster regimen comprising a dose of 30 ug of RNA, wherein the second booster regimen is administered at least 3 months (e.g., at least 4, at least 5, or at least 6 months) after administration of a first booster regimen.

In some embodiments, patients receiving dose(s) of RNA compositions as described herein are monitored for one or more particular conditions, e.g., following administration of one or more doses. In some embodiments, such condition(s) may be or comprise allergic reaction(s) (particularly in subject(s) with a history of relevant allergies or allergic reactions), myocarditis (inflammation of the heart muscle, particularly where the subject is a young male and/or may have experienced prior such inflammation), pericarditis (inflammation of the lining outside the heart, particularly where the subject is a young males and/or may have experienced prior such inflammation), fever, bleeding (particularly where the subject is known to have a bleeding disorder or to be receiving therapy with a blood thinner). Alternatively or additionally, patients who may receive closer monitoring may be or include patients who are immunocompromised or are receiving therapy with a medicine that affects the immune system, are pregnant or planning to become pregnant, are breastfeeding, have received another COVID-19 vaccine, and/or have ever fainted in association with an injection. In some embodiments, patients are monitored for myocarditis following administration of one of the compositions disclosed herein. In some embodiments, patients are monitored for pericarditis following administration of one of the compositions disclosed herein. Patients may be monitored and/or treated for the condition using current standards of care.

In some embodiments, efficacy for RNA (e.g., mRNA) compositions described in pediatric populations (e.g., described herein) may be assessed by various metrics described herein (including, e.g., but not limited to COVID-19 incidence per 1000 person-years in subjects with no serological or virological evidence of past SARS-CoV-2 infection; geometric mean ratio (GMR) of SARS CoV-2 neutralizing titers measured, e.g., 7 days after a second dose; etc.) In some embodiments, pediatric populations described herein (e.g., from 12 to less than 16 years of age) may be monitored for occurrence of multisystem inflammatory syndrome (MIS) (e.g., inflammation in different body parts such as, e.g., heart, lung, kidneys, brain, skin, eyes, and/or gastrointestinal organs), after administration of an RNA composition (e.g., mRNA) described herein. Exemplary symptoms of MIS in children may include, but are not limited to fever, abdominal pain, vomiting, diarrhea, neck pain, rash, bloodshot eyes, feeling extra tried, and combinations thereof.

In one embodiment, RNA administered as described above is nucleoside modified messenger RNA (modRNA) described herein as BNT162b1(RBP020.3), BNT162b2 (RBP020.1 or RBP020.2), or BNT162b3 (e.g., BNT162b3c). In one embodiment, RNA administered as described above is nucleoside modified messenger RNA (modRNA) described herein as RBP020.2. In one embodiment, RNA encoding a vaccine antigen is nucleoside modified messenger RNA (modRNA) described herein as BNT162b3 (e.g., BNT162b3c).

In one embodiment, RNA administered as described above is nucleoside modified messenger RNA (modRNA) and (i) comprises the nucleotide sequence of SEQ ID NO: 21, a nucleotide sequence having at least 99%, 98%, 97%, 96%, 95%, 90%, 85%, or 80% identity to the nucleotide sequence of SEQ ID NO: 21, and/or (ii) encodes an amino acid sequence comprising the amino acid sequence of SEQ ID NO: 5, or an amino acid sequence having at least 99%, 98%, 97%, 96%, 95%, 90%, 85%, or 80% identity to the amino acid sequence of SEQ ID NO: 5. In one embodiment, RNA administered as described above is nucleoside modified messenger RNA (modRNA) and (i) comprises the nucleotide sequence of SEQ ID NO: 21; and/or (ii) encodes an amino acid sequence comprising the amino acid sequence of SEQ ID NO: 5.

In one embodiment, RNA administered as described above is nucleoside modified messenger RNA (modRNA) and (i) comprises the nucleotide sequence of SEQ ID NO: 19, or 20, a nucleotide sequence having at least 99%, 98%, 97%, 96%, 95%, 90%, 85%, or 80% identity to the nucleotide sequence of SEQ ID NO: 19, or 20, and/or (ii) encodes an amino acid sequence comprising the amino acid sequence of SEQ ID NO: 7, or an amino acid sequence having at least 99%, 98%, 97%, 96%, 95%, 90%, 85%, or 80% identity to the amino acid sequence of SEQ ID NO: 7. In one embodiment, RNA administered as described above is nucleoside modified messenger RNA (modRNA) and (i) comprises the nucleotide sequence of SEQ ID NO: 19, or 20; and/or (ii) encodes an amino acid sequence comprising the amino acid sequence of SEQ ID NO: 7.

In one embodiment, RNA administered as described above is nucleoside modified messenger RNA (modRNA) and (i) comprises the nucleotide sequence of SEQ ID NO: 20, a nucleotide sequence having at least 99%, 98%, 97%, 96%, 95%, 90%, 85%, or 80% identity to the nucleotide sequence of SEQ ID NO: 20, and/or (ii) encodes an amino acid sequence comprising the amino acid sequence of SEQ ID NO: 7, or an amino acid sequence having at least 99%, 98%, 97%, 96%, 95%, 90%, 85%, or 80% identity to the amino acid sequence of SEQ ID NO: 7. In one embodiment, RNA administered as described above is nucleoside modified messenger RNA (modRNA) and (i) comprises the nucleotide sequence of SEQ ID NO: 20; and/or (ii) encodes an amino acid sequence comprising the amino acid sequence of SEQ ID NO: 7.

In one embodiment, RNA administered as described above is nucleoside modified messenger RNA (modRNA) and (i) comprises the nucleotide sequence of SEQ ID NO: 30, a nucleotide sequence having at least 99%, 98%, 97%, 96%, 95%, 90%, 85%, or 80% identity to the nucleotide sequence of SEQ ID NO: 30, and/or (ii) encodes an amino acid sequence comprising the amino acid sequence of SEQ ID NO: 29, or an amino acid sequence having at least 99%, 98%, 97%, 96%, 95%, 90%, 85%, or 80% identity to the amino acid sequence of SEQ ID NO: 29. In one embodiment, RNA administered as described above is nucleoside modified messenger RNA (modRNA) and (i) comprises the nucleotide sequence of SEQ ID NO: 30; and/or (ii) encodes an amino acid sequence comprising the amino acid sequence of SEQ ID NO: 29.

In one embodiment, RNA administered is nucleoside modified messenger RNA (modRNA), (i) comprises the nucleotide sequence of SEQ ID NO: 20; and/or (ii) encodes an amino acid sequence comprising the amino acid sequence of SEQ ID NO: 7, and is administered in an amount of about 30 ug per dose. In one embodiment, at least two of such doses are administered. For example, a second dose may be administered about 21 days following administration of the first dose.

In some embodiments, populations to be treated with RNA described herein comprise, essentially consist of, or consist of subjects of age of at least 50, at least 55, at least 60, or at least 65. In some embodiments, populations to be treated with RNA described herein comprise, essentially consist of, or consist of subjects of age of between 55 to 90, 60 to 85, or 65 to 85.

In some embodiments, the period of time between the doses administered is at least 7 days, at least 14 days, or at least 21 days. In some embodiments, the period of time between the doses administered is between 7 days and 28 days such as between 14 days and 23 days.

In some embodiments, no more than 5 doses, no more than 4 doses, or no more than 3 doses of the RNA described herein may be administered to a subject.

In some embodiments, the methods and agents described herein are administered (in a regimen, e.g., at a dose, frequency of doses and/or number of doses) such that adverse events (AE), i.e., any unwanted medical occurrence in a patient, e.g., any unfavourable and unintended sign, symptom, or disease associated with the use of a medicinal product, whether or not related to the medicinal product, are mild or moderate in intensity. In some embodiments, the methods and agents described herein are administered such that adverse events (AE) can be managed with interventions such as treatment with, e.g., paracetamol or other drugs that provide analgesic, antipyretic (fever-reducing) and/or anti-inflammatory effects, e.g., nonsteroidal anti-inflammatory drugs (NSAIDs), e.g., aspirin, ibuprofen, and naproxen. Paracetamol or "acetaminophen" which is not classified as a NSAID exerts weak anti-inflammatory effects and can be administered as analgesic according to the present disclosure.

In some embodiments, the methods and agents described herein provide a neutralizing effect in a subject to coronavirus, coronavirus infection, or to a disease or disorder associated with coronavirus.

In some embodiments, the methods and agents described herein following administration to a subject induce an immune response that blocks or neutralizes coronavirus in the subject. In some embodiments, the methods and agents described herein following administration to a subject induce the generation of antibodies such as IgG antibodies that block or neutralize coronavirus in the subject. In some embodiments, the methods and agents described herein following administration to a subject induce an immune response that blocks or neutralizes coronavirus S protein binding to ACE2 in the subject. In some embodiments, the methods and agents described herein following administration to a subject induce the generation of antibodies that block or neutralize coronavirus S protein binding to ACE2 in the subject.

In some embodiments, the methods and agents described herein following administration to a subject induce geometric mean concentrations (GMCs) of RBD domain-binding antibodies such as IgG antibodies of at least 500 U/ml, 1000 U/ml, 2000 U/ml, 3000 U/ml, 4000 U/ml, 5000 U/ml, 10000 U/ml, 15000 U/ml, 20000 U/ml, 25000 U/ml, 30000 U/ml or even higher. In some embodiments, the elevated GMCs of RBD domain-binding antibodies persist for at least 14 days, 21 days, 28 days, 1 month, 3 months, 6 months, 12 months or even longer.

In some embodiments, the methods and agents described herein following administration to a subject induce geometric mean titers (GMTs) of neutralizing antibodies such as IgG antibodies of at least 100 U/ml, 200 U/ml, 300 U/ml, 400 U/ml, 500 U/ml, 1000 U/ml, 1500 U/ml, or even higher. In some embodiments, the elevated GMTs of neutralizing antibodies persist for at least 14 days, 21 days, 28 days, 1 month, 3 months, 6 months, 12 months or even longer.

As used herein, the term "neutralization" refers to an event in which binding agents such as antibodies bind to a biological active site of a virus such as a receptor binding protein, thereby inhibiting the viral infection of cells. As used herein, the term "neutralization" with respect to coronavirus, in particular coronavirus S protein, refers to an event in which binding agents such as antibodies bind to the RBD domain of the S protein, thereby inhibiting the viral infection of cells. In particular, the term "neutralization" refers to an event in which binding agents eliminate or significantly reduce virulence (e.g. ability of infecting cells) of viruses of interest.

The type of immune response generated in response to an antigenic challenge can generally be distinguished by the subset of T helper (Th) cells involved in the response. Immune responses can be broadly divided into two types: Th1 and Th2. Th1 immune activation is optimized for intracellular infections such as viruses, whereas Th2 immune responses are optimized for humoral (antibody) responses. Th1 cells produce interleukin 2 (IL-2), tumor necrosis factor (TNFα) and interferon gamma (IFNγ). Th2 cells produce IL-4, IL-5, IL-6, IL-9, IL-10 and IL-13. Th1 immune activation is the most highly desired in many clinical situations. Vaccine compositions specialized in eliciting Th2 or humoral immune responses are generally not effective against most viral diseases.

In some embodiments, the methods and agents described herein following administration to a subject induce or promote a Th1-mediated immune response in the subject. In some embodiments, the methods and agents described herein following administration to a subject induce or promote a cytokine profile that is typical for a Th1-mediated immune response in the subject. In some embodiments, the methods and agents described herein following administration to a subject induce or promote the production of interleukin 2 (IL-2), tumor necrosis factor (TNFα) and/or interferon gamma (IFNγ) in the subject. In some embodiments, the methods and agents described herein following administration to a subject induce or promote the production of interleukin 2 (IL-2) and interferon gamma (IFNγ) in the subject. In some embodiments, the methods and agents described herein following administration to a subject do not induce or promote a Th2-mediated immune response in the subject, or induce or promote a Th2-mediated immune response in the subject to a significant lower extent compared to the induction or promotion of a Th1-mediated immune response. In some embodiments, the methods and agents described herein following administration to a subject do not induce or promote a cytokine profile that is typical for a Th2-mediated immune response in the subject, or induce or promote a cytokine profile that is typical for a Th2-mediated immune response in the subject to a significant lower extent compared to the induction or promotion of a cytokine profile that is typical for a Th1-mediated immune response. In some embodiments, the methods and agents described herein following administration to a subject do not induce or promote the production of IL-4, IL-5, IL-6, IL-9, IL-10 and/or IL-13, or induce or promote the production of IL-4, IL-5, IL-6, IL-9, IL-10 and/or IL-13 in the subject to a significant lower extent compared to the induction or promotion of interleukin 2 (IL-2), tumor necrosis factor (TNFα) and/or interferon gamma (IFNγ) in the subject. In some embodiments, the methods and agents described herein following administration to a subject do not induce or promote the production of IL-4, or induce or promote the production of IL-4 in the subject to a significant lower extent compared to the induction or promotion of interleukin 2 (IL-2) and interferon gamma (IFNγ) in the subject.

In some embodiments, the methods and agents described herein following administration to a subject induce an antibody response, in particular a neutralizing antibody response, in the subject that targets a panel of different S protein variants such as SARS-CoV-2 S protein variants, in particular naturally occurring S protein variants. In some embodiments, the panel of different S protein variants comprises at least 5, at least 10, at least 15, or even more S protein variants. In some embodiments, such S protein variants comprise variants having amino acid modifications in the RBD domain and/or variants having amino acid modifications outside the RBD domain. In one embodiment, such S protein variant comprises SARS-CoV-2 S protein or a naturally occurring variant thereof wherein the amino acid corresponding to position 321 (Q) in SEQ ID NO: 1 is S. In one embodiment, such S protein variant comprises SARS-CoV-2 S protein or a naturally occurring variant thereof wherein the amino acid corresponding to position 321 (Q) in SEQ ID NO: 1 is L. In one embodiment, such S protein variant comprises SARS-CoV-2 S protein or a naturally occurring variant thereof wherein the amino acid corresponding to position 341 (V) in SEQ ID NO: 1 is I. In one embodiment, such S protein variant comprises SARS-CoV-2 S protein or a naturally occurring variant thereof wherein the amino acid corresponding to position 348 (A) in SEQ ID NO: 1 is T. In one embodiment, such S protein variant comprises SARS-CoV-2 S protein or a naturally occurring variant thereof wherein the amino acid corresponding to position 354 (N) in SEQ ID NO: 1 is D. In one embodiment, such S protein variant comprises SARS-CoV-2 S protein or a naturally occurring variant thereof wherein the amino acid corresponding to position 359 (S) in SEQ ID NO: 1 is N. In one embodiment, such S protein variant comprises SARS-CoV-2 S protein or a naturally occurring variant thereof wherein the amino acid corresponding to position 367 (V) in SEQ ID NO: 1 is F. In one embodiment, such S protein variant comprises SARS-CoV-2 S protein or a naturally occurring variant thereof wherein the amino acid corresponding to position 378 (K) in SEQ ID NO: 1 is S. In one embodiment, such S protein variant comprises SARS-CoV-2 S protein or a naturally occurring variant thereof wherein the amino acid corresponding to position 378 (K) in SEQ ID NO: 1 is R. In one embodiment, such S protein variant comprises SARS-CoV-2 S protein or a naturally occurring variant thereof wherein the amino acid corresponding to position 408 (R) in SEQ ID NO: 1 is I. In one embodiment, such S protein variant comprises SARS-CoV-2 S protein or a naturally occurring variant thereof wherein the amino acid corresponding to position 409 (Q) in SEQ ID NO: 1 is E. In one embodiment, such S protein variant comprises SARS-CoV-2 S protein or a naturally occurring variant thereof wherein the amino acid corresponding to position 435 (A) in SEQ ID NO: 1 is S. In one embodiment, such S protein variant comprises SARS-CoV-2 S protein or a naturally occurring variant thereof wherein the amino acid corresponding to position 439 (N) in SEQ ID NO: 1 is K. In one embodiment, such S protein variant comprises SARS-CoV-2 S protein or a naturally occurring variant thereof wherein the amino acid corresponding to position 458 (K) in SEQ ID NO: 1 is R. In one embodiment, such S protein variant comprises SARS-CoV-2 S protein or a naturally occurring variant thereof wherein the amino acid corresponding to position 472 (1) in SEQ ID NO: 1 is V. In one embodiment, such S protein variant comprises SARS-CoV-2 S protein or a naturally occurring variant thereof wherein the amino acid corresponding to position 476 (G) in SEQ ID NO: 1 is S. In one embodiment, such S protein variant comprises SARS-CoV-2 S protein or a naturally occurring variant thereof wherein the amino acid corresponding to position 477 (S) in SEQ ID NO: 1 is N. In one embodiment, such S protein variant comprises SARS-CoV-2 S protein or a naturally occurring variant thereof wherein the amino acid corresponding to position 483 (V) in SEQ ID NO: 1 is A. In one embodiment, such S protein variant comprises SARS-CoV-2 S protein or a naturally occurring variant thereof wherein the amino acid corresponding to position 508 (Y) in SEQ ID NO: 1 is H. In one embodiment, such S protein variant comprises SARS-CoV-2 S protein or a naturally occurring variant thereof wherein the amino acid corresponding to position 519 (H) in SEQ ID NO: 1 is P. In one embodiment, such S protein variant comprises SARS-CoV-2 S protein or a naturally occurring variant thereof wherein the amino acid corresponding to position 614 (D) in SEQ ID NO: 1 is G.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at a position corresponding to position 501(N) in SEQ ID NO: 1. In one embodiment, the amino acid corresponding to position 501 (N) in SEQ ID NO: 1 is Y.

Said S protein variant comprising a mutation at a position corresponding to position 501 (N) in SEQ ID NO: 1 may comprise one or more further mutations. Such one or more further mutations may be selected from mutations at positions corresponding to the following positions in SEQ ID NO: 1: 69 (H), 70 (V), 144 (Y), 570 (A), 614 (D), 681 (P), 716 (T), 982 (S), 1118 (D), 80 (D), 215 (D), 484 (E), 701 (A), 18 (L), 246 (R), 417 (K), 242 (L), 243 (A), and 244 (L). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 484 (E) in SEQ ID NO: 1 is K. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted.

In some embodiments, the methods and agents described herein following administration to a subject induce an antibody response, in particular a neutralizing antibody response, in the subject that targets VOC-202012/01.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: deletion 69-70, deletion 144, N501Y, A570D, D614G, P681H, T716I, S982A, and D1118H.

In some embodiments, the methods and agents described herein following administration to a subject induce an antibody response, in particular a neutralizing antibody response, in the subject that targets 501.V2.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y and A701V, and optionally: L18F, R246I, K417N, and deletion 242-244. Said S protein variant may also comprise a D→G mutation at a position corresponding to position 614 in SEQ ID NO: 1.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a deletion at a position corresponding to positions 69 (H) and 70 (V) in SEQ ID NO: 1.

In some embodiments, a S protein variant comprising a deletion at a position corresponding to positions 69 (H) and 70 (V) in SEQ ID NO: 1 may comprise one or more further mutations. Such one or more further mutations may be selected from mutations at positions corresponding to the following positions in SEQ ID NO: 1: 144 (Y), 501 (N), 570 (A), 614 (D), 681 (P), 716 (T), 982 (S), 1118 (D), 80 (D), 215 (D), 484 (E), 701 (A), 18 (L), 246 (R), 417 (K), 242 (L), 243 (A), 244 (L), 453 (Y), 692 (1), 1147 (S), and 1229 (M). In one embodiment, the amino acid corresponding to position 144 (Y) in SEQ ID NO: 1 is deleted. In one embodiment, the amino acid corresponding to position 501 (N) in SEQ ID NO: 1 is Y. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 484 (E) in SEQ ID NO: 1 is K. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (1) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I.

In some embodiments, the methods and agents described herein following administration to a subject induce an antibody response, in particular a neutralizing antibody response, in the subject that targets VOC-202012/01.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: deletion 69-70, deletion 144, N501Y, A570D, D614G, P681H, T716I, S982A, and D1118H.

In some embodiments, the methods and agents described herein following administration to a subject induce an antibody response, in particular a neutralizing antibody response, in the subject that targets "Cluster 5".

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: deletion 69-70, Y453F, I692V, M1229I, and optionally S1147L.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at a position corresponding to position 614 (D) in SEQ ID NO: 1. In one embodiment, the amino acid corresponding to position 614 (D) in SEQ ID NO: 1 is G.

In some embodiments, a S protein variant comprising a mutation at a position corresponding to position 614 (D) in SEQ ID NO: 1 may comprise one or more further mutations. Such one or more further mutations may be selected from mutations at positions corresponding to the following positions in SEQ ID NO: 1: 69 (H), 70 (V), 144 (Y), 501 (N), 570 (A), 681 (P), 716 (T), 982 (S), 1118 (D), 80 (D), 215 (D), 484 (E), 701 (A), 18 (L), 246 (R), 417 (K), 242 (L), 243 (A), 244 (L), 453 (Y), 692 (1), 1147 (S), and 1229 (M). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 501 (N) in SEQ ID NO: 1 is Y. In one embodiment, the amino acid corresponding to position 570 (A) in SEQ ID NO: 1 is D. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 484 (E) in SEQ ID NO: 1 is K. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (1) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I.

In some embodiments, the methods and agents described herein following administration to a subject induce an antibody response, in particular a neutralizing antibody response, in the subject that targets VOC-202012/01.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: deletion 69-70, deletion 144, N501Y, A570D, D614G, P681H, T716I, S982A, and D1118H.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y, D614G and A701V, and optionally: L18F, R246I, K417N, and deletion 242-244.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at positions corresponding to positions 501 (N) and 614 (D) in SEQ ID NO: 1. In one embodiment, the amino acid corresponding to position 501 (N) in SEQ ID NO: 1 is Y and the amino acid corresponding to position 614 (D) in SEQ ID NO: 1 is G.

In some embodiments, a S protein variant comprising a mutation at positions corresponding to positions 501 (N) and 614 (D) in SEQ ID NO: 1 may comprise one or more further mutations. Such one or more further mutations may be selected from mutations at positions corresponding to the following positions in SEQ ID NO: 1: 69 (H), 70 (V), 144 (Y), 570 (A), 681 (P), 716 (T), 982 (S), 1118 (D), 80 (D), 215 (D), 484 (E), 701 (A), 18 (L), 246 (R), 417 (K), 242 (L), 243 (A), 244 (L), 453 (Y), 692 (1), 1147 (S), and 1229 (M). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 570 (A) in SEQ ID NO: 1 is D. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 484 (E) in SEQ ID NO: 1 is K. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (1) in SEQ ID NO: 1 is V. In one embodiment, the amino acid corresponding to position 1147

(S) in SEQ ID NO: 1 is L. In one embodiment, the amino acid corresponding to position 1229 (M) in SEQ ID NO: 1 is I.

In some embodiments, the methods and agents described herein following administration to a subject induce an antibody response, in particular a neutralizing antibody response, in the subject that targets VOC-202012/01.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: deletion 69-70, deletion 144, N501Y, A570D, D614G, P681H, T716I, S982A, and D1118H.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y, D614G and A701V, and optionally: L18F, R246I, K417N, and deletion 242-244.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at a position corresponding to position 484 (E) in SEQ ID NO: 1. In one embodiment, the amino acid corresponding to position 484 (E) in SEQ ID NO: 1 is K.

In some embodiments, a S protein variant comprising a mutation at a position corresponding to position 484 (E) in SEQ ID NO: 1 may comprise one or more further mutations. Such one or more further mutations may be selected from mutations at positions corresponding to the following positions in SEQ ID NO: 1: 69 (H), 70 (V), 144 (Y), 501 (N), 570 (A), 614 (D), 681 (P), 716 (T), 982 (S), 1118 (D), 80 (D), 215 (D), 701 (A), 18 (L), 246 (R), 417 (K), 242 (L), 243 (A), 244 (L), 453 (Y), 692 (1), 1147 (S), 1229 (M), 20 (T), 26 (P), 138 (D), 190 (R), 417 (K), 655 (H), 1027 (T), and 1176 (V). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 501 (N) in SEQ ID NO: 1 is Y. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (1) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I. In one embodiment, the amino acid corresponding to position 20 (T) in SEQ ID NO: 1 is N. In one embodiment, the amino acid corresponding to position 26 (P) in SEQ ID NO: 1 is S. In one embodiment, the amino acid corresponding to position 138 (D) in SEQ ID NO: 1 is Y. In one embodiment, the amino acid corresponding to position 190 (R) in SEQ ID NO: 1 is S. In one embodiment, the amino acid corresponding to position 417 (K) in SEQ ID NO: 1 is T. In one embodiment, the amino acid corresponding to position 655 (H) in SEQ ID NO: 1 is Y. In one embodiment, the amino acid corresponding to position 1027 (T) in SEQ ID NO: 1 is I. In one embodiment, the amino acid corresponding to position 1176 (V) in SEQ ID NO: 1 is F.

In some embodiments, the methods and agents described herein following administration to a subject induce an antibody response, in particular a neutralizing antibody response, in the subject that targets 501.V2.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y and A701V, and optionally: L18F, R246I, K417N, and deletion 242-244. Said S protein variant may also comprise a D→G mutation at a position corresponding to position 614 in SEQ ID NO: 1. In some embodiments, the methods and agents described herein following administration to a subject induce an antibody response, in particular a neutralizing antibody response, in the subject that targets "B.1.1.28".

In some embodiments, the methods and agents described herein following administration to a subject induce an antibody response, in particular a neutralizing antibody response, in the subject that targets "B.1.1.248".

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: L18F, T20N, P26S, D138Y, R190S, K417T, E484K, N501Y, H655Y, T1027I, and V1176F.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at positions corresponding to positions 501 (N) and 484 (E) in SEQ ID NO: 1. In one embodiment, the amino acid corresponding to position 501 (N) in SEQ ID NO: 1 is Y and the amino acid corresponding to position 484 (E) in SEQ ID NO: 1 is K.

In some embodiments, a S protein variant comprising a mutation at positions corresponding to positions 501 (N) and 484 (E) in SEQ ID NO: 1 may comprise one or more further mutations.

Such one or more further mutations may be selected from mutations at positions corresponding to the following positions in SEQ ID NO: 1: 69 (H), 70 (V), 144 (Y), 570 (A), 614 (D), 681 (P), 716 (T), 982 (S), 1118 (D), 80 (D), 215 (D), 701 (A), 18 (L), 246 (R), 417 (K), 242 (L), 243 (A), 244 (L), 453 (Y), 692 (1), 1147 (S), 1229 (M), 20 (T), 26 (P), 138 (D), 190 (R), 417 (K), 655 (H), 1027 (T), and 1176 (V). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (1) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I. In one embodiment, the amino acid corresponding to position 20 (T) in SEQ ID NO: 1 is N. In one embodiment, the amino acid corresponding to position 26 (P) in SEQ ID NO: 1 is S. In one embodiment, the amino acid corresponding to position 138 (D) in SEQ ID NO: 1 is Y. In one embodiment, the amino acid corresponding to position 190 (R) in SEQ ID NO: 1 is S. In one embodiment, the amino acid corresponding to position 417 (K) in SEQ ID NO: 1 is T. In one embodiment, the amino acid corresponding to position 655 (H) in SEQ ID NO: 1 is Y. In one embodiment, the amino acid corresponding to position 1027 (T) in SEQ ID NO: 1 is I. In one embodiment, the amino acid corresponding to position 1176 (V) in SEQ ID NO: 1 is F.

In some embodiments, the methods and agents described herein following administration to a subject induce an antibody response, in particular a neutralizing antibody response, in the subject that targets 501.V2.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y and A701V, and optionally: L18F, R246I, K417N, and deletion 242-244. Said S protein variant may also comprise a D→G mutation at a position corresponding to position 614 in SEQ ID NO: 1.

In some embodiments, the methods and agents described herein following administration to a subject induce an antibody response, in particular a neutralizing antibody response, in the subject that targets "B.1.1.248".

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: L18F, T20N, P26S, D138Y, R190S, K417T, E484K, N501Y, H655Y, T1027I, and V1176F.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at positions corresponding to positions 501 (N), 484 (E) and 614 (D) in SEQ ID NO: 1. In one embodiment, the amino acid corresponding to position 501 (N) in SEQ ID NO: 1 is Y, the amino acid corresponding to position 484 (E) in SEQ ID NO: 1 is K and the amino acid corresponding to position 614 (D) in SEQ ID NO: 1 is G.

In some embodiments, a S protein variant comprising a mutation at positions corresponding to positions 501 (N), 484 (E) and 614 (D) in SEQ ID NO: 1 may comprise one or more further mutations. Such one or more further mutations may be selected from mutations at positions corresponding to the following positions in SEQ ID NO: 1: 69 (H), 70 (V), 144 (Y), 570 (A), 681 (P), 716 (T), 982 (S), 1118 (D), 80 (D), 215 (D), 701 (A), 18 (L), 246 (R), 417 (K), 242 (L), 243 (A), 244 (L), 453 (Y), 692 (1), 1147 (S), 1229 (M), 20 (T), 26 (P), 138 (D), 190 (R), 417 (K), 655 (H), 1027 (T), and 1176 (V). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 570 (A) in SEQ ID NO: 1 is D. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 242 (L) in SEQ ID NO: 1 is deleted. In one embodiment, the amino acid corresponding to position 243

(A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (I) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I. In one embodiment, the amino acid corresponding to position 20 (T) in SEQ ID NO: 1 is N. In one embodiment, the amino acid corresponding to position 26 (P) in SEQ ID NO: 1 is S. In one embodiment, the amino acid corresponding to position 138 (D) in SEQ ID NO: 1 is Y. In one embodiment, the amino acid corresponding to position 190 (R) in SEQ ID NO: 1 is S. In one embodiment, the amino acid corresponding to position 417 (K) in SEQ ID NO: 1 is T. In one embodiment, the amino acid corresponding to position 655 (H) in SEQ ID NO: 1 is Y. In one embodiment, the amino acid corresponding to position 1027 (T) in SEQ ID NO: 1 is I. In one embodiment, the amino acid corresponding to position 1176 (V) in SEQ ID NO: 1 is F.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y, A701V, and D614G, and optionally: L18F, R246I, K417N, and deletion 242-244.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a deletion at a position corresponding to positions 242 (L), 243 (A) and 244 (L) in SEQ ID NO: 1.

In some embodiments, a S protein variant comprising a deletion at a position corresponding to positions 242 (L), 243 (A) and 244 (L) in SEQ ID NO: 1 may comprise one or more further mutations. Such one or more further mutations may be selected from mutations at positions corresponding to the following positions in SEQ ID NO: 1: 69 (H), 70 (V), 144 (Y), 501 (N), 570 (A), 614 (D), 681 (P), 716 (T), 982 (S), 1118 (D), 80 (D), 215 (D), 484 (E), 701 (A), 18 (L), 246 (R), 417 (K), 453 (Y), 692 (1), 1147 (S), 1229 (M), 20 (T), 26 (P), 138 (D), 190 (R), 417 (K), 655 (H), 1027 (T), and 1176 (V). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 501 (N) in SEQ ID NO: 1 is Y. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 484 (E) in SEQ ID NO: 1 is K. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 417 (K) in SEQ ID NO: 1 is N. In one embodiment, the amino acid corresponding to position 453 (Y) in SEQ ID NO: 1 is F. In one embodiment, the amino acid corresponding to position 692 (I) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I. In one embodiment, the amino acid corresponding to position 20 (T) in SEQ ID NO: 1 is N. In one embodiment, the amino acid corresponding to position 26 (P) in SEQ ID NO: 1 is S. In one embodiment, the amino acid corresponding to position 138 (D) in SEQ ID NO: 1 is Y. In one embodiment, the amino acid corresponding to position 190 (R) in SEQ ID NO: 1 is S. In one embodiment, the amino acid corresponding to position 417 (K) in SEQ ID NO: 1 is T. In one embodiment, the amino acid corresponding to position 655 (H) in SEQ ID NO: 1 is Y. In one embodiment, the amino acid corresponding to position 1027 (T) in SEQ ID NO: 1 is I. In one embodiment, the amino acid corresponding to position 1176 (V) in SEQ ID NO: 1 is F.

In some embodiments, the methods and agents described herein following administration to a subject induce an antibody response, in particular a neutralizing antibody response, in the subject that targets 501.V2.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y, A701V and deletion 242-244, and optionally: L18F, R246I, and K417N. Said S protein variant may also comprise a D→G mutation at a position corresponding to position 614 in SEQ ID NO: 1.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at a position corresponding to position 417 (K) in SEQ ID NO: 1. In one embodiment, the amino acid corresponding to position 417 (K) in SEQ ID NO: 1 is N. In one embodiment, the amino acid corresponding to position 417 (K) in SEQ ID NO: 1 is T.

In some embodiments, a S protein variant comprising a mutation at a position corresponding to position 417 (K) in SEQ ID NO: 1 may comprise one or more further mutations. Such one or more further mutations may be selected from mutations at positions corresponding to the following positions in SEQ ID NO: 1: 69 (H), 70 (V), 144 (Y), 501 (N), 570 (A), 614 (D), 681 (P), 716 (T), 982 (S), 1118 (D), 80 (D), 215 (D), 484 (E), 701 (A), 18 (L), 246 (R), 242 (L), 243 (A), 244 (L), 453 (Y), 692 (1), 1147 (S), 1229 (M), 20 (T), 26 (P), 138 (D), 190 (R), 655 (H), 1027 (T), and 1176 (V). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 501 (N) in SEQ ID NO: 1 is Y. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 484 (E) in SEQ ID NO: 1 is K. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (1) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I. In one embodiment, the amino acid corresponding to position 20 (T) in SEQ ID NO: 1 is N. In one embodiment, the amino acid corresponding to position 26 (P) in SEQ ID NO: 1 is S. In one embodiment, the amino acid corresponding to position 138 (D) in SEQ ID NO: 1 is Y. In one embodiment, the amino acid corresponding to position 190 (R) in SEQ ID NO: 1 is S. In one embodiment, the amino acid corresponding to position 655 (H) in SEQ ID NO: 1 is Y. In one embodiment, the amino acid corresponding to position 1027 (T) in SEQ ID NO: 1 is I. In one embodiment, the amino acid corresponding to position 1176 (V) in SEQ ID NO: 1 is F.

In some embodiments, the methods and agents described herein following administration to a subject induce an antibody response, in particular a neutralizing antibody response, in the subject that targets 501.V2.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y, A701V, and K417N, and optionally: L18F, R246I, and deletion 242-244. Said S protein variant may also comprise a D→G mutation at a position corresponding to position 614 in SEQ ID NO: 1.

In some embodiments, the methods and agents described herein following administration to a subject induce an antibody response, in particular a neutralizing antibody response, in the subject that targets "B.1.1.248".

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: L18F, T20N, P26S, D138Y, R190S, K417T, E484K, N501Y, H655Y, T1027I, and V1176F.

In some embodiments, the methods and agents described herein following administration to a subject induce an antibody response, in particular a neutralizing antibody response, in the subject that targets a S protein variant such as SARS-CoV-2 S protein variant, in particular naturally occurring S protein variant comprising a mutation at positions corresponding to positions 417 (K) and 484 (E) and/or 501 (N) in SEQ ID NO: 1. In one embodiment, the amino acid corresponding to position 417 (K) in SEQ ID NO: 1 is N, and the amino acid corresponding to position 484 (E) in SEQ ID NO: 1 is K and/or the amino acid corresponding to position 501 (N) in SEQ ID NO: 1 is Y. In one embodiment, the amino acid corresponding to position 417 (K) in SEQ ID NO: 1 is T, and the amino acid corresponding to position 484 (E) in SEQ ID NO: 1 is K and/or the amino acid corresponding to position 501 (N) in SEQ ID NO: 1 is Y.

In some embodiments, a S protein variant comprising a mutation at positions corresponding to positions 417 (K) and 484 (E) and/or 501 (N) in SEQ ID NO: 1 may comprise one or more further mutations. Such one or more further mutations may be selected from mutations at positions corresponding to the following positions in SEQ ID NO: 1: 69 (H), 70 (V), 144 (Y), 570 (A), 614 (D), 681 (P), 716 (T), 982 (S), 1118 (D), 80 (D), 215 (D), 701 (A), 18 (L), 246 (R), 242 (L), 243 (A), 244 (L), 453 (Y), 692 (1), 1147 (S), 1229 (M), 20 (T), 26 (P), 138 (D), 190 (R), 655 (H), 1027 (T), and 1176 (V). In one embodiment, the amino acid corresponding to position 69 (H) in SEQ ID NO: 1 is deleted. In one embodiment, the amino acid corresponding to position 70 (V) in SEQ ID NO: 1 is deleted. In one embodiment, the amino acid corresponding to position 144 (Y) in SEQ ID NO: 1 is deleted. In one embodiment, the amino acid corresponding to position 570 (A) in SEQ ID NO: 1 is D. In one embodiment, the amino acid corresponding to position 614 (D) in SEQ ID NO: 1 is G. In one embodiment, the amino acid corresponding to position 681 (P) in SEQ ID NO: 1 is H. In one embodiment, the amino acid corresponding to position 716 (T) in SEQ ID NO: 1 is I. In one embodiment, the amino acid corresponding to position 982 (S) in SEQ ID NO: 1 is A. In one embodiment, the amino acid corresponding to position 1118 (D) in SEQ ID NO: 1 is H. In one embodiment, the amino acid corresponding to position 80 (D) in SEQ ID NO: 1 is A. In one embodiment, the amino acid corresponding to position 215 (D) in SEQ ID NO: 1 is G. In one embodiment, the amino acid corresponding to position 701 (A) in SEQ ID NO: 1 is V. In one embodiment, the amino acid corresponding to position 18 (L) in SEQ ID NO: 1 is F. In one embodiment, the amino acid corresponding to position 246 (R) in SEQ ID NO: 1 is I. In one embodiment, the amino acid corresponding to position 242 (L) in SEQ ID NO: 1 is deleted. In one embodiment, the amino acid corresponding to position 243 (A) in SEQ ID NO: 1 is deleted. In one embodiment, the amino acid corresponding to position 244 (L) in SEQ ID NO: 1 is deleted. In one embodiment, the amino acid corresponding to position 453 (Y) in SEQ ID NO: 1 is F. In one embodiment, the amino acid corresponding to position 692 (1) in SEQ ID NO: 1 is V. In one embodiment, the amino acid corresponding to position 1147 (S) in SEQ ID NO: 1 is L. In one embodiment, the amino acid corresponding to position 1229 (M) in SEQ ID NO: 1 is I. In one embodiment, the amino acid corresponding to position 20 (T) in SEQ ID NO: 1 is N. In one embodiment, the amino acid corresponding to position 26 (P) in SEQ ID NO: 1 is S. In one embodiment, the amino acid corresponding to position 138 (D) in SEQ ID NO: 1 is Y. In one embodiment, the amino acid corresponding to position 190 (R) in SEQ ID NO: 1 is S. In one embodiment, the amino acid corresponding to position 655 (H) in SEQ ID NO: 1 is Y. In one embodiment, the amino acid corresponding to position 1027 (T) in SEQ ID NO: 1 is I. In one embodiment, the amino acid corresponding to position 1176 (V) in SEQ ID NO: 1 is F.

In some embodiments, the methods and agents described herein following administration to a subject induce an antibody response, in particular a neutralizing antibody response, in the subject that targets 501.V2.

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: D80A, D215G, E484K, N501Y, A701V, and K417N and optionally: L18F, R246I, and deletion 242-244. Said S protein variant may also comprise a D→G mutation at a position corresponding to position 614 in SEQ ID NO: 1.

In some embodiments, the methods and agents described herein following administration to a subject induce an antibody response, in particular a neutralizing antibody response, in the subject that targets "B.1.1.248".

In some embodiments, the methods and agents described herein following administration to a subject induce an antibody response, in particular a neutralizing antibody response, in the subject that targets a S protein variant comprising the following mutations at positions corresponding to the following positions in SEQ ID NO: 1: L18F, T20N, P26S, D138Y, R190S, K417T, E484K, N501Y, H655Y, T1027I, and V1176F.

In some embodiments, the methods and agents described herein following administration to a subject induce an antibody response, in particular a neutralizing antibody response, in the subject that targets the Omicron (B.1.1.529) variant.

In some embodiments, the methods and agents described herein following administration to a subject induce an antibody response, in particular a neutralizing antibody response, in the subject that targets a S protein variant comprising at least 10, at least 15, at least 20, at least 21, at least 22, at least 23, at least 24, at least 25, at least 26, at least 27, at least 28, at least 29, at least 30, at least 31, at least 32, at least 33, at least 34, at least 35, at least 36, or at least 37 of the following mutations: T547K, H655Y, D614G, N679K, P681H, N969K, S373P, S371L, N440K, G339D, G446S, N856K, N764K, K417N, D796Y, Q954H, T95I, A67V, L981F, S477N, G496S, T478K, Q498R, Q493R, E484A, N501Y, S375F, Y505H, V143del, H69del, V70del, N211del, L212I, ins214EPE, G142D, Y144del, Y145del, L141del, Y144F, Y145D, G142del, as compared to SEQ ID NO: 1.

In some embodiments, the methods and agents described herein following administration to a subject induce an antibody response, in particular a neutralizing antibody response, in the subject that targets a S protein variant comprising at least 10, at least 15, at least 20, at least 21, at least 22, at least 23, at least 24, or all of the following mutations: T547K, H655Y, D614G, N679K, P681H, N969K, S373P, S371L, N440K, G339D, G446S, N856K, N764K, K417N, D796Y, Q954H, T95I, A67V, L981F, S477N, G496S, T478K, Q498R, Q493R, E484A, as compared to SEQ ID NO: 1. Said S protein variant may include at least 1, at least 2, at least 3, at least 4, at least 5, or all of the following mutations: N501Y, S375F, Y505H, V143del, H69del, V70del, as compared to SEQ ID NO: 1 and/or may include at least 1, at least 2, at least 3, at least 4, at least 5, or all of the following mutations: N211del, L212I, ins214EPE, G142D, Y144del, Y145del, as compared to SEQ ID NO: 1. In some embodiments, said S protein variant may include at least 1, at least 2, at least 3, or all of the following mutations: L141del, Y144F, Y145D, G142del, as compared to SEQ ID NO: 1.

In some embodiments, the methods and agents described herein following administration to a subject induce an antibody response, in particular a neutralizing antibody response, in the subject that targets a S protein variant comprising at least 10, at least 15, at least 20, at least 21, at least 22, at least 23, at least 24, at least 25, at least 26, at least 27, at least 28, at least 29, at least 30, at least 31, at least 32, or at least 33 of the following mutations:

A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, and L981F, as compared to SEQ ID NO: 1.

In some embodiments, the methods and agents described herein following administration to a subject induce an antibody response, in particular a neutralizing antibody response, in the subject that targets a S protein variant comprising the following mutations:

A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, and L981F, as compared to SEQ ID NO: 1.

In some embodiments, the methods and agents described herein following administration to a subject induce an antibody response, in particular a neutralizing antibody response, in the subject that targets a S protein variant comprising the following mutations:

A67V, Δ69-70, T95I, G142D, Δ143-145, Δ211, L212I, ins214EPE, G339D, S371L, S373P, S375F, S477N, T478K, E484A, Q493R, G496S, Q498R, N501Y, Y505H, T547K, D614G, H655Y, N679K, P681H, N764K, D796Y, N856K, Q954H, N969K, and L981F, as compared to SEQ ID NO: 1.

In some embodiments, the methods and agents described herein following administration to a subject induce an immune response (cellular and/or antibody response, in particular neutralizing antibody response) in the subject that targets the Omicron (B.1.1.529) variant.

In some embodiments, the methods and agents described herein following administration to a subject induce an immune response (cellular and/or antibody response, in particular neutralizing antibody response) in the subject that targets a S protein variant comprising at least 10, at least 15, at least 20, at least 21, at least 22, at least 23, at least 24, at least 25, at least 26, at least 27, at least 28, at least 29, at least 30, at least 31, at least 32, at least 33, at least 34, at least 35, at least 36, or at least 37 of the following mutations: T547K, H655Y, D614G, N679K, P681H, N969K, S373P, S371L, N440K, G339D, G446S, N856K, N764K, K417N, D796Y, Q954H, T95I, A67V, L981F, S477N, G496S, T478K, Q498R, Q493R, E484A, N501Y, S375F, Y505H, V143del, H69del, V70del, N211del, L212I, ins214EPE, G142D, Y144del, Y145del, L141del, Y144F, Y145D, G142del, as compared to SEQ ID NO: 1.

In some embodiments, the methods and agents described herein following administration to a subject induce an immune response (cellular and/or antibody response, in particular neutralizing antibody response) in the subject that targets a S protein variant comprising at least 10, at least 15, at least 20, at least 21, at least 22, at least 23, at least 24, or all of the following mutations: T547K, H655Y, D614G, N679K, P681H, N969K, S373P, S371L, N440K, G339D, G446S, N856K, N764K, K417N, D796Y, Q954H, T95I, A67V, L981F, S477N, G496S, T478K, Q498R, Q493R, E484A, as compared to SEQ ID NO: 1. Said S protein variant may include at least 1, at least 2, at least 3, at least 4, at least 5, or all of the following mutations: N501Y, S375F, Y505H, V143del, H69del, V70del, as compared to SEQ ID NO: 1 and/or may include at least 1, at least 2, at least 3, at least 4, at least 5, or all of the following mutations: N211del, L212I, ins214EPE, G142D, Y144del, Y145del, as compared to SEQ ID NO: 1. In some embodiments, said S protein variant may include at least 1, at least 2, at least 3, or all of the following mutations: L141del, Y144F, Y145D, G142del, as compared to SEQ ID NO: 1.

In some embodiments, the methods and agents described herein following administration to a subject induce an immune response (cellular and/or antibody response, in particular neutralizing antibody response) in the subject that targets a S protein variant comprising at least 10, at least 15, at least 20, at least 21, at least 22, at least 23, at least 24, at least 25, at least 26, at least 27, at least 28, at least 29, at least 30, at least 31, at least 32, or at least 33 of the following mutations:

A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, and L981F, as compared to SEQ ID NO: 1.

In some embodiments, the methods and agents described herein following administration to a subject induce an immune response (cellular and/or antibody response, in particular neutralizing antibody response) in the subject that targets a S protein variant comprising the following mutations:

A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, and L981F, as compared to SEQ ID NO: 1.

In some embodiments, the methods and agents described herein following administration to a subject induce an immune response (cellular and/or antibody response, in particular neutralizing antibody response) in the subject that targets a S protein variant comprising the following mutations:

A67V, Δ69-70, T95I, G142D, Δ143-145, Δ211, L212I, ins214EPE, G339D, S371L, S373P, S375F, S477N, T478K, E484A, Q493R, G496S, Q498R, N501Y, Y505H, T547K, D614G, H655Y, N679K, P681H, N764K, D796Y, N856K, Q954H, N969K, and L981F, as compared to SEQ ID NO: 1.

The term "amino acid corresponding to position . . . " as used herein refers to an amino acid position number corresponding to an amino acid position number in SARS-CoV-2 S protein, in particular the amino acid sequence shown in SEQ ID NO: 1. The phrase "as compared to SEQ ID NO: 1" is equivalent to "at positions corresponding to the following positions in SEQ ID NO: 1". Corresponding amino acid positions in other coronavirus S protein variants such as SARS-CoV-2 S protein variants may be found by alignment with SARS-CoV-2 S protein, in particular the amino acid sequence shown in SEQ ID NO: 1. It is considered well-known in the art how to align a sequence or segment in a sequence and thereby determine the corresponding position in a sequence to an amino acid position according to the present disclosure. Standard sequence alignment programs such as ALIGN, ClustalW or similar, typically at default settings may be used.

In some embodiments, the panel of different S protein variants to which an antibody response is targeted comprises at least 5, at least 10, at least 15, or even more S protein variants selected from the group consisting of the Q321S, V341I, Δ348T, N354D, S359N, V367F, K378S, R408I, Q409E, Δ435S, K458R, I472V, G476S, V483A, Y508H, H519P and D614G variants described above. In some embodiments, the panel of different S protein variants to which an antibody response is targeted comprises all S protein variants from the group consisting of the Q321S, V341I, Δ348T, N354D, S359N, V367F, K378S, R408I, Q409E, Δ435S, K458R, I472V, G476S, V483A, Y508H, H519P and D614G variants described above.

In some embodiments, the panel of different S protein variants to which an antibody response is targeted comprises at least 5, at least 10, at least 15, or even more S protein variants selected from the group consisting of the Q321L, V341I, Δ348T, N354D, S359N, V367F, K378R, R408I, Q409E, Δ435S, N439K, K458R, I472V, G476S, S477N, V483A, Y508H, H519P and D614G variants described above. In some embodiments, the panel of different S protein variants to which an antibody response is targeted comprises all S protein variants from the group consisting of the Q321L, V341I, Δ348T, N354D, S359N, V367F, K378R, R408I, Q409E, Δ435S, N439K, K458R, I472V, G476S, S477N, V483A, Y508H, H519P and D614G variants described above.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises one or more of the mutations described herein for S protein variants such as SARS-CoV-2 S protein variants, in particular naturally occurring S protein variants. In one embodiment, a SARS-CoV-2 S protein, an immunogenic variant thereof, or an immunogenic fragment of the SARS-CoV-2 S protein or the immunogenic variant thereof, e.g., as encoded by the RNA described herein, comprises a mutation at a position corresponding to position 501 (N) in SEQ ID NO: 1. In one embodiment, the amino acid corresponding to position 501 (N) in SEQ ID NO: 1 is Y. In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises one or more mutations, such as all mutations, of a SARS-CoV-2 S protein of a SARS-CoV-2 variant selected from the group consisting of VOC-202012/01, 501.V2, Cluster 5 and B.1.1.248. In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises an amino acid sequence with alanine substitution at position 80, glycine substitution at position 215, lysine substitution at position 484, tyrosine substitution at position 501, valine substitution at position 701, phenylalanine substitution at position 18, isoleucine substitution at position 246, asparagine substitution at position 417, glycine substitution at position 614, deletions at positions 242 to 244, and proline substitutions at positions 986 and 987 of SEQ ID NO:1.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises at least 10, at least 15, at least 20, at least 21, at least 22, at least 23, at least 24, at least 25, at least 26, at least 27, at least 28, at least 29, at least 30, at least 31, at least 32, at least 33, at least 34, at least 35, at least 36, or at least 37 of the following mutations: T547K, H655Y, D614G, N679K, P681H, N969K, S373P, S371L, N440K, G339D, G446S, N856K, N764K, K417N, D796Y, Q954H, T95I, A67V, L981F, S477N, G496S, T478K, Q498R, Q493R, E484A, N501Y, S375F, Y505H, V143del, H69del, V70del, N211del, L212I, ins214EPE, G142D, Y144del, Y145del, L141del, Y144F, Y145D, G142del, as compared to SEQ ID NO: 1. In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprising said mutations comprises K986P and V987P, as compared to SEQ ID NO: 1.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises at least 10, at least 15, at least 20, at least 21, at least 22, at least 23, at least 24, or all of the following mutations: T547K, H655Y, D614G, N679K, P681H, N969K, S373P, S371L, N440K, G339D, G446S, N856K, N764K, K417N, D796Y, Q954H, T95I, A67V, L981F, S477N, G496S, T478K, Q498R, Q493R, E484A, as compared to SEQ ID NO: 1. Said SARs-CoV-2 S protein, variant, or fragment may include at least 1, at least 2, at least 3, at least 4, at least 5, or all of the following mutations: N501Y, S375F, Y505H, V143del, H69del, V70del, as compared to SEQ ID NO: 1 and/or may include at least 1, at least 2, at least 3, at least 4, at least 5, or all of the following mutations: N211del, L212I, ins214EPE, G142D, Y144del, Y145del, as compared to SEQ ID NO: 1. In some embodiments, said SARs-CoV-2 S protein, variant, or fragment may include at least 1, at least 2, at least 3, or all of the following mutations: L141del, Y144F, Y145D, G142del, as compared to SEQ ID NO: 1. In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprising said mutations comprises K986P and V987P, as compared to SEQ ID NO: 1.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises at least 10, at least 15, at least 20, at least 21, at least 22, at least 23, at least 24, at least 25, at least 26, at least 27, at least 28, at least 29, at least 30, at least 31, at least 32, or at least 33 of the following mutations:

A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, and L981F, as compared to SEQ ID NO: 1. In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprising said mutations comprises K986P and V987P, as compared to SEQ ID NO: 1.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises the following mutations:

A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, and L981F, as compared to SEQ ID NO: 1.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprising said mutations comprises K986P and V987P, as compared to SEQ ID NO: 1.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises the following mutations:

A67V, Δ69-70, T95I, G142D, Δ143-145, Δ211, L212I, ins214EPE, G339D, S371L, S373P, S375F, S477N, T478K, E484A, Q493R, G496S, Q498R, N501Y, Y505H, T547K, D614G, H655Y, N679K, P681H, N764K, D796Y, N856K, Q954H, N969K, and L981F, as compared to SEQ ID NO: 1.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprising said mutations comprises K986P and V987P, as compared to SEQ ID NO: 1.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises the following mutations:

A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F, K986P and V987P, as compared to SEQ ID NO: 1.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises the following mutations:

A67V, Δ69-70, T95I, G142D, Δ143-145, Δ211, L212I, ins214EPE, G339D, S371L, 5373P, S375F, 5477N, T478K, E484A, Q493R, G496S, Q498R, N501Y, Y505H, T547K, D614G, H655Y, N679K, P681H, N764K, D796Y, N856K, Q954H, N969K, L981F, K986P and V987P, as compared to SEQ ID NO: 1.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises the following mutations:

In some embodiments, the spike changes in Omicron BA.2 variant include T19I, Δ24-26, A27S, G142D, V213G, G339D, S371F, S373P, S375F, T376A, D405N, R408S, K417N, N440K, 5477N, T478K, E484A, Q493R, Q498R, N501Y, Y505H, D614G, H655Y, N679K, P681H, N764K, D796Y, Q954H, N969K, K986P, and V987P, as compared to SEQ ID NO: 1.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprises the following mutations:

T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K, K986P, and V987P, as compared to SEQ ID NO: 1. In some embodiments, administration of a variant specific vaccine (e.g., a variant specific vaccine disclosed herein) may result in an improved immune response in a patient as compared to administration of vaccine encoding or comprising a SARS-CoV-2 S protein from a Wuhan strain, or an immunogenic fragment thereof. In some embodiments, administration of a variant-specific vaccine may result in induction of a broader immune response in a subject as compared to a patient administered a vaccine comprising or encoding a SARS-CoV-2 S protein from a Wuhan strain (or an immunogenic fragment thereof) (e.g., induce a stronger neutralization response against a greater number of SARS-CoV-2 variants and/or a neutralization response that recognizes epitopes in a greater number of SARS-CoV-2 variants).

In particular embodiments, a broader immune response may be induced when a variant specific vaccine is administered in combination with a vaccine comprising or encoding a SARS-CoV-2 S protein from a different variant or from a Wuhan strain (e.g., in some embodiments, a broader immune response may be induced when a variant specific vaccine is administered in combination with a vaccine comprising or encoding a SARS-CoV-2 S protein from a Wuhan strain or a vaccine comprising or encoding a SARS-CoV-2 S protein comprising mutations characteristic of a different SARS-CoV-2 variant). For example, a broader immune response may be induced when an RNA vaccine encoding a SARS-CoV-2 S protein from a Wuhan strain is administered in combination with an RNA vaccine encoding a SARS-CoV-2 S protein having mutations characteristic of an Omicron variant. In another embodiment, a broader immune response may be induced when an RNA vaccine encoding a SARS-CoV-2 S protein comprising one or more mutations characteristic of a delta variant is administered in combination with an RNA vaccine encoding a SARS-CoV-2 S protein comprising one or more mutations characteristic of an Omicron variant. In such embodiments, a "broader" immune response may be defined relative to a patient administered a vaccine comprising or encoding a SARS-CoV-2 S protein from a single variant (e.g., an RNA vaccine encoding a SARS-CoV-2 S protein from a Wuhan strain). Vaccines comprising or encoding S proteins from different SARS-CoV-2 variants, or immunogenic fragments thereof, may be administered in combination by administering at different time points (e.g., administering a vaccine encoding a SARS-CoV-2 S protein from a Wuhan strain and a vaccine encoding a SARS-CoV-2 S protein having one or more mutations characteristic of a variant strain at different time points, e.g., both administered as part of a primary regimen or part of a booster regimen; or one is administered as part of a primary regimen while another is administered as part of a booster regimen). In some embodiments, vaccines comprising or encoding S proteins from different SARS-CoV-2 variants, or immunogenic fragments thereof, may be administered in combination by administering a multivalent vaccine (e.g., a composition comprising RNA encoding a SARS-CoV-2 S protein from a Wuhan strain and RNA encoding a SARS-CoV-2 S protein having mutations characteristic of an Omicron variant). In some embodiments, a variant specific vaccine may induce a superior immune response (e.g., inducing higher concentrations of neutralizing antibodies) against a variant against which the vaccine is specifically designed to immunize, and an immune response against one or more other variants. In some such embodiments, an immune response against other variant(s) may be comparable to or higher than that as observed with a vaccine that encodes or comprises a SARS-CoV-2 S protein from a Wuhan strain.

In some embodiments, the geometric mean ratio (GMR) or geometric mean fold rise (GMFR) of neutralization antibodies induced by a variant specific vaccine is at least 1.1, 1.2, 1.3, 1.4, 1.5, 1.6, 1.7, 1.8, 1.9, or 2.0 (e.g., 1.1 to 4, 1.1 to 3.5, 1.1 to 3, 1.5 to 3, or 1.1 to 1.5) fold higher than that induced by a non-variant specific vaccine (e.g., as measured 1 day to 3 months after immunization, 7 days to 2 months after administration, about 7 days, or about 1 month after administration).

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprising said mutations comprises the amino acid sequence of SEQ ID NO: 49, an amino acid sequence having at least 99.5%, 99%, 98.5%, 98%, 98.5%, 97%, 96%, 95%, 90%, 85%, or 80% identity to the amino acid sequence of SEQ ID NO: 49, or an immunogenic fragment of the amino acid sequence of SEQ ID NO: 49, or the amino acid sequence having at least 99.5%, 99%, 98.5%, 98%, 98.5%, 97%, 96%, 95%, 90%, 85%, or 80% identity to the amino acid sequence of SEQ ID NO: 49. In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprising said mutations comprises the amino acid sequence of SEQ ID NO: 49.

In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprising said mutations comprises the amino acid sequence of SEQ ID NO: 52, an amino acid sequence having at least 99.5%, 99%, 98.5%, 98%, 98.5%, 97%, 96%, 95%, 90%, 85%, or 80% identity to the amino acid sequence of SEQ ID NO: 52, or an immunogenic fragment of the amino acid sequence of SEQ ID NO: 52, or the amino acid sequence having at least 99.5%, 99%, 98.5%, 98%, 98.5%, 97%, 96%, 95%, 90%, 85%, or 80% identity to the amino acid sequence of SEQ ID NO: 52. In some embodiments, a SARS-CoV-2 S protein, an immunogenic variant thereof, or an immunogenic fragment of the SARS-CoV-2 S protein or the immunogenic variant thereof, e.g., as encoded by the RNA described herein, comprising said mutations comprises the amino acid sequence of SEQ ID NO: 52.

In some embodiments, the methods and agents, e.g., RNA (e.g., mRNA) compositions, described herein following administration to a subject induce a cell-mediated immune response (e.g., CD4+ and/or CD8+ T cell response). In some embodiments, T cells are induced that recognize one or more epitopes (e.g., MHC class I-restricted epitopes) selected from the group consisting of LPFNDGVYF (SEQ ID NO: 145), GVYFASTEK (SEQ ID NO: 146), YLQPRTFLL (SEQ ID NO: 138), QPTESIVRF (SEQ ID NO: 143), CVADYSVLY (SEQ ID NO: 147), KCYGVSPTK (SEQ ID NO: 151), NYNYLYRLF (SEQ ID NO: 141), FQPTNGVGY (SEQ ID NO: 148), IPFAMQMAY (SEQ ID NO: 144), RLQSLQTYV (SEQ ID NO: 139), GTHWFVTQR (SEQ ID NO: 149), VYDPLQPEL (SEQ ID NO: 150), QYIKWPWYI (SEQ ID NO: 140), and KWPWYIWLGF (SEQ ID NO: 142). In one embodiment, T cells are induced that recognize the epitope YLQPRTFLL (SEQ ID NO: 138). In one embodiment, T cells are induced that recognize the epitope NYNYLYRLF (SEQ ID NO: 141). In one embodiment, T cells are induced that recognize the epitope QYIKWPWYI (SEQ ID NO: 140). In one embodiment, T cells are induced that recognize the epitope KCYGVSPTK (SEQ ID NO: 151). In one embodiment, T cells are induced that recognize the epitope RLQSLQTYV (SEQ ID NO: 139). In some embodiments, the methods and agents, e.g., RNA (e.g., mRNA) compositions, described herein are administered according to a regimen which achieves such induction of T cells.

In some embodiments, the methods and agents, e.g., RNA (e.g., mRNA) compositions, described herein following administration to a subject induce a cell-mediated immune response (e.g., CD4+ and/or CD8+ T cell response) that is detectable 15 weeks or later, 16 weeks or later, 17 weeks or later, 18 weeks or later, 19 weeks or later, 20 weeks or later, 21 weeks or later, 22 weeks or later, 23 weeks or later, 24 weeks or later or 25 weeks or later after administration, e.g., using two doses of the RNA described herein (wherein the second dose may be administered about 21 days following administration of the first dose). In some embodiments, the methods and agents, e.g., RNA (e.g., mRNA) compositions, described herein are administered according to a regimen which achieves such induction of a cell-mediated immune response.

In one embodiment, vaccination against Coronavirus described herein, e.g., using RNA described herein which may be administered in the amounts and regimens described herein, e.g., at two doses of 30 μg per dose e.g. administered 21 days apart, may be repeated after a certain period of time, e.g., once it is observed that protection against Coronavirus infection diminishes, using the same or a different vaccine as used for the first vaccination. Such certain period of time may be at least 6 months, 1 year, two years etc. In one embodiment, the same RNA as used for the first vaccination is used for the second or further vaccination, however, at a lower dose or a lower frequency of administration. For example, the first vaccination may comprise vaccination using a dose of about 30 μg per dose, wherein in one embodiment, at least two of such doses are administered, (for example, a second dose may be administered about 21 days following administration of the first dose) and the second or further vaccination may comprise vaccination using a dose of less than about 30 μg per dose, wherein in one embodiment, only one of such doses is administered. In one embodiment, a different RNA as used for the first vaccination is used for the second or further vaccination, e.g., BNT162b2 is used for the first vaccination and BNT162B1 or BNT162b3 is used for the second or further vaccination.

In one embodiment, the vaccination regimen comprises a first vaccination using at least two doses of the RNA described herein, e.g., two doses of the RNA described herein (wherein the second dose may be administered about 21 days following administration of the first dose), and a second vaccination using a single dose or multiple doses, e.g., two doses, of the RNA described herein. In various embodiments, the second vaccination is administered 3 to 24 months, 6 to 18 months, 6 to 12 months, or 5 to 7 months after administration of the first vaccination, e.g., after the initial two-dose regimen. The amount of RNA used in each dose of the second vaccination may be equal or different to the amount of RNA used in each dose of the first vaccination. In one embodiment, the amount of RNA used in each dose of the second vaccination is equal to the amount of RNA used in each dose of the first vaccination. In one embodiment, the amount of RNA used in each dose of the second vaccination and the amount of RNA used in each dose of the first vaccination is about 30 μg per dose. In one embodiment, the same RNA as used for the first vaccination is used for the second vaccination.

In one embodiment, the RNA used for the first vaccination and for the second vaccination is BNT162b2.

In some embodiments, when the RNA used for the first vaccination and for the second vaccination is BNT162b2, the aim is to induce an immune response that targets SARS-CoV-2 variants including, but not limited to, the Omicron (B.1.1.529) variant. Accordingly, in some embodiments, when the RNA used for the first vaccination and for the second vaccination is BNT162b2, the aim is to protect a subject from infection with SARS-CoV-2 variants including, but not limited to, the Omicron (B.1.1.529) variant.

In one embodiment, a different RNA as used for the first vaccination is used for the second vaccination. In one embodiment, the RNA used for the first vaccination is BNT162b2 and the RNA used for the second vaccination is RNA encoding a SARS-CoV-2 S protein of a SARS-CoV-2 variant strain, e.g., a strain discussed herein. In one embodiment, the RNA used for the first vaccination is BNT162b2 and the RNA used for the second vaccination is RNA encoding a SARS-CoV-2 S protein of a SARS-CoV-2 variant strain that is prevalent or rapidly spreading at the time of the second vaccination. In one embodiment, the RNA used for the first vaccination is BNT162b2 and the RNA used for the second vaccination is RNA encoding a SARS-CoV-2 S protein, an immunogenic variant thereof, or an immunogenic fragment of the SARS-CoV-2 S protein or the immunogenic variant thereof comprising one or more of the mutations described herein for S protein variants such as SARS-CoV-2 S protein variants, in particular naturally occurring S protein variants. In one embodiment, the RNA used for the first vaccination is BNT162b2 and the RNA used for the second vaccination is RNA encoding a SARS-CoV-2 S protein, an immunogenic variant thereof, or an immunogenic fragment of the SARS-CoV-2 S protein or the immunogenic variant thereof comprising one or more mutations, such as all mutations, of a SARS-CoV-2 S protein of a SARS-CoV-2 variant selected from the group consisting of VOC-202012/01, 501.V2, Cluster 5, B.1.1.248, and Omicron (B.1.1.529).

In one embodiment, the RNA used for the first vaccination encodes a polypeptide comprising an amino acid sequence with proline residue substitutions at positions 986 and 987 of SEQ ID NO:1 and the RNA used for the second vaccination is RNA encoding a polypeptide comprising an amino acid sequence with alanine substitution at position 80, glycine substitution at position 215, lysine substitution at position 484, tyrosine substitution at position 501, valine substitution at position 701, phenylalanine substitution at position 18, isoleucine substitution at position 246, asparagine substitution at position 417, glycine substitution at position 614, deletions at positions 242 to 244, and proline substitutions at positions 986 and 987 of SEQ ID NO:1.

In one embodiment, the RNA used for the first vaccination encodes a polypeptide comprising an amino acid sequence with proline residue substitutions at positions 986 and 987 of SEQ ID NO:1 and the RNA used for the second vaccination is RNA encoding a polypeptide comprising an amino acid sequence with the following mutations in SEQ ID NO:1:

A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F, K986P and V987P, as compared to SEQ ID NO: 1.

In one embodiment, the RNA used for the first vaccination encodes a polypeptide comprising an amino acid sequence with following mutations in SEQ ID NO: 1: residue substitutions at positions 986 and 987 of SEQ ID NO:1 and the RNA used for the second vaccination is RNA encoding a polypeptide comprising an amino acid sequence with the following mutations in SEQ ID NO:1:

T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K, K986P, and V987P, as compared to SEQ ID NO: 1.

In one embodiment, the RNA used for the first vaccination encodes a polypeptide comprising an amino acid sequence with proline residue substitutions at positions 986 and 987 of SEQ ID NO:1 and the RNA used for the second vaccination is RNA encoding a polypeptide comprising an amino acid sequence with the following mutations in SEQ ID NO:1:

T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K, K986P, and V987P, as compared to SEQ ID NO: 1.

In one embodiment, the RNA used for the first vaccination encodes a polypeptide comprising an amino acid sequence with following mutations in SEQ ID NO: 1:

A67V, Δ69-70, T95I, G142D, Δ143-145, Δ211, L212I, ins214EPE, G339D, S371L, 5373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F, K986P and V987P, and the RNA used for the second vaccination encodes a polypeptide comprising an amino acid sequence with the following mutations in SEQ ID NO: 1:

T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K, K986P, and V987P, as compared to SEQ ID NO: 1.

In one embodiment, the RNA used for the first vaccination encodes a polypeptide comprising an amino acid sequence with following mutations in SEQ ID NO: 1:

A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F, K986P and V987P, and the RNA used for the second vaccination encodes a polypeptide comprising an amino acid sequence with the following mutations in SEQ ID NO: 1:

T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K, K986P, and V987P, as compared to SEQ ID NO: 1.

In one embodiment, the RNA used for the first vaccination encodes a polypeptide comprising an amino acid sequence with following mutations in SEQ ID NO: 1:

T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K, K986P, and V987P, as compared to SEQ ID NO: 1, and the RNA used for the second vaccination encodes a polypeptide comprising an amino acid sequence with the following mutations in SEQ ID NO: 1:

T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K, K986P, and V987P, as compared to SEQ ID NO: 1.

In one embodiment, the RNA used for the first vaccination encodes a polypeptide comprising the amino acid sequence of SEQ ID NO: 7 and the RNA used for the second vaccination is RNA encoding a polypeptide comprising the amino acid sequence of SEQ ID NO: 49.

In one embodiment, the RNA used for the first vaccination comprises the nucleotide sequence of SEQ ID NO: 20 and the RNA used for the second vaccination is RNA comprising the nucleotide sequence of SEQ ID NO: 51.

In one embodiment, the RNA used for the first vaccination encodes a polypeptide comprising the amino acid sequence of SEQ ID NO: 7 and the RNA used for the second vaccination is RNA encoding a polypeptide comprising the amino acid sequence of SEQ ID NO: 55, 58 or 61.

In one embodiment, the RNA used for the first vaccination comprises the nucleotide sequence of SEQ ID NO: 20 and the RNA used for the second vaccination is RNA comprising the nucleotide sequence of SEQ ID NO: 57, 60, or 63a.

In one embodiment, the RNA used for the first vaccination encodes a polypeptide comprising the amino acid sequence of SEQ ID NO: 58 and the RNA used for the second vaccination is RNA encoding a polypeptide comprising the amino acid sequence of SEQ ID NO: 49, 55 or 61.

In one embodiment, the RNA used for the first vaccination comprises the nucleotide sequence of SEQ ID NO: 60 and the RNA used for the second vaccination is RNA comprising the nucleotide sequence of SEQ ID NO: 51, 57, or 63a.

In one embodiment, the RNA used for the first vaccination encodes a polypeptide comprising the amino acid sequence of SEQ ID NO: 49 and the RNA used for the second vaccination is RNA encoding a polypeptide comprising the amino acid sequence of SEQ ID NO: 55 or 61.

In one embodiment, the RNA used for the first vaccination comprises the nucleotide sequence of SEQ ID NO: 51 and the RNA used for the second vaccination is RNA comprising the nucleotide sequence of SEQ ID NO: 57 or 63a.

In one embodiment, the RNA used for the first vaccination encodes a polypeptide comprising the amino acid sequence of SEQ ID NO: 55 and the RNA used for the second vaccination is RNA encoding a polypeptide comprising the amino acid sequence of SEQ ID NO: 61.

In one embodiment, the RNA used for the first vaccination comprises the nucleotide sequence of SEQ ID NO: 57 and the RNA used for the second vaccination is RNA comprising the nucleotide sequence of SEQ ID NO: 63a.

In one embodiment, the RNA used for the first vaccination encodes a polypeptide comprising an amino acid sequence with proline residue substitutions at positions 986 and 987 of SEQ ID NO:1 and the RNA used for the second vaccination is RNA encoding a polypeptide comprising an amino acid sequence with the following mutations in SEQ ID NO:1:

A67V, 669-70, T95I, G142D, Δ143-145, Δ211, L212I, ins214EPE, G339D, S371L, S373P, S375F, S477N, T478K, E484A, Q493R, G496S, Q498R, N501Y, Y505H, T547K, D614G, H655Y, N679K, P681H, N764K, D796Y, N856K, Q954H, N969K, L981F, K986P and V987P, as compared to SEQ ID NO: 1. In some embodiments, the polypeptide encoded by the RNA used in the second vaccination further comprises proline residue substitutions at positions corresponding to 986 and 987 of SEQ ID NO:1.

In one embodiment, the RNA used for the first vaccination encodes a polypeptide comprising the amino acid sequence of SEQ ID NO: 7 and the RNA used for the second vaccination is RNA encoding a polypeptide comprising the amino acid sequence of SEQ ID NO: 52.

In one embodiment, a subject is administered a primary regimen comprising two 30 ug doses of RNA comprising a sequence encoding a polypeptide comprising the amino acid sequence of SEQ ID NO: 7, and a booster regimen comprising at least one dose of 30 ug of RNA comprising a sequence encoding a polypeptide comprising the amino acid sequence of SEQ ID NO: 7, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a sequence encoding a polypeptide comprising the amino acid sequence of SEQ ID NO: 7.

In one embodiment, a subject is administered a primary regimen comprising two 30 ug doses of RNA comprising a sequence encoding a polypeptide comprising the amino acid sequence of SEQ ID NO: 7, and a booster regimen comprising at least one dose of 50 ug of RNA comprising a sequence encoding a polypeptide comprising the amino acid sequence of SEQ ID NO: 7, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a sequence encoding a polypeptide comprising the amino acid sequence of SEQ ID NO: 7.

In one embodiment, a subject is administered a primary regimen comprising two 30 ug doses of RNA comprising a sequence encoding a polypeptide comprising the amino acid sequence of SEQ ID NO: 7, and a booster regimen comprising at least one dose of 60 ug of RNA comprising a sequence encoding a polypeptide comprising the amino acid sequence of SEQ ID NO: 7, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a sequence encoding a polypeptide comprising the amino acid sequence of SEQ ID NO: 7.

In one embodiment, a subject is administered a primary regimen comprising two 30 ug doses of RNA comprising a sequence encoding a polypeptide comprising the amino acid sequence of SEQ ID NO: 7, and a booster regimen comprising at least one dose of 30 ug of RNA comprising a sequence encoding a polypeptide comprising the amino acid sequence of SEQ ID NO: 49, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a sequence encoding a polypeptide comprising the amino acid sequence of SEQ ID NO: 7.

In one embodiment, a subject is administered a primary regimen comprising at least two 30 ug doses of RNA comprising a sequence encoding a polypeptide comprising the amino acid sequence of SEQ ID NO: 7, and a booster regimen comprising at least two doses of 30 ug of RNA comprising a sequence encoding a polypeptide comprising the amino acid sequence of SEQ ID NO: 49, wherein in some embodiments the two doses of the booster regimen are administered at least 2 months apart from each other (e.g., at least 3 months, at least 4 months, at least 5 months, or at least 6 months apart from each other). In some embodiments, such a subject may have previously been administered a 30 ug dose of RNA comprising a sequence encoding a polypeptide comprising the amino acid sequence of SEQ ID NO: 7 as a booster dose.

In one embodiment, a subject is administered a primary regimen comprising two 30 ug doses of RNA comprising a sequence encoding a polypeptide comprising the amino acid sequence of SEQ ID NO: 7, and a booster regimen comprising at least one dose of 50 ug of RNA comprising a nucleotide sequence that encodes the amino acid sequence of SEQ ID NO: 49, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a sequence encoding a polypeptide comprising the amino acid sequence of SEQ ID NO: 7.

In one embodiment, a subject is administered a primary regimen comprising two 30 ug doses of RNA comprising a sequence encoding a polypeptide comprising the amino acid sequence of SEQ ID NO: 7, and a booster regimen comprising at least one dose of 60 ug of RNA comprising a nucleotide sequence that encodes the amino acid sequence of SEQ ID NO: 49, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a sequence encoding a polypeptide comprising the amino acid sequence of SEQ ID NO: 7.

In some embodiments, a subject is administered a primary regimen comprising two doses of 30 ug of RNA (administered, e.g., about 21 days after one another), wherein each 30 ug dose of RNA comprises 15 ug of RNA comprising a nucleotide sequence encoding the amino acid sequence of SEQ ID NO: 7 and 15 ug of RNA comprising a nucleotide sequence encoding the amino acid sequence of SEQ ID NO: 49. In some embodiments, such a primary regimen is administered to a vaccine naive subject.

In some embodiments, a subject is administered a primary regimen comprising two doses of 30 ug of RNA (administered, e.g., about 21 days after one another), wherein each 30 ug dose of RNA comprises a nucleotide sequence encoding the amino acid sequence of SEQ ID NO: 49. In some embodiments, such a primary regimen is administered to a vaccine naive subject.

In one embodiment, a subject is administered a primary regimen comprising two 30 ug doses of RNA comprising a sequence encoding a polypeptide comprising the amino acid sequence of SEQ ID NO: 7, and a booster regimen comprising at least one dose of 30 ug of RNA, wherein the 30 ug of RNA comprises 15 ug of RNA comprising a nucleotide sequence encoding the amino acid sequence of SEQ ID NO: 7 and 15 ug of RNA comprising a nucleotide sequence encoding the amino acid sequence of SEQ ID NO: 49, wherein the two RNAs are optionally administered in the same composition, and wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a sequence encoding a polypeptide comprising the amino acid sequence of SEQ ID NO: 7.

In one embodiment, a subject is administered a primary regimen comprising two 30 ug doses of RNA comprising a sequence encoding a polypeptide comprising the amino acid sequence of SEQ ID NO: 7, and a booster regimen comprising at least one dose of 50 ug of RNA, wherein the 50 ug of RNA comprises 25 ug of RNA comprising a nucleotide sequence encoding the amino acid sequence of SEQ ID NO: 7 and 25 ug of RNA comprising a nucleotide sequence encoding the amino acid sequence of SEQ ID NO: 49, wherein the two RNAs are optionally administered in the same composition (e.g., a formulation comprising both RNAs), and wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a sequence encoding a polypeptide comprising the amino acid sequence of SEQ ID NO: 7.

In one embodiment, a subject is administered a primary regimen comprising two 30 ug doses of RNA comprising a sequence encoding a polypeptide comprising the amino acid sequence of SEQ ID NO: 7, and a booster regimen comprising at least one dose of 60 ug of RNA, wherein the 60 ug of RNA comprises 30 ug of RNA comprising a nucleotide sequence encoding the amino acid sequence of SEQ ID NO: 7 and 30 ug of an RNA comprising a nucleotide sequence encoding the amino acid sequence of SEQ ID NO: 49, wherein the two RNAs are optionally administered in the same composition, and wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a sequence encoding a polypeptide comprising the amino acid sequence of SEQ ID NO: 7.

In one embodiment, the RNA used for the first vaccination comprises the nucleotide sequence of SEQ ID NO: 20 and the RNA used for the second vaccination is RNA comprising the nucleotide sequence of SEQ ID NO: 54.

In one embodiment, a subject is administered a primary regimen comprising two 30 ug doses of RNA comprising a nucleotide sequence of SEQ ID NO: 20, and a booster regimen comprising at least one dose of 30 ug of RNA comprising a nucleotide sequence of SEQ ID NO: 20, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 50 ug of RNA comprising a nucleotide sequence of SEQ ID NO: 20, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 60 ug of RNA comprising a nucleotide sequence of SEQ ID NO: 20, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 30 ug of RNA comprising a nucleotide sequence of SEQ ID NO: 51, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 50 ug of RNA comprising a nucleotide sequence of SEQ ID NO: 51, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 60 ug of RNA comprising a nucleotide sequence of SEQ ID NO: 51, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 30 ug of RNA, wherein the 30 ug of RNA comprises 15 ug of RNA comprising a nucleotide sequence of SEQ ID NO: 20 and 15 ug of RNA comprising a nucleotide sequence of SEQ ID NO: 51, wherein the two RNAs are optionally administered in the same composition, and wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose comprising 50 ug of a RNA, wherein the 50 ug of RNA comprises 25 ug of RNA comprising a nucleotide sequence of SEQ ID NO: 20 and 25 ug of RNA comprising a nucleotide sequence of SEQ ID NO: 51, wherein the two RNAs are optionally administered in the same composition, and wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose comprising 60 ug of RNA, wherein the 60 ug of RNA comprises 30 ug of an RNA comprising a nucleotide sequence of SEQ ID NO: 20 and 30 ug of an RNA comprising a nucleotide sequence of SEQ ID NO: 51, wherein the two RNAs are optionally administered in the same composition, and wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 30 ug of RNA comprising a nucleotide sequence of SEQ ID NO: 57, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 50 ug of RNA comprising a nucleotide sequence of SEQ ID NO: 57, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 60 ug of RNA comprising a nucleotide sequence of SEQ ID NO: 57, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 30 ug of RNA comprising a nucleotide sequence of SEQ ID NO: 60, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 50 ug of RNA comprising a nucleotide sequence of SEQ ID NO: 60, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 60 ug of RNA comprising a nucleotide sequence of SEQ ID NO: 60, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 30 ug of RNA comprising a nucleotide sequence of SEQ ID NO: 63a, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 20, and a booster regimen comprising at least one dose of 50 ug of RNA comprising a nucleotide sequence of SEQ ID NO: 63a, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, a subject is administered a primary regimen comprising two 30 ug doses of RNA comprising a nucleotide sequence of SEQ ID NO: 63a, and a booster regimen comprising at least one dose of 60 ug of RNA comprising a nucleotide sequence of SEQ ID NO: 57, wherein the booster regimen is administered at least 2 months (e.g., at least 3 months, at least 4 months, at least 5 months, or at least 6 months) after administration of the primary regimen, and wherein the subject has optionally previously been administered a first booster regimen comprising a 30 ug dose of RNA comprising a nucleotide sequence of SEQ ID NO: 20.

In one embodiment, the vaccination regimen comprises a first vaccination using two doses of RNA encoding a polypeptide comprising an amino acid sequence with proline residue substitutions at positions 986 and 987 of SEQ ID NO:1 administered about 21 days apart and a second vaccination using a single dose or multiple doses of RNA encoding a polypeptide comprising an amino acid sequence with proline residue substitutions at positions 986 and 987 of SEQ ID NO:1 administered about 4 to 12 months, 5 to 12 months, or 6 to 12 months after administration of the first vaccination, i.e., after the initial two-dose regimen. In one embodiment, each RNA dose comprises 30 ug RNA. In this embodiment, the aim in one embodiment is to induce an immune response that targets SARS-CoV-2 variants including, but not limited to, the Omicron (B.1.1.529) variant. Accordingly, in this embodiment, the aim in one embodiment is to protect a subject from infection with SARS-CoV-2 variants including, but not limited to, the Omicron (B.1.1.529) variant.

In one embodiment, the vaccination regimen comprises a first vaccination using two doses of RNA encoding a polypeptide comprising an amino acid sequence with proline residue substitutions at positions 986 and 987 of SEQ ID NO:1 administered about 21 days apart and a second vaccination using a single dose or multiple doses of RNA encoding a polypeptide comprising an amino acid sequence with alanine substitution at position 80, glycine substitution at position 215, lysine substitution at position 484, tyrosine substitution at position 501, valine substitution at position 701, phenylalanine substitution at position 18, isoleucine substitution at position 246, asparagine substitution at position 417, glycine substitution at position 614, deletions at positions 242 to 244, and proline substitutions at positions 986 and 987 of SEQ ID NO:1 administered about 6 to 12 months after administration of the first vaccination, i.e., after the initial two-dose regimen. In one embodiment, each RNA dose comprises 30 μg RNA.

In one embodiment, the vaccination regimen comprises a first vaccination using two doses of RNA encoding a polypeptide comprising an amino acid sequence with proline residue substitutions at positions 986 and 987 of SEQ ID NO:1 administered about 21 days apart and a second vaccination using a single dose or multiple doses of RNA encoding a polypeptide comprising an amino acid sequence with the following mutations in SEQ ID NO:1:

A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F, K986P and V987P, as compared to SEQ ID NO: 1, administered after, e.g., about 6 to 12 months after administration of the first vaccination, i.e., after the initial two-dose regimen. In one embodiment, each RNA dose comprises 30 μg RNA.

In one embodiment, the vaccination regimen comprises a first vaccination using two doses of RNA encoding a polypeptide comprising an amino acid sequence with proline residue substitutions at positions 986 and 987 of SEQ ID NO:1 administered about 21 days apart and a second vaccination using a single dose or multiple doses of RNA encoding a polypeptide comprising an amino acid sequence with the following mutations in SEQ ID NO:1:

A67V, Δ69-70, T95I, G142D, Δ143-145, Δ211, L212I, ins214EPE, G339D, S371L, S373P, S375F, S477N, T478K, E484A, Q493R, G496S, Q498R, N501Y, Y505H, T547K, D614G, H655Y, N679K, P681H, N764K, D796Y, N856K, Q954H, N969K, L981F, K986P and V987P, as compared to SEQ ID NO: 1, administered after, e.g., about 6 to 12 months after administration of the first vaccination, i.e., after the initial two-dose regimen. In one embodiment, each RNA dose comprises 30 μg RNA. In some embodiments, the encoded polypeptide further comprises proline residue substitutions at positions corresponding to 986 and 987 of SEQ ID NO:1.

In one embodiment, the vaccination regimen comprises a first vaccination involving at least two doses of RNA encoding a polypeptide comprising an amino acid sequence with proline residue substitutions at positions 986 and 987 of SEQ ID NO: 1 administered about 21 days apart and a second vaccination involving a single dose or multiple doses of RNA encoding a polypeptide comprising an amino acid sequence with the following mutations in SEQ ID NO: 1:

T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K, K986P, and V987P, as compared to SEQ ID NO: 1, administered after, e.g., about 6 to 12 months after administration of the first vaccination, i.e., after the initial two-dose regimen. In one embodiment, each or at least one RNA dose comprises 30 μg RNA.

In one embodiment, the vaccination regimen comprises a first vaccination involving at least two doses of RNA encoding a polypeptide comprising an amino acid sequence with proline residue substitutions at positions 986 and 987 of SEQ ID NO:1 administered about 21 days apart and a second vaccination involving a single dose or multiple doses of RNA encoding a polypeptide comprising an amino acid sequence with the following mutations in SEQ ID NO:1:

T19I, Δ24-26, A27S, Δ69/70, G142D, V213G, G339D, 5371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K, K986P, and V987P, as compared to SEQ ID NO: 1 administered after, e.g., about 6 to 12 months after administration of the first vaccination, i.e., after the initial two-dose regimen. In one embodiment, each or at least one RNA dose comprises 30 μg RNA.

In one embodiment, the vaccination regimen comprises a first vaccination involving at least two doses of RNA encoding a polypeptide comprising an amino acid sequence with the following mutations in SEQ ID NO:1:

A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F, K986P and V987P, wherein the two doses of the first vaccination are administered about 21 days apart and wherein the vaccination regimen comprises a second vaccination involving a single dose or multiple doses of RNA encoding a polypeptide comprising an amino acid sequence with the following mutations in SEQ ID NO:1:

T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K, K986P, and V987P, as compared to SEQ ID NO: 1 administered after, e.g., about 6 to 12 months after administration of the first vaccination, i.e., after the initial two-dose regimen. In one embodiment, each or at least one RNA dose comprises 30 ug RNA.

In one embodiment, the vaccination regimen comprises a first vaccination involving at least two doses of RNA encoding a polypeptide comprising an amino acid sequence with the following mutations in SEQ ID NO:1:

A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F, K986P and V987P, wherein the two doses of the first vaccination are administered about 21 days apart and wherein the vaccination regimen comprises a second vaccination involving a single dose or multiple doses of RNA encoding a polypeptide comprising an amino acid sequence with the following mutations in SEQ ID NO:1:

T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K, K986P, and V987P, as compared to SEQ ID NO: 1 administered after, e.g., about 6 to 12 months after administration of the first vaccination, i.e., after the initial two-dose regimen. In one embodiment, each or at least one RNA dose comprises 30 ug RNA.

In one embodiment, the vaccination regimen comprises a first vaccination involving at least two doses of RNA encoding a polypeptide comprising an amino acid sequence with the following mutations in SEQ ID NO:1:

T19I, Δ24-26, A27S, G142D, V213G, G339D, S371F, 5373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K, K986P, and V987P, as compared to SEQ ID NO: 1, wherein the two doses of the first vaccination are administered about 21 days apart and wherein the vaccination regimen comprises a second vaccination involving a single dose or multiple doses of RNA encoding a polypeptide comprising an amino acid sequence with the following mutations in SEQ ID NO:1:

T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K, K986P, and V987P, as compared to SEQ ID NO: 1 administered after, e.g., about 6 to 12 months after administration of the first vaccination, i.e., after the initial two-dose regimen. In one embodiment, each or at least one RNA dose comprises 30 μg RNA.

In one embodiment, a vaccination regimen comprises (i) a first vaccination comprising at least three doses of an RNA described herein (e.g., where each dose comprises about 30 μg of an RNA comprising a nucleotide sequence of SEQ ID NO: 20), wherein a second dose may be administered about 21 days following administration of a first dose, and a third dose may be administered at least about 1, 2, 3, 4, 5, 6, 7, 8, 9, 10, 11, or 12 months after a second dose; and (ii) a second vaccination comprising at least one dose of an RNA described herein (e.g., wherein each dose comprises about 30 μg RNA per dose). In some embodiments, a second vaccination comprises at least one dose of a bivalent vaccine described herein, e.g., about 30 μg total of a bivalent vaccine, e.g., a bivalent vaccine comprising about 15 μg RNA encoding a SARS-CoV-2 S protein from a Wuhan strain and about 15 μg RNA encoding a SARS-CoV-2 S protein comprising mutations characteristic of an Omicron variant (b2+Omi). In some embodiments, the bivalent vaccine comprises about 15 μg RNA encoding a SARS-CoV-2 S protein from a Wuhan strain and about 15 μg RNA encoding a SARS-CoV-2 S protein comprising mutations characteristic of a BA.1 Omicron variant (e.g., 15 μg RNA comprising a sequence of SEQ ID NO: 20 and 15 μg of RNA comprising a sequence of SEQ ID NO: 51). In some embodiments, the bivalent vaccine comprises about 15 μg RNA encoding a SARS-CoV-2 S protein from a Wuhan strain and about 15 lag RNA encoding a SARS-CoV-2 S protein comprising mutations characteristic of a BA.4/5 Omicron variant (e.g., 15 μg RNA comprising a sequence of SEQ ID NO: 20 and 15 μg of RNA comprising a sequence of SEQ ID NO: 72). In some embodiments, the vaccination regimen is administered to a subject who is at least about 12 years old. In some embodiments, the vaccination regimen is administered to a subject who is at least about 6 months old to less than about 12 years old.

In one embodiment, the second vaccination results in a boosting of the immune response.

In one embodiment, RNA described herein is co-administered with other vaccines. In some embodiments, RNA described herein is co-administered with a composition comprising one or more T-cell epitopes of SARS-CoV-2 or RNA encoding the same. In some embodiments, RNA described herein is co-administered one or more T-cell epitopes, or RNA encoding the same, derived from an M protein, an N protein, and/or an ORF1ab protein of SARS-CoV-2, e.g., a composition disclosed in WO2021188969, the contents of which is incorporated by reference herein in its entirety. In some embodiments, RNA described herein (e.g., RNA encoding a SARS-CoV-2 S protein comprising mutations characteristic of a BA.1, BA.2, or BA.4/5 Omicron variant, optionally administered with RNA encoding a SARS-CoV-2 S protein of a Wuhan variant) is co-administered with a T-string construct described in WO2021188969 (e.g., an RNA encoding SEQ ID NO: RS C7p2full of WO2021/188969). In some embodiments, RNA described herein and a T-string construct described in WO2021188969 are administered in a combination of up to about 100 ug RNA total. In some embodiments, subjects are administered with at least 2 doses of RNA described herein (e.g., in some embodiments at 30 ug each) in combination with a T-string construct (e.g., an RNA encoding SEQ ID NO: RS C7p2full of WO2021/188969), e.g., each dose of a combination of RNA described herein and an RNA encoding SEQ ID NO: RS C7p2full of up to about 100 ug RNA total, wherein the two doses are administered, for example, at least 4 weeks or longer (including, e.g., at least 5 weeks, at least 6 weeks, at least 7 weeks, at least 8 weeks, at least 9 weeks, at least 10 weeks, at least 11 weeks, or at least 12 weeks, or longer) apart from one another. In some embodiments, subjects are administered at least 3 doses of RNA described herein (e.g., in some embodiments at 30 ug each) in combination with a T-string construct (e.g., an RNA encoding SEQ ID NO: RS C7p2full of WO2021/188969), e.g., each dose of a combination of RNA described herein and an RNA encoding SEQ ID NO: RS C7p2full of up to about 100 ug RNA total, wherein the first and the second doses and the second and third doses are each independently administered at least 4 weeks or longer (including, e.g., at least 5 weeks, at least 6 weeks, at least 7 weeks, at least 8 weeks, at least 9 weeks, at least 10 weeks, at least 11 weeks, or at least 12 weeks, or longer) apart from one another. In some embodiments, the RNA described herein and the T-string construct may be co-administered as separate formulations (e.g., formulations administered on the same day to separate injection sites). In some embodiments, the RNA described herein and the T-string construct may be co-administered as a co-formulation (e.g., a formulation comprising RNA described herein and the T-string construct as separate LNP formulations or as LNP formulations comprising both a T-string construct and RNA described herein).

In some embodiments, an RNA composition described herein is co-administered with one or more vaccines against a non-SARS-CoV-2 disease. In some embodiments, an RNA composition described herein is co-administered with one or more vaccines against a non-SARS-COV-2 viral disease. In some embodiments, an RNA composition described herein is co-administered with one or more vaccines against a non-SARS-CoV-2 respiratory disease. In some embodiments, the non-SARS-CoV-2 respiratory disease is a non-SARS-CoV-2 Coronavirus, an Influenza virus, a Pneumoviridae virus, or a Paramyxoviridae virus. In some embodiments, the Pneumoviridae virus is a Respiratory syncytial virus or a Metapneumovirus. In some embodiments, the Metapneumovirus is a human metapneumovirus (hMPV). In some embodiments, the Paramyxoviridae virus is a Parainfluenza virus or a Henipavirus. In some embodiments the parainfluenzavirus is PIV3. In some embodiments, the non-SAR-CoV-2 coronavirus is a betacoronavirus (e.g., SARS-CoV-1). In come embodiments the non-SARS-CoV-2 coronavirus is a Merbecovirus (e.g., a MERS-CoV virus).

In some embodiments, an RNA composition described herein is co-administered with an RSV vaccine (e.g., an RSV A or RSV B vaccine). In some embodiments, the RSV vaccine comprises an RSV fusion protein (F), an RSV attachment protein (G), an RSV small hydrophobic protein (SH), an RSV matrix protein (M), an RSV nucleoprotein (N), an RSV M2-1 protein, an RSV Large polymerase (L), and/or an RSV phosphoprotein (P), or an immunogenic fragment of immunogenic variant thereof, or a nucleic acid (e.g., RNA), encoding any one of the same.

In some embodiments, an RNA composition described herein is co-administered with an influenza vaccine. In some embodiments, the influenza vaccine is an alphainfluenza virus, a betainfluenza virus, a gammainfluenza virus or a deltainfluenza virus vaccine. In some embodiments the vaccine is an Influenza A virus, an Influenza B virus, an Influenza C virus, or an Influenza D virus vaccine. In some embodiments, the influenza A virus vaccine comprises a hemagglutinin selected from H1, H2, H3, H4, H5, H6, H7, H8, H9, H10, H11, H12, H13, H14, H15, H16, H17, and H18, or an immunogenic fragment or variant of the same, or a nucleic acid (e.g., RNA) encoding any one of the same. In some embodiments the influenza A vaccine comprises or encodes a neuraminidase (NA) selected from N1, N2, N3, N4, N5, N6, N7, N8, N9, N10, and N11, or an immunogenic fragment or variant of the same, or a nucleic acid (e.g., RNA) encoding any one of the same. In some embodiments, the influenza vaccine comprises at least one Influenza virus hemagglutinin (HA), neuraminidase (NA), nucleoprotein (NP), matrix protein 1 (M1), matrix protein 2 (M2), non-structural protein 1 (NS1), non-structural protein 2 (NS2), nuclear export protein (NEP), polymerase acidic protein (PA), polymerase basic protein PB16, PB1-F2, and/or polymerase basic protein 2 (PB2), or an immunogenic fragment or variant thereof, or a nucleic acid (e.g., RNA) encoding any of one of the same.

In some embodiments, an RNA composition provided herein and other injectable vaccine(s) are administered at different times. In some embodiments, an RNA composition provided herein is administered at the same time as other injectable vaccine(s). In some such embodiments, an RNA composition provided herein and at least one another injectable vaccine(s) are administered at different injection sites. In some embodiments, an RNA composition provided herein is not mixed with any other vaccine in the same syringe. In some embodiments, an RNA composition provided herein is not combined with other coronavirus vaccines as part of vaccination against coronavirus, e.g., SARS-CoV-2.

The term "disease" refers to an abnormal condition that affects the body of an individual. A disease is often construed as a medical condition associated with specific symptoms and signs. A disease may be caused by factors originally from an external source, such as infectious disease, or it may be caused by internal dysfunctions, such as autoimmune diseases. In humans, "disease" is often used more broadly to refer to any condition that causes pain, dysfunction, distress, social problems, or death to the individual afflicted, or similar problems for those in contact with the individual. In this broader sense, it sometimes includes injuries, disabilities, disorders, syndromes, infections, isolated symptoms, deviant behaviors, and atypical variations of structure and function, while in other contexts and for other purposes these may be considered distinguishable categories. Diseases usually affect individuals not only physically, but also emotionally, as contracting and living with many diseases can alter one's perspective on life, and one's personality.

In the present context, the term "treatment", "treating" or "therapeutic intervention" relates to the management and care of a subject for the purpose of combating a condition such as a disease or disorder. The term is intended to include the full spectrum of treatments for a given condition from which the subject is suffering, such as administration of the therapeutically effective compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of an individual for the purpose of combating the disease, condition or disorder and includes the administration of the active compounds to prevent the onset of the symptoms or complications.

The term "therapeutic treatment" relates to any treatment which improves the health status and/or prolongs (increases) the lifespan of an individual. Said treatment may eliminate the disease in an individual, arrest or slow the development of a disease in an individual, inhibit or slow the development of a disease in an individual, decrease the frequency or severity of symptoms in an individual, and/or decrease the recurrence in an individual who currently has or who previously has had a disease.

The terms "prophylactic treatment" or "preventive treatment" relate to any treatment that is intended to prevent a disease from occurring in an individual. The terms "prophylactic treatment" or "preventive treatment" are used herein interchangeably.

The terms "individual" and "subject" are used herein interchangeably. They refer to a human or another mammal (e.g. mouse, rat, rabbit, dog, cat, cattle, swine, sheep, horse or primate) that can be afflicted with or is susceptible to a disease or disorder but may or may not have the disease or disorder. In many embodiments, the individual is a human being. Unless otherwise stated, the terms "individual" and "subject" do not denote a particular age, and thus encompass adults, elderlies, children, and newborns. In some embodiments, the term "subject" includes humans of age of at least 50, at least 55, at least 60, at least 65, at least 70, or older. In some embodiments, the term "subject" includes humans of age of at least 65, such as 65 to 80, 65 to 75, or 65 to 70. In embodiments of the present disclosure, the "individual" or "subject" is a "patient".

The term "patient" means an individual or subject for treatment, in particular a diseased individual or subject.

In one embodiment of the present disclosure, the aim is to provide an immune response against coronavirus, and to prevent or treat coronavirus infection.

A pharmaceutical composition comprising RNA encoding a peptide or protein comprising an epitope may be administered to a subject to elicit an immune response against an antigen comprising said epitope in the subject which may be therapeutic or partially or fully protective.

A person skilled in the art will know that one of the principles of immunotherapy and vaccination is based on the fact that an immunoprotective reaction to a disease is produced by immunizing a subject with an antigen or an epitope, which is immunologically relevant with respect to the disease to be treated. Accordingly, pharmaceutical compositions described herein are applicable for inducing or enhancing an immune response. Pharmaceutical compositions described herein are thus useful in a prophylactic and/or therapeutic treatment of a disease involving an antigen or epitope.

As used herein, "immune response" refers to an integrated bodily response to an antigen or a cell expressing an antigen and refers to a cellular immune response and/or a humoral immune response. The immune system is divided into a more primitive innate immune system, and acquired or adaptive immune system of vertebrates, each of which contains humoral and cellular components.

"Cell-mediated immunity", "cellular immunity", "cellular immune response", or similar terms are meant to include a cellular response directed to cells characterized by expression of an antigen, in particular characterized by presentation of an antigen with class I or class II MHC. The cellular response relates to immune effector cells, in particular to cells called T cells or T lymphocytes which act as either "helpers" or "killers". The helper T cells (also termed $CD4^+$ T cells) play a central role by regulating the immune response and the killer cells (also termed cytotoxic T cells, cytolytic T cells, $CD8^+$ T cells or CTLs) kill diseased cells such as virus-infected cells, preventing the production of more diseased cells.

An immune effector cell includes any cell which is responsive to vaccine antigen. Such responsiveness includes activation, differentiation, proliferation, survival and/or indication of one or more immune effector functions. The cells include, in particular, cells with lytic potential, in particular lymphoid cells, and are preferably T cells, in particular cytotoxic lymphocytes, preferably selected from cytotoxic T cells, natural killer (NK) cells, and lymphokine-activated killer (LAK) cells. Upon activation, each of these cytotoxic lymphocytes triggers the destruction of target cells. For example, cytotoxic T cells trigger the destruction of target cells by either or both of the following means. First, upon activation T cells release cytotoxins such as perforin, granzymes, and granulysin. Perforin and granulysin create pores in the target cell, and granzymes enter the cell and trigger a caspase cascade in the cytoplasm that induces apoptosis (programmed cell death) of the cell. Second, apoptosis can be induced via Fas-Fas ligand interaction between the T cells and target cells.

The term "effector functions" in the context of the present disclosure includes any functions mediated by components of the immune system that result, for example, in the neutralization of a pathogenic agent such as a virus and/or in the killing of diseased cells such as virus-infected cells. In one embodiment, the effector functions in the context of the present disclosure are T cell mediated effector functions. Such functions comprise in the case of a helper T cell ($CD4^+$ T cell) the release of cytokines and/or the activation of $CD8^+$ lymphocytes (CTLs) and/or B cells, and in the case of CTL the elimination of cells, i.e., cells characterized by expression of an antigen, for example, via apoptosis or perforin-mediated cell lysis, production of cytokines such as IFN-γ and TNF-α, and specific cytolytic killing of antigen expressing target cells.

The term "immune effector cell" or "immunoreactive cell" in the context of the present disclosure relates to a cell which exerts effector functions during an immune reaction. An "immune effector cell" in one embodiment is capable of binding an antigen such as an antigen presented in the context of MHC on a cell or expressed on the surface of a cell and mediating an immune response. For example, immune effector cells comprise T cells (cytotoxic T cells, helper T cells, tumor infiltrating T cells), B cells, natural killer cells, neutrophils, macrophages, and dendritic cells.

Preferably, in the context of the present disclosure, "immune effector cells" are T cells, preferably $CD4^+$ and/or $CD8^+$ T cells, most preferably $CD8^+$ T cells. According to the present disclosure, the term "immune effector cell" also includes a cell which can mature into an immune cell (such as T cell, in particular T helper cell, or cytolytic T cell) with suitable stimulation. Immune effector cells comprise $CD34^+$ hematopoietic stem cells, immature and mature T cells and immature and mature B cells. The differentiation of T cell precursors into a cytolytic T cell, when exposed to an antigen, is similar to clonal selection of the immune system.

A "lymphoid cell" is a cell which is capable of producing an immune response such as a cellular immune response, or a precursor cell of such cell, and includes lymphocytes, preferably T lymphocytes, lymphoblasts, and plasma cells. A lymphoid cell may be an immune effector cell as described herein. A preferred lymphoid cell is a T cell.

The terms "T cell" and "T lymphocyte" are used interchangeably herein and include T helper cells (CD4+ T cells) and cytotoxic T cells (CTLs, CD8+ T cells) which comprise cytolytic T cells. The term "antigen-specific T cell" or similar terms relate to a T cell which recognizes the antigen to which the T cell is targeted and preferably exerts effector functions of T cells.

T cells belong to a group of white blood cells known as lymphocytes, and play a central role in cell-mediated immunity. They can be distinguished from other lymphocyte types, such as B cells and natural killer cells by the presence of a special receptor on their cell surface called T cell receptor (TCR). The thymus is the principal organ responsible for the maturation of T cells. Several different subsets of T cells have been discovered, each with a distinct function.

T helper cells assist other white blood cells in immunologic processes, including maturation of B cells into plasma cells and activation of cytotoxic T cells and macrophages, among other functions. These cells are also known as CD4+ T cells because they express the CD4 glycoprotein on their surface. Helper T cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T cells destroy virally infected cells and tumor cells, and are also implicated in transplant rejection. These cells are also known as CD8+ T cells since they express the CD8 glycoprotein on their surface. These cells recognize their targets by binding to antigen associated with MHC class I, which is present on the surface of nearly every cell of the body. A majority of T cells have a T cell receptor (TCR) existing as a complex of several proteins. The TCR of a T cell is able to interact with immunogenic peptides (epitopes) bound to major histocompatibility complex (MHC) molecules and presented on the surface of target cells. Specific binding of the TCR triggers a signal cascade inside the T cell leading to proliferation and differentiation into a maturated effector T cell. The actual T cell receptor is composed of two separate peptide chains, which are produced from the independent T cell receptor alpha and beta (TCRα and TCRβ) genes and are called α- and β-TCR chains. γδ T cells (gamma delta T cells) represent a small subset of T cells that possess a distinct T cell receptor (TCR) on their surface. However, in γδ T cells, the TCR is made up of one γ-chain and one δ-chain. This group of T cells is much less common (2% of total T cells) than the αβ T cells.

"Humoral immunity" or "humoral immune response" is the aspect of immunity that is mediated by macromolecules found in extracellular fluids such as secreted antibodies, complement proteins, and certain antimicrobial peptides. It contrasts with cell-mediated immunity. Its aspects involving antibodies are often called antibody-mediated immunity.

Humoral immunity refers to antibody production and the accessory processes that accompany it, including: Th2 activation and cytokine production, germinal center formation and isotype switching, affinity maturation and memory cell generation. It also refers to the effector functions of antibodies, which include pathogen neutralization, classical complement activation, and opsonin promotion of phagocytosis and pathogen elimination.

In humoral immune response, first the B cells mature in the bone marrow and gain B-cell receptors (BCR's) which are displayed in large number on the cell surface. These membrane-bound protein complexes have antibodies which are specific for antigen detection. Each B cell has a unique antibody that binds with an antigen. The mature B cells migrate from the bone marrow to the lymph nodes or other lymphatic organs, where they begin to encounter pathogens. When a B cell encounters an antigen, the antigen is bound to the receptor and taken inside the B cell by endocytosis. The antigen is processed and presented on the B cell's surface again by MHC-II proteins. The B cell waits for a helper T cell (TH) to bind to the complex. This binding will activate the TH cell, which then releases cytokines that induce B cells to divide rapidly, making thousands of identical clones of the B cell. These daughter cells either become plasma cells or memory cells. The memory B cells remain inactive here; later when these memory B cells encounter the same antigen due to reinfection, they divide and form plasma cells. On the other hand, the plasma cells produce a large number of antibodies which are released free into the circulatory system. These antibodies will encounter antigens and bind with them. This will either interfere with the chemical interaction between host and foreign cells, or they may form bridges between their antigenic sites hindering their proper functioning, or their presence will attract macrophages or killer cells to attack and phagocytose them.

The term "antibody" includes an immunoglobulin comprising at least two heavy (H) chains and two light (L) chains inter-connected by disulfide bonds. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system. An antibody binds, preferably specifically binds with an antigen.

Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

An “antibody heavy chain”, as used herein, refers to the larger of the two types of polypeptide chains present in antibody molecules in their naturally occurring conformations.

An “antibody light chain”, as used herein, refers to the smaller of the two types of polypeptide chains present in antibody molecules in their naturally occurring conformations, K and A light chains refer to the two major antibody light chain isotypes.

The present disclosure contemplates an immune response that may be protective, preventive, prophylactic and/or therapeutic. As used herein, “induces [or inducing] an immune response” may indicate that no immune response against a particular antigen was present before induction or it may indicate that there was a basal level of immune response against a particular antigen before induction, which was enhanced after induction. Therefore, “induces [or inducing] an immune response” includes “enhances [or enhancing] an immune response”.

The term “immunotherapy” relates to the treatment of a disease or condition by inducing, or enhancing an immune response. The term “immunotherapy” includes antigen immunization or antigen vaccination.

The terms “immunization” or “vaccination” describe the process of administering an antigen to an individual with the purpose of inducing an immune response, for example, for therapeutic or prophylactic reasons.

The term “macrophage” refers to a subgroup of phagocytic cells produced by the differentiation of monocytes. Macrophages which are activated by inflammation, immune cytokines or microbial products nonspecifically engulf and kill foreign pathogens within the macrophage by hydrolytic and oxidative attack resulting in degradation of the pathogen.

Peptides from degraded proteins are displayed on the macrophage cell surface where they can be recognized by T cells, and they can directly interact with antibodies on the B cell surface, resulting in T and B cell activation and further stimulation of the immune response.

Macrophages belong to the class of antigen presenting cells. In one embodiment, the macrophages are splenic macrophages.

The term “dendritic cell” (DC) refers to another subtype of phagocytic cells belonging to the class of antigen presenting cells. In one embodiment, dendritic cells are derived from hematopoietic bone marrow progenitor cells. These progenitor cells initially transform into immature dendritic cells. These immature cells are characterized by high phagocytic activity and low T cell activation potential. Immature dendritic cells constantly sample the surrounding environment for pathogens such as viruses and bacteria. Once they have come into contact with a presentable antigen, they become activated into mature dendritic cells and begin to migrate to the spleen or to the lymph node. Immature dendritic cells phagocytose pathogens and degrade their proteins into small pieces and upon maturation present those fragments at their cell surface using MHC molecules. Simultaneously, they upregulate cell-surface receptors that act as co-receptors in T cell activation such as CD80, CD86, and CD40 greatly enhancing their ability to activate T cells. They also upregulate CCR7, a chemotactic receptor that induces the dendritic cell to travel through the blood stream to the spleen or through the lymphatic system to a lymph node. Here they act as antigen-presenting cells and activate helper T cells and killer T cells as well as B cells by presenting them antigens, alongside non-antigen specific co-stimulatory signals. Thus, dendritic cells can actively induce a T cell- or B cell-related immune response. In one embodiment, the dendritic cells are splenic dendritic cells.

The term “antigen presenting cell” (APC) is a cell of a variety of cells capable of displaying, acquiring, and/or presenting at least one antigen or antigenic fragment on (or at) its cell surface. Antigen-presenting cells can be distinguished in professional antigen presenting cells and non-professional antigen presenting cells.

The term “professional antigen presenting cells” relates to antigen presenting cells which constitutively express the Major Histocompatibility Complex class II (MHC class II) molecules required for interaction with naive T cells. If a T cell interacts with the MHC class II molecule complex on the membrane of the antigen presenting cell, the antigen presenting cell produces a co-stimulatory molecule inducing activation of the T cell. Professional antigen presenting cells comprise dendritic cells and macrophages.

The term “non-professional antigen presenting cells” relates to antigen presenting cells which do not constitutively express MHC class II molecules, but upon stimulation by certain cytokines such as interferon-gamma. Exemplary, non-professional antigen presenting cells include fibroblasts, thymic epithelial cells, thyroid epithelial cells, glial cells, pancreatic beta cells or vascular endothelial cells.

“Antigen processing” refers to the degradation of an antigen into procession products, which are fragments of said antigen (e.g., the degradation of a protein into peptides) and the association of one or more of these fragments (e.g., via binding) with MHC molecules for presentation by cells, such as antigen presenting cells to specific T cells.

The term “disease involving an antigen” refers to any disease which implicates an antigen, e.g. a disease which is characterized by the presence of an antigen. The disease involving an antigen can be an infectious disease. As mentioned above, the antigen may be a disease-associated antigen, such as a viral antigen. In one embodiment, a disease involving an antigen is a disease involving cells expressing an antigen, preferably on the cell surface.

The term “infectious disease” refers to any disease which can be transmitted from individual to individual or from organism to organism, and is caused by a microbial agent (e.g. common cold). Infectious diseases are known in the art and include, for example, a viral disease, a bacterial disease, or a parasitic disease, which diseases are caused by a virus, a bacterium, and a parasite, respectively. In this regard, the infectious disease can be, for example, hepatitis, sexually transmitted diseases (e.g. chlamydia or gonorrhea), tuberculosis, HIV/acquired immune deficiency syndrome (AIDS), diphtheria, hepatitis B, hepatitis C, cholera, severe acute respiratory syndrome (SARS), the bird flu, and influenza.

Exemplary Dosing Regimens

In some embodiments, compositions and methods disclosed herein can be used in accordance with an exemplary vaccination regimen as illustrated in FIG. 14.

Primary Dosing Regimens

In some embodiments, subjects are administered a primary dosing regimen. A primary dosing regimen can comprise one or more doses. For example, in some embodiments, a primary dosing regimen comprises a single dose ($PD_1$). In some embodiments a primary dosing regimen comprises a first dose ($PD_1$) and a second dose ($PD_2$). In some embodiments, a primary dosing regimen comprises a first dose, a second dose, and a third dose ($PD_3$). In some embodiments, a primary dosing regimen comprises a first dose, a second dose, a third dose, and one or more additional doses ($PD_n$) of any one of the pharmaceutical compositions described herein.

In some embodiments, $PD_1$ comprises administering 1 to 100 ug of RNA. In some embodiments, $PD_1$ comprises administering 1 to 60 ug of RNA In some embodiments, PD1 comprises administering 1 to 50 ug of RNA. In some embodiments, $PD_1$ comprises administering 1 to 30 ug of RNA. In some embodiments, $PD_1$ comprises administering about 3 ug of RNA. In some embodiments, $PD_1$ comprises administering about 5 ug of RNA. In some embodiments, $PD_1$ comprises administering about 10 ug of RNA. In some embodiments, $PD_1$ comprises administering about 15 ug of RNA. In some embodiments, $PD_1$ comprises administering about 20 ug of RNA. In some embodiments, $PD_1$ comprises administering about 30 ug of RNA. In some embodiments, $PD_1$ comprises administering about 50 ug of RNA. In some embodiments, $PD_1$ comprises administering about 60 ug of RNA.

In some embodiments, $PD_2$ comprises administering 1 to 100 ug of RNA. In some embodiments, $PD_2$ comprises administering 1 to 60 ug of RNA. In some embodiments, $PD_2$ comprises administering 1 to 50 ug of RNA. In some embodiments, $PD_2$ comprises administering 1 to 30 ug of RNA. In some embodiments, $PD_2$ comprises administering about 3 ug. In some embodiments, $PD_2$ comprises administering about 5 ug of RNA. In some embodiments, $PD_2$ comprises administering about 10 ug of RNA. In some embodiments, $PD_2$ comprises administering about 15 ug of RNA. In some embodiments, $PD_2$ comprises administering about 20 ug RNA. In some embodiments, $PD_2$ comprises administering about 30 ug of RNA. In some embodiments, $PD_2$ comprises administering about 50 ug of RNA. In some embodiments, $PD_2$ comprises administering about 60 ug of RNA.

In some embodiments, $PD_3$ comprises administering 1 to 100 ug of RNA. In some embodiments, $PD_3$ comprises administering 1 to 60 ug of RNA. In some embodiments, $PD_3$ comprises administering 1 to 50 ug of RNA. In some embodiments, $PD_3$ comprises administering 1 to 30 ug of RNA. In some embodiments, $PD_3$ comprises administering about 3 ug of RNA. In some embodiments, $PD_3$ comprises administering about 5 ug of RNA. In some embodiments, $PD_3$ comprises administering about 10 ug of RNA. In some embodiments, $PD_3$ comprises administering about 15 ug of RNA. In some embodiments, $PD_3$ comprises administering about 20 ug of RNA. In some embodiments, $PD_3$ comprises administering about 30 ug of RNA. In some embodiments, $PD_3$ comprises administering about 50 ug of RNA. In some embodiments, $PD_3$ comprises administering about 60 ug of RNA.

In some embodiments, $PD_n$ comprises administering 1 to 100 ug of RNA. In some embodiments, $PD_n$ comprises administering 1 to 60 ug of RNA. In some embodiments, $PD_n$ comprises administering 1 to 50 ug of RNA. In some embodiments, $PD_n$ comprises administering 1 to 30 ug of RNA. In some embodiments, $PD_n$ comprises administering about 3 ug of RNA. In some embodiments, $PD_n$ comprises administering about 5 ug of RNA. In some embodiments, $PD_n$ comprises administering about 10 ug of RNA. In some embodiments, $PD_n$ comprises administering about 15 ug of RNA. In some embodiments, $PD_n$ comprises administering about 20 ug of RNA. In some embodiments, $PD_n$ comprises administering about 30 ug of RNA. In some embodiments, $PD_n$ comprises administering about 50 ug of RNA. In some embodiments, $PD_n$ comprises administering about 60 ug of RNA.

In some embodiments, $PD_1$ comprises an RNA encoding a SARS-CoV-2 Spike protein or an immunogenic fragment thereof from the Wuhan strain. In some embodiments, $PD_1$ comprises an RNA encoding a Spike protein or an immunogenic fragment thereof from a SARS-CoV-2 strain that is prevalent and/or spreading rapidly in a relevant jurisdiction. In some embodiments, $PD_1$ comprises an RNA encoding a SARS-CoV-2 Spike protein or an immunogenic fragment thereof comprising one or more mutations from an alpha variant. In some embodiments, $PD_1$ comprises an RNA encoding a SARS-CoV-2 Spike protein or an immunogenic fragment thereof comprising one or more mutations from a delta variant. In some embodiments, $PD_1$ comprises an RNA encoding a SARS-CoV-2 Spike protein or an immunogenic fragment thereof comprising one or more mutations from a beta variant. In some embodiments, $PD_1$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant). In some embodiments, $PD_1$ comprises an RNA encoding a SARS-CoV-2 Spike protein or an immunogenic fragment thereof from the Wuhan strain and one or more additional RNAs encoding a Spike protein or an immunogenic fragment thereof from a SARS-CoV-2 strain that is prevalent and/or spreading rapidly in a relevant jurisdiction. In some embodiments, $PD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an alpha variant. In some embodiments, $PD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $PD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $PD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $PD_2$ comprises an RNA encoding a SARS-CoV-2 Spike protein or an immunogenic fragment thereof from the Wuhan strain. In some embodiments, $PD_2$ comprises an RNA encoding a Spike protein or an immunogenic fragment thereof from a SARS-CoV-2 strain that is prevalent and/or spreading rapidly in a relevant jurisdiction. In some embodiments, $PD_2$ comprises an RNA encoding a SARS-CoV-2 Spike protein or an immunogenic fragment thereof comprising one or more mutations from an alpha variant. In some embodiments, $PD_2$ comprises an RNA encoding a SARS-CoV-2 Spike protein or an immunogenic fragment thereof comprising one or more mutations from a delta variant. In some embodiments, $PD_2$ comprises an RNA encoding a SARS-CoV-2 Spike protein or an immunogenic fragment thereof comprising one or more mutations from a beta variant. In some embodiments, $PD_2$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant). In some embodiments, $PD_2$ comprises an RNA encoding a SARS-CoV-2 Spike protein or an immunogenic fragment thereof from the Wuhan strain and one or more additional RNAs encoding a Spike protein or an immunogenic fragment thereof from a SARS-CoV-2 strain that is prevalent and/or spreading rapidly in a relevant jurisdiction. In some embodiments, $PD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an alpha variant. In some embodiments, $PD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $PD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $PD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $PD_3$ comprises an RNA encoding a SARS-CoV-2 Spike protein or an immunogenic fragment thereof from the Wuhan strain. In some embodiments, $PD_3$ comprises an RNA encoding a Spike protein or an immunogenic fragment thereof from a SARS-CoV-2 strain that is prevalent and/or spreading rapidly in a relevant jurisdiction. In some embodiments, $PD_3$ comprises an RNA encoding a SARS-CoV-2 Spike protein or an immunogenic fragment thereof comprising one or more mutations from an alpha variant. In some embodiments, $PD_3$ comprises an RNA encoding a SARS-CoV-2 Spike protein or an immunogenic fragment thereof comprising one or more mutations from a delta variant. In some embodiments, $PD_3$ comprises an RNA encoding a SARS-CoV-2 Spike protein or an immunogenic fragment thereof comprising one or more mutations from a beta variant. In some embodiments, $PD_3$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant). In some embodiments, $PD_3$ comprises an RNA encoding a SARS-CoV-2 Spike protein or an immunogenic fragment thereof from the Wuhan strain and one or more additional RNAs encoding a Spike protein or an immunogenic fragment thereof from a SARS-CoV-2 strain that is prevalent and/or spreading rapidly in a relevant jurisdiction. In some embodiments, $PD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an alpha variant. In some embodiments, $PD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $PD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $PD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $PD_n$ comprises an RNA encoding a SARS-CoV-2 Spike protein or an immunogenic fragment thereof from the Wuhan strain. In some embodiments, $PD_n$ comprises an RNA encoding a Spike protein or an immunogenic fragment thereof from a SARS-CoV-2 strain that is prevalent and/or spreading rapidly in a relevant jurisdiction. In some embodiments, $PD_n$ comprises an RNA encoding a SARS-CoV-2 Spike protein or an immunogenic fragment thereof comprising one or more mutations from an alpha variant. In some embodiments, $PD_n$ comprises an RNA encoding a SARS-CoV-2 Spike protein or an immunogenic fragment thereof comprising one or more mutations from a delta variant. In some embodiments, $PD_n$ comprises an RNA encoding a SARS-CoV-2 Spike protein or an immunogenic fragment thereof comprising one or more mutations from a beta variant. In some embodiments, $PD_n$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant). In some embodiments, $PD_n$ comprises an RNA encoding a SARS-CoV-2 Spike protein or an immunogenic fragment thereof from the Wuhan strain and one or more additional RNAs encoding a Spike protein or an immunogenic fragment thereof from a SARS-CoV-2 strain that is prevalent and/or spreading rapidly in a relevant jurisdiction. In some embodiments, $PD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an alpha variant. In some embodiments, $PD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $PD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $PD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $PD_1$, $PD_2$, $PD_3$, and $PD_n$ can each independently comprise a plurality of (e.g., at least two) mRNA compositions described herein. In some embodiments $PD_1$, $PD_2$, $PD_3$, and $PD_n$ can each independently comprise a first and a second mRNA composition. In some embodiments, at least one of a plurality of mRNA compositions comprises BNT162b2 (e.g., as described herein). In some embodiments, at least one of a plurality of mRNA compositions comprises an mRNA encoding a SARS-CoV-2 S protein or an immunogenic fragment thereof from a different SARS-CoV-2 variant. In some embodiments, at least one of a plurality of mRNA compositions comprises an mRNA encoding a SARS-CoV-2 S protein or an immunogenic fragment thereof from a Wuhan strain of SARS-CoV-2. In some embodiments, at least one of a plurality of mRNA compositions comprises an RNA encoding a SARS-CoV-2 S protein or an immunogenic fragment thereof comprising one or more mutations from a variant that is prevalent and/or spreading rapidly in a relevant jurisdiction. In some embodiments, at least one of a plurality of mRNA compositions comprises an mRNA encoding a SARS-CoV-2 S protein or an immunogenic fragment thereof comprising one or more mutations from an alpha variant. In some embodiments, at least one of a plurality of mRNA compositions comprises an mRNA encoding a SARS-CoV-2 S protein or an immunogenic fragment thereof comprising one or more mutations from a delta variant. In some embodiments, at least one of a plurality of mRNA compositions comprises an mRNA encoding a SARS-CoV-2 S protein or an immunogenic fragment thereof comprising one or more mutations from an Omicron variant (e.g., a BA.4/5, BA.1, BA.2, XBB, XBB.1, or BQ.1 Omicron variant).

In some embodiments, a plurality of mRNA compositions given in $PD_1$, $PD_2$, $PD_3$, and/or $PD_n$ can each independently comprise at least two different mRNA constructs (e.g., differing in at protein-encoding sequences). For example, in some embodiments a plurality of mRNA compositions given in $PD_1$, $PD_2$, $PD_3$, and/or $PD_n$ can each independently comprise an mRNA encoding a SARS-CoV-2 S protein or an immunogenic fragment thereof from a Wuhan strain of SARS-CoV-2 and an mRNA encoding a SARS-CoV-2 S protein or an immunogenic fragment thereof comprising one or more mutations from a variant that is prevalent and/or spreading rapidly in a relevant jurisdiction. In some embodiments a plurality of mRNA compositions given in $PD_1$, $PD_2$, $PD_3$, and/or $PD_n$ can each independently comprise an mRNA encoding a SARS-CoV-2 S protein or an immunogenic fragment thereof derived from a Wuhan strain of SARS-CoV-2 and an mRNA encoding a SARS-CoV-2 S protein or an immunogenic fragment thereof comprising one or more mutations from a variant that is prevalent and/or spreading rapidly in a relevant jurisdiction. In some such embodiments, a variant can be an alpha variant. In some such embodiments, a variant can be a delta variant. In some such embodiments a variant can be an Omicron variant (e.g., a BA.4/5, BA.1, BA.2, XBB, XBB.1, or BQ.1 Omicron variant). In some embodiments, each of a plurality of mRNA compositions given in PD1, PD2, $PD_3$, and/or $PD_n$ can independently comprise at least two mRNAs, each encoding a SARS-CoV-2 S protein or an immunogenic fragment thereof comprising one or more mutations from a distinct variant that is prevalent and/or spreading rapidly in a relevant jurisdiction. In some embodiments, each of a plurality of mRNA compositions given in $PD_1$, $PD_2$, $PD_3$, and/or $PD_n$ can independently comprise an mRNA encoding a SARS-CoV-2 S protein or an immunogenic fragment thereof from an alpha variant and an mRNA encoding a SARS-CoV-2 S protein or an immunogenic fragment thereof comprising one or more mutations from a delta variant. In some embodiments, each of a plurality of mRNA compositions given in PD1, $PD_2$, $PD_3$, and/or $PD_n$ can independently comprise an mRNA encoding a SARS-CoV-2 S protein or an immunogenic fragment thereof from an alpha variant and an mRNA encoding a SARS-CoV-2 S protein or an immunogenic fragment thereof comprising one or more mutations from an Omicron variant (e.g., a BA.4/S, BA.1, BA.2, XBB, XBB.1, or BQ.1 Omicron variant). In some embodiments, each of a plurality of mRNA compositions given in $PD_1$, $PD_2$,$PD_3$, and/or $PD_n$ can independently comprise an mRNA encoding a SARS-CoV-2 S protein or an immunogenic fragment thereof from a delta variant and an mRNA encoding a SARS-CoV-2 S protein or an immunogenic fragment thereof comprising one or more mutations from an Omicron variant (e.g., a BA.4/5, BA.1, BA.2, XBB, XBB.1, or BQ.1 Omicron variant).

In some embodiments, $PD_1$, $PD_2$, $PD_3$, and/or $PD_n$ each comprise a plurality of mRNA compositions, wherein each mRNA composition is separately administered to a subject. For example, in some embodiments each mRNA composition is administered via intramuscular injection at different injection sites. For example, in some embodiments, a first and second mRNA composition given in $PD_1$, $PD_2$, $PD_3$, and/or $PD_n$ are separately administered to different arms of a subject via intramuscular injection.

In some embodiments, $PD_1$, $PD_2$, $PD_3$, and/or $PD_n$ comprise administering a plurality of RNA molecules, wherein each RNA molecule encodes a Spike protein comprising mutations from a different SARS-CoV-2 variant, and wherein the plurality of RNA molecules are administered to the subject in a single formulation. In some embodiments, the single formulation comprises an RNA encoding a Spike protein or an immunogenic variant thereof from the Wuhan strain and an RNA encoding a SARS-CoV-2 Spike protein or an immunogenic fragment thereof comprising one or more mutations from an alpha variant. In some embodiments, the single formulation comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, the single formulation comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, the single formulation comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, the length of time between $PD_1$ and $PD_2$ ($PI_1$) is at least about 1 week, at least about 2 weeks, at least about 3 weeks, or at least about 4 weeks. In some embodiments, $PI_1$ is about 1 week to about 12 weeks. In some embodiments, $PI_1$ is about 1 week to about 10 weeks. In some embodiments, $PI_1$ is about 2 weeks to about 10 weeks. In some embodiments, $PI_1$ is about 2 weeks to about 8 weeks. In some embodiments, $PI_1$ is about 3 weeks to about 8 weeks. In some embodiments, $PI_1$ is about 4 weeks to about 8 weeks. In some embodiments, $PI_1$ is about 6 weeks to about 8 weeks. In some embodiments $PI_1$ is about 3 to about 4 weeks. In some embodiments, $PI_1$ is about 1 week. In some embodiments, $PI_1$ is about 2 weeks. In some embodiments, $PI_1$ is about 3 weeks. In some embodiments, $PI_1$ is about 4 weeks. In some embodiments, $PI_1$ is about 5 weeks. In some embodiments, $PI_1$ is about 6 weeks. In some embodiments, $PI_1$ is about 7 weeks. In some embodiments, $PI_1$ is about 8 weeks. In some embodiments, $PI_1$ is about 9 weeks. In some embodiments, $PI_1$ is about 10 weeks. In some embodiments, $PI_1$ is about 11 weeks. In some embodiments, $PI_1$ is about 12 weeks.

In some embodiments, the length of time between $PD_2$ and $PD_3$ ($PI_2$) is at least about 1 week, at least about 2 weeks, or at least about 3 weeks. In some embodiments, $PI_2$ is about 1 week to about 12 weeks. In some embodiments, $PI_2$ is about 1 week to about 10 weeks. In some embodiments, $PI_2$ is about 2 weeks to about 10 weeks. In some embodiments, $PI_2$ is about 2 weeks to about 8 weeks. In some embodiments, $PI_2$ is about 3 weeks to about 8 weeks. In some embodiments, $PI_2$ is about 4 weeks to about 8 weeks. In some embodiments, $PI_2$ is about 6 weeks to about 8 weeks. In some embodiments $PI_2$ is about 3 to about 4 weeks. In some embodiments, $PI_2$ is about 1 week. In some embodiments, $PI_2$ is about 2 weeks. In some embodiments, $PI_2$ is about 3 weeks. In some embodiments, $PI_2$ is about 4 weeks. In some embodiments, $PI_2$ is about 5 weeks. In some embodiments, $PI_2$ is about 6 weeks. In some embodiments, $PI_2$ is about 7 weeks. In some embodiments, $PI_2$ is about 8 weeks. In some embodiments, $PI_2$ is about 9 weeks. In some embodiments, $PI_2$ is about 10 weeks. In some embodiments, $PI_2$ is about 11 weeks. In some embodiments, $PI_2$ is about 12 weeks.

In some embodiments, the length of time between $PD_3$ and a subsequent dose that is part of the Primary Dosing Regimen, or between doses for any dose beyond $PD_3$ ($PI_n$) is each separately and independently selected from: about 1 week or more, about 2 weeks or more, or about 3 weeks or more. In some embodiments, $PI_n$ is about 1 week to about 12 weeks. In some embodiments, $PI_n$ is about 1 week to about 10 weeks. In some embodiments, $PI_n$ is about 2 weeks to about 10 weeks. In some embodiments, $PI_n$ is about 2 weeks to about 8 weeks. In some embodiments, $PI_n$ is about 3 weeks to about 8 weeks. In some embodiments, $PI_n$ is about 4 weeks to about 8 weeks. In some embodiments, $PI_n$ is about 6 weeks to about 8 weeks. In some embodiments $PI_n$ is about 3 to about 4 weeks. In some embodiments, $PI_2$ is about 1 week. In some embodiments, $PI_n$ is about 2 weeks. In some embodiments, $PI_n$ is about 3 weeks. In some embodiments, $PI_n$ is about 4 weeks. In some embodiments, $PI_n$ is about 5 weeks. In some embodiments, $PI_n$ is about 6 weeks. In some embodiments, $PI_n$ is about 7 weeks. In some embodiments, $PI_n$ is about 8 weeks. In some embodiments, $PI_n$ is about 9 weeks. In some embodiments, $PI_n$ is about 10 weeks. In some embodiments, $PI_n$ is about 11 weeks. In some embodiments, $PI_n$ is about 12 weeks.

In some embodiments, one or more compositions adminstered in $PD_1$ are formulated in a Tris buffer. In some embodiments, one or more compositions administered in $PD_2$ are formulated in a Tris buffer. In some embodiments, one or more compositions administering in $PD_3$ are formulated in a Tris buffer. In some embodiments, one or more compositions administered in $PD_n$ are formulated in a Tris buffer.

In some embodiments, the primary dosing regimen comprises administering two or more mRNA compositions described herein, and at least two of the mRNA compositions have different formulations. In some embodiments, the primary dosing regimen comprises $PD_1$ and $PD_2$, where $PD_1$ comprises administering an mRNA formulated in a Tris buffer and $PD_2$ comprises administering an mRNA formulated in a PBS buffer. In some embodiments, the primary dosing regimen comprises $PD_1$ and $PD_2$, where $PD_1$ comprises administering an mRNA formulated in a PBS buffer and $PD_2$ comprises administering an mRNA formulated in a Tris buffer.

In some embodiments, one or more mRNA compositions given in $PD_1$, $PD_2$, $PD_3$, and/or $PD_n$ can be administered in combination with another vaccine. In some embodiments, another vaccine is for a disease that is not COVID-19. In some embodiments, the disease is one that increases deleterious effects of SARS-CoV-2 when a subject is coinfected with the disease and SARS-CoV-2. In some embodiments, the disease is one that increases the transmission rate of SARS-CoV-2 when a subject is coinfected with the disease and SARS-CoV-2. In some embodiments, another vaccine is a different commerically available vaccine. In some embodiments, the different commercially available vaccine is an RNA vaccine. In some embodiments, the different commercially available vaccine is a polypeptide-based vaccine. In some embodiments, another vaccine (e.g., as described herein) and one or more mRNA compositions given in $PD_1$, $PD_2$, $PD_3$, and/or $PD_n$ are separately administered, for example, in some embodiments via intramuscular injection, at different injection sites. For example, in some embodiments, an influenza vaccine and one or more SARS-CoV-2 mRNA compositions described herein given in $PD_1$, $PD_2$, $PD_3$, and/or $PD_n$ are separately administered to different arms of a subject via intramuscular injection.

Booster Dosing Regimens

In some embodiments, methods of vaccination disclosed herein comprise one or more Booster Dosing Regimens. The Booster Dosing Regimens disclosed herein comprise one or more doses. In some embodiments, a Booster Dosing Regimen is administered to patients who have been administered a Primary Dosing Regimen (e.g., as described herein). In some embodiments a Booster Dosing Regimen is administered to patients who have not received a pharmaceutical composition disclosed herein. In some embodiments a Booster Dosing Regimen is administered to patients who have been previously vaccinated with a COVID-19 vaccine that is different from the vaccine administered in a Primary Dosing Regimen.

In some embodiments, the length of time between the Primary Dosing Regimen and the Booster Dosing Regimen is at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 2 months, at least 3 months, at least 4 months, at least 5 months, at least 6 months, at least 7 months, at least 8 months, at least 9 months, at least 10 months, at least 11 months, or at least 12 months or longer. In some embodiments, the length of time between the Primary Dosing Regimen and the Booster Dosing Regimen is about 1 month. In some embodiments, the length of time between the Primary Dosing Regimen and the Booster Dosing Regimen is at least about 2 months. In some embodiments, the length of time between the Primary Dosing Regimen and the Booster Dosing Regimen is at least about 3 months. In some embodiments, the length of time between the Primary Dosing Regimen and the Booster Dosing Regimen is at least about 4 months. In some embodiments, the length of time between the Primary Dosing Regimen and the Booster Dosing Regimen is at least about 5 months. In some embodiments, the length of time between the Primary Dosing Regimen and the Booster Dosing Regimen is at least about 6 months. In some embodiments, the length of time between the Primary Dosing Regimen and the Booster Dosing Regimen is from about 1 month to about 48 months. In some embodiments, the length of time between the Primary Dosing Regimen and the Booster Dosing Regimen is from about 1 month to about 36 months. In some embodiments, the length of time between the primary dosing regimen and the Booster Dosing Regimen is from about 1 month to about 24 months. In some embodiments, the length of time between the Primary Dosing Regimen and the Booster Dosing Regimen is from about 2 months to about 24 months. In some embodiments, the length of time between the Primary Dosing Regimen and the Booster Dosing Regimen is from about 3 months to about 24 months. In some embodiments, the length of time between the primary dosing regimen and the Booster Dosing Regimen is from about 3 months to about 18 months. In some embodiments, the length of time between the primary dosing regimen and the Booster Dosing Regimen is from about 3 months to about 12 months. In some embodiments, the length of time between the primary dosing regimen and the Booster Dosing Regimen is from about 6 months to about 12 months. In some embodiments, the length of time between the Primary Dosing Regimen and the Booster Dosing Regimen is from about 3 months to about 9 months. In some embodiments, the length of time between the Primary Dosing Regimen and the Booster Dosing Regimen is from about 5 months to about 7 months. In some embodiments, the length of time between the Primary Dosing Regimen and the Booster Dosing Regimen is about 6 months.

In some embodiments, subjects are administered a Booster Dosing Regimen. A Booster dosing regimen can comprise one or more doses. For example, in some embodiments, a Booster Dosing Regimen comprises a single dose ($BD_1$). In some embodiments a Booster Dosing Regimen comprises a first dose ($BD_1$) and a second dose ($BD_2$). In some embodiments, a Booster Dosing Regimen comprises a first dose, a second dose, and a third dose ($BD_3$). In some embodiments, a Booster Dosing Regimen comprises a first dose, a second dose, a third dose, and one or more additional doses ($BD_n$) of any one of the pharmaceutical compositions described herein.

In some embodiments, $BD_1$ comprises administering 1 to 100 ug of RNA. In some embodiments, $BD_1$ comprises administering 1 to 60 ug of RNA. In some embodiments, $BD_1$ comprises administering 1 to 50 ug of RNA. In some embodiments, $BD_1$ comprises administering 1 to 30 ug of RNA. In some embodiments, $BD_1$ comprises administering about 3 ug of RNA. In some embodiments, $BD_1$ comprises administering about 5 ug of RNA. In some embodiments, $BD_1$ comprises administering about 10 ug of RNA. In some embodiments, $BD_1$ comprises administering about 15 ug of RNA. In some embodiments, $BD_1$ comprises administering about 20 ug of RNA. In some embodiments, $BD_1$ comprises administering about 30 ug of RNA. In some embodiments, $BD_1$ comprises administering about 50 ug of RNA. In some embodiments, $BD_1$ comprises administering about 60 ug of RNA.

In some embodiments, $BD_2$ comprises administering 1 to 100 ug of RNA. In some embodiments, $BD_2$ comprises administering 1 to 60 ug of RNA. In some embodiments, $BD_2$ comprises administering 1 to 50 ug of RNA. In some embodiments, $BD_2$ comprises administering 1 to 30 ug of RNA. In some embodiments, $BD_2$ comprises administering about 3 ug. In some embodiments, $BD_2$ comprises administering about 5 ug of RNA. In some embodiments, $BD_2$ comprises administering about 10 ug of RNA. In some embodiments, $BD_2$ comprises administering about 15 ug of RNA. In some embodiments, $BD_2$ comprises administering about 20 ug RNA. In some embodiments, $BD_2$ comprises administering about 30 ug of RNA. In some embodiments, $BD_2$ comprises administering about 50 ug of RNA. In some embodiments, $BD_2$ comprises administering about 60 ug of RNA.

In some embodiments, $BD_3$ comprises administering 1 to 100 ug of RNA. In some embodiments, $BD_3$ comprises administering 1 to 60 ug of RNA. In some embodiments, $BD_3$ comprises administering 1 to 50 ug of RNA. In some embodiments, $BD_3$ comprises administering 1 to 30 ug of RNA. In some embodiments, $BD_3$ comprises administering about 3 ug of RNA. In some embodiments, $BD_3$ comprises administering about 5 ug of RNA. In some embodiments, $BD_3$ comprises administering about 10 ug of RNA. In some embodiments, $BD_3$ comprises administering about 15 ug of RNA. In some embodiments, $BD_3$ comprises administering about 20 ug of RNA. In some embodiments, $BD_3$ comprises administering about 30 ug of RNA. In some embodiments, $BD_3$ comprises administering about 50 ug of RNA. In some embodiments, $BD_3$ comprises administering about 60 ug of RNA.

In some embodiments, $BD_n$ comprises administering 1 to 100 ug of RNA. In some embodiments, $BD_n$ comprises administering 1 to 60 ug of RNA. In some embodiments, $BD_n$ comprises administering 1 to 50 ug of RNA. In some embodiments, $BD_n$ comprises administering 1 to 30 ug of RNA. In some embodiments, $BD_n$ comprises administering about 3 ug of RNA. In some embodiments, $BD_n$ comprises administering about 5 ug of RNA. In some embodiments, $BD_n$ comprises administering about 10 ug of RNA. In some embodiments, $BD_n$ comprises administering about 15 ug of RNA. In some embodiments, $BD_n$ comprises administering about 20 ug of RNA. In some embodiments, $BD_n$ comprises administering about 30 ug of RNA. In some embodiments, $BD_0$ comprises administering about 60 ug of RNA. In some embodiments, $BD_n$ comprises administering about 50 ug of RNA.

In some embodiments, $BD_1$ comprises an RNA encoding a SARS-CoV-2 Spike protein or an immunogenic fragment thereof from the Wuhan strain. In some embodiments, $BD_1$ comprises an RNA encoding a Spike protein or an immunogenic fragment thereof from a SARS-CoV-2 strain that is prevalent and/or spreading rapidly in a relevant jurisdiction. In some embodiments, $BD_1$ comprises an RNA encoding a SARS-CoV-2 Spike protein or an immunogenic fragment thereof comprising one or more mutations from an alpha variant. In some embodiments, $BD_1$ comprises an RNA encoding a SARS-CoV-2 Spike protein or an immunogenic fragment thereof comprising one or more mutations from a delta variant. In some embodiments, $BD_1$ comprises an RNA encoding a SARS-CoV-2 Spike protein or an immunogenic fragment thereof comprising one or more mutations from a beta variant. In some embodiments, $BD_1$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $BD_1$ comprises an RNA encoding a SARS-CoV-2 Spike protein or an immunogenic fragment thereof from the Wuhan strain and one or more RNA encoding a Spike protein or an immunogenic fragment thereof from a SARS-CoV-2 strain that is prevalent and/or spreading rapidly in a relevant jurisdiction. In some embodiments, $BD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a alpha variant. In some embodiments, $BD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $BD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $BD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $BD_2$ comprises an RNA encoding a SARS-CoV-2 Spike protein or an immunogenic fragment thereof from the Wuhan strain. In some embodiments, $BD_2$ comprises an RNA encoding a Spike protein or an immunogenic fragment thereof from a SARS-CoV-2 strain that is prevalent and/or spreading rapidly in a relevant jurisdiction. In some embodiments, $BD_2$ comprises an RNA encoding a SARS-CoV-2 Spike protein or an immunogenic fragment thereof comprising one or more mutations from an alpha variant. In some embodiments, $BD_2$ comprises an RNA encoding a SARS-CoV-2 Spike protein or an immunogenic fragment thereof comprising one or more mutations from a delta variant. In some embodiments, $BD_2$ comprises an RNA encoding a SARS-CoV-2 Spike protein or an immunogenic fragment thereof comprising one or more mutations from a beta variant. In some embodiments, $BD_2$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant). In some embodiments, $BD_2$ comprises an RNA encoding a SARS-CoV-2 Spike protein or an immunogenic fragment thereof from the Wuhan strain and one or more RNA encoding a Spike protein or an immunogenic fragment thereof from a SARS-CoV-2 strain that is prevalent and/or spreading rapidly in a relevant jurisdiction. In some embodiments, $BD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a alpha variant. In some embodiments, $BD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $BD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $BD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/S, BA.1, BA.2, XBB, XBB.1, or BQ.1 Omicron variant).

In some embodiments, $BD_3$ comprises an RNA encoding a SARS-CoV-2 Spike protein or an immunogenic fragment thereof from the Wuhan strain. In some embodiments, $BD_3$ comprises an RNA encoding a Spike protein or an immunogenic fragment thereof from a SARS-CoV-2 strain that is prevalent and/or spreading rapidly in a relevant jurisdiction. In some embodiments, $BD_3$ comprises an RNA encoding a SARS-CoV-2 Spike protein or an immunogenic fragment thereof comprising one or more mutations from an alpha variant. In some embodiments, $BD_3$ comprises an RNA encoding a SARS-CoV-2 Spike protein or an immunogenic fragment thereof comprising one or more mutations from a delta variant. In some embodiments, $BD_3$ comprises an RNA encoding a SARS-CoV-2 Spike protein or an immunogenic fragment thereof comprising one or more mutations from a beta variant. In some embodiments, $BD_3$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $BD_3$ comprises an RNA encoding a SARS-CoV-2 Spike protein or an immunogenic fragment thereof from the Wuhan strain and one or more RNA encoding a Spike protein or an immunogenic fragment thereof from a SARS-CoV-2 strain that is prevalent and/or spreading rapidly in a relevant jurisdiction. In some embodiments, $BD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a alpha variant. In some embodiments, $BD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $BD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $BD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $BD_n$ comprises an RNA encoding a SARS-CoV-2 Spike protein or an immunogenic fragment thereof from the Wuhan strain. In some embodiments, $BD_n$ comprises an RNA encoding a Spike protein or an immunogenic fragment thereof from a SARS-CoV-2 strain that is prevalent and/or spreading rapidly in a relevant jurisdiction. In some embodiments, $BD_n$ comprises an RNA encoding a SARS-CoV-2 Spike protein or an immunogenic fragment thereof comprising one or more mutations from an alpha variant. In some embodiments, $BD_n$ comprises an RNA encoding a SARS-CoV-2 Spike protein or an immunogenic fragment thereof comprising one or more mutations from a delta variant. In some embodiments, $BD_n$ comprises an RNA encoding a SARS-CoV-2 Spike protein or an immunogenic fragment thereof comprising one or more mutations from a beta variant. In some embodiments, $BD_n$ comprises an RNA encoding a SARS-CoV-2 Spike protein or an immunogenic fragment thereof comprising one or more mutations from an Omicron variant(e.g., a BA.4/5, BA.1, BA.2, XBB, XBB.1, or BQ.1 Omicron variant).

In some embodiments, $BD_n$ comprises an RNA encoding a SARS-CoV-2 Spike protein or an immunogenic fragment thereof from the Wuhan strain and one or more RNA encoding a Spike protein or an immunogenic fragment thereof from a SARS-CoV-2 strain that is prevalent and/or spreading rapidly in a relevant jurisdiction. In some embodiments, $BD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a alpha variant. In some embodiments, $BD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $BD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $BD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $BD_1$, $BD_2$, $BD_3$, and $BD_n$ can each independently comprise a plurality of (e.g., at least two) mRNA compositions described herein. In some embodiments $BD_1$, $BD_2$, $BD_3$, and $BD_n$ can each independently comprise a first and a second mRNA composition. In some embodiments, $BD_1$, $BD_2$, $BD_3$, and $BD_n$ can each independently comprise a plurality of (e.g., at least two) mRNA compositions, wherein, at least one of the plurality of mRNA compositions comprises BNT162b2 (e.g., as described herein). In some embodiments, at least one of a plurality of mRNA compositions comprises an mRNA encoding a SARS-CoV-2 S protein or an immunogenic fragment thereof from a different SARS-CoV-2 variant (e.g., a variant that is prevalent or rapidly spreading in a relevant jurisdiction, e.g., a variant disclosed herein). In some embodiments, at least one of a plurality of mRNA compositions comprises an mRNA encoding a SARS-CoV-2 S protein or an immunogenic fragment thereof from a Wuhan strain of SARS-CoV-2. In some embodiments, at least one of a plurality of mRNA compositions comprises an RNA encoding a SARS-CoV-2 S protein or an immunogenic fragment thereof comprising one or more mutations from a variant that is prevalent and/or spreading rapidly in a relevant jurisdiction. In some embodiments, at least one of a plurality of mRNA compositions comprises an mRNA encoding a SARS-CoV-2 S protein or an immunogenic fragment thereof comprising one or more mutations from an alpha variant. In some embodiments, at least one of a plurality of mRNA compositions comprises an mRNA encoding a SARS-CoV-2 S protein or an immunogenic fragment thereof comprising one or more mutations from a delta variant. In some embodiments, at least one of a plurality of mRNA compositions comprises an mRNA encoding a SARS-CoV-2 S protein or an immunogenic fragment thereof comprising one or more mutations from an Omicron variant (e.g., a BA.4/5, BA.1, BA.2, XBB, XBB.1, or BQ.1 Omicron variant).

In some embodiments, a plurality of mRNA compositions given in $BD_1$, $BD_2$, $BD_3$, and/or $BD_n$ can each independently comprise at least two different mRNA constructs (e.g., mRNA constructs having differing protein-encoding sequences). For example, in some embodiments a plurality of mRNA compositions given in $BD_1$, $BD_2$, $BD_3$, and/or $BD_n$ can each independently comprise an mRNA encoding a SARS-CoV-2 S protein or an immunogenic fragment thereof from a Wuhan strain of SARS-CoV-2 and an mRNA encoding a SARS-CoV-2 S protein or an immunogenic fragment thereof comprising one or more mutations from a variant that is prevalent and/or spreading rapidly in a relevant jurisdiction. In some embodiments a plurality of mRNA compositions given in $BD_1$, $BD_2$, $BD_3$, and/or $BD_n$ can each independently comprise an mRNA encoding a SARS-CoV-2 S protein or an immunogenic fragment thereof derived from a Wuhan strain of SARS-CoV-2 and an mRNA encoding a SARS-CoV-2 S protein or an immunogenic fragment thereof comprising one or more mutations from a variant that is prevalent and/or spreading rapidly in a relevant jurisdiction. In some such embodiments, a variant can be an alpha variant. In some such embodiments, a variant can be a delta variant. In some such embodiments a variant can be an Omicron variant (e.g., a BA.4/5, BA.1, BA.2, XBB, XBB.1, or BQ.1 Omicron variant).

In some embodiments, a plurality of mRNA compositions given in $BD_1$, $BD_2$, $BD_3$, and/or $BD_n$ can each independently comprise at least two mRNAs each encoding a SARS-CoV-2 S protein or an immunogenic fragment thereof comprising one or more mutations from a distinct variant that is prevalent and/or spreading rapidly in a relevant jurisdiction. In some embodiments a plurality of mRNA compositions given in $BD_1$, $BD_2$, $BD_3$, and/or $BD_n$ can each independently comprise an mRNA encoding a SARS-CoV-2 S protein or an immunogenic fragment thereof from an alpha variant and an mRNA encoding a SARS-CoV-2 S protein or an immunogenic fragment thereof comprising one or more mutations from a delta variant. In some embodiments a plurality of mRNA compositions given in $BD_1$, $BD_2$, $BD_3$, and/or $BD_n$ can each independently comprise an mRNA encoding a SARS-CoV-2 S protein or an immunogenic fragment thereof from an alpha variant and an mRNA encoding a SARS-CoV-2 S protein or an immunogenic fragment thereof comprising one or more mutations from an Omicron variant (e.g., a BA.4/5, BA.1, BA.2, XBB, XBB.1, or BQ.1 Omicron variant). In some embodiments a plurality of mRNA compositions given in $BD_1$, $BD_2$, $BD_3$, and/or $BD_n$ can each independently comprise an mRNA encoding a SARS-CoV-2 S protein or an immunogenic fragment thereof from a delta variant and an mRNA encoding a SARS-CoV-2 S protein or an immunogenic fragment thereof comprising one or more mutations from an Omicron variant (e.g., a BA.4/5, BA.1, BA.2, XBB, XBB.1, or BQ.1 Omicron variant).

In some embodiments, a plurality of mRNA compositions given in $BD_1$, $BD_2$, $BD_3$, and/or $BD_n$ are separately administered to a subject, for example, in some embodiments via intramuscular injection, at different injection sites. For example, in some embodiments, a first and second mRNA composition given in $BD_1$, $BD_2$, $BD_3$, and/or $BD_n$ are separately administered to different arms of a subject via intramuscular injection.

In some embodiments, the length of time between $BD_1$ and $BD_2$ (B1I1) is at least about 1 week, at least about 2 weeks, at least about 3 weeks, or at least about 4 weeks. In some embodiments, $BI_1$ is about 1 week to about 12 weeks. In some embodiments, $BI_1$ is about 1 week to about 10 weeks. In some embodiments, $BI_1$ is about 2 weeks to about 10 weeks. In some embodiments, $BI_1$ is about 2 weeks to about 8 weeks. In some embodiments, $BI_1$ is about 3 weeks to about 8 weeks. In some embodiments, $BI_1$ is about 4 weeks to about 8 weeks. In some embodiments, $BI_1$ is about 6 weeks to about 8 weeks. In some embodiments $BI_1$ is about 3 to about 4 weeks. In some embodiments, $BI_1$ is about 1 week. In some embodiments, $BI_1$ is about 2 weeks. In some embodiments, $BI_1$ is about 3 weeks. In some embodiments, $BI_1$ is about 4 weeks. In some embodiments, $BI_1$ is about 5 weeks. In some embodiments, $BI_1$ is about 6 weeks. In some embodiments, B1 is about 7 weeks. In some embodiments, $BI_1$ is about 8 weeks. In some embodiments, $BI_1$ is about 9 weeks. In some embodiments, $BI_1$ is about 10 weeks.

In some embodiments, the length of time between $BD_2$ and $BD_3$ ($BI_2$) is at least about 1 week, at least about 2 weeks, or at least about 3 weeks. In some embodiments, $BI_2$ is about 1 week to about 12 weeks. In some embodiments, $BI_2$ is about 1 week to about 10 weeks. In some embodiments, $BI_2$ is about 2 weeks to about 10 weeks. In some embodiments, B12 is about 2 weeks to about 8 weeks. In some embodiments, $BI_2$ is about 3 weeks to about 8 weeks. In some embodiments, $BI_2$ is about 4 weeks to about 8 weeks. In some embodiments, $BI_2$ is about 6 weeks to about 8 weeks. In some embodiments B12 is about 3 to about 4 weeks. In some embodiments, B12 is about 1 week. In some embodiments, B12 is about 2 weeks. In some embodiments, B12 is about 3 weeks. In some embodiments, B12 is about 4 weeks. In some embodiments, B12 is about 5 weeks. In some embodiments, $BI_2$ is about 6 weeks. In some embodiments, $BI_2$ is about 7 weeks. In some embodiments, $BI_2$ is about 8 weeks. In some embodiments, B12 is about 9 weeks. In some embodiments, $BI_2$ is about 10 weeks.

In some embodiments, the length of time between $BD_3$ and a subsequent dose that is part of the Booster Dosing Regimen, or between doses for any dose beyond $BD_3$ ($BI_n$) is each separately and independently selected from: about 1 week or more, about 2 weeks or more, or about 3 weeks or more. In some embodiments, $BI_n$ is about 1 week to about 12 weeks. In some embodiments, $BI_n$ is about 1 week to about 10 weeks. In some embodiments, $BI_n$ is about 2 weeks to about 10 weeks. In some embodiments, $BI_n$ is about 2 weeks to about 8 weeks. In some embodiments, $BI_n$ is about 3 weeks to about 8 weeks. In some embodiments, $BI_n$ is about 4 weeks to about 8 weeks. In some embodiments, $BI_n$ is about 6 weeks to about 8 weeks. In some embodiments $BI_n$ is about 3 to about 4 weeks. In some embodiments, $BI_n$ is about 1 week. In some embodiments, $BI_n$ is about 2 weeks. In some embodiments, $BI_n$ is about 3 weeks. In some embodiments, $BI_n$ is about 4 weeks. In some embodiments, $BI_n$ is about 5 weeks. In some embodiments, $BI_n$ is about 6 weeks. In some embodiments, $BI_n$ is about 7 weeks. In some embodiments, $BI_n$ is about 8 weeks. In some embodiments, $BI_n$ is about 9 weeks. In some embodiments, $BI_n$ is about 10 weeks.

In some embodiments, one or more compositions adminstered in $BD_1$ are formulated in a Tris buffer. In some embodiments, one or more compositions administered in $BD_2$ are formulated in a Tris buffer. In some embodiments, one or more compositions administering in $BD_3$ are formulated in a Tris buffer. In some embodiments, one or more compositions administered in $BD_3$ are formulated in a Tris buffer.

In some embodiments, the Booster dosing regimen comprises administering two or more mRNA compositions described herein, and at least two of the mRNA compositions have different formulations. In some embodiments, the Booster dosing regimen comprises $BD_1$ and $BD_2$, where $BD_1$ comprises administering an mRNA formulated in a Tris buffer and $BD_2$ comprises administering an mRNA formulated in a PBS buffer. In some embodiments, the Booster dosing regimen comprises $BD_1$ and $BD_2$, where $BD_1$ comprises administering an mRNA formulated in a PBS buffer and $BD_2$ comprises administering an mRNA formulated in a Tris buffer.

In some embodiments, one or more mRNA compositions given in $BD_1$, $BD_2$, $BD_3$, and/or $BD_n$ can be administered in combination with another vaccine. In some embodiments, another vaccine is for a disease that is not COVID-19. In some embodiments, the disease is one that increases deleterious effects of SARS-CoV-2 when a subject is coinfected with the disease and SARS-CoV-2. In some embodiments, the disease is one that increases the transmission rate of SARS-CoV-2 when a subject is coinfected with the disease and SARS-CoV-2. In some embodiments, another vaccine is a different commerically available vaccine. In some embodiments, the different commercially available vaccine is an RNA vaccine. In some embodiments, the different commercially available vaccine is a polypeptide-based vaccine. In some embodiments, another vaccine (e.g., as described herein) and one or more mRNA compositions given in $BD_1$, $BD_2$, $BD_3$, and/or $BD_n$ are separately administered, for example, in some embodiments via intramuscular injection, at different injection sites. For example, in some embodiments, an influenza vaccine and one or more SARS-CoV-2 mRNA compositions described herein given in $BD_1$, $BD_2$, $BD_3$, and/or $BD_n$ are separately administered to different arms of a subject via intramuscular injection.

Additional Booster Regimens

In some embodiments, methods of vaccination disclosed herein comprise administering more than one Booster Dosing Regimen. In some embodiments, more than one Booster Dosing Regimen may need to be administered to increase neutralizing antibody response. In some embodiments, more than one booster dosing regimen may be needed to counteract a SARS-CoV-2 strain that has been shown to have a high likelihood of evading immune response elicited by vaccines that a patient has previously received. In some embodiments, an additional Booster Dosing Regimen is administered to a patient who has been determined to produce low concentrations of neutralizing antibodies. In some embodiments, an additional booster dosing regimen is administered to a patient who has been determined to have a high likelihood of being susceptible to SARS-CoV-2 infection, despite previous vaccination (e.g., an immunocompromised patient, a cancer patient, and/or an organ transplant patient).

The description provided above for the first Booster Dosing Regimen also describes the one or more additional Booster Dosing Regimens. The interval of time between the first Booster Dosing Regimen and a second Booster Dosing Regimen, or between subsequent Booster Dosing Regimens can be any of the acceptable intervals of time described above between the Primary Dosing Regimen and the First Booster Dosing Regimen.

In some embodiments, a dosing regimen comprises a primary regimen and a booster regimen, wherein at least one dose given in the primary regimen and/or the booster regimen comprises a composition comprising an RNA that encodes a S protein or immunogenic fragment thereof from a variant that is prevalent or is spreading rapidly in a relevant jurisdiction (e.g., Omicron variant as described herein). For example, in some embodiments, a primary regimen comprises at least 2 doses of BNT162b2 (e.g., encoding a Wuhan strain), for example, given at least 3 weeks apart, and a booster regimen comprises at least 1 dose of a composition comprising RNA that encodes a S protein or immunogenic fragment thereof from a variant that is prevalent or is spreading rapidly in a relevant jurisdiction (e.g., Omicron variant as described herein). In some such embodiments, such a dose of a booster regimen may further comprise an RNA that encodes a S protein or immunogenic fragment thereof from a Wuhan strain, which can be administered with an RNA that encodes a S protein or immunogenic fragment thereof from a variant that is prevalent or is spreading rapidly in a relevant jurisdiction (e.g., Omicron variant as described herein), as a single mixture, or as two separate compositions, for example, in 1:1 weight ratio. In some embodiments, a booster regimen can also comprise at least 1 dose of BNT162b2, which can be administered as a first booster dose or a subsequent booster dose.

In some embodiments, an RNA composition described herein is given as a booster at a dose that is higher than the doses given during a primary regimen (primary doses) and/or the dose given for a first booster, if any. For example, in some embodiments, such a dose may be 60 ug; or in some embodiments such a dose may be higher than 30 ug and lower than 60 ug (e.g., 55 ug, 50 ug, or lower). In some embodiments, an RNA composition described herein is given as a booster at least 3-12 months or 4-12 months, or 5-12 months, or 6-12 months after the last dose (e.g., the last dose of a primary regimen or a first dose of a booster regimen). In some embodiments, the primary doses and/or the first booster dose (if any) may comprise BNT162b2, for example at 30 ug per dose.

In some embodiments, an RNA composition described herein comprises an RNA encoding a polypeptide as set forth in SEQ ID NO: 49 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 49). In some embodiments, an RNA composition comprises an RNA that includes the sequence of SEQ ID NO: 50 or a variant thereof (e.g., having at least 70% or more, including, e.g., at least 80%, at least 85%, at least 90%, at least 95%, at least 96%, at least 97%, at least 98%, or higher, identity to SEQ ID NO: 50). In some embodiments, an RNA composition comprises an RNA that includes the sequence of SEQ ID NO: 51 or a variant thereof (e.g., having at least 70% or more, including, e.g., at least 80%, at least 85%, at least 90%, at least 95%, at least 96%, at least 97%, at least 98%, or higher, identity to SEQ ID NO: 51).

In some embodiments, an RNA composition described herein comprises an RNA encoding a polypeptide as set forth in SEQ ID NO: 55 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 55. In some embodiments, an RNA composition comprises an RNA that includes the sequence of SEQ ID NO: 56 or a variant thereof (e.g., having at least 70% or more, including, e.g., at least 80%, at least 85%, at least 90%, at least 95%, at least 96%, at least 97%, at least 98%, or higher, identity to SEQ ID NO: 56). In some embodiments, an RNA composition comprises an RNA that includes the sequence of SEQ ID NO: 57 or a variant thereof (e.g., having at least 70% or more, including, e.g., at least 80%, at least 85%, at least 90%, at least 95%, at least 96%, at least 97%, at least 98%, or higher, identity to SEQ ID NO: 57).

In some embodiments, an RNA composition described herein comprises an RNA encoding a polypeptide as set forth in SEQ ID NO: 58 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 58). In some embodiments, an RNA composition comprises an RNA that includes the sequence of SEQ ID NO: 59 or a variant thereof (e.g., having at least 70% or more, including, e.g., at least 80%, at least 85%, at least 90%, at least 95%, at least 96%, at least 97%, at least 98%, or higher, identity to SEQ ID NO: 59). In some embodiments, an RNA composition comprises an RNA that includes the sequence of SEQ ID NO: 60 or a variant thereof (e.g., having at least 70% or more, including, e.g., at least 80%, at least 85%, at least 90%, at least 95%, at least 96%, at least 97%, at least 98%, or higher, identity to SEQ ID NO: 60).

In some embodiments, an RNA composition described herein comprises an RNA encoding a polypeptide as set forth in SEQ ID NO: 61 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 61). In some embodiments, an RNA composition comprises an RNA that includes the sequence of SEQ ID NO: 62a or a variant thereof (e.g., having at least 70% or more, including, e.g., at least 80%, at least 85%, at least 90%, at least 95%, at least 96%, at least 97%, at least 98%, or higher, identity to SEQ ID NO: 62a). In some embodiments, an RNA composition comprises an RNA that includes the sequence of SEQ ID NO: 63a or a variant thereof (e.g., having at least 70% or more, including, e.g., at least 80%, at least 85%, at least 90%, at least 95%, at least 96%, at least 97%, at least 98%, or higher, identity to SEQ ID NO: 63a).

In some embodiments, the formulations disclosed herein can be used to carry out any of the dosing regimens described in Table C (below).

TABLE C

Exemplary Dosing Regimens:

| | Primary Regimen | | | | Time between the last dose of a Primary regimen and a first dose of Booster Regimen | Booster Regimen | | | |
|---|---|---|---|---|---|---|---|---|---|
| # | Dose 1 (μg RNA) | Dose 2 (μg RNA) | Time Between Doses 1 and 2 | Dose 1 and Dose 2 Formulation | | Dose 1 (μg RNA) | Dose 2 (μg RNA) | Time Between Doses 1 and 2 | Dose 1 and Dose 2 Formulation |
| 1 | 30 | 30 | 2 to 8 weeks | PBS | At least 2 months | 30 | N/A[1] | N/A | PBS |
| 2 | 30 | 30 | 2 to 8 weeks | PBS | At least 3 months | 30 | N/A[1] | N/A | PBS |
| 3 | 30 | 30 | 2 to 8 weeks | PBS | 6 to 12 months | 30 | N/A[1] | N/A | PBS |
| 4 | 30 | 30 | 2 to 8 weeks | PBS or Tris | 4 to 12 months | 15 | N/A[1] | N/A | PBS or Tris |
| 5 | 30 | 30 | 2 to 8 weeks | PBS or Tris | 4 to 12 months | 10 | N/A[1] | N/A | PBS or Tris |
| 6 | 30 | 30 | 2 to 8 weeks | PBS or Tris | 4 to 12 months | 30 | 30 | 4 to 12 months | PBS or Tris |

TABLE C-continued

| Exemplary Dosing Regimens: | | | | | | | | | |
|---|---|---|---|---|---|---|---|---|---|
| | Primary Regimen | | | | Time between the | Booster Regimen | | | |
| # | Dose 1 (μg RNA) | Dose 2 (μg RNA) | Time Between Doses 1 and 2 | Dose 1 and Dose 2 Formulation | last dose of a Primary regimen and a first dose of Booster Regimen | Dose 1 (μg RNA) | Dose 2 (μg RNA) | Time Between Doses 1 and 2 | Dose 1 and Dose 2 Formulation |
| 7 | 30 | 30 | 2 to 8 weeks | PBS or Tris | 4 to 12 months | 30 | 15 | 4 to 12 months | PBS or Tris |
| 8 | 30 | 30 | 2 to 8 weeks | PBS or Tris | 4 to 12 months | 30 | 10 | 4 to 12 months | PBS or Tris |
| 9 | 30 | 30 | 2 to 8 weeks | PBS or Tris | 4 to 12 months | 30 | 60 | 4 to 12 months | PBS or Tris |
| 10 | 30 | 30 | 2 to 8 weeks | PBS or Tris | 4 to 12 months | 30 | >30 to <60 | 4 to 12 months | PBS or Tris |
| 11 | 30 | 30 | 2 to 8 weeks | PBS or Tris | 4 to 12 months | 30 | 50 | 4 to 12 months | PBS or Tris |
| 12 | 30 | 30 | 2 to 8 weeks | PBS | At least 6 months | 30 | N/A[1] | N/A | PBS |
| 13 | 30 | 30 | ~21 days | PBS | At least 2 months | 30 | N/A[1] | N/A | PBS |
| 14 | 30 | 30 | ~21 days | PBS | At least 3 months | 30 | N/A[1] | N/A | PBS |
| 15 | 30 | 30 | ~21 days | PBS | 6 to 12 months | 30 | N/A[1] | N/A | PBS |
| 16 | 30 | 30 | ~21 days | PBS | At least 6 months | 30 | N/A[1] | N/A | PBS |
| 17 | 30 | 30 | 21 days | PBS | At least 6 months | 15 | 15 | ~21 days | PBS |
| 18 | 30 | 30 | 21 days | PBS | At least 6 months | 15 | 15 | ~21 days | PBS |
| 19 | 30 | 30 | 2 to 8 weeks | PBS | At least 2 months | 30 | N/A[1] | N/A | Tris |
| 20 | 30 | 30 | 2 to 8 weeks | PBS | At least 3 months | 30 | N/A[1] | N/A | Tris |
| 21 | 30 | 30 | 2 to 8 weeks | PBS | 6 to 12 months | 30 | N/A[1] | N/A | Tris |
| 22 | 30 | 30 | 2 to 8 weeks | PBS | At least 6 months | 30 | N/A[1] | N/A | Tris |
| 23 | 30 | 30 | ~21 days | PBS | At least 2 months | 30 | N/A[1] | N/A | Tris |
| 24 | 30 | 30 | ~21 days | PBS | At least 3 months | 30 | N/A[1] | N/A | Tris |
| 25 | 30 | 30 | ~21 days | PBS | 6 to 12 months | 30 | N/A[1] | N/A | Tris |
| 26 | 30 | 30 | ~21 days | PBS | At least 6 months | 30 | N/A[1] | N/A | Tris |
| 27 | 30 | 30 | 21 days | PBS | At least 6 months | 15 | 15 | ~21 days | Tris |
| 28 | 30 | 30 | 21 days | PBS | At least 6 months | 15 | 15 | ~21 days | Tris |
| 29 | 30 | 30 | 2 to 8 weeks | Tris | At least 2 months | 30 | N/A[1] | N/A | Tris |
| 30 | 30 | 30 | 2 to 8 weeks | Tris | At least 3 months | 30 | N/A[1] | N/A | Tris |
| 31 | 30 | 30 | 2 to 8 weeks | Tris | 6 to 12 months | 30 | N/A[1] | N/A | Tris |
| 32 | 30 | 30 | 2 to 8 weeks | Tris | At least 6 months | 30 | N/A[1] | N/A | Tris |
| 33 | 30 | 30 | ~21 days | Tris | At least 2 months | 30 | N/A[1] | N/A | Tris |
| 34 | 30 | 30 | ~21 days | Tris | At least 3 months | 30 | N/A[1] | N/A | Tris |
| 35 | 30 | 30 | ~21 days | Tris | 6 to 12 months | 30 | N/A[1] | N/A | Tris |
| 36 | 30 | 30 | ~21 days | Tris | At least 6 months | 30 | N/A[1] | N/A | Tris |
| 37 | 30 | 30 | 21 days | Tris | At least 6 months | 15 | 15 | ~21 days | Tris |
| 38 | 30 | 30 | 21 days | Tris | At least 6 months | 15 | 15 | ~21 days | Tris |
| 39 | 10 | 10 | 2 to 8 weeks | Tris | At least 2 months | 10 | N/A[1] | N/A | Tris |
| 40 | 10 | 10 | 2 to 8 weeks | Tris | At least 3 months | 10 | N/A[1] | N/A | Tris |
| 41 | 10 | 10 | 2 to 8 weeks | Tris | 6 to 12 months | 10 | N/A[1] | N/A | Tris |
| 42 | 10 | 10 | 2 to 8 weeks | Tris | At least 6 months | 10 | N/A[1] | N/A | Tris |
| 43 | 10 | 10 | ~21 days | Tris | At least 2 months | 10 | N/A[1] | N/A | Tris |
| 44 | 10 | 10 | ~21 days | Tris | At least 3 months | 10 | N/A[1] | N/A | Tris |
| 45 | 10 | 10 | ~21 days | Tris | 6 to 12 months | 10 | N/A[1] | N/A | Tris |
| 46 | 10 | 10 | ~21 days | Tris | At least 6 months | 10 | N/A[1] | N/A | Tris |
| 47 | 3 | 3 | 2 to 8 weeks | Tris | At least 2 months | 3 | N/A[1] | N/A | Tris |
| 48 | 3 | 3 | 2 to 8 weeks | Tris | At least 3 months | 3 | N/A[1] | N/A | Tris |
| 49 | 3 | 3 | 2 to 8 weeks | Tris | 6 to 12 months | 3 | N/A[1] | N/A | Tris |
| 50 | 3 | 3 | 2 to 8 weeks | Tris | At least 6 months | 3 | N/A[1] | N/A | Tris |
| 51 | 3 | 3 | ~21 days | Tris | At least 2 months | 3 | N/A[1] | N/A | Tris |
| 52 | 3 | 3 | ~21 days | Tris | At least 3 months | 3 | N/A[1] | N/A | Tris |
| 53 | 3 | 3 | ~21 days | Tris | 6 to 12 months | 3 | N/A[1] | N/A | Tris |
| 54 | 3 | 3 | ~21 days | Tris | At least 6 months | 3 | N/A[1] | N/A | Tris |

[1]N/A refers to no dose necessary.

In some embodiments of certain exemplary dosing regimens as described in Table C above, an RNA composition described herein (e.g., comprising RNA encoding a variant described herein) is given in a first dose of a primary regimen. In some embodiments of certain exemplary dosing regimens as described in Table C above, an RNA composition described herein (e.g., comprising RNA encoding a variant described herein) is given in a second dose of a primary regimen. In some embodiments of certain exemplary dosing regimens as described in Table C above, an RNA composition described herein (e.g., comprising RNA encoding a variant described herein) is given in a first dose and a second dose of a primary regimen. In some embodiments of certain exemplary dosing regimens as described in Table C above, an RNA composition described herein (e.g., comprising RNA encoding a variant described herein) is given in a first dose of a booster regimen. In some embodiments of certain exemplary dosing regimens as described in Table C above, an RNA composition described herein (e.g., comprising RNA encoding a variant described herein) is given in a second dose of a booster regimen. In some embodiments of certain exemplary dosing regimens as described in Table C above, an RNA composition described herein (e.g., comprising RNA encoding a variant described herein) is given in a first dose and a second dose of a booster regimen. In some embodiments of certain exemplary dosing regimens as described in Table C above, an RNA composition described herein (e.g., comprising RNA encoding a variant described herein) is given in a first dose and a second dose of a primary regimen and also in at least one dose of a booster regimen. In some embodiments of certain exemplary dosing regimens as described in Table C above, an RNA composition described herein (e.g., comprising RNA encoding a variant described herein) is given in at least one dose (including, e.g., at least two doses) of a booster regimen and BNT162b2 is given in a primary regimen. In some embodiments of certain exemplary dosing regimens as described in Table C above, an RNA composition described herein (e.g., comprising RNA encoding a variant described herein) is given in a second dose of a booster regimen and BNT162b2 is given in a primary regimen and in a first dose of a booster regimen. In some embodiments, an RNA composition described herein (e.g., comprising RNA encoding a variant described herein) comprises an RNA encoding a polypeptide as set forth in SEQ ID NO: 49 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 49). In some embodiments, an RNA composition described herein (e.g., comprising RNA encoding a variant described herein) comprises an RNA that includes the sequence of SEQ ID NO: 50 or a variant thereof (e.g., having at least 70% or more, including, e.g., at least 80%, at least 85%, at least 90%, at least 95%, at least 96%, at least 97%, at least 98%, or higher, identity to SEQ ID NO: 50). In some embodiments, an RNA composition described herein (e.g., comprising RNA encoding a variant described herein) comprises an RNA that includes the sequence of SEQ ID NO: 51 or a variant thereof (e.g., having at least 70% or more, including, e.g., at least 80%, at least 85%, at least 90%, at least 95%, at least 96%, at least 97%, at least 98%, or higher, identity to SEQ ID NO: 51).

In some embodiments, an RNA composition described herein comprises an RNA encoding a polypeptide as set forth in SEQ ID NO: 55 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 55). In some embodiments, an RNA composition comprises an RNA that includes the sequence of SEQ ID NO: 56 or a variant thereof (e.g., having at least 70% or more, including, e.g., at least 80%, at least 85%, at least 90%, at least 95%, at least 96%, at least 97%, at least 98%, or higher, identity to SEQ ID NO: 56). In some embodiments, an RNA composition comprises an RNA that includes the sequence of SEQ ID NO: 57 or a variant thereof (e.g., having at least 70% or more, including, e.g., at least 80%, at least 85%, at least 90%, at least 95%, at least 96%, at least 97%, at least 98%, or higher, identity to SEQ ID NO: 57).

In some embodiments, an RNA composition described herein comprises an RNA encoding a polypeptide as set forth in SEQ ID NO: 58 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 58). In some embodiments, an RNA composition comprises an RNA that includes the sequence of SEQ ID NO: 59 or a variant thereof (e.g., having at least 70% or more, including, e.g., at least 80%, at least 85%, at least 90%, at least 95%, at least 96%, at least 97%, at least 98%, or higher, identity to SEQ ID NO: 59). In some embodiments, an RNA composition comprises an RNA that includes the sequence of SEQ ID NO: 60 or a variant thereof (e.g., having at least 70% or more, including, e.g., at least 80%, at least 85%, at least 90%, at least 95%, at least 96%, at least 97%, at least 98%, or higher, identity to SEQ ID NO: 60).

In some embodiments, an RNA composition described herein comprises an RNA encoding a polypeptide as set forth in SEQ ID NO: 61 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 61). In some embodiments, an RNA composition comprises an RNA that includes the sequence of SEQ ID NO: 62a or a variant thereof (e.g., having at least 70% or more, including, e.g., at least 80%, at least 85%, at least 90%, at least 95%, at least 96%, at least 97%, at least 98%, or higher, identity to SEQ ID NO: 62a). In some embodiments, an RNA composition comprises an RNA that includes the sequence of SEQ ID NO: 63a or a variant thereof (e.g., having at least 70% or more, including, e.g., at least 80%, at least 85%, at least 90%, at least 95%, at least 96%, at least 97%, at least 98%, or higher, identity to SEQ ID NO: 63a).

In some embodiments, such an RNA composition described herein (e.g., comprising RNA encoding a variant described herein) can further comprise RNA encoding a S protein or an immunogenic fragment thereof of a different strain (e.g., a Wuhan strain). By way of example, in some embodiments, a second dose of a booster regimen of Regimens #9-11 as described in Table C above can comprise an RNA composition described herein (e.g., comprising RNA encoding a variant described herein such as Omicron, for example, in one embodiment RNA as described in this Example) and a BNT162b2 construct, for example, in 1: 1 weight ratio.

In some embodiments of Regimen #6 as described in Table C above, a first dose and a second dose of a primary regimen and a first dose and a second dose of a booster regimen each comprise an RNA composition described herein (e.g., comprising RNA encoding a variant described herein such as Omicron, for example, in one embodiment RNA as described in this Example). In some such embodiments, a second dose of a booster regimen may not be necessary.

In some embodiments of Regimen #6 as described in Table C above, a first dose and a second dose of a primary regimen and a first dose and a second dose of a booster regimen each comprise an RNA composition described herein (e.g., comprising RNA encoding a variant described herein such as Omicron, for example, in one embodiment RNA as described in this Example). In some such embodiments, a second dose of a booster regimen may not be necessary.

In some embodiments of Regimen #6 as described in Table C above, a first dose and a second dose of a primary regimen each comprise a BNT162b2 construct, and a first dose and a second dose of a booster regimen each comprise an RNA composition described herein (e.g., comprising RNA encoding a variant described herein such as Omicron, for example, in one embodiment RNA as described in this Example). In some such embodiments, a second dose of a booster regimen may not be necessary.

In some embodiments of Regimen #6 as described in Table C above, a first dose and a second dose of a primary regimen and a first dose of a booster regimen each comprise a BNT162b2 construct, and a second dose of a booster regimen comprises an RNA composition described herein (e.g., comprising RNA encoding a variant described herein such as Omicron, for example, in one embodiment RNA as described in this Example).

Certain exemplary embodiments below are also within the scope of the present disclosure:

1. A composition or medical preparation comprising RNA comprising a nucleotide sequence encoding a SARS-CoV-2 S protein comprising one or more mutations characteristic of a SARS-CoV-2 variant (e.g., in some embodiments a SARS-CoV-2 Omicron variant), or an immunogenic fragment thereof.

2. The composition or medical preparation of embodiment 1, wherein the immunogenic fragment of the SARS-CoV-2 S protein comprises the S1 subunit of the SARS-CoV-2 S protein, or the receptor binding domain (RBD) of the S1 subunit of the SARS-CoV-2 S protein.

3. The composition or medical preparation of embodiment 1 or 2, wherein the SARS-CoV-2 S protein or immunogenic fragment thereof comprises one or more mutations characteristic of a BA.1, BA.2, BA.4/5, XBB, XBB.1, BQ.1.1, or a BA.4.6/BF.7 Omicron variant or sublineages thereof.

4. The composition or medical preparation of embodiment 3, wherein the SARS-CoV-2 S protein or immunogenic fragment thereof comprises one or more mutations characteristic of a BA.4/5 variant, wherein the one or more mutations are selected from the group consisting of T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, and N969K.

5. The composition or medical preparation of embodiment 3, wherein the SARS-CoV-2 S protein or immunogenic fragment thereof comprises one or more mutations characteristic of a BA.1 variant, wherein the one or more mutations are selected from the group consisting of A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F.

6. The composition or medical preparation of embodiment 3, wherein the SARS-CoV-2 S protein or immunogenic fragment thereof comprises one or more mutations characteristic of a BA.2 variant, wherein the one or more mutations are selected from the group consisting of T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, and N969K.

7. The composition or medical preparation of embodiment 3, wherein the SARS-CoV-2 S protein or immunogenic fragment thereof comprises one or more mutations characteristic of a BA.2.75.1 variant, wherein the one or more mutations are selected from the group consisting of T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, and N969K.

8. The composition or medical preparation of embodiment 3, wherein the SARS-CoV-2 S protein or immunogenic fragment thereof comprises one or more mutations characteristic of a BA.4.6/BF.7 variant, wherein the one or more mutations are selected from the group consisting of T19I, Δ24-26, Δ275, Δ69/70, G142D, V213G, G339D, R346T, S371F, S373P, S375F, T376A, D405N, R408S, K417N, N440K, L452R, S477N, T478K, E484A, F486V, Q498R, N501Y, Y505H, D614G, H655Y, N658S, N679K, P681H, N764K, D796Y, Q954H, and N969K.

9. The composition or medical preparation of embodiment 3, wherein the SARS-CoV-2 S protein or immunogenic fragment thereof comprises one or more mutations characteristic of an XBB variant, wherein the one or more mutations are selected from the group consisting of T19I, Δ24-26, A27S, V83A, G142D, Δ144, H146Q, Q183E, V213E, G339H, R346T, L368I, S371F, S373P, S375F, T376A, D405N, R408S, K417N, N440K, V445P, G446S, N460K, S477N, T478K, E484A, F486S, F490S, Q493R, Q498R, N501Y, Y505H, D614G, H655Y, N679K, P681H, N764K, D796Y, Q954H, and N969K.

10. The composition or medical preparation of embodiment 3, wherein the SARS-CoV-2 S protein or immunogenic fragment thereof comprises one or more mutations characteristic of an XBB.1 variant, wherein the one or more mutations are selected from the group consisting of T19I, Δ24-26, A27S, V83A, G142D, Δ144, H146Q, Q183E, V213E, G252V, G339H, R346T, L368I, S371F, S373P, S375F, T376A, D405N, R408S, K417N, N440K, V445P, G446S, N460K, S477N, T478K, E484A, F486S, F490S, Q493R, Q498R, N501Y, Y505H, D614G, H655Y, N679K, P681H, N764K, D796Y, Q954H, and N969K.

11. The composition or medical preparation of embodiment 3, wherein the SARS-CoV-2 S protein or immunogenic fragment thereof comprises one or more mutations characteristic of a BQ.1.1 variant, wherein the one or more mutations are selected from the group consisting of T19I, Δ24-26, A27S, Δ69/70, G142D, V213G, G339D, R346T, S371F, S373P, S375F, T376A, D405N, R408S, K417N, N440K, K444T, L452R, N460K, S477N, T478K, E484A, F486V, Q498R, N501Y, Y505H, D614G, H655Y, N679K, P681H, N764K, D796Y, Q954H, N969K.

12. The composition or medical preparation of any one of embodiments 1-11, wherein the SARS-CoV-2 S protein comprising one or more mutations characteristic of an Omicron variant, or an immunogenic fragment thereof is encoded by a sequence that is codon-optimized (e.g., codon-optimized for expression in human cells) and/or which has a G/C content that is increased compared to a wild type coding sequence.

13. The composition or medical preparation of embodiment 3 or 4, wherein the SARS-CoV-2 S protein comprises one or more mutations characteristic of an Omicron BA.4/5 variant and wherein:

a) the SARS-CoV-2 S protein comprises an amino acid sequence having at least 99%, 98%, 97%, 96%, 95%, 90%, 85%, or 80% identity to SEQ ID NO: 69, or an immunogenic fragment thereof; and/or b) the RNA encoding the SARS-CoV-2 S protein comprises a nucleotide sequence having at least 99%, 98%, 97%, 96%, 95%, 90%, 85%, or 80% identity to SEQ ID NO: 70; and/or at least 99%, 98%, 97%, 96%, 95%, 90%, 85%, or 80% identity to SEQ ID NO: 71.

14. The composition or medical preparation of embodiment 3 or 5, wherein the SARS-CoV-2 S protein comprises one or more mutations characteristic of an Omicron BA.1 variant and wherein:

a) the SARS-CoV-2 S protein comprises an amino acid sequence having at least 99%, 98%, 97%, 96%, 95%, 90%, 85%, or 80% identity to SEQ ID NO: 49, or an immunogenic fragment thereof; and/or
b) the RNA encoding the SARS-CoV-2 S protein comprises a nucleotide sequence having at least 99%, 98%, 97%, 96%, 95%, 90%, 85%, or 80% identity to SEQ ID NO: 50 and/or at least 99%, 98%, 97%, 96%, 95%, 90%, 85%, or 80% identity to SEQ ID NO: 51.

15. The composition or medical preparation of embodiment 3 or 6, wherein the SARS-CoV-2 S protein comprises one or more mutations characteristic of an Omicron BA.2 variant and wherein:
a) the SARS-CoV-2 S protein comprises an amino acid sequence having at least 99%, 98%, 97%, 96%, 95%, 90%, 85%, or 80% identity to SEQ ID NO: 64, or an immunogenic fragment thereof; and/or
b) the RNA encoding the SARS-CoV-2 S protein comprises a nucleotide sequence having at least 99%, 98%, 97%, 96%, 95%, 90%, 85%, or 80% identity to SEQ ID NO: 65 and/or at least 99%, 98%, 97%, 96%, 95%, 90%, 85%, or 80% identity to SEQ ID NO: 66.

16. The composition or medical preparation of embodiment 3 or 7, wherein the SARS-CoV-2 S protein comprises one or more mutations characteristic of an Omicron BA.2.75.1 variant and wherein:
a) the SARS-CoV-2 S protein comprises an amino acid sequence having at least 99%, 98%, 97%, 96%, 95%, 90%, 85%, or 80% identity to SEQ ID NO: 80, or an immunogenic fragment thereof; and/or
b) the RNA encoding the SARS-CoV-2 S protein comprises a nucleotide sequence having at least 99%, 98%, 97%, 96%, 95%, 90%, 85%, or 80% identity to SEQ ID NO: 81 and/or at least 99%, 98%, 97%, 96%, 95%, 90%, 85%, or 80% identity to SEQ ID NO: 83.

17. The composition or medical preparation of embodiment 3 or 8, wherein the SARS-CoV-2 S protein comprises one or more mutations characteristic of an Omicron BA.4.6/BF.7 variant and wherein:
a) the SARS-CoV-2 S protein comprises an amino acid sequence having at least 99%, 98%, 97%, 96%, 95%, 90%, 85%, or 80% identity to SEQ ID NO: 90, or an immunogenic fragment thereof; and/or
b) the RNA encoding the SARS-CoV-2 S protein comprises a nucleotide sequence having at least 99%, 98%, 97%, 96%, 95%, 90%, 85%, or 80% identity to SEQ ID NO: 91 and/or at least 99%, 98%, 97%, 96%, 95%, 90%, 85%, or 80% identity to SEQ ID NO: 92.

18. The composition or medical preparation of embodiment 3 or 9, wherein the SARS-CoV-2 S protein comprises one or more mutations characteristic of an Omicron XBB variant and wherein:
a) the SARS-CoV-2 S protein comprises an amino acid sequence having at least 99%, 98%, 97%, 96%, 95%, 90%, 85%, or 80% identity to SEQ ID NO: 95, or an immunogenic fragment thereof; and/or
b) the RNA encoding the SARS-CoV-2 S protein comprises a nucleotide sequence having at least 99%, 98%, 97%, 96%, 95%, 90%, 85%, or 80% identity to SEQ ID NO: 96; and/or at least 99%, 98%, 97%, 96%, 95%, 96%, 85%, or 80% identity to SEQ ID NO: 98.

19. The composition or medical preparation of embodiment 3 or 11, wherein the SARS-CoV-2 S protein comprises one or more mutations characteristic of an Omicron BQ.1.1 variant and wherein:
a) the SARS-CoV-2 S protein comprises an amino acid sequence having at least 99%, 98%, 97%, 96%, 95%, 90%, 85%, or 80% identity to SEQ ID NO: 100, or an immunogenic fragment thereof; and/or
b) the RNA encoding the SARS-CoV-2 S protein comprises a nucleotide sequence having at least 99%, 98%, 97%, 96%, 95%, 90%, 85%, or 80% identity to SEQ ID NO: 101 and/or at least 99%, 98%, 97%, 96%, 95%, 90%, 85%, or 80% identity to SEQ ID NO: 102.

20. The composition or medical preparation of any one of embodiments 1-19, wherein the SARS-CoV-2 S protein comprises one or more mutations that improves expression, stability, and/or immunogenicity.

21. The composition or medical preparation of embodiment 20, wherein the SARS-CoV-2 S protein comprises one or more mutations that stabilizes the prefusion conformation.

22. The composition or medical preparation of embodiment 20, wherein the SARS-CoV-2 S protein comprises proline mutations at positions corresponding to residues 986 and 987 of SEQ ID NO: 1.

23. The composition or medical preparation of embodiment 21 or 22, wherein the SARS-CoV-2 S protein comprises one or more proline residues at positions corresponding to positions 817, 892, 899, and/or 942 of SEQ ID NO: 1.

24. The composition or medical preparation of any one of embodiments 20-23, wherein the SARS-CoV-2 S protein comprises a mutation that prevents furin cleavage.

25. The composition or medical preparation of embodiment 24, wherein the SARS-CoV-2 S protein comprises a mutation at a location corresponding to residues 682-685 of SEQ ID NO: 1 that prevents cleavage by a furin protease (e.g., a GSAS mutation).

26. The composition or medical preparation of any one of embodiments 20-25, wherein the SARS-CoV-2 S protein comprises one or more mutations that decreases S protein shedding (e.g., an aspartate to glycine mutation at a position corresponding to residue 614 of SEQ ID NO: 1).

27. The composition or medical preparation of any one of embodiments 1-26, wherein the RNA comprises a modified nucleoside in place of uridine.

28. The composition or medical preparation of embodiment 27, wherein the RNA comprises a modified nucleoside in place of each uridine.

29. The composition or medical preparation of embodiment 27 or 28, wherein the modified nucleoside is selected from pseudouridine (ψ), N1-methyl-pseudouridine (m1ψ), and 5-methyl-uridine (m5U).

30. The composition or medical preparation of embodiment 29, wherein the modified nucleoside is N1-methyl-pseudouridine (m1ψ).

31. The composition or medical preparation of any one of embodiments 1-30, wherein the RNA comprises a 5' cap.

32. The composition or medical preparation of embodiment 31, wherein the 5' cap is or comprises a cap1 structure.

33. The composition or medical preparation of embodiment 32, wherein the RNA comprises a 5'-cap that is or comprises $m_2^{7,3'-O}Gppp(m_1^{2'-O})ApG$.

34. The composition or medical preparation of any one of embodiments 1-33, wherein the composition comprises a poly(A) sequence.

35. The composition or medical preparation of embodiment 34, wherein the poly(A) sequence comprises at least 100 A nucleotides.

36. The composition or medical preparation of embodiment 34 or 35, wherein the poly(A) sequence is an interrupted sequence of A nucleotides.

37. The composition or medical preparation of embodiment 36, wherein the poly(A) sequence comprises 30 adenine nucleotides followed by 70 adenine nucleotides, wherein the 30 adenine nucleotides and 70 adenine nucleotides are separated by a linker sequence.

38. The composition or medical preparation of embodiment 37, wherein the poly(A) sequence comprises or consists of the nucleotide sequence of SEQ ID NO: 14, or a nucleotide sequence that is at least 99%, 98%, 97%, 96%, 95%, 90%, 85%, or 80% identical to the nucleotide sequence of SEQ ID NO: 14.

39. The composition or medical preparation of any one of embodiments 1-38, wherein the RNA comprises a 5'-UTR that is or comprises a modified human alpha-globin 5'-UTR.

40. The composition or medical preparation of embodiment 39, wherein the 5' UTR comprises the nucleotide sequence of SEQ ID NO: 12, or a nucleotide sequence that is at least 99%, 98%, 97%, 96%, 95%, 90%, 85%, or 80% identical to the nucleotide sequence of SEQ ID NO: 12.

41. The composition or medical preparation of any one of embodiments 1-40, wherein the RNA comprises a 3'-UTR that is or comprises a first sequence from the amino terminal enhancer of split (AES) messenger RNA and a second sequence from the mitochondrial encoded 125 ribosomal RNA.

42. The composition or medical preparation of embodiment 41, wherein the RNA comprises a 3' UTR comprising the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

43. The composition or medical preparation of any one of embodiments 1-42, wherein the RNA is formulated or is to be formulated as particles.

44. The composition or medical preparation of embodiment 43, wherein the particles are lipid nanoparticles (LNP) or lipoplex (LPX) particles.

45. The composition or medical preparation of embodiment 44, wherein the LNPs comprise a cationically ionizable lipid, a neutral lipid, a sterol and a polymer-lipid conjugate.

46. The composition or medical preparation of embodiment 45, wherein the neutral lipid is present in a concentration ranging from about 5 to about 15 mol percent of the total lipids.

47. The composition or medical preparation of embodiment 45 or 46, wherein the cationically ionizable lipid is present in a concentration ranging from about 40 to about 50 mol percent of the total lipids.

48. The composition or medical preparation of any one of embodiments 45-47, wherein the sterol is present in a concentration ranging from about 30 to about 50 mol percent of the total lipids.

49. The composition or medical preparation of any one of embodiments 45-48, wherein the polymer-lipid conjugate is present in a concentration ranging from about 1 to about 10 mol percent of the total lipids.

50. The composition or medical preparation of any one of embodiments 45-49, wherein the lipid nanoparticles comprise from about 40 to about 50 mol percent of the cationically ionizable lipid; from about 5 to about 15 mol percent of the neutral lipid; from about 35 to about 45 mol percent of the sterol; and from about 1 to about 10 mol percent of the polymer conjugated-lipid.

51. The composition or medical preparation of embodiment 44, wherein the RNA lipoplex particles are obtainable by mixing the RNA with liposomes.

52. A composition or medical preparation comprising: a lipid nanoparticle (LNP) comprising an RNA, wherein the RNA comprises a nucleotide sequence that (a) encodes a SARS-CoV-2 S protein comprising one or more mutations characteristic of an Omicron BA.1 variant and comprising an amino acid sequence of SEQ ID NO: 49 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 49 and/or (b) comprises the nucleotide sequence of SEQ ID NO: 50 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 50, and wherein the RNA comprises:

(a) modified uridines;

(b) a 5' cap; and wherein the LNP comprises a cationically ionizable lipid, a neutral lipid, a sterol and a polymer-lipid conjugate.

53. The composition or medical preparation of embodiment 52, wherein the nucleotide sequence includes modified uridines in place of all uridines.

54. The composition or medical preparation of embodiment 52 or 53, wherein the modified uridines are each N1-methyl-pseudouridine.

55. The composition or medical preparation of any one of embodiments 52-54, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

56. The composition or medical preparation of embodiment 55, wherein the poly-A sequence comprises 30 adenine nucleotides followed by 70 adenine nucleotides, wherein the 30 adenine nucleotides and 70 adenine nucleotides are separated by a linker sequence.

57. The composition or medical preparation of embodiment 56, wherein the poly-A sequence comprises SEQ ID NO: 14.

58. The composition or medical preparation of any one of embodiments 52-57, wherein the RNA comprises SEQ ID NO: 51.

59. A composition or medical preparation comprising a lipid nanoparticle (LNP) comprising an RNA, wherein the RNA comprises a nucleotide sequence (a) that encodes a SARS-CoV-2 S protein comprising one or more mutations characteristic of a Beta variant and comprising the amino acid sequence of SEQ ID NO: 55 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 55 and/or (b) comprises the nucleotide sequence of SEQ ID NO: 56 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 56, and wherein the RNA comprises:

(a) modified uridines;

(b) a 5' cap; and wherein the LNP comprises a cationically ionizable lipid, a neutral lipid, a sterol and a polymer-lipid conjugate.

60. The composition or medical preparation of embodiment 59, wherein the nucleotide sequence includes modified uridines in place of all uridines.

61. The composition or medical preparation of embodiment 59 or 60, wherein the modified uridines are each N1-methyl-pseudouridine.

62. The composition or medical preparation of any one of embodiments 59 to 61, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

63. The composition or medical preparation of embodiment 62, wherein the poly-A sequence comprises 30 adenine nucleotides followed by 70 adenine nucleotides, wherein the 30 adenine nucleotides and 70 adenine nucleotides are separated by a linker sequence.

64. The composition or medical preparation of embodiment 63, wherein the poly-A sequence comprises SEQ ID NO: 14.

65. The composition or medical preparation of any one of embodiments 59-64, wherein the RNA comprises SEQ ID NO: 57.

66. A composition or medical preparation comprising a a lipid nanoparticle (LNP) comprising an RNA, wherein the RNA comprises a nucleotide sequence that (a) encodes a SARS-CoV-2 S protein comprising one or more mutations characteristic of an Alpha variant and comprising the polypeptide of SEQ ID NO: 58 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 58 and/or (b) comprises the nucleotide sequence of SEQ ID NO: 59 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 59, and wherein the RNA comprises:

(a) modified uridines;

(b) a 5' cap; and wherein the LNP comprises a cationically ionizable lipid, a neutral lipid, a sterol and a polymer-lipid conjugate.

67. The composition or medical preparation of embodiment 66, wherein the nucleotide sequence includes modified uridines in place of all uridines.

68. The composition or medical preparation of embodiment 66 or 67, wherein the modified uridines are each N1-methyl-pseudouridine.

69. The composition or medical preparation of any one of embodiments 66-68, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

70. The composition or medical preparation of embodiment 69, wherein the poly-A sequence comprises 30 adenine nucleotides followed by 70 adenine nucleotides, wherein the 30 adenine nucleotides and 70 adenine nucleotides are separated by a linker sequence.

71. The composition or medical preparation of embodiment 70, wherein the poly-A sequence comprises SEQ ID NO: 14.

72. The composition or medical preparation of any one of embodiments 66-71, wherein the RNA comprises SEQ ID NO: 60.

73. A composition or medical preparation comprising a lipid nanoparticle (LNP) comprising an RNA, wherein the RNA comprises a nucleotide sequence that (a) encodes a SARS-CoV-2 S protein comprising one or more mutations characteristic of a Delta variant and comprises an amino acid sequence of SEQ ID NO: 61 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 61 and/or (b) comprises the nucleotide sequence of SEQ ID NO: 62a or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 62a, and wherein the RNA comprises:

(a) modified uridines;

(b) a 5' cap; and wherein the LNP comprises a cationically ionizable lipid, a neutral lipid, a sterol and a polymer-lipid conjugate.

74. The composition or medical preparation of embodiment 73, wherein the nucleotide sequence includes modified uridines in place of all uridines.

75. The composition or medical preparation of embodiment 73 or 74, wherein the modified uridines are each N1-methyl-pseudouridine.

76. The composition or medical preparation of any one of embodiments 73-75, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

77. The composition or medical preparation of embodiment 76, wherein the poly-A sequence comprises 30 adenine nucleotides followed by 70 adenine nucleotides, wherein the 30 adenine nucleotides and 70 adenine nucleotides are separated by a linker sequence.

78. The composition or medical preparation of embodiment 77, wherein the poly-A sequence comprises SEQ ID NO: 14.

79. The composition or medical preparation of any one of embodiments 73-78, wherein the RNA comprises SEQ ID NO: 63a.

80. A composition or medical preparation comprising a lipid nanoparticle (LNP) comprising an RNA, wherein the RNA comprises a nucleotide sequence that (a) encodes a SARS-CoV-2 S protein comprising one or more mutations characteristic of a BA.2 Omicron variant and encodes a polypeptide comprising an amino acid sequence of SEQ ID NO: 64 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 64 and/or (b) comprises the nucleotide sequence of SEQ ID NO: 65 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 65, and wherein the RNA comprises:

(a) modified uridines;

(b) a 5' cap; and wherein the LNP comprises a cationically ionizable lipid, a neutral lipid, a sterol and a polymer-lipid conjugate.

81. The composition or medical preparation of embodiment 80, wherein the nucleotide sequence includes modified uridines in place of all uridines.

82. The composition or medical preparation of embodiment 80 or 81, wherein the modified uridines are each N1-methyl-pseudouridine.

83. The composition or medical preparation of any one of embodiments 80-82, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

84. The composition or medical preparation of embodiment 83, wherein the poly-A sequence comprises 30 adenine nucleotides followed by 70 adenine nucleotides, wherein the 30 adenine nucleotides and 70 adenine nucleotides are separated by a linker sequence.

85. The composition or medical preparation of embodiment 84, wherein the poly-A sequence comprises SEQ ID NO: 14.

86. The composition or medical preparation of any one of embodiments 80-85, wherein the RNA comprises SEQ ID NO: 67.

87. A composition or medical preparation comprising a lipid nanoparticle (LNP) comprising an RNA, wherein the RNA comprises a nucleotide sequence that (a) encodes a SARS-CoV-2 S protein that comprises one or more mutations characteristic of a BA.2.75 Omicron variant and comprises an amino acid sequence of SEQ ID NO 80 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 80 and/or (b) comprises the nucleotide sequence of SEQ ID NO: 81 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 81, and wherein the RNA comprises:

(a) modified uridines;

(b) a 5' cap; and wherein the LNP comprises a cationically ionizable lipid, a neutral lipid, a sterol and a polymer-lipid conjugate.

88. The composition or medical preparation of embodiment 87, wherein the nucleotide sequence includes modified uridines in place of all uridines.

89. The composition or medical preparation of embodiment 87 or 88, wherein the modified uridines are each N1-methyl-pseudouridine.

90. The composition or medical preparation of any one of embodiments 87-89, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

91. The composition or medical preparation of embodiment 90, wherein the poly-A sequence comprises 30 adenine nucleotides followed by 70 adenine nucleotides, wherein the 30 adenine nucleotides and 70 adenine nucleotides are separated by a linker sequence.

92. The composition or medical preparation of embodiment 91, wherein the poly-A sequence comprises SEQ ID NO: 14.

93. The composition or medical preparation of any one of embodiments 90-92, wherein the RNA comprises SEQ ID NO: 83.

94. A composition or medical preparation comprising a lipid nanoparticle (LNP) comprising an RNA, wherein the RNA comprises a nucleotide sequence that encodes a SARS-CoV-2 S protein comprising one or more mutations characteristic of a BA.2.75.2 Omicron variant and comprises an amino acid sequence of SEQ ID NO 85 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 85 and/or (b) comprises the nucleotide sequence of 86 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 86, and wherein the RNA comprises:

(a) modified uridines;

(b) a 5' cap; and wherein the LNP comprises a cationically ionizable lipid, a neutral lipid, a sterol and a polymer-lipid conjugate.

95. The composition or medical preparation of embodiment 94, wherein the nucleotide sequence includes modified uridines in place of all uridines.

96. The composition or medical preparation of embodiment 94 or 95, wherein the modified uridines are each N1-methyl-pseudouridine.

97. The composition or medical preparation of any one of embodiments 94-96, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

98. The composition or medical preparation of embodiment 97, wherein the poly-A sequence comprises 30 adenine nucleotides followed by 70 adenine nucleotides, wherein the 30 adenine nucleotides and 70 adenine nucleotides are separated by a linker sequence.

99. The composition or medical preparation of embodiment 98, wherein the poly-A sequence comprises SEQ ID NO: 14.

100. The composition or medical preparation of any one of embodiments 94-99, wherein the RNA comprises SEQ ID NO: 88.

101. A composition or medical preparation comprising a lipid nanoparticle (LNP) comprising an RNA, wherein the RNA comprises a nucleotide sequence that (a) encodes a SARS-CoV-2 S protein comprising one or more mutations characteristic of an Omicron BA.4/5 variant and comprises an amino acid sequence of SEQ ID NO: 69 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 69 and/or (b) comprises the nucleotide sequence of SEQ ID NO: 70 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 70, and wherein the RNA comprises:

(a) modified uridines;

(b) a 5' cap; and wherein the LNP comprises a cationically ionizable lipid, a neutral lipid, a sterol and a polymer-lipid conjugate.

102. The composition or medical preparation of embodiment 101, wherein the nucleotide sequence includes modified uridines in place of all uridines.

103. The composition or medical preparation of embodiment 101 or 102, wherein the modified uridines are each N1-methyl-pseudouridine.

104. The composition or medical preparation of any one of embodiments 101-103, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

105. The composition or medical preparation of embodiment 104, wherein the poly-A sequence comprises 30 adenine nucleotides followed by 70 adenine nucleotides, wherein the 30 adenine nucleotides and 70 adenine nucleotides are separated by a linker sequence.

106. The composition or medical preparation of embodiment 105, wherein the poly-A sequence comprises SEQ ID NO: 14.

107. The composition or medical preparation of any one of embodiments 101-106, wherein the RNA comprises SEQ ID NO: 72.

108. A composition or medical preparation comprising a lipid nanoparticle (LNP) comprising an RNA, wherein the RNA comprises a nucleotide sequence that (a) encodes a SARS-CoV-2 S protein comprising one or more mutations that are characteristic of an Omicron BA.4.6/BF.7 variant and comprising an amino acid sequence of SEQ ID NO: 90 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 90 and (b) comprises the nucleotide sequence of SEQ ID NO: 91 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 91, and wherein the RNA comprises:

(a) modified uridines;

(b) a 5' cap; and wherein the LNP comprises a cationically ionizable lipid, a neutral lipid, a sterol and a polymer-lipid conjugate.

109. The composition or medical preparation of embodiment 108, wherein the nucleotide sequence includes modified uridines in place of all uridines.

110. The composition or medical preparation of embodiment 108 or 109, wherein the modified uridines are each N1-methyl-pseudouridine.

111. The composition or medical preparation of any one of embodiments 108-110, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

112. The composition or medical preparation of embodiment 111, wherein the poly-A sequence comprises 30 adenine nucleotides followed by 70 adenine nucleotides, wherein the 30 adenine nucleotides and 70 adenine nucleotides are separated by a linker sequence.

113. The composition or medical preparation of embodiment 112, wherein the poly-A sequence comprises SEQ ID NO: 14.

114. The composition or medical preparation of any one of embodiments 108-112, wherein the RNA comprises SEQ ID NO: 93.

115. A composition or medical preparation comprising a lipid nanoparticle (LNP) comprising an RNA, wherein the RNA comprises a nucleotide sequence that (a) encodes a SARS-CoV-2 S protein comprising one or more mutations characteristic of an XBB Omicron variant and comprises an amino acid sequence of SEQ ID NO 85 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 95 and/or (b) comprises the nucleotide sequence of SEQ ID NO: 96 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 96, and wherein the RNA comprises:

(a) modified uridines;

(b) a 5' cap; and wherein the LNP comprises a cationically ionizable lipid, a neutral lipid, a sterol and a polymer-lipid conjugate.

116. The composition or medical preparation of embodiment 115, wherein the nucleotide sequence includes modified uridines in place of all uridines.

117. The composition or medical preparation of embodiment 115 or 116, wherein the modified uridines are each N1-methyl-pseudouridine.

118. The composition or medical preparation of any one of embodiments 115-117, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

119. The composition or medical preparation of embodiment 118, wherein the poly-A sequence comprises 30 adenine nucleotides followed by 70 adenine nucleotides, wherein the 30 adenine nucleotides and 70 adenine nucleotides are separated by a linker sequence.

120. The composition or medical preparation of embodiment 119, wherein the poly-A sequence comprises SEQ ID NO: 14.

121. The composition or medical preparation of any one of embodiments 115-120, wherein the RNA comprises SEQ ID NO: 98.

122. A composition or medical preparation comprising a lipid nanoparticle (LNP) comprising an RNA, wherein the RNA comprises a nucleotide sequence that (a) encodes a SARS-CoV-2 S protein comprising one or more mutations characteristic of a BQ.1.1 Omicron variant and comprising an amino acid sequence of SEQ ID NO 100 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 100 and/or (b) comprises a nucleotide sequence of SEQ ID NO: 101 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 101, and wherein the RNA comprises:

(a) modified uridines;

(b) a 5' cap; and wherein the LNP comprises a cationically ionizable lipid, a neutral lipid, a sterol and a polymer-lipid conjugate.

123. The composition or medical preparation of embodiment 122, wherein the nucleotide sequence includes modified uridines in place of all uridines.

124. The composition or medical preparation of embodiment 122 or 123, wherein the modified uridines are each N1-methyl-pseudouridine.

125. The composition or medical preparation of any one of embodiments 122-124, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

126. The composition or medical preparation of embodiment 125, wherein the poly-A sequence comprises 30 adenine nucleotides followed by 70 adenine nucleotides, wherein the 30 adenine nucleotides and 70 adenine nucleotides are separated by a linker sequence.

127. The composition or medical preparation of embodiment 126, wherein the poly-A sequence comprises SEQ ID NO: 14.

128. The composition or medical preparation of any one of embodiments 121-127, wherein the RNA comprises SEQ ID NO: 103.

129. The composition or medical preparation of any one of embodiments 1-128, wherein the RNA is present in an amount within a range of about 1 μg to about 100 μg per dose in the composition.

130. The composition or medical preparation of embodiment 129, wherein the RNA is present in an amount within a range of about 1 μg to about 60 μg per dose in the composition.

131. The composition or medical preparation of embodiment 130, wherein the RNA is present in an amount of about 1.5 μg, about 2.5 μg, about 3.0 μg, about 5.0 μg, about 10 μg, about 15 μg, about 30 μg, or about 60 μg per dose in the composition.

132. The composition or medical preparation of any one of embodiments 1-131, further comprising a second RNA comprising a nucleotide sequence encoding a SARS-CoV-2 S protein, or an immunogenic fragment thereof, wherein the SARS-CoV-2 S protein comprises one or more mutations that are characteristic of a second SARS-CoV-2 variant.

133. A composition or medical preparation comprising:

(a) a first RNA comprising a nucleotide sequence encoding a SARS-CoV-2 S protein of a first strain or variant, or an immunogenic fragment thereof; and (b) a second RNA comprising a nucleotide sequence encoding a SARS-CoV-2 S protein of a second variant, or an immunogenic fragment thereof, wherein the first variant is different from the second variant, and optionally wherein the first and/or second variant is an Omicron variant.

134. The composition or medical preparation of embodiment 133, wherein the first RNA comprises a nucleotide sequence that encodes a SARS-CoV-2 S protein of a Wuhan strain, or an immunogenic fragment thereof, and the second RNA comprises a nucleotide sequence that encodes a SARS-CoV-2 S protein comprising one or more mutations that are characteristic of an Omicron variant, or an immunogenic fragment thereof.

135. The composition or medical preparation of embodiments 133 or 134, wherein the first RNA comprises a nucleotide sequence that encodes a SARS-CoV-2 S protein of a Wuhan strain, or an immunogenic fragment thereof, and the second RNA comprises a nucleotide sequence that encodes a SARS-CoV-2 S protein comprising one or more mutations that are characteristic of a BA.4/5, BA.1, BA.2, XBB, XBB.1, or BQ.1.1 Omicron variant, or sublineages thereof or an immunogenic fragment thereof.

136. The composition or medical preparation of embodiment 133, wherein the second RNA comprises a nucleotide sequence that encodes a SARS-CoV-2 S protein that is antigenically distinct from the S protein encoded by the first RNA, or an immunogenic fragment thereof.

137. A composition or medical preparation comprising (a) a first RNA comprising a nucleotide sequence encoding a SARS-CoV-2 S protein of a Wuhan strain, an Alpha variant, a Beta variant, a Delta variant, or a BA.1 Omicron variant, or an immunogenic fragment thereof and (b) a second RNA comprising a nucleotide sequence encoding a SARS-CoV-2 S protein comprising one or more mutations that are characteristic of an Omicron variant that is not a BA.1 Omicron variant, or an immunogenic fragment thereof.

138. The composition or medical preparation of any one of embodiments 133-137, wherein the second RNA comprises a nucleotide sequence that encodes a SARS-CoV-2 S protein comprising one or more mutations characteristic of a BA.4/5 Omicron variant, or a variant that has evolved from a BA.4/5 Omicron variant, or an immunogenic fragment thereof.

139. The composition or medical preparation of any one of embodiments 133-135, wherein the first RNA comprises a nucleotide sequence encoding a SARS-CoV-2 S protein of a Wuhan strain, or an immunogenic fragment thereof, and the second RNA comprises a nucleotide sequence that encodes a SARS-CoV-2 S protein comprising one or more mutations that are characteristic of a BA.1 Omicron variant, or an immunogenic fragment thereof.

140. The composition or medical preparation of any one of embodiments 133-138, wherein the first RNA comprises a nucleotide sequence that encodes a SARS-CoV-2 S protein of a Wuhan strain, or an immunogenic fragment thereof, and the second RNA comprises a nucleotide sequence that encodes a SARS-CoV-2 S protein comprising one or more mutations characteristic of a BA.2 Omicron variant, or an immunogenic fragment thereof.

141. The composition or medical preparation of any one of embodiments 133-138, wherein the first RNA comprises a nucleotide sequence that encodes a SARS-CoV-2 S protein of a Wuhan strain, or an immunogenic fragment thereof, and the second RNA comprises a nucleotide sequence that encodes a SARS-CoV-2 S protein comprising one or more mutations characteristic of a BA.4 or BA.5 Omicron variant, or an immunogenic fragment thereof.

142. The composition or medical preparation of any one of embodiments 133-138, wherein the first RNA comprises a nucleotide sequence encoding a SARS-CoV-2 S protein of a Wuhan strain, or an immunogenic fragment thereof, and the second RNA comprises a nucleotide sequence encoding a SARS-CoV-2 S protein comprising one or more mutations characteristic of a BA.2 Omicron variant, or an immunogenic fragment thereof.

143. The composition or medical preparation of any one of embodiments 133-138, wherein the first RNA comprises a nucleotide sequence encoding a SARS-CoV-2 S protein of a Wuhan strain, or an immunogenic fragment thereof, and the second RNA comprises a nucleotide sequence encoding a SARS-CoV-2 S protein comprising one or more mutations characteristic of a BA.4 or BA.5 Omicron variant, or an immunogenic fragment thereof.

144. The composition or medical preparation of any one of embodiments 133-143, wherein the first RNA comprises a nucleotide sequence encoding a SARS-CoV-2 S protein of a Wuhan strain, or an immunogenic fragment thereof, and the second RNA comprises a nucleotide sequence encoding a SARS-CoV-2 S protein comprising one or more mutations characteristic of an XBB Omicron variant, or an immunogenic fragment thereof.

145. The composition or medical preparation of any one of embodiments 133-138, wherein the first RNA comprises a nucleotide sequence encoding a SARS-CoV-2 S protein of a Wuhan strain, or an immunogenic fragment thereof, and the second RNA comprises a nucleotide sequence encoding a SARS-CoV-2 S protein comprising one or more mutations characteristic of a BQ.1.1 Omicron variant or sublineages thereof, or an immunogenic fragment thereof.

146. The composition or medical preparation of any one of embodiments 133-145, wherein the immunogenic fragment of the SARS-CoV-2 S protein encoded by the first RNA and/or the second RNA comprises the S1 subunit of the SARS-CoV-2 S protein, or the receptor binding domain (RBD) of the S1 subunit of the SARS-CoV-2 S protein.

147. The composition or medical preparation of any one of embodiments 133-146, wherein each of the first RNA and the second RNA is codon-optimized (e.g., codon-optimized for expression in human cells) and/or has a G/C content that is increased compared to a wild type coding sequence.

148. A composition or medical preparation comprising a first RNA and a second RNA, wherein:

a) the first RNA comprises a nucleotide sequence encoding a SARS-CoV-2 S protein of a Wuhan strain wherein (i) the SARS-CoV-2 S protein of a Wuhan strain comprises SEQ ID NO: 7 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 7, and/or (ii) the first RNA comprises a nucleotide sequence of SEQ ID NO: 9 or 20 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 9 or 20, and b) the second RNA comprises a nucleotide sequence encoding a SARS-CoV-2 protein comprising one or more mutations characteristic of a BA.4/5 Omicron variant, wherein (i) the SARS-CoV-2 S protein comprising one or more mutations characteristic of a BA.4/5 Omicron variant comprises an amino acid sequence of 90 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 90 and/or (ii) the second RNA comprises the nucleotide sequence of SEQ ID NO: 91 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 91.

149. A composition or medical preparation comprising a first RNA and a second RNA, wherein:

a) the first RNA comprises a nucleotide sequence encoding a SARS-CoV-2 S protein of a Wuhan strain wherein (i) the SARS-CoV-2 S protein of a Wuhan strain comprises SEQ ID NO: 7 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 7, and/or (ii) the first RNA comprises a nucleotide sequence of SEQ ID NO: 9 or 20 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 9 or 20, and b) the second RNA comprises a nucleotide sequence encoding a SARS-CoV-2 protein comprising one or more mutations characteristic of a BA.1 Omicron variant, wherein (i) the SARS-CoV-2 S protein comprising one or more mutations characteristic of a BA.1 Omicron variant comprises an amino acid sequence of SEQ ID NO: 49 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 49 and/or (ii) the second RNA comprises the nucleotide sequence of SEQ ID NO: 70 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 70.

150. A composition or medical preparation comprising a first RNA and a second RNA, wherein:

a) the first RNA comprises a nucleotide sequence encoding a SARS-CoV-2 S protein of a Wuhan strain wherein (i) the SARS-CoV-2 S protein of a Wuhan strain comprises SEQ ID NO: 7 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 7, and/or (ii) the first RNA comprises a nucleotide sequence of SEQ ID NO: 9 or 20 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 9 or 20, and b) the second RNA comprises a nucleotide sequence encoding a SARS-CoV-2 protein comprising one or more mutations characteristic of a BA.2 Omicron variant, wherein (i) the SARS-CoV-2 S protein comprising one or more mutations characteristic of a BA.2 Omicron variant comprises an amino acid sequence of SEQ ID NO: 64 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 69 and/or (ii) the second RNA comprises the nucleotide sequence of SEQ ID NO: 70 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 70.

151. A composition or medical preparation comprising a first RNA and a second RNA, wherein:

a) the first RNA comprises a nucleotide sequence encoding a SARS-CoV-2 S protein of a Wuhan strain wherein (i) the SARS-CoV-2 S protein of a Wuhan strain comprises SEQ ID NO: 7 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 7, and/or (ii) the first RNA comprises a nucleotide sequence of SEQ ID NO: 9 or 20 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 9 or 20, and b) the second RNA comprises a nucleotide sequence encoding a SARS-CoV-2 protein comprising one or more mutations characteristic of a BA.2.75 Omicron variant, wherein (i) the SARS-CoV-2 S protein comprising one or more mutations characteristic of a BA.2.75 Omicron variant comprises an amino acid sequence of SEQ ID NO: 80 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 80 and/or (ii) the second RNA comprises the nucleotide sequence of SEQ ID NO: 81 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 81.

152. A composition or medical preparation comprising a first RNA and a second RNA, wherein:

a) the first RNA comprises a nucleotide sequence encoding a SARS-CoV-2 S protein of a Wuhan strain wherein (i) the SARS-CoV-2 S protein of a Wuhan strain comprises SEQ ID NO: 7 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 7, and/or (ii) the first RNA comprises a nucleotide sequence of SEQ ID NO: 9 or 20 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 9 or 20, and b) the second RNA comprises a nucleotide sequence encoding a SARS-CoV-2 protein comprising one or more mutations characteristic of a BA.2.75.2 Omicron variant, wherein (i) the SARS-CoV-2 S protein comprising one or more mutations characteristic of a BA.2.75.2 Omicron variant comprises an amino acid sequence of SEQ ID NO: 85 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 85 and/or (ii) the second RNA comprises the nucleotide sequence of SEQ ID NO: 86 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 86.

153. A composition or medical preparation comprising a first RNA and a second RNA, wherein:

a) the first RNA comprises a nucleotide sequence encoding a SARS-CoV-2 S protein of a Wuhan strain wherein (i) the SARS-CoV-2 S protein of a Wuhan strain comprises SEQ ID NO: 7 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 7, and/or (ii) the first RNA comprises a nucleotide sequence of SEQ ID NO: 9 or 20 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 9 or 20, and b) the second RNA comprises a nucleotide sequence encoding a SARS-CoV-2 protein comprising one or more mutations characteristic of a BA.4.6 or BF.7 Omicron variant, wherein (i) the SARS-CoV-2 S protein comprising one or more mutations characteristic of a BA.4.6 or BF.7 Omicron variant comprises an amino acid sequence of SEQ ID NO: 90 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 90 and/or (ii) the second RNA comprises the nucleotide sequence of SEQ ID NO: 91 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 91.

154. A composition or medical preparation comprising a first RNA and a second RNA, wherein:

a) the first RNA comprises a nucleotide sequence encoding a SARS-CoV-2 S protein of a Wuhan strain wherein (i) the SARS-CoV-2 S protein of a Wuhan strain comprises SEQ ID NO: 7 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 7, and/or (ii) the first RNA comprises a nucleotide sequence of SEQ ID NO: 9 or 20 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 9 or 20, and b) the second RNA comprises a nucleotide sequence encoding a SARS-CoV-2 protein comprising one or more mutations characteristic of an XBB Omicron variant, wherein (i) the SARS-CoV-2 S protein comprising one or more mutations characteristic of an XBB Omicron variant comprises an amino acid sequence of SEQ ID NO: 95 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 95 and/or (ii) the second RNA comprises the nucleotide sequence of SEQ ID NO: 96 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 96.

155. A composition or medical preparation comprising a first RNA and a second RNA, wherein:

a) the first RNA comprises a nucleotide sequence encoding a SARS-CoV-2 S protein of a Wuhan strain wherein (i) the SARS-CoV-2 S protein of a Wuhan strain comprises SEQ ID NO: 7 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 7, and/or (ii) the first RNA comprises a nucleotide sequence of SEQ ID NO: 9 or 20 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 9 or 20, and b) the second RNA comprises a nucleotide sequence encoding a SARS-CoV-2 protein comprising one or more mutations characteristic of an BQ.1.1 Omicron variant, wherein (i) the SARS-CoV-2 S protein comprising one or more mutations characteristic of a BQ.1.1 Omicron variant comprises an amino acid sequence of SEQ ID NO: 100 or an amino acid sequence that is at least 80% (e.g., at 85%, at least 90%, at least 91%, at least 92%, at least 93%, at least 94%, at least 95%, at least 97%, at least 98%, or 99% or higher) identical to SEQ ID NO: 100 and/or (ii) the second RNA comprises the nucleotide sequence of SEQ ID NO: 100 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 100.

156. The composition or medical preparation of any one of embodiments 133-155, wherein each of the first RNA and the second RNA encode a SARS-CoV-2 S protein comprising one or more mutations that improves expression, stability, and/or immunogenicity.

157. The composition or medical preparation of embodiment 156, wherein each of the first RNA and the second RNA encode a SARS-CoV-2 S protein comprising one or more mutations that stabilize the prefusion confirmation.

158. The composition or medical preparation of embodiment 157, wherein each of the first RNA and the second RNA encode a SARS-CoV-2 S protein comprising proline mutations at positions corresponding to residues 986 and 987 of SEQ ID NO: 1.

159. The composition or medical preparation of embodiment 157 or 158, wherein each of the first RNA and the second RNA encode a SARS-CoV-2 S protein comprising one or more proline mutations at positions corresponding to residues 817, 892, 899, and/or 942 of SEQ ID NO: 1.

160. The composition or medical preparation of any one of embodiments 156-159, wherein each of the first RNA and the second RNA encode a SARS-CoV-2 S protein comprising a mutation that prevents furin cleavage.

161. The composition or medical preparation of embodiment 160, wherein each of the first RNA and the second RNA encode a SARS-CoV-2 S protein comprising a mutation at a location corresponding to residues 682-685 of SEQ ID NO: 1 that prevents cleavage by a furin protease (e.g., a GSAS mutation).

162. The composition or medical preparation of any one of embodiments 156-161, wherein each of the first RNA and the second RNA encode a SARS-CoV-2 S protein comprising one or more mutations that decreases S protein shedding (e.g., an aspartate to glycine mutation at a position corresponding to residue 614 of SEQ ID NO: 1).

163. The composition or medical preparation of any one of embodiments 133-162, wherein the first RNA and the second RNA each comprise a modified nucleoside in place of uridine.

164. The composition or medical preparation of embodiment 163, wherein the first RNA and the second RNA each comprise a modified nucleoside in place of each uridine.

165. The composition or medical preparation of embodiment 163 or 164, wherein the modified nucleoside is selected from pseudouridine (ψ), N1-methyl-pseudouridine (m1ψ), and 5-methyl-uridine (m5U).

166. The composition or medical preparation of embodiment 165, wherein the modified nucleoside is N1-methyl-pseudouridine (m1ψ).

167. The composition or medical preparation of any one of embodiments 133-166, wherein the first RNA and the second RNA each comprise a 5' cap.

168. The composition or medical preparation of embodiment 167, wherein the 5' cap is or comprises a cap1 structure.

169. The composition or medical preparation of embodiment 168, wherein the 5'-cap is or comprises $m_2^{7,3'-O}$Gppp$(m_1^{2'-O})$ApG.

170. The composition or medical preparation or medical preparation of any one of embodiments 133-169, wherein the first RNA and the second RNA each comprise a poly(A) sequence.

171. The composition or medical preparation of embodiment 170, wherein the poly(A) sequence comprises at least 100 A nucleotides.

172. The composition or medical preparation of embodiment 170 or 171, wherein the poly(A) sequence is an interrupted sequence of A nucleotides.

173. The composition or medical preparation of embodiment 172, wherein the poly(A) sequence comprises 30 adenine nucleotides followed by 70 adenine nucleotides, wherein the 30 adenine nucleotides and 70 adenine nucleotides are separated by a linker sequence.

174. The composition or medical preparation of any one of embodiments 170-173, wherein the poly(A) sequence comprises or consists of the nucleotide sequence of SEQ ID NO: 14, or a nucleotide sequence that is at least 99%, 98%, 97%, 96%, 95%, 90%, 85%, or 80% identical to the nucleotide sequence of SEQ ID NO: 14.

175. The composition or medical preparation of any one of embodiments 133-174, wherein the first RNA and the second RNA each comprise a 5'-UTR that is or comprises a modified human alpha-globin 5'-UTR.

176. The composition or medical preparation of embodiment 175, wherein the 5' UTR comprises the nucleotide sequence of SEQ ID NO: 12, or a nucleotide sequence that is at least 99%, 98%, 97%, 96%, 95%, 90%, 85%, or 80% identical to the nucleotide sequence of SEQ ID NO: 12.

178. The composition or medical preparation of any one of embodiments 133-176, wherein the first RNA and the second RNA each comprise a 3'-UTR that is or comprises a first sequence from the amino terminal enhancer of split (AES) messenger RNA and a second sequence from the mitochondrial encoded 12S ribosomal RNA.

179. The composition or medical preparation of embodiment 178, wherein the first RNA and the second RNA each comprise a 3' UTR comprises the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

180. The composition or medical preparation of any one of embodiments 133-179, wherein the first RNA and the second RNA are each formulated or are to be formulated as particles.

181. The composition or medical preparation of embodiment 180, wherein the particles are lipid nanoparticles (LNP) or lipoplex (LPX) particles.

182. The composition or medical preparation of embodiment 181, wherein the LNPs comprise a cationically ionizable lipid, a neutral lipid, a sterol and a polymer-lipid conjugate.

183. The composition or medical preparation of embodiment 181 or 182, wherein the first RNA and the second RNA are formulated in separate lipid nanoparticles.

184. The composition or medical preparation of embodiment 181 or 182, wherein the first RNA and the second RNA are formulated in the same lipid nanoparticles.

185. The composition or medical preparation of any one of embodiments 182-184, wherein the neutral lipid is present in a concentration ranging from about 5 to about 15 mol percent of the total lipids.

186. The composition or medical preparation of any one of embodiments 182-185, wherein the cationically ionizable lipid is present in a concentration ranging from about 40 to about 50 mol percent of the total lipids.

187. The composition or medical preparation of any one of embodiments 182-186, wherein the sterol is present in a concentration ranging from about 30 to about 50 mol percent of the total lipids.

188. The composition or medical preparation of any one of embodiments 182-187, wherein the polymer-lipid conjugate is present in a concentration ranging from about 1 to about 10 mol percent of the total lipids.

189. The composition or medical preparation of any one of embodiments 182-188, wherein the lipid nanoparticles comprise from about 40 to about 50 mol percent of the cationically ionizable lipid; from about 5 to about 15 mol percent of the neutral lipid; from about 35 to about 45 mol percent of the sterol; and from about 1 to about 10 mol percent of the polymer conjugated-lipid.

190. The composition or medical preparation of embodiment 181, wherein the RNA lipoplex particles are obtainable by mixing the first RNA and the second RNA with liposomes.

191. The composition or medical preparation of any one of embodiments 133-190, wherein the first RNA and the second RNA are present in a combined amount within a range of about 1 μg to about 100 μg per dose.

192. The composition or medical preparation of any one of embodiments 133-191, wherein the first RNA and the second RNA are present in a combined amount within a range of about 1 μg to about 60 μg per dose.

193. The composition or medical preparation of any one of embodiments 133-192, wherein the first RNA and the second RNA are present in a combined amount of about 3.0 μg, about 10 μg, about 30 μg, or about 60 μg per dose.

194. The composition or medical preparation of any one of embodiments 133-193, wherein the ratio of the first RNA to the second RNA is about 1:10 to about 10:1.

195. The composition or medical preparation of any one of embodiments 133-194, wherein the ratio of the first RNA to the second RNA is about 1:1.

196. The composition or medical preparation of any one of embodiments 133-195, wherein:

a) the first RNA and the second RNA are each present in an amount of about 1.5 μg per dose in the composition;
b) the first RNA and the second RNA are each present in an amount of about 5 μg per dose in the composition;
c) the first RNA and the second RNA are each present in an amount of about 15 μg per dose in the composition; or
d) the first RNA and the second RNA are each present in an amount of about 15 μg per dose in the composition.

197. The composition or medical preparation of any one of embodiments 124-169, further comprising an RNA encoding one or more T cell epitopes of SARS-CoV-2.

198. The composition or medical preparation of embodiment 170, wherein the RNA encoding one or more T cell epitopes of SARS-CoV-2 comprises one or more epitopes of each of the ORF1ab, M, and N regions of the SARS-CoV-2 genome.

199. The composition or medical preparation of any one of embodiments 1-198, which is formulated or is to be formulated as a liquid, a solid, or a combination thereof.

200. The composition or medical preparation of any one of embodiments 1-199, which is formulated or is to be formulated for injection.

201. The composition or medical preparation of any one of embodiments 1-200, wherein the composition or medical preparation is formulated or is to be formulated for intramuscular administration.

202. The composition or medical preparation of any one of embodiments 1-201, which is a pharmaceutical composition.

203. The composition or medical preparation of any one of embodiments 1-202, which is a vaccine.

204. The composition or medical preparation of embodiment 202 or 203, wherein the pharmaceutical composition further comprises one or more pharmaceutically acceptable carriers, diluents and/or excipients.

205. The composition or medical preparation of any one of embodiments 1-204, which is a kit.

206. The composition or medical preparation of embodiment 205, further comprising instructions for use of the composition or medical preparation for inducing an immune response against coronavirus in a subject.

207. The composition or medical preparation of any one of embodiments 1-206 for pharmaceutical use.

208. The composition or medical preparation of embodiment 207, wherein the pharmaceutical use comprises inducing an immune response against coronavirus in a subject.

209. The composition or medical preparation of embodiment 207 or 208, wherein the pharmaceutical use comprises a therapeutic or prophylactic treatment of a coronavirus infection.

210. The composition or medical preparation of embodiment 208 or 209, wherein the coronavirus is a sarbecovirus.

211. The composition or medical preparation of any one of embodiments 208-211, wherein the coronavirus is a betacoronavirus.

212. The composition or medical preparation of any one of embodiments 208-212, wherein the coronavirus is SARS-CoV-2.

213. The composition or medical preparation of any one of embodiments 1-212, which is for administration to a human.

214. A method of eliciting an immune response against SARS-CoV-2 in a subject comprising administering the composition or medical preparation of any one of embodiments 1-213.

215. The method of embodiment 214, wherein the immune response is elicited against an Omicron variant of SARS-CoV-2.

216. The method of embodiment 214 or 215, wherein the subject has previously been infected with or vaccinated against SARS-CoV-2.

217. The method of any one of embodiments 214-216, wherein an antigen of a Wuhan strain of SARS-CoV-2 has previously been delivered to the subject (e.g., as a polypeptide or an RNA encoding such a polypeptide).

218. The method of any one of embodiments 214-217, wherein the subject has previously been administered RNA encoding a SARS-CoV-2 S protein of a Wuhan strain.

219. The method of any one of embodiments 214-218, wherein the subject has previously been administered two or more doses of RNA encoding a SARS-CoV-2 S protein of a Wuhan strain.

220. The method of embodiment 219, wherein the RNA of any one of embodiments 1-206 is administered at least about 2 months after the two or more doses of RNA encoding a SARS-CoV-2 S protein of a Wuhan strain.

221. The method of any one of embodiments 214-220, wherein the method comprises administering RNA encoding an antigen of a SARS-CoV-2 virus that is not a BA.1 Omicron variant.

222. The method of any one of embodiments 214-221, wherein the method comprises administering RNA comprising a nucleotide sequence encoding a SARS-Cov-2 S protein comprising one or more mutations characteristic of an Omicron variant, wherein the Omicron variant is not a BA.1 Omicron variant.

223. The method of any one of embodiments 214-222, wherein the method comprises administering RNA comprising a nucleotide sequence encoding a SARS-CoV-2 S protein comprising one or more mutations characteristic of a BA.2 Omicron variant.

224. The method of any one of embodiments 214-222, wherein the method comprises administering RNA comprising a nucleotide sequence encoding a SARS-CoV-2 S protein comprising one or more mutations characteristic of a BA.4 or BA.5 Omicron variant.

225. A method for inducing an immune response in a subject, wherein the method comprises administering (a) a first RNA comprising a nucleotide sequence encoding a SARS-CoV-2 S protein of a Wuhan strain, or comprising one or more mutations characteristic of an Alpha variant, a Beta variant, or a Delta variant, and (b) a second RNA comprising a nucleotide sequence encoding a SARS-CoV-2 S protein comprising one or more mutations characteristic of an Omicron variant that is not a BA.1 Omicron variant.

226. The method of embodiment 225, where the second RNA comprises a nucleotide sequence encoding a SARS-CoV-2 S protein of a BA.2 Omicron variant.

227. The method of embodiment 225, where the second RNA comprises a nucleotide sequence encoding an S protein comprising one or more mutations characteristic of a BA.4 or BA.5 Omicron variant.

228. A method for inducing an immune response in a subject, wherein the method comprises administering (a) a first RNA comprising a nucleotide sequence encoding a SARS-CoV-2 S protein of a Wuhan strain, or comprising one or more mutations characteristic of an Alpha variant, a Beta variant, a Delta variant, or a BA.1 Omicron variant and (b) a second RNA comprising a nucleotide sequence encoding a SARS-CoV-2 S protein that is antigenically distinct from the S protein encoded by the first RNA.

229. The method of embodiment 228, wherein the second RNA comprises a nucleotide sequence encoding a SARS-CoV-2 S protein comprising one or more mutations that are characteristic of an Omicron variant that is not a BA.1 Omicron variant.

230. The method of embodiment 228, wherein the second RNA comprises a nucleotide sequence encoding a SARS-CoV-2 S protein comprising one or more mutations that are characteristic of a BA.2 Omicron variant.

231. The method of embodiment 228, wherein the second RNA comprises a nucleotide sequence encoding a SARS-CoV-2 S protein comprising one or more mutations characteristic of a BA.4 or BA.5 Omicron variant.

232. The method of any one of embodiments 214-231, wherein the first RNA and the second RNA are encapsulated in separate LNPs.

233. The method of any one of embodiments 214-231, wherein the first RNA and the second RNA are encapsulated in the same LNP.

234. The method of any one of embodiments 214-232, wherein the first RNA and the second RNA are administered separately, e.g., at different injection sites.

235. The method of any one of embodiments 214-234, further comprising administering an RNA comprising a nucleotide sequence encoding one or more T cell epitopes of SARS-CoV-2.

236. The method of embodiment 235, wherein the nucleotide sequence encoding one or more T cell epitopes of SARS-CoV-2 encodes one or more epitopes of each of the ORF1ab, M, and N regions of the SARS-CoV-2 genome.

237. The method of embodiment 235 or 236, wherein the first RNA, the second RNA, and the RNA encoding one or more T cell epitopes of SARS-CoV-2 are each formulated in separate LNPs.

238. The method of embodiment 235 or 236, wherein the first RNA and the second RNA are co-formulated in the same LNP, and the RNA encoding one or more T cell epitopes of SARS-CoV-2 is formulated in a separate LNP.

239. The method of embodiment 235 or 236, wherein each of the first RNA, the second RNA, and the RNA encoding one or more T cell epitopes of SARS-CoV-2 is co-formulated in the same LNP.

240. The method of any one of embodiments 235-239, wherein the first RNA, the second RNA, and the RNA encoding one or more T cell epitopes of SARS-CoV-2 are administered in a dose comprising:

(a) 30 μg of the first RNA and the second RNA combined (e.g., 15 μg of the first RNA and 15 μg of the second RNA), and 5 μg of the RNA encoding one or more T cell epitopes of SARS-CoV-2;

(b) 30 μg of the first RNA and the second RNA combined (e.g., 15 μg of the first RNA and 15 μg of the second RNA), and 10 μg of the RNA encoding one or more T cell epitopes of SARS-CoV-2; or (c) 30 μg of the first RNA and the second RNA combined (e.g., 15 μg of the first RNA and 15 μg of the second RNA), and 15 μg of the RNA encoding one or more T cell epitopes of SARS-CoV-2.

241. The method of any one of embodiments 235-240, wherein the RNA encoding one or more T-cell epitopes of SARS-CoV-2 encodes a polypeptide sequence of SEQ ID NO: RS C7p2full.

242. The method of any one of embodiments 207-241, further comprising administering one or more vaccines against a respiratory disease.

243. The method of embodiment 242, wherein the respiratory disease is RSV or influenza.

244. The method of embodiment 242 or 243, comprising administering a vaccine against RSV and a vaccine against influenza.

245. The method of any one of embodiments 242-244, wherein the one or more vaccines against a respiratory disease are RNA vaccines each comprise one or more RNAs encoding an antigenic protein.

246. The method of embodiment 245, comprising administering one or more RNAs encoding antigen(s) from an influenza virus and/or one or more RNAs encoding antigen(s) from an RSV.

247. The method of embodiment 246, wherein each RNA is formulated in a separate LNP.

248. The method of embodiment 246, wherein each RNA encoding a SARS-CoV-2 S protein or an immunogenic fragment thereof is co-formulated together in the same LNP, each RNA encoding an antigenic protein from an influenza virus is co-formulated together in the same LNP, and each RNA encoding an antigenic protein from an RSV is co-formulated together in the same LNP.

249. The method of embodiment 246, wherein each RNA encoding a SARS-CoV-2 S protein or an immunogenic fragment thereof, each RNA encoding an antigenic protein from an influenza virus, and each RNA encoding an antigenic protein from an RSV are co-formulated together in the same LNP.

250. A composition or medical preparation comprising RNA encoding an amino acid sequence comprising a SARS-CoV-2 S protein, an immunogenic variant thereof, or an immunogenic fragment of the SARS-CoV-2 S protein or the immunogenic variant thereof.

251. The composition or medical preparation of embodiment 250, wherein an immunogenic fragment of the SARS-CoV-2 S protein comprises the S1 subunit of the SARS-CoV-2 S protein, or the receptor binding domain (RBD) of the S1 subunit of the SARS-CoV-2 S protein.

252. The composition or medical preparation of embodiments 250 or 251, wherein the amino acid sequence comprising a SARS-CoV-2 S protein, an immunogenic variant thereof, or an immunogenic fragment of the SARS-CoV-2 S protein or the immunogenic variant thereof is encoded by a coding sequence which is codon-optimized and/or the G/C content of which is increased compared to wild type coding sequence, wherein the codon-optimization and/or the increase in the G/C content preferably does not change the sequence of the encoded amino acid sequence.

253. The composition or medical preparation of any one of embodiments 250 to 252, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 979 to 1584 of SEQ ID NO: 2, 8 or 9, a nucleotide sequence having at least 99%, 98%, 97%, 96%, 95%, 90%, 85%, or 80% identity to the nucleotide sequence of nucleotides 979 to 1584 of SEQ ID NO: 2, 8 or 9, or a fragment of the nucleotide sequence of nucleotides 979 to 1584 of SEQ ID NO: 2, 8 or 9, or the nucleotide sequence having at least 99%, 98%, 97%, 96%, 95%, 90%, 85%, or 80% identity to the nucleotide sequence of nucleotides 979 to 1584 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 327 to 528 of SEQ ID NO: 1, an amino acid sequence having at least 99%, 98%, 97%, 96%, 95%, 90%, 85%, or 80% identity to the amino acid sequence of amino acids 327 to 528 of SEQ ID NO: 1, or an immunogenic fragment of the amino acid sequence of amino acids 327 to 528 of SEQ ID NO: 1, or the amino acid sequence having at least 99%, 98%, 97%, 96%, 95%, 90%, 85%, or 80% identity to the amino acid sequence of amino acids 327 to 528 of SEQ ID NO: 1.

254. The composition or medical preparation of any one of embodiments 250 to 253, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 111 to 986 of SEQ ID NO: 30, a nucleotide sequence having at least 99%, 98%, 97%, 96%, 95%, 90%, 85%, or 80% identity to the nucleotide sequence of nucleotides 111 to 986 of SEQ ID NO: 30, or a fragment of the nucleotide sequence of nucleotides 111 to 986 of SEQ ID NO: 30, or the nucleotide sequence having at least 99%, 98%, 97%, 96%, 95%, 90%, 85%, or 80% identity to the nucleotide sequence of nucleotides 111 to 986 of SEQ ID NO: 30; and/or (ii) a SARS-CoV-2 S protein, an immunogenic variant thereof, or an immunogenic fragment of the SARS-CoV-2 S protein or the immunogenic variant thereof comprises the amino acid sequence of amino acids 20 to 311 of SEQ ID NO: 29, an amino acid sequence having at least 99%, 98%, 97%, 96%, 95%, 90%, 85%, or 80% identity to the amino acid sequence of amino acids 20 to 311 of SEQ ID NO: 29, or an immunogenic fragment of the amino acid sequence of amino acids 20 to 311 of SEQ ID NO: 29, or the amino acid sequence having at least 99%, 98%, 97%, 96%, 95%, 90%, 85%, or 80% identity to the amino acid sequence of amino acids 20 to 311 of SEQ ID NO: 29..

255. The composition or medical preparation of any one of embodiments 250 to 254, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 3819 of SEQ ID NO: 2, 8 or 9, a nucleotide sequence having at least 99%, 98%, 97%, 96%, 95%, 90%, 85%, or 80% identity to the nucleotide sequence of nucleotides 49 to 3819 of SEQ ID NO: 2, 8 or 9, or a fragment of the nucleotide sequence of nucleotides 49 to 3819 of SEQ ID NO: 2, 8 or 9, or the nucleotide sequence having at least 99%, 98%, 97%, 96%, 95%, 90%, 85%, or 80% identity to the nucleotide sequence of nucleotides 49 to 3819 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 1273 of SEQ ID NO: 1 or 7, an amino acid sequence having at least 99%, 98%, 97%, 96%, 95%, 90%, 85%, or 80% identity to the amino acid sequence of amino acids 17 to 1273 of SEQ ID NO: 1 or 7, or an immunogenic fragment of the amino acid sequence of amino acids 17 to 1273 of SEQ ID NO: 1 or 7, or the amino acid sequence having at least 99%, 98%, 97%, 96%, 95%, 90%, 85%, or 80% identity to the amino acid sequence of amino acids 17 to 1273 of SEQ ID NO: 1 or 7.

256. The composition or medical preparation of any one of embodiments 250 to 255, wherein the amino acid sequence comprising a SARS-CoV-2 S protein, an immunogenic variant thereof, or an immunogenic fragment of the SARS-CoV-2 S protein or the immunogenic variant thereof comprises a secretory signal peptide.

257. The composition or medical preparation of embodiment 256, wherein the secretory signal peptide is fused, preferably N-terminally, to a SARS-CoV-2 S protein, an immunogenic variant thereof, or an immunogenic fragment of the SARS-CoV-2 S protein or the immunogenic variant thereof.

258. The composition or medical preparation of embodiment 256 or 257, wherein (i) the RNA encoding the secretory signal peptide comprises the nucleotide sequence of nucleotides 1 to 48 of SEQ ID NO: 2, 8 or 9, a nucleotide sequence having at least 99%, 98%, 97%, 96%, 95%, 90%, 85%, or 80% identity to the nucleotide sequence of nucleotides 1 to 48 of SEQ ID NO: 2, 8 or 9, or a fragment of the nucleotide sequence of nucleotides 1 to 48 of SEQ ID NO: 2, 8 or 9, or the nucleotide sequence having at least 99%, 98%, 97%, 96%, 95%, 90%, 85%, or 80% identity to the nucleotide sequence of nucleotides 1 to 48 of SEQ ID NO: 2, 8 or 9; and/or (ii) the secretory signal peptide comprises the amino acid sequence of amino acids 1 to 16 of SEQ ID NO: 1, an amino acid sequence having at least 99%, 98%, 97%, 96%, 95%, 90%, 85%, or 80% identity to the amino acid sequence of amino acids 1 to 16 of SEQ ID NO: 1, or a functional fragment of the amino acid sequence of amino acids 1 to 16 of SEQ ID NO: 1, or the amino acid sequence having at least 99%, 98%, 97%, 96%, 95%, 90%, 85%, or 80% identity to the amino acid sequence of amino acids 1 to 16 of SEQ ID NO: 1.

259. The composition or medical preparation of any one of embodiments 250 to 258, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of SEQ ID NO: 6, a nucleotide sequence having at least 99%, 98%, 97%, 96%, 95%, 90%, 85%, or 80% identity to the nucleotide sequence of SEQ ID NO: 6, or a fragment of the nucleotide sequence of SEQ ID NO: 6, or the nucleotide sequence having at least 99%, 98%, 97%, 96%, 95%, 90%, 85%, or 80% identity to the nucleotide sequence of SEQ ID NO: 6; and/or (ii) a SARS-CoV-2 S protein, an immunogenic variant thereof, or an immunogenic fragment of the SARS-CoV-2 S protein or the immunogenic variant thereof comprises the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5.

260. The composition or medical preparation of any one of embodiments 250 to 259, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 54 to 986 of SEQ ID NO: 30, a nucleotide sequence having at least 99%, 98%, 97%, 96%, 95%, 90%, 85%, or 80% identity to the nucleotide sequence of nucleotides 54 to 986 of SEQ ID NO: 30, or a fragment of the nucleotide sequence of nucleotides 54 to 986 of SEQ ID NO: 30, or the nucleotide sequence having at least 99%, 98%, 97%, 96%, 95%, 90%, 85%, or 80% identity to the nucleotide sequence of nucleotides 54 to 986 of SEQ ID NO: 30; and/or (ii) a SARS-CoV-2 S protein, an immunogenic variant thereof, or an immunogenic fragment of the SARS-CoV-2 S protein or the immunogenic variant thereof comprises the amino acid sequence of amino acids 1 to 311 of SEQ ID NO: 29, an amino acid sequence having at least 99%, 98%, 97%, 96%, 95%, 90%, 85%, or 80% identity to the amino acid sequence of amino acids 1 to 311 of SEQ ID NO: 29, or an immunogenic fragment of the amino acid sequence of amino acids 1 to 311 of SEQ ID NO: 29, or the amino acid sequence having at least 99%, 98%, 97%, 96%, 95%, 90%, 85%, or 80% identity to the amino acid sequence of amino acids 1 to 311 of SEQ ID NO: 29.

261. The composition or medical preparation of any one of embodiments 250 to 258, wherein the RNA comprises a modified nucleoside in place of uridine, in particular wherein the modified nucleoside is selected from pseudouridine (ψ), N1-methyl-pseudouridine (m1ψ), and 5-methyluridine (m5U), in particular wherein the modified nucleoside is N1-methyl-pseudouridine (m1ψ).

262. The composition or medical preparation of any one of embodiments 250 to 261, wherein the RNA comprises a 5' cap.

263. The composition or medical preparation of any one of embodiments 250 to 262, wherein the RNA encoding an amino acid sequence comprising a SARS-CoV-2 S protein, an immunogenic variant thereof, or an immunogenic fragment of the SARS-CoV-2 S protein or the immunogenic variant thereof comprises a 5' UTR comprising the nucleotide sequence of SEQ ID NO: 12, or a nucleotide sequence having at least 99%, 98%, 97%, 96%, 95%, 90%, 85%, or 80% identity to the nucleotide sequence of SEQ ID NO: 12.

264. The composition or medical preparation of any one of embodiments 250 to 263, wherein the RNA encoding an amino acid sequence comprising a SARS-CoV-2 S protein, an immunogenic variant thereof, or an immunogenic fragment of the SARS-CoV-2 S protein or the immunogenic variant thereof comprises a 3' UTR comprising the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

265. The composition or medical preparation of any one of embodiments 250 to 264, wherein the RNA encoding an amino acid sequence comprising a SARS-CoV-2 S protein, an immunogenic variant thereof, or an immunogenic fragment of the SARS-CoV-2 S protein or the immunogenic variant thereof comprises a poly-A sequence.

266. The composition or medical preparation of embodiment 265, wherein the poly-A sequence comprises at least 100 nucleotides.

267. The composition or medical preparation of embodiment 265 or 266, wherein the poly-A sequence comprises or consists of the nucleotide sequence of SEQ ID NO: 14.

268. The composition or medical preparation of any one of embodiments 250 to 267, wherein the RNA is formulated or is to be formulated as a liquid, a solid, or a combination thereof.

269. The composition or medical preparation of any one of embodiments 250 to 268, wherein the RNA is formulated or is to be formulated for injection.

270. The composition or medical preparation of any one of embodiments 250 to 269, wherein the RNA is formulated or is to be formulated for intramuscular administration.

271. The composition or medical preparation of any one of embodiments 250 to 270, wherein the RNA is formulated or is to be formulated as particles.

272. The composition or medical preparation of embodiment 271, wherein the particles are lipid nanoparticles (LNP) or lipoplex (LPX) particles.

273. The composition or medical preparation of embodiment 272, wherein the LNP particles comprise ((4-hydroxybutyl)azanediyl)bis(hexane-6,1-diyl)bis(2-hexyldecanoate), 2-[(polyethylene glycol)-2000]-N,N-ditetradecylacetamide, 1,2-Distearoyl-sn-glycero-3-phosphocholine, and cholesterol.

274. The composition or medical preparation of embodiment 272, wherein the RNA lipoplex particles are obtainable by mixing the RNA with liposomes.

275. The composition or medical preparation of any one of embodiments 250 to 274, wherein the RNA is mRNA or saRNA.

276. The composition or medical preparation of any one of embodiments 250 to 275, which is a pharmaceutical composition.

277. The composition or medical preparation of any one of embodiments 250 to 276, which is a vaccine.

278. The composition or medical preparation of embodiment 276 or 277, wherein the pharmaceutical composition further comprises one or more pharmaceutically acceptable carriers, diluents and/or excipients.

279. The composition or medical preparation of any one of embodiments 250 to 275, which is a kit.

280. The composition or medical preparation of embodiment 279, wherein the RNA and optionally the particle forming components are in separate vials.

281. The composition or medical preparation of embodiment 279 or 280, further comprising instructions for use of the composition or medical preparation for inducing an immune response against coronavirus in a subject.

282. The composition or medical preparation of any one of embodiments 250 to 281 for pharmaceutical use.

283. The composition or medical preparation of embodiment 282, wherein the pharmaceutical use comprises inducing an immune response against coronavirus in a subject.

284. The composition or medical preparation of embodiment 282 or 283, wherein the pharmaceutical use comprises a therapeutic or prophylactic treatment of a coronavirus infection.

285. The composition or medical preparation of any one of embodiments 250 to 284, which is for administration to a human.

286. The composition or medical preparation of any one of embodiments 282 to 285, wherein the coronavirus is a betacoronavirus.

287. The composition or medical preparation of any one of embodiments 282 to 286, wherein the coronavirus is a sarbecovirus.

288. The composition or medical preparation of any one of embodiments 282 to 287, wherein the coronavirus is SARS-CoV-2.

289. A method of inducing an immune response against coronavirus in a subject comprising administering to the subject a composition comprising RNA encoding an amino acid sequence comprising a SARS-CoV-2 S protein, an immunogenic variant thereof, or an immunogenic fragment of the SARS-CoV-2 S protein or the immunogenic variant thereof.

290. The method of embodiment 289, wherein an immunogenic fragment of the SARS-CoV-2 S protein comprises the S1 subunit of the SARS-CoV-2 S protein, or the receptor binding domain (RBD) of the S1 subunit of the SARS-CoV-2 S protein.

291. The method of any one of embodiments 289 or 290, wherein the amino acid sequence comprising a SARS-CoV-2 S protein, an immunogenic variant thereof, or an immunogenic fragment of the SARS-CoV-2 S protein or the immunogenic variant thereof is encoded by a coding sequence which is codon-optimized and/or the G/C content of which is increased compared to wild type coding sequence, wherein the codon-optimization and/or the increase in the G/C content preferably does not change the sequence of the encoded amino acid sequence.

292. The method of any one of embodiments 289 to 291, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 979 to 1584 of SEQ ID NO: 2, 8 or 9, a nucleotide sequence having at least 99%, 98%, 97%, 96%, 95%, 90%, 85%, or 80% identity to the nucleotide sequence of nucleotides 979 to 1584 of SEQ ID NO: 2, 8 or 9, or a fragment of the nucleotide sequence of nucleotides 979 to 1584 of SEQ ID NO: 2, 8 or 9, or the nucleotide sequence having at least 99%, 98%, 97%, 96%, 95%, 90%, 85%, or 80% identity to the nucleotide sequence of nucleotides 979 to 1584 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 327 to 528 of SEQ ID NO: 1, an amino acid sequence having at least 99%, 98%, 97%, 96%, 95%, 90%, 85%, or 80% identity to the amino acid sequence of amino acids 327 to 528 of SEQ ID NO: 1, or an immunogenic fragment of the amino acid sequence of amino acids 327 to 528 of SEQ ID NO: 1, or the amino acid sequence having at least 99%, 98%, 97%, 96%, 95%, 90%, 85%, or 80% identity to the amino acid sequence of amino acids 327 to 528 of SEQ ID NO:1.

293. The method of any one of embodiments 289 to 292, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 111 to 986 of SEQ ID NO: 30, a nucleotide sequence having at least 99%, 98%, 97%, 96%, 95%, 90%, 85%, or 80% identity to the nucleotide sequence of nucleotides 111 to 986 of SEQ ID NO: 30, or a fragment of the nucleotide sequence of nucleotides 111 to 986 of SEQ ID NO: 30, or the nucleotide sequence having at least 99%, 98%, 97%, 96%, 95%, 90%, 85%, or 80% identity to the nucleotide sequence of nucleotides 111 to 986 of SEQ ID NO: 30; and/or (ii) a SARS-CoV-2 S protein, an immunogenic variant thereof, or an immunogenic fragment of the SARS-CoV-2 S protein or the immunogenic variant thereof comprises the amino acid sequence of amino acids 20 to 311 of SEQ ID NO: 29, an amino acid sequence having at least 99%, 98%, 97%, 96%, 95%, 90%, 85%, or 80% identity to the amino acid sequence of amino acids 20 to 311 of SEQ ID NO: 29, or an immunogenic fragment of the amino acid sequence of amino acids 20 to 311 of SEQ ID NO: 29, or the amino acid sequence having at least 99%, 98%, 97%, 96%, 95%, 90%, 85%, or 80% identity to the amino acid sequence of amino acids 20 to 311 of SEQ ID NO: 29.

294. The method of any one of embodiments 289 to 293, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 49 to 3819 of SEQ ID NO: 2, 8 or 9, a nucleotide sequence having at least 99%, 98%, 97%, 96%, 95%, 90%, 85%, or 80% identity to the nucleotide sequence of nucleotides 49 to 3819 of SEQ ID NO: 2, 8 or 9, or a fragment of the nucleotide sequence of nucleotides 49 to 3819 of SEQ ID NO: 2, 8 or 9, or the nucleotide sequence having at least 99%, 98%, 97%, 96%, 95%, 90%, 85%, or 80% identity to the nucleotide sequence of nucleotides 49 to 3819 of SEQ ID NO: 2, 8 or 9; and/or (ii) a SARS-CoV-2 S protein, an immunogenic variant thereof, or an immunogenic fragment of the SARS-CoV-2 S protein or the immunogenic variant thereof comprises the amino acid sequence of amino acids 17 to 1273 of SEQ ID NO: 1 or 7, an amino acid sequence having at least 99%, 98%, 97%, 96%, 95%, 90%, 85%, or 80% identity to the amino acid sequence of amino acids 17 to 1273 of SEQ ID NO: 1 or 7, or an immunogenic fragment of the amino acid sequence of amino acids 17 to 1273 of SEQ ID NO: 1 or 7, or the amino acid sequence having at least 99%, 98%, 97%, 96%, 95%, 90%, 85%, or 80% identity to the amino acid sequence of amino acids 17 to 1273 of SEQ ID NO: 1 or 7.

295. The method of any one of embodiments 289 to 294, wherein the amino acid sequence comprising a SARS-CoV-2 S protein, an immunogenic variant thereof, or an immunogenic fragment of the SARS-CoV-2 S protein or the immunogenic variant thereof comprises a secretory signal peptide.

296. The method of embodiment 295, wherein the secretory signal peptide is fused, preferably N-terminally, to a SARS-CoV-2 S protein, an immunogenic variant thereof, or an immunogenic fragment of the SARS-CoV-2 S protein or the immunogenic variant thereof.

297. The method of embodiment 295 or 297, wherein (i) the RNA encoding the secretory signal peptide comprises the nucleotide sequence of nucleotides 1 to 48 of SEQ ID NO: 2, 8 or 9, a nucleotide sequence having at least 99%, 98%, 97%, 96%, 95%, 90%, 85%, or 80% identity to the nucleotide sequence of nucleotides 1 to 48 of SEQ ID NO: 2, 8 or 9, or a fragment of the nucleotide sequence of nucleotides 1 to 48 of SEQ ID NO: 2, 8 or 9, or the nucleotide sequence having at least 99%, 98%, 97%, 96%, 95%, 90%, 85%, or 80% identity to the nucleotide sequence of nucleotides 1 to 48 of SEQ ID NO: 2, 8 or 9; and/or (ii) the secretory signal peptide comprises the amino acid sequence of amino acids 1 to 16 of SEQ ID NO: 1, an amino acid sequence having at least 99%, 98%, 97%, 96%, 95%, 90%, 85%, or 80% identity to the amino acid sequence of amino acids 1 to 16 of SEQ ID NO: 1, or a functional fragment of the amino acid sequence of amino acids 1 to 16 of SEQ ID NO: 1, or the amino acid sequence having at least 99%, 98%, 97%, 96%, 95%, 90%, 85%, or 80% identity to the amino acid sequence of amino acids 1 to 16 of SEQ ID NO: 1.

298. The method of any one of embodiments 289 to 297, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of SEQ ID NO: 6, a nucleotide sequence having at least 99%, 98%, 97%, 96%, 95%, 90%, 85%, or 80% identity to the nucleotide sequence of SEQ ID NO: 6, or a fragment of the nucleotide sequence of SEQ ID NO: 6, or the nucleotide sequence having at least 99%, 98%, 97%, 96%, 95%, 90%, 85%, or 80% identity to the nucleotide sequence of SEQ ID NO: 6; and/or (ii) a SARS-CoV-2 S protein, an immunogenic variant thereof, or an immunogenic fragment of the SARS-CoV-2 S protein or the immunogenic variant thereof comprises the amino acid sequence of SEQ ID NO: 5, an amino acid sequence having at least 99%, 98%, 97%, 96%, 95%, 90%, 85%, or 80% identity to the amino acid sequence of SEQ ID NO: 5, or an immunogenic fragment of the amino acid sequence of SEQ ID NO: 5, or the amino acid sequence having at least 99%, 98%, 97%, 96%, 95%, 90%, 85%, or 80% identity to the amino acid sequence of SEQ ID NO: 5.

299. The method of any one of embodiments 289 to 298, wherein (i) the RNA encoding a SARS-CoV-2 S protein, an immunogenic variant thereof, or an immunogenic fragment of the SARS-CoV-2 S protein or the immunogenic variant thereof comprises the nucleotide sequence of nucleotides 54 to 986 of SEQ ID NO: 30, a nucleotide sequence having at least 99%, 98%, 97%, 96%, 95%, 90%, 85%, or 80% identity to the nucleotide sequence of nucleotides 54 to 986 of SEQ ID NO: 30, or a fragment of the nucleotide sequence of nucleotides 54 to 986 of SEQ ID NO: 30, or the nucleotide sequence having at least 99%, 98%, 97%, 96%, 95%, 90%, 85%, or 80% identity to the nucleotide sequence of nucleotides 54 to 986 of SEQ ID NO: 30; and/or (ii) a SARS-CoV-2 S protein, an immunogenic variant thereof, or an immunogenic fragment of the SARS-CoV-2 S protein or the immunogenic variant thereof comprises the amino acid sequence of amino acids 1 to 311 of SEQ ID NO: 29, an amino acid sequence having at least 99%, 98%, 97%, 96%, 95%, 90%, 85%, or 80% identity to the amino acid sequence of amino acids 1 to 311 of SEQ ID NO: 29, or an immunogenic fragment of the amino acid sequence of amino acids 1 to 311 of SEQ ID NO: 29, or the amino acid sequence having at least 99%, 98%, 97%, 96%, 95%, 90%, 85%, or 80% identity to the amino acid sequence of amino acids 1 to 311 of SEQ ID NO: 29.

300. The method of any one of embodiments 289 to 298, wherein the RNA comprises a modified nucleoside in place of uridine, in particular wherein the modified nucleoside is selected from pseudouridine (ψ), N1-methyl-pseudouridine (m1ψ), and 5-methyl-uridine (m5U), in particular wherein the modified nucleoside is N1-methyl-pseudouridine (m1ψ).

301. The method of any one of embodiments 289 to 300, wherein the RNA comprises a cap.

302. The method of any one of embodiments 289 to 301, wherein the RNA encoding an amino acid sequence comprising a SARS-CoV-2 S protein, an immunogenic variant thereof, or an immunogenic fragment of the SARS-CoV-2 S protein or the immunogenic variant thereof comprises a 5' UTR comprising the nucleotide sequence of SEQ ID NO: 12, or a nucleotide sequence having at least 99%, 98%, 97%, 96%, 95%, 90%, 85%, or 80% identity to the nucleotide sequence of SEQ ID NO: 12.

303. The method of any one of embodiments 289 to 302, wherein the RNA encoding an amino acid sequence comprising a SARS-CoV-2 S protein, an immunogenic variant thereof, or an immunogenic fragment of the SARS-CoV-2 S protein or the immunogenic variant thereof comprises a 3' UTR comprising the nucleotide sequence of SEQ ID NO: 13, or a nucleotide sequence having at least 99%, 98%, 97%, 96%, 95%, 90%, 85%, or 80% identity to the nucleotide sequence of SEQ ID NO: 13.

304. The method of any one of embodiments 289 to 303, wherein the RNA encoding an amino acid sequence comprising a SARS-CoV-2 S protein, an immunogenic variant thereof, or an immunogenic fragment of the SARS-CoV-2 S protein or the immunogenic variant thereof comprises a poly-A sequence.

305. The method of embodiment 304, wherein the poly-A sequence comprises at least 100 nucleotides.

306. The method of embodiment 304 or 305, wherein the poly-A sequence comprises or consists of the nucleotide sequence of SEQ ID NO: 14.

307. The method of any one of embodiments 289 to 306, wherein the RNA is formulated as a liquid, a solid, or a combination thereof.

308. The method of any one of embodiments 289 to 307, wherein the RNA is administered by injection.

309. The method of any one of embodiments 289 to 308, wherein the RNA is administered by intramuscular administration.

310. The method of any one of embodiments 289 to 309, wherein the RNA is formulated as particles.

311. The method of embodiment 310, wherein the particles are lipid nanoparticles (LNP) or lipoplex (LPX) particles.

312. The method of embodiment 311, wherein the LNP particles comprise ((4-hydroxybutyl)azanediyl)bis(hexane-6,1-diyl)bis(2-hexyldecanoate), 2-[(polyethylene glycol)-2000]-N,N-ditetradecylacetamide, 1,2-Distearoyl-sn-glycero-3-phosphocholine, and cholesterol.

313. The method of any one of embodiment 311, wherein the RNA lipoplex particles are obtainable by mixing the RNA with liposomes.

314. The method of any one of embodiments 289 to 313, wherein the RNA is mRNA or saRNA.

315. The method of any one of embodiments 289 to 314, which is a method for vaccination against coronavirus.

316. The method of any one of embodiments 289 to 315, which is a method for therapeutic or prophylactic treatment of a coronavirus infection.

317. The method of any one of embodiments 289 to 316, wherein the subject is a human.

318. The method of any one of embodiments 289 to 317, wherein the coronavirus is a betacoronavirus.

319. The method of any one of embodiments 289 to 318, wherein the coronavirus is a sarbecovirus.

320. The method of any one of embodiments 289 to 319, wherein the coronavirus is SARS-CoV-2.

321. The method of any one of embodiments 289 to 320, wherein the composition is a composition of any one of embodiments 1 to 39.

322. A composition or medical preparation of any one of embodiments 250 to 288 for use in a method of any one of embodiments 289 to 320.

323. An immunogenic composition comprising: a lipid nanoparticle (LNP) comprising an RNA, wherein the RNA encodes the polypeptide of SEQ ID NO: 49 and comprises the nucleotide sequence of SEQ ID NO: 50 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 50, and wherein the RNA comprises:

(a) modified uridines;

(b) a 5' cap; and wherein the LNP comprises ((4-hydroxybutyl)azanediyl) bis(hexane-6,1-diyl)bis(2-hexyldecanoate), 2-[(polyethylene glycol)-2000]-N,N-ditetradecylacetamide, 1,2-Distearoyl-sn-glycero-3-phosphocholine, and cholesterol.

324. The immunogenic composition of embodiment 323, wherein the nucleotide sequence includes modified uridines in place of all uridines.

325. The immunogenic of embodiment 323 or 324, wherein the modified uridines are each N1-methyl-pseudouridine.

326. The immunogenic composition of any one of embodiments 323 to 325, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

327. The immunogenic composition of embodiment 326, wherein the poly-A sequence comprises 30 adenine nucleotides followed by 70 adenine nucleotides, wherein the 30 adenine nucleotides and 70 adenine nucleotides are separated by a linker sequence.

328. The immunogenic composition of embodiment 326, wherein the poly-A sequence comprises SEQ ID NO: 14.

329. The immunogenic composition of any one of embodiments 323 to 328, wherein the RNA comprises SEQ ID NO: 51.

330. An immunogenic composition comprising a lipid nanoparticle (LNP) comprising an RNA, wherein the RNA encodes the polypeptide of SEQ ID NO: 55 and comprises the nucleotide sequence of SEQ ID NO: 56 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 56, and wherein the RNA comprises:

(a) modified uridines;

(b) a 5' cap; and wherein the LNP comprises ((4-hydroxybutyl)azanediyl) bis(hexane-6,1-diyl)bis(2-hexyldecanoate), 2-[(polyethylene glycol)-2000]-N,N-ditetradecylacetamide, 1,2-Distearoyl-sn-glycero-3-phosphocholine, and cholesterol.

331. The immunogenic composition of embodiment 330, wherein the nucleotide sequence includes modified uridines in place of all uridines.

332. The immunogenic of embodiment 330 or 331, wherein the modified uridines are each N1-methyl-pseudouridine.

333. The immunogenic composition of any one of embodiments 330 to 332, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

334. The immunogenic composition of embodiment 333, wherein the poly-A sequence comprises 30 adenine nucleotides followed by 70 adenine nucleotides, wherein the 30 adenine nucleotides and 70 adenine nucleotides are separated by a linker sequence.

335. The immunogenic composition of embodiment 334, wherein the poly-A sequence comprises SEQ ID NO: 14.

336. The immunogenic composition of any one of embodiments 330 to 335, wherein the RNA comprises SEQ ID NO: 57.

337. An immunogenic composition comprising a lipid nanoparticle (LNP) comprising an RNA, wherein the RNA encodes the polypeptide of SEQ ID NO: 58 and comprises the nucleotide sequence of SEQ ID NO: 59 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 59, and wherein the RNA comprises:

(a) modified uridines;

(b) a 5' cap; and wherein the LNP comprises ((4-hydroxybutyl)azanediyl) bis(hexane-6,1-diyl)bis(2-hexyldecanoate), 2-[(polyethylene glycol)-2000]-N,N-ditetradecylacetamide, 1,2-Distearoyl-sn-glycero-3-phosphocholine, and cholesterol.

338. The immunogenic composition of embodiment 337, wherein the nucleotide sequence includes modified uridines in place of all uridines.

339. The immunogenic of embodiment 337 or 338, wherein the modified uridines are each N1-methyl-pseudouridine.

340. The immunogenic composition of any one of embodiments 337 to 339, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

341. The immunogenic composition of embodiment 340, wherein the poly-A sequence comprises 30 adenine nucleotides followed by 70 adenine nucleotides, wherein the 30 adenine nucleotides and 70 adenine nucleotides are separated by a linker sequence.

342. The immunogenic composition of embodiment 341, wherein the poly-A sequence comprises SEQ ID NO: 14.

343. The immunogenic composition of any one of embodiments 337 to 342, wherein the RNA comprises SEQ ID NO: 60.

344. An immunogenic composition comprising a lipid nanoparticle (LNP) comprising an RNA, wherein the RNA encodes the polypeptide of SEQ ID NO: 61 and comprises the nucleotide sequence of SEQ ID NO: 62a or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 62a, and wherein the RNA comprises:

(a) modified uridines;

(b) a 5' cap; and wherein the LNP comprises ((4-hydroxybutyl)azanediyl) bis(hexane-6,1-diyl)bis(2-hexyldecanoate), 2-[(polyethylene glycol)-2000]-N,N-ditetradecylacetamide, 1,2-Distearoyl-sn-glycero-3-phosphocholine, and cholesterol.

345. The immunogenic composition of embodiment 344, wherein the nucleotide sequence includes modified uridines in place of all uridines.

346. The immunogenic of embodiment 344 or 345, wherein the modified uridines are each N1-methyl-pseudouridine.

347. The immunogenic composition of any one of embodiments 344 to 346, wherein the RNA further comprises at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

348. The immunogenic composition of embodiment 347, wherein the poly-A sequence comprises 30 adenine nucleotides followed by 70 adenine nucleotides, wherein the 30 adenine nucleotides and 70 adenine nucleotides are separated by a linker sequence.

349. The immunogenic composition of embodiment 348, wherein the poly-A sequence comprises SEQ ID NO: 14.

350. The immunogenic composition of any one of embodiments 344 to 349, wherein the RNA comprises SEQ ID NO: 63a.

351. An immunogenic composition comprising a first RNA and a second RNA, wherein: the first RNA encodes the polypeptide of SEQ ID NO: 7 and comprises the nucleotide sequence of SEQ ID NO: 9 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 9, and the second RNA encodes the polypeptide of SEQ ID NO: 49 and comprises the nucleotide sequence of SEQ ID NO: 50 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 50, and wherein each of the first RNA and the second RNA comprise:

(a) modified uridines; and (b) a 5' cap, and wherein the first RNA and the second RNA are formulated in lipid nanoparticles (LNPs), wherein the LNPs comprise ((4-hydroxybutyl)azanediyl)bis(hexane-6,1-diyl) bis(2-hexyldecanoate), 2-[(polyethylene glycol)-2000]-N,N-ditetradecylacetamide, 1,2-Distearoyl-sn-glycero-3-phosphocholine, and cholesterol.

352. The immunogenic composition of embodiment 351, wherein the first RNA and the second RNA are formulated in the same lipid nanoparticles.

353. The immunogenic composition of embodiment 351, wherein the first RNA and the second RNA are formulated in separate lipid nanoparticles.

354. The immunogenic composition of any one of embodiments 351 to 353, wherein each of the first RNA and the second RNA include modified uridines in place of all uridines.

355. The immunogenic of any one of embodiments 351 to 354, wherein the modified uridines are each N1-methyl-pseudouridine.

356. The immunogenic composition of any one of embodiments 351 to 355, wherein the first RNA and the second RNA each independently comprise at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

357. The immunogenic composition of embodiment 357, wherein the poly-A sequence comprises 30 adenine nucleotides followed by 70 adenine nucleotides, wherein the 30 adenine nucleotides and 70 adenine nucleotides are separated by a linker sequence.

358. The immunogenic composition of embodiment 357, wherein the poly-A sequence comprises SEQ ID NO: 14.

359. The immunogenic composition of any one of embodiments 351 to 358, wherein the first RNA comprises SEQ ID NO: 20 and the second RNA comprises SEQ ID NO: 51.

360. An immunogenic composition comprising a first RNA and a second RNA, wherein:

the first RNA encodes the polypeptide of SEQ ID NO: 7 and comprises the nucleotide sequence of SEQ ID NO: 9 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 9, and the second RNA encodes the polypeptide of SEQ ID NO: 55, 58, or 61 and comprises the nucleotide sequence of SEQ ID NO: 56, 59, or 62a, or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 56, 59, or 62a, and wherein each of the first RNA and the second RNA comprise:

(a) modified uridines; and (b) a 5' cap, and wherein the first RNA and the second RNA are formulated in lipid nanoparticles (LNPs), wherein the LNPs comprise ((4-hydroxybutyl)azanediyl)bis(hexane-6,1-diyl) bis(2-hexyldecanoate), 2-[(polyethylene glycol)-2000]-N,N-ditetradecylacetamide, 1,2-Distearoyl-sn-glycero-3-phosphocholine, and cholesterol.

361. The immunogenic composition of embodiment 360, wherein the first RNA and the second RNA are formulated in separate lipid nanoparticles.

362. The immunogenic composition of embodiment 360, wherein the first RNA and the second RNA are formulated in the same lipid nanoparticles.

363. The immunogenic composition of any one of embodiments 360 to 362, wherein the first RNA and the second RNA each include modified uridines in place of all uridines.

364. The immunogenic composition of any one of embodiments 360 to 363, wherein the modified uridines are each N1-methyl-pseudouridine.

365. The immunogenic composition of any one of embodiments 360 to 364, wherein the first RNA and the second RNA each independently further comprise at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

366. The immunogenic composition of any one of embodiments 360 to 365, wherein the poly-A sequence comprises 30 adenine nucleotides followed by 70 adenine nucleotides, wherein the 30 adenine nucleotides and 70 adenine nucleotides are separated by a linker sequence.

367. The immunogenic composition of embodiment 366, wherein the poly-A sequence comprises SEQ ID NO: 14.

368. The immunogenic composition of any one of embodiments 360 to 367, wherein the first RNA comprises SEQ ID NO: 9 and the second RNA comprises SEQ ID NO: 56.

369. The immunogenic composition of any one of embodiments 360 to 368, wherein the first RNA comprises SEQ ID NO: 9 and the second RNA comprises SEQ ID NO: 59.

370. The immunogenic composition of any one of embodiments 360 to 368, wherein the first RNA comprises SEQ ID NO: 9 and the second RNA comprises SEQ ID NO: 62a.

371. The immunogenic composition of any one of embodiments 360 to 368, wherein the first RNA comprises SEQ ID NO: 20 and the second RNA comprises SEQ ID NO: 57.

372. The immunogenic composition of any one of embodiments 360 to 368, wherein the first RNA comprises SEQ ID NO: 20 and the second RNA comprises SEQ ID NO: 60.

373. The immunogenic composition of any one of embodiments 360 to 368, wherein the first RNA comprises SEQ ID NO: 20 and the second RNA comprises SEQ ID NO: 63a.

374. An immunogenic composition comprising a first RNA and a second RNA, wherein:

the first RNA encodes the polypeptide of SEQ ID NO: 58 and comprises the nucleotide sequence of SEQ ID NO: 59 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 59, and the second RNA encodes the polypeptide of SEQ ID NO: 49, 55, or 61 and comprises the nucleotide sequence of SEQ ID NO: 50, 56, or 62a, or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 50, 56, or 62a, and wherein each of the first RNA and the second RNA comprise:

(a) modified uridines; and (b) a 5' cap, and wherein the first RNA and the second RNA are formulated in lipid nanoparticles (LNPs), wherein the LNPs comprise ((4-hydroxybutyl)azanediyl)bis(hexane-6,1-diyl) bis(2-hexyldecanoate), 2-[(polyethylene glycol)-2000]-N,N-ditetradecylacetamide, 1,2-Distearoyl-sn-glycero-3-phosphocholine, and cholesterol.

375. The immunogenic composition of embodiment 374, wherein the first RNA and the second RNA are formulated in separate lipid nanoparticles.

376. The immunogenic composition of embodiment 374, wherein the first RNA and the second RNA are formulated in the same lipid nanoparticles.

377. The immunogenic composition of any one of embodiments 374 to 376, wherein the first RNA and the second RNA each include modified uridines in place of all uridines.

378. The immunogenic of any one of embodiments 374 to 377, wherein the modified uridines are each N1-methyl-pseudouridine.

379. The immunogenic composition of any one of embodiments 374 to 378, wherein the first RNA and the second RNA each independently further comprise at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

380. The immunogenic composition of embodiment 379, wherein the poly-A sequence comprises 30 adenine nucleotides followed by 70 adenine nucleotides, wherein the 30 adenine nucleotides and 70 adenine nucleotides are separated by a linker sequence.

381. The immunogenic composition of embodiment 379, wherein the poly-A sequence comprises SEQ ID NO: 14.

382. The immunogenic composition of any one of embodiments 374 to 381, wherein the first RNA comprises SEQ ID NO: 59 and the second RNA comprises SEQ ID NO: 50.

383. The immunogenic composition of any one of embodiments 374 to 381, wherein the first RNA comprises SEQ ID NO: 59 and the second RNA comprises SEQ ID NO: 56.

384. The immunogenic composition of any one of embodiments 374 to 381, wherein the first RNA comprises SEQ ID NO: 59 and the second RNA comprises SEQ ID NO: 62a.

385. The immunogenic composition of any one of embodiments 374 to 381, wherein the first RNA comprises SEQ ID NO: 60 and the second RNA comprises SEQ ID NO: 51.

386. The immunogenic composition of any one of embodiments 374 to 381, wherein the first RNA comprises SEQ ID NO: 60 and the second RNA comprises SEQ ID NO: 57.

387. The immunogenic composition of any one of embodiments 374 to 381, wherein the first RNA comprises SEQ ID NO: 60 and the second RNA comprises SEQ ID NO: 63a.

388. An immunogenic composition comprising a first RNA and a second RNA, wherein:

the first RNA encodes the polypeptide of SEQ ID NO: 49 and comprises the nucleotide sequence of SEQ ID NO: 50 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 50, and the second RNA encodes the polypeptide of SEQ ID NO: 55 or 61 and comprises the nucleotide sequence of SEQ ID NO: 56 or 62a, or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 56 or 62a, and wherein each of the first RNA and the second RNA comprise:

(a) modified uridines; and (b) a 5' cap, and wherein the first RNA and the second RNA are formulated in lipid nanoparticles (LNPs), wherein the LNPs comprise ((4-hydroxybutyl)azanediyl)bis(hexane-6,1-diyl) bis(2-hexyldecanoate), 2-[(polyethylene glycol)-2000]-N,N-ditetradecylacetamide, 1,2-Distearoyl-sn-glycero-3-phosphocholine, and cholesterol.

389. The immunogenic composition of embodiment 388, wherein the first RNA and the second RNA are formulated in separate lipid nanoparticles.

390. The immunogenic composition of embodiment 388, wherein the first RNA and the second RNA are formulated in the same lipid nanoparticles.

391. The immunogenic composition of any one of embodiments 388 to 390, wherein the first RNA and the second RNA each include modified uridines in place of all uridines.

392. The immunogenic of any one of embodiments 388 to 391, wherein the modified uridines are each N1-methyl-pseudouridine.

393. The immunogenic composition of any one of embodiments 388 to 392, wherein the first RNA and the second RNA further each independently further comprise at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

394. The immunogenic composition of embodiment 393, wherein the poly-A sequence comprises 30 adenine nucleotides followed by 70 adenine nucleotides, wherein the 30 adenine nucleotides and 70 adenine nucleotides are separated by a linker sequence.

395. The immunogenic composition of embodiment 393, wherein the poly-A sequence comprises SEQ ID NO: 14.

396. The immunogenic composition of any one of embodiments 388 to 395, wherein the first RNA comprises SEQ ID NO: 50 and the second RNA comprises SEQ ID NO: 56.

397. The immunogenic composition of any one of embodiments 388 to 395, wherein the first RNA comprises SEQ ID NO: 50 and the second RNA comprises SEQ ID NO: 62a.

398. The immunogenic composition of any one of embodiments 388 to 395, wherein the first RNA comprises SEQ ID NO: 51 and the second RNA comprises SEQ ID NO: 57.

399. The immunogenic composition of any one of embodiments 388 to 395, wherein the first RNA comprises SEQ ID NO: 51 and the second RNA comprises SEQ ID NO: 63a.

400. An immunogenic composition comprising a first RNA and a second RNA, wherein:

the first RNA encodes the polypeptide of SEQ ID NO: 55 and comprises the nucleotide sequence of SEQ ID NO: 56 or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 56, and the second RNA encodes the polypeptide of SEQ ID NO: 61 and comprises the nucleotide sequence of SEQ ID NO: 62a, or a nucleotide sequence that is at least 80% (e.g., at 85%, at least 90%, at least 91%, at least 92%, at least 93%, at least 94%, at least 95%, at least 97%, at least 98%, or 99% or higher) identical to SEQ ID NO: 62a, and wherein each of the first RNA and the second RNA comprise:

(a) modified uridines; and (b) a 5' cap, and wherein the first RNA and the second RNA are formulated in lipid nanoparticles (LNPs), wherein the LNPs comprise ((4-hydroxybutyl)azanediyl)bis(hexane-6,1-diyl) bis(2-hexyldecanoate), 2-[(polyethylene glycol)-2000]-N,N-ditetradecylacetamide, 1,2-Distearoyl-sn-glycero-3-phosphocholine, and cholesterol.

401. The immunogenic composition of embodiment 400, wherein the first RNA and the second RNA are formulated in separate lipid nanoparticles.

402. The immunogenic composition of embodiment 400, wherein the first RNA and the second RNA are formulated in the same lipid nanoparticles.

403. The immunogenic composition of any one of embodiments 400 to 402, wherein the first RNA and the second RNA each include modified uridines in place of all uridines.

404. The immunogenic of any one of embodiments 400 to 403, wherein the modified uridines are each N1-methyl-pseudouridine.

405. The immunogenic composition of any one of embodiments 400 to 404, wherein the first RNA and the second RNA each independently further comprise at least one, at least two, or all of the following features:

a 5' untranslated region (UTR) comprising SEQ ID NO: 12;

a 3' untranslated region (UTR) comprising SEQ ID NO: 13; and a poly-A sequence of at least 100 A nucleotides.

406. The immunogenic composition of embodiment 405, wherein the poly-A sequence comprises 30 adenine nucleotides followed by 70 adenine nucleotides, wherein the 30 adenine nucleotides and 70 adenine nucleotides are separated by a linker sequence.

407. The immunogenic composition of embodiment 405, wherein the poly-A sequence comprises SEQ ID NO: 14.

408. The immunogenic composition of any one of embodiments 400 to 407, wherein the first RNA comprises SEQ ID NO: 57 and the second RNA comprises SEQ ID NO: 63a.

409. The immunogenic composition of any one of embodiments 323 to 408, wherein the 5'-cap is or comprises $m_{273}$-0Gppp(m12-O)ApG.

410. The immunogenic composition of any one of embodiments 323 to 409, wherein the LNP comprises about 40 to about 50 mole percent ((4-hydroxybutyl)azanediyl)bis (hexane-6,1-diyl)bis(2-hexyldecanoate), about 35 to about 45 mole percent cholesterol, about 5 to about 15 mole percent 1,2-Distearoyl-sn-glycero-3-phosphocholine, and about 1 to about 10 mole percent 2-[(polyethylene glycol)-2000]-N,N-ditetradecylacetamide.

411. The immunogenic composition of any one of embodiments 323 to 410, wherein the composition comprises a plurality of LNPs, wherein the average diameter of the plurality of LNPs is about 30 nm to about 200 nm or about 60 nm to about 120 nm (e.g., as determined by dynamic light scattering measurements).

412. A method of eliciting an immune response against SARS-CoV-2 comprising administering the immunogenic composition of any one of embodiments 74 to 162.

413. The method of embodiment 413, wherein the immune response is elicited against an Omicron variant of SARS-CoV-2.

414. The method of embodiment 412, wherein the immune response is elicited against a Beta variant of SARS-CoV-2.

415. The method of embodiment 412, wherein the immune response is elicited against an Alpha variant of SARS-CoV-2.

416. The method of embodiment 412, wherein the immune response is elicited against a Delta variant of SARS-CoV-2.

417. The method of embodiment 412, wherein the immune response is elicited against a Wuhan strain, an Omicron variant, a Beta variant, an Alpha variant, and a Delta variant of SARS-CoV-2.

418. A method for inducing an immune response in a subject, wherein the method comprises delivering (e.g., as a polypeptide or an RNA encoding such a polypeptide) an antigen of a SARS-CoV-2 virus that is not a BA.1 Omicron variant of SARS-CoV-2.

419. The method of embodiment 418, wherein the subject has previously been infected with or vaccinated against SARS-CoV-2.

420. The method of embodiment 418 or 419, wherein the subject has previously been delivered (e.g., as a polypeptide or an RNA encoding such a polypeptide) an antigen of a Wuhan strain of SARS-CoV-2.

421. The method of any one of embodiments 418-420, wherein the subject has previously been administered RNA encoding a SARS-CoV-2 S protein of a Wuhan strain.

422. The method of any one of embodiments 418-421, wherein the subject has previously been administered two or more doses of RNA encoding a SARS-CoV-2 S protein of a Wuhan strain.

423. The method of any one of embodiments 418-422, wherein the method comprises administering RNA encoding an antigen of a SARS-CoV-2 virus that is not a BA.1 Omicron variant.

424. The method of any one of embodiments 418-423, wherein the method comprises administering RNA encoding a SARS-CoV-2 S protein from a SARS-CoV-2 variant that is a BA.1 Omicron variant.

425. The method of any one of embodiments 418-424, wherein the method comprises administering RNA encoding an S protein of an Omicron variant of SARS-CoV-2, wherein the Omicron variant is not a BA.1 Omicron variant.

426. The method of any one of embodiments 418-425, wherein the method comprises administering RNA encoding an S protein of a BA.2 Omicron variant of SARS-CoV-2.

427. The method of any one of embodiments 418-425, wherein the method comprises administering RNA encoding an S protein of a BA.4 or BA.5 Omicron variant of SARS-CoV-2.

428. A method for inducing an immune response in a subject, wherein the method comprises administering (a) a first RNA encoding a SARS-CoV-2 S protein of a Wuhan strain, an Alpha variant, a Beta variant, or a Delta variant, and (b) a second RNA encoding a SARS-CoV-2 S protein of an Omicron variant that is not a BA.1 Omicron variant.

429. The method of embodiment 428, where the second RNA encodes an S protein of a BA.2 Omicron variant.

430. The method of embodiment 428, where the second RNA encodes an S protein of a BA.4 or BA.5 Omicron variant.

431. A method for inducing an immune response in a subject, wherein the method comprises administering (a) a first RNA encoding a SARS-CoV-2 S protein of a Wuhan strain, an Alpha variant, a Beta variant, a Delta variant, or a BA.1 Omicron variant and (b) a second RNA encoding a SARS-CoV-2 S protein that is antigenically distinct from the S protein encoded by the first RNA.

432. The method of embodiment 431, wherein the second RNA encodes a SARS-CoV-2 S protein of an Omicron variant that is not a BA.1 Omicron variant.

433. The method of embodiment 431, wherein the second RNA encodes a SARS-CoV-2 S protein of a BA.2 Omicron variant.

434. The method of embodiment 431, wherein the second RNA encodes a SARS-CoV-2 S protein of a BA.4 or BA.5 Omicron variant.

435. The method of any one of embodiments 418-434, wherein the first RNA and the second RNA are encapsulated in separate LNPs.

436. The method of any one of embodiments 418-435, wherein the first RNA and the second RNA are encapsulated in the same LNP.

437. The method of any one of embodiments 418-436, wherein the first RNA and the second RNA are administered separately, e.g., at different injection sites.

438. A composition comprising (a) a first RNA encoding a SARS-CoV-2 S protein of a Wuhan strain, an Alpha variant, a Beta variant, a Delta variant, or a BA.1 Omicron variant and (b) a second RNA encoding a SARS-CoV-2 S protein that is antigenically distinct from the S protein encoded by the first RNA.

439. A composition comprising (a) a first RNA encoding a SARS-CoV-2 S protein of a Wuhan strain, an Alpha variant, a Beta variant, a Delta variant, or a BA.1 Omicron variant and (b) a second RNA encoding a SARS-CoV-2 S protein an Omicron variant that is not a BA.1 Omicron variant.

440. The composition of embodiment 439, wherein the second RNA encodes a SARS-CoV-2 S protein of a BA.2 Omicron variant.

441. The composition of embodiment 439, wherein the second RNA encodes a SARS-CoV-2 S protein of a BA.4 or BA.5 Omicron variant.

442. The composition of embodiment 439, wherein the first RNA encodes a SARS-CoV-2 S protein of a Wuhan strain and the second RNA encodes a SARS-CoV-2 S protein of a BA.2 Omicron variant.

443. The composition of embodiment 439, wherein the first RNA encodes a SARS-CoV-2 S protein of a Wuhan strain and the second RNA encodes a SARS-CoV-2 S protein of a BA.4 or BA.5 Omicron variant.

444. The composition of embodiment 439, wherein the first RNA encodes a SARS-CoV-2 S protein of a BA.1 Omicron variant and the second RNA encodes a SARS-CoV-2 S protein of a BA.2 Omicron variant.

445. The composition of embodiment 439, wherein the first RNA encodes a SARS-CoV-2 S protein of a BA.1 Omicron variant and the second RNA encodes a SARS-CoV-2 S protein of a BA.4 or BA.5 Omicron variant.

446. The composition of any one of embodiments 438-445, wherein the first RNA and the second RNA are administered in encapsulated in the same LNP.

447. The composition of any one of embodiments 438-446, wherein the first RNA and the second RNA are encapsulated in separate LNPs.

448. The method of any one of embodiments 214 to 249, 289 to 321, or 412 to 437, wherein the composition is a composition of any one of embodiments 1 to 213, 250 to 288, 322 to 411, or 438 to 448.

448. A composition or medical preparation of any one of embodiments 1 to 213, 250 to 288, 322 to 411, or 438 to 448 for use in a method of any one of embodiments 214 to 249, 289 to 321, or 412 to 437.

449. The composition or medical preparation of any one of embodiments 1 to 213, 250 to 288, 322 to 411, or 438 to 448, which is a pharmaceutical composition.

450. The composition or medical preparation of any one of embodiments 1 to 213, 250 to 288, 322 to 411, or 438 to 448, which is a vaccine.

451. The composition or medical preparation of embodiment 449 or 450, wherein the pharmaceutical composition or vaccine further comprises one or more pharmaceutically acceptable carriers, diluents and/or excipients.

452. The composition or medical preparation of any one of embodiment 1 to 213, 250 to 288, 322 to 411, or 438 to 448, which is a kit.

453. The composition or medical preparation of embodiment 452, wherein the RNA and optionally the particle forming components are in separate vials.

454. The composition or medical preparation of embodiment 452 or 453, further comprising instructions for use of the composition or medical preparation for inducing an immune response against coronavirus in a subject.

455. The composition or medical preparation of any one of embodiments 1 to 213, 250 to 288, 322 to 411, or 438 to 448 for pharmaceutical use.

456. The composition or medical preparation of embodiment 455, wherein the pharmaceutical use comprises inducing an immune response against coronavirus in a subject.

457. The composition or medical preparation of embodiment 455 or 456, wherein the pharmaceutical use comprises a therapeutic or prophylactic treatment of a coronavirus infection.

458. The composition or medical preparation of any one of embodiments 1 to 213, 250 to 288, 322 to 411, or 438 to 448 for use in the manufacture of a medicament.

459. The composition or medical preparation of embodiment 458, wherein the medicament is for inducing an immune response against coronavirus in a subject.

460. The composition or medical preparation of embodiment 458 or 459, wherein the medicament is for therapeutic or prophylactic treatment of a coronavirus infection.

461. The composition or medical preparation of any one of embodiments 1 to 213, 250 to 288, 322 to 411, or 438 to 448, which is for administration to a human.

462. The composition or medical preparation of any one of embodiments 454, 456, 457, 459, or 460, wherein the coronavirus is a betacoronavirus.

463. The composition or medical preparation of embodiment 462, wherein the coronavirus is a sarbecovirus.

464. The composition or medical preparation of embodiment 463, wherein the coronavirus is SARS-CoV-2.

Citation of documents and studies referenced herein is not intended as an admission that any of the foregoing is pertinent prior art. All statements as to the contents of these documents are based on the information available to the applicants and do not constitute any admission as to the correctness of the contents of these documents.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

EXAMPLES

Example 1: Immunogenicity Study of BNT162b3 Variants BNT162b3c and BNT162b3d To get an idea about the potential potency of transmembrane-anchored RBD-based vaccine antigens (Schematic in FIG. 6; BNT162b3c (1) and BNT162b3d (2)), BALB/c mice were immunized IM once with 4 ug LNP-C12 formulated mRNA or with buffer as control. The non-clinical LNP-C12 formulated mRNAs were used as surrogate for the BNT162b3 variants BNT162b3c and BNT162b3d. The immunogenicity of the RNA vaccine was investigated by focusing on the antibody immune response.

ELISA data 6, 14 and 21 d after the first immunization show an early, dose-dependent immune activation against the S1 protein and the receptor binding domain (FIG. 7). Sera obtained 6, 14 and 21 d after immunization show high SARS-CoV-2 pseudovirus neutralization, correlating with the increase of IgG antibody titers (FIG. 8).

Example 2: Neutralization of SARS-CoV-2 BA.1 Omicron Lineage (a.k.a. B.1.1.529) Pseudovirus by BNT162b2 Vaccine-Elicited Human Sera Materials and Methods A recombinant replication-deficient VSV vector that encodes green fluorescent protein (GFP) and luciferase (Luc) instead of the VSV-glycoprotein (VSV-G) was pseudotyped with Wuhan-Hu-1 isolate SARS-CoV-2 spike (S) (GenBank: QHD43416.1), and a variant spike harbouring the mutations found in the S protein of the Omicron (B.1.1.529) BA.1 lineage (A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F) according to published pseudotyping protocols. In brief, HEK293T/17 monolayers transfected to express the respective SARS-CoV-2 S protein truncated of the C-terminal cytoplasmic 19 amino acids (SARS-CoV-2-S(CΔ19)) were inoculated with VSVΔG-GFP/Luc vector. After incubation for 2 h at 37° C., the inoculum was removed, and cells were washed with PBS before medium supplemented with anti-VSV-G antibody (clone 8G5F11, Kerafast) was added to neutralise residual input virus. VSV-SARS-CoV-2 pseudovirus-containing medium was collected 20 h after inoculation, 0.2-μm-filtered and stored at −80° C.

For pseudovirus neutralisation assays, 40,000 Vero 76 cells were seeded per 96-well. Sera were serially diluted 1:2 in culture medium starting with a 1:10 dilution (dilution range of 1:10 to 1:10,240). VSV-SARS-CoV-2-S pseudoparticles were diluted in culture medium for a fluorescent focus unit (ffu) count in the assay of ~200 TU in the assay. Serum dilutions were mixed 1:1 with pseudovirus for 30 minutes at room temperature prior to addition to Vero 76 cell monolayers in 96-well plates and incubation at 37° C. for 16-24 hours. Supernatants were removed, and the cells were lysed with luciferase reagent (Promega). Luminescence was recorded, and neutralisation titers were calculated as the reciprocal of the highest serum dilution that still resulted in 50% reduction in luminescence. Results were reported as GMT of duplicates. If no neutralization was observed, an arbitrary titer value of 5 (half of the limit of detection [LOD]) was reported.

Sera (N=19-20) were collected from subjects 21 days after receiving the second 30 μg dose or one month after receiving the third 30 μg dose of BNT162b2. Each serum was tested for its neutralizing antibody titer against wild-type SARS-CoV-2 Wuhan Hu-1 and Omicron BA.1 lineage (B.1.1.529) spike protein pseudotyped VSV by a 50% neutralization assay ($pVNT_{50}$). The Omicron BA.1-strain spike protein used in the neutralization assay carried the following amino acid changes compared to the Wuhan reference: A67V, Δ69-70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F.

BNT162b2-immune sera generated at 21 days after the second dose displayed effective neutralization of the SARS-CoV-2 Wuhan Hu-1 pseudotyped reference. However, more than a 25-fold reduction in neutralization titers against the Omicron BA.1 variant was observed when compared to the Wuhan reference (geometric mean titer [GMT] of 6 vs. 155). Importantly, the third dose significantly increased the neutralizing antibody titers against the Omicron BA.1 strain pseudovirus by 25-fold. Hence, neutralization titers against the Omicron BA.1 variant pseudovirus after three doses of BNT162b2 were comparable to the neutralization titers against the wild-type strain observed in sera from individuals who received two doses of BNT162b2 (GMT of 154 vs. 155).

Example 3: Additional Data for Neutralization of SARS-CoV-2 Omicron BA.1 Lineage (a.k.a. B.1.1.529) Pseudovirus by BNT162b2 Vaccine-Elicited Human Sera Further to the study and data as described in Example 2, a longitudinal analysis of neutralizing titers was also performed in an independent smaller subset of subjects. Sera drawn at 21 days after dose 2 exhibited a 19.6-fold reduction in GMT against the Omicron BA.1 variant compared to the Wuhan reference pseudovirus (FIG. 12; GMT of 6 vs. 118). Serum obtained from study participants just prior to receiving the third dose of BNT162b2 (at a median 251 days following dose 2) had considerably reduced neutralizing titers against the Wuhan pseudovirus (GMT of 14) while the Omicron BA.1-specific titers were below the limit of detection. The third dose of BNT162b2 resulted in a significant increase in neutralizing titers against the Wuhan pseudovirus (GMT of 254) and a >26.6-fold increase in neutralizing titers against Omicron BA.1 at 1 month after dose 3 compared to titers at 21 days after dose 2 (GMT of 160 vs. 6). In all 9 subjects reduced but effective neutralization of Omicron BA.1 was observed up to 3 months after the third dose (3.2-fold reduction compared to 1 month after dose 3; GMT of 50 vs. 160), whereas Wuhan-specific neutralizing GMTs remained stable.

In summary, a third dose of BNT162b2 boosts Omicron BA.1 neutralization capability to a level similar to the one observed after two doses against the Wuhan pseudovirus. Thus, the data indicate that providing a third dose of BNT162b2 can improve protection against infection with the Omicron BA.1 variant.

Example 4: Neutralization of Other SARS-CoV-2 Lineage Pseudovirus by BNT162b2 Vaccine-Elicited Human Sera As described in Example 2 and Example 3, each serum was also tested for its neutralizing antibody titer against Beta and Delta lineage spike protein pseudotyped VSV by a 50% neutralization assay ($pVNT_{50}$) (data not shown).

A recombinant replication-deficient VSV vector that encodes green fluorescent protein (GFP) and luciferase (Luc) instead of the VSV-glycoprotein (VSV-G) was pseudotyped with Wuhan-Hu-1 isolate SARS-CoV-2 spike (S) (GenBank: QHD43416.1), and a variant spike harbouring the mutations found in the S protein of the Beta lineage (mutations: L18F, D80A, D215G, R246I, Δ242-244, K417N, E484K, N501Y, D614G, A701V), and the Delta lineage (mutations: T19R, G142D, Δ157/158, K417N, L452R, T478K, D614G, P681R, D950N, K986P, V987P), according to published pseudotyping protocols.

For sera collected 21 days after a second dose of BNT162b2, $PVNT_{50}$ was reduced by approximately 6.7-fold (GMT of 24 vs 155) for the Beta variant and approximately 2.2-fold for the Delta variant (GMT of 73 vs 155) as compared to the Wuhan variant, but were significantly higher than the neutralization response against the delta variant. The third dose of BNT162b2 also increased neutralizing activity against Beta and Delta pseudoviruses, with GMTs of 279 and 413, respectively.

Example 5: T Cell Epitope Conservation in the Omicron BA.1 Spike Variant

In addition to humoral immunity, T-cell mediated immunity is another layer of defense, in particular for preventing severe COVID-19. Previous observations that efficacy against disease is already established about 12 days after the first dose of BNT162b2 before the second dose has been administered and prior to the onset of high neutralizing titers further highlights the potential protective role of the T cell response. Prior reports have shown that CD8 T cell responses in individuals vaccinated with BNT162b2 are polyepitopic.

To assess the risk of immune evasion of CD8+ T cell responses by Omicron BA.1, a set of HLA class I restricted T cell epitopes from the Wuhan spike protein sequence that were reported in the Immune Epitope Database to be immunogenic (IEDB, n=244) were investigated (the procedure used to identify these epitopes is described in the below paragraph). Despite the multitude of mutations in the Omicron BA.1 spike protein, 85.25% (n=208) of the described epitopes were not impacted on the amino acid sequence level, indicating that the targets of the vast majority of T cell responses elicited by BNT162b2 may still be conserved in the Omicron BA.1 variant (FIG. 13). Early laboratory studies confirm that CD8+ T cell recognition of Omicron epitopes are preserved in COVID-19 recovered individuals exposed early in the pandemic and that the Omicron BA.1 VOC has not evolved extensive T-cell escape mutations at this time.

To estimate the rate of nonsynonymous mutation in T cell epitopes in the spike glycoprotein, the Immune Epitope Database (www_iedb_org/) was used to obtain epitopes confirmed for T cell reactivity in experimental assays. The database was filtered using the following criteria: Organism: SARS-COV2; Antigen: Spike glycoprotein; Positive Assay; No B cell assays; No MHC assays; MHC Restriction Type: Class I; Host: *Homo sapiens* (human). The resulting table was filtered by removing epitopes that were "deduced from a reactive overlapping peptide pool", as well as epitopes longer than 14 amino acids in order to restrict the dataset to confirmed minimal epitopes only. Of the 251 unique epitope sequences obtained in this approach, 244 were found in the Wuhan strain Spike glycoprotein. Of these, 36 epitopes (14.75%) included a position reported to be mutated in Omicron by the sequence analysis disclosed herein. Results are summarized in FIG. 10. Also shown are the numbers of predicted MHC-I epitopes mutated in each of the Alpha, Beta, Gamma, Delta SARS-CoV-2 variants. FIG. 13 depicts the locations of the T cell epitopes within the Spike Protein, and indicates which epitopes are conserved or mutated in the Spike protein from the Omicron BA.1 variant.

Example 6: Exemplary Dosing Regimens

In some embodiments, compositions and methods disclosed herein can be used in accordance with an exemplary vaccination regimen as illustrated in FIG. 14.

Primary Dosing Regimens

In some embodiments, subjects are administered a primary dosing regimen. A primary dosing regimen can comprise one or more doses. For example, in some embodiments, a primary dosing regimen comprises a single dose ($PD_1$). In some embodiments a primary dosing regimen comprises a first dose ($PD_1$) and a second dose ($PD_2$). In some embodiments, a primary dosing regimen comprises a first dose, a second dose, and a third dose ($PD_3$). In some embodiments, a primary dosing regimen comprises a first dose, a second dose, a third dose, and one or more additional doses ($PD_n$) of any one of the pharmaceutical compositions described herein.

In some embodiments, $PD_1$ comprises administering 1 to 100 ug of RNA. In some embodiments, $PD_1$ comprises administering 1 to 60 ug of RNA In some embodiments, $PD_1$ comprises administering 1 to 50 ug of RNA. In some embodiments, PD1 comprises administering 1 to 30 ug of RNA. In some embodiments, $PD_1$ comprises administering about 3 ug of RNA. In some embodiments, $PD_1$ comprises administering about 5 ug of RNA. In some embodiments, $PD_1$ comprises administering about 10 ug of RNA. In some embodiments, $PD_1$ comprises administering about 15 ug of RNA. In some embodiments, $PD_1$ comprises administering about 20 ug of RNA. In some embodiments, $PD_1$ comprises administering about 30 ug of RNA. In some embodiments, $PD_1$ comprises administering about 50 ug of RNA. In some embodiments, $PD_1$ comprises administering about 60 ug of RNA.

In some embodiments, $PD_2$ comprises administering 1 to 100 ug of RNA. In some embodiments, $PD_2$ comprises administering 1 to 60 ug of RNA. In some embodiments, $PD_2$ comprises administering 1 to 50 ug of RNA. In some embodiments, $PD_2$ comprises administering 1 to 30 ug of RNA. In some embodiments, $PD_2$ comprises administering about 3 ug. In some embodiments, $PD_2$ comprises administering about 5 ug of RNA. In some embodiments, $PD_2$ comprises administering about 10 ug of RNA. In some embodiments, $PD_2$ comprises administering about 15 ug of RNA. In some embodiments, $PD_2$ comprises administering about 20 ug RNA. In some embodiments, $PD_2$ comprises administering about 30 ug of RNA. In some embodiments, $PD_2$ comprises administering about 50 ug of RNA. In some embodiments, $PD_2$ comprises administering about 60 ug of RNA.

In some embodiments, $PD_3$ comprises administering 1 to 100 ug of RNA. In some embodiments, $PD_3$ comprises administering 1 to 60 ug of RNA. In some embodiments, $PD_3$ comprises administering 1 to 50 ug of RNA. In some embodiments, $PD_3$ comprises administering 1 to 30 ug of RNA. In some embodiments, $PD_3$ comprises administering about 3 ug of RNA. In some embodiments, $PD_3$ comprises administering about 5 ug of RNA. In some embodiments, $PD_3$ comprises administering about 10 ug of RNA. In some embodiments, $PD_3$ comprises administering about 15 ug of RNA. In some embodiments, $PD_3$ comprises administering about 20 ug of RNA. In some embodiments, $PD_3$ comprises administering about 30 ug of RNA. In some embodiments, $PD_3$ comprises administering about 50 ug of RNA. In some embodiments, $PD_3$ comprises administering about 60 ug of RNA.

In some embodiments, $PD_n$ comprises administering 1 to 100 ug of RNA. In some embodiments, $PD_n$ comprises administering 1 to 60 ug of RNA. In some embodiments, $PD_n$ comprises administering 1 to 50 ug of RNA. In some embodiments, $PD_n$ comprises administering 1 to 30 ug of RNA. In some embodiments, $PD_n$ comprises administering about 3 ug of RNA. In some embodiments, $PD_n$ comprises administering about 5 ug of RNA. In some embodiments, $PD_n$ comprises administering about 10 ug of RNA. In some embodiments, $PD_n$ comprises administering about 15 ug of RNA. In some embodiments, $PD_n$ comprises administering about 20 ug of RNA. In some embodiments, $PD_n$ comprises administering about 30 ug of RNA. In some embodiments, $PD_n$ comprises administering about 50 ug of RNA. In some embodiments, $PD_n$ comprises administering about 60 ug of RNA.

In some embodiments, $PD_1$ comprises an RNA encoding a SARS-CoV-2 Spike protein or an immunogenic fragment thereof from the Wuhan strain. In some embodiments, $PD_1$ comprises an RNA encoding a Spike protein or an immunogenic fragment thereof from a SARS-CoV-2 strain that is prevalent and/or spreading rapidly in a relevant jurisdiction. In some embodiments, $PD_1$ comprises an RNA encoding a SARS-CoV-2 Spike protein or an immunogenic fragment thereof comprising one or more mutations from an alpha variant. In some embodiments, $PD_1$ comprises an RNA encoding a SARS-CoV-2 Spike protein or an immunogenic fragment thereof comprising one or more mutations from a delta variant. In some embodiments, $PD_1$ comprises an RNA encoding a SARS-CoV-2 Spike protein or an immunogenic fragment thereof comprising one or more mutations from a beta variant. In some embodiments, $PD_1$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant). In some embodiments, PD1 comprises an RNA encoding a SARS-CoV-2 Spike protein or an immunogenic fragment thereof from the Wuhan strain and one or more additional RNAs encoding a Spike protein or an immunogenic fragment thereof from a SARS-CoV-2 strain that is prevalent and/or spreading rapidly in a relevant jurisdiction. In some embodiments, $PD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an alpha variant. In some embodiments, $PD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $PD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, PD1 comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $PD_2$ comprises an RNA encoding a SARS-CoV-2 Spike protein or an immunogenic fragment thereof from the Wuhan strain. In some embodiments, $PD_2$ comprises an RNA encoding a Spike protein or an immunogenic fragment thereof from a SARS-CoV-2 strain that is prevalent and/or spreading rapidly in a relevant jurisdiction. In some embodiments, $PD_2$ comprises an RNA encoding a SARS-CoV-2 Spike protein or an immunogenic fragment thereof comprising one or more mutations from an alpha variant. In some embodiments, $PD_2$ comprises an RNA encoding a SARS-CoV-2 Spike protein or an immunogenic fragment thereof comprising one or more mutations from a delta variant. In some embodiments, $PD_2$ comprises an RNA encoding a SARS-CoV-2 Spike protein or an immunogenic fragment thereof comprising one or more mutations from a beta variant. In some embodiments, $PD_2$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant). In some embodiments, $PD_2$ comprises an RNA encoding a SARS-CoV-2 Spike protein or an immunogenic fragment thereof from the Wuhan strain and one or more additional RNAs encoding a Spike protein or an immunogenic fragment thereof from a SARS-CoV-2 strain that is prevalent and/or spreading rapidly in a relevant jurisdiction. In some embodiments, $PD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an alpha variant. In some embodiments, $PD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $PD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $PD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $PD_3$ comprises an RNA encoding a SARS-CoV-2 Spike protein or an immunogenic fragment thereof from the Wuhan strain. In some embodiments, $PD_3$ comprises an RNA encoding a Spike protein or an immunogenic fragment thereof from a SARS-CoV-2 strain that is prevalent and/or spreading rapidly in a relevant jurisdiction. In some embodiments, $PD_3$ comprises an RNA encoding a SARS-CoV-2 Spike protein or an immunogenic fragment thereof comprising one or more mutations from an alpha variant. In some embodiments, $PD_3$ comprises an RNA encoding a SARS-CoV-2 Spike protein or an immunogenic fragment thereof comprising one or more mutations from a delta variant. In some embodiments, $PD_3$ comprises an RNA encoding a SARS-CoV-2 Spike protein or an immunogenic fragment thereof comprising one or more mutations from a beta variant. In some embodiments, $PD_3$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant). In some embodiments, $PD_3$ comprises an RNA encoding a SARS-CoV-2 Spike protein or an immunogenic fragment thereof from the Wuhan strain and one or more additional RNAs encoding a Spike protein or an immunogenic fragment thereof from a SARS-CoV-2 strain that is prevalent and/or spreading rapidly in a relevant jurisdiction. In some embodiments, $PD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an alpha variant. In some embodiments, $PD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $PD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $PD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $PD_n$ comprises an RNA encoding a SARS-CoV-2 Spike protein or an immunogenic fragment thereof from the Wuhan strain. In some embodiments, $PD_n$ comprises an RNA encoding a Spike protein or an immunogenic fragment thereof from a SARS-CoV-2 strain that is prevalent and/or spreading rapidly in a relevant jurisdiction. In some embodiments, $PD_n$ comprises an RNA encoding a SARS-CoV-2 Spike protein or an immunogenic fragment thereof comprising one or more mutations from an alpha variant. In some embodiments, $PD_n$ comprises an RNA encoding a SARS-CoV-2 Spike protein or an immunogenic fragment thereof comprising one or more mutations from a delta variant. In some embodiments, $PD_n$ comprises an RNA encoding a SARS-CoV-2 Spike protein or an immunogenic fragment thereof comprising one or more mutations from a beta variant. In some embodiments, $PD_n$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant). In some embodiments, $PD_n$ comprises an RNA encoding a SARS-CoV-2 Spike protein or an immunogenic fragment thereof from the Wuhan strain and one or more additional RNAs encoding a Spike protein or an immunogenic fragment thereof from a SARS-CoV-2 strain that is prevalent and/or spreading rapidly in a relevant jurisdiction. In some embodiments, $PD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an alpha variant. In some embodiments, $PD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $PD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $PD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $PD_1$, $PD_2$, $PD_3$, and $PD_n$ can each independently comprise a plurality of (e.g., at least two) mRNA compositions described herein. In some embodiments PD1, $PD_2$, $PD_3$, and $PD_n$ can each independently comprise a first and a second mRNA composition. In some embodiments, at least one of a plurality of mRNA compositions comprises BNT162b2 (e.g., as described herein). In some embodiments, at least one of a plurality of mRNA compositions comprises an mRNA encoding a SARS-CoV-2 S protein or an immunogenic fragment thereof from a different SARS-CoV-2 variant. In some embodiments, at least one of a plurality of mRNA compositions comprises an mRNA encoding a SARS-CoV-2 S protein or an immunogenic fragment thereof from a Wuhan strain of SARS-CoV-2. In some embodiments, at least one of a plurality of mRNA compositions comprises an RNA encoding a SARS-CoV-2 S protein or an immunogenic fragment thereof comprising one or more mutations from a variant that is prevalent and/or spreading rapidly in a relevant jurisdiction. In some embodiments, at least one of a plurality of mRNA compositions comprises an mRNA encoding a SARS-CoV-2 S protein or an immunogenic fragment thereof comprising one or more mutations from an alpha variant. In some embodiments, at least one of a plurality of mRNA compositions comprises an mRNA encoding a SARS-CoV-2 S protein or an immunogenic fragment thereof comprising one or more mutations from a delta variant. In some embodiments, at least one of a plurality of mRNA compositions comprises an mRNA encoding a SARS-CoV-2 S protein or an immunogenic fragment thereof comprising one or more mutations from an Omicron variant (e.g., a BA.4/5, BA.1, BA.2, XBB, XBB.1, or BQ.1 Omicron variant).

In some embodiments, a plurality of mRNA compositions given in PD1, $PD_2$, $PD_3$,and/or $PD_n$ can each independently comprise at least two different mRNA constructs (e.g., differing in at protein-encoding sequences). For example, in some embodiments a plurality of mRNA compositions given in $PD_1$, $PD_2$, $PD_3$, and/or $PD_n$ can each independently comprise an mRNA encoding a SARS-CoV-2 S protein or an immunogenic fragment thereof from a Wuhan strain of SARS-CoV-2 and an mRNA encoding a SARS-CoV-2 S protein or an immunogenic fragment thereof comprising one or more mutations from a variant that is prevalent and/or spreading rapidly in a relevant jurisdiction. In some embodiments a plurality of mRNA compositions given in $PD_1$, $PD_2$, $PD_3$, and/or $PD_n$ can each independently comprise an mRNA encoding a SARS-CoV-2 S protein or an immunogenic fragment thereof derived from a Wuhan strain of SARS-CoV-2 and an mRNA encoding a SARS-CoV-2 S protein or an immunogenic fragment thereof comprising one or more mutations from a variant that is prevalent and/or spreading rapidly in a relevant jurisdiction. In some such embodiments, a variant can be an alpha variant. In some such embodiments, a variant can be a delta variant. In some such embodiments a variant can be an Omicron variant (e.g., a BA.4/5, BA.1, BA.2, XBB, XBB.1, or BQ.1 Omicron variant).

In some embodiments, each of a plurality of mRNA compositions given in $PD_1$, $PD_2$, $PD_3$, and/or $PD_n$ can independently comprise at least two mRNAs, each encoding a SARS-CoV-2 S protein or an immunogenic fragment thereof comprising one or more mutations from a distinct variant that is prevalent and/or spreading rapidly in a relevant jurisdiction. In some embodiments, each of a plurality of mRNA compositions given in $PD_1$, $PD_2$, $PD_3$, and/or $PD_n$ can independently comprise an mRNA encoding a SARS-CoV-2 S protein or an immunogenic fragment thereof from an alpha variant and an mRNA encoding a SARS-CoV-2 S protein or an immunogenic fragment thereof comprising one or more mutations from a delta variant. In some embodiments, each of a plurality of mRNA compositions given in PD1, $PD_2$, $PD_3$, and/or $PD_n$ can independently comprise an mRNA encoding a SARS-CoV-2 S protein or an immunogenic fragment thereof from an alpha variant and an mRNA encoding a SARS-CoV-2 S protein or an immunogenic fragment thereof comprising one or more mutations from an Omicron variant (e.g., a BA.4/5, BA.1, BA.2, XBB, XBB.1, or BQ.1 Omicron variant). In some embodiments, each of a plurality of mRNA compositions given in PD1, $PD_2$, $PD_3$, and/or $PD_n$ can independently comprise an mRNA encoding a SARS-CoV-2 S protein or an immunogenic fragment thereof from a delta variant and an mRNA encoding a SARS-CoV-2 S protein or an immunogenic fragment thereof comprising one or more mutations from an Omicron variant (e.g., a BA.4/5, BA.1, BA.2, XBB, XBB.1, or BQ.1 Omicron variant).

In some embodiments, $PD_1$, $PD_2$, $PD_3$, and/or $PD_n$ each comprise a plurality of mRNA compositions, wherein each mRNA composition is separately administered to a subject. For example, in some embodiments each mRNA composition is administered via intramuscular injection at different injection sites. For example, in some embodiments, a first and second mRNA composition given in $PD_1$, $PD_2$, $PD_3$, and/or $PD_n$ are separately administered to different arms of a subject via intramuscular injection.

In some embodiments, $PD_1$, $PD_2$, $PD_3$, and/or $PD_n$ comprise administering a plurality of RNA molecules, wherein each RNA molecule encodes a Spike protein comprising mutations from a different SARS-CoV-2 variant, and wherein the plurality of RNA molecules are administered to the subject in a single formulation. In some embodiments, the single formulation comprises an RNA encoding a Spike protein or an immunogenic variant thereof from the Wuhan strain and an RNA encoding a SARS-CoV-2 Spike protein or an immunogenic fragment thereof comprising one or more mutations from an alpha variant. In some embodiments, the single formulation comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, the single formulation comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, the single formulation comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, the length of time between PD1 and $PD_2$ ($PI_1$) is at least about 1 week, at least about 2 weeks, at least about 3 weeks, or at least about 4 weeks. In some embodiments, $PI_1$ is about 1 week to about 12 weeks. In some embodiments, $PI_1$ is about 1 week to about 10 weeks. In some embodiments, $PI_1$ is about 2 weeks to about 10 weeks. In some embodiments, $PI_1$ is about 2 weeks to about 8 weeks. In some embodiments, $PI_1$ is about 3 weeks to about 8 weeks. In some embodiments, $PI_1$ is about 4 weeks to about 8 weeks. In some embodiments, $PI_1$ is about 6 weeks to about 8 weeks. In some embodiments $PI_1$ is about 3 to about 4 weeks. In some embodiments, $PI_1$ is about 1 week. In some embodiments, P1 is about 2 weeks. In some embodiments, $PI_1$ is about 3 weeks. In some embodiments, $PI_1$ is about 4 weeks. In some embodiments, $PI_1$ is about 5 weeks. In some embodiments, $PI_1$ is about 6 weeks. In some embodiments, $PI_1$ is about 7 weeks. In some embodiments, $PI_1$ is about 8 weeks. In some embodiments, $PI_1$ is about 9 weeks. In some embodiments, $PI_1$ is about 10 weeks. In some embodiments, $PI_1$ is about 11 weeks. In some embodiments, $PI_1$ is about 12 weeks.

In some embodiments, the length of time between $PD_2$ and $PD_3$ ($PI_2$) is at least about 1 week, at least about 2 weeks, or at least about 3 weeks. In some embodiments, $PI_2$ is about 1 week to about 12 weeks. In some embodiments, $PI_2$ is about 1 week to about 10 weeks. In some embodiments, $PI_2$ is about 2 weeks to about 10 weeks. In some embodiments, $PI_2$ is about 2 weeks to about 8 weeks. In some embodiments, $PI_2$ is about 3 weeks to about 8 weeks. In some embodiments, $PI_2$ is about 4 weeks to about 8 weeks. In some embodiments, $PI_2$ is about 6 weeks to about 8 weeks. In some embodiments $PI_2$ is about 3 to about 4 weeks. In some embodiments, $PI_2$ is about 1 week. In some embodiments, $PI_2$ is about 2 weeks. In some embodiments, $PI_2$ is about 3 weeks. In some embodiments, $PI_2$ is about 4 weeks. In some embodiments, $PI_2$ is about 5 weeks. In some embodiments, $PI_2$ is about 6 weeks. In some embodiments, $PI_2$ is about 7 weeks. In some embodiments, $PI_2$ is about 8 weeks. In some embodiments, $PI_2$ is about 9 weeks. In some embodiments, $PI_2$ is about 10 weeks. In some embodiments, $PI_2$ is about 11 weeks. In some embodiments, $PI_2$ is about 12 weeks.

In some embodiments, the length of time between $PD_3$ and a subsequent dose that is part of the Primary Dosing Regimen, or between doses for any dose beyond $PD_3$ ($PI_n$) is each separately and independently selected from: about 1 week or more, about 2 weeks or more, or about 3 weeks or more. In some embodiments, $PI_n$ is about 1 week to about 12 weeks. In 20 some embodiments, $PI_n$ is about 1 week to about 10 weeks. In some embodiments, $PI_n$ is about 2 weeks to about 10 weeks. In some embodiments, $PI_n$ is about 2 weeks to about 8 weeks. In some embodiments, $PI_n$ is about 3 weeks to about 8 weeks. In some embodiments, $PI_c$ is about 4 weeks to about 8 weeks. In some embodiments, $PI_n$ is about 6 weeks to about 8 weeks. In some embodiments $PI_n$ is about 3 to about 4 weeks. In some embodiments, $PI_2$ is about 1 week. In some embodiments, $PI_n$ is about 2 weeks. In some embodiments, $PI_n$ is about 3 weeks. In some embodiments, $PI_n$ is about 4 weeks. In some embodiments, $PI_n$ is about 5 weeks. In some embodiments, $PI_n$ is about 6 weeks. In some embodiments, $PI_n$ is about 7 weeks. In some embodiments, $PI_n$ is about 8 weeks. In some embodiments, $PI_n$ is about 9 weeks. In some embodiments, $PI_a$ is about 10 weeks. In some embodiments, $PI_n$ is about 11 weeks. In some embodiments, $PI_n$ is about 12 weeks.

In some embodiments, one or more compositions adminstered in $PD_1$ are formulated in a Tris buffer. In some embodiments, one or more compositions administered in $PD_2$ are formulated in a Tris buffer. In some embodiments, one or more compositions administering in $PD_3$ are formulated in a Tris buffer. In some embodiments, one or more compositions administered in $PD_n$ are formulated in a Tris buffer.

In some embodiments, the primary dosing regimen comprises administering two or more mRNA compositions described herein, and at least two of the mRNA compositions have different formulations. In some embodiments, the primary dosing regimen comprises $PD_1$ and $PD_2$, where $PD_1$ comprises administering an mRNA formulated in a Tris buffer and $PD_2$ comprises administering an mRNA formulated in a PBS buffer. In some embodiments, the primary dosing regimen comprises $PD_1$ and $PD_2$, where $PD_1$ comprises administering an mRNA formulated in a PBS buffer and $PD_2$ comprises administering an mRNA formulated in a Tris buffer.

In some embodiments, one or more mRNA compositions given in $PD_1$, $PD_2$, $PD_3$, and/or $PD_n$ can be administered in combination with another vaccine. In some embodiments, another vaccine is for a disease that is not COVID-19. In some embodiments, the disease is one that increases deleterious effects of SARS-CoV-2 when a subject is coinfected with the disease and SARS-CoV-2. In some embodiments, the disease is one that increases the transmission rate of SARS-CoV-2 when a subject is coinfected with the disease and SARS-CoV-2. In some embodiments, another vaccine is a different commerically available vaccine. In some embodiments, the different commercially available vaccine is an RNA vaccine. In some embodiments, the different commercially available vaccine is a polypeptide-based vaccine. In some embodiments, another vaccine (e.g., as described herein) and one or more mRNA compositions given in $PD_1$, $PD_2$, $PD_3$, and/or $PD_n$ are separately administered, for example, in some embodiments via intramuscular injection, at different injection sites. For example, in some embodiments, an influenza vaccine and one or more SARS-CoV-2 mRNA compositions described herein given in $PD_1$, $PD_2$, $PD_3$, and/or $PD_n$ are separately administered to different arms of a subject via intramuscular injection.

Booster Dosing Regimens

In some embodiments, methods of vaccination disclosed herein comprise one or more Booster Dosing Regimens. The Booster Dosing Regimens disclosed herein comprise one or more doses. In some embodiments, a Booster Dosing Regimen is administered to patients who have been administered a Primary Dosing Regimen (e.g., as described herein). In some embodiments a Booster Dosing Regimen is administered to patients who have not received a pharmaceutical composition disclosed herein. In some embodiments a Booster Dosing Regimen is administered to patients who have been previously vaccinated with a COVID-19 vaccine that is different from the vaccine administered in a Primary Dosing Regimen.

In some embodiments, the length of time between the Primary Dosing Regimen and the Booster Dosing Regimen is at least 1 week, at least 2 weeks, at least 3 weeks, at least 4 weeks, at least 5 weeks, at least 6 weeks, at least 7 weeks, at least 8 weeks, at least 9 weeks, at least 10 weeks, at least 11 weeks, at least 12 weeks, at least 2 months, at least 3 months, at least 4 months, at least 5 months, at least 6 months, at least 7 months, at least 8 months, at least 9 months, at least 10 months, at least 11 months, or at least 12 months or longer. In some embodiments, the length of time between the Primary Dosing Regimen and the Booster Dosing Regimen is about 1 month. In some embodiments, the length of time between the Primary Dosing Regimen and the Booster Dosing Regimen is at least about 2 months. In some embodiments, the length of time between the Primary Dosing Regimen and the Booster Dosing Regimen is at least about 3 months. In some embodiments, the length of time between the Primary Dosing Regimen and the Booster Dosing Regimen is at least about 4 months. In some embodiments, the length of time between the Primary Dosing Regimen and the Booster Dosing Regimen is at least about 5 months. In some embodiments, the length of time between the Primary Dosing Regimen and the Booster Dosing Regimen is at least about 6 months. In some embodiments, the length of time between the Primary Dosing Regimen and the Booster Dosing Regimen is from about 1 month to about 48 months. In some embodiments, the length of time between the Primary Dosing Regimen and the Booster Dosing Regimen is from about 1 month to about 36 months. In some embodiments, the length of time between the primary dosing regimen and the Booster Dosing Regimen is from about 1 month to about 24 months. In some embodiments, the length of time between the Primary Dosing Regimen and the Booster Dosing Regimen is from about 2 months to about 24 months. In some embodiments, the length of time between the Primary Dosing Regimen and the Booster Dosing Regimen is from about 3 months to about 24 months. In some embodiments, the length of time between the primary dosing regimen and the Booster Dosing Regimen is from about 3 months to about 18 months. In some embodiments, the length of time between the primary dosing regimen and the Booster Dosing Regimen is from about 3 months to about 12 months. In some embodiments, the length of time between the primary dosing regimen and the Booster Dosing Regimen is from about 6 months to about 12 months. In some embodiments, the length of time between the Primary Dosing Regimen and the Booster Dosing Regimen is from about 3 months to about 9 months. In some embodiments, the length of time between the Primary Dosing Regimen and the Booster Dosing Regimen is from about 5 months to about 7 months. In some embodiments, the length of time between the Primary Dosing Regimen and the Booster Dosing Regimen is about 6 months.

In some embodiments, subjects are administered a Booster Dosing Regimen. A Booster dosing regimen can comprise one or more doses. For example, in some embodiments, a Booster Dosing Regimen comprises a single dose ($BD_1$). In some embodiments a Booster Dosing Regimen comprises a first dose ($BD_1$) and a second dose ($BD_2$). In some embodiments, a Booster Dosing Regimen comprises a first dose, a second dose, and a third dose ($BD_3$). In some embodiments, a Booster Dosing Regimen comprises a first dose, a second dose, a third dose, and one or more additional doses ($BD_n$) of any one of the pharmaceutical compositions described herein.

In some embodiments, $BD_1$ comprises administering 1 to 100 ug of RNA. In some embodiments, $BD_1$ comprises administering 1 to 60 ug of RNA. In some embodiments, $BD_1$ comprises administering 1 to 50 ug of RNA. In some embodiments, $BD_1$ comprises administering 1 to 30 ug of RNA. In some embodiments, $BD_1$ comprises administering about 3 ug of RNA. In some embodiments, $BD_1$ comprises administering about 5 ug of RNA. In some embodiments, $BD_1$ comprises administering about 10 ug of RNA. In some embodiments, $BD_1$ comprises administering about 15 ug of RNA. In some embodiments, $BD_1$ comprises administering about 20 ug of RNA. In some embodiments, $BD_1$ comprises administering about 30 ug of RNA. In some embodiments, $BD_1$ comprises administering about 50 ug of RNA. In some embodiments, $BD_1$ comprises administering about 60 ug of RNA.

In some embodiments, $BD_2$ comprises administering 1 to 100 ug of RNA. In some embodiments, $BD_2$ comprises administering 1 to 60 ug of RNA. In some embodiments, $BD_2$ comprises administering 1 to 50 ug of RNA. In some embodiments, $BD_2$ comprises administering 1 to 30 ug of RNA. In some embodiments, $BD_2$ comprises administering about 3 ug. In some embodiments, $BD_2$ comprises administering about 5 ug of RNA. In some embodiments, $BD_2$ comprises administering about 10 ug of RNA. In some embodiments, $BD_2$ comprises administering about 15 ug of RNA. In some embodiments, $BD_2$ comprises administering about 20 ug RNA. In some embodiments, $BD_2$ comprises administering about 30 ug of RNA. In some embodiments, $BD_2$ comprises administering about 50 ug of RNA. In some embodiments, $BD_2$ comprises administering about 60 ug of RNA.

In some embodiments, $BD_3$ comprises administering 1 to 100 ug of RNA. In some embodiments, $BD_3$ comprises administering 1 to 60 ug of RNA. In some embodiments, $BD_3$ comprises administering 1 to 50 ug of RNA. In some embodiments, $BD_3$ comprises administering 1 to 30 ug of RNA. In some embodiments, $BD_3$ comprises administering about 3 ug of RNA. In some embodiments, $BD_3$ comprises administering about 5 ug of RNA. In some embodiments, $BD_3$ comprises administering about 10 ug of RNA. In some embodiments, $BD_3$ comprises administering about 15 ug of RNA. In some embodiments, $BD_3$ comprises administering about 20 ug of RNA. In some embodiments, $BD_3$ comprises administering about 30 ug of RNA. In some embodiments, $BD_3$ comprises administering about 50 ug of RNA. In some embodiments, $BD_3$ comprises administering about 60 ug of RNA.

In some embodiments, $BD_n$ comprises administering 1 to 100 ug of RNA. In some embodiments, $BD_n$ comprises administering 1 to 60 ug of RNA. In some embodiments, $BD_n$ comprises administering 1 to 50 ug of RNA. In some embodiments, $BD_n$ comprises administering 1 to 30 ug of RNA. In some embodiments, $BD_n$ comprises administering about 3 ug of RNA. In some embodiments, $BD_n$ comprises administering about 5 ug of RNA. In some embodiments, $BD_n$ comprises administering about 10 ug of RNA. In some embodiments, $BD_n$ comprises administering about 15 ug of RNA. In some embodiments, $BD_n$ comprises administering about 20 ug of RNA. In some embodiments, $BD_n$ comprises administering about 30 ug of RNA. In some embodiments, $BD_n$ comprises administering about 60 ug of RNA. In some embodiments, $BD_n$ comprises administering about 50 ug of RNA.

In some embodiments, $BD_1$ comprises an RNA encoding a SARS-CoV-2 Spike protein or an immunogenic fragment thereof from the Wuhan strain. In some embodiments, $BD_1$ comprises an RNA encoding a Spike protein or an immunogenic fragment thereof from a SARS-CoV-2 strain that is prevalent and/or spreading rapidly in a relevant jurisdiction. In some embodiments, $BD_1$ comprises an RNA encoding a SARS-CoV-2 Spike protein or an immunogenic fragment thereof comprising one or more mutations from an alpha variant. In some embodiments, $BD_1$ comprises an RNA encoding a SARS-CoV-2 Spike protein or an immunogenic fragment thereof comprising one or more mutations from a delta variant. In some embodiments, $BD_1$ comprises an RNA encoding a SARS-CoV-2 Spike protein or an immunogenic fragment thereof comprising one or more mutations from a beta variant. In some embodiments, $BD_1$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $BD_1$ comprises an RNA encoding a SARS-CoV-2 Spike protein or an immunogenic fragment thereof from the Wuhan strain and one or more RNA encoding a Spike protein or an immunogenic fragment thereof from a SARS-CoV-2 strain that is prevalent and/or spreading rapidly in a relevant jurisdiction. In some embodiments, $BD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a alpha variant. In some embodiments, $BD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $BD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $BD_1$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $BD_2$ comprises an RNA encoding a SARS-CoV-2 Spike protein or an immunogenic fragment thereof from the Wuhan strain. In some embodiments, $BD_2$ comprises an RNA encoding a Spike protein or an immunogenic fragment thereof from a SARS-CoV-2 strain that is prevalent and/or spreading rapidly in a relevant jurisdiction. In some embodiments, $BD_2$ comprises an RNA encoding a SARS-CoV-2 Spike protein or an immunogenic fragment thereof comprising one or more mutations from an alpha variant. In some embodiments, $BD_2$ comprises an RNA encoding a SARS-CoV-2 Spike protein or an immunogenic fragment thereof comprising one or more mutations from a delta variant. In some embodiments, $BD_2$ comprises an RNA encoding a SARS-CoV-2 Spike protein or an immunogenic fragment thereof comprising one or more mutations from a beta variant. In some embodiments, $BD_2$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant). In some embodiments, $BD_2$ comprises an RNA encoding a SARS-CoV-2 Spike protein or an immunogenic fragment thereof from the Wuhan strain and one or more RNA encoding a Spike protein or an immunogenic fragment thereof from a SARS-CoV-2 strain that is prevalent and/or spreading rapidly in a relevant jurisdiction. In some embodiments, $BD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a alpha variant. In some embodiments, $BD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $BD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $BD_2$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $BD_3$ comprises an RNA encoding a SARS-CoV-2 Spike protein or an immunogenic fragment thereof from the Wuhan strain. In some embodiments, $BD_3$ comprises an RNA encoding a Spike protein or an immunogenic fragment thereof from a SARS-CoV-2 strain that is prevalent and/or spreading rapidly in a relevant jurisdiction. In some embodiments, $BD_3$ comprises an RNA encoding a SARS-CoV-2 Spike protein or an immunogenic fragment thereof comprising one or more mutations from an alpha variant. In some embodiments, $BD_3$ comprises an RNA encoding a SARS-CoV-2 Spike protein or an immunogenic fragment thereof comprising one or more mutations from a delta variant. In some embodiments, $BD_3$ comprises an RNA encoding a SARS-CoV-2 Spike protein or an immunogenic fragment thereof comprising one or more mutations from a beta variant. In some embodiments, $BD_3$ comprises an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $BD_3$ comprises an RNA encoding a SARS-CoV-2 Spike protein or an immunogenic fragment thereof from the Wuhan strain and one or more RNA encoding a Spike protein or an immunogenic fragment thereof from a SARS-CoV-2 strain that is prevalent and/or spreading rapidly in a relevant jurisdiction. In some embodiments, $BD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a alpha variant. In some embodiments, $BD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $BD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $BD_3$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $BD_n$ comprises an RNA encoding a SARS-CoV-2 Spike protein or an immunogenic fragment thereof from the Wuhan strain. In some embodiments, $BD_n$ comprises an RNA encoding a Spike protein or an immunogenic fragment thereof from a SARS-CoV-2 strain that is prevalent and/or spreading rapidly in a relevant jurisdiction. In some embodiments, $BD_n$ comprises an RNA encoding a SARS-CoV-2 Spike protein or an immunogenic fragment thereof comprising one or more mutations from an alpha variant. In some embodiments, $BD_n$ comprises an RNA encoding a SARS-CoV-2 Spike protein or an immunogenic fragment thereof comprising one or more mutations from a delta variant. In some embodiments, $BD_n$ comprises an RNA encoding a SARS-CoV-2 Spike protein or an immunogenic fragment thereof comprising one or more mutations from a beta variant. In some embodiments, $BD_n$ comprises an RNA encoding a SARS-CoV-2 Spike protein or an immunogenic fragment thereof comprising one or more mutations from an Omicron variant(e.g., a BA.4/5, BA.1, BA.2, XBB, XBB.1, or BQ.1 Omicron variant).

In some embodiments, $BD_n$ comprises an RNA encoding a SARS-CoV-2 Spike protein or an immunogenic fragment thereof from the Wuhan strain and one or more RNA encoding a Spike protein or an immunogenic fragment thereof from a SARS-CoV-2 strain that is prevalent and/or spreading rapidly in a relevant jurisdiction, In some embodiments, $BD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a alpha variant. In some embodiments, $BD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a delta variant. In some embodiments, $BD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from a beta variant. In some embodiments, $BD_n$ comprises an RNA encoding a SARS-CoV-2 Spike protein or an immunogenic fragment thereof from the Wuhan strain and an RNA encoding a SARS-CoV-2 Spike protein or an immunogenic fragment thereof comprising one or more mutations from an Omicron variant (e.g., a BA.4/5, BA.1, BA.2, XBB, XBB.1, or BQ.1 Omicron variant).

In some embodiments, $BD_1$, $BD_2$, $BD_3$, and $BD_n$ can each independently comprise a plurality of (e.g., at least two) mRNA compositions described herein. In some embodiments $BD_1$, $BD_2$, $BD_3$, and $BD_n$ can each independently comprise a first and a second mRNA composition. In some embodiments, $BD_1$, $BD_2$, $BD_3$, and $BD_n$ can each independently comprise a plurality of (e.g., at least two) mRNA compositions, wherein, at least one of the plurality of mRNA compositions comprises BNT162b2 (e.g., as described herein). In some embodiments, at least one of a plurality of mRNA compositions comprises an mRNA encoding a SARS-CoV-2 S protein or an immunogenic fragment thereof from a different SARS-CoV-2 variant (e.g., a variant that is prevalent or rapidly spreading in a relevant jurisdiction, e.g., a variant disclosed herein). In some embodiments, at least one of a plurality of mRNA compositions comprises an mRNA encoding a SARS-CoV-2 S protein or an immunogenic fragment thereof from a Wuhan strain of SARS-CoV-2. In some embodiments, at least one of a plurality of mRNA compositions comprises an RNA encoding a SARS-CoV-2 S protein or an immunogenic fragment thereof comprising one or more mutations from a variant that is prevalent and/or spreading rapidly in a relevant jurisdiction. In some embodiments, at least one of a plurality of mRNA compositions comprises an mRNA encoding a SARS-CoV-2 S protein or an immunogenic fragment thereof comprising one or more mutations from an alpha variant. In some embodiments, at least one of a plurality of mRNA compositions comprises an mRNA encoding a SARS-CoV-2 S protein or an immunogenic fragment thereof comprising one or more mutations from a delta variant. In some embodiments, at least one of a plurality of mRNA compositions comprises an mRNA encoding a SARS-CoV-2 S protein or an immunogenic fragment thereof comprising one or more mutations from an Omicron variant (e.g., a BA.4/5, BA.1, BA.2, XBB, XBB.1, or BQ.1 Omicron variant).

In some embodiments, a plurality of mRNA compositions given in $BD_1$, $BD_2$, $BD_3$, and/or $BD_n$ can each independently comprise at least two different mRNA constructs (e.g., mRNA constructs having differing protein-encoding sequences). For example, in some embodiments a plurality of mRNA compositions given in $BD_1$, $BD_2$, $BD_3$, and/or $BD_n$ can each independently comprise an mRNA encoding a SARS-CoV-2 S protein or an immunogenic fragment thereof from a Wuhan strain of SARS-CoV-2 and an mRNA encoding a SARS-CoV-2 S protein or an immunogenic fragment thereof comprising one or more mutations from a variant that is prevalent and/or spreading rapidly in a relevant jurisdiction. In some embodiments a plurality of mRNA compositions given in $BD_1$, $BD_2$, $BD_3$, and/or $BD_n$ can each independently comprise an mRNA encoding a SARS-CoV-2 S protein or an immunogenic fragment thereof derived from a Wuhan strain of SARS-CoV-2 and an mRNA encoding a SARS-CoV-2 S protein or an immunogenic fragment thereof comprising one or more mutations from a variant that is prevalent and/or spreading rapidly in a relevant jurisdiction. In some such embodiments, a variant can be an alpha variant. In some such embodiments, a variant can be a delta variant. In some such embodiments a variant can be an Omicron variant (e.g., a BA.4/5, BA.1, BA.2, XBB, XBB.1, or BQ.1 Omicron variant).

In some embodiments, a plurality of mRNA compositions given in $BD_1$, $BD_2$, $BD_3$, and/or $BD_n$ can each independently comprise at least two mRNAs each encoding a SARS-CoV-2 S protein or an immunogenic fragment thereof comprising one or more mutations from a distinct variant that is prevalent and/or spreading rapidly in a relevant jurisdiction. In some embodiments a plurality of mRNA compositions given in $BD_1$, $BD_2$, $BD_3$, and/or $BD_n$ can each independently comprise an mRNA encoding a SARS-CoV-2 S protein or an immunogenic fragment thereof from an alpha variant and an mRNA encoding a SARS-CoV-2 S protein or an immunogenic fragment thereof comprising one or more mutations from a delta variant. In some embodiments a plurality of mRNA compositions given in $BD_1$, $BD_2$, $BD_3$, and/or $BD_n$ can each independently comprise an mRNA encoding a SARS-CoV-2 S protein or an immunogenic fragment thereof from an alpha variant and an mRNA encoding a SARS-CoV-2 S protein or an immunogenic fragment thereof comprising one or more mutations from an Omicron variant (e.g., a BA.4/5, BA.1, BA.2, XBB, XBB.1, or BQ.1 Omicron variant). In some embodiments a plurality of mRNA compositions given in $BD_1$, $BD_2$, $BD_3$, and/or $BD_n$ can each independently comprise an mRNA encoding a SARS-CoV-2 S protein or an immunogenic fragment thereof from a delta variant and an mRNA encoding a SARS-CoV-2 S protein or an immunogenic fragment thereof comprising one or more mutations from an Omicron variant (e.g., a BA.4/5, BA.1, BA.2, XBB, XBB.1, or BQ.1 Omicron variant).

In some embodiments, a plurality of mRNA compositions given in $BD_1$, $BD_2$, $BD_3$,and/or $BD_n$ are separately administered to a subject, for example, in some embodiments via intramuscular injection, at different injection sites. For example, in some embodiments, a first and second mRNA composition given in $BD_1$, $BD_2$, $BD_3$, and/or $BD_n$ are separately administered to different arms of a subject via intramuscular injection.

In some embodiments, the length of time between $BD_1$ and $BD_2$ (BI) is at least about 1 week, at least about 2 weeks, at least about 3 weeks, or at least about 4 weeks. In some embodiments, $BI_1$ is about 1 week to about 12 weeks. In some embodiments, $BI_1$ is about 1 week to about 10 weeks. In some embodiments, $BI_1$ is about 2 weeks to about 10 weeks. In some embodiments, $BI_1$ is about 2 weeks to about 8 weeks. In some embodiments, $BI_1$ is about 3 weeks to about 8 weeks. In some embodiments, $BI_1$ is about 4 weeks to about 8 weeks. In some embodiments, $BI_1$ is about 6 weeks to about 8 weeks. In some embodiments $BI_1$ is about 3 to about 4 weeks. In some embodiments, $BI_1$ is about 1 week. In some embodiments, $BI_1$ is about 2 weeks. In some embodiments, $BI_1$ is about 3 weeks. In some embodiments, $BI_1$ is about 4 weeks. In some embodiments, $BI_1$ is about 5 weeks. In some embodiments, $BI_1$ is about 6 weeks. In some embodiments, $BI_1$ is about 7 weeks. In some embodiments, $BI_1$ is about 8 weeks. In some embodiments, $BI_1$ is about 9 weeks. In some embodiments, $BI_1$ is about 10 weeks.

In some embodiments, the length of time between $BD_2$ and $BD_3$ ($BI_2$) is at least about 1 week, at least about 2 weeks, or at least about 3 weeks. In some embodiments, B12 is about 1 week to about 12 weeks. In some embodiments, $BI_2$ is about 1 week to about 10 weeks. In some embodiments, $BI_2$ is about 2 weeks to about 10 weeks. In some embodiments, $BI_2$ is about 2 weeks to about 8 weeks. In some embodiments, $BI_2$ is about 3 weeks to about 8 weeks. In some embodiments, $BI_2$ is about 4 weeks to about 8 weeks. In some embodiments, B12 is about 6 weeks to about 8 weeks. In some embodiments $BI_2$ is about 3 to about 4 weeks. In some embodiments, $BI_2$ is about 1 week. In some embodiments, B12 is about 2 weeks. In some embodiments, $BI_2$ is about 3 weeks. In some embodiments, $BI_2$ is about 4 weeks. In some embodiments, $BI_2$ is about 5 weeks. In some embodiments, $BI_2$ is about 6 weeks. In some embodiments, $BI_2$ is about 7 weeks. In some embodiments, B12 is about 8 weeks. In some embodiments, B12 is about 9 weeks. In some embodiments, B12 is about 10 weeks.

In some embodiments, the length of time between $BD_3$ and a subsequent dose that is part of the Booster Dosing Regimen, or between doses for any dose beyond $BD_3$ (Bin) is each separately and independently selected from: about 1 week or more, about 2 weeks or more, or about 3 weeks or more. In some embodiments, $BI_n$ is about 1 week to about 12 weeks. In some embodiments, $BI_n$ is about 1 week to about 10 weeks. In some embodiments, $BI_n$ is about 2 weeks to about 10 weeks. In some embodiments, $BI_n$ is about 2 weeks to about 8 weeks. In some embodiments, $BI_n$ is about 3 weeks to about 8 weeks. In some embodiments, $BI_n$ is about 4 weeks to about 8 weeks. In some embodiments, $BI_n$ is about 6 weeks to about 8 weeks. In some embodiments $BI_n$ is about 3 to about 4 weeks. In some embodiments, $BI_n$ is about 1 week. In some embodiments, $BI_n$ is about 2 weeks. In some embodiments, $BI_n$ is about 3 weeks. In some embodiments, $BI_n$ is about 4 weeks. In some embodiments, $BI_n$ is about 5 weeks. In some embodiments, $BI_n$ is about 6 weeks. In some embodiments, $BI_n$ is about 7 weeks. In some embodiments, $BI_n$ is about 8 weeks. In some embodiments, $BI_n$ is about 9 weeks. In some embodiments, $BI_n$ is about 10 weeks.

In some embodiments, one or more compositions adminstered in $BD_1$ are formulated in a Tris buffer. In some embodiments, one or more compositions administered in $BD_2$ are formulated in a Tris buffer. In some embodiments, one or more compositions administering in $BD_3$ are formulated in a Tris buffer. In some embodiments, one or more compositions administered in $BD_3$ are formulated in a Tris buffer.

In some embodiments, the Booster dosing regimen comprises administering two or more mRNA compositions described herein, and at least two of the mRNA compositions have different formulations. In some embodiments, the Booster dosing regimen comprises $BD_1$ and $BD_2$, where $BD_1$ comprises administering an mRNA formulated in a Tris buffer and $BD_2$ comprises administering an mRNA formulated in a PBS buffer. In some embodiments, the Booster dosing regimen comprises $BD_1$ and $BD_2$, where $BD_1$ comprises administering an mRNA formulated in a PBS buffer and $BD_2$ comprises administering an mRNA formulated in a Tris buffer.

In some embodiments, one or more mRNA compositions given in $BD_1$, $BD_2$, $BD_3$, and/or $BD_n$ can be administered in combination with another vaccine. In some embodiments, another vaccine is for a disease that is not COVID-19. In some embodiments, the disease is one that increases deleterious effects of SARS-CoV-2 when a subject is coinfected with the disease and SARS-CoV-2. In some embodiments, the disease is one that increases the transmission rate of SARS-CoV-2 when a subject is coinfected with the disease and SARS-CoV-2. In some embodiments, another vaccine is a different commerically available vaccine. In some embodiments, the different commercially available vaccine is an RNA vaccine. In some embodiments, the different commercially available vaccine is a polypeptide-based vaccine. In some embodiments, another vaccine (e.g., as described herein) and one or more mRNA compositions given in $BD_1$, $BD_2$, $BD_3$, and/or $BD_n$ are separately administered, for example, in some embodiments via intramuscular injection, at different injection sites. For example, in some embodiments, an influenza vaccine and one or more SARS-CoV-2 mRNA compositions described herein given in $BD_1$, $BD_2$, $BD_3$, and/or $BD_n$ are separately administered to different arms of a subject via intramuscular injection.

Additional Booster Regimens

In some embodiments, methods of vaccination disclosed herein comprise administering more than one Booster Dosing Regimen. In some embodiments, more than one Booster Dosing Regimen may need to be administered to increase neutralizing antibody response. In some embodiments, more than one booster dosing regimen may be needed to counteract a SARS-CoV-2 strain that has been shown to have a high likelihood of evading immune response elicited by vaccines that a patient has previously received. In some embodiments, an additional Booster Dosing Regimen is administered to a patient who has been determined to produce low concentrations of neutralizing antibodies. In some embodiments, an additional booster dosing regimen is administered to a patient who has been determined to have a high likelihood of being susceptible to SARS-CoV-2 infection, despite previous vaccination (e.g., an immunocompromised patient, a cancer patient, and/or an organ transplant patient).

The description provided above for the first Booster Dosing Regimen also describes the one or more additional Booster Dosing Regimens. The interval of time between the first Booster Dosing Regimen and a second Booster Dosing Regimen, or between subsequent Booster Dosing Regimens can be any of the acceptable intervals of time described above between the Primary Dosing Regimen and the First Booster Dosing Regimen.

In some embodiments, a dosing regimen comprises a primary regimen and a booster regimen, wherein at least one dose given in the primary regimen and/or the booster regimen comprises a composition comprising an RNA that encodes a S protein or immunogenic fragment thereof from a variant that is prevalent or is spreading rapidly in a relevant jurisdiction (e.g., Omicron variant as described herein). For example, in some embodiments, a primary regimen comprises at least 2 doses of BNT162b2 (e.g., encoding a Wuhan strain), for example, given at least 3 weeks apart, and a booster regimen comprises at least 1 dose of a composition comprising RNA that encodes a S protein or immunogenic fragment thereof from a variant that is prevalent or is spreading rapidly in a relevant jurisdiction (e.g., Omicron variant as described herein). In some such embodiments, such a dose of a booster regimen may further comprise an RNA that encodes a S protein or immunogenic fragment thereof from a Wuhan strain, which can be administered with an RNA that encodes a S protein or immunogenic fragment thereof from a variant that is prevalent or is spreading rapidly in a relevant jurisdiction (e.g., Omicron variant as described herein), as a single mixture, or as two separate compositions, for example, in 1:1 weight ratio. In some embodiments, a booster regimen can also comprise at least 1 dose of BNT162b2, which can be administered as a first booster dose or a subsequent booster dose.

In some embodiments, an RNA composition described herein is given as a booster at a dose that is higher than the doses given during a primary regimen (primary doses) and/or the dose given for a first booster, if any. For example, in some embodiments, such a dose may be 60 ug; or in some embodiments such a dose may be higher than 30 ug and lower than 60 ug (e.g., 55 ug, 50 ug, or lower). In some embodiments, an RNA composition described herein is given as a booster at least 3-12 months or 4-12 months, or 5-12 months, or 6-12 months after the last dose (e.g., the last dose of a primary regimen or a first dose of a booster regimen). In some embodiments, the primary doses and/or the first booster dose (if any) may comprise BNT162b2, for example at 30 ug per dose.

In some embodiments, an RNA composition described herein comprises an RNA encoding a polypeptide as set forth in SEQ ID NO: 49 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 49). In some embodiments, an RNA composition comprises an RNA that includes the sequence of SEQ ID NO: 50 or a variant thereof (e.g., having at least 70% or more, including, e.g., at least 80%, at least 85%, at least 90%, at least 95%, at least 96%, at least 97%, at least 98%, or higher, identity to SEQ ID NO: 50). In some embodiments, an RNA composition comprises an RNA that includes the sequence of SEQ ID NO: 51 or a variant thereof (e.g., having at least 70% or more, including, e.g., at least 80%, at least 85%, at least 90%, at least 95%, at least 96%, at least 97%, at least 98%, or higher, identity to SEQ ID NO: 51).

In some embodiments, an RNA composition described herein comprises an RNA encoding a polypeptide as set forth in SEQ ID NO: 55 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 55. In some embodiments, an RNA composition comprises an RNA that includes the sequence of SEQ ID NO: 56 or a variant thereof (e.g., having at least 70% or more, including, e.g., at least 80%, at least 85%, at least 90%, at least 95%, at least 96%, at least 97%, at least 98%, or higher, identity to SEQ ID NO: 56). In some embodiments, an RNA composition comprises an RNA that includes the sequence of SEQ ID NO: 57 or a variant thereof (e.g., having at least 70% or more, including, e.g., at least 80%, at least 85%, at least 90%, at least 95%, at least 96%, at least 97%, at least 98%, or higher, identity to SEQ ID NO: 57).

In some embodiments, an RNA composition described herein comprises an RNA encoding a polypeptide as set forth in SEQ ID NO: 58 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 58). In some embodiments, an RNA composition comprises an RNA that includes the sequence of SEQ ID NO: 59 or a variant thereof (e.g., having at least 70% or more, including, e.g., at least 80%, at least 85%, at least 90%, at least 95%, at least 96%, at least 97%, at least 98%, or higher, identity to SEQ ID NO: 59). In some embodiments, an RNA composition comprises an RNA that includes the sequence of SEQ ID NO: 60 or a variant thereof (e.g., having at least 70% or more, including, e.g., at least 80%, at least 85%, at least 90%, at least 95%, at least 96%, at least 97%, at least 98%, or higher, identity to SEQ ID NO: 60).

In some embodiments, an RNA composition described herein comprises an RNA encoding a polypeptide as set forth in SEQ ID NO: 61 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 61). In some embodiments, an RNA composition comprises an RNA that includes the sequence of SEQ ID NO: 62a or a variant thereof (e.g., having at least 70% or more, including, e.g., at least 80%, at least 85%, at least 90%, at least 95%, at least 96%, at least 97%, at least 98%, or higher, identity to SEQ ID NO: 62a). In some embodiments, an RNA composition comprises an RNA that includes the sequence of SEQ ID NO: 63a or a variant thereof (e.g., having at least 70% or more, including, e.g., at least 80%, at least 85%, at least 90%, at least 95%, at least 96%, at least 97%, at least 98%, or higher, identity to SEQ ID NO: 63a).

In some embodiments, the formulations disclosed herein can be used to carry out any of the dosing regimens described in Table 19 (below).

TABLE 19

| Exemplary Dosing Regimens: | | | | | | | | | |
|---|---|---|---|---|---|---|---|---|---|
| | Primary Regimen | | | | Time between the | Booster Regimen | | | |
| # | Dose 1 (μg RNA) | Dose 2 (μg RNA) | Time Between Doses 1 and 2 | Dose 1 and Dose 2 Formulation | last dose of a Primary regimen and a first dose of Booster Regimen | Dose 1 (μg RNA) | Dose 2 (μg RNA) | Time Between Doses 1 and 2 | Dose 1 and Dose 2 Formulation |
| 1 | 30 | 30 | 2 to 8 weeks | PBS | At least 2 months | 30 | N/A[1] | N/A | PBS |
| 2 | 30 | 30 | 2 to 8 weeks | PBS | At least 3 months | 30 | N/A[1] | N/A | PBS |
| 3 | 30 | 30 | 2 to 8 weeks | PBS | 6 to 12 months | 30 | N/A[1] | N/A | PBS |
| 4 | 30 | 30 | 2 to 8 weeks | PBS or Tris | 4 to 12 months | 15 | N/A[1] | N/A | PBS or Tris |
| 5 | 30 | 30 | 2 to 8 weeks | PBS or Tris | 4 to 12 months | 10 | N/A[1] | N/A | PBS or Tris |
| 6 | 30 | 30 | 2 to 8 weeks | PBS or Tris | 4 to 12 months | 30 | 30 | 4 to 12 months | PBS or Tris |
| 7 | 30 | 30 | 2 to 8 weeks | PBS or Tris | 4 to 12 months | 30 | 15 | 4 to 12 months | PBS or Tris |
| 8 | 30 | 30 | 2 to 8 weeks | PBS or Tris | 4 to 12 months | 30 | 10 | 4 to 12 months | PBS or Tris |
| 9 | 30 | 30 | 2 to 8 weeks | PBS or Tris | 4 to 12 months | 30 | 60 | 4 to 12 months | PBS or Tris |
| 10 | 30 | 30 | 2 to 8 weeks | PBS or Tris | 4 to 12 months | 30 | >30 to <60 | 4 to 12 months | PBS or Tris |
| 11 | 30 | 30 | 2 to 8 weeks | PBS or Tris | 4 to 12 months | 30 | 50 | 4 to 12 months | PBS or Tris |
| 12 | 30 | 30 | 2 to 8 weeks | PBS | At least 6 months | 30 | N/A[1] | N/A | PBS |
| 13 | 30 | 30 | ~21 days | PBS | At least 2 months | 30 | N/A[1] | N/A | PBS |
| 14 | 30 | 30 | ~21 days | PBS | At least 3 months | 30 | N/A[1] | N/A | PBS |
| 15 | 30 | 30 | ~21 days | PBS | 6 to 12 months | 30 | N/A[1] | N/A | PBS |
| 16 | 30 | 30 | ~21 days | PBS | At least 6 months | 30 | N/A[1] | N/A | PBS |
| 17 | 30 | 30 | 21 days | PBS | At least 6 months | 15 | 15 | ~21 days | PBS |
| 18 | 30 | 30 | 21 days | PBS | At least 6 months | 15 | 15 | ~21 days | PBS |
| 19 | 30 | 30 | 2 to 8 weeks | PBS | At least 2 months | 30 | N/A[1] | N/A | Tris |
| 20 | 30 | 30 | 2 to 8 weeks | PBS | At least 3 months | 30 | N/A[1] | N/A | Tris |
| 21 | 30 | 30 | 2 to 8 weeks | PBS | 6 to 12 months | 30 | N/A[1] | N/A | Tris |
| 22 | 30 | 30 | 2 to 8 weeks | PBS | At least 6 months | 30 | N/A[1] | N/A | Tris |
| 23 | 30 | 30 | ~21 days | PBS | At least 2 months | 30 | N/A[1] | N/A | Tris |
| 24 | 30 | 30 | ~21 days | PBS | At least 3 months | 30 | N/A[1] | N/A | Tris |
| 25 | 30 | 30 | ~21 days | PBS | 6 to 12 months | 30 | N/A[1] | N/A | Tris |
| 26 | 30 | 30 | ~21 days | PBS | At least 6 months | 30 | N/A[1] | N/A | Tris |
| 27 | 30 | 30 | 21 days | PBS | At least 6 months | 15 | 15 | ~21 days | Tris |
| 28 | 30 | 30 | 21 days | PBS | At least 6 months | 15 | 15 | ~21 days | Tris |
| 29 | 30 | 30 | 2 to 8 weeks | Tris | At least 2 months | 30 | N/A[1] | N/A | Tris |
| 30 | 30 | 30 | 2 to 8 weeks | Tris | At least 3 months | 30 | N/A[1] | N/A | Tris |
| 31 | 30 | 30 | 2 to 8 weeks | Tris | 6 to 12 months | 30 | N/A[1] | N/A | Tris |
| 32 | 30 | 30 | 2 to 8 weeks | Tris | At least 6 months | 30 | N/A[1] | N/A | Tris |
| 33 | 30 | 30 | ~21 days | Tris | At least 2 months | 30 | N/A[1] | N/A | Tris |
| 34 | 30 | 30 | ~21 days | Tris | At least 3 months | 30 | N/A[1] | N/A | Tris |
| 35 | 30 | 30 | ~21 days | Tris | 6 to 12 months | 30 | N/A[1] | N/Å | Tris |
| 36 | 30 | 30 | ~21 days | Tris | At least 6 months | 30 | N/A[1] | N/A | Tris |
| 37 | 30 | 30 | 21 days | Tris | At least 6 months | 15 | 15 | ~21 days | Tris |
| 38 | 30 | 30 | 21 days | Tris | At least 6 months | 15 | 15 | ~21 days | Tris |
| 39 | 10 | 10 | 2 to 8 weeks | Tris | At least 2 months | 10 | N/A[1] | N/A | Tris |
| 40 | 10 | 10 | 2 to 8 weeks | Tris | At least 3 months | 10 | N/A[1] | N/A | Tris |
| 41 | 10 | 10 | 2 to 8 weeks | Tris | 6 to 12 months | 10 | N/A[1] | N/A | Tris |
| 42 | 10 | 10 | 2 to 8 weeks | Tris | At least 6 months | 10 | N/A[1] | N/A | Tris |
| 43 | 10 | 10 | ~21 days | Tris | At least 2 months | 10 | N/A[1] | N/A | Tris |
| 44 | 10 | 10 | ~21 days | Tris | At least 3 months | 10 | N/A[1] | N/A | Tris |

TABLE 19-continued

Exemplary Dosing Regimens:

| | Primary Regimen | | | | Time between the last dose of a Primary regimen and a first dose of Booster Regimen | Booster Regimen | | | |
|---|---|---|---|---|---|---|---|---|---|
| # | Dose 1 (µg RNA) | Dose 2 (µg RNA) | Time Between Doses 1 and 2 | Dose 1 and Dose 2 Formulation | | Dose 1 (µg RNA) | Dose 2 (µg RNA) | Time Between Doses 1 and 2 | Dose 1 and Dose 2 Formulation |
| 45 | 10 | 10 | ~21 days | Tris | 6 to 12 months | 10 | N/A[1] | N/A | Tris |
| 46 | 10 | 10 | ~21 days | Tris | At least 6 months | 10 | N/A[1] | N/A | Tris |
| 47 | 3 | 3 | 2 to 8 weeks | Tris | At least 2 months | 3 | N/A[1] | N/A | Tris |
| 48 | 3 | 3 | 2 to 8 weeks | Tris | At least 3 months | 3 | N/A[1] | N/A | Tris |
| 49 | 3 | 3 | 2 to 8 weeks | Tris | 6 to 12 months | 3 | N/A[1] | N/A | Tris |
| 50 | 3 | 3 | 2 to 8 weeks | Tris | At least 6 months | 3 | N/A[1] | N/A | Tris |
| 51 | 3 | 3 | ~21 days | Tris | At least 2 months | 3 | N/A[1] | N/A | Tris |
| 52 | 3 | 3 | ~21 days | Tris | At least 3 months | 3 | N/A[1] | N/A | Tris |
| 53 | 3 | 3 | ~21 days | Tris | 6 to 12 months | 3 | N/A[1] | N/A | Tris |
| 54 | 3 | 3 | ~21 days | Tris | At least 6 months | 3 | N/A[1] | N/A | Tris |

[1]N/A refers to no dose necessary.

In some embodiments of certain exemplary dosing regimens as described in Table 19 above, an RNA composition described herein (e.g., comprising RNA encoding a variant described herein) is given in a first dose of a primary regimen. In some embodiments of certain exemplary dosing regimens as described in Table 19 above, an RNA composition described herein (e.g., comprising RNA encoding a variant described herein) is given in a second dose of a primary regimen. In some embodiments of certain exemplary dosing regimens as described in Table 19 above, an RNA composition described herein (e.g., comprising RNA encoding a variant described herein) is given in a first dose and a second dose of a primary regimen. In some embodiments of certain exemplary dosing regimens as described in Table 19 above, an RNA composition described herein (e.g., comprising RNA encoding a variant described herein) is given in a first dose of a booster regimen. In some embodiments of certain exemplary dosing regimens as described in Table 19 above, an RNA composition described herein (e.g., comprising RNA encoding a variant described herein) is given in a second dose of a booster regimen. In some embodiments of certain exemplary dosing regimens as described in Table 19 above, an RNA composition described herein (e.g., comprising RNA encoding a variant described herein) is given in a first dose and a second dose of a booster regimen. In some embodiments of certain exemplary dosing regimens as described in Table 19 above, an RNA composition described herein (e.g., comprising RNA encoding a variant described herein) is given in a first dose and a second dose of a primary regimen and also in at least one dose of a booster regimen. In some embodiments of certain exemplary dosing regimens as described in Table 19 above, an RNA composition described herein (e.g., comprising RNA encoding a variant described herein) is given in at least one dose (including, e.g., at least two doses) of a booster regimen and BNT162b2 is given in a primary regimen. In some embodiments of certain exemplary dosing regimens as described in Table 19 above, an RNA composition described herein (e.g., comprising RNA encoding a variant described herein) is given in a second dose of a booster regimen and BNT162b2 is given in a primary regimen and in a first dose of a booster regimen. In some embodiments, an RNA composition described herein (e.g., comprising RNA encoding a variant described herein) comprises an RNA encoding a polypeptide as set forth in SEQ ID NO: 49 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 49). In some embodiments, an RNA composition described herein (e.g., comprising RNA encoding a variant described herein) comprises an RNA that includes the sequence of SEQ ID NO: 50 or a variant thereof (e.g., having at least 70% or more, including, e.g., at least 80%, at least 85%, at least 90%, at least 95%, at least 96%, at least 97%, at least 98%, or higher, identity to SEQ ID NO: 50). In some embodiments, an RNA composition described herein (e.g., comprising RNA encoding a variant described herein) comprises an RNA that includes the sequence of SEQ ID NO: 51 or a variant thereof (e.g., having at least 70% or more, including, e.g., at least 80%, at least 85%, at least 90%, at least 95%, at least 96%, at least 97%, at least 98%, or higher, identity to SEQ ID NO: 51).

In some embodiments, an RNA composition described herein comprises an RNA encoding a polypeptide as set forth in SEQ ID NO: 55 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 55). In some embodiments, an RNA composition comprises an RNA that includes the sequence of SEQ ID NO: 56 or a variant thereof (e.g., having at least 70% or more, including, e.g., at least 80%, at least 85%, at least 90%, at least 95%, at least 96%, at least 97%, at least 98%, or higher, identity to SEQ ID NO: 56). In some embodiments, an RNA composition comprises an RNA that includes the sequence of SEQ ID NO: 57 or a variant thereof (e.g., having at least 70% or more, including, e.g., at least 80%, at least 85%, at least 90%, at least 95%, at least 96%, at least 97%, at least 98%, or higher, identity to SEQ ID NO: 57).

In some embodiments, an RNA composition described herein comprises an RNA encoding a polypeptide as set forth in SEQ ID NO: 58 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 58). In some embodiments, an RNA composition comprises an RNA that includes the sequence of SEQ ID NO: 59 or a variant thereof (e.g., having at least 70% or more, including, e.g., at least 80%, at least 85%, at least 90%, at least 95%, at least 96%, at least 97%, at least 98%, or higher, identity to SEQ ID NO: 59). In some embodiments, an RNA composition comprises an RNA that includes the sequence of SEQ ID NO: 60 or a variant thereof (e.g., having at least 70% or more, including, e.g., at least 80%, at least 85%, at least 90%, at least 95%, at least 96%, at least 97%, at least 98%, or higher, identity to SEQ ID NO: 60).

In some embodiments, an RNA composition described herein comprises an RNA encoding a polypeptide as set forth in SEQ ID NO: 61 or an immunogenic fragment thereof, or a variant thereof (e.g., having at least 70% or more, including, e.g., at least 80%, at least 85%, at least 90%, at least 95%, at least 96%, at least 97%, at least 98%, or higher, identity to SEQ ID NO: 61). In some embodiments, an RNA composition comprises an RNA that includes the sequence of SEQ ID NO: 62a or a variant thereof (e.g., having at least 70% or more, including, e.g., at least 80%, at least 85%, at least 90%, at least 95%, at least 96%, at least 97%, at least 98%, or higher, identity to SEQ ID NO: 62a). In some embodiments, an RNA composition comprises an RNA that includes the sequence of SEQ ID NO: 63a or a variant thereof (e.g., having at least 70% or more, including, e.g., at least 80%, at least 85%, at least 90%, at least 95%, at least 96%, at least 97%, at least 98%, or higher, identity to SEQ ID NO: 63a).

In some embodiments, such an RNA composition described herein (e.g., comprising RNA encoding a variant described herein) can further comprise RNA encoding a S protein or an immunogenic fragment thereof of a different strain (e.g., a Wuhan strain). By way of example, in some embodiments, a second dose of a booster regimen of Regimens #9-11 as described in Table 19 above can comprise an RNA composition described herein (e.g., comprising RNA encoding a variant described herein such as Omicron, for example, in one embodiment RNA as described in this Example) and a BNT162b2 construct, for example, in 1: 1 weight ratio.

In some embodiments of Regimen #6 as described in Table 19 above, a first dose and a second dose of a primary regimen and a first dose and a second dose of a booster regimen each comprise an RNA composition described herein (e.g., comprising RNA encoding a variant described herein such as Omicron, for example, in one embodiment RNA as described in this Example). In some such embodiments, a second dose of a booster regimen may not be necessary.

In some embodiments of Regimen #6 as described in Table 19 above, a first dose and a second dose of a primary regimen and a first dose and a second dose of a booster regimen each comprise an RNA composition described herein (e.g., comprising RNA encoding a variant described herein such as Omicron, for example, in one embodiment RNA as described in this Example). In some such embodiments, a second dose of a booster regimen may not be necessary.

In some embodiments of Regimen #6 as described in Table 19 above, a first dose and a second dose of a primary regimen each comprise a BNT162b2 construct, and a first dose and a second dose of a booster regimen each comprise an RNA composition described herein (e.g., comprising RNA encoding a variant described herein such as Omicron, for example, in one embodiment RNA as described in this Example). In some such embodiments, a second dose of a booster regimen may not be necessary.

In some embodiments of Regimen #6 as described in Table 19 above, a first dose and a second dose of a primary regimen and a first dose of a booster regimen each comprise a BNT162b2 construct, and a second dose of a booster regimen comprises an RNA composition described herein (e.g., comprising RNA encoding a variant described herein such as Omicron, for example, in one embodiment RNA as described in this Example).

Example 7: Omicron BA.1 Breakthrough Infection Drives Cross-Variant Neutralization and Memory B Cell Formation The present Example shows that an Omicron BA.1 breakthrough infection in individuals double- and triple-vaccinated with BNT162b2 drives cross variant neutralization and memory B cell formation, including production of neutralizing antibodies and B cell responses toward an Omicron BA.1 variant. One of ordinary skill in the art reading the present Example will understand that such findings can be extended to administration of an mRNA vaccine comprising an RNA encoding a SARS-CoV-2 S protein having mutations characteristic of an Omicron BA.1 variant (e.g., ones as described herein) to subjects who were previously administered two or three doses of SARS-CoV-2 vaccines (e.g., in some embodiments developed based on a S protein from a Wuhan-Hu-1 strain).

Omicron is the evolutionarily most distinct SARS-CoV-2 variant of concern (VOC) to date. To address how Omicron breakthrough infection can potentially reshape SARS-CoV-2 recognition in vaccinated individuals, the effects of Omicron BA.1 breakthrough infection were investigated on serum neutralization and $B_{MEM}$ cell antigen recognition in BNT162b2 double- and triple-vaccinated individuals. Omicron BA.1 breakthrough infection induced broad neutralization of VOCs including Omicron BA.1, with substantially stronger neutralization compared to Omicron BA.1-naïve double- and triple-vaccinees. Broad recognition of VOCs by BMEM cells from BNT162b2 double- and triple-vaccinated individuals was boosted by Omicron BA.1 breakthrough infection, with recognition primarily against conserved epitopes shared broadly between variants rather than Omicron BA.1-specific epitopes. The data presented herein demonstrate that an Omicron BA.1 breakthrough infection efficiently broadens neutralizing antibody and/or B cell responses towards multiple variants and suggest that a vaccine adapted to the Omicron BA.1 S protein may be able to reshape the immune repertoire.

INTRODUCTION

Containment of the current COVID-19 pandemic requires the generation of durable and sufficiently broad immunity that provides protection against circulating and future variants of SARS-CoV-2. The titer of neutralizing antibodies to SARS-CoV-2, and the binding of antibodies to the spike (5) glycoprotein and its receptor-binding domain (RBD) are considered correlates of protection against infection (D. S. Khoury et al., "Neutralizing antibody levels are highly predictive of immune protection from symptomatic SARS-CoV-2 infection," Nature medicine. 27, 1205-1211 (2021), doi:10.1038/s41591-021-01377-8; and P. B. Gilbert et al., "Immune correlates analysis of the mRNA-1273 COVID-19 vaccine efficacy clinical trial," Science (New York, N.Y.). 375, 43-50 (2022), doi:10.1126/science.abm3425). Currently available vaccines are based on the ancestral Wuhan-Hu-1 strain and induce antibodies with a neutralizing capacity that exceeds the breadth elicited by infection with the Wuhan strain, or with variants of concern (VOCs) (K. Röltgen et al., "Immune imprinting, breadth of variant recognition, and germinal center response in human SARS-CoV-2 infection and vaccination," Cell (2022), doi:10.1016/j.cell.2022.01.018). However, protective titers wane over time (J. P. Evans et al., "Neutralizing antibody responses elicited by SARS-CoV-2 mRNA vaccination wane over time and are boosted by breakthrough infection," Science translational medicine, eabn8057 (2022), doi:10.1126/scitranslmed.abn8057; S. Yamayoshi et al., "Antibody titers against SARS-CoV-2 decline, but do not disappear for several months," Eclinical Medicine, 32, 100734 (2021), doi: 10.1016/j.eclinm.2021.100734; W. N. Chia et al., "Dynamics of SARS-CoV-2 neutralising antibody responses and duration of immunity," The Lancet Microbe, 2, e240-e249 (2021), doi:10.1016/52666-5247(21)00025-2; Y. Goldberg et al., "Waning Immunity after the BNT162b2 Vaccine in Israel," The New England journal of medicine. 385, e85 (2021), doi:10.1056/NEJMoa2114228. and routine booster vaccinations are thought to be needed to trigger recall immunity and maintain efficacy against new VOCs (A. R. Falsey et al., "SARS-CoV-2 Neutralization with BNT162b2 Vaccine Dose 3," The New England journal of medicine. 385, 1627-1629 (2021), doi:10.1056/NEJMc2113468; A. Choi et al., "Safety and immunogenicity of SARS-CoV-2 variant mRNA vaccine boosters in healthy adults," Nature medicine. 27, 2025-2031 (2021), doi:10.1038/s41591-021-01527-y; and N. Andrews et al., "Effectiveness of COVID-19 booster vaccines against covid-19 related symptoms, hospitalisation and death in England," Nature medicine (2022), doi:10.1038/s41591-022-01699-1.

Long-lived memory B ($B_{MEM}$) cells are the basis for the recall response upon antigen reencounter either by infection or booster vaccination. They play an important role in the maintenance and evolution of the antiviral antibody response against variants, since low-affinity selection mechanisms during the germinal center reaction and continued hypermutation of $B_{MEM}$ cells expand the breadth of viral variant recognition over time (W. E. Purtha, et al., "Memory B cells, but not long-lived plasma cells, possess antigen specificities for viral escape mutants," The Journal of experimental medicine, 208, 2599-2606 (2011) doi: 10.1084/jem.20110740; and Y. Adachi et al., "Distinct germinal center selection at local sites shapes memory B cell response to viral escape," The Journal of experimental medicine. 212, 1709-1723 (2015), doi:10.1084/jem.20142284).

How vaccine-mediated protective immunity will evolve over time and will be modified by iterations of exposure to COVID-19 vaccines and infections with increasingly divergent viral variants, is of particular relevance with the emergence of antigenically distinct VOCs. Omicron is the evolutionarily most distant reported VOC with a hitherto unprecedented number of amino acid alterations in its S glycoprotein, including at least 15 amino acid changes in the RBD and extensive changes in the N-terminal domain (NTD). These alterations are predicted to affect most neutralizing antibody epitopes. In addition, Omicron is highly transmissible, and its sublineages BA.1 and BA.2 have spread rapidly across the globe, outcompeting Delta within weeks to become the dominant circulating VOC (W. Dejnirattisai et al., "SARS-CoV-2 Omicron-B.1.1.529 leads to widespread escape from neutralizing antibody responses," Cell. 185, 467-484.e15 (2022), doi:10.1016/j.cell.2021.12.046; and M. Hoffmann et al., "The Omicron variant is highly resistant against antibody-mediated neutralization," Cell. 185, 447-456.e11 (2022), doi:10.1016/j.cell.2021.12.032).

To date, over 1 billion people worldwide have been vaccinated with the mRNA-based COVID-19 vaccine BNT162b2 and have received the primary 2-dose series or further boosters. This vaccine is contributing substantially to the pattern of population immunity in many regions on which further immune editing and effects of currently spreading variants will build upon.

To characterize the effect of Omicron BA.1 breakthrough infection on the magnitude and breadth of serum neutralizing activity and $B_{MEM}$ cells, blood samples from individuals that were double- or triple-vaccinated with BNT162b2 were studied.

As understanding of the antigen-specific B cell memory pool is a critical determinant of an individual's ability to respond to newly emerging variants, this data can help to guide vaccine development.

Results and Discussion

Cohorts and Sampling

Blood samples have been sourced from the biosample collection of BNT162b2 vaccine trials, and a biobank of prospectively collected samples from vaccinated individuals with subsequent SARS-CoV-2 Omicron BA.1 breakthrough infection. Samples were selected to investigate biomarkers in four independent groups, namely individuals who were (i) double- or (ii) triple-vaccinated with BNT162b2 without a prior or breakthrough infection at the time of sample collection ($BNT162b2^2$, $BNT162b2^3$) and individuals who were (iii) double- or (iv) triple-vaccinated with BNT162b2 and who experienced breakthrough infection with the SARS-CoV-2 Omicron BA.1 variant after a median of approximately 5 months or 4 weeks, respectively ($BNT162b2^2$+Omi, $BNT162b2^3$+Omi) (see materials and methods below). Immune sera were used to characterize Omicron BA.1 infection-associated changes to the magnitude and the breadth of serum neutralizing activity. PBMCs were used to characterize the VOC-specificity of peripheral $B_{MEM}$ cells recognizing the respective full-length SARS-CoV-2 S protein or its RBD (FIG. 15).

Omicron Breakthrough Infection of BNT162b2 Double- and Triple-Vaccinated Individuals Induces Broad Neutralization of Omicron BA.1, BA.2 and Other VOCs To evaluate the neutralizing activity of immune sera, two orthogonal test systems were used: a well-characterized pseudovirus neutralization test (pVNT) to investigate the breadth of inhibition of virus entry in a propagation-deficient set-up, as well as a live SARS-CoV-2 neutralization test (VNT) designed to evaluate neutralization during multicycle replication of authentic virus with the antibodies maintained throughout the entire test period. For the former, pseudoviruses bearing S proteins comprising mutations characteristic of Omicron sublineages BA.1 or BA.2, other SARS-CoV-2 VOCs (Wuhan, Alpha, Beta, Delta) were used to assess breadth while pseudoviruses bearing the S proteins of SARS-CoV-1 (T. Li et al., "Phylogenetic supertree reveals detailed evolution of SARS-CoV-2," Scientific reports, 10, 22366 (2020), doi:10.1038/s41598-020-79484-8) was used to detect potential pan-Sarbecovirus neutralizing activity (C.-W. Tan et al., "Pan-Sarbecovirus Neutralizing Antibodies in BNT162b2-Immunized SARS-CoV-1 Survivors," The New England journal of medicine, 385, 1401-1406 (2021), doi:10.1056/NEJMoa2108453).

As reported previously (A. R. Falsey et al., "SARS-CoV-2 Neutralization with BNT162b2 Vaccine Dose 3," The New England journal of medicine, 385, 1627-1629 (2021), doi: 10.1056/NEJMc2113468; and C.-W. Tan et al., "Pan-Sarbecovirus Neutralizing Antibodies in BNT162b2-Immunized SARS-CoV-1 Survivors," The New England journal of medicine. 385, 1401-1406 (2021), doi:10.1056/NEJMoa2108453), in Omicron-naïve double-vaccinated individuals 50% pseudovirus neutralization ($pVN_{50}$) geometric mean titers (GMTs) of Beta and Delta VOCs were reduced, and neutralization of both Omicron sublineages was virtually undetectable. In Omicron-naïve triple-vaccinated individuals, $pVN_{50}$ GMTs against all tested VOCs were substantially higher with robust neutralization of Alpha, Beta and Delta variants. While GMTs against Omicron BA.1 were significantly lower compared to Wuhan (GMT 160 vs 398), titers against Omicron BA.2 were also considerably reduced at 211. Thus, triple vaccination induced a similar level of neutralization against the two Omicron sublineages (FIG. 16, A) (A. Muik et al., "Neutralization of SARS-CoV-2 Omicron by BNT162b2 mRNA vaccine-elicited human sera," Science (New York, N.Y.), 375, 678-680 (2022), doi:10.1126/science.abn7591; C.-W. Tan et al., "Pan-Sarbecovirus Neutralizing Antibodies in BNT162b2-Immunized SARS-CoV-1 Survivors," The New England journal of medicine, 385, 1401-1406 (2021), doi:10.1056/NEJMoa2108453; J. Liu et al., "BNT162b2-elicited neutralization of B.1.617 and other SARS-CoV-2 variants," Nature, 596, 273-275 (2021), doi:10.1038/s41586-021-03693-y; A. Muik et al., "Neutralization of SARS-CoV-2 lineage B.1.1.7 pseudovirus by BNT162b2 vaccine-elicited human sera," Science (New York, N.Y.), 371, 1152-1153 (2021), doi: 10.1126/science.abg6105; and Y. Liu et al., "Neutralizing Activity of BNT162b2-Elicited Serum," The New England journal of medicine, 384, 1466-1468 (2021), doi:10.1056/NEJMc2102017).

Omicron BA.1-breakthrough infection had a marked effect on magnitude and breadth of the neutralizing antibody response of both double- and triple-vaccinated individuals, with slightly higher $pVN_{50}$ GMTs observed in the triple-vaccinated individuals (FIG. 16, A). The $pVN_{50}$ GMT of double-vaccinated individuals with breakthrough infection against Omicron BA.1 and BA.2 was more than 100-fold and 35-fold above the GMTs of Omicron BA.1-naïve double-vaccinated individuals. Immune sera from double-vaccinated individuals with breakthrough infection had broad neutralizing activity, with higher $pVN_{50}$ GMTs against Beta and Delta than observed in Omicron-naïve triple-vaccinated individuals (GMT 740 vs. 222 and 571 vs. 370).

The effect of Omicron BA.1-breakthrough infection on the neutralization of Omicron BA.1 and BA.2 pseudovirus was less pronounced when looking at triple-vaccinated individuals (approximately 7-fold and 4-fold increased neutralization compared to Omicron-naïve triple-vaccinated individuals). $pVN_{50}$ GMTs against Omicron BA.1, BA.2 and Delta were 1029, 836 and 1103 in triple-vaccinated Omicron breakthrough individuals as compared to 160, 211 and 370 in the Omicron-naïve triple-vaccinated. GMTs against all SARS-CoV-2 VOCs, including Beta and Omicron, were close to titers against the Wuhan reference, while noticeably reduced in triple-vaccinated Omicron-naïve individuals.

Likewise, while sera from vaccinated Omicron-naïve individuals had no detectable or only poor $pVN_{50}$ titers against the phylogenetically more distant SARS-CoV-1, convalescent sera of double- and even more markedly of triple-vaccinated Omicron infected individuals robustly neutralized SARS-CoV-1 pseudovirus (FIGS. 16, A and B). Nine out of 18 breakthrough infected individuals (four double-vaccinated and five triple-vaccinated) had SARS-CoV-1 $pVN_{50}$ GMTs comparable to or above those against the Wuhan reference in Omicron-naïve double-vaccinated individuals (GMT≥120).

Authentic live SARS-CoV-2 virus neutralization assays conducted with Wuhan, Beta, Delta and Omicron BA.1 pseudoviruses also showed similar findings (FIG. 16, B). In BNT162b2 double- and triple-vaccinated individuals, Omicron BA.1 infection was associated with a strongly increased neutralizing activity against Omicron BA.1 with 50% virus neutralization ($VN_{50}$) GMTs in the same range as against the Wuhan strain (FIG. 16, B; GMT 493 vs. 381 and GMT 538 vs. 613). Similarly, Omicron BA.1 convalescent double- and triple-vaccinated individuals showed comparable levels of neutralization against other variants as well (e.g., GMT 493 and 729 against Beta), indicating a wide breadth of neutralizing activity.

In aggregate, these data demonstrate that SARS-CoV-2 Omicron BA.1 breakthrough infection induces neutralization activity of profound breadth in vaccine-experienced individuals, a finding further supported by the calculated ratios of $VN_{50}$ GMTs against the Wuhan strain and SARS-CoV-2 VOCs (FIG. 16, C). While double- and to a lesser extent also triple-BNT162b2 vaccinated Omicron-naïve individuals displayed marked differences in neutralization proficiency against VOCs, neutralization activity of Omicron BA.1 convalescent subjects was leveled to almost the same range of high performance against all variant strains tested.

Likewise, Omicron BA.1 breakthrough infection had a similarly broad neutralization augmenting effect in individuals vaccinated with other approved COVID-19 vaccines or heterologous regimens (FIG. 19; Table 20).

TABLE 20

Individuals vaccinated with other approved COVID-19 vaccines or mixed regimens after subsequent Omicron BA.1 breakthrough infection

| Vaccination | Omicron subtype | Dose 1-2 interval | Dose 2-3 interval | Positive test after last vaccination | Blood draw after positive test |
|---|---|---|---|---|---|
| AZ/BNT | n/a | 62 | N/A | 142 | 46 |
| AZ/BNT | n/a | 68 | N/A | 135 | 45 |
| J&J | n/a | N/A | N/A | 161 | 44 |
| $MOD^3$ | BA.1 | 42 | 172 | 3 | 35 |
| $MOD^2$ | n/a | 42 | N/A | 169 | 44 |
| J&J/BNT | n/a | 138 | N/A | 45 | 40 |
| AZ/BNT/MOD | BA.1 | 68 | 154 | 9 | 43 |
| $MOD^2$/BNT | n/a | 28 | 252 | 22 | 40 |
| $MOD^2$/BNT | n/a | 42 | 154 | 13 | 42 |
| $MOD^2$/BNT | n/a | 28 | 256 | 45 | 31 |
| | | | Median: | 45 | 43 |

n/a, not available;
N/A, not applicable;
AZ, AstraZeneca AZD1222;
BNT, BioNTech/Pfizer BNT162b2;
J&J, Johnson & Johnson Ad26.COV2.S;
MOD, Moderna mRNA-1273;
$BNT^4$, BNT162b2 four-dose series;
$MOD^2$, mRNA-1273 two-dose series;
$MOD^3$, mRNA-1273 three-dose series $B_{MEM}$ Cells of BNT162b2 Double- and of Triple-Vaccinated Individuals Broadly Recognize VOCs and are Further Boosted by Omicron Breakthrough Infection Next, the phenotype and quantity of SARS-CoV-2 S protein specific B cells were investigated. Flow cytometry-based B cell phenotyping assays were used for differential detection of variant-specific S protein-binding B cells in bulk PBMCs. All S protein- and RBD-specific B cells in the peripheral blood were found to be of a $B_{MEM}$ phenotype ($B_{MEM}$; $CD^{20high}CD^{38int/neg}$), as antigen-specific plasmablasts or naïve B cells were not detected (data not shown). The assays therefore allowed the differentiation for each of the SARS-CoV-2 variants between $B_{MEM}$ cells recognizing the full S protein or its RBD that is a hotspot for amino acid alterations, and variant-specific antigenic epitopes (FIG. 17, A).

The overall frequency of antigen-specific $B_{MEM}$ cells varied across the different groups. The frequency of $B_{MEM}$ cells in Omicron-naïve double-vaccinated individuals was low at an early time point after vaccination and increased over time: At 5 months as compared to 3 weeks after the second BNT162b2 dose, S protein-specific $B_{MEM}$ cells almost quadrupled, RBD-specific ones tripled across all VOCs thereby reaching quantities similar to those observed in Omicron-naïve triple-vaccinated individuals (FIGS. 17, B and C).

Double or triple BNT162b2-vaccinated individuals with a SARS-CoV-2 Omicron BA.1 breakthrough infection exhibited a strongly increased frequency of $B_{MEM}$ cells, which was higher than those of Omicron-naïve triple-vaccinated individuals (FIGS. 17, B and D).

In all groups, including Omicron-naïve and Omicron infected individuals, $B_{MEM}$ cells against Omicron BA.1 S protein were detectable at frequencies comparable to those against Wuhan and other tested VOCs (FIGS. 17, B and D), whereas the frequency of $B_{MEM}$ cells against Omicron BA.1 RBD was slightly lower compared to the other variants (FIGS. 17, C and E).

The ratios of RBD protein to S protein binding within the different groups was then compared and found to be biased towards S protein recognition for the Omicron BA.1 VOC, particularly in the Omicron-naïve groups (FIG. 17, F). In the Omicron BA.1-experienced groups this ratio is higher, indicating that an Omicron BA.1 breakthrough infection improved Omicron BA.1 RBD recognition.

Omicron BA.1 Breakthrough Infection in BNT162b2 Double- and Triple-Vaccinated Individuals Primarily Boosts $B_{MEM}$ Cells Against Conserved Epitopes Shared Broadly Between S Proteins of Wuhan and other VOCs rather than strictly Omicron S-specific epitopes. These findings indicate that Omicron BA.1 infection in vaccinated individuals boosts not only neutralizing activity and $B_{MEM}$ cells against Omicron BA.1, but broadly augments immunity against various VOCs. To investigate the specificity of antibody responses at a cellular level, multi-parameter analyses of $B_{MEM}$ cells stained with fluorescently labeled variant-specific S or RBD proteins were performed.

A combinatorial gating strategy was applied to distinguish between $B_{MEM}$ cell subsets that could identify only single variant-specific epitopes of Wuhan, Alpha, Delta or Omicron BA.1, versus those that could identify any given combination thereof (FIG. 18, A).

In a first analysis, $B_{MEM}$ cell recognition of Wuhan and Omicron BA.1 S and RBD proteins was evaluated (FIGS. 18, B, C, and D). The SARS-CoV-2 Omicron BA.1 variant has 37 amino acid alterations in the S protein compared to the Wuhan parental strain, of which 15 alterations are in the RBD, an immunodominant target of neutralizing antibodies induced by COVID-19 vaccines or by SARS-CoV-2 infections.

Staining with full length S proteins showed that the largest proportion of $B_{MEM}$ cells from Omicron-naïve double-vaccinated individuals, and even more predominantly from triple-vaccinated individuals were directed against epitopes shared by both Wuhan and Omicron BA.1 SARS-CoV-2 variants. Consistent with the observation that vaccination with BNT162b2 can elicit immune responses against wild-type epitopes that do not recognize the corresponding altered epitopes in the Omicron BA.1 S protein (FIGS. 18, B and C), in most individuals a smaller but clearly detectable proportion of $B_{MEM}$ cells was found that recognized only Wuhan S protein or RBD. Consistent with the lack of exposure, no $B_{ME}$M cells binding exclusively to Omicron BA.1 S or RBD protein were detected in these Omicron-naïve individuals.

In Omicron BA.1 convalescent individuals, frequencies of $B_{MEM}$ cells recognizing S protein epitopes shared between Wuhan and Omicron BA.1 were significantly higher than in the Omicron-naïve ones (FIGS. 18, B and C). In most of these subjects, a small proportion of exclusively Wuhan S protein-specific $B_{MEM}$ cells was found, as well as a slightly lower frequency of exclusively Omicron BA.1 variant S protein-specific ones.

A similar but slightly different pattern was observed by B cell staining with labeled RBD proteins (FIGS. 18, B and D). Again, Omicron BA.1 breakthrough infection of double-/triple-vaccinated individuals was found to primarily boost $B_{MEM}$ cells reactive with conserved epitopes. A moderate boost of Wuhan-specific reactivities was observed; however, only small populations of Omicron-RBD-specific $B_{MEM}$ cells were detected in the tested individuals (FIG. 18, D).

Next, the combinatorial gating approach was used to identify the subsets of S protein or RBD binding $B_{MEM}$ cells that either bind exclusively to Wuhan or Omicron BA.1, or to common epitopes conserved broadly across all four variants, Wuhan, Alpha, Delta and Omicron BA.1 (FIG. 18, E). Across all four study groups, the frequency of $B_{MEM}$ cells recognizing S protein epitopes was found to be conserved across all tested variants, accounting for the largest fraction of the pool of S protein-binding $B_{MEM}$ cells (FIG. 18, F, all 4+ve). The S protein of the Wuhan strain does not have an exclusive amino acid change that distinguishes it from the spike proteins of the Alpha, Delta, or Omicron BA.1 VOCs. Accordingly, $B_{MEM}$ cells exclusively recognizing the Wuhan S protein were hardly detected in any individual (FIG. 18, F). In several individuals with Omicron BA.1 breakthrough infection, a small proportion of $B_{MEM}$ cells was detected that bound exclusively to Omicron BA.1 S protein (FIG. 18, F), whereas almost none of the individuals displayed a strictly Omicron BA.1 RBD-specific response (FIG. 18, G).

These findings indicate that SARS-CoV-2 Omicron BA.1 breakthrough infection in vaccinated individuals primarily expands a broad $B_{MEM}$ cell repertoire against conserved S protein and RBD epitopes, rather than inducing large numbers of Omicron-specific $B_{MEM}$ cells.

To further dissect this response, the $B_{MEM}$ subsets directed against the RBD were characterized. The combinatorial Boolean gating approach was used to discern $B_{MEM}$ cells with distinct binding patterns in the spectrum of strictly variant-specific and common epitopes shared by several variants. Multiple sequence alignments revealed that the Omicron BA.1 RBD diverges from the RBD sequence regions conserved in Wuhan, Alpha and Delta by 13 single amino acid alterations. All Omicron BA.1 convalescent individuals were found to have robust frequencies of $B_{MEM}$ cells that recognized Wuhan, Alpha as well as the Delta VOC RBDs, but not Omicron BA.1 RBD, while $B_{MEM}$ cells exclusively reactive with Omicron BA.1 RBD were almost absent in most of those individuals (FIG. 18, H). $B_{MEM}$ cells that exclusively recognized the Omicron BA.1 and Alpha RBDs, or the Omicron BA.1 and Delta RBDs were also not detected.

Furthermore, in all individuals two additional subsets of RBD-specific $B_{MEM}$ cells were identified. One subset was characterized by binding to Wuhan, Alpha and Omicron BA.1, but not Delta, RBD. The other population exhibited binding to Wuhan and Alpha but not Omicron BA.1 or Delta RBD (FIG. 18, H). Sequence alignment identified L452R as the only RBD mutation unique for Delta that is not shared by the other 3 variant RBDs (FIG. 18, I top). Similarly, the only RBD site conserved in Wuhan and Alpha but altered in Delta and Omicron BA.1 was found to be T478K (FIG. 18, I bottom). Both L452R and T478K alterations are known to be associated with the evasion of vaccine induced neutralizing antibody responses. Of note, no $B_{MEM}$ cells were detected in all combinatorial subgroups in which multiple sequence alignment failed to identify unique epitopes in the RBD sequence that satisfied the Boolean selection criteria (e.g., Wuhan only or Wuhan and Omicron BA.1, but not Alpha, Delta). These findings indicate that the $B_{MEM}$ cell response against RBD is driven by specificities induced through prior vaccination with BNT162b2 and not substantially redirected against new RBD epitopes mutated in the Omicron variant after infection.

Summary

SARS-CoV-2 Omicron is a partial immune escape variant with an unprecedented number of amino acid alterations in the S protein at sites of neutralizing antibody binding, distinguishing it from previously reported variants. Recent neutralizing antibody mapping and molecular modeling studies strongly support the functional relevance of these alterations, and their importance is confirmed by the observation that double-vaccinated individuals have no detectable neutralizing activity against SARS-CoV-2 Omicron.

The findings presented herein show that Omicron BA.1 breakthrough infection of vaccinated individuals boosts not only neutralizing activity and $B_{MEM}$ cells against Omicron BA.1 but broadly augments immunity against various VOCs, and also provide insights into how broad immunity is achieved The data presented herein indicate that initial exposure to the Wuhan strain S protein may have shaped the formation of $B_{MEM}$ cells and imprinted against the formation of novel $B_{MEM}$ cell responses against the more distinctive epitopes of the Omicron BA.1 variant. Similar observations have been reported from vaccinated individuals who experienced breakthrough infections with the delta variant (K. Röltgen et al., "Immune imprinting, breadth of variant recognition, and germinal center response in human SARS-CoV-2 infection and vaccination," Cell (2022), doi:10.1016/j.cell.2022.01.018.). As demonstrated in the present Example, Omicron BA.1 breakthrough infection primarily expands a broad $B_{MEM}$ cell repertoire against conserved S protein and RBD epitopes, rather than inducing considerable numbers of strictly Omicron-specific $B_{MEM}$ cells.

Thus, Omicron BA.1 breakthrough infection in double-vaccinated individuals leads to expansion of the pre-existing $B_{MEM}$ cell pool, similar to a third dose of booster vaccination. However, there are clear differences in the immune response pattern induced by a homologous vaccine booster as compared to an Omicron BA.1 breakthrough infection. Despite the focus of the B cell memory response on conserved epitopes, Omicron BA.1 breakthrough infection leads to a more substantial increase in antibody neutralization titers against Omicron BA.1, as well as pronounced cross-neutralization of both the ancestral and the novel SARS CoV-2 variants. These effects are particularly striking in double-vaccinated individuals.

Without wishing to be bound by theory, three findings may point to potentially complementary and synergistic mechanisms responsible for these results:

First, an overall increase of S protein-specific $B_{MEM}$ cells. Omicron BA.1-convalescent double-vaccinated individuals have a higher frequency of $B_{MEM}$ cells and higher neutralizing antibody titers against all VOCs as compared to triple-vaccinated individuals. That breakthrough infection elicits a stronger neutralizing antibody response than the 3rd vaccine dose in double-vaccinated individuals is not apparent from previous studies describing breakthrough infections with other variants (Evans et al., Science Translational Medicine (2022) 14, eabn8057) and may be explained by poor neutralization of the Omicron BA.1 variant in the initial phase of infection, potentially causing a greater or prolonged antigen exposure of the immune system to the altered S protein.

Second, a stronger bias on RBD-specific $B_{MEM}$ cell responses. Omicron BA.1 breakthrough infection promotes proportionally more pronounced boosting of RBD-specific $B_{MEM}$ cells than of $B_{MEM}$ cells that recognize S protein-specific epitopes outside the RBD. Therefore, Omicron BA.1-infected individuals have a significantly higher ratio of RBD/S protein-specific $B_{ME}$M cells compared to vaccinated Omicron-naïve individuals. The RBD is a key domain of the S protein that binds to the SARS-CoV-2 receptor ACE2 and has multiple neutralizing antibody binding sites in regions that are not affected by Omicron BA.1 alterations, e.g., position L452. An increased focus of the immune response on this domain could promote $B_{MEM}$ cells producing neutralizing antibodies against RBD epitopes that are not altered in Omicron BA.1.

Third, the induction of broadly neutralizing antibodies. The majority of sera from Omicron-BA.1 convalescent but not from Omicron-naïve vaccinated individuals was found to robustly neutralize SARS-CoV-1. This may indicate that Omicron BA.1 infection in vaccinated individuals stimulates $B_{MEM}$ cells that form neutralizing antibodies against spike protein epitopes conserved in the SARS-CoV-1 and SARS-CoV-2 families. It was reported that broadly neutralizing antibodies are present in SARS-CoV-1 infected individuals vaccinated with BNT162b2. Such pan-Serbecovirus immune responses are thought to be triggered by neutralizing antibodies to highly conserved S protein domains. The greater antigenic distance of the Omicron BA.1 spike protein from the other SARS-Cov-2 strains may promote targeting of conserved subdominant neutralizing epitopes as recently described to be located in the C-terminal portion of the spike protein.

In aggregate, these results indicate that despite possible imprinting of the immune response by previous vaccination, the preformed B-cell memory pool can be refocused and quantitatively remodeled by exposure to heterologous S proteins to allow neutralization of variants that evade a previously established neutralizing antibody response.

In conclusion, while the data are based on samples from individuals exposed to the Omicron BA.1 S protein as a result of infection, the findings presented herein support that a vaccine adapted to the Omicron BA.1 S protein can similarly reshape the B-cell memory repertoire and therefore can be more beneficial than an extended series of boosters with the existing Wuhan-Hu-1 spike based vaccines.

Materials and Methods

Recruitment of Participants and Sample Collection

Individuals from the SARS-CoV-2 Omicron-naïve BNT162b2 double-vaccinated (BNT162b$2^2$) and triple-vaccinated (BNT162b$2^3$) cohorts provided informed consent as part of their participation in a clinical trial (the Phase 1/2 trial BNT162-01 [NCT04380701], the Phase 2 rollover trial BNT162-14 [NCT04949490], or as part of the BNT162-17 [NCT05004181] trial).

Participants from the SARS-CoV-2 Omicron BA.1 convalescent double- and triple vaccinated cohorts (BNT162b$2^2$+Omi and BNT162b$2^3$+Omi cohorts, respectively) and individuals vaccinated with other approved COVID-19 vaccines or mixed regimens with subsequent Omicron BA.1 breakthrough infection were recruited from University Hospital, Goethe University Frankfurt as part of a research program that recruited patients that had experienced Omicron BA.1 breakthrough infection following vaccination for COVID-19, to provide blood samples and clinical data for research. Infection with the Omicron BA.1 strain was confirmed with variant-specific PCR or sequencing, and participants were free of symptoms at the time of blood collection.

Sampling Timepoints are Provided in FIG. 15.

Serum was isolated by centrifugation 2000×g for 10 minutes and cryopreserved until use. Li-Heparin blood samples were isolated by density gradient centrifugation using Ficoll-Paque PLUS (Cytiva) and were subsequently cryopreserved until use.

VSV-SARS-CoV-2 S Variant Pseudovirus Generation

A recombinant replication-deficient vesicular stomatitis virus (VSV) vector that encodes green fluorescent protein (GFP) and luciferase instead of the VSV-glycoprotein (VSV-G) was pseudotyped with SARS-CoV-1 spike (S) (UniProt Ref: P59594) and with SARS-CoV-2 S derived from either the Wuhan reference strain (NCBI Ref: 43740568), the Alpha variant (mutations: Δ69/70, Δ144, N501Y, A570D, D614G, P681H, T716I, 5982A, D1118H), the Beta variant (mutations: L18F, D80A, D215G, Δ242-244, R246I, K417N, E484K, N501Y, D614G, A701V), the Delta variant (mutations: T19R, G142D, E156G, Δ157/158, K417N, L452R, T478K, D614G, P681R, D950N) the Omicron BA.1 variant (mutations: A67V, Δ69/70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F) or the Omicron BA.2 variant (mutations: T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K) according to published pseudotyping protocols (M. Berger Rentsch, G. Zimmer, A vesicular stomatitis virus replicon-based bioassay for the rapid and sensitive determination of multi-species type I interferon. PloS one. 6, e25858 (2011), doi:10.1371/journal.pone.0025858).

In brief, HEK293T/17 monolayers (ATCC® CRL-11268™) cultured in Dulbecco's modified Eagle's medium (DMEM) with GlutaMAX™ (Gibco) supplemented with 10% heat-inactivated fetal bovine serum (FBS [Sigma-Aldrich]) (referred to as medium) were transfected with Sanger sequencing-verified SARS-CoV-1 or variant-specific SARS-CoV-2 S expression plasmid with Lipofectamine LTX (Life Technologies) following the manufacturer's instructions. At 24 hours VSV-G complemented VSVΔG vector. After incubation for 2 hours at 37° C. with 7.5% $CO_2$, cells were washed twice with phosphate buffered saline (PBS) before medium supplemented with anti-VSV-G antibody (clone 8G5F11, Kerafast Inc.) was added to neutralize residual VSV-G-complemented input virus. VSV-SARS-CoV-2-S pseudotype-containing medium was harvested 20 hours after inoculation, passed through a 0.2 μm filter (Nalgene) and stored at −80° C. The pseudovirus batches were titrated on Vero 76 cells (ATCC® CRL-1587™) cultured in medium. The relative luciferase units induced by a defined volume of a Wuhan spike pseudovirus reference batch previously described in Muik et al. (Muik et al., "Neutralization of SARS-CoV-2 lineage B.1.1.7 pseudovirus by BNT162b2 vaccine-elicited human sera. Science (New York, N.Y.). 371, 1152-1153 (2021), doi:10.1126/science.abg6105") that corresponds to an infectious titer of 200 transducing units (TU) per mL, was used as a comparator. Input volumes for the SARS-CoV-2 variant pseudovirus batches were calculated to normalize the infectious titer based on the relative luciferase units relative to the reference.

Pseudovirus Neutralization Assay

Vero 76 cells were seeded in 96-well white, flat-bottom plates (Thermo Fisher Scientific®) at 40,000 cells/well in medium 4 hours prior to the assay and cultured at 37° C. with 7.5% $CO_2$. Each serum was serially diluted 2-fold in medium with the first dilution being 1:5 (Omicron naïve double- and triple BNT162b2 vaccinated; dilution range of 1:5 to 1:5,120) or 1:30 (double- and triple BNT162b2 vaccinated after subsequent Omicron breakthrough infection; dilution range of 1:30 to 1:30,720). VSV-SARS-CoV-2-S/VSV-SARS-CoV-1-S particles were diluted in medium to obtain 200 TU in the assay. Serum dilutions were mixed 1:1 with pseudovirus (n=2 technical replicates per serum per pseudovirus) for 30 minutes at room temperature before being added to Vero 76 cell monolayers and incubated at 37° C. with 7.5% $CO_2$ for 24 hours. Supernatants were removed and the cells were lysed with luciferase reagent (Promega). Luminescence was recorded on a CLARIOstar® Plus microplate reader (BMG Labtech), and neutralization titers were calculated as the reciprocal of the highest serum dilution that still resulted in 50% reduction in luminescence. Results were expressed as geometric mean titers (GMT) of duplicates. If no neutralization was observed, an arbitrary titer value of half of the limit of detection [LOD] was reported.

Live SARS-CoV-2 Neutralization Assay

SARS-CoV-2 virus neutralization titers were determined by a microneutralization assay based on cytopathic effect (CPE) at VisMederi S.r.l., Siena, Italy. In brief, heat-inactivated serum samples from participants were serially diluted 1:2 (starting at 1:10) and incubated for 1 hour at 37° C. with 100 TCID50 of live Wuhan-like SARS-CoV-2 virus strain 2019-nCOV/ITALY-INMI1 (GenBank: MT066156), Beta virus strain Human nCoV19 isolate/England ex-SA/HCM002/2021 (mutations: D80A, D215G, Δ242-244, K417N, E484K, N501Y, D614G, A701V), sequence-verified Delta strain isolated from a nasopharyngeal swab (mutations: T19R, G142D, E156G, Δ157/158, L452R, T478K, D614G, P681R, R682Q, D950N) or Omicron BA.1 strain hCoV-19/Belgium/rega-20174/2021 (mutations: A67V, Δ69/70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F) to allow any antigen-specific antibodies to bind to the virus. The 2019-nCOV/ITALY-INMI1 strain S protein is identical in sequence to the wild-type SARS-CoV-2 S (Wuhan-Hu-1 isolate). Vero E6 (ATCC® CRL-1586™) cell monolayers were inoculated with the serum/virus mix in 96-well plates and incubated for 3 days (2019-nCOV/ITALY-INM11 strain) or 4 days (Beta, Delta and Omicron BA.1 variant strain) to allow infection by non-neutralized virus. The plates were observed under an inverted light microscope and the wells were scored as positive for SARS-CoV-2 infection (i.e., showing CPE) or negative for SARS-CoV-2 infection (i.e., cells were alive without CPE). The neutralization titer was determined as the reciprocal of the highest serum dilution that protected more than 50% of cells from CPE and reported as GMT of duplicates. If no neutralization was observed, an arbitrary titer value of 5 (half of the limit of detection [LOD]) was reported.

Detection and Characterization of SARS-CoV-2-Specific B Cells with Flow Cytometry Spike/RBD-specific B cells were detected using recombinant, biotinylated SARS-CoV-2 Spike (Acro Biosystems: Wuhan—SPN-C82E9, Alpha—SPN-C82E5, Delta—SPN-C82Ec, Omicron—SPN-C82Ee) and RBD (Acro Biosystems: Wuhan—SPD-B28E9, Alpha—SPD-C82E6, Delta—SPD-C82Ed, Omicron—SPD-C82E4) proteins. Recombinant Spike and RBD proteins were tetramerized with fluorescently labeled Streptavidin (BioLegend, BD Biosciences) in a 4:1 molar ratio for 1 h at 4° C. in the dark. Afterwards samples were spun down for 10 min at 4° C. to remove eventual precipitates.

For flow cytometric analysis, PBMCs were thawed and $5\times10^6$ cells per sample were seeded into 96 U-bottom plates. Cells were blocked for Fc-receptor-binding (Human BD Fc Block™, BD Biosciences) and statured with free biotin (D-Biotin, Invitrogen, 1 pM) in flow buffer (DPBS (Gibco) supplemented with 2% FBS (Sigma), 2 mM EDTA (Sigma-Aldrich)) for 20 min at 4° C. Cells were washed and labeled with BCR bait tetramers supplemented with free Biotin in flow buffer (D-Biotin, Invitrogen, 2 μg/ml) for 1 h at 4° C. in the dark (2 μg/ml for Spike and 0.25 μg/ml for RBD proteins). Cells were washed with flow buffer and stained for viability (Fixable Viability Dye eFluor™ 780, eBioscience) and surface markers (CD3—clone: UCHT1(BD Biosciences), CD4—clone: SK3 (BD Biosciences), CD185 (CXCR5)—clone: RF8B2 (BioLegend), CD279 (PD-1)—clone: EH12.1(BD Biosciences), CD278 (ICOS)—clone: C398.4A (BioLegend), CD19—clone: SJ25C1(BD Biosciences), CD20—clone: 2H7(BD Biosciences), CD21—clone: B-ly4(BD Biosciences), CD27—clone: L128(BD Biosciences), CD38—clone: HIT2(BD Biosciences), CD11c—clone: S-HCL-3(BD Biosciences), CD138—clone: M115(BD Biosciences), IgG—clone: G18-145(BD Biosciences), IgM—clone: G20-127(BD Biosciences), IgD—clone: IA6-2(BD Biosciences), CD14—clone: M<bP9 (BD Biosciences, dump channel), CD16—clone: 3G8 (BD Biosciences, dump channel)) in flow buffer supplemented with Brilliant Stain Buffer Plus (BD Biosciences, according to the manufacturer's instructions) for 20 min at 4° C. Samples were washed and fixed with BDTM Stabilizing Fixative (BD Biosciences, according to the manufacturer's instructions) prior to data acquisition on a BD Symphony Δ3 flow cytometer. FCS 3.0 files were exported from BD Diva Software and analyzed using FlowJo software (Version 10.7.1.).

Debris and doublets were discriminated via FSC/SSC. Then dead cells and monocytes (CD14, CD16-Viability/Dump channel) were excluded. CD19 positive B cells were analyzed for IgD and CD27 expression, thereby naïve B cells were discriminated as IgD® cells with the Boolean 'make non-gate' function. Within non-naïve B cells Plasmablasts ($CD38^{high}$ $CD20^{low}$) and memory B cells ($B_{MEM}$s $CD38^{int/low}CD20^{high}$) were distinguished. $B_{MEM}$ cells were analyzed for B cell bait binding. SARS-CoV-2 Spike reactivities were assessed by gating on each Spike/RBD variant tested by plotting against the CD20 signal. Bait gates were overlayed onto total $B_{MEM}$ cells and displayed as N×N-Plots for the four bait channels.

Statistical Analysis

The statistical method of aggregation used for the analysis of antibody titers is the geometric mean and for the ratio of SARS-CoV-2 VOC titer and Wuhan titer the geometric mean and the corresponding 95% confidence interval. The use of the geometric mean accounts for the non-normal distribution of antibody titers, which span several orders of magnitude. The Friedman test with Dunn's correction for multiple comparisons was used to conduct pairwise signed-rank tests of group geometric mean neutralizing antibody titers with a common control group. Flow cytometric frequencies were analyzed with and tables were exported from FlowJo software (Version 10.7.1.). Statistical analysis of cumulative memory B cell frequencies was the mean and standard errors of the mean (SEM). All statistical analyses were performed using GraphPad Prism software version 9.

Example 8: Induced Antibody Response of Vaccines Encoding a SARS-CoV-2 S Protein from an Omicron Variant To test the efficacy of an RNA vaccine encoding a SARS-CoV-2 S protein comprising one or more mutations characteristic of an Omicron variant, subjects previously administered a primary regimen comprising two doses of 30 ug of RNA encoding a SARS-CoV-2 S protein from a Wuhan strain (e.g., BNT162b2), and a booster regimen comprising a dose of 30 ug of RNA encoding a SARS-CoV-2 S protein from a Wuhan strain (i.e., a Wuhan specific booster, e.g., BNT162b2) were administered a further booster dose comprising either (i) 30 ug of RNA encoding an SARS-CoV-2 S protein from a Wuhan strain (e.g., BNT162b2), or (ii) 30 ug of RNA encoding a SARS-CoV-2 S protein comprising mutations that are characteristic of an Omicron BA.1 variant (i.e., an Omicron BA.1-specific booster, e.g., RNA encoding a SARS-CoV-2 S protein comprising an amino acid sequence of SEQ ID NO: 49, and/or comprising a nucleotide sequence of SEQ ID NOs: 50 and/or 51) (the dose administered as part of the second booster regimen is referred to as a "4th dose" in the figures). Sera was collected from subjects at the time of administering the second booster regimen and one month afterwards.

Neutralization antibody titers were determined using a Fluorescent Focus Reduction Neutralization Test ("FFRNT"). Suitable FFRNT assays are known in the art, and include, e.g., the assays described in Zou J, Xia H, Xie X, et al. "Neutralization against Omicron SARS-CoV-2 from previous non-Omicron infection," Nat Commun 2022; 13:852, the contents of which is incorporated by reference herein in its entirety. Additional exemplary neutralization assays include those described in the previous examples, as well as those described in Bewley, Kevin R., et al. "Quantification of SARS-CoV-2 neutralizing antibody by wild-type plaque reduction neutralization, microneutralization and pseudotyped virus neutralization assays." Nature Protocols 16.6 (2021): 3114-3140. As shown in FIG. 20, A, subjects administered a second booster regimen comprising a dose of RNA encoding a SARS-CoV-2 S protein comprising mutations characteristic of an Omicron BA.1 variant exhibited significant increases in concentrations of neutralization antibodies against an Omicron BA.1 variant, as compared to subjects administered a second booster regimen comprising a dose of RNA encoding a SARS-CoV-2 S protein of a Wuhan strain. Specifically, subjects administered an Omicron BA.1 specific booster exhibited a GMR that was 1.79-fold higher and a GMFR that was 2.31 fold higher than that observed in subjects administered a fourth dose of RNA encoding a SARS-CoV-2 S protein from a Wuhan strain. The superior immune response induced by an Omicron BA.1-specific booster against an Omicron BA.1 variant was further increased in subjects previously infected with SARS-CoV-2 (as determined by an antigen test) or currently infected with SARS-CoV-2 (as determined by PCR). See FIG. 20, B, which shows that a subject population including previously and/or currently infected subjects exhibited a GMR that is 2.94 fold higher, and a GMFR ratio that is 1.97 fold higher that observed in a subject population comprising previously and/or currently infected subjects administered an RNA vaccine encoding a SARS-CoV-2 S protein from a Wuhan strain.

Pseudovirus neutralization assays were also performed using a pseudovirus comprising a SARS-CoV-2 S protein of a Wuhan strain, using the same sera samples discussed above. Subjects administered RNA encoding a SARS-CoV-2 S protein from a Wuhan strain (e.g., BNT162b2) exhibited titers of neutralization antibodies that were similar to those observed in subjects administered an Omicron BA.1-specific booster, demonstrating that the two vaccines are at least similarly effective in their ability to induce an antibody response against a Wuhan strain. See FIG. 20C, which shows that the GMR and GMFR observed in subjects administered a Wuhan specific booster (e.g., BNT162b2) is similar to that observed in subjects administered an Omicron BA.1 specific booster (OMI). In subjects previously infected with SARS-CoV-2 (e.g., as determined by an antigen assay) or currently infected with SARS-CoV-2 (e.g., as determined by a PCR assay), subjects administered an Omicron BA.1 specific booster demonstrated an improved immune response as compared to subjects administered a booster specific for a Wuhan strain. See FIG. 20D, which shows that the GMR for subjects administered an Omicron BA.1 specific booster is about 1.4 fold that of subjects administered a Wuhan specific booster. Subjects administered an Omicron BA.1 specific booster also demonstrated a superior immune response against a delta variant in pseudovirus neutralization assays. See FIG. 20E, showing that the GMFR for subjects administered an Omicron BA.1-specific booster is about 1.20 fold higher than that observed in subjects administered a Wuhan specific booster. The superior immune response induced by an Omicron BA.1-specific booster against a delta variant was further increased in sera from subjects previously and/or currently infected with SARS-CoV-2. See FIG. 20F.

Example 9: Immunogenicity Study of Vaccines Encoding S Proteins of SARS-CoV-2 Variants in Vaccine-Naïve Subjects To test the immunogenicity of various variant specific vaccines in vaccine naïve subjects, vaccine naïve mice were immunized twice with (a) saline (negative control), (b) an RNA vaccine encoding a SARS-CoV-2 S protein from a Wuhan strain, (c) an RNA vaccine encoding a SARS-CoV-2 S protein having mutations characteristic of an Omicron BA.1 variant (Omi), (d) an RNA vaccine encoding a SARS-CoV-2 S protein having mutations characteristic of a delta variant (Delta), (e) a bivalent vaccine comprising RNA encoding a SARS-CoV-2 S protein from a Wuhan strain and a SARS-CoV-2 S protein comprising mutations characteristic of an Omicron BA.1 variant (b2+Omi), and (f) a bivalent vaccine comprising RNA encoding a SARS-CoV-2 S protein having mutations characteristic of a delta variant and RNA encoding a SARS-CoV-2 S protein having mutations characteristics of an Omicron BA.1 variant (Delta+Omi). The immunogenicity of the RNA vaccines was investigated by focusing on the antibody immune response.

Sera was obtained 7 days after immunization, and analyzed using a pseudovirus neutralization assay (e.g., the assay described in Example 2), using pseudoviruses comprising a SARS-CoV-2 S protein from a Wuhan strain, a SARS-CoV-2 S protein comprising mutations characteristic of a beta variant, a SARS-CoV-2 S protein comprising mutations characteristic of a delta variant, or a SARS-CoV-2 S protein comprising mutations characteristic of an Omicron BA.1 variant. As shown in FIG. 21, bivalent vaccines were found to elicit the broadest immune response in vaccine naïve mice.

Example 10: Induced Antibody Response of Vaccines Encoding a SARS-CoV-2 S Protein Comprising One or More Mutations Characteristic of a Beta Variant in Subjects Previously Administered an RNA Vaccine Encoding a SARS-CoV-2 S Protein from a Wuhan Strain To test the efficacy of an RNA vaccine encoding a SARS-CoV-2 S protein comprising one or more mutations characteristic of a Beta variant, subjects previously administered a primary regimen comprising two doses each of 30 ug of RNA encoding a SARS-CoV-2 S protein from a Wuhan strain (in the present example, BNT162b2 (SEQ ID NO: 20)), were administered two booster doses, each comprising 30 ug of RNA encoding a SARS-CoV-2 S protein comprising one or more mutations characteristic of a Beta variant (referred to hereafter as a Beta-specific vaccine). In the present Example, construct RBP020.11 was administered as the Beta-specific vaccine. While in the present Example, the two booster doses were administered approximately one month apart, in some embodiments, the two booster doses can be administered at least 3 weeks apart, at least 4 weeks apart, at least 5 weeks apart, at least 6 weeks apart, at least 7 weeks apart, at least 8 weeks apart, or longer (e.g., in accordance with exemplary dosing regimens as described herein).

Sera were collected from subjects before administration of BNT162b2, one month after administering two primary doses of BNT162b2, one month after administering a first dose of a Beta-specific vaccine, and one month after administering a second dose of a Beta-specific vaccine. Neutralization antibody titers against a pseudovirus comprising a SARS-CoV-2 S protein of a Wuhan strain or a SARS-CoV-2 S protein comprising one or more mutations characteristic of a Beta variant were measured using a pseudovirus neutralization assay (results shown in FIG. 22). Subjects exhibited an increase in neutralization antibody titers against both a Wuhan strain of SARS-CoV-2 and a Beta varaint following administration of the third and fourth doses of a Beta-specific vaccine.

Example 11: Induced Antibody Response of Vaccines Encoding a SARS-CoV-2 S Protein Comprising One or More Mutations Characteristic of a Beta Variant in Vaccine Naïve Subjects To test the efficacy of an RNA vaccine encoding a SARS-CoV-2 S protein comprising one or more mutations characteristic of a Beta variant in vaccine naïve subjects, subjects who had not previously been administered a SARS-CoV-2 vaccine, and did not show evidence of prior or current infection with SARS-CoV-2 (e.g., as assessed by an antibody test and/or a PCR test) were administered two doses each of 30 ug of RNA encoding a SARS-CoV-2 S protein comprising one or more mutations characteristic of a Beta variant (in the present example, RBP020.11). Sera was collected one month after administration of a second dose, and neutralization antibody titers were measured using a viral neutralization assay, using viral particles comprising either a SARS-CoV-2 S protein from a Wuhan strain or a SARS-CoV-2 S protein having one or more mutations characteristic of a Beta variant. Tables 15 and 16, below, show the results for the neutralization assay against Beta variant (results for the neutralization assay against a Wuhan strain are not shown). As shown in the tables, compared to vaccine-naïve subjects administered two doses of an RNA vaccine encoding a SARS-CoV-2 S protein from a Wuhan strain (in the present Example, BNT162b2), an RNA vaccine encoding a SARS-CoV-2 S protein having mutations characteristic of a Beta variant was found to induce a significantly stronger antibody response against a Beta variant.

TABLE 21

Geometric Mean Fold Rise (GMFR) of titers of neutralization antibodies, from before Dose 1 to each subsequent time points, in BNT162b2-naïve subjects without evidence of infection up to 1 month after dose 2 and administered BNT162b2 or an RNA vaccine encoding a SARS-CoV-2 S protein having one or more mutations characteristic of a Beta variant

| | | Vaccine Group (as Assigned/Randomized)[a] | | | |
|---|---|---|---|---|---|
| | Dose/ Sampling | $BNT162b2_{SA}$ (30 μg) | | BNT162b2 (30 μg) | |
| Assay | Time Point[b] | n[c] | GMFR[d] (95% CI[d]) | n[c] | GMFR[d] (95% CI[d]) |
| SARS-CoV-2 neutralization assay - SA variant - NT50 | 2/1 Month | 272 | 40.0 (36.2, 44.2) | 304 | 8.3 (7.4, 9.2) |

Abbreviations: GMFR = geometric mean fold rise; LLOQ = lower limit of quantitation; N-binding = SARS-CoV-2 nucleoprotein-binding; NAAT = nucleic acid amplification test; NE = not estimable; NT50 = 50% neutralizing titer; SA = South Africa (Beta variant); SARS-CoV-2 = severe acute respiratory syndrome coronavirus 2.

Note:

Subjects who had no serological or virological evidence (up to 1 month after receipt of Dose 2) of past SARS-CoV-2 infection (i.e., N-binding antibody [serum] negative at Dose 1 visit, 1-month post-Dose 2 visit, SARS-CoV-2 not detected by NAAT[nasal swab] at Dose 1 visit, Dose 2 visit, and negative NAAT[nasal swab] at any unscheduled visit up to 1 month after Dose 2) were included in the analysis.

[a]Subjects in the $BNT162b2_{SA}$/Beta-specific vaccine (30 μg) vaccine group were not randomized.

[b]Protocol-specified timing for blood sample collection.

[c]n = Number of subjects with valid and determinate assay results for the specified assay at both prevaccinationtime point and the given dose/sampling time point.

[d]GMFRs and 2-sided 95% CIs were calculated by exponentiating the mean logarithm of fold rises and the corresponding CIs (based on the Student t distribution). Assay results below the LLOQwere set to 0.5 × LLOQ in the analysis.

TABLE 22

Geometric Mean Titers (GMT) of neutralization antibodies measured in vaccine-naïve subjects without evidence of infection up to 1 month after dose 2 and administered BNT162b2 or an RNA vaccine encoding a SARS-CoV-2 S protein having one or more mutations characteristic of a Beta variant

| | | Vaccine Group (as Assigned/Randomized)[a] | | | |
|---|---|---|---|---|---|
| | | $BNT162b2_{SA}$ (30 μg) | | BNT162b2 (30 μg) | |
| Assay | Dose/Sampling Time Point[b] | n[c] | GMT[d] (95% CI[d]) | n[c] | GMT[d] (95% CI[d]) |
| SARS-CoV-2 neutralization assay - SA variant - NT50 (titer) | 1/Prevax | 272 | 34.0 (32.6, 35.3) | 304 | 33.0 (33.0, 33.0) |
| | 2/1 Month | 272 | 1358.0 (1242.2, 1484.5) | 304 | 273.1 (245.6, 303.7) |

Abbreviations: GMT = geometric mean titer; LLOQ = lower limit of quantitation; N-binding = SARS-CoV-2 nucleoprotein-binding; NAAT = nucleic acid amplification test; NE = not estimable; NT50 = 50% neutralizing titer; Prevax = prevaccination; SA = South Africa (Beta-variant); SARS-CoV-2 = severe acute respiratory syndrome coronavirus 2.

Note:

Subjects who had no serological or virological evidence (up to 1 month after receipt of Dose 2) of past SARS-CoV-2 infection (ie, N-binding antibody [serum] negative at Dose 1 visit, 1-month post-Dose 2 visit, SARS-CoV-2 not detected by NAAT[nasal swab] at Dose 1 visit, Dose 2 visit, and negative NAAT[nasal swab] at any unscheduled visit up to 1 month after Dose 2) were included in the analysis.

[a]Subjects in the $BNT162b2_{SA}$/Beta-specific vaccine (30 μg) vaccine group were not randomized.

[b]Protocol-specified timing for blood sample collection.

[c]n = Number of subjects with valid and determinate assay results for the specified assay at the given dose/sampling time point.

[d]GMTs and 2-sided 95% CIs were calculated by exponentiating the mean logarithm of the titers and the corresponding CIs (based on the Student t distribution).

Assay results below the LLOQwere set to 0.5 × LLOQ.

Example 12: Induced Antibody Response and Reactogenicity of BNT162b2 or Omicron BA.1-Specific Vaccine as Monovalent, Bivalent and High Dose in Participants 55+ Years of Age To test the efficacy and safety of (i) higher doses of RNA vaccines (e.g., as described herein), (ii) RNA vaccines encoding a SARS-CoV-2 S protein having one or more mutations characteristic of an Omicron BA.1 variant (an Omicron BA.1-specific vaccine), and (iii) a bivalent vaccine comprising an RNA encoding a SARS-CoV-2 S protein from a Wuhan variant and RNA encoding a SARS-CoV-2 S protein having one or more mutations characteristic of an Omicron BA.1 variant, subjects previously administered at least one dose of an RNA vaccine encoding a SARS-CoV-2 S protein of a Wuhan strain were administered one of several booster doses (e.g., as described herein). Specifically, subjects who had previously been administered two doses of 30 ug of an RNA vaccine encoding a SARS-CoV-2 S protein from a Wuhan strain (in the present example, BNT162b2), and a third dose of 30 ug of RNA encoding a SARS-CoV-2 S protein of a Wuhan strain (also BNT162b2 in the present example), were administered a fourth dose comprising:

(a) 30 ug of RNA encoding a SARS-CoV-2 S protein from a Wuhan strain,
(b) 60 ug of RNA encoding a SARS-CoV-2 S protein from a Wuhan strain,
(c) 30 ug of an Omicron BA.1-specific vaccine,
(d) 60 ug of an Omicron BA.1-specific vaccine,
e) 30 ug of a bivalent RNA vaccine (Omicron BA.1-adapted bivalent vaccine), comprising 15 ug of RNA encoding a SARS-CoV-2 S protein from a Wuhan strain and 15 ug of RNA encoding a SARS-CoV-2 S protein comprising mutations characteristic of an Omicron BA.1 variant, or
(f) 60 ug of a bivalent RNA vaccine (Omicron BA.1-adapted bivalent vaccine), comprising 30 ug of RNA encoding a SARS-CoV-2 S protein from a Wuhan strain and 30 ug of RNA encoding a SARS-CoV-2 S protein comprising mutations characteristic of an Omicron BA.1 variant.

In the present example, for the fourth dose, the RNA encoding a SARS-CoV-2 S protein from a Wuhan variant was BNT162b2, and the RNA encoding a SARS-CoV-2 S protein having mutations characteristic of an Omicron BA.1 variant comprised the nucleotide sequence of SEQ ID NO: 51.

Sera samples were collected at the time of administering the 4th dose and 7 days afterward, and tested for neutralization antibody titers against a viral particle comprising a SARS-CoV-2 S protein from a Wuhan strain, or a SARS-CoV-2 S protein comprising mutations characteristic of a Delta variant or an Omicron BA.1 variant.

Neutralization antibody titers were determined using a Fluorescent Focus Reduction Neutralization Test ("FFRNT"). Suitable FFRNT assays are known in the art, as discussed in Example 8. The neutralization responses are shown in FIG. 23.

As shown in FIG. 23 (A) subjects administered a fourth dose of 30 ug of an Omciron BA.1-specific vaccine exhibited an increase in neutralization antibodies against an Omicron BA.1 variant as compared to subjects administered a fourth dose of 30 ug of BNT162b2. Administering 60 ug of RNA increased neutralization responses both for BNT162b2 and an Omicron BA.1-specific vaccine, with 60 ug of an Omicron BA.1-specific vaccine showing a stronger immune response against an Omicron BA.1 variant. As shown in FIG. 23 (B), similar effects were observed in a population that included subjects previously or currently infected with SARS-CoV-2 (e.g., as determined by an antibody test and a PCR test, respectively).

FIG. 23 (C-D) provides data for neutralization responses against a Wuhan strain of SARS-CoV-2 in a population of subjects excluding subjects previously or currently infected with SARS-CoV-2 (FIG. 23(C)) and a population of subjects including these subjects (FIG. 23(D)).

FIG. 23 (E-F)-provides data for neutralization responses against a Delta variant in a population of subjects excluding subjects previously or currently infected with SARS-CoV-2 (FIG. 23(E)) and a population of subjects including these subjects (FIG. 23(F)).

FIG. 23 (G) shows neutralization responses as compared to subjects administered a 4th dose of 30 ug of BNT162b2. As can be seen in the table, an Omicron BA.1-specific vaccine induced a strong response against an Omicron BA.1 variant, and responses that were at least comparable to that of BNT162b2 for other variants. A bivalent vaccine (Omicron BA.1-adapted bivalent vaccine) produced a strong immune response against each SARS-CoV-2 variant tested, both at 30 ug and 60 ug doses.

Reactogenicity of the tested $4^{th}$ doses was also monitored in patients for 7 days following administration of the $4^{th}$ dose. FIG. 24 (A) shows local immune responses observed in subjects of different groups as indicated. As can be seen in the figure, 60 ug doses of an Omicron BA.1 specific vaccine and a bivalent vaccine were found to be more likely to produce pain at the injection site, as compared to that observed with other tested booster doses; however, the pain was rated as mild or moderate for both doses. Redness and swelling responses were low and comparable at each dose tested.

FIG. 24 (B) shows systemic immune responses observed in subjects of different groups as indicated. Systemic responses (as characterized by fever, fatigue, headache, chills, vomiting, diarrhea, muscle pain, or joint pain) were similar for each dose, while fatigue trended higher with the 60 ug doses.

The immune responses and reactogenicity of Omicron BA.1-adapted vaccines (monovalent and bivalent vaccines as described in this Example) as a booster dose are also confirmed in a Phase 2/3 trial in over 1,000 participants 56 years of age and older. The geometric mean titers (GMTs) of each of the tested doses, as well as the geometric mean ratios (GMRs) as compared to subjects administered a 4th dose of 30 ug of BNT162b2 are shown in Table 23, below

TABLE 23

Neutralization Responses in Subjects Administered 30 ug or 60 ug of a monovalent or bivalent Omicron BA.1-specific vaccine.

| | | | Vaccine group/BNT162b2 30 ug | |
|---|---|---|---|---|
| Vaccine Group | n | GMT (95% CI) 1 M post-dose | GMR (95% CI) | Met Superiority (Y/N) |
| BNT162b2 30 ug | 163 | 455.8 (365.9, 567.6) | | |
| BNT162b2 OMI 30 ug | 169 | 1014.5 (825.6, 1246.7) | 2.23 (1.65, 3.00) | Y |
| BNT162b2 OMI 60 ug | 174 | 1435.2 (1208.1, 1704.8) | 3.15 (2.38, 4.16) | Y |
| Bivalent OMI 30 ug | 178 | 711.0 (588.3, 829.2) | 1.56 (1.17, 2.08) | Y |
| Bivalent OMI 60 ug | 175 | 900.1 (726.3, 1115.6) | 1.97 (1.45, 2.68) | Y |

Seroresponse rates are summarized in Table 24, below. As shown in the below table, each of the tested doses was found to be non-inferior to BNT162b2 30 ug.

TABLE 24

Omicron BA.1 seroresponse rates

| Vaccine Group | N | n (%) | (95% CI) 1 M post-dose | Seroresponse difference in % (relative to BNT162b2 30 ug group) % (95% CI) | Met Non-Inferiority (Y/N)[1] |
|---|---|---|---|---|---|
| BNT162b2 30 ug | 149 | 85 (57.0) | (48.7, 65.1) | — | — |
| BNT162b2 OMI 30 ug | 163 | 125 (76.7) | (69.4, 82.9) | 19.6 (9.3, 29.7) | Y |
| BNT162b2 OMI 60 ug | 166 | 143 (86.1) | (79.9, 91.0) | 29.1 (19.4, 38.5) | Y |
| Bivalent OMI 30 ug | 169 | 121 (71.6) | (64.2, 78.3) | 14.6 (4.0, 24.9) | Y |
| Bivalent OMI 60 ug | 162 | 110 (67.9) | (60.1, 75.0) | 10.9 (0.1, 21.4) | Y |

[1]Non-inferiority criterion: the lower bound of the 95% confidence interval is >−5%

Followng the collection of the data summarized in Table 24, data continued to be collected on subjects administered an Omicron monovalent vaccine. The further data is summarized in Table 25, below, and confirms the findings shown in Table 24.

TABLE 25

Further data on Omicron BA.1 seroresponse rates

| | | Vaccine group (as randomized) | | | | |
|---|---|---|---|---|---|---|
| | | BNT162b2 OMI (30 ug) | | BNT162b2 (30 ug) | | Difference |
| Assay | Dose/sampling time point[a] | N[a] | n[b] (%) (95% CI[c]) | N[a] | n[b] (%) (95% CI[c]) | %[d] (95% CI[e]) |
| SARS-CoV-2 neutralization assay - Omicron BA.1 - $NT_{50}$ (titre) | 1/1 month | 206 | 127 (61.7) (54.6, 68.3 | 226 | 91 (40.3) (33.8, 47.0) | 21.4 (12.0, 30.4) |

Abbreviations: $NT_{50}$ = 50% neutralizing titer; SARS-CoV-2 = severe acute respiratory syndrome coronavirus 2.

Note:

Seroresponse is defined as achieving a ≥4-fold rise from baseline (before the first dose of study vaccination). If the baseline measurement is below the LLOQ, the postvaccination measure of ≥4 × LLOQ is considered seroresponse.

Note:

Participants who had no serological or virological evidence (prior to the 1-month post-first study vaccination blood sample collection) of past SARS-CoV-2 infection (i.e., N-binding antibody [serum] negative at the first study vaccination and the 1-month post-first study vaccination visits, negative NAAT [nasal swab] at the first study vaccination visit, and any unscheduled visit prior to the 1-month post-first study vaccination blood sample collection) and had no medical history of COVID-19 were included in the analysis.

a. N = number of participants with valid and determinate assay results for the specified assay at both the prevaccination time point and the given sampling time point. This value is the denominator for the percentage calculations.

b. n = Number of participants with seroresponse for the given assay at the given sampling time point.

c. Exact 2-sided CI based on the Clopper and Pearson method.

d. Difference in proportions, expressed as a percentage (monovalent Omicron BA.1 [30 mcg] - Comirnaty [30 mcg]).

e. 2-sided CI based on the Miettinen and Nurminen method for the difference in proportions, expressed as a percentage.

Changes in titers for each dose before administration of a 4th booster dose and 1 month after administration of a 4th booster dose are shown in FIG. 25. As shown in FIG. 25, one month after administration, a booster dose of the Omicron BA.1-adapted monovalent vaccine (30 µg and 60 µg) increased neutralizing geometric mean titers (GMT) against Omicron BA.1 13.5 and 19.6-fold above pre-booster dose levels, while a booster dose of the Omicron BA.1-adapted bivalent vaccine (30 µg and 60 µg) conferred a 9.1 and 10.9-fold increase in neutralizing GMTs against Omicron BA.1. A booster dose of the Omicron BA.1-adapted bivalent vaccine (30 µg) induced neutralization titers that were approximately 3-fold lower than those induced against BA.1. Both Omicron BA.1-adapted vaccines (e.g., monovalent and bivalent vaccines) were well-tolerated in participants who received one or the other Omicron BA.1-adapted vaccine, and demonstrated a favorable safety and tolerability profile similar to that of BNT162b2 (encoding a SARS-CoV-2 S protein from a Wuhan strain).

Additionally, in a SARS-CoV-2 live virus neutralization assay tested on sera from participants over 56 years of age and older receiving an Omicron-adapted vaccine (e.g., monovalent or bivalent vaccine as described in this Example), sera also neutralized Omicron BA.4/BA.5 with titers lower than Omicron BA.1.

Example 13: Omicron Breakthrough Infection Drives Cross-Variant Neutralization and Memory B Cell Formation, but to a Lesser Extent Against Omicron BA.4 and BA.5

New Omicron sublineages that harbor further alterations in the SARS-CoV-2 S protein continue to arise, with BA.4 and BA.5 deemed VOCs by the European Centre for Disease Prevention and Control (ECDC) on the May 12, 2022 (European Centre for Disease Prevention and Control, Epidemiological update: SARS-CoV-2 Omicron sub-lineages BA.4 and BA.5 (2022) (available at www_ecdc_europa_eu/en/news-events/epidemiological-update-sarscov-2-omicron-sub-lineages-ba4-and-ba5)).

The present Example 13 is an extension of Example 7, in which the serum samples collected from BA.1-breakthrough cases as described in Example 7 were further analyzed for their neutralization activity against Omicron BA.4 and BA.5 variants.

As described in Example 7, in Omicron-naïve double-vaccinated individuals, 50% pseudovirus neutralization ($pVN_{50}$) geometric mean titers (GMTs) of Beta and Delta VOCs were found to be reduced as compared to the Wuhan strain, while neutralization of Omicron sublineages BA.1 and BA.2 was virtually undetectable. In this present Example, FIG. 26(*a*) shows that neutralization titers of BA.4/5 was also virtually undetectable in double-vaccinated, BA.1-breakthrough patients.

As described in Example 7, Omicron-naïve triple-vaccinated individuals exhibited $pVN_{50}$ GMTs against all tested VOCs that were substantially higher as compared to double-vaccinated individuals. Robust neutralization of Alpha, Beta and Delta variants was observed, while neutralization of Omicron BA.1 and BA.2 was reduced as compared to Wuhan (GMT 160 and 211 vs 398). As shown in FIG. 26(A) of the present Example, neutralization of Omicron BA.4/5 was further reduced (GMT 74) in Omicron-naïve triple-vaccinating patients, corresponding to a 5-fold lower titer as compared to the Wuhan strain.

As shown in FIG. 26(*b*), Omicron BA.1 breakthrough infection was found to have only a minor boosting effect on neutralization of BA.4/5. In double-vaccinated patients, $pVN_{50}$ GMTs against Omicron BA.4/5 were significantly below those against Wuhan (GMT 135 vs. 740). A similar pattern was observed with BA.1 convalescent and control sera from triple-vaccinated individuals. As noted in Example 7, BA.1 convalescent sera exhibited high $pVN_{50}$ GMTs against previous SARS-CoV-2 VOCs, including Beta (1182), Omicron BA.1 (1029), and Omicron BA.2 (836), which were close to titers against the Wuhan reference (1182). In contrast, as shown in FIG. 26(*b*), neutralization of BA.4/5 in triple-vaccinated individuals with a breakthrough infection of BA.1 was significantly reduced as compared to the Wuhan strain, with $pVN_5o$ GMTs of 197, 6-fold lower than against the Wuhan strain.

Of note, in all cohorts, neutralizing titers against BA.4/5 were closer to the low level observed against the phylogenetically more distant SARS-CoV-1 pseudovirus than that seen against Wuhan. Comparing the ratios of SARS-CoV-2 VOC and SARS-CoV-1 pVN5 GMTs normalized against Wuhan (FIG. 26(*c*)), it is remarkable that breakthrough infection with Omicron BA.1 does not lead to more efficient cross-neutralization of Omicron BA.4/5 in double-vaccinated and triple-vaccinated individuals. In aggregate, these data demonstrate that Omicron BA.1 breakthrough infection of vaccine-experienced individuals mediates broadly neutralizing activity against BA.1, BA.2 and several previous SARS-CoV-2 variants, but not for BA.4/5.

As shown in FIG. 27, similar results were found for patients previously administered a non-BNT162b2 vaccine and who had a BA.1 breakthrough infection.

As described in Example 7, Omicron BA.1 breakthrough infection in BNT162b2-vaccinated individuals was found to produce strong neutralizing activity against Omicron BA.1, BA.2 and previous SARS-CoV-2 VOCs, primarily by expanding $B_{MEM}$ cells against epitopes shared broadly across the different SARS-CoV-2 strains. These data demonstrate that a vaccination-imprinted $B_{MEM}$ cell pool has sufficient plasticity to be remodeled by exposure to a heterologous SARS-CoV-2 S protein. While selective amplification of $B_{MEM}$ cells recognizing shared epitopes allows for effective neutralization of most variants that evade previously established immunity, susceptibility to escape by variants that acquire alterations at hitherto conserved sites may be heightened. The significantly reduced neutralizing activity against the Omicron BA.4/5 pseudovirus, which harbors the additional alterations L452R and F486V in the RBD, supports a mechanism of immune evasion by loss of the few remaining conserved epitopes.

Discussion

Surprisingly, and contrary to the results observed in Example 7, neutralization of Omicron sublineages BA.4 and BA.5 was not enhanced in BA.1-breakthrough patients, with titers instead comparable to those against the phylogenetically more distant SARS-CoV-1. While the present Example focused on individuals vaccinated with the BNT162b2 mRNA vaccine, in individuals vaccinated with CoronaVac (a whole, inactivated virus vaccine developed by Sinovac Biotech), similar observations have recently been reported, suggesting that Omicron BA.4/5 can bypass BA.1 infection-mediated boosting of humoral immunity (Y. Cao et al., BA.2.12.1, BA.4 and BA.5 escape antibodies elicited by Omicron infection, bioRxiv: the preprint server for biology (2022)).

The present disclosure provides insights into how immunity against multiple variants is achieved in BA.1 breakthrough cases, why Omicron BA.4 and BA.5 sublineages can partially escape neutralization, and provides vaccination protocols and technologies to enhance protection across coronavirus strains and lineages, specifically including across Omicron lineages (e.g., including BA.4 and/or BA.5). Without wishing to be bound by any particular theory, the present disclosure proposes that initial exposure to the Wuhan strain S protein may shape formation of $B_{MEM}$ cells and imprint against novel $B_{MEM}$ cell responses recognizing epitopes distinctive for the Omicron BA.1 variant.

Omicron BA.1 breakthrough infection in BNT162b2-vaccinated individuals primarily expands a broad $B_{MEM}$ cell repertoire against conserved SARS-CoV-2 S protein and RBD epitopes, rather than inducing strictly Omicron BA.1-specific $B_{MEM}$ cells. As compared to the immune response induced by a homologous vaccine booster, an Omicron BA.1 breakthrough infection leads to a more substantial increase in antibody neutralization titers against Omicron and a robust cross-neutralization of many SARS CoV-2 variants.

As noted in Example 7, one potential explanation for the broad neutralization elicited by a BA.1 breakthrough infection is the induction of broadly neutralizing antibodies. Sera from Omicron BA.1-convalescent vaccinated individuals was found to neutralize SARS-CoV-2 Omicron BA.4/5 and SARS-CoV-1 to a far lesser extent than previous SARS-CoV-2 VOCs including BA.1 and BA.2. This finding indicates that Omicron BA.1 infection in vaccinated individuals stimulates $B_{MEM}$ cells that produce neutralizing antibodies against S protein epitopes conserved in the SARS-CoV-2 variants up to and including Omicron BA.2, but that have mostly been lost in BA.4/5 and are for the most part not shared by SARS-CoV-1.

The greater antigenic distance of the Omicron BA.1 S protein from earlier SARS-CoV-2 strains may promote targeting of conserved subdominant neutralizing epitopes as recently described to be located, e.g., in cryptic sites within a portion of the RBD distinct from the receptor-binding motif (Li, Tingting, et al. "Cross-neutralizing antibodies bind a SARS-CoV-2 cryptic site and resist circulating variants," Nature communications 12.1 (2021): 1-12, and Yuan, Meng, et al. "A highly conserved cryptic epitope in the receptor binding domains of SARS-CoV-2 and SARS-CoV" Science 368.6491 (2020): 630-633) or in the membrane proximal S glycoprotein subunit designated S2 (Pinto, Dora, et al. "Broad betacoronavirus neutralization by a stem helix-specific human antibody." Science 373.6559 (2021): 1109-1116. Li, Wenwei, et al. "Structural basis and mode of action for two broadly neutralizing antibodies against SARS-CoV-2 emerging variants of concern." Cell reports 38.2 (2022): 110210; Hurlburt, Nicholas K., et al. "Structural definition of a pan-sarbecovirus neutralizing epitope on the spike S2 subunit." Communications biology 5.1 (2022): 1-13).

As noted in Example 7, Omicron BA.1-infected individuals appear to have a significantly higher RBD/S protein-specific $B_{MEM}$ cell ratio as compared to vaccinated Omicron-naïve individuals. Omicron BA.1 carries multiple S protein alterations in key neutralizing antibody binding sites of the NTD (such as del69/70 and del143-145) that dramatically reduce the targeting surface for memory B cell responses in this region. Although the Omicron BA.1 RBD harbors multiple alterations, some neutralizing antibody binding sites are unaffected (20). An expansion of $B_{MEM}$ cells that produce neutralizing antibodies against RBD epitopes that are not altered in Omicron BA.1, such as those at position L452 as indicated in the present Example, could help to rapidly restore neutralization of the BA.1 and BA.2 variants. Importantly, the strong neutralization of Omicron BA.1 and BA.2 should not mask the fact that the neutralizing $B_{MEM}$ immune response in Omicron BA.1 convalescent vaccinated individuals is driven by a smaller number of epitopes. The significantly reduced neutralizing activity against the Omicron BA.4/5 pseudovirus, which harbors the additional alterations L452R and F486V in the RBD, demonstrates the mechanism of immune evasion by loss of the few remaining conserved epitopes. Meanwhile, further sublineages with L452 alterations (e.g., BA.2.12.1) are being reported to evade humoral immunity elicited by BA.1 breakthrough infection (Y. Cao et al., cited above).

The present disclosure proposes that immunity in the early stages of Omicron BA.1 infection in vaccinated individuals may be based on recognition of conserved epitopes, and narrowly focused on a small number of neutralizing sites that are not altered in Omicron BA.1 and BA.2. Such a narrow immune response bears a high risk that those few epitopes may be lost by acquisition of further alterations in the course of the on-going evolution of Omicron and may result in immune escape, as experienced with sublineages BA.2.12.1, BA.4 and BA.5 (Y. Cao et al., cited above, and K. Khan et al., Omicron sub-lineages BA.4/BA.5 escape BA.1 infection elicited neutralizing immunity (2022)). Importantly, Omicron BA.1 breakthrough infection does not appear to reduce the overall spectrum of (Wuhan) S glycoprotein-specific memory B cells, as memory B cells that do not recognize Omicron BA.1 S remain detectable in blood at similar frequencies. Wuhan-specific (non-Omicron BA.1 reactive) $B_{MEM}$ cells were consistently detected in Omicron BA.1 breakthrough infected individuals at levels similar to those in Omicron-naïve double-/triple-vaccinated individuals. Without wishing to be bound by any particular theory, the present disclosure notes that these findings may reflect an increase of the total $B_{MEM}$ cell repertoire by selective amplification of $B_{MEM}$ cells that recognize shared epitopes.

The present Example, among other things, provides insights that it may be more beneficial for a subject who has been infected or administered at least one dose (including, e.g., at least two, at least three doses) of vaccine(s) adapted to a Wuhan strain (e.g., but not limited to a protein based vaccine or RNA-based vaccines such as BNT162b2, Moderna mRNA-1273) to receive at least one dose of a vaccine (e.g., a protein or RNA-based vaccine) adapted to a strain that is not an Omicron BA.1. In some embodiments, a vaccine that is adapted to a strain that is not an Omicron BA.1 can be or comprise a vaccine that is adapted to Omicron BA.4 and/or Omicron BA.5. The present Example, among other things, also provides insights that vaccine-naïve subjects without prior SARS-CoV-2 infection may be desirable to be administered a combination of vaccines, which comprises at least one dose of a vaccine adapted to a Wuhan strain (e.g., RNA vaccine such as in some embodiment BNT162b2) and at least one dose of a vaccine adapted to a strain that is not an Omicron BA.1. In some embodiments, such vaccines in a combination may be administered at different times, for example, in some embodiments as primary doses and/or booster doses administered apart by a pre-determined period of time (e.g., according to certain dosing regimens as described herein). In some embodiments, such vaccines in a combination may be administered as a single multivalent vaccine.

Materials and Methods

Serum samples, neutralization assays, and all other experiments described in the present Example were performed as in Example 7. The BA.4/5 VSV-SARS-CoV-2 S variant pseudovirus generation A recombinant replication-deficient vesicular stomatitis virus (VSV) vector that encodes green fluorescent protein (GFP) and luciferase instead of the VSV-glycoprotein (VSV-G) was pseudotyped comprised a SARS-CoV-2 S protein comprising the following mutations relative to the Wuhan strain: T19I, A 24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K).

Example 14. Omicron BA.2 Breakthrough Infection of Vaccinated Individuals Induces Broad Cross Neutralization Against Omicron BA.1, BA.2 and Other VOCs, Including BA.4 and BA.5

The present Example shows that a BA.2 Omicron breakthrough infection in individuals triple-vaccinated with BNT162b2 surprisingly drives superior cross variant neutralization as compared to a BA.1-breakthrough infection in individuals triple-vaccinated with BN162b2, including improved production of neutralizing antibodies against a BA.4/5 Omicron variant. Thus, among other things, the present disclosure demonstrates feasibility of defining immunologically synergistic categories of coronavirus strains and/or sequences (e.g., spike protein sequences).

In some embodiments of improved coronavirus vaccination strategies provided by the present disclosure, a subject is exposed to each of at least two different such synergistic categories. In some embodiments, a subject is, has been or becomes infected with a virus of a first category, and receives at least one dose of a vaccine of a second category, characterized by immunologic synergy with the first category. Alternatively or additionally, in some embodiments, a subject receives or has received doses of first and second vaccines of such first and second categories. In some embodiments, vaccines of different categories may be separately administered (e.g., at different points in time and/or to different sites on a subject). In some embodiments, vaccines of different categories may be administered together (e.g., at substantially the same time and/or to approximately or exactly the same site and/or in a single composition).

As compared to Omicron BA.1 breakthrough infection of vaccinated individuals, which induces lower neutralization against Omicron BA.4/BA.5 relative to neutralization against other SARS-CoV-2 variants (including, e.g., Wuhan-Hu-1 strain, alpha variant, beta variant, delta variant, Omicron BA.1, Omicron BA.2, and Omicron BA.2.11.2), the present Example shows that a BA.2 Omicron breakthrough infection in individuals vaccinated with BNT162b2 surprisingly drives superior cross variant neutralization, including improved production of neutralizing antibodies against a BA.4/5 Omicron variant. Thus, in some embodiments, the present disclosure, among other things, demonstrates that SARS-CoV-2 strains and/or variants can be grouped into at least two different categories such that a subject who is exposed to a SARS-CoV-2 strain and/or variant from each of such two different categories can benefit from immunologically synergistic protection conferred by such two different categories. In some embodiments, a first category of SARS-CoV-2 strains/variants comprises: Wuhan-Hu-1 strain, alpha variant, beta variant, delta variant, Omicron BA.1, and subvariants derived from aforementioned strains and/or variants; while a second category comprises Omicron BA.2, Omicron BA.2.12.1, Omicron BA.4/BA.5, and subvariants derived from aforementioned strains and/or variants. Thus, in some embodiments, the present disclosure, among other things, provide insights that a combination of at least one dose (including, e.g., at least 1, at least 2, at least 3, at least 4, or more) of a first vaccine (e.g., an mRNA vaccine as described herein that encodes a spike protein polypeptide) that comprises or delivers a SARS-CoV-2 spike protein polypeptide with a sequence characteristic of a first category as described above, and at least one dose (including, e.g., at least 1, at least 2, at least 3, at least 4, or more) of a second vaccine (e.g., an mRNA vaccine described herein that encodes a spike protein polypeptide) that comprises or delivers a SARS-CoV-2 spike protein polypeptide with a sequence characteristic of a second category as described above can synergistically provide superior cross variant neutralization, including enhanced production of neutralizing antibodies toward a BA.4/5 Omicron variant. In some embodiments, the present disclosure specifically teaches surprising efficacy of administering at least one dose of a vaccine (e.g., an mRNA vaccine that encodes a spike protein polypeptide as described herein) that comprises or delivers a SARS-CoV-2 spike protein polypeptide with sequences characteristic of a BA.2 Omicron variant to subjects who have received at least one (e.g., 2, 3, or more) doses of a vaccine (e.g., vaccine that encodes a spike protein polypeptide as described herein) that comprises or delivers a SARS-CoV-2 spike protein polypeptide with sequences characteristic of a Wuhan-Hu-1 strain).

Background

Emergence of the SARS-CoV-2 Omicron variant of concern (VOC) in November 2021 (Ref. 1) can be considered a turning point in the COVID-19 pandemic, owing to its ability to substantially escape previously established immunity. Omicron BA.1, which displaced Delta within weeks as the predominant circulating VOC, had acquired significant alterations in the receptor binding domain (RBD) and N-terminal domain (NTD) (Ref. 2). These changes resulted in a loss of many epitopes recognized by neutralizing antibodies (Refs. 3-4) and drastically impaired humoral immunity induced by vaccines based on the ancestral Wuhan strain or exposure to the ancestral strain or previous variants (Refs. 5-7). BA.1 was subsequently displaced by the BA.2 variant, which in turn gave rise to further sub-lineages. BA.4 and BA.5, which are derived from BA.2, are currently becoming the dominant variants in many countries across the globe with multiple studies suggesting a significant change in antigenic properties compared to BA.2, and especially compared to BA.1 (Refs. 8-9). As BA.4 and BA.5 share an identical S glycoprotein sequence, they are referred herein as BA.4/5. While many of the amino acid changes in the RBD are shared between Omicron sub-lineages, alterations within the NTD of BA.2-derived sub-lineages including BA.4/5 are mostly distinct from those found in BA.1 (FIG. 33).

A vast majority worldwide have been immunized with the vaccines adapted Wuhan strain, including, e.g., mRNA vaccines such as BNT162b2 and mRNA-1273 (Ref. 10), which have thus substantially shaped SARS-CoV-2 population immunity. However, emergence of the immune escape variant Omicron BA.1 led to a steep increase in the occurrence of breakthrough infections in vaccinated individuals. It has been reported that SARS-CoV-2 variant breakthrough infection can reshape humoral immunity, thereby modulating neutralizing antibody titers against other variants (Refs. 8, 11, 12). However, as previously reported, BA.1 breakthrough infection may not provide strong immunity against Omicron BA.4/5.

Certain Findings

In order to determine if BA.2 breakthrough infection would refocus immunity against Omicron BA.2 and BA.2-derived sub-lineages such as BA.4/5, the magnitude and breadth of the neutralizing antibody response was studied in samples from individuals who had received a triple vaccination scheme with mRNA vaccines (BNT162b2/mRNA-1273) and subsequently experienced SARS-CoV-2 breakthrough infections between March and May 2022, during which period the BA.2 lineage was dominant in Germany (All Vax+Omi BA.2). Such findings have important implications for ongoing efforts of vaccine design, as containment of the COVID-19 pandemic requires the generation of durable and sufficiently broad immunity to provide protection against current and future variants of SARS-CoV-2.

Two reference cohorts were generated from data previously published in Quandt et al. (Ref. 12), comprising (i) individuals triple-vaccinated with BNT162b2 without a prior or breakthrough SARS-CoV-2 infection at the time of sample collection ($BNT162b2^3$) and (ii) individuals who were triple-vaccinated with mRNA vaccines with subsequent breakthrough-infection during a period of Omicron BA.1 dominance (All Vax+Omi BA.1).

Breakthrough infection with the SARS-CoV-2 Omicron BA.1 and BA.2 occurred at a median of approximately 4 months or 3 weeks, respectively, after triple-vaccination with an mRNA-based COVID-19 vaccine (BNT162b2, mRNA-1273, or heterologous regimens comprising both vaccines; all Vax+Omi BA.1, all Vax+Omi BA.2) (FIG. 29). Immune sera used to characterize serum neutralizing activity were collected at a median 28 days post-vaccination for the $BNT162b2^3$ cohort, 43 days post-BA.1 breakthrough for the All Vax+Omi BA.1 cohort, and 39 days post BA.2 breakthrough infection for the All Vax+Omi BA.2 cohort. Median ages of the cohorts were similar (32-38 years). The BA.2.12.1 neutralization data was generated from serum samples from cohorts $BNT162b^3$ and All Vax+Om BA. 1 for this study.

To evaluate the neutralizing activity of immune sera, a pseudovirus neutralization test (pVNT), for example, as described in Refs. 13, 14, were used. Pseudoviruses bearing the S glycoproteins of SARS-CoV-2 Wuhan, Alpha, Beta, Delta, Omicron BA.1, BA.2, BA.2.12.1, as well as the recently emerged Omicron sub-lineages BA.4 and BA.5 were applied to assess neutralization breadth. As BA.4 and BA.5 share an identical S glycoprotein sequence, including key alterations L452R and F486V, they are referred herein as BA.4/5. In addition, SARS-CoV (herein referred to as SARS-CoV-1; Ref. 15) was assayed to detect potential pan-Sarbecovirus neutralizing activity.

As reported previously in Ref. 12, 50% pseudovirus neutralization ($pVN_{50}$) geometric mean titers (GMTs) against Omicron BA.1 and BA.2 of immune sera from SARS-CoV-2 naïve triple-vaccinated individuals were considerably reduced compared to the Wuhan strain (GMT 160 and 221 versus 398). Neutralizing activity against BA.2.12.1 and BA.4/5 was even further reduced (GMTs 111 and 74), corresponding to a 5.4-fold lower titer for BA.4/5 as compared to the Wuhan strain (FIG. 30(A)).

Omicron BA.2 breakthrough infection markedly increased $pVN_{50}$ GMTs against BA.2 and BA.2.12.1 compared to SARS-CoV-2-naïve triple-vaccinated immune sera, such that neutralization of BA.2 after breakthrough infection was comparable to the Wuhan strain (FIG. 31 (B-C)). Similarly, BA.1 breakthrough infection conferred robust neutralizing activity against BA.1 (FIG. 30(B), FIG. 31(A). Importantly, while $pVN_{50}$ GMTs against BA.4/5 in BA.2 convalescent sera were lower than against the Wuhan strain (GMTs 391 versus 922, i.e., 2.4-fold reduction), this reduction was still less than that observed in the Omicron-naïve BNT162b2[3] cohort, whose sera showed a 5.4-fold reduction of BA.4/5 neutralizing activity (FIG. 31(C)). By contrast, $pVN_{50}$ GMTs against BA.4/5 and Wuhan after BA.1 breakthrough infection were 266 and 1327, respectively (i.e., 5-fold reduction; FIG. 30(B)). Hence, Omicron BA.1 breakthrough infection of triple-vaccinated individuals did not lead to more efficient cross-neutralization of Omicron BA.4/5 as compared with triple-vaccinated Omicron-naïve individuals. In both cohorts, neutralizing titers against BA.4/5 were closer to the low level observed against the phylogenetically more distant SARS-CoV-1 than that seen against Wuhan (FIG. 30). Of note, the $pVN_{50}$ GMTs against the Wuhan strain after BA.1 breakthrough infection were slightly higher than those observed for BA.2 breakthrough infection (GMTs 1327 versus 922), which, without wishing to be bound by a particular theory, may relate to the longer interval between the third vaccination and the infection (median 22 days for BA.1 versus 127.5 days for BA.2) (FIG. 31). A separate analysis was conducted including only individuals triple-vaccinated with BNT162b2 (with BA.2 or BA.1 breakthrough infections, or Omicron-naïve). In these analyses similar observations regarding BA.4/5 neutralizing activities were made: $pVN_{50}$ GMTs against BA.4/5 in BA.2 convalescent sera were 2.4-fold lower than against the Wuhan strain, whereas the reduction was 6-fold after BA.1 breakthrough infections (FIG. 31). While relative neutralization of BA.2 and BA.2.12.1 was comparable in BA.2 and BA.1 convalescent sera, neutralizing activity against these variants remained slightly above that seen in Omicron-naïve sera.

Immune sera from triple-vaccinated Omicron naïve individuals had broad neutralizing activity against ancestral SARS-CoV-2 VOCs. Neutralizing activity against Beta was slightly higher in BA.1 convalescent sera, whereas neutralization of Alpha and Delta was not affected by BA.1 or BA.2 breakthrough infections (FIG. 31(C)).

In aggregate, these data demonstrate that Omicron BA.2 breakthrough infections of vaccine-experienced individuals mediate broadly neutralizing activity against BA.1, BA.2, BA.2.12.1 and several ancestral SARS-CoV-2 variants. Moreover, neutralizing activity against BA.4/5, while lower than against the Wuhan reference, is provided to a larger extent than in BA.1 convalescent sera.

Recent studies have demonstrated that Omicron BA.1 breakthrough infection in individuals vaccinated with an mRNA vaccine (BNT162b2 or mRNA-1273) boosts serum neutralizing titers not only against the ancestral Wuhan strain, but also against VOCs including BA.2 (Refs. 8, 11, 12). This effect was seen in triple-vaccinated individuals but was particularly evident in double-vaccinated individuals, whose sera contain little to no neutralizing activity against BA.2. However, BA.1 breakthrough infection did not induce strong neutralizing activity against BA.4/5, VOCs that are currently establishing dominance worldwide. Without wishing to be bound by a particular theory, this immune escape has been attributed to the amplification and/or recall of pre-existing neutralizing antibody responses that recognize epitopes absent in the Omicron sub-lineages BA.2.12.1, BA.4, and BA.5.

The present Example, among other things, provide insights that BA.2 breakthrough infections trigger recall responses which mediate enhanced neutralization of the BA.2-derived sub-lineages, including BA.4/5, indicating that higher S protein sequence similarity among BA.2, BA.2.12.1, and BA.4/5 drives more efficient cross-neutralization compared to breakthrough infections with the more distant BA.1 variant. Notwithstanding the importance of vaccination with currently approved Wuhan-derived vaccines such as BNT162b2 that offer effective protection from severe disease by current VOCs including Omicron BA.1 and BA.2, the present findings of broadly cross-neutralizing activity against current VOCs including BA.4/5 after BA.2 breakthrough infection provides insights, among other things, that a combination of a vaccine adapted to Wuhan strain sequence or a variant sequence from the same immunologically-related category as discussed above (e.g., alpha strain, beta strain, delta strain, Omicron BA.1) and a vaccine adapted to the BA.2 variant sequence or a variant sequence from the same immunologically-related category as discussed above (e.g., Omicron BA.2.12.1, Omicron BA.4/BA.5) can provide enhanced cross-neutralization activity against variants from two different categories. In some embodiments, the present Example provides evidence that supports implementation of licensure procedures modelled on that of seasonal flu vaccines that use the latest epidemiological data to select for COVID-19 vaccine strains. In some embodiments, the present Example further provides evidence that supports establishment of rapid strain selection for seasonal updates of COVID-19 vaccines, similar to the selection process practiced by the World Health Organization (WHO) Global Influenza Surveillance and Response System (GISRS), and/or agreement on accelerated approval pathways based on surrogate immunogenicity endpoints.

Neutralization titers from subjects vaccinated against SARS-CoV-2 and who have had a BA.1 or a BA.2 breakthrough infection are shown in FIGS. 31(A) and (B), respectively, and GMRs for both groups of subjects are shown in FIG. 31(C). As shown in FIGS. 31(A) and (B), sera from subjects previously vaccinated against SARS-CoV-2, and who had a breakthrough infection with either BA.1 or BA.2, were found to have significant neutralization titers against pseudovirus comprising a SARS-CoV-2 S protein of a Wuhan strain, an Alpha variant, a Beta variant, a Delta Variant, and an Omicron BA.1 variant. As noted previously, neutralization titers against BA.2 are somewhat lower in sera from BA.1 breakthrough patients (GMT of 875 for BA.2 vs 1327 for Wuhan strain) and are lower still against BA.2.12.1 and BA.4/5 (GMTs of 584 and 266, respectively as compared to 1327 for Wuhan). BA.2 breakthrough patients show similar neutralization responses as BA.1 breakthrough patients against a SARS-CoV-2 Wuhan strain, Alpha variant, Beta variant, and Delta variant. The neutralization response against Omicron BA.1 is somewhat higher in BA.1-breakthrough patients than in BA.2-breakthrough patients (GMR of 0.76 as compared to 0.60), while neutralization titers against Omicron BA.2 are higher in BA.2-breakthrough patients than in BA.1-breakthrough patients (GMR of 0.94 vs 0.66). Surprisingly, however, neutralization responses against BA.4/5 are significantly higher in BA.2-breakthrough patients (GMR of 0.39 in BA.2 breakthrough patients, as compared to a GMR of 0.2 in BA.1 breakthrough subjects). The present disclosure therefore documents that a broader immune response can be elicited by a BA.2-breakthrough infection as compared to a BA.1 breakthrough infection in subject vaccinated against SARS-CoV-2, and teaches that administering a booster vaccine comprising RNA encoding an S protein comprising mutations characteristic of a BA.2 Omicron variant can achieve surprising and unexpected benefits.

Furthermore, the present disclosure provides an insight that, given similarities among S protein sequences of BA.2 and BA.4/5 variants, combining vaccination doses that comprise or deliver BA.4 and/or BA.5 variant spike sequences with those of that comprise or deliver Wuhan spike sequences may also achieve particularly broad immunization (i.e., synergistic immunization as described herein).

In some embodiments, these findings suggest that synergistic categories of coronavirus strain and/or variant sequences (e.g., SARS-CoV-2 strain and/or variant sequences) can be defined, for example, in some embodiments based on shared amino acid alterations in S glycoprotein of coronavirus strain and/or variant sequences. For example, while many of the amino acid changes in the RBD of S protein are shared between Omicron sub-lineages (e.g., BA.1, BA.2, BA.2.12.1, and BA.4/5), alterations within the NTD of BA.2 and BA.2-derived sub-lineages including BA.4/5 are mostly distinct from those found in BA.1. Therefore, in some embodiments, synergistic categories of coronavirus strain and/or variant sequences (e.g., SARS-CoV-2 strain and/or variant sequences) can be defined based on the degree of shared amino acid mutations present with the NTD of a S protein. For example, in some embodiments where two SARS-CoV-2 strain and/or variant sequences share at least 50% (including, e.g., at least 60%, at least 70%, at least 80%, at least 90%, or more) of the amino acid mutations present in the NTD of a S protein, both SARS-CoV-2 strain and variant sequences can be grouped into the same category. In some embodiments where two SARS-CoV-2 strain and/or variant sequences share no more 50% (including, e.g., no more than 45%, no more than 40%, no more than 30%, or lower) of the amino acid mutations present in the NTD of a S protein, both SARS-CoV-2 strain and variant sequences can be grouped into different categories. Among other things, the present findings provide insights that exposing subjects (e.g., via infection and/or vaccination) to at least two antigens that are of different synergistic categories (e.g., as shown in the table below) can produce a more robust immune response (e.g., broadening the spectrum of cross-neutralization against different variants and/or producing an immune response that is less prone to immune escape).

| Category I | Category II |
|---|---|
| Wuhan strain | Omicron BA.2 |
| Alpha variant | Omicron BA.2.11.2 |
| Beta variant | Omicron BA.4 |
| Delta variant | Omicron BA.5 |
| Omicron BA.1 | |
| | Sublineages derived from any one of the above |
| Sublineages derived from any one of the above | |

For example, in some embodiments, vaccine-naïve subjects without prior infection may be administered a combination of vaccines, at least two of which are each adapted to a SARS-CoV-2 strain of different synergistic categories (e.g., as described herein). In some embodiments, such vaccines in a combination may be administered at different times, for example, in some embodiments as a first dose and a second dose administered apart by a pre-determined period of time (e.g., according to certain dosing regimens as described herein). In some embodiments, such vaccines in a combination may be administered as a multivalent vaccine. In some embodiments, subject infected or vaccinated with a SARS-CoV-2 strain of one category may be administered with a vaccine adapted to a SARS-CoV-2 strain of a different category (e.g., as described herein). In some embodiments, such a vaccine may be a polypeptide-based or RNA-based vaccine.

In some embodiments, a combination of vaccines comprising a vaccine from Category I and a BA.4/5 vaccine may provide a particularly superior immune response (e.g., an immune response with particularly strong cross-neutralization effects).

Due to the large number of differences between XBB and its variants, in some embodiments, a particularly improved synergistic effect can be produced by a combination comprising a vaccine of Category I and an XBB vaccine. In some embodiments, a particularly improved synergistic effect can be produced by a combination comprising a BA.4/5 vaccine and an XBB vaccine.

While the present findings are based on retrospective analyses of samples derived from different studies, using relatively small samples sizes and cohorts that are not fully aligned regarding immunization intervals and demographic characteristics such as age and sex of individuals, the present findings provide useful insights for vaccine design and vaccination strategies for improving cross-neutralization against a broader spectrum of SARS-COV-2 variants.

In some embodiments, a vaccine can comprise a polypeptide (e.g., a non-natural polypeptide, e.g., a chimeric polypeptide) comprising one or more mutations that are characteristic of one or more different SARS-CoV-2 variants, or a nucleic acid (e.g., in some embodiments an RNA) encoding the polypeptide. In some embodiments, a vaccine can comprise a polypeptide (e.g., a non-natural polypeptide, e.g., a chimeric polypeptide) comprising one or more mutations that are characteristic of a first SARS-CoV-2 variant and one or more mutations that are characteristic of a second SARS-CoV-2 variant, or a nucleic acid (e.g., in some embodiments an RNA) encoding the polypeptide. In some embodiments, a first SARS-CoV-2 variant can be a SARS-CoV-2 strain/variant from Category I of the table above, while a second SARS-CoV-2 variant can be a SARS-CoV-2 strain/variant from Category II of the table above. For example, in some embodiments, a vaccine can comprise a polypeptide that comprises an RBD comprising one or more mutations that are characteristic of a first SARS-CoV-2 variant and an NTD comprising one or more mutations that are characteristic of a second SARS-CoV-2 variant, or a nucleic acid (e.g., in some embodiments an RNA) encoding the polypeptide.

In some embodiments, a vaccine can comprise a polypeptide that comprises an RBD comprising one or more mutations characteristic of a BA.1 Omicron variant and an NTD comprising one or more mutations characteristic of a second SARS-CoV-2 variant that is not a BA.1 Omicron variant, or a nucleic acid (e.g., in some embodiments an RNA) encoding the polypeptide. In some embodiments, a vaccine can comprise or encode a polypeptide comprising an NTD comprising one or more mutations characteristic of a BA.1 Omicron variant and an RBD comprising one or more mutations characteristic of a second SARS-CoV-2 variant that is not a BA.1 Omicron variant. In some embodiments, a vaccine can comprise a polypeptide that comprises an RBD comprising one or more mutations characteristic of a BA.1 Omicron variant and an NTD comprising one or more mutations characteristic of a BA.2 Omicron variant, or a nucleic acid (e.g., in some embodiments an RNA) encoding the polypeptide. In some embodiments, a vaccine can comprise a polypeptide that comprises an RBD comprising one or more mutations characteristic of a BA.1 Omicron variant and an NTD comprising one or more mutations characteristic of a BA.4/5 Omicron variant, or a nucleic acid (e.g., in some embodiments an RNA) encoding the polypeptide.

In some embodiments, a vaccine can comprise a polypeptide that comprises an NTD comprising one or more mutations characteristic of a BA.1 Omicron variant and an RBD comprising one or more mutations characteristic of a second SARS-CoV-2 variant that is not a BA.1 Omicron variant, or a nucleic acid (e.g., in some embodiments an RNA) encoding the polypeptide. In some embodiments, a vaccine can comprise a polypeptide that comprises an RBD comprising one or more mutations characteristic of a BA.1 Omicron variant and an NTD comprising one or more mutations characteristic of a second SARS-CoV-2 variant that is not a BA.1 Omicron variant, or a nucleic acid (e.g., in some embodiments an RNA) encoding the polypeptide. In some embodiments, a vaccine can comprise a polypeptide that comprises an NTD comprising one or more mutations characteristic of a BA.1 Omicron variant and an RBD comprising one or more mutations characteristic of a BA.2 Omicron variant, or a nucleic acid (e.g., in some embodiments an RNA) encoding the polypeptide. In some embodiments, a vaccine can comprise a polypeptide that comprises one or more mutations characteristic of an NTD of a BA.1 Omicron variant and an RBD comprising one or more mutations characteristic of a BA.4/5 Omicron variant, or a nucleic acid (e.g., in some embodiments an RNA) encoding the polypeptide.

In some embodiments, a vaccine can comprise a polypeptide that comprises an RBD comprising one or more mutations characteristic of a BA.1 Omicron variant and an NTD of a Wuhan S protein, or a nucleic acid (e.g., in some embodiments an RNA) encoding the polypeptide. In some embodiments, a vaccine can comprise a polypeptide that comprises an RBD comprising one or more mutations characteristic of a BA.2 Omicron variant and an NTD of a Wuhan S protein, or a nucleic acid (e.g., in some embodiments an RNA) encoding the polypeptide. In some embodiments, a vaccine can comprise a polypeptide that comprises an RBD comprising one or more mutations characteristic of a BA.4/5 Omicron variant and an NTD of a Wuhan S protein, or a nucleic acid (e.g., in some embodiments an RNA) encoding the polypeptide.

In some embodiments, a vaccine can comprise a polypeptide that comprises an NTD comprising one or more mutations characteristic of a BA.1 Omicron variant and an RBD of a Wuhan S protein, or a nucleic acid (e.g., in some embodiments an RNA) encoding the polypeptide. In some embodiments, a vaccine can comprise a polypeptide that comprises an NTD comprising one or more mutations characteristic of a BA.2 Omicron variant and an RBD of a Wuhan S protein, or a nucleic acid (e.g., in some embodiments an RNA) encoding the polypeptide. In some embodiments, a vaccine can comprise a polypeptide that comprises an NTD comprising one or more mutations characteristic of a BA.4/5 Omicron variant and an RBD of a Wuhan S protein, or a nucleic acid (e.g., in some embodiments an RNA) encoding the polypeptide.

Materials and Methods

Recruitment of Participants and Sample Collection

Individuals from the SARS-CoV-2-naïve BNT162b2 triple-vaccinated (BNT162b2$^3$) cohort provided informed consent as part of their participation in the Phase 2 trial BNT162-17 (NCT05004181). Individuals with Omicron BA.1 or BA.2 breakthrough infection (All Vax+Omi BA.1 and All Vax+Omi BA.2 cohorts) were triple-vaccinated, e.g., with one or more doses of BNT162b2, Moderna mRNA-1273, AstraZeneca ChAdOx1-S recombinant vaccine, or a combination thereof, and were recruited to provide blood samples and clinical data for research. Omicron infections were confirmed with variant-specific PCR either between November 2021 and mid-January 2022 (All Vax+Omi BA.1) or between March 2022 and May 2022, at times were sub-lineages BA.1 or BA.2, respectively, were dominant (Ref. 24). The infections of certain participants (e.g., at least 7 participants) in this study were further characterized by genome sequencing, and genome sequencing confirmed Omicron BA.1 or BA.2 infection.

Participants were free of symptoms at the time of blood collection. Table 26 is a summary of characteristics of vaccinated individuals analyzed for neutralizing antibody responses. All participants had no documented history of SARS-CoV-2 infection prior to vaccination.

TABLE 26

| Characteristic | all Vax + Omi BA.2 (n = 14) | all Vax + Omi BA.1 (n = 15) | BNT16262$^3$ (n = 19) |
|---|---|---|---|
| Sex, n (%) | | | |
| Male | 6 (43) | 12 (80) | 10 (53) |
| Female | 8 (57) | 3 (20) | 9 (47) |
| Age, median (range) | 34 (25-57) | 32 (23-60) | 38 (23-54) |
| Age group at vaccination, n (%) | | | |
| 18-55 yrs | 12 (86) | 13 (87) | 19 (100) |
| 56-85 yrs | 2 (14) | 2 (13) | 0 (0) |
| Baseline SARS-CoV-2 status, n (%) | | | |
| Positive | 14 (100)† | 15 (100)† | 0 (0) |
| Negative | 0 (0) | 0 (0) | 19 (100)# |
| Unknown | 0 (0) | 0 (0) | 0 (0) |
| Interval, median (range) | | | |
| Days between D 1/D 2 | 41 (15-88) | 39 (20-92) | ‡ |
| Days between D 2/D 3 | 189 (152-249) | 189 (156-256) | 202 (181-266) |
| Days until serum draw after D 3 | N/A | N/A | 28 (26-30) |
| Days between last dose/infection | 127.5 (36-188) | 22 (3-112) | N/A |
| Days until serum draw after infection | 43 (34-99) | 43 (25-55) | N/A |

N/A: not applicable; n/a, not available; D, Dose; Yrs, Years; n, Number.

*Negative SARS-CoV-2 PCR test at the time of enrollment

#No evidence of prior SARS-CoV-2 infection (based on COVID-19 symptoms/signs and SARS-CoV-2 PCR test)

‡, Participants received the primary 2-dose series of BNT162b2 vaccine as part of a governmental vaccination program and the interval between doses was not recorded †Omicron BA.1 infection confirmed at time of recruitment to the research study.

Serum was isolated by centrifugation of drawn blood at 2000×g for 10 minutes and cryopreserved until use.

VSV-SARS-CoV-2 S Variant Pseudovirus Generation

A recombinant replication-deficient vesicular stomatitis virus (VSV) vector that encodes green fluorescent protein (GFP) and luciferase instead of the VSV-glycoprotein (VSV-G) was pseudotyped with SARS-CoV-1 S glycoprotein (UniProt Ref: P59594) and with SARS-CoV-2 S glycoprotein derived from either the Wuhan reference strain (NCBI Ref: 43740568), the Alpha variant (alterations: Δ69/70, Δ144, N501Y, A570D, D614G, P681H, T716I, S982A, D1118H), the Beta variant (alterations: L18F, D80A, D215G, Δ242-244, R246I, K417N, E484K, N501Y, D614G, A701V), the Delta variant (alterations: T19R, G142D, E156G, Δ157/158, K417N, L452R, T478K, D614G, P681R, D950N) the Omicron BA.1 variant (alterations: A67V, Δ69/70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F), the Omicron BA.2 variant (alterations: T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K), the Omicron BA.2.12.1 variant (alterations: T19I, Δ24-26, A27S, G142D, V213G, G339D, S371F, 5373P, S375F, T376A, D405N, R408S, K417N, N440K, L452Q, S477N, T478K, E484A, Q493R, Q498R, N501Y, Y505H, D614G, H655Y, N679K, P681H, S704L, N764K, D796Y, Q954H, N969K), or the Omicron BA.4/5 variant (alterations: T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K) according to published pseudotyping protocols (Ref. 49).

A diagram of SARS-CoV-2 S glycoprotein alterations is shown in FIG. 32 and a separate alignment of S glycoprotein alterations in Omicron sub-lineages is displayed in FIG. 33. In brief, HEK293T/17 monolayers (ATCC® CRL-11268™) cultured in Dulbecco's modified Eagle's medium (DMEM) with GlutaMAX™ (Gibco) supplemented with 10% heat-inactivated fetal bovine serum (FBS [Sigma-Aldrich]) (referred to as medium) were transfected with Sanger sequencing-verified SARS-CoV-1 or variant-specific SARS-CoV-2 S expression plasmid with Lipofectamine LTX (Life Technologies) following the manufacturer's instructions. At 24 hours VSV-G complemented VSVΔG vector. After incubation for 2 hours at 37° C. with 7.5% CO2, cells were washed twice with phosphate buffered saline (PBS) before medium supplemented with anti-VSV-G antibody (clone 8G5F11, Kerafast Inc.) was added to neutralize residual VSV-G-complemented input virus. VSV-SARS-CoV-2-S pseudotype-containing medium was harvested 20 hours after inoculation, passed through a 0.2 μm filter (Nalgene) and stored at −80° C. The pseudovirus batches were titrated on Vero 76 cells (ATCC® CRL-1587"') cultured in medium. The relative luciferase units induced by a defined volume of a Wuhan S glycoprotein pseudovirus reference batch previously described in Muik et al., 2021, that corresponds to an infectious titer of 200 transducing units (TU) per mL, was used as a comparator. Input volumes for the SARS-CoV-2 variant pseudovirus batches were calculated to normalize the infectious titer based on the relative luciferase units relative to the reference.

Pseudovirus Neutralization Assay

Vero 76 cells were seeded in 96-well white, flat-bottom plates (Thermo Fisher Scientific®) at 40,000 cells/well in medium 4 hours prior to the assay and cultured at 37° C. with 7.5% CO2. Each individual serum was serially diluted 2-fold in medium with the first dilution being 1:5 (Omicron-naïve triple BNT162b2 vaccinated; dilution range of 1:5 to 1:5,120) or 1:30 (triple vaccinated after subsequent Omicron BA.1 or BA.2 breakthrough infection; dilution range of 1:30 to 1:30,720). In the case of the SARS-CoV-1 pseudovirus assay, the serum of all individuals was initially diluted 1:5 (dilution range of 0.1:5 to 1:5,120). VSV-SARS-CoV-2-S/VSV-SARS-CoV-1-S particles were diluted in medium to obtain 200 TU in the assay. Serum dilutions were mixed 1:1 with pseudovirus (n=2 technical replicates per serum per pseudovirus) for 30 minutes at room temperature before being added to Vero 76 cell monolayers and incubated at 37° C. with 7.5% CO2 for 24 hours. Supernatants were removed and the cells were lysed with luciferase reagent (Promega). Luminescence was recorded on a CLARIOstar® Plus microplate reader (BMG Labtech), and neutralization titers were calculated as the reciprocal of the highest serum dilution that still resulted in 50% reduction in luminescence. Results were expressed as geometric mean titers (GMT) of duplicates. If no neutralization was observed, an arbitrary titer value of half of the limit of detection [LOD] was reported.

Statistical Analysis

The statistical method of aggregation used for the analysis of antibody titers is the geometric mean and for the ratio of SARS-CoV-2 VOC titer and Wuhan titer the geometric mean and the corresponding 95% confidence interval. The use of the geometric mean accounts for the non-normal distribution of antibody titers, which span several orders of magnitude. The Friedman test with Dunn's correction for multiple comparisons was used to conduct pairwise signed-rank tests of group geometric mean neutralizing antibody titers with a common control group. All statistical analyses were performed using GraphPad Prism software version 9.

References Cited in Example 14

1. WHO Technical Advisory Group on SARS-CoV-2 Virus Evolution (TAG-VE), Classification of Omicron (B.1.1.529): SARS-CoV-2 Variant of Concern (2021).
2. WHO Headquarters (HQ), WHO Health Emergencies Programme, Enhancing response to Omicron SARS-CoV-2 variant: Technical brief and priority actions for Member States (2022).
3. M. Hoffmann et al., The Omicron variant is highly resistant against antibody-mediated neutralization. Cell. 185, 447-456.e11 (2022), doi:10.1016/j.cell.2021.12.032.
4. W. Dejnirattisai et al., SARS-CoV-2 Omicron-B.1.1.529 leads to widespread escape from neutralizing antibody responses. Cell. 185, 467-484.e15 (2022), doi:10.1016/j.cell.2021.12.046.
5. V. Servellita et al., Neutralizing immunity in vaccine breakthrough infections from the SARS-CoV-2 Omicron and Delta variants. Cell. 185, 1539-1548.e5 (2022), doi:10.1016/j.cell.2022.03.019.
6. C. Kurhade et al., Neutralization of Omicron BA.1, BA.2, and BA.3 SARS-CoV-2 by 3 doses of BNT162b2 vaccine. Nature communications. 13, 255 (2022), doi:10.1038/s41467-022-30681-1.
7. Y. Cao et al., Omicron escapes the majority of existing SARS-CoV-2 neutralizing antibodies. Nature. 602, 657-663 (2022), doi:10.1038/s41586-021-04385-3.

8. Y. Cao et al., BA.2.12.1, BA.4 and BA.5 escape antibodies elicited by Omicron infection. Nature (2022), doi: 10.1038/s41586-022-04980-y.
9. N. P. Hachmann et al., Neutralization Escape by SARS-CoV-2 Omicron Subvariants BA.2.12.1, BA.4, and BA.5. The New England journal of medicine (2022), doi: 10.1056/NEJMc2206576.
10. E. Mathieu et al., A global database of COVID-19 vaccinations. Nature human behaviour. 5, 947-953 (2021), doi:10.1038/s41562-021-01122-8.
11. C. I. Kaku et al., Recall of pre-existing cross-reactive B cell memory following Omicron BA.1 breakthrough infection. Science immunology, eabq3511 (2022), doi: 10.1126/sciimmunol.abq3511.
12. J. Quandt et al., Omicron BA.1 breakthrough infection drives cross-variant neutralization and memory B cell formation against conserved epitopes. Science immunology, eabq2427 (2022), doi:10.1126/sciimmunol.abq2427.
13. A. Muik et al., Neutralization of SARS-CoV-2 Omicron by BNT162b2 mRNA vaccine-elicited human sera. Science (New York, N.Y.). 375, 678-680 (2022), doi: 10.1126/science.abn7591.
14. A. Muik et al., Neutralization of SARS-CoV-2 lineage B.1.1.7 pseudovirus by BNT162b2 vaccine-elicited human sera. Science (New York, N.Y.). 371, 1152-1153 (2021), doi:10.1126/science.abg6105.
15. C.-W. Tan et al., Pan-Sarbecovirus Neutralizing Antibodies in BNT162b2-Immunized SARS-CoV-1 Survivors. The New England journal of medicine. 385, 1401-1406 (2021), doi:10.1056/NEJMoa2108453.

Example 15: Further Updates on Immune Responses Elicited by Vaccines Encoding a SARS-CoV-2 S Protein from an Omicron Variant Following the experiment described in Example 8, further subjects were enrolled in a clinical trial investigating RNA vaccines encoding a SARS-CoV-2 S protein comprising one or more mutations characteristic of a BA.1 Omicron variant. In the present Example, subjects (18 to 55 years of age with or without evidence of prior infection) were administered a $2^{nd}$ booster ($4^{th}$ dose) of either 30 μg of RNA encoding a SARS-CoV-2 S protein of a Wuhan strain (in the present Example, BNT162b2) or 30 μg of RNA encoding an SARS-CoV-2 S protein having one or more mutations characteristic of an Omicron variant (in the present example, BNT162b2 OMI, which encodes a SARS-CoV-2 S protein having mutations characteristic of a BA.1 Omicron variant, comprises SEQ ID NOs: 50 and 51, and encodes an amino acid of SEQ ID NO: 49).

In a primary immunogenicity analysis of participants without evidence of prior infection, BNT162b2 OMI (N=132) elicited a superior neutralizing antibody response to the BA.1 Omicron SARS-CoV-2 virus compared to BNT162b2 (N=141). The BNT162b2 OMI GMT against BA.1 Omicron was 1929 (CI: 1632, 2281) compared to a BNT162b2 GMT of 1100 (CI: 932, 1297); GMT ratio 1.75 (95% Cl: 1.39, 2.22).

Compared to BNT162b2, BNT162b2 OMI elicited a similar neutralizing antibody response to a Wuhan strain of SARS-CoV-2. BNT162b2 OMI GMT was 11997 (CI: 10554, 13638) compared to a BNT162b2 GMT of 12009 (CI: 10744, 13425).

The data suggests that an Omicron monovalent vaccine as the $2^{nd}$ booster vaccination ($4^{th}$ dose) improves a neutralizing antibody response to BA.1 Omicron compared to an RNA vaccine encoding an S protein of a Wuhan strain, and does not negatively affect a neutralizing antibody response to a Wuhan strain of SARS-CoV-2.

Example 16. Immunological Impact of VOC Vaccination

The present Example describes immunological impacts of administration of BNT162b2 vaccines encoding spike proteins from certain variants of concern ("VOC"). In particular, the present Example describes immunological impacts of administration of a "booster dose" to subjects (in this Example, mice) who have received two doses (i.e., according to an established model immunization protocol) of the "original" BNT162b2 vaccine (i.e., encoding the Wuhan spike protein, as described herein).

FIG. 34 presents the immunization protocol utilized in the present Example. Specifically, BALB/c mice were immunized twice (1 ug each dose) with BNT 162b2, and then at a later time point with a BNT162b2/VOC (1 ug each dose). Immunization occurred up to 3 or 4 times. Animals were bled regularly to analyze antibody immune response by ELISA and pseudovirus neutralization assay. At the end of the trial, animals were euthanized and T cell response in the spleen was analyzed.

Boosting was performed with: (a) the original BNT162b2 ("BNT162b2"); (b) BNT162b2 OMI BA.1 ("OMI BA.1"); (c) BNT162b2 OMI BA.4/5 ("OMI BA.4/5"); (d) BNT162b2+OMI BA.1 (0.5 g each) € BNT162b2+OMI BA.4/5 (0.5 ug each); (f) OMI BA.1+OMI BA.4/5 (0.5 ug each); and (g) BNT162b2+OMI BA.1+OMI BA.4/5 (0.33 ug each).

Omicron variants BA.4 and BA.5 were first reported in circulation in January 2022, and were becoming dominant variants by June 2022. Both of these lineages contain the amino-acid substitutions F486V, and R493Q. Preliminary studies suggest a significant change in antigenic properties of BA.4 and BA.5 compared to BA.1 and BA.2, especially compared to BA.1. Additionally, as increasing trends in BA.5 variant proportions are observed in particular locations (e.g., in Portugal), COVID-19 case numbers and test positivity rate have also increased. The present disclosure proposes that BA.4/5 (which, given their common spike protein mutations, are considered together in the present Example) could represent escape VOC. The present disclosure demonstrates particular benefits of dosing regimens (e.g., as described herein and specifically as exemplified in the present Example) that include one or more doses of a vaccine that comprises or delivers (e.g., via expression of an administered RNA) a spike protein that includes relevant BA.4/5 sequences (e.g., amino acid substitutions).

FIGS. 35 and 36 present baseline (determined at day 104, pre-boost) geometric mean titers ("GMT"s) relative to various SARS-CoV-2 strains, as indicated. As can be seen, baseline immunization of the different mouse cohorts was comparable. Specifically, group GMTs per pseudovirus were consistently in the same ballpark between cohorts; no difference greater than about 2-fold was observed. Consistent with observations made in human populations, as noted above, neutralizing GMTs against the Wuhan strain were considerably higher (GMT of up to 3,044) as compared to those against VOCs. Overall, the order of GMTs was Wuhan>BA.1≅BA.2>BA.2.12.1>BA.4/5.

FIG. 37 shows baseline (determined at day 104, pre-boost) cross-neutralization analysis and demonstrates that baseline immunization of cohorts with respect to cross-neutralization capacity is comparable. Specifically, at baseline, calculated variant/Wuhan ref GMT ratios indicated that cross-neutralization capacity was quite comparable between cohorts (only one outlier in the BNT162b2 monovalent group re. BA.1 neutralization was observed). Again consistent with observations of human populations, BA.1=BA.2>BA.2.12.1>BA.4/5Figures—8-40 present data obtained seven days post-boost and document remarkable effectiveness of BA.4/5, and in particular of monovalent BA.4/5, in achieving significant geometric mean fold increase of GMTs (FIGS. 38 and 39) and effective cross-neutralization (FIG. 40). As can be seen, BNT162b2 booster immunization resulted in a comparable titer increase against all VOCs (3.9-7.1 fold), whereas monovalent BA.1 and BA.4/5 boosters resulted in a considerably stronger increase in the homologous VOC titer (16.8-fold for BA.1, 67.3-fold for BA.4/5).

The monovalent BA.4/5 booster was the most effective in driving titer increases across the pseudovirus panel tested. Bivalent boosters showed a similar but attenuated trend compared to the monovalent VOC boosters; amongst bivalent boosters the b2+BA.4/5 combination was most effective in driving broad cross-neutralization. The trivalent booster (b2+BA.1+BA.4/5) was superior to the bivalent boosters and gave intermediate immunization between the bivalent b2+BA.4/5 and monovalent BA.4/5 booster.

FIG. 40, among other things, presents calculated variant/Wuhan ref GMT ratios, which indicate that:

(i) BNT162b2 booster results in relatively poor cross-neutralization, especially of BA.2 and descendants (BA.2.12.1, BA.4/5)

(ii) BA.1 booster results in superior cross-neutralization of BA.1, but still relatively poor neutralization of BA.2.12.1, BA.4/5

(iii) BA.4/5 booster results in balanced pan-Omicron neutralization with very encouraging neutralization against BA.2, BA.2.12.1 and BA.4/5

Bivalent boosters showed a similar but attenuated trend compared to the monovalent VOC boosters; among bivalent boosters the b2+BA.4/5 combination was most effective in driving broad cross-neutralization; the trivalent booster (b2+BA.1+BA.4/5) elicited comparable cross-neutralization to the BA.1/BA.4/5 booster.

Mice can also be administered two RNA molecules, where the ratio of the two RNA molecules is not 1:1. For example, mice can be administered a bivalent vaccine comprising BNT162b2 and BA.4/5 at a ratio of 1:2 (e.g., by administering 0.33 ug of BNT162b2 and 0.66 ug of BA.4/5). Mice can also be administered a bivalent vaccine comprising BNT162b2 and BA.4/5 at a ratio of 1:3 (e.g., by administering 0.25 ug of BNT162b2 and 0.75 ug of BA.4/5). Such compositions can be administered to vaccine naive mice or to mice previously vaccinated with BNT162b2 (e.g., previously administered two doses of 1 ug of BNT162b2).

The present specification demonstrates remarkable efficacy of BA.4/5 immunization (and specifically of BNT162b2+BA.4/5 immunization, e.g., with sequences provided herein). Furthermore, the present specification demonstrates efficacy of BA.4/5 immunization in monovalent, bivalent, and trivalent formats, and documents surprising efficacy of monovalent BA.4/5.

The present disclosure specifically demonstrates remarkable usefulness of one or more BA.4/5 doses administered to subjects who have previously been immunized (e.g., with a Wuhan vaccine, such as with at least (or exactly) two doses of a Wuhan vaccine. Without wishing to be bound by any particular theory, the present disclosure teaches that immunological characteristics of the omicron BA.4/5 spike may render it particularly useful or effective for immunization of subjects, including those who have been immunized (e.g., via prior administration of one or more vaccine doses and/or by prior infection) with the Wuhan strain (and/or with one or more strains immunologically related to the Wuhan strain), including specifically by vaccination with one or more (e.g., 1, 2, 3, 4 or more) doses of original BNT162b2.

Example 17: Omicron BA.2 Breakthrough Infection Enhances Cross-Neutralization of BA.2.12.1 and BA.4/BA.5

The present Example 17 is an extension of Example 14, and describes experiments in which serum samples collected from BA.1- and BA.2-breakthrough cases were analyzed for neutralization activity against Omicron BA.4 and BA.5 variants. In addition to confirming the results described in Example 14, the present Example 17 also provides further characterization of antibody responses induced by BA.1 and BA.2 breakthrough infections, and provides insights as to what aspects may contribute to increased neutralization of a BA.4/5 Omicron variant as observed in a BA.2 breakthrough infection, as compared to a BA.1 breakthrough infection. In particular, the present Example demonstrates that a BA.2 breakthrough infection can induce higher titers of neutralization antibodies that bind the N-terminal domain (NTD) of a SARS-CoV-2 S protein (e.g., a BA.4/5 SARS-CoV-2 Omicron variant), which can result in increased neutralization of a BA.4/5 Omicron variant.

As demonstrated in the previous examples, individuals previously administered RNA encoding a SARS-CoV-2 S protein from a Wuhan strain, who subsequently had an Omicron BA.1 breakthrough infection, have strong serum neutralizing activity against Omicron BA.1, BA.2, and previous SARS-CoV-2 variants of concern (VOCs), yet less against highly contagious Omicron sublineages BA.4 and BA.5 that have displaced previous variants. As the latter sublineages are derived from Omicron BA.2, the serum neutralizing activity of COVID-19 mRNA vaccine triple-immunized individuals who experienced BA.2 breakthrough infection was analyzed. The present Example demonstrates that sera of these individuals have broadly neutralizing activity against previous VOCs as well as all tested Omicron sublineages, including BA.2 derived variants BA.2.12.1, BA.4/BA.5 (confirming the results of previous Example 14). Furthermore, applying antibody depletion the present Example shows that neutralization of BA.2 and BA.4/BA.5 sublineages by BA.2 convalescent sera is driven to a significant extent by antibodies targeting the N-terminal domain (NTD) of the spike glycoprotein, whereas their neutralization by Omicron BA.1 convalescent sera depends exclusively on antibodies targeting the receptor binding domain (RBD). These findings suggest that exposure to Omicron BA.2, in contrast to BA.1 spike glycoprotein, triggers significant NTD specific recall responses in vaccinated individuals and thereby enhances the neutralization of BA.4/BA.5 sublineages. Given the current epidemiology with a predominance of BA.2 derived sublineages like BA.4/BA.5 and rapidly ongoing evolution, these findings are of high relevance for the development of Omicron adapted vaccines.

Introduction

Emergence of the SARS-CoV-2 Omicron variant of concern (VOC) in November 2021 (Ref. 1) can be considered a turning point in the COVID-19 pandemic. Omicron BA.1, which is significantly altered in the spike (S) glycoprotein receptor binding domain (RBD) and N-terminal domain (NTD) relative to an S protein from a Wuhan strain, partially escapes previously established immunity (Ref. 2). The loss of many epitopes (Refs. 3, 4) decreased susceptibility to neutralizing antibodies induced by wild-type strain (Wuhan-Hu-1) S glycoprotein-based vaccines or by infection with previous strains (Refs. 5-7), necessitating a third vaccine dose to establish full immunity (Refs. 8-10). Omicron BA.1 was displaced by the BA.2 variant, which in turn was displaced by its descendants BA.2.12.1, BA.4 and BA.5 that now dominate in many regions (Refs. 11-14).

Antigenically, BA.2.12.1 exhibits high similarity with BA.2 but not BA.1, whereas BA.4 and BA.5 differ considerably from BA.2 and even more so from BA.1, in line with their genealogy (Refs. 15 and 16). While some amino acid changes in the RBD are shared between all Omicron sublineages, the alteration L452Q is only found in BA.2.12.1 and is the only residue which distinguishes its RBD from that of the BA.2 variant. The L452R and F486V alterations are BA.4/BA.5-specific, whereas S371F, T376A, D405N, and R408S are shared by BA.2 and its descendants BA.2.12.1 and BA.4/BA.5, but not BA.1 (FIG. 33). These amino acid exchanges are associated with further escape from vaccine-induced neutralizing antibodies and therapeutic antibody drugs targeting the wild-type S glycoprotein (Refs. 6, 15, 17-20). The NTDs of BA.2 and its descendants are antigenically closer to the wild-type strain and lack several amino acid changes, insertions, and deletions that occurred in BA.1 (FIG. 33). For instance, Δ143-145, L212I, or ins214EPE, which rendered the BA.1 variant resistant to a panel of NTD-directed monoclonal antibodies raised against the wild-type S glycoprotein, are not found in BA.2 and descendants (Refs. 21, 22).

As demonstrated in the previous Examples, Omicron BA.1 breakthrough infection of BNT162b2 vaccinated individuals augments broadly neutralizing activity against Omicron BA.1, BA.2 and previous VOCs at levels similar to those observed against SARS-CoV-2 wild-type. BA.1 breakthrough infection of triple BNT162b2-vaccinated individuals induces a robust recall response, primarily expanding memory B cells against epitopes shared broadly amongst variants, rather than inducing B cells specific to BA.1 only. Neutralization of Omicron sublineages BA.4 and BA.5 was increased to a lesser extent in BA.1 breakthrough patients as compared to the BA.1 variant, and geometric mean titers were comparable to those against the phylogenetically more distant SARS-CoV-1.

Given that Omicron BA.2 is more closely related to BA.4/BA.5 than to BA.1, whether BA.2 breakthrough infection would shift cross-neutralization activity more towards these most recent Omicron sublineages, as compared to BA.1 breakthrough infection, was assessed. The neutralization of different Omicron sublineages by serum samples was compared from three different cohorts of individuals triple-vaccinated with mRNA COVID-19 vaccines, namely from individuals with no history of SARS-CoV-2 infection and individuals that experienced breakthrough infection with either BA.1 or BA.2. In addition, the contribution of serum antibodies targeting the S glycoprotein RBD versus the NTD to Omicron sublineage neutralization was characterized. The resulting data increase current understanding on Omicron immune escape mechanisms and the effects of immunization on variant cross-neutralization, and thus help guide further vaccine development.

Results

Cohorts and Sampling

This study investigated serum samples from three cohorts: from BNT162b2 triple-vaccinated individuals who were SARS-CoV-2-naïve at the time of sampling ($BNT162b2^3$, n=18), from individuals vaccinated with three doses of mRNA COVID-19 vaccine (BNT162b2/mRNA-1273 homologous or heterologous regimens) who subsequently had a breakthrough infection with Omicron at a time of BA.1 dominance ($mRNA\text{-}Vax^3$+BA.1, n=14), or from triple mRNA vaccinated individuals with a breakthrough infection at a time of BA.2 dominance ($mRNA\text{-}Vax^3$+BA.2, n=13). For convalescent cohorts, relevant intervals between key events such as the most recent vaccination and infection are provided in FIG. 41. Sera were derived from the biosample collections of BNT162b2 vaccine trials and from a non-interventional study researching vaccinated patients that had experienced Omicron breakthrough infection.

Omicron BA.2 Breakthrough Infection of Triple mRNA-Vaccinated Individuals Induces Broad Neutralization of VOCs Including Omicron BA.4/BA.5

Neutralizing activity of immune sera was tested in a well-characterized pseudovirus neutralization test (pVNT) (Refs. 24, 25) by determining 50% pseudovirus neutralization ($pVN_{50}$) geometric mean titers (GMTs) with pseudoviruses bearing the S glycoproteins of the SARS-CoV-2 wild-type strain, or Alpha, Beta, Delta, Omicron BA.1, BA.2, and the BA.2-derived sublineages BA.2.12.1, BA.4 and BA.5. As BA.4 and BA.5 share an identical S glycoprotein sequence, in the present Example they are referred to as BA.4/5 in the context of the pVNT. In addition, SARS-CoV (herein referred to as SARS-CoV-1) was assayed to detect potential pan-Sarbecovirus neutralizing activity (Ref. 26). As an orthogonal test system, a live SARS-CoV 2 neutralization test (VNT) was also used that analyzes neutralization during multicycle replication of authentic virus (SARS-CoV-2 wild-type strain and VOCs including BA.4, except Omicron BA.2.12.1) with the antibodies present during the entire test period.

In the pVNT, sera from all three cohorts robustly neutralized the wild-type strain, Alpha, Beta, Delta VOCs as well as Omicron BA.1 and BA.2 lineages with neutralization activity being more pronounced in the breakthrough infected individuals, particularly in the BA.1 breakthrough infection cohort (mRNA-Vax3+BA.1). However, serum neutralizing activity of BNT162b2 triple-vaccinated SARS-CoV-2 naïve ($BNT162b2^3$) and $mRNA\text{-}Vax^3$+BA.1 individuals against BA.2.12.1 was significantly reduced compared to wild-type ($p<0.05$) and even more so for BA.4/5 ($p<0.001$; >5-fold compared to the wild-type strain) (FIG. 42(A)). In contrast, sera from triple mRNA-vaccinated individuals with Omicron BA.2 breakthrough infection (mRNA-Vax3+BA.2) neutralized the BA.2.12.1 pseudovirus as robustly as the wild-type strain. Neutralization of BA.4/5 was broadly similar to that of BA.2.12.1, and the reduction relative to the wild-type strain significant ($p<0.05$) yet less pronounced ("2.5-fold) as compared to the two other cohorts.

To compare the cohorts with regard to neutralization breadth irrespective of the magnitude of antibody titers, the VOC $pVN_{50}$ GMTs was normalized against the Wuhan strain. The ratios showed that BA.4/5 cross-neutralization was substantially stronger in $mRNA\text{-}Vax^3$+BA.2 (GMT ratio 0.38) as compared to $mRNA\text{-}Vax^3$+BA.1 and $BNT162b2^3$ sera (GMT ratios 0.18 and 0.17) (FIG. 42(B)). Similarly, cross-neutralization of Omicron BA.2.12.1 by $mRNA\text{-}Vax^3$+BA.2 sera (GMT ratio 0.52) was stronger than by $mRNA\text{-}Vax^3$+BA.1 sera (GMT ratio 0.43), and even more so than by $BNT162b2^3$ sera (GMT ratio 0.26).

A separate analysis including only the BNT162b2 vaccinated individuals within those three cohorts confirmed that BA.2 breakthrough infection is associated with considerable BA.4/5 cross-neutralization (BA.4/5 to wild-type GMT ratio 0.42), whereas after BA.1 breakthrough infection $pVN_{50}$ GMTs against BA.4/5 were ~6-fold lower than those against wild-type (i.e., GMT ratio 0.17) (FIG. 45 ((A)-(C)). Cross-neutralization of BA.2 and BA.2.12.1 by sera of the BA.1 or BA.2 convalescents was superior to that of BNT162b2 triple-vaccinated SARS-CoV-2 naïve individuals.

The authentic live SARS-CoV-2 virus neutralization assay provided VOC neutralizing titers that strongly correlated with those from the pVNT assay (FIG. 46) and confirmed the major findings in FIG. 42. In this assay, 50% virus neutralization ($VN_{50}$) GMT against Omicron BA.2 in $BNT162b2^3$ sera was strongly reduced compared to that against wild-type ($p<0.0001$), whereas sera from both convalescent groups exhibited strong neutralizing activity, with $VN_{50}$ GMTs comparable to those against the wild-type strain (FIG. 43(A)). Reduction of neutralizing activity against Omicron BA.4 was less pronounced in the BA.2 convalescent cohort as compared to $BNT162b2^3$ and mRNA-$Vax^3$+BA.1 cohorts ($VN_{50}$ GMTs ~2.5-fold as compared to ~15-fold and 5-fold lower than against the wild-type strain, respectively).

In line with the pVNT data, magnitude-independent analyses via the calculated ratios of VOC $VN_{50}$ GMTs against the wild-type strain showed that BA.4 cross-neutralization was stronger in the mRNA-$Vax^3$+BA.2 cohort (GMT ratio 0.39) as compared to the mRNA-$Vax^3$+BA.1 (GMT ratio 0.20) and $BNT162b2^3$ (GMT ratio 0.07) cohorts (FIG. 43(B)) and similarly so within the sub-cohort of BNT162b2 triple-vaccinated individuals (FIGS. 45(D)-(F)).

In aggregate, these data demonstrate that Omicron BA.2 breakthrough infection of vaccinated individuals was associated with broad neutralizing activity against all tested Omicron-sublineages and previous SARS-CoV-2 VOCs. In particular, these data indicate that breakthrough infection with BA.2 was more effective ("2-fold higher cross neutralization) than that with BA.1 at refocusing neutralizing antibody responses towards the BA.4/BA.5 S glycoprotein.

Neutralization of Omicron BA.2 and BA.4/5 by sera of triple mRNA vaccinated BA.2 convalescent individuals is mediated to a large extent by NTD-targeting antibodies.

To dissect the role of serum antibodies binding either to the RBD or the NTD of the S glycoprotein for neutralization of SARS-CoV-2 wild-type, Omicron BA.1, BA.2, and BA.4/5, these antibody fractions were depleted separately from sera of the three cohorts (n=6 each, FIG. 47(A)). The SARS-CoV-2 wild-type strain S glycoprotein RBD and NTD baits was used for depletion, as VOC breakthrough infections have been demonstrated to predominantly elicit recall responses recognizing epitopes conserved across known VOCs (Refs. 10, 23, and 27). The depletion experiments removed >97% of all RBD-binding antibodies and >74% of all NTD-binding antibodies (FIG. 47(B)). Depleted sera were subsequently tested in pVNT assays. RBD-antibody depletion strongly diminished neutralizing activity against the wild-type strain in sera from all cohorts, whereas neutralizing activity was mostly retained (>80% remaining activity) upon depletion of NTD-binding antibodies (FIG. 44 (A)). Neutralization of Omicron BA.1 was completely abrogated upon depletion of RBD-binding antibodies and largely unaffected by NTD-binding antibody depletion. For neutralization of BA.2, RBD-antibody depletion almost completely abolished neutralizing activity of mRNA-$Vax^3$+BA.1 sera (about 2% residual neutralization activity). The reduction of neutralizing titers for $BNT162b2^3$ and particularly mRNA-$Vax^3$+BA.2 sera was less severe with ~12% and ~24% remaining neutralizing activity, respectively. In contrast, depletion of NTD-binding antibodies did not considerably impact the neutralizing activity of $BNT162b2^3$ and mRNA-$Vax^3$+BA.1 sera (~91 and ~99% of undepleted control, respectively), while neutralizing activity of mRNA-$Vax^3$+BA.2 sera was reduced to ~50%. A similar pattern was seen following RBD-antibody depletion for neutralization of BA.4/5, with strongly reduced neutralizing activity of mRNA-$Vax^3$+BA.1 sera (~3% residual activity) versus less severe reductions for $BNT162b2^3$ and mRNA-$Vax^3$+BA.2 sera (~20 and ~26% remaining activity, respectively). Depletion of NTD-binding antibodies had a larger impact for BA.4/5 neutralization compared to BA.2, with remaining neutralizing activity of $BNT162b2^3$ and mRNA-$Vax^3$+BA.1 sera of ~70 and ~90% respectively, again with the strongest effect (~48% of undepleted control) of mRNA-$Vax^3$+BA.2 sera.

As an orthogonal approach the neutralizing activity of sera was assessed from those 3 cohorts of vaccinated individuals against a pseudovirus harboring an engineered hybrid S glycoprotein consisting of the Omicron BA.1 N-terminus including the NTD (amino acids 1-338) and the BA.4/5 C terminus including the RBD.

The $pVN_{50}$ GMT against the Omicron BA.1-BA.4/5 hybrid pseudovirus in sera from $BNT162b2^3$ was moderately below (1.86-fold) the GMT for the BA.4/5 pseudovirus, and in the BA.1 convalescents the GMT was only marginally affected (<1.5-fold reduction) (FIG. 44(B)). In contrast, in BA.2 convalescent sera titers against the hybrid pseudovirus were considerably lower than those against the BA.4/5 pseudovirus (>3-fold reduction of GMT) (FIG. 44(B)), suggesting that substantial neutralizing activity can be attributed to NTD epitopes that are shared between Omicron BA.2 and BA.4/5.

In aggregate the data obtained in both experiments indicate that across all these VOCs RBD-binding antibodies provided a major contribution to neutralization. Additionally, exposure to BA.1 (that differs substantially from previous VOCs in its NTD; FIG. 33) boosted recall responses of vaccine-induced neutralizing antibodies that primarily bind the RBD, whereas exposure to BA.2 S glycoprotein (with an NTD closer related to previous VOCs) can build on existing memory and elicited a considerable recall of NTD-targeting antibodies that in turn contributed substantially to the neutralization of BA.2 and BA.4/5.

Discussion

Recent studies have demonstrated that Omicron BA.1 breakthrough infection in individuals vaccinated with mRNA vaccines BNT162b2 or mRNA-1273 or an inactivated virus vaccine boosts serum neutralizing titers against VOCs including BA.2 (Refs. 10, 15, 23), but not against BA.2.12.1 or BA.4/BA.5. The immune escape has been attributed to boosting of pre-existing neutralizing antibody responses that recognize epitopes shared between the SARS-CoV-2 wild-type strain and Omicron BA.1 but are in part absent in BA.2.12.1, BA.4, and BA.5 due to alterations at key residues including L4520/L452R, and F486V (Ref. 15).

In the present Example, BA.2 breakthrough infection was associated with broadly neutralizing activity including BA.2 and its descendants BA.2.12.1, BA.4 and BA.5. These findings suggest that the higher sequence similarity of BA.2 with BA.2.12.1 and BA.4/5 in the S glycoprotein RBD as well as the NTD drives more efficient cross-neutralization as compared to breakthrough infections with the antigenically more distant BA.1 variant. In particular, BA.1 breakthrough infection may not elicit a strong recall of NTD-specific memory B cells owing to the substantial alterations within the BA.1 NTD (FIG. 33) given that breakthrough infection with heterologous SARS-CoV-2 strains primarily expands a memory B cell repertoire against conserved S glycoprotein epitopes (Refs. 10, 23). The data described herein that was obtained in antibody-depletion and hybrid pseudovirus experiments show that NTD-binding antibodies have a substantial contribution to neutralizing activity against Omicron BA.4/5 in triple-vaccinated BA.2 convalescent sera, whereas neutralizing activity in BA.1 convalescent sera largely relies on RBD-binding antibodies. This finding is consistent with the observation that NTD-binding antibodies isolated from BA.2 breakthrough infected individuals do not neutralize BA.1 (Ref. 29). Together these important findings extend our knowledge on how vaccinations and boosters with the current wild-type strain-based vaccines together with breakthrough infections with the various VOCs shape the immunity patterns within the population and are material to inform further vaccine development and adaptation in response to current and emerging VOCs.

Notwithstanding the importance of vaccination with currently approved wild-type-strain based vaccines such as BNT162b2 that offer effective protection from severe disease by current VOCs including Omicron BA.1 and BA.2 (Refs. 30 and 31), the present findings highlight that consideration of rapidly evolving epidemiological landscapes and newly emerging SARS-CoV-2 variants is important for guiding vaccine adaptation programs. For instance, while the efficacy of vaccine adaptation to the BA.1 strain S glycoprotein sequence is currently under investigation in clinical trials, the present data suggest that further benefit may be derived from a vaccine adapted to the sequence of BA.2 or descendants.

Materials and Methods

Study Design, Recruitment of Participants and Sample Collection

The objective of this study was to investigate the effect of Omicron BA.2 breakthrough infection on the cross-variant neutralization capacity of human sera. Immune responses in triple-mRNA (BNT162b2/mRNA-1273)-vaccinated individuals with a confirmed subsequent SARS-CoV-2 breakthrough infection in a period of Omicron BA.2 lineage-dominance in Germany (March to May 2022; mRNA-Vax3+BA.2), was compared to that of triple-mRNA-vaccinated individuals with a confirmed subsequent SARS-CoV-2 breakthrough infection in a period of Omicron BA.1 lineage-dominance (November 2021 to mid-January 2022; mRNA-Vax$^3$+BA.1) (Refs. 1 and 2) and triple-BNT162b2-vaccinated individuals that were SARS-CoV-2-naïve (nucleocapsid seronegative) at the time of sample collection (BNT162b2$^3$). Serum neutralizing capability was characterized using pseudovirus and live SARS-CoV-2 neutralization assays. Data for the reference cohorts BNT162b2$^3$ and mRNA-Vax$^3$+BA.1 were previously published (Ref. 10), except for newly generated BA.2.12.1 neutralization data. Cross-neutralization of variants was further characterized in smaller sub-cohorts after depletion of either wild-type S glycoprotein NTD- or RBD-targeted neutralizing antibodies. Individuals from the BNT162b2$^3$ cohort provided informed consent as part of their participation in the Phase 2 trial BNT162-17 (NCT05004181). Participants from the mRNA-Vax$^3$+Omi BA.1 and mRNA-Vax$^3$+BA.2 cohorts were recruited from University Hospital, Goethe University Frankfurt as part of a non-interventional study (protocol approved by the Ethics Board of the University Hospital [No. 2021-560]) researching patients that had experienced Omicron breakthrough infection following vaccination for COVID-19. Omicron BA.1 infections were confirmed with variant-specific PCR. The infections of 4 BA.1 convalescent participants in this study were further characterized by genome sequencing. In all 4 cases, genome sequencing confirmed Omicron BA.1 infection.

Demographic and clinical data for all participants and sampling timepoints are provided (FIG. 41). All participants had no documented history of SARS-CoV-2 infection prior to vaccination.

Participants were free of symptoms at the time of blood collection.

Serum was isolated by centrifugation of drawn blood at 2000×g for 10 minutes and cryopreserved until use.

VSV-SARS-CoV-2 S Variant Pseudovirus Generation

A recombinant replication-deficient vesicular stomatitis virus (VSV) vector that encodes green fluorescent protein (GFP) and luciferase instead of the VSV-glycoprotein (VSV-G) was pseudotyped with SARS-CoV-1 S glycoprotein (UniProt Ref: P59594) and with SARS-CoV-2 S glycoprotein derived from either the Wuhan-Hu-1 reference strain (NCBI Ref: 43740568), the Alpha variant (alterations: Δ69/70, Δ144, N501Y, A570D, D614G, P681H, T716I, S982A, D1118H), the Beta variant (alterations: L18F, D80A, D215G, Δ242-244, R246I, K417N, E484K, N501Y, D614G, A701V), the Delta variant (alterations: T19R, G142D, E156G, Δ157/158, K417N, L452R, T478K, D614G, P681R, D950N), the Omicron BA.1 variant (alterations: A67V, Δ69/70, T95I, G142D, 6143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F),the Omicron BA.2 variant (alterations: T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K), the Omicron BA.2.12.1 variant (alterations: T19I, Δ24-26, A27S, G142D, V213G, G339D, S371F, S373P, S375F, T376A, D405N, R408S, K417N, N440K, L452Q, S477N, T478K, E484A, Q493R, Q498R, N501Y, Y505H, D614G, H655Y, N679K, P681H, S704L, N764K, D796Y, Q954H, N969K), the Omicron BA.4/5 variant (alterations: T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K), or an artificial Omicron BA.1-BA.4/5 hybrid S glycoprotein (alterations: A67V, Δ69/70, T95I, G142D, Δ143-145, Δ211, L212I, ins214EPE, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K) according to published pseudotyping protocols (Ref. 3). A diagram of SARS-CoV-2 S glycoprotein alterations is shown in FIG. 48 and a separate alignment of S glycoprotein alterations in Omicron sub-lineages is displayed in FIG. 33.

In brief, HEK293T/17 monolayers (ATCC® CRL-11268™) cultured in Dulbecco's modified Eagle's medium (DMEM) with GlutaMAX™ (Gibco) supplemented with 10% heat-inactivated fetal bovine serum (FBS [Sigma-Aldrich]) (referred to as medium) were transfected with Sanger sequencing-verified SARS-CoV-1 or variant-specific SARS-CoV-2 S expression plasmid with Lipofectamine LTX (Life Technologies) following the manufacturer's instructions. At 24 hours after transfection, the cells were infected at a multiplicity of infection (MOI) of three with VSV-G complemented VSVΔG vector. After incubation for 2 hours at 37° C. with 7.5% $CO_2$, cells were washed twice with phosphate buffered saline (PBS) before medium supplemented with anti-VSV-G antibody (clone 8G5F11, Kerafast Inc.) was added to neutralize residual VSV-G-complemented input virus. VSV-SARS-CoV-2-S pseudotype-containing medium was harvested 20 hours after inoculation, passed through a 0.2 μm filter (Nalgene) and stored at −80° C. The pseudovirus batches were titrated on Vero 76 cells (ATCC® CRL-1587™) cultured in medium. The relative luciferase units induced by a defined volume of a SARS-CoV-2 wild-type strain S glycoprotein pseudovirus reference batch previously described in Muik et al., 2021 (Ref. 4), that corresponds to an infectious titer of 200 transducing units (TU) per mL, was used as a comparator. Input volumes for the SARS-CoV-2 variant pseudovirus batches were calculated to normalize the infectious titer based on the relative luciferase units relative to the reference.

Pseudovirus Neutralization Assay

Vero 76 cells were seeded in 96-well white, flat-bottom plates (Thermo Fisher Scientific®) at 40,000 cells/well in medium 4 hours prior to the assay and cultured at 37° C. with 7.5% $CO_2$. Each individual serum was serially diluted 2-fold in medium with the first dilution being 1:5 (SARS-CoV-2-naïve triple BNT162b2 vaccinated; dilution range of 1:5 to 1:5,120) or 1:30 (triple vaccinated after subsequent Omicron BA.1 or BA.2 breakthrough infection; dilution range of 1:30 to 1:30,720). In the case of the SARS-CoV-1 pseudovirus assay, the serum of all individuals was initially diluted 1:5 (dilution range of 1:5 to 1:5,120). VSV-SARS-CoV-2-S/VSV-SARS-CoV-1-S particles were diluted in medium to obtain 200 TU in the assay. Serum dilutions were mixed 1:1 with pseudovirus (n=2 technical replicates per serum per pseudovirus) for 30 minutes at room temperature before being added to Vero 76 cell monolayers and incubated at 37° C. with 7.5% $CO_2$ for 24 hours. Supernatants were removed and the cells were lysed with luciferase reagent (Promega). Luminescence was recorded on a CLARIOstar® Plus microplate reader (BMG Labtech), and neutralization titers were calculated as the reciprocal of the highest serum dilution that still resulted in 50% reduction in luminescence. For depletion studies resolution with regards to neutralization titers was increased, in order to discriminate smaller than 2-fold differences on an individual serum level. Neutralization titers were determined by generating a 4-parameter logistical (4PL) fit of the percent neutralization at each serial serum dilution. The 50% pseudovirus neutralization ($pVN_{50}$) titer was reported as the interpolated reciprocal of the dilution yielding a 50% reduction in luminescence. Results for all pseudovirus neutralization experiments were expressed as geometric mean titers (GMT) of duplicates. If no neutralization was observed, an arbitrary titer value of half of the limit of detection [LOD] was reported. SARS-CoV-2 wild-type strain, and Alpha, Beta, Delta, BA.1, BA.4/5 VOC, as well as SARS-CoV-1 pseudovirus neutralizing GMTs for the SARS-CoV-2 naïve BNT162b2 triple-vaccinated cohort and the triple-vaccinated BA.1 convalescent cohort were previously reported in Quandt. et al. (Ref. 10). Only the BA.2.12.1 neutralization data was newly generated from serum samples for this study.

Live SARS-CoV-2 Neutralization Assay

SARS-CoV-2 virus neutralization titers were determined by a microneutralization assay based on cytopathic effect (CPE) at VisMederi S.r.l., Siena, Italy. In brief, heat-inactivated serum samples from individuals were serially diluted 1:2 (starting at 1:10; n=2 technical replicates per serum per virus) and incubated for 1 hour at 37° C. with 100 TCID50 of the live wild-type-like SARS-CoV-2 virus strain 2019-nCOV/ITALY-INMI1 (GenBank: MT066156), Alpha virus strain nCoV19 isolate/England/MIG457/2020 (alterations: Δ69/70, Δ144, N501Y, A570D, D614G, P681H, T716I, S982A, D1118H), Beta virus strain nCoV19 isolate/England ex-SA/HCM002/2021 (alterations: D80A, D215G, Δ242-244, K417N, E484K, N501Y, D614G, A701V), sequence-verified Delta strain isolated from a nasopharyngeal swab (alterations: T19R, G142D, E156G, Δ157/158, L452R, T478K, D614G, P681R, R682Q, D950N), Omicron BA.1 strain hCoV-19/Belgium/rega-20174/2021 (alterations: A67V, Δ69/70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F), sequence-verified Omicron BA.2 strain (alterations: T19I, Δ24-26, A27S, V213G, G339D, S371F, S373P, S375F, T376A, D405N, R408S, K417N, 5477N, T478K, E484A, Q493R, Q498R, N501Y, Y505H, D614G, H655Y, N679K, P681H, R682W, N764K, D796Y, Q954H, N969K), or sequence-verified Omicron BA.4 strain (alterations: V3G, T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K) to allow any antigen-specific antibodies to bind to the virus. A diagram of S glycoprotein alterations is shown in FIG. 48. The 2019-nCOV/ITALY-INM11 strain S glycoprotein is identical in sequence to the wild-type SARS-CoV-2 S (Wuhan-Hu-1 isolate). Vero E6 (ATCC® CRL-1586™) cell monolayers were inoculated with the serum/virus mix in 96-well plates and incubated for 3 days (2019-nCOV/ITALY-INMI1 strain) or 4 days (Alpha, Beta, Delta, Omicron BA.1, BA.2 and BA.4 variant strain) to allow infection by non-neutralized virus. The plates were observed under an inverted light microscope and the wells were scored as positive for SARS-CoV-2 infection (i.e., showing CPE) or negative for SARS-CoV-2 infection (i.e., cells were alive without CPE). The neutralization titer was determined as the reciprocal of the highest serum dilution that protected more than 50% of cells from CPE and reported as GMT of duplicates. If no neutralization was observed, an arbitrary titer value of 5 (half of the LOD) was reported.

Depletion of RBD- or NTD-binding antibodies from human sera

SARS-CoV-2 wild-type strain S glycoprotein RBD- and NTD-coupled magnetic beads (Acro Biosystems, Cat. no. MBS-K002 and MBS-K019; 40 μg RBD/mg beads and 38 μg NTD/mg beads, respectively) were prepared according to the manufacturer's instructions. Beads were resuspended in ultrapure water at 1 mg beads/mL and a magnet was used to collect and wash the beads with PBS. Beads were resuspended in serum to obtain 20 μg RBD- or NTD-bait per 100 μL serum. A mock depletion (undepleted control) was performed for each serum by adding 0.5 mg Biotin-saturated MyOne™ Streptavidin T1 Dynabeads™ (Thermo Fisher Scientific®, Cat. no. 65601) per 100 μL serum. Beads were incubated with human sera for 1 hour with gentle rotation. A magnet was used to separate bead-bound antibodies from the depleted supernatant. Depleted and undepleted sera were analyzed for cross-neutralization capacity using pseudovirus neutralization assays. Depletion efficacy for both RBD- and NTD-binding antibodies was determined by a multiplexed electrochemiluminescence immunoassay (Meso Scale Discovery, V-Plex SARS-CoV-2 Panel 1 Kit, Cat. No. K15359U-2).

Statistical Analysis

The statistical method of aggregation used for the analysis of antibody titers is the geometric mean and for the ratio of SARS-CoV-2 VOC titer and wild-type strain titer the geometric mean and the corresponding 95% confidence interval. The use of the geometric mean accounts for the non-normal distribution of antibody titers, which span several orders of magnitude. The Friedman test with Dunn's correction for multiple comparisons was used to conduct pairwise signed-rank tests of group geometric mean neutralizing antibody titers with a common control group. Spearman correlation was used to evaluate the monotonic relationship between non-normally distributed datasets. All statistical analyses were performed using GraphPad Prism software version 9.

References for Example 17

1. WHO Technical Advisory Group on SARS-CoV-2 Virus Evolution (TAG-VE): Classification of Omicron (B.1.1.259): SARS-CoV-2 Variant of Concern. (2021).
2. WHO Headquarters (HQ), WHO Health Emergencies Programme, Enhancing Response to Omicron SARS-CoV-2 variant: Technical brief and priority actions for Member States. (2022).
3. M. Hoffmann et al., The Omicron variant is highly resistant against antibody-mediated neutralization: Implications for control of the COVID-19 pandemic. Cell 185, 447-456 e411 (2022).
4. W. Dejnirattisai et al., SARS-CoV-2 Omicron-B.1.1.529 leads to widespread escape from neutralizing antibody responses. Cell 185, 467-484 e415 (2022).
5. V. Servellita et al., Neutralizing immunity in vaccine breakthrough infections from the SARS-CoV-2 Omicron and Delta variants. Cell 185, 1539-1548 e1535 (2022).
6. C. Kurhade et al., Neutralization of Omicron BA.1, BA.2, and BA.3 SARS-CoV-2 by 3 doses of BNT162b2 vaccine. Nat Commun 13, 3602 (2022).
7. Y. Cao et al., Omicron escapes the majority of existing SARS-CoV-2 neutralizing antibodies. Nature 602, 657-663 (2022).
8. WHO Technical Advisory Group on COVID-19 Vaccine Composition (TAG-CO-VAC): Interim statement on the composition of current COVID-19 vaccines. (2022).
9. M. E. McMenamin et al., Vaccine effectiveness of one, two, and three doses of BNT162b2 and CoronaVac against COVID-19 in Hong Kong: a population-based observational study. Lancet Infect Dis, (2022).
10. J. Quandt et al., Omicron BA.1 breakthrough infection drives cross-variant neutralization and memory B cell formation against conserved epitopes. Sci Immunol, eabq2427 (2022).
11. E. Callaway, What Omicron's BA.4 and BA.5 variants mean for the pandemic. Nature 606, 848-849 (2022).
12. H. Tegally et al., Emergence of SARS-CoV-2 Omicron lineages BA.4 and BA.5 in South Africa. Nat Med, (2022).
13. S. Xia, L. Wang, Y. Zhu, L. Lu, S. Jiang, Origin, virological features, immune evasion and intervention of SARS-CoV-2 Omicron sublineages. Signal Transduct Target Ther 7, 241 (2022).
14. European Centre for Disease Prevention and Control, Weekly COVID-19 country overview—Country overview report: week 27 2022 (2022).
15. Y. Cao et al., BA.2.12.1, BA.4 and BA.5 escape antibodies elicited by Omicron infection. Nature, (2022).
16. N. P. Hachmann et al., Neutralization Escape by SARS-CoV-2 Omicron Subvariants BA.2.12.1, BA.4, and BA.5. N Engl J Med 387, 86-88 (2022).
17. T. N. Starr, A. J. Greaney, A. S. Dingens, J. D. Bloom, Complete map of SARS-CoV-2 RBD mutations that escape the monoclonal antibody LY-CoV555 and its cocktail with LY-CoV016. Cell Rep Med 2, 100255 (2021).
18. A. Tuekprakhon et al., Antibody escape of SARS-CoV-2 Omicron BA.4 and BA.5 from vaccine and BA.1 serum. Cell 185, 2422-2433 e2413 (2022).
19. Q. Wang et al., Antibody evasion by SARS-CoV-2 Omicron subvariants BA.2.12.1, BA.4, & BA.5. Nature, (2022).
20. Y. Wang et al., Structural basis for SARS-CoV-2 Delta variant recognition of ACE2 receptor and broadly neutralizing antibodies. Nat Commun 13, 871 (2022).
21. P. Wang et al., Antibody resistance of SARS-CoV-2 variants B.1.351 and B.1.1.7. Nature 593, 130-135 (2021).
22. L. Liu et al., Striking antibody evasion manifested by the Omicron variant of SARS-CoV-2. Nature 602, 676-681 (2022).
23. C. I. Kaku et al., Recall of pre-existing cross-reactive B cell memory following Omicron BA.1 breakthrough infection. Sci Immunol, eabq3511 (2022).
24. A. Muik et al., Neutralization of SARS-CoV-2 Omicron by BNT162b2 mRNA vaccine-elicited human sera. Science 375, 678-680 (2022).
25. A. Muik et al., Neutralization of SARS-CoV-2 lineage B.1.1.7 pseudovirus by BNT162b2 vaccine-elicited human sera. Science 371, 1152-1153 (2021).
26. C. W. Tan et al., Pan-Sarbecovirus Neutralizing Antibodies in BNT162b2-Immunized SARS-CoV-1 Survivors. N Engl J Med 385, 1401-1406 (2021).
27. R. Nutalai et al., Potent cross-reactive antibodies following Omicron breakthrough in vaccinees. Cell 185, 2116-2131 e2118 (2022).
28. P. Arora et al., Augmented neutralisation resistance of emerging omicron subvariants BA.2.12.1, BA.4, and BA.5. Lancet Infect Dis, (2022).
29. E. Andreano et al., Anatomy of Omicron BA.1 and BA.2 neutralizing antibodies in COVID-19 mRNA vaccinees. Nat Commun 13, 3375 (2022).
30. N. Andrews et al., Covid-19 Vaccine Effectiveness against the Omicron (B.1.1.529) Variant. N Engl J Med 386, 1532-1546 (2022).
31. S. Y. Tartof et al., Immunocompromise and durability of BNT162b2 vaccine against severe outcomes due to omicron and delta variants. Lancet Respir Med 10, e61-e62 (2022).

Example 18: Exposure to BA.4/BA.5 Spike Glycoprotein Drives Pan-Omicron Neutralization in Vaccine-Experienced Humans and Mice The present Example is an extension of Examples 7, 13, 16, and 17, and describes (i) immune response data from human subjects previously vaccinated against SARS-CoV-2 who have had a BA.4/5-breakthrough infection (in the present example, human subjects who have previously been administered three doses of RNA vaccine(s) encoding the SARS-CoV-2 S protein of a Wuhan variant), and (ii) further mouse data, showing immune responses induced by RNA encoding SARS-CoV-2 S proteins comprising mutations characteristic of certain Omicron variants.

Abstract

The SARS-CoV-2 Omicron variant and its sublineages show pronounced viral escape from neutralizing antibodies owing to numerous amino acid alterations within the spike (5) glycoprotein. As demonstrated in the previous Examples, breakthrough infection of vaccinated individuals with Omicron sublineages BA.1 and BA.2 has been associated with distinct patterns of cross-neutralizing activity against SARS-CoV-2 variants of concern (VOCs), most notably against the recently emerged BA.2 descendants Omicron BA.4 and BA.5. Here, the effect of Omicron BA.4/BA.5 S glycoprotein exposure on the magnitude and breadth of the neutralizing antibody response is investigated in vaccine-experienced humans and mice. The immune sera from triple mRNA-vaccinated individuals with Omicron BA.4/BA.5 breakthrough infection is shown to display broad and robust neutralizing activity against Omicron BA.1, BA.2, BA.2.12.1, and BA.4/BA.5. Administration of a BA.4/BA.5-adapted mRNA booster vaccine to mice following SARS-CoV-2 wild-type (Wuhan) strain-based primary immunization is associated with similarly broad neutralizing activity. Immunization of vaccine-naïve mice with a bivalent mRNA vaccine encoding BA.4/BA.5-adapted and wild-type-based S glycoprotein immunogens is further shown to induce strong and broad neutralizing activity against Omicron and non-Omicron VOCs. These findings support the conclusion that, when administered as monovalent or bivalent boosters, Omicron BA.4/BA.5-adapted vaccines (e.g., RNA encoding a SARS-CoV-2 S protein comprising mutations characteristic of these variants) can lead to improved neutralization breadth against current and newly emerging VOCs (improved, in particular, as compared to a BA.1-adapted vaccine). These findings also show that a BA.4/BA.5 vaccine, when administered in a bivalent format has the potential to confer protection to subjects with no pre-existing immunity against SARS-CoV-2 (e.g., to exposure-naïve subjects).

Introduction

The SARS-CoV-2 Omicron variant of concern (VOC) has had a major impact on the epidemiological landscape of the COVID-19 pandemic since its emergence in November 2021 (Refs. 1-2). Significant alterations in the spike (S) glycoprotein of the initial Omicron variant BA.1 led to the loss of many neutralizing antibody epitopes (Ref. 3) and rendered BA.1 capable of partially escaping previously established SARS-CoV-2 wild-type strain (Wuhan-Hu-1)-based immunity (Refs. 4-6). Hence, breakthrough infections of vaccinated individuals with Omicron are more common than with previous VOCs. While Omicron BA.1 was displaced by the BA.2 variant in many countries around the globe, other variants such as BA.1.1 and BA.3 temporarily and/or locally gained momentum but did not become globally dominant (Refs. 7-9). Omicron BA.2.12.1 displaced BA.2 to become dominant in the United States in the interim, whereas BA.4 and BA.5 displaced BA.2 in Europe, parts of Africa, and Asia/Pacific (Refs. 8, 10-12. Currently the VOCs Omicron BA.4 and BA.5 are predominant in large parts of the world, including the United States where they eventually displaced BA.2.12.1 (Ref. 13).

Omicron lineage VOCs have acquired numerous alterations (amino acid exchanges, insertions, or deletions) in the S glycoprotein, among which some are shared between all Omicron VOCs while others are specific to one or more sublineages (see FIG. 33). Antigenically, BA.2.12.1 exhibits high similarity with BA.2 but not BA.1, whereas BA.4 and BA.5 differ considerably from BA.2 and even more so from BA.1, in line with their genealogy (Ref. 14). Major differences of BA.1 from the remaining Omicron VOCs include 0143-145, L212I, or ins214EPE in the S glycoprotein N-terminal domain and G446S or G496S in the receptor binding domain (RBD). Amino acid changes T376A, D405N, and R408S in the RBD are in turn common to BA.2 and its descendants but not found in BA.1. In addition, some alterations are specific for certain BA.2-descendant VOCs, including L452Q for BA.2.12.1 or L452R and F486V for BA.4 and BA.5. Most of these shared and sublineage-specific alterations were shown to play an important role in immune escape from monoclonal antibodies and polyclonal sera raised against the wild-type S glycoprotein (Ref. 15).

As described in the previous Examples, breakthrough infection with Omicron BA.1 or BA.2 of individuals immunized with mRNA vaccines or an inactivated virus vaccine has been associated with potent neutralizing activity against Omicron BA.1, BA.2 and previous VOCs (see also, Refs. 16-21). A considerable boost of Omicron BA.2.12.1 and BA.4/BA.5 neutralization relative to SARS-CoV-2 naïve vaccinee sera was only evident in BA.2 breakthrough cases, with titers against BA.4/BA.5 being lower than those against the remaining VOCs (see also Refs. 19-21). Administration of an Omicron BA.1-adapted booster to mice after wild-type strain-based primary immunization has previously been shown to enhance neutralizing activity against BA.1 compared to a wild-type booster (see previous Example 16 and Ref. 22). Preliminary analyses of a Phase 2 clinical trial have also shown that sera from SARS-CoV-2 naïve individuals vaccinated with an Omicron BA.1-adapted mRNA vaccine as a 4$^{th}$ dose showed significantly increased neutralizing responses against BA.1 compared to sera from individuals boosted with the prototypic mRNA vaccine (Ref. 23). However, the BA.1-adapted booster was not associated with increased BA.4/BA.5 cross-neutralization, as responses against BA.4/BA.5 were approximately three-fold and five-fold lower than responses against BA.1 and the prototypic strain, respectively, in sera from both BA.1 and prototype-boosted individuals.

Given the current predominance of the highly contagious VOCs Omicron BA.4 and BA.5 in large parts of the globe, the present Example was designed to investigate whether exposure to an Omicron BA.4/BA.5 S glycoprotein would trigger a broader neutralizing antibody response against relevant Omicron sublineages. The breadth of neutralizing activity was tested against Omicron VOCs in immune sera from vaccinated individuals with Omicron BA.4/BA.5 breakthrough infection and in sera from mice that received Omicron BA.4/BA.5-adapted booster vaccines following primary immunization with BNT162b2. In addition, the breadth of neutralizing activity was evaluated in sera from mice immunized with Omicron BA.4/BA.5-adapted vaccines without prior exposure to the wild-type S glycoprotein. The data described in the present Example provides further insight into Omicron immune escape mechanisms and the effects of immunization on variant cross-neutralization, and thus is useful for guiding selection of vaccination strategies.

Results

Study Design, Cohorts, and Sampling

The effect of Omicron BA.4/BA.5 breakthrough infection in individuals vaccinated with three doses of mRNA COVID-19 vaccine (BNT162b2/mRNA-1273 homologous or heterologous regimens) (FIG. 49(A)) and of Omicron BA.4/BA.5-adapted booster vaccination of BNT162b2 pre-immunized mice on the breadth of neutralizing activity in immune sera (FIG. 49(B)) was investigated. In addition, the effect of primary immunization with Omicron BA.4/BA.5-adapted vaccines was investigated in naïve mice (i.e., mice without previous exposure to a SARS-CoV-2 S protein, see FIG. 49(C)).

For the breakthrough infection study, serum samples were collected from triple mRNA vaccinated individuals who subsequently experienced a breakthrough infection with Omicron BA.4 or BA.5 (mRNA-Vax$^3$+BA.4/BA.5, n=17, FIG. 53). Three cohorts were included for reference: triple mRNA vaccinated individuals with a breakthrough infection with Omicron BA.2 (mRNA-Vax$^3$+BA.2, n=19) or with BA.1 (mRNA-Vax$^3$+BA.2, n=14), and BNT162b2 triple-vaccinated individuals who were SARS-CoV-2-naïve at the time of sampling (BNT162b2$^3$, n=18, FIG. 53). Sera were derived the study previously described in Examples 7, 13, and 17.

Omicron BA.4/BA.5 Breakthrough Infection of Triple mRNA-Vaccinated Individuals Results in Pan-Omicron Neutralizing Activity Neutralizing activity of immune sera was tested in a well-characterized pseudovirus neutralization test (pVNT) (Refs. 24-25) by determining 50% pseudovirus neutralization (pVN$_{50}$) geometric mean titers (GMTs) with pseudoviruses bearing the S glycoproteins of the SARS-CoV-2 wild-type strain or Omicron BA.1, BA.2, and the BA.2-derived sublineages BA.2.12.1, BA.4 and BA.5. As BA.4 and BA.5 are identical in their S glycoprotein sequence, in the context of pVNT, BA.4/5 is used. In addition, SARS-CoV was assayed (herein referred to as SARS-CoV-1) to detect potential pan-Sarbecovirus neutralizing activity (Ref. 26). As an orthogonal test system, a live SARS-CoV-2 neutralization test (VNT) was also used that analyzes neutralization during multicycle replication of authentic virus (SARS-CoV-2 wild-type strain and Omicron VOCs BA.1, BA.2, and BA.4) with immune serum present during the entire test period.

In the pVNT assay, sera from the Omicron BA.4/BA.5 breakthrough infection cohort (mRNA-Vax$^3$+BA.4/BA.5) robustly neutralized the wild-type strain and all tested Omicron VOCs (FIG. 50(A)). The pVN$_{50}$ GMTs against Omicron BA.2 and BA.2.12.1 pseudoviruses were within a 2-fold range of the GMT against the wild-type strain (GMTs 613 against Omicron vs. GMT 1085 against wild-type). Neutralization of BA.1 and BA.4/5 (GMTs 500-521) was broadly similar to that of BA.2, and the reduction relative to the wild-type strain significant (p<0.05) yet also within a ~2-fold range. The GMT against SARS-CoV-1 was significantly lower (p<0.0001; >50-fold lower than wild-type).

To compare mRNA-Vax$^3$+BA.4/BA.5 to the reference cohorts with Omicron BA.1 or BA.2 breakthrough infection (mRNA-Vax$^3$+BA.1 and mRNA-Vax$^3$+BA.2) and SARS-CoV-2 naïve triple BNT162b2-vaccinated individuals (BNT162b2$^3$), the VOC pVN$_{50}$ GMTs was normalized against the wild-type strain to allow for assessment of neutralization breadth irrespective of the magnitude of antibody titers, which expectedly differs between triple-vaccinated individuals with a breakthrough infection and triple-vaccinated individuals without infection (Refs. 16 and 21). While BNT162b2$^3$ sera mediated considerable cross-neutralization of Omicron BA.1 and BA.2, breakthrough infection with Omicron BA.1 and BA.2 was associated with higher cross-neutralization of the respective homologous strains (FIG. 50(B)). Cross-neutralization of BA.2.12.1, and especially BA.4/5, was less effective in the mRNA-Vax$^3$+BA.1 cohort (GMT ratios 0.43 and 0.18, respectively) compared to mRNA-Vax$^3$+BA.4/BA.5 (GMT ratios 0.57 and 0.48). Cross-neutralization of BA.2.12.1 and BA.4/5 was less reduced in the mRNA-Vax$^3$+BA.2 cohort (GMT ratios 0.53 and 0.37, respectively). Surprisingly, in the reciprocal case, cross-neutralization of Omicron BA.1 and BA.2 was maintained at comparatively higher levels in the mRNA-Vax$^3$+BA.4/BA.5 cohort (GMT ratios 0.46 and 0.57, respectively). Hence, BA.4/BA.5 breakthrough infection resulted in the most efficient cross-neutralization across all tested VOCs (GMT ratios 20.46) of all cohorts evaluated.

The authentic live SARS-CoV-2 virus neutralization assay largely confirmed the major pVNT assay findings shown in FIG. 50(A)-(B). 50% virus neutralization (VN$_{50}$) GMTs in Omicron BA.4/BA.5 breakthrough sera against BA.2 and BA.4 were comparable (i.e., within a 1.5-fold range) to that against the wild-type strain (FIG. 50(C)). Reduction of BA.1 neutralization was significant (p<0.01) yet within a 2.5-fold range. The GMTs normalized against the wild-type strain showed robust cross-neutralization of Omicron BA.1, BA.2, and BA.4 by mRNA-Vax$^3$+BA.4/BA.5 sera (GMT ratio >0.40), whereas BA.4 cross-neutralization was considerably less efficient in mRNA-Vax$^3$+BA.1 (GMT ratio 0.20) and mRNA-Vax$^3$+BA.2 (GMT ratio 0.39) sera (FIG. 50(D)) (Refs. 16, 21). Hence, the findings in both the pVNT and the VNT assay system showed that Omicron BA.4/BA.5 breakthrough infection was associated with broad neutralizing activity against all Omicron sublineages tested.

Booster Immunization with an Omicron BA.4/BA.5 S Glycoprotein Adapted mRNA Vaccine Drives Pan-Omicron Neutralization in BNT162b2 Double-Vaccinated Mice The heightened neutralization breadth seen after Omicron BA.4/BA.5 breakthrough infection suggested that variant-adapted vaccines based on the Omicron BA.4/5 S glycoprotein sequence can elicit a recall response with broader cross-neutralization than those based on Omicron BA.1. To test this hypothesis, booster studies were performed in BNT162b2-preimmunized mice (FIG. 49(B)). Mice were administered a primary series of two immunizations with BNT162b2 on days 0 and 21 and a third dose of either BNT162b2 (1 µg), or a BNT162b2-derived variant-adapted vaccine encoding Omicron BA.1 or BA.4/BA.5 S glycoprotein (FIG. 54) on day 104. The adapted vaccines were either administered as monovalent vaccines encoding Omicron BA.1 or BA.4/5 S glycoprotein (1 µg), or bivalent vaccines comprising BNT162b2 and the Omicron BA.1 or BA.4/5 S glycoprotein adapted vaccine (0.5 µg each). Comparable RNA purity and integrity, and expression of antigens in vitro were confirmed for BNT162b2 and Omicron-adapted vaccines (FIG. 55(A)-(B)).

Neutralizing titers against pseudoviruses expressing the wild-type strain, Omicron BA.1, BA.2, BA.2.12.1, or BA.4/5 S glycoprotein were determined in pVNT assays using sera drawn before the booster (day 104, pre-D3) and on days 7, 21, and 35 after the booster (d7D3, d21D3 and d35D3). The live SARS-CoV-2 neutralization test was used as an orthogonal test system to confirm the observed pseudovirus neutralizing activity post-boost on d21D3 and d35D3.

Baseline immunization of the mice was assessed by determination of SARS-CoV-2 pseudovirus neutralizing activity in sera drawn on pre-D3. pVN$_{50}$ GMTs of the groups dedicated for the various boosters were comparable, i.e., within a range of 3-fold difference (FIG. 56). pVN$_{50}$ GMTs against Omicron BA.1 and BA.2 were 3 to 11-fold lower than those against the wild-type strain (GMT ratios <0.32, FIG. 56(B)). GMTs against BA.2.12.1 and BA.4/5 were 10 to 25-fold lower than those against wild-type (GMT ratios 0.10).

On d7D3, neutralizing GMTs had increased substantially across groups and against all tested variants (FIG. 57) with peak titers reached on d21D3 (FIG. 51). In sera from BNT162b2 boosted mice, strong neutralizing activity against the wild-type strain was observed, whereas pVN$_{50}$ GMTs against Omicron variants were substantially lower (FIG. 51(A)). The Omicron BA.1 booster led to comparable neutralization of BA.1 and the wild-type strain, while the pVN$_{50}$ GMTs against the remaining VOCs were considerably lower. In particular, GMTs against BA.4/5 were reduced 13-fold compared to those against wild-type. In contrast, administration of the BA.4/5 booster resulted in broad neutralizing activity against all Omicron variants, with pVN$_{50}$ GMTs comparable (within a 1.5-fold range) to that against the wild-type strain. Sera from mice that received the BNT162b2/BA.1 bivalent booster had a high pVN$_{50}$ GMT against the wild-type strain, and robust neutralization of Omicron BA.1, whereas the GMTs against BA.2 and its descendants were slightly lower. The BNT162b2/Omicron BA.4/5 bivalent booster gave rise to high titers against the wild-type strain, comparable to the BNT162b2 monovalent booster. Omicron neutralization was broadly comparable across all sublineages (within a 2-fold range), with pVN$_{50}$ GMTs modestly below that against the wild-type strain.

To quantify the booster effect of the third dose of vaccine variants on neutralization of individual VOCs, the fold-changes in pVN$_{50}$ GMTs detected on d21D3 was evaluated relative to the baseline GMTs determined before administration of the third dose. BNT162b2 comparably increased neutralization of all tested variants (pVN$_{50}$ GMTs 6 to 10-fold higher than at baseline), whereas the most pronounced effect of the BA.1 booster was detected for the neutralization of the homologous VOC (26-fold increase) (FIG. 51(B)). The BA.4/5 booster strongly potentiated neutralizing activity against BA.2.12.1 and BA.4/5 (>120-fold) and also had a substantial effect on BA.1 and BA.2 neutralization (increases of 34 and 37-fold, respectively). The BNT162b2/BA.1 and BNT162b2/BA.4/5 bivalent vaccines showed patterns of potentiation similar to the BA.1 and BA.4/5 monovalent vaccines, respectively, albeit with less focused increases in neutralization against the homologous VOCs.

To compare the groups with regard to neutralization breadth irrespective of the magnitude, the VOC pVN$_{50}$ GMTs was normalized against the wild-type strain. The GMT ratios showed that the Omicron BA.4/5 booster vaccine mediated pan-Omicron neutralization (>0.65 for all tested variants) (FIG. 51(C)). In contrast, the BA.1 booster vaccine was beneficial for neutralization of BA.1 (GMT ratio 0.77), whereas ratios for BA.2 (0.39) and especially for BA.2.12.1 and BA.4/5 (50.16) were substantially lower. The bivalent BNT162b2/BA.4/5 vaccine also mediated broad neutralizing activity with enhanced cross-neutralization of BA.2, BA.2.12.1 and BA.4/5 compared to the BNT162b2/BA.1 bivalent vaccine, albeit with lower GMT ratios (between 0.27 and 0.46) than the BA.4/5 monovalent vaccine.

Again, the authentic live SARS-CoV-2 virus neutralization assay largely confirmed the major pVNT assay findings shown in FIG. 51(A)-(C). Sera from mice administered the BA.4/5 booster dose robustly neutralized all the variants tested (FIG. 51(D)), thereby confirming the capacity of this approach to mediate pan-Omicron neutralization (GMT ratios >0.39) (FIG. 51(E)).

While neutralization of Omicron variants in sera from mice boosted with the BNT162b2/BA.4/5 bivalent vaccine was lower compared to the BA.4/5 monovalent vaccine, both BA.4/5-containing vaccines exhibited stronger cross-neutralization of the Omicron variants than the BNT162b2/BA.1 vaccine, and even more so than the monovalent BA.1 vaccine and BNT162b2.

While absolute titers were slightly lower on d7D3 compared to d21D3, the Omicron BA.4/5 vaccine mediated a similarly broad neutralizing activity against all variants (FIG. 57). BNT162b2/BA.4/5 bivalent booster mediated comparable neutralization breadth (GMT ratios≥0.35), whereas sera from all other booster groups exhibited considerably lower cross-neutralization of BA.2, BA.2.12.1 (and BA.4/5). Similarly, later analysis of sera on d35D3 showed substantial potentiation of neutralizing activity against Omicron variants by the BA.4/5 vaccine booster compared to baseline, resulting in pan-Omicron neutralization (FIG. 58(A)-(C)). The bivalent BNT162b2/BA.4/5 booster also exhibited broad neutralization across all variants tested, whereas the BA.1 and the BNT162b2/BA.1 vaccines manifested with lower capacity of cross-neutralization, especially against BA.2.12.1 and BA.4/5. Similarly, in the VNT assay, sera from both groups boosted with BA.4/5-containing vaccines exhibited substantially stronger cross-neutralization of all tested Omicron variants compared to the BA.1-containing vaccines and BNT162b2 (FIG. 58(D)-(E)).

These mouse booster results were consistent with those observed in humans with BA.4/5 breakthrough infections, described above, and further suggest that a booster with an Omicron BA.4/5 S glycoprotein adapted vaccine following primary immunization with a wild-type strain-based vaccine can elicit pan-Omicron neutralizing activity superior in breadth to a BA.1 S glycoprotein-based booster.

Immunization with an Omicron BA.4/BA.5 S Glycoprotein Adapted mRNA Vaccine Drives Pan-Omicron Neutralization in Previously Unvaccinated Mice Next, experiments were performed to better understand the neutralizing capacity of serum samples after immunization with the Omicron-adapted vaccine in mice with no pre-existing immune response against SARS-CoV-2. Naïve mice were immunized twice at day 0 and day 21 with either BNT162b2, with BA.1 or BA.4/5 S glycoprotein adapted monovalent vaccines, or the bivalent BNT162b2/BA.4/5 vaccine (FIG. 49(C)). Neutralizing titers against pseudoviruses expressing the wild-type strain S glycoprotein, that of the previous VOCs Alpha or Delta, or Omicron BA.1, BA.2, BA.2.12.1, or BA.4/5 were determined in pVNT assays using sera drawn 14 days after the second immunization (d14D2). In sera from BNT162b2 immunized mice, strong neutralizing activity against the wild-type strain was observed. In these sera, robust neutralizing activity against Alpha and Delta was also detected (within a 4-fold range of wild-type), whereas pVN$_{50}$ GMTs against Omicron variants were substantially (14 to 37-fold) lower than against wild-type (FIG. 52). Immunization with the Omicron BA.1 monovalent vaccine led to high neutralization of BA.1. In these sera, robust neutralization of Omicron BA.2 and BA.2.12.1 was also detected (within a 3-fold range of BA.1), while the pVN$_{50}$ GMTs against the wild-type strain and remaining VOCs were considerably (7 to 32-fold) lower than BA.1. Immunization with the Omicron BA.4/5 monovalent vaccine led to high neutralization of BA.4/5. In these sera, robust neutralization of Omicron BA.2 and BA.2.12.1 was also detected (within a 2.5-fold range of BA.4/5), while the pVN$_{50}$ GMTs against the wild-type strain and remaining VOCs were considerably (14 to >42-fold lower than BA.4/5. Immunization with the BNT162b2/BA.4/5 bivalent vaccine resulted in high neutralizing activity against BA.4/5. In contrast to the other vaccines, robust neutralizing activity against the wild-type strain and all remaining VOCs (within a 6-fold range of BA.4/5) were also detected in these sera.

These results show that a monovalent vaccine in naïve animals (e.g., animals that have not been previously administered against and/or infected with SARS-CoV-2) can induce a high neutralizing antibody response mostly in a variant-specific manner but can lose potency when testing against more distant variants. In contrast, a bivalent vaccine can induce strong and broad neutralizing antibody responses in naïve animals.

Discussion

In the present Example, BA.4/BA.5 breakthrough infection of triple-mRNA vaccinated individuals is associated with robust neutralization of all currently or previously predominant Omicron subvariants, i.e., pan-Omicron neutralization is observed in BA.4/5-breakthrough patients. These findings are consistent with a recent report showing strong cross-neutralization of Omicron BA.1, BA.2, as well as Beta and Delta in sera from individuals vaccinated with BNT162b2 or an adenovirus-based vaccine and subsequent BA.4 breakthrough infection (Ref. 27). In line with those observations in humans, pan-Omicron neutralizing activity was also observed in the sera of mice that received an Omicron BA.4/5 booster vaccine following primary immunization with BNT162b2, whereas an Omicron BA.1 boost induced strongly reduced neutralizing antibody titers against BA.4/BA.5. A bivalent BNT162b2/BA.4/5 boost elicited broad Omicron neutralization, albeit less pronounced than the BA.4/5 monovalent booster. Together, these findings provide further understanding on how breakthrough infections or vaccine boosters adapted to Omicron VOCs in a mono- or bivalent format shape immunity and suggest that exposure to Omicron BA.4/5 S glycoprotein may confer heightened protection against the currently circulating and potential future Omicron sublineage VOCs. The finding that immunization of naïve mice with the BNT162b2/BA.4/5 bivalent vaccine elicits strong neutralizing antibody responses against the wild-type strain as well as Omicron and non-Omicron VOCs suggest that this bivalent approach can confer broad protection to unvaccinated individuals not previously infected SARS-CoV-2 (e.g., young pediatric patients), and thus may be particularly suitable for these individuals.

While currently approved SARS-CoV-2 wild-type strain-based vaccines such as BNT162b2 have proven effective at protecting against severe disease (Refs. 28-30), prevention of transmission remains a significant challenge as new variants continue to emerge that are antigenically distant from the wild-type strain (Refs. 16-18, 20). The data described in the present Example suggest that a mono- or bivalent BA.4/BA.5 S glycoprotein adapted booster vaccine (e.g., a mono- or bivalent vaccine described herein), can confer higher benefit against the highly prevalent BA.4 and BA.5 VOCs than a vaccine based on a previously dominant Omicron sublineage such as BA.1. Given their predominance in many regions around the world and their high transmissibility (see, e.g., Refs., 8, 10, 11, and 13), it is possible that new variants with further growth advantage will emerge from Omicron BA.4 or BA.5 that retain partial or full susceptibility to an Omicron BA.4/BA.5-adapted vaccine. Boosting pre-existing immunity with an Omicron BA.4/5 S glycoprotein-based adapted vaccine could therefore represent a suitable strategy to address the current pandemic situation, while close monitoring of virus evolution and epidemiological landscapes remains instrumental for guidance on potential further vaccine adaptations in response to emerging threats.

Materials and Methods

Human study design, recruitment of participants and sample collection The objective of the study described in the present Example was to investigate the effect of Omicron BA.4/BA.5 breakthrough infection on the cross-variant neutralization capacity of human sera. Neutralizing activity was assessed in immune sera from triple-mRNA (BNT162b2/mRNA-1273)-vaccinated individuals with a confirmed subsequent SARS-CoV-2 breakthrough infection, which either occurred in a period of Omicron BA.4/BA.5 lineage-dominance in Germany (mid-June to mid-July 2022;) or was variant-confirmed (BA.4 or BA.5) by genome sequencing (mRNA-Vax$^3$+BA.4/5) (FIG. 53). The neutralizing activity was compared to that in immune sera from triple mRNA vaccinated individuals with a confirmed subsequent SARS-CoV-2 breakthrough infection in a period of Omicron BA.2 lineage-dominance (March to May 2022; mRNA-Vax$^3$+BA.2), a period of Omicron BA.1 lineage-dominance in Germany (November 2021 to mid-January 2022; mRNA-Vax$^3$+BA.1) (Refs. 1, 2), and triple-BNT162b2-vaccinated individuals that were SARS-CoV-2-naïve (nucleocapsid seronegative) at the time of sample collection (BNT162b2$^3$). Serum neutralizing capability was characterized using pseudovirus and live SARS-CoV-2 neutralization assays. Data for the reference cohorts mRNA-Vax$^3$+BA.2, mRNA-Vax$^3$+BA.1, and BNT162b2$^3$ were previously published (Refs. 16, 21).

Participants from the mRNA-Vax$^3$+Omi BA.4/5, mRNA-Vax$^3$+Omi BA.2, and mRNA-Vax$^3$+BA.1 cohorts were recruited from University Hospital, Goethe University Frankfurt as part of a non-interventional study (protocol approved by the Ethics Board of the University Hospital [No. 2021-560]) researching patients that had experienced Omicron breakthrough infection following vaccination for COVID-19. Individuals from the BNT162b2$^3$ cohort provided informed consent as part of their participation in the Phase 2 trial BNT162-17 (NCT05004181).

The infections of 5 BA.4/5 and 4 BA.1 convalescent participants in this study were confirmed by genome sequencing (Ref. 16).

All participants had no documented history of SARS-CoV-2 infection prior to vaccination.

Participants were free of symptoms at the time of blood collection.

Serum was isolated by centrifugation of drawn blood at 2000×g for 10 minutes and cryopreserved until use.

In Vitro Transcription and Lipid-Nonoparticle (LNP)Formulation of the RNA

The BNT162b2 vaccine was designed on a background of S sequences from SARS-CoV-2 isolate Wuhan-Hu-1 (GenBank: MN908947.3) with pre-fusion conformation-stabilizing K986P and V987P mutations. Omicron BA.1 and Omicron BA.4/5 vaccine candidates were designed based on BNT162b2 including sequence changes as shown in FIG. 54. RNA production as well as formulation were performed as described elsewhere (see, e.g., Ref. 32 the contents of which are incorporated herein by reference in their entirety). In brief, DNA templates were cloned into a plasmid vector with backbone sequence elements (T7 promoter, 5' and 3'

UTR, 100 nucleotide poly(A) tail) interrupted by a linker (Δ30LA70, 10 nucleotides) for improved RNA stability and translational efficiency (see, e.g., Refs. 33, 34), amplified via PCR and purified. RNA was in vitro transcribed by T7 RNA polymerase in the presence of a trinucleotide cap1 analogue ((m27,3'-O)Gppp(m2'-O)ApG; TriLink) and with N1-methylpseudouridine-5'-triphosphate (m1LPTP; Thermo Fisher Scientific®) replacing uridine-5'-triphosphate (UTP) (Ref. 35). RNA was purified using magnetic particles (Ref. 36) and RNA integrity was assessed by microfluidic capillary electrophoresis (Agilent 2100 Bioanalyzer) and all three RNAs show single sharp peaks resulting in comparable and high purity as well as integrity (FIG. 55(A)). In addition, the concentration, pH, osmolality, endotoxin level and bioburden of the solution were determined.

One ionizable lipid ((4-hydroxybutyl)azanediyl)bis (hexane-6,1-diyl)bis(2-hexyldecanoate)), two structural lipids (1,2-distearoyl-sn-glycero-3-phosphocholine [DSPC] and cholesterol) and one PEGylated lipid (2-[(polyethylene glycol)-2000]-N,N-ditetradecylacetamide) were used for formulation of RNA. After transfer into an aqueous buffer system via diafiltration, the LNP compositions were analyzed ensuring but not limited to high RNA integrity and encapsulation efficacy, as well as a particle size below 100 nm. The vaccine candidates were stored at −70 to −80° C. at a concentration of 0.5 mg/mL till time point of usage.

In Vitro Expression of RNAs and Vaccines

HEK293T cells were transfected with 0.15 μg BNT162b2 or Omicron-adapted vaccines (lipid-nanoparticle-formulated), or with vaccine RNAs using RiboJuice™ mRNA Transfection Kit (Merck Millipore) according to the manufacturer's instructions and incubated for 18 h. Transfected HEK293T cells were stained with Fixable Viability Dye (eBioscience) and incubated with mFc-tagged recombinant human ACE-2 (Sino Biological). A secondary donkey anti-mouse antibody conjugated with AF647 was used for detection of surface expression. Cells were fixed (Fixation Buffer, Biolegend) prior to flow cytometry analysis using a FACS-Celesta flow cytometer (BD Biosciences, BD FACSDiva software version 8.0.1) and FlowJo software version 10.6.2 (FlowJo, BD Biosciences).

Mouse Studies

All mouse studies were performed at BioNTech SE, and protocols were approved by the local authorities (local welfare committee) and conducted according to Federation of European Laboratory Animal Science Associations recommendations. Study execution and housing were in compliance with the German Animal Welfare Act and Directive 2010/63/EU. Mice were kept in individually ventilated cages with a 12-h light/dark cycle, controlled environmental conditions (22±2° C., 45% to 65% relative humidity) and under specific-pathogen-free conditions. Food and water were available ad libitum. Only mice with an unobjectionable health status were selected for testing procedures.

For immunization, female BALB/c mice (Janvier) (9-21 weeks old) were randomly allocated to groups. BNT162b2 and Omicron-based vaccines candidates were diluted in 0.9% NaCl and 1 μg of the vaccine candidate was injected into the gastrocnemius muscle at a volume of 20 μl under isoflurane anesthesia. For the mouse booster study, mice were immunized twice (day 0 and 21) with BNT162b2. Third immunization with BNT162b2 and Omicron-based vaccines candidates occurred at day 104 after study start and mice were bled shortly before third immunization and as indicated in FIG. 49. For the naïve moue study, animals were immunized at day 0 and 21 with BNT162b2 and Omicron-based vaccines candidates. 14 days after second immunization, blood was withdrawn. Peripheral blood was collected from the vena facialis without anesthesia. Final bleeding was performed under isoflurane anesthesia from the retro-orbital venous plexus. For serum generation, blood was centrifuged for 5 min at 16,000 g and the serum was immediately used for downstream assays or stored at −20° C. till timepoint of usage.

VSV-SARS-CoV-2 S Variant Pseudovirus Generation

A recombinant replication-deficient vesicular stomatitis virus (VSV) vector that encodes green fluorescent protein (GFP) and luciferase instead of the VSV-glycoprotein (VSV-G) was pseudotyped with SARS-CoV-1 S glycoprotein (UniProt Ref: P59594) and with SARS-CoV-2 S glycoprotein derived from either the wild-type strain (Wuhan-Hu-1, NCBI Ref: 43740568), the Alpha variant (alterations: Δ69/70, Δ144, N501Y, A570D, D614G, P681H, T716I, S982A, D1118H), the Delta variant (alterations: T19R, G142D, E156G, Δ157/158, K417N, L452R, T478K, D614G, P681R, D950N), the Omicron BA.1 variant (alterations: A67V, Δ69/70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F), the Omicron BA.2 variant (alterations: T19I, Δ24-26, A27S, G142D, V213G, G339D, S371F, S373P, S375F, T376A, D405N, R408S, K417N, N440K, S477N, T478K, E484A, Q493R, Q498R, N501Y, Y505H, D614G, H655Y, N679K, P681H, N764K, D796Y, Q954H, N969K), the Omicron BA.2.12.1 variant (alterations: T19I, Δ24-26, A27S, G142D, V213G, G339D, S371F, S373P, S375F, T376A, D405N, R408S, K417N, N440K, L452Q, S477N, T478K, E484A, Q493R, Q498R, N501Y, Y505H, D614G, H655Y, N679K, P681H, S704L, N764K, D796Y, Q954H, N969K), and the Omicron BA.4/5 variant (alterations: T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K) according to published pseudotyping protocols (e.g., as described in Ref. 3, the contents of which are incorporated by reference herein in their entirety). A diagram of SARS-CoV-2 S glycoprotein alterations is shown in FIG. 32 and a separate alignment of S glycoprotein alterations in Omicron sublineages is displayed in FIG. 33.

In brief, HEK293T/17 monolayers (ATCC® CRL-11268™) cultured in Dulbecco's modified Eagle's medium (DMEM) with GlutaMAX™ (Gibco) supplemented with 10% heat-inactivated fetal bovine serum (FBS [Sigma-Aldrich]) (referred to as medium) were transfected with Sanger sequencing-verified SARS-CoV-1 or variant-specific SARS-CoV-2 S expression plasmid with Lipofectamine LTX (Life Technologies) following the manufacturer's instructions. At 24 hours after transfection, the cells were infected at a multiplicity of infection (MOI) of three with VSV-G complemented VSVΔG vector. After incubation for 2 hours at 37° C. with 7.5% $CO_2$, cells were washed twice with phosphate buffered saline (PBS) before medium supplemented with anti-VSV-G antibody (clone 8G5F11, Kerafast Inc.) was added to neutralize residual VSV-G-complemented input virus. VSV-SARS-CoV-2-S pseudotype-containing medium was harvested 20 hours after inoculation, passed through a 0.2 μm filter (Nalgene) and stored at −80° C. The pseudovirus batches were titrated on Vero 76 cells (ATCC® CRL-1587™) cultured in medium. The relative luciferase units induced by a defined volume of a SARS-CoV-2 wild-type strain S glycoprotein pseudovirus reference batch previously described in Muik et al., 2021 (Ref. 31), that corresponds to an infectious titer of 200 transducing units (TU) per mL, was used as a comparator. Input volumes for the SARS-CoV-2 variant pseudovirus batches were calculated to normalize the infectious titer based on the relative luciferase units relative to the reference.

Pseudovirus Neutralization Assay

Vero 76 cells were seeded in 96-well white, flat-bottom plates (Thermo Fisher Scientific®) at 40,000 cells/well in medium 4 hours prior to the assay and cultured at 37° C. with 7.5% $CO_2$. Human and mouse serum samples were 2-fold serially diluted in medium with dilutions ranging from 1:5 to 1:30,720 (human sera), from 1:40 to 1:102,400 for mouse booster study (mouse sera; starting dilution was 1:40 [pre-D3], 1:200 [d7D3]) as well as 1:100 [d21D3, d35D3]) and in the naïve setting (mouse sera; monovalent vaccinated groups starting dilution 1:120 to 1:15,360 and bivalent vaccinated groups starting 1:100). VSV-SARS-CoV-2-S/VSV-SARS-CoV-1-S particles were diluted in medium to obtain 200 TU in the assay. Serum dilutions were mixed 1:1 with pseudovirus (n=2 technical replicates per serum per pseudovirus) for 30 minutes at room temperature before being added to Vero 76 cell monolayers and incubated at 37° C. with 7.5% $CO_2$ for 24 hours. Supernatants were removed and the cells were lysed with luciferase reagent (Promega). Luminescence was recorded on a CLARIOstar® Plus microplate reader (BMG Labtech), and neutralization titers were calculated as the reciprocal of the highest serum dilution that still resulted in 50% reduction in luminescence. Results for all pseudovirus neutralization experiments were expressed as geometric mean titers (GMT) of duplicates. If no neutralization was observed, an arbitrary titer value of half of the limit of detection [LOD] was reported. Tables of the neutralization titers in human sera are provided.

Live SARS-CoV-2 Neutralization Assay

SARS-CoV-2 virus neutralization titers were determined by a microneutralization assay based on cytopathic effect (CPE) at VisMederi S.r.l., Siena, Italy. In brief, human and mouse serum samples were serially diluted 1:2 (n=2 technical replicates per serum per virus; starting at 1:10 for human samples and starting at 1:100 [post-boost, day 125] or at 1:50 [post-boost, day 139] for murine samples) and incubated for 1 hour at 37° C. with 100 $TCID_{50}$ of the live wild-type-like SARS-CoV-2 virus strain 2019-nCOV/ITALY-INM11 (GenBank: MT066156), Omicron BA.1 strain hCoV-19/Belgium/rega-20174/2021 (alterations: A67V, Δ69/70, T95I, G142D, Δ143-145, Δ211, L212I, ins214EPE, G339D, S371L, S373P, S375F, K417N, N440K, G446S, S477N, T478K, E484A, Q493R, G496S, Q498R, N501Y, Y505H, T547K, D614G, H655Y, N679K, P681H, N764K, D796Y, N856K, Q954H, N969K, L981F), sequence-verified Omicron BA.2 strain (alterations: T19I, Δ24-26, A27S, V213G, G339D, S371F, S373P, S375F, T376A, D405N, R408S, K417N, S477N, T478K, E484A, Q493R, Q498R, N501Y, Y505H, D614G, H655Y, N679K, P681H, R682W, N764K, D796Y, Q954H, N969K), or sequence-verified Omicron BA.4 strain (alterations: V3G, T19I, Δ24-26, A27S, Δ69/70, G142D, V213G, G339D, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K) to allow any antigen-specific antibodies to bind to the virus. A diagram of S glycoprotein alterations is shown in FIG. 48. The 2019-nCOV/ITALY-INM11 strain S glycoprotein is identical in sequence to the wild-type SARS-CoV-2 S (Wuhan-Hu-1 isolate). Vero E6 (ATCC® CRL-1586™) cell monolayers were inoculated with the serum/virus mix in 96-well plates and incubated for 3 days (2019-nCOV/ITALY-INM11 strain) or 4 days (Omicron BA.1, BA.2 and BA.4 variant strain) to allow infection by non-neutralized virus. The plates were observed under an inverted light microscope and the wells were scored as positive for SARS-CoV-2 infection (i.e., showing CPE) or negative for SARS-CoV-2 infection (i.e., cells were alive without CPE). The neutralization titer was determined as the reciprocal of the highest serum dilution that protected more than 50% of cells from CPE and reported as GMT of duplicates. If no neutralization was observed, an arbitrary titer value of 5 (half of the LOD) was reported.

Statistical Analysis

The statistical method of aggregation used for the analysis of antibody titers is the geometric mean and for the ratio of SARS-CoV-2 VOC titer and wild-type strain titer the geometric mean and the corresponding 95% confidence interval. The use of the geometric mean accounts for the non-normal distribution of antibody titers, which span several orders of magnitude. The Friedman test with Dunn's correction for multiple comparisons was used to conduct pairwise signed-rank tests of group geometric mean neutralizing antibody titers with a common control group. Spearman correlation was used to evaluate the monotonic relationship between non-normally distributed datasets. All statistical analyses were performed using GraphPad Prism software version 9.

References for Example 18

1. WHO Technical Advisory Group on SARS-CoV-2 Virus Evolution (TAG-VE): Classification of Omicron (B.1.1.259): SARS-CoV-2 Variant of Concern. (2021).
2. WHO Headquarters (HQ), WHO Health Emergencies Programme, Enhancing Response to Omicron SARS-CoV-2 variant: Technical brief and priority actions for Member States. (2022).
3. M. Hoffmann et al., The Omicron variant is highly resistant against antibody-mediated neutralization: Implications for control of the COVID-19 pandemic. *Cell* 185, 447-456 e411 (2022).
4. V. Servellita et al., Neutralizing immunity in vaccine breakthrough infections from the SARS-CoV-2 Omicron and Delta variants. *Cell* 185, 1539-1548 e1535 (2022).
5. C. Kurhade et al., Neutralization of Omicron BA.1, BA.2, and BA.3 SARS-CoV-2 by 3 doses of BNT162b2 vaccine. *Nat Commun* 13, 3602 (2022).
6. Y. Cao et al., Omicron escapes the majority of existing SARS-CoV-2 neutralizing antibodies. *Nature* 602, 657-663 (2022).
7. S. Xia, L. Wang, Y. Zhu, L. Lu, S. Jiang, Origin, virological features, immune evasion and intervention of SARS-CoV-2 Omicron sublineages. *Signal Transduct Target Ther* 7, 241 (2022).
8. H. Gruell et al., SARS-CoV-2 Omicron sublineages exhibit distinct antibody escape patterns. *Cell Host Microbe*, (2022).
9. Y. Fan et al., SARS-CoV-2 Omicron variant: recent progress and future perspectives. *Signal Transduct Target Ther* 7, 141 (2022).
10. H. Tegally et al., Emergence of SARS-CoV-2 Omicron lineages BA.4 and BA.5 in South Africa. Nat Med, (2022).
11. European Centre for Disease Prevention and Control, Weekly COVID-19 country overview—Country overview report: week 31 2022 (2022).

12. J. Hadfield et al., Nextstrain: real-time tracking of pathogen evolution nextstrain_org/ncov/gisaid_. *Bioinformatics* 34, 4121-4123 (2018).
13. Centers for Disease Control and Prevention. COVID Data Tracker. Atlanta, GA: US Department of Health and Human Services, CDC; 2022, August 12. covid_cdc_gov/covid-data-tracker. (2022).
14. A. Z. Mykytyn et al., Antigenic cartography of SARS-CoV-2 reveals that Omicron BA.1 and BA.2 are antigenically distinct. *Sci Immunol*, eabq4450 (2022).
15. P. Wang et al., Antibody resistance of SARS-CoV-2 variants B.1.351 and B.1.1.7. *Nature* 593, 130-135 (2021).
16. J. Quandt et al., Omicron BA.1 breakthrough infection drives cross-variant neutralization and memory B cell formation against conserved epitopes. *Sci Immunol*, eabq2427 (2022).
17. C. I. Kaku et al., Recall of pre-existing cross-reactive B cell memory following Omicron BA.1 breakthrough infection. *Sci Immunol*, eabq3511 (2022).
18. Y. Cao et al., BA.2.12.1, BA.4 and BA.5 escape antibodies elicited by Omicron infection. *Nature*, (2022).
19. P. Arora et al., Augmented neutralisation resistance of emerging omicron subvariants BA.2.12.1, BA.4, and BA.5. *Lancet Infect Dis*, (2022).
20. Q. Wang et al., Antibody evasion by SARS-CoV-2 Omicron subvariants BA.2.12.1, BA.4, & BA.5. *Nature*, (2022).
21. A. Muik et al., Omicron BA.2 breakthrough infection enhances cross-neutralization of BA.2.12.1 and BA.4/BA.5. *bioRxiv*, (2022).
22. P. Du et al., A bivalent vaccine containing D614G and BA.1 spike trimer proteins or a BA.1 spike trimer protein booster shows broad neutralizing immunity. *J Med Viral* 94, 4287-4293 (2022).
23. A. R. Branche et al., SARS-CoV-2 Variant Vaccine Boosters Trial: Preliminary Analyses. *medRxiv*, (2022).
24. A. Muik et al., Neutralization of SARS-CoV-2 lineage B.1.1.7 pseudovirus by BNT162b2 vaccine-elicited human sera. *Science* 371, 1152-1153 (2021).
25. A. Muik et al., Neutralization of SARS-CoV-2 Omicron by BNT162b2 mRNA vaccine-elicited human sera. *Science* 375, 678-680 (2022).
26. C. W. Tan et al., Pan-Sarbecovirus Neutralizing Antibodies in BNT162b2-Immunized SARS-CoV-1 Survivors. *N Engl J Med* 385, 1401-1406 (2021).
27. S. I. Richardson et al., SARS-CoV-2 BA.4 infection triggers more cross-reactive neutralizing antibodies than BA.1. *bioRxiv*, (2022).
28. S. Y. Tartof et al., Immunocompromise and durability of BNT162b2 vaccine against severe outcomes due to omicron and delta variants. *Lancet Respir Med* 10, e61-e62 (2022).
29. N. Andrews et al., Covid-19 Vaccine Effectiveness against the Omicron (B.1.1.529) Variant. *N Engl J Med* 386, 1532-1546 (2022).
30. F. P. Polack et al., Safety and Efficacy of the BNT162b2 mRNA Covid-19 Vaccine. *N Engl J Med* 383, 2603-2615 (2020).
31. W. Dejnirattisai et al., SARS-CoV-2 Omicron-B.1.1.529 leads to widespread escape from neutralizing antibody responses. Cell 185, 467-484 e415 (2022).
32. A. B. Vogel et al., BNT162b vaccines protect rhesus macaques from SARS-CoV-2. *Nature* 592, 283-289 (2021).
33. A. G. Orlandini von Niessen et al., Improving mRNA-Based Therapeutic Gene Delivery by Expression-Augmenting 3' UTRs Identified by Cellular Library Screening. *Mol Ther* 27, 824-836 (2019).
34. S. Holtkamp et al., Modification of antigen-encoding RNA increases stability, translational efficacy, and T-cell stimulatory capacity of dendritic cells. *Blood* 108, 4009-4017 (2006).
35. E. Grudzien-Nogalska et al., Synthetic mRNAs with superior translation and stability properties. *Methods Mol Biol* 969, 55-72 (2013).
36. S. Berensmeier, Magnetic particles for the separation and purification of nucleic acids. *Appl Microbial Biotechnol* 73, 495-504 (2006).

Example 19: Influence of BA.4/BA.5 Breakthrough Infections on Omicron Immune Responses The present Example 19 is an extension of Examples 14, 17, and 18, and describes experiments in which serum samples collected from BA.1-, BA.2-, and BA.4/5-breakthrough cases were analyzed for neutralization activity against Omicron BA.4, BA.5, BA.4.6, BF.7, and BA.2.75 variants. In addition to confirming the results described in the previous Examples, the present Example 19 also provides further characterization of antibody responses induced by BA.1-, BA.2-, and BA.4/5-breakthrough infections in relation to BA.4.6, BF.7, and BA.2.75 variants. The present Example further demonstrates that a BA.4/5 breakthrough infection can produce a broader neutralization response than BA.1- and BA.2-breakthrough infections, with superior neutralization titers induced against BA.4/5 and BA.4.6/BF.7 variants as compared to BA.1- and BA.2-breakthrough infections, and comparable neutralization titers against a BA.2.75 virus.

Continued evolution of the SARS-CoV-2 Omicron variant has led to the emergence of numerous sublineages with distinct patterns of neutralizing antibody evasion. The recently emerged sublineages BA.4.6, BF.7, and BA.2.75 have raised concerns as their prevalence slowly but steadily increases in many regions. The present Example investigated neutralizing activity against these Omicron sublineages as well as the currently dominant BA.4/BA.5 in immune sera of COVID-19 mRNA triple-vaccinated individuals with subsequent breakthrough infection with BA.1, BA.2, or BA.4/BA.5 SARS-CoV-2 variants. Sera from SARS-CoV-2 naïve triple- or quadruple mRNA-vaccinated individuals were also tested. Sera from BA.1, BA.2, and BA.4/BA.5 convalescents were broadly comparable in their proficiency to cross-neutralize BA.2.75 relative to the SARS-CoV-2 wild-type strain. The strongest cross-neutralization of Omicron BA.4.6/BF.7 was detected in BA.4/BA.5 convalescent sera. These findings indicate that breakthrough infection with recent Omicron sublineages may confer at least partial protection against infection with newly emerging sublineages, and provides further evidence supporting the efficacy of a BA.4/5-specific vaccine (in particular, further evidence that a BA.4/5-specific vaccine can provide a broad immune response against Omciron variants). The SARS-CoV-2 Omicron variant of concern (VOC) contains over 30 amino acid alterations in its spike (S) glycoprotein, which mediate partial escape from previously established immunity.

As a result, breakthrough infections with Omicron have been more frequent than with previously circulating VOCs among vaccinated populations. Since Omicron's first emergence in November 2021, sublineages BA.1, BA.2, BA.4, and BA.5 consecutively dominated the pandemic landscape. While BA.5 has been the globally dominant sublineage since mid-2022, virus evolution continues to give rise to new sublineages that harbor additional amino acid alterations in their S glycoprotein. Descendants of previous Omicron sublineages with slow but steady increases in prevalence have been reported in many countries across continents. These descendants include Omicron BA.2.75, BA.4.6, and BF.7, which have emerged from BA.2, BA.4, and BA.5, respectively.

Omicron BA.2.75 contains five amino acid alterations within the N-terminal domain (NTD) of the S protein that distinguishes it from previous Omicron Variants of Concern (VOCs), including its parental sublineage BA.2 (FIG. 60). In addition, BA.2.75 has three alterations in its receptor-binding domain (RBD) that are not found in BA.2, of which G446S is shared with BA.1. The most prevalent strains of Omicron BA.4.6 and BF.7 have identical S glycoprotein sequences, which show high similarity with their respective parental lineages BA.4 and BA.5, which also share their S glycoprotein sequence. A single R346T alteration within the RBD differentiates BA.4.6/BF.7 from BA.4/BA.5, and abrogates neutralization by the therapeutic monoclonal antibody (mAb) cilgavimab (Ref. 1). The combination of cilgavimab and tixagevimab (Evusheld™), which has high clinical relevance for pre-exposure COVID-19 prophylaxis in immunocompromised patients, is expected to be ineffective against Omicron BA.4.6 and BF.7 given that tixagevimab lacks neutralizing activity against Omicron BA.4/BA.5 and their descendants (Refs. 1 and 2).

Primary SARS-CoV-2 immunity in many parts of the world is based on infections with the original wild-type virus or wild-type strain-based vaccines, such as the mRNA vaccines BNT162b2 and mRNA-1273. Immune responses are commonly further shaped through breakthrough infections with antigenically distinct Omicron sublineage viruses or recently authorized Omicron-adapted vaccine boosters. An important question is whether breakthrough infections and Omicron-adapted vaccine boosters elicit substantial neutralizing antibody responses against recently emerged Omicron sublineages currently gaining momentum.

The present example investigated neutralizing activity against Omicron BA.4.6/BF.7 and BA.2.75 from immune sera isolated from five cohorts of individuals who received three or four doses of mRNA COVID-19 vaccines (BNT162b2/mRNA-1273 homologous or heterologous regimens), with or without subsequent breakthrough infections with Omicron sublineage variants. Individual cohorts were BNT162b2 triple-vaccinated SARS-CoV-2-naïve individuals ($BNT162b2^3$; n=18), BNT162b2 quadruple-vaccinated SARS-CoV-2-naïve elderly individuals ($BNT162b2^4$; n=15), and triple mRNA-vaccinated individuals who experienced breakthrough infection with Omicron BA.1 ($mRNA\text{-}Vax^3$+BA.1; n=14), BA.2 ($mRNA\text{-}Vax^3$+BA.2, n=19), or BA.4/BA.5 ($mRNA\text{-}Vax^3$+BA.4/BA.5, n=17) (FIG. 61). The study design includes cohorts that are thought to represent a large proportion of the European and North American population, given the local health authorities' recommendation of a fourth vaccine dose for elderly individuals and the high frequency of breakthrough infections with Omicron compared to previous variants. Serum neutralizing activity was tested in a well-characterized pseudovirus neutralization test (pVNT) (Refs. 3-5) by determining 50% pseudovirus neutralization ($pVN_{50}$) geometric mean titers (GMTs) with pseudoviruses bearing the S glycoproteins of the SARS-CoV-2 wild-type strain or Omicron BA.4/BA.5 (BA.4 and BA.5 are identical in their S glycoprotein sequence), BA.4.6/BF.7 (BA.4.6 and BF.7 are identical in their S glycoprotein sequence), or BA.2.75.

In the $BNT162b2^3$, $BNT162b2^4$, and $mRNA\text{-}Vax^3$+BA.1 cohorts, $pVN_5o$ titers against Omicron BA.4/BA.5 were significantly lower (GMTs reduced 5 to 6-fold) than titers against the wild-type strain (FIG. 59(A)). The reduction of BA.4/BA.5 neutralization in the $mRNA\text{-}Vax^3$+BA.2 and $mRNA\text{-}Vax^3$+BA.4/BA.5 cohorts was also statistically significant yet less pronounced (GMTs 2 to 3-fold lower compared to wild-type) than in the other cohorts. $pVN_5o$ titers against Omicron BA.4.6/BF.7 were further significantly reduced compared to BA.4/BA.5 in $mRNA\text{-}Vax^3$+BA.2 (GMT 239 vs. 386; $P<0.05$). A considerable but statistically non-significant reduction in BA.4.6/BF.7 neutralization relative to BA.4/BA.5 was also seen in $BNT162b2^4$ (GMT 55 vs. 121). For all other cohorts, Omicron BA.4.6/BF.7 GMTs were largely comparable to those against Omicron BA.4/BA.5 and titers in the $mRNA\text{-}Vax^3$+BA.4/BA.5 were the most robust (GMT 443). In $mRNA\text{-}Vax^3$+BA.4/BA.5, titers against BA.2.75 were reduced 1.8-fold compared to BA.4/BA.5 (GMT 295 vs. 521), while neutralizing GMTs against BA.2.75 were even increased 2-fold compared to those against BA.4/BA.5 in $mRNA\text{-}Vax^3$+BA.1 (GMT 525 vs. 263). Titers against BA.2.75 were comparable to those against BA.4/5 in the other cohorts.

To allow for assessment of neutralization breadth irrespective of the magnitude of antibody titers, the Omicron sublineage $pVN_{50}$ GMTs were normalized against the wild-type strain. GMT ratios for all Omicron subvariant pseudoviruses were comparable in the $BNT162b2^3$ and $BNT162b2^4$ cohorts (ratios 50.22 for all pseudoviruses, FIG. 59(B)), indicating that a fourth dose of BNT162b2 did not improve cross-neutralization of the tested subvariants despite a slight overall increase in antibody titers. Cross-neutralization of BA.4/BA.5 and BA.4.6/BF.7 were significantly ($p<0.05$) stronger in sera from $mRNA\text{-}Vax^3$+BA.2 compared to $BNT162b2^3$ (GMT ratios 0.37 vs 0.17 for BA.4/BA.5, and 0.23 vs 0.12 for BA.4.6/BF.7). The GMT ratios were even higher in the $mRNA\text{-}Vax^3$+BA.4/BA.5 cohort for both the BA.4/BA.5 pseudovirus (GMT ratio 0.48, $p<0.01$ versus $BNT162b2^3$) and the BA.4.6/BF.7 pseudovirus (0.41, $p<0.0001$). Cross-neutralization of the Omicron BA.2.75 pseudovirus was broadly comparable in most cohorts, with a significant ($p<0.05$) increase seen only in $mRNA\text{-}Vax^3$+BA.1 compared to $BNT162b2^3$.

The finding that neutralizing activity against Omicron BA.4.6/BF.7 is further reduced compared to BA.4/BA.5 in sera of vaccinated individuals and BA.2 convalescents suggests that the R346T alteration mediates further escape from neutralizing antibodies in polyclonal sera. Convergent evolution of the RBD at this site in Omicron BA.4.6, BF.7, and additional currently less prevalent strains (Ref. 1) indicates that the resulting immune escape may confer considerable growth advantage. The findings summarized here indicate that Omicron BA.4/BA.5 breakthrough infection refocuses neutralizing antibody responses to partially restore BA.4.6/BF.7 neutralization. A similar cross-neutralization pattern of the Omicron lineage in BA.4/BA.5 breakthrough infected humans and in mice boosted with an Omicron BA.4/5-adapted vaccine has also been observed, as demonstrated in Example 18. Hence, such findings provide evidence supporting that Omicron BA.4/5-adapted vaccine boosters can also elicit relevant neutralizing antibody responses against BA.4.6/BF.7 in humans.

The observation that cross-neutralization of Omicron BA.2.75 is broadly comparable to that of BA.4/5 is consistent with previous reports (Refs. 2, 6, and 7). Without wishing to be bound by a particular theory, this observation suggests that the growth advantage of BA.2.75 over BA.5 may be related to factors other than immune evasion. For example, in some embodiments, minor differences in the susceptibility of Omicron BA.2.75 and BA.4/BA.5 to neutralization by BA.1 and BA.4/BA.5 convalescent sera may point towards amino acid alterations with a potential context-dependent role in immune evasion.

The investigation summarized in the present Example focused on neutralization of the new Omicron sublineages BA.4.6/BF.7, and BA.2.75, as these sublineages could potentially displace BA.5 in the future according to their current trajectory. The finding that Omicron breakthrough infection is associated with enhanced cross-neutralization of the new sublineages is consistent with the data provided in the previous Examples, showing enhanced neutralization breadth, including against earlier Omicron sublineages and previous SARS-CoV-2 VOCs. Together these findings show that Omicron BA.4/BA.5 breakthrough infection is associated with the broadest neutralization against all variants, including Omicron sublineages, providing evidence supporting that vaccination with RNA encoding a SARS-CoV-2 S protein comprising mutations characteristic of the BA.4/5 variant can produce a broad neutralization response.

Materials and Methods

Study Design, Recruitment of Participants and Sample Collection

The objective of this study was to investigate the cross-neutralizing activity of five different panels of sera against Omicron BA.4.6/BF.7 and BA.2.75 sub-lineages compared to SARS-CoV-2 wild-type and Omicron BA.4/BA.5. Neutralizing activity was assessed in immune sera from (i) SARS-CoV-2-naïve triple-BNT162b2-vaccinated younger adult individuals (BNT162b2$^3$), (ii) SARS-CoV-2-naïve quadruple-BNT162b2-vaccinated older adult individuals (BNT162b2$^4$), and triple-mRNA (BNT162b2/mRNA-1273)-vaccinated individuals with a confirmed subsequent SARS-CoV-2 breakthrough infection which either occurred (iii) in a period of Omicron BA.1 lineage-dominance (November 2021 to mid-January 2022; mRNA-Vax$^3$+BA.1), (iv) in a period of Omicron BA.2 lineage-dominance (March to May 2022; mRNA-Vax$^3$+BA.2), or (v) in a period of Omicron BA.4/BA.5 lineage-dominance in Germany (mid-June to mid-July 2022; mRNA-Vax$^3$+BA.4/5). Serum neutralizing capability was characterized using pseudovirus neutralization assays. SARS-CoV-2 wild-type and Omicron BA.4/BA.5 neutralization data for cohorts BNT162b2$^3$, mRNA-Vax$^3$+BA.1, mRNA-Vax$^3$+BA.2, mRNA-Vax$^3$+BA.4/5 were previously published.

Participants from the mRNA-Vax$^3$+Omi BA.1, mRNA-Vax$^3$+Omi BA.2, and mRNA-Vax$^3$+BA.4/5 cohorts were recruited from University Hospital, Goethe University Frankfurt as part of a non-interventional study (protocol approved by the Ethics Board of the University Hospital [No. 2021-560]) researching patients that had experienced Omicron breakthrough infection following vaccination for COVID-19. Individuals from the BNT162b2$^3$ and BNT162b2$^4$ cohort provided informed consent as part of their participation in the Phase 2 trial BNT162-17 (NCT05004181) and BNT162-16 Substudy F (NCT04955626), respectively. All participants had no documented history of SARS-CoV-2 infection prior to vaccination. Participants were free of symptoms at the time of blood collection.

Serum was isolated by centrifugation of drawn blood at 2000×g for 10 minutes and cryopreserved until use.

A recombinant replication-deficient vesicular stomatitis virus (VSV) vector that encodes green fluorescent protein (GFP) and luciferase instead of the VSV-glycoprotein (VSV-G) was pseudotyped with SARS-CoV-1 S glycoprotein (UniProt Ref: P59594) or with SARS-CoV-2 S glycoprotein derived from either the wild-type strain (Wuhan-Hu-1, NCBI Ref: 43740568), the Omicron BA.4/BA.5 variant (alterations: T19I, Δ24-26, A27S, Δ69/70, G142D, V213G, G339D, S371F, S373P, S375F, T376A, D405N, R408S, K417N, N440K, L452R, 5477N, T478K, E484A, F486V, Q498R, N501Y, Y505H, D614G, H655Y, N679K, P681H, N764K, D796Y, Q954H, N969K), the Omicron BA.4.6/BF.7 variant (alterations: T19I, Δ24-26, A27S, Δ69/70, G142D, V213G, G339D, R346T, S371F, S373P, S375F, T376A, D405N, R408S, K417N, N440K, L452R, S477N, T478K, E484A, F486V, Q498R, N501Y, Y505H, D614G, H655Y, N679K, P681H, N764K, D796Y, Q954H, N969K), and the Omicron BA.2.75 variant (alterations: T19I, Δ24-26, A27S, G142D, K147E, W152R, F157L, I210V, V213G, G257S, G339H, S371F, S373P, S375F, T376A, D405N, R408S, K417N, N440K, G446S, N460K, S477N, T478K, E484A, Q498R, N501Y, Y505H, D614G, H655Y, N679K, P681H, N764K, D796Y, Q954H, N969K) according to published pseudotyping protocols (Berger Rentsch, Marianne, and Gert Zimmer. "A vesicular stomatitis virus replicon-based bioassay for the rapid and sensitive determination of multi-species type I interferon." PloS one 6.10 (2011): e25858). A diagram of SARS-CoV-2 S glycoprotein alterations is shown in FIG. 62 and a separate alignment of S glycoprotein alterations in Omicron VOCs is displayed in FIG. 60.

In brief, HEK293T/17 monolayers (ATCC® CRL-11268™) cultured in Dulbecco's modified Eagle's medium (DMEM) with GlutaMAX™ (Gibco) supplemented with 10% heat-inactivated fetal bovine serum (FBS [Sigma-Aldrich]) (referred to as medium) were transfected with Sanger sequencing-verified variant-specific SARS-CoV-2 S expression plasmid with Lipofectamine LTX (Life Technologies) following the manufacturer's instructions. At 24 hours after transfection, the cells were infected at a multiplicity of infection (MOI) of three with VSV-G complemented VSVΔG vector. After incubation for 2 hours at 37° C. with 7.5% $CO_2$, cells were washed twice with phosphate buffered saline (PBS) before medium supplemented with anti-VSV-G antibody (clone 8G5F11, Kerafast Inc.) was added to neutralize residual VSV-G-complemented input virus. VSV-SARS-CoV-2-S pseudotype-containing medium was harvested 20 hours after inoculation, passed through a 0.2 μm filter (Nalgene) and stored at −80° C. The pseudovirus batches were titrated on Vero 76 cells (ATCC® CRL-1587™) cultured in medium. The relative luciferase units induced by a defined volume of a SARS-CoV-2 wild-type strain S glycoprotein pseudovirus reference batch previously described in Muik et al., 2021 (Muik, Alexander, et al. "Neutralization of SARS-CoV-2 lineage B. 1.1. 7 pseudovirus by BNT162b2 vaccine-elicited human sera." Science 371.6534 (2021): 1152-1153), that corresponds to an infectious titer of 200 transducing units (TU) per mL, was used as a comparator. Input volumes for the SARS-CoV-2 variant pseudovirus batches were calculated to normalize the infectious titer based on the relative luciferase units relative to the reference.

Pseudovirus Neutralization Assay

Vero 76 cells were seeded in 96-well white, flat-bottom plates (Thermo Fisher Scientific®) at 40,000 cells/well in medium 4 hours prior to the assay and cultured at 37° C. with 7.5% $CO_2$. Human serum samples were 2-fold serially diluted in medium with dilutions ranging from 1:10 to 1:10,240. VSV-SARS-CoV-2-S particles were diluted in medium to obtain 200 TU in the assay. Serum dilutions were mixed 1:1 with pseudovirus (n=2 technical replicates per serum per pseudovirus) for 30 minutes at room temperature before being added to Vero 76 cell monolayers and incubated at 37° C. with 7.5% $CO_2$ for 24 hours. Supernatants were removed and the cells were lysed with luciferase reagent (Promega). Luminescence was recorded on a CLARIOstar® Plus microplate reader (BMG Labtech), and neutralization titers were calculated as the reciprocal of the highest serum dilution that still resulted in 50% reduction in luminescence. Results for all pseudovirus neutralization experiments were expressed as geometric mean titers (GMT) of duplicates. If no neutralization was observed, an arbitrary titer value of half of the limit of detection [LOD] was reported.

Statistical analysis The statistical method of aggregation used for analysis of antibody titers was the geometric mean and for the ratio of SARS-CoV-2 VOC titer and wild-type strain titer the geometric mean and the corresponding 95% confidence interval. The use of the geometric mean accounts for the non-normal distribution of antibody titers, which span several orders of magnitude. The Friedman test with Dunn's correction for multiple comparisons was used to conduct pairwise signed-rank tests of group geometric mean neutralizing antibody titers with a common control group. The Kruskal-Wallis test with Dunn's correction for multiple comparisons was used to conduct unpaired signed-rank tests of group GMT ratios. All statistical analyses were performed using GraphPad Prism software version 9.

References Cited in Example 19

1. F. Jian, Y. Yu, W. Song, A. Yisimayi, L. Yu, Y. Gao, N. Zhang, Y. Wang, F. Shao, X. Hao, Y. Xu, R. Jin, Y. Wang, X. S. Xie, Y. Cao, Further humoral immunity evasion of emerging SARS-CoV-2 BA.4 and BA.5 subvariants. *Lancet Infect Dis*, (2022).
2. Q. Wang, S. Iketani, Z. Li, Y. Guo, A. Y. Yeh, M. Liu, J. Yu, Z. Sheng, Y. Huang, L. Liu, D. D. Ho, Antigenic characterization of the SARS-CoV-2 Omicron subvariant BA.2.75. *Cell Host Microbe*, (2022).
3. A. Muik, A. K. Wallisch, B. Sanger, K. A. Swanson, J. Muhl, W. Chen, H. Cai, D. Maurus, R. Sarkar, O. Tureci, P. R. Dormitzer, U. Sahin, Neutralization of SARS-CoV-2 lineage B.1.1.7 pseudovirus by BNT162b2 vaccine-elicited human sera. *Science* 371, 1152-1153 (2021).
4. A. Muik, B. G. Lui, A. K. Wallisch, M. Bacher, J. Muhl, J. Reinholz, O. Ozhelvaci, N. Beckmann, R. C. Guimil Garcia, A. Poran, S. Shpyro, A. Finlayson, H. Cai, Q. Yang, K. A. Swanson, O. Tureci, U. Sahin, Neutralization of SARS-CoV-2 Omicron by BNT162b2 mRNA vaccine-elicited human sera. *Science* 375, 678-680 (2022).
5. A. Muik, B. G. Lui, M. Bacher, A. K. Wallisch, A. Toker, A. Finlayson, K. Kruger, O. Ozhelvaci, K. Grikscheit, S. Hoehl, S. Ciesek, O. Tureci, U. Sahin, Omicron BA.2 breakthrough infection enhances cross-neutralization of BA.2.12.1 and BA.4/BA.5. *bioRxiv*, (2022).
6. X. Shen, S. Chalkias, J. Feng, X. Chen, H. Zhou, J. C. Marshall, B. Girard, J. E. Tomassini, A. Aunins, R. Das, D. C. Montefiori, Neutralization of SARS-CoV-2 Omicron BA.2.75 after mRNA-1273 Vaccination. *N Engl J Med* 387, 1234-1236 (2022).
7. H. Gruell, K. Vanshylla, P. Tober-Lau, D. Hillus, L. E. Sander, F. Kurth, F. Klein, Neutralisation sensitivity of the SARS-CoV-2 omicron BA.2.75 sublineage. *Lancet Infect Dis* 22, 1422-1423 (2022).
8. WHO Technical Advisory Group on SARS-CoV-2 Virus Evolution (TAG-VE): Classification of Omicron (B.1.1.259): SARS-CoV-2 Variant of Concern. (2021).
9. WHO Headquarters (HQ), WHO Health Emergencies Programme, Enhancing Response to Omicron SARS-CoV-2 variant: Technical brief and priority actions for Member States. (2022).
10. M. Hoffmann et al., The Omicron variant is highly resistant against antibody-mediated neutralization: Implications for control of the COVID-19 pandemic. Cell 185, 447-456 e411 (2022).
11. V. Servellita et al., Neutralizing immunity in vaccine breakthrough infections from the SARS-CoV-2 Omicron and Delta variants. Cell 185, 1539-1548 e1535 (2022).
12. C. Kurhade et al., Neutralization of Omicron BA.1, BA.2, and BA.3 SARS-CoV-2 by 3 doses of BNT162b2 vaccine. Nat Commun 13, 3602 (2022).
13. Y. Cao et al., Omicron escapes the majority of existing SARS-CoV-2 neutralizing antibodies. Nature 602, 657-663 (2022).
14. S. Xia, L. Wang, Y. Zhu, L. Lu, S. Jiang, Origin, virological features, immune evasion and intervention of SARS-CoV-2 Omicron sublineages. Signal Transduct Target Ther 7, 241 (2022).
15. H. Gruell et al., SARS-CoV-2 Omicron sublineages exhibit distinct antibody escape patterns. Cell Host Microbe, (2022).
16. Y. Fan et al., SARS-CoV-2 Omicron variant: recent progress and future perspectives. Signal Transduct Target Ther 7, 141 (2022).
17. H. Tegally et al., Emergence of SARS-CoV-2 Omicron lineages BA.4 and BA.5 in South Africa. Nat Med, (2022).
18. European Centre for Disease Prevention and Control, Weekly COVID-19 country overview—Country overview report: week 31 2022 (2022).
19. J. Hadfield et al., Nextstrain: real-time tracking of pathogen evolution nextstrain_org/ncov/gisaid. Bioinformatics 34, 4121-4123 (2018).
20. Centers for Disease Control and Prevention. COVID Data Tracker. Atlanta, GA: US Department of Health and Human Services, CDC; 2022, August 12. covid_cdc_gov/covid-data-tracker. (2022).
21. A. Z. Mykytyn et al., Antigenic cartography of SARS-CoV-2 reveals that Omicron BA.1 and BA.2 are antigenically distinct. Sci Immunol, eabq4450 (2022).
22. P. Wang et al., Antibody resistance of SARS-CoV-2 variants B.1.351 and B.1.1.7. Nature 593, 130-135 (2021).
23. J. Quandt et al., Omicron BA.1 breakthrough infection drives cross-variant neutralization and memory B cell formation against conserved epitopes. Sci Immunol, eabq2427 (2022).
24. C. I. Kaku et al., Recall of pre-existing cross-reactive B cell memory following Omicron BA.1 breakthrough infection. Sci Immunol, eabq3511 (2022).
25. Y. Cao et al., BA.2.12.1, BA.4 and BA.5 escape antibodies elicited by Omicron infection. Nature, (2022).
26. P. Arora et al., Augmented neutralisation resistance of emerging omicron subvariants BA.2.12.1, BA.4, and BA.5. Lancet Infect Dis, (2022).

27. Q. Wang et al., Antibody evasion by SARS-CoV-2 Omicron subvariants BA.2.12.1, BA.4, & BA.5. Nature, (2022).
28. A. Muik et al., Omicron BA.2 breakthrough infection enhances cross-neutralization of BA.2.12.1 and BA.4/BA.5. bioRxiv, (2022).
29. P. Du et al., A bivalent vaccine containing D614G and BA.1 spike trimer proteins or a BA.1 spike trimer protein booster shows broad neutralizing immunity. J Med Virol 94, 4287-4293 (2022).
30. A. R. Branche et al., SARS-CoV-2 Variant Vaccine Boosters Trial: Preliminary Analyses. medRxiv, (2022).
31. A. Muik et al., Neutralization of SARS-CoV-2 lineage B.1.1.7 pseudovirus by BNT162b2 vaccine-elicited human sera. Science 371, 1152-1153 (2021).
32. A. Muik et al., Neutralization of SARS-CoV-2 Omicron by BNT162b2 mRNA vaccine-elicited human sera. Science 375, 678-680 (2022).
33. C. W. Tan et al., Pan-Sarbecovirus Neutralizing Antibodies in BNT162b2-Immunized SARS-CoV-1 Survivors. N Engl J Med 385, 1401-1406 (2021).
34. S. I. Richardson et al., SARS-CoV-2 BA.4 infection triggers more cross-reactive neutralizing antibodies than BA.1. bioRxiv, (2022).
35. S. Y. Tartof et al., Immunocompromise and durability of BNT162b2 vaccine against severe outcomes due to omicron and delta variants. Lancet Respir Med 10, e61-e62 (2022).
36. N. Andrews et al., Covid-19 Vaccine Effectiveness against the Omicron (8.1.1.529) Variant. N Engl J Med 386, 1532-1546 (2022).
37. F. P. Polack et al., Safety and Efficacy of the BNT162b2 mRNA Covid-19 Vaccine. N Engl J Med 383, 2603-2615 (2020).
38. W. Dejnirattisai et al., SARS-CoV-2 Omicron-B.1.1.529 leads to widespread escape from neutralizing antibody responses. Cell 185, 467-484 e415 (2022).
39. A. B. Vogel et al., BNT162b vaccines protect rhesus macaques from SARS-CoV-2. Nature 592, 283-289 (2021).
40. A. G. Orlandini von Niessen et al., Improving mRNA-Based Therapeutic Gene Delivery by Expression-Augmenting 3' UTRs Identified by Cellular Library Screening. Mol Ther 27, 824-836 (2019).
41. S. Holtkamp et al., Modification of antigen-encoding RNA increases stability, translational efficacy, and T-cell stimulatory capacity of dendritic cells. Blood 108, 4009-4017 (2006).
42. E. Grudzien-Nogalska et al., Synthetic mRNAs with superior translation and stability properties. Methods Mol Biol 969, 55-72 (2013).
43. S. Berensmeier, Magnetic particles for the separation and purification of nucleic acids. Appl Microbiol Biotechnol 73, 495-504 (2006).

Example 20: Clinical Trial Results Confirming that a Booster Dose that Includes Omicron BA.4/5-Specific Vaccine can Induce a Strong Immune Response Against Omicron BA.4/5 Variants The present Example provides clinical trial data confirming that a BA.4/5-specific vaccine (e.g., a bivalent RNA vaccine comprising a first RNA encoding a SARS-CoV-2 S protein of a Wuhan strain and a second RNA encoding a SARS-CoV-2 S protein comprising one or more mutations characteristic of a BA.4/5 Omicron variant as described herein) can induce a strong immune response in subjects. Specifically, the present Example provides data demonstrating that such an RNA vaccine can induce an immune response (e.g., neutralization antibody titers) that are higher against a BA.4/5 variant than an immune response induced by an RNA vaccine encoding a SARS-CoV-2 S protein of a Wuhan strain.

These results confirm the insights provided by the BA.4/5-breakthrough infection data and mouse experiment data described in the previous Examples, with respect to the benefits of administering a BA.4/5-specific vaccine (e.g., ones described herein).

The present Example provides immune response data from a Phase 2/3 clinical trial in which a 30-μg booster dose of an Omicron BA.4/BA.5-adapted bivalent COVID-19 vaccine (comprising 15 μg of RNA encoding a full length SARS-CoV-2 S protein of a Wuhan variant, for example, in some embodiments an RNA comprising a nucleotide sequence that is at least 95% or higher (including and up to 100%) identical to SEQ ID NO: 20 (e.g., in some embodiments BNT 162b2), and 15 μg of RNA encoding a full length SARS-CoV-2 S protein comprising one or more mutations characteristic of an Omicron BA.4/BA.5, for example, in some embodiments, an RNA comprising a nucleotide sequence that is at least 95% or higher (including and up to 100%) identical to SEQ ID NO:72) was administered to individuals 18 to 55 years of age (n=38) and those older than 55 years of age (n=36) who had previously received three doses of an RNA vaccine encoding a SARS-CoV-2 S protein of a Wuhan strain (e.g., BNT162b2). A comparator group of participants older than 55 years of age (n=40) were administered a 30-μg booster dose (as a fourth dose) of an RNA vaccine encoding a SARS-CoV-2 S protein of a Wuhan strain. In the present Example, subjects who were administered a bivalent vaccine as described herein received their last dose of the vaccine that encodes a SARS-CoV-2 S protein of a Wuhan strain on an average of 11 months prior to administration of a bivalent vaccine, whereas subjects who were administered an RNA vaccine encoding a SARS-CoV-2 protein of a Wuhan strain, e.g., BNT162b2 (as a fourth dose) received their third dose on an average of 6 months previously. Despite this difference, pre-booster antibody titers were similar in both groups. Both groups included subjects with evidence of prior SARS-CoV-2 infection and subjects without prior SARS-CoV-2 infection.

Among subjects administered an Omicron BA.4/BA.5-specific bivalent vaccine, a substantially higher increase in Omicron BA.4/BA.5-neutralizing antibody titers was observed as compared to pre-booster levels. For individuals 18 to 55 years of age administered a bivalent vaccine, the geometric mean titer (GMT) against Omicron BA.4/BA.5 was about 600 (e.g., 606), which was a 9.5-fold rise (95% Cl: 6.7, 13.6) from pre-booster levels. For individuals older than 55 years administered a BA.4/5 bivalent vaccine, the GMT was about 900 (e.g., 896), which was a 13.2-fold rise (95% Cl: 8.0, 21.6) from pre-booster levels. By contrast, participants over 55 years of age who received a 30-μg booster dose of an RNA vaccine encoding a SARS-CoV-2 S protein of a Wuhan strain, a lower neutralizing antibody response was observed against Omicron BA.4/BA.5 measured 1-month post booster. For these participants, the GMT was about 230 (e.g., 236), representing a 2.9-fold rise (95% Cl: 2.1, 3.9) from pre-booster levels. The safety profile observed in the clinical trial for the bivalent vaccine was favorable, and consistent with BNT162b2.

In addition, when examining populations of subjects with and without evidence of a prior SARS-CoV-2 infection, an increase in neutralizing antibodies against Omicron BA.4/BA.5 following a booster dose of a bivalent vaccine was observed in both populations, demonstrating that a BA.4/5-bivalent vaccine can improve protection in subjects that receive such a vaccine, regardless of prior infection status.

Example 21: Improved Neutralization of Omicron BA.4/5, BA.4.6, BA.2.75.2, BQ.1.1, and XBB.1 with a Bivalent BA.4/5 Vaccine The present Example provides further data demonstrating that a bivalent RNA vaccine comprising RNA encoding a SARS-CoV-2 S protein of a Wuhan strain and RNA encoding a SARS-CoV-2 S protein comprising one or more mutations characteristic of a BA.4/5 Omicron variant (e.g., a bivalent vaccine described herein) can provide an improved immune response as compared to a monovalent RNA vaccine encoding a SARS-CoV-2 S protein of a Wuhan strain. For example, in some embodiments, such an improved immune response includes increased neutralization titers against one or more, including, two or more, three or more, four or more, five or more, six or more, SARS-CoV-2 variants of concern. In some embodiments, such an improved immune response includes increased neutralization titers against one or more, including, two or more, three or more, four or more, five or more, six or more, Omicron variants of concern. In some embodiments, such an improved immune response includes increased neutralization titers against a larger number of Omicron variants of concern, as compared to that observed with a monovalent RNA vaccine encoding a SARS-CoV-2 S protein of a Wuhan strain.

In particular, the present Example provides data demonstrating that such a bivalent vaccine can induce an improved immune response (e.g., in some embodiments higher neutralizing responses) against BA.5-derived sublineages (e.g., BA.4.6, BQ.1.1, and XBB.1) and BA.2-derived sublineages (e.g., BA.2.75.2) as compared to a monovalent RNA vaccine encoding a SARS-CoV-2 S protein of a Wuhan strain when administered as a 4th dose booster. The present Example also provides data demonstrating that subjects with SARS-CoV-2 infection history (e.g., subjects with previous or current SARS-CoV-2 infection) can develop higher immune responses (e.g., higher neutralizing titers) after administration of a $4^{th}$ booster dose (e.g., of a monovalent or a bivalent vaccine) relative to subjects who have not been infected with SARS-COV-2. The present Example demonstrates that a BA.4/5 bivalent vaccine can induce an improved immune response (e.g., improved neutralizing response) as compared to a monovalent RNA vaccine encoding a SARS-CoV-2 S protein of a Wuhan strain regardless of SARS-CoV-2 infection history. The present Example also provides data demonstrating that improvements in immune response against certain Omicron sublineages (e.g., Omicron sublineages tested herein) provided by a BA.4/5 bivalent vaccine relative to a Wuhan monovalent vaccine are greater for subjects who have not been previously infected with SARS-CoV-2 as compared to subjects who have been previously infected with SARS-CoV-2.

Severe acute respiratory syndrome coronavirus 2 (SARS-CoV-2) Omicron variant has continued to evolve globally into many sublineages since its emergence in November 2021. To mitigate the ongoing Omicron pandemic, the U.S. FDA authorized emergency use of a bivalent BA.4/5-vaccine in September 2022. The U.S. FDA authorized bivalent vaccine contains two mRNAs: one encoding original (Wuhan) SARS-CoV-2 Spike protein (BNT162b2) and another encoding a SARS-CoV-2 S protein comprising mutations characteristic of an Omicron BA.4/5 variant (comprising in some embodiments an amino acid sequence of SEQ ID NO: 69, and in some embodiments SEQ ID NO: 72). Since U.S. FDA approval, new Omicron BA.2- and BA.5-descendent sublineages (e.g., BA.4.6, BA.2.75.2, BQ.1.1, and XBB.1) have emerged and become prevalent (covid_cdc_gov/covid-data-tracker/#variant-proportions). Although early epidemiological data suggest no increase in disease severity, these new sublineages have accumulated additional spike mutations that could further evade vaccine- and/or infection-elicited antibody neutralization (Refs. 2-4).

The present Example describes data from a clinical trial in which neutralization titers against Omicron sublineages BA.4/5, BA.4.6, BA.2.75.2, BQ.1.1, and XBB.1 were measured in sera collected from subjects administered as a fourth dose (a) a 30-μg booster dose of an Omicron BA.4/BA.5-adapted bivalent COVID-19 vaccine, which in some embodiments comprises 15 μg of RNA comprising a nucleotide sequence that is at least 95% (including and up to 100%) identical to SEQ ID NO: 20, and 15 μg of RNA encoding a full length SARS-CoV-2 S protein comprising one or more mutations characteristic of an Omicron BA.4/BA.5 variant and comprising a nucleotide sequence that is at least 95% (including and up to 100%) identical to SEQ ID NO:72. In the present Example, an Omicron BA.4/BA.5-adapted bivalent COVID-19 vaccine comprising (i) 15 μg of RNA comprising the sequence of SEQ ID NO: 20 and (ii) 15 μg of RNA comprising the sequence of SEQ ID NO: 72 was administered to the tested subjects.

Participants >55-years-old who had previously received 3 doses of a vaccine that delivered a SARS-CoV-2 S protein of a Wuhan strain (in the present Example, subjects had previously received three 30-μg doses of BNT162b2) were administered a 4th booster dose comprising 30-μg of monovalent BNT162b2 at ~6.6-months-post-dose-3 or 30-μg of a bivalent vaccine (15-μg BNT162b2 plus 15-μg BA.4/5) at ~11-months-post-dose-3. Serum was collected on the day dose 4 was administered (Pre serum samples) and at 1-month-post-dose-4 (1MPD4 serum samples). All participants were screened for evidence of previous and current SARS-CoV-2 infection by viral nucleocapsid antibodies and RT-PCR tests; both vaccine groups in the neutralization analysis were equally distributed among those with or without evidence of infection. For neutralization testing, the complete spike gene from Omicron BA.4/5 (BA.4 and BA.5 encode an identical spike sequence), BA.2.75.2, BQ.1.1, or XBB.1 was cloned into the backbone of fluorescent reporter USA-WA1/2020 SARS-CoV-2 (a strain isolated in January 2020, see Ref. 5). The resulting wild-type-(WT), BA.4/5-, BA.2.75.2-, BQ.1.1-, and XBB.1-spike mNG USA-WA1/2020 were used to measure 50% fluorescent focus reduction neutralization titers ($FFRNT_{50}$) for each serum sample collected.

For all participants (including subjects with and without evidence of SARS-CoV-2 infection), a $4^{th}$ dose of monovalent BNT162b2 vaccine was found to induce a 3.0×, 2.9×, 2.3×, 2.1×, 1.9×, and 1.5× geometric mean neutralizing titer fold rise (GMFR) against Wuhan, BA.4/5, BA.4.6, BA.2.75.2, BQ.1.1, and XBB.1, respectively; a bivalent vaccine was found to induce 5.8×, 13.0×, 11.1×, 6.7×, 8.7×, and 4.8×GMFRs (FIG. 63(A)). For individuals without SARS-CoV-2 infection history, BNT162b2 induced 4.4×, 3.0×, 2.6×, 2.1×, 1.5×, and 1.3×GMFRs, respectively; the bivalent vaccine induced 9.9×, 25.9×, 21.2×, 8.6×, 13.0×, and 4.6×GMFRs (FIG. 63(B)). For individuals with previous SARS-CoV-2 infection, BNT162b2 induced 2.0×, 2.8×, 2.1×, 2.1×, 2.2×, and 1.8×GMFRs, respectively; the bivalent vaccine induced 3.5×, 6.7×, 6.2×, 5.3×, 6.3×, and 4.9× GMFRs (FIG. 63C). Despite different intervals between doses 3 and 4, pre-dose-4 neutralizing titers were similar in the monovalent and bivalent vaccine groups in the all participants and the without infection groups.

The present Example provides at least three findings. First, a bivalent BA.4/5 vaccine consistently elicited higher neutralizing responses against BA.5-derived sublineages (BA.4.6, BQ.1.1, and XBB.1) and BA.2-derived sublineage (BA.2.75.2) than a monovalent RNA vaccine encoding a SARS-CoV-2 S protein when administered as a 4th dose booster. Second, individuals with evidence of previous or current SARS-CoV-2 infection developed higher neutralizing titers than those without infection after a 4th dose booster. The improved neutralizing responses induced by a bivalent vaccine was observed regardless of SARS-CoV-2 infection history. Third, for each tested Omicron sublineage, the difference between BNT162b2- and bivalent-GMFR was greater for sera without previous infection than those with previous infection.

Among all Omicron sublineages, BA.2.75.2, BQ.1.1, and XBB.1 exhibited the greatest evasion of vaccine-elicited neutralization; however, neutralizing titers following a bivalent booster were several fold higher than those following a monovalent RNA encoding a SARS-CoV-2 S protein of a Wuhan strain. These data demonstrate that a bivalent vaccine is more immunogenic against circulating Omicron sublineages and underscore the importance of monitoring real-world effectiveness.

Methods

Cells

Vero E6 (ATCC® CRL-1586) purchased from the American Type Culture Collection (ATCC, Bethesda, MD) and Vero E6 cells expressing TMPRSS2 purchased from SEKISUI XenoTech, LLC were maintained in a high-glucose Dulbecco's modified Eagle's medium (DMEM) containing 10% fetal bovine serum (FBS; HyClone Laboratories, South Logan, UT) and 1% penicillin/streptomycin at 37° C. with 5% C02. Culture media and antibiotics were purchased from Thermo Fisher Scientific® (Waltham, MA). The cell line was tested negative for *Mycoplasma.*

Human Serum

In participants >55 years of age who previously received three 30-μg BNT162b2 doses, serum samples were collected just prior to and 1 month post-boost with a 4th dose booster of monovalent original 30-μg BNT162b2 or 30-μg bivalent BA.4/BA.5 vaccine (15 μg original with 15 μg BA.4/BA.5). The protocol and informed consent were approved by institutional review boards for each of the investigational centers participating in the study. The study was conducted in compliance with all International Council for Harmonisation Good Clinical Practice guidelines and the ethical principles of the Declaration of Helsinki. The median time between dose-3 and -4 was 6.3 and 11.3 months for BNT162b2 and the bivalent BA.4/5 vaccine, respectively. All participants were screened by SARS-CoV-2 nucleocapsid Ig serological test for preexisting SARS-CoV-2 or RT-PCR for existing infection. The subset of participant's sera (approximately 40 per vaccine group) selected for neutralization testing were equally distributed between those with and without evidence of infection by either test. Human sera were heat-inactivated at 56° C. for 30 min before the neutralization test.

Recombinant Omicron Sublineages-FP SARS CoV-2 Viruses

Recombinant Omicron sublineage BA.4/5-, BA.4.6-, BA.2.75.2-, BQ.1.1-, and XBB.1-spike fluorescent protein (FP) SARS-CoV-2s was constructed by engineering the complete spike gene from the indicated variants into an infectious cDNA clone of mNG USA-WA1/2020 and reported previously (Refs. 6-10). Viruses were rescued post 2-3 days after electroporation and served as P0 stock. P0 stock was further passaged once on Vero E6 cells to produce P1 stock. The spike gene was sequenced from all P1 stock viruses to ensure no undesired mutation. The infectious titer of the P1 virus was quantified by fluorescent focus assay on Vero E6 cells. The P1 virus was used for the neutralization test.

Fluorescent Focus Reduction Neutralization Test (FFRNT)

Neutralization titers of human sera were measured by FFRNT using the USA-WA1/2020-, BA.4/5, BA.4.6-, BA.2.75.2-, BQ.1.1- and XBB.1-spike FP SARS-CoV-2s. All sera were tested sequentially, USA-WA1/2020 and BA.4/5 followed by the remaining Omicron sublineages. The details of the FFRNT protocol were reported previously (see Refs. 6 and 10-13). Briefly, $2.5\times10^4$ Vero E6 cells per well were seeded in 96-well plates (Greiner Bio-One™). The cells were incubated overnight. On the next day, each serum was 2-fold serially diluted in the culture medium with the first dilution of 1:20 (final dilution range of 1:20 to 1:20,480). The diluted serum was incubated with 100-150 FFUs of FP SARS-CoV-2 at 37° C. for 1 h, after which the serum virus mixtures were loaded onto the pre-seeded Vero E6 cell monolayer in 96-well plates. After 1 h infection, the inoculum was removed and 100 μl of overlay medium (supplemented with 0.8% methylcellulose) was added to each well. After incubating the plates at 37° C. for 16 h, raw images of FP foci were acquired using Cytation™ 7 (BioTek) armed with 2.5× FL Zeiss objective with a wide-field of view and processed using the Gene 5 software settings (GFP [469,525] threshold 4000, object selection size 50-1000 μm). The foci in each well were counted and normalized to the non-serum-treated controls to calculate the relative infectivities. The $FFRNT_{50}$ value was defined as the minimal serum dilution that suppressed >50% of fluorescent foci. The neutralization titer of each serum was determined in duplicate assays, and the geometric mean was taken. All attempts at replication were successful. Data were initially plotted in GraphPad Prism 9 software and assembled in Adobe Illustrator.

References Cited in Example 21 (Each Incorporated by Reference Herein in its Entirety)

1. Cele S, Jackson L, Khoury D S, et al. Omicron extensively but incompletely escapes Pfizer BNT162b2 neutralization. Nature 2022; 602(7898): 654-6.
2. Kurhade C, Zou J, Xia H, et al. Neutralization of Omicron sublineages and Deltacron SARS-CoV-2 by 3 doses of BNT162b2 vaccine or BA.1 infection. Emerg Microbes Infect 2022: 1-18.
3. Liu Z, VanBlargan L A, Bloyet L M, et al. Identification of SARS-CoV-2 spike mutations that attenuate monoclonal and serum antibody neutralization. Cell Host Microbe 2021; 29(3): 477-88 e4.
4. Davis-Gardner M E, Lai L, Wali B, et al. mRNA bivalent booster 1 enhances neutralization against BA.2.75.2 and BQ.1.1. bioRxiv 2022: doi_org/10.1101/2022_10_31_514636.

5. Muruato A E, Fontes-Garfias C R, Ren P, et al. A high-throughput neutralizing antibody assay for COVID-19 diagnosis and vaccine evaluation. Nat Commun 2020; 11(1): 4059.
6. Kurhade C, Zou J, Xia H, et al. Low neutralization of SARS-CoV-2 Omicron BA.2.75.2, BQ.1.1, and XBB.1 by 4 doses of parental mRNA vaccine or a BA.5-bivalent booster. bioRxiv 2022: 2022.10.31.514580.
7. Xie X, Muruato A, Lokugamage K G, et al. An Infectious cDNA Clone of SARS-CoV-2. Cell host & microbe 2020: 51931-3128(20)30231-6.
8. Xie X, Lokugamage K G, Zhang X, et al. Engineering SARS-CoV-2 using a reverse genetic system. Nature Protocols 2021; 16(3): 1761-84.
9. Muruato A E, Fontes-Garfias C R, Ren P, et al. A high-throughput neutralizing antibody assay for COVID-19 diagnosis and vaccine evaluation. Nat Commun 2020; 11(1): 4059.
10. Xie X, Zou J, Liu M, Ren P, Shi P Y. Neutralization of SARS-CoV-2 Omicron sublineages by 4 doses of mRNA vaccine. bioRxiv 2022.
11. Zou J, Xie X, Liu M, Shi P Y, Ren P. Neutralization Titers in Vaccinated Patients with SARS-CoV-2 Delta Breakthrough Infections. mBio 2022; 13(4): e0199622.
12. Zou J, Xia H, Xie X, et al. Neutralization against Omicron SARS-CoV-2 from previous non-Omicron infection. Nat Commun 2022; 13(1): 852.
13. Kurhade C, Zou J, Xia H, et al. Neutralization of Omicron sublineages and Deltacron SARS-CoV-2 by 3 doses of BNT162b2 vaccine or BA.1 infection. Emerg Microbes Infect 2022: 1-18.

Example 22: Distinct Cross-Neutralization of Omicron Sublineages by Vaccine-Elicited and Convalescent Immune Sera Serum samples were drawn from (i) SARS-CoV-2-naïve individuals triple-vaccinated with BNT162b2 or (ii) quadruple-vaccinated with BNT162b2, and individuals with three doses of mRNA COVID-19 vaccine (BNT162b2/mRNA-1273 homologous or heterologous regimens) who subsequently had a breakthrough infection with (iii) Omicron BA.1, (iv) Omicron BA.2 or (v) Omicron BA.4/BA.5. Breakthrough infections occurred at a time of respective variant of concern dominance (BA.1: November 2021 to January 2021, BA.2: March to May 2022, BA.4/5: mid-June to mid-July 2022) and/or were variant confirmed by genome sequencing. Neutralization titers were measured using a pseudovirus neutralization assay, using pseudoviruses bearing the SARS-CoV-2 S protein of a BA.4/5, BA.4.6/BF.7, BQ.1.1, BA.2.75, BA.2.75.2, or XBB Omicron variants on the surface (e.g., using methods described in the previous Examples; FIG. 65). 50% pseudovirus neutralization titers ($pVNT_{50}$) are shown in FIG. 64(A). Neutralization breadth irrespective of the magnitude of antibody titers was assessed by normalizing the Omicron sublineage $pVNT_{50}$ against those for the wild-type strain (FIG. 64(B)). In the triple-/quadruple-vaccinated individuals without breakthrough infection, $pVN_{50}$ GMTs against Omicron BA.4/5 were 5 to 6-fold lower than GMTs against the wild-type strain (GMTs against BA.4/5 in the range of 69-121) (FIG. 64(A)). GMTs against BA.4/5 were similarly reduced in BA.1 convalescents (GMT 263, 5-fold lower than wild-type), whereas in the BA.2 and BA.4/BA.5 convalescent cohorts titers against BA.4/5 remained higher (GMTs of 386 and 521, respectively; 3 and 2-fold lower than wild-type).

In all three convalescent cohorts, neutralizing titers against Omicron BA.4.6/BF.7 and BA.2.75 were robustly above those of triple-/quadruple-vaccinated SARS-CoV-2 naïve individuals (GMT range 239-525 for convalescents as compared to 55-139 for naïves). In the convalescents, Omicron BA.4.6/BF.7 and BA.2.75 GMTs were largely comparable with no significant differences to those against Omicron BA.4/BA.5. In contrast, $pVN_{50}$ titers against Omicron BQ.1.1, BA.2.75.2, and XBB were lower than those against BA.4/5 across cohorts. Titers against BQ.1.1 were overall low in the SARS-CoV-2 naïve vaccinated cohorts and BA.1 convalescents (GMTs ≤38), and higher in the BA.2 and BA.4/BA.5 convalescent cohorts (GMTs 100 and 154, respectively). Titers against BA.2.75.2 and XBB were relatively low across cohorts (GMTs ≤88 and ≤33, respectively).

To assess neutralization breadth irrespective of the magnitude of antibody titers, Omicron sublineage $pVN_{50}$ GMTs were normalized against those for the wild-type strain. GMT ratios for all Omicron subvariant pseudoviruses were comparable in the $BNT162b2^3$ and $BNT162b2^4$ cohorts (FIG. 64(B)), indicating that a fourth dose did not improve cross-neutralization of the tested sublineages. GMT ratios were in the range of 0.09-0.22 for BA.4/5, BA.4.6/BF.7, and BA.2.75 and 50.05 for BQ.1.1, BA.2.75.2, and XBB in both cohorts.

Cross-neutralization of BA.4/BA.5 and BA.4.6/BF.7 was significantly ($p<0.05$) higher in sera from BA.2.convalescents as compared to triple-vaccinated individuals (GMT ratios 0.37 vs 0.17 for BA.4/BA.5, and 0.23 vs 0.12 for BA.4.6/BF.7) and even more so in BA.4/BA.5-convalescents for both the BA.4/BA.5 pseudovirus (GMT ratio 0.48, $p<0.01$ versus $BNT162b2^3$) and the BA.4.6/BF.7 pseudovirus (GMT ratio 0.41, $p<0.0001$). Cross-neutralization of BA.4.6/BF.7 was also significantly ($p<0.0001$) stronger in BA.4/BA.5 convalescents compared to quadruple-vaccinated individuals. While BQ.1.1 was cross-neutralized less efficiently than BA.4/5 in all cohorts (GMT ratios 50.14), cross-neutralization in BA.4/BA.5 and BA.2 convalescents remained significantly stronger compared to SARS-CoV-2 naïve triple or quadruple vaccinated and BA.1 breakthrough infected cohorts. Cross-neutralization of BA.2.75, BA.2.75.2, and XBB pseudoviruses was broadly comparable across cohorts. Together these data show that partial neutralization of some Omicron sublineages is retained especially in BA.4/BA.5 convalescent individuals, and that neutralizating antibody responses observed in vaccinated and breakthrough infected individuals appeared to be less effective against sublineases BA.2.75.2 and XBB. These data also suggest that, in some embodiments, an improved immune response (e.g., increased neutralization titers) may be provided by a vaccine comprising RNA encoding a SARS-CoV-2 S protein comprising one or more mutations characteristic of an XBB variant, a BQ.1.1 variant, or any lineage derived therefrom).

Example 23: T Cell Epitope and Neutralizing B Cell Epitope Conservedness Across SARS-CoV-2 Variants of Concern To estimate the rate of nonsynonymous mutation in T cell epitopes in the S glycoprotein, the Immune Epitope Database (www_iedb_org/) was used to obtain epitopes confirmed for T cell reactivity in experimental assays. The database was filtered using the following criteria: Organism: SARS-COV2; Antigen: Spike glycoprotein; Positive Assay; No B cell assays; No MHC assays; MHC Restriction Type: Class I; Host: *Homo sapiens* (human). The resulting table was filtered by removing epitopes that were "deduced from a reactive overlapping peptide pool", as well as epitopes longer than 14 amino acids in order to restrict the dataset to confirmed minimal epitopes only. The experimental assays confirming the reactivity of these epitopes relied on multimer analysis, ELISpot or ELISpot-like assays, T cell activation assays, etc. The epitopes were reported for at least 27 different HLA-I alleles, including HLA-A, HLA-B, and HLA-C alleles. Of the 251 unique epitope sequences obtained in this approach, 244 were found in the Wuhan strain spike glycoprotein. Of these, 36 epitopes (14.8%) included a position reported to be mutated by sequence analysis described herein.

In addition, conservedness of neutralizing B cell epitopes was calculated by counting the number of antibody neutralising epitopes potentially impacted by mutations. It was calculated by first mapping 719 binding epitopes observed in 332 experimentally resolved structures of nAbs onto the S protein using available protein structures (as described in www_biorxiv_org/content/10_1101/2021_12_24_ 474095 v2). For each structure, an epitope per antibody was calculated as the set of positions that were in contact with an antibody, where two residues were considered to be in contact if the smallest Euclidean distance between their atoms was smaller than 4 Ångstroms. Each nAb was evaluated and considered to be evaded by a variant if any position of its epitope was mutated.

Figure 66:
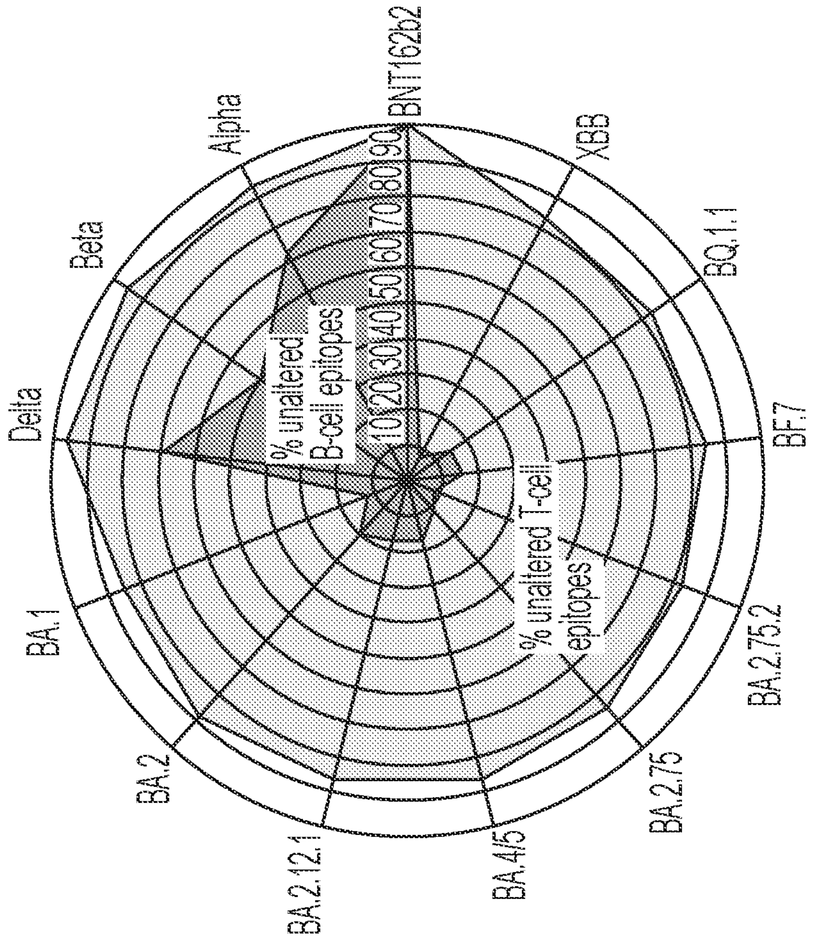
Figure 66:
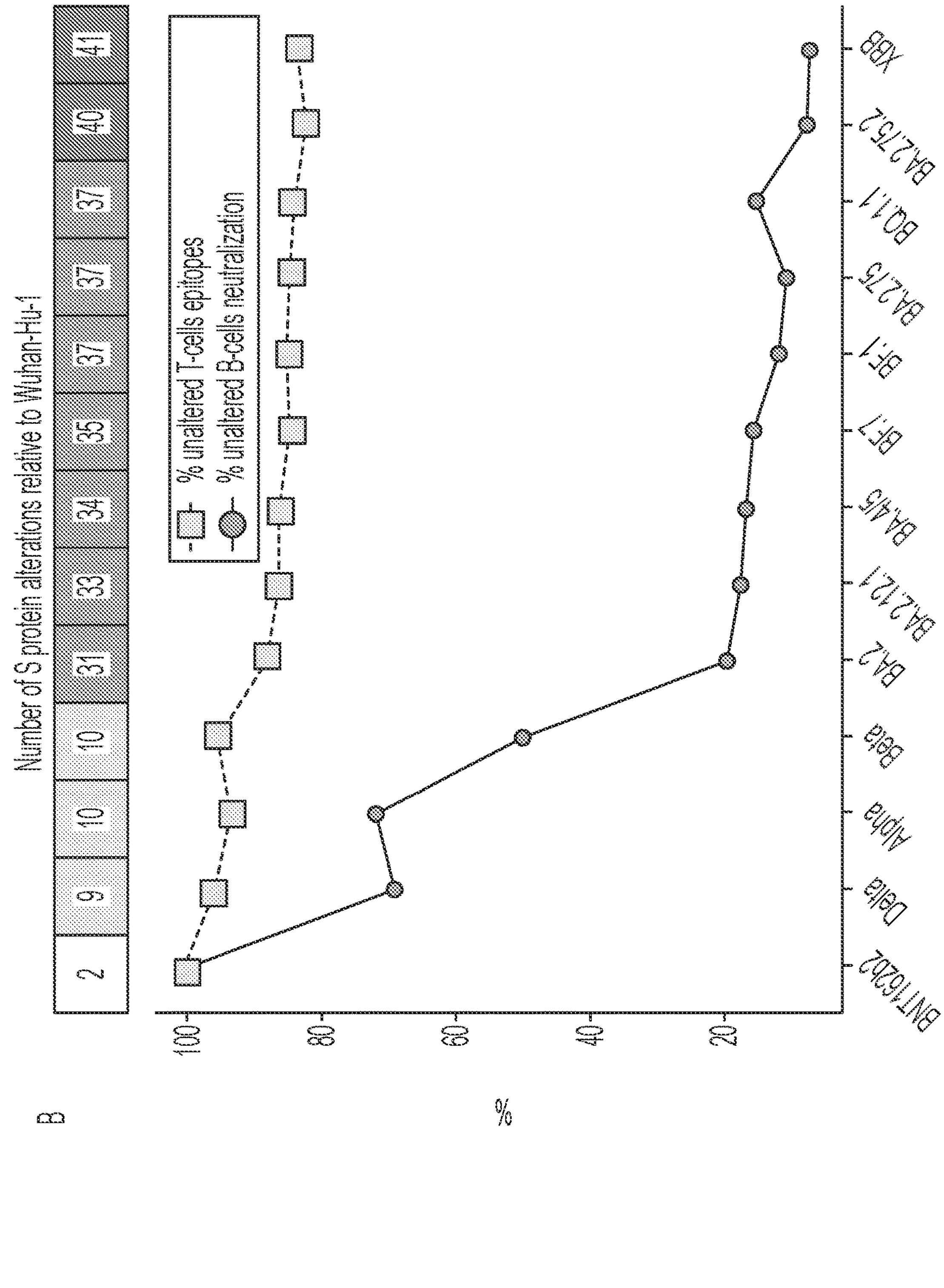

Given that humoral and cell-mediated immunity together determine susceptibility to severe COVID-19 disease, the degree of conservation among neutralizing B-cell and T-cell epitopes of the S glycoprotein in Omicron sublineages was assessed. The findings presented herein show that over 80% of the BNT162b2 encoded S glycoprotein T-cell epitopes were fully conserved in Omicron sublineages including BA.2.75.2, BQ.1.1, and XBB (FIG. 66). In striking contrast, B-cell epitopes were partially conserved in the earlier variants Alpha, Beta, and Delta (≥50%) but most of these epitopes were altered in the Omicron lineage (≤20% conservation), particularly in BA.2.75.2 and XBB (≤10%). These findings suggest that in the vaccinated population robust T-cell mediated immunity may be maintained against the Omicron variant, including sublineages that evade neutralizing antibodies.

The invention claimed is:

1. A composition comprising: an RNA molecule having a nucleotide sequence that is at least 99% identical to that set forth in SEQ ID NO: 98;

wherein the RNA molecule comprises a 5' cap; and wherein the RNA molecule optionally comprises a modified uridine in place of one or more uridines.

2. The composition of claim 1, wherein each of the uridines in the RNA molecule is replaced with a modified uridine.

3. The composition of claim 2, wherein the modified uridine is N1-methyl-pseudouridine.

4. The composition of claim 1, wherein the 5' cap comprises $m_2^{7,3'-O}Gppp(m_1^{2'-O})ApG$.

5. The composition of claim 1, wherein the RNA molecule is encapsulated in a lipid nanoparticle (LNP).

6. A composition comprising an RNA molecule having a nucleotide sequence that is at least 99% identical to that set forth in SEQ ID NO: 98, wherein:

the RNA molecule comprises N1-methyl-pseudouridine in place of each uridine;

the RNA molecule comprises a 5' cap that comprises $m_2^{7,3'-O}Gppp(m_1^{2'-O})ApG$; and the RNA molecule is encapsulated in a lipid nanoparticle (LNP).

7. The composition of claim 6, comprising about 10 mM Tris buffer and about 10% sucrose.

8. The composition of claim 7, wherein the composition is formulated as a multidose formulation in a vial.

9. A method of inducing an immune response, comprising administering to a subject the composition of claim 1.

10. The method of claim 9, wherein the RNA molecule comprises N1-methyl-pseudouridine in place of each uridine.

11. The method of claim 9, wherein the 5' cap comprises $m_2^{7,3'-O}Gppp(m_1^{2'-O})ApG$.

12. The method of claim 9, wherein the RNA molecule is encapsulated in an LNP.

13. The method of claim 9, wherein the subject is 12 years or older, and the composition comprises 30 μg of the RNA molecule.

14. The method of claim 9, wherein the subject is 5 years to less than 12 years old, and the composition comprises 10 μg of the RNA molecule.

15. The method of claim 9, wherein the subject is 6 months to less than 5 years old, and the composition comprises 3 μg of the RNA molecule.

16. The method of claim 9, wherein, prior to administering the composition of claim 1, the subject is administered a first dose and a second dose of an RNA molecule comprising a sequence that is at least 99% identical to SEQ ID NO: 20;

wherein the second dose is administered about 21 days after the first dose; and wherein the composition of claim 1 is administered at least about two months after the second dose.

17. The method of claim 9, wherein the composition of claim 1 is administered in a volume of about 200 μL to 300 μL.

18. The method of claim 9, wherein the subject was previously administered one or more doses of a SARS-CoV-2 vaccine.

19. The method of claim 18, wherein the subject was previously administered a complete dosing regimen of a SARS-CoV-2 vaccine.

20. The method of claim 9, wherein the composition is administered in conjunction with one or more vaccines targeting a different infectious agent.

21. The method of claim 20, wherein the one or more vaccines targeting a different infectious agent comprise an influenza vaccine and/or an RSV vaccine.

22. A composition comprising at least one unit dose of a population of lipid nanoparticles (LNPs), wherein each LNP in the population encapsulates at least one RNA molecule, wherein the at least one RNA molecule comprises:

(a) a nucleotide sequence that is at least 95% identical to SEQ ID NO: 98 and which encodes a polypeptide, wherein the polypeptide:

(i) has an amino acid sequence that is at least 95% identical to SEQ ID NO: 95;

(ii) comprises a proline substitution at one or both positions corresponding to residues 986 and 987 of SEQ ID NO: 1; and (iii) comprises at least 10 of the following mutations as compared to SEQ ID NO: 1: T19I, Δ24-26, A27S, V83A, G142D, Δ144, H146Q, Q183E, V213E, G339H, R346T, L368I, S371F, S373P, S375F, T376A, D405N, R408S, K417N, N440K, V445P, G446S, N460K, S477N, T478K, E484A, F486S, F490S, Q498R, N501Y, Y505H, D614G, H655Y, N679K, P681H, N764K, D796Y, and Q954H;

(b) N1-methyl-pseudouridine in place of each uridine; and (c) a 5' cap that comprises $m_2^{7,3'-O}Gppp(m_1^{2'-O})ApG$.

23. The composition of claim 22, comprising about 10 mM Tris buffer and about 10% sucrose.

24. The composition of claim 22, wherein the unit dose comprises the RNA molecule in an amount of about 3 μg to about 30 μg.

25. The composition of claim 1, wherein the SARS-CoV-2 S protein comprises a proline mutation at one or both positions corresponding to residues 986 and 987 of SEQ ID NO: 1.

26. The composition of claim 25, wherein the SARS-CoV-2 S protein comprises at least 10 of the following mutations as compared to SEQ ID NO: 1: T19I, Δ24-26, A27S, V83A, G142D, Δ144, H146Q, Q183E, V213E, G339H, R346T, L368I, S371F, S373P, S375F, T376A, D405N, R408S, K417N, N440K, V445P, G446S, N460K, S477N, T478K, E484A, F486S, F490S, Q498R, N501Y, Y505H, D614G, H655Y, N679K, P681H, N764K, D796Y, and Q954H.

27. The composition of claim 1, wherein:

(a) the 5'-cap comprises $m_2^{7,3'-O}Gppp(m_1^{2'O})ApG$;

(b) the RNA molecule comprises a 5'-UTR that comprises a modified human alpha-globin 5'-UTR;

(c) the RNA molecule comprises a 3'-UTR that comprises a first sequence from the amino terminal enhancer of split (AES) messenger RNA and a second sequence from the mitochondrial encoded 12S ribosomal RNA; and (d) the RNA molecule comprises a poly(A) sequence comprising at least 100 A nucleotides.

28. The composition of claim 22, wherein the RNA molecule comprises each of the following:

(a) a 5'-UTR that comprises a modified human alpha-globin 5'-UTR;

(b) a 3'-UTR that comprises a first sequence from the amino terminal enhancer of split (AES) messenger RNA and a second sequence from the mitochondrial encoded 12S ribosomal RNA; and (c) a poly(A) sequence that comprises at least 100 A nucleotides.

* * * * *